United States Patent
Umetani et al.

(10) Patent No.: US 11,000,038 B2
(45) Date of Patent: May 11, 2021

(54) PYRIDONE COMPOUNDS AND AGRICULTURAL AND HORTICULTURAL FUNGICIDES CONTAINING THE SAME AS ACTIVE INGREDIENTS

(71) Applicant: MITSUI CHEMICALS AGRO, INC., Tokyo (JP)

(72) Inventors: Hideki Umetani, Ritto (JP); Kazuki Kitajima, Mobara (JP); Takeshi Fukumoto, Chiba (JP); Masanori Yanagi, Mobara (JP); Akihiro Nishida, Chiba (JP); Ryohei Naito, Kusatsu (JP); Koya Saito, Mobara (JP); Tomomi Shirakawa, Ritto (JP); Hikaru Koishihara, Chiba (JP); Akane Sakurada, Mobara (JP); Satoshi Yutani, Ratchaburi (TH); Toshiaki Ohara, Moriyama (JP)

(73) Assignee: MITSUI CHEMICALS AGRO, INC., Tokyo (JP)

( * ) Notice: Subject to any disclaimer, the term of this patent is extended or adjusted under 35 U.S.C. 154(b) by 75 days.

(21) Appl. No.: 16/500,480

(22) PCT Filed: Apr. 10, 2018

(86) PCT No.: PCT/JP2018/015141
§ 371 (c)(1),
(2) Date: Oct. 3, 2019

(87) PCT Pub. No.: WO2018/190351
PCT Pub. Date: Oct. 18, 2018

(65) Prior Publication Data
US 2020/0196600 A1    Jun. 25, 2020

(30) Foreign Application Priority Data
Apr. 10, 2017  (JP) .............................. JP2017-077802

(51) Int. Cl.
*A01N 43/40*  (2006.01)
*C07D 213/68*  (2006.01)
*C07D 413/04*  (2006.01)
*C07D 401/04*  (2006.01)

(52) U.S. Cl.
CPC ........... *A01N 43/40* (2013.01); *C07D 213/68* (2013.01); *C07D 401/04* (2013.01); *C07D 413/04* (2013.01)

(58) Field of Classification Search
CPC .............................. C07D 213/68; A01N 43/40
See application file for complete search history.

(56) References Cited

FOREIGN PATENT DOCUMENTS

| EP | 0304057 A2 | 2/1989 |
|---|---|---|
| JP | S53065882 A | 6/1978 |
| JP | S61246163 A | 11/1986 |
| JP | S6447767 A | 2/1989 |
| JP | H01207274 A | 8/1989 |

OTHER PUBLICATIONS

International Search Report (PCT/ISA/210) and translation and Written Opinion (PCT/ISA/237) dated Jun. 19, 2019, by the Japanese Patent Office as the International Searching Authority for International Application No. PCT/JP2018/015141.

*Primary Examiner* — Kamal A Saeed
(74) *Attorney, Agent, or Firm* — Buchanan, Ingersoll & Rooney PC

(57) ABSTRACT

A pyridone compound represented by Formula (1):

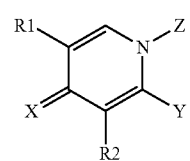

wherein R1, R2, X, Y and Z are defined. The pyridone compound can control plant diseases.

7 Claims, No Drawings

PYRIDONE COMPOUNDS AND AGRICULTURAL AND HORTICULTURAL FUNGICIDES CONTAINING THE SAME AS ACTIVE INGREDIENTS

TECHNICAL FIELD

The present invention relates to a pyridone compound and a pesticide containing the compound as an active ingredient.

BACKGROUND ART

Protection of agricultural and horticultural crops from diseases is important to ensure stable agricultural production. For this purpose, various fungicides are used. However, use of fungicides over years causes emergence of fungi resistant to drugs. Thus, novel fungicides that are effective not only to drug-sensitive fungi but also to drug-resistant fungi are demanded.

By the way, prior examples related to 1,2,3,5-substituted-4-pyridone compounds have been known. For example, 1,2,3,5-substituted-4-pyridone compounds each having a carboxyl group at the 5-position have been disclosed as antibacterial drugs (for example, JP Sho.53-65882A and JP Sho.61-246163A).

CITATION LIST

Patent Literature

Patent Literature 1: JP Sho.53-65882A
Patent Literature 2: JP Sho.61-246163A

SUMMARY OF INVENTION

Problems to be Solved by Invention

However, the uses of the compounds disclosed in JP Sho.53-65882A and JP Sho.61-246163A are each medicine and differ from the technical field to which the agricultural and horticultural fungicide according to the present invention belongs.

An object of the present invention is to provide a novel compound effective as an agricultural and horticultural fungicide.

Means to Solve the Problems

In order to solve the problems above, the present inventors have extensively studied a 1,2,3,5-substituted-pyridone compound group. As a result, it has been found that a group of novel compounds each in which a halogen atom, an alkyl group or the like is introduced at each of the 3- and 5-positions in the 4-pyridone skeleton exhibit an excellent activity in the control of plant diseases, thus completing the present invention.

That is, the present invention resides in the following aspects.

[1] A compound represented by Formula (1):

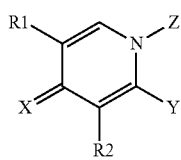
(1)

[wherein:
R1 represents
  a cyano group,
  a halogen atom,
  a C1-C6 alkyl group optionally substituted with substituent A,
  a C1-C6 haloalkyl group,
  a C3-C8 cycloalkyl group optionally substituted with substituent A,
  a C2-C6 alkenyl group optionally substituted with substituent A,
  a C2-C6 haloalkenyl group,
  a C2-C6 alkynyl group optionally substituted with substituent A,
  a C2-C6 haloalkynyl group,
  a C1-C6 alkoxy group optionally substituted with substituent A,
  a C1-C6 haloalkoxy group,
  a C3-C8 cycloalkoxy group optionally substituted with substituent A,
  a C2-C6 alkenyloxy group optionally substituted with substituent A,
  a C2-C6 haloalkenyloxy group,
  a C3-C6 alkynyloxy group optionally substituted with substituent A,
  a C3-C6 haloalkynyloxy group,
  an Rc-L- (wherein Rc represents a C1-C6 alkyl group or a C1-C6 haloalkyl group, and L represents S, SO or $SO_2$), or
  an RgC(=O)— (wherein Rg represents a C1-C6 alkyl group optionally substituted with substituent B, a C1-C6 haloalkyl group or a C3-C8 cycloalkyl group);
R2 represents
  a cyano group,
  a halogen atom,
  a C1-C6 alkyl group optionally substituted with substituent A,
  a C1-C6 haloalkyl group,
  a C3-C8 cycloalkyl group optionally substituted with substituent A,
  a C2-C6 alkenyl group optionally substituted with substituent A,
  a C2-C6 haloalkenyl group,
  a C2-C6 alkynyl group optionally substituted with substituent A,
  a C2-C6 haloalkynyl group,
  an Rc-L- (wherein Rc and L are the same as defined above), or
  an RgC(=O)— (wherein Rg is the same as defined above);
X represents an oxygen atom or a sulfur atom;
Y represents
  a phenyl group optionally substituted with 0 to 5 R3 (with the proviso that when there are two or more substituents R3, they are independent to each other),
  a pyridyl group optionally substituted with 0 to 4 R3 (with the proviso that when there are two or more substituents R3, they are independent to each other),
  a pyridazinyl group optionally substituted with 0 to 3 R3 (with the proviso that when there are two or more substituents R3, they are independent to each other),
  a pyrimidinyl group optionally substituted with 0 to 3 R3 (with the proviso that when there are two or more substituents R3, they are independent to each other),
  a pyrazinyl group optionally substituted with 0 to 3 R3 (with the proviso that when there are two or more substituents R3, they are independent to each other), a triazinyl group optionally substituted with 0 to 2 R3 (with the proviso that when there are two substituents R3, they are independent to each other), a tetrazinyl group optionally substituted with R3, a thienyl group optionally substituted with 0 to 3 R3 (with the proviso that when there are two or more substituents R3, they are independent to each other), a thiazolyl group optionally substituted with 0 to 2 R3 (with the proviso that when there are two substituents R3, they are independent to each other), an isothiazolyl group optionally substituted with 0 to 2 R3 (with the proviso that when there are two substituents R3, they are independent to each other), a thiadiazolyl group optionally substituted with R3, a furanyl group optionally substituted with 0 to 3 R3 (with the proviso that when there are two or more substituents R3, they are independent to each other), an oxazolyl group optionally substituted with 0 to 2 R3 (with the proviso that when there are two substituents R3, they are independent to each other), an isoxazolyl group optionally substituted with 0 to 2 R3 (with the proviso that when there are two substituents R3, they are independent to each other), or an oxadiazolyl group optionally substituted with R3, R3 represents a hydroxyl group, a cyano group, a nitro group, a halogen atom, a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C, a C2-C6 haloalkynyl group, a C1-C6 alkoxy group optionally substituted with substituent C, a C1-C6 haloalkoxy group, a C3-C8 cycloalkoxy group optionally substituted with substituent C, a C2-C6 alkenyloxy group optionally substituted with substituent C, a C2-C6 haloalkenyloxy group, a C3-C6 alkynyloxy group optionally substituted with substituent C, a C3-C6 haloalkynyloxy group, an RdC(=O)— (wherein Rd represents a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group)), an RdC(=O)O— (wherein Rd is the same as defined above), a group of a 3-6 membered ring containing 1-2 oxygen atoms, an Rc-L- (wherein Rc and L are the same as defined above), an RaRbN— (wherein Ra and Rb are the same as defined above), or an ReC(=O)N(Rf)— (wherein Re and Rf are independent to each other, and each represents a hydrogen atom, a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are the same as defined above));

Z represents a C1-C9 alkyl group optionally substituted with substituent C, a C1-C6 haloalkyl group, a C3-C8 cycloalkyl group optionally substituted with substituent D, a C2-C6 alkenyl group optionally substituted with substituent C, a C2-C6 haloalkenyl group, a C2-C6 alkynyl group optionally substituted with substituent C, a C2-C6 haloalkynyl group, a phenyl group optionally substituted with 0 to 5 R4 (with the proviso that when there are two or more substituents R4, they are independent to each other), a C1-C6 alkyl group having a phenyl group optionally substituted with 0 to 5 R4 (with the proviso that when there are two or more substituents R4, they are independent to each other), a C1-C6 haloalkyl group having a phenyl group optionally substituted with 0 to 5 R4 (with the proviso that when there are two or more substituents R4, they are independent to each other), a pyridyl group optionally substituted with 0 to 4 R4 (with the proviso that when there are two or more substituents R4, they are independent to each other), a pyridazinyl group optionally substituted with 0 to 3 R4 (with the proviso that when there are two or more substituents R4, they are independent to each other), a pyrimidinyl group optionally substituted with 0 to 3 R4 (with the proviso that when there are two or more substituents R4, they are independent to each other), a pyrazinyl group optionally substituted with 0 to 3 R4 (with the proviso that when there are two or more substituents R4, they are independent to each other), a triazinyl group optionally substituted with 0 to 2 R4 (with the proviso that when there are two substituents R4, they are independent to each other), a tetrazinyl group optionally substituted with R4, a thienyl group optionally substituted with 0 to 3 R4 (with the proviso that when there are two or more substituents R4, they are independent to each other), a thiazolyl group optionally substituted with 0 to 2 R4 (with the proviso that when there are two substituents R4, they are independent to each other), an isothiazolyl group optionally substituted with 0 to 2 R4 (with the proviso that when there are two substituents R4, they are independent to each other), a thiadiazolyl group optionally substituted with R4, an oxazolyl group optionally substituted with 0 to 2 R4 (with the proviso that when there are two substituents R4, they are independent to each other), an isoxazolyl group optionally substituted with 0 to 2 R4 (with the proviso that when there are two substituents R4, they are independent to each other), an oxadiazolyl group optionally substituted with R4, or a pyrazolyl group optionally substituted with 0 to 2 R4 (with the proviso that when there are two substituents R4, they are independent to each other), R4 has the same meaning as R3; and the substituent A is at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, an RaRbN— (wherein Ra and Rb are the same as defined above) and an Rc-L- (wherein Rc and L are the same as defined above);

the substituent B is at least one member selected from the group consisting of a cyano group, a C1-C6 alkoxy group, a C1-C6 haloalkoxy group and a C3-C8 cycloalkoxy group;

the substituent C is at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, a C2-C5 alkoxyalkoxy group, an RaRbN— (wherein Ra and Rb are the same as defined above), an Rc-L- (wherein Rc and L are the same as defined above), an RdC(=O)— (wherein Rd is the same as defined above) and a group of a 3-6 membered ring containing 1-2 oxygen atoms; and the substituent D is at least one member selected from the group consisting of a cyano group, a C1-C6 alkyl group, a C1-C6 alkoxy group, a C1-C6 haloalkoxy group and a C3-C8 cycloalkoxy group], or a salt thereof.

[2] The compound of [1], wherein:

R1 represents
  a halogen atom,
  a C1-C6 alkyl group optionally substituted with substituent A,
  a C1-C6 haloalkyl group,
  a C3-C8 cycloalkyl group optionally substituted with substituent A,
  a C2-C6 alkenyl group optionally substituted with substituent A,
  a C2-C6 haloalkenyl group,
  a C2-C6 alkynyl group optionally substituted with substituent A,
  a C2-C6 haloalkynyl group,
  a C1-C6 alkoxy group optionally substituted with substituent A,
  a C1-C6 haloalkoxy group,
  a C2-C6 alkenyloxy group optionally substituted with substituent A,
  a C3-C6 alkynyloxy group optionally substituted with substituent A, or
  an RgC(=O)— (wherein Rg represents a C1-C6 alkyl group optionally substituted with substituent B, a C1-C6 haloalkyl group or a C3-C8 cycloalkyl group);

R2 represents
  a halogen atom,
  a C1-C6 alkyl group optionally substituted with substituent A,
  a C1-C6 haloalkyl group,
  a C3-C8 cycloalkyl group optionally substituted with substituent A,
  a C2-C6 alkenyl group optionally substituted with substituent A,
  a C2-C6 haloalkenyl group,
  a C2-C6 alkynyl group optionally substituted with substituent A, or
  a C2-C6 haloalkynyl group;

Y represents
  a phenyl group optionally substituted with 0 to 5 R3 (with the proviso that when there are two or more substituents R3, they are independent to each other),
  a pyridyl group optionally substituted with 0 to 4 R3 (with the proviso that when there are two or more substituents R3, they are independent to each other), or
  a furanyl group optionally substituted with 0 to 3 R3 (with the proviso that when there are two or more substituents R3, they are independent to each other), R3 represents
  a hydroxyl group,
  a cyano group,
  a halogen atom,
  a C1-C6 alkyl group optionally substituted with substituent C,
  a C1-C6 haloalkyl group,
  a C1-C6 alkoxy group optionally substituted with substituent C,
  a C1-C6 haloalkoxy group,
  a C2-C6 alkenyloxy group optionally substituted with substituent C,
  a C2-C6 haloalkenyloxy group,
  a C3-C6 alkynyloxy group optionally substituted with substituent C,
  a C3-C6 haloalkynyloxy group,
  an RdC(=O)— (wherein Rd represents a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group)),
  an RdC(=O)O— (wherein Rd is the same as defined above), or
  an Rc-L- (wherein Rc represents a C1-C6 alkyl group or a C1-C6 haloalkyl group, and L represents S, SO or SO$_2$);

Z represents
  a C1-C9 alkyl group optionally substituted with substituent C,
  a C1-C6 haloalkyl group,
  a C3-C8 cycloalkyl group optionally substituted with substituent D,
  a C2-C6 alkenyl group optionally substituted with substituent C,
  a C2-C6 alkynyl group optionally substituted with substituent C,
  a phenyl group optionally substituted with 0 to 5 R4 (with the proviso that when there are two or more substituents R4, they are independent to each other),
  a C1-C6 alkyl group having a phenyl group optionally substituted with 0 to 5 R4 (with the proviso that when there are two or more substituents R4, they are independent to each other),
  a pyridyl group optionally substituted with 0 to 4 R4 (with the proviso that when there are two or more substituents R4, they are independent to each other),
  an oxazolyl group optionally substituted with 0 to 2 R4 (with the proviso that when there are two substituents R4, they are independent to each other),
  an isoxazolyl group optionally substituted with 0 to 2 R4 (with the proviso that when there are two substituents R4, they are independent to each other), or
  an oxadiazolyl group optionally substituted with R4, R4 represents
  a hydroxyl group, a cyano group,
a nitro group,
a halogen atom,
a C1-C6 alkyl group optionally substituted with substituent C,
a C1-C6 haloalkyl group,
a C2-C6 alkenyl group optionally substituted with substituent C,
a C2-C6 alkynyl group optionally substituted with substituent C,
a C1-C6 alkoxy group optionally substituted with substituent C,
a C1-C6 haloalkoxy group,
a C2-C6 alkenyloxy group optionally substituted with substituent C,
a C3-C6 alkynyloxy group optionally substituted with substituent C,
an RdC(=O)O— (wherein Rd is the same as defined above),
an RaRbN— (wherein Ra and Rb are the same as defined above), or
an ReC(=O)N(Rf)— (wherein Re and Rf are independent to each other, and each represents a hydrogen atom, a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are the same as defined above)), or a salt thereof.

[3] The compound of [2], wherein:
R1 represents
a halogen atom,
a C1-C6 alkyl group optionally substituted with substituent A,
a C1-C6 haloalkyl group,
a C2-C6 alkenyl group optionally substituted with substituent A,
a C2-C6 alkynyl group optionally substituted with substituent A, or
an RgC(=O)— (wherein Rg represents a C1-C6 alkyl group optionally substituted with substituent B, a C1-C6 haloalkyl group or a C3-C8 cycloalkyl group);
R2 represents
a halogen atom,
a C1-C6 alkyl group optionally substituted with substituent A, or
a C1-C6 haloalkyl group;
Y represents
a phenyl group optionally substituted with 0 to 5 R3 (with the proviso that when there are two or more substituents R3, they are independent to each other),
a pyridyl group optionally substituted with 0 to 4 R3 (with the proviso that when there are two or more substituents R3, they are independent to each other), or
a furanyl group optionally substituted with 0 to 3 R3 (with the proviso that when there are two or more substituents R3, they are independent to each other),
R3 represents
a hydroxyl group,
a cyano group,
a halogen atom,
a C1-C6 alkyl group optionally substituted with substituent C,
a C1-C6 haloalkyl group,
a C1-C6 alkoxy group optionally substituted with substituent C,
a C2-C6 alkenyloxy group optionally substituted with substituent C,
a C3-C6 alkynyloxy group optionally substituted with substituent C,
an RdC(=O)— (wherein Rd represents a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group)),
an RdC(=O)O— (wherein Rd is the same as defined above), or
an Rc-L- (wherein Rc represents a C1-C6 alkyl group or a C1-C6 haloalkyl group, and L represents S, SO or SO$_2$);
Z represents
a C1-C9 alkyl group optionally substituted with substituent C,
a C1-C6 haloalkyl group,
a C3-C8 cycloalkyl group optionally substituted with substituent D,
a C2-C6 alkenyl group optionally substituted with substituent C,
a C2-C6 alkynyl group optionally substituted with substituent C,
a phenyl group optionally substituted with 0 to 5 R4 (with the proviso that when there are two or more substituents R4, they are independent to each other),
a C1-C6 alkyl group having a phenyl group optionally substituted with 0 to 5 R4 (with the proviso that when there are two or more substituents R4, they are independent to each other),
a pyridyl group optionally substituted with 0 to 4 R4 (with the proviso that when there are two or more substituents R4, they are independent to each other), or
an isoxazolyl group optionally substituted with 0 to 2 R4 (with the proviso that when there are two substituents R4, they are independent to each other),
R4 represents
a hydroxyl group,
a cyano group,
a nitro group,
a halogen atom,
a C1-C6 alkyl group optionally substituted with substituent C,
a C1-C6 haloalkyl group,
a C1-C6 alkoxy group optionally substituted with substituent C,
a C2-C6 alkenyloxy group optionally substituted with substituent C,
a C3-C6 alkynyloxy group optionally substituted with substituent C,
an RaRbN— (wherein Ra and Rb are the same as defined above) or
an ReC(=O)N(Rf)— (wherein Re and Rf are independent to each other, and each represents a hydrogen atom, a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are the same as defined above)), or a salt thereof.

[4] The compound of any one of [1] to [3], wherein R1 is a fluorine atom, a chlorine atom, a bromine atom, an iodine atom, a methyl group, an ethyl group, a trifluoromethyl group, a vinyl group, an ethynyl group or an acetyl group, or a salt thereof.

[5] The compound of any one of [1] to [4], wherein R2 is a fluorine atom, a chlorine atom, a bromine atom, an iodine atom, a methyl group, an ethyl group, a propyl group or a 2,2,2-trifluoroethyl group, or a salt thereof.

[6] The compound of any one of [1] to [5], wherein X is an oxygen atom, or a salt thereof.

[7] The compound of any one of [1] to [5], wherein X is a sulfur atom, or a salt thereof.

[8] The compound of any one of [1] to [7], wherein Y represents a phenyl group optionally substituted with 0 to 5 R3 (with the proviso that when there are two or more substituents R3, they are independent to each other), or a pyridyl group optionally substituted with 0 to 4 R3 (with the proviso that when there are two or more substituents R3, they are independent to each other), R3 represents a hydroxyl group, a cyano group, a halogen atom, a C1-C6 alkyl group optionally substituted with substituent C, a C1-C6 alkoxy group optionally substituted with substituent C, a C2-C6 alkenyloxy group optionally substituted with substituent C, a C3-C6 alkynyloxy group optionally substituted with substituent C, or an RdC(=O)O— (wherein Rd represents a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group)), or a salt thereof.

[9] The compound of any one of [1] to [7], wherein R3 is a hydroxyl group, a cyano group, a fluorine atom, a chlorine atom, a bromine atom, a methyl group, a trifluoromethyl group, a methoxy group, an ethoxy group, an allyloxy group, a propargyloxy group, a methoxycarbonyl group, an acetyloxy group, a methylthio group, a methanesulfinyl group or a methanesulfonyl group, or a salt thereof.

[10] The compound of any one of [1] to [9], wherein Y is a phenyl group optionally substituted with 0 to 5 R3 (with the proviso that when there are two or more substituents R3, they are independent to each other), or a salt thereof.

[11] The compound of any one of [1] to [9], wherein Y is a pyridyl group optionally substituted with 0 to 4 R3 (with the proviso that when there are two or more substituents R3, they are independent to each other), or a salt thereof.

[12] The compound of any one of [1] to [7], wherein Y is a phenyl group, a 4-cyanophenyl group, a 2-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 2,4,6-trifluorophenyl group, a 4-chloro-2-fluorophenyl group, a 2-chloro-4-fluorophenyl group, a 2-chloro-6-fluorophenyl group, a 2-bromo-4-fluorophenyl group, a 2-bromo-6-fluorophenyl group, a 2,4-dichlorophenyl group, a 3,5-dichlorophenyl group, a 2-chlorophenyl group, a 2-bromophenyl group, a 2,6-difluoro-4-hydroxyphenyl group, a 2-fluoro-6-methylphenyl group, a 4-fluoro-2-methylphenyl group, a 2-fluoro-6-(trifluoromethyl)phenyl group, a 2,6-difluoro-4-methoxyphenyl group, a 2,6-difluoro-4-ethoxyphenyl group, a 2-fluoro-6-methoxyphenyl group, a 2-bromo-4-methoxyphenyl group, a 2,6-difluoro-4-(allyloxy)phenyl group, a 2,6-difluoro-4-(propargyloxy)phenyl group, a 2,6-difluoro-4-(acetyloxy)phenyl group, a 2-methylphenyl group, a 4-methylphenyl group, a 2-(trifluoromethyl)phenyl group, a 4-(trifluoromethyl)phenyl group, a 2-methoxyphenyl group, a 4-methoxyphenyl group, a 4-(methoxycarbonyl)phenyl group, a 4-(methylthio)phenyl group, a 4-(methanesulfinyl) phenyl group, a 4-(methanesulfonyl)phenyl group, a 4-pyridyl group, a 3,5-difluoro-4-pyridyl group, a 3,5-dichloro-4-pyridyl group or a 3-furanyl group, or a salt thereof.

[13] The compound of any one of [1] to [7], wherein Y is a phenyl group, a 4-cyanophenyl group, a 2-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 2,4,6-trifluorophenyl group, a 4-chloro-2-fluorophenyl group, a 2-chloro-4-fluorophenyl group, a 2-chloro-6-fluorophenyl group, a 2-bromo-4-fluorophenyl group, a 2-bromo-6-fluorophenyl group, a 2,4-dichlorophenyl group, a 3,5-dichlorophenyl group, a 2-chlorophenyl group, a 2-bromophenyl group, a 2,6-difluoro-4-hydroxyphenyl group, a 2-fluoro-6-methylphenyl group, a 4-fluoro-2-methylphenyl group, a 2-fluoro-6-(trifluoromethyl)phenyl group, a 2,6-difluoro-4-methoxyphenyl group, a 2,6-difluoro-4-ethoxyphenyl group, a 2-fluoro-6-methoxyphenyl group, a 2-bromo-4-methoxyphenyl group, a 2,6-difluoro-4-(allyloxy)phenyl group, a 2,6-difluoro-4-(propargyloxy)phenyl group, a 2,6-difluoro-4-(acetyloxy)phenyl group, a 2-methylphenyl group, a 4-methylphenyl group, a 2-(trifluoromethyl)phenyl group, a 4-(trifluoromethyl)phenyl group, a 2-methoxyphenyl group, a 4-methoxyphenyl group, a 4-(methoxycarbonyl)phenyl group, a 4-(methylthio)phenyl group or a 4-(methanesulfinyl)phenyl group, or a salt thereof.

[14] The compound of any one of [1] to [7], wherein Y is a 4-pyridyl group, a 3,5-difluoro-4-pyridyl group or a 3,5-dichloro-4-pyridyl group, or a salt thereof.

[15] The compound of any one of [1] to [14], wherein R4 represents a hydroxyl group, a nitro group, a halogen atom, a C1-C6 alkyl group optionally substituted with substituent C, a C1-C6 haloalkyl group, a C1-C6 alkoxy group optionally substituted with substituent C, a C2-C6 alkenyloxy group optionally substituted with substituent C, a C3-C6 alkynyloxy group optionally substituted with substituent C, or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group), or a salt thereof.

[16] The compound of any one of [1] to [14], wherein R4 is a hydroxyl group, a cyano group, a nitro group, a fluorine atom, a chlorine atom, a bromine atom, a methyl group, an ethyl group, a propyl group, an isopropyl group, a trifluoromethyl group, a methoxy group, an ethoxy group, a propyloxy group, an isopropyloxy group, an isobutoxy group, a cyanomethoxy group, a methoxymethoxy group, an ethoxymethoxy group, a 2-methoxyethoxy group, an allyloxy group, a propargyloxy group, an amino group, a methylamino group, a dimethylamino group or an acetylamino group, or a salt thereof.

[17] The compound of any one of [1] to [16], wherein Z represents a phenyl group optionally substituted with 0 to 5 R4 (with the proviso that when there are two or more substituents R4, they are independent to each other), or a salt thereof.

[18] The compound of any one of [1] to [16], wherein Z represents a pyridyl group optionally substituted with 0 to 4 R4 (with the proviso that when there are two or more substituents R4, they are independent to each other), or a salt thereof.

[19] The compound of any one of [1] to [14], wherein Z is a propyl group, an isopropyl group, a butyl group, an isobutyl group, a 2-methylbutyl group, a neopentyl group, an isopentyl group, a 1,2-dimethylpropyl group, a cyanomethyl group, a cyclohexylmethyl group, a methoxymethyl group, a 2-methoxyethyl group, a methylthiomethyl group, an ethoxycarbonylmethyl group, a 2,2-difluoroethyl group, a 4,4,4-trifluorobutyl group, a cyclohexyl group, a 2-methylcyclohexyl group, an allyl group, a propargyl group, a phenyl group, a 2-fluorophenyl group, a 2-chlorophenyl group, a 3-chlorophenyl group, a 2-bromophenyl group, a 3-bromophenyl group, a 4-bromophenyl group, a 2-chloro-4-fluorophenyl group, a 2-chloro-5-fluorophenyl group, a 4-bromo-2-chlorophenyl group, a 2-fluoro-6-methylphenyl group, a 3-fluoro-2-methylphenyl group, a 4-fluoro-2-methylphenyl group, a 5-fluoro-2-methylphenyl group, a 2-chloro-6-methylphenyl group, a 3-chloro-2-methylphenyl group, a 4-chloro-2-methylphenyl group, a 5-chloro-2-methylphenyl group, a 3-bromo-2-methylphenyl group, a 5-bromo-2-methylphenyl group, a 2-bromo-5-methoxyphenyl group, 2-methylphenyl group, a 2-ethylphenyl group, a 2-propylphenyl group, a 2-isopropylphenyl group, a 2,3-dimethylphenyl group, a 2,4-dimethylphenyl group, a 2,5-dimethylphenyl group, a 2,6-dimethylphenyl group, a 2-methyl-3-hydroxyphenyl group, a 2-methyl-5-hydroxyphenyl group, a 2-ethyl-5-hydroxyphenyl group, a 2-methyl-3-nitrophenyl group, a 2-methyl-5-nitrophenyl group, a 2-methyl-5-cyanophenyl group, a 2-methyl-3-methoxyphenyl group, a 2-methyl-4-methoxyphenyl group, a 2-methyl-5-methoxyphenyl group, a 2-methyl-3-ethoxyphenyl group, a 2-methyl-5-ethoxyphenyl group, a 2-methyl-3-propyloxyphenyl group, a 2-methyl-5-isopropyloxyphenyl group, a 2-methyl-3-isobutoxyphenyl group, a 2-ethyl-5-methoxyphenyl group, a 2-methyl-5-(cyanomethoxy)phenyl group, a 2-ethyl-5-(cyanomethoxy)phenyl group, a 2-methyl-5-(methoxymethoxy)phenyl group, a 2-methyl-5-(ethoxymethoxy)phenyl group, a 2-ethyl-5-(methoxymethoxy)phenyl group, a 2-methyl-5-(2-methoxyethoxy)phenyl group, a 2-ethyl-5-(2-methoxyethoxy)phenyl group, a 2-methyl-3-(trifluoromethyl)phenyl group, a 2-methyl-5-(trifluoromethyl)phenyl group, a 2-methyl-5-(allyloxy)phenyl group, a 2-methyl-5-(propargyloxy)phenyl group, a 2-ethyl-5-(propargyloxy)phenyl group, a 2-methyl-3-aminophenyl group, a 2-methyl-5-aminophenyl group, a 2-methyl-3-(methylamino)phenyl group, a 2-methyl-5-(methylamino) phenyl group, a 2-methyl-3-(dimethylamino)phenyl group, a 2-methyl-5-(dimethylamino)phenyl group, a 2-methyl-3-(acetylamino)phenyl group, a 2-(trifluoromethyl)phenyl group, a 2-methoxyphenyl group, 3-methoxyphenyl group, a 4-bromo-2-methyl-3-nitrophenyl group, a 4-bromo-2-methyl-5-methoxyphenyl group, benzyl group, a 2-chlorobenzyl group, a 2,4-dimethoxybenzyl group, a 1-phenylethyl group, a phenethyl group, a 2-chloro-3-pyridyl group, a 2-methyl-3-pyridyl group, a 2-methoxy-3-pyridyl group, an isoxazol-3-yl group, a 5-methylisoxazol-3-yl group or a 4-bromo-5-methylisoxazol-3-yl group, or a salt thereof.

[20] The compound of any one of [1] to [14], wherein Z is a phenyl group, a 2-fluorophenyl group, a 2-chlorophenyl group, a 3-chlorophenyl group, a 2-bromophenyl group, a 3-bromophenyl group, a 4-bromophenyl group, a 2-chloro-4-fluorophenyl group, a 2-chloro-5-fluorophenyl group, a 4-bromo-2-chlorophenyl group, a 2-fluoro-6-methylphenyl group, a 3-fluoro-2-methylphenyl group, a 4-fluoro-2-methylphenyl group, a 5-fluoro-2-methylphenyl group, a 2-chloro-6-methylphenyl group, a 3-chloro-2-methylphenyl group, a 4-chloro-2-methylphenyl group, a 5-chloro-2-methylphenyl group, a 3-bromo-2-methylphenyl group, a 5-bromo-2-methylphenyl group, a 2-bromo-5-methoxyphenyl group, a 2-methylphenyl group, a 2-ethylphenyl group, a 2-propylphenyl group, a 2-isopropylphenyl group, a 2,3-dimethylphenyl group, a 2,4-dimethylphenyl group, a 2,5-dimethylphenyl group, a 2,6-dimethylphenyl group, a 2-methyl-3-hydroxyphenyl group, a 2-methyl-5-hydroxyphenyl group, a 2-ethyl-5-hydroxyphenyl group, a 2-methyl-3-nitrophenyl group, a 2-methyl-5-nitrophenyl group, a 2-methyl-5-cyanophenyl group, a 2-methyl-3-methoxy-phenyl group, a 2-methyl-4-methoxyphenyl group, a 2-methyl-5-methoxyphenyl group, a 2-methyl-3-ethoxyphenyl group, a 2-methyl-5-ethoxyphenyl group, a 2-methyl-3-propyloxyphenyl group, a 2-methyl-5-isopropyloxyphenyl group, a 2-methyl-3-isobutoxyphenyl group, a 2-ethyl-5-methoxyphenyl group, a 2-methyl-5-(cyanomethoxy)phenyl group, a 2-ethyl-5-(cyanomethoxy)phenyl group, a 2-methyl-5-(methoxymethoxy)phenyl group, a 2-methyl-5-(ethoxymethoxy)phenyl group, a 2-ethyl-5-(methoxymethoxy)phenyl group, a 2-methyl-5-(2-methoxyethoxy)phenyl group, a 2-ethyl-5-(2-methoxyethoxy)phenyl group, a 2-methyl-3-(trifluoromethyl)phenyl group, a 2-methyl-5-(trifluoromethyl)phenyl group, a 2-methyl-5-(allyloxy) phenyl group, a 2-methyl-5-(propargyloxy)phenyl group, a 2-ethyl-5-(propargyloxy)phenyl group, a 2-methyl-3-aminophenyl group, a 2-methyl-5-aminophenyl group, a 2-methyl-3-(methylamino)phenyl group, a 2-methyl-5-(methylamino) phenyl group, a 2-methyl-3-(dimethylamino)phenyl group, a 2-methyl-5-(dimethylamino)phenyl group, a 2-methyl-3-(acetylamino)phenyl group, a 2-(trifluoromethyl)phenyl group, a 2-methoxyphenyl group, 3-methoxyphenyl group, a 4-bromo-2-methyl-3-nitrophenyl group or a 4-bromo-2-methyl-5-methoxyphenyl group, or a salt thereof.

[21] The compound of any one of [1] to [14], wherein Z is a 2-chloro-3-pyridyl group, a 2-methyl-3-pyridyl group or a 2-methoxy-3-pyridyl group, or a salt thereof.

[22] An agricultural and horticultural pest control agent comprising the compound any one of [1] to [21] or a salt thereof as an active ingredient.

[23] An agricultural and horticultural fungicide comprising the compound of any one of [1] to [21] or a salt thereof as an active ingredient.

[24] A method for controlling plant diseases, which comprises applying the agricultural and horticultural pest control agent of [22] to a plant, a plant seed or a soil for growing a plant.

[25] A method for controlling plant diseases, which comprises applying the agricultural and horticultural fungicides of [23] to a plant, a seed of a plant or a soil for growing a plant.

[26] Use of the compound of any one of [1] to [21] as an agricultural and horticultural pest control agent.

[27] Use of the compound of any one of [1] to [21] as an agricultural and horticultural fungicide.

Effects of Invention

According to the present invention, a novel compound effective as an agricultural and horticultural fungicide can be provided.

DESCRIPTION OF EMBODIMENTS

Hereinbelow, embodiments for carrying out the present invention will be explained in detail.

The terminologies used in the claims and the specification are understood in accordance with the definitions which are usually used in the art unless otherwise specified.

The abbreviations used in the present specification are explained below.

DMF: N,N-dimethylformamide, THF: tetrahydrofuran, Me: methyl group, Et: ethyl group, Pr: propyl group, Bu: butyl group, Pent: pentyl group, Hex: hexyl group, Hept: heptyl group, Oct: octyl group, Non: nonyl group, Ac: acetyl group, Ph: phenyl group, Py: pyridyl group, c: cyclo, is iso, sec: secondary, t: tertiary, =: double bond and ≡: triple bond. Each of Pr, Bu, Pent, Hex, Hept, Oct and Non in columns of tables with no prefix means that the group is in a normal form.

The definitions of the terminologies used in the present specification will be explained below.

The description Cx-Cy indicates that it has carbon atoms from the number of x to y. Here, x and y each represents an integer and it is to be understood that all the integers between x and y are each independently disclosed. For example, C1-C9 means that 1, 2, 3, 4, 5, 6, 7, 8 or 9 carbon atom(s) is/are present, C1-C6 means that 1, 2, 3, 4, 5 or 6 carbon atom(s) is/are present, C1-C5 means that 1, 2, 3, 4 or 5 carbon atom(s) is/are present, C2-C6 means that 2, 3, 4, 5 or 6 carbon atoms are present, C3-C8 means that 3, 4, 5, 6, 7 or 8 carbon atoms are present and C3-C6 means that 3, 4, 5 or 6 carbon atoms are present, respectively.

The term "optionally substituted" mean that it may be substituted or unsubstituted. Use of this term with no explicitly indicated number of substituent indicates that the number of the substituent is 1. On the other hand, for example, when the number of the substituent(s) is specified as "optionally substituted with 0 to 5", it is to be understood that all the integers between 0 and 5 are independently disclosed. That is, it is meant that the number of the substituent is none, 1, 2, 3, 4 or 5. Similarly, by "optionally substituted with 0 to 4", it is meant that the number of the substituent is none, 1, 2, 3 or 4, by "optionally substituted with 0 to 3", it is meant that the number of the substituent is none, 1, 2 or 3 and by"optionally substituted with 0 to 2", it is meant that the number of the substituent is none, 1 or 2, respectively.

A C1-C6 alkyl group may be linear or branched, and specific examples include a methyl group, an ethyl group, a propyl group, an isopropyl group, a butyl group, an isobutyl group, a sec-butyl group, a t-butyl group, a pentyl group, an isopentyl group, a 1-methylbutyl group, a 2-methylbutyl group, a neopentyl group, a 1-ethylpropyl group, a 1,2-dimethylpropyl group, a hexyl group, a 1-methylpentyl group, a 2-methylpentyl group, a 3-methylpentyl group, a 4-methylpentyl group, a 1,1-dimethylbutyl group, a 2,2-dimethylbutyl group, a 3,3-dimethylbutyl group, a 1,2-dimethylbutyl group, a 1,3-dimethylbutyl group, a 2,3-dimethylbutyl group, a 2-ethylbutyl group, a 1-isopropylpropyl group, a 1,1,2-trimethylpropyl group, a 1,2,2-trimethylpropyl group, and the like.

A C1-C9 alkyl group may be linear or branched, and specific examples include, in addition to the examples of the above-mentioned C1-C6 alkyl group, a heptyl group, a 2-methyl-1-isopropylpropyl group, a 1-t-butylpropyl group, a 1-isopropylbutyl group, a 1,1-dimethylpentyl group, a 2,2-dimethylpentyl group, a 3,3-dimethylpentyl group, a 4,4-dimethylpentyl group, a 1,2-dimethylpentyl group, a 1,3-dimethylpentyl group, a 1,4-dimethylpentyl group, a 1-methylhexyl group, a 1-ethylpentyl group, a 1-propylbutyl group, an octyl group, a 1-t-butylbutyl group, a 5,5-dimethylhexyl group, a 1,1-dimethylhexyl group, a 2,2-dimethylhexyl group, a 3,3-dimethylhexyl group, a 4,4-dimethylhexyl group, a 1-methylheptyl group, a 1-ethylhexyl group, a 1-propylpentyl group, a nonyl group, a 1,1-dimethylheptyl group, a 2,2-dimethylheptyl group, a 3,3-dimethylheptyl group, a 4,4-dimethylheptyl group, a 5,5-dimethylheptyl group, a 6,6-dimethylheptyl group, a 1-methyloctyl group, a 1-ethylheptyl group, a 1-propylhexyl group, a 1-butylpentyl group, and the like.

Specific examples of halogen atoms include a fluorine atom, a chlorine atom, a bromine atom, an iodine atom, and the like.

A C1-C6 haloalkyl group refers to the above-mentioned C1-C6 alkyl group with any hydrogen atom(s) therein substituted with 1 or 2 or more halogen atom(s). When this group is substituted with two or more halogen atoms, these halogen atoms may be the same or different, and the number of the substituents is not particularly limited as long as this group can exist as a substituent. Specific examples of the C1-C6 haloalkyl group include a monofluoromethyl group, a difluoromethyl group, a trifluoromethyl group, a monochloromethyl group, a monobromomethyl group, a monoiodomethyl group, a chlorodifluoromethyl group, a bromodifluoromethyl group, a 1-fluoroethyl group, a 2-fluoroethyl group, a 1,1-difluoroethyl group, a 2,2-difluoroethyl group, a 2,2,2-trifluoroethyl group, a 1,1,2,2-tetrafluoroethyl group, a pentafluoroethyl group, a 2,2,2-trichloroethyl group, a 3,3-difluoropropyl group, a 3,3,3-trifluoropropyl group, a heptafluoropropyl group, a heptafluoroisopropyl group, a 2,2,2-trifluoro-1-(trifluoromethyl)ethyl group, a 4,4-difluorobutyl group, a 4,4,4-trifluorobutyl group, a nonafluorobutyl group, a nonafluoro-sec-butyl group, a 5,5-difluoropentyl group, a 5,5,5-trifluoropentyl group, a 3,3,4,4,5,5,5-heptafluoropentyl group, an undecafluoropentyl group, a tridecafluorohexyl group, and the like.

Specific examples of C3-C8 cycloalkyl groups include a cyclopropyl group, a cyclobutyl group, a cyclopentyl group, a cyclohexyl group, a cycloheptyl group, a cyclooctyl group, and the like.

A C2-C6 alkenyl group refers to a linear or branched, unsaturated hydrocarbon group having 1 or 2 or more double bond(s). When a geometric isomer is present, this group may be either one of the E-isomer or the Z-isomer, or a mixture of the E-isomer and Z-isomer in any ratio, and there is no particular limitation as long as the number of carbon atoms falls within the specified range. Specific examples of the C2-C6 alkenyl group include a vinyl group, a 1-propenyl group, an allyl group, a 1-butenyl group, a 2-butenyl group, a 3-butenyl group, a 2-methyl-1-propenyl group, a 1-pentenyl group, a 2-pentenyl group, a 3-pentenyl group, a 4-pentenyl group, a 2-methyl-1-butenyl group, a 3-methyl-2-butenyl group, a 1-hexenyl group, a 2-hexenyl group, a 3-hexenyl group, a 4-hexenyl group, a 5-hexenyl group, a 3-methyl-2-pentenyl group, a 4-methyl-3-pentenyl group, and the like.

A C2-C6 haloalkenyl group refers to the above-mentioned C2-C6 alkenyl group with any hydrogen atom(s) therein substituted with 1 or 2 or more halogen atom(s). When this group is substituted with two or more halogen atoms, these halogen atoms may be the same different, and the number of the substituents is not particularly limited as long as this group can exist as a substituent. Specific examples of the C2-C6 haloalkenyl group include a 2-fluorovinyl group, a 2,2-difluorovinyl group, a 2,2-dichlorovinyl group, a 3-fluoroallyl group, a 3,3-difluoroallyl group, a 3,3-dichloroallyl group, a 4,4-difluoro-3-butenyl group, a 5,5-difluoro-4-pentenyl group, a 6,6-difluoro-5-hexenyl group, and the like.

A C2-C6 alkynyl group refers to a linear or branched, unsaturated hydrocarbon group having 1 or 2 or more triple bond(s). Specific examples of the C2-C6 alkynyl group include an ethynyl group, a 1-propynyl group, a propargyl group, a 1-butynyl group, a 2-butynyl group, a 3-butynyl group, a 1-pentynyl group, a 2-pentynyl group, a 3-pentynyl group, a 4-pentynyl group, a 1,1-dimethyl-2-propynyl group, a 1-hexynyl group, a 2-hexynyl group, a 3-hexynyl group, a 4-hexynyl group, a 5-hexynyl group, and the like.

A C2-C6 haloalkynyl group refers to the above-mentioned C2-C6 alkynyl group with any hydrogen atom(s) therein substituted with 1 or 2 or more halogen atom(s). When this group is substituted with two or more halogen atoms, these halogen atoms may be the same different, and the number of the substituents is not particularly limited as long as this group can exist as a substituent. Specific examples of the C2-C6 haloalkynyl group include a 2-fluoroethynyl group, a 2-chloroethynyl group, a 2-bromoethynyl group, a 2-iodoethynyl group, a 3,3-difluoro-1-propynyl group, a 3-chloro-3,3-difluoro-1-propynyl group, a 3-bromo-3,3-difluoro-1-propynyl group, a 3,3,3-trifluoro-1-propynyl group, a 4,4-difluoro-1-butynyl group, a 4,4-difluoro-2-butynyl group, a 4-chloro-4,4-difluoro-1-butynyl group, a 4-chloro-4,4-difluoro-2-butynyl group, a 4-bromo-4,4-difluoro-1-butynyl group, a 4-bromo-4,4-difluoro-2-butynyl group, a 4,4,4-trifluoro-1-butynyl group, a 4,4,4-trifluoro-2-butynyl group, a 5,5-difluoro-3-pentynyl group, a 5-chloro-5,5-difluoro-3-pentynyl group, a 5-bromo-5,5-difluoro-3-pentynyl group, a 5,5,5-trifluoro-3-pentynyl group, a 6,6-difluoro-4-hexynyl group, a 6-chloro-6,6-difluoro-4-hexynyl group, a 6-bromo-6,6-difluoro-4-hexynyl group, a 6,6,6-trifluoro-4-hexynyl group, and the like.

A C1-C6 alkoxy group refers to the above-mentioned C1-C6 alkyl group being bonded through an oxygen atom. Specific examples of the C1-C6 alkoxy group include a methoxy group, an ethoxy group, a propyloxy group, an isopropyloxy group, a butoxy group, an isobutoxy group, a sec-butoxy group, a t-butoxy group, a pentyloxy group, an isopentyloxy group, a 1-methylbutoxy group, a 2-methylbutoxy group, a neopentyloxy group, a 1-ethylpropyloxy group, a 1,2-dimethylpropyloxy group, a hexyloxy group, a 1-methylpentyloxy group, a 2-methylpentyloxy group, a 3-methylpentyloxy group, a 4-methylpentyloxy group, a 1,1-dimethylbutoxy group, a 2,2-dimethylbutoxy group, a 3,3-dimethylbutoxy group, a 1,2-dimethylbutoxy group, a 1,3-dimethylbutoxy group, a 2,3-dimethylbutoxy group, a 2-ethylbutoxy group, a 1-isopropylpropyloxy group, a 1,1,2-trimethylpropyloxy group, a 1,2,2-trimethylpropyloxy group, and the like.

A C1-C6 haloalkoxy group refers to the above-mentioned C1-C6 alkoxy group with any hydrogen atom(s) therein substituted with 1 or 2 or more halogen atom(s). When this group is substituted with two or more halogen atoms, these halogen atoms may be the same different, and the number of the substituents is not particularly limited as long as this group can exist as a substituent. Specific examples of the C1-C6 haloalkoxy group include a difluoromethoxy group, a trifluoromethoxy group, a chlorodifluoromethoxy group, a bromodifluoromethoxy group, a 2-fluoroethoxy group, a 2,2-difluoroethoxy group, a 2,2,2-trifluoroethoxy group, a 1,1,2,2-tetrafluoroethoxy group, a pentafluoroethoxy group, a 2,2,2-trichloroethoxy group, a 3,3-difluoropropyloxy group, a 3,3,3-trifluoropropyloxy group, a heptafluoropropyloxy group, a heptafluoroisopropyloxy group, a 2,2,2-trifluoro-1-(trifluoromethyl)-ethoxy group, a 4,4-difluorobutoxy group, a 4,4,4-trifluorobutoxy group, a nonafluorobutoxy group, a nonafluoro-sec-butoxy group, a 5,5-difluoropentyloxy group, a 5,5,5-trifluoropentyloxy group, a 3,3,4,4,5,5,5-heptafluoropentyloxy group, an undecafluoropentyloxy group, a tridecafluorohexyloxy group, and the like.

A C3-C8 cycloalkoxy group refers to the above-mentioned C3-C8 cycloalkyl group being bonded through an oxygen atom. Specific examples of the C3-C8 cycloalkoxy group include a cyclopropyloxy group, a cyclobutoxy group, a cyclopentyloxy group, a cyclohexyloxy group, a cycloheptyloxy group, a cyclooctyloxy group, and the like.

A C2-C6 alkenyloxy group refers to the above-mentioned C2-C6 alkenyl group being bonded through an oxygen atom. When a geometric isomer is present, this group may be either one of the E-isomer or the Z-isomer, or a mixture of the E-isomer and Z-isomer in any ratio, and there is no particular limitation as long as the number of carbon atoms falls within the specified range. Specific examples of the C2-C6 alkenyloxy group include a vinyloxy group, a 1-propenyloxy group, an allyloxy group, a 1-butenyloxy group, a 2-butenyloxy group, a 3-butenyloxy group, a 2-methyl-1-propenyloxy group, a 1-pentenyloxy group, a 2-pentenyloxy group, a 3-pentenyloxy group, a 4-pentenyloxy group, a 2-methyl-1-butenyloxy group, a 3-methyl-2-butenyloxy group, a 1-hexenyloxy group, a 2-hexenyloxy group, a 3-hexenyloxy group, a 4-hexenyloxy group, a 5-hexenyloxy group, a 3-methyl-2-pentenyloxy group, a 4-methyl-3-pentenyloxy group, and the like.

A C2-C6 haloalkenyloxy group refers to the above-mentioned C2-C6 alkenyloxy group with any hydrogen atom(s) therein substituted with 1 or 2 or more halogen atom(s). When this group is substituted with two or more halogen atoms, these halogen atoms may be the same different, and the number of the substituents is not particularly limited as long as this group can exist as a substituent. Specific examples of the C2-C6 haloalkenyloxy group include a 2-fluorovinyloxy group, a 2,2-difluorovinyloxy group, a 2,2-dichlorovinyloxy group, a 3-fluoroallyloxy group, a 3,3-difluoroallyloxy group, a 3,3-dichloroallyloxy group, a 4,4-difluoro-3-butenyloxy group, a 5,5-difluoro-4-pentenyloxy group, a 6,6-difluoro-5-hexenyloxy group, and the like.

A C3-C6 alkynyloxy group refers to a C3-C6 alkynyl group among the above-mentioned C2-C6 alkynyl group being bonded through an oxygen atom. Specific examples of the C3-C6 alkynyloxy group include a propargyloxy group, a 2-butynyloxy group, a 3-butynyloxy group, a 2-pentynyloxy group, a 3-pentynyloxy group, a 4-pentynyloxy group, a 1,1-dimethyl-2-propynyloxy group, a 2-hexynyloxy group, a 3-hexynyloxy group, a 4-hexynyloxy group, a 5-hexynyloxy group, and the like.

A C3-C6 haloalkynyloxy group refers to the above-mentioned C3-C6 alkynyloxy group with any hydrogen atom(s) therein substituted with 1 or 2 or more halogen atom(s). When this group is substituted with two or more halogen atoms, these halogen atoms may be the same different, and the number of the substituents is not particularly limited as long as this group can exist as a substituent. Specific examples of the C3-C6 haloalkynyloxy group include a 1,1-difluoro-2-propynyloxy group, a 4,4-difluoro-2-butynyloxy group, a 4-chloro-4,4-difluoro-2-butynyloxy group, a 4-bromo-4,4-difluoro-2-butynyloxy group, a 4,4,4-trifluoro-2-butynyloxy group, a 5,5-difluoro-3-pentynyloxy group, a 5-chloro-5,5-difluoro-3-pentynyloxy group, a 5-bromo-5,5-difluoro-3-pentynyloxy group, a 5,5,5-trifluoro-3-pentynyloxy group, a 6,6-difluoro-4-hexynyloxy group, a 6-chloro-6,6-difluoro-4-hexynyloxy group, a 6-bromo-6,6-difluoro-4-hexynyloxy group, a 6,6,6-trifluoro-4-hexynyloxy group, and the like.

Specific examples of the group of a 3-6 membered ring containing 1-2 oxygen atoms include a 1,2-epoxyethanyl group, an oxetanyl group, an oxolanyl group, an oxanyl group, a 1,3-dioxolanyl group, a 1,3-dioxanyl group, a 1,4-dioxanyl group, and the like.

A C2-C6 alkoxyalkoxy group refers to a C1-C5 alkoxy group among the above-mentioned C1-C6 alkoxy group with any hydrogen atom(s) therein substituted with 1 or 2 or more C1-C5 alkoxy group(s). There is no particular limitation as long as the total number of carbon atoms falls within the specified range. Specific examples of the C2-C6 alkoxyalkoxy group include a methoxymethoxy group, an ethoxymethoxy group, a propyloxymethoxy group, an isopropyloxymethoxy group, a methoxyethoxy group, an ethoxyethoxy group, a propyloxyethoxy group, an isopropyloxyethoxy group, a methoxypropyloxy group, an ethoxypropyloxy group, a propyloxypropyloxy group, an isopropyloxypropyloxy group, and the like.

The pyridone compound of the present invention (hereinafter also referred to as the "compound of the present invention") encompasses the compound represented by Formula (1) below and a salt thereof.

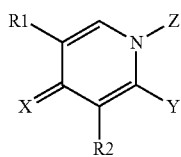

(1)

In the following, Formula (1) will be explained.

R1 in Formula (1) represents a cyano group, a halogen atom, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, a C1-C6 alkoxy group optionally substituted with substituent A, a C1-C6 haloalkoxy group, a C3-C8 cycloalkoxy group optionally substituted with substituent A, a C2-C6 alkenyloxy group optionally substituted with substituent A, a C2-C6 haloalkenyloxy group, a C3-C6 alkynyloxy group optionally substituted with substituent A, a C3-C6 haloalkynyloxy group, an Rc-L- (wherein Rc represents a C1-C6 alkyl group or a C1-C6 haloalkyl group, and L represents S, SO or SO$_2$) or an RgC(=O)— (wherein Rg represents a C1-C6 alkyl group optionally substituted with substituent B, a C1-C6 haloalkyl group or a C3-C8 cycloalkyl group), among them, R1 is preferably a halogen atom, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, a C1-C6 alkoxy group optionally substituted with substituent A, a C1-C6 haloalkoxy group, a C2-C6 alkenyloxy group optionally substituted with substituent A, a C3-C6 alkynyloxy group optionally substituted with substituent A or an RgC(=O)— (wherein Rg is the same as defined above), in particular, R1 is preferably a halogen atom, a C1-C6 alkyl group optionally substituted with substituent A, a C1-C6 haloalkyl group, a C2-C6 alkenyl group optionally substituted with substituent A, a C2-C6 alkynyl group optionally substituted with substituent A or an RgC(=O)— (wherein Rg is the same as defined above).

In R1 of Formula (1), a cyano group is included.

The halogen atom as R1 of Formula (1) is the same as defined above, and preferably a fluorine atom, a chlorine atom, a bromine atom or an iodine atom.

The C1-C6 alkyl group for the "C1-C6 alkyl group optionally substituted with substituent A" as R1 of Formula (1) is the same as defined above, and preferably a methyl group, an ethyl group, a propyl group, an isopropyl group, a butyl group or an isobutyl group, more preferably a methyl group, an ethyl group, a propyl group or an isopropyl group. When substituent A is present, any hydrogen atom in the C1-C6 alkyl group is substituted with substituent A.

The "C1-C6 haloalkyl group" as R1 of Formula (1) is the same as defined above, and preferably a difluoromethyl group, a trifluoromethyl group, a 2,2-difluoroethyl group, a 2,2,2-trifluoroethyl group, a 3,3-difluoropropyl group or a 3,3,3-trifluoropropyl group, more preferably a difluoromethyl group, a trifluoromethyl group, a 2,2-difluoroethyl group or a 2,2,2-trifluoroethyl group.

The C3-C8 cycloalkyl group for the "C3-C8 cycloalkyl group optionally substituted with substituent A" as R1 of Formula (1) is the same as defined above, and preferably a cyclopropyl group, a cyclobutyl group, a cyclopentyl group or a cyclohexyl group, more preferably a cyclopropyl group or a cyclobutyl group. When substituent A is present, any hydrogen atom in the C3-C8 cycloalkyl group is substituted with substituent A.

The C2-C6 alkenyl group for the "C2-C6 alkenyl group optionally substituted with substituent A" as R1 of Formula (1) is the same as defined above, and preferably a vinyl group, a 1-propenyl group, an allyl group, a 1-butenyl group, a 2-butenyl group or a 3-butenyl group, more preferably a vinyl group, a 1-propenyl group or an allyl group. When substituent A is present, any hydrogen atom in the C2-C6 alkenyl group is substituted with substituent A.

The "C2-C6 haloalkenyl group" as R1 of Formula (1) is the same as defined above, and preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, more preferably a 2-fluorovinyl group or a 2,2-difluorovinyl group.

The C2-C6 alkynyl group for the "C2-C6 alkynyl group optionally substituted with substituent A" as R1 of Formula (1) is the same as defined above, and preferably an ethynyl group, a 1-propynyl group, a propargyl group, a 1-butynyl group, a 2-butynyl group or a 3-butynyl group, more preferably an ethynyl group, a 1-propynyl group or a propargyl group. When substituent A is present, any hydrogen atom in the C2-C6 alkynyl group is substituted with substituent A.

The "C2-C6 haloalkynyl group" as R1 of Formula (1) is the same as defined above, and preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, more preferably a 3,3-difluoro-1-propynyl group or a 3,3,3-trifluoro-1-propynyl group.

The C1-C6 alkoxy group for the "C1-C6 alkoxy group optionally substituted with substituent A" as R1 of Formula (1) is the same as defined above, and preferably a methoxy group, an ethoxy group, a propyloxy group or an isopropyloxy group, more preferably a methoxy group or an ethoxy group. When substituent A is present, any hydrogen atom in the C1-C6 alkoxy group is substituted with substituent A.

The "C1-C6 haloalkoxy group" as R1 of Formula (1) is the same as defined above, and preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, more preferably a difluoromethoxy group, a trifluoromethoxy group, a 2,2-difluoroethoxy group or a 2,2,2-trifluoroethoxy group.

The C3-C8 cycloalkoxy group for the "C3-C8 cycloalkoxy group optionally substituted with substituent A" as R1 of Formula (1) is the same as defined above, and preferably a cyclopropyloxy group, a cyclobutoxy group, a cyclopentyloxy group or a cyclohexyloxy group, more preferably a cyclopropyloxy group or a cyclobutoxy group. When substituent A is present, any hydrogen atom in the C3-C8 cycloalkoxy group is substituted with substituent A.

The C2-C6 alkenyloxy group for the "C2-C6 alkenyloxy group optionally substituted with substituent A" as R1 of Formula (1) is the same as defined above, and preferably a vinyloxy group, a 1-propenyloxy group, an allyloxy group, a 1-butenyloxy group, a 2-butenyloxy group or a 3-butenyloxy group, more preferably a vinyloxy group, a 1-propenyloxy group or an allyloxy group. When substituent A is present, any hydrogen atom in the C2-C6 alkenyloxy group is substituted with substituent A.

The "C2-C6 haloalkenyloxy group" as R1 of Formula (1) is the same as defined above, and preferably a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group, more preferably a 2-fluorovinyloxy group or a 2,2-difluorovinyloxy group.

The C3-C6 alkynyloxy group for the "C3-C6 alkynyloxy group optionally substituted with substituent A" as R1 of Formula (1) is the same as defined above, and preferably a propargyloxy group, a 2-butynyloxy group or a 3-butynyloxy group, more preferably a propargyloxy group. When substituent A is present, any hydrogen atom in the C3-C6 alkynyloxy group is substituted with substituent A.

The "C3-C6 haloalkynyloxy group" as R1 of Formula (1) is the same as defined above, and preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, more preferably a 4,4-difluoro-2-butynyloxy group or a 4,4,4-trifluoro-2-butynyloxy group.

Each of the terms for the "Rc-L-" (wherein Rc represents a C1-C6 alkyl group or a C1-C6 haloalkyl group, and L represents S, SO or $SO_2$) as R1 of Formula (1) is the same as defined above. The "Rc-L-" is preferably a methylthio group, a methanesulfinyl group, a methanesulfonyl group, a trifluoromethylthio group, a trifluoromethanesulfinyl group or a trifluoromethanesulfonyl group, more preferably a methylthio group, a methanesulfinyl group or a methanesulfonyl group.

Each of the terms for the "RgC(=O)—" (wherein Rg represents a C1-C6 alkyl group optionally substituted with substituent B, a C1-C6 haloalkyl group or a C3-C8 cycloalkyl group) as R1 of Formula (1) is the same as defined above. Incidentally, with regard to the "C1-C6 alkyl group optionally substituted with substituent B", when substituent B is present, any hydrogen atom in the C1-C6 alkyl group is substituted with substituent B. Rg is preferably a C1-C6 alkyl group optionally substituted with the substituent B. The "RgC(=O)—" is preferably an acetyl group, a methoxyacetyl group, a cyanoacetyl group, a propionyl group, a difluoroacetyl group, a trifluoroacetyl group or a cyclopropanecarbonyl group, and more preferably an acetyl group or a propionyl group.

R2 in Formula (1) represents a cyano group, a halogen atom, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, an Rc-L-(wherein Rc and L are the same as defined above) or an RgC(=O)— (wherein Rg is the same as defined above), among them, R2 is preferably a halogen atom, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A or a C2-C6 haloalkynyl group, in particular, R2 is preferably a halogen atom, a C1-C6 alkyl group optionally substituted with substituent A or a C1-C6 haloalkyl group.

In R2 of Formula (1), a cyano group is included.

The halogen atom as R2 of Formula (1) is the same as defined above, and preferably a fluorine atom, a chlorine atom, a bromine atom or an iodine atom.

The C1-C6 alkyl group for the "C1-C6 alkyl group optionally substituted with substituent A" as R2 of Formula (1) is the same as defined above, and preferably a methyl group, an ethyl group, a propyl group, an isopropyl group, a butyl group or an isobutyl group, more preferably a methyl group, an ethyl group, a propyl group or a butyl group. When substituent A is present, any hydrogen atom in the C1-C6 alkyl group is substituted with substituent A.

The "C1-C6 haloalkyl group" as R2 of Formula (1) is the same as defined above, and preferably a difluoromethyl group, a trifluoromethyl group, a 2,2-difluoroethyl group, a 2,2,2-trifluoroethyl group, a 3,3-difluoropropyl group or a 3,3,3-trifluoropropyl group, more preferably a difluoromethyl group, a trifluoromethyl group, a 2,2-difluoroethyl group or a 2,2,2-trifluoroethyl group.

The C3-C8 cycloalkyl group for the "C3-C8 cycloalkyl group optionally substituted with substituent A" as R2 of Formula (1) is the same as defined above, and preferably a cyclopropyl group, a cyclobutyl group, a cyclopentyl group or a cyclohexyl group, more preferably a cyclopropyl group or a cyclobutyl group. When substituent A is present, any hydrogen atom in the C3-C8 cycloalkyl group is substituted with substituent A.

The C2-C6 alkenyl group for the "C2-C6 alkenyl group optionally substituted with substituent A" as R2 of Formula (1) is the same as defined above, and preferably a vinyl group, a 1-propenyl group, an allyl group, a 1-butenyl group, a 2-butenyl group or a 3-butenyl group, more preferably a vinyl group, a 1-propenyl group or an allyl group. When substituent A is present, any hydrogen atom in the C2-C6 alkenyl group is substituted with substituent A.

The "C2-C6 haloalkenyl group" as R2 of Formula (1) is the same as defined above, and preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, more preferably a 2-fluorovinyl group or a 2,2-difluorovinyl group.

The C2-C6 alkynyl group for the "C2-C6 alkynyl group optionally substituted with substituent A" as R2 of Formula (1) is the same as defined above, and preferably an ethynyl group, a 1-propynyl group, a propargyl group, a 1-butynyl group, a 2-butynyl group or a 3-butynyl group, more preferably an ethynyl group, a 1-propynyl group or a propargyl group. When substituent A is present, any hydrogen atom in the C2-C6 alkynyl group is substituted with substituent A.

The "C2-C6 haloalkynyl group" as R2 of Formula (1) is the same as defined above, and preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, more preferably a 3,3-difluoro-1-propynyl group or a 3,3,3-trifluoro-1-propynyl group.

Rc and L for the "Rc-L-" as R2 of Formula (1) are the same as defined above. The "Rc-L-" is preferably a methylthio group, a methanesulfinyl group, a methanesulfonyl group, a trifluoromethylthio group, a trifluoromethanesulfinyl group or a trifluoromethanesulfonyl group, and more preferably a methylthio group, a methanesulfinyl group or a methanesulfonyl group.

Rg for the "RgC(=O)—" as R2 of Formula (1) is the same as defined above. As Rg, preferred is a C1-C6 alkyl group optionally substituted with substituent B. As "RgC(=O)—", preferred is an acetyl group, a methoxyacetyl group, a cyanoacetyl group, a propionyl group, a difluoroacetyl group, a trifluoroacetyl group or a cyclopropanecarbonyl group, and more preferred is an acetyl group or a propionyl group.

X in Formula (1) is an oxygen atom or a sulfur atom, preferably an oxygen atom.

Y in Formula (1) represents a phenyl group optionally substituted with 0 to 5 R3 (with the proviso that when there are two or more substituents R3, they are independent to each other), a pyridyl group optionally substituted with 0 to 4 R3 (with the proviso that when there are two or more substituents R3, they are independent to each other), a pyridazinyl group optionally substituted with 0 to 3 R3 (with the proviso that when there are two or more substituents R3, they are independent to each other), a pyrimidinyl group optionally substituted with 0 to 3 R3 (with the proviso that when there are two or more substituents R3, they are independent to each other), a pyrazinyl group optionally substituted with 0 to 3 R3 (with the proviso that when there are two or more substituents R3, they are independent to each other), a triazinyl group optionally substituted with 0 to 2 R3 (with the proviso that when there are two substituents R3, they are independent to each other), a tetrazinyl group optionally substituted with R3, a thienyl group optionally substituted with 0 to 3 R3 (with the proviso that when there are two or more substituents R3, they are independent to each other), a thiazolyl group optionally substituted with 0 to 2 R3 (with the proviso that when there are two substituents R3, they are independent to each other), an isothiazolyl group optionally substituted with 0 to 2 R3 (with the proviso that when there are two substituents R3, they are independent to each other), a thiadiazolyl group optionally substituted with R3, a furanyl group optionally substituted with 0 to 3 R3 (with the proviso that when there are two or more substituents R3, they are independent to each other), an oxazolyl group optionally substituted with 0 to 2 R3 (with the proviso that when there are two substituents R3, they are independent to each other), an isoxazolyl group optionally substituted with 0 to 2 R3 (with the proviso that when there are two substituents R3, they are independent to each other) or an oxadiazolyl group optionally substituted with R3, among these, Y is preferably a phenyl group optionally substituted with 0 to 5 R3 (with the proviso that when there are two or more substituents R3, they are independent to each other), a pyridyl group optionally substituted with 0 to 4 R3 (with the proviso that when there are two or more substituents R3, they are independent to each other) or a furanyl group optionally substituted with 0 to 3 R3 (with the proviso that when there are two or more substituents R3, they are independent to each other), in particular, Y represents a phenyl group optionally substituted with 0 to 5 R3 (with the proviso that when there are two or more substituents R3, they are independent to each other), a pyridyl group optionally substituted with 0 to 4 R3 (with the proviso that when there are two or more substituents R3, they are independent to each other) or a furanyl group optionally substituted with 0 to 3 R3 (with the proviso that when there are two or more substituents R3, they are independent to each other), further, Y is preferably a phenyl group optionally substituted with 0 to 5 R3 (with the proviso that when there are two or more substituents R3, they are independent to each other) or a pyridyl group optionally substituted with 0 to 4 R3 (with the proviso that when there are two or more substituents R3, they are independent to each other).

The "phenyl group optionally substituted with 0 to 5 R3" (with the proviso that when there are two or more substituents R3, they are independent to each other) as Y of Formula (1) refers to the partial structure represented by Formula (a) shown below.

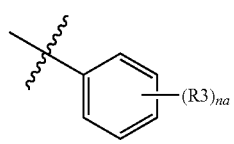

(a)

In Formula (a), na represents an integer of 0 to 5 and, when na is 2 or more, the substituents which two or more R3's represent are independent to each other and may be the same or different and arbitrarily selected.

The "pyridyl group optionally substituted with 0 to 4 R3" (with the proviso that when there are two or more substituents R3, they are independent to each other) as Y of Formula (1) refers to the partial structure represented by one formula selected from the group consisting of Formula (b-1), Formula (b-2) and Formula (b-3) shown below.

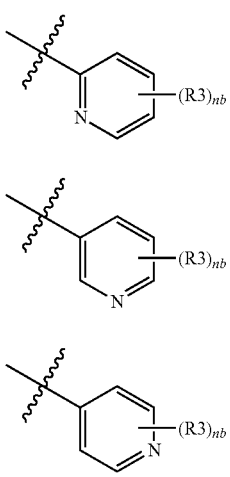

(b-1)

(b-2)

(b-3)

In each of Formula (b-1), Formula (b-2) and Formula (b-3), nb represents an integer of 0 to 4 and, when nb is 2 or more, the substituents which two or more R3's represent are independent to each other and may be the same or different and arbitrarily selected.

The "pyridazinyl group optionally substituted with 0 to 3 R3" (with the proviso that when there are two or more substituents R3, they are independent to each other)" as Y of Formula (1) refers to the partial structure represented by one formula selected from the group consisting of Formula (c-1), Formula (c-2) and Formula (c-3) shown below.

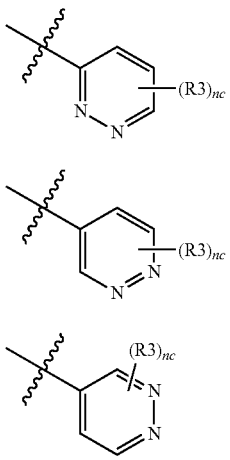

(c-1)

(c-2)

(c-3)

In each of Formula (c-1), Formula (c-2) and Formula (c-3), nc represents an integer of 0 to 3 and, when nc is 2 or more, the substituents which two or more R3's represent are independent to each other and may be the same or different and arbitrarily selected.

The "pyrimidinyl group optionally substituted with 0 to 3 R3" (with the proviso that when there are two or more substituents R3, they are independent to each other)" as Y of Formula (1) refers to the partial structure represented by one formula selected from the group consisting of Formula (d-1), Formula (d-2) and Formula (d-3) shown below.

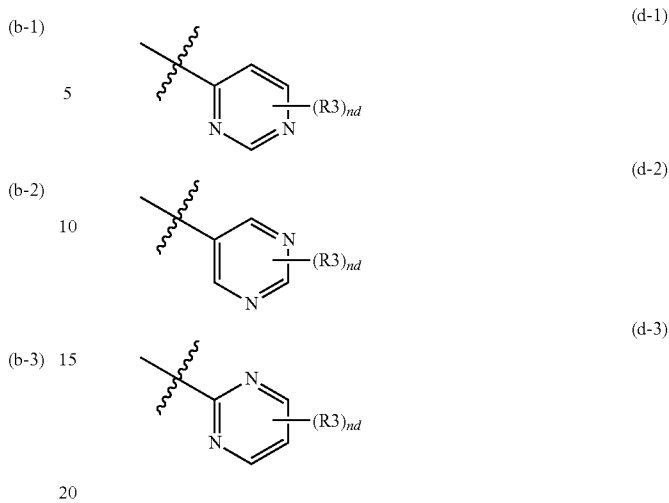

(d-1)

(d-2)

(d-3)

In each of Formula (d-1), Formula (d-2) and Formula (d-3), nd represents an integer of 0 to 3 and, when nd is 2 or more, the substituents which two or more R3's represent are independent to each other and may be the same or different and arbitrarily selected.

The "pyrazinyl group optionally substituted with 0 to 3 R3 (with the proviso that when there are two or more substituents R3, they are independent to each other)" as Y of Formula (1) refers to the partial structure represented by Formula (e) shown below.

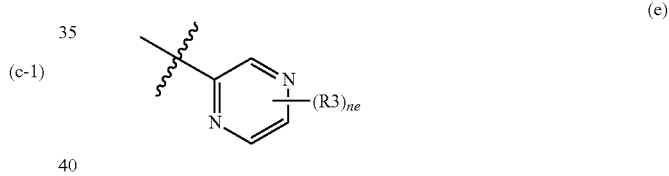

(e)

In Formula (e), ne represents an integer of 0 to 3 and, when ne is 2 or more, the substituents which two or more R3's represent are independent to each other and may be the same or different and arbitrarily selected.

The "triazinyl group optionally substituted with 0 to 2 R3" (with the proviso that when there are two substituents R3, they are independent to each other) as Y of Formula (1) refers to the partial structure represented by one formula selected from the group consisting of Formula (f-1), Formula (f-2), Formula (f-3), Formula (f-4) and Formula (f-5) shown below.

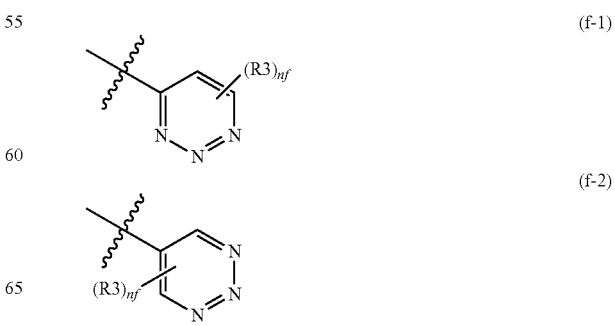

(f-1)

(f-2)

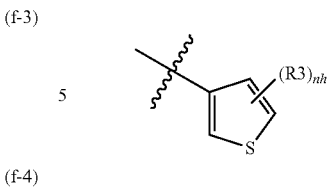

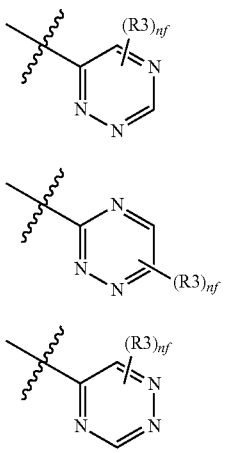

In each of Formula (f-1), Formula (f-2), Formula (f-3), Formula (f-4) and Formula (f-5), nf represents an integer of 0 to 2 and, when nf is 2, the substituents which two R3's represent are independent to each other and may be the same or different and arbitrarily selected.

The "tetradinyl group optionally substituted with R3" as Y of Formula (1) refers to the partial structure represented by one formula selected from the group consisting of Formula (g-1), Formula (g-2) and Formula (g-3) shown below.

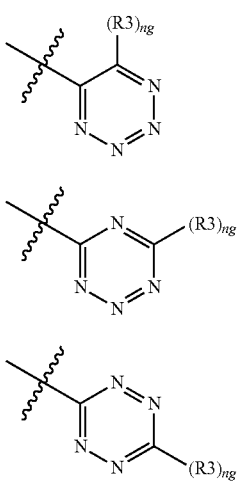

In each of Formula (g-1), Formula (g-2) and Formula (g-3), ng represents an integer of 0 to 1.

The "thienyl group optionally substituted with 0 to 3 R3" (with the proviso that when there are two or more substituents R3, they are independent to each other) as Y of Formula (1) refers to the partial structure represented by one formula selected from the group consisting of Formula (h-1) and Formula (h-2) shown below.

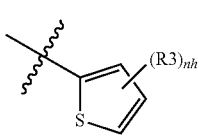

In each of Formula (h-1) and Formula (h-2), nh represents an integer of 0 to 3 and, when nh is 2 or more, the substituents which two or more R3's represent are independent to each other and may be the same or different and arbitrarily selected.

The "thiazolyl group optionally substituted with 0 to 2 R3" (with the proviso that when there are two substituents R3, they are independent to each other) as Y of Formula (1) refers to the partial structure represented by one formula selected from the group consisting of Formula (i-1), Formula (i-2) and Formula (i-3) shown below.

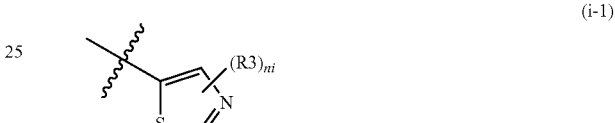

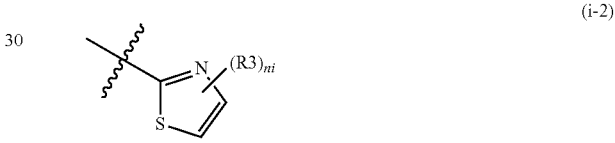

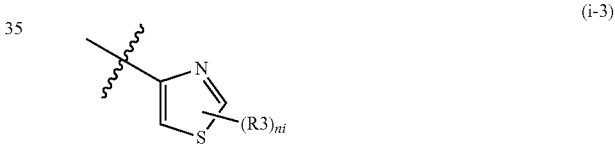

In each of Formula (i-1), Formula (i-2) and Formula (i-3), ni represents an integer of 0 to 2 and, when ni is 2, the substituents which two R3's represent are independent to each other and may be the same or different and arbitrarily selected.

The "isothiazolyl group optionally substituted with 0 to 2 R3" (with the proviso that when there are two substituents R3, they are independent to each other) as Y of Formula (1) refers to the partial structure represented by one formula selected from the group consisting of Formula (j-1), Formula (j-2) and Formula (j-3) shown below.

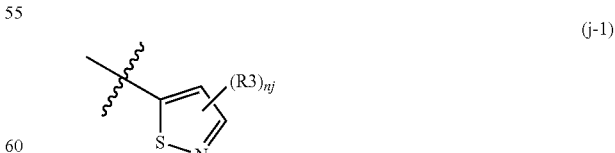

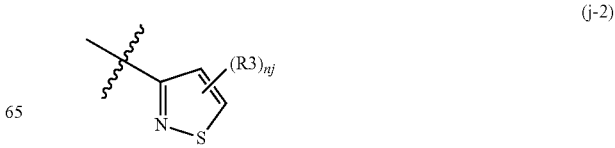

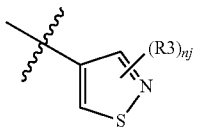
(j-3)

In each of Formula (j-1), Formula (j-2) and Formula (j-3), nj represents an integer of 0 to 2 and, when nj is 2, the substituents which two or more R3's represent are independent to each other and may be the same or different and arbitrarily selected.

The "thiadiazolyl group optionally substituted with R3" as Y of Formula (1) refers to the partial structure represented by one formula selected from the group consisting of Formula (k-1), Formula (k-2), Formula (k-3), Formula (k-4), Formula (k-5) and Formula (k-6) shown below.

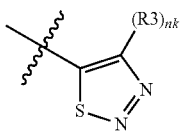
(k-1)

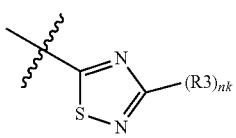
(k-2)

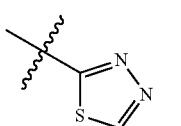
(k-3)

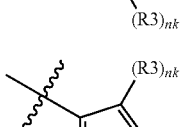
(k-4)

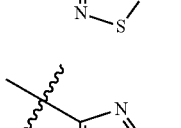
(k-5)

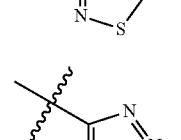
(k-6)

In each of Formula (k-1), Formula (k-2), Formula (k-3), Formula (k-4), Formula (k-5) and Formula (k-6), nk represents an integer of 0 to 1.

The "furanyl group optionally substituted with 0 to 3 R3" (with the proviso that when there are two or more substituents R3, they are independent to each other) as Y of Formula (1) refers to the partial structure represented by one formula selected from the group consisting of Formula (l-1) and Formula (l-2) shown below.

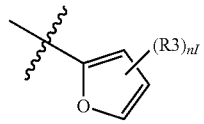
(l-1)

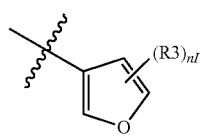
(l-2)

In each of Formula (l-1) and Formula (l-2), nl represents an integer of 0 to 3 and, when nl is 2 or more, the substituents which two or more R3's represent are independent to each other and may be the same or different and arbitrarily selected.

The "oxazolyl group optionally substituted with 0 to 2 R3" (with the proviso that when there are two substituents R3, they are independent to each other) as Y of Formula (1) refers to the partial structure represented by one formula selected from the group consisting of Formula (m-1), Formula (m-2) and Formula (m-3) shown below.

(m-1)

(m-2)

(m-3)

In each of Formula (m-1), Formula (m-2) and Formula (m-3), nm represents an integer of 0 to 2 and, when nm is 2, the substituents which two R3's represent are independent to each other and may be the same or different and arbitrarily selected.

The "isoxazolyl group optionally substituted with 0 to 2 R3" (with the proviso that when there are two substituents R3, they are independent to each other) as Y of Formula (1) refers to the partial structure represented by one formula selected from the group consisting of Formula (n-1), Formula (n-2) and Formula (n-3) shown below.

(n-1)

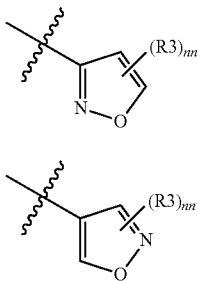

In each of Formula (n-1), Formula (n-2) and Formula (n-3), nn represents an integer of 0 to 2 and, when nn is 2, the substituents which two R3's represent are independent to each other and may be the same or different and arbitrarily selected.

The "oxadiazolyl group optionally substituted with R3" as Y of Formula (1) refers to the partial structure represented by one formula selected from the group consisting of Formula (o-1), Formula (o-2), Formula (o-3), Formula (o-4), Formula (o-5) and Formula (o-6) shown below.

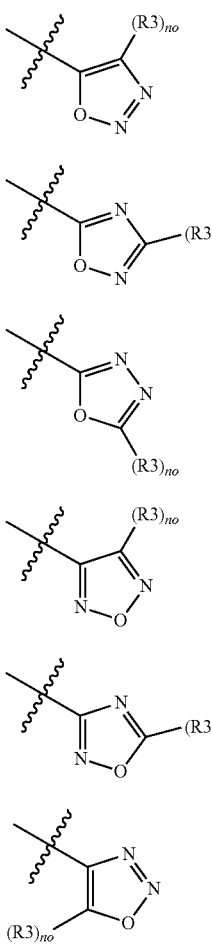

In each of Formula (o-1), Formula (o-2), Formula (o-3), Formula (o-4), Formula (o-5) and Formula (0-6), no represents an integer of 0 to 1.

R3 in Formula (1) represents a hydroxyl group, a cyano group, a nitro group, a halogen atom, a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C, a C2-C6 haloalkynyl group, a C1-C6 alkoxy group optionally substituted with substituent C, a C1-C6 haloalkoxy group, a C3-C8 cycloalkoxy group optionally substituted with substituent C, a C2-C6 alkenyloxy group optionally substituted with substituent C, a C2-C6 haloalkenyloxy group, a C3-C6 alkynyloxy group optionally substituted with substituent C, a C3-C6 haloalkynyloxy group, an RdC(=O)— (wherein Rd represents a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group)), an RdC(=O)O— (wherein Rd is the same as defined above), a group of a 3-6 membered ring containing 1-2 oxygen atoms, an Rc-L- (wherein Rc and L are the same as defined above), an RaRbN— (wherein Ra and Rb are the same as defined above) or an ReC(=O)N (Rf)— (wherein Re and Rf are independent to each other, and each represents a hydrogen atom, a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are the same as defined above)), among these, R3 is preferably a hydroxyl group, a cyano group, a halogen atom, a C1-C6 alkyl group optionally substituted with substituent C, a C1-C6 haloalkyl group, a C1-C6 alkoxy group optionally substituted with substituent C, a C1-C6 haloalkoxy group, a C2-C6 alkenyloxy group optionally substituted with substituent C, a C2-C6 haloalkenyloxy group, a C3-C6 alkynyloxy group optionally substituted with substituent C, a C3-C6 haloalkynyloxy group, an RdC(=O)— (wherein Rd is the same as defined above), an RdC(=O)O— (wherein Rd is the same as defined above) or an Rc-L-(wherein Rc and L are the same as defined above), in particular, R3 is preferably a hydroxyl group, a cyano group, a halogen atom, a C1-C6 alkyl group optionally substituted with substituent C, a C1-C6 haloalkyl group, a C1-C6 alkoxy group optionally substituted with substituent C, a C2-C6 alkenyloxy group optionally substituted with substituent C, a C3-C6 alkynyloxy group optionally substituted with substituent C, an RdC(=O)— (wherein Rd is the same as defined above), an RdC(=O)O— (wherein Rd is the same as defined above) or an Rc-L- (wherein Rc and L are the same as defined above), further, R3 is preferably a hydroxyl group, a cyano group, a halogen atom, a C1-C6 alkyl group optionally substituted with substituent C, a C1-C6 alkoxy group optionally substituted with substituent C, a C2-C6 alkenyloxy group optionally substituted with substituent C, a C3-C6 alkynyloxy group optionally substituted with substituent C or an RdC(=O)O— (wherein Rd is the same as defined above).

In R3 of Formula (1), a hydroxyl group, a cyano group and a nitro group are included.

The halogen atom as R3 of Formula (1) is the same as defined above, and preferably a fluorine atom, a chlorine atom, a bromine atom or an iodine atom.

The C1-C6 alkyl group for the "C1-C6 alkyl group optionally substituted with substituent C" as R3 of Formula (1) is the same as defined above, and preferably a methyl group, an ethyl group, a propyl group, an isopropyl group, a butyl group or an isobutyl group, more preferably a methyl group or an ethyl group. When substituent C is present, any hydrogen atom in the C1-C6 alkyl group is substituted with substituent C.

The "C1-C6 haloalkyl group" as R3 of Formula (1) is the same as defined above, and preferably a difluoromethyl group, a trifluoromethyl group, a 2,2-difluoroethyl group, a 2,2,2-trifluoroethyl group, a 3,3-difluoropropyl group or a 3,3,3-trifluoropropyl group, more preferably a difluoromethyl group or a trifluoromethyl group.

The C3-C8 cycloalkyl group for the "C3-C8 cycloalkyl group optionally substituted with substituent C" as R3 of Formula (1) is the same as defined above, and preferably a cyclopropyl group, a cyclobutyl group, a cyclopentyl group or a cyclohexyl group, more preferably a cyclopropyl group or a cyclobutyl group. When substituent C is present, any hydrogen atom in the C3-C8 cycloalkyl group is substituted with substituent C.

The C2-C6 alkenyl group for the "C2-C6 alkenyl group optionally substituted with substituent C" as R3 of Formula (1) is the same as defined above, and preferably a vinyl group, a 1-propenyl group, an allyl group, a 1-butenyl group, a 2-butenyl group or a 3-butenyl group, more preferably a vinyl group, a 1-propenyl group or an allyl group. When substituent C is present, any hydrogen atom in the C2-C6 alkenyl group is substituted with substituent C.

The "C2-C6 haloalkenyl group" as R3 of Formula (1) is the same as defined above, and preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, more preferably a 2-fluorovinyl group or a 2,2-difluorovinyl group.

The C2-C6 alkynyl group for the "C2-C6 alkynyl group optionally substituted with substituent C" as R3 of Formula (1) is the same as defined above, and preferably an ethynyl group, a 1-propynyl group, a propargyl group, a 1-butynyl group, a 2-butynyl group or a 3-butynyl group, more preferably an ethynyl group, a 1-propynyl group or a propargyl group. When substituent C is present, any hydrogen atom in the C2-C6 alkynyl group is substituted with substituent C.

The "C2-C6 haloalkynyl group" as R3 of Formula (1) is the same as defined above, and preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, more preferably a 3,3-difluoro-1-propynyl group or a 3,3,3-trifluoro-1-propynyl group.

The C1-C6 alkoxy group for the "C1-C6 alkoxyl group optionally substituted with substituent C" as R3 of Formula (1) is the same as defined above, and preferably a methoxy group, an ethoxy group, a propyloxy group, an isopropyloxy group, a butoxy group, an isobutoxy group or a pentyloxy group, more preferably a methoxy group, an ethoxy group, a propyloxy group or an isopropyloxy group. When substituent C is present, any hydrogen atom in the C1-C6 alkoxy group is substituted with substituent C.

The "C1-C6 haloalkoxy group" as R3 of Formula (1) is the same as defined above, and preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, more preferably a difluoromethoxy group, a trifluoromethoxy group, a 2,2-difluoroethoxy group or a 2,2,2-trifluoroethoxy group.

The C3-C8 cycloalkoxy group for the "C3-C8 cycloalkoxy group optionally substituted with substituent C" as R3 of Formula (1) is the same as defined above, and preferably a cyclopropyloxy group, a cyclobutoxy group, a cyclopentyloxy group or a cyclohexyloxy group, more preferably a cyclopropyloxy group or a cyclobutoxy group. When substituent C is present, any hydrogen atom in the C3-C8 cycloalkoxy group is substituted with substituent C.

The C2-C6 alkenyloxy group for the "C2-C6 alkenyloxy group optionally substituted with substituent C" as R3 of Formula (1) is the same as defined above, and preferably a vinyloxy group, a 1-propenyloxy group, an allyloxy group, a 1-butenyloxy group, a 2-butenyloxy group or a 3-butenyloxy group, more preferably a vinyloxy group, a 1-propenyloxy group or an allyloxy group. When substituent C is present, any hydrogen atom in the C2-C6 alkenyloxy group is substituted with substituent C.

The "C2-C6 haloalkenyloxy group" as R3 of Formula (1) is the same as defined above, and preferably a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group, more preferably a 2-fluorovinyloxy group or a 2,2-difluorovinyloxy group.

The C3-C6 alkynyloxy group for the "C3-C6 alkynyloxy group optionally substituted with substituent C" as R3 of Formula (1) is the same as defined above, and preferably a propargyloxy group, a 2-butynyloxy group or a 3-butynyloxy group, more preferably a propargyloxy group or a 2-butynyloxy group. When substituent C is present, any hydrogen atom in the C3-C6 alkynyloxy group is substituted with substituent C.

The "C3-C6 haloalkynyloxy group" as R3 of Formula (1) is the same as defined above, and preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, more preferably a 4,4-difluoro-2-butynyloxy group or a 4,4,4-trifluoro-2-butynyloxy group.

Each of the terms for the "RdC(=O)—" (wherein Rd represents a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group)) as R3 of Formula (1) is the same as defined above. Incidentally, with regard to the "C1-C6 alkyl group optionally substituted with substituent B", when substituent B is present, any hydrogen atom in the C1-C6 alkyl group is substituted with substituent B. Rd is preferably a C1-C6 alkyl group optionally substituted with substituent B or a C1-C6 alkoxy group, and more preferably a C1-C6 alkoxy group. The "RdC(=O)—" is preferably an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethyl(methyl)aminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a cyclopropyl(methyl)aminocarbonyl group, a pyrrolidinylcarbonyl group or a piperidinylcarbonyl group, further preferably an acetyl group, a methoxyacetyl group, a cyanoacetyl group, a methoxycarbonyl group or an ethoxycarbonyl group, and particularly preferably a methoxycarbonyl group or an ethoxycarbonyl group.

Rd of the "RdC(=O)O—" as R3 of Formula (1) is the same as defined above. Rd is preferably a C1-C6 alkyl group optionally substituted with substituent B or a C1-C6 alkoxy group, and more preferably a C1-C6 alkyl group optionally substituted with substituent B. The "RdC(=O)O—" is preferably an acetyloxy group, a methoxyacetyloxy group, a cyanoacetyloxy group, a propionyloxy group, a difluoroacetyloxy group, a trifluoroacetyloxy group, a cyclopropanecarbonyloxy group, a methoxycarbonyloxy group, an ethoxycarbonyloxy group, a 2,2-difluoroethoxycarbonyloxy group, a 2,2,2-trifluoroethoxycarbonyloxy group, a 3,3,3-trifluoropropyloxycarbonyloxy group, a cyclopropyloxycarbonyloxy group, an aminocarbonyloxy group, a methylaminocarbonyloxy group, an ethylaminocarbonyloxy group, a (methoxymethyl)aminocarbonyloxy group, a (2-methoxyethyl)aminocarbonyloxy group, a (cyanomethyl)aminocarbonyloxy group, a (2-cyanoethyl)aminocarbonyloxy group, a dimethylaminocarbonyloxy group, an ethyl(methyl)aminocarbonyloxy group, a diethylaminocarbonyloxy group, a (methoxymethyl)methylaminocarbonyloxy group, a (2-methoxyethyl)methylaminocarbonyloxy group, a (cyanomethyl)methylaminocarbonyloxy group, a (2-cyanoethyl)methylaminocarbonyloxy group, a 2,2-difluoroethylaminocarbonyloxy group, a 2,2,2-trifluoroethylaminocarbonyloxy group, a cyclopropylaminocarbonyloxy group, a cyclopropyl(methyl)aminocarbonyloxy group, a pyrrolidinylcarbonyloxy group or a piperidinylcarbonyloxy group, further preferably an acetyloxy group, a methoxyacetyloxy group, a cyanoacetyloxy group, a methoxycarbonyloxy group or an ethoxycarbonyloxy group, and particularly preferably an acetyloxy group, a methoxyacetyloxy group or a cyanoacetyloxy group.

The "group of a 3-6 membered ring containing 1-2 oxygen atoms" as R3 of Formula (1) is the same as defined above, and preferably an oxolanyl group, an oxanyl group, a 1,3-dioxolanyl group or a 1,3-dioxanyl group, more preferably a 1,3-dioxolanyl group or a 1,3-dioxanyl group.

Rc and L of the "Rc-L-" as R3 of Formula (1) are the same as defined above. The "Rc-L-" is preferably a methylthio group, a methanesulfinyl group, a methanesulfonyl group, a trifluoromethylthio group, a trifluoromethanesulfinyl group or a trifluoromethanesulfonyl group, more preferably a methylthio group, a methanesulfinyl group or a methanesulfonyl group.

Ra and Rb of the "RaRbN—" as R3 of Formula (1) are the same as defined above. The "RaRbN—" is preferably an amino group, a methylamino group, an ethylamino group, a propylamino group, an isopropylamino group, a (methoxymethyl)amino group, a (2-methoxyethyl)amino group, a (cyanomethyl)amino group, a (2-cyanoethyl)amino group, a dimethylamino group, an ethyl(methyl)amino group, a methyl(propyl)amino group, an isopropyl(methyl)amino group, a (methoxymethyl)methylamino group, a (2-methoxyethyl)methylamino group, a (cyanomethyl)methylamino group, a (2-cyanoethyl)methylamino group, a diethylamino group, an ethyl(propyl)amino group, an ethyl(isopropyl)amino group, an ethyl(methoxymethyl)amino group, an ethyl(2-methoxyethyl)amino group, a (cyanomethyl)ethylamino group, a (2-cyanoethyl)ethylamino group, a 2,2-difluoroethylamino group, a 2,2,2-trifluoroethylamino group, a cyclopropylamino group, a (cyclopropyl)methylamino group, a pyrrolidinyl group or a piperidinyl group, and more preferably a dimethylamino group, an ethyl(methyl)amino group, an isopropyl(methyl)amino group, a diethylamino group or an ethyl(isopropyl)amino group.

Each of the terms for the "ReC(=O)N(Rf)—" (wherein Re and Rf are independent to each other, and each represents a hydrogen atom, a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are the same as defined above)) as R3 of Formula (1) is the same as defined above. Incidentally, with regard to the "C1-C6 alkyl group optionally substituted with substituent B", when substituent B is present, any hydrogen atom in the C1-C6 alkyl group is substituted with substituent B. The "ReC(=O)N(Rf)—" is preferably a formylamino group, an acetylamino group, a methoxyacetylamino group, a cyanoacetylamino group, a propionylamino group, a difluoroacetylamino group, a trifluoroacetylamino group, a cyclopropanecarbonylamino group, a methoxycarbonylamino group, an ethoxycarbonylamino group, a 2,2-difluoroethoxycarbonylamino group, a 2,2,2-trifluoroethoxycarbonylamino group, a 3,3,3-trifluoropropyloxycarbonylamino group, a cyclopropyloxycarbonylamino group, an aminocarbonylamino group, a methylaminocarbonylamino group, an ethylaminocarbonylamino group, a (methoxymethyl)aminocarbonylamino group, a (2-methoxyethyl)aminocarbonylamino group, a (cyanomethyl)aminocarbonylamino group, a (2-cyanoethyl)aminocarbonylamino group, a dimethylaminocarbonylamino group, an ethyl(methyl)aminocarbonylamino group, a diethylaminocarbonylamino group, a (methoxymethyl)methylaminocarbonylamino group, a (2-methoxyethyl)methylaminocarbonylamino group, a (cyanomethyl)methylaminocarbonylamino group, a (2-cyanoethyl)methylaminocarbonylamino group, a 2,2-difluoroethylaminocarbonylamino group, a 2,2,2-trifluoroethylaminocarbonylamino group, a cyclopropylaminocarbonylamino group, a cyclopropyl(methyl)aminocarbonylamino group, a pyrrolidinylcarbonylamino group, a piperidinylcarbonylamino group, a formyl(methyl)amino group, an acetyl(methyl)amino group, a methoxyacetyl(methyl)amino group, a cyanoacetyl(methyl)amino group, a propionyl(methyl)amino group, a difluoroacetyl(methyl)amino group, a trifluoroacetyl(methyl)amino group, a cyclopropanecarbonyl(methyl)amino group, a methoxycarbonyl(methyl)amino group, an ethoxycarbonyl(methyl)amino group, a 2,2-difluoroethoxycarbonyl(methyl)amino group, a 2,2,2-trifluoroethoxycarbonyl(methyl)amino group, a 3,3,3-trifluoropropyloxycarbonyl (methyl)amino group, a cyclopropyloxycarbonyl(methyl) amino group, an aminocarbonyl(methyl)amino group, a methylaminocarbonyl(methyl)amino group, an ethylaminocarbonyl(methyl)amino group, a (methoxymethyl)aminocarbonyl(methyl)amino group, a (2-methoxyethyl)aminocarbonyl(methyl)amino group, a (cyanomethyl)aminocarbonyl(methyl)amino group, a (2-cyanoethyl)aminocarbonyl(methyl)amino group, a dimethylaminocarbonyl(methyl)amino group, an ethyl(methyl)aminocarbonyl(methyl)amino group, a diethylaminocarbonyl(methyl)amino group, a (methoxymethyl)methylaminocarbonyl(methyl)amino group, a (2-methoxyethyl)methylaminocarbonyl(methyl)amino group, a (cyanomethyl)methylaminocarbonyl(methyl)amino group, a (2-cyanoethyl)methylaminocarbonyl(methyl)amino group, a 2,2-difluoroethylaminocarbonyl(methyl)amino group, a 2,2,2-trifluoroethylaminocarbonyl(methyl)amino group, a cyclopropylaminocarbonyl(methyl)amino group, a cyclopropyl(methyl)aminocarbonyl(methyl)amino group, a pyrrolidinylcarbonyl(methyl)amino group, a piperidinylcarbonyl(methyl)amino group, a formyl(ethyl)amino group, an acetyl(ethyl)amino group, a methoxyacetyl(ethyl)amino group, a cyanoacetyl(ethyl)amino group, a propionyl(ethyl)amino group, a difluoroacetyl(ethyl)amino group, a trifluoroacetyl(ethyl)amino group, a cyclopropanecarbonyl(ethyl)amino group, a methoxycarbonyl(ethyl)amino group, an ethoxycarbonyl(ethyl)amino group, a 2,2-difluoroethoxycarbonyl(ethyl)amino group, a 2,2,2-trifluoroethoxycarbonyl(ethyl)amino group, a 3,3,3-trifluoropropyloxycarbonyl(ethyl)amino group, a cyclopropyloxycarbonyl(ethyl)amino group, an aminocarbonyl(ethyl)amino group, a methylaminocarbonyl(ethyl)amino group, an ethylaminocarbonyl(ethyl)amino group, a (methoxymethyl)aminocarbonyl(ethyl)amino group, a (2-methoxyethyl)aminocarbonyl(ethyl)amino group, a (cyanomethyl)aminocarbonyl(ethyl)amino group, a (2-cyanoethyl)aminocarbonyl(ethyl)amino group, a dimethylaminocarbonyl(ethyl)amino group, an ethyl(methyl)aminocarbonyl(ethyl)amino group, a diethylaminocarbonyl(ethyl)amino group, a (methoxymethyl)methylaminocarbonyl(ethyl)amino group, a (2-methoxyethyl)methylaminocarbonyl(ethyl)amino group, a (cyanomethyl)methylaminocarbonyl(ethyl)amino group, a (2-cyanoethyl)methylaminocarbonyl(ethyl)amino group, a 2,2-difluoroethylaminocarbonyl(ethyl)amino group, a 2,2,2-trifluoroethylaminocarbonyl(ethyl)amino group, a cyclopropylaminocarbonyl(ethyl)amino group, a cyclopropyl(methyl)aminocarbonyl(ethyl)amino group, a pyrrolidinylcarbonyl(ethyl)amino group, a piperidinylcarbonyl(ethyl)amino group, a formyl(methoxy)amino group, an acetyl(methoxy)amino group, a methoxyacetyl(methoxy)amino group, a cyanoacetyl(methoxy)amino group, a propionyl(methoxy)amino group, a difluoroacetyl(methoxy)amino group, a trifluoroacetyl(methoxy)amino group, a cyclopropanecarbonyl(methoxy)amino group, a methoxycarbonyl(methoxy)amino group, an ethoxycarbonyl(methoxy)amino group, a 2,2-difluoroethoxycarbonyl(methoxy)amino group, a 2,2,2-trifluoroethoxycarbonyl(methoxy)amino group, a 3,3,3-trifluoropropyloxycarbonyl(methoxy)amino group, a cyclopropyloxycarbonyl(methoxy)amino group, an aminocarbonyl(methoxy)amino group, a methylaminocarbonyl(methoxy)amino group, an ethylaminocarbonyl(methoxy) amino group, a (methoxymethyl)aminocarbonyl(methoxy) amino group, a (2-methoxyethyl)aminocarbonyl(methoxy) amino group, a (cyanomethyl)aminocarbonyl(methoxy) amino group, a (2-cyanoethyl)aminocarbonyl(methoxy) amino group, a dimethylaminocarbonyl(methoxy)amino group, an ethyl(methyl)aminocarbonyl(methoxy)amino group, a diethylaminocarbonyl(methoxy)amino group, a (methoxymethyl)methylaminocarbonyl(methoxy)amino group, a (2-methoxyethyl)methylaminocarbonyl(methoxy) amino group, a (cyanomethyl)methylaminocarbonyl (methoxy)amino group, a (2-cyanoethyl)methylaminocarbonyl(methoxy)amino group, a 2,2-difluoroethylaminocarbonyl(methoxy)amino group, a 2,2,2-trifluoroethylaminocarbonyl(methoxy)amino group, a cyclopropylaminocarbonyl(methoxy)amino group, a cyclopropyl(methyl)aminocarbonyl(methoxy)amino group, a pyrrolidinylcarbonyl(methoxy)amino group, a piperidinylcarbonyl(methoxy)amino group, a formyl(ethoxy)amino group, an acetyl(ethoxy)amino group, a methoxyacetyl(ethoxy)amino group, a cyanoacetyl(ethoxy)amino group, a propionyl(ethoxy)amino group, a difluoroacetyl(ethoxy)amino group, a trifluoroacetyl(ethoxy)amino group, a cyclopropanecarbonyl(ethoxy)amino group, a methoxycarbonyl(ethoxy)amino group, an ethoxycarbonyl(ethoxy)amino group, a 2,2-difluoroethoxycarbonyl(ethoxy)amino group, a 2,2,2-trifluoroethoxycarbonyl(ethoxy)amino group, a 3,3,3-trifluoropropyloxycarbonyl(ethoxy)amino group, a cyclopropyloxycarbonyl(ethoxy)amino group, an aminocarbonyl(ethoxy)amino group, a methylaminocarbonyl(ethoxy) amino group, an ethylaminocarbonyl(ethoxy)amino group, a (methoxymethyl)aminocarbonyl(ethoxy)amino group, a (2-methoxyethyl)aminocarbonyl(ethoxy)amino group, a (cyanomethyl)aminocarbonyl(ethoxy)amino group, a (2-cyanoethyl)aminocarbonyl(ethoxy)amino group, a dimethylaminocarbonyl(ethoxy)amino group, an ethyl(methyl) aminocarbonyl(ethoxy)amino group, a diethylaminocarbonyl(ethoxy)amino group, a (methoxymethyl) methylaminocarbonyl(ethoxy)amino group, a (2-methoxyethyl)methylaminocarbonyl(ethoxy)amino group, a (cyanomethyl)methylaminocarbonyl(ethoxy)amino group, a (2-cyanoethyl)methylaminocarbonyl(ethoxy)amino group, a 2,2-difluoroethylaminocarbonyl(ethoxy)amino group, a 2,2,2-trifluoroethylaminocarbonyl(ethoxy)amino group, a cyclopropylaminocarbonyl(ethoxy)amino group, a cyclopropyl(methyl)aminocarbonyl(ethoxy)amino group, a pyrrolidinylcarbonyl(ethoxy)amino group or a piperidinylcarbonyl(ethoxy)amino group, and more preferably an acetylamino group, an acetyl(methyl)amino group, an acetyl (ethyl)amino group, an acetyl(methoxy)amino group, an acetyl(ethoxy)amino group, a methoxycarbonylamino group, an ethoxycarbonylamino group, a methoxycarbonyl (methyl)amino group, an ethoxycarbonyl(methyl)amino group, a methoxycarbonyl(ethyl)amino group, an ethoxycarbonyl(ethyl)amino group, a methoxycarbonyl(methoxy) amino group, an ethoxycarbonyl(methoxy)amino group, a methoxycarbonyl(ethoxy)amino group or an ethoxycarbonyl(ethoxy)amino group.

Z in Formula (1) represents a C1-C9 alkyl group optionally substituted with substituent C, a C1-C6 haloalkyl group, a C3-C8 cycloalkyl group optionally substituted with substituent D, a C2-C6 alkenyl group optionally substituted with substituent C, a C2-C6 haloalkenyl group, a C2-C6 alkynyl group optionally substituted with substituent C, a C2-C6 haloalkynyl group, a phenyl group optionally substituted with 0 to 5 R4 (with the proviso that when there are two or more substituents R4, they are independent to each other), a C1-C6 alkyl group having a phenyl group optionally substituted with 0 to 5 R4 (with the proviso that when there are two or more substituents R4, they are independent to each other), a C1-C6 haloalkyl group having a phenyl group optionally substituted with 0 to 5 R4 (with the proviso that when there are two or more substituents R4, they are independent to each other), a pyridyl group optionally substituted with 0 to 4 R4 (with the proviso that when there are two or more substituents R4, they are independent to each other), a pyridazinyl group optionally substituted with 0 to 3 R4 (with the proviso that when there are two or more substituents R4, they are independent to each other), a pyrimidinyl group optionally substituted with 0 to 3 R4 (with the proviso that when there are two or more substituents R4, they are independent to each other), a pyrazinyl group optionally substituted with 0 to 3 R4 (with the proviso that when there are two or more substituents R4, they are independent to each other), a triazinyl group optionally substituted with 0 to 2 R4 (with the proviso that when there are two substituents R4, they are independent to each other), a tetrazinyl group optionally substituted with R4, a thienyl group optionally substituted with 0 to 3 R4 (with the proviso that when there are two or more substituents R4, they are independent to each other), a thiazolyl group optionally substituted with 0 to 2 R4 (with the proviso that when there are two substituents R4, they are independent to each other), an isothiazolyl group optionally substituted with 0 to 2 R4 (with the proviso that when there are two substituents R4, they are independent to each other), a thiadiazolyl group optionally substituted with R4, an oxazolyl group optionally substituted with 0 to 2 R4 (with the proviso that when there are two substituents R4, they are independent to each other), an isoxazolyl group optionally substituted with 0 to 2 R4 (with the proviso that when there are two substituents R4, they are independent to each other), an oxadiazolyl group optionally substituted with R4, or a pyrazolyl group optionally substituted with 0 to 2 R4 (with the proviso that when there are two substituents R4, they are independent to each other), among these, Z is preferably a C1-C9 alkyl group optionally substituted with substituent C, a C1-C6 haloalkyl group, a C3-C8 cycloalkyl group optionally substituted with substituent D, a C2-C6 alkenyl group optionally substituted with substituent C, a C2-C6 alkynyl group optionally substituted with substituent C, a phenyl group optionally substituted with 0 to 5 R4 (with the proviso that when there are two or more substituents R4, they are independent to each other), a C1-C6 alkyl group having a phenyl group optionally substituted with 0 to 5 R4 (with the proviso that when there are two or more substituents R4, they are independent to each other), a pyridyl group optionally substituted with 0 to 4 R4 (with the proviso that when there are two or more substituents R4, they are independent to each other), an oxazolyl group optionally substituted with 0 to 2 R4 (with the proviso that when there are two substituents R4, they are independent to each other), an isoxazolyl group optionally substituted with 0 to 2 R4 (with the proviso that when there are two substituents R4, they are independent to each other) or an oxadiazolyl group optionally substituted with R4, and in particular, Z is preferably a C1-C9 alkyl group optionally substituted with substituent C, a C1-C6 haloalkyl group, a C3-C8 cycloalkyl group optionally substituted with substituent D, a C2-C6 alkenyl group optionally substituted with substituent C, a C2-C6 alkynyl group optionally substituted with substituent C, a phenyl group optionally substituted with 0 to 5 R4 (with the proviso that when there are two or more substituents R4, they are independent to each other), a C1-C6 alkyl group having a phenyl group optionally substituted with 0 to 5 R4 (with the proviso that when there are two or more substituents R4, they are independent to each other), a pyridyl group optionally substituted with 0 to 4 R4 (with the proviso that when there are two or more substituents R4, they are independent to each other) or an isoxazolyl group optionally substituted with 0 to 2 R4 (with the proviso that when there are two substituents R4, they are independent to each other).

The C1-C9 alkyl group for the "C1-C9 alkyl group optionally substituted with substituent C" as Z of Formula (1) is the same as defined above, and preferably a methyl group, an ethyl group, a propyl group, an isopropyl group, a butyl group, an isobutyl group, a sec-butyl group, a t-butyl group, a pentyl group, an isopentyl group, a 1-methylbutyl group, a 2-methylbutyl group, a neopentyl group, a 1,2-dimethylpropyl group, a hexyl group, a 1-isopropylpropyl group, a 1,2,2-trimethylpropyl group, a heptyl group, a 2-methyl-1-isopropylpropyl group, a 1-t-butylpropyl group, a 1-isopropylbutyl group, a octyl group or a nonyl group, more preferably a methyl group, an ethyl group, a propyl group, an isopropyl group, a butyl group, an isobutyl group, a sec-butyl group, a t-butyl group, a pentyl group, an isopentyl group, a 2-methylbutyl group, a neopentyl group, a 1,2-dimethylpropyl group, a hexyl group, a 1-isopropylpropyl group, a 1,2,2-trimethylpropyl group or a heptyl group. When substituent C is present, any hydrogen atom in the C1-C9 alkyl group is substituted with substituent C.

The "C1-C6 haloalkyl group" as Z of Formula (1) is the same as defined above, and preferably a difluoromethyl group, a trifluoromethyl group, a 2,2-difluoroethyl group, a 2,2,2-trifluoroethyl group, a 3,3-difluoropropyl group, a 3,3,3-trifluoropropyl group, a 4,4-difluorobutyl group or a 4,4,4-trifluorobutyl group, more preferably a 2,2-difluoroethyl group, a 2,2,2-trifluoroethyl group, a 3,3-difluoropropyl group, a 3,3,3-trifluoropropyl group, a 4,4-difluorobutyl group or a 4,4,4-trifluorobutyl group.

The C3-C8 cycloalkyl group for the "C3-C8 cycloalkyl group optionally substituted with substituent D" as Z of Formula (1) is the same as defined above, and preferably a cyclopropyl group, a cyclobutyl group, a cyclopentyl group, a cyclohexyl group or a cycloheptyl group, more preferably a cyclopropyl group, a cyclobutyl group, a cyclopentyl group or a cyclohexyl group. When substituent D is present, any hydrogen atom in the C3-C8 cycloalkyl group is substituted with substituent D.

The C2-C6 alkenyl group for the "C2-C6 alkenyl group optionally substituted with substituent C" as Z of Formula (1) is the same as defined above, and preferably a vinyl group, a 1-propenyl group, an allyl group, a 1-butenyl group, a 2-butenyl group or a 3-butenyl group, more preferably a vinyl group, a 1-propenyl group or an allyl group. When substituent C is present, any hydrogen atom in the C2-C6 alkenyl group is substituted with substituent C.

The "C2-C6 haloalkenyl group" as Z of Formula (1) is the same as defined above, and preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, more preferably a 2-fluorovinyl group or a 2,2-difluorovinyl group.

The C2-C6 alkynyl group for the "C2-C6 alkynyl group optionally substituted with substituent C" as Z of Formula (1) is the same as defined above, and preferably an ethynyl group, a 1-propynyl group, a propargyl group, a 1-butynyl group, a 2-butynyl group or a 3-butynyl group, more preferably an ethynyl group, a 1-propynyl group or a propargyl group. When substituent C is present, any hydrogen atom in the C2-C6 alkynyl group is substituted with substituent C.

The "C2-C6 haloalkynyl group" as Z of Formula (1) is the same as defined above, and preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, more preferably a 3,3-difluoro-1-propynyl group or a 3,3,3-trifluoro-1-propynyl group.

The "phenyl group optionally substituted with 0 to 5 R4" (with the proviso that when there are two or more substituents R4, they are independent to each other) as Z of Formula (1) refers to the partial structure represented by Formula (A) shown below.

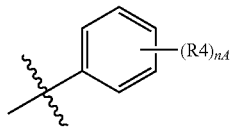

In Formula (A), nA represents an integer of 0 to 5 and, when nA is 2 or more, the substituents which two or more R4's represent are independent to each other and may be the same or different and arbitrarily selected.

Each of the "phenyl group optionally substituted with 0 to 5 R4" and "C1-C6 alkyl group" for the "C1-C6 alkyl group having a phenyl group optionally substituted with 0 to 5 R4" (with the proviso that when there are two or more substituents R4, they are independent to each other) as Z of Formula (1) is the same as defined above. The "C1-C6 alkyl group having a phenyl group" is preferably a phenylmethyl group, a 2-phenylethyl group, a 1-phenylethyl group, a 3-phenylpropyl group, a 2-phenylpropyl group, a 1-phenylpropyl group, a 4-phenylbutyl group or a 5-phenylpentyl group, and more preferably a phenylmethyl group, a 2-phenylethyl group, a 1-phenylethyl group or a 1-phenylpropyl group. When R4 is present, any hydrogen atom of the phenyl group is substituted with R4.

Each of the "phenyl group optionally substituted with 0 to 5 R4" and "C1-C6 haloalkyl group" for the "C1-C6 haloalkyl group having a phenyl group optionally substituted with 0 to 5 R4" (with the proviso that when there are two or more substituents R4, they are independent to each other) as Z of Formula (1) is the same as defined above. The "C1-C6 haloalkyl group having a phenyl group" is preferably a 2,2,2-trifluoro-1-phenylethyl group or a 2,2-difluoro-1-phenylethyl group, and more preferably a 2,2,2-trifluoro-1-phenylethyl group. When R4 is present, any hydrogen atom of the phenyl group is substituted with R4.

The "pyridyl group optionally substituted with 0 to 4 R4" (with the proviso that when there are two or more substituents R4, they are independent to each other) as Z of Formula (1) refers to the partial structure represented by one formula selected from the group consisting of Formula (B-1), Formula (B-2) and Formula (B-3) shown below.

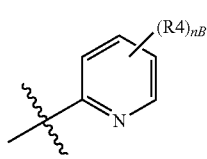

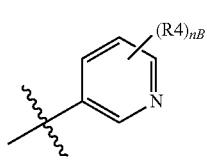

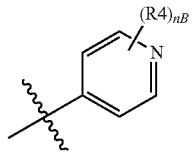

In each of Formula (B-1), Formula (B-2) and Formula (B-3), nB represents an integer of 0 to 4 and, when nB is 2 or more, the substituents which two or more R4's represent are independent to each other and may be the same or different and arbitrarily selected.

The "pyridazinyl group optionally substituted with 0 to 3 R4" (with the proviso that when there are two or more substituents R4, they are independent to each other) as Z of Formula (1) refers to the partial structure represented by one formula selected from the group consisting of Formula (C-1), Formula (C-2) and Formula (C-3) shown below.

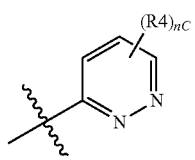

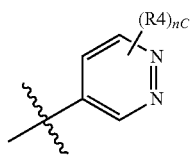

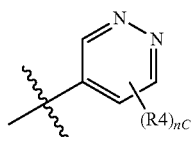

In each of Formula (C-1), Formula (C-2) and Formula (C-3), nC represents an integer of 0 to 3 and, when nC is 2 or more, the substituents which two or more R4's represent are independent to each other and may be the same or different and arbitrarily selected.

The "pyrimidinyl group optionally substituted with 0 to 3 R4" (with the proviso that when there are two or more substituents R4, they are independent to each other) as Z of Formula (1) refers to the partial structure represented by one formula selected from the group consisting of Formula (D-1), Formula (D-2) and Formula (D-3) shown below.

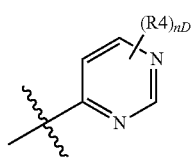

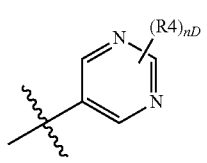

(D-2)

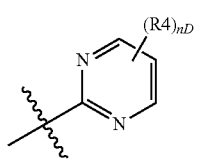

(D-3)

In each of Formula (D-1), Formula (D-2) and Formula (D-3), nD represents an integer of 0 to 3 and, when nD is 2 or more, the substituents which two or more R4's represent are independent to each other and may be the same or different and arbitrarily selected.

The "pyrazinyl group optionally substituted with 0 to 3 R4 (with the proviso that when there are two or more substituents R4, they are independent to each other)" as Z of Formula (1) refers to the partial structure represented by Formula (E) shown below.

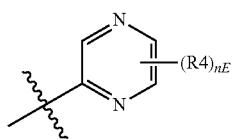

(E)

In Formula (E), nE represents an integer of 0 to 3 and, when nE is 2 or more, the substituents which two or more R4's represent are independent to each other and may be the same or different and arbitrarily selected.

The "triazinyl group optionally substituted with 0 to 2 R4" (with the proviso that when there are two substituents R4, they are independent to each other) as Z of Formula (1) refers to the partial structure represented by one formula selected from the group consisting of Formula (F-1), Formula (F-2), Formula (F-3), Formula (F-4) and Formula (F-5) shown below.

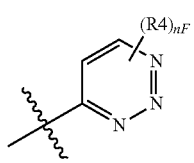

(F-1)

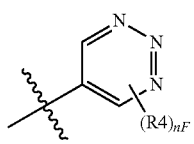

(F-2)

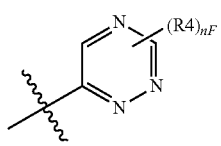

(F-3)

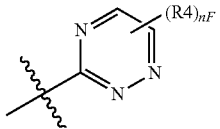

(F-4)

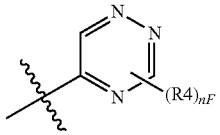

(F-5)

In each of Formula (F-1), Formula (F-2), Formula (F-3), Formula (F-4) and Formula (F-5), nF represents an integer of 0 to 2 and, when nF is 2, the substituents which two R4's represent are independent to each other and may be the same or different and arbitrarily selected.

The "tetrazinyl group optionally substituted with R4" as Z of Formula (1) refers to the partial structure represented by one formula selected from the group consisting of Formula (G-1), Formula (G-2) and Formula (G-3) shown below.

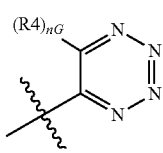

(G-1)

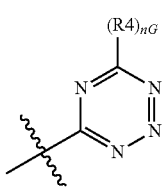

(G-2)

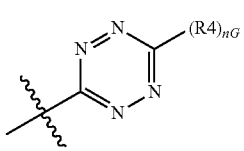

(G-3)

In each of Formula (G-1), Formula (G-2) and Formula (G-3), nG represents an integer of 0 to 1.

The "thienyl group optionally substituted with 0 to 3 R4" (with the proviso that when there are two or more substituents R4, they are independent to each other) as Z of Formula (1) refers to the partial structure represented by one formula selected from the group consisting of Formula (H-1) and Formula (H-2) shown below.

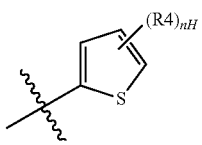

(H-1)

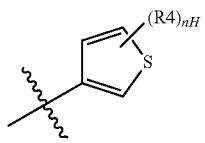
(H-2)

In each of Formula (H-1) and Formula (H-2), nH represents an integer of 0 to 3 and, when nH is 2 or more, the substituents which two or more R4's represent are independent to each other and may be the same or different and arbitrarily selected.

The "thiazolyl group optionally substituted with 0 to 2 R4" (with the proviso that when there are two substituents R4, they are independent to each other) as Z of Formula (1) refers to the partial structure represented by one formula selected from the group consisting of Formula (I-1), Formula (I-2) and Formula (I-3) shown below.

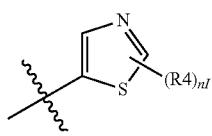
(I-1)

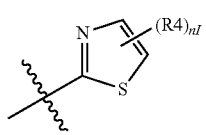
(I-2)

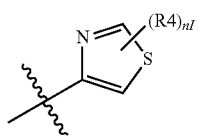
(I-3)

In each of Formula (I-1), Formula (I-2) and Formula (I-3), nI represents an integer of 0 to 2 and, when nI is 2, the substituents which two R4's represent are independent to each other and may be the same or different and arbitrarily selected.

The "isothiazolyl group optionally substituted with 0 to 2 R4" (with the proviso that when there are two substituents R4, they are independent to each other) as Z of Formula (1) refers to the partial structure represented by one formula selected from the group consisting of Formula (J-1), Formula (J-2) and Formula (J-3) shown below.

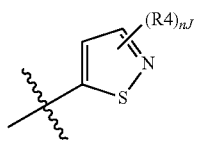
(J-1)

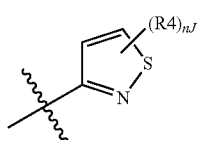
(J-2)

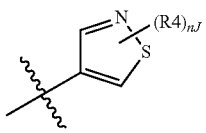
(J-3)

In each of Formula (J-1), Formula (J-2) and Formula (J-3), nJ represents an integer of 0 to 2 and, when nJ is 2, the substituents which two R4's represent are independent to each other and may be the same or different and arbitrarily selected.

The "thiadiazolyl group optionally substituted with R4" as Z of Formula (1) refers to the partial structure represented by one formula selected from the group consisting of Formula (K-1), Formula (K-2), Formula (K-3), Formula (K-4), Formula (K-5) and Formula (K-6) shown below.

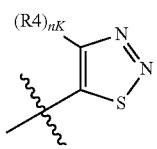
(K-1)

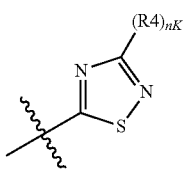
(K-2)

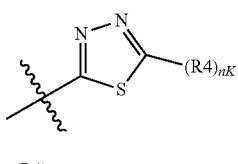
(K-3)

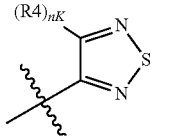
(K-4)

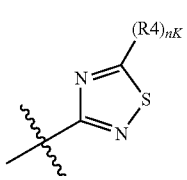
(K-5)

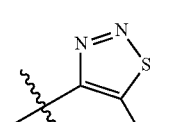
(K-6)

In each of Formula (K-1), Formula (K-2), Formula (K-3), Formula (K-4), Formula (K-5) and Formula (K-6), nK represents an integer of 0 to 1.

The "oxazolyl group optionally substituted with 0 to 2 R4" (with the proviso that when there are two substituents R4, they are independent to each other) as Z of Formula (1) refers to the partial structure represented by one formula selected from the group consisting of Formula (L-1), Formula (L-2) and Formula (L-3) shown below.

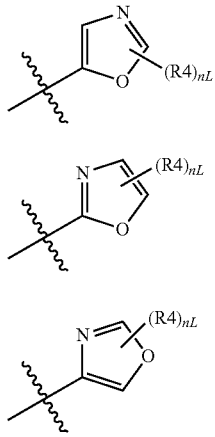

In each of Formula (L-1), Formula (L-2) and Formula (L-3), nL represents an integer of 0 to 2 and, when nL is 2, the substituents which two R4's represent are independent to each other and may be the same or different and arbitrarily selected.

The "isoxazolyl group optionally substituted with 0 to 2 R4" (with the proviso that when there are two substituents R4, they are independent to each other) as Z of Formula (1) refers to the partial structure represented by one formula selected from the group consisting of Formula (M-1), Formula (M-2) and Formula (M-3) shown below.

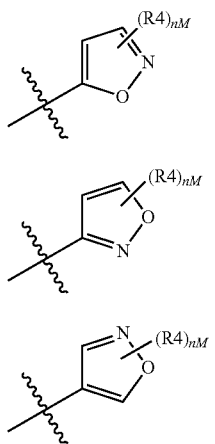

In each of Formula (M-1), Formula (M-2) and Formula (M-3), nM represents an integer of 0 to 2 and, when nM is 2, the substituents which two R4's represent are independent to each other and may be the same or different and arbitrarily selected.

The "oxadiazolyl group optionally substituted with R4" as Z of Formula (1) refers to the partial structure represented by one formula selected from the group consisting of Formula (N-1), Formula (N-2), Formula (N-3), Formula (N-4), Formula (N-5) and Formula (N-6) shown below.

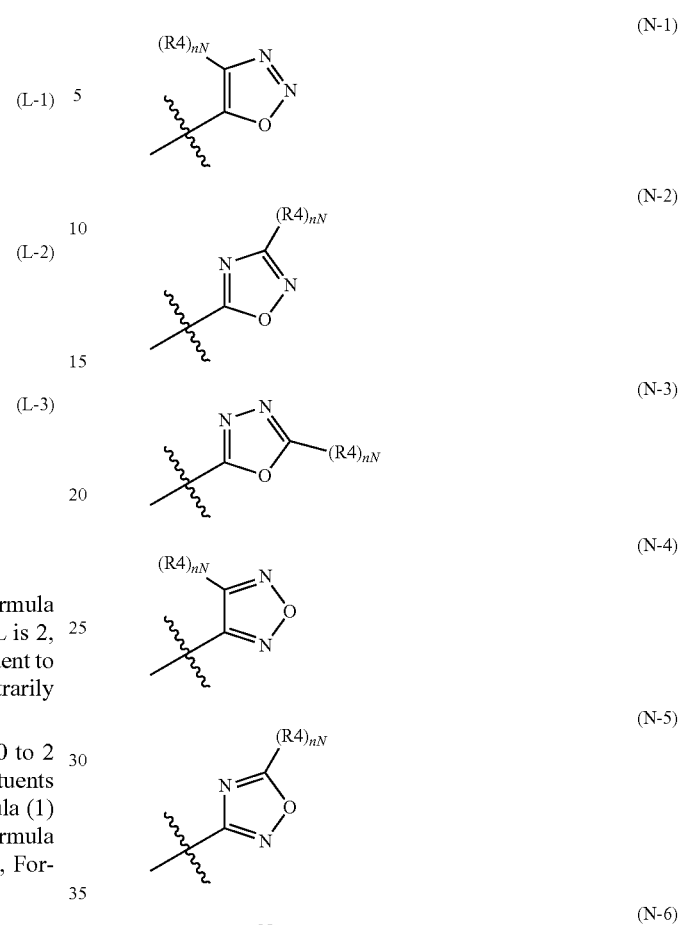

In each of Formula (N-1), Formula (N-2), Formula (N-3), Formula (N-4), Formula (N-5) and Formula (N-6), nN represents an integer of 0 to 1.

The "pyrazolyl group optionally substituted with 0 to 2 R4" (with the proviso that when there are two substituents R4, they are independent to each other) as Z of Formula (1) refers to the partial structure represented by one formula selected from the group consisting of Formula (O-1), Formula (O-2) and Formula (O-3) shown below.

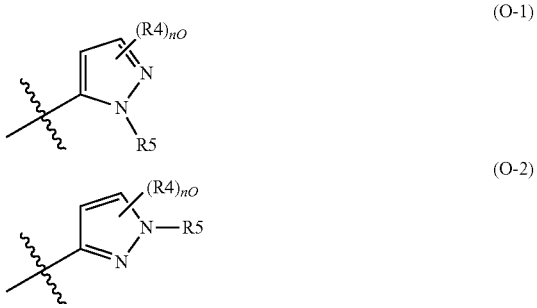

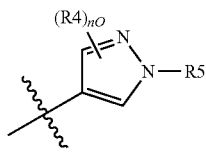

(O-3)

In each of Formula (0-1), Formula (0-2) and Formula (0-3), R5 represents a hydrogen atom, a C1-C6 alkyl group or a C1-C6 haloalkyl group, and nO represents an integer of 0 to 2. When nO is 2, the substituents which two R4's represent are independent to each other and may be the same or different and arbitrarily selected.

R4 in Formula (1) has the same meaning as R3. That is, it represents a hydroxyl group, a cyano group, a nitro group, a halogen atom, a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C, a C2-C6 haloalkynyl group, a C1-C6 alkoxy group optionally substituted with substituent C, a C1-C6 haloalkoxy group, a C3-C8 cycloalkoxy group optionally substituted with substituent C, a C2-C6 alkenyloxy group optionally substituted with substituent C, a C2-C6 haloalkenyloxy group, a C3-C6 alkynyloxy group optionally substituted with substituent C, a C3-C6 haloalkynyloxy group, an RdC(=O)— (wherein Rd is the same as defined above), an RdC(=O)O— (wherein Rd is the same as defined above), a group of a 3-6 membered ring containing 1-2 oxygen atoms, an Rc-L- (wherein Rc and L are the same as defined above), an RaRbN— (wherein Ra and Rb are the same as defined above) or an ReC(=O)N (Rf)— (wherein Re and Rf are the same as defined above).

Among these, R4 is preferably a hydroxyl group, a cyano group, a nitro group, a halogen atom, a C1-C6 alkyl group optionally substituted with substituent C, a C1-C6 haloalkyl group, a C2-C6 alkenyl group optionally substituted with substituent C, a C2-C6 alkynyl group optionally substituted with substituent C, a C1-C6 alkoxy group optionally substituted with substituent C, a C1-C6 haloalkoxy group, a C2-C6 alkenyloxy group optionally substituted with substituent C, a C3-C6 alkynyloxy group optionally substituted with substituent C, an RdC(=O)O— (wherein Rd is the same as defined above), an RaRbN— (wherein Ra and Rb are the same as defined above) or an ReC(=O)N(Rf)— (wherein Re and Rf are the same as defined above), in particular, R4 is preferably a hydroxyl group, a cyano group, a nitro group, a halogen atom, a C1-C6 alkyl group optionally substituted with substituent C, a C1-C6 haloalkyl group, a C1-C6 alkoxy group optionally substituted with substituent C, a C2-C6 alkenyloxy group optionally substituted with substituent C, a C3-C6 alkynyloxy group optionally substituted with substituent C, an RaRbN— (wherein Ra and Rb are the same as defined above) or an ReC(=O)N(Rf)— (wherein Re and Rf are the same as defined above), and R4 is further preferably a hydroxyl group, a nitro group, a halogen atom, a C1-C6 alkyl group optionally substituted with substituent C, a C1-C6 haloalkyl group, a C1-C6 alkoxy group optionally substituted with substituent C, a C2-C6 alkenyloxy group optionally substituted with substituent C, a C3-C6 alkynyloxy group optionally substituted with substituent C or an RaRbN— (wherein Ra and Rb are the same as defined above).

In R4 of Formula (1), a hydroxyl group, a cyano group and a nitro group are included.

The halogen atom as R4 of Formula (1) is the same as defined above, preferably a fluorine atom, a chlorine atom, a bromine atom or an iodine atom.

The C1-C6 alkyl group for the "C1-C6 alkyl group optionally substituted with substituent C" as R4 of Formula (1) is the same as defined above, and preferably a methyl group, an ethyl group, a propyl group, an isopropyl group, a butyl group, an isobutyl group or a pentyl group, more preferably a methyl group, an ethyl group, a propyl group, an isopropyl group or a butyl group. When substituent C is present, any hydrogen atom in the C1-C6 alkyl group is substituted with substituent C.

The "C1-C6 haloalkyl group" as R4 of Formula (1) is the same as defined above, and preferably a difluoromethyl group, a trifluoromethyl group, a 2,2-difluoroethyl group or a 2,2,2-trifluoroethyl group, more preferably a difluoromethyl group or a trifluoromethyl group.

The C3-C8 cycloalkyl group for the "C3-C8 cycloalkyl group optionally substituted with substituent C" as R4 of Formula (1) is the same as defined above, and preferably a cyclopropyl group, a cyclobutyl group, a cyclopentyl group or a cyclohexyl group, more preferably a cyclopropyl group or a cyclobutyl group. When substituent C is present, any hydrogen atom in the C3-C8 cycloalkyl group is substituted with substituent C.

The C2-C6 alkenyl group for the "C2-C6 alkenyl group optionally substituted with substituent C" as R4 of Formula (1) is the same as defined above, and preferably a vinyl group, a 1-propenyl group, an allyl group, a 1-butenyl group, a 2-butenyl group or a 3-butenyl group, more preferably a vinyl group, a 1-propenyl group or an allyl group. When substituent C is present, any hydrogen atom in the C2-C6 alkenyl group is substituted with substituent C.

The "C2-C6 haloalkenyl group" as R4 of Formula (1) is the same as defined above, and preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, more preferably a 2-fluorovinyl group or a 2,2-difluorovinyl group.

The C2-C6 alkynyl group for the "C2-C6 alkynyl group optionally substituted with substituent C" as R4 of Formula (1) is the same as defined above, and preferably an ethynyl group, a 1-propynyl group, a propargyl group, a 1-butynyl group, a 2-butynyl group or a 3-butynyl group, more preferably an ethynyl group, a 1-propynyl group or a propargyl group. When substituent C is present, any hydrogen atom in the C2-C6 alkynyl group is substituted with substituent C.

The "C2-C6 haloalkynyl group" as R4 of Formula (1) is the same as defined above, and preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, more preferably a 3,3-difluoro-1-propynyl group or a 3,3,3-trifluoro-1-propynyl group.

The C1-C6 alkoxy group for the "C1-C6 alkoxy group optionally substituted with substituent C" as R4 of Formula (1) is the same as defined above, and preferably a methoxy group, an ethoxy group, a propyloxy group, an isopropyloxy group, a butoxy group, an isobutoxy group, a sec-butoxy group, a t-butoxy group, a pentyloxy group or an isopentyloxy group, more preferably a methoxy group, an ethoxy group, a propyloxy group, an isopropyloxy group, a butoxy group, an isobutoxy group, a sec-butoxy group or a t-butoxy group. When substituent C is present, any hydrogen atom in the C1-C6 alkoxy group is substituted with substituent C.

The "C1-C6 haloalkoxy group" as R4 of Formula (1) is the same as defined above, and preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, more preferably a difluoromethoxy group, a trifluoromethoxy group, a 2,2-difluoroethoxy group or a 2,2,2-trifluoroethoxy group.

The C3-C8 cycloalkoxy group for the "C3-C8 cycloalkoxy group optionally substituted with substituent C" as R4 of Formula (1) is the same as defined above, and preferably a cyclopropyloxy group, a cyclobutoxy group, a cyclopentyloxy group or a cyclohexyloxy group, more preferably a cyclopropyloxy group or a cyclobutoxy group. When substituent C is present, any hydrogen atom in the C3-C8 cycloalkoxy group is substituted with substituent C.

The C2-C6 alkenyloxy group for the "C2-C6 alkenyloxy group optionally substituted with substituent C" as R4 of Formula (1) is the same as defined above, and preferably a vinyloxy group, a 1-propenyloxy group, an allyloxy group, a 1-butenyloxy group, a 2-butenyloxy group or a 3-butenyloxy group, more preferably a vinyloxy group, a 1-propenyloxy group or an allyloxy group. When substituent C is present, any hydrogen atom in the C2-C6 alkenyloxy group is substituted with substituent C.

The "C2-C6 haloalkenyloxy group" as R4 of Formula (1) is the same as defined above, and preferably a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group, more preferably a 2-fluorovinyloxy group or a 2,2-difluorovinyloxy group.

The C3-C6 alkynyloxy group for the "C3-C6 alkynyloxy group optionally substituted with substituent C" as R4 of Formula (1) is the same as defined above, and preferably a propargyloxy group, a 2-butynyloxy group or a 3-butynyloxy group, more preferably a propargyloxy group or a 2-butynyloxy group. When substituent C is present, any hydrogen atom in the C3-C6 alkynyloxy group is substituted with substituent C.

The "C3-C6 haloalkynyloxy group" as R4 of Formula (1) is the same as defined above, and preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, more preferably a 4,4-difluoro-2-butynyloxy group or a 4,4,4-trifluoro-2-butynyloxy group.

Rd of the "RdC(=O)—" as R4 of Formula (1) is the same as defined above. Rd is preferably a C1-C6 alkyl group optionally substituted with substituent B, a C1-C6 haloalkyl group or a C1-C6 alkoxy group, and more preferably a C1-C6 alkyl group optionally substituted with substituent B or a C1-C6 alkoxy group. The "RdC(=O)—" is preferably an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethyl(methyl)aminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a cyclopropyl(methyl)aminocarbonyl group, a pyrrolidinylcarbonyl group or a piperidinylcarbonyl group, and more preferably an acetyl group, a methoxyacetyl group, a cyanoacetyl group, a methoxycarbonyl group or an ethoxycarbonyl group.

Rd of the "RdC(=O)O—" as R4 of Formula (1) is the same as defined above. Rd is preferably a C1-C6 alkyl group optionally substituted with substituent B, a C1-C6 haloalkyl group or a C1-C6 alkoxy group, and more preferably a C1-C6 alkyl group optionally substituted with substituent B or a C1-C6 alkoxy group. The "RdC(=O)O—" is preferably an acetyloxy group, a methoxyacetyloxy group, a cyanoacetyloxy group, a propionyloxy group, a difluoroacetyloxy group, a trifluoroacetyloxy group, a cyclopropanecarbonyloxy group, a methoxycarbonyloxy group, an ethoxycarbonyloxy group, a 2,2-difluoroethoxycarbonyloxy group, a 2,2,2-trifluoroethoxycarbonyloxy group, a 3,3,3-trifluoropropyloxycarbonyloxy group, a cyclopropyloxycarbonyloxy group, an aminocarbonyloxy group, a methylaminocarbonyloxy group, an ethylaminocarbonyloxy group, a (methoxymethyl)aminocarbonyloxy group, a (2-methoxyethyl)aminocarbonyloxy group, a (cyanomethyl)aminocarbonyloxy group, a (2-cyanoethyl)aminocarbonyloxy group, a dimethylaminocarbonyloxy group, an ethyl(methyl)aminocarbonyloxy group, a diethylaminocarbonyloxy group, a (methoxymethyl)methylaminocarbonyloxy group, a (2-methoxyethyl)methylaminocarbonyloxy group, a (cyanomethyl)methylaminocarbonyloxy group, a (2-cyanoethyl)methylaminocarbonyloxy group, a 2,2-difluoroethylaminocarbonyloxy group, a 2,2,2-trifluoroethylaminocarbonyloxy group, a cyclopropylaminocarbonyloxy group, a cyclopropyl(methyl)aminocarbonyloxy group, a pyrrolidinylcarbonyloxy group or a piperidinylcarbonyloxy group, and more preferably an acetyloxy group, a methoxyacetyloxy group, a cyanoacetyloxy group, a methoxycarbonyloxy group or an ethoxycarbonyloxy group.

The "group of a 3-6 membered ring containing 1-2 oxygen atoms" as R4 of Formula (1) is the same as defined above, and preferably an oxolanyl group, an oxanyl group, a 1,3-dioxolanyl group or a 1,3-dioxanyl group, more preferably a 1,3-dioxolanyl group or a 1,3-dioxanyl group.

Rc and L of the "Rc-L-" as R4 of Formula (1) are the same as defined above. The "Rc-L-" is preferably a methylthio group, a methanesulfinyl group, a methanesulfonyl group, a trifluoromethylthio group, a trifluoromethanesulfinyl group or a trifluoromethanesulfonyl group, and more preferably a methylthio group, a methanesulfinyl group or a methanesulfonyl group.

Ra and Rb of the "RaRbN—" as R4 of Formula (1) are the same as defined above. Ra and Rb are each preferably a hydrogen atom, a C1-C6 alkyl group optionally substituted with substituent B or a C1-C6 haloalkyl group, further preferably a hydrogen atom or a C1-C6 alkyl group optionally substituted with substituent B. The "RaRbN—" is preferably an amino group, a methylamino group, an ethylamino group, a propylamino group, an isopropylamino group, a (methoxymethyl)amino group, a (2-methoxyethyl)amino group, a (cyanomethyl)amino group, a (2-cyanoethyl)amino group, a dimethylamino group, an ethyl(methyl)amino group, a methyl(propyl)amino group, an isopropyl(methyl)amino group, a (methoxymethyl)methylamino group, a (2-methoxyethyl)methylamino group, a (cyanomethyl)methylamino group, a (2-cyanoethyl)methylamino group, a diethylamino group, an ethyl(propyl)amino group, an ethyl(isopropyl)amino group, an ethyl(methoxymethyl)amino group, an ethyl(2-methoxyethyl)amino group, a (cyanomethyl)ethylamino group, a (2-cyanoethyl)ethylamino group, a 2,2-difluoroethylamino group, a 2,2,2-trifluoroethylamino group, a cyclopropylamino group, a (cyclopropyl)methylamino group, a pyrrolidinyl group or a piperidinyl group, and more preferably an amino group, a methylamino group, an ethylamino group, a dimethylamino group, an ethyl(methyl)amino group or a diethylamino group.

Re and Rf of the "ReC(=O)N(Rf)—" as R4 of Formula (1) are the same as defined above. Re and Rf are each preferably a hydrogen atom, a C1-C6 alkyl group optionally substituted with substituent B, a C1-C6 haloalkyl group, and more preferably a hydrogen atom or a C1-C6 alkyl group optionally substituted with substituent B. The "ReC(=O)N(Rf)—" is preferably a formylamino group, an acetylamino group, a methoxyacetylamino group, a cyanoacetylamino group, a propionylamino group, a difluoroacetylamino group, a trifluoroacetylamino group, a cyclopropanecarbonylamino group, a methoxycarbonylamino group, an ethoxycarbonylamino group, a 2,2-difluoroethoxycarbonylamino group, a 2,2,2-trifluoroethoxycarbonylamino group, a 3,3,3-trifluoropropyloxycarbonylamino group, a cyclopropyloxycarbonylamino group, an aminocarbonylamino group, a methylaminocarbonylamino group, an ethylaminocarbonylamino group, a (methoxymethyl)aminocarbonylamino group, a (2-methoxyethyl)aminocarbonylamino group, a (cyanomethyl)aminocarbonylamino group, a (2-cyanoethyl)aminocarbonylamino group, a dimethylaminocarbonylamino group, an ethyl(methyl)aminocarbonylamino group, a diethylaminocarbonylamino group, a (methoxymethyl)methylaminocarbonylamino group, a (2-methoxyethyl)methylaminocarbonylamino group, a (cyanomethyl)methylaminocarbonylamino group, a (2-cyanoethyl)methylaminocarbonylamino group, a 2,2-difluoroethylaminocarbonylamino group, a 2,2,2-trifluoroethylaminocarbonylamino group, a cyclopropylaminocarbonylamino group, a cyclopropyl(methyl)aminocarbonylamino group, a pyrrolidinylcarbonylamino group, a piperidinylcarbonylamino group, a formyl(methyl)amino group, an acetyl(methyl)amino group, a methoxyacetyl(methyl)amino group, a cyanoacetyl(methyl)amino group, a propionyl(methyl)amino group, a difluoroacetyl(methyl)amino group, a trifluoroacetyl(methyl)amino group, a cyclopropanecarbonyl(methyl)amino group, a methoxycarbonyl(methyl)amino group, an ethoxycarbonyl(methyl)amino group, a 2,2-difluoroethoxycarbonyl(methyl)amino group, a 2,2,2-trifluoroethoxycarbonyl(methyl)amino group, a 3,3,3-trifluoropropyloxycarbonyl(methyl)amino group, a cyclopropyloxycarbonyl(methyl)amino group, an aminocarbonyl(methyl)amino group, a methylaminocarbonyl(methyl)amino group, an ethylaminocarbonyl(methyl)amino group, a (methoxymethyl)aminocarbonyl(methyl)amino group, a (2-methoxyethyl)aminocarbonyl(methyl)amino group, a (cyanomethyl)aminocarbonyl(methyl)amino group, a (2-cyanoethyl)aminocarbonyl(methyl)amino group, a dimethylaminocarbonyl(methyl)amino group, an ethyl(methyl)aminocarbonyl(methyl)amino group, a diethylaminocarbonyl(methyl)amino group, a (methoxymethyl)methylaminocarbonyl(methyl)amino group, a (2-methoxyethyl)methylaminocarbonyl(methyl)amino group, a (cyanomethyl)methylaminocarbonyl(methyl)amino group, a (2-cyanoethyl)methylaminocarbonyl(methyl)amino group, a 2,2-difluoroethylaminocarbonyl(methyl)amino group, a 2,2,2-trifluoroethylaminocarbonyl(methyl)amino group, a cyclopropylaminocarbonyl(methyl)amino group, a cyclopropyl(methyl)aminocarbonyl(methyl)amino group, a pyrrolidinylcarbonyl(methyl)amino group, a piperidinylcarbonyl(methyl)amino group, a formyl(ethyl)amino group, an acetyl(ethyl)amino group, a methoxyacetyl(ethyl)amino group, a cyanoacetyl(ethyl)amino group, a propionyl(ethyl)amino group, a difluoroacetyl(ethyl)amino group, a trifluoroacetyl(ethyl)amino group, a cyclopropanecarbonyl(ethyl)amino group, a methoxycarbonyl(ethyl)amino group, an ethoxycarbonyl(ethyl)amino group, a 2,2-difluoroethoxycarbonyl(ethyl)amino group, a 2,2,2-trifluoroethoxycarbonyl(ethyl)amino group, a 3,3,3-trifluoropropyloxycarbonyl(ethyl)amino group, a cyclopropyloxycarbonyl(ethyl)amino group, an aminocarbonyl(ethyl)amino group, a methylaminocarbonyl(ethyl)amino group, an ethylaminocarbonyl(ethyl)amino group, a (methoxymethyl)aminocarbonyl(ethyl)amino group, a (2-methoxyethyl)aminocarbonyl(ethyl)amino group, a (cyanomethyl)aminocarbonyl(ethyl)amino group, a (2-cyanoethyl)aminocarbonyl(ethyl)amino group, a dimethylaminocarbonyl(ethyl)amino group, an ethyl(methyl)aminocarbonyl(ethyl)amino group, a diethylaminocarbonyl(ethyl)amino group, a (methoxymethyl)methylaminocarbonyl(ethyl)amino group, a (2-methoxyethyl)methylaminocarbonyl(ethyl)amino group, a (cyanomethyl)methylaminocarbonyl(ethyl)amino group, a (2-cyanoethyl)methylaminocarbonyl(ethyl)amino group, a 2,2-difluoroethylaminocarbonyl(ethyl)amino group, a 2,2,2-trifluoroethylaminocarbonyl(ethyl)amino group, a cyclopropylaminocarbonyl(ethyl)amino group, a cyclopropyl(methyl)aminocarbonyl(ethyl)amino group, a pyrrolidinylcarbonyl(ethyl)amino group, a piperidinylcarbonyl(ethyl)amino group, a formyl(methoxy)amino group, an acetyl(methoxy)amino group, a methoxyacetyl(methoxy)amino group, a cyanoacetyl(methoxy)amino group, a propionyl(methoxy)amino group, a difluoroacetyl(methoxy)amino group, a trifluoroacetyl(methoxy)amino group, a cyclopropanecarbonyl(methoxy)amino group, a methoxycarbonyl(methoxy)amino group, an ethoxycarbonyl(methoxy)amino group, a 2,2-difluoroethoxycarbonyl(methoxy)amino group, a 2,2,2-trifluoroethoxycarbonyl(methoxy)amino group, a 3,3,3-trifluoropropyloxycarbonyl(methoxy)amino group, a cyclopropyloxycarbonyl(methoxy)amino group, an aminocarbonyl(methoxy)amino group, a methylaminocarbonyl(methoxy)amino group, an ethylaminocarbonyl(methoxy)amino group, a (methoxymethyl)aminocarbonyl(methoxy)amino group, a (2-methoxyethyl)aminocarbonyl(methoxy)amino group, a (cyanomethyl)aminocarbonyl(methoxy)amino group, a (2-cyanoethyl)aminocarbonyl(methoxy)amino group, a dimethylaminocarbonyl(methoxy)amino group, an ethyl(methyl)aminocarbonyl(methoxy)amino group, a diethylaminocarbonyl(methoxy)amino group, a (methoxymethyl)methylaminocarbonyl(methoxy)amino group, a (2-methoxyethyl)methylaminocarbonyl(methoxy)amino group, a (cyanomethyl)methylaminocarbonyl(methoxy)amino group, a (2-cyanoethyl)methylaminocarbonyl(methoxy)amino group, a 2,2-difluoroethylaminocarbonyl(methoxy)amino group, a 2,2,2-trifluoroethylaminocarbonyl(methoxy)amino group, a cyclopropylaminocarbonyl(methoxy)amino group, a cyclopropyl(methyl)aminocarbonyl(methoxy)amino group, a pyrrolidinylcarbonyl(methoxy)amino group, a piperidinylcarbonyl(methoxy)amino group, a formyl(ethoxy)amino group, an acetyl(ethoxy)amino group, a methoxyacetyl(ethoxy)amino group, a cyanoacetyl(ethoxy)amino group, a propionyl(ethoxy)amino group, a difluoroacetyl(ethoxy)amino group, a trifluoroacetyl(ethoxy)amino group, a cyclopropane-carbonyl(ethoxy)amino group, a methoxycarbonyl (ethoxy)amino group, an ethoxycarbonyl(ethoxy)amino group, a 2,2-difluoroethoxycarbonyl(ethoxy)amino group, a 2,2,2-trifluoroethoxycarbonyl(ethoxy)amino group, a 3,3,3-trifluoropropyloxycarbonyl(ethoxy)amino group, a cyclopropyloxycarbonyl(ethoxy)amino group, an aminocarbonyl (ethoxy)amino group, a methylaminocarbonyl(ethoxy) amino group, an ethylaminocarbonyl(ethoxy)amino group, a (methoxymethyl)aminocarbonyl(ethoxy)amino group, a (2-methoxyethyl)aminocarbonyl(ethoxy)amino group, a (cyanomethyl)aminocarbonyl(ethoxy)amino group, a (2-cyanoethyl)aminocarbonyl(ethoxy)amino group, a dimethylaminocarbonyl(ethoxy)amino group, an ethyl(methyl) aminocarbonyl(ethoxy)amino group, a diethylaminocarbonyl(ethoxy)amino group, a (methoxymethyl) methylaminocarbonyl(ethoxy)amino group, a (2-methoxyethyl)methylaminocarbonyl(ethoxy)amino group, a (cyanomethyl)methylaminocarbonyl(ethoxy)amino group, a (2-cyanoethyl)methylaminocarbonyl(ethoxy)amino group, a 2,2-difluoroethylaminocarbonyl(ethoxy)amino group, a 2,2,2-trifluoroethylaminocarbonyl(ethoxy)amino group, a cyclopropylaminocarbonyl(ethoxy)amino group, a cyclopropyl(methyl)aminocarbonyl(ethoxy)amino group, a pyrrolidinylcarbonyl(ethoxy)amino group or a piperidinylcarbonyl(ethoxy)amino group, further preferably an acetylamino group, an acetyl(methyl)amino group, an acetyl (ethyl)amino group, an acetyl(methoxy)amino group, an acetyl(ethoxy)amino group, a methoxycarbonylamino group, an ethoxycarbonylamino group, a methoxycarbonyl (methyl)amino group, an ethoxycarbonyl(methyl)amino group, a methoxycarbonyl(ethyl)amino group, an ethoxycarbonyl(ethyl)amino group, a methoxycarbonyl(methoxy) amino group, an ethoxycarbonyl(methoxy)amino group, a methoxycarbonyl(ethoxy)amino group or an ethoxycarbonyl(ethoxy)amino group, and particularly preferably an acetylamino group, an acetyl(methyl)amino group, a propionylamino group or a propionyl(methyl)amino group.

"Substituent A" of Formula (1) refers to at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, an RaRbN— (wherein Ra and Rb are the same as defined above) and an Rc-L- (wherein Rc and L are the same as defined above).

Among these, substituent A is preferably a cyano group, a C1-C6 alkoxy group or an Rc-L- (wherein Rc and L are the same as defined above), in particular, a cyano group or a C1-C6 alkoxy group.

Each of the terms for substituent A is the same as defined above.

Preferred specific examples of substituent A include:
a hydroxyl group; a cyano group;
a cyclopropyl group, a cyclobutyl group, a cyclopentyl group and a cyclohexyl group as the C3-C8 cycloalkyl group;
a methoxy group, an ethoxy group, a propyloxy group and an isopropyloxy group as the C1-C6 alkoxy group;
a difluoromethoxy group, a trifluoromethoxy group, a 2,2-difluoroethoxy group, a 2,2,2-trifluoroethoxy group, a 3,3-difluoropropyloxy group and a 3,3,3-trifluoropropyloxy group as the C1-C6 haloalkoxy group;
a cyclopropyloxy group, a cyclobutoxy group, a cyclopentyloxy group and a cyclohexyloxy group as the C3-C8 cycloalkoxy group;
an amino group, a methylamino group, an ethylamino group, a propylamino group, an isopropylamino group, a (methoxymethyl)amino group, a (2-methoxyethyl)amino group, a (cyanomethyl)amino group, a (2-cyanoethyl)amino group, a dimethylamino group, an ethyl(methyl)amino group, a methyl(propyl)amino group, an isopropyl(methyl) amino group, a (methoxymethyl)methylamino group, a (2-methoxyethyl)methylamino group, a (cyanomethyl)methylamino group, a (2-cyanoethyl)methylamino group, a diethylamino group, an ethyl(propyl)amino group, an ethyl (isopropyl)amino group, an ethyl(methoxymethyl)amino group, an ethyl(2-methoxyethyl)amino group, a (cyanomethyl)ethylamino group, a (2-cyanoethyl)ethylamino group, a 2,2-difluoroethylamino group, a 2,2,2-trifluoroethylamino group, a cyclopropylamino group, a (cyclopropyl)methylamino group, a pyrrolidinyl group and a piperidinyl group as the RaRbN— (wherein Ra and Rb are the same as defined above); and
a methylthio group, a methanesulfinyl group, a methanesulfonyl group, a trifluoromethylthio group, a trifluoromethanesulfinyl group and a trifluoromethanesulfonyl group as the Rc-L- (wherein Rc and L are the same as defined above).

More preferred specific examples of substituent A include:
a hydroxyl group; a cyano group;
a cyclopropyl group and a cyclobutyl group as the C3-C8 cycloalkyl group;
a methoxy group and an ethoxy group as the C1-C6 alkoxy group;
a difluoromethoxy group, a trifluoromethoxy group, a 2,2-difluoroethoxy group and a 2,2,2-trifluoroethoxy group as the C1-C6 haloalkoxy group;
a cyclopropyloxy group and a cyclobutoxy group as the C3-C8 cycloalkoxy group;
a dimethylamino group, an ethyl(methyl)amino group and a diethylamino group as the RaRbN— (wherein Ra and Rb are the same as defined above); and
a methylthio group, a methanesulfinyl group and a methanesulfonyl group as the Rc-L-(wherein Rc and L are the same as defined above).

"Substituent B" of Formula (1) refers to at least one member selected from the group consisting of a cyano group, a C1-C6 alkoxy group, a C1-C6 haloalkoxy group and a C3-C8 cycloalkoxy group.

Among these, substituent B is preferably a cyano group or a C1-C6 alkoxy group.

Each of the terms for substituent B is the same as defined above.

Preferred specific examples of substituent B include:
a cyano group;
a methoxy group, an ethoxy group, a propyloxy group and an isopropyloxy group as the
C1-C6 alkoxy group;
a difluoromethoxy group, a trifluoromethoxy group, a 2,2-difluoroethoxy group, a 2,2,2-trifluoroethoxy group, a 3,3-difluoropropyloxy group and a 3,3,3-trifluoropropyloxy group as the C1-C6 haloalkoxy group; and
a cyclopropyloxy group, a cyclobutoxy group, a cyclopentyloxy group and a cyclohexyloxy group as the C3-C8 cycloalkoxy group.

More preferred specific examples of the substituent B include:
a cyano group;
a methoxy group and an ethoxy group as the C1-C6 alkoxy group;
a difluoromethoxy group, a trifluoromethoxy group, a 2,2-difluoroethoxy group and a 2,2,2-trifluoroethoxy group as the C1-C6 haloalkoxy group; and
a cyclopropyloxy group and a cyclobutoxy group as the C3-C8 cycloalkoxy group.

"Substituent C" of Formula (1) refers to at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, an RaRbN— (wherein Ra and Rb are the same as defined above), an Rc-L- (wherein Rc and L are the same as defined above), an RdC(=O)— (wherein Rd is the same as defined above) and a group of a 3-6 membered ring containing 1-2 oxygen atoms.

Among these, substituent C is preferably a cyano group, a C3-C8 cycloalkyl group, a C1-C6 alkoxy group, a C1-C6 haloalkoxy group, a C3-C8 cycloalkoxy group, a C2-C6 alkoxyalkoxy group, an Rc-L- (wherein Rc and L are the same as defined above) or an RdC(=O)— (wherein Rd is the same as defined above), in particular, a cyano group, a C3-C8 cycloalkyl group, a C1-C6 alkoxy group, an Rc-L- (wherein Rc and L are the same as defined above) or an RdC(=O)— (wherein Rd is the same as defined above).

Each of the terms for substituent C is the same as defined above.

Preferable Rd of the "RdC(C=O)" as substituent C is a C1-C6 alkyl group optionally substituted with substituent B or a C1-C6 alkoxy group, and more preferably a C1-C6 alkoxy group.

In the "Rc-L-" as substituent C, preferable Rc is a C1-C6 alkyl group and preferable L is S.

Preferred specific examples of substituent C include:
a hydroxyl group; a cyano group;
a cyclopropyl group, a cyclobutyl group, a cyclopentyl group and a cyclohexyl group as the C3-C8 cycloalkyl group;
a methoxy group, an ethoxy group, a propyloxy group, an isopropyloxy group, a butoxy group, an isobutoxy group and a t-butoxy group as the C1-C6 alkoxy group;
a difluoromethoxy group, a trifluoromethoxy group, a 2,2-difluoroethoxy group, a 2,2,2-trifluoroethoxy group, a 3,3-difluoropropyloxy group and a 3,3,3-trifluoropropyloxy group as the C1-C6 haloalkoxy group;
a cyclopropyloxy group, a cyclobutoxy group, a cyclopentyloxy group and a cyclohexyloxy group as the C3-C8 cycloalkoxy group;
a methoxymethoxy group, an ethoxymethoxy group, a methoxyethoxy group, an ethoxyethoxy group and a methoxypropyloxy group as the C2-C6 alkoxyalkoxy group;
an amino group, a methylamino group, an ethylamino group, a propylamino group, an isopropylamino group, a (methoxymethyl)amino group, a (2-methoxyethyl)amino group, a (cyanomethyl)amino group, a (2-cyanoethyl)amino group, a dimethylamino group, an ethyl(methyl)amino group, a methyl(propyl)amino group, an isopropyl(methyl)amino group, a (methoxymethyl)methylamino group, a (2-methoxyethyl)methylamino group, a (cyanomethyl)methylamino group, a (2-cyanoethyl)methylamino group, a diethylamino group, an ethyl(propyl)amino group, an ethyl(isopropyl)amino group, an ethyl(methoxymethyl)amino group, an ethyl(2-methoxyethyl)amino group, a (cyanomethyl)ethylamino group, a (2-cyanoethyl)ethylamino group, a 2,2-difluoroethylamino group, a 2,2,2-trifluoroethylamino group, a cyclopropylamino group, a (cyclopropyl)methylamino group, a pyrrolidinyl group and a piperidinyl group as the RaRbN— (wherein Ra and Rb are the same as defined above);
a methylthio group, an ethylthio group, a propylthio group, an isopropylthio group, a methanesulfinyl group, a methanesulfonyl group, a trifluoromethylthio group, a trifluoromethanesulfinyl group and a trifluoromethanesulfonyl group as the Rc-L-(wherein Rc and L are the same as defined above);
an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethyl(methyl)aminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a (cyclopropyl)methylaminocarbonyl group, a pyrrolidinylcarbonyl group and a piperidinylcarbonyl group as the RdC(=O)— (wherein Rd is the same as defined above); and
an oxolanyl group, an oxanyl group, a 1,3-dioxolanyl group and a 1,3-dioxanyl group as the group of a 3-6 membered ring containing 1-2 oxygen atoms.

More preferred specific examples of substituent C include:
a hydroxyl group; a cyano group;
a cyclopentyl group and a cyclohexyl group as the C3-C8 cycloalkyl group; a methoxy group, an ethoxy group, a propyloxy group, and an isopropyloxy group as the C1-C6 alkoxy group;
a difluoromethoxy group, a trifluoromethoxy group, a 2,2-difluoroethoxy group, a 2,2,2-trifluoroethoxy group as the C1-C6 haloalkoxy group;
a cyclopropyloxy group and a cyclobutoxy group as the C3-C8 cycloalkoxy group;
a methoxymethoxy group, an ethoxymethoxy group, a methoxyethoxy group and an ethoxyethoxy group as the C2-C6 alkoxyalkoxy group;
a dimethylamino group, an ethyl(methyl)amino group and a diethylamino group as the RaRbN— (wherein Ra and Rb are the same as defined above);
a methylthio group, an ethylthio group, a propylthio group and an isopropylthio group as the Rc-L- (wherein Rc and L are the same as defined above);
an acetyl group, a methoxyacetyl group, a cyanoacetyl group, a difluoroacetyl group, a trifluoroacetyl group, a methoxycarbonyl group, an ethoxycarbonyl group, an aminocarbonyl group, a dimethylaminocarbonyl group, an ethyl(methyl)aminocarbonyl group and a diethylaminocarbonyl group as the RdC(=O)— (wherein Rd is the same as defined above); and
a 1,3-dioxolanyl group and a 1,3-dioxanyl group as the group of a 3-6 membered ring containing 1-2 oxygen atoms.

"Substituent D" of Formula (1) refers to at least one member selected from the group consisting of a cyano group, a C1-C6 alkyl group, a C1-C6 alkoxy group, a C1-C6 haloalkoxy group and a C3-C8 cycloalkoxy group.

Among these, substituent D is preferably a C1-C6 alkyl group or a C1-C6 alkoxy group, in particular, a C1-C6 alkyl group.

Each of the terms for substituent D is the same as defined above.

Preferred specific examples of substituent D include:
a cyano group;
a methyl group, an ethyl group, a propyl group and an isopropyl group as the C1-C6 alkyl group;
a methoxy group, an ethoxy group, a propyloxy group and an isopropyloxy group as the C1-C6 alkoxy group;
a difluoromethoxy group, a trifluoromethoxy group, a 2,2-difluoroethoxy group, a 2,2,2-trifluoroethoxy group, a 3,3-difluoropropyloxy group and a 3,3,3-trifluoropropyloxy group as the C1-C6 haloalkoxy group; and
a cyclopropyloxy group, a cyclobutoxy group, a cyclopentyloxy group and a cyclohexyloxy group as the C3-C8 cycloalkoxy group.

More preferred specific examples of substituent D include:
a cyano group;
a methyl group and an ethyl group as the C1-C6 alkyl group;
a methoxy group and an ethoxy group as the C1-C6 alkoxy group;
a difluoromethoxy group, a trifluoromethoxy group, a 2,2-difluoroethoxy group and a 2,2,2-trifluoroethoxy group as the C1-C6 haloalkoxy group; and
a cyclopropyloxy group and a cyclobutoxy group as the C3-C8 cycloalkoxy group.

A compound within the scope of compounds obtainable by arbitrarily combining the above-explained R1, R2, R3, R4, X, Y, Z, substituent A, substituent B, substituent C and substituent D each within the preferable scope is regarded as being described herein as a compound within the scope of the compound of the present invention represented by Formula (1).

The compound represented by Formula (1) may have axial chirality. There is no particular limitation with respect to the ratio of isomers related to this matter, and the compound may be present as a single isomer or a mixture of isomers of any ratio.

The compound represented by Formula (1) may contain an asymmetric atom. There is no particular limitation with respect to the ratio of isomers related to this matter, and the compound may be present as a single isomer or a mixture of isomers of any ratio.

The compound represented by Formula (1) may contain a geometric isomer. There is no particular limitation with respect to the ratio of isomers related to this matter, and the compound may be present as a single isomer or a mixture of isomers of any ratio.

The compound represented by Formula (1) may form a salt. Examples of such salts include a salt with an acid, such as hydrochloric acid, sulfuric acid, acetic acid, fumaric acid and maleic acid; and a salt with a metal, such as sodium, potassium and calcium. There is no particular limitation with respect to the salt as long as the salt can be used as an agricultural and horticultural fungicide.

Next, specific compounds of the present invention are shown as combinations of the structural formulae given in Table 1 (P-1 to P-80, wherein X in the structural formulae is an oxygen atom or a sulfur atom), Zs given in Table 2 (No. 1 to No. 10,748) and Ys given in Table 3 (Y-1 to Y-283).

These compounds are shown only for illustrative purpose and the present invention is not limited to these compounds.

TABLE 1

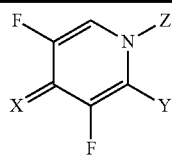
P-1

TABLE 1-continued

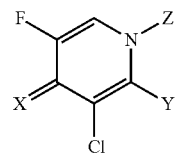 P-2

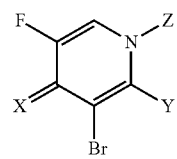 P-3

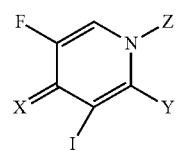 P-4

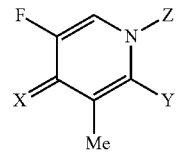 P-5

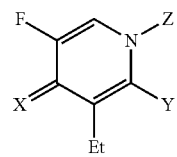 P-6

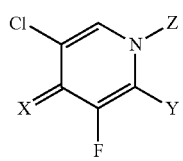 P-7

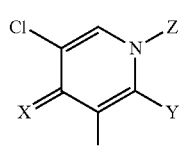 P-8

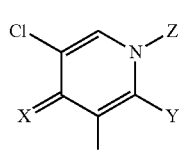 P-9

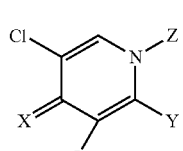 P-10

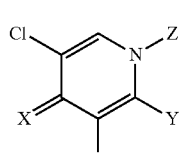 P-11

TABLE 1-continued
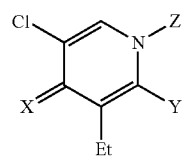 P-12
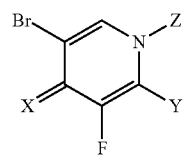 P-13
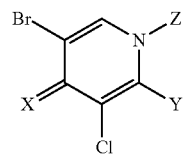 P-14
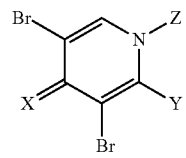 P-15
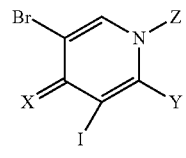 P-16
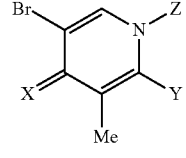 P-17
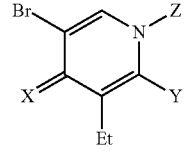 P-18
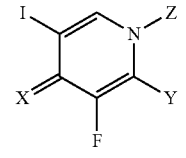 P-19
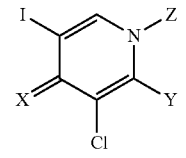 P-20
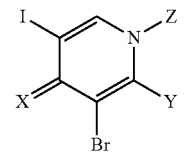 P-21
TABLE 1-continued
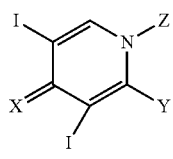 P-22
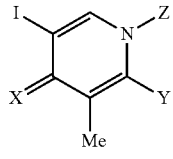 P-23
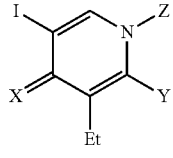 P-24
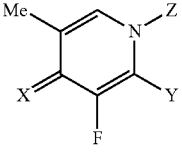 P-25
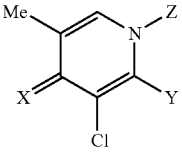 P-26
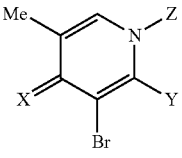 P-27
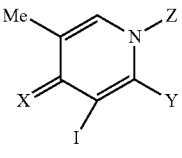 P-28
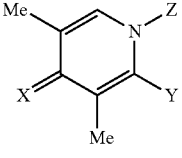 P-29
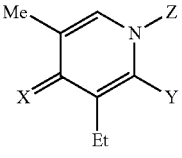 P-30
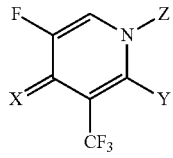 P-31

TABLE 1-continued

| Structure | ID |
|---|---|
| 5-F, 3-CF₂H pyridine | P-32 |
| 5-Cl, 3-CF₃ pyridine | P-33 |
| 5-Cl, 3-CF₂H pyridine | P-34 |
| 5-Br, 3-CF₃ pyridine | P-35 |
| 5-Br, 3-CF₂H pyridine | P-36 |
| 5-I, 3-CF₃ pyridine | P-37 |
| 5-I, 3-CF₂H pyridine | P-38 |
| 5-Me, 3-CF₃ pyridine | P-39 |
| 5-Me, 3-CF₂H pyridine | P-40 |
| 5-Et, 3-F pyridine | P-41 |
| 5-Et, 3-Cl pyridine | P-42 |
| 5-Et, 3-Br pyridine | P-43 |
| 5-Et, 3-I pyridine | P-44 |
| 5-Et, 3-Me pyridine | P-45 |
| 5-Et, 3-Et pyridine | P-46 |
| 5-Et, 3-CF₃ pyridine | P-47 |
| 5-Et, 3-CF₂H pyridine | P-48 |
| 5-CF₃, 3-F pyridine | P-49 |

TABLE 1-continued
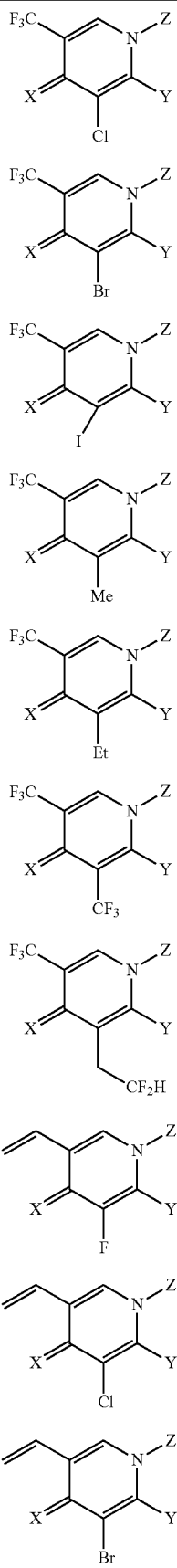
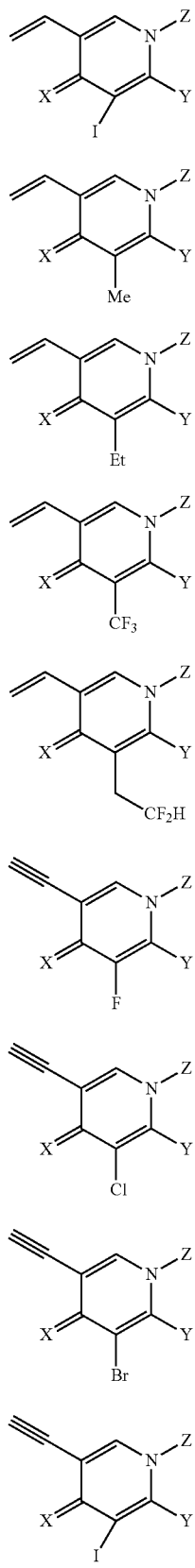

TABLE 1-continued
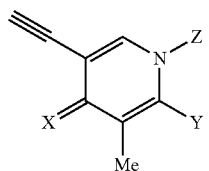 P-69
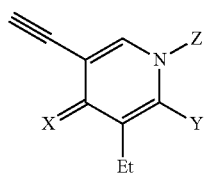 P-70
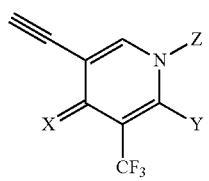 P-71
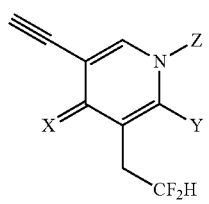 P-72
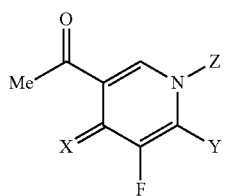 P-73
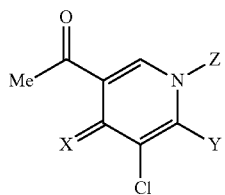 P-74
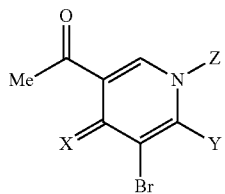 P-75
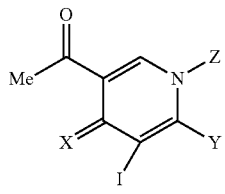 P-76
TABLE 1-continued
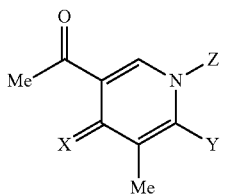 P-77
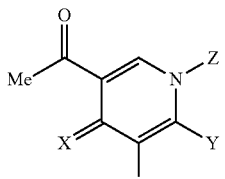 P-78
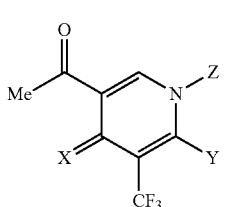 P-79
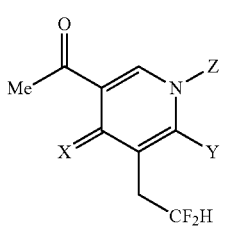 P-80
TABLE 2
| No. | Z |
|---|---|
| 1 | Ph |
| 2 | 2-F—Ph |
| 3 | 3-F—Ph |
| 4 | 4-F—Ph |
| 5 | 2-Cl—Ph |
| 6 | 3-Cl—Ph |
| 7 | 4-Cl—Ph |
| 8 | 2-Br—Ph |
| 9 | 3-Br—Ph |
| 10 | 4-Br—Ph |
| 11 | 2-I—Ph |
| 12 | 3-I—Ph |
| 13 | 4-I—Ph |
| 14 | 2-HO—Ph |
| 15 | 3-HO—Ph |
| 16 | 4-HO—Ph |
| 17 | 2-N≡C—Ph |
| 18 | 3-N≡C—Ph |
| 19 | 4-N≡C—Ph |
| 20 | 2-O2N—Ph |
| 21 | 3-O2N—Ph |
| 22 | 4-O2N—Ph |
| 23 | 2-Me—Ph |
| 24 | 3-Me—Ph |
| 25 | 4-Me—Ph |
| 26 | 2-Et—Ph |
| 27 | 3-Et—Ph |
| 28 | 4-Et—Ph |
| 29 | 2-Pr—Ph |
| 30 | 3-Pr—Ph |
| 31 | 4-Pr—Ph |
| 32 | 2-iPr—Ph |

TABLE 2-continued

| No. | Z |
|---|---|
| 33 | 3-iPr—Ph |
| 34 | 4-iPr—Ph |
| 35 | 2-N≡CCH2—Ph |
| 36 | 3-N≡CCH2—Ph |
| 37 | 4-N≡CCH2—Ph |
| 38 | 2-N≡CCH2CH2—Ph |
| 39 | 3-N≡CCH2CH2—Ph |
| 40 | 4-N≡CCH2CH2—Ph |
| 41 | 2-cPrCH2—Ph |
| 42 | 3-cPrCH2—Ph |
| 43 | 4-cPrCH2—Ph |
| 44 | 2-cBuCH2—Ph |
| 45 | 3-cBuCH2—Ph |
| 46 | 4-cBuCH2—Ph |
| 47 | 2-MeOCH2—Ph |
| 48 | 3-MeOCH2—Ph |
| 49 | 4-MeOCH2—Ph |
| 50 | 2-MeOCH2CH2—Ph |
| 51 | 3-MeOCH2CH2—Ph |
| 52 | 4-MeOCH2CH2—Ph |
| 53 | 2-MeOCH2CH2CH2—Ph |
| 54 | 3-MeOCH2CH2CH2—Ph |
| 55 | 4-MeOCH2CH2CH2—Ph |
| 56 | 2-EtOCH2—Ph |
| 57 | 3-EtOCH2—Ph |
| 58 | 4-EtOCH2—Ph |
| 59 | 2-EtOCH2CH2—Ph |
| 60 | 3-EtOCH2CH2—Ph |
| 61 | 4-EtOCH2CH2—Ph |
| 62 | 2-cPrOCH2—Ph |
| 63 | 3-cPrOCH2—Ph |
| 64 | 4-cPrOCH2—Ph |
| 65 | 2-F3COCH2—Ph |
| 66 | 3-F3COCH2—Ph |
| 67 | 4-F3COCH2—Ph |
| 68 | 2-F2CHOCH2—Ph |
| 69 | 3-F2CHOCH2—Ph |
| 70 | 4-F2CHOCH2—Ph |
| 71 | 2-MeOCH2CH2OCH2—Ph |
| 72 | 3-MeOCH2CH2OCH2—Ph |
| 73 | 4-MeOCH2CH2OCH2—Ph |
| 74 | 2-Me2NCH2—Ph |
| 75 | 3-Me2NCH2—Ph |
| 76 | 4-Me2NCH2—Ph |
| 77 | 2-MeSCH2—Ph |
| 78 | 3-MeSCH2—Ph |
| 79 | 4-MeSCH2—Ph |
| 80 | 2-MeS(O)CH2—Ph |
| 81 | 3-MeS(O)CH2—Ph |
| 82 | 4-MeS(O)CH2—Ph |
| 83 | 2-MeSO2CH2—Ph |
| 84 | 3-MeSO2CH2—Ph |
| 85 | 4-MeSO2CH2—Ph |
| 86 | 2-cPr—Ph |
| 87 | 3-cPr—Ph |
| 88 | 4-cPr—Ph |
| 89 | 2-cBu—Ph |
| 90 | 3-cBu—Ph |
| 91 | 4-cBu—Ph |
| 92 | 2-F3C—Ph |
| 93 | 3-F3C—Ph |
| 94 | 4-F3C—Ph |
| 95 | 2-F2CH—Ph |
| 96 | 3-F2CH—Ph |
| 97 | 4-F2CH—Ph |
| 98 | 2-H2C=CH—Ph |
| 99 | 3-H2C=CH—Ph |
| 100 | 4-H2C=CH—Ph |
| 101 | 2-H2C=CHCH2—Ph |
| 102 | 3-H2C=CHCH2—Ph |
| 103 | 4-H2C=CHCH2—Ph |
| 104 | 2-F2C=CH—Ph |
| 105 | 3-F2C=CH—Ph |
| 106 | 4-F2C=CH—Ph |
| 107 | 2-F2C=CHCH2—Ph |
| 108 | 3-F2C=CHCH2—Ph |
| 109 | 4-F2C=CHCH2—Ph |
| 110 | 2-HC≡C—Ph |
| 111 | 3-HC≡C—Ph |
| 112 | 4-HC≡C—Ph |
| 113 | 2-HC≡CCH2—Ph |
| 114 | 3-HC≡CCH2—Ph |
| 115 | 4-HC≡CCH2—Ph |
| 116 | 2-F3CC≡C—Ph |
| 117 | 3-F3CC≡C—Ph |
| 118 | 4-F3CC≡C—Ph |
| 119 | 2-F3CC≡CCH2—Ph |
| 120 | 3-F3CC≡CCH2—Ph |
| 121 | 4-F3CC≡CCH2—Ph |
| 122 | 2-MeO—Ph |
| 123 | 3-MeO—Ph |
| 124 | 4-MeO—Ph |
| 125 | 2-EtO—Ph |
| 126 | 3-EtO—Ph |
| 127 | 4-EtO—Ph |
| 128 | 2-PrO—Ph |
| 129 | 3-PrO—Ph |
| 130 | 4-PrO—Ph |
| 131 | 2-iPrO—Ph |
| 132 | 3-iPrO—Ph |
| 133 | 4-iPrO—Ph |
| 134 | 2-BuO—Ph |
| 135 | 3-BuO—Ph |
| 136 | 4-BuO—Ph |
| 137 | 2-iBuO—Ph |
| 138 | 3-iBuO—Ph |
| 139 | 4-iBuO—Ph |
| 140 | 2-PentylO—Ph |
| 141 | 3-PentylO—Ph |
| 142 | 4-PentylO—Ph |
| 143 | 2-N≡CCH2O—Ph |
| 144 | 3-N≡CCH2O—Ph |
| 145 | 4-N≡CCH2O—Ph |
| 146 | 2-N≡CCH2CH2O—Ph |
| 147 | 3-N≡CCH2CH2O—Ph |
| 148 | 4-N≡CCH2CH2O—Ph |
| 149 | 2-cPrCH2O—Ph |
| 150 | 3-cPrCH2O—Ph |
| 151 | 4-cPrCH2O—Ph |
| 152 | 2-cBuCH2O—Ph |
| 153 | 3-cBuCH2O—Ph |
| 154 | 4-cBuCH2O—Ph |
| 155 | 2-cPentylCH2O—Ph |
| 156 | 3-cPentylCH2O—Ph |
| 157 | 4-cPentylCH2O—Ph |
| 158 | 2-cHexylCH2O—Ph |
| 159 | 3-cHexylCH2O—Ph |
| 160 | 4-cHexylCH2O—Ph |
| 161 | 2-MeOCH2O—Ph |
| 162 | 3-MeOCH2O—Ph |
| 163 | 4-MeOCH2O—Ph |
| 164 | 2-EtOCH2O—Ph |
| 165 | 3-EtOCH2O—Ph |
| 166 | 4-EtOCH2O—Ph |
| 167 | 2-MeOCH2CH2O—Ph |
| 168 | 3-MeOCH2CH2O—Ph |
| 169 | 4-MeOCH2CH2O—Ph |
| 170 | 2-MeOCH2CH2CH2O—Ph |
| 171 | 3-MeOCH2CH2CH2O—Ph |
| 172 | 4-MeOCH2CH2CH2O—Ph |
| 173 | 2-MeOCH2CH2OCH2O—Ph |
| 174 | 3-MeOCH2CH2OCH2O—Ph |
| 175 | 4-MeOCH2CH2OCH2O—Ph |
| 176 | 2-MeSCH2O—Ph |
| 177 | 3-MeSCH2O—Ph |
| 178 | 4-MeSCH2O—Ph |
| 179 | 2-MeS(O)CH2O—Ph |
| 180 | 3-MeS(O)CH2O—Ph |
| 181 | 4-MeS(O)CH2O—Ph |
| 182 | 2-MeSO2CH2O—Ph |
| 183 | 3-MeSO2CH2O—Ph |
| 184 | 4-MeSO2CH2O—Ph |
| 185 | 2-AcCH2O—Ph |
| 186 | 3-AcCH2O—Ph |
| 187 | 4-AcCH2O—Ph |
| 188 | 2-MeOC(=O)CH2O—Ph |

TABLE 2-continued

| No. | Z |
|---|---|
| 189 | 3-MeOC(=O)CH2O—Ph |
| 190 | 4-MeOC(=O)CH2O—Ph |
| 191 | 2-EtOC(=O)CH2O—Ph |
| 192 | 3-EtOC(=O)CH2O—Ph |
| 193 | 4-EtOC(=O)CH2O—Ph |
| 194 | 2-(1,3-dioxolan-2-yl)CH2O—Ph |
| 195 | 3-(1,3-dioxolan-2-yl)CH2O—Ph |
| 196 | 4-(1,3-dioxolan-2-yl)CH2O—Ph |
| 197 | 2-(1,3-dioxolan-2-yl)CH2CH2O—Ph |
| 198 | 3-(1,3-dioxolan-2-yl)CH2CH2O—Ph |
| 199 | 4-(1,3-dioxolan-2-yl)CH2CH2O—Ph |
| 200 | 2-(1,3-dioxan-2-yl)CH2O—Ph |
| 201 | 3-(1,3-dioxan-2-yl)CH2O—Ph |
| 202 | 4-(1,3-dioxan-2-yl)CH2O—Ph |
| 203 | 2-(1,3-dioxan-2-yl)CH2CH2O—Ph |
| 204 | 3-(1,3-dioxan-2-yl)CH2CH2O—Ph |
| 205 | 4-(1,3-dioxan-2-yl)CH2CH2O—Ph |
| 206 | 2-cPrO—Ph |
| 207 | 3-cPrO—Ph |
| 208 | 4-cPrO—Ph |
| 209 | 2-cBuO—Ph |
| 210 | 3-cBuO—Ph |
| 211 | 4-cBuO—Ph |
| 212 | 2-cPentylO—Ph |
| 213 | 3-cPentylO—Ph |
| 214 | 4-cPentylO—Ph |
| 215 | 2-cHexylO—Ph |
| 216 | 3-cHexylO—Ph |
| 217 | 4-cHexylO—Ph |
| 218 | 2-F3CO—Ph |
| 219 | 3-F3CO—Ph |
| 220 | 4-F3CO—Ph |
| 221 | 2-F2CHO—Ph |
| 222 | 3-F2CHO—Ph |
| 223 | 4-F2CHO—Ph |
| 224 | 2-F3CCH2O—Ph |
| 225 | 3-F3CCH2O—Ph |
| 226 | 4-F3CCH2O—Ph |
| 227 | 2-F2CHCH2O—Ph |
| 228 | 3-F2CHCH2O—Ph |
| 229 | 4-F2CHCH2O—Ph |
| 230 | 2-H2C=CHCH2O—Ph |
| 231 | 3-H2C=CHCH2O—Ph |
| 232 | 4-H2C=CHCH2O—Ph |
| 233 | 2-HC≡CCH2O—Ph |
| 234 | 3-HC≡CCH2O—Ph |
| 235 | 4-HC≡CCH2O—Ph |
| 236 | 2-AcPh |
| 237 | 3-AcPh |
| 238 | 4-AcPh |
| 239 | 2-MeOC(=O)—Ph |
| 240 | 3-MeOC(=O)—Ph |
| 241 | 4-MeOC(=O)—Ph |
| 242 | 2-EtOC(=O)—Ph |
| 243 | 3-EtOC(=O)—Ph |
| 244 | 4-EtOC(=O)—Ph |
| 245 | 2-AcO—Ph |
| 246 | 3-AcO—Ph |
| 247 | 4-AcO—Ph |
| 248 | 2-MeOC(=O)O—Ph |
| 249 | 3-MeOC(=O)O—Ph |
| 250 | 4-MeOC(=O)O—Ph |
| 251 | 2-EtOC(=O)O—Ph |
| 252 | 3-EtOC(=O)O—Ph |
| 253 | 4-EtOC(=O)O—Ph |
| 254 | 2-(1,3-dioxolan-2-yl)-Ph |
| 255 | 3-(1,3-dioxolan-2-yl)-Ph |
| 256 | 4-(1,3-dioxolan-2-yl)-Ph |
| 257 | 2-(1,3-dioxan-2-yl)-Ph |
| 258 | 3-(1,3-dioxan-2-yl)-Ph |
| 259 | 4-(1,3-dioxan-2-yl)-Ph |
| 260 | 2-MeS—Ph |
| 261 | 3-MeS—Ph |
| 262 | 4-MeS—Ph |
| 263 | 2-MeS(O)—Ph |
| 264 | 3-MeS(O)—Ph |
| 265 | 4-MeS(O)—Ph |
| 266 | 2-MeSO2—Ph |
| 267 | 3-MeSO2—Ph |
| 268 | 4-MeSO2—Ph |
| 269 | 2-ClCH2S—Ph |
| 270 | 3-ClCH2S—Ph |
| 271 | 4-ClCH2S—Ph |
| 272 | 2-ClCH2S(O)—Ph |
| 273 | 3-ClCH2S(O)—Ph |
| 274 | 4-ClCH2S(O)—Ph |
| 275 | 2-ClCH2SO2—Ph |
| 276 | 3-ClCH2SO2—Ph |
| 277 | 4-ClCH2SO2—Ph |
| 278 | 2-F-3-HO—Ph |
| 279 | 2-F-4-HO—Ph |
| 280 | 2-F-5-HO—Ph |
| 281 | 2-F-6-HO—Ph |
| 282 | 2-Cl-3-HO—Ph |
| 283 | 2-Cl-4-HO—Ph |
| 284 | 2-Cl-5-HO—Ph |
| 285 | 2-Cl-6-HO—Ph |
| 286 | 2-Br-3-HO—Ph |
| 287 | 2-Br-4-HO—Ph |
| 288 | 2-Br-5-HO—Ph |
| 289 | 2-Br-6-HO—Ph |
| 290 | 2-I-3-HO—Ph |
| 291 | 2-I-4-HO—Ph |
| 292 | 2-I-5-HO—Ph |
| 293 | 2-I-6-HO—Ph |
| 294 | 2-Me-3-HO—Ph |
| 295 | 2-Me-4-HO—Ph |
| 296 | 2-Me-5-HO—Ph |
| 297 | 2-Me-6-HO—Ph |
| 298 | 2,3-di-F—Ph |
| 299 | 2,4-di-F—Ph |
| 300 | 2,5-di-F—Ph |
| 301 | 2,6-di-F—Ph |
| 302 | 2-Cl-3-F—Ph |
| 303 | 2-Cl-4-F—Ph |
| 304 | 2-Cl-5-F—Ph |
| 305 | 2-Cl-6-F—Ph |
| 306 | 2-Br-3-F—Ph |
| 307 | 2-Br-4-F—Ph |
| 308 | 2-Br-5-F—Ph |
| 309 | 2-Br-6-F—Ph |
| 310 | 3-F-2-I—Ph |
| 311 | 4-F-2-I—Ph |
| 312 | 5-F-2-I—Ph |
| 313 | 6-F-2-I—Ph |
| 314 | 3-F-2-Me—Ph |
| 315 | 4-F-2-Me—Ph |
| 316 | 5-F-2-Me—Ph |
| 317 | 6-F-2-Me—Ph |
| 318 | 3-Cl-2-F—Ph |
| 319 | 4-Cl-2-F—Ph |
| 320 | 5-Cl-2-F—Ph |
| 321 | 6-Cl-2-F—Ph |
| 322 | 2,3-di-Cl—Ph |
| 323 | 2,4-di-Cl—Ph |
| 324 | 2,5-di-Cl—Ph |
| 325 | 2,6-di-Cl—Ph |
| 326 | 2-Br-3-Cl—Ph |
| 327 | 2-Br-4-Cl—Ph |
| 328 | 2-Br-5-Cl—Ph |
| 329 | 2-Br-6-Cl—Ph |
| 330 | 3-Cl-2-I—Ph |
| 331 | 4-Cl-2-I—Ph |
| 332 | 5-Cl-2-I—Ph |
| 333 | 6-Cl-2-I—Ph |
| 334 | 3-Cl-2-Me—Ph |
| 335 | 4-Cl-2-Me—Ph |
| 336 | 5-Cl-2-Me—Ph |
| 337 | 6-Cl-2-Me—Ph |
| 338 | 3-Br-2-F—Ph |
| 339 | 4-Br-2-F—Ph |
| 340 | 5-Br-2-F—Ph |
| 341 | 6-Br-2-F—Ph |
| 342 | 3-Br-2-Cl—Ph |
| 343 | 4-Br-2-Cl—Ph |
| 344 | 5-Br-2-Cl—Ph |

TABLE 2-continued

| No. | Z |
|---|---|
| 345 | 6-Br-2-Cl—Ph |
| 346 | 2,3-di-Br—Ph |
| 347 | 2,4-di-Br—Ph |
| 348 | 2,5-di-Br—Ph |
| 349 | 2,6-di-Br—Ph |
| 350 | 3-Br-2-I—Ph |
| 351 | 4-Br-2-I—Ph |
| 352 | 5-Br-2-I—Ph |
| 353 | 6-Br-2-I—Ph |
| 354 | 3-Br-2-Me—Ph |
| 355 | 4-Br-2-Me—Ph |
| 356 | 5-Br-2-Me—Ph |
| 357 | 6-Br-2-Me—Ph |
| 358 | 2-F-3-I—Ph |
| 359 | 2-F-4-I—Ph |
| 360 | 2-F-5-I—Ph |
| 361 | 2-F-6-I—Ph |
| 362 | 2-Cl-3-I—Ph |
| 363 | 2-Cl-4-I—Ph |
| 364 | 2-Cl-5-I—Ph |
| 365 | 2-Cl-6-I—Ph |
| 366 | 2-Br-3-I—Ph |
| 367 | 2-Br-4-I—Ph |
| 368 | 2-Br-5-I—Ph |
| 369 | 2-Br-6-I—Ph |
| 370 | 2,3-di-I—Ph |
| 371 | 2,4-di-I—Ph |
| 372 | 2,5-di-I—Ph |
| 373 | 2,6-di-I—Ph |
| 374 | 2-Me-3-I—Ph |
| 375 | 2-Me-4-I—Ph |
| 376 | 2-Me-5-I—Ph |
| 377 | 2-Me-6-I—Ph |
| 378 | 2-F-3-N≡C—Ph |
| 379 | 2-F-4-N≡C—Ph |
| 380 | 2-F-5-N≡C—Ph |
| 381 | 2-F-6-N≡C—Ph |
| 382 | 2-Cl-3-N≡C—Ph |
| 383 | 2-Cl-4-N≡C—Ph |
| 384 | 2-Cl-5-N≡C—Ph |
| 385 | 2-Cl-6-N≡C—Ph |
| 386 | 2-Br-3-N≡C—Ph |
| 387 | 2-Br-4-N≡C—Ph |
| 388 | 2-Br-5-N≡C—Ph |
| 389 | 2-Br-6-N≡C—Ph |
| 390 | 2-I-3-N≡C—Ph |
| 391 | 2-I-4-N≡C—Ph |
| 392 | 2-I-5-N≡C—Ph |
| 393 | 2-I-6-N≡C—Ph |
| 394 | 2-Me-3-N≡C—Ph |
| 395 | 2-Me-4-N≡C—Ph |
| 396 | 2-Me-5-N≡C—Ph |
| 397 | 2-Me-6-N≡C—Ph |
| 398 | 2-F-3-O2N—Ph |
| 399 | 2-F-4-O2N—Ph |
| 400 | 2-F-5-O2N—Ph |
| 401 | 2-F-6-O2N—Ph |
| 402 | 2-Cl-3-O2N—Ph |
| 403 | 2-Cl-4-O2N—Ph |
| 404 | 2-Cl-5-O2N—Ph |
| 405 | 2-Cl-6-O2N—Ph |
| 406 | 2-Br-3-O2N—Ph |
| 407 | 2-Br-4-O2N—Ph |
| 408 | 2-Br-5-O2N—Ph |
| 409 | 2-Br-6-O2N—Ph |
| 410 | 2-I-3-O2N—Ph |
| 411 | 2-I-4-O2N—Ph |
| 412 | 2-I-5-O2N—Ph |
| 413 | 2-I-6-O2N—Ph |
| 414 | 2-Me-3-O2N—Ph |
| 415 | 2-Me-4-O2N—Ph |
| 416 | 2-Me-5-O2N—Ph |
| 417 | 2-Me-6-O2N—Ph |
| 418 | 2-F-3-Me—Ph |
| 419 | 2-F-4-Me—Ph |
| 420 | 2-F-5-Me—Ph |
| 421 | 2-F-6-Me—Ph |
| 422 | 2-Cl-3-Me—Ph |
| 423 | 2-Cl-4-Me—Ph |
| 424 | 2-Cl-5-Me—Ph |
| 425 | 2-Cl-6-Me—Ph |
| 426 | 2-Br-3-Me—Ph |
| 427 | 2-Br-4-Me—Ph |
| 428 | 2-Br-5-Me—Ph |
| 429 | 2-Br-6-Me—Ph |
| 430 | 2-I-3-Me—Ph |
| 431 | 2-I-4-Me—Ph |
| 432 | 2-I-5-Me—Ph |
| 433 | 2-I-6-Me—Ph |
| 434 | 2,3-di-Me—Ph |
| 435 | 2,4-di-Me—Ph |
| 436 | 2,5-di-Me—Ph |
| 437 | 2,6-di-Me—Ph |
| 438 | 2-F-3-Et—Ph |
| 439 | 2-F-4-Et—Ph |
| 440 | 2-F-5-Et—Ph |
| 441 | 2-F-6-Et—Ph |
| 442 | 2-Cl-3-Et—Ph |
| 443 | 2-Cl-4-Et—Ph |
| 444 | 2-Cl-5-Et—Ph |
| 445 | 2-Cl-6-Et—Ph |
| 446 | 2-Br-3-Et—Ph |
| 447 | 2-Br-4-Et—Ph |
| 448 | 2-Br-5-Et—Ph |
| 449 | 2-Br-6-Et—Ph |
| 450 | 2-I-3-Et—Ph |
| 451 | 2-I-4-Et—Ph |
| 452 | 2-I-5-Et—Ph |
| 453 | 2-I-6-Et—Ph |
| 454 | 2-Me-3-Et—Ph |
| 455 | 2-Me-4-Et—Ph |
| 456 | 2-Me-5-Et—Ph |
| 457 | 2-Me-6-Et—Ph |
| 458 | 2-F-3-Pr—Ph |
| 459 | 2-F-4-Pr—Ph |
| 460 | 2-F-5-Pr—Ph |
| 461 | 2-F-6-Pr—Ph |
| 462 | 2-Cl-3-Pr—Ph |
| 463 | 2-Cl-4-Pr—Ph |
| 464 | 2-Cl-5-Pr—Ph |
| 465 | 2-Cl-6-Pr—Ph |
| 466 | 2-Br-3-Pr—Ph |
| 467 | 2-Br-4-Pr—Ph |
| 468 | 2-Br-5-Pr—Ph |
| 469 | 2-Br-6-Pr—Ph |
| 470 | 2-I-3-Pr—Ph |
| 471 | 2-I-4-Pr—Ph |
| 472 | 2-I-5-Pr—Ph |
| 473 | 2-I-6-Pr—Ph |
| 474 | 2-Me-3-Pr—Ph |
| 475 | 2-Me-4-Pr—Ph |
| 476 | 2-Me-5-Pr—Ph |
| 477 | 2-Me-6-Pr—Ph |
| 478 | 2-F-3-iPr—Ph |
| 479 | 2-F-4-iPr—Ph |
| 480 | 2-F-5-iPr—Ph |
| 481 | 2-F-6-iPr—Ph |
| 482 | 2-Cl-3-iPr—Ph |
| 483 | 2-Cl-4-iPr—Ph |
| 484 | 2-Cl-5-iPr—Ph |
| 485 | 2-Cl-6-iPr—Ph |
| 486 | 2-Br-3-iPr—Ph |
| 487 | 2-Br-4-iPr—Ph |
| 488 | 2-Br-5-iPr—Ph |
| 489 | 2-Br-6-iPr—Ph |
| 490 | 2-I-3-iPr—Ph |
| 491 | 2-I-4-iPr—Ph |
| 492 | 2-I-5-iPr—Ph |
| 493 | 2-I-6-iPr—Ph |
| 494 | 2-Me-3-iPr—Ph |
| 495 | 2-Me-4-iPr—Ph |
| 496 | 2-Me-5-iPr—Ph |
| 497 | 2-Me-6-iPr—Ph |
| 498 | 2-F-3-N≡CCH2—Ph |
| 499 | 2-F-4-N≡CCH2—Ph |
| 500 | 2-F-5-N≡CCH2—Ph |

TABLE 2-continued

| No. | Z |
|---|---|
| 501 | 2-F-6-N≡CCH2—Ph |
| 502 | 2-Cl-3-N≡CCH2—Ph |
| 503 | 2-Cl-4-N≡CCH2—Ph |
| 504 | 2-Cl-5-N≡CCH2—Ph |
| 505 | 2-Cl-6-N≡CCH2—Ph |
| 506 | 2-Br-3-N≡CCH2—Ph |
| 507 | 2-Br-4-N≡CCH2—Ph |
| 508 | 2-Br-5-N≡CCH2—Ph |
| 509 | 2-Br-6-N≡CCH2—Ph |
| 510 | 2-I-3-N≡CCH2—Ph |
| 511 | 2-I-4-N≡CCH2—Ph |
| 512 | 2-I-5-N≡CCH2—Ph |
| 513 | 2-I-6-N≡CCH2—Ph |
| 514 | 2-Me-3-N≡CCH2—Ph |
| 515 | 2-Me-4-N≡CCH2—Ph |
| 516 | 2-Me-5-N≡CCH2—Ph |
| 517 | 2-Me-6-N≡CCH2—Ph |
| 518 | 2-F-3-N≡CCH2CH2—Ph |
| 519 | 2-F-4-N≡CCH2CH2—Ph |
| 520 | 2-F-5-N≡CCH2CH2—Ph |
| 521 | 2-F-6-N≡CCH2CH2—Ph |
| 522 | 2-Cl-3-N≡CCH2CH2—Ph |
| 523 | 2-Cl-4-N≡CCH2CH2—Ph |
| 524 | 2-Cl-5-N≡CCH2CH2—Ph |
| 525 | 2-Cl-6-N≡CCH2CH2—Ph |
| 526 | 2-Br-3-N≡CCH2CH2—Ph |
| 527 | 2-Br-4-N≡CCH2CH2—Ph |
| 528 | 2-Br-5-N≡CCH2CH2—Ph |
| 529 | 2-Br-6-N≡CCH2CH2—Ph |
| 530 | 2-I-3-N≡CCH2CH2—Ph |
| 531 | 2-I-4-N≡CCH2CH2—Ph |
| 532 | 2-I-5-N≡CCH2CH2—Ph |
| 533 | 2-I-6-N≡CCH2CH2—Ph |
| 534 | 2-Me-3-N≡CCH2CH2—Ph |
| 535 | 2-Me-4-N≡CCH2CH2—Ph |
| 536 | 2-Me-5-N≡CCH2CH2—Ph |
| 537 | 2-Me-6-N≡CCH2CH2—Ph |
| 538 | 2-F-3-cPrCH2—Ph |
| 539 | 2-F-4-cPrCH2—Ph |
| 540 | 2-F-5-cPrCH2—Ph |
| 541 | 2-F-6-cPrCH2—Ph |
| 542 | 2-Cl-3-cPrCH2—Ph |
| 543 | 2-Cl-4-cPrCH2—Ph |
| 544 | 2-Cl-5-cPrCH2—Ph |
| 545 | 2-Cl-6-cPrCH2—Ph |
| 546 | 2-Br-3-cPrCH2—Ph |
| 547 | 2-Br-4-cPrCH2—Ph |
| 548 | 2-Br-5-cPrCH2—Ph |
| 549 | 2-Br-6-cPrCH2—Ph |
| 550 | 2-I-3-cPrCH2—Ph |
| 551 | 2-I-4-cPrCH2—Ph |
| 552 | 2-I-5-cPrCH2—Ph |
| 553 | 2-I-6-cPrCH2—Ph |
| 554 | 2-Me-3-cPrCH2—Ph |
| 555 | 2-Me-4-cPrCH2—Ph |
| 556 | 2-Me-5-cPrCH2—Ph |
| 557 | 2-Me-6-cPrCH2—Ph |
| 558 | 2-F-3-cBuCH2—Ph |
| 559 | 2-F-4-cBuCH2—Ph |
| 560 | 2-F-5-cBuCH2—Ph |
| 561 | 2-F-6-cBuCH2—Ph |
| 562 | 2-Cl-3-cBuCH2—Ph |
| 563 | 2-Cl-4-cBuCH2—Ph |
| 564 | 2-Cl-5-cBuCH2—Ph |
| 565 | 2-Cl-6-cBuCH2—Ph |
| 566 | 2-Br-3-cBuCH2—Ph |
| 567 | 2-Br-4-cBuCH2—Ph |
| 568 | 2-Br-5-cBuCH2—Ph |
| 569 | 2-Br-6-cBuCH2—Ph |
| 570 | 2-I-3-cBuCH2—Ph |
| 571 | 2-I-4-cBuCH2—Ph |
| 572 | 2-I-5-cBuCH2—Ph |
| 573 | 2-I-6-cBuCH2—Ph |
| 574 | 2-Me-3-cBuCH2—Ph |
| 575 | 2-Me-4-cBuCH2—Ph |
| 576 | 2-Me-5-cBuCH2—Ph |
| 577 | 2-Me-6-cBuCH2—Ph |
| 578 | 2-F-3-MeOCH2—Ph |
| 579 | 2-F-4-MeOCH2—Ph |
| 580 | 2-F-5-MeOCH2—Ph |
| 581 | 2-F-6-MeOCH2—Ph |
| 582 | 2-Cl-3-MeOCH2—Ph |
| 583 | 2-Cl-4-MeOCH2—Ph |
| 584 | 2-Cl-5-MeOCH2—Ph |
| 585 | 2-Cl-6-MeOCH2—Ph |
| 586 | 2-Br-3-MeOCH2—Ph |
| 587 | 2-Br-4-MeOCH2—Ph |
| 588 | 2-Br-5-MeOCH2—Ph |
| 589 | 2-Br-6-MeOCH2—Ph |
| 590 | 2-I-3-MeOCH2—Ph |
| 591 | 2-I-4-MeOCH2—Ph |
| 592 | 2-I-5-MeOCH2—Ph |
| 593 | 2-I-6-MeOCH2—Ph |
| 594 | 2-Me-3-MeOCH2—Ph |
| 595 | 2-Me-4-MeOCH2—Ph |
| 596 | 2-Me-5-MeOCH2—Ph |
| 597 | 2-Me-6-MeOCH2—Ph |
| 598 | 2-F-3-MeOCH2CH2—Ph |
| 599 | 2-F-4-MeOCH2CH2—Ph |
| 600 | 2-F-5-MeOCH2CH2—Ph |
| 601 | 2-F-6-MeOCH2CH2—Ph |
| 602 | 2-Cl-3-MeOCH2CH2—Ph |
| 603 | 2-Cl-4-MeOCH2CH2—Ph |
| 604 | 2-Cl-5-MeOCH2CH2—Ph |
| 605 | 2-Cl-6-MeOCH2CH2—Ph |
| 606 | 2-Br-3-MeOCH2CH2—Ph |
| 607 | 2-Br-4-MeOCH2CH2—Ph |
| 608 | 2-Br-5-MeOCH2CH2—Ph |
| 609 | 2-Br-6-MeOCH2CH2—Ph |
| 610 | 2-I-3-MeOCH2CH2—Ph |
| 611 | 2-I-4-MeOCH2CH2—Ph |
| 612 | 2-I-5-MeOCH2CH2—Ph |
| 613 | 2-I-6-MeOCH2CH2—Ph |
| 614 | 2-Me-3-MeOCH2CH2—Ph |
| 615 | 2-Me-4-MeOCH2CH2—Ph |
| 616 | 2-Me-5-MeOCH2CH2—Ph |
| 617 | 2-Me-6-MeOCH2CH2—Ph |
| 618 | 2-F-3-MeOCH2CH2CH2—Ph |
| 619 | 2-F-4-MeOCH2CH2CH2—Ph |
| 620 | 2-F-5-MeOCH2CH2CH2—Ph |
| 621 | 2-F-6-MeOCH2CH2CH2—Ph |
| 622 | 2-Cl-3-MeOCH2CH2CH2—Ph |
| 623 | 2-Cl-4-MeOCH2CH2CH2—Ph |
| 624 | 2-Cl-5-MeOCH2CH2CH2—Ph |
| 625 | 2-Cl-6-MeOCH2CH2CH2—Ph |
| 626 | 2-Br-3-MeOCH2CH2CH2—Ph |
| 627 | 2-Br-4-MeOCH2CH2CH2—Ph |
| 628 | 2-Br-5-MeOCH2CH2CH2—Ph |
| 629 | 2-Br-6-MeOCH2CH2CH2—Ph |
| 630 | 2-I-3-MeOCH2CH2CH2—Ph |
| 631 | 2-I-4-MeOCH2CH2CH2—Ph |
| 632 | 2-I-5-MeOCH2CH2CH2—Ph |
| 633 | 2-I-6-MeOCH2CH2CH2—Ph |
| 634 | 2-Me-3-MeOCH2CH2CH2—Ph |
| 635 | 2-Me-4-MeOCH2CH2CH2—Ph |
| 636 | 2-Me-5-MeOCH2CH2CH2—Ph |
| 637 | 2-Me-6-MeOCH2CH2CH2—Ph |
| 638 | 2-F-3-EtOCH2—Ph |
| 639 | 2-F-4-EtOCH2—Ph |
| 640 | 2-F-5-EtOCH2—Ph |
| 641 | 2-F-6-EtOCH2—Ph |
| 642 | 2-Cl-3-EtOCH2—Ph |
| 643 | 2-Cl-4-EtOCH2—Ph |
| 644 | 2-Cl-5-EtOCH2—Ph |
| 645 | 2-Cl-6-EtOCH2—Ph |
| 646 | 2-Br-3-EtOCH2—Ph |
| 647 | 2-Br-4-EtOCH2—Ph |
| 648 | 2-Br-5-EtOCH2—Ph |
| 649 | 2-Br-6-EtOCH2—Ph |
| 650 | 2-I-3-EtOCH2—Ph |
| 651 | 2-I-4-EtOCH2—Ph |
| 652 | 2-I-5-EtOCH2—Ph |
| 653 | 2-I-6-EtOCH2—Ph |
| 654 | 2-Me-3-EtOCH2—Ph |
| 655 | 2-Me-4-EtOCH2—Ph |
| 656 | 2-Me-5-EtOCH2—Ph |

TABLE 2-continued

| No. | Z |
|---|---|
| 657 | 2-Me-6-EtOCH2—Ph |
| 658 | 2-F-3-EtOCH2CH2—Ph |
| 659 | 2-F-4-EtOCH2CH2—Ph |
| 660 | 2-F-5-EtOCH2CH2—Ph |
| 661 | 2-F-6-EtOCH2CH2—Ph |
| 662 | 2-Cl-3-EtOCH2CH2—Ph |
| 663 | 2-Cl-4-EtOCH2CH2—Ph |
| 664 | 2-Cl-5-EtOCH2CH2—Ph |
| 665 | 2-Cl-6-EtOCH2CH2—Ph |
| 666 | 2-Br-3-EtOCH2CH2—Ph |
| 667 | 2-Br-4-EtOCH2CH2—Ph |
| 668 | 2-Br-5-EtOCH2CH2—Ph |
| 669 | 2-Br-6-EtOCH2CH2—Ph |
| 670 | 2-I-3-EtOCH2CH2—Ph |
| 671 | 2-I-4-EtOCH2CH2—Ph |
| 672 | 2-I-5-EtOCH2CH2—Ph |
| 673 | 2-I-6-EtOCH2CH2—Ph |
| 674 | 2-Me-3-EtOCH2CH2—Ph |
| 675 | 2-Me-4-EtOCH2CH2—Ph |
| 676 | 2-Me-5-EtOCH2CH2—Ph |
| 677 | 2-Me-6-EtOCH2CH2—Ph |
| 678 | 2-F-3-cPrOCH2—Ph |
| 679 | 2-F-4-cPrOCH2—Ph |
| 680 | 2-F-5-cPrOCH2—Ph |
| 681 | 2-F-6-cPrOCH2—Ph |
| 682 | 2-Cl-3-cPrOCH2—Ph |
| 683 | 2-Cl-4-cPrOCH2—Ph |
| 684 | 2-Cl-5-cPrOCH2—Ph |
| 685 | 2-Cl-6-cPrOCH2—Ph |
| 686 | 2-Br-3-cPrOCH2—Ph |
| 687 | 2-Br-4-cPrOCH2—Ph |
| 688 | 2-Br-5-cPrOCH2—Ph |
| 689 | 2-Br-6-cPrOCH2—Ph |
| 690 | 2-I-3-cPrOCH2—Ph |
| 691 | 2-I-4-cPrOCH2—Ph |
| 692 | 2-I-5-cPrOCH2—Ph |
| 693 | 2-I-6-cPrOCH2—Ph |
| 694 | 2-Me-3-cPrOCH2—Ph |
| 695 | 2-Me-4-cPrOCH2—Ph |
| 696 | 2-Me-5-cPrOCH2—Ph |
| 697 | 2-Me-6-cPrOCH2—Ph |
| 698 | 2-F-3-F3COCH2—Ph |
| 699 | 2-F-4-F3COCH2—Ph |
| 700 | 2-F-5-F3COCH2—Ph |
| 701 | 2-F-6-F3COCH2—Ph |
| 702 | 2-Cl-3-F3COCH2—Ph |
| 703 | 2-Cl-4-F3COCH2—Ph |
| 704 | 2-Cl-5-F3COCH2—Ph |
| 705 | 2-Cl-6-F3COCH2—Ph |
| 706 | 2-Br-3-F3COCH2—Ph |
| 707 | 2-Br-4-F3COCH2—Ph |
| 708 | 2-Br-5-F3COCH2—Ph |
| 709 | 2-Br-6-F3COCH2—Ph |
| 710 | 2-I-3-F3COCH2—Ph |
| 711 | 2-I-4-F3COCH2—Ph |
| 712 | 2-I-5-F3COCH2—Ph |
| 713 | 2-I-6-F3COCH2—Ph |
| 714 | 2-Me-3-F3COCH2—Ph |
| 715 | 2-Me-4-F3COCH2—Ph |
| 716 | 2-Me-5-F3COCH2—Ph |
| 717 | 2-Me-6-F3COCH2—Ph |
| 718 | 2-F-3-F2CHOCH2—Ph |
| 719 | 2-F-4-F2CHOCH2—Ph |
| 720 | 2-F-5-F2CHOCH2—Ph |
| 721 | 2-F-6-F2CHOCH2—Ph |
| 722 | 2-Cl-3-F2CHOCH2—Ph |
| 723 | 2-Cl-4-F2CHOCH2—Ph |
| 724 | 2-Cl-5-F2CHOCH2—Ph |
| 725 | 2-Cl-6-F2CHOCH2—Ph |
| 726 | 2-Br-3-F2CHOCH2—Ph |
| 727 | 2-Br-4-F2CHOCH2—Ph |
| 728 | 2-Br-5-F2CHOCH2—Ph |
| 729 | 2-Br-6-F2CHOCH2—Ph |
| 730 | 2-I-3-F2CHOCH2—Ph |
| 731 | 2-I-4-F2CHOCH2—Ph |
| 732 | 2-I-5-F2CHOCH2—Ph |
| 733 | 2-I-6-F2CHOCH2—Ph |
| 734 | 2-Me-3-F2CHOCH2—Ph |
| 735 | 2-Me-4-F2CHOCH2—Ph |
| 736 | 2-Me-5-F2CHOCH2—Ph |
| 737 | 2-Me-6-F2CHOCH2—Ph |
| 738 | 2-F-3-MeOCH2CH2OCH2—Ph |
| 739 | 2-F-4-MeOCH2CH2OCH2—Ph |
| 740 | 2-F-5-MeOCH2CH2OCH2—Ph |
| 741 | 2-F-6-MeOCH2CH2OCH2—Ph |
| 742 | 2-Cl-3-MeOCH2CH2OCH2—Ph |
| 743 | 2-Cl-4-MeOCH2CH2OCH2—Ph |
| 744 | 2-Cl-5-MeOCH2CH2OCH2—Ph |
| 745 | 2-Cl-6-MeOCH2CH2OCH2—Ph |
| 746 | 2-Br-3-MeOCH2CH2OCH2—Ph |
| 747 | 2-Br-4-MeOCH2CH2OCH2—Ph |
| 748 | 2-Br-5-MeOCH2CH2OCH2—Ph |
| 749 | 2-Br-6-MeOCH2CH2OCH2—Ph |
| 750 | 2-I-3-MeOCH2CH2OCH2—Ph |
| 751 | 2-I-4-MeOCH2CH2OCH2—Ph |
| 752 | 2-I-5-MeOCH2CH2OCH2—Ph |
| 753 | 2-I-6-MeOCH2CH2OCH2—Ph |
| 754 | 2-Me-3-MeOCH2CH2OCH2—Ph |
| 755 | 2-Me-4-MeOCH2CH2OCH2—Ph |
| 756 | 2-Me-5-MeOCH2CH2OCH2—Ph |
| 757 | 2-Me-6-MeOCH2CH2OCH2—Ph |
| 758 | 2-F-3-Me2NCH2—Ph |
| 759 | 2-F-4-Me2NCH2—Ph |
| 760 | 2-F-5-Me2NCH2—Ph |
| 761 | 2-F-6-Me2NCH2—Ph |
| 762 | 2-Cl-3-Me2NCH—Ph |
| 763 | 2-Cl-4-Me2NCH—Ph |
| 764 | 2-Cl-5-Me2NCH—Ph |
| 765 | 2-Cl-6-Me2NCH—Ph |
| 766 | 2-Br-3-Me2NCH2—Ph |
| 767 | 2-Br-4-Me2NCH2—Ph |
| 768 | 2-Br-5-Me2NCH2—Ph |
| 769 | 2-Br-6-Me2NCH2—Ph |
| 770 | 2-I-3-Me2NCH2—Ph |
| 771 | 2-I-4-Me2NCH2—Ph |
| 772 | 2-I-5-Me2NCH2—Ph |
| 773 | 2-I-6-Me2NCH2—Ph |
| 774 | 2-Me-3-Me2NCH2—Ph |
| 775 | 2-Me-4-Me2NCH2—Ph |
| 776 | 2-Me-5-Me2NCH2—Ph |
| 777 | 2-Me-6-Me2NCH2—Ph |
| 778 | 2-F-3-MeSCH2—Ph |
| 779 | 2-F-4-MeSCH2—Ph |
| 780 | 2-F-5-MeSCH2—Ph |
| 781 | 2-F-6-MeSCH2—Ph |
| 782 | 2-Cl-3-MeSCH2—Ph |
| 783 | 2-Cl-4-MeSCH2—Ph |
| 784 | 2-Cl-5-MeSCH2—Ph |
| 785 | 2-Cl-6-MeSCH2—Ph |
| 786 | 2-Br-3-MeSCH2—Ph |
| 787 | 2-Br-4-MeSCH2—Ph |
| 788 | 2-Br-5-MeSCH2—Ph |
| 789 | 2-Br-6-MeSCH2—Ph |
| 790 | 2-I-3-MeSCH2—Ph |
| 791 | 2-I-4-MeSCH2—Ph |
| 792 | 2-I-5-MeSCH2—Ph |
| 793 | 2-I-6-MeSCH2—Ph |
| 794 | 2-Me-3-MeSCH2—Ph |
| 795 | 2-Me-4-MeSCH2—Ph |
| 796 | 2-Me-5-MeSCH2—Ph |
| 797 | 2-Me-6-MeSCH2—Ph |
| 798 | 2-F-3-MeS(O)CH2—Ph |
| 799 | 2-F-4-MeS(O)CH2—Ph |
| 800 | 2-F-5-MeS(O)CH2—Ph |
| 801 | 2-F-6-MeS(O)CH2—Ph |
| 802 | 2-Cl-3-MeS(O)CH2—Ph |
| 803 | 2-Cl-4-MeS(O)CH2—Ph |
| 804 | 2-Cl-5-MeS(O)CH2—Ph |
| 805 | 2-Cl-6-MeS(O)CH2—Ph |
| 806 | 2-Br-3-MeS(O)CH2—Ph |
| 807 | 2-Br-4-MeS(O)CH2—Ph |
| 808 | 2-Br-5-MeS(O)CH2—Ph |
| 809 | 2-Br-6-MeS(O)CH2—Ph |
| 810 | 2-I-3-MeS(O)CH2—Ph |
| 811 | 2-I-4-MeS(O)CH2—Ph |
| 812 | 2-I-5-MeS(O)CH2—Ph |

TABLE 2-continued

| No. | Z |
|---|---|
| 813 | 2-I-6-MeS(O)CH2—Ph |
| 814 | 2-Me-3-MeS(O)CH2—Ph |
| 815 | 2-Me-4-MeS(O)CH2—Ph |
| 816 | 2-Me-5-MeS(O)CH2—Ph |
| 817 | 2-Me-6-MeS(O)CH2—Ph |
| 818 | 2-F-3-MeSO2CH2—Ph |
| 819 | 2-F-4-MeSO2CH2—Ph |
| 820 | 2-F-5-MeSO2CH2—Ph |
| 821 | 2-F-6-MeSO2CH2—Ph |
| 822 | 2-Cl-3-MeSO2CH2—Ph |
| 823 | 2-Cl-4-MeSO2CH2—Ph |
| 824 | 2-Cl-5-MeSO2CH2—Ph |
| 825 | 2-Cl-6-MeSO2CH2—Ph |
| 826 | 2-Br-3-MeSO2CH2—Ph |
| 827 | 2-Br-4-MeSO2CH2—Ph |
| 828 | 2-Br-5-MeSO2CH2—Ph |
| 829 | 2-Br-6-MeSO2CH2—Ph |
| 830 | 2-I-3-MeSO2CH2—Ph |
| 831 | 2-I-4-MeSO2CH2—Ph |
| 832 | 2-I-5-MeSO2CH2—Ph |
| 833 | 2-I-6-MeSO2CH2—Ph |
| 834 | 2-Me-3-MeSO2CH2—Ph |
| 835 | 2-Me-4-MeSO2CH2—Ph |
| 836 | 2-Me-5-MeSO2CH2—Ph |
| 837 | 2-Me-6-MeSO2CH2—Ph |
| 838 | 2-F-3-cPr—Ph |
| 839 | 2-F-4-cPr—Ph |
| 840 | 2-F-5-cPr—Ph |
| 841 | 2-F-6-cPr—Ph |
| 842 | 2-Cl-3-cPr—Ph |
| 843 | 2-Cl-4-cPr—Ph |
| 844 | 2-Cl-5-cPr—Ph |
| 845 | 2-Cl-6-cPr—Ph |
| 846 | 2-Br-3-cPr—Ph |
| 847 | 2-Br-4-cPr—Ph |
| 848 | 2-Br-5-cPr—Ph |
| 849 | 2-Br-6-cPr—Ph |
| 850 | 2-I-3-cPr—Ph |
| 851 | 2-I-4-cPr—Ph |
| 852 | 2-I-5-cPr—Ph |
| 853 | 2-I-6-cPr—Ph |
| 854 | 2-Me-3-cPr—Ph |
| 855 | 2-Me-4-cPr—Ph |
| 856 | 2-Me-5-cPr—Ph |
| 857 | 2-Me-6-cPr—Ph |
| 858 | 2-F-3-cBu—Ph |
| 859 | 2-F-4-cBu—Ph |
| 860 | 2-F-5-cBu—Ph |
| 861 | 2-F-6-cBu—Ph |
| 862 | 2-Cl-3-cBu—Ph |
| 863 | 2-Cl-4-cBu—Ph |
| 864 | 2-Cl-5-cBu—Ph |
| 865 | 2-Cl-6-cBu—Ph |
| 866 | 2-Br-3-cBu—Ph |
| 867 | 2-Br-4-cBu—Ph |
| 868 | 2-Br-5-cBu—Ph |
| 869 | 2-Br-6-cBu—Ph |
| 870 | 2-I-3-cBu—Ph |
| 871 | 2-I-4-cBu—Ph |
| 872 | 2-I-5-cBu—Ph |
| 873 | 2-I-6-cBu—Ph |
| 874 | 2-Me-3-cBu—Ph |
| 875 | 2-Me-4-cBu—Ph |
| 876 | 2-Me-5-cBu—Ph |
| 877 | 2-Me-6-cBu—Ph |
| 878 | 2-F-3-F3C—Ph |
| 879 | 2-F-4-F3C—Ph |
| 880 | 2-F-5-F3C—Ph |
| 881 | 2-F-6-F3C—Ph |
| 882 | 2-Cl-3-F3C—Ph |
| 883 | 2-Cl-4-F3C—Ph |
| 884 | 2-Cl-5-F3C—Ph |
| 885 | 2-Cl-6-F3C—Ph |
| 886 | 2-Br-3-F3C—Ph |
| 887 | 2-Br-4-F3C—Ph |
| 888 | 2-Br-5-F3C—Ph |
| 889 | 2-Br-6-F3C—Ph |
| 890 | 2-I-3-F3C—Ph |
| 891 | 2-I-4-F3C—Ph |
| 892 | 2-I-5-F3C—Ph |
| 893 | 2-I-6-F3C—Ph |
| 894 | 2-Me-3-F3C—Ph |
| 895 | 2-Me-4-F3C—Ph |
| 896 | 2-Me-5-F3C—Ph |
| 897 | 2-Me-6-F3C—Ph |
| 898 | 2-F-3-F2CH—Ph |
| 899 | 2-F-4-F2CH—Ph |
| 900 | 2-F-5-F2CH—Ph |
| 901 | 2-F-6-F2CH—Ph |
| 902 | 2-Cl-3-F2CH—Ph |
| 903 | 2-Cl-4-F2CH—Ph |
| 904 | 2-Cl-5-F2CH—Ph |
| 905 | 2-Cl-6-F2CH—Ph |
| 906 | 2-Br-3-F2CH—Ph |
| 907 | 2-Br-4-F2CH—Ph |
| 908 | 2-Br-5-F2CH—Ph |
| 909 | 2-Br-6-F2CH—Ph |
| 910 | 2-I-3-F2CH—Ph |
| 911 | 2-I-4-F2CH—Ph |
| 912 | 2-I-5-F2CH—Ph |
| 913 | 2-I-6-F2CH—Ph |
| 914 | 2-Me-3-F2CH—Ph |
| 915 | 2-Me-4-F2CH—Ph |
| 916 | 2-Me-5-F2CH—Ph |
| 917 | 2-Me-6-F2CH—Ph |
| 918 | 2-F-3-H2C=CH—Ph |
| 919 | 2-F-4-H2C=CH—Ph |
| 920 | 2-F-5-H2C=CH—Ph |
| 921 | 2-F-6-H2C=CH—Ph |
| 922 | 2-Cl-3-H2C=CH—Ph |
| 923 | 2-Cl-4-H2C=CH—Ph |
| 924 | 2-Cl-5-H2C=CH—Ph |
| 925 | 2-Cl-6-H2C=CH—Ph |
| 926 | 2-Br-3-H2C=CH—Ph |
| 927 | 2-Br-4-H2C=CH—Ph |
| 928 | 2-Br-5-H2C=CH—Ph |
| 929 | 2-Br-6-H2C=CH—Ph |
| 930 | 2-I-3-H2C=CH—Ph |
| 931 | 2-I-4-H2C=CH—Ph |
| 932 | 2-I-5-H2C=CH—Ph |
| 933 | 2-I-6-H2C=CH—Ph |
| 934 | 2-Me-3-H2C=CH—Ph |
| 935 | 2-Me-4-H2C=CH—Ph |
| 936 | 2-Me-5-H2C=CH—Ph |
| 937 | 2-Me-6-H2C=CH—Ph |
| 938 | 2-F-3-H2C=CHCH2—Ph |
| 939 | 2-F-4-H2C=CHCH2—Ph |
| 940 | 2-F-5-H2C=CHCH2—Ph |
| 941 | 2-F-6-H2C=CHCH2—Ph |
| 942 | 2-Cl-3-H2C=CHCH2—Ph |
| 943 | 2-Cl-4-H2C=CHCH2—Ph |
| 944 | 2-Cl-5-H2C=CHCH2—Ph |
| 945 | 2-Cl-6-H2C=CHCH2—Ph |
| 946 | 2-Br-3-H2C=CHCH2—Ph |
| 947 | 2-Br-4-H2C=CHCH2—Ph |
| 948 | 2-Br-5-H2C=CHCH2—Ph |
| 949 | 2-Br-6-H2C=CHCH2—Ph |
| 950 | 2-I-3-H2C=CHCH2—Ph |
| 951 | 2-I-4-H2C=CHCH2—Ph |
| 952 | 2-I-5-H2C=CHCH2—Ph |
| 953 | 2-I-6-H2C=CHCH2—Ph |
| 954 | 2-Me-3-H2C=CHCH2—Ph |
| 955 | 2-Me-4-H2C=CHCH2—Ph |
| 956 | 2-Me-5-H2C=CHCH2—Ph |
| 957 | 2-Me-6-H2C=CHCH2—Ph |
| 958 | 2-F-3-F2C=CH—Ph |
| 959 | 2-F-4-F2C=CH—Ph |
| 960 | 2-F-5-F2C=CH—Ph |
| 961 | 2-F-6-F2C=CH—Ph |
| 962 | 2-Cl-3-F2C=CH—Ph |
| 963 | 2-Cl-4-F2C=CH—Ph |
| 964 | 2-Cl-5-F2C=CH—Ph |
| 965 | 2-Cl-6-F2C=CH—Ph |
| 966 | 2-Br-3-F2C=CH—Ph |
| 967 | 2-Br-4-F2C=CH—Ph |
| 968 | 2-Br-5-F2C=CH—Ph |

TABLE 2-continued

| No. | Z |
|---|---|
| 969 | 2-Br-6-F2C=CH—Ph |
| 970 | 2-I-3-F2C=CH—Ph |
| 971 | 2-I-4-F2C=CH—Ph |
| 972 | 2-I-5-F2C=CH—Ph |
| 973 | 2-I-6-F2C=CH—Ph |
| 974 | 2-Me-3-F2C=CH—Ph |
| 975 | 2-Me-4-F2C=CH—Ph |
| 976 | 2-Me-5-F2C=CH—Ph |
| 977 | 2-Me-6-F2C=CH—Ph |
| 978 | 2-F-3-F2C=CHCH2—Ph |
| 979 | 2-F-4-F2C=CHCH2—Ph |
| 980 | 2-F-5-F2C=CHCH2—Ph |
| 981 | 2-F-6-F2C=CHCH2—Ph |
| 982 | 2-Cl-3-F2C=CHCH2—Ph |
| 983 | 2-Cl-4-F2C=CHCH2—Ph |
| 984 | 2-Cl-5-F2C=CHCH2—Ph |
| 985 | 2-Cl-6-F2C=CHCH2—Ph |
| 986 | 2-Br-3-F2C=CHCH2—Ph |
| 987 | 2-Br-4-F2C=CHCH2—Ph |
| 988 | 2-Br-5-F2C=CHCH2—Ph |
| 989 | 2-Br-6-F2C=CHCH2—Ph |
| 990 | 2-I-3-F2C=CHCH2—Ph |
| 991 | 2-I-4-F2C=CHCH2—Ph |
| 992 | 2-I-5-F2C=CHCH2—Ph |
| 993 | 2-I-6-F2C=CHCH2—Ph |
| 994 | 2-Me-3-F2C=CHCH2—Ph |
| 995 | 2-Me-4-F2C=CHCH2—Ph |
| 996 | 2-Me-5-F2C=CHCH2—Ph |
| 997 | 2-Me-6-F2C=CHCH2—Ph |
| 998 | 2-F-3-HC≡C—Ph |
| 999 | 2-F-4-HC≡C—Ph |
| 1000 | 2-F-5-HC≡C—Ph |
| 1001 | 2-F-6-HC≡C—Ph |
| 1002 | 2-Cl-3-HC≡C—Ph |
| 1003 | 2-Cl-4-HC≡C—Ph |
| 1004 | 2-Cl-5-HC≡C—Ph |
| 1005 | 2-Cl-6-HC≡C—Ph |
| 1006 | 2-Br-3-HC≡C—Ph |
| 1007 | 2-Br-4-HC≡C—Ph |
| 1008 | 2-Br-5-HC≡C—Ph |
| 1009 | 2-Br-6-HC≡C—Ph |
| 1010 | 2-I-3-HC≡C—Ph |
| 1011 | 2-I-4-HC≡C—Ph |
| 1012 | 2-I-5-HC≡C—Ph |
| 1013 | 2-I-6-HC≡C—Ph |
| 1014 | 2-Me-3-HC≡C—Ph |
| 1015 | 2-Me-4-HC≡C—Ph |
| 1016 | 2-Me-5-HC≡C—Ph |
| 1017 | 2-Me-6-HC≡C—Ph |
| 1018 | 2-F-3-HC≡CCH2—Ph |
| 1019 | 2-F-4-HC≡CCH2—Ph |
| 1020 | 2-F-5-HC≡CCH2—Ph |
| 1021 | 2-F-6-HC≡CCH2—Ph |
| 1022 | 2-Cl-3-HC≡CCH2—Ph |
| 1023 | 2-Cl-4-HC≡CCH2—Ph |
| 1024 | 2-Cl-5-HC≡CCH2—Ph |
| 1025 | 2-Cl-6-HC≡CCH2—Ph |
| 1026 | 2-Br-3-HC≡CCH2—Ph |
| 1027 | 2-Br-4-HC≡CCH2—Ph |
| 1028 | 2-Br-5-HC≡CCH2—Ph |
| 1029 | 2-Br-6-HC≡CCH2—Ph |
| 1030 | 2-I-3-HC≡CCH2—Ph |
| 1031 | 2-I-4-HC≡CCH2—Ph |
| 1032 | 2-I-5-HC≡CCH2—Ph |
| 1033 | 2-I-6-HC≡CCH2—Ph |
| 1034 | 2-Me-3-HC≡CCH2—Ph |
| 1035 | 2-Me-4-HC≡CCH2—Ph |
| 1036 | 2-Me-5-HC≡CCH2—Ph |
| 1037 | 2-Me-6-HC≡CCH2—Ph |
| 1038 | 2-F-3-F3CC≡C—Ph |
| 1039 | 2-F-4-F3CC≡C—Ph |
| 1040 | 2-F-5-F3CC≡C—Ph |
| 1041 | 2-F-6-F3CC≡C—Ph |
| 1042 | 2-Cl-3-F3CC≡C—Ph |
| 1043 | 2-Cl-4-F3CC≡C—Ph |
| 1044 | 2-Cl-5-F3CC≡C—Ph |
| 1045 | 2-Cl-6-F3CC≡C—Ph |
| 1046 | 2-Br-3-F3CC≡C—Ph |
| 1047 | 2-Br-4-F3CC≡C—Ph |
| 1048 | 2-Br-5-F3CC≡C—Ph |
| 1049 | 2-Br-6-F3CC≡C—Ph |
| 1050 | 2-I-3-F3CC≡C—Ph |
| 1051 | 2-I-4-F3CC≡C—Ph |
| 1052 | 2-I-5-F3CC≡C—Ph |
| 1053 | 2-I-6-F3CC≡C—Ph |
| 1054 | 2-Me-3-F3CC≡C—Ph |
| 1055 | 2-Me-4-F3CC≡C—Ph |
| 1056 | 2-Me-5-F3CC≡C—Ph |
| 1057 | 2-Me-6-F3CC≡C—Ph |
| 1058 | 2-F-4-F3CC≡CCH2—Ph |
| 1059 | 2-F-3-F3CC≡CCH2—Ph |
| 1060 | 2-F-5-F3CC≡CCH2—Ph |
| 1061 | 2-F-6-F3CC≡CCH2—Ph |
| 1062 | 2-Cl-3-F3CC≡CCH2—Ph |
| 1063 | 2-Cl-4-F3CC≡CCH2—Ph |
| 1064 | 2-Cl-5-F3CC≡CCH2—Ph |
| 1065 | 2-Cl-6-F3CC≡CCH2—Ph |
| 1066 | 2-Br-3-F3CC≡CCH2—Ph |
| 1067 | 2-Br-4-F3CC≡CCH2—Ph |
| 1068 | 2-Br-5-F3CC≡CCH2—Ph |
| 1069 | 2-Br-6-F3CC≡CCH2—Ph |
| 1070 | 2-I-3-F3CC≡CCH2—Ph |
| 1071 | 2-I-4-F3CC≡CCH2—Ph |
| 1072 | 2-I-5-F3CC≡CCH2—Ph |
| 1073 | 2-I-6-F3CC≡CCH2—Ph |
| 1074 | 2-Me-3-F3CC≡CCH2—Ph |
| 1075 | 2-Me-4-F3CC≡CCH2—Ph |
| 1076 | 2-Me-5-F3CC≡CCH2—Ph |
| 1077 | 2-Me-6-F3CC≡CCH2—Ph |
| 1078 | 2-F-3-MeO—Ph |
| 1079 | 2-F-4-MeO—Ph |
| 1080 | 2-F-5-MeO—Ph |
| 1081 | 2-F-6-MeO—Ph |
| 1082 | 2-Cl-3-MeO—Ph |
| 1083 | 2-Cl-4-MeO—Ph |
| 1084 | 2-Cl-5-MeO—Ph |
| 1085 | 2-Cl-6-MeO—Ph |
| 1086 | 2-Br-3-MeO—Ph |
| 1087 | 2-Br-4-MeO—Ph |
| 1088 | 2-Br-5-MeO—Ph |
| 1089 | 2-Br-6-MeO—Ph |
| 1090 | 2-I-3-MeO—Ph |
| 1091 | 2-I-4-MeO—Ph |
| 1092 | 2-I-5-MeO—Ph |
| 1093 | 2-I-6-MeO—Ph |
| 1094 | 2-Me-3-MeO—Ph |
| 1095 | 2-Me-4-MeO—Ph |
| 1096 | 2-Me-5-MeO—Ph |
| 1097 | 2-Me-6-MeO—Ph |
| 1098 | 2-F-3-EtO—Ph |
| 1099 | 2-F-4-EtO—Ph |
| 1100 | 2-F-5-EtO—Ph |
| 1101 | 2-F-6-EtO—Ph |
| 1102 | 2-Cl-3-EtO—Ph |
| 1103 | 2-Cl-4-EtO—Ph |
| 1104 | 2-Cl-5-EtO—Ph |
| 1105 | 2-Cl-6-EtO—Ph |
| 1106 | 2-Br-3-EtO—Ph |
| 1107 | 2-Br-4-EtO—Ph |
| 1108 | 2-Br-5-EtO—Ph |
| 1109 | 2-Br-6-EtO—Ph |
| 1110 | 2-I-3-EtO—Ph |
| 1111 | 2-I-4-EtO—Ph |
| 1112 | 2-I-5-EtO—Ph |
| 1113 | 2-I-6-EtO—Ph |
| 1114 | 2-Me-3-EtO—Ph |
| 1115 | 2-Me-4-EtO—Ph |
| 1116 | 2-Me-5-EtO—Ph |
| 1117 | 2-Me-6-EtO—Ph |
| 1118 | 2-F-3-PrO—Ph |
| 1119 | 2-F-4-PrO—Ph |
| 1120 | 2-F-5-PrO—Ph |
| 1121 | 2-F-6-PrO—Ph |
| 1122 | 2-Cl-3-PrO—Ph |
| 1123 | 2-Cl-4-PrO—Ph |
| 1124 | 2-Cl-5-PrO—Ph |

TABLE 2-continued

| No. | Z |
|---|---|
| 1125 | 2-Cl-6-PrO—Ph |
| 1126 | 2-Br-3-PrO—Ph |
| 1127 | 2-Br-4-PrO—Ph |
| 1128 | 2-Br-5-PrO—Ph |
| 1129 | 2-Br-6-PrO—Ph |
| 1130 | 2-I-3-PrO—Ph |
| 1131 | 2-I-4-PrO—Ph |
| 1132 | 2-I-5-PrO—Ph |
| 1133 | 2-I-6-PrO—Ph |
| 1134 | 2-Me-3-PrO—Ph |
| 1135 | 2-Me-4-PrO—Ph |
| 1136 | 2-Me-5-PrO—Ph |
| 1137 | 2-Me-6-PrO—Ph |
| 1138 | 2-F-3-iPrO—Ph |
| 1139 | 2-F-4-iPrO—Ph |
| 1140 | 2-F-5-iPrO—Ph |
| 1141 | 2-F-6-iPrO—Ph |
| 1142 | 2-Cl-3-iPrO—Ph |
| 1143 | 2-Cl-4-iPrO—Ph |
| 1144 | 2-Cl-5-iPrO—Ph |
| 1145 | 2-Cl-6-iPrO—Ph |
| 1146 | 2-Br-3-iPrO—Ph |
| 1147 | 2-Br-4-iPrO—Ph |
| 1148 | 2-Br-5-iPrO—Ph |
| 1149 | 2-Br-6-iPrO—Ph |
| 1150 | 2-I-3-iPrO—Ph |
| 1151 | 2-I-4-iPrO—Ph |
| 1152 | 2-I-5-iPrO—Ph |
| 1153 | 2-I-6-iPrO—Ph |
| 1154 | 2-Me-3-iPrO—Ph |
| 1155 | 2-Me-4-iPrO—Ph |
| 1156 | 2-Me-5-iPrO—Ph |
| 1157 | 2-Me-6-iPrO—Ph |
| 1158 | 2-F-3-BuO—Ph |
| 1159 | 2-F-4-BuO—Ph |
| 1160 | 2-F-5-BuO—Ph |
| 1161 | 2-F-6-BuO—Ph |
| 1162 | 2-Cl-3-BuO—Ph |
| 1163 | 2-Cl-4-BuO—Ph |
| 1164 | 2-Cl-5-BuO—Ph |
| 1165 | 2-Cl-6-BuO—Ph |
| 1166 | 2-Br-3-BuO—Ph |
| 1167 | 2-Br-4-BuO—Ph |
| 1168 | 2-Br-5-BuO—Ph |
| 1169 | 2-Br-6-BuO—Ph |
| 1170 | 2-I-3-BuO—Ph |
| 1171 | 2-I-4-BuO—Ph |
| 1172 | 2-I-5-BuO—Ph |
| 1173 | 2-I-6-BuO—Ph |
| 1174 | 2-Me-3-BuO—Ph |
| 1175 | 2-Me-4-BuO—Ph |
| 1176 | 2-Me-5-BuO—Ph |
| 1177 | 2-Me-6-BuO—Ph |
| 1178 | 2-F-3-iBuO—Ph |
| 1179 | 2-F-4-iBuO—Ph |
| 1180 | 2-F-5-iBuO—Ph |
| 1181 | 2-F-6-iBuO—Ph |
| 1182 | 2-Cl-3-iBuO—Ph |
| 1183 | 2-Cl-4-iBuO—Ph |
| 1184 | 2-Cl-5-iBuO—Ph |
| 1185 | 2-Cl-6-iBuO—Ph |
| 1186 | 2-Br-3-iBuO—Ph |
| 1187 | 2-Br-4-iBuO—Ph |
| 1188 | 2-Br-5-iBuO—Ph |
| 1189 | 2-Br-6-iBuO—Ph |
| 1190 | 2-I-3-iBuO—Ph |
| 1191 | 2-I-4-iBuO—Ph |
| 1192 | 2-I-5-iBuO—Ph |
| 1193 | 2-I-6-iBuO—Ph |
| 1194 | 2-Me-3-iBuO—Ph |
| 1195 | 2-Me-4-iBuO—Ph |
| 1196 | 2-Me-5-iBuO—Ph |
| 1197 | 2-Me-6-iBuO—Ph |
| 1198 | 2-F-3-PentylO—Ph |
| 1199 | 2-F-4-PentylO—Ph |
| 1200 | 2-F-5-PentylO—Ph |
| 1201 | 2-F-6-PentylO—Ph |
| 1202 | 2-Cl-3-PentylO—Ph |
| 1203 | 2-Cl-4-PentylO—Ph |
| 1204 | 2-Cl-5-PentylO—Ph |
| 1205 | 2-Cl-6-PentylO—Ph |
| 1206 | 2-Br-3-PentylO—Ph |
| 1207 | 2-Br-4-PentylO—Ph |
| 1208 | 2-Br-5-PentylO—Ph |
| 1209 | 2-Br-6-PentylO—Ph |
| 1210 | 2-I-3-PentylO—Ph |
| 1211 | 2-I-4-PentylO—Ph |
| 1212 | 2-I-5-PentylO—Ph |
| 1213 | 2-I-6-PentylO—Ph |
| 1214 | 2-Me-3-PentylO—Ph |
| 1215 | 2-Me-4-PentylO—Ph |
| 1216 | 2-Me-5-PentylO—Ph |
| 1217 | 2-Me-6-PentylO—Ph |
| 1218 | 2-F-3-N≡CCH2O—Ph |
| 1219 | 2-F-4-N≡CCH2O—Ph |
| 1220 | 2-F-5-N≡CCH2O—Ph |
| 1221 | 2-F-6-N≡CCH2O—Ph |
| 1222 | 2-Cl-3-N≡CCH2O—Ph |
| 1223 | 2-Cl-4-N≡CCH2O—Ph |
| 1224 | 2-Cl-5-N≡CCH2O—Ph |
| 1225 | 2-Cl-6-N≡CCH2O—Ph |
| 1226 | 2-Br-3-N≡CCH2O—Ph |
| 1227 | 2-Br-4-N≡CCH2O—Ph |
| 1228 | 2-Br-5-N≡CCH2O—Ph |
| 1229 | 2-Br-6-N≡CCH2O—Ph |
| 1230 | 2-I-3-N≡CCH2O—Ph |
| 1231 | 2-I-4-N≡CCH2O—Ph |
| 1232 | 2-I-5-N≡CCH2O—Ph |
| 1233 | 2-I-6-N≡CCH2O—Ph |
| 1234 | 2-Me-3-N≡CCH2O—Ph |
| 1235 | 2-Me-4-N≡CCH2O—Ph |
| 1236 | 2-Me-5-N≡CCH2O—Ph |
| 1237 | 2-Me-6-N≡CCH2O—Ph |
| 1238 | 2-F-3-N≡CCH2CH2O—Ph |
| 1239 | 2-F-4-N≡CCH2CH2O—Ph |
| 1240 | 2-F-5-N≡CCH2CH2O—Ph |
| 1241 | 2-F-6-N≡CCH2CH2O—Ph |
| 1242 | 2-Cl-3-N≡CCH2CH2O—Ph |
| 1243 | 2-Cl-4-N≡CCH2CH2O—Ph |
| 1244 | 2-Cl-5-N≡CCH2CH2O—Ph |
| 1245 | 2-Cl-6-N≡CCH2CH2O—Ph |
| 1246 | 2-Br-3-N≡CCH2CH2O—Ph |
| 1247 | 2-Br-4-N≡CCH2CH2O—Ph |
| 1248 | 2-Br-5-N≡CCH2CH2O—Ph |
| 1249 | 2-Br-6-N≡CCH2CH2O—Ph |
| 1250 | 2-I-3-N≡CCH2CH2O—Ph |
| 1251 | 2-I-4-N≡CCH2CH2O—Ph |
| 1252 | 2-I-5-N≡CCH2CH2O—Ph |
| 1253 | 2-I-6-N≡CCH2CH2O—Ph |
| 1254 | 2-Me-3-N≡CCH2CH2O—Ph |
| 1255 | 2-Me-4-N≡CCH2CH2O—Ph |
| 1256 | 2-Me-5-N≡CCH2CH2O—Ph |
| 1257 | 2-Me-6-N≡CCH2CH2O—Ph |
| 1258 | 2-F-3-cPrCH2O—Ph |
| 1259 | 2-F-4-cPrCH2O—Ph |
| 1260 | 2-F-5-cPrCH2O—Ph |
| 1261 | 2-F-6-cPrCH2O—Ph |
| 1262 | 2-Cl-3-cPrCH2O—Ph |
| 1263 | 2-Cl-4-cPrCH2O—Ph |
| 1264 | 2-Cl-5-cPrCH2O—Ph |
| 1265 | 2-Cl-6-cPrCH2O—Ph |
| 1266 | 2-Br-3-cPrCH2O—Ph |
| 1267 | 2-Br-4-cPrCH2O—Ph |
| 1268 | 2-Br-5-cPrCH2O—Ph |
| 1269 | 2-Br-6-cPrCH2O—Ph |
| 1270 | 2-I-3-cPrCH2O—Ph |
| 1271 | 2-I-4-cPrCH2O—Ph |
| 1272 | 2-I-5-cPrCH2O—Ph |
| 1273 | 2-I-6-cPrCH2O—Ph |
| 1274 | 2-Me-3-cPrCH2O—Ph |
| 1275 | 2-Me-4-cPrCH2O—Ph |
| 1276 | 2-Me-5-cPrCH2O—Ph |
| 1277 | 2-Me-6-cPrCH2O—Ph |
| 1278 | 2-F-3-cBuCH2O—Ph |
| 1279 | 2-F-4-cBuCH2O—Ph |
| 1280 | 2-F-5-cBuCH2O—Ph |

TABLE 2-continued

| No. | Z |
|---|---|
| 1281 | 2-F-6-cBuCH2O—Ph |
| 1282 | 2-Cl-3-cBuCH2O—Ph |
| 1283 | 2-Cl-4-cBuCH2O—Ph |
| 1284 | 2-Cl-5-cBuCH2O—Ph |
| 1285 | 2-Cl-6-cBuCH2O—Ph |
| 1286 | 2-Br-3-cBuCH2O—Ph |
| 1287 | 2-Br-4-cBuCH2O—Ph |
| 1288 | 2-Br-5-cBuCH2O—Ph |
| 1289 | 2-Br-6-cBuCH2O—Ph |
| 1290 | 2-I-3-cBuCH2O—Ph |
| 1291 | 2-I-4-cBuCH2O—Ph |
| 1292 | 2-I-5-cBuCH2O—Ph |
| 1293 | 2-I-6-cBuCH2O—Ph |
| 1294 | 2-Me-3-cBuCH2O—Ph |
| 1295 | 2-Me-4-cBuCH2O—Ph |
| 1296 | 2-Me-5-cBuCH2O—Ph |
| 1297 | 2-Me-6-cBuCH2O—Ph |
| 1298 | 2-F-3-cPentylCH2O—Ph |
| 1299 | 2-F-4-cPentylCH2O—Ph |
| 1300 | 2-F-5-cPentylCH2O—Ph |
| 1301 | 2-F-6-cPentylCH2O—Ph |
| 1302 | 2-Cl-3-cPentylCH2O—Ph |
| 1303 | 2-Cl-4-cPentylCH2O—Ph |
| 1304 | 2-Cl-5-cPentylCH2O—Ph |
| 1305 | 2-Cl-6-cPentylCH2O—Ph |
| 1306 | 2-Br-3-cPentylCH2O—Ph |
| 1307 | 2-Br-4-cPentylCH2O—Ph |
| 1308 | 2-Br-5-cPentylCH2O—Ph |
| 1309 | 2-Br-6-cPentylCH2O—Ph |
| 1310 | 2-I-3-cPentylCH2O—Ph |
| 1311 | 2-I-4-cPentylCH2O—Ph |
| 1312 | 2-I-5-cPentylCH2O—Ph |
| 1313 | 2-I-6-cPentylCH2O—Ph |
| 1314 | 2-Me-3-cPentylCH2O—Ph |
| 1315 | 2-Me-4-cPentylCH2O—Ph |
| 1316 | 2-Me-5-cPentylCH2O—Ph |
| 1317 | 2-Me-6-cPentylCH2O—Ph |
| 1318 | 2-F-3-cHexylCH2O—Ph |
| 1319 | 2-F-4-cHexylCH2O—Ph |
| 1320 | 2-F-5-cHexylCH2O—Ph |
| 1321 | 2-F-6-cHexylCH2O—Ph |
| 1322 | 2-Cl-3-cHexylCH2O—Ph |
| 1323 | 2-Cl-4-cHexylCH2O—Ph |
| 1324 | 2-Cl-5-cHexylCH2O—Ph |
| 1325 | 2-Cl-6-cHexylCH2O—Ph |
| 1326 | 2-Br-3-cHexylCH2O—Ph |
| 1327 | 2-Br-4-cHexylCH2O—Ph |
| 1328 | 2-Br-5-cHexylCH2O—Ph |
| 1329 | 2-Br-6-cHexylCH2O—Ph |
| 1330 | 2-I-3-cHexylCH2O—Ph |
| 1331 | 2-I-4-cHexylCH2O—Ph |
| 1332 | 2-I-5-cHexylCH2O—Ph |
| 1333 | 2-I-6-cHexylCH2O—Ph |
| 1334 | 2-Me-3-cHexylCH2O—Ph |
| 1335 | 2-Me-4-cHexylCH2O—Ph |
| 1336 | 2-Me-5-cHexylCH2O—Ph |
| 1337 | 2-Me-6-cHexylCH2O—Ph |
| 1338 | 2-F-3-MeOCH2O—Ph |
| 1339 | 2-F-4-MeOCH2O—Ph |
| 1340 | 2-F-5-MeOCH2O—Ph |
| 1341 | 2-F-6-MeOCH2O—Ph |
| 1342 | 2-Cl-3-MeOCH2O—Ph |
| 1343 | 2-Cl-4-MeOCH2O—Ph |
| 1344 | 2-Cl-5-MeOCH2O—Ph |
| 1345 | 2-Cl-6-MeOCH2O—Ph |
| 1346 | 2-Br-3-MeOCH2O—Ph |
| 1347 | 2-Br-4-MeOCH2O—Ph |
| 1348 | 2-Br-5-MeOCH2O—Ph |
| 1349 | 2-Br-6-MeOCH2O—Ph |
| 1350 | 2-I-3-MeOCH2O—Ph |
| 1351 | 2-I-4-MeOCH2O—Ph |
| 1352 | 2-I-5-MeOCH2O—Ph |
| 1353 | 2-I-6-MeOCH2O—Ph |
| 1354 | 2-Me-3-MeOCH2O—Ph |
| 1355 | 2-Me-4-MeOCH2O—Ph |
| 1356 | 2-Me-5-MeOCH2O—Ph |
| 1357 | 2-Me-6-MeOCH2O—Ph |
| 1358 | 2-F-3-EtOCH2O—Ph |
| 1359 | 2-F-4-EtOCH2O—Ph |
| 1360 | 2-F-5-EtOCH2O—Ph |
| 1361 | 2-F-6-EtOCH2O—Ph |
| 1362 | 2-Cl-3-EtOCH2O—Ph |
| 1363 | 2-Cl-4-EtOCH2O—Ph |
| 1364 | 2-Cl-5-EtOCH2O—Ph |
| 1365 | 2-Cl-6-EtOCH2O—Ph |
| 1366 | 2-Br-3-EtOCH2O—Ph |
| 1367 | 2-Br-4-EtOCH2O—Ph |
| 1368 | 2-Br-5-EtOCH2O—Ph |
| 1369 | 2-Br-6-EtOCH2O—Ph |
| 1370 | 2-I-3-EtOCH2O—Ph |
| 1371 | 2-I-4-EtOCH2O—Ph |
| 1372 | 2-I-5-EtOCH2O—Ph |
| 1373 | 2-I-6-EtOCH2O—Ph |
| 1374 | 2-Me-3-EtOCH2O—Ph |
| 1375 | 2-Me-4-EtOCH2O—Ph |
| 1376 | 2-Me-5-EtOCH2O—Ph |
| 1377 | 2-Me-6-EtOCH2O—Ph |
| 1378 | 2-F-3-MeOCH2CH2O—Ph |
| 1379 | 2-F-4-MeOCH2CH2O—Ph |
| 1380 | 2-F-5-MeOCH2CH2O—Ph |
| 1381 | 2-F-6-MeOCH2CH2O—Ph |
| 1382 | 2-Cl-3-MeOCH2CH2O—Ph |
| 1383 | 2-Cl-4-MeOCH2CH2O—Ph |
| 1384 | 2-Cl-5-MeOCH2CH2O—Ph |
| 1385 | 2-Cl-6-MeOCH2CH2O—Ph |
| 1386 | 2-Br-3-MeOCH2CH2O—Ph |
| 1387 | 2-Br-4-MeOCH2CH2O—Ph |
| 1388 | 2-Br-5-MeOCH2CH2O—Ph |
| 1389 | 2-Br-6-MeOCH2CH2O—Ph |
| 1390 | 2-I-3-MeOCH2CH2O—Ph |
| 1391 | 2-I-4-MeOCH2CH2O—Ph |
| 1392 | 2-I-5-MeOCH2CH2O—Ph |
| 1393 | 2-I-6-MeOCH2CH2O—Ph |
| 1394 | 2-Me-3-MeOCH2CH2O—Ph |
| 1395 | 2-Me-4-MeOCH2CH2O—Ph |
| 1396 | 2-Me-5-MeOCH2CH2O—Ph |
| 1397 | 2-Me-6-MeOCH2CH2O—Ph |
| 1398 | 2-F-3-MeOCH2CH2CH2O—Ph |
| 1399 | 2-F-4-MeOCH2CH2CH2O—Ph |
| 1400 | 2-F-5-MeOCH2CH2CH2O—Ph |
| 1401 | 2-F-6-MeOCH2CH2CH2O—Ph |
| 1402 | 2-Cl-3-MeOCH2CH2CH2O—Ph |
| 1403 | 2-Cl-4-MeOCH2CH2CH2O—Ph |
| 1404 | 2-Cl-5-MeOCH2CH2CH2O—Ph |
| 1405 | 2-Cl-6-MeOCH2CH2CH2O—Ph |
| 1406 | 2-Br-3-MeOCH2CH2CH2O—Ph |
| 1407 | 2-Br-4-MeOCH2CH2CH2O—Ph |
| 1408 | 2-Br-5-MeOCH2CH2CH2O—Ph |
| 1409 | 2-Br-6-MeOCH2CH2CH2O—Ph |
| 1410 | 2-I-3-MeOCH2CH2CH2O—Ph |
| 1411 | 2-I-4-MeOCH2CH2CH2O—Ph |
| 1412 | 2-I-5-MeOCH2CH2CH2O—Ph |
| 1413 | 2-I-6-MeOCH2CH2CH2O—Ph |
| 1414 | 2-Me-3-MeOCH2CH2CH2O—Ph |
| 1415 | 2-Me-4-MeOCH2CH2CH2O—Ph |
| 1416 | 2-Me-5-MeOCH2CH2CH2O—Ph |
| 1417 | 2-Me-6-MeOCH2CH2CH2O—Ph |
| 1418 | 2-F-3-MeOCH2CH2OCH2O—Ph |
| 1419 | 2-F-4-MeOCH2CH2OCH2O—Ph |
| 1420 | 2-F-5-MeOCH2CH2OCH2O—Ph |
| 1421 | 2-F-6-MeOCH2CH2OCH2O—Ph |
| 1422 | 2-Cl-3-MeOCH2CH2OCH2O—Ph |
| 1423 | 2-Cl-4-MeOCH2CH2OCH2O—Ph |
| 1424 | 2-Cl-5-MeOCH2CH2OCH2O—Ph |
| 1425 | 2-Cl-6-MeOCH2CH2OCH2O—Ph |
| 1426 | 2-Br-3-MeOCH2CH2OCH2O—Ph |
| 1427 | 2-Br-4-MeOCH2CH2OCH2O—Ph |
| 1428 | 2-Br-5-MeOCH2CH2OCH2O—Ph |
| 1429 | 2-Br-6-MeOCH2CH2OCH2O—Ph |
| 1430 | 2-I-3-MeOCH2CH2OCH2O—Ph |
| 1431 | 2-I-4-MeOCH2CH2OCH2O—Ph |
| 1432 | 2-I-5-MeOCH2CH2OCH2O—Ph |
| 1433 | 2-I-6-MeOCH2CH2OCH2O—Ph |
| 1434 | 2-Me-3-MeOCH2CH2OCH2O—Ph |
| 1435 | 2-Me-4-MeOCH2CH2OCH2O—Ph |
| 1436 | 2-Me-5-MeOCH2CH2OCH2O—Ph |

TABLE 2-continued

| No. | Z |
|---|---|
| 1437 | 2-Me-6-MeOCH2CH2OCH2O—Ph |
| 1438 | 2-F-3-MeSCH2O—Ph |
| 1439 | 2-F-4-MeSCH2O—Ph |
| 1440 | 2-F-5-MeSCH2O—Ph |
| 1441 | 2-F-6-MeSCH2O—Ph |
| 1442 | 2-Cl-3-MeSCH2O—Ph |
| 1443 | 2-Cl-4-MeSCH2O—Ph |
| 1444 | 2-Cl-5-MeSCH2O—Ph |
| 1445 | 2-Cl-6-MeSCH2O—Ph |
| 1446 | 2-Br-3-MeSCH2O—Ph |
| 1447 | 2-Br-4-MeSCH2O—Ph |
| 1448 | 2-Br-5-MeSCH2O—Ph |
| 1449 | 2-Br-6-MeSCH2O—Ph |
| 1450 | 2-I-3-MeSCH2O—Ph |
| 1451 | 2-I-4-MeSCH2O—Ph |
| 1452 | 2-I-5-MeSCH2O—Ph |
| 1453 | 2-I-6-MeSCH2O—Ph |
| 1454 | 2-Me-3-MeSCH2O—Ph |
| 1455 | 2-Me-4-MeSCH2O—Ph |
| 1456 | 2-Me-5-MeSCH2O—Ph |
| 1457 | 2-Me-6-MeSCH2O—Ph |
| 1458 | 2-F-3-MeS(O)CH2O—Ph |
| 1459 | 2-F-4-MeS(O)CH2O—Ph |
| 1460 | 2-F-5-MeS(O)CH2O—Ph |
| 1461 | 2-F-6-MeS(O)CH2O—Ph |
| 1462 | 2-Cl-3-MeS(O)CH2O—Ph |
| 1463 | 2-Cl-4-MeS(O)CH2O—Ph |
| 1464 | 2-Cl-5-MeS(O)CH2O—Ph |
| 1465 | 2-Cl-6-MeS(O)CH2O—Ph |
| 1466 | 2-Br-3-MeS(O)CH2O—Ph |
| 1467 | 2-Br-4-MeS(O)CH2O—Ph |
| 1468 | 2-Br-5-MeS(O)CH2O—Ph |
| 1469 | 2-Br-6-MeS(O)CH2O—Ph |
| 1470 | 2-I-3-MeS(O)CH2O—Ph |
| 1471 | 2-I-4-MeS(O)CH2O—Ph |
| 1472 | 2-I-5-MeS(O)CH2O—Ph |
| 1473 | 2-I-6-MeS(O)CH2O—Ph |
| 1474 | 2-Me-3-MeS(O)CH2O—Ph |
| 1475 | 2-Me-4-MeS(O)CH2O—Ph |
| 1476 | 2-Me-5-MeS(O)CH2O—Ph |
| 1477 | 2-Me-6-MeS(O)CH2O—Ph |
| 1478 | 2-F-3-MeSO2CH2O—Ph |
| 1479 | 2-F-4-MeSO2CH2O—Ph |
| 1480 | 2-F-5-MeSO2CH2O—Ph |
| 1481 | 2-F-6-MeSO2CH2O—Ph |
| 1482 | 2-Cl-3-MeSO2CH2O—Ph |
| 1483 | 2-Cl-4-MeSO2CH2O—Ph |
| 1484 | 2-Cl-5-MeSO2CH2O—Ph |
| 1485 | 2-Cl-6-MeSO2CH2O—Ph |
| 1486 | 2-Br-3-MeSO2CH2O—Ph |
| 1487 | 2-Br-4-MeSO2CH2O—Ph |
| 1488 | 2-Br-5-MeSO2CH2O—Ph |
| 1489 | 2-Br-6-MeSO2CH2O—Ph |
| 1490 | 2-I-3-MeSO2CH2O—Ph |
| 1491 | 2-I-4-MeSO2CH2O—Ph |
| 1492 | 2-I-5-MeSO2CH2O—Ph |
| 1493 | 2-I-6-MeSO2CH2O—Ph |
| 1494 | 2-Me-3-MeSO2CH2O—Ph |
| 1495 | 2-Me-4-MeSO2CH2O—Ph |
| 1496 | 2-Me-5-MeSO2CH2O—Ph |
| 1497 | 2-Me-6-MeSO2CH2O—Ph |
| 1498 | 2-F-3-AcCH2O—Ph |
| 1499 | 2-F-4-AcCH2O—Ph |
| 1500 | 2-F-5-AcCH2O—Ph |
| 1501 | 2-F-6-AcCH2O—Ph |
| 1502 | 2-Cl-3-AcCH2O—Ph |
| 1503 | 2-Cl-4-AcCH2O—Ph |
| 1504 | 2-Cl-5-AcCH2O—Ph |
| 1505 | 2-Cl-6-AcCH2O—Ph |
| 1506 | 2-Br-3-AcCH2O—Ph |
| 1507 | 2-Br-4-AcCH2O—Ph |
| 1508 | 2-Br-5-AcCH2O—Ph |
| 1509 | 2-Br-6-AcCH2O—Ph |
| 1510 | 2-I-3-AcCH2O—Ph |
| 1511 | 2-I-4-AcCH2O—Ph |
| 1512 | 2-I-5-AcCH2O—Ph |
| 1513 | 2-I-6-AcCH2O—Ph |
| 1514 | 2-Me-3-AcCH2O—Ph |
| 1515 | 2-Me-4-AcCH2O—Ph |
| 1516 | 2-Me-5-AcCH2O—Ph |
| 1517 | 2-Me-6-AcCH2O—Ph |
| 1518 | 2-F-3-MeOC(=O)CH2O—Ph |
| 1519 | 2-F-4-MeOC(=O)CH2O—Ph |
| 1520 | 2-F-5-MeOC(=O)CH2O—Ph |
| 1521 | 2-F-6-MeOC(=O)CH2O—Ph |
| 1522 | 2-Cl-3-MeOC(=O)CH2O—Ph |
| 1523 | 2-Cl-4-MeOC(=O)CH2O—Ph |
| 1524 | 2-Cl-5-MeOC(=O)CH2O—Ph |
| 1525 | 2-Cl-6-MeOC(=O)CH2O—Ph |
| 1526 | 2-Br-3-MeOC(=O)CH2O—Ph |
| 1527 | 2-Br-4-MeOC(=O)CH2O—Ph |
| 1528 | 2-Br-5-MeOC(=O)CH2O—Ph |
| 1529 | 2-Br-6-MeOC(=O)CH2O—Ph |
| 1530 | 2-I-3-MeOC(=O)CH2O—Ph |
| 1531 | 2-I-4-MeOC(=O)CH2O—Ph |
| 1532 | 2-I-5-MeOC(=O)CH2O—Ph |
| 1533 | 2-I-6-MeOC(=O)CH2O—Ph |
| 1534 | 2-Me-3-MeOC(=O)CH2O—Ph |
| 1535 | 2-Me-4-MeOC(=O)CH2O—Ph |
| 1536 | 2-Me-5-MeOC(=O)CH2O—Ph |
| 1537 | 2-Me-6-MeOC(=O)CH2O—Ph |
| 1538 | 2-F-3-EtOC(=O)CH2O—Ph |
| 1539 | 2-F-4-EtOC(=O)CH2O—Ph |
| 1540 | 2-F-5-EtOC(=O)CH2O—Ph |
| 1541 | 2-F-6-EtOC(=O)CH2O—Ph |
| 1542 | 2-Cl-3-EtOC(=O)CH2O—Ph |
| 1543 | 2-Cl-4-EtOC(=O)CH2O—Ph |
| 1544 | 2-Cl-5-EtOC(=O)CH2O—Ph |
| 1545 | 2-Cl-6-EtOC(=O)CH2O—Ph |
| 1546 | 2-Br-3-EtOC(=O)CH2O—Ph |
| 1547 | 2-Br-4-EtOC(=O)CH2O—Ph |
| 1548 | 2-Br-5-EtOC(=O)CH2O—Ph |
| 1549 | 2-Br-6-EtOC(=O)CH2O—Ph |
| 1550 | 2-I-3-EtOC(=O)CH2O—Ph |
| 1551 | 2-I-4-EtOC(=O)CH2O—Ph |
| 1552 | 2-I-5-EtOC(=O)CH2O—Ph |
| 1553 | 2-I-6-EtOC(=O)CH2O—Ph |
| 1554 | 2-Me-3-EtOC(=O)CH2O—Ph |
| 1555 | 2-Me-4-EtOC(=O)CH2O—Ph |
| 1556 | 2-Me-5-EtOC(=O)CH2O—Ph |
| 1557 | 2-Me-6-EtOC(=O)CH2O—Ph |
| 1558 | 2-F-3-(1,3-dioxolan-2-yl)CH2O—Ph |
| 1559 | 2-F-4-(1,3-dioxolan-2-yl)CH2O—Ph |
| 1560 | 2-F-5-(1,3-dioxolan-2-yl)CH2O—Ph |
| 1561 | 2-F-6-(1,3-dioxolan-2-yl)CH2O—Ph |
| 1562 | 2-Cl-3-(1,3-dioxolan-2-yl)CH2O—Ph |
| 1563 | 2-Cl-4-(1,3-dioxolan-2-yl)CH2O—Ph |
| 1564 | 2-Cl-5-(1,3-dioxolan-2-yl)CH2O—Ph |
| 1565 | 2-Cl-6-(1,3-dioxolan-2-yl)CH2O—Ph |
| 1566 | 2-Br-3-(1,3-dioxolan-2-yl)CH2O—Ph |
| 1567 | 2-Br-4-(1,3-dioxolan-2-yl)CH2O—Ph |
| 1568 | 2-Br-5-(1,3-dioxolan-2-yl)CH2O—Ph |
| 1569 | 2-Br-6-(1,3-dioxolan-2-yl)CH2O—Ph |
| 1570 | 2-I-3-(1,3-dioxolan-2-yl)CH2O—Ph |
| 1571 | 2-I-4-(1,3-dioxolan-2-yl)CH2O—Ph |
| 1572 | 2-I-5-(1,3-dioxolan-2-yl)CH2O—Ph |
| 1573 | 2-I-6-(1,3-dioxolan-2-yl)CH2O—Ph |
| 1574 | 2-Me-3-(1,3-dioxolan-2-yl)CH2O—Ph |
| 1575 | 2-Me-4-(1,3-dioxolan-2-yl)CH2O—Ph |
| 1576 | 2-Me-5-(1,3-dioxolan-2-yl)CH2O—Ph |
| 1577 | 2-Me-6-(1,3-dioxolan-2-yl)CH2O—Ph |
| 1578 | 2-F-3-(1,3-dioxolan-2-yl)CH2CH2O—Ph |
| 1579 | 2-F-4-(1,3-dioxolan-2-yl)CH2CH2O—Ph |
| 1580 | 2-F-5-(1,3-dioxolan-2-yl)CH2CH2O—Ph |
| 1581 | 2-F-6-(1,3-dioxolan-2-yl)CH2CH2O—Ph |
| 1582 | 2-Cl-3-(1,3-dioxolan-2-yl)CH2CH2O—Ph |
| 1583 | 2-Cl-4-(1,3-dioxolan-2-yl)CH2CH2O—Ph |
| 1584 | 2-Cl-5-(1,3-dioxolan-2-yl)CH2CH2O—Ph |
| 1585 | 2-Cl-6-(1,3-dioxolan-2-yl)CH2CH2O—Ph |
| 1586 | 2-Br-3-(1,3-dioxolan-2-yl)CH2CH2O—Ph |
| 1587 | 2-Br-4-(1,3-dioxolan-2-yl)CH2CH2O—Ph |
| 1588 | 2-Br-5-(1,3-dioxolan-2-yl)CH2CH2O—Ph |
| 1589 | 2-Br-6-(1,3-dioxolan-2-yl)CH2CH2O—Ph |
| 1590 | 2-I-3-(1,3-dioxolan-2-yl)CH2CH2O—Ph |
| 1591 | 2-I-4-(1,3-dioxolan-2-yl)CH2CH2O—Ph |
| 1592 | 2-I-5-(1,3-dioxolan-2-yl)CH2CH2O—Ph |

TABLE 2-continued

| No. | Z |
|---|---|
| 1593 | 2-I-6-(1,3-dioxolan-2-yl)CH2CH2O—Ph |
| 1594 | 2-Me-3-(1,3-dioxolan-2-yl)CH2CH2O—Ph |
| 1595 | 2-Me-4-(1,3-dioxolan-2-yl)CH2CH2O—Ph |
| 1596 | 2-Me-5-(1,3-dioxolan-2-yl)CH2CH2O—Ph |
| 1597 | 2-Me-6-(1,3-dioxolan-2-yl)CH2CH2O—Ph |
| 1598 | 2-F-3-(1,3-dioxan-2-yl)CH2O—Ph |
| 1599 | 2-F-4-(1,3-dioxan-2-yl)CH2O—Ph |
| 1600 | 2-F-5-(1,3-dioxan-2-yl)CH2O—Ph |
| 1601 | 2-F-6-(1,3-dioxan-2-yl)CH2O—Ph |
| 1602 | 2-Cl-3-(1,3-dioxan-2-yl)CH2O—Ph |
| 1603 | 2-Cl-4-(1,3-dioxan-2-yl)CH2O—Ph |
| 1604 | 2-Cl-5-(1,3-dioxan-2-yl)CH2O—Ph |
| 1605 | 2-Cl-6-(1,3-dioxan-2-yl)CH2O—Ph |
| 1606 | 2-Br-3-(1,3-dioxan-2-yl)CH2O—Ph |
| 1607 | 2-Br-4-(1,3-dioxan-2-yl)CH2O—Ph |
| 1608 | 2-Br-5-(1,3-dioxan-2-yl)CH2O—Ph |
| 1609 | 2-Br-6-(1,3-dioxan-2-yl)CH2O—Ph |
| 1610 | 2-I-3-(1,3-dioxan-2-yl)CH2O—Ph |
| 1611 | 2-I-4-(1,3-dioxan-2-yl)CH2O—Ph |
| 1612 | 2-I-5-(1,3-dioxan-2-yl)CH2O—Ph |
| 1613 | 2-I-6-(1,3-dioxan-2-yl)CH2O—Ph |
| 1614 | 2-Me-3-(1,3-dioxan-2-yl)CH2O—Ph |
| 1615 | 2-Me-4-(1,3-dioxan-2-yl)CH2O—Ph |
| 1616 | 2-Me-5-(1,3-dioxan-2-yl)CH2O—Ph |
| 1617 | 2-Me-6-(1,3-dioxan-2-yl)CH2O—Ph |
| 1618 | 2-F-3-(1,3-dioxan-2-yl)CH2CH2O—Ph |
| 1619 | 2-F-4-(1,3-dioxan-2-yl)CH2CH2O—Ph |
| 1620 | 2-F-5-(1,3-dioxan-2-yl)CH2CH2O—Ph |
| 1621 | 2-F-6-(1,3-dioxan-2-yl)CH2CH2O—Ph |
| 1622 | 2-Cl-3-(1,3-dioxan-2-yl)CH2CH2O—Ph |
| 1623 | 2-Cl-4-(1,3-dioxan-2-yl)CH2CH2O—Ph |
| 1624 | 2-Cl-5-(1,3-dioxan-2-yl)CH2CH2O—Ph |
| 1625 | 2-Cl-6-(1,3-dioxan-2-yl)CH2CH2O—Ph |
| 1626 | 2-Br-3-(1,3-dioxan-2-yl)CH2CH2O—Ph |
| 1627 | 2-Br-4-(1,3-dioxan-2-yl)CH2CH2O—Ph |
| 1628 | 2-Br-5-(1,3-dioxan-2-yl)CH2CH2O—Ph |
| 1629 | 2-Br-6-(1,3-dioxan-2-yl)CH2CH2O—Ph |
| 1630 | 2-I-3-(1,3-dioxan-2-yl)CH2CH2O—Ph |
| 1631 | 2-I-4-(1,3-dioxan-2-yl)CH2CH2O—Ph |
| 1632 | 2-I-5-(1,3-dioxan-2-yl)CH2CH2O—Ph |
| 1633 | 2-I-6-(1,3-dioxan-2-yl)CH2CH2O—Ph |
| 1634 | 2-Me-3-(1,3-dioxan-2-yl)CH2CH2O—Ph |
| 1635 | 2-Me-4-(1,3-dioxan-2-yl)CH2CH2O—Ph |
| 1636 | 2-Me-5-(1,3-dioxan-2-yl)CH2CH2O—Ph |
| 1637 | 2-Me-6-(1,3-dioxan-2-yl)CH2CH2O—Ph |
| 1638 | 2-F-3-cPrO—Ph |
| 1639 | 2-F-4-cPrO—Ph |
| 1640 | 2-F-5-cPrO—Ph |
| 1641 | 2-F-6-cPrO—Ph |
| 1642 | 2-Cl-3-cPrO—Ph |
| 1643 | 2-Cl-4-cPrO—Ph |
| 1644 | 2-Cl-5-cPrO—Ph |
| 1645 | 2-Cl-6-cPrO—Ph |
| 1646 | 2-Br-3-cPrO—Ph |
| 1647 | 2-Br-4-cPrO—Ph |
| 1648 | 2-Br-5-cPrO—Ph |
| 1649 | 2-Br-6-cPrO—Ph |
| 1650 | 2-I-3-cPrO—Ph |
| 1651 | 2-I-4-cPrO—Ph |
| 1652 | 2-I-5-cPrO—Ph |
| 1653 | 2-I-6-cPrO—Ph |
| 1654 | 2-Me-3-cPrO—Ph |
| 1655 | 2-Me-4-cPrO—Ph |
| 1656 | 2-Me-5-cPrO—Ph |
| 1657 | 2-Me-6-cPrO—Ph |
| 1658 | 2-F-3-cBuO—Ph |
| 1659 | 2-F-4-cBuO—Ph |
| 1660 | 2-F-5-cBuO—Ph |
| 1661 | 2-F-6-cBuO—Ph |
| 1662 | 2-Cl-3-cBuO—Ph |
| 1663 | 2-Cl-4-cBuO—Ph |
| 1664 | 2-Cl-5-cBuO—Ph |
| 1665 | 2-Cl-6-cBuO—Ph |
| 1666 | 2-Br-3-cBuO—Ph |
| 1667 | 2-Br-4-cBuO—Ph |
| 1668 | 2-Br-5-cBuO—Ph |
| 1669 | 2-Br-6-cBuO—Ph |
| 1670 | 2-I-3-cBuO—Ph |
| 1671 | 2-I-4-cBuO—Ph |
| 1672 | 2-I-5-cBuO—Ph |
| 1673 | 2-I-6-cBuO—Ph |
| 1674 | 2-Me-3-cBuO—Ph |
| 1675 | 2-Me-4-cBuO—Ph |
| 1676 | 2-Me-5-cBuO—Ph |
| 1677 | 2-Me-6-cBuO—Ph |
| 1678 | 2-F-3-cPentylO—Ph |
| 1679 | 2-F-4-cPentylO—Ph |
| 1680 | 2-F-5-cPentylO—Ph |
| 1681 | 2-F-6-cPentylO—Ph |
| 1682 | 2-Cl-3-cPentylO—Ph |
| 1683 | 2-Cl-4-cPentylO—Ph |
| 1684 | 2-Cl-5-cPentylO—Ph |
| 1685 | 2-Cl-6-cPentylO—Ph |
| 1686 | 2-Br-3-cPentylO—Ph |
| 1687 | 2-Br-4-cPentylO—Ph |
| 1688 | 2-Br-5-cPentylO—Ph |
| 1689 | 2-Br-6-cPentylO—Ph |
| 1690 | 2-I-3-cPentylO—Ph |
| 1691 | 2-I-4-cPentylO—Ph |
| 1692 | 2-I-5-cPentylO—Ph |
| 1693 | 2-I-6-cPentylO—Ph |
| 1694 | 2-Me-3-cPentylO—Ph |
| 1695 | 2-Me-4-cPentylO—Ph |
| 1696 | 2-Me-5-cPentylO—Ph |
| 1697 | 2-Me-6-cPentylO—Ph |
| 1698 | 2-F-3-cHexylO—Ph |
| 1699 | 2-F-4-cHexylO—Ph |
| 1700 | 2-F-5-cHexylO—Ph |
| 1701 | 2-F-6-cHexylO—Ph |
| 1702 | 2-Cl-3-cHexylO—Ph |
| 1703 | 2-Cl-4-cHexylO—Ph |
| 1704 | 2-Cl-5-cHexylO—Ph |
| 1705 | 2-Cl-6-cHexylO—Ph |
| 1706 | 2-Br-3-cHexylO—Ph |
| 1707 | 2-Br-4-cHexylO—Ph |
| 1708 | 2-Br-5-cHexylO—Ph |
| 1709 | 2-Br-6-cHexylO—Ph |
| 1710 | 2-I-3-cHexylO—Ph |
| 1711 | 2-I-4-cHexylO—Ph |
| 1712 | 2-I-5-cHexylO—Ph |
| 1713 | 2-I-6-cHexylO—Ph |
| 1714 | 2-Me-3-cHexylO—Ph |
| 1715 | 2-Me-4-cHexylO—Ph |
| 1716 | 2-Me-5-cHexylO—Ph |
| 1717 | 2-Me-6-cHexylO—Ph |
| 1718 | 2-F-3-F3CO—Ph |
| 1719 | 2-F-4-F3CO—Ph |
| 1720 | 2-F-5-F3CO—Ph |
| 1721 | 2-F-6-F3CO—Ph |
| 1722 | 2-Cl-3-F3CO—Ph |
| 1723 | 2-Cl-4-F3CO—Ph |
| 1724 | 2-Cl-5-F3CO—Ph |
| 1725 | 2-Cl-6-F3CO—Ph |
| 1726 | 2-Br-3-F3CO—Ph |
| 1727 | 2-Br-4-F3CO—Ph |
| 1728 | 2-Br-5-F3CO—Ph |
| 1729 | 2-Br-6-F3CO—Ph |
| 1730 | 2-I-3-F3CO—Ph |
| 1731 | 2-I-4-F3CO—Ph |
| 1732 | 2-I-5-F3CO—Ph |
| 1733 | 2-I-6-F3CO—Ph |
| 1734 | 2-Me-3-F3CO—Ph |
| 1735 | 2-Me-4-F3CO—Ph |
| 1736 | 2-Me-5-F3CO—Ph |
| 1737 | 2-Me-6-F3CO—Ph |
| 1738 | 2-F-3-F2CHO—Ph |
| 1739 | 2-F-4-F2CHO—Ph |
| 1740 | 2-F-5-F2CHO—Ph |
| 1741 | 2-F-6-F2CHO—Ph |
| 1742 | 2-Cl-3-F2CHO—Ph |
| 1743 | 2-Cl-4-F2CHO—Ph |
| 1744 | 2-Cl-5-F2CHO—Ph |
| 1745 | 2-Cl-6-F2CHO—Ph |
| 1746 | 2-Br-3-F2CHO—Ph |
| 1747 | 2-Br-4-F2CHO—Ph |
| 1748 | 2-Br-5-F2CHO—Ph |

TABLE 2-continued

| No. | Z |
|---|---|
| 1749 | 2-Br-6-F2CHO—Ph |
| 1750 | 2-I-3-F2CHO—Ph |
| 1751 | 2-I-4-F2CHO—Ph |
| 1752 | 2-I-5-F2CHO—Ph |
| 1753 | 2-I-6-F2CHO—Ph |
| 1754 | 2-Me-3-F2CHO—Ph |
| 1755 | 2-Me-4-F2CHO—Ph |
| 1756 | 2-Me-5-F2CHO—Ph |
| 1757 | 2-Me-6-F2CHO—Ph |
| 1758 | 2-F-3-F3CCH2O—Ph |
| 1759 | 2-F-4-F3CCH2O—Ph |
| 1760 | 2-F-5-F3CCH2O—Ph |
| 1761 | 2-F-6-F3CCH2O—Ph |
| 1762 | 2-Cl-3-F3CCH2O—Ph |
| 1763 | 2-Cl-4-F3CCH2O—Ph |
| 1764 | 2-Cl-5-F3CCH2O—Ph |
| 1765 | 2-Cl-6-F3CCH2O—Ph |
| 1766 | 2-Br-3-F3CCH2O—Ph |
| 1767 | 2-Br-4-F3CCH2O—Ph |
| 1768 | 2-Br-5-F3CCH2O—Ph |
| 1769 | 2-Br-6-F3CCH2O—Ph |
| 1770 | 2-I-3-F3CCH2O—Ph |
| 1771 | 2-I-4-F3CCH2O—Ph |
| 1772 | 2-I-5-F3CCH2O—Ph |
| 1773 | 2-I-6-F3CCH2O—Ph |
| 1774 | 2-Me-3-F3CCH2O—Ph |
| 1775 | 2-Me-4-F3CCH2O—Ph |
| 1776 | 2-Me-5-F3CCH2O—Ph |
| 1777 | 2-Me-6-F3CCH2O—Ph |
| 1778 | 2-F-3-F2CHCH2O—Ph |
| 1779 | 2-F-4-F2CHCH2O—Ph |
| 1780 | 2-F-5-F2CHCH2O—Ph |
| 1781 | 2-F-6-F2CHCH2O—Ph |
| 1782 | 2-Cl-3-F2CHCH2O—Ph |
| 1783 | 2-Cl-4-F2CHCH2O—Ph |
| 1784 | 2-Cl-5-F2CHCH2O—Ph |
| 1785 | 2-Cl-6-F2CHCH2O—Ph |
| 1786 | 2-Br-3-F2CHCH2O—Ph |
| 1787 | 2-Br-4-F2CHCH2O—Ph |
| 1788 | 2-Br-5-F2CHCH2O—Ph |
| 1789 | 2-Br-6-F2CHCH2O—Ph |
| 1790 | 2-I-3-F2CHCH2O—Ph |
| 1791 | 2-I-4-F2CHCH2O—Ph |
| 1792 | 2-I-5-F2CHCH2O—Ph |
| 1793 | 2-I-6-F2CHCH2O—Ph |
| 1794 | 2-Me-3-F2CHCH2O—Ph |
| 1795 | 2-Me-4-F2CHCH2O—Ph |
| 1796 | 2-Me-5-F2CHCH2O—Ph |
| 1797 | 2-Me-6-F2CHCH2O—Ph |
| 1798 | 2-F-3-H2C=CHCH2O—Ph |
| 1799 | 2-F-4-H2C=CHCH2O—Ph |
| 1800 | 2-F-5-H2C=CHCH2O—Ph |
| 1801 | 2-F-6-H2C=CHCH2O—Ph |
| 1802 | 2-Cl-3-H2C=CHCH2O—Ph |
| 1803 | 2-Cl-4-H2C=CHCH2O—Ph |
| 1804 | 2-Cl-5-H2C=CHCH2O—Ph |
| 1805 | 2-Cl-6-H2C=CHCH2O—Ph |
| 1806 | 2-Br-3-H2C=CHCH2O—Ph |
| 1807 | 2-Br-4-H2C=CHCH2O—Ph |
| 1808 | 2-Br-5-H2C=CHCH2O—Ph |
| 1809 | 2-Br-6-H2C=CHCH2O—Ph |
| 1810 | 2-I-3-H2C=CHCH2O—Ph |
| 1811 | 2-I-4-H2C=CHCH2O—Ph |
| 1812 | 2-I-5-H2C=CHCH2O—Ph |
| 1813 | 2-I-6-H2C=CHCH2O—Ph |
| 1814 | 2-Me-3-H2C=CHCH2O—Ph |
| 1815 | 2-Me-4-H2C=CHCH2O—Ph |
| 1816 | 2-Me-5-H2C=CHCH2O—Ph |
| 1817 | 2-Me-6-H2C=CHCH2O—Ph |
| 1818 | 2-F-3-HC≡CCH2O—Ph |
| 1819 | 2-F-4-HC≡CCH2O—Ph |
| 1820 | 2-F-5-HC≡CCH2O—Ph |
| 1821 | 2-F-6-HC≡CCH2O—Ph |
| 1822 | 2-Cl-3-HC≡CCH2O—Ph |
| 1823 | 2-Cl-4-HC≡CCH2O—Ph |
| 1824 | 2-Cl-5-HC≡CCH2O—Ph |
| 1825 | 2-Cl-6-HC≡CCH2O—Ph |
| 1826 | 2-Br-3-HC≡CCH2O—Ph |
| 1827 | 2-Br-4-HC≡CCH2O—Ph |
| 1828 | 2-Br-5-HC≡CCH2O—Ph |
| 1829 | 2-Br-6-HC≡CCH2O—Ph |
| 1830 | 2-I-3-HC≡CCH2O—Ph |
| 1831 | 2-I-4-HC≡CCH2O—Ph |
| 1832 | 2-I-5-HC≡CCH2O—Ph |
| 1833 | 2-I-6-HC≡CCH2O—Ph |
| 1834 | 2-Me-3-HC≡CCH2O—Ph |
| 1835 | 2-Me-4-HC≡CCH2O—Ph |
| 1836 | 2-Me-5-HC≡CCH2O—Ph |
| 1837 | 2-Me-6-HC≡CCH2O—Ph |
| 1838 | 2-F-3-Ac—Ph |
| 1839 | 2-F-4-Ac—Ph |
| 1840 | 2-F-5-Ac—Ph |
| 1841 | 2-F-6-Ac—Ph |
| 1842 | 2-Cl-3-Ac—Ph |
| 1843 | 2-Cl-4-Ac—Ph |
| 1844 | 2-Cl-5-Ac—Ph |
| 1845 | 2-Cl-6-Ac—Ph |
| 1846 | 2-Br-3-Ac—Ph |
| 1847 | 2-Br-4-Ac—Ph |
| 1848 | 2-Br-5-Ac—Ph |
| 1849 | 2-Br-6-Ac—Ph |
| 1850 | 2-I-3-Ac—Ph |
| 1851 | 2-I-4-Ac—Ph |
| 1852 | 2-I-5-Ac—Ph |
| 1853 | 2-I-6-Ac—Ph |
| 1854 | 2-Me-3-Ac—Ph |
| 1855 | 2-Me-4-Ac—Ph |
| 1856 | 2-Me-5-Ac—Ph |
| 1857 | 2-Me-6-Ac—Ph |
| 1858 | 2-F-3-MeOC(=O)—Ph |
| 1859 | 2-F-4-MeOC(=O)—Ph |
| 1860 | 2-F-5-MeOC(=O)—Ph |
| 1861 | 2-F-6-MeOC(=O)—Ph |
| 1862 | 2-Cl-3-MeOC(=O)—Ph |
| 1863 | 2-Cl-4-MeOC(=O)—Ph |
| 1864 | 2-Cl-5-MeOC(=O)—Ph |
| 1865 | 2-Cl-6-MeOC(=O)—Ph |
| 1866 | 2-Br-3-MeOC(=O)—Ph |
| 1867 | 2-Br-4-MeOC(=O)—Ph |
| 1868 | 2-Br-5-MeOC(=O)—Ph |
| 1869 | 2-Br-6-MeOC(=O)—Ph |
| 1870 | 2-I-3-MeOC(=O)—Ph |
| 1871 | 2-I-4-MeOC(=O)—Ph |
| 1872 | 2-I-5-MeOC(=O)—Ph |
| 1873 | 2-I-6-MeOC(=O)—Ph |
| 1874 | 2-Me-3-MeOC(=O)—Ph |
| 1875 | 2-Me-4-MeOC(=O)—Ph |
| 1876 | 2-Me-5-MeOC(=O)—Ph |
| 1877 | 2-Me-6-MeOC(=O)—Ph |
| 1878 | 2-F-3-EtOC(=O)—Ph |
| 1879 | 2-F-4-EtOC(=O)—Ph |
| 1880 | 2-F-5-EtOC(=O)—Ph |
| 1881 | 2-F-6-EtOC(=O)—Ph |
| 1882 | 2-Cl-3-EtOC(=O)—Ph |
| 1883 | 2-Cl-4-EtOC(=O)—Ph |
| 1884 | 2-Cl-5-EtOC(=O)—Ph |
| 1885 | 2-Cl-6-EtOC(=O)—Ph |
| 1886 | 2-Br-3-EtOC(=O)—Ph |
| 1887 | 2-Br-4-EtOC(=O)—Ph |
| 1888 | 2-Br-5-EtOC(=O)—Ph |
| 1889 | 2-Br-6-EtOC(=O)—Ph |
| 1890 | 2-I-3-EtOC(=O)—Ph |
| 1891 | 2-I-4-EtOC(=O)—Ph |
| 1892 | 2-I-5-EtOC(=O)—Ph |
| 1893 | 2-I-6-EtOC(=O)—Ph |
| 1894 | 2-Me-3-EtOC(=O)—Ph |
| 1895 | 2-Me-4-EtOC(=O)—Ph |
| 1896 | 2-Me-5-EtOC(=O)—Ph |
| 1897 | 2-Me-6-EtOC(=O)—Ph |
| 1898 | 2-F-3-AcO—Ph |
| 1899 | 2-F-4-AcO—Ph |
| 1900 | 2-F-5-AcO—Ph |
| 1901 | 2-F-6-AcO—Ph |
| 1902 | 2-Cl-3-AcO—Ph |
| 1903 | 2-Cl-4-AcO—Ph |
| 1904 | 2-Cl-5-AcO—Ph |

TABLE 2-continued

| No. | Z |
|---|---|
| 1905 | 2-Cl-6-AcO—Ph |
| 1906 | 2-Br-3-AcO—Ph |
| 1907 | 2-Br-4-AcO—Ph |
| 1908 | 2-Br-5-AcO—Ph |
| 1909 | 2-Br-6-AcO—Ph |
| 1910 | 2-I-3-AcO—Ph |
| 1911 | 2-I-4-AcO—Ph |
| 1912 | 2-I-5-AcO—Ph |
| 1913 | 2-I-6-AcO—Ph |
| 1914 | 2-Me-3-AcO—Ph |
| 1915 | 2-Me-4-AcO—Ph |
| 1916 | 2-Me-5-AcO—Ph |
| 1917 | 2-Me-6-AcO—Ph |
| 1918 | 2-F-3-MeOC(=O)O—Ph |
| 1919 | 2-F-4-MeOC(=O)O—Ph |
| 1920 | 2-F-5-MeOC(=O)O—Ph |
| 1921 | 2-F-6-MeOC(=O)O—Ph |
| 1922 | 2-Cl-3-MeOC(=O)O—Ph |
| 1923 | 2-Cl-4-MeOC(=O)O—Ph |
| 1924 | 2-Cl-5-MeOC(=O)O—Ph |
| 1925 | 2-Cl-6-MeOC(=O)O—Ph |
| 1926 | 2-Br-3-MeOC(=O)O—Ph |
| 1927 | 2-Br-4-MeOC(=O)O—Ph |
| 1928 | 2-Br-5-MeOC(=O)O—Ph |
| 1929 | 2-Br-6-MeOC(=O)O—Ph |
| 1930 | 2-I-3-MeOC(=O)O—Ph |
| 1931 | 2-I-4-MeOC(=O)O—Ph |
| 1932 | 2-I-5-MeOC(=O)O—Ph |
| 1933 | 2-I-6-MeOC(=O)O—Ph |
| 1934 | 2-Me-3-MeOC(=O)O—Ph |
| 1935 | 2-Me-4-MeOC(=O)O—Ph |
| 1936 | 2-Me-5-MeOC(=O)O—Ph |
| 1937 | 2-Me-6-MeOC(=O)O—Ph |
| 1938 | 2-F-3-EtOC(=O)O—Ph |
| 1939 | 2-F-4-EtOC(=O)O—Ph |
| 1940 | 2-F-5-EtOC(=O)O—Ph |
| 1941 | 2-F-6-EtOC(=O)O—Ph |
| 1942 | 2-Cl-3-EtOC(=O)O—Ph |
| 1943 | 2-Cl-4-EtOC(=O)O—Ph |
| 1944 | 2-Cl-5-EtOC(=O)O—Ph |
| 1945 | 2-Cl-6-EtOC(=O)O—Ph |
| 1946 | 2-Br-3-EtOC(=O)O—Ph |
| 1947 | 2-Br-4-EtOC(=O)O—Ph |
| 1948 | 2-Br-5-EtOC(=O)O—Ph |
| 1949 | 2-Br-6-EtOC(=O)O—Ph |
| 1950 | 2-I-3-EtOC(=O)O—Ph |
| 1951 | 2-I-4-EtOC(=O)O—Ph |
| 1952 | 2-I-5-EtOC(=O)O—Ph |
| 1953 | 2-I-6-EtOC(=O)O—Ph |
| 1954 | 2-Me-3-EtOC(=O)O—Ph |
| 1955 | 2-Me-4-EtOC(=O)O—Ph |
| 1956 | 2-Me-5-EtOC(=O)O—Ph |
| 1957 | 2-Me-6-EtOC(=O)O—Ph |
| 1958 | 2-F-3-(1,3-dioxolan-2-yl)-Ph |
| 1959 | 2-F-4-(1,3-dioxolan-2-yl)-Ph |
| 1960 | 2-F-5-(1,3-dioxolan-2-yl)-Ph |
| 1961 | 2-F-6-(1,3-dioxolan-2-yl)-Ph |
| 1962 | 2-Cl-3-(1,3-dioxolan-2-yl)-Ph |
| 1963 | 2-Cl-4-(1,3-dioxolan-2-yl)-Ph |
| 1964 | 2-Cl-5-(1,3-dioxolan-2-yl)-Ph |
| 1965 | 2-Cl-6-(1,3-dioxolan-2-yl)-Ph |
| 1966 | 2-Br-3-(1,3-dioxolan-2-yl)-Ph |
| 1967 | 2-Br-4-(1,3-dioxolan-2-yl)-Ph |
| 1968 | 2-Br-5-(1,3-dioxolan-2-yl)-Ph |
| 1969 | 2-Br-6-(1,3-dioxolan-2-yl)-Ph |
| 1970 | 2-I-3-(1,3-dioxolan-2-yl)-Ph |
| 1971 | 2-I-4-(1,3-dioxolan-2-yl)-Ph |
| 1972 | 2-I-5-(1,3-dioxolan-2-yl)-Ph |
| 1973 | 2-I-6-(1,3-dioxolan-2-yl)-Ph |
| 1974 | 2-Me-3-(1,3-dioxolan-2-yl)-Ph |
| 1975 | 2-Me-4-(1,3-dioxolan-2-yl)-Ph |
| 1976 | 2-Me-5-(1,3-dioxolan-2-yl)-Ph |
| 1977 | 2-Me-6-(1,3-dioxolan-2-yl)-Ph |
| 1978 | 2-F-3-(1,3-dioxan-2-yl)-Ph |
| 1979 | 2-F-4-(1,3-dioxan-2-yl)-Ph |
| 1980 | 2-F-5-(1,3-dioxan-2-yl)-Ph |
| 1981 | 2-F-6-(1,3-dioxan-2-yl)-Ph |
| 1982 | 2-Cl-3-(1,3-dioxan-2-yl)-Ph |
| 1983 | 2-Cl-4-(1,3-dioxan-2-yl)-Ph |
| 1984 | 2-Cl-5-(1,3-dioxan-2-yl)-Ph |
| 1985 | 2-Cl-6-(1,3-dioxan-2-yl)-Ph |
| 1986 | 2-Br-3-(1,3-dioxan-2-yl)-Ph |
| 1987 | 2-Br-4-(1,3-dioxan-2-yl)-Ph |
| 1988 | 2-Br-5-(1,3-dioxan-2-yl)-Ph |
| 1989 | 2-Br-6-(1,3-dioxan-2-yl)-Ph |
| 1990 | 2-I-3-(1,3-dioxan-2-yl)-Ph |
| 1991 | 2-I-4-(1,3-dioxan-2-yl)-Ph |
| 1992 | 2-I-5-(1,3-dioxan-2-yl)-Ph |
| 1993 | 2-I-6-(1,3-dioxan-2-yl)-Ph |
| 1994 | 2-Me-3-(1,3-dioxan-2-yl)-Ph |
| 1995 | 2-Me-4-(1,3-dioxan-2-yl)-Ph |
| 1996 | 2-Me-5-(1,3-dioxan-2-yl)-Ph |
| 1997 | 2-Me-6-(1,3-dioxan-2-yl)-Ph |
| 1998 | 2-F-3-MeS—Ph |
| 1999 | 2-F-4-MeS—Ph |
| 2000 | 2-F-5-MeS—Ph |
| 2001 | 2-F-6-MeS—Ph |
| 2002 | 2-Cl-3-MeS—Ph |
| 2003 | 2-Cl-4-MeS—Ph |
| 2004 | 2-Cl-5-MeS—Ph |
| 2005 | 2-Cl-6-MeS—Ph |
| 2006 | 2-Br-3-MeS—Ph |
| 2007 | 2-Br-4-MeS—Ph |
| 2008 | 2-Br-5-MeS—Ph |
| 2009 | 2-Br-6-MeS—Ph |
| 2010 | 2-I-3-MeS—Ph |
| 2011 | 2-I-4-MeS—Ph |
| 2012 | 2-I-5-MeS—Ph |
| 2013 | 2-I-6-MeS—Ph |
| 2014 | 2-Me-3-MeS—Ph |
| 2015 | 2-Me-4-MeS—Ph |
| 2016 | 2-Me-5-MeS—Ph |
| 2017 | 2-Me-6-MeS—Ph |
| 2018 | 2-F-3-MeS(O)—Ph |
| 2019 | 2-F-4-MeS(O)—Ph |
| 2020 | 2-F-5-MeS(O)—Ph |
| 2021 | 2-F-6-MeS(O)—Ph |
| 2022 | 2-Cl-3-MeS(O)—Ph |
| 2023 | 2-Cl-4-MeS(O)—Ph |
| 2024 | 2-Cl-5-MeS(O)—Ph |
| 2025 | 2-Cl-6-MeS(O)—Ph |
| 2026 | 2-Br-3-MeS(O)—Ph |
| 2027 | 2-Br-4-MeS(O)—Ph |
| 2028 | 2-Br-5-MeS(O)—Ph |
| 2029 | 2-Br-6-MeS(O)—Ph |
| 2030 | 2-I-3-MeS(O)—Ph |
| 2031 | 2-I-4-MeS(O)—Ph |
| 2032 | 2-I-5-MeS(O)—Ph |
| 2033 | 2-I-6-MeS(O)—Ph |
| 2034 | 2-Me-3-MeS(O)—Ph |
| 2035 | 2-Me-4-MeS(O)—Ph |
| 2036 | 2-Me-5-MeS(O)—Ph |
| 2037 | 2-Me-6-MeS(O)—Ph |
| 2038 | 2-F-3-MeSO2—Ph |
| 2039 | 2-F-4-MeSO2—Ph |
| 2040 | 2-F-5-MeSO2—Ph |
| 2041 | 2-F-6-MeSO2—Ph |
| 2042 | 2-Cl-3-MeSO2—Ph |
| 2043 | 2-Cl-4-MeSO2—Ph |
| 2044 | 2-Cl-5-MeSO2—Ph |
| 2045 | 2-Cl-6-MeSO2—Ph |
| 2046 | 2-Br-3-MeSO2—Ph |
| 2047 | 2-Br-4-MeSO2—Ph |
| 2048 | 2-Br-5-MeSO2—Ph |
| 2049 | 2-Br-6-MeSO2—Ph |
| 2050 | 2-I-3-MeSO2—Ph |
| 2051 | 2-I-4-MeSO2—Ph |
| 2052 | 2-I-5-MeSO2—Ph |
| 2053 | 2-I-6-MeSO2—Ph |
| 2054 | 2-Me-3-MeSO2—Ph |
| 2055 | 2-Me-4-MeSO2—Ph |
| 2056 | 2-Me-5-MeSO2—Ph |
| 2057 | 2-Me-6-MeSO2—Ph |
| 2058 | 2-F-3-ClCH2S—Ph |
| 2059 | 2-F-4-ClCH2S—Ph |
| 2060 | 2-F-5-ClCH2S—Ph |

TABLE 2-continued

| No. | Z |
|---|---|
| 2061 | 2-F-6-ClCH2S—Ph |
| 2062 | 2-Cl-3-ClCH2S—Ph |
| 2063 | 2-Cl-4-ClCH2S—Ph |
| 2064 | 2-Cl-5-ClCH2S—Ph |
| 2065 | 2-Cl-6-ClCH2S—Ph |
| 2066 | 2-Br-3-ClCH2S—Ph |
| 2067 | 2-Br-4-ClCH2S—Ph |
| 2068 | 2-Br-5-ClCH2S—Ph |
| 2069 | 2-Br-6-ClCH2S—Ph |
| 2070 | 2-I-3-ClCH2S—Ph |
| 2071 | 2-I-4-ClCH2S—Ph |
| 2072 | 2-I-5-ClCH2S—Ph |
| 2073 | 2-I-6-ClCH2S—Ph |
| 2074 | 2-Me-3-ClCH2S—Ph |
| 2075 | 2-Me-4-ClCH2S—Ph |
| 2076 | 2-Me-5-ClCH2S—Ph |
| 2077 | 2-Me-6-ClCH2S—Ph |
| 2078 | 2-F-3-ClCH2S(O)—Ph |
| 2079 | 2-F-4-ClCH2S(O)—Ph |
| 2080 | 2-F-5-ClCH2S(O)—Ph |
| 2081 | 2-F-6-ClCH2S(O)—Ph |
| 2082 | 2-Cl-3-ClCH2S(O)—Ph |
| 2083 | 2-Cl-4-ClCH2S(O)—Ph |
| 2084 | 2-Cl-5-ClCH2S(O)—Ph |
| 2085 | 2-Cl-6-ClCH2S(O)—Ph |
| 2086 | 2-Br-3-ClCH2S(O)—Ph |
| 2087 | 2-Br-4-ClCH2S(O)—Ph |
| 2088 | 2-Br-5-ClCH2S(O)—Ph |
| 2089 | 2-Br-6-ClCH2S(O)—Ph |
| 2090 | 2-I-3-ClCH2S(O)—Ph |
| 2091 | 2-I-4-ClCH2S(O)—Ph |
| 2092 | 2-I-5-ClCH2S(O)—Ph |
| 2093 | 2-I-6-ClCH2S(O)—Ph |
| 2094 | 2-Me-3-ClCH2S(O)—Ph |
| 2095 | 2-Me-4-ClCH2S(O)—Ph |
| 2096 | 2-Me-5-ClCH2S(O)—Ph |
| 2097 | 2-Me-6-ClCH2S(O)—Ph |
| 2098 | 2-F-3-ClCH2SO2—Ph |
| 2099 | 2-F-4-ClCH2SO2—Ph |
| 2100 | 2-F-5-ClCH2SO2—Ph |
| 2101 | 2-F-6-ClCH2SO2—Ph |
| 2102 | 2-Cl-3-ClCH2SO2—Ph |
| 2103 | 2-Cl-4-ClCH2SO2—Ph |
| 2104 | 2-Cl-5-ClCH2SO2—Ph |
| 2105 | 2-Cl-6-ClCH2SO2—Ph |
| 2106 | 2-Br-3-ClCH2SO2—Ph |
| 2107 | 2-Br-4-ClCH2SO2—Ph |
| 2108 | 2-Br-5-ClCH2SO2—Ph |
| 2109 | 2-Br-6-ClCH2SO2—Ph |
| 2110 | 2-I-3-ClCH2SO2—Ph |
| 2111 | 2-I-4-ClCH2SO2—Ph |
| 2112 | 2-I-5-ClCH2SO2—Ph |
| 2113 | 2-I-6-ClCH2SO2—Ph |
| 2114 | 2-Me-3-ClCH2SO2—Ph |
| 2115 | 2-Me-4-ClCH2SO2—Ph |
| 2116 | 2-Me-5-ClCH2SO2—Ph |
| 2117 | 2-Me-6-ClCH2SO2—Ph |
| 2118 | 3,5-di-MeO—Ph |
| 2119 | 3,5-di-EtO—Ph |
| 2120 | 3,5-di-F—Ph |
| 2121 | 3,5-di-Cl—Ph |
| 2122 | 3,5-di-Br—Ph |
| 2123 | 3,5-di-I—Ph |
| 2124 | 3,5-di-Me—Ph |
| 2125 | 3-F-5-Me—Ph |
| 2126 | 3-Cl-5-Me—Ph |
| 2127 | 3-Br-5-Me—Ph |
| 2128 | 3-I-5-Me—Ph |
| 2129 | 3-F-5-MeO—Ph |
| 2130 | 3-Cl-5-MeO—Ph |
| 2131 | 3-Br-5-MeO—Ph |
| 2132 | 3-I-5-MeO—Ph |
| 2133 | 5-F-3-EtO—Ph |
| 2134 | 3-Cl-5-EtO—Ph |
| 2135 | 3-Br-5-EtO—Ph |
| 2136 | 5-I-3-EtO—Ph |
| 2137 | 3-F-5-N≡CCH2O—Ph |
| 2138 | 3-Cl-5-N≡CCH2O—Ph |
| 2139 | 3-Br-5-N≡CCH2O—Ph |
| 2140 | 3-I-5-N≡CCH2O—Ph |
| 2141 | 3-F-5-MeOCH2O—Ph |
| 2142 | 3-Cl-5-MeOCH2O—Ph |
| 2143 | 3-Br-5-MeOCH2O—Ph |
| 2144 | 3-I-5-MeOCH2O—Ph |
| 2145 | 5-F-2-MeO—Ph |
| 2146 | 5-Cl-2-MeO—Ph |
| 2147 | 5-Br-2-MeO—Ph |
| 2148 | 5-I-2-MeO—Ph |
| 2149 | 5-Me-2-MeO—Ph |
| 2150 | 2-F-3,5-di-MeO—Ph |
| 2151 | 2-F-3,5-di-EtO—Ph |
| 2152 | 2,3,5-tri-F—Ph |
| 2153 | 2-F-3,5-di-Cl—Ph |
| 2154 | 3,5-di-Br-2-F—Ph |
| 2155 | 2-F-3,5-di-I—Ph |
| 2156 | 2-F-3,5-di-Me—Ph |
| 2157 | 2,3-di-F-5-Me—Ph |
| 2158 | 2,5-di-F-3-Me—Ph |
| 2159 | 3-Cl-2-F-5-Me—Ph |
| 2160 | 5-Cl-2-F-3-Me—Ph |
| 2161 | 3-Br-2-F-5-Me—Ph |
| 2162 | 5-Br-2-F-3-Me—Ph |
| 2163 | 2-F-3-I-5-Me—Ph |
| 2164 | 2-F-5-I-3-Me—Ph |
| 2165 | 2,3-di-F-5-MeO—Ph |
| 2166 | 2,5-di-F-3-MeO—Ph |
| 2167 | 3-Cl-2-F-5-MeO—Ph |
| 2168 | 5-Cl-2-F-3-MeO—Ph |
| 2169 | 3-Br-2-F-5-MeO—Ph |
| 2170 | 5-Br-2-F-3-MeO—Ph |
| 2171 | 2-F-3-I-5-MeO—Ph |
| 2172 | 2-F-5-I-3-MeO—Ph |
| 2173 | 2,3-di-F-5-EtO—Ph |
| 2174 | 2,5-di-F-3-EtO—Ph |
| 2175 | 3-Cl-2-F-5-EtO—Ph |
| 2176 | 5-Cl-2-F-3-EtO—Ph |
| 2177 | 3-Br-2-F-5-EtO—Ph |
| 2178 | 5-Br-2-F-3-EtO—Ph |
| 2179 | 2-F-3-I-5-EtO—Ph |
| 2180 | 2-F-5-I-3-EtO—Ph |
| 2181 | 2,3-di-F-5-N≡CCH2O—Ph |
| 2182 | 2,5-di-F-3-N≡CCH2O—Ph |
| 2183 | 3-Cl-2-F-5-N≡CCH2O—Ph |
| 2184 | 5-Cl-2-F-3-N≡CCH2O—Ph |
| 2185 | 3-Br-2-F-5-N≡CCH2O—Ph |
| 2186 | 5-Br-2-F-3-N≡CCH2O—Ph |
| 2187 | 2-F-3-I-5-N≡CCH2O—Ph |
| 2188 | 2-F-5-I-3-N≡CCH2O—Ph |
| 2189 | 2,3-di-F-5-MeOCH2O—Ph |
| 2190 | 2,5-di-F-3-MeOCH2O—Ph |
| 2191 | 3-Cl-2-F-5-MeOCH2O—Ph |
| 2192 | 5-Cl-2-F-3-MeOCH2O—Ph |
| 2193 | 3-Br-2-F-5-MeOCH2O—Ph |
| 2194 | 5-Br-2-F-3-MeOCH2O—Ph |
| 2195 | 2-F-3-I-5-MeOCH2O—Ph |
| 2196 | 2-F-5-I-3-MeOCH2O—Ph |
| 2197 | 2-Cl-3,5-di-MeO—Ph |
| 2198 | 2-Cl-3,5-di-EtO—Ph |
| 2199 | 2-Cl-3,5-di-F—Ph |
| 2200 | 2,3,5-tri-Cl—Ph |
| 2201 | 3,5-di-Br-2-Cl—Ph |
| 2202 | 2-Cl-3,5-di-I—Ph |
| 2203 | 2-Cl-3,5-di-Me—Ph |
| 2204 | 2-Cl-3-F-5-Me—Ph |
| 2205 | 2-Cl-5-F-3-Me—Ph |
| 2206 | 2,3-di-Cl-5-Me—Ph |
| 2207 | 2,5-di-Cl-3-Me—Ph |
| 2208 | 3-Br-2-Cl-5-Me—Ph |
| 2209 | 5-Br-2-Cl-3-Me—Ph |
| 2210 | 2-Cl-3-I-5-Me—Ph |
| 2211 | 2-Cl-5-I-3-Me—Ph |
| 2212 | 2-Cl-3-F-5-MeO—Ph |
| 2213 | 2-Cl-5-F-3-MeO—Ph |
| 2214 | 2,3-di-Cl-5-MeO—Ph |
| 2215 | 2,5-di-Cl-3-MeO—Ph |
| 2216 | 3-Br-2-Cl-5-MeO—Ph |

TABLE 2-continued

| No. | Z |
|---|---|
| 2217 | 5-Br-2-Cl-3-MeO—Ph |
| 2218 | 2-Cl-3-I-5-MeO—Ph |
| 2219 | 2-Cl-5-I-3-MeO—Ph |
| 2220 | 2-Cl-3-F-5-EtO—Ph |
| 2221 | 2-Cl-5-F-3-EtO—Ph |
| 2222 | 2,3-di-Cl-5-EtO—Ph |
| 2223 | 2,5-di-Cl-3-EtO—Ph |
| 2224 | 3-Br-2-Cl-5-EtO—Ph |
| 2225 | 5-Br-2-Cl-3-EtO—Ph |
| 2226 | 2-Cl-3-I-5-EtO—Ph |
| 2227 | 2-Cl-5-I-3-EtO—Ph |
| 2228 | 2-Cl-3-F-5-N≡CCH2O—Ph |
| 2229 | 2-Cl-5-F-3-N≡CCH2O—Ph |
| 2230 | 2,3-di-Cl-5-N≡CCH2O—Ph |
| 2231 | 2,5-di-Cl-3-N≡CCH2O—Ph |
| 2232 | 3-Br-2-Cl-5-N≡CCH2O—Ph |
| 2233 | 5-Br-2-Cl-3-N≡CCH2O—Ph |
| 2234 | 2-Cl-3-I-5-N≡CCH2O—Ph |
| 2235 | 2-Cl-5-I-3-N≡CCH2O—Ph |
| 2236 | 2-Cl-3-F-5-MeOCH2O—Ph |
| 2237 | 2-Cl-5-F-3-MeOCH2O—Ph |
| 2238 | 2,3-di-Cl-5-MeOCH2O—Ph |
| 2239 | 2,5-di-Cl-3-MeOCH2O—Ph |
| 2240 | 3-Br-2-Cl-5-MeOCH2O—Ph |
| 2241 | 5-Br-2-Cl-3-MeOCH2O—Ph |
| 2242 | 2-Cl-3-I-5-MeOCH2O—Ph |
| 2243 | 2-Cl-5-I-3-MeOCH2O—Ph |
| 2244 | 2-Br-3,5-di-MeO—Ph |
| 2245 | 2-Br-3,5-di-EtO—Ph |
| 2246 | 2-Br-3,5-di-F—Ph |
| 2247 | 2-Br-3,5-di-Cl—Ph |
| 2248 | 2,3,5-tri-Br—Ph |
| 2249 | 2-Br-3,5-di-I—Ph |
| 2250 | 2-Br-3,5-di-Me—Ph |
| 2251 | 2-Br-3-F-5-Me—Ph |
| 2252 | 2-Br-5-F-3-Me—Ph |
| 2253 | 2-Br-3-Cl-5-Me—Ph |
| 2254 | 2-Br-5-Cl-3-Me—Ph |
| 2255 | 2,3-di-Br-5-Me—Ph |
| 2256 | 2,5-di-Br-3-Me—Ph |
| 2257 | 2-Br-3-I-5-Me—Ph |
| 2258 | 2-Br-5-I-3-Me—Ph |
| 2259 | 2-Br-3-F-5-MeO—Ph |
| 2260 | 2-Pr-5-F-3-MeO—Ph |
| 2261 | 2-Br-3-Cl-5-MeO—Ph |
| 2262 | 2-Br-5-Cl-3-MeO—Ph |
| 2263 | 2,3-di-Br-5-MeO—Ph |
| 2264 | 2,5-di-Br-3-MeO—Ph |
| 2265 | 2-Br-3-I-5-MeO—Ph |
| 2266 | 2-Br-5-I-3-MeO—Ph |
| 2267 | 2-Br-3-F-5-EtO—Ph |
| 2268 | 2-Br-5-F-3-EtO—Ph |
| 2269 | 2-Br-3-Cl-5-EtO—Ph |
| 2270 | 2-Br-5-Cl-3-EtO—Ph |
| 2271 | 2,3-di-Br-5-EtO—Ph |
| 2272 | 2,5-di-Br-3-EtO—Ph |
| 2273 | 2-Br-3-I-5-EtO—Ph |
| 2274 | 2-Br-5-I-3-EtO—Ph |
| 2275 | 2-Br-3-F-5-N≡CCH2O—Ph |
| 2276 | 2-Br-5-F-3-N≡CCH2O—Ph |
| 2277 | 2-Br-3-Cl-5-N≡CCH2O—Ph |
| 2278 | 2-Br-5-Cl-3-N≡CCH2O—Ph |
| 2279 | 2,3-di-Br-5-N≡CCH2O—Ph |
| 2280 | 2,5-di-Br-3-N≡CCH2O—Ph |
| 2281 | 2-Br-3-I-5-N≡CCH2O—Ph |
| 2282 | 2-Br-5-I-3-N≡CCH2O—Ph |
| 2283 | 2-Br-3-F-5-MeOCH2O—Ph |
| 2284 | 2-Br-5-F-3-MeOCH2O—Ph |
| 2285 | 2-Br-3-Cl-5-MeOCH2O—Ph |
| 2286 | 2-Br-5-Cl-3-MeOCH2O—Ph |
| 2287 | 2,3-di-Br-5-MeOCH2O—Ph |
| 2288 | 2,5-di-Br-3-MeOCH2O—Ph |
| 2289 | 2-Br-3-I-5-MeOCH2O—Ph |
| 2290 | 2-Br-5-I-3-MeOCH2O—Ph |
| 2291 | 2-I-3,5-di-MeO—Ph |
| 2292 | 2-I-3,5-di-EtO—Ph |
| 2293 | 3,5-di-F-2-I—Ph |
| 2294 | 3,5-di-Cl-2-I—Ph |
| 2295 | 3,5-di-Br-2-I—Ph |
| 2296 | 2,3,5-Tri-I—Ph |
| 2297 | 3,5-di-Me-2-I—Ph |
| 2298 | 3-F-2-I-5-Me—Ph |
| 2299 | 5-F-2-I-3-Me—Ph |
| 2300 | 3-Cl-2-I-5-Me—Ph |
| 2301 | 5-Cl-2-I-3-Me—Ph |
| 2302 | 3-Br-2-I-5-Me—Ph |
| 2303 | 5-Br-2-I-3-Me—Ph |
| 2304 | 2,3-di-I-5-Me—Ph |
| 2305 | 2,5-di-I-3-Me—Ph |
| 2306 | 3-F-2-I-5-MeO—Ph |
| 2307 | 5-F-2-I-3-MeO—Ph |
| 2308 | 3-Cl-2-I-5-MeO—Ph |
| 2309 | 5-Cl-2-I-3-MeO—Ph |
| 2310 | 3-Br-2-I-5-MeO—Ph |
| 2311 | 5-Br-2-I-3-MeO—Ph |
| 2312 | 2,3-di-I-5-MeO—Ph |
| 2313 | 2,5-di-I-3-MeO—Ph |
| 2314 | 3-F-2-I-5-EtO—Ph |
| 2315 | 5-F-2-I-3-EtO—Ph |
| 2316 | 3-Cl-2-I-5-EtO—Ph |
| 2317 | 5-Cl-2-I-3-EtO—Ph |
| 2318 | 3-Br-2-I-5-EtO—Ph |
| 2319 | 5-Br-2-I-3-EtO—Ph |
| 2320 | 2,3-di-I-5-EtO—Ph |
| 2321 | 2,5-di-I-3-EtO—Ph |
| 2322 | 3-F-2-I-5-N≡CCH2O—Ph |
| 2323 | 5-F-2-I-3-N≡CCH2O—Ph |
| 2324 | 3-Cl-2-I-5-N≡CCH2O—Ph |
| 2325 | 5-Cl-2-I-3-N≡CCH2O—Ph |
| 2326 | 3-Br-2-I-5-N≡CCH2O—Ph |
| 2327 | 5-Br-2-I-3-N≡CCH2O—Ph |
| 2328 | 2,3-di-I-5-N≡CCH2O—Ph |
| 2329 | 2,5-di-I-3-N≡CCH2O—Ph |
| 2330 | 3-F-2-I-5-MeOCH2O—Ph |
| 2331 | 5-F-2-I-3-MeOCH2O—Ph |
| 2332 | 3-Cl-2-I-5-MeOCH2O—Ph |
| 2333 | 5-Cl-2-I-3-MeOCH2O—Ph |
| 2334 | 3-Br-2-I-5-MeOCH2O—Ph |
| 2335 | 5-Br-2-I-3-MeOCH2O—Ph |
| 2336 | 2,3-di-I-5-MeOCH2O—Ph |
| 2337 | 2,5-di-I-3-MeOCH2O—Ph |
| 2338 | 2-Me-3,5-di-MeO—Ph |
| 2339 | 2-Me-3,5-di-EtO—Ph |
| 2340 | 3,5-di-F-2-Me—Ph |
| 2341 | 3,5-di-Cl-2-Me—Ph |
| 2342 | 3,5-di-Br-2-Me—Ph |
| 2343 | 3,5-di-I-2-Me—Ph |
| 2344 | 2,3,5-tri-Me—Ph |
| 2345 | 3-F-2,5-di-Me—Ph |
| 2346 | 5-F-2,3-di-Me—Ph |
| 2347 | 3-Cl-2,5-di-Me—Ph |
| 2348 | 5-Cl-2,3-di-Me—Ph |
| 2349 | 3-Br-2,5-di-Me—Ph |
| 2350 | 5-Br-2,3-di-Me—Ph |
| 2351 | 3-I-2,5-di-Me—Ph |
| 2352 | 5-I-2,3-di-Me—Ph |
| 2353 | 3-F-2-Me-5-MeO—Ph |
| 2354 | 5-F-2-Me-3-MeO—Ph |
| 2355 | 3-Cl-2-Me-5-MeO—Ph |
| 2356 | 5-Cl-2-Me-3-MeO—Ph |
| 2357 | 3-Br-2-Me-5-MeO—Ph |
| 2358 | 5-Br-2-Me-3-MeO—Ph |
| 2359 | 3-I-2-Me-5-MeO—Ph |
| 2360 | 5-I-2-Me-3-MeO—Ph |
| 2361 | 3-F-2-Me-5-EtO—Ph |
| 2362 | 5-F-2-Me-3-EtO—Ph |
| 2363 | 3-Cl-2-Me-5-EtO—Ph |
| 2364 | 5-Cl-2-Me-3-EtO—Ph |
| 2365 | 3-Br-2-Me-5-EtO—Ph |
| 2366 | 5-Br-2-Me-3-EtO—Ph |
| 2367 | 3-I-2-Me-5-EtO—Ph |
| 2368 | 5-I-2-Me-3-EtO—Ph |
| 2369 | 3-F-2-Me-5-N≡CCH2O—Ph |
| 2370 | 5-F-2-Me-3-N≡CCH2O—Ph |
| 2371 | 3-Cl-2-Me-5-N≡CCH2O—Ph |
| 2372 | 5-Cl-2-Me-3-N≡CCH2O—Ph |

TABLE 2-continued

| No. | Z |
|---|---|
| 2373 | 3-Br-2-Me-5-N≡CCH2O—Ph |
| 2374 | 5-Br-2-Me-3-N≡CCH2O—Ph |
| 2375 | 3-I-2-Me-5-N≡CCH2O—Ph |
| 2376 | 5-I-2-Me-3-N≡CCH2O—Ph |
| 2377 | 3-F-2-Me-5-MeOCH2O—Ph |
| 2378 | 5-F-2-Me-3-MeOCH2O—Ph |
| 2379 | 3-Cl-2-Me-5-MeOCH2O—Ph |
| 2380 | 5-Cl-2-Me-3-MeOCH2O—Ph |
| 2381 | 3-Br-2-Me-5-MeOCH2O—Ph |
| 2382 | 5-Br-2-Me-3-MeOCH2O—Ph |
| 2383 | 3-I-2-Me-5-MeOCH2O—Ph |
| 2384 | 5-I-2-Me-3-MeOCH2O—Ph |
| 2385 | 2,3,6-tri-F—Ph |
| 2386 | 2,6-di-Cl-3-F—Ph |
| 2387 | 2-Cl-3,6-di-F—Ph |
| 2388 | 6-Cl-2,3-di-F—Ph |
| 2389 | 3-Cl-2,6-di-F—Ph |
| 2390 | 2,3,6-Tri-Cl—Ph |
| 2391 | 2,3-di-Cl-6-F—Ph |
| 2392 | 3,6-di-Cl-2-F—Ph |
| 2393 | 3-Br-2,6-di-F—Ph |
| 2394 | 3-Br-2,6-di-Cl—Ph |
| 2395 | 3-Br-2-Cl-6-F—Ph |
| 2396 | 3-Br-6-Cl-2-F—Ph |
| 2397 | 2,6-di-F-3-I—Ph |
| 2398 | 2,6-di-Cl-3-I—Ph |
| 2399 | 2-Cl-6-F-3-I—Ph |
| 2400 | 6-Cl-2-F-3-I—Ph |
| 2401 | 2,6-di-F-3-Me—Ph |
| 2402 | 2,6-di-Cl-3-Me—Ph |
| 2403 | 2-Cl-6-F-3-Me—Ph |
| 2404 | 6-Cl-2-F-3-Me—Ph |
| 2405 | 2,6-di-F-3-MeO—Ph |
| 2406 | 2,6-di-Cl-3-MeO—Ph |
| 2407 | 2-Cl-6-F-3-MeO—Ph |
| 2408 | 6-Cl-2-F-3-MeO—Ph |
| 2409 | 2,6-di-F-3-EtO—Ph |
| 2410 | 2,6-di-Cl-3-EtO—Ph |
| 2411 | 2-Cl-6-F-3-EtO—Ph |
| 2412 | 6-Cl-2-F-3-EtO—Ph |
| 2413 | 2,6-di-F-3-N≡CCH2O—Ph |
| 2414 | 2,6-di-Cl-3-N≡CCH2O—Ph |
| 2415 | 2-Cl-6-F-3-N≡CCH2O—Ph |
| 2416 | 6-Cl-2-F-3-N≡CCH2O—Ph |
| 2417 | 2,6-di-F-3-MeOCH2O—Ph |
| 2418 | 2,6-di-Cl-3-MeOCH2O—Ph |
| 2419 | 2-Cl-6-F-3-MeOCH2O—Ph |
| 2420 | 6-Cl-2-F-3-MeOCH2O—Ph |
| 2421 | 3,4,5-tri-F—Ph |
| 2422 | 4-Cl-3,5-di-F—Ph |
| 2423 | 4-Br-3,5-di-F—Ph |
| 2424 | 3,5-di-F-4-I—Ph |
| 2425 | 3,5-di-F-4-Me—Ph |
| 2426 | 3,5-di-Cl-4-F—Ph |
| 2427 | 3,4,5-tri-Cl—Ph |
| 2428 | 4-Br-3,5-di-Cl—Ph |
| 2429 | 3,5-di-Cl-4-I—Ph |
| 2430 | 3,5-di-Cl-4-Me—Ph |
| 2431 | 3,5-di-Br-4-F—Ph |
| 2432 | 3,5-di-Br-4-Cl—Ph |
| 2433 | 3,4,5-tri-Br—Ph |
| 2434 | 3,5-di-Br-4-I—Ph |
| 2435 | 3,5-di-Br-4-Me—Ph |
| 2436 | 4-F-3,5-di-I—Ph |
| 2437 | 4-Cl-3,5-di-I—Ph |
| 2438 | 4-Br-3,5-di-I—Ph |
| 2439 | 3,4,5-tri-I—Ph |
| 2440 | 4-Me-3,5-di-I—Ph |
| 2441 | 4-F-3,5-di-Me—Ph |
| 2442 | 4-Cl-3,5-di-Me—Ph |
| 2443 | 4-Br-3,5-di-Me—Ph |
| 2444 | 4-I-3,5-di-Me—Ph |
| 2445 | 3,4,5-tri-Me—Ph |
| 2446 | 4-F-3,5-di-Me—Ph |
| 2447 | 4-Cl-3,5-di-Me—Ph |
| 2448 | 4-Br-3,5-di-Me—Ph |
| 2449 | 4-I-3,5-di-Me—Ph |
| 2450 | 4-MeO-3,5-di-Me—Ph |
| 2451 | 4-F-3,5-di-MeO—Ph |
| 2452 | 4-Cl-3,5-di-MeO—Ph |
| 2453 | 4-Br-3,5-di-MeO—Ph |
| 2454 | 44-3,5-di-MeO—Ph |
| 2455 | 4-Me-3,5-di-MeO—Ph |
| 2456 | 4-F-3,5-di-EtO—Ph |
| 2457 | 4-Cl-3,5-di-EtO—Ph |
| 2458 | 4-Br-3,5-di-EtO—Ph |
| 2459 | 4-I-3,5-di-EtO—Ph |
| 2460 | 4-Me-3,5-di-EtO—Ph |
| 2461 | 2,3,4-tri-F—Ph |
| 2462 | 2-Cl-3,4-di-F—Ph |
| 2463 | 2-Br-3,4-di-F—Ph |
| 2464 | 3,4-di-F-2-I—Ph |
| 2465 | 3,4-di-F-2-Me—Ph |
| 2466 | 2,4,5-tri-F—Ph |
| 2467 | 2-Cl-4,5-di-F—Ph |
| 2468 | 2-Br-4,5-di-F—Ph |
| 2469 | 4,5-di-F-2-I—Ph |
| 2470 | 4,5-di-F-2-Me—Ph |
| 2471 | 2,4-F-3-Cl—Ph |
| 2472 | 2,3-di-Cl-4-F—Ph |
| 2473 | 2-Br-3-Cl-4-F—Ph |
| 2474 | 3-Cl-4-F-2-I—Ph |
| 2475 | 3-Cl-4-F-2-Me—Ph |
| 2476 | 2,4-di-F-5-Cl—Ph |
| 2477 | 2,5-di-Cl-4-F—Ph |
| 2478 | 2-Br-5-Cl-4-F—Ph |
| 2479 | 5-Cl-4-F-2-I—Ph |
| 2480 | 5-Cl-4-F-2-Me—Ph |
| 2481 | 2-F-3,4-di-Cl—Ph |
| 2482 | 2,3,4-tri-Cl—Ph |
| 2483 | 2-Br-3,4-di-Cl—Ph |
| 2484 | di-3,4-Cl-2-I—Ph |
| 2485 | di-3,4-Cl-2-Me—Ph |
| 2486 | 2-F-3,5-di-Cl—Ph |
| 2487 | 2,3,5-tri-Cl—Ph |
| 2488 | 2-Br-3,5-di-Cl—Ph |
| 2489 | 3,5-di-Cl-2-I—Ph |
| 2490 | 3,5-di-Cl-2-Me—Ph |
| 2491 | 4-Cl-2,3-di-F—Ph |
| 2492 | 2,4-di-Cl-3-F—Ph |
| 2493 | 2-Br-4-Cl-3-F—Ph |
| 2494 | 4-Cl-3-F-2-I—Ph |
| 2495 | 4-Cl-3-F-2-Me—Ph |
| 2496 | 4-Cl-2,5-di-F—Ph |
| 2497 | 2,4-di-Cl-5-F—Ph |
| 2498 | 2-Br-4-Cl-5-F—Ph |
| 2499 | 4-Cl-5-F-2-I—Ph |
| 2500 | 4-Cl-5-F-2-Me—Ph |
| 2501 | 2,4-di-F-3-MeO—Ph |
| 2502 | 2-Cl-4-F-3-MeO—Ph |
| 2503 | 2-Br-4-F-3-MeO—Ph |
| 2504 | 4-F-2-I-3-MeO—Ph |
| 2505 | 4-F-2-Me-3-MeO—Ph |
| 2506 | 2,4-F-5-MeO—Ph |
| 2507 | 2-Cl-4-F-5-MeO—Ph |
| 2508 | 2-Br-4-F-5-MeO—Ph |
| 2509 | 4-F-2-I-5-MeO—Ph |
| 2510 | 4-F-2-Me-5-MeO—Ph |
| 2511 | 4-Cl-2-F-3-MeO—Ph |
| 2512 | 2,4-di-Cl-3-MeO—Ph |
| 2513 | 2-Br-4-Cl-3-MeO—Ph |
| 2514 | 4-Cl-2-I-3-MeO—Ph |
| 2515 | 4-Cl-2-Me-3-MeO—Ph |
| 2516 | 4-Cl-2-F-5-MeO—Ph |
| 2517 | 2,4-di-Cl-5-MeO—Ph |
| 2518 | 2-Br-4-Cl-5-MeO—Ph |
| 2519 | 4-Cl-2-I-5-MeO—Ph |
| 2520 | 4-Cl-2-Me-5-MeO—Ph |
| 2521 | 2,6-di-F-3,5-di-MeO—Ph |
| 2522 | 2,6-di-Cl-3,5-di-MeO—Ph |
| 2523 | 6-Cl-2-F-3,5-di-MeO—Ph |
| 2524 | 6-Br-2-F-3,5-di-MeO—Ph |
| 2525 | 2-Br-6-Cl-3,5-di-MeO—Ph |
| 2526 | 2,3,4,5,-tetra-F—Ph |
| 2527 | 2,3,5,6,-tetra-F—Ph |
| 2528 | 2,3,4,5,6 -penta-F—Ph |

TABLE 2-continued

| No. | Z |
|---|---|
| 2529 | 2,3-di-F-5-MeS—Ph |
| 2530 | 2-F-3-MeO-5-MeS—Ph |
| 2531 | 2,5-di-F-3-MeS—Ph |
| 2532 | 2-Cl-3-F-5-MeS—Ph |
| 2533 | 2-Cl-5-F-3-MeS—Ph |
| 2534 | 2-F-5-MeO-3-MeS—Ph |
| 2535 | 2-Cl-5-MeO-3-MeS—Ph |
| 2536 | 2-Br-3-F-5-MeS—Ph |
| 2537 | 2-Cl-3-MeO-5-MeS—Ph |
| 2538 | 2-Br-3-MeO-5-MeS—Ph |
| 2539 | 2-Br-5-MeO-3-MeS—Ph |
| 2540 | 2-Br-5-F-3-MeS—Ph |
| 2541 | 2-I-5-F-3-MeS—Ph |
| 2542 | 2-I-3-MeO-5-MeS—Ph |
| 2543 | 2-I-3-F-5-MeS—Ph |
| 2544 | 3-F-2-Me-5-MeS—Ph |
| 2545 | 5-F-2-Me-3-MeS—Ph |
| 2546 | 2-I-5-MeO-3-MeS—Ph |
| 2547 | 2-Me-5-MeO-3-MeS—Ph |
| 2548 | 2-F-3,5-di-MeS—Ph |
| 2549 | 2-Me-3-MeO-5-MeS—Ph |
| 2550 | 2-Br-3,5-di-MeS—Ph |
| 2551 | 2-I-3,5-di-MeS—Ph |
| 2552 | 2-Cl-3,5-di-MeS—Ph |
| 2553 | 2,5-di-F-3-MeS(O)—Ph |
| 2554 | 2,3-di-F-5-MeS(O)—Ph |
| 2555 | 2-Me-3,5-di-MeS—Ph |
| 2556 | 2-F-5-MeO-3-MeS(O)—Ph |
| 2557 | 2-Cl-3-F-5-MeS(O)—Ph |
| 2558 | 2-F-3-MeO-5-MeS(O)—Ph |
| 2559 | 2-Cl-3-MeO-5-MeS(O)—Ph |
| 2560 | 2-Cl-5-MeO-3-MeS(O)—Ph |
| 2561 | 2-Cl-5-F-3-MeS(O)—Ph |
| 2562 | 2-Br-5-F-3-MeS(O)—Ph |
| 2563 | 2-Br-3-MeO-5-MeS(O)—Ph |
| 2564 | 2-Br-3-F-5-MeS(O)—Ph |
| 2565 | 2-I-3-F-5-MeS(O)—Ph |
| 2566 | 5-F-2-I-3-MeS(O)—Ph |
| 2567 | 2-Br-5-MeO-3-MeS(O)—Ph |
| 2568 | 2-I-5-MeO-3-MeS(O)—Ph |
| 2569 | 3-F-2-Me-5-MeS(O)—Ph |
| 2570 | 2-I-3-MeO-5-MeS(O)—Ph |
| 2571 | 2-Me-3-MeO-5-MeS(O)—Ph |
| 2572 | 2-Me-5-MeO-3-MeS(O)—Ph |
| 2573 | 5-F-2-Me-3-MeS(O)—Ph |
| 2574 | 2-Cl-3,5-di-MeS(O)—Ph |
| 2575 | 2-Br-3,5-di-MeS(O)—Ph |
| 2576 | 2-F-3,5-di-MeS(O)—Ph |
| 2577 | 2-Me-3,5-di-MeS(O)—Ph |
| 2578 | 2,5-di-F-3-MeSO2—Ph |
| 2579 | 2-I-3,5-di-MeS(O)—Ph |
| 2580 | 2-F-3-MeO-5-MeSO2—Ph |
| 2581 | 2-F-5-MeO-3-MeSO2—Ph |
| 2582 | 2,3-di-F-5-MeSO2—Ph |
| 2583 | 2-Cl-5-F-3-MeSO2—Ph |
| 2584 | 2-Cl-3-MeO-5-MeSO2—Ph |
| 2585 | 2-Cl-3-F-5-MeSO2—Ph |
| 2586 | 2-Br-3-F-5-MeSO2—Ph |
| 2587 | 2-Br-5-F-3-MeSO2—Ph |
| 2588 | 2-Cl-5-MeO-3-MeSO2—Ph |
| 2589 | 2-Br-5-MeO-3-MeSO2—Ph |
| 2590 | 3-F-2-I-5-MeSO2—Ph |
| 2591 | 2-Br-3-MeO-5-MeSO2—Ph |
| 2592 | 2-I-3-MeO-5-MeSO2—Ph |
| 2593 | 2-I-5-MeO-3-MeSO2—Ph |
| 2594 | 5-F-2-I-3-MeSO2—Ph |
| 2595 | 5-F-2-Me-3-MeSO2—Ph |
| 2596 | 2-Me-3-MeO-5-MeSO2—Ph |
| 2597 | 3-F-2-Me-5-MeSO2—Ph |
| 2598 | 2-F-3,5-di-MeSO2—Ph |
| 2599 | 2-Cl-3,5-di-MeSO2—Ph |
| 2600 | 2-Me-5-MeO-3-MeSO2—Ph |
| 2601 | 2-I-3,5-di-MeSO2—Ph |
| 2602 | 2-Me-3,5-di-MeSO2—Ph |
| 2603 | 2-Br-3,5-di-MeSO2—Ph |
| 2604 | 2,4,6-tri-F—Ph |
| 2605 | PhCH2— |
| 2606 | 2-F—PhCH2— |
| 2607 | 3-F—PhCH2— |
| 2608 | 4-F—PhCH2— |
| 2609 | 2-Cl—PhCH2— |
| 2610 | 3-Cl—PhCH2— |
| 2611 | 4-Cl—PhCH2— |
| 2612 | 2-Br—PhCH2— |
| 2613 | 3-Br—PhCH2— |
| 2614 | 4-Br—PhCH2— |
| 2615 | 2-I—PhCH2— |
| 2616 | 3-I—PhCH2— |
| 2617 | 4-I—PhCH2— |
| 2618 | 2-HO—PhCH2— |
| 2619 | 3-HO—PhCH2— |
| 2620 | 4-HO—PhCH2— |
| 2621 | 2-N≡C—PhCH2— |
| 2622 | 3-N≡C—PhCH2— |
| 2623 | 4-N≡C—PhCH2— |
| 2624 | 2-O2N—PhCH2— |
| 2625 | 3-O2N—PhCH2— |
| 2626 | 4-O2N—PhCH2— |
| 2627 | 2-Me—PhCH2— |
| 2628 | 3-Me—PhCH2— |
| 2629 | 4-Me—PhCH2— |
| 2630 | 2-Et—PhCH2— |
| 2631 | 3-Et—PhCH2— |
| 2632 | 4-Et—PhCH2— |
| 2633 | 2-Pr—PhCH2— |
| 2634 | 3-Pr—PhCH2— |
| 2635 | 4-Pr—PhCH2— |
| 2636 | 2-iPr—PhCH2— |
| 2637 | 3-iPr—PhCH2— |
| 2638 | 4-iPr—PhCH2— |
| 2639 | 2-N≡CCH2—PhCH2— |
| 2640 | 3-N≡CCH2—PhCH2— |
| 2641 | 4-N≡CCH2—PhCH2— |
| 2642 | 2-N≡CCH2CH2—PhCH2— |
| 2643 | 3-N≡CCH2CH2—PhCH2— |
| 2644 | 4-N≡CCH2CH2—PhCH2— |
| 2645 | 2-cPrCH2—PhCH2— |
| 2646 | 3-cPrCH2—PhCH2— |
| 2647 | 4-cPrCH2—PhCH2— |
| 2648 | 2-cBuCH2—PhCH2— |
| 2649 | 3-cBuCH2—PhCH2— |
| 2650 | 4-cBuCH2—PhCH2— |
| 2651 | 2-MeOCH—PhCH2— |
| 2652 | 3-MeOCH—PhCH2— |
| 2653 | 4-MeOCH—PhCH2— |
| 2654 | 2-MeOCH2CH2—PhCH2— |
| 2655 | 3-MeOCH2CH2—PhCH2— |
| 2656 | 4-MeOCH2CH2—PhCH2— |
| 2657 | 2-MeOCH2CH2CH2—PhCH2— |
| 2658 | 3-MeOCH2CH2CH2—PhCH2— |
| 2659 | 4-MeOCH2CH2CH2—PhCH2— |
| 2660 | 2-EtOCH2—PhCH2— |
| 2661 | 3-EtOCH2—PhCH2— |
| 2662 | 4-EtOCH2—PhCH2— |
| 2663 | 2-EtOCH2CH2—PhCH2— |
| 2664 | 3-EtOCH2CH2—PhCH2— |
| 2665 | 4-EtOCH2CH2—PhCH2— |
| 2666 | 2-cPrOCH2—PhCH2— |
| 2667 | 3-cPrOCH2—PhCH2— |
| 2668 | 4-cPrOCH2—PhCH2— |
| 2669 | 2-F3COCH2—PhCH2— |
| 2670 | 3-F3COCH2—PhCH2— |
| 2671 | 4-F3COCH2—PhCH2— |
| 2672 | 2-F2CHOCH2—PhCH2— |
| 2673 | 3-F2CHOCH2—PhCH2— |
| 2674 | 4-F2CHOCH2—PhCH2— |
| 2675 | 2-MeOCH2CH2OCH2—PhCH2— |
| 2676 | 3-MeOCH2CH2OCH2—PhCH2— |
| 2677 | 4-MeOCH2CH2OCH2—PhCH2— |
| 2678 | 2-Me2NCH2—PhCH2— |
| 2679 | 3-Me2NCH2—PhCH2— |
| 2680 | 4-Me2NCH2—PhCH2— |
| 2681 | 2-MeSCH2—PhCH2— |
| 2682 | 3-MeSCH2—PhCH2— |
| 2683 | 4-MeSCH2—PhCH2— |
| 2684 | 2-MeS(O)CH2—PhCH2— |

TABLE 2-continued

| No. | Z |
|---|---|
| 2685 | 3-MeS(O)CH2—PhCH2— |
| 2686 | 4-MeS(O)CH2—PhCH2— |
| 2687 | 2-MeSO2CH2—PhCH2— |
| 2688 | 3-MeSO2CH2—PhCH2— |
| 2689 | 4-MeSO2CH2—PhCH2— |
| 2690 | 2-cPr—PhCH2— |
| 2691 | 3-cPr—PhCH2— |
| 2692 | 4-cPr—PhCH2— |
| 2693 | 2-cBu—PhCH2— |
| 2694 | 3-cBu—PhCH2— |
| 2695 | 4-cBu—PhCH2— |
| 2696 | 2-F3C—PhCH2— |
| 2697 | 3-F3C—PhCH2— |
| 2698 | 4-F3C—PhCH2— |
| 2699 | 2-F2CH—PhCH2— |
| 2700 | 3-F2CH—PhCH2— |
| 2701 | 4-F2CH—PhCH2— |
| 2702 | 2-H2C=CH—PhCH2— |
| 2703 | 3-H2C=CH—PhCH2— |
| 2704 | 4-H2C=CH—PhCH2— |
| 2705 | 2-H2C=CHCH2—PhCH2— |
| 2706 | 3-H2C=CHCH2—PhCH2— |
| 2707 | 4-H2C=CHCH2—PhCH2— |
| 2708 | 2-F2C=CH—PhCH2— |
| 2709 | 3-F2C=CH—PhCH2— |
| 2710 | 4-F2C=CH—PhCH2— |
| 2711 | 2-F2C=CHCH2—PhCH2— |
| 2712 | 3-F2C=CHCH2—PhCH2— |
| 2713 | 4-F2C=CHCH2—PhCH2— |
| 2714 | 2-HC≡C—PhCH2— |
| 2715 | 3-HC≡C—PhCH2— |
| 2716 | 4-HC≡C—PhCH2— |
| 2717 | 2-HC≡CCH2—PhCH2— |
| 2718 | 3-HC≡CCH2—PhCH2— |
| 2719 | 4-HC≡CCH2—PhCH2— |
| 2720 | 2-F3CC≡C—PhCH2— |
| 2721 | 3-F3CC≡C—PhCH2— |
| 2722 | 4-F3CC≡C—PhCH2— |
| 2723 | 2-F3CC≡CCH2—PhCH2— |
| 2724 | 3-F3CC≡CCH2—PhCH2— |
| 2725 | 4-F3CC≡CCH2—PhCH2— |
| 2726 | 2-MeO—PhCH2— |
| 2727 | 3-MeO—PhCH2— |
| 2728 | 4-MeO—PhCH2— |
| 2729 | 2-EtO—PhCH2— |
| 2730 | 3-EtO—PhCH2— |
| 2731 | 4-EtO—PhCH2— |
| 2732 | 2-PrO—PhCH2— |
| 2733 | 3-PrO—PhCH2— |
| 2734 | 4-PrO—PhCH2— |
| 2735 | 2-iPrO—PhCH2— |
| 2736 | 3-iPrO—PhCH2— |
| 2737 | 4-iPrO—PhCH2— |
| 2738 | 2-BuO—PhCH2— |
| 2739 | 3-BuO—PhCH2— |
| 2740 | 4-BuO—PhCH2— |
| 2741 | 2-iBuO—PhCH2— |
| 2742 | 3-iBuO—PhCH2— |
| 2743 | 4-iBuO—PhCH2— |
| 2744 | 2-PentylO—PhCH2— |
| 2745 | 3-PentylO—PhCH2— |
| 2746 | 4-PentylO—PhCH2— |
| 2747 | 2-N≡CCH2O—PhCH2— |
| 2748 | 3-N≡CCH2O—PhCH2— |
| 2749 | 4-N≡CCH2O—PhCH2— |
| 2750 | 2-N≡CCH2CH2O—PhCH2— |
| 2751 | 3-N≡CCH2CH2O—PhCH2— |
| 2752 | 4-N≡CCH2CH2O—PhCH2— |
| 2753 | 2-cPrCH2O—PhCH2— |
| 2754 | 3-cPrCH2O—PhCH2— |
| 2755 | 4-cPrCH2O—PhCH2— |
| 2756 | 2-cBuCH2O—PhCH2— |
| 2757 | 3-cBuCH2O—PhCH2— |
| 2758 | 4-cBuCH2O—PhCH2— |
| 2759 | 2-cPentylCH2O—PhCH2— |
| 2760 | 3-cPentylCH2O—PhCH2— |
| 2761 | 4-cPentylCH2O—PhCH2— |
| 2762 | 2-cHexylCH2O—PhCH2— |
| 2763 | 3-cHexylCH2O—PhCH2— |
| 2764 | 4-cHexylCH2O—PhCH2— |
| 2765 | 2-MeOCH2O—PhCH2— |
| 2766 | 3-MeOCH2O—PhCH2— |
| 2767 | 4-MeOCH2O—PhCH2— |
| 2768 | 2-EtOCH2O—PhCH2— |
| 2769 | 3-EtOCH2O—PhCH2— |
| 2770 | 4-EtOCH2O—PhCH2— |
| 2771 | 2-MeOCH2CH2O—PhCH2— |
| 2772 | 3-MeOCH2CH2O—PhCH2— |
| 2773 | 4-MeOCH2CH2O—PhCH2— |
| 2774 | 2-MeOCH2CH2CH2O—PhCH2— |
| 2775 | 3-MeOCH2CH2CH2O—PhCH2— |
| 2776 | 4-MeOCH2CH2CH2O—PhCH2— |
| 2777 | 2-MeOCH2CH2OCH2O—PhCH2— |
| 2778 | 3-MeOCH2CH2OCH2O—PhCH2— |
| 2779 | 4-MeOCH2CH2OCH2O—PhCH2— |
| 2780 | 2-MeSCH2O—PhCH2— |
| 2781 | 3-MeSCH2O—PhCH2— |
| 2782 | 4-MeSCH2O—PhCH2— |
| 2783 | 2-MeS(O)CH2O—PhCH2— |
| 2784 | 3-MeS(O)CH2O—PhCH2— |
| 2785 | 4-MeS(O)CH2O—PhCH2— |
| 2786 | 2-MeSO2CH2O—PhCH2— |
| 2787 | 3-MeSO2CH2O—PhCH2— |
| 2788 | 4-MeSO2CH2O—PhCH2— |
| 2789 | 2-AcCH2O—PhCH2— |
| 2790 | 3-AcCH2O—PhCH2— |
| 2791 | 4-AcCH2O—PhCH2— |
| 2792 | 2-MeOC(=O)CH2O—PhCH2— |
| 2793 | 3-MeOC(=O)CH2O—PhCH2— |
| 2794 | 4-MeOC(=O)CH2O—PhCH2— |
| 2795 | 2-EtOC(=O)CH2O—PhCH2— |
| 2796 | 3-EtOC(=O)CH2O—PhCH2— |
| 2797 | 4-EtOC(=O)CH2O—PhCH2— |
| 2798 | 2-(1,3-dioxolan-2-yl)CH2O—PhCH2— |
| 2799 | 3-(1,3-dioxolan-2-yl)CH2O—PhCH2— |
| 2800 | 4-(1,3-dioxolan-2-yl)CH2O—PhCH2— |
| 2801 | 2-(1,3-dioxolan-2-yl)CH2CH2O—PhCH2— |
| 2802 | 3-(1,3-dioxolan-2-yl)CH2CH2O—PhCH2— |
| 2803 | 4-(1,3-dioxolan-2-yl)CH2CH2O—PhCH2— |
| 2804 | 2-(1,3-dioxan-2-yl)CH2O—PhCH2— |
| 2805 | 3-(1,3-dioxan-2-yl)CH2O—PhCH2— |
| 2806 | 4-(1,3-dioxan-2-yl)CH2O—PhCH2— |
| 2807 | 2-(1,3-dioxan-2-yl)CH2CH2O—PhCH2— |
| 2808 | 3-(1,3-dioxan-2-yl)CH2CH2O—PhCH2— |
| 2809 | 4-(1,3-dioxan-2-yl)CH2CH2O—PhCH2— |
| 2810 | 2-cPrO—PhCH2— |
| 2811 | 3-cPrO—PhCH2— |
| 2812 | 4-cPrO—PhCH2— |
| 2813 | 2-cBuO—PhCH2— |
| 2814 | 3-cBuO—PhCH2— |
| 2815 | 4-cBuO—PhCH2— |
| 2816 | 2-cPentylO—PhCH2— |
| 2817 | 3-cPentylO—PhCH2— |
| 2818 | 4-cPentylO—PhCH2— |
| 2819 | 2-cHexylO—PhCH2— |
| 2820 | 3-cHexylO—PhCH2— |
| 2821 | 4-cHexylO—PhCH2— |
| 2822 | 2-F3CO—PhCH2— |
| 2823 | 3-F3CO—PhCH2— |
| 2824 | 4-F3CO—PhCH2— |
| 2825 | 2-F2CHO—PhCH2— |
| 2826 | 3-F2CHO—PhCH2— |
| 2827 | 4-F2CHO—PhCH2— |
| 2828 | 2-F3CCH2O—PhCH2— |
| 2829 | 3-F3CCH2O—PhCH2— |
| 2830 | 4-F3CCH2O—PhCH2— |
| 2831 | 2-F2CHCH2O—PhCH2— |
| 2832 | 3-F2CHCH2O—PhCH2— |
| 2833 | 4-F2CHCH2O—PhCH2— |
| 2834 | 2-H2C=CHCH2O—PhCH2— |
| 2835 | 3-H2C=CHCH2O—PhCH2— |
| 2836 | 4-H2C=CHCH2O—PhCH2— |
| 2837 | 2-HC≡CCH2O—PhCH2— |
| 2838 | 3-HC≡CCH2O—PhCH2— |
| 2839 | 4-HC≡CCH2O—PhCH2— |
| 2840 | 2-AcPhCH2— |

TABLE 2-continued

| No. | Z |
|---|---|
| 2841 | 3-AcPhCH2— |
| 2842 | 4-AcPhCH2— |
| 2843 | 2-MeOC(=O)—PhCH2— |
| 2844 | 3-MeOC(=O)—PhCH2— |
| 2845 | 4-MeOC(=O)—PhCH2— |
| 2846 | 2-EtOC(=O)—PhCH2— |
| 2847 | 3-EtOC(=O)—PhCH2— |
| 2848 | 4-EtOC(=O)—PhCH2— |
| 2849 | 2-AcO—PhCH2— |
| 2850 | 3-AcO—PhCH2— |
| 2851 | 4-AcO—PhCH2— |
| 2852 | 2-MeOC(=O)—PhCH2— |
| 2853 | 3-MeOC(=O)—PhCH2— |
| 2854 | 4-MeOC(=O)—PhCH2— |
| 2855 | 2-EtOC(=O)—PhCH2— |
| 2856 | 3-EtOC(=O)—PhCH2— |
| 2857 | 4-EtOC(=O)—PhCH2— |
| 2858 | 2-(1,3-dioxolan-2-yl)-PhCH2— |
| 2859 | 3-(1,3-dioxolan-2-yl)-PhCH2— |
| 2860 | 4-(1,3-dioxolan-2-yl)-PhCH2— |
| 2861 | 2-(1,3-dioxan-2-yl)-PhCH2— |
| 2862 | 3-(1,3-dioxan-2-yl)-PhCH2— |
| 2863 | 4-(1,3-dioxan-2-yl)-PhCH2— |
| 2864 | 2-MeS—PhCH2— |
| 2865 | 3-MeS—PhCH2— |
| 2866 | 4-MeS—PhCH2— |
| 2867 | 2-MeS(O)—PhCH2— |
| 2868 | 3-MeS(O)—PhCH2— |
| 2869 | 4-MeS(O)—PhCH2— |
| 2870 | 2-MeSO2—PhCH2— |
| 2871 | 3-MeSO2—PhCH2— |
| 2872 | 4-MeSO2—PhCH2— |
| 2873 | 2-ClCH2S—PhCH2— |
| 2874 | 3-ClCH2S—PhCH2— |
| 2875 | 4-ClCH2S—PhCH2— |
| 2876 | 2-ClCH2S(O)—PhCH2— |
| 2877 | 3-ClCH2S(O)—PhCH2— |
| 2878 | 4-ClCH2S(O)—PhCH2— |
| 2879 | 2-ClCH2SO2—PhCH2— |
| 2880 | 3-ClCH2SO2—PhCH2— |
| 2881 | 4-ClCH2SO2—PhCH2— |
| 2882 | 2-F-3-HO—PhCH2— |
| 2883 | 2-F-4-HO—PhCH2— |
| 2884 | 2-F-5-HO—PhCH2— |
| 2885 | 2-F-6-HO—PhCH2— |
| 2886 | 2-Cl-3-HO—PhCH2— |
| 2887 | 2-Cl-4-HO—PhCH2— |
| 2888 | 2-Cl-5-HO—PhCH2— |
| 2889 | 2-Cl-6-HO—PhCH2— |
| 2890 | 2-Br-3-HO—PhCH2— |
| 2891 | 2-Br-4-HO—PhCH2— |
| 2892 | 2-Br-5-HO—PhCH2— |
| 2893 | 2-Br-6-HO—PhCH2— |
| 2894 | 2-I-3-HO—PhCH2— |
| 2895 | 2-I-4-HO—PhCH2— |
| 2896 | 2-I-5-HO—PhCH2— |
| 2897 | 2-I-6-HO—PhCH2— |
| 2898 | 2-Me-3-HO—PhCH2— |
| 2899 | 2-Me-4-HO—PhCH2— |
| 2900 | 2-Me-5-HO—PhCH2— |
| 2901 | 2-Me-6-HO—PhCH2— |
| 2902 | 2,3-di-F—PhCH2— |
| 2903 | 2,4-di-F—PhCH2— |
| 2904 | 2,5-di-F—PhCH2— |
| 2905 | 2,6-di-F—PhCH2— |
| 2906 | 2-Cl-3-F—PhCH2— |
| 2907 | 2-Cl-4-F—PhCH2— |
| 2908 | 2-Cl-5-F—PhCH2— |
| 2909 | 2-Cl-6-F—PhCH2— |
| 2910 | 2-Br-3-F—PhCH2— |
| 2911 | 2-Br-4-F—PhCH2— |
| 2912 | 2-Br-5-F—PhCH2— |
| 2913 | 2-Br-6-F—PhCH2— |
| 2914 | 3-F-2-I—PhCH2— |
| 2915 | 4-F-2-I—PhCH2— |
| 2916 | 5-F-2-I—PhCH2— |
| 2917 | 6-F-2-I—PhCH2— |
| 2918 | 3-F-2-Me—PhCH2— |
| 2919 | 4-F-2-Me—PhCH2— |
| 2920 | 5-F-2-Me—PhCH2— |
| 2921 | 6-F-2-Me—PhCH2— |
| 2922 | 3-Cl-2-F—PhCH2— |
| 2923 | 4-Cl-2-F—PhCH2— |
| 2924 | 5-Cl-2-F—PhCH2— |
| 2925 | 6-Cl-2-F—PhCH2— |
| 2926 | 2,3-di-Cl—PhCH2— |
| 2927 | 2,4-di-Cl—PhCH2— |
| 2928 | 2,5-di-Cl—PhCH2— |
| 2929 | 2,6-di-Cl—PhCH2— |
| 2930 | 2-Br-3-Cl—PhCH2— |
| 2931 | 2-Br-4-Cl—PhCH2— |
| 2932 | 2-Br-5-Cl—PhCH2— |
| 2933 | 2-Br-6-Cl—PhCH2— |
| 2934 | 3-Cl-2-I—PhCH2— |
| 2935 | 4-Cl-2-I—PhCH2— |
| 2936 | 5-Cl-2-I—PhCH2— |
| 2937 | 6-Cl-2-I—PhCH2— |
| 2938 | 3-Cl-2-Me—PhCH2— |
| 2939 | 4-Cl-2-Me—PhCH2— |
| 2940 | 5-Cl-2-Me—PhCH2— |
| 2941 | 6-Cl-2-Me—PhCH2— |
| 2942 | 3-Br-2-F—PhCH2— |
| 2943 | 4-Br-2-F—PhCH2— |
| 2944 | 5-Br-2-F—PhCH2— |
| 2945 | 6-Br-2-F—PhCH2— |
| 2946 | 3-Br-2-Cl—PhCH2— |
| 2947 | 4-Br-2-Cl—PhCH2— |
| 2948 | 5-Br-2-Cl—PhCH2— |
| 2949 | 6-Br-2-Cl—PhCH2— |
| 2950 | 2,3-di-Br—PhCH2— |
| 2951 | 2,4-di-Br—PhCH2— |
| 2952 | 2,5-di-Br—PhCH2— |
| 2953 | 2,6-di-Br—PhCH2— |
| 2954 | 3-Br-2-I—PhCH2— |
| 2955 | 4-Br-2-I—PhCH2— |
| 2956 | 5-Br-2-I—PhCH2— |
| 2957 | 6-Br-2-I—PhCH2— |
| 2958 | 3-Br-2-Me—PhCH2— |
| 2959 | 4-Br-2-Me—PhCH2— |
| 2960 | 5-Br-2-Me—PhCH2— |
| 2961 | 6-Br-2-Me—PhCH2— |
| 2962 | 2-F-3-I—PhCH2— |
| 2963 | 2-F-4-I—PhCH2— |
| 2964 | 2-F-5-I—PhCH2— |
| 2965 | 2-F-6-I—PhCH2— |
| 2966 | 2-Cl-3-I—PhCH2— |
| 2967 | 2-Cl-4-I—PhCH2— |
| 2968 | 2-Cl-5-I—PhCH2— |
| 2969 | 2-Cl-6-I—PhCH2— |
| 2970 | 2-Br-3-I—PhCH2— |
| 2971 | 2-Br-4-I—PhCH2— |
| 2972 | 2-Br-5-I—PhCH2— |
| 2973 | 2-Br-6-I—PhCH2— |
| 2974 | 2,3-di-I—PhCH2— |
| 2975 | 2,4-di-I—PhCH2— |
| 2976 | 2,5-di-I—PhCH2— |
| 2977 | 2,6-di-I—PhCH2— |
| 2978 | 2-Me-3-I—PhCH2— |
| 2979 | 2-Me-4-I—PhCH2— |
| 2980 | 2-Me-5-I—PhCH2— |
| 2981 | 2-Me-6-I—PhCH2— |
| 2982 | 2-F-3-N≡C—PhCH2— |
| 2983 | 2-F-4-N≡C—PhCH2— |
| 2984 | 2-F-5-N≡C—PhCH2— |
| 2985 | 2-F-6-N≡C—PhCH2— |
| 2986 | 2-Cl-3-N≡C—PhCH2— |
| 2987 | 2-Cl-4-N≡C—PhCH2— |
| 2988 | 2-Cl-5-N≡C—PhCH2— |
| 2989 | 2-Cl-6-N≡C—PhCH2— |
| 2990 | 2-Br-3-N≡C—PhCH2— |
| 2991 | 2-Br-4-N≡C—PhCH2— |
| 2992 | 2-Br-5-N≡C—PhCH2— |
| 2993 | 2-Br-6-N≡C—PhCH2— |
| 2994 | 2-I-3-N≡C—PhCH2— |
| 2995 | 2-I-4-N≡C—PhCH2— |
| 2996 | 2-I-5-N≡C—PhCH2— |

TABLE 2-continued

| No. | Z |
|---|---|
| 2997 | 2-I-6-N≡C—PhCH2— |
| 2998 | 2-Me-3-N≡C—PhCH2— |
| 2999 | 2-Me-4-N≡C—PhCH2— |
| 3000 | 2-Me-5-N≡C—PhCH2— |
| 3001 | 2-Me-6-N≡C—PhCH2— |
| 3002 | 2-F-3-O2N—PhCH2— |
| 3003 | 2-F-4-O2N—PhCH2— |
| 3004 | 2-F-5-O2N—PhCH2— |
| 3005 | 2-F-6-O2N—PhCH2— |
| 3006 | 2-Cl-3-O2N—PhCH2— |
| 3007 | 2-Cl-4-O2N—PhCH2— |
| 3008 | 2-Cl-5-O2N—PhCH2— |
| 3009 | 2-Cl-6-O2N—PhCH2— |
| 3010 | 2-Br-3-O2N—PhCH2— |
| 3011 | 2-Br-4-O2N—PhCH2— |
| 3012 | 2-Br-5-O2N—PhCH2— |
| 3013 | 2-Br-6-O2N—PhCH2— |
| 3014 | 2-I-3-O2N—PhCH2— |
| 3015 | 2-I-4-O2N—PhCH2— |
| 3016 | 2-I-5-O2N—PhCH2— |
| 3017 | 2-I-6-O2N—PhCH2— |
| 3018 | 2-Me-3-O2N—PhCH2— |
| 3019 | 2-Me-4-O2N—PhCH2— |
| 3020 | 2-Me-5-O2N—PhCH2— |
| 3021 | 2-Me-6-O2N—PhCH2— |
| 3022 | 2-F-3-Me—PhCH2— |
| 3023 | 2-F-4-Me—PhCH2— |
| 3024 | 2-F-5-Me—PhCH2— |
| 3025 | 2-F-6-Me—PhCH2— |
| 3026 | 2-Cl-3-Me—PhCH2— |
| 3027 | 2-Cl-4-Me—PhCH2— |
| 3028 | 2-Cl-5-Me—PhCH2— |
| 3029 | 2-Cl-6-Me—PhCH2— |
| 3030 | 2-Br-3-Me—PhCH2— |
| 3031 | 2-Br-4-Me—PhCH2— |
| 3032 | 2-Br-5-Me—PhCH2— |
| 3033 | 2-Br-6-Me—PhCH2— |
| 3034 | 2-I-3-Me—PhCH2— |
| 3035 | 2-I-4-Me—PhCH2— |
| 3036 | 2-I-5-Me—PhCH2— |
| 3037 | 2-I-6-Me—PhCH2— |
| 3038 | 2,3-di-Me—PhCH2— |
| 3039 | 2,4-di-Me—PhCH2— |
| 3040 | 2,5-di-Me—PhCH2— |
| 3041 | 2,6-di-Me—PhCH2— |
| 3042 | 2-F-3-Et—PhCH2— |
| 3043 | 2-F-4-Et—PhCH2— |
| 3044 | 2-F-5-Et—PhCH2— |
| 3045 | 2-F-6-Et—PhCH2— |
| 3046 | 2-Cl-3-Et—PhCH2— |
| 3047 | 2-Cl-4-Et—PhCH2— |
| 3048 | 2-Cl-5-Et—PhCH2— |
| 3049 | 2-Cl-6-Et—PhCH2— |
| 3050 | 2-Br-3-Et—PhCH2— |
| 3051 | 2-Br-4-Et—PhCH2— |
| 3052 | 2-Br-5-Et—PhCH2— |
| 3053 | 2-Br-6-Et—PhCH2— |
| 3054 | 2-I-3-Et—PhCH2— |
| 3055 | 2-I-4-Et—PhCH2— |
| 3056 | 2-I-5-Et—PhCH2— |
| 3057 | 2-I-6-Et—PhCH2— |
| 3058 | 2-Me-3-Et—PhCH2— |
| 3059 | 2-Me-4-Et—PhCH2— |
| 3060 | 2-Me-5-Et—PhCH2— |
| 3061 | 2-Me-6-Et—PhCH2— |
| 3062 | 2-F-3-Pr—PhCH2— |
| 3063 | 2-F-4-Pr—PhCH2— |
| 3064 | 2-F-5-Pr—PhCH2— |
| 3065 | 2-F-6-Pr—PhCH2— |
| 3066 | 2-Cl-3-Pr—PhCH2— |
| 3067 | 2-Cl-4-Pr—PhCH2— |
| 3068 | 2-Cl-5-Pr—PhCH2— |
| 3069 | 2-Cl-6-Pr—PhCH2— |
| 3070 | 2-Br-3-Pr—PhCH2— |
| 3071 | 2-Br-4-Pr—PhCH2— |
| 3072 | 2-Br-5-Pr—PhCH2— |
| 3073 | 2-Br-6-Pr—PhCH2— |
| 3074 | 2-I-3-Pr—PhCH2— |
| 3075 | 2-I-4-Pr—PhCH2— |
| 3076 | 2-I-5-Pr—PhCH2— |
| 3077 | 2-I-6-Pr—PhCH2— |
| 3078 | 2-Me-3-Pr—PhCH2— |
| 3079 | 2-Me-4-Pr—PhCH2— |
| 3080 | 2-Me-5-Pr—PhCH2— |
| 3081 | 2-Me-6-Pr—PhCH2— |
| 3082 | 2-F-3-iPr—PhCH2— |
| 3083 | 2-F-4-iPr—PhCH2— |
| 3084 | 2-F-5-iPr—PhCH2— |
| 3085 | 2-F-6-iPr—PhCH2— |
| 3086 | 2-Cl-3-iPr—PhCH2— |
| 3087 | 2-Cl-4-iPr—PhCH2— |
| 3088 | 2-Cl-5-iPr—PhCH2— |
| 3089 | 2-Cl-6-iPr—PhCH2— |
| 3090 | 2-Br-3-iPr—PhCH2— |
| 3091 | 2-Br-4-iPr—PhCH2— |
| 3092 | 2-Br-5-iPr—PhCH2— |
| 3093 | 2-Br-6-iPr—PhCH2— |
| 3094 | 2-I-3-iPr—PhCH2— |
| 3095 | 2-I-4-iPr—PhCH2— |
| 3096 | 2-I-5-iPr—PhCH2— |
| 3097 | 2-I-6-iPr—PhCH2— |
| 3098 | 2-Me-3-iPr—PhCH2— |
| 3099 | 2-Me-4-iPr—PhCH2— |
| 3100 | 2-Me-5-iPr—PhCH2— |
| 3101 | 2-Me-6-iPr—PhCH2— |
| 3102 | 2-F-3-N≡CCH2—PhCH2— |
| 3103 | 2-F-4-N≡CCH2—PhCH2— |
| 3104 | 2-F-5-N≡CCH2—PhCH2— |
| 3105 | 2-F-6-N≡CCH2—PhCH2— |
| 3106 | 2-Cl-3-N≡CCH2—PhCH2— |
| 3107 | 2-Cl-4-N≡CCH2—PhCH2— |
| 3108 | 2-Cl-5-N≡CCH2—PhCH2— |
| 3109 | 2-Cl-6-N≡CCH2—PhCH2— |
| 3110 | 2-Br-3-N≡CCH2—PhCH2— |
| 3111 | 2-Br-4-N≡CCH2—PhCH2— |
| 3112 | 2-Br-5-N≡CCH2—PhCH2— |
| 3113 | 2-Br-6-N≡CCH2—PhCH2— |
| 3114 | 2-I-3-N≡CCH2—PhCH2— |
| 3115 | 2-I-4-N≡CCH2—PhCH2— |
| 3116 | 2-I-5-N≡CCH2—PhCH2— |
| 3117 | 2-I-6-N≡CCH2—PhCH2— |
| 3118 | 2-Me-3-N≡CCH2—PhCH2— |
| 3119 | 2-Me-4-N≡CCH2—PhCH2— |
| 3120 | 2-Me-5-N≡CCH2—PhCH2— |
| 3121 | 2-Me-6-N≡CCH2—PhCH2— |
| 3122 | 2-F-3-N≡CCH2CH2—PhCH2— |
| 3123 | 2-F-4-N≡CCH2CH2—PhCH2— |
| 3124 | 2-F-5-N≡CCH2CH2—PhCH2— |
| 3125 | 2-F-6-N≡CCH2CH2—PhCH2— |
| 3126 | 2-Cl-3-N≡CCH2CH2—PhCH2— |
| 3127 | 2-Cl-4-N≡CCH2CH2—PhCH2— |
| 3128 | 2-Cl-5-N≡CCH2CH2—PhCH2— |
| 3129 | 2-Cl-6-N≡CCH2CH2—PhCH2— |
| 3130 | 2-Br-3-N≡CCH2CH2—PhCH2— |
| 3131 | 2-Br-4-N≡CCH2CH2—PhCH2— |
| 3132 | 2-Br-5-N≡CCH2CH2—PhCH2— |
| 3133 | 2-Br-6-N≡CCH2CH2—PhCH2— |
| 3134 | 2-I-3-N≡CCH2CH2—PhCH2— |
| 3135 | 2-I-4-N≡CCH2CH2—PhCH2— |
| 3136 | 2-I-5-N≡CCH2CH2—PhCH2— |
| 3137 | 2-I-6-N≡CCH2CH2—PhCH2— |
| 3138 | 2-Me-3-N≡CCH2CH2—PhCH2— |
| 3139 | 2-Me-4-N≡CCH2CH2—PhCH2— |
| 3140 | 2-Me-5-N≡CCH2CH2—PhCH2— |
| 3141 | 2-Me-6-N≡CCH2CH2—PhCH2— |
| 3142 | 2-F-3-cPrCH2—PhCH2— |
| 3143 | 2-F-4-cPrCH2—PhCH2— |
| 3144 | 2-F-5-cPrCH2—PhCH2— |
| 3145 | 2-F-6-cPrCH2—PhCH2— |
| 3146 | 2-Cl-3-cPrCH2—PhCH2— |
| 3147 | 2-Cl-4-cPrCH2—PhCH2— |
| 3148 | 2-Cl-5-cPrCH2—PhCH2— |
| 3149 | 2-Cl-6-cPrCH2—PhCH2— |
| 3150 | 2-Br-3-cPrCH2—PhCH2— |
| 3151 | 2-Br-4-cPrCH2—PhCH2— |
| 3152 | 2-Br-5-cPrCH2—PhCH2— |

TABLE 2-continued

| No. | Z |
|---|---|
| 3153 | 2-Br-6-cPrCH2—PhCH2— |
| 3154 | 2-I-3-cPrCH2—PhCH2— |
| 3155 | 2-I-4-cPrCH2—PhCH2— |
| 3156 | 2-I-5-cPrCH2—PhCH2— |
| 3157 | 2-I-6-cPrCH2—PhCH2— |
| 3158 | 2-Me-3-cPrCH2—PhCH2— |
| 3159 | 2-Me-4-cPrCH2—PhCH2— |
| 3160 | 2-Me-5-cPrCH2—PhCH2— |
| 3161 | 2-Me-6-cPrCH2—PhCH2— |
| 3162 | 2-F-3-cBuCH2—PhCH2— |
| 3163 | 2-F-4-cBuCH2—PhCH2— |
| 3164 | 2-F-5-cBuCH2—PhCH2— |
| 3165 | 2-F-6-cBuCH2—PhCH2— |
| 3166 | 2-Cl-3-cBuCH2—PhCH2— |
| 3167 | 2-Cl-4-cBuCH2—PhCH2— |
| 3168 | 2-Cl-5-cBuCH2—PhCH2— |
| 3169 | 2-Cl-6-cBuCH2—PhCH2— |
| 3170 | 2-Br-3-cBuCH2—PhCH2— |
| 3171 | 2-Br-4-cBuCH2—PhCH2— |
| 3172 | 2-Br-5-cBuCH2—PhCH2— |
| 3173 | 2-Br-6-cBuCH2—PhCH2— |
| 3174 | 2-I-3-cBuCH2—PhCH2— |
| 3175 | 2-I-4-cBuCH2—PhCH2— |
| 3176 | 2-I-5-cBuCH2—PhCH2— |
| 3177 | 2-I-6-cBuCH2—PhCH2— |
| 3178 | 2-Me-3-cBuCH2—PhCH2— |
| 3179 | 2-Me-4-cBuCH2—PhCH2— |
| 3180 | 2-Me-5-cBuCH2—PhCH2— |
| 3181 | 2-Me-6-cBuCH2—PhCH2— |
| 3182 | 2-F-3-MeOCH2—PhCH2— |
| 3183 | 2-F-4-MeOCH2—PhCH2— |
| 3184 | 2-F-5-MeOCH2—PhCH2— |
| 3185 | 2-F-6-MeOCH2—PhCH2— |
| 3186 | 2-Cl-3-MeOCH2—PhCH2— |
| 3187 | 2-Cl-4-MeOCH2—PhCH2— |
| 3188 | 2-Cl-5-MeOCH2—PhCH2— |
| 3189 | 2-Cl-6-MeOCH2—PhCH2— |
| 3190 | 2-Br-3-MeOCH2—PhCH2— |
| 3191 | 2-Br-4-MeOCH2—PhCH2— |
| 3192 | 2-Br-5-MeOCH2—PhCH2— |
| 3193 | 2-Br-6-MeOCH2—PhCH2— |
| 3194 | 2-I-3-MeOCH2—PhCH2— |
| 3195 | 2-I-4-MeOCH2—PhCH2— |
| 3196 | 2-I-5-MeOCH2—PhCH2— |
| 3197 | 2-I-6-MeOCH2—PhCH2— |
| 3198 | 2-Me-3-MeOCH2—PhCH2— |
| 3199 | 2-Me-4-MeOCH2—PhCH2— |
| 3200 | 2-Me-5-MeOCH2—PhCH2— |
| 3201 | 2-Me-6-MeOCH2—PhCH2— |
| 3202 | 2-F-3-MeOCH2CH2—PhCH2— |
| 3203 | 2-F-4-MeOCH2CH2—PhCH2— |
| 3204 | 2-F-5-MeOCH2CH2—PhCH2— |
| 3205 | 2-F-6-MeOCH2CH2—PhCH2— |
| 3206 | 2-Cl-3-MeOCH2CH2—PhCH2— |
| 3207 | 2-Cl-4-MeOCH2CH2—PhCH2— |
| 3208 | 2-Cl-5-MeOCH2CH2—PhCH2— |
| 3209 | 2-Cl-6-MeOCH2CH2—PhCH2— |
| 3210 | 2-Br-3-MeOCH2CH2—PhCH2— |
| 3211 | 2-Br-4-MeOCH2CH2—PhCH2— |
| 3212 | 2-Br-5-MeOCH2CH2—PhCH2— |
| 3213 | 2-Br-6-MeOCH2CH2—PhCH2— |
| 3214 | 2-I-3-MeOCH2CH2—PhCH2— |
| 3215 | 2-I-4-MeOCH2CH2—PhCH2— |
| 3216 | 2-I-5-MeOCH2CH2—PhCH2— |
| 3217 | 2-I-6-MeOCH2CH2—PhCH2— |
| 3218 | 2-Me-3-MeOCH2CH2—PhCH2— |
| 3219 | 2-Me-4-MeOCH2CH2—PhCH2— |
| 3220 | 2-Me-5-MeOCH2CH2—PhCH2— |
| 3221 | 2-Me-6-MeOCH2CH2—PhCH2— |
| 3222 | 2-F-3-MeOCH2CH2CH2—PhCH2— |
| 3223 | 2-F-4-MeOCH2CH2CH2—PhCH2— |
| 3224 | 2-F-5-MeOCH2CH2CH2—PhCH2— |
| 3225 | 2-F-6-MeOCH2CH2CH2—PhCH2— |
| 3226 | 2-Cl-3-MeOCH2CH2CH2—PhCH2— |
| 3227 | 2-Cl-4-MeOCH2CH2CH2—PhCH2— |
| 3228 | 2-Cl-5-MeOCH2CH2CH2—PhCH2— |
| 3229 | 2-Cl-6-MeOCH2CH2CH2—PhCH2— |
| 3230 | 2-Br-3-MeOCH2CH2CH2—PhCH2— |
| 3231 | 2-Br-4-MeOCH2CH2CH2—PhCH2— |
| 3232 | 2-Br-5-MeOCH2CH2CH2—PhCH2— |
| 3233 | 2-Br-6-MeOCH2CH2CH2—PhCH2— |
| 3234 | 2-I-3-MeOCH2CH2CH2—PhCH2— |
| 3235 | 2-I-4-MeOCH2CH2CH2—PhCH2— |
| 3236 | 2-I-5-MeOCH2CH2CH2—PhCH2— |
| 3237 | 2-I-6-MeOCH2CH2CH2—PhCH2— |
| 3238 | 2-Me-3-MeOCH2CH2CH2—PhCH2— |
| 3239 | 2-Me-4-MeOCH2CH2CH2—PhCH2— |
| 3240 | 2-Me-5-MeOCH2CH2CH2—PhCH2— |
| 3241 | 2-Me-6-MeOCH2CH2CH2—PhCH2— |
| 3242 | 2-F-3-EtOCH2—PhCH2— |
| 3243 | 2-F-4-EtOCH2—PhCH2— |
| 3244 | 2-F-5-EtOCH2—PhCH2— |
| 3245 | 2-F-6-EtOCH2—PhCH2— |
| 3246 | 2-Cl-3-EtOCH2—PhCH2— |
| 3247 | 2-Cl-4-EtOCH2—PhCH2— |
| 3248 | 2-Cl-5-EtOCH2—PhCH2— |
| 3249 | 2-Cl-6-EtOCH2—PhCH2— |
| 3250 | 2-Br-3-EtOCH2—PhCH2— |
| 3251 | 2-Br-4-EtOCH2—PhCH2— |
| 3252 | 2-Br-5-EtOCH2—PhCH2— |
| 3253 | 2-Br-6-EtOCH2—PhCH2— |
| 3254 | 2-I-3-EtOCH2—PhCH2— |
| 3255 | 2-I-4-EtOCH2—PhCH2— |
| 3256 | 2-I-5-EtOCH2—PhCH2— |
| 3257 | 2-I-6-EtOCH2—PhCH2— |
| 3258 | 2-Me-3-EtOCH2—PhCH2— |
| 3259 | 2-Me-4-EtOCH2—PhCH2— |
| 3260 | 2-Me-5-EtOCH2—PhCH2— |
| 3261 | 2-Me-6-EtOCH2—PhCH2— |
| 3262 | 2-F-3-EtOCH2CH2—PhCH2— |
| 3263 | 2-F-4-EtOCH2CH2—PhCH2— |
| 3264 | 2-F-5-EtOCH2CH2—PhCH2— |
| 3265 | 2-F-6-EtOCH2CH2—PhCH2— |
| 3266 | 2-Cl-3-EtOCH2CH2—PhCH2— |
| 3267 | 2-Cl-4-EtOCH2CH2—PhCH2— |
| 3268 | 2-Cl-5-EtOCH2CH2—PhCH2— |
| 3269 | 2-Cl-6-EtOCH2CH2—PhCH2— |
| 3270 | 2-Br-3-EtOCH2CH2—PhCH2— |
| 3271 | 2-Br-4-EtOCH2CH2—PhCH2— |
| 3272 | 2-Br-5-EtOCH2CH2—PhCH2— |
| 3273 | 2-Br-6-EtOCH2CH2—PhCH2— |
| 3274 | 2-I-3-EtOCH2CH2—PhCH2— |
| 3275 | 2-I-4-EtOCH2CH2—PhCH2— |
| 3276 | 2-I-5-EtOCH2CH2—PhCH2— |
| 3277 | 2-I-6-EtOCH2CH2—PhCH2— |
| 3278 | 2-Me-3-EtOCH2CH2—PhCH2— |
| 3279 | 2-Me-4-EtOCH2CH2—PhCH2— |
| 3280 | 2-Me-5-EtOCH2CH2—PhCH2— |
| 3281 | 2-Me-6-EtOCH2CH2—PhCH2— |
| 3282 | 2-F-3-cPrOCH2—PhCH2— |
| 3283 | 2-F-4-cPrOCH2—PhCH2— |
| 3284 | 2-F-5-cPrOCH2—PhCH2— |
| 3285 | 2-F-6-cPrOCH2—PhCH2— |
| 3286 | 2-Cl-3-cPrOCH2—PhCH2— |
| 3287 | 2-Cl-4-cPrOCH2—PhCH2— |
| 3288 | 2-Cl-5-cPrOCH2—PhCH2— |
| 3289 | 2-Cl-6-cPrOCH2—PhCH2— |
| 3290 | 2-Br-3-cPrOCH2—PhCH2— |
| 3291 | 2-Br-4-cPrOCH2—PhCH2— |
| 3292 | 2-Br-5-cPrOCH2—PhCH2— |
| 3293 | 2-Br-6-cPrOCH2—PhCH2— |
| 3294 | 2-I-3-cPrOCH2—PhCH2— |
| 3295 | 2-I-4-cPrOCH2—PhCH2— |
| 3296 | 2-I-5-cPrOCH2—PhCH2— |
| 3297 | 2-I-6-cPrOCH2—PhCH2— |
| 3298 | 2-Me-3-cPrOCH2—PhCH2— |
| 3299 | 2-Me-4-cPrOCH2—PhCH2— |
| 3300 | 2-Me-5-cPrOCH2—PhCH2— |
| 3301 | 2-Me-6-cPrOCH2—PhCH2— |
| 3302 | 2-F-3-F3COCH2—PhCH2— |
| 3303 | 2-F-4-F3COCH2—PhCH2— |
| 3304 | 2-F-5-F3COCH2—PhCH2— |
| 3305 | 2-F-6-F3COCH2—PhCH2— |
| 3306 | 2-Cl-3-F3COCH2—PhCH2— |
| 3307 | 2-Cl-4-F3COCH2—PhCH2— |
| 3308 | 2-Cl-5-F3COCH2—PhCH2— |

TABLE 2-continued

| No. | Z |
|---|---|
| 3309 | 2-Cl-6-F3COCH2—PhCH2— |
| 3310 | 2-Br-3-F3COCH2—PhCH2— |
| 3311 | 2-Br-4-F3COCH2—PhCH2— |
| 3312 | 2-Br-5-F3COCH2—PhCH2— |
| 3313 | 2-Br-6-F3COCH2—PhCH2— |
| 3314 | 2-I-3-F3COCH2—PhCH2— |
| 3315 | 2-I-4-F3COCH2—PhCH2— |
| 3316 | 2-I-5-F3COCH2—PhCH2— |
| 3317 | 2-I-6-F3COCH2—PhCH2— |
| 3318 | 2-Me-3-F3COCH2—PhCH2— |
| 3319 | 2-Me-4-F3COCH2—PhCH2— |
| 3320 | 2-Me-5-F3COCH2—PhCH2— |
| 3321 | 2-Me-6-F3COCH2—PhCH2— |
| 3322 | 2-F-3-F2CHOCH2—PhCH2— |
| 3323 | 2-F-4-F2CHOCH2—PhCH2— |
| 3324 | 2-F-5-F2CHOCH2—PhCH2— |
| 3325 | 2-F-6-F2CHOCH2—PhCH2— |
| 3326 | 2-Cl-3-F2CHOCH2—PhCH2— |
| 3327 | 2-Cl-4-F2CHOCH2—PhCH2— |
| 3328 | 2-Cl-5-F2CHOCH2—PhCH2— |
| 3329 | 2-Cl-6-F2CHOCH2—PhCH2— |
| 3330 | 2-Br-3-F2CHOCH2—PhCH2— |
| 3331 | 2-Br-4-F2CHOCH2—PhCH2— |
| 3332 | 2-Br-5-F2CHOCH2—PhCH2— |
| 3333 | 2-Br-6-F2CHOCH2—PhCH2— |
| 3334 | 2-I-3-F2CHOCH2—PhCH2— |
| 3335 | 2-I-4-F2CHOCH2—PhCH2— |
| 3336 | 2-I-5-F2CHOCH2—PhCH2— |
| 3337 | 2-I-6-F2CHOCH2—PhCH2— |
| 3338 | 2-Me-3-F2CHOCH2—PhCH2— |
| 3339 | 2-Me-4-F2CHOCH2—PhCH2— |
| 3340 | 2-Me-5-F2CHOCH2—PhCH2— |
| 3341 | 2-Me-6-F2CHOCH2—PhCH2— |
| 3342 | 2-F-3-MeOCH2CH2OCH2—PhCH2— |
| 3343 | 2-F-4-MeOCH2CH2OCH2—PhCH2— |
| 3344 | 2-F-5-MeOCH2CH2OCH2—PhCH2— |
| 3345 | 2-F-6-MeOCH2CH2OCH2—PhCH2— |
| 3346 | 2-Cl-3-MeOCH2CH2OCH2—PhCH2— |
| 3347 | 2-Cl-4-MeOCH2CH2OCH2—PhCH2— |
| 3348 | 2-Cl-5-MeOCH2CH2OCH2—PhCH2— |
| 3349 | 2-Cl-6-MeOCH2CH2OCH2—PhCH2— |
| 3350 | 2-Br-3-MeOCH2CH2OCH2—PhCH2— |
| 3351 | 2-Br-4-MeOCH2CH2OCH2—PhCH2— |
| 3352 | 2-Br-5-MeOCH2CH2OCH2—PhCH2— |
| 3353 | 2-Br-6-MeOCH2CH2OCH2—PhCH2— |
| 3354 | 2-I-3-MeOCH2CH2OCH2—PhCH2— |
| 3355 | 2-I-4-MeOCH2CH2OCH2—PhCH2— |
| 3356 | 2-I-5-MeOCH2CH2OCH2—PhCH2— |
| 3357 | 2-I-6-MeOCH2CH2OCH2—PhCH2— |
| 3358 | 2-Me-3-MeOCH2CH2OCH2—PhCH2— |
| 3359 | 2-Me-4-MeOCH2CH2OCH2—PhCH2— |
| 3360 | 2-Me-5-MeOCH2CH2OCH2—PhCH2— |
| 3361 | 2-Me-6-MeOCH2CH2OCH2—PhCH2— |
| 3362 | 2-F-3-Me2NCH2—PhCH2— |
| 3363 | 2-F-4-Me2NCH2—PhCH2— |
| 3364 | 2-F-5-Me2NCH2—PhCH2— |
| 3365 | 2-F-6-Me2NCH2—PhCH2— |
| 3366 | 2-Cl-3-Me2NCH2—PhCH2— |
| 3367 | 2-Cl-4-Me2NCH2—PhCH2— |
| 3368 | 2-Cl-5-Me2NCH2—PhCH2— |
| 3369 | 2-Cl-6-Me2NCH2—PhCH2— |
| 3370 | 2-Br-3-Me2NCH2—PhCH2— |
| 3371 | 2-Br-4-Me2NCH2—PhCH2— |
| 3372 | 2-Br-5-Me2NCH2—PhCH2— |
| 3373 | 2-Br-6-Me2NCH2—PhCH2— |
| 3374 | 2-I-3-Me2NCH2—PhCH2— |
| 3375 | 2-I-4-Me2NCH2—PhCH2— |
| 3376 | 2-I-5-Me2NCH2—PhCH2— |
| 3377 | 2-I-6-Me2NCH2—PhCH2— |
| 3378 | 2-Me-3-Me2NCH2—PhCH2— |
| 3379 | 2-Me-4-Me2NCH2—PhCH2— |
| 3380 | 2-Me-5-Me2NCH2—PhCH2— |
| 3381 | 2-Me-6-Me2NCH2—PhCH2— |
| 3382 | 2-F-3-MeSCH2—PhCH2— |
| 3383 | 2-F-4-MeSCH2—PhCH2— |
| 3384 | 2-F-5-MeSCH2—PhCH2— |
| 3385 | 2-F-6-MeSCH2—PhCH2— |
| 3386 | 2-Cl-3MeSCH2—PhCH2— |
| 3387 | 2-Cl-4-MeSCH2—PhCH2— |
| 3388 | 2-Cl-5-MeSCH2—PhCH2— |
| 3389 | 2-Cl-6-MeSCH2—PhCH2— |
| 3390 | 2-Br-3-MeSCH2—PhCH2— |
| 3391 | 2-Br-4-MeSCH2—PhCH2— |
| 3392 | 2-Br-5-MeSCH2—PhCH2— |
| 3393 | 2-Br-6-MeSCH2—PhCH2— |
| 3394 | 2-I-3-MeSCH2—PhCH2— |
| 3395 | 2-I-4-MeSCH2—PhCH2— |
| 3396 | 2-I-5-MeSCH2—PhCH2— |
| 3397 | 2-I-6-MeSCH2—PhCH2— |
| 3398 | 2-Me-3-MeSCH2—PhCH2— |
| 3399 | 2-Me-4-MeSCH2—PhCH2— |
| 3400 | 2-Me-5-MeSCH2—PhCH2— |
| 3401 | 2-Me-6-MeSCH2—PhCH2— |
| 3402 | 2-F-3-MeS(O)CH2—PhCH2— |
| 3403 | 2-F-4-MeS(O)CH2—PhCH2— |
| 3404 | 2-F-5-MeS(O)CH2—PhCH2— |
| 3405 | 2-F-6-MeS(O)CH2—PhCH2— |
| 3406 | 2-Cl-3-MeS(O)CH2—PhCH2— |
| 3407 | 2-Cl-4-MeS(O)CH2—PhCH2— |
| 3408 | 2-Cl-5-MeS(O)CH2—PhCH2— |
| 3409 | 2-Cl-6-MeS(O)CH2—PhCH2— |
| 3410 | 2-Br-3-MeS(O)CH2—PhCH2— |
| 3411 | 2-Br-4-MeS(O)CH2—PhCH2— |
| 3412 | 2-Br-5-MeS(O)CH2—PhCH2— |
| 3413 | 2-Br-6-MeS(O)CH2—PhCH2— |
| 3414 | 2-I-3-MeS(O)CH2—PhCH2— |
| 3415 | 2-I-4-MeS(O)CH2—PhCH2— |
| 3416 | 2-I-5-MeS(O)CH2—PhCH2— |
| 3417 | 2-I-6-MeS(O)CH2—PhCH2— |
| 3418 | 2-Me-3-MeS(O)CH2—PhCH2— |
| 3419 | 2-Me-4-MeS(O)CH2—PhCH2— |
| 3420 | 2-Me-5-MeS(O)CH2—PhCH2— |
| 3421 | 2-Me-6-MeS(O)CH2—PhCH2— |
| 3422 | 2-F-3-MeSO2CH2—PhCH2— |
| 3423 | 2-F-4-MeSO2CH2—PhCH2— |
| 3424 | 2-F-5-MeSO2CH2—PhCH2— |
| 3425 | 2-F-6-MeSO2CH2—PhCH2— |
| 3426 | 2-Cl-3-MeSO2CH2—PhCH2— |
| 3427 | 2-Cl-4-MeSO2CH2—PhCH2— |
| 3428 | 2-Cl-5-MeSO2CH2—PhCH2— |
| 3429 | 2-Cl-6-MeSO2CH2—PhCH2— |
| 3430 | 2-Br-3-MeSO2CH2—PhCH2— |
| 3431 | 2-Br-4-MeSO2CH2—PhCH2— |
| 3432 | 2-Br-5-MeSO2CH2—PhCH2— |
| 3433 | 2-Br-6-MeSO2CH2—PhCH2— |
| 3434 | 2-I-3-MeSO2CH2—PhCH2— |
| 3435 | 2-I-4-MeSO2CH2—PhCH2— |
| 3436 | 2-I-5-MeSO2CH2—PhCH2— |
| 3437 | 2-I-6-MeSO2CH2—PhCH2— |
| 3438 | 2-Me-3-MeSO2CH2—PhCH2— |
| 3439 | 2-Me-4-MeSO2CH2—PhCH2— |
| 3440 | 2-Me-5-MeSO2CH2—PhCH2— |
| 3441 | 2-Me-6-MeSO2CH2—PhCH2— |
| 3442 | 2-F-3-cPr—PhCH2— |
| 3443 | 2-F-4-cPr—PhCH2— |
| 3444 | 2-F-5-cPr—PhCH2— |
| 3445 | 2-F-6-cPr—PhCH2— |
| 3446 | 2-Cl-3-cPr—PhCH2— |
| 3447 | 2-Cl-4-cPr—PhCH2— |
| 3448 | 2-Cl-5-cPr—PhCH2— |
| 3449 | 2-Cl-6-cPr—PhCH2— |
| 3450 | 2-Br-3-cPr—PhCH2— |
| 3451 | 2-Br-4-cPr—PhCH2— |
| 3452 | 2-Br-5-cPr—PhCH2— |
| 3453 | 2-Br-6-cPr—PhCH2— |
| 3454 | 2-I-3-cPr—PhCH2— |
| 3455 | 2-I-4-cPr—PhCH2— |
| 3456 | 2-I-5-cPr—PhCH2— |
| 3457 | 2-I-6-cPr—PhCH2— |
| 3458 | 2-Me-3-cPr—PhCH2— |
| 3459 | 2-Me-4-cPr—PhCH2— |
| 3460 | 2-Me-5-cPr—PhCH2— |
| 3461 | 2-Me-6-cPr—PhCH2— |
| 3462 | 2-F-3-cBu—PhCH2— |
| 3463 | 2-F-4-cBu—PhCH2— |
| 3464 | 2-F-5-cBu—PhCH2— |

TABLE 2-continued

| No. | Z |
|---|---|
| 3465 | 2-F-6-cBu—PhCH2— |
| 3466 | 2-Cl-3-cBu—PhCH2— |
| 3467 | 2-Cl-4-cBu—PhCH2— |
| 3468 | 2-Cl-5-cBu—PhCH2— |
| 3469 | 2-Cl-6-cBu—PhCH2— |
| 3470 | 2-Br-3-cBu—PhCH2— |
| 3471 | 2-Br-4-cBu—PhCH2— |
| 3472 | 2-Br-5-cBu—PhCH2— |
| 3473 | 2-Br-6-cBu—PhCH2— |
| 3474 | 2-I-3-cBu—PhCH2— |
| 3475 | 2-I-4-cBu—PhCH2— |
| 3476 | 2-I-5-cBu—PhCH2— |
| 3477 | 2-I-6-cBu—PhCH2— |
| 3478 | 2-Me-3-cBu—PhCH2— |
| 3479 | 2-Me-4-cBu—PhCH2— |
| 3480 | 2-Me-5-cBu—PhCH2— |
| 3481 | 2-Me-6-cBu—PhCH2— |
| 3482 | 2-F-3-F3C—PhCH2— |
| 3483 | 2-F-4-F3C—PhCH2— |
| 3484 | 2-F-5-F3C—PhCH2— |
| 3485 | 2-F-6-F3C—PhCH2— |
| 3486 | 2-Cl-3-F3C—PhCH2— |
| 3487 | 2-Cl-4-F3C—PhCH2— |
| 3488 | 2-Cl-5-F3C—PhCH2— |
| 3489 | 2-Cl-6-F3C—PhCH2— |
| 3490 | 2-Br-3-F3C—PhCH2— |
| 3491 | 2-Br-4-F3C—PhCH2— |
| 3492 | 2-Br-5-F3C—PhCH2— |
| 3493 | 2-Br-6-F3C—PhCH2— |
| 3494 | 2-I-3-F3C—PhCH2— |
| 3495 | 2-I-4-F3C—PhCH2— |
| 3496 | 2-I-5-F3C—PhCH2— |
| 3497 | 2-I-6-F3C—PhCH2— |
| 3498 | 2-Me-3-F3C—PhCH2— |
| 3499 | 2-Me-4-F3C—PhCH2— |
| 3500 | 2-Me-5-F3C—PhCH2— |
| 3501 | 2-Me-6-F3C—PhCH2— |
| 3502 | 2-F-3-F2CH—PhCH2— |
| 3503 | 2-F-4-F2CH—PhCH2— |
| 3504 | 2-F-5-F2CH—PhCH2— |
| 3505 | 2-F-6-F2CH—PhCH2— |
| 3506 | 2-Cl-3-F2CH—PhCH2— |
| 3507 | 2-Cl-4-F2CH—PhCH2— |
| 3508 | 2-Cl-5-F2CH—PhCH2— |
| 3509 | 2-Cl-6-F2CH—PhCH2— |
| 3510 | 2-Br-3-F2CH—PhCH2— |
| 3511 | 2-Br-4-F2CH—PhCH2— |
| 3512 | 2-Br-5-F2CH—PhCH2— |
| 3513 | 2-Br-6-F2CH—PhCH2— |
| 3514 | 2-I-3-F2CH—PhCH2— |
| 3515 | 2-I-4-F2CH—PhCH2— |
| 3516 | 2-I-5-F2CH—PhCH2— |
| 3517 | 2-I-6-F2CH—PhCH2— |
| 3518 | 2-Me-3-F2CH—PhCH2— |
| 3519 | 2-Me-4-F2CH—PhCH2— |
| 3520 | 2-Me-5-F2CH—PhCH2— |
| 3521 | 2-Me-6-F2CH—PhCH2— |
| 3522 | 2-F-3-H2C=CH—PhCH2— |
| 3523 | 2-F-4-H2C=CH—PhCH2— |
| 3524 | 2-F-5-H2C=CH—PhCH2— |
| 3525 | 2-F-6-H2C=CH—PhCH2— |
| 3526 | 2-Cl-3-H2C=CH—PhCH2— |
| 3527 | 2-Cl-4-H2C=CH—PhCH2— |
| 3528 | 2-Cl-5-H2C=CH—PhCH2— |
| 3529 | 2-Cl-6-H2C=CH—PhCH2— |
| 3530 | 2-Br-3-H2C=CH—PhCH2— |
| 3531 | 2-Br-4-H2C=CH—PhCH2— |
| 3532 | 2-Br-5-H2C=CH—PhCH2— |
| 3533 | 2-Br-6-H2C=CH—PhCH2— |
| 3534 | 2-I-3-H2C=CH—PhCH2— |
| 3535 | 2-I-4-H2C=CH—PhCH2— |
| 3536 | 2-I-5-H2C=CH—PhCH2— |
| 3537 | 2-I-6-H2C=CH—PhCH2— |
| 3538 | 2-Me-3-H2C=CH—PhCH2— |
| 3539 | 2-Me-4-H2C=CH—PhCH2— |
| 3540 | 2-Me-5-H2C=CH—PhCH2— |
| 3541 | 2-Me-6-H2C=CH—PhCH2— |
| 3542 | 2-F-3-H2C=CHCH2—PhCH2— |
| 3543 | 2-F-4-H2C=CHCH2—PhCH2— |
| 3544 | 2-F-5-H2C=CHCH2—PhCH2— |
| 3545 | 2-F-6-H2C=CHCH2—PhCH2— |
| 3546 | 2-Cl-3-H2C=CHCH2—PhCH2— |
| 3547 | 2-Cl-4-H2C=CHCH2—PhCH2— |
| 3548 | 2-Cl-5-H2C=CHCH2—PhCH2— |
| 3549 | 2-Cl-6-H2C=CHCH2—PhCH2— |
| 3550 | 2-Br-3-H2C=CHCH2—PhCH2— |
| 3551 | 2-Br-4-H2C=CHCH2—PhCH2— |
| 3552 | 2-Br-5-H2C=CHCH2—PhCH2— |
| 3553 | 2-Br-6-H2C=CHCH2—PhCH2— |
| 3554 | 2-I-3-H2C=CHCH2—PhCH2— |
| 3555 | 2-I-4-H2C=CHCH2—PhCH2— |
| 3556 | 2-I-5-H2C=CHCH2—PhCH2— |
| 3557 | 2-I-6-H2C=CHCH2—PhCH2— |
| 3558 | 2-Me-3-H2C=CHCH2—PhCH2— |
| 3559 | 2-Me-4-H2C=CHCH2—PhCH2— |
| 3560 | 2-Me-5-H2C=CHCH2—PhCH2— |
| 3561 | 2-Me-6-H2C=CHCH2—PhCH2— |
| 3562 | 2-F-3-F2C=CH—PhCH2— |
| 3563 | 2-F-4-F2C=CH—PhCH2— |
| 3564 | 2-F-5-F2C=CH—PhCH2— |
| 3565 | 2-F-6-F2C=CH—PhCH2— |
| 3566 | 2-Cl-3-F2C=CH—PhCH2— |
| 3567 | 2-Cl-4-F2C=CH—PhCH2— |
| 3568 | 2-Cl-5-F2C=CH—PhCH2— |
| 3569 | 2-Cl-6-F2C=CH—PhCH2— |
| 3570 | 2-Br-3-F2C=CH—PhCH2— |
| 3571 | 2-Br-4-F2C=CH—PhCH2— |
| 3572 | 2-Br-5-F2C=CH—PhCH2— |
| 3573 | 2-Br-6-F2C=CH—PhCH2— |
| 3574 | 2-I-3-F2C=CH—PhCH2— |
| 3575 | 2-I-4-F2C=CH—PhCH2— |
| 3576 | 2-I-5-F2C=CH—PhCH2— |
| 3577 | 2-I-6-F2C=CH—PhCH2— |
| 3578 | 2-Me-3-F2C=CH—PhCH2— |
| 3579 | 2-Me-4-F2C=CH—PhCH2— |
| 3580 | 2-Me-5-F2C=CH—PhCH2— |
| 3581 | 2-Me-6-F2C=CH—PhCH2— |
| 3582 | 2-F-3-F2C=CHCH2—PhCH2— |
| 3583 | 2-F-4-F2C=CHCH2—PhCH2— |
| 3584 | 2-F-5-F2C=CHCH2—PhCH2— |
| 3585 | 2-F-6-F2C=CHCH2—PhCH2— |
| 3586 | 2-Cl-3-F2C=CHCH2—PhCH2— |
| 3587 | 2-Cl-4-F2C=CHCH2—PhCH2— |
| 3588 | 2-Cl-5-F2C=CHCH2—PhCH2— |
| 3589 | 2-Cl-6-F2C=CHCH2—PhCH2— |
| 3590 | 2-Br-3-F2C=CHCH2—PhCH2— |
| 3591 | 2-Br-4-F2C=CHCH2—PhCH2— |
| 3592 | 2-Br-5-F2C=CHCH2—PhCH2— |
| 3593 | 2-Br-6-F2C=CHCH2—PhCH2— |
| 3594 | 2-I-3-F2C=CHCH2—PhCH2— |
| 3595 | 2-I-4-F2C=CHCH2—PhCH2— |
| 3596 | 2-I-5-F2C=CHCH2—PhCH2— |
| 3597 | 2-I-6-F2C=CHCH2—PhCH2— |
| 3598 | 2-Me-3-F2C=CHCH2—PhCH2— |
| 3599 | 2-Me-4-F2C=CHCH2—PhCH2— |
| 3600 | 2-Me-5-F2C=CHCH2—PhCH2— |
| 3601 | 2-Me-6-F2C=CHCH2—PhCH2— |
| 3602 | 2-F-3-HC≡C—PhCH2— |
| 3603 | 2-F-4-HC≡C—PhCH2— |
| 3604 | 2-F-5-HC≡C—PhCH2— |
| 3605 | 2-F-6-HC≡C—PhCH2— |
| 3606 | 2-Cl-3-HC≡C—PhCH2— |
| 3607 | 2-Cl-4-HC≡C—PhCH2— |
| 3608 | 2-Cl-5-HC≡C—PhCH2— |
| 3609 | 2-Cl-6-HC≡C—PhCH2— |
| 3610 | 2-Br-3-HC≡C—PhCH2— |
| 3611 | 2-Br-4-HC≡C—PhCH2— |
| 3612 | 2-Br-5-HC≡C—PhCH2— |
| 3613 | 2-Br-6-HC≡C—PhCH2— |
| 3614 | 2-I-3-HC≡C—PhCH2— |
| 3615 | 2-I-4-HC≡C—PhCH2— |
| 3616 | 2-I-5-HC≡C—PhCH2— |
| 3617 | 2-I-6-HC≡C—PhCH2— |
| 3618 | 2-Me-3-HC≡C—PhCH2— |
| 3619 | 2-Me-4-HC≡C—PhCH2— |
| 3620 | 2-Me-5-HC≡C—PhCH2— |

TABLE 2-continued

| No. | Z |
|---|---|
| 3621 | 2-Me-6-HC≡C—PhCH2— |
| 3622 | 2-F-3-HC≡CCH2—PhCH2— |
| 3623 | 2-F-4-HC≡CCH2—PhCH2— |
| 3624 | 2-F-5-HC≡CCH2—PhCH2— |
| 3625 | 2-F-6-HC≡CCH2—PhCH2— |
| 3626 | 2-Cl-3-HC≡CCH2—PhCH2— |
| 3627 | 2-Cl-4-HC≡CCH2—PhCH2— |
| 3628 | 2-Cl-5-HC≡CCH2—PhCH2— |
| 3629 | 2-Cl-6-HC≡CCH2—PhCH2— |
| 3630 | 2-Br-3-HC≡CCH2—PhCH2— |
| 3631 | 2-Br-4-HC≡CCH2—PhCH2— |
| 3632 | 2-Br-5-HC≡CCH2—PhCH2— |
| 3633 | 2-Br-6-HC≡CCH2—PhCH2— |
| 3634 | 2-I-3-HC≡CCH2—PhCH2— |
| 3635 | 2-I-4-HC≡CCH2—PhCH2— |
| 3636 | 2-I-5-HC≡CCH2—PhCH2— |
| 3637 | 2-I-6-HC≡CCH2—PhCH2— |
| 3638 | 2-Me-3-HC≡CCH2—PhCH2— |
| 3639 | 2-Me-4-HC≡CCH2—PhCH2— |
| 3640 | 2-Me-5-HC≡CCH2—PhCH2— |
| 3641 | 2-Me-6-HC≡CCH2—PhCH2— |
| 3642 | 2-F-3-F3CC≡C—PhCH2— |
| 3643 | 2-F-4-F3CC≡C—PhCH2— |
| 3644 | 2-F-5-F3CC≡C—PhCH2— |
| 3645 | 2-F-6-F3CC≡C—PhCH2— |
| 3646 | 2-Cl-3-F3CC≡C—PhCH2— |
| 3647 | 2-Cl-4-F3CC≡C—PhCH2— |
| 3648 | 2-Cl-5-F3CC≡C—PhCH2— |
| 3649 | 2-Cl-6-F3CC≡C—PhCH2— |
| 3650 | 2-Br-3-F3CC≡C—PhCH2— |
| 3651 | 2-Br-4-F3CC≡C—PhCH2— |
| 3652 | 2-Br-5-F3CC≡C—PhCH2— |
| 3653 | 2-Br-6-F3CC≡C—PhCH2— |
| 3654 | 2-I-3-F3CC≡C—PhCH2— |
| 3655 | 2-I-4-F3CC≡C—PhCH2— |
| 3656 | 2-I-5-F3CC≡C—PhCH2— |
| 3657 | 2-I-6-F3CC≡C—PhCH2— |
| 3658 | 2-Me-3-F3CC≡C—PhCH2— |
| 3659 | 2-Me-4-F3CC≡C—PhCH2— |
| 3660 | 2-Me-5-F3CC≡C—PhCH2— |
| 3661 | 2-Me-6-F3CC≡C—PhCH2— |
| 3662 | 2-F-3-F3CC≡CCH2—PhCH2— |
| 3663 | 2-F-4-F3CC≡CCH2—PhCH2— |
| 3664 | 2-F-5-F3CC≡CCH2—PhCH2— |
| 3665 | 2-F-6-F3CC≡CCH2—PhCH2— |
| 3666 | 2-Cl-3-F3CC≡CCH2—PhCH2— |
| 3667 | 2-Cl-4-F3CC≡CCH2—PhCH2— |
| 3668 | 2-Cl-5-F3CC≡CCH2—PhCH2— |
| 3669 | 2-Cl-6-F3CC≡CCH2—PhCH2— |
| 3670 | 2-Br-3-F3CC≡CCH2—PhCH2— |
| 3671 | 2-Br-4-F3CC≡CCH2—PhCH2— |
| 3672 | 2-Br-5-F3CC≡CCH2—PhCH2— |
| 3673 | 2-Br-6-F3CC≡CCH2—PhCH2— |
| 3674 | 2-I-3-F3CC≡CCH2—PhCH2— |
| 3675 | 2-I-4-F3CC≡CCH2—PhCH2— |
| 3676 | 2-I-5-F3CC≡CCH2—PhCH2— |
| 3677 | 2-I-6-F3CC≡CCH2—PhCH2— |
| 3678 | 2-Me-3-F3CC≡CCH2—PhCH2— |
| 3679 | 2-Me-4-F3CC≡CCH2—PhCH2— |
| 3680 | 2-Me-5-F3CC≡CCH2—PhCH2— |
| 3681 | 2-Me-6-F3CC≡CCH2—PhCH2— |
| 3682 | 2-F-3-MeO—PhCH2— |
| 3683 | 2-F-4-MeO—PhCH2— |
| 3684 | 2-F-5-MeO—PhCH2— |
| 3685 | 2-F-6-MeO—PhCH2— |
| 3686 | 2-Cl-3-MeO—PhCH2— |
| 3687 | 2-Cl-4-MeO—PhCH2— |
| 3688 | 2-Cl-5-MeO—PhCH2— |
| 3689 | 2-Cl-6-MeO—PhCH2— |
| 3690 | 2-Br-3-MeO—PhCH2— |
| 3691 | 2-Br-4-MeO—PhCH2— |
| 3692 | 2-Br-5-MeO—PhCH2— |
| 3693 | 2-Br-6-MeO—PhCH2— |
| 3694 | 2-I-3-MeO—PhCH2— |
| 3695 | 2-I-4-MeO—PhCH2— |
| 3696 | 2-I-5-MeO—PhCH2— |
| 3697 | 2-I-6-MeO—PhCH2— |
| 3698 | 2-Me-3-MeO—PhCH2— |
| 3699 | 2-Me-4-MeO—PhCH2— |
| 3700 | 2-Me-5-MeO—PhCH2— |
| 3701 | 2-Me-6-MeO—PhCH2— |
| 3702 | 2-F-3-EtO—PhCH2— |
| 3703 | 2-F-4-EtO—PhCH2— |
| 3704 | 2-F-5-EtO—PhCH2— |
| 3705 | 2-F-6-EtO—PhCH2— |
| 3706 | 2-Cl-3-EtO—PhCH2— |
| 3707 | 2-Cl-4-EtO—PhCH2— |
| 3708 | 2-Cl-5-EtO—PhCH2— |
| 3709 | 2-Cl-6-EtO—PhCH2— |
| 3710 | 2-Br-3-EtO—PhCH2— |
| 3711 | 2-Br-4-EtO—PhCH2— |
| 3712 | 2-Br-5-EtO—PhCH2— |
| 3713 | 2-Br-6-EtO—PhCH2— |
| 3714 | 2-I-3-EtO—PhCH2— |
| 3715 | 2-I-4-EtO—PhCH2— |
| 3716 | 2-I-5-EtO—PhCH2— |
| 3717 | 2-I-6-EtO—PhCH2— |
| 3718 | 2-Me-3-EtO—PhCH2— |
| 3719 | 2-Me-4-EtO—PhCH2— |
| 3720 | 2-Me-5-EtO—PhCH2— |
| 3721 | 2-Me-6-EtO—PhCH2— |
| 3722 | 2-F-3-PrO—PhCH2— |
| 3723 | 2-F-4-PrO—PhCH2— |
| 3724 | 2-F-5-PrO—PhCH2— |
| 3725 | 2-F-6-PrO—PhCH2— |
| 3726 | 2-Cl-3-PrO—PhCH2— |
| 3727 | 2-Cl-4-PrO—PhCH2— |
| 3728 | 2-Cl-5-PrO—PhCH2— |
| 3729 | 2-Cl-6-PrO—PhCH2— |
| 3730 | 2-Br-3-PrO—PhCH2— |
| 3731 | 2-Br-4-PrO—PhCH2— |
| 3732 | 2-Br-5-PrO—PhCH2— |
| 3733 | 2-Br-6-PrO—PhCH2— |
| 3734 | 2-I-3-PrO—PhCH2— |
| 3735 | 2-I-4-PrO—PhCH2— |
| 3736 | 2-I-5-PrO—PhCH2— |
| 3737 | 2-I-6-PrO—PhCH2— |
| 3738 | 2-Me-3-PrO—PhCH2— |
| 3739 | 2-Me-4-PrO—PhCH2— |
| 3740 | 2-Me-5-PrO—PhCH2— |
| 3741 | 2-Me-6-PrO—PhCH2— |
| 3742 | 2-F-3-iPrO—PhCH2— |
| 3743 | 2-F-4-iPrO—PhCH2— |
| 3744 | 2-F-5-iPrO—PhCH2— |
| 3745 | 2-F-6-iPrO—PhCH2— |
| 3746 | 2-Cl-3-iPrO—PhCH2— |
| 3747 | 2-Cl-4-iPrO—PhCH2— |
| 3748 | 2-Cl-5-iPrO—PhCH2— |
| 3749 | 2-Cl-6-iPrO—PhCH2— |
| 3750 | 2-Br-3-iPrO—PhCH2— |
| 3751 | 2-Br-4-iPrO—PhCH2— |
| 3752 | 2-Br-5-iPrO—PhCH2— |
| 3753 | 2-Br-6-iPrO—PhCH2— |
| 3754 | 2-I-3-iPrO—PhCH2— |
| 3755 | 2-I-4-iPrO—PhCH2— |
| 3756 | 2-I-5-iPrO—PhCH2— |
| 3757 | 2-I-6-iPrO—PhCH2— |
| 3758 | 2-Me-3-iPrO—PhCH2— |
| 3759 | 2-Me-4-iPrO—PhCH2— |
| 3760 | 2-Me-5-iPrO—PhCH2— |
| 3761 | 2-Me-6-iPrO—PhCH2— |
| 3762 | 2-F-3-BuO—PhCH2— |
| 3763 | 2-F-4-BuO—PhCH2— |
| 3764 | 2-F-5-BuO—PhCH2— |
| 3765 | 2-F-6-BuO—PhCH2— |
| 3766 | 2-Cl-3-BuO—PhCH2— |
| 3767 | 2-Cl-4-BuO—PhCH2— |
| 3768 | 2-Cl-5-BuO—PhCH2— |
| 3769 | 2-Cl-6-BuO—PhCH2— |
| 3770 | 2-Br-3-BuO—PhCH2— |
| 3771 | 2-Br-4-BuO—PhCH2— |
| 3772 | 2-Br-5-BuO—PhCH2— |
| 3773 | 2-Br-6-BuO—PhCH2— |
| 3774 | 2-I-3-BuO—PhCH2— |
| 3775 | 2-I-4-BuO—PhCH2— |
| 3776 | 2-I-5-BuO—PhCH2— |

TABLE 2-continued

| No. | Z |
|---|---|
| 3777 | 2-I-6-BuO—PhCH2— |
| 3778 | 2-Me-3-BuO—PhCH2— |
| 3779 | 2-Me-4-BuO—PhCH2— |
| 3780 | 2-Me-5-BuO—PhCH2— |
| 3781 | 2-Me-6-BuO—PhCH2— |
| 3782 | 2-F-3-iBuO—PhCH2— |
| 3783 | 2-F-4-iBuO—PhCH2— |
| 3784 | 2-F-5-iBuO—PhCH2— |
| 3785 | 2-F-6-iBuO—PhCH2— |
| 3786 | 2-Cl-3-iBuO—PhCH2— |
| 3787 | 2-Cl-4-iBuO—PhCH2— |
| 3788 | 2-Cl-5-iBuO—PhCH2— |
| 3789 | 2-Cl-6-iBuO—PhCH2— |
| 3790 | 2-Br-3-iBuO—PhCH2— |
| 3791 | 2-Br-4-iBuO—PhCH2— |
| 3792 | 2-Br-5-iBuO—PhCH2— |
| 3793 | 2-Br-6-iBuO—PhCH2— |
| 3794 | 2-I-3-iBuO—PhCH2— |
| 3795 | 2-I-4-iBuO—PhCH2— |
| 3796 | 2-I-5-iBuO—PhCH2— |
| 3797 | 2-I-6-iBuO—PhCH2— |
| 3798 | 2-Me-3-iBuO—PhCH2— |
| 3799 | 2-Me-4-iBuO—PhCH2— |
| 3800 | 2-Me-5-iBuO—PhCH2— |
| 3801 | 2-Me-6-iBuO—PhCH2— |
| 3802 | 2-F-3-PentylO—PhCH2— |
| 3803 | 2-F-4-PentylO—PhCH2— |
| 3804 | 2-F-5-PentylO—PhCH2— |
| 3805 | 2-F-6-PentylO—PhCH2— |
| 3806 | 2-Cl-3-PentylO—PhCH2— |
| 3807 | 2-Cl-4-PentylO—PhCH2— |
| 3808 | 2-Cl-5-PentylO—PhCH2— |
| 3809 | 2-Cl-6-PentylO—PhCH2— |
| 3810 | 2-Br-3-PentylO—PhCH2— |
| 3811 | 2-Br-4-PentylO—PhCH2— |
| 3812 | 2-Br-5-PentylO—PhCH2— |
| 3813 | 2-Br-6-PentylO—PhCH2— |
| 3814 | 2-I-3-PentylO—PhCH2— |
| 3815 | 2-I-4-PentylO—PhCH2— |
| 3816 | 2-I-5-PentylO—PhCH2— |
| 3817 | 2-I-6-PentylO—PhCH2— |
| 3818 | 2-Me-3-PentylO—PhCH2— |
| 3819 | 2-Me-4-PentylO—PhCH2— |
| 3820 | 2-Me-5-PentylO—PhCH2— |
| 3821 | 2-Me-6-PentylO—PhCH2— |
| 3822 | 2-F-3-N≡CCH2O—PhCH2— |
| 3823 | 2-F-4-N≡CCH2O—PhCH2— |
| 3824 | 2-F-5-N≡CCH2O—PhCH2— |
| 3825 | 2-F-6-N≡CCH2O—PhCH2— |
| 3826 | 2-Cl-3-N≡CCH2O—PhCH2— |
| 3827 | 2-Cl-4-N≡CCH2O—PhCH2— |
| 3828 | 2-Cl-5-N≡CCH2O—PhCH2— |
| 3829 | 2-Cl-6-N≡CCH2O—PhCH2— |
| 3830 | 2-Br-3-N≡CCH2O—PhCH2— |
| 3831 | 2-Br-4-N≡CCH2O—PhCH2— |
| 3832 | 2-Br-5-N≡CCH2O—PhCH2— |
| 3833 | 2-Br-6-N≡CCH2O—PhCH2— |
| 3834 | 2-I-3-N≡CCH2O—PhCH2— |
| 3835 | 2-I-4-N≡CCH2O—PhCH2— |
| 3836 | 2-I-5-N≡CCH2O—PhCH2— |
| 3837 | 2-I-6-N≡CCH2O—PhCH2— |
| 3838 | 2-Me-3-N≡CCH2O—PhCH2— |
| 3839 | 2-Me-4-N≡CCH2O—PhCH2— |
| 3840 | 2-Me-5-N≡CCH2O—PhCH2— |
| 3841 | 2-Me-6-N≡CCH2O—PhCH2— |
| 3842 | 2-F-3-N≡CCH2CH2O—PhCH2— |
| 3843 | 2-F-4-N≡CCH2CH2O—PhCH2— |
| 3844 | 2-F-5-N≡CCH2CH2O—PhCH2— |
| 3845 | 2-F-6-N≡CCH2CH2O—PhCH2— |
| 3846 | 2-Cl-3-N≡CCH2CH2O—PhCH2— |
| 3847 | 2-Cl-4-N≡CCH2CH2O—PhCH2— |
| 3848 | 2-Cl-5-N≡CCH2CH2O—PhCH2— |
| 3849 | 2-Cl-6-N≡CCH2CH2O—PhCH2— |
| 3850 | 2-Br-3-N≡CCH2CH2O—PhCH2— |
| 3851 | 2-Br-4-N≡CCH2CH2O—PhCH2— |
| 3852 | 2-Br-5-N≡CCH2CH2O—PhCH2— |
| 3853 | 2-Br-6-N≡CCH2CH2O—PhCH2— |
| 3854 | 2-I-3-N≡CCH2CH2O—PhCH2— |
| 3855 | 2-I-4-N≡CCH2CH2O—PhCH2— |
| 3856 | 2-I-5-N≡CCH2CH2O—PhCH2— |
| 3857 | 2-I-6-N≡CCH2CH2O—PhCH2— |
| 3858 | 2-Me-3-N≡CCH2CH2O—PhCH2— |
| 3859 | 2-Me-4-N≡CCH2CH2O—PhCH2— |
| 3860 | 2-Me-5-N≡CCH2CH2O—PhCH2— |
| 3861 | 2-Me-6-N≡CCH2CH2O—PhCH2— |
| 3862 | 2-F-3-cPrCH2O—PhCH2— |
| 3863 | 2-F-4-cPrCH2O—PhCH2— |
| 3864 | 2-F-5-cPrCH2O—PhCH2— |
| 3865 | 2-F-6-cPrCH2O—PhCH2— |
| 3866 | 2-Cl-3-cPrCH2O—PhCH2— |
| 3867 | 2-Cl-4-cPrCH2O—PhCH2— |
| 3868 | 2-Cl-5-cPrCH2O—PhCH2— |
| 3869 | 2-Cl-6-cPrCH2O—PhCH2— |
| 3870 | 2-Br-3-cPrCH2O—PhCH2— |
| 3871 | 2-Br-4-cPrCH2O—PhCH2— |
| 3872 | 2-Br-5-cPrCH2O—PhCH2— |
| 3873 | 2-Br-6-cPrCH2O—PhCH2— |
| 3874 | 2-I-3-cPrCH2O—PhCH2— |
| 3875 | 2-I-4-cPrCH2O—PhCH2— |
| 3876 | 2-I-5-cPrCH2O—PhCH2— |
| 3877 | 2-I-6-cPrCH2O—PhCH2— |
| 3878 | 2-Me-3-cPrCH2O—PhCH2— |
| 3879 | 2-Me-4-cPrCH2O—PhCH2— |
| 3880 | 2-Me-5-cPrCH2O—PhCH2— |
| 3881 | 2-Me-6-cPrCH2O—PhCH2— |
| 3882 | 2-F-3-cBuCH2O—PhCH2— |
| 3883 | 2-F-4-cBuCH2O—PhCH2— |
| 3884 | 2-F-5-cBuCH2O—PhCH2— |
| 3885 | 2-F-6-cBuCH2O—PhCH2— |
| 3886 | 2-Cl-3-cBuCH2O—PhCH2— |
| 3887 | 2-Cl-4-cBuCH2O—PhCH2— |
| 3888 | 2-Cl-5-cBuCH2O—PhCH2— |
| 3889 | 2-Cl-6-cBuCH2O—PhCH2— |
| 3890 | 2-Br-3-cBuCH2O—PhCH2— |
| 3891 | 2-Br-4-cBuCH2O—PhCH2— |
| 3892 | 2-Br-5-cBuCH2O—PhCH2— |
| 3893 | 2-Br-6-cBuCH2O—PhCH2— |
| 3894 | 2-I-3-cBuCH2O—PhCH2— |
| 3895 | 2-I-4-cBuCH2O—PhCH2— |
| 3896 | 2-I-5-cBuCH2O—PhCH2— |
| 3897 | 2-I-6-cBuCH2O—PhCH2— |
| 3898 | 2-Me-3-cBuCH2O—PhCH2— |
| 3899 | 2-Me-4-cBuCH2O—PhCH2— |
| 3900 | 2-Me-5-cBuCH2O—PhCH2— |
| 3901 | 2-Me-6-cBuCH2O—PhCH2— |
| 3902 | 2-F-3-cPentylCH2O—PhCH2— |
| 3903 | 2-F-4-cPentylCH2O—PhCH2— |
| 3904 | 2-F-5-cPentylCH2O—PhCH2— |
| 3905 | 2-F-6-cPentylCH2O—PhCH2— |
| 3906 | 2-Cl-3-cPentylCH2O—PhCH2— |
| 3907 | 2-Cl-4-cPentylCH2O—PhCH2— |
| 3908 | 2-Cl-5-cPentylCH2O—PhCH2— |
| 3909 | 2-Cl-6-cPentylCH2O—PhCH2— |
| 3910 | 2-Br-3-cPentylCH2O—PhCH2— |
| 3911 | 2-Br-4-cPentylCH2O—PhCH2— |
| 3912 | 2-Br-5-cPentylCH2O—PhCH2— |
| 3913 | 2-Br-6-cPentylCH2O—PhCH2— |
| 3914 | 2-I-3-cPentylCH2O—PhCH2— |
| 3915 | 2-I-4-cPentylCH2O—PhCH2— |
| 3916 | 2-I-5-cPentylCH2O—PhCH2— |
| 3917 | 2-I-6-cPentylCH2O—PhCH2— |
| 3918 | 2-Me-3-cPentylCH2O—PhCH2— |
| 3919 | 2-Me-4-cPentylCH2O—PhCH2— |
| 3920 | 2-Me-5-cPentylCH2O—PhCH2— |
| 3921 | 2-Me-6-cPentylCH2O—PhCH2— |
| 3922 | 2-F-3-cHexylCH2O—PhCH2— |
| 3923 | 2-F-4-cHexylCH2O—PhCH2— |
| 3924 | 2-F-5-cHexylCH2O—PhCH2— |
| 3925 | 2-F-6-cHexylCH2O—PhCH2— |
| 3926 | 2-Cl-3-cHexylCH2O—PhCH2— |
| 3927 | 2-Cl-4-cHexylCH2O—PhCH2— |
| 3928 | 2-Cl-5-cHexylCH2O—PhCH2— |
| 3929 | 2-Cl-6-cHexylCH2O—PhCH2— |
| 3930 | 2-Br-3-cHexylCH2O—PhCH2— |
| 3931 | 2-Br-4-cHexylCH2O—PhCH2— |
| 3932 | 2-Br-5-cHexylCH2O—PhCH2— |

TABLE 2-continued

| No. | Z |
|---|---|
| 3933 | 2-Br-6-cHexylCH2O—PhCH2— |
| 3934 | 2-I-3-cHexylCH2O—PhCH2— |
| 3935 | 2-I-4-cHexylCH2O—PhCH2— |
| 3936 | 2-I-5-cHexylCH2O—PhCH2— |
| 3937 | 2-I-6-cHexylCH2O—PhCH2— |
| 3938 | 2-Me-3-cHexylCH2O—PhCH2— |
| 3939 | 2-Me-4-cHexylCH2O—PhCH2— |
| 3940 | 2-Me-5-cHexylCH2O—PhCH2— |
| 3941 | 2-Me-6-cHexylCH2O—PhCH2— |
| 3942 | 2-F-3-MeOCH2O—PhCH2— |
| 3943 | 2-F-4-MeOCH2O—PhCH2— |
| 3944 | 2-F-5-MeOCH2O—PhCH2— |
| 3945 | 2-F-6-MeOCH2O—PhCH2— |
| 3946 | 2-Cl-3-MeOCH2O—PhCH2— |
| 3947 | 2-Cl-4-MeOCH2O—PhCH2— |
| 3948 | 2-Cl-5-MeOCH2O—PhCH2— |
| 3949 | 2-Cl-6-MeOCH2O—PhCH2— |
| 3950 | 2-Br-3-MeOCH2O—PhCH2— |
| 3951 | 2-Br-4-MeOCH2O—PhCH2— |
| 3952 | 2-Br-5-MeOCH2O—PhCH2— |
| 3953 | 2-Br-6-MeOCH2O—PhCH2— |
| 3954 | 2-I-3-MeOCH2O—PhCH2— |
| 3955 | 2-I-4-MeOCH2O—PhCH2— |
| 3956 | 2-I-5-MeOCH2O—PhCH2— |
| 3957 | 2-I-6-MeOCH2O—PhCH2— |
| 3958 | 2-Me-3-MeOCH2O—PhCH2— |
| 3959 | 2-Me-4-MeOCH2O—PhCH2— |
| 3960 | 2-Me-5-MeOCH2O—PhCH2— |
| 3961 | 2-Me-6-MeOCH2O—PhCH2— |
| 3962 | 2-F-3-EtOCH2O—PhCH2— |
| 3963 | 2-F-4-EtOCH2O—PhCH2— |
| 3964 | 2-F-5-EtOCH2O—PhCH2— |
| 3965 | 2-F-6-EtOCH2O—PhCH2— |
| 3966 | 2-Cl-3-EtOCH2O—PhCH2— |
| 3967 | 2-Cl-4-EtOCH2O—PhCH2— |
| 3968 | 2-Cl-5-EtOCH2O—PhCH2— |
| 3969 | 2-Cl-6-EtOCH2O—PhCH2— |
| 3970 | 2-Br-3-EtOCH2O—PhCH2— |
| 3971 | 2-Br-4-EtOCH2O—PhCH2— |
| 3972 | 2-Br-5-EtOCH2O—PhCH2— |
| 3973 | 2-Br-6-EtOCH2O—PhCH2— |
| 3974 | 2-I-3-EtOCH2O—PhCH2— |
| 3975 | 2-I-4-EtOCH2O—PhCH2— |
| 3976 | 2-I-5-EtOCH2O—PhCH2— |
| 3977 | 2-I-6-EtOCH2O—PhCH2— |
| 3978 | 2-Me-3-EtOCH2O—PhCH2— |
| 3979 | 2-Me-4-EtOCH2O—PhCH2— |
| 3980 | 2-Me-5-EtOCH2O—PhCH2— |
| 3981 | 2-Me-6-EtOCH2O—PhCH2— |
| 3982 | 2-F-3-MeOCH2CH2O—PhCH2— |
| 3983 | 2-F-4-MeOCH2CH2O—PhCH2— |
| 3984 | 2-F-5-MeOCH2CH2O—PhCH2— |
| 3985 | 2-F-6-MeOCH2CH2O—PhCH2— |
| 3986 | 2-Cl-3-MeOCH2CH2O—PhCH2— |
| 3987 | 2-Cl-4-MeOCH2CH2O—PhCH2— |
| 3988 | 2-Cl-5-MeOCH2CH2O—PhCH2— |
| 3989 | 2-Cl-6-MeOCH2CH2O—PhCH2— |
| 3990 | 2-Br-3-MeOCH2CH2O—PhCH2— |
| 3991 | 2-Br-4-MeOCH2CH2O—PhCH2— |
| 3992 | 2-Br-5-MeOCH2CH2O—PhCH2— |
| 3993 | 2-Br-6-MeOCH2CH2O—PhCH2— |
| 3994 | 2-I-3-MeOCH2CH2O—PhCH2— |
| 3995 | 2-I-4-MeOCH2CH2O—PhCH2— |
| 3996 | 2-I-5-MeOCH2CH2O—PhCH2— |
| 3997 | 2-I-6-MeOCH2CH2O—PhCH2— |
| 3998 | 2-Me-3-MeOCH2CH2O—PhCH2— |
| 3999 | 2-Me-4-MeOCH2CH2O—PhCH2— |
| 4000 | 2-Me-5-MeOCH2CH2O—PhCH2— |
| 4001 | 2-Me-6-MeOCH2CH2O—PhCH2— |
| 4002 | 2-F-3-MeOCH2CH2CH2O—PhCH2— |
| 4003 | 2-F-4-MeOCH2CH2CH2O—PhCH2— |
| 4004 | 2-F-5-MeOCH2CH2CH2O—PhCH2— |
| 4005 | 2-F-6-MeOCH2CH2CH2O—PhCH2— |
| 4006 | 2-Cl-3-MeOCH2CH2CH2O—PhCH2— |
| 4007 | 2-Cl-4-MeOCH2CH2CH2O—PhCH2— |
| 4008 | 2-Cl-5-MeOCH2CH2CH2O—PhCH2— |
| 4009 | 2-Cl-6-MeOCH2CH2CH2O—PhCH2— |
| 4010 | 2-Br-3-MeOCH2CH2CH2O—PhCH2— |
| 4011 | 2-Br-4-MeOCH2CH2CH2O—PhCH2— |
| 4012 | 2-Br-5-MeOCH2CH2CH2O—PhCH2— |
| 4013 | 2-Br-6-MeOCH2CH2CH2O—PhCH2— |
| 4014 | 2-I-3-MeOCH2CH2CH2O—PhCH2— |
| 4015 | 2-I-4-MeOCH2CH2CH2O—PhCH2— |
| 4016 | 2-I-5-MeOCH2CH2CH2O—PhCH2— |
| 4017 | 2-I-6-MeOCH2CH2CH2O—PhCH2— |
| 4018 | 2-Me-3-MeOCH2CH2CH2O—PhCH2— |
| 4019 | 2-Me-4-MeOCH2CH2CH2O—PhCH2— |
| 4020 | 2-Me-5-MeOCH2CH2CH2O—PhCH2— |
| 4021 | 2-Me-6-MeOCH2CH2CH2O—PhCH2— |
| 4022 | 2-F-3-MeOCH2CH2OCH2O—PhCH2— |
| 4023 | 2-F-4-MeOCH2CH2OCH2O—PhCH2— |
| 4024 | 2-F-5-MeOCH2CH2OCH2O—PhCH2— |
| 4025 | 2-F-6-MeOCH2CH2OCH2O—PhCH2— |
| 4026 | 2-Cl-3-MeOCH2CH2OCH2O—PhCH2— |
| 4027 | 2-Cl-4-MeOCH2CH2OCH2O—PhCH2— |
| 4028 | 2-Cl-5-MeOCH2CH2OCH2O—PhCH2— |
| 4029 | 2-Cl-6-MeOCH2CH2OCH2O—PhCH2— |
| 4030 | 2-Br-3-MeOCH2CH2OCH2O—PhCH2— |
| 4031 | 2-Br-4-MeOCH2CH2OCH2O—PhCH2— |
| 4032 | 2-Br-5-MeOCH2CH2OCH2O—PhCH2— |
| 4033 | 2-Br-6-MeOCH2CH2OCH2O—PhCH2— |
| 4034 | 2-I-3-MeOCH2CH2OCH2O—PhCH2— |
| 4035 | 2-I-4-MeOCH2CH2OCH2O—PhCH2— |
| 4036 | 2-I-5-MeOCH2CH2OCH2O—PhCH2— |
| 4037 | 2-I-6-MeOCH2CH2OCH2O—PhCH2— |
| 4038 | 2-Me-3-MeOCH2CH2OCH2O—PhCH2— |
| 4039 | 2-Me-4-MeOCH2CH2OCH2O—PhCH2— |
| 4040 | 2-Me-5-MeOCH2CH2OCH2O—PhCH2— |
| 4041 | 2-Me-6-MeOCH2CH2OCH2O—PhCH2— |
| 4042 | 2-F-3-MeSCH2O—PhCH2— |
| 4043 | 2-F-4-MeSCH2O—PhCH2— |
| 4044 | 2-F-5-MeSCH2O—PhCH2— |
| 4045 | 2-F-6-MeSCH2O—PhCH2— |
| 4046 | 2-Cl-3-MeSCH2O—PhCH2— |
| 4047 | 2-Cl-4-MeSCH2O—PhCH2— |
| 4048 | 2-Cl-5-MeSCH2O—PhCH2— |
| 4049 | 2-Cl-6-MeSCH2O—PhCH2— |
| 4050 | 2-Br-3-MeSCH2O—PhCH2— |
| 4051 | 2-Br-4-MeSCH2O—PhCH2— |
| 4052 | 2-Br-5-MeSCH2O—PhCH2— |
| 4053 | 2-Br-6-MeSCH2O—PhCH2— |
| 4054 | 2-I-3-MeSCH2O—PhCH2— |
| 4055 | 2-I-4-MeSCH2O—PhCH2— |
| 4056 | 2-I-5-MeSCH2O—PhCH2— |
| 4057 | 2-I-6-MeSCH2O—PhCH2— |
| 4058 | 2-Me-3-MeSCH2O—PhCH2— |
| 4059 | 2-Me-4-MeSCH2O—PhCH2— |
| 4060 | 2-Me-5-MeSCH2O—PhCH2— |
| 4061 | 2-Me-6-MeSCH2O—PhCH2— |
| 4062 | 2-F-3-MeS(O)CH2O—PhCH2— |
| 4063 | 2-F-4-MeS(O)CH2O—PhCH2— |
| 4064 | 2-F-5-MeS(O)CH2O—PhCH2— |
| 4065 | 2-F-6-MeS(O)CH2O—PhCH2— |
| 4066 | 2-Cl-3-MeS(O)CH2O—PhCH2— |
| 4067 | 2-Cl-4-MeS(O)CH2O—PhCH2— |
| 4068 | 2-Cl-5-MeS(O)CH2O—PhCH2— |
| 4069 | 2-Cl-6-MeS(O)CH2O—PhCH2— |
| 4070 | 2-Br-3-MeS(O)CH2O—PhCH2— |
| 4071 | 2-Br-4-MeS(O)CH2O—PhCH2— |
| 4072 | 2-Br-5-MeS(O)CH2O—PhCH2— |
| 4073 | 2-Br-6-MeS(O)CH2O—PhCH2— |
| 4074 | 2-I-3-MeS(O)CH2O—PhCH2— |
| 4075 | 2-I-4-MeS(O)CH2O—PhCH2— |
| 4076 | 2-I-5-MeS(O)CH2O—PhCH2— |
| 4077 | 2-I-6-MeS(O)CH2O—PhCH2— |
| 4078 | 2-Me-3-MeS(O)CH2O—PhCH2— |
| 4079 | 2-Me-4-MeS(O)CH2O—PhCH2— |
| 4080 | 2-Me-5-MeS(O)CH2O—PhCH2— |
| 4081 | 2-Me-6-MeS(O)CH2O—PhCH2— |
| 4082 | 2-F-3-MeSO2CH2O—PhCH2— |
| 4083 | 2-F-4-MeSO2CH2O—PhCH2— |
| 4084 | 2-F-5-MeSO2CH2O—PhCH2— |
| 4085 | 2-F-6-MeSO2CH2O—PhCH2— |
| 4086 | 2-Cl-3-MeSO2CH2O—PhCH2— |
| 4087 | 2-Cl-4-MeSO2CH2O—PhCH2— |
| 4088 | 2-Cl-5-MeSO2CH2O—PhCH2— |

TABLE 2-continued

| No. | Z |
|---|---|
| 4089 | 2-Cl-6-MeSO2CH2O—PhCH2— |
| 4090 | 2-Br-3-MeSO2CH2O—PhCH2— |
| 4091 | 2-Br-4-MeSO2CH2O—PhCH2— |
| 4092 | 2-Br-5-MeSO2CH2O—PhCH2— |
| 4093 | 2-Br-6-MeSO2CH2O—PhCH2— |
| 4094 | 2-I-3-MeSO2CH2O—PhCH2— |
| 4095 | 2-I-4-MeSO2CH2O—PhCH2— |
| 4096 | 2-I-5-MeSO2CH2O—PhCH2— |
| 4097 | 2-I-6-MeSO2CH2O—PhCH2— |
| 4098 | 2-Me-3-MeSO2CH2O—PhCH2— |
| 4099 | 2-Me-4-MeSO2CH2O—PhCH2— |
| 4100 | 2-Me-5-MeSO2CH2O—PhCH2— |
| 4101 | 2-Me-6-MeSO2CH2O—PhCH2— |
| 4102 | 2-F-3-AcCH2O—PhCH2— |
| 4103 | 2-F-4-AcCH2O—PhCH2— |
| 4104 | 2-F-5-AcCH2O—PhCH2— |
| 4105 | 2-F-6-AcCH2O—PhCH2— |
| 4106 | 2-Cl-3-AcCH2O—PhCH2— |
| 4107 | 2-Cl-4-AcCH2O—PhCH2— |
| 4108 | 2-Cl-5-AcCH2O—PhCH2— |
| 4109 | 2-Cl-6-AcCH2O—PhCH2— |
| 4110 | 2-Br-3-AcCH2O—PhCH2— |
| 4111 | 2-Br-4-AcCH2O—PhCH2— |
| 4112 | 2-Br-5-AcCH2O—PhCH2— |
| 4113 | 2-Br-6-AcCH2O—PhCH2— |
| 4114 | 2-I-3-AcCH2O—PhCH2— |
| 4115 | 2-I-4-AcCH2O—PhCH2— |
| 4116 | 2-I-5-AcCH2O—PhCH2— |
| 4117 | 2-I-6-AcCH2O—PhCH2— |
| 4118 | 2-Me-3-AcCH2O—PhCH2— |
| 4119 | 2-Me-4-AcCH2O—PhCH2— |
| 4120 | 2-Me-5-AcCH2O—PhCH2— |
| 4121 | 2-Me-6-AcCH2O—PhCH2— |
| 4122 | 2-F-3-MeOC(=O)CH2O—PhCH2— |
| 4123 | 2-F-4-MeOC(=O)CH2O—PhCH2— |
| 4124 | 2-F-5-MeOC(=O)CH2O—PhCH2— |
| 4125 | 2-F-6-MeOC(=O)CH2O—PhCH2— |
| 4126 | 2-Cl-3-MeOC(=O)CH2O—PhCH2— |
| 4127 | 2-Cl-4-MeOC(=O)CH2O—PhCH2— |
| 4128 | 2-Cl-5-MeOC(=O)CH2O—PhCH2— |
| 4129 | 2-Cl-6-MeOC(=O)CH2O—PhCH2— |
| 4130 | 2-Br-3-MeOC(=O)CH2O—PhCH2— |
| 4131 | 2-Br-4-MeOC(=O)CH2O—PhCH2— |
| 4132 | 2-Br-5-MeOC(=O)CH2O—PhCH2— |
| 4133 | 2-Br-6-MeOC(=O)CH2O—PhCH2— |
| 4134 | 2-I-3-MeOC(=O)CH2O—PhCH2— |
| 4135 | 2-I-4-MeOC(=O)CH2O—PhCH2— |
| 4136 | 2-I-5-MeOC(=O)CH2O—PhCH2— |
| 4137 | 2-I-6-MeOC(=O)CH2O—PhCH2— |
| 4138 | 2-Me-3-MeOC(=O)CH2O—PhCH2— |
| 4139 | 2-Me-4-MeOC(=O)CH2O—PhCH2— |
| 4140 | 2-Me-5-MeOC(=O)CH2O—PhCH2— |
| 4141 | 2-Me-6-MeOC(=O)CH2O—PhCH2— |
| 4142 | 2-F-3-EtOC(=O)CH2O—PhCH2— |
| 4143 | 2-F-4-EtOC(=O)CH2O—PhCH2— |
| 4144 | 2-F-5-EtOC(=O)CH2O—PhCH2— |
| 4145 | 2-F-6-EtOC(=O)CH2O—PhCH2— |
| 4146 | 2-Cl-3-EtOC(=O)CH2O—PhCH2— |
| 4147 | 2-Cl-4-EtOC(=O)CH2O—PhCH2— |
| 4148 | 2-Cl-5-EtOC(=O)CH2O—PhCH2— |
| 4149 | 2-Cl-6-EtOC(=O)CH2O—PhCH2— |
| 4150 | 2-Br-3-EtOC(=O)CH2O—PhCH2— |
| 4151 | 2-Br-4-EtOC(=O)CH2O—PhCH2— |
| 4152 | 2-Br-5-EtOC(=O)CH2O—PhCH2— |
| 4153 | 2-Br-6-EtOC(=O)CH2O—PhCH2— |
| 4154 | 2-I-3-EtOC(=O)CH2O—PhCH2— |
| 4155 | 2-I-4-EtOC(=O)CH2O—PhCH2— |
| 4156 | 2-I-5-EtOC(=O)CH2O—PhCH2— |
| 4157 | 2-I-6-EtOC(=O)CH2O—PhCH2— |
| 4158 | 2-Me-3-EtOC(=O)CH2O—PhCH2— |
| 4159 | 2-Me-4-EtOC(=O)CH2O—PhCH2— |
| 4160 | 2-Me-5-EtOC(=O)CH2O—PhCH2— |
| 4161 | 2-Me-6-EtOC(=O)CH2O—PhCH2— |
| 4162 | 2-F-3-(1,3-dioxolan-2-yl)CH2O—PhCH2— |
| 4163 | 2-F-4-(1,3-dioxolan-2-yl)CH2O—PhCH2— |
| 4164 | 2-F-5-(1,3-dioxolan-2-yl)CH2O—PhCH2— |
| 4165 | 2-F-6-(1,3-dioxolan-2-yl)CH2O—PhCH2— |
| 4166 | 2-Cl-3-(1,3-dioxolan-2-yl)CH2O—PhCH2— |
| 4167 | 2-Cl-4-(1,3-dioxolan-2-yl)CH2O—PhCH2— |
| 4168 | 2-Cl-5-(1,3-dioxolan-2-yl)CH2O—PhCH2— |
| 4169 | 2-Cl-6-(1,3-dioxolan-2-yl)CH2O—PhCH2— |
| 4170 | 2-Br-3-(1,3-dioxolan-2-yl)CH2O—PhCH2— |
| 4171 | 2-Br-4-(1,3-dioxolan-2-yl)CH2O—PhCH2— |
| 4172 | 2-Br-5-(1,3-dioxolan-2-yl)CH2O—PhCH2— |
| 4173 | 2-Br-6-(1,3-dioxolan-2-yl)CH2O—PhCH2— |
| 4174 | 2-I-3-(1,3-dioxolan-2-yl)CH2O—PhCH2— |
| 4175 | 2-I-4-(1,3-dioxolan-2-yl)CH2O—PhCH2— |
| 4176 | 2-I-5-(1,3-dioxolan-2-yl)CH2O—PhCH2— |
| 4177 | 2-I-6-(1,3-dioxolan-2-yl)CH2O—PhCH2— |
| 4178 | 2-Me-3-(1,3-dioxolan-2-yl)CH2O—PhCH2— |
| 4179 | 2-Me-4-(1,3-dioxolan-2-yl)CH2O—PhCH2— |
| 4180 | 2-Me-5-(1,3-dioxolan-2-yl)CH2O—PhCH2— |
| 4181 | 2-Me-6-(1,3-dioxolan-2-yl)CH2O—PhCH2— |
| 4182 | 2-F-3-(1,3-dioxolan-2-yl)CH2CH2O—PhCH2— |
| 4183 | 2-F-4-(1,3-dioxolan-2-yl)CH2CH2O—PhCH2— |
| 4184 | 2-F-5-(1,3-dioxolan-2-yl)CH2CH2O—PhCH2— |
| 4185 | 2-F-6-(1,3-dioxolan-2-yl)CH2CH2O—PhCH2— |
| 4186 | 2-Cl-3-(1,3-dioxolan-2-yl)CH2CH2O—PhCH2— |
| 4187 | 2-Cl-4-(1,3-dioxolan-2-yl)CH2CH2O—PhCH2— |
| 4188 | 2-Cl-5-(1,3-dioxolan-2-yl)CH2CH2O—PhCH2— |
| 4189 | 2-Cl-6-(1,3-dioxolan-2-yl)CH2CH2O—PhCH2— |
| 4190 | 2-Br-3-(1,3-dioxolan-2-yl)CH2CH2O—PhCH2— |
| 4191 | 2-Br-4-(1,3-dioxolan-2-yl)CH2CH2O—PhCH2— |
| 4192 | 2-Br-5-(1,3-dioxolan-2-yl)CH2CH2O—PhCH2— |
| 4193 | 2-Br-6-(1,3-dioxolan-2-yl)CH2CH2O—PhCH2— |
| 4194 | 2-I-3-(1,3-dioxolan-2-yl)CH2CH2O—PhCH2— |
| 4195 | 2-I-4-(1,3-dioxolan-2-yl)CH2CH2O—PhCH2— |
| 4196 | 2-I-5-(1,3-dioxolan-2-yl)CH2CH2O—PhCH2— |
| 4197 | 2-I-6-(1,3-dioxolan-2-yl)CH2CH2O—PhCH2— |
| 4198 | 2-Me-3-(1,3-dioxolan-2-yl)CH2CH2O—PhCH2— |
| 4199 | 2-Me-4-(1,3-dioxolan-2-yl)CH2CH2O—PhCH2— |
| 4200 | 2-Me-5-(1,3-dioxolan-2-yl)CH2CH2O—PhCH2— |
| 4201 | 2-Me-6-(1,3-dioxolan-2-yl)CH2CH2O—PhCH2— |
| 4202 | 2-F-3-(1,3-dioxan-2-yl)CH2O—PhCH2— |
| 4203 | 2-F-4-(1,3-dioxan-2-yl)CH2O—PhCH2— |
| 4204 | 2-F-5-(1,3-dioxan-2-yl)CH2O—PhCH2— |
| 4205 | 2-F-6-(1,3-dioxan-2-yl)CH2O—PhCH2— |
| 4206 | 2-Cl-3-(1,3-dioxan-2-yl)CH2O—PhCH2— |
| 4207 | 2-Cl-4-(1,3-dioxan-2-yl)CH2O—PhCH2— |
| 4208 | 2-Cl-5-(1,3-dioxan-2-yl)CH2O—PhCH2— |
| 4209 | 2-Cl-6-(1,3-dioxan-2-yl)CH2O—PhCH2— |
| 4210 | 2-Br-3-(1,3-dioxan-2-yl)CH2O—PhCH2— |
| 4211 | 2-Br-4-(1,3-dioxan-2-yl)CH2O—PhCH2— |
| 4212 | 2-Br-5-(1,3-dioxan-2-yl)CH2O—PhCH2— |
| 4213 | 2-Br-6-(1,3-dioxan-2-yl)CH2O—PhCH2— |
| 4214 | 2-I-3-(1,3-dioxan-2-yl)CH2O—PhCH2— |
| 4215 | 2-I-4-(1,3-dioxan-2-yl)CH2O—PhCH2— |
| 4216 | 2-I-5-(1,3-dioxan-2-yl)CH2O—PhCH2— |
| 4217 | 2-I-6-(1,3-dioxan-2-yl)CH2O—PhCH2— |
| 4218 | 2-Me-3-(1,3-dioxan-2-yl)CH2O—PhCH2— |
| 4219 | 2-Me-4-(1,3-dioxan-2-yl)CH2O—PhCH2— |
| 4210 | 2-Me-5-(1,3-dioxan-2-yl)CH2O—PhCH2— |
| 4221 | 2-Me-6-(1,3-dioxan-2-yl)CH2O—PhCH2— |
| 4222 | 2-F-3-(1,3-dioxan-2-yl)CH2CH2O—PhCH2— |
| 4223 | 2-F-4-(1,3-dioxan-2-yl)CH2CH2O—PhCH2— |
| 4224 | 2-F-5-(1,3-dioxan-2-yl)CH2CH2O—PhCH2— |
| 4225 | 2-F-6-(1,3-dioxan-2-yl)CH2CH2O—PhCH2— |
| 4226 | 2-Cl-3-(1,3-dioxan-2-yl)CH2CH2O—PhCH2— |
| 4227 | 2-Cl-4-(1,3-dioxan-2-yl)CH2CH2O—PhCH2— |
| 4228 | 2-Cl-5-(1,3-dioxan-2-yl)CH2CH2O—PhCH2— |
| 4229 | 2-Cl-6-(1,3-dioxan-2-yl)CH2CH2O—PhCH2— |
| 4220 | 2-Br-3-(1,3-dioxan-2-yl)CH2CH2O—PhCH2— |
| 4231 | 2-Br-4-(1,3-dioxan-2-yl)CH2CH2O—PhCH2— |
| 4232 | 2-Br-5-(1,3-dioxan-2-yl)CH2CH2O—PhCH2— |
| 4233 | 2-Br-6-(1,3-dioxan-2-yl)CH2CH2O—PhCH2— |
| 4234 | 2-I-3-(1,3-dioxan-2-yl)CH2CH2O—PhCH2— |
| 4235 | 2-I-4-(1,3-dioxan-2-yl)CH2CH2O—PhCH2— |
| 4236 | 2-I-5-(1,3-dioxan-2-yl)CH2CH2O—PhCH2— |
| 4237 | 2-I-6-(1,3-dioxan-2-yl)CH2CH2O—PhCH2— |
| 4238 | 2-Me-3-(1,3-dioxan-2-yl)CH2CH2O—PhCH2— |
| 4239 | 2-Me-4-(1,3-dioxan-2-yl)CH2CH2O—PhCH2— |
| 4240 | 2-Me-5-(1,3-dioxan-2-yl)CH2CH2O—PhCH2— |
| 4241 | 2-Me-6-(1,3-dioxan-2-yl)CH2CH2O—PhCH2— |
| 4243 | 2-F-4-cPrO—PhCH2— |
| 4244 | 2-F-5-cPrO—PhCH2— |
| 4245 | 2-F-6-cPrO—PhCH2— |

TABLE 2-continued

| No. | Z |
|---|---|
| 4246 | 2-Cl-3-cPrO—PhCH2— |
| 4247 | 2-Cl-4-cPrO—PhCH2— |
| 4248 | 2-Cl-5-cPrO—PhCH2— |
| 4249 | 2-Cl-6-cPrO—PhCH2— |
| 4250 | 2-Br-3-cPrO—PhCH2— |
| 4251 | 2-Br-4-cPrO—PhCH2— |
| 4252 | 2-Br-5-cPrO—PhCH2— |
| 4253 | 2-Br-6-cPrO—PhCH2— |
| 4254 | 2-I-3-cPrO—PhCH2— |
| 4255 | 2-I-4-cPrO—PhCH2— |
| 4256 | 2-I-5-cPrO—PhCH2— |
| 4257 | 2-I-6-cPrO—PhCH2— |
| 4258 | 2-Me-3-cPrO—PhCH2— |
| 4259 | 2-Me-4-cPrO—PhCH2— |
| 4260 | 2-Me-5-cPrO—PhCH2— |
| 4261 | 2-Me-6-cPrO—PhCH2— |
| 4262 | 2-F-3-cBuO—PhCH2— |
| 4263 | 2-F-4-cBuO—PhCH2— |
| 4264 | 2-F-5-cBuO—PhCH2— |
| 4265 | 2-F-6-cBuO—PhCH2— |
| 4266 | 2-Cl-3-cBuO—PhCH2— |
| 4267 | 2-Cl-4-cBuO—PhCH2— |
| 4268 | 2-Cl-5-cBuO—PhCH2— |
| 4269 | 2-Cl-6-cBuO—PhCH2— |
| 4270 | 2-Br-3-cBuO—PhCH2— |
| 4271 | 2-Br-4-cBuO—PhCH2— |
| 4272 | 2-Br-5-cBuO—PhCH2— |
| 4273 | 2-Br-6-cBuO—PhCH2— |
| 4274 | 2-I-3-cBuO—PhCH2— |
| 4275 | 2-I-4-cBuO—PhCH2— |
| 4276 | 2-I-5-cBuO—PhCH2— |
| 4277 | 2-I-6-cBuO—PhCH2— |
| 4278 | 2-Me-3-cBuO—PhCH2— |
| 4279 | 2-Me-4-cBuO—PhCH2— |
| 4280 | 2-Me-5-cBuO—PhCH2— |
| 4281 | 2-Me-6-cBuO—PhCH2— |
| 4282 | 2-F-3-cPentylO—PhCH2— |
| 4283 | 2-F-4-cPentylO—PhCH2— |
| 4284 | 2-F-5-cPentylO—PhCH2— |
| 4285 | 2-F-6-cPentylO—PhCH2— |
| 4286 | 2-Cl-3-cPentylO—PhCH2— |
| 4287 | 2-Cl-4-cPentylO—PhCH2— |
| 4288 | 2-Cl-5-cPentylO—PhCH2— |
| 4289 | 2-Cl-6-cPentylO—PhCH2— |
| 4290 | 2-Br-3-cPentylO—PhCH2— |
| 4291 | 2-Br-4-cPentylO—PhCH2— |
| 4292 | 2-Br-5-cPentylO—PhCH2— |
| 4293 | 2-Br-6-cPentylO—PhCH2— |
| 4294 | 2-I-3-cPentylO—PhCH2— |
| 4295 | 2-I-4-cPentylO—PhCH2— |
| 4296 | 2-I-5-cPentylO—PhCH2— |
| 4297 | 2-I-6-cPentylO—PhCH2— |
| 4298 | 2-Me-3-cPentylO—PhCH2— |
| 4299 | 2-Me-4-cPentylO—PhCH2— |
| 4300 | 2-Me-5-cPentylO—PhCH2— |
| 4301 | 2-Me-6-cPentylO—PhCH2— |
| 4302 | 2-F-3-cHexylO—PhCH2— |
| 4303 | 2-F-4-cHexylO—PhCH2— |
| 4304 | 2-F-5-cHexylO—PhCH2— |
| 4305 | 2-F-6-cHexylO—PhCH2— |
| 4306 | 2-Cl-3-cHexylO—PhCH2— |
| 4307 | 2-Cl-4-cHexylO—PhCH2— |
| 4308 | 2-Cl-5-cHexylO—PhCH2— |
| 4309 | 2-Cl-6-cHexylO—PhCH2— |
| 4310 | 2-Br-3-cHexylO—PhCH2— |
| 4311 | 2-Br-4-cHexylO—PhCH2— |
| 4312 | 2-Br-5-cHexylO—PhCH2— |
| 4313 | 2-Br-6-cHexylO—PhCH2— |
| 4314 | 2-I-3-cHexylO—PhCH2— |
| 4315 | 2-I-4-cHexylO—PhCH2— |
| 4316 | 2-I-5-cHexylO—PhCH2— |
| 4317 | 2-I-6-cHexylO—PhCH2— |
| 4318 | 2-Me-3-cHexylO—PhCH2— |
| 4319 | 2-Me-4-cHexylO—PhCH2— |
| 4320 | 2-Me-5-cHexylO—PhCH2— |
| 4321 | 2-Me-6-cHexylO—PhCH2— |
| 4322 | 2-F-3-F3CO—PhCH2— |
| 4323 | 2-F-4-F3CO—PhCH2— |
| 4324 | 2-F-5-F3CO—PhCH2— |
| 4325 | 2-F-6-F3CO—PhCH2— |
| 4326 | 2-Cl-3-F3CO—PhCH2— |
| 4327 | 2-Cl-4-F3CO—PhCH2— |
| 4328 | 2-Cl-5-F3CO—PhCH2— |
| 4329 | 2-Cl-6-F3CO—PhCH2— |
| 4330 | 2-Br-3-F3CO—PhCH2— |
| 4331 | 2-Br-4-F3CO—PhCH2— |
| 4332 | 2-Br-5-F3CO—PhCH2— |
| 4333 | 2-Br-6-F3CO—PhCH2— |
| 4334 | 2-I-3-F3CO—PhCH2— |
| 4335 | 2-I-4-F3CO—PhCH2— |
| 4336 | 2-I-5-F3CO—PhCH2— |
| 4337 | 2-I-6-F3CO—PhCH2— |
| 4338 | 2-Me-3-F3CO—PhCH2— |
| 4339 | 2-Me-4-F3CO—PhCH2— |
| 4340 | 2-Me-5-F3CO—PhCH2— |
| 4341 | 2-Me-6-F3CO—PhCH2— |
| 4342 | 2-F-3-F2CHO—PhCH2— |
| 4343 | 2-F-4-F2CHO—PhCH2— |
| 4344 | 2-F-5-F2CHO—PhCH2— |
| 4345 | 2-F-6-F2CHO—PhCH2— |
| 4346 | 2-Cl-3-F2CHO—PhCH2— |
| 4347 | 2-Cl-4-F2CHO—PhCH2— |
| 4348 | 2-Cl-5-F2CHO—PhCH2— |
| 4349 | 2-Cl-6-F2CHO—PhCH2— |
| 4350 | 2-Br-3-F2CHO—PhCH2— |
| 4351 | 2-Br-4-F2CHO—PhCH2— |
| 4352 | 2-Br-5-F2CHO—PhCH2— |
| 4353 | 2-Br-6-F2CHO—PhCH2— |
| 4354 | 2-I-3-F2CHO—PhCH2— |
| 4355 | 2-I-4-F2CHO—PhCH2— |
| 4356 | 2-I-5-F2CHO—PhCH2— |
| 4357 | 2-I-6-F2CHO—PhCH2— |
| 4358 | 2-Me-3-F2CHO—PhCH2— |
| 4359 | 2-Me-4-F2CHO—PhCH2— |
| 4360 | 2-Me-5-F2CHO—PhCH2— |
| 4361 | 2-Me-6-F2CHO—PhCH2— |
| 4362 | 2-F-3-F3CCH2O—PhCH2— |
| 4363 | 2-F-4-F3CCH2O—PhCH2— |
| 4364 | 2-F-5-F3CCH2O—PhCH2— |
| 4365 | 2-F-6-F3CCH2O—PhCH2— |
| 4366 | 2-Cl-3-F3CCH2O—PhCH2— |
| 4367 | 2-Cl-4-F3CCH2O—PhCH2— |
| 4368 | 2-Cl-5-F3CCH2O—PhCH2— |
| 4369 | 2-Cl-6-F3CCH2O—PhCH2— |
| 4370 | 2-Br-3-F3CCH2O—PhCH2— |
| 4371 | 2-Br-4-F3CCH2O—PhCH2— |
| 4372 | 2-Br-5-F3CCH2O—PhCH2— |
| 4373 | 2-Br-6-F3CCH2O—PhCH2— |
| 4374 | 2-I-3-F3CCH2O—PhCH2— |
| 4375 | 2-I-4-F3CCH2O—PhCH2— |
| 4376 | 2-I-5-F3CCH2O—PhCH2— |
| 4377 | 2-I-6-F3CCH2O—PhCH2— |
| 4378 | 2-Me-3-F3CCH2O—PhCH2— |
| 4379 | 2-Me-4-F3CCH2O—PhCH2— |
| 4380 | 2-Me-5-F3CCH2O—PhCH2— |
| 4381 | 2-Me-6-F3CCH2O—PhCH2— |
| 4382 | 2-F-3-F2CHCH2O—PhCH2— |
| 4383 | 2-F-4-F2CHCH2O—PhCH2— |
| 4384 | 2-F-5-F2CHCH2O—PhCH2— |
| 4385 | 2-F-6-F2CHCH2O—PhCH2— |
| 4386 | 2-Cl-3-F2CHCH2O—PhCH2— |
| 4387 | 2-Cl-4-F2CHCH2O—PhCH2— |
| 4388 | 2-Cl-5-F2CHCH2O—PhCH2— |
| 4389 | 2-Cl-6-F2CHCH2O—PhCH2— |
| 4390 | 2-Br-3-F2CHCH2O—PhCH2— |
| 4391 | 2-Br-4-F2CHCH2O—PhCH2— |
| 4392 | 2-Br-5-F2CHCH2O—PhCH2— |
| 4393 | 2-Br-6-F2CHCH2O—PhCH2— |
| 4394 | 2-I-3-F2CHCH2O—PhCH2— |
| 4395 | 2-I-4-F2CHCH2O—PhCH2— |
| 4396 | 2-I-5-F2CHCH2O—PhCH2— |
| 4397 | 2-I-6-F2CHCH2O—PhCH2— |
| 4398 | 2-Me-3-F2CHCH2O—PhCH2— |
| 4399 | 2-Me-4-F2CHCH2O—PhCH2— |
| 4400 | 2-Me-5-F2CHCH2O—PhCH2— |
| 4401 | 2-Me-6-F2CHCH2O—PhCH2— |

TABLE 2-continued

| No. | Z |
|---|---|
| 4402 | 2-F-3-H2C=CHCH2O—PhCH2— |
| 4403 | 2-F-4-H2C=CHCH2O—PhCH2— |
| 4404 | 2-F-5-H2C=CHCH2O—PhCH2— |
| 4405 | 2-F-6-H2C=CHCH2O—PhCH2— |
| 4406 | 2-Cl-3-H2C=CHCH2O—PhCH2— |
| 4407 | 2-Cl-4-H2C=CHCH2O—PhCH2— |
| 4408 | 2-Cl-5-H2C=CHCH2O—PhCH2— |
| 4409 | 2-Cl-6-H2C=CHCH2O—PhCH2— |
| 4410 | 2-Br-3-H2C=CHCH2O—PhCH2— |
| 4411 | 2-Br-4-H2C=CHCH2O—PhCH2— |
| 4412 | 2-Br-5-H2C=CHCH2O—PhCH2— |
| 4413 | 2-Br-6-H2C=CHCH2O—PhCH2— |
| 4414 | 2-I-3-H2C=CHCH2O—PhCH2— |
| 4415 | 2-I-4-H2C=CHCH2O—PhCH2— |
| 4416 | 2-I-5-H2C=CHCH2O—PhCH2— |
| 4417 | 2-I-6-H2C=CHCH2O—PhCH2— |
| 4418 | 2-Me-3-H2C=CHCH2O—PhCH2— |
| 4419 | 2-Me-4-H2C=CHCH2O—PhCH2— |
| 4420 | 2-Me-5-H2C=CHCH2O—PhCH2— |
| 4421 | 2-Me-6-H2C=CHCH2O—PhCH2— |
| 4422 | 2-F-3-HC≡CCH2O—PhCH2— |
| 4423 | 2-F-4-HC≡CCH2O—PhCH2— |
| 4424 | 2-F-5-HC≡CCH2O—PhCH2— |
| 4425 | 2-F-6-HC≡CCH2O—PhCH2— |
| 4426 | 2-Cl-3-HC≡CCH2O—PhCH2— |
| 4427 | 2-Cl-4-HC≡CCH2O—PhCH2— |
| 4428 | 2-Cl-5-HC≡CCH2O—PhCH2— |
| 4429 | 2-Cl-6-HC≡CCH2O—PhCH2— |
| 4430 | 2-Br-3-HC≡CCH2O—PhCH2— |
| 4431 | 2-Br-4-HC≡CCH2O—PhCH2— |
| 4432 | 2-Br-5-HC≡CCH2O—PhCH2— |
| 4433 | 2-Br-6-HC≡CCH2O—PhCH2— |
| 4434 | 2-I-3-HC≡CCH2O—PhCH2— |
| 4435 | 2-I-4-HC≡CCH2O—PhCH2— |
| 4436 | 2-I-5-HC≡CCH2O—PhCH2— |
| 4437 | 2-I-6-HC≡CCH2O—PhCH2— |
| 4438 | 2-Me-3-HC≡CCH2O—PhCH2— |
| 4439 | 2-Me-4-HC≡CCH2O—PhCH2— |
| 4440 | 2-Me-5-HC≡CCH2O—PhCH2— |
| 4441 | 2-Me-6-HC≡CCH2O—PhCH2— |
| 4442 | 2-F-3-Ac—PhCH2— |
| 4443 | 2-F-4-Ac—PhCH2— |
| 4444 | 2-F-5-Ac—PhCH2— |
| 4445 | 2-F-6-Ac—PhCH2— |
| 4446 | 2-Cl-3-Ac—PhCH2— |
| 4447 | 2-Cl-4-Ac—PhCH2— |
| 4448 | 2-Cl-5-Ac—PhCH2— |
| 4449 | 2-Cl-6-Ac—PhCH2— |
| 4450 | 2-Br-3-Ac—PhCH2— |
| 4451 | 2-Br-4-Ac—PhCH2— |
| 4452 | 2-Br-5-Ac—PhCH2— |
| 4453 | 2-Br-6-Ac—PhCH2— |
| 4454 | 2-I-3-Ac—PhCH2— |
| 4455 | 2-I-4-Ac—PhCH2— |
| 4456 | 2-I-5-Ac—PhCH2— |
| 4457 | 2-I-6-Ac—PhCH2— |
| 4458 | 2-Me-3-Ac—PhCH2— |
| 4459 | 2-Me-4-Ac—PhCH2— |
| 4460 | 2-Me-5-Ac—PhCH2— |
| 4461 | 2-Me-6-Ac—PhCH2— |
| 4462 | 2-F-3-MeOC(=O)—PhCH2— |
| 4463 | 2-F-4-MeOC(=O)—PhCH2— |
| 4464 | 2-F-5-MeOC(=O)—PhCH2— |
| 4465 | 2-F-6-MeOC(=O)—PhCH2— |
| 4466 | 2-Cl-3-MeOC(=O)—PhCH2— |
| 4467 | 2-Cl-4-MeOC(=O)—PhCH2— |
| 4468 | 2-Cl-5-MeOC(=O)—PhCH2— |
| 4469 | 2-Cl-6-MeOC(=O)—PhCH2— |
| 4470 | 2-Br-3-MeOC(=O)—PhCH2— |
| 4471 | 2-Br-4-MeOC(=O)—PhCH2— |
| 4472 | 2-Br-5-MeOC(=O)—PhCH2— |
| 4473 | 2-Br-6-MeOC(=O)—PhCH2— |
| 4474 | 2-I-3-MeOC(=O)—PhCH2— |
| 4475 | 2-I-4-MeOC(=O)—PhCH2— |
| 4476 | 2-I-5-MeOC(=O)—PhCH2— |
| 4477 | 2-I-6-MeOC(=O)—PhCH2— |
| 4478 | 2-Me-3-MeOC(=O)—PhCH2— |
| 4479 | 2-Me-4-MeOC(=O)—PhCH2— |
| 4480 | 2-Me-5-MeOC(=O)—PhCH2— |
| 4481 | 2-Me-6-MeOC(=O)—PhCH2— |
| 4482 | 2-F-3-EtOC(=O)—PhCH2— |
| 4483 | 2-F-4-EtOC(=O)—PhCH2— |
| 4484 | 2-F-5-EtOC(=O)—PhCH2— |
| 4485 | 2-F-6-EtOC(=O)—PhCH2— |
| 4486 | 2-Cl-3-EtOC(=O)—PhCH2— |
| 4487 | 2-Cl-4-EtOC(=O)—PhCH2— |
| 4488 | 2-Cl-5-EtOC(=O)—PhCH2— |
| 4489 | 2-Cl-6-EtOC(=O)—PhCH2— |
| 4490 | 2-Br-3-EtOC(=O)—PhCH2— |
| 4491 | 2-Br-4-EtOC(=O)—PhCH2— |
| 4492 | 2-Br-5-EtOC(=O)—PhCH2— |
| 4493 | 2-Br-6-EtOC(=O)—PhCH2— |
| 4494 | 2-I-3-EtOC(=O)—PhCH2— |
| 4495 | 2-I-4-EtOC(=O)—PhCH2— |
| 4496 | 2-I-5-EtOC(=O)—PhCH2— |
| 4497 | 2-I-6-EtOC(=O)—PhCH2— |
| 4498 | 2-Me-3-EtOC(=O)—PhCH2— |
| 4499 | 2-Me-4-EtOC(=O)—PhCH2— |
| 4500 | 2-Me-5-EtOC(=O)—PhCH2— |
| 4501 | 2-Me-6-EtOC(=O)—PhCH2— |
| 4502 | 2-F-3-AcO—PhCH2— |
| 4503 | 2-F-4-AcO—PhCH2— |
| 4504 | 2-F-5-AcO—PhCH2— |
| 4505 | 2-F-6-AcO—PhCH2— |
| 4506 | 2-Cl-3-AcO—PhCH2— |
| 4507 | 2-Cl-4-AcO—PhCH2— |
| 4508 | 2-Cl-5-AcO—PhCH2— |
| 4509 | 2-Cl-6-AcO—PhCH2— |
| 4510 | 2-Br-3-AcO—PhCH2— |
| 4511 | 2-Br-4-AcO—PhCH2— |
| 4512 | 2-Br-5-AcO—PhCH2— |
| 4513 | 2-Br-6-AcO—PhCH2— |
| 4514 | 2-I-3-AcO—PhCH2— |
| 4515 | 2-I-4-AcO—PhCH2— |
| 4516 | 2-I-5-AcO—PhCH2— |
| 4517 | 2-I-6-AcO—PhCH2— |
| 4518 | 2-Me-3-AcO—PhCH2— |
| 4519 | 2-Me-4-AcO—PhCH2— |
| 4520 | 2-Me-5-AcO—PhCH2— |
| 4521 | 2-Me-6-AcO—PhCH2— |
| 4522 | 2-F-3-MeOC(=O)O—PhCH2— |
| 4523 | 2-F-4-MeOC(=O)O—PhCH2— |
| 4524 | 2-F-5-MeOC(=O)O—PhCH2— |
| 4525 | 2-F-6-MeOC(=O)O—PhCH2— |
| 4526 | 2-Cl-3-MeOC(=O)O—PhCH2— |
| 4527 | 2-Cl-4-MeOC(=O)O—PhCH2— |
| 4528 | 2-Cl-5-MeOC(=O)O—PhCH2— |
| 4529 | 2-Cl-6-MeOC(=O)O—PhCH2— |
| 4530 | 2-Br-3-MeOC(=O)O—PhCH2— |
| 4531 | 2-Br-4-MeOC(=O)O—PhCH2— |
| 4532 | 2-Br-5-MeOC(=O)O—PhCH2— |
| 4533 | 2-Br-6-MeOC(=O)O—PhCH2— |
| 4534 | 2-I-3-MeOC(=O)O—PhCH2— |
| 4535 | 2-I-4-MeOC(=O)O—PhCH2— |
| 4536 | 2-I-5-MeOC(=O)O—PhCH2— |
| 4537 | 2-I-6-MeOC(=O)O—PhCH2— |
| 4538 | 2-Me-3-MeOC(=O)O—PhCH2— |
| 4539 | 2-Me-4-MeOC(=O)O—PhCH2— |
| 4540 | 2-Me-5-MeOC(=O)O—PhCH2— |
| 4541 | 2-Me-6-MeOC(=O)O—PhCH2— |
| 4542 | 2-F-3-EtOC(=O)O—PhCH2— |
| 4543 | 2-F-4-EtOC(=O)O—PhCH2— |
| 4544 | 2-F-5-EtOC(=O)O—PhCH2— |
| 4545 | 2-F-6-EtOC(=O)O—PhCH2— |
| 4546 | 2-Cl-3-EtOC(=O)O—PhCH2— |
| 4547 | 2-Cl-4-EtOC(=O)O—PhCH2— |
| 4548 | 2-Cl-5-EtOC(=O)O—PhCH2— |
| 4549 | 2-Cl-6-EtOC(=O)O—PhCH2— |
| 4550 | 2-Br-3-EtOC(=O)O—PhCH2— |
| 4551 | 2-Br-4-EtOC(=O)O—PhCH2— |
| 4552 | 2-Br-5-EtOC(=O)O—PhCH2— |
| 4553 | 2-Br-6-EtOC(=O)O—PhCH2— |
| 4554 | 2-I-3-EtOC(=O)O—PhCH2— |
| 4555 | 2-I-4-EtOC(=O)O—PhCH2— |
| 4556 | 2-I-5-EtOC(=O)O—PhCH2— |
| 4557 | 2-I-6-EtOC(=O)O—PhCH2— |

TABLE 2-continued

| No. | Z |
|---|---|
| 4558 | 2-Me-3-EtOC(=O)O—PhCH2— |
| 4559 | 2-Me-4-EtOC(=O)O—PhCH2— |
| 4560 | 2-Me-5-EtOC(=O)O—PhCH2— |
| 4561 | 2-Me-6-EtOC(=O)O—PhCH2— |
| 4562 | 2-F-3-(1,3-dioxolan-2-yl)-PhCH2— |
| 4563 | 2-F-4-(1,3-dioxolan-2-yl)-PhCH2— |
| 4564 | 2-F-5-(1,3-dioxolan-2-yl)-PhCH2— |
| 4565 | 2-F-6-(1,3-dioxolan-2-yl)-PhCH2— |
| 4566 | 2-Cl-3-(1,3-dioxolan-2-yl)-PhCH2— |
| 4567 | 2-Cl-4-(1,3-dioxolan-2-yl)-PhCH2— |
| 4568 | 2-Cl-5-(1,3-dioxolan-2-yl)-PhCH2— |
| 4569 | 2-Cl-6-(1,3-dioxolan-2-yl)-PhCH2— |
| 4570 | 2-Br-3-(1,3-dioxolan-2-yl)-PhCH2— |
| 4571 | 2-Br-4-(1,3-dioxolan-2-yl)-PhCH2— |
| 4572 | 2-Br-5-(1,3-dioxolan-2-yl)-PhCH2— |
| 4573 | 2-Br-6-(1,3-dioxolan-2-yl)-PhCH2— |
| 4574 | 2-I-3-(1,3-dioxolan-2-yl)-PhCH2— |
| 4575 | 2-I-4-(1,3-dioxolan-2-yl)-PhCH2— |
| 4576 | 2-I-5-(1,3-dioxolan-2-yl)-PhCH2— |
| 4577 | 2-I-6-(1,3-dioxolan-2-yl)-PhCH2— |
| 4578 | 2-Me-3-(1,3-dioxolan-2-yl)-PhCH2— |
| 4579 | 2-Me-4-(1,3-dioxolan-2-yl)-PhCH2— |
| 4580 | 2-Me-5-(1,3-dioxolan-2-yl)-PhCH2— |
| 4581 | 2-Me-6-(1,3-dioxolan-2-yl)-PhCH2— |
| 4582 | 2-F-3-(1,3-dioxan-2-yl)-PhCH2— |
| 4583 | 2-F-4-(1,3-dioxan-2-yl)-PhCH2— |
| 4584 | 2-F-5-(1,3-dioxan-2-yl)-PhCH2— |
| 4585 | 2-F-6-(1,3-dioxan-2-yl)-PhCH2— |
| 4586 | 2-Cl-3-(1,3-dioxan-2-yl)-PhCH2— |
| 4587 | 2-Cl-4-(1,3-dioxan-2-yl)-PhCH2— |
| 4588 | 2-Cl-5-(1,3-dioxan-2-yl)-PhCH2— |
| 4589 | 2-Cl-6-(1,3-dioxan-2-yl)-PhCH2— |
| 4590 | 2-Br-3-(1,3-dioxan-2-yl)-PhCH2— |
| 4591 | 2-Br-4-(1,3-dioxan-2-yl)-PhCH2— |
| 4592 | 2-Br-5-(1,3-dioxan-2-yl)-PhCH2— |
| 4593 | 2-Br-6-(1,3-dioxan-2-yl)-PhCH2— |
| 4594 | 2-I-3-(1,3-dioxan-2-yl)-PhCH2— |
| 4595 | 2-I-4-(1,3-dioxan-2-yl)-PhCH2— |
| 4596 | 2-I-5-(1,3-dioxan-2-yl)-PhCH2— |
| 4597 | 2-I-6-(1,3-dioxan-2-yl)-PhCH2— |
| 4598 | 2-Me-3-(1,3-dioxan-2-yl)-PhCH2— |
| 4599 | 2-Me-4-(1,3-dioxan-2-yl)-PhCH2— |
| 4600 | 2-Me-5-(1,3-dioxan-2-yl)-PhCH2— |
| 4597 | 2-Me-6-(1,3-dioxan-2-yl)-PhCH2— |
| 4602 | 2-F-3-MeS—PhCH2— |
| 4603 | 2-F-4-MeS—PhCH2— |
| 4604 | 2-F-5-MeS—PhCH2— |
| 4605 | 2-F-6-MeS—PhCH2— |
| 4606 | 2-Cl-3-MeS—PhCH2— |
| 4607 | 2-Cl-4-MeS—PhCH2— |
| 4608 | 2-Cl-5-MeS—PhCH2— |
| 4609 | 2-Cl-6-MeS—PhCH2— |
| 4610 | 2-Br-3-MeS—PhCH2— |
| 4611 | 2-Br-4-MeS—PhCH2— |
| 4612 | 2-Br-5-MeS—PhCH2— |
| 4613 | 2-Br-6-MeS—PhCH2— |
| 4614 | 2-I-3-MeS—PhCH2— |
| 4615 | 2-I-4-MeS—PhCH2— |
| 4616 | 2-I-5-MeS—PhCH2— |
| 4617 | 2-I-6-MeS—PhCH2— |
| 4618 | 2-Me-3-MeS—PhCH2— |
| 4619 | 2-Me-4-MeS—PhCH2— |
| 4620 | 2-Me-5-MeS—PhCH2— |
| 4621 | 2-Me-6-MeS—PhCH2— |
| 4622 | 2-F-3-MeS(O)—PhCH2— |
| 4623 | 2-F-4-MeS(O)—PhCH2— |
| 4694 | 2-F-5-MeS(O)—PhCH2— |
| 4695 | 2-F-6-MeS(O)—PhCH2— |
| 4696 | 2-Cl-3-MeS(O)—PhCH2— |
| 4627 | 2-Cl-4-MeS(O)—PhCH2— |
| 4628 | 2-Cl-5-MeS(O)—PhCH2— |
| 4629 | 2-Cl-6-MeS(O)—PhCH2— |
| 4630 | 2-Br-3-MeS(O)—PhCH2— |
| 4631 | 2-Br-4-MeS(O)—PhCH2— |
| 4632 | 2-Br-5-MeS(O)—PhCH2— |
| 4633 | 2-Br-6-MeS(O)—PhCH2— |
| 4634 | 2-I-2-MeS(O)—PhCH2— |
| 4635 | 2-I-4-MeS(O)—PhCH2— |
| 4636 | 2-I-5-MeS(O)—PhCH2— |
| 4637 | 2-I-6-MeS(O)—PhCH2— |
| 4638 | 2-Me-3-MeS(O)—PhCH2— |
| 4639 | 2-Me-4-MeS(O)—PhCH2— |
| 4640 | 2-Me-5-MeS(O)—PhCH2— |
| 4641 | 2-Me-6-MeS(O)—PhCH2— |
| 4642 | 2-F-3-MeSO2—PhCH2— |
| 4643 | 2-F-4-MeSO2—PhCH2— |
| 4644 | 2-F-5-MeSO2—PhCH2— |
| 4645 | 2-F-6-MeSO2—PhCH2— |
| 4646 | 2-Cl-3-MeSO2—PhCH2— |
| 4647 | 2-Cl-4-MeSO2—PhCH2— |
| 4648 | 2-Cl-5-MeSO2—PhCH2— |
| 4649 | 2-Cl-6-MeSO2—PhCH2— |
| 4650 | 2-Br-3-MeSO2—PhCH2— |
| 4651 | 2-Br-4-MeSO2—PhCH2— |
| 4652 | 2-Br-5-MeSO2—PhCH2— |
| 4653 | 2-Br-6-MeSO2—PhCH2— |
| 4654 | 2-I-3-MeSO2—PhCH2— |
| 4655 | 2-I-4-MeSO2—PhCH2— |
| 4656 | 2-I-5-MeSO2—PhCH2— |
| 4657 | 2-I-6-MeSO2—PhCH2— |
| 4658 | 2-Me-3-MeSO2—PhCH2— |
| 4659 | 2-Me-4-MeSO2—PhCH2— |
| 4660 | 2-Me-5-MeSO2—PhCH2— |
| 4661 | 2-Me-6-MeSO2—PhCH2— |
| 4662 | 2-F-3-ClCH2S—PhCH2— |
| 4663 | 2-F-4-ClCH2S—PhCH2— |
| 4664 | 2-F-5-ClCH2S—PhCH2— |
| 4665 | 2-F-6-ClCH2S—PhCH2— |
| 4666 | 2-Cl-3-ClCH2S—PhCH2— |
| 4667 | 2-Cl-4-ClCH2S—PhCH2— |
| 4668 | 2-Cl-5-ClCH2S—PhCH2— |
| 4669 | 2-Cl-6-ClCH2S—PhCH2— |
| 4670 | 2-Br-3-ClCH2S—PhCH2— |
| 4671 | 2-Br-4-ClCH2S—PhCH2— |
| 4672 | 2-Br-5-ClCH2S—PhCH2— |
| 4673 | 2-Br-6-ClCH2S—PhCH2— |
| 4674 | 2-I-3-ClCH2S—PhCH2— |
| 4675 | 2-I-4-ClCH2S—PhCH2— |
| 4676 | 2-I-5-ClCH2S—PhCH2— |
| 4677 | 2-I-6-ClCH2S—PhCH2— |
| 4678 | 2-Me-3-ClCH2S—PhCH2— |
| 4679 | 2-Me-4-ClCH2S—PhCH2— |
| 4680 | 2-Me-5-ClCH2S—PhCH2— |
| 4681 | 2-Me-6-ClCH2S—PhCH2— |
| 4682 | 2-F-3-ClCH2S(O)—PhCH2— |
| 4683 | 2-F-4-ClCH2S(O)—PhCH2— |
| 4684 | 2-F-5-ClCH2S(O)—PhCH2— |
| 4685 | 2-F-6-ClCH2S(O)—PhCH2— |
| 4686 | 2-Cl-3-ClCH2S(O)—PhCH2— |
| 4687 | 2-Cl-4-ClCH2S(O)—PhCH2— |
| 4688 | 2-Cl-5-ClCH2S(O)—PhCH2— |
| 4689 | 2-Cl-6-ClCH2S(O)—PhCH2— |
| 4690 | 2-Br-3-ClCH2S(O)—PhCH2— |
| 4691 | 2-Br-4-ClCH2S(O)—PhCH2— |
| 4692 | 2-Br-5-ClCH2S(O)—PhCH2— |
| 4693 | 2-Br-6-ClCH2S(O)—PhCH2— |
| 4694 | 2-I-3-ClCH2S(O)—PhCH2— |
| 4695 | 2-I-4-ClCH2S(O)—PhCH2— |
| 4696 | 2-I-5-ClCH2S(O)—PhCH2— |
| 4697 | 2-I-6-ClCH2S(O)—PhCH2— |
| 4698 | 2-Me-3-ClCH2S(O)—PhCH2— |
| 4699 | 2-Me-4-ClCH2S(O)—PhCH2— |
| 4700 | 2-Me-5-ClCH2S(O)—PhCH2— |
| 4701 | 2-Me-6-ClCH2S(O)—PhCH2— |
| 4702 | 2-F-3-ClCH2SO2—PhCH2— |
| 4703 | 2-F-4-ClCH2SO2—PhCH2— |
| 4704 | 2-F-5-ClCH2SO2—PhCH2— |
| 4705 | 2-F-6-ClCH2SO2—PhCH2— |
| 4706 | 2-Cl-3-ClCH2SO2—PhCH2— |
| 4707 | 2-Cl-4-ClCH2SO2—PhCH2— |
| 4708 | 2-Cl-5-ClCH2SO2—PhCH2— |
| 4709 | 2-Cl-6-ClCH2SO2—PhCH2— |
| 4710 | 2-Br-3-ClCH2SO2—PhCH2— |
| 4711 | 2-Br-4-ClCH2SO2—PhCH2— |
| 4712 | 2-Br-5-ClCH2SO2—PhCH2— |
| 4713 | 2-Br-6-ClCH2SO2—PhCH2— |

TABLE 2-continued

| No. | Z |
|---|---|
| 4714 | 2-I-3-ClCH2SO2—PhCH2— |
| 4715 | 2-I-4-ClCH2SO2—PhCH2— |
| 4716 | 2-I-5-ClCH2SO2—PhCH2— |
| 4717 | 2-I-6-ClCH2SO2—PhCH2— |
| 4718 | 2-Me-3-ClCH2SO2—PhCH2— |
| 4719 | 2-Me-4-ClCH2SO2—PhCH2— |
| 4720 | 2-Me-5-ClCH2SO2—PhCH2— |
| 4721 | 2-Me-6-ClCH2SO2—PhCH2— |
| 4722 | 3,5-di-MeO—PhCH2— |
| 4723 | 3,5-di-EtO—PhCH2— |
| 4724 | 3,5-di-F—PhCH2— |
| 4725 | 3,5-di-Cl—PhCH2— |
| 4726 | 3,5-di-Br—PhCH2— |
| 4727 | 3,5-di-I—PhCH2— |
| 4728 | 3,5-di-Me—PhCH2— |
| 4729 | 3-F-5-Me—PhCH2— |
| 4730 | 3-Cl-5-Me—PhCH2— |
| 4731 | 3-Br-5-Me—PhCH2— |
| 4732 | 3-I-5-Me—PhCH2— |
| 4733 | 3-F-5-MeO—PhCH2— |
| 4734 | 3-Cl-5-MeO—PhCH2— |
| 4735 | 3-Br-5-MeO—PhCH2— |
| 4736 | 3-I-5-MeO—PhCH2— |
| 4737 | 5-F-3-EtO—PhCH2— |
| 4738 | 3-Cl-5-EtO—PhCH2— |
| 4739 | 3-Br-5-EtO—PhCH2— |
| 4740 | 5-I-3-EtO—PhCH2— |
| 4741 | 3-F-5-N≡CCH2O—PhCH2— |
| 4742 | 3-Cl-5-N≡CCH2O—PhCH2— |
| 4743 | 3-Br-5-N≡CCH2O—PhCH2— |
| 4744 | 3-I-5-N≡CCH2O—PhCH2— |
| 4745 | 3-F-5-MeOCH2O—PhCH2— |
| 4746 | 3-Cl-5-MeOCH2O—PhCH2— |
| 4747 | 3-Br-5-MeOCH2O—PhCH2— |
| 4748 | 3-I-5-MeOCH2O—PhCH2— |
| 4749 | 5-F-2-MeO—PhCH2— |
| 4750 | 5-Cl-2-MeO—PhCH2— |
| 4751 | 5-Br-2-MeO—PhCH2— |
| 4752 | 5-I-2-MeO—PhCH2— |
| 4753 | 5-Me-2-MeO—PhCH2— |
| 4754 | 2-F-3,5-di-MeO—PhCH2— |
| 4755 | 2-F-3,5-di-EtO—PhCH2— |
| 4756 | 2,3,5-tri-F—PhCH2— |
| 4757 | 2-F-3,5-di-Cl—PhCH2— |
| 4758 | 3,5-di-Br-2-F—PhCH2— |
| 4759 | 2-F-3,5-di-I—PhCH2— |
| 4760 | 2-F-3,5-di-Me—PhCH2— |
| 4761 | 2,3-di-F-5-Me—PhCH2— |
| 4762 | 2,5-di-F-3-Me—PhCH2— |
| 4763 | 3-Cl-2-F-5-Me—PhCH2— |
| 4764 | 5-Cl-2-F-3-Me—PhCH2— |
| 4765 | 3-Br-2-F-5-Me—PhCH2— |
| 4766 | 5-Br-2-F-3-Me—PhCH2— |
| 4767 | 2-F-3-I-5-Me—PhCH2— |
| 4768 | 2-F-5-I-3-Me—PhCH2— |
| 4769 | 2,3-di-F-5-MeO—PhCH2— |
| 4770 | 2,5-di-F-3-MeO—PhCH2— |
| 4771 | 3-Cl-2-F-5-MeO—PhCH2— |
| 4772 | 5-Cl-2-F-3-MeO—PhCH2— |
| 4773 | 3-Br-2-F-5-MeO—PhCH2— |
| 4774 | 5-Br-2-F-3-MeO—PhCH2— |
| 4775 | 2-F-3-I-5-MeO—PhCH2— |
| 4776 | 2-F-5-I-3-MeO—PhCH2— |
| 4777 | 2,3-di-F-5-EtO—PhCH2— |
| 4778 | 2,5-di-F-3-EtO—PhCH2— |
| 4779 | 3-Cl-2-F-5-EtO—PhCH2— |
| 4780 | 5-Cl-2-F-3-EtO—PhCH2— |
| 4781 | 3-Br-2-F-5-EtO—PhCH2— |
| 4782 | 5-Br-2-F-3-EtO—PhCH2— |
| 4783 | 2-F-3-I-5-EtO—PhCH2— |
| 4784 | 2-F-5-I-3-EtO—PhCH2— |
| 4785 | 2,3-di-F-5-N≡CCH2O—PhCH2— |
| 4786 | 2,5-di-F-3-N≡CCH2O—PhCH2— |
| 4787 | 3-Cl-2-F-5-N≡CCH2O—PhCH2— |
| 4788 | 5-Cl-2-F-3-N≡CCH2O—PhCH2— |
| 4789 | 3-Br-2-F-5-N≡CCH2O—PhCH2— |
| 4790 | 5-Br-2-F-3-N≡CCH2O—PhCH2— |
| 4791 | 2-F-3-I-5-N≡CCH2O—PhCH2— |
| 4792 | 2-F-5-I-3-N≡CCH2O—PhCH2— |
| 4793 | 2,3-di-F-5-MeOCH2O—PhCH2— |
| 4794 | 2,5-di-F-3-MeOCH2O—PhCH2— |
| 4795 | 3-Cl-2-F-5-MeOCH2O—PhCH2— |
| 4796 | 5-Cl-2-F-3-MeOCH2O—PhCH2— |
| 4797 | 3-Br-2-F-5-MeOCH2O—PhCH2— |
| 4798 | 5-Br-2-F-3-MeOCH2O—PhCH2— |
| 4799 | 2-F-3-I-5-MeOCH2O—PhCH2— |
| 4800 | 2-F-5-I-3-MeOCH2O—PhCH2— |
| 4801 | 2-Cl-3,5-di-MeO—PhCH2— |
| 4802 | 2-Cl-3,5-di-EtO—PhCH2— |
| 4803 | 2-Cl-3,5-di-F—PhCH2— |
| 4804 | 2,3,5-tri-Cl—PhCH2— |
| 4805 | 3,5-di-Br-2-Cl—PhCH2— |
| 4806 | 2-Cl-3,5-di-I—PhCH2— |
| 4807 | 2-Cl-3,5-di-Me—PhCH2— |
| 4808 | 2-Cl-3-F-5-Me—PhCH2— |
| 4809 | 2-Cl-5-F-3-Me—PhCH2— |
| 4810 | 2,3-di-Cl-5-Me—PhCH2— |
| 4811 | 2,5-di-Cl-3-Me—PhCH2— |
| 4812 | 3-Br-2-Cl-5-Me—PhCH2— |
| 4813 | 5-Br-2-Cl-3-Me—PhCH2— |
| 4814 | 2-Cl-3-I-5-Me—PhCH2— |
| 4815 | 2-Cl-5-I-3-Me—PhCH2— |
| 4816 | 2-Cl-3-F-5-MeO—PhCH2— |
| 4817 | 2-Cl-5-F-3-MeO—PhCH2— |
| 4818 | 2,3-di-Cl-5-MeO—PhCH2— |
| 4819 | 2,5-di-Cl-3-MeO—PhCH2— |
| 4820 | 3-Br-2-Cl-5-MeO—PhCH2— |
| 4821 | 5-Br-2-Cl-3-MeO—PhCH2— |
| 4822 | 2-Cl-3-I-5-MeO—PhCH2— |
| 4823 | 2-Cl-5-I-3-MeO—PhCH2— |
| 4824 | 2-Cl-3-F-5-EtO—PhCH2— |
| 4825 | 2-Cl-5-F-3-EtO—PhCH2— |
| 4826 | 2,3-di-Cl-5-EtO—PhCH2— |
| 4827 | 2,5-di-Cl-3-EtO—PhCH2— |
| 4828 | 3-Br-2-Cl-5-EtO—PhCH2— |
| 4829 | 5-Br-2-Cl-3-EtO—PhCH2— |
| 4830 | 2-Cl-3-I-5-EtO—PhCH2— |
| 4831 | 2-Cl-5-I-3-EtO—PhCH2 |
| 4832 | 2-Cl-3-F-5-N≡CCH2O—PhCH2— |
| 4833 | 2-Cl-5-F-3-N≡CCH2O—PhCH2— |
| 4834 | 2,3-di-Cl-5-N≡CCH2O—PhCH2— |
| 4835 | 2,5-di-Cl-3-N≡CCH2O—PhCH2— |
| 4836 | 3-Br-2-Cl-5-N≡CCH2O—PhCH2— |
| 4837 | 5-Br-2-Cl-3-N≡CCH2O—PhCH2— |
| 4838 | 2-Cl-3-I-5-N≡CCH2O—PhCH2— |
| 4839 | 2-Cl-5-I-3-N≡CCH2O—PhCH2— |
| 4840 | 2-Cl-3-F-5-MeOCH2O—PhCH2— |
| 4841 | 2-Cl-5-F-3-MeOCH2O—PhCH2— |
| 4842 | 2,3-di-Cl-5-MeOCH2O—PhCH2— |
| 4843 | 2,5-di-Cl-3-MeOCH2O—PhCH2— |
| 4844 | 3-Br-2-Cl-5-MeOCH2O—PhCH2— |
| 4845 | 5-Br-2-Cl-3-MeOCH2O—PhCH2— |
| 4846 | 2-Cl-3-I-5-MeOCH2O—PhCH2— |
| 4847 | 2-Cl-5-I-3-MeOCH2O—PhCH2— |
| 4848 | 2-Br-3,5-di-MeO—PhCH2— |
| 4849 | 2-Br-3,5-di-EtO—PhCH2— |
| 4850 | 2-Br-3,5-di-F—PhCH2— |
| 4851 | 2-Br-3,5-di-Cl—PhCH2— |
| 4852 | 2,3,5-tri-Br—PhCH2— |
| 4853 | 2-Br-3,5-di-I—PhCH2— |
| 4854 | 2-Br-3,5-di-Me—PhCH2— |
| 4855 | 2-Br-3-F-5-Me—PhCH2— |
| 4856 | 2-Br-5-F-3-Me—PhCH2— |
| 4857 | 2-Br-3-Cl-5-Me—PhCH2— |
| 4858 | 2-Br-5-Cl-3-Me—PhCH2— |
| 4859 | 2,3-di-Br-5-Me—PhCH2— |
| 4860 | 2,5-di-Br-3-Me—PhCH2— |
| 4861 | 2-Br-3-I-5-Me—PhCH2— |
| 4862 | 2-Br-5-I-3-Me—PhCH2— |
| 4863 | 2-Br-3-F-5-MeO—PhCH2— |
| 4864 | 2-Br-5-F-3-MeO—PhCH2— |
| 4865 | 2-Br-3-Cl-5-MeO—PhCH2— |
| 4866 | 2-Br-5-Cl-3-MeO—PhCH2— |
| 4867 | 2,3-di-Br-5-MeO—PhCH2— |
| 4868 | 2,5-di-Br-3-MeO—PhCH2— |
| 4869 | 2-Br-3-I-5-MeO—PhCH2— |

TABLE 2-continued

| No. | Z |
|---|---|
| 4870 | 2-Br-5-I-3-MeO—PhCH2— |
| 4871 | 2-Br-3-F-5-EtO—PhCH2— |
| 4872 | 2-Br-5-F-3-EtO—PhCH2— |
| 4873 | 2-Br-3-Cl-5-EtO—PhCH2— |
| 4874 | 2-Br-5-Cl-3-EtO—PhCH2— |
| 4875 | 2,3-di-Br-5-EtO—PhCH2— |
| 4876 | 2,5-di-Br-3-EtO—PhCH2— |
| 4877 | 2-Br-3-I-5-EtO—PhCH2— |
| 4878 | 2-Br-5-I-3-EtO—PhCH2— |
| 4879 | 2-Br-3-F-5-N≡CCH2O—PhCH2— |
| 4880 | 2-Br-5-F-3-N≡CCH2O—PhCH2— |
| 4881 | 2-Br-3-Cl-5-N≡CCH2O—PhCH2— |
| 4882 | 2-Br-5-Cl-3-N≡CCH2O—PhCH2— |
| 4883 | 2,3-di-Br-5-N≡CCH2O—PhCH2— |
| 4884 | 2,5-di-Br-3-N≡CCH2O—PhCH2— |
| 4885 | 2-Br-3-I-5-N≡CCH2O—PhCH2— |
| 4886 | 2-Br-5-I-3-N≡CCH2O—PhCH2— |
| 4887 | 2-Br-3-F-5-MeOCH2O—PhCH2— |
| 4888 | 2-Br-5-F-3-MeOCH2O—PhCH2— |
| 4889 | 2-Br-3-Cl-5-MeOCH2O—PhCH2— |
| 4890 | 2-Br-5-Cl-3-MeOCH2O—PhCH2— |
| 4891 | 2,3-di-Br-5-MeOCH2O—PhCH2— |
| 4892 | 2,5-di-Br-3-MeOCH2O—PhCH2— |
| 4893 | 2-Br-3-I-5-MeOCH2O—PhCH2— |
| 4894 | 2-Br-5-I-3-MeOCH2O—PhCH2— |
| 4895 | 2-I-3,5-di-MeO—PhCH2— |
| 4896 | 2-I-3,5-di-EtO—PhCH2— |
| 4897 | 3,5-di-F-2-I—PhCH2— |
| 4898 | 3,5-di-Cl-2-I—PhCH2— |
| 4899 | 3,5-di-Br-2-I—PhCH2— |
| 4900 | 2,3,5-Tri-I—PhCH2— |
| 4901 | 3,5-di-Me-2-I—PhCH2— |
| 4902 | 3-F-2-I-5-Me—PhCH2— |
| 4903 | 5-F-2-I-3-Me—PhCH2— |
| 4904 | 3-Cl-2-I-5-Me—PhCH2— |
| 4905 | 5-Cl-2-I-3-Me—PhCH2— |
| 4906 | 3-Br-2-I-5-Me—PhCH2— |
| 4907 | 5-Br-2-I-3-Me—PhCH2— |
| 4908 | 2,3-di-I-5-Me—PhCH2— |
| 4909 | 2,5-di-I-3-Me—PhCH2— |
| 4910 | 3-F-2-I-5-MeO—PhCH2— |
| 4911 | 5-F-2-I-3-MeO—PhCH2— |
| 4912 | 3-Cl-2-I-5-MeO—PhCH2— |
| 4913 | 5-Cl-2-I-3-MeO—PhCH2— |
| 4914 | 3-Br-2-I-5-MeO—PhCH2— |
| 4915 | 5-Br-2-I-3-MeO—PhCH2— |
| 4916 | 2,3-di-I-5-MeO—PhCH2— |
| 4917 | 2,5-di-I-3-MeO—PhCH2— |
| 4918 | 3-F-2-I-5-EtO—PhCH2— |
| 4919 | 5-F-2-I-3-EtO—PhCH2— |
| 4920 | 3-Cl-2-I-5-EtO—PhCH2— |
| 4921 | 5-Cl-2-I-3-EtO—PhCH2— |
| 4922 | 3-Br-2-I-5-EtO—PhCH2— |
| 4923 | 5-Br-2-I-3-EtO—PhCH2— |
| 4924 | 2,3-di-I-5-EtO—PhCH2— |
| 4925 | 2,5-di-I-3-EtO—PhCH2— |
| 4926 | 3-F-2-I-5-N≡CCH2O—PhCH2— |
| 4927 | 5-F-2-I-3-N≡CCH2O—PhCH2— |
| 4928 | 3-Cl-2-I-5-N≡CCH2O—PhCH2— |
| 4929 | 5-Cl-2-I-3-N≡CCH2O—PhCH2— |
| 4930 | 3-Br-2-I-5-N≡CCH2O—PhCH2— |
| 4931 | 5-Br-2-I-3-N≡CCH2O—PhCH2— |
| 4932 | 2,3-di-I-5-N≡CCH2O—PhCH2— |
| 4933 | 2,5-di-I-3-N≡CCH2O—PhCH2— |
| 4934 | 3-F-2-I-5-MeOCH2O—PhCH2— |
| 4935 | 5-F-2-I-3-MeOCH2O—PhCH2— |
| 4936 | 3-Cl-2-I-5-MeOCH2O—PhCH2— |
| 4937 | 5-Cl-2-I-3-MeOCH2O—PhCH2— |
| 4938 | 3-Br-2-I-5-MeOCH2O—PhCH2— |
| 4939 | 5-Br-2-I-3-MeOCH2O—PhCH2— |
| 4940 | 2,3-di-I-5-MeOCH2O—PhCH2— |
| 4941 | 2,5-di-I-3-MeOCH2O—PhCH2— |
| 4942 | 2-Me-3,5-di-MeO—PhCH2— |
| 4943 | 2-Me-3,5-di-EtO—PhCH2— |
| 4914 | 3,5-di-F-2-Me—PhCH2— |
| 4945 | 3,5-di-Cl-2-Me—PhCH2— |
| 4946 | 3,5-di-Br-2-Me—PhCH2— |
| 4947 | 3,5-di-I-2-Me—PhCH2— |
| 4948 | 2,3,5-tri-Me—PhCH2— |
| 4949 | 3-F-2,5-di-Me—PhCH2— |
| 4950 | 5-F-2,3-di-Me—PhCH2— |
| 4951 | 3-Cl-2,5-di-Me—PhCH2— |
| 4952 | 5-Cl-2,3-di-Me—PhCH2— |
| 4953 | 3-Br-2,5-di-Me—PhCH2— |
| 4954 | 5-Br-2,3-di-Me—PhCH2— |
| 4955 | 3-I-2,5-di-Me—PhCH2— |
| 4956 | 5-I-2,3-di-Me—PhCH2— |
| 4957 | 3-F-2-Me-5-MeO—PhCH2— |
| 4958 | 5-F-2-Me-3-MeO—PhCH2— |
| 4959 | 3-Cl-2-Me-5-MeO—PhCH2— |
| 4960 | 5-Cl-2-Me-3-MeO—PhCH2— |
| 4961 | 3-Br-2-Me-5-MeO—PhCH2— |
| 4962 | 5-Br-2-Me-3-MeO—PhCH2— |
| 4963 | 3-I-2-Me-5-MeO—PhCH2— |
| 4964 | 5-I-2-Me-3-MeO—PhCH2— |
| 4965 | 3-F-2-Me-5-EtO—PhCH2— |
| 4966 | 5-F-2-Me-3-EtO—PhCH2— |
| 4967 | 3-Cl-2-Me-5-EtO—PhCH2— |
| 4968 | 5-Cl-2-Me-3-EtO—PhCH2— |
| 4969 | 3-Br-2-Me-5-EtO—PhCH2— |
| 4970 | 5-Br-2-Me-3-EtO—PhCH2— |
| 4971 | 3-I-2-Me-5-EtO—PhCH2— |
| 4972 | 5-I-2-Me-3-EtO—PhCH2— |
| 4973 | 3-F-2-Me-5-N≡CCH2O—PhCH2— |
| 4974 | 5-F-2-Me-3-N≡CCH2O—PhCH2— |
| 4975 | 3-Cl-2-Me-5-N≡CCH2O—PhCH2— |
| 4976 | 5-Cl-2-Me-3-N≡CCH2O—PhCH2— |
| 4977 | 3-Br-2-Me-5-N≡CCH2O—PhCH2— |
| 4978 | 5-Br-2-Me-3-N≡CCH2O—PhCH2— |
| 4979 | 3-I-2-Me-5-N≡CCH2O—PhCH2— |
| 4980 | 5-I-2-Me-3-N≡CCH2O—PhCH2— |
| 4981 | 3-F-2-Me-5-MeOCH2O—PhCH2— |
| 4982 | 5-F-2-Me-3-MeOCH2O—PhCH2— |
| 4983 | 3-Cl-2-Me-5-MeOCH2O—PhCH2— |
| 4984 | 5-Cl-2-Me-3-MeOCH2O—PhCH2— |
| 4985 | 3-Br-2-Me-5-MeOCH2O—PhCH2— |
| 4986 | 5-Br-2-Me-3-MeOCH2O—PhCH2— |
| 4987 | 3-I-2-Me-5-MeOCH2O—PhCH2— |
| 4988 | 5-I-2-Me-3-MeOCH2O—PhCH2— |
| 4989 | 2,3,6-tri-F—PhCH2— |
| 4990 | 2,6-di-Cl-3-F—PhCH2— |
| 4991 | 2-Cl-3,6-di-F—PhCH2— |
| 4992 | 6-Cl-2,3-di-F—PhCH2— |
| 4993 | 3-Cl-2,6-di-F—PhCH2— |
| 4994 | 2,3,6-Tri-Cl—PhCH2— |
| 4995 | 2,3-di-Cl-6-F—PhCH2— |
| 4996 | 3,6-di-Cl-2-F—PhCH2— |
| 4997 | 3-Br-2,6-di-F—PhCH2— |
| 4998 | 3-Br-2,6-di-Cl—PhCH2— |
| 4999 | 3-Br-2-Cl-6-F—PhCH2— |
| 5000 | 3-Br-6-Cl-2-F—PhCH2— |
| 5001 | 2,6-di-F-3-I—PhCH2— |
| 5002 | 2,6-di-Cl-3-I—PhCH2— |
| 5003 | 2-Cl-6-F-3-I—PhCH2— |
| 5004 | 6-Cl-2-F-3-I—PhCH2— |
| 5005 | 2,6-di-F-3-Me—PhCH2— |
| 5006 | 2,6-di-Cl-3-Me—PhCH2— |
| 5007 | 2-Cl-6-F-3-Me—PhCH2— |
| 5008 | 6-Cl-2-F-3-Me—PhCH2— |
| 5009 | 2,6-di-F-3-MeO—PhCH2— |
| 5010 | 2,6-di-Cl-3-MeO—PhCH2— |
| 5011 | 2-Cl-6-F-3-MeO—PhCH2— |
| 5012 | 6-Cl-2-F-3-MeO—PhCH2— |
| 5013 | 2,6-di-F-3-EtO—PhCH2— |
| 5014 | 2,6-di-Cl-3-EtO—PhCH2— |
| 5015 | 2-Cl-6-F-3-EtO—PhCH2— |
| 5016 | 6-Cl-2-F-3-EtO—PhCH2— |
| 5017 | 2,6-di-F-3-N≡CCH2O—PhCH2— |
| 5018 | 2,6-di-Cl-3-N≡CCH2O—PhCH2— |
| 5019 | 2-Cl-6-F-3-N≡CCH2O—PhCH2— |
| 5020 | 6-Cl-2-F-3-N≡CCH2O—PhCH2— |
| 5021 | 2,6-di-F-3-MeOCH2O—PhCH2— |
| 5022 | 2,6-di-Cl-3-MeOCH2O—PhCH2— |
| 5023 | 2-Cl-6-F-3-MeOCH2O—PhCH2— |
| 5024 | 6-Cl-2-F-3-MeOCH2O—PhCH2— |
| 5025 | 3,4,5-tri-F—PhCH2— |

TABLE 2-continued

| No. | Z |
|---|---|
| 5026 | 4-Cl-3,5-di-F—PhCH2— |
| 5027 | 4-Br-3,5-di-F—PhCH2— |
| 5028 | 3,5-di-F-4-I—PhCH2— |
| 5029 | 3,5-di-F-4-Me—PhCH2— |
| 5030 | 3,5-di-Cl-4-F—PhCH2— |
| 5031 | 3,4,5-tri-Cl—PhCH2— |
| 5032 | 4-Br-3,5-di-Cl—PhCH2— |
| 5033 | 3,5-di-Cl-4-I—PhCH2— |
| 5034 | 3,5-di-Cl-4-Me—PhCH2 |
| 5035 | 3,5-di-Br-4-F—PhCH2— |
| 5036 | 3,5-di-Br-4-Cl—PhCH2— |
| 5037 | 3,4,5-tri-Br—PhCH2— |
| 5038 | 3,5-di-Br-4-I—PhCH2— |
| 5039 | 3,5-di-Br-4-Me—PhCH2— |
| 5040 | 4-F-3,5-di-I—PhCH2— |
| 5041 | 4-Cl-3,5-di-I—PhCH2— |
| 5042 | 4-Br-3,5-di-I—PhCH2— |
| 5043 | 3,4,5-tri-I—PhCH2— |
| 5044 | 4-Me-3,5-di-I—PhCH2— |
| 5045 | 4-F-3,5-di-Me—PhCH2— |
| 5046 | 4-Cl-3,5-di-Me—PhCH2 |
| 5047 | 4-Br-3,5-di-Me—PhCH2 |
| 5048 | 4-I-3,5-di-Me—PhCH2— |
| 5049 | 3,4,5-tri-Me—PhCH2— |
| 5050 | 4-F-3,5-di-Me—PhCH2— |
| 5051 | 4-Cl-3,5-di-Me—PhCH2— |
| 5052 | 4-Br-3,5-di-Me—PhCH2— |
| 5053 | 4-I-3,5-di-Me—PhCH2— |
| 5054 | 4-MeO-3,5-di-Me—PhCH2— |
| 5055 | 4-F-3,5-di-MeO—PhCH2— |
| 5056 | 4-Cl-3,5-di-MeO—PhCH2— |
| 5057 | 4-Br-3,5-di-MeO—PhCH2— |
| 5058 | 4-I-3,5-di-MeO—PhCH2— |
| 5059 | 4-Me-3,5-di-MeO—PhCH2— |
| 5060 | 4-F-3,5-di-EtO—PhCH2— |
| 5061 | 4-Cl-3,5-di-EtO—PhCH2— |
| 5062 | 4-Br-3,5-di-EtO—PhCH2— |
| 5063 | 4-I-3,5-di-EtO—PhCH2— |
| 5064 | 4-Me-3,5-di-EtO—PhCH2— |
| 5065 | 2,3,4-tri-F—PhCH2— |
| 5066 | 2-Cl-3,4-di-F—PhCH2— |
| 5067 | 2-Br-3,4-di-F—PhCH2— |
| 5068 | 3,4-di-F-2-I—PhCH2— |
| 5069 | 3,4-di-F-2-Me—PhCH2— |
| 5070 | 2,4,5-tri-F—PhCH2— |
| 5071 | 2-Cl-4,5-di-F—PhCH2— |
| 5072 | 2-Br-4,5-di-F—PhCH2— |
| 5073 | 4,5-di-F-2-I—PhCH2— |
| 5074 | 4,5-di-F-2-Me—PhCH2— |
| 5075 | 2,4-di-F-3-Cl—PhCH2— |
| 5076 | 2,3-di-Cl-4-F—PhCH2— |
| 5077 | 2-Br-3-Cl-4-F—PhCH2— |
| 5078 | 3-Cl-4-F-2-I—PhCH2— |
| 5079 | 3-Cl-4-F-2-Me—PhCH2— |
| 5080 | 2,4-di-F-5-Cl—PhCH2— |
| 5081 | 2,5-di-Cl-4-F—PhCH2— |
| 5082 | 2-Br-5-Cl-4-F—PhCH2— |
| 5083 | 5-Cl-4-F-2-I—PhCH2— |
| 5084 | 5-Cl-4-F-2-Me—PhCH2— |
| 5085 | 2-F-3,4-di-Cl—PhCH2— |
| 5086 | 2,3,4-tri-Cl—PhCH2— |
| 5087 | 2-Br-3,4-di-Cl—PhCH2— |
| 5088 | di-3,4-Cl-2-I—PhCH2— |
| 5089 | di-3,4-Cl-2-Me—PhCH2— |
| 5090 | 2-F-3,5-di-Cl—PhCH2— |
| 5091 | 2,3,5-tri-Cl—PhCH2— |
| 5092 | 2-Br-3,5-di-Cl—PhCH2— |
| 5093 | 3,5-di-Cl-2-I—PhCH2— |
| 5094 | 3,5-di-Cl-2-Me—PhCH2— |
| 5095 | 4-Cl-2,3-di-F—PhCH2— |
| 5096 | 2,4-di-Cl-3-F—PhCH2— |
| 5097 | 2-Br-4-Cl-3-F—PhCH2— |
| 5098 | 4-Cl-3-F-2-I—PhCH2— |
| 5099 | 4-Cl-3-F-2-Me—PhCH2— |
| 5100 | 4-Cl-2,5-di-F—PhCH2— |
| 5101 | 2,4-di-Cl-5-F—PhCH2— |
| 5102 | 2-Br-4-Cl-5-F—PhCH2— |
| 5103 | 4-Cl-5-F-2-I—PhCH2— |
| 5104 | 4-Cl-5-F-2-Me—PhCH2— |
| 5105 | 2,4-di-F-3-MeO—PhCH2— |
| 5106 | 2-Cl-4-F-3-MeO—PhCH2— |
| 5107 | 2-Br-4-F-3-MeO—PhCH2— |
| 5108 | 4-F-2-I-3-MeO—PhCH2— |
| 5109 | 4-F-2-Me-3-MeO—PhCH2— |
| 5110 | 2,4-F-5-MeO—PhCH2— |
| 5111 | 2-Cl-4-F-5-MeO—PhCH2— |
| 5112 | 2-Br-4-F-5-MeO—PhCH2— |
| 5113 | 4-F-2-I-5-MeO—PhCH2— |
| 5114 | 4-F-2-Me-5-MeO—PhCH2— |
| 5115 | 4-Cl-2-F-3-MeO—PhCH2— |
| 5116 | 2,4-di-Cl-3-MeO—PhCH2— |
| 5117 | 2-Br-4-Cl-3-MeO—PhCH2— |
| 5118 | 4-Cl-2-I-3-MeO—PhCH2— |
| 5119 | 4-Cl-2-Me-3-MeO—PhCH2— |
| 5120 | 4-Cl-2-F-5-MeO—PhCH2— |
| 5121 | 2,4-di-Cl-5-MeO—PhCH2— |
| 5122 | 2-Br-4-Cl-5-MeO—PhCH2— |
| 5123 | 4-Cl-2-I-5-MeO—PhCH2— |
| 5124 | 4-Cl-2-Me-5-MeO—PhCH2— |
| 5125 | 2,6-di-F-3,5-di-MeO—PhCH2— |
| 5126 | 2,6-di-Cl-3,5-di-MeO—PhCH2— |
| 5127 | 6-Cl-2-F-3,5-di-MeO—PhCH2— |
| 5128 | 6-Br-2-F-3,5-di-MeO—PhCH2— |
| 5129 | 2-Br-6-Cl-3,5-di-MeO—PhCH2— |
| 5130 | 2,3,4,5,-tetra-F—PhCH2— |
| 5131 | 2,3,5,6,-tetra-F—PhCH2— |
| 5132 | 2,3,4,5,6-penta-F—PhCH2— |
| 5133 | 2,3-di-F-5-MeS—PhCH2— |
| 5134 | 2-F-3-MeO-5-MeS—PhCH2— |
| 5135 | 2,5-di-F-3-MeS—PhCH2— |
| 5136 | 2-Cl-3-F-5-MeS—PhCH2— |
| 5137 | 2-Cl-5-F-3-MeS—PhCH2— |
| 5138 | 2-F-5-MeO-3-MeS—PhCH2— |
| 5139 | 2-Cl-5-MeO-3-MeS—PhCH2— |
| 5140 | 2-Br-3-F-5-MeS—PhCH2— |
| 5141 | 2-Cl-3-MeO-5-MeS—PhCH2— |
| 5142 | 2-Br-3-MeO-5-MeS—PhCH2— |
| 5143 | 2-Br-5-MeO-3-MeS—PhCH2— |
| 5144 | 2-Br-5-F-3-MeS—PhCH2— |
| 5145 | 2-I-5-F-3-MeS—PhCH2— |
| 5146 | 2-I-3-MeO-5-MeS—PhCH2— |
| 5147 | 2-I-3-F-5-MeS—PhCH2— |
| 5148 | 3-F-2-Me-5-MeS—PhCH2— |
| 5149 | 5-F-2-Me-3-MeS—PhCH2— |
| 5150 | 2-I-5-MeO-3-MeS—PhCH2— |
| 5151 | 2-Me-5-MeO-3-MeS—PhCH2— |
| 5152 | 2-F-3,5-di-MeS—PhCH2— |
| 5153 | 2-Me-3-MeO-5-MeS—PhCH2— |
| 5154 | 2-Br-3,5-di-MeS—PhCH2— |
| 5155 | 2-I-3,5-di-MeS—PhCH2— |
| 5156 | 2-Cl-3,5-di-MeS—PhCH2— |
| 5157 | 2,5-di-F-3-MeS(O)—PhCH2— |
| 5158 | 2,3-di-F-5-MeS(O)—PhCH2— |
| 5159 | 2-Me-3,5-di-MeS—PhCH2— |
| 5160 | 2-F-5-MeO-3-MeS(O)—PhCH2— |
| 5161 | 2-Cl-3-F-5-MeS(O)—PhCH2— |
| 5162 | 2-F-3-MeO-5-MeS(O)—PhCH2— |
| 5163 | 2-Cl-3-MeO-5-MeS(O)—PhCH2— |
| 5164 | 2-Cl-5-MeO-3-MeS(O)—PhCH2— |
| 5165 | 2-Cl-5-F-3-MeS(O)—PhCH2— |
| 5166 | 2-Br-5-F-3-MeS(O)—PhCH2— |
| 5167 | 2-Br-3-MeO-5-MeS(O)—PhCH2— |
| 5168 | 2-Br-3-F-5-MeS(O)—PhCH2— |
| 5169 | 2-I-3-F-5-MeS(O)—PhCH2— |
| 5170 | 5-F-2-I-3-MeS(O)—PhCH2— |
| 5171 | 2-Br-5-MeO-3-MeS(O)—PhCH2— |
| 5172 | 2-I-5-MeO-3-MeS(O)—PhCH2— |
| 5173 | 3-F-2-Me-5-MeS(O)—PhCH2— |
| 5174 | 2-I-3-MeO-5-MeS(O)—PhCH2— |
| 5175 | 2-Me-3-MeO-5-MeS(O)—PhCH2— |
| 5176 | 2-Me-5-MeO-3-MeS(O)—PhCH2— |
| 5177 | 5-F-2-Me-3-MeS(O)—PhCH2— |
| 5178 | 2-Cl-3,5-di-MeS(O)—PhCH2— |
| 5179 | 2-Br-3,5-di-MeS(O)—PhCH2— |
| 5180 | 2-F-3,5-di-MeS(O)—PhCH2— |
| 5181 | 2-Me-3,5-di-MeS(O)—PhCH2— |

TABLE 2-continued

| No. | Z |
|---|---|
| 5182 | 2,5-di-F-3-MeSO2—PhCH2— |
| 5183 | 2-I-3,5-di-MeS(O)—PhCH2— |
| 5184 | 2-F-3-MeO-5-MeSO2—PhCH2— |
| 5185 | 2-F-5-MeO-3-MeSO2—PhCH2— |
| 5186 | 2,3-di-F-5-MeSO2—PhCH2— |
| 5187 | 2-Cl-5-F-3-MeSO2—PhCH2— |
| 5188 | 2-Cl-3-MeO-5-MeSO2—PhCH2— |
| 5189 | 2-Cl-3-F-5-MeSO2—PhCH2— |
| 5190 | 2-Br-3-F-5-MeSO2—PhCH2— |
| 5191 | 2-Br-5-F-3-MeSO2—PhCH2— |
| 5192 | 2-Cl-5-MeO-3-MeSO2—PhCH2— |
| 5193 | 2-Br-5-MeO-3-MeSO2—PhCH2— |
| 5194 | 3-F-2-I-5-MeSO2—PhCH2— |
| 5195 | 2-Br-3-MeO-5-MeSO2—PhCH2— |
| 5196 | 2-I-MeO-5-MeSO2—PhCH2— |
| 5197 | 2-I-5-MeO-3-MeSO2—PhCH2— |
| 5198 | 5-F-2-I-3-MeSO2—PhCH2— |
| 5199 | 5-F-2-Me-3-MeSO2—PhCH2— |
| 5200 | 2-Me-3-MeO-5-MeSO2—PhCH2— |
| 5201 | 3-F-2-Me-5-MeSO2—PhCH2— |
| 5202 | 2-F-3,5-di-MeSO2—PhCH2— |
| 5203 | 2-Cl-3,5-di-MeSO2—PhCH2— |
| 5204 | 2-Me-5-MeO-3-MeSO—PhCH2— |
| 5205 | 2-I-3,5-di-MeSO2—PhCH2— |
| 5206 | 2-Me-3,5-di-MeSO2—PhCH2— |
| 5207 | 2-Br-3,5-di-MeSO2—PhCH2— |
| 5208 | 2,4,6-tri-F—PhCH2— |
| 5209 | Ph(Me)CH— |
| 5210 | 2-F—Ph(Me)CH— |
| 5211 | 3-F—Ph(Me)CH— |
| 5212 | 4-F—Ph(Me)CH— |
| 5213 | 2-Cl—Ph(Me)CH— |
| 5214 | 3-Cl—Ph(Me)CH— |
| 5215 | 4-Cl—Ph(Me)CH— |
| 5216 | 2-Br—Ph(Me)CH— |
| 5217 | 3-Br—Ph(Me)CH— |
| 5218 | 4-Br—Ph(Me)CH— |
| 5219 | 2-I—Ph(Me)CH— |
| 5220 | 3-I—Ph(Me)CH— |
| 5221 | 4-I—Ph(Me)CH— |
| 5222 | 2-HO—Ph(Me)CH— |
| 5223 | 3-HO—Ph(Me)CH— |
| 5224 | 4-HO—Ph(Me)CH— |
| 5225 | 2-N≡C—Ph(Me)CH— |
| 5226 | 3-N≡C—Ph(Me)CH— |
| 5227 | 4-N≡C—Ph(Me)CH— |
| 5228 | 2-O2N—Ph(Me)CH— |
| 5229 | 3-O2N—Ph(Me)CH— |
| 5230 | 4-O2N—Ph(Me)CH— |
| 5231 | 2-Me—Ph(Me)CH— |
| 5232 | 3-Me—Ph(Me)CH— |
| 5233 | 4-Me—Ph(Me)CH— |
| 5234 | 2-Et—Ph(Me)CH— |
| 5235 | 3-Et—Ph(Me)CH— |
| 5236 | 4-Et—Ph(Me)CH— |
| 5237 | 2-Pr—Ph(Me)CH— |
| 5238 | 3-Pr—Ph(Me)CH— |
| 5239 | 4-Pr—Ph(Me)CH— |
| 5240 | 2-iPr—Ph(Me)CH— |
| 5241 | 3-iPr—Ph(Me)CH— |
| 5242 | 4-iPr—Ph(Me)CH— |
| 5243 | 2-N≡CCH2—Ph(Me)CH— |
| 5244 | 3-N≡CCH2—Ph(Me)CH— |
| 5245 | 4-N≡CCH2—Ph(Me)CH— |
| 5246 | 2-N≡CCH2CH2—Ph(Me)CH— |
| 5247 | 3-N≡CCH2CH2—Ph(Me)CH— |
| 5248 | 4-N≡CCH2CH2—Ph(Me)CH— |
| 5249 | 2-cPrCH2—Ph(Me)CH— |
| 5250 | 3-cPrCH2—Ph(Me)CH— |
| 5251 | 4-cPrCH2—Ph(Me)CH— |
| 5252 | 2-cBuCH2—Ph(Me)CH— |
| 5253 | 3-cBuCH2—Ph(Me)CH— |
| 5254 | 4-cBuCH2—Ph(Me)CH— |
| 5255 | 2-MeOCH2—Ph(Me)CH— |
| 5256 | 3-MeOCH2—Ph(Me)CH— |
| 5257 | 4-MeOCH2—Ph(Me)CH— |
| 5258 | 2-MeOCH2CH2—Ph(Me)CH— |
| 5259 | 3-MeOCH2CH2—Ph(Me)CH— |
| 5260 | 4-MeOCH2CH2—Ph(Me)CH— |
| 5261 | 2-MeOCH2CH2CH2—Ph(Me)CH— |
| 5262 | 3-MeOCH2CH2CH2—Ph(Me)CH— |
| 5263 | 4-MeOCH2CH2CH2—Ph(Me)CH— |
| 5264 | 2-EtOCH2—Ph(Me)CH— |
| 5265 | 3-EtOCH2—Ph(Me)CH— |
| 5266 | 4-EtOCH2—Ph(Me)CH— |
| 5267 | 2-EtOCH2CH2—Ph(Me)CH— |
| 5268 | 3-EtOCH2CH2—Ph(Me)CH— |
| 5269 | 4-EtOCH2CH2—Ph(Me)CH— |
| 5270 | 2-cPrOCH2—Ph(Me)CH— |
| 5271 | 3-cPrOCH2—Ph(Me)CH— |
| 5272 | 4-cPrOCH2—Ph(Me)CH— |
| 5273 | 2-F3COCH2—Ph(Me)CH— |
| 5274 | 3-F3COCH2—Ph(Me)CH— |
| 5275 | 4-F3COCH2—Ph(Me)CH— |
| 5276 | 2-F2CHOCH2—Ph(Me)CH— |
| 5277 | 3-F2CHOCH2—Ph(Me)CH— |
| 5278 | 4-F2CHOCH2—Ph(Me)CH— |
| 5279 | 2-MeOCH2CH2OCH2—Ph(Me)CH— |
| 5280 | 3-MeOCH2CH2OCH2—Ph(Me)CH— |
| 5281 | 4-MeOCH2CH2OCH2—Ph(Me)CH— |
| 5282 | 2-Me2NCH2—Ph(Me)CH— |
| 5283 | 3-Me2NCH2—Ph(Me)CH— |
| 5284 | 4-Me2NCH2—Ph(Me)CH— |
| 5285 | 2-MeSCH2—Ph(Me)CH— |
| 5286 | 3-MeSCH2—Ph(Me)CH— |
| 5287 | 4-MeSCH2—Ph(Me)CH— |
| 5288 | 2-MeS(O)CH2—Ph(Me)CH— |
| 5289 | 3-MeS(O)CH2—Ph(Me)CH— |
| 5290 | 4-MeS(O)CH2—Ph(Me)CH— |
| 5291 | 2-MeSO2CH2—Ph(Me)CH— |
| 5292 | 3-MeSO2CH2—Ph(Me)CH— |
| 5293 | 4-MeSO2CH2—Ph(Me)CH— |
| 5294 | 2-cPr—Ph(Me)CH— |
| 5295 | 3-cPr—Ph(Me)CH— |
| 5296 | 4-cPr—Ph(Me)CH— |
| 5297 | 2-cBu—Ph(Me)CH— |
| 5298 | 3-cBu—Ph(Me)CH— |
| 5299 | 4-cBu—Ph(Me)CH— |
| 5300 | 2-F3C—Ph(Me)CH— |
| 5301 | 3-F3C—Ph(Me)CH— |
| 5302 | 4-F3C—Ph(Me)CH— |
| 5303 | 2-F2CH—Ph(Me)CH— |
| 5304 | 3-F2CH—Ph(Me)CH— |
| 5305 | 4-F2CH—Ph(Me)CH— |
| 5306 | 2-H2C=CH—Ph(Me)CH— |
| 5307 | 3-H2C=CH—Ph(Me)CH— |
| 5308 | 4-H2C=CH—Ph(Me)CH— |
| 5309 | 2-H2C=CHCH2—Ph(Me)CH— |
| 5310 | 3-H2C=CHCH2—Ph(Me)CH— |
| 5311 | 4-H2C=CHCH2—Ph(Me)CH— |
| 5312 | 2-F2C=CH—Ph(Me)CH— |
| 5313 | 3-F2C=CH—Ph(Me)CH— |
| 5314 | 4-F2C=CH—Ph(Me)CH— |
| 5315 | 2-F2C=CHCH2—Ph(Me)CH— |
| 5316 | 3-F2C=CHCH2—Ph(Me)CH— |
| 5317 | 4-F2C=CHCH2—Ph(Me)CH— |
| 5318 | 2-HC≡C—Ph(Me)CH— |
| 5319 | 3-HC≡C—Ph(Me)CH— |
| 5320 | 4-HC≡C—Ph(Me)CH— |
| 5321 | 2-HC≡CCH2—Ph(Me)CH— |
| 5322 | 3-HC≡CCH2—Ph(Me)CH— |
| 5323 | 4-HC≡CCH2—Ph(Me)CH— |
| 5324 | 2-F3CC≡C—Ph(Me)CH— |
| 5325 | 3-F3CC≡C—Ph(Me)CH— |
| 5326 | 4-F3CC≡C—Ph(Me)CH— |
| 5327 | 2-F3CC≡C—Ph(Me)CH— |
| 5328 | 3-F3CC≡C—Ph(Me)CH— |
| 5329 | 4-F3CC≡C—Ph(Me)CH— |
| 5330 | 2-MeO—Ph(Me)CH— |
| 5331 | 3-MeO—Ph(Me)CH— |
| 5332 | 4-MeO—Ph(Me)CH— |
| 5333 | 2-EtO—Ph(Me)CH— |
| 5334 | 3-EtO—Ph(Me)CH— |
| 5335 | 4-EtO—Ph(Me)CH— |
| 5336 | 2-PrO—Ph(Me)CH— |
| 5337 | 3-PrO—Ph(Me)CH— |

TABLE 2-continued

| No. | Z |
|---|---|
| 5338 | 4-PrO—Ph(Me)CH— |
| 5339 | 2-iPrO—Ph(Me)CH— |
| 5340 | 3-iPrO—Ph(Me)CH— |
| 5341 | 4-iPrO—Ph(Me)CH— |
| 5342 | 2-BuO—Ph(Me)CH— |
| 5343 | 3-BuO—Ph(Me)CH— |
| 5344 | 4-BuO—Ph(Me)CH— |
| 5345 | 2-iBuO—Ph(Me)CH— |
| 5346 | 3-iBuO—Ph(Me)CH— |
| 5347 | 4-iBuO—Ph(Me)CH— |
| 5348 | 2-PentylO—Ph(Me)CH— |
| 5349 | 3-PentylO—Ph(Me)CH— |
| 5350 | 4-PentylO—Ph(Me)CH— |
| 5351 | 2-N≡CCH2O—Ph(Me)CH— |
| 5352 | 3-N≡CCH2O—Ph(Me)CH— |
| 5353 | 4-N≡CCH2O—Ph(Me)CH— |
| 5354 | 2-N≡CCH2CH2O—Ph(Me)CH— |
| 5355 | 3-N≡CCH2CH2O—Ph(Me)CH— |
| 5356 | 4-N≡CCH2CH2O—Ph(Me)CH— |
| 5357 | 2-cPrCH2O—Ph(Me)CH— |
| 5358 | 3-cPrCH2O—Ph(Me)CH— |
| 5359 | 4-cPrCH2O—Ph(Me)CH— |
| 5360 | 2-cBuCH2O—Ph(Me)CH— |
| 5361 | 3-cBuCH2O—Ph(Me)CH— |
| 5362 | 4-cBuCH2O—Ph(Me)CH— |
| 5363 | 2-cPentylCH2O—Ph(Me)CH— |
| 5364 | 3-cPentylCH2O—Ph(Me)CH— |
| 5365 | 4-cPentylCH2O—Ph(Me)CH— |
| 5366 | 2-cHexylCH2O—Ph(Me)CH— |
| 5367 | 3-cHexylCH2O—Ph(Me)CH— |
| 5368 | 4-cHexylCH2O—Ph(Me)CH— |
| 5369 | 2-MeOCH2O—Ph(Me)CH— |
| 5370 | 3-MeOCH2O—Ph(Me)CH— |
| 5371 | 4-MeOCH2O—Ph(Me)CH— |
| 5372 | 2-EtOCH2O—Ph(Me)CH— |
| 5373 | 3-EtOCH2O—Ph(Me)CH— |
| 5374 | 4-EtOCH2O—Ph(Me)CH— |
| 5375 | 2-MeOCH2CH2O—Ph(Me)CH— |
| 5376 | 3-MeOCH2CH2O—Ph(Me)CH— |
| 5377 | 4-MeOCH2CH2O—Ph(Me)CH— |
| 5378 | 2-MeOCH2CH2CH2O—Ph(Me)CH— |
| 5379 | 3-MeOCH2CH2CH2O—Ph(Me)CH— |
| 5380 | 4-MeOCH2CH2CH2O—Ph(Me)CH— |
| 5381 | 2-MeOCH2CH2OCH2O—Ph(Me)CH— |
| 5382 | 3-MeOCH2CH2OCH2O—Ph(Me)CH— |
| 5383 | 4-MeOCH2CH2OCH2O—Ph(Me)CH— |
| 5384 | 2-MeSCH2O—Ph(Me)CH— |
| 5385 | 3-MeSCH2O—Ph(Me)CH— |
| 5386 | 4-MeSCH2O—Ph(Me)CH— |
| 5387 | 2-MeS(O)CH2O—Ph(Me)CH— |
| 5388 | 3-MeS(O)CH2O—Ph(Me)CH— |
| 5389 | 4-MeS(O)CH2O—Ph(Me)CH— |
| 5390 | 2-MeSO2CH2O—Ph(Me)CH— |
| 5391 | 3-MeSO2CH2O—Ph(Me)CH— |
| 5392 | 4-MeSO2CH2O—Ph(Me)CH— |
| 5393 | 2-AcCH2O—Ph(Me)CH— |
| 5394 | 3-AcCH2O—Ph(Me)CH— |
| 5395 | 4-AcCH2O—Ph(Me)CH— |
| 5396 | 2-MeOC(=O)CH2O—Ph(Me)CH— |
| 5397 | 3-MeOC(=O)CH2O—Ph(Me)CH— |
| 5398 | 4-MeOC(=O)CH2O—Ph(Me)CH— |
| 5399 | 2-EtOC(=O)CH2O—Ph(Me)CH— |
| 5400 | 3-EtOC(=O)CH2O—Ph(Me)CH— |
| 5401 | 4-EtOC(=O)CH2O—Ph(Me)CH— |
| 5402 | 2-(1,3-dioxolan-2-yl)CH2O—Ph(Me)CH— |
| 5403 | 3-(1,3-dioxolan-2-yl)CH2O—Ph(Me)CH— |
| 5404 | 4-(1,3-dioxolan-2-yl)CH2O—Ph(Me)CH— |
| 5405 | 2-(1,3-dioxolan-2-yl)CH2CH2O—Ph(Me)CH— |
| 5406 | 3-(1,3-dioxolan-2-yl)CH2CH2O—Ph(Me)CH— |
| 5407 | 4-(1,3-dioxolan-2-yl)CH2CH2O—Ph(Me)CH— |
| 5408 | 2-(1,3-dioxan-2-yl)CH2O—Ph(Me)CH— |
| 5409 | 3-(1,3-dioxan-2-yl)CH2O—Ph(Me)CH— |
| 5410 | 4-(1,3-dioxan-2-yl)CH2O—Ph(Me)CH— |
| 5411 | 2-(1,3-dioxan-2-yl)CH2CH2O—Ph(Me)CH— |
| 5412 | 3-(1,3-dioxan-2-yl)CH2CH2O—Ph(Me)CH— |
| 5413 | 4-(1,3-dioxan-2-yl)CH2CH2O—Ph(Me)CH— |
| 5414 | 2-cPrO—Ph(Me)CH— |
| 5415 | 3-cPrO—Ph(Me)CH— |
| 5416 | 4-cPrO—Ph(Me)CH— |
| 5417 | 2-cBuO—Ph(Me)CH— |
| 5418 | 3-cBuO—Ph(Me)CH— |
| 5419 | 4-cBuO—Ph(Me)CH— |
| 5420 | 2-cPentylO—Ph(Me)CH— |
| 5421 | 3-cPentylO—Ph(Me)CH— |
| 5422 | 4-cPentylO—Ph(Me)CH— |
| 5423 | 2-cHexylO—Ph(Me)CH— |
| 5424 | 3-cHexylO—Ph(Me)CH— |
| 5425 | 4-cHexylO—Ph(Me)CH— |
| 5426 | 2-F3CO—Ph(Me)CH— |
| 5427 | 3-F3CO—Ph(Me)CH— |
| 5428 | 4-F3CO—Ph(Me)CH— |
| 5429 | 2-F2CHO—Ph(Me)CH— |
| 5430 | 3-F2CHO—Ph(Me)CH— |
| 5431 | 4-F2CHO—Ph(Me)CH— |
| 5432 | 2-F3CCH2O—Ph(Me)CH— |
| 5433 | 3-F3CCH2O—Ph(Me)CH— |
| 5434 | 4-F3CCH2O—Ph(Me)CH— |
| 5435 | 2-F2CHCH2O—Ph(Me)CH— |
| 5436 | 3-F2CHCH2O—Ph(Me)CH— |
| 5437 | 4-F2CHCH2O—Ph(Me)CH— |
| 5438 | 2-H2C=CHCH2O—Ph(Me)CH— |
| 5439 | 3-H2C=CHCH2O—Ph(Me)CH— |
| 5440 | 4-H2C=CHCH2O—Ph(Me)CH— |
| 5411 | 2-HC≡CCH2O—Ph(Me)CH— |
| 5442 | 3-HC≡CCH2O—Ph(Me)CH— |
| 5443 | 4-HC≡CCH2O—Ph(Me)CH— |
| 5444 | 2-AcPh(Me)CH— |
| 5445 | 3-AcPh(Me)CH— |
| 5446 | 4-AcPh(Me)CH— |
| 5447 | 2-MeOC(=O)—Ph(Me)CH— |
| 5448 | 3-MeOC(=O)—Ph(Me)CH— |
| 5449 | 4-MeOC(=O)—Ph(Me)CH— |
| 5450 | 2-EtOC(=O)—Ph(Me)CH— |
| 5451 | 3-EtOC(=O)—Ph(Me)CH— |
| 5452 | 4-EtOC(=O)—Ph(Me)CH— |
| 5453 | 2-AcO—Ph(Me)CH— |
| 5454 | 3-AcO—Ph(Me)CH— |
| 5455 | 4-AcO—Ph(Me)CH— |
| 5456 | 3-MeOC(=O)O—Ph(Me)CH— |
| 5457 | 2-MeOC(=O)O—Ph(Me)CH— |
| 5458 | 4-MeOC(=O)O—Ph(Me)CH— |
| 5459 | 2-EtOC(=O)O—Ph(Me)CH— |
| 5460 | 3-EtOC(=O)O—Ph(Me)CH— |
| 5461 | 4-EtOC(=O)O—Ph(Me)CH— |
| 5462 | 2-(1,3-dioxolan-2-yl)-Ph(Me)CH— |
| 5463 | 3-(1,3-dioxolan-2-yl)-Ph(Me)CH— |
| 5464 | 4-(1,3-dioxolan-2-yl)-Ph(Me)CH— |
| 5465 | 2-(1,3-dioxan-2-yl)-Ph(Me)CH— |
| 5466 | 3-(1,3-dioxan-2-yl)-Ph(Me)CH— |
| 5467 | 4-(1,3-dioxan-2-yl)-Ph(Me)CH— |
| 5468 | 2-MeS—Ph(Me)CH— |
| 5469 | 3-MeS—Ph(Me)CH— |
| 5470 | 4-MeS—Ph(Me)CH— |
| 5471 | 2-MeS(O)—Ph(Me)CH— |
| 5472 | 3-MeS(O)—Ph(Me)CH— |
| 5473 | 4-MeS(O)—Ph(Me)CH— |
| 5474 | 2-MeSO2—Ph(Me)CH— |
| 5475 | 3-MeSO2—Ph(Me)CH— |
| 5476 | 4-MeSO2—Ph(Me)CH— |
| 5477 | 2-ClCH2S—Ph(Me)CH— |
| 5478 | 3-ClCH2S—Ph(Me)CH— |
| 5479 | 4-ClCH2S—Ph(Me)CH— |
| 5480 | 2-ClCH2S(O)—Ph(Me)CH— |
| 5481 | 3-ClCH2S(O)—Ph(Me)CH— |
| 5482 | 4-ClCH2S(O)—Ph(Me)CH— |
| 5483 | 2-ClCH2SO2—Ph(Me)CH— |
| 5484 | 3-ClCH2SO2—Ph(Me)CH— |
| 5485 | 4-ClCH2SO2—Ph(Me)CH— |
| 5486 | 2-F-3-HO—Ph(Me)CH— |
| 5487 | 2-F-4-HO—Ph(Me)CH— |
| 5488 | 2-F-5-HO—Ph(Me)CH— |
| 5489 | 2-F-6-HO—Ph(Me)CH— |
| 5490 | 2-Cl-3-HO—Ph(Me)CH— |
| 5491 | 2-Cl-4-HO—Ph(Me)CH— |
| 5492 | 2-Cl-5-HO—Ph(Me)CH— |
| 5493 | 2-Cl-6-HO—Ph(Me)CH— |

TABLE 2-continued

| No. | Z |
|---|---|
| 5494 | 2-Br-3-HO—Ph(Me)CH— |
| 5495 | 2-Br-4-HO—Ph(Me)CH— |
| 5496 | 2-Br-5-HO—Ph(Me)CH— |
| 5497 | 2-Br-6-HO—Ph(Me)CH— |
| 5498 | 2-I-3-HO—Ph(Me)CH— |
| 5499 | 2-I-4-HO—Ph(Me)CH— |
| 5500 | 2-I-5-HO—Ph(Me)CH— |
| 5501 | 2-I-6-HO—Ph(Me)CH— |
| 5502 | 2-Me-3-HO—Ph(Me)CH— |
| 5503 | 2-Me-4-HO—Ph(Me)CH— |
| 5504 | 2-Me-5-HO—Ph(Me)CH— |
| 5505 | 2-Me-6-HO—Ph(Me)CH— |
| 5506 | 2,3-di-F—Ph(Me)CH— |
| 5507 | 2,4-di-F—Ph(Me)CH— |
| 5508 | 2,5-di-F—Ph(Me)CH— |
| 5509 | 2,6-di-F—Ph(Me)CH— |
| 5510 | 2-Cl-3-F—Ph(Me)CH— |
| 5511 | 2-Cl-4-F—Ph(Me)CH— |
| 5512 | 2-Cl-5-F—Ph(Me)CH— |
| 5513 | 2-Cl-6-F—Ph(Me)CH— |
| 5514 | 2-Br-3-F—Ph(Me)CH— |
| 5515 | 2-Br-4-F—Ph(Me)CH— |
| 5516 | 2-Br-5-F—Ph(Me)CH— |
| 5517 | 2-Br-6-F—Ph(Me)CH— |
| 5518 | 3-F-2-I—Ph(Me)CH— |
| 5519 | 4-F-2-I—Ph(Me)CH— |
| 5520 | 5-F-2-I—Ph(Me)CH— |
| 5521 | 6-F-2-I—Ph(Me)CH— |
| 5522 | 3-F-2-Me—Ph(Me)CH— |
| 5523 | 4-F-2-Me—Ph(Me)CH— |
| 5524 | 5-F-2-Me—Ph(Me)CH— |
| 5525 | 6-F-2-Me—Ph(Me)CH— |
| 5526 | 3-Cl-2-F—Ph(Me)CH— |
| 5527 | 4-Cl-2-F—Ph(Me)CH— |
| 5528 | 5-Cl-2-F—Ph(Me)CH— |
| 5529 | 6-Cl-2-F—Ph(Me)CH— |
| 5530 | 2,3-di-Cl—Ph(Me)CH— |
| 5531 | 2,4-di-Cl—Ph(Me)CH— |
| 5532 | 2,5-di-Cl—Ph(Me)CH— |
| 5533 | 2,6-di-Cl—Ph(Me)CH— |
| 5534 | 2-Br-3-Cl—Ph(Me)CH— |
| 5535 | 2-Br-4-Cl—Ph(Me)CH— |
| 5536 | 2-Br-5-Cl—Ph(Me)CH— |
| 5537 | 2-Br-6-Cl—Ph(Me)CH— |
| 5538 | 3-Cl-2-I—Ph(Me)CH— |
| 5539 | 4-Cl-2-I—Ph(Me)CH— |
| 5540 | 5-Cl-2-I—Ph(Me)CH— |
| 5541 | 6-Cl-2-1—Ph(Me)CH— |
| 5542 | 3-Cl-2-Me—Ph(Me)CH— |
| 5543 | 4-Cl-2-Me—Ph(Me)CH— |
| 55/11 | 5-Cl-2-Me—Ph(Me)CH— |
| 5545 | 6-Cl-2-Me—Ph(Me)CH— |
| 5546 | 3-Br-2-F—Ph(Me)CH— |
| 5547 | 4-Br-2-F—Ph(Me)CH— |
| 5548 | 5-Br-2-F—Ph(Me)CH— |
| 5549 | 6-Br-2-F—Ph(Me)CH— |
| 5550 | 3-Br-2-Cl—Ph(Me)CH— |
| 5551 | 4-Br-2-Cl—Ph(Me)CH— |
| 5552 | 5-Br-2-Cl—Ph(Me)CH— |
| 5553 | 6-Br-2-Cl—Ph(Me)CH— |
| 5554 | 2,3-di-Br—Ph(Me)CH— |
| 5555 | 2,4-di-Br—Ph(Me)CH— |
| 5556 | 2,5-di-Br—Ph(Me)CH— |
| 5557 | 2,6-di-Br—Ph(Me)CH— |
| 5558 | 3-Br-2-I—Ph(Me)CH— |
| 5559 | 4-Br-2-I—Ph(Me)CH— |
| 5560 | 5-Br-2-I—Ph(Me)CH— |
| 5561 | 6-Br-2-I—Ph(Me)CH— |
| 5562 | 3-Br-2-Me—Ph(Me)CH— |
| 5563 | 4-Br-2-Me—Ph(Me)CH— |
| 5564 | 5-Br-2-Me—Ph(Me)CH— |
| 5565 | 6-Br-2-Me—Ph(Me)CH— |
| 5566 | 2-F-3-I—Ph(Me)CH— |
| 5567 | 2-F-4-I—Ph(Me)CH— |
| 5568 | 2-F-5-I—Ph(Me)CH— |
| 5569 | 2-F-6-I—Ph(Me)CH— |
| 5570 | 2-Cl-3-I—Ph(Me)CH— |
| 5571 | 2-Cl-4-I—Ph(Me)CH— |
| 5572 | 2-Cl-5-I—Ph(Me)CH— |
| 5573 | 2-Cl-6-I—Ph(Me)CH— |
| 5574 | 2-Br-3-I—Ph(Me)CH— |
| 5575 | 2-Br-4-I—Ph(Me)CH— |
| 5576 | 2-Br-5-I—Ph(Me)CH— |
| 5577 | 2-Br-6-I—Ph(Me)CH— |
| 5578 | 2,3-di-I—Ph(Me)CH— |
| 5579 | 2,4-di-I—Ph(Me)CH— |
| 5580 | 2,5-di-I—Ph(Me)CH— |
| 5581 | 2,6-di-I—Ph(Me)CH— |
| 5582 | 2-Me-3-I—Ph(Me)CH— |
| 5583 | 2-Me-4-I—Ph(Me)CH— |
| 5584 | 2-Me-5-I—Ph(Me)CH— |
| 5585 | 2-Me-6-I—Ph(Me)CH— |
| 5586 | 2-F-3-N≡C—Ph(Me)CH— |
| 5587 | 2-F-4-N≡C—Ph(Me)CH— |
| 5588 | 2-F-5-N≡C—Ph(Me)CH— |
| 5589 | 2-F-6-N≡C—Ph(Me)CH— |
| 5590 | 2-Cl-3-N≡C—Ph(Me)CH— |
| 5591 | 2-Cl-4-N≡C—Ph(Me)CH— |
| 5592 | 2-Cl-5-N≡C—Ph(Me)CH— |
| 5593 | 2-Cl-6-N≡C—Ph(Me)CH— |
| 5594 | 2-Br-3-N≡C—Ph(Me)CH— |
| 5595 | 2-Br-4-N≡C—Ph(Me)CH— |
| 5596 | 2-Br-5-N≡C—Ph(Me)CH— |
| 5597 | 2-Br-6-N≡C—Ph(Me)CH— |
| 5598 | 2-I-3-N≡C—Ph(Me)CH— |
| 5599 | 2-I-4-N≡C—Ph(Me)CH— |
| 5600 | 2-I-5-N≡C—Ph(Me)CH— |
| 5601 | 2-I-6-N≡C—Ph(Me)CH— |
| 5602 | 2-Me-3-N≡C—Ph(Me)CH— |
| 5603 | 2-Me-4-N≡C—Ph(Me)CH— |
| 5604 | 2-Me-5-N≡C—Ph(Me)CH— |
| 5605 | 2-Me-6-N≡C—Ph(Me)CH— |
| 5606 | 2-F-3-O2N—Ph(Me)CH— |
| 5607 | 2-F-4-O2N—Ph(Me)CH— |
| 5608 | 2-F-5-O2N—Ph(Me)CH— |
| 5609 | 2-F-6-O2N—Ph(Me)CH— |
| 5610 | 2-Cl-3-O2N—Ph(Me)CH— |
| 5611 | 2-Cl-4-O2N—Ph(Me)CH— |
| 5612 | 2-Cl-5-O2N—Ph(Me)CH— |
| 5613 | 2-Cl-6-O2N—Ph(Me)CH— |
| 5614 | 2-Br-3-O2N—Ph(Me)CH— |
| 5615 | 2-Br-4-O2N—Ph(Me)CH— |
| 5616 | 2-Br-5-O2N—Ph(Me)CH— |
| 5617 | 2-Br-6-O2N—Ph(Me)CH— |
| 5618 | 2-I-3-O2N—Ph(Me)CH— |
| 5619 | 2-I-4-O2N—Ph(Me)CH— |
| 5620 | 2-I-5-O2N—Ph(Me)CH— |
| 5621 | 2-I-6-O2N—Ph(Me)CH— |
| 5622 | 2-Me-3-O2N—Ph(Me)CH— |
| 5623 | 2-Me-4-O2N—Ph(Me)CH— |
| 5624 | 2-Me-5-O2N—Ph(Me)CH— |
| 5625 | 2-Me-6-O2N—Ph(Me)CH— |
| 5626 | 2-F-3-Me—Ph(Me)CH— |
| 5627 | 2-F-4-Me—Ph(Me)CH— |
| 5628 | 2-F-5-Me—Ph(Me)CH— |
| 5629 | 2-F-6-Me—Ph(Me)CH— |
| 5630 | 2-Cl-3-Me—Ph(Me)CH— |
| 5631 | 2-Cl-4-Me—Ph(Me)CH— |
| 5632 | 2-Cl-5-Me—Ph(Me)CH— |
| 5633 | 2-Cl-6-Me—Ph(Me)CH— |
| 5634 | 2-Br-3-Me—Ph(Me)CH— |
| 5635 | 2-Br-4-Me—Ph(Me)CH— |
| 5636 | 2-Br-5-Me—Ph(Me)CH— |
| 5637 | 2-Br-6-Me—Ph(Me)CH— |
| 5638 | 2-I-3-Me—Ph(Me)CH— |
| 5639 | 2-I-4-Me—Ph(Me)CH— |
| 5640 | 2-I-5-Me—Ph(Me)CH— |
| 5641 | 2-I-6-Me—Ph(Me)CH— |
| 5642 | 2,3-di-Me—Ph(Me)CH— |
| 5643 | 2,4-di-Me—Ph(Me)CH— |
| 5644 | 2,5-di-Me—Ph(Me)CH— |
| 5645 | 2,6-di-Me—Ph(Me)CH— |
| 5646 | 2-F-3-Et—Ph(Me)CH— |
| 5647 | 2-F-4-Et—Ph(Me)CH— |
| 5648 | 2-F-5-Et—Ph(Me)CH— |
| 5649 | 2-F-6-Et—Ph(Me)CH— |

TABLE 2-continued

| No. | Z |
|---|---|
| 5650 | 2-Cl-3-Et—Ph(Me)CH— |
| 5651 | 2-Cl-4-Et—Ph(Me)CH— |
| 5652 | 2-Cl-5-Et—Ph(Me)CH— |
| 5653 | 2-Cl-6-Et—Ph(Me)CH— |
| 5654 | 2-Br-3-Et—Ph(Me)CH— |
| 5655 | 2-Br-4-Et—Ph(Me)CH— |
| 5656 | 2-Br-5-Et—Ph(Me)CH— |
| 5657 | 2-Br-6-Et—Ph(Me)CH— |
| 5658 | 2-I-3-Et—Ph(Me)CH— |
| 5659 | 2-I-4-Et—Ph(Me)CH— |
| 5660 | 2-I-5-Et—Ph(Me)CH— |
| 5661 | 2-I-6-Et—Ph(Me)CH— |
| 5662 | 2-Me-3-Et—Ph(Me)CH— |
| 5663 | 2-Me-4-Et—Ph(Me)CH— |
| 5664 | 2-Me-5-Et—Ph(Me)CH— |
| 5665 | 2-Me-6-Et—Ph(Me)CH— |
| 5666 | 2-F-3-Pr—Ph(Me)CH— |
| 5667 | 2-F-4-Pr—Ph(Me)CH— |
| 5668 | 2-F-5-Pr—Ph(Me)CH— |
| 5669 | 2-F-6-Pr—Ph(Me)CH— |
| 5670 | 2-Cl-3-Pr—Ph(Me)CH— |
| 5671 | 2-Cl-4-Pr—Ph(Me)CH— |
| 5672 | 2-Cl-5-Pr—Ph(Me)CH— |
| 5673 | 2-Cl-6-Pr—Ph(Me)CH— |
| 5674 | 2-Br-3-Pr—Ph(Me)CH— |
| 5675 | 2-Br-4-Pr—Ph(Me)CH— |
| 5676 | 2-Br-5-Pr—Ph(Me)CH— |
| 5677 | 2-Br-6-Pr—Ph(Me)CH— |
| 5678 | 2-I-3-Pr—Ph(Me)CH— |
| 5679 | 2-I-4-Pr—Ph(Me)CH— |
| 5680 | 2-I-5-Pr—Ph(Me)CH— |
| 5681 | 2-I-6-Pr—Ph(Me)CH— |
| 5682 | 2-Me-3-Pr—Ph(Me)CH— |
| 5683 | 2-Me-4-Pr—Ph(Me)CH— |
| 5684 | 2-Me-5-Pr—Ph(Me)CH— |
| 5685 | 2-Me-6-Pr—Ph(Me)CH— |
| 5686 | 2-F-3-iPr—Ph(Me)CH— |
| 5687 | 2-F-4-iPr—Ph(Me)CH— |
| 5688 | 2-F-5-iPr—Ph(Me)CH— |
| 5689 | 2-F-6-iPr—Ph(Me)CH— |
| 5690 | 2-Cl-3-iPr—Ph(Me)CH— |
| 5691 | 2-Cl-4-iPr—Ph(Me)CH— |
| 5692 | 2-Cl-5-iPr—Ph(Me)CH— |
| 5693 | 2-Cl-6-iPr—Ph(Me)CH— |
| 5694 | 2-Br-3-iPr—Ph(Me)CH— |
| 5695 | 2-Br-4-iPr—Ph(Me)CH— |
| 5696 | 2-Br-5-iPr—Ph(Me)CH— |
| 5697 | 2-Br-6-iPr—Ph(Me)CH— |
| 5698 | 2-I-3-iPr—Ph(Me)CH— |
| 5699 | 2-I-4-iPr—Ph(Me)CH— |
| 5700 | 2-I-5-iPr—Ph(Me)CH— |
| 5701 | 2-I-6-iPr—Ph(Me)CH— |
| 5702 | 2-Me-3-iPr—Ph(Me)CH— |
| 5703 | 2-Me-4-iPr—Ph(Me)CH— |
| 5704 | 2-Me-5-iPr—Ph(Me)CH— |
| 5705 | 2-Me-6-iPr—Ph(Me)CH— |
| 5706 | 2-F-3-N≡CCH2—Ph(Me)CH— |
| 5707 | 2-F-4-N≡CCH2—Ph(Me)CH— |
| 5708 | 2-F-5-N≡CCH2—Ph(Me)CH— |
| 5709 | 2-F-6-N≡CCH2—Ph(Me)CH— |
| 5710 | 2-Cl-3-N≡CCH2—Ph(Me)CH— |
| 5711 | 2-Cl-4-N≡CCH2—Ph(Me)CH— |
| 5712 | 2-Cl-5-N≡CCH2—Ph(Me)CH— |
| 5713 | 2-Cl-6-N≡CCH2—Ph(Me)CH— |
| 5714 | 2-Br-3-N≡CCH2—Ph(Me)CH— |
| 5715 | 2-Br-4-N≡CCH2—Ph(Me)CH— |
| 5716 | 2-Br-5-N≡CCH2—Ph(Me)CH— |
| 5717 | 2-Br-6-N≡CCH2—Ph(Me)CH— |
| 5718 | 2-I-3-N≡CCH2—Ph(Me)CH— |
| 5719 | 2-I-4-N≡CCH2—Ph(Me)CH— |
| 5720 | 2-I-5-N≡CCH2—Ph(Me)CH— |
| 5721 | 2-I-6-N≡CCH2—Ph(Me)CH— |
| 5722 | 2-Me-3-N≡CCH2—Ph(Me)CH— |
| 5723 | 2-Me-4-N≡CCH2—Ph(Me)CH— |
| 5724 | 2-Me-5-N≡CCH2—Ph(Me)CH— |
| 5725 | 2-Me-6-N≡CCH2—Ph(Me)CH— |
| 5726 | 2-F-3-N≡CCH2CH2—Ph(Me)CH— |
| 5727 | 2-F-4-N≡CCH2CH2—Ph(Me)CH— |
| 5728 | 2-F-5-N≡CCH2CH2—Ph(Me)CH— |
| 5729 | 2-F-6-N≡CCH2CH2—Ph(Me)CH— |
| 5730 | 2-Cl-3-N≡CCH2CH2—Ph(Me)CH— |
| 5731 | 2-Cl-4-N≡CCH2CH2—Ph(Me)CH— |
| 5732 | 2-Cl-5-N≡CCH2CH2—Ph(Me)CH— |
| 5733 | 2-Cl-6-N≡CCH2CH2—Ph(Me)CH— |
| 5734 | 2-Br-3-N≡CCH2CH2—Ph(Me)CH— |
| 5735 | 2-Br-4-N≡CCH2CH2—Ph(Me)CH— |
| 5736 | 2-Br-5-N≡CCH2CH2—Ph(Me)CH— |
| 5737 | 2-Br-6-N≡CCH2CH2—Ph(Me)CH— |
| 5738 | 2-I-3-N≡CCH2CH2—Ph(Me)CH— |
| 5739 | 2-I-4-N≡CCH2CH2—Ph(Me)CH— |
| 5740 | 2-I-5-N≡CCH2CH2—Ph(Me)CH— |
| 5741 | 2-I-6-N≡CCH2CH2—Ph(Me)CH— |
| 5742 | 2-Me-3-N≡CCH2CH2—Ph(Me)CH— |
| 5743 | 2-Me-4-N≡CCH2CH2—Ph(Me)CH— |
| 5744 | 2-Me-5-N≡CCH2CH2—Ph(Me)CH— |
| 5745 | 2-Me-6-N≡CCH2CH2—Ph(Me)CH— |
| 5746 | 2-F-3-cPrCH2—Ph(Me)CH— |
| 5747 | 2-F-4-cPrCH2—Ph(Me)CH— |
| 5748 | 2-F-5-cPrCH2—Ph(Me)CH— |
| 5749 | 2-F-6-cPrCH2—Ph(Me)CH— |
| 5750 | 2-Cl-3-cPrCH2—Ph(Me)CH— |
| 5751 | 2-Cl-4-cPrCH2—Ph(Me)CH— |
| 5752 | 2-Cl-5-cPrCH2—Ph(Me)CH— |
| 5753 | 2-Cl-6-cPrCH2—Ph(Me)CH— |
| 5754 | 2-Br-3-cPrCH2—Ph(Me)CH— |
| 5755 | 2-Br-4-cPrCH2—Ph(Me)CH— |
| 5756 | 2-Br-5-cPrCH2—Ph(Me)CH— |
| 5757 | 2-Br-6-cPrCH2—Ph(Me)CH— |
| 5758 | 2-Br-3-cPrCH2—Ph(Me)CH— |
| 5759 | 2-I-4-cPrCH2—Ph(Me)CH— |
| 5760 | 2-I-5-cPrCH2—Ph(Me)CH— |
| 5761 | 2-I-6-cPrCH2—Ph(Me)CH— |
| 5762 | 2-Me-3-cPrCH2—Ph(Me)CH— |
| 5763 | 2-Me-4-cPrCH2—Ph(Me)CH— |
| 5764 | 2-Me-5-cPrCH2—Ph(Me)CH— |
| 5765 | 2-Me-6-cPrCH2—Ph(Me)CH— |
| 5766 | 2-F-3-cBuCH2—Ph(Me)CH— |
| 5767 | 2-F-4-cBuCH2—Ph(Me)CH— |
| 5768 | 2-F-5-cBuCH2—Ph(Me)CH— |
| 5769 | 2-F-6-cBuCH2—Ph(Me)CH— |
| 5770 | 2-Cl-3-cBuCH2—Ph(Me)CH— |
| 5771 | 2-Cl-4-cBuCH2—Ph(Me)CH— |
| 5772 | 2-Cl-5-cBuCH2—Ph(Me)CH— |
| 5773 | 2-Cl-6-cBuCH2—Ph(Me)CH— |
| 5774 | 2-Br-3-cBuCH2—Ph(Me)CH— |
| 5775 | 2-Br-4-cBuCH2—Ph(Me)CH— |
| 5776 | 2-Br-5-cBuCH2—Ph(Me)CH— |
| 5777 | 2-Br-6-cBuCH2—Ph(Me)CH— |
| 5778 | 2-I-3-cBuCH2—Ph(Me)CH— |
| 5779 | 2-I-4-cBuCH2—Ph(Me)CH— |
| 5780 | 2-I-5-cBuCH2—Ph(Me)CH— |
| 5781 | 2-I-6-cBuCH2—Ph(Me)CH— |
| 5782 | 2-Me-3-cBuCH2—Ph(Me)CH— |
| 5783 | 2-Me-4-cBuCH2—Ph(Me)CH— |
| 5784 | 2-Me-5-cBuCH2—Ph(Me)CH— |
| 5785 | 2-Me-6-cBuCH2—Ph(Me)CH— |
| 5786 | 2-F-3-MeOCH2—Ph(Me)CH— |
| 5787 | 2-F-4-MeOCH2—Ph(Me)CH— |
| 5788 | 2-F-5-MeOCH2—Ph(Me)CH— |
| 5789 | 2-F-6-MeOCH2—Ph(Me)CH— |
| 5790 | 2-Cl-3-MeOCH2—Ph(Me)CH— |
| 5791 | 2-Cl-4-MeOCH2—Ph(Me)CH— |
| 5792 | 2-Cl-5-MeOCH2—Ph(Me)CH— |
| 5793 | 2-Cl-6-MeOCH2—Ph(Me)CH— |
| 5794 | 2-Br-3-MeOCH2—Ph(Me)CH— |
| 5795 | 2-Br-4-MeOCH2—Ph(Me)CH— |
| 5796 | 2-Br-5-MeOCH2—Ph(Me)CH— |
| 5797 | 2-Br-6-MeOCH2—Ph(Me)CH— |
| 5798 | 2-I-3-MeOCH2—Ph(Me)CH— |
| 5799 | 2-I-4-MeOCH2—Ph(Me)CH— |
| 5800 | 2-I-5-MeOCH2—Ph(Me)CH— |
| 5801 | 2-I-6-MeOCH2—Ph(Me)CH— |
| 5802 | 2-Me-3-MeOCH2—Ph(Me)CH— |
| 5803 | 2-Me-4-MeOCH2—Ph(Me)CH— |
| 5804 | 2-Me-5-MeOCH2—Ph(Me)CH— |
| 5805 | 2-Me-6-MeOCH2—Ph(Me)CH— |

TABLE 2-continued

| No. | Z |
|---|---|
| 5806 | 2-F-3-MeOCH2CH2—Ph(Me)CH— |
| 5807 | 2-F-4-MeOCH2CH2—Ph(Me)CH— |
| 5808 | 2-F-5-MeOCH2CH2—Ph(Me)CH— |
| 5809 | 2-F-6-MeOCH2CH2—Ph(Me)CH— |
| 5810 | 2-Cl-3-MeOCH2CH2—Ph(Me)CH— |
| 5811 | 2-Cl-4-MeOCH2CH2—Ph(Me)CH— |
| 5812 | 2-Cl-5-MeOCH2CH2—Ph(Me)CH— |
| 5813 | 2-Cl-6-MeOCH2CH2—Ph(Me)CH— |
| 5814 | 2-Br-3-MeOCH2CH2—Ph(Me)CH— |
| 5815 | 2-Br-4-MeOCH2CH2—Ph(Me)CH— |
| 5816 | 2-Br-5-MeOCH2CH2—Ph(Me)CH— |
| 5817 | 2-Br-6-MeOCH2CH2—Ph(Me)CH— |
| 5818 | 2-I-3-MeOCH2CH2—Ph(Me)CH— |
| 5819 | 2-I-4-MeOCH2CH2—Ph(Me)CH— |
| 5820 | 2-I-5-MeOCH2CH2—Ph(Me)CH— |
| 5821 | 2-I-6-MeOCH2CH2—Ph(Me)CH— |
| 5822 | 2-Me-3-MeOCH2CH2—Ph(Me)CH— |
| 5823 | 2-Me-4-MeOCH2CH2—Ph(Me)CH— |
| 5824 | 2-Me-5-MeOCH2CH2—Ph(Me)CH— |
| 5825 | 2-Me-6-MeOCH2CH2—Ph(Me)CH— |
| 5826 | 2-F-3-MeOCH2CH2CH2—Ph(Me)CH— |
| 5827 | 2-F-4-MeOCH2CH2CH2—Ph(Me)CH— |
| 5828 | 2-F-5-MeOCH2CH2CH2—Ph(Me)CH— |
| 5829 | 2-F-6-MeOCH2CH2CH2—Ph(Me)CH— |
| 5830 | 2-Cl-3-MeOCH2CH2CH2—Ph(Me)CH— |
| 5831 | 2-Cl-4-MeOCH2CH2CH2—Ph(Me)CH— |
| 5832 | 2-Cl-5-MeOCH2CH2CH2—Ph(Me)CH— |
| 5833 | 2-Cl-6-MeOCH2CH2CH2—Ph(Me)CH— |
| 5834 | 2-Br-3-MeOCH2CH2CH2—Ph(Me)CH— |
| 5835 | 2-Br-4-MeOCH2CH2CH2—Ph(Me)CH— |
| 5836 | 2-Br-5-MeOCH2CH2CH2—Ph(Me)CH— |
| 5837 | 2-Br-6-MeOCH2CH2CH2—Ph(Me)CH— |
| 5838 | 2-I-3-MeOCH2CH2CH2—Ph(Me)CH— |
| 5839 | 2-I-4-MeOCH2CH2CH2—Ph(Me)CH— |
| 5840 | 2-I-5-MeOCH2CH2CH2—Ph(Me)CH— |
| 5841 | 2-I-6-MeOCH2CH2CH2—Ph(Me)CH— |
| 5842 | 2-Me-3-MeOCH2CH2CH2—Ph(Me)CH— |
| 5843 | 2-Me-4-MeOCH2CH2CH2—Ph(Me)CH— |
| 5844 | 2-Me-5-MeOCH2CH2CH2—Ph(Me)CH— |
| 5845 | 2-Me-6-MeOCH2CH2CH2—Ph(Me)CH— |
| 5846 | 2-F-3-EtOCH2—Ph(Me)CH— |
| 5847 | 2-F-4-EtOCH2—Ph(Me)CH— |
| 5848 | 2-F-5-EtOCH2—Ph(Me)CH— |
| 5849 | 2-F-6-EtOCH2—Ph(Me)CH— |
| 5850 | 2-Cl-3-EtOCH2—Ph(Me)CH— |
| 5851 | 2-Cl-4-EtOCH2—Ph(Me)CH— |
| 5852 | 2-Cl-5-EtOCH2—Ph(Me)CH— |
| 5853 | 2-Cl-6-EtOCH2—Ph(Me)CH— |
| 5854 | 2-Br-3-EtOCH2—Ph(Me)CH— |
| 5855 | 2-Br-4-EtOCH2—Ph(Me)CH— |
| 5856 | 2-Br-5-EtOCH2—Ph(Me)CH— |
| 5857 | 2-Br-6-EtOCH2—Ph(Me)CH— |
| 5858 | 2-I-3-EtOCH2—Ph(Me)CH— |
| 5859 | 2-I-4-EtOCH2—Ph(Me)CH— |
| 5860 | 2-I-5-EtOCH2—Ph(Me)CH— |
| 5861 | 2-I-6-EtOCH2—Ph(Me)CH— |
| 5862 | 2-Me-3-EtOCH2—Ph(Me)CH— |
| 5863 | 2-Me-4-EtOCH2—Ph(Me)CH— |
| 5864 | 2-Me-5-EtOCH2—Ph(Me)CH— |
| 5865 | 2-Me-6-EtOCH2—Ph(Me)CH— |
| 5866 | 2-F-3-EtOCH2CH2—Ph(Me)CH— |
| 5867 | 2-F-4-EtOCH2CH2—Ph(Me)CH— |
| 5868 | 2-F-5-EtOCH2CH2—Ph(Me)CH— |
| 5869 | 2-F-6-EtOCH2CH2—Ph(Me)CH— |
| 5870 | 2-Cl-3-EtOCH2CH2—Ph(Me)CH— |
| 5871 | 2-Cl-4-EtOCH2CH2—Ph(Me)CH— |
| 5872 | 2-Cl-5-EtOCH2CH2—Ph(Me)CH— |
| 5873 | 2-Cl-6-EtOCH2CH2—Ph(Me)CH— |
| 5874 | 2-Br-3-EtOCH2CH2—Ph(Me)CH— |
| 5875 | 2-Br-4-EtOCH2CH2—Ph(Me)CH— |
| 5876 | 2-Br-5-EtOCH2CH2—Ph(Me)CH— |
| 5877 | 2-Br-6-EtOCH2CH2—Ph(Me)CH— |
| 5878 | 2-I-3-EtOCH2CH2—Ph(Me)CH— |
| 5879 | 2-I-4-EtOCH2CH2—Ph(Me)CH— |
| 5880 | 2-I-5-EtOCH2CH2—Ph(Me)CH— |
| 5881 | 2-I-6-EtOCH2CH2—Ph(Me)CH— |
| 5882 | 2-Me-3-EtOCH2CH2—Ph(Me)CH— |
| 5883 | 2-Me-4-EtOCH2CH2—Ph(Me)CH— |
| 5884 | 2-Me-5-EtOCH2CH2—Ph(Me)CH— |
| 5885 | 2-Me-6-EtOCH2CH2—Ph(Me)CH— |
| 5886 | 2-F-3-cPrOCH2—Ph(Me)CH— |
| 5887 | 2-F-4-cPrOCH2—Ph(Me)CH— |
| 5888 | 2-F-5-cPrOCH2—Ph(Me)CH— |
| 5889 | 2-F-6-cPrOCH2—Ph(Me)CH— |
| 5890 | 2-Cl-3-cPrOCH2—Ph(Me)CH— |
| 5891 | 2-Cl-4-cPrOCH2—Ph(Me)CH— |
| 5892 | 2-Cl-5-cPrOCH2—Ph(Me)CH— |
| 5893 | 2-Cl-6-cPrOCH2—Ph(Me)CH— |
| 5894 | 2-Br-3-cPrOCH2—Ph(Me)CH— |
| 5895 | 2-Br-4-cPrOCH2—Ph(Me)CH— |
| 5896 | 2-Br-5-cPrOCH2—Ph(Me)CH— |
| 5897 | 2-Br-6-cPrOCH2—Ph(Me)CH— |
| 5898 | 2-I-3-cPrOCH2—Ph(Me)CH— |
| 5899 | 2-I-4-cPrOCH2—Ph(Me)CH— |
| 5900 | 2-I-5-cPrOCH2—Ph(Me)CH— |
| 5901 | 2-I-6-cPrOCH2—Ph(Me)CH— |
| 5902 | 2-Me-3-cPrOCH2—Ph(Me)CH— |
| 5903 | 2-Me-4-cPrOCH2—Ph(Me)CH— |
| 5904 | 2-Me-5-cPrOCH2—Ph(Me)CH— |
| 5905 | 2-Me-6-cPrOCH2—Ph(Me)CH— |
| 5906 | 2-F-3-F3COCH2—Ph(Me)CH— |
| 5907 | 2-F-4-F3COCH2—Ph(Me)CH— |
| 5908 | 2-F-5-F3COCH2—Ph(Me)CH— |
| 5909 | 2-F-6-F3COCH2—Ph(Me)CH— |
| 5910 | 2-Cl-3-F3COCH2—Ph(Me)CH— |
| 5911 | 2-Cl-4-F3COCH2—Ph(Me)CH— |
| 5912 | 2-Cl-5-F3COCH2—Ph(Me)CH— |
| 5913 | 2-Cl-6-F3COCH2—Ph(Me)CH— |
| 5914 | 2-Br-3-F3COCH2—Ph(Me)CH— |
| 5915 | 2-Br-4-F3COCH2—Ph(Me)CH— |
| 5916 | 2-Br-5-F3COCH2—Ph(Me)CH— |
| 5917 | 2-Br-6-F3COCH2—Ph(Me)CH— |
| 5918 | 2-I-3-F3COCH2—Ph(Me)CH— |
| 5919 | 2-I-4-F3COCH2—Ph(Me)CH— |
| 5920 | 2-I-5-F3COCH2—Ph(Me)CH— |
| 5921 | 2-I-6-F3COCH2—Ph(Me)CH— |
| 5922 | 2-Me-3-F3COCH2—Ph(Me)CH— |
| 5923 | 2-Me-4-F3COCH2—Ph(Me)CH— |
| 5924 | 2-Me-5-F3COCH2—Ph(Me)CH— |
| 5925 | 2-Me-6-F3COCH2—Ph(Me)CH— |
| 5926 | 2-F-3-F2CHOCH2—Ph(Me)CH— |
| 5927 | 2-F-4-F2CHOCH2—Ph(Me)CH— |
| 5928 | 2-F-5-F2CHOCH2—Ph(Me)CH— |
| 5929 | 2-F-6-F2CHOCH2—Ph(Me)CH— |
| 5930 | 2-Cl-3-F2CHOCH2—Ph(Me)CH— |
| 5931 | 2-Cl-4-F2CHOCH2—Ph(Me)CH— |
| 5932 | 2-Cl-5-F2CHOCH2—Ph(Me)CH— |
| 5933 | 2-Cl-6-F2CHOCH2—Ph(Me)CH— |
| 5934 | 2-Br-3-F2CHOCH2—Ph(Me)CH— |
| 5935 | 2-Br-4-F2CHOCH2—Ph(Me)CH— |
| 5936 | 2-Br-5-F2CHOCH2—Ph(Me)CH— |
| 5937 | 2-Br-6-F2CHOCH2—Ph(Me)CH— |
| 5938 | 2-I-3-F2CHOCH2—Ph(Me)CH— |
| 5939 | 2-I-4-F2CHOCH2—Ph(Me)CH— |
| 5940 | 2-I-5-F2CHOCH2—Ph(Me)CH— |
| 5941 | 2-I-6-F2CHOCH2—Ph(Me)CH— |
| 5942 | 2-Me-3-F2CHOCH2—Ph(Me)CH— |
| 5943 | 2-Me-4-F2CHOCH2—Ph(Me)CH— |
| 5944 | 2-Me-5-F2CHOCH2—Ph(Me)CH— |
| 5945 | 2-Me-6-F2CHOCH2—Ph(Me)CH— |
| 5946 | 2-F-3-MeOCH2CH2OCH2—Ph(Me)CH— |
| 5947 | 2-F-4-MeOCH2CH2OCH2—Ph(Me)CH— |
| 5948 | 2-F-5-MeOCH2CH2OCH2—Ph(Me)CH— |
| 5949 | 2-F-6-MeOCH2CH2OCH2—Ph(Me)CH— |
| 5950 | 2-Cl-3-MeOCH2CH2OCH2—Ph(Me)CH— |
| 5951 | 2-Cl-4-MeOCH2CH2OCH2—Ph(Me)CH— |
| 5952 | 2-Cl-5-MeOCH2CH2OCH2—Ph(Me)CH— |
| 5953 | 2-Cl-6-MeOCH2CH2OCH2—Ph(Me)CH— |
| 5954 | 2-Br-3-MeOCH2CH2OCH2—Ph(Me)CH— |
| 5955 | 2-Br-4-MeOCH2CH2OCH2—Ph(Me)CH— |
| 5956 | 2-Br-5-MeOCH2CH2OCH2—Ph(Me)CH— |
| 5957 | 2-Br-6-MeOCH2CH2OCH2—Ph(Me)CH— |
| 5958 | 2-I-3-MeOCH2CH2OCH2—Ph(Me)CH— |
| 5959 | 2-I-4-MeOCH2CH2OCH2—Ph(Me)CH— |
| 5960 | 2-I-5-MeOCH2CH2OCH2—Ph(Me)CH— |
| 5961 | 2-I-6-MeOCH2CH2OCH2—Ph(Me)CH— |

TABLE 2-continued

| No. | Z |
|---|---|
| 5962 | 2-Me-3-MeOCH2CH2OCH2—Ph(Me)CH— |
| 5963 | 2-Me-4-MeOCH2CH2OCH2—Ph(Me)CH— |
| 5964 | 2-Me-5-MeOCH2CH2OCH2—Ph(Me)CH— |
| 5965 | 2-Me-6-MeOCH2CH2OCH2—Ph(Me)CH— |
| 5966 | 2-F-3-Me2NCH2—Ph(Me)CH— |
| 5967 | 2-F-4-Me2NCH2—Ph(Me)CH— |
| 5968 | 2-F-5-Me2NCH2—Ph(Me)CH— |
| 5969 | 2-F-6-Me2NCH2—Ph(Me)CH— |
| 5970 | 2-Cl-3-Me2NCH2—Ph(Me)CH— |
| 5971 | 2-Cl-4-Me2NCH2—Ph(Me)CH— |
| 5972 | 2-Cl-5-Me2NCH2—Ph(Me)CH— |
| 5973 | 2-Cl-6-Me2NCH2—Ph(Me)CH— |
| 5974 | 2-Br-3-Me2NCH2—Ph(Me)CH— |
| 5975 | 2-Br-4-Me2NCH2—Ph(Me)CH— |
| 5976 | 2-Br-5-Me2NCH2—Ph(Me)CH— |
| 5977 | 2-Br-6-Me2NCH2—Ph(Me)CH— |
| 5978 | 2-I-3-Me2NCH2—Ph(Me)CH— |
| 5979 | 2-I-4-Me2NCH2—Ph(Me)CH— |
| 5980 | 2-I-5-Me2NCH2—Ph(Me)CH— |
| 5981 | 2-I-6-Me2NCH2—Ph(Me)CH— |
| 5982 | 2-Me-3-Me2NCH2—Ph(Me)CH— |
| 5983 | 2-Me-4-Me2NCH2—Ph(Me)CH— |
| 5984 | 2-Me-5-Me2NCH2—Ph(Me)CH— |
| 5985 | 2-Me-6-Me2NCH2—Ph(Me)CH— |
| 5986 | 2-F-3-MeSCH2—Ph(Me)CH— |
| 5987 | 2-F-4-MeSCH2—Ph(Me)CH— |
| 5988 | 2-F-5-MeSCH2—Ph(Me)CH— |
| 5989 | 2-Cl-6-MeSCH2—Ph(Me)CH— |
| 5990 | 2-Cl-3-MeSCH2—Ph(Me)CH— |
| 5991 | 2-Cl-4-MeSCH2—Ph(Me)CH— |
| 5992 | 2-Cl-5-MeSCH2—Ph(Me)CH— |
| 5993 | 2-Cl-6-MeSCH2—Ph(Me)CH— |
| 5994 | 2-Br-3-MeSCH2—Ph(Me)CH— |
| 5995 | 2-Br-4-MeSCH2—Ph(Me)CH— |
| 5996 | 2-Br-5-MeSCH2—Ph(Me)CH— |
| 5997 | 2-Br-6-MeSCH2—Ph(Me)CH— |
| 5998 | 2-I-3-MeSCH2—Ph(Me)CH— |
| 5999 | 2-I-4-MeSCH2—Ph(Me)CH— |
| 6000 | 2-I-5-MeSCH2—Ph(Me)CH— |
| 6001 | 2-I-6-MeSCH2—Ph(Me)CH— |
| 6002 | 2-Me-3-MeSCH2—Ph(Me)CH— |
| 6003 | 2-Me-4-MeSCH2—Ph(Me)CH— |
| 6004 | 2-Me-5-MeSCH2—Ph(Me)CH— |
| 6005 | 2-Me-6-MeSCH2—Ph(Me)CH— |
| 6006 | 2-F-3-MeS(O)CH2—Ph(Me)CH— |
| 6007 | 2-F-4-MeS(O)CH2—Ph(Me)CH— |
| 6008 | 2-F-5-MeS(O)CH2—Ph(Me)CH— |
| 6009 | 2-F-6-MeS(O)CH2—Ph(Me)CH— |
| 6010 | 2-Cl-3-MeS(O)CH2—Ph(Me)CH— |
| 6011 | 2-Cl-4-MeS(O)CH2—Ph(Me)CH— |
| 6012 | 2-Cl-5-MeS(O)CH2—Ph(Me)CH— |
| 6013 | 2-Cl-6-MeS(O)CH2—Ph(Me)CH— |
| 6014 | 2-Br-3-MeS(O)CH2—Ph(Me)CH— |
| 6015 | 2-Br-4-MeS(O)CH2—Ph(Me)CH— |
| 6016 | 2-Br-5-MeS(O)CH2—Ph(Me)CH— |
| 6017 | 2-Br-6-MeS(O)CH2—Ph(Me)CH— |
| 6018 | 2-I-3-MeS(O)CH2—Ph(Me)CH— |
| 6019 | 2-I-4-MeS(O)CH2—Ph(Me)CH— |
| 6020 | 2-I-5-MeS(O)CH2—Ph(Me)CH— |
| 6021 | 2-I-6-MeS(O)CH2—Ph(Me)CH— |
| 6022 | 2-Me-3-MeS(O)CH2—Ph(Me)CH— |
| 6023 | 2-Me-4-MeS(O)CH2—Ph(Me)CH— |
| 6024 | 2-Me-5-MeS(O)CH2—Ph(Me)CH— |
| 6025 | 2-Me-6-MeS(O)CH2—Ph(Me)CH— |
| 6026 | 2-F-3-MeSO2CH2—Ph(Me)CH— |
| 6027 | 2-F-4-MeSO2CH2—Ph(Me)CH— |
| 6028 | 2-F-5-MeSO2CH2—Ph(Me)CH— |
| 6029 | 2-F-6-MeSO2CH2—Ph(Me)CH— |
| 6030 | 2-Cl-3-MeSO2CH2—Ph(Me)CH— |
| 6031 | 2-Cl-4-MeSO2CH2—Ph(Me)CH— |
| 6032 | 2-Cl-5-MeSO2CH2—Ph(Me)CH— |
| 6033 | 2-Cl-6-MeSO2CH2—Ph(Me)CH— |
| 6034 | 2-Br-3-MeSO2CH2—Ph(Me)CH— |
| 6035 | 2-Br-4-MeSO2CH2—Ph(Me)CH— |
| 6036 | 2-Br-5-MeSO2CH2—Ph(Me)CH— |
| 6037 | 2-Br-6-MeSO2CH2—Ph(Me)CH— |
| 6038 | 2-I-3-MeSO2CH2—Ph(Me)CH— |
| 6039 | 2-I-4-MeSO2CH2—Ph(Me)CH— |
| 6040 | 2-I-5-MeSO2CH2—Ph(Me)CH— |
| 6041 | 2-I-6-MeSO2CH2—Ph(Me)CH— |
| 6042 | 2-Me-3-MeSO2CH2—Ph(Me)CH— |
| 6043 | 2-Me-4-MeSO2CH2—Ph(Me)CH— |
| 6044 | 2-Me-5-MeSO2CH2—Ph(Me)CH— |
| 6045 | 2-Me-6-MeSO2CH2—Ph(Me)CH— |
| 6046 | 2-F-3-cPr—Ph(Me)CH— |
| 6047 | 2-F-4-cPr—Ph(Me)CH— |
| 6048 | 2-F-5-cPr—Ph(Me)CH— |
| 6049 | 2-F-6-cPr—Ph(Me)CH— |
| 6050 | 2-Cl-3-cPr—Ph(Me)CH— |
| 6051 | 2-Cl-4-cPr—Ph(Me)CH— |
| 6052 | 2-Cl-5-cPr—Ph(Me)CH— |
| 6053 | 2-Cl-6-cPr—Ph(Me)CH— |
| 6054 | 2-Br-3-cPr—Ph(Me)CH— |
| 6055 | 2-Br-4-cPr—Ph(Me)CH— |
| 6056 | 2-Br-5-cPr—Ph(Me)CH— |
| 6057 | 2-Br-6-cPr—Ph(Me)CH— |
| 6058 | 2-I-3-cPr—Ph(Me)CH— |
| 6059 | 2-I-4-cPr—Ph(Me)CH— |
| 6060 | 2-I-5-cPr—Ph(Me)CH— |
| 6061 | 2-I-6-cPr—Ph(Me)CH— |
| 6062 | 2-Me-3-cPr—Ph(Me)CH— |
| 6063 | 2-Me-4-cPr—Ph(Me)CH— |
| 6064 | 2-Me-5-cPr—Ph(Me)CH— |
| 6065 | 2-Me-6-cPr—Ph(Me)CH— |
| 6066 | 2-F-3-cBu—Ph(Me)CH— |
| 6067 | 2-F-4-cBu—Ph(Me)CH— |
| 6068 | 2-F-5-cBu—Ph(Me)CH— |
| 6069 | 2-F-6-cBu—Ph(Me)CH— |
| 6070 | 2-Cl-3-cBu—Ph(Me)CH— |
| 6071 | 2-Cl-4-cBu—Ph(Me)CH— |
| 6072 | 2-Cl-5-cBu—Ph(Me)CH— |
| 6073 | 2-Cl-6-cBu—Ph(Me)CH— |
| 6074 | 2-Br-3-cBu—Ph(Me)CH— |
| 6075 | 2-Br-4-cBu—Ph(Me)CH— |
| 6076 | 2-Br-5-cBu—Ph(Me)CH— |
| 6077 | 2-Br-6-cBu—Ph(Me)CH— |
| 6078 | 2-I-3-cBu—Ph(Me)CH— |
| 6079 | 2-I-4-cBu—Ph(Me)CH— |
| 6080 | 2-I-5-cBu—Ph(Me)CH— |
| 6081 | 2-I-6-cBu—Ph(Me)CH— |
| 6082 | 2-Me-3-cBu—Ph(Me)CH— |
| 6083 | 2-Me-4-cBu—Ph(Me)CH— |
| 6084 | 2-Me-5-cBu—Ph(Me)CH— |
| 6085 | 2-Me-6-cBu—Ph(Me)CH— |
| 6086 | 2-F-3-F3C—Ph(Me)CH— |
| 6087 | 2-F-4-F3C—Ph(Me)CH— |
| 6088 | 2-F-5-F3C—Ph(Me)CH— |
| 6089 | 2-F-6-F3C—Ph(Me)CH— |
| 6090 | 2-Cl-3-F3C—Ph(Me)CH— |
| 6091 | 2-Cl-4-F3C—Ph(Me)CH— |
| 6092 | 2-Cl-5-F3C—Ph(Me)CH— |
| 6093 | 2-Cl-6-F3C—Ph(Me)CH— |
| 6094 | 2-Br-3-F3C—Ph(Me)CH— |
| 6095 | 2-Br-4-F3C—Ph(Me)CH— |
| 6096 | 2-Br-5-F3C—Ph(Me)CH— |
| 6097 | 2-Br-6-F3C—Ph(Me)CH— |
| 6098 | 2-I-3-F3C—Ph(Me)CH— |
| 6099 | 2-I-4-F3C—Ph(Me)CH— |
| 6100 | 2-I-5-F3C—Ph(Me)CH— |
| 6101 | 2-I-6-F3C—Ph(Me)CH— |
| 6102 | 2-Me-3-F3C—Ph(Me)CH— |
| 6103 | 2-Me-4-F3C—Ph(Me)CH— |
| 6104 | 2-Me-5-F3C—Ph(Me)CH— |
| 6105 | 2-Me-6-F3C—Ph(Me)CH— |
| 6106 | 2-F-3-F2CH—Ph(Me)CH— |
| 6107 | 2-F-4-F2CH—Ph(Me)CH— |
| 6108 | 2-F-5-F2CH—Ph(Me)CH— |
| 6109 | 2-F-6-F2CH—Ph(Me)CH— |
| 6110 | 2-Cl-3-F2CH—Ph(Me)CH— |
| 6111 | 2-Cl-4-F2CH—Ph(Me)CH— |
| 6112 | 2-Cl-5-F2CH—Ph(Me)CH— |
| 6113 | 2-Cl-6-F2CH—Ph(Me)CH— |
| 6114 | 2-Br-3-F2CH—Ph(Me)CH— |
| 6115 | 2-Br-5-F2CH—Ph(Me)CH— |
| 6116 | 2-Br-5-F2CH—Ph(Me)CH— |
| 6117 | 2-Br-6-F2CH—Ph(Me)CH— |

TABLE 2-continued

| No. | Z |
|---|---|
| 6118 | 2-I-3-F2CH—Ph(Me)CH— |
| 6119 | 2-I-4-F2CH—Ph(Me)CH— |
| 6120 | 2-I-5-F2CH—Ph(Me)CH— |
| 6121 | 2-I-6-F2CH—Ph(Me)CH— |
| 6122 | 2-Me-3-F2CH—Ph(Me)CH— |
| 6123 | 2-Me-4-F2CH—Ph(Me)CH— |
| 6124 | 2-Me-5-F2CH—Ph(Me)CH— |
| 6125 | 2-Me-6-F2CH—Ph(Me)CH— |
| 6126 | 2-F-3-H2C=CH—Ph(Me)CH— |
| 6127 | 2-F-4-H2C=CH—Ph(Me)CH— |
| 6128 | 2-F-5-H2C=CH—Ph(Me)CH— |
| 6129 | 2-F-6-H2C=CH—Ph(Me)CH— |
| 6130 | 2-Cl-3-H2C=CH—Ph(Me)CH— |
| 6131 | 2-Cl-4-H2C=CH—Ph(Me)CH— |
| 6132 | 2-Cl-5-H2C=CH—Ph(Me)CH— |
| 6133 | 2-Cl-6-H2C=CH—Ph(Me)CH— |
| 6134 | 2-Br-3-H2C=CH—Ph(Me)CH— |
| 6135 | 2-Br-4-H2C=CH—Ph(Me)CH— |
| 6136 | 2-Br-5-H2C=CH—Ph(Me)CH— |
| 6137 | 2-Br-6-H2C=CH—Ph(Me)CH— |
| 6138 | 2-I-3-H2C=CH—Ph(Me)CH— |
| 6139 | 2-I-4-H2C=CH—Ph(Me)CH— |
| 6140 | 2-I-5-H2C=CH—Ph(Me)CH— |
| 6141 | 2-I-6-H2C=CH—Ph(Me)CH— |
| 6142 | 2-Me-3-H2C=CH—Ph(Me)CH— |
| 6143 | 2-Me-4-H2C=CH—Ph(Me)CH— |
| 6144 | 2-Me-5-H2C=CH—Ph(Me)CH— |
| 6145 | 2-Me-6-H2C=CH—Ph(Me)CH— |
| 6146 | 2-F-3-H2C=CHCH2—Ph(Me)CH— |
| 6147 | 2-F-4-H2C=CHCH2—Ph(Me)CH— |
| 6148 | 2-F-5-H2C=CHCH2—Ph(Me)CH— |
| 6149 | 2-F-6-H2C=CHCH2—Ph(Me)CH— |
| 6150 | 2-Cl-3-H2C=CHCH2—Ph(Me)CH— |
| 6151 | 2-Cl-4-H2C=CHCH2—Ph(Me)CH— |
| 6152 | 2-Cl-5-H2C=CHCH2—Ph(Me)CH— |
| 6153 | 2-Cl-6-H2C=CHCH2—Ph(Me)CH— |
| 6154 | 2-Br-3-H2C=CHCH2—Ph(Me)CH— |
| 6155 | 2-Br-4-H2C=CHCH2—Ph(Me)CH— |
| 6156 | 2-Br-5-H2C=CHCH2—Ph(Me)CH— |
| 6157 | 2-Br-6-H2C=CHCH2—Ph(Me)CH— |
| 6158 | 2-I-3-H2C=CHCH2—Ph(Me)CH— |
| 6159 | 2-I-4-H2C=CHCH2—Ph(Me)CH— |
| 6160 | 2-I-5-H2C=CHCH2—Ph(Me)CH— |
| 6161 | 2-I-6-H2C=CHCH2—Ph(Me)CH— |
| 6162 | 2-Me-3-H2C=CHCH2—Ph(Me)CH— |
| 6163 | 2-Me-4-H2C=CHCH2—Ph(Me)CH— |
| 6164 | 2-Me-5-H2C=CHCH2—Ph(Me)CH— |
| 6165 | 2-Me-6-H2C=CHCH2—Ph(Me)CH— |
| 6166 | 2-F-3-F2C=CH—Ph(Me)CH— |
| 6167 | 2-F-4-F2C=CH—Ph(Me)CH— |
| 6168 | 2-F-5-F2C=CH—Ph(Me)CH— |
| 6169 | 2-F-6-F2C=CH—Ph(Me)CH— |
| 6170 | 2-Cl-3-F2C=CH—Ph(Me)CH— |
| 6171 | 2-Cl-4-F2C=CH—Ph(Me)CH— |
| 6172 | 2-Cl-5-F2C=CH—Ph(Me)CH— |
| 6173 | 2-Cl-6-F2C=CH—Ph(Me)CH— |
| 6174 | 2-Br-3-F2C=CH—Ph(Me)CH— |
| 6175 | 2-Br-4-F2C=CH—Ph(Me)CH— |
| 6176 | 2-Br-5-F2C=CH—Ph(Me)CH— |
| 6177 | 2-Br-6-F2C=CH—Ph(Me)CH— |
| 6178 | 2-I-3-F2C=CH—Ph(Me)CH— |
| 6179 | 2-I-4-F2C=CH—Ph(Me)CH— |
| 6180 | 2-I-5-F2C=CH—Ph(Me)CH— |
| 6181 | 2-I-6-F2C=CH—Ph(Me)CH— |
| 6182 | 2-Me-3-F2C=CH—Ph(Me)CH— |
| 6183 | 2-Me-4-F2C=CH—Ph(Me)CH— |
| 6184 | 2-Me-5-F2C=CH—Ph(Me)CH— |
| 6185 | 2-Me-6-F2C=CH—Ph(Me)CH— |
| 6186 | 2-F-3-F2C=CHCH2—Ph(Me)CH— |
| 6187 | 2-F-4-F2C=CHCH2—Ph(Me)CH— |
| 6188 | 2-F-5-F2C=CHCH2—Ph(Me)CH— |
| 6189 | 2-F-6-F2C=CHCH2—Ph(Me)CH— |
| 6190 | 2-Cl-3-F2C=CHCH2—Ph(Me)CH— |
| 6191 | 2-Cl-4-F2C=CHCH2—Ph(Me)CH— |
| 6192 | 2-Cl-5-F2C=CHCH2—Ph(Me)CH— |
| 6193 | 2-Cl-6-F2C=CHCH2—Ph(Me)CH— |
| 6194 | 2-Br-3-F2C=CHCH2—Ph(Me)CH— |
| 6195 | 2-Br-4-F2C=CHCH2—Ph(Me)CH— |
| 6196 | 2-Br-5-F2C=CHCH2—Ph(Me)CH— |
| 6197 | 2-Br-6-F2C=CHCH2—Ph(Me)CH— |
| 6198 | 2-I-3-F2C=CHCH2—Ph(Me)CH— |
| 6199 | 2-I-4-F2C=CHCH2—Ph(Me)CH— |
| 6200 | 2-I-5-F2C=CHCH2—Ph(Me)CH— |
| 6201 | 2-I-6-F2C=CHCH2—Ph(Me)CH— |
| 6202 | 2-Me-3-F2C=CHCH2—Ph(Me)CH— |
| 6203 | 2-Me-4-F2C=CHCH2—Ph(Me)CH— |
| 6204 | 2-Me-5-F2C=CHCH2—Ph(Me)CH— |
| 6205 | 2-Me-6-F2C=CHCH2—Ph(Me)CH— |
| 6206 | 2-F-3-HC≡C—Ph(Me)CH— |
| 6207 | 2-F-4-HC≡C—Ph(Me)CH— |
| 6208 | 2-F-5-HC≡C—Ph(Me)CH— |
| 6209 | 2-F-6-HC≡C—Ph(Me)CH— |
| 6210 | 2-Cl-3-HC≡C—Ph(Me)CH— |
| 6211 | 2-Cl-4-HC≡C—Ph(Me)CH— |
| 6212 | 2-Cl-5-HC≡C—Ph(Me)CH— |
| 6213 | 2-Cl-6-HC≡C—Ph(Me)CH— |
| 6214 | 2-Br-3-HC≡C—Ph(Me)CH— |
| 6215 | 2-Br-4-HC≡C—Ph(Me)CH— |
| 6216 | 2-Br-5-HC≡C—Ph(Me)CH— |
| 6217 | 2-Br-6-HC≡C—Ph(Me)CH— |
| 6218 | 2-I-3-HC≡C—Ph(Me)CH— |
| 6219 | 2-I-4-HC≡C—Ph(Me)CH— |
| 6220 | 2-I-5-HC≡C—Ph(Me)CH— |
| 6221 | 2-I-6-HC≡C—Ph(Me)CH— |
| 6222 | 2-Me-3-HC≡C—Ph(Me)CH— |
| 6223 | 2-Me-4-HC≡C—Ph(Me)CH— |
| 6224 | 2-Me-5-HC≡C—Ph(Me)CH— |
| 6225 | 2-Me-6-HC≡C—Ph(Me)CH— |
| 6226 | 2-F-3-HC≡CCH2—Ph(Me)CH— |
| 6227 | 2-F-4-HC≡CCH2—Ph(Me)CH— |
| 6228 | 2-F-5-HC≡CCH2—Ph(Me)CH— |
| 6229 | 2-F-6-HC≡CCH2—Ph(Me)CH— |
| 6230 | 2-Cl-3-HC≡CCH2—Ph(Me)CH— |
| 6231 | 2-Cl-4-HC≡CCH2—Ph(Me)CH— |
| 6232 | 2-Cl-5-HC≡CCH2—Ph(Me)CH— |
| 6233 | 2-Cl-6-HC≡CCH2—Ph(Me)CH— |
| 6234 | 2-Br-3-HC≡CCH2—Ph(Me)CH— |
| 6235 | 2-Br-4-HC≡CCH2—Ph(Me)CH— |
| 6236 | 2-Br-5-HC≡CCH2—Ph(Me)CH— |
| 6237 | 2-Br-6-HC≡CCH2—Ph(Me)CH— |
| 6238 | 2-I-3-HC≡CCH2—Ph(Me)CH— |
| 6239 | 2-I-4-HC≡CCH2—Ph(Me)CH— |
| 6240 | 2-I-5-HC≡CCH2—Ph(Me)CH— |
| 6241 | 2-I-6-HC≡CCH2—Ph(Me)CH— |
| 6242 | 2-Me-3-HC≡CCH2—Ph(Me)CH— |
| 6243 | 2-Me-4-HC≡CCH2—Ph(Me)CH— |
| 6244 | 2-Me-5-HC≡CCH2—Ph(Me)CH— |
| 6245 | 2-Me-6-HC≡CCH2—Ph(Me)CH— |
| 6246 | 2-F-3-F3CC≡C—Ph(Me)CH— |
| 6247 | 2-F-4-F3CC≡C—Ph(Me)CH— |
| 6248 | 2-F-5-F3CC≡C—Ph(Me)CH— |
| 6249 | 2-F-6-F3CC≡C—Ph(Me)CH— |
| 6250 | 2-Cl-3-F3CC≡C—Ph(Me)CH— |
| 6251 | 2-Cl-4-F3CC≡C—Ph(Me)CH— |
| 6252 | 2-Cl-5-F3CC≡C—Ph(Me)CH— |
| 6253 | 2-Cl-6-F3CC≡C—Ph(Me)CH— |
| 6254 | 2-Br-3-F3CC≡C—Ph(Me)CH— |
| 6255 | 2-Br-4-F3CC≡C—Ph(Me)CH— |
| 6256 | 2-Br-5-F3CC≡C—Ph(Me)CH— |
| 6257 | 2-Br-6-F3CC≡C—Ph(Me)CH— |
| 6258 | 2-I-3-F3CC≡C—Ph(Me)CH— |
| 6259 | 2-I-4-F3CC≡C—Ph(Me)CH— |
| 6260 | 2-I-5-F3CC≡C—Ph(Me)CH— |
| 6261 | 2-I-6-F3CC≡C—Ph(Me)CH— |
| 6262 | 2-Me-3-F3CC≡C—Ph(Me)CH— |
| 6263 | 2-Me-4-F3CC≡C—Ph(Me)CH— |
| 6264 | 2-Me-5-F3CC≡C—Ph(Me)CH— |
| 6265 | 2-Me-6-F3CC≡C—Ph(Me)CH— |
| 6266 | 2-F-3-F3CC≡CCH2—Ph(Me)CH— |
| 6267 | 2-F-4-F3CC≡CCH2—Ph(Me)CH— |
| 6268 | 2-F-5-F3CC≡CCH2—Ph(Me)CH— |
| 6269 | 2-F-6-F3CC≡CCH2—Ph(Me)CH— |
| 6270 | 2-Cl-3-F3CC≡CCH2—Ph(Me)CH— |
| 6271 | 2-Cl-4-F3CC≡CCH2—Ph(Me)CH— |
| 6272 | 2-Cl-5-F3CC≡CCH2—Ph(Me)CH— |
| 6273 | 2-Cl-6-F3CC≡CCH2—Ph(Me)CH— |

TABLE 2-continued

| No. | Z |
|---|---|
| 6274 | 2-Br-3-F3CC≡CCH2—Ph(Me)CH— |
| 6275 | 2-Br-4-F3CC≡CCH2—Ph(Me)CH— |
| 6276 | 2-Br-5-F3CC≡CCH2—Ph(Me)CH— |
| 6277 | 2-Br-6-F3CC≡CCH2—Ph(Me)CH— |
| 6278 | 2-I-3-F3CC≡CCH2—Ph(Me)CH— |
| 6279 | 2-I-4-F3CC≡CCH2—Ph(Me)CH— |
| 6280 | 2-I-5-F3CC≡CCH2—Ph(Me)CH— |
| 6281 | 2-I-6-F3CC≡CCH2—Ph(Me)CH— |
| 6282 | 2-Me-3-F3CC≡CCH2—Ph(Me)CH— |
| 6283 | 2-Me-4-F3CC≡CCH2—Ph(Me)CH— |
| 6284 | 2-Me-5-F3CC≡CCH2—Ph(Me)CH— |
| 6285 | 2-Me-6-F3CC≡CCH2—Ph(Me)CH— |
| 6286 | 2-F-3-MeO—Ph(Me)CH— |
| 6287 | 2-F-4-MeO—Ph(Me)CH— |
| 6288 | 2-F-5-MeO—Ph(Me)CH— |
| 6289 | 2-F-6-MeO—Ph(Me)CH— |
| 6290 | 2-Cl-3-MeO—Ph(Me)CH— |
| 6291 | 2-Cl-4-MeO—Ph(Me)CH— |
| 6292 | 2-Cl-5-MeO—Ph(Me)CH— |
| 6293 | 2-Cl-6-MeO—Ph(Me)CH— |
| 6294 | 2-Br-3-MeO—Ph(Me)CH— |
| 6295 | 2-Br-4-MeO—Ph(Me)CH— |
| 6296 | 2-Br-5-MeO—Ph(Me)CH— |
| 6297 | 2-Br-6-MeO—Ph(Me)CH— |
| 6298 | 2-I-3-MeO—Ph(Me)CH— |
| 6299 | 2-I-4-MeO—Ph(Me)CH— |
| 6300 | 2-I-5-MeO—Ph(Me)CH— |
| 6301 | 2-I-6-MeO—Ph(Me)CH— |
| 6302 | 2-Me-3-MeO—Ph(Me)CH— |
| 6303 | 2-Me-4-MeO—Ph(Me)CH— |
| 6304 | 2-Me-5-MeO—Ph(Me)CH— |
| 6305 | 2-Me-6-MeO—Ph(Me)CH— |
| 6306 | 2-F-3-EtO—Ph(Me)CH— |
| 6307 | 2-F-4-EtO—Ph(Me)CH— |
| 6308 | 2-F-5-EtO—Ph(Me)CH— |
| 6309 | 2-F-6-EtO—Ph(Me)CH— |
| 6310 | 2-Cl-3-EtO—Ph(Me)CH— |
| 6311 | 2-Cl-4-EtO—Ph(Me)CH— |
| 6312 | 2-Cl-5-EtO—Ph(Me)CH— |
| 6313 | 2-Cl-6-EtO—Ph(Me)CH— |
| 6314 | 2-Br-3-EtO—Ph(Me)CH— |
| 6315 | 2-Br-4-EtO—Ph(Me)CH— |
| 6316 | 2-Br-5-EtO—Ph(Me)CH— |
| 6317 | 2-Br-6-EtO—Ph(Me)CH— |
| 6318 | 2-I-3-EtO—Ph(Me)CH— |
| 6319 | 2-I-4-EtO—Ph(Me)CH— |
| 6320 | 2-I-5-EtO—Ph(Me)CH— |
| 6321 | 2-I-6-EtO—Ph(Me)CH— |
| 6322 | 2-Me-3-EtO—Ph(Me)CH— |
| 6323 | 2-Me-4-EtO—Ph(Me)CH— |
| 6324 | 2-Me-5-EtO—Ph(Me)CH— |
| 6325 | 2-Me-6-EtO—Ph(Me)CH— |
| 6326 | 2-F-3-PrO—Ph(Me)CH— |
| 6327 | 2-F-4-PrO—Ph(Me)CH— |
| 6328 | 2-F-5-PrO—Ph(Me)CH— |
| 6329 | 2-F-6-PrO—Ph(Me)CH— |
| 6330 | 2-Cl-3-PrO—Ph(Me)CH— |
| 6331 | 2-Cl-4-PrO—Ph(Me)CH— |
| 6332 | 2-Cl-5-PrO—Ph(Me)CH— |
| 6333 | 2-Cl-6-PrO—Ph(Me)CH— |
| 6334 | 2-Br-3-PrO—Ph(Me)CH— |
| 6335 | 2-Br-4-PrO—Ph(Me)CH— |
| 6336 | 2-Br-5-PrO—Ph(Me)CH— |
| 6337 | 2-Br-6-PrO—Ph(Me)CH— |
| 6338 | 2-I-3-PrO—Ph(Me)CH— |
| 6339 | 2-I-4-PrO—Ph(Me)CH— |
| 6340 | 2-I-5-PrO—Ph(Me)CH— |
| 6341 | 2-I-6-PrO—Ph(Me)CH— |
| 6342 | 2-Me-3-PrO—Ph(Me)CH— |
| 6343 | 2-Me-4-PrO—Ph(Me)CH— |
| 6344 | 2-Me-5-PrO—Ph(Me)CH— |
| 6345 | 2-Me-6-PrO—Ph(Me)CH— |
| 6346 | 2-F-3-iPrO—Ph(Me)CH— |
| 6347 | 2-F-4-iPrO—Ph(Me)CH— |
| 6348 | 2-F-5-iPrO—Ph(Me)CH— |
| 6349 | 2-F-6-iPrO—Ph(Me)CH— |
| 6350 | 2-Cl-3-iPrO—Ph(Me)CH— |
| 6351 | 2-Cl-4-iPrO—Ph(Me)CH— |
| 6352 | 2-Cl-5-iPrO—Ph(Me)CH— |
| 6353 | 2-Cl-6-iPrO—Ph(Me)CH— |
| 6354 | 2-Br-3-iPrO—Ph(Me)CH— |
| 6355 | 2-Br-4-iPrO—Ph(Me)CH— |
| 6356 | 2-Br-5-iPrO—Ph(Me)CH— |
| 6357 | 2-Br-6-iPrO—Ph(Me)CH— |
| 6358 | 2-I-3-iPrO—Ph(Me)CH— |
| 6359 | 2-I-4-iPrO—Ph(Me)CH— |
| 6360 | 2-I-5-iPrO—Ph(Me)CH— |
| 6361 | 2-I-6-iPrO—Ph(Me)CH— |
| 6362 | 2-Me-3-iPrO—Ph(Me)CH— |
| 6363 | 2-Me-4-iPrO—Ph(Me)CH— |
| 6364 | 2-Me-5-iPrO—Ph(Me)CH— |
| 6365 | 2-Me-6-iPrO—Ph(Me)CH— |
| 6366 | 2-F-3-BuO—Ph(Me)CH— |
| 6367 | 2-F-4-BuO—Ph(Me)CH— |
| 6368 | 2-F-5-BuO—Ph(Me)CH— |
| 6369 | 2-F-6-BuO—Ph(Me)CH— |
| 6370 | 2-Cl-3-BuO—Ph(Me)CH— |
| 6371 | 2-Cl-4-BuO—Ph(Me)CH— |
| 6372 | 2-Cl-5-BuO—Ph(Me)CH— |
| 6373 | 2-Cl-6-BuO—Ph(Me)CH— |
| 6374 | 2-Br-3-BuO—Ph(Me)CH— |
| 6375 | 2-Br-4-BuO—Ph(Me)CH— |
| 6376 | 2-Br-5-BuO—Ph(Me)CH— |
| 6377 | 2-Br-6-BuO—Ph(Me)CH— |
| 6378 | 2-I-3-BuO—Ph(Me)CH— |
| 6379 | 2-I-4-BuO—Ph(Me)CH— |
| 6380 | 2-I-5-BuO—Ph(Me)CH— |
| 6381 | 2-I-6-BuO—Ph(Me)CH— |
| 6382 | 2-Me-3-BuO—Ph(Me)CH— |
| 6383 | 2-Me-4-BuO—Ph(Me)CH— |
| 6384 | 2-Me-5-BuO—Ph(Me)CH— |
| 6385 | 2-Me-6-BuO—Ph(Me)CH— |
| 6386 | 2-F-3-iBuO—Ph(Me)CH— |
| 6387 | 2-F-4-iBuO—Ph(Me)CH— |
| 6388 | 2-F-5-iBuO—Ph(Me)CH— |
| 6389 | 2-F-6-iBuO—Ph(Me)CH— |
| 6390 | 2-Cl-3-iBuO—Ph(Me)CH— |
| 6391 | 2-Cl-4-iBuO—Ph(Me)CH— |
| 6392 | 2-Cl-5-iBuO—Ph(Me)CH— |
| 6393 | 2-Cl-6-iBuO—Ph(Me)CH— |
| 6394 | 2-Br-3-iBuO—Ph(Me)CH— |
| 6395 | 2-Br-4-iBuO—Ph(Me)CH— |
| 6396 | 2-Br-5-iBuO—Ph(Me)CH— |
| 6397 | 2-Br-6-iBuO—Ph(Me)CH— |
| 6398 | 2-I-3-iBuO—Ph(Me)CH— |
| 6399 | 2-I-4-iBuO—Ph(Me)CH— |
| 6400 | 2-I-5-iBuO—Ph(Me)CH— |
| 6401 | 2-I-6-iBuO—Ph(Me)CH— |
| 6402 | 2-Me-3-iBuO—Ph(Me)CH— |
| 6403 | 2-Me-4-iBuO—Ph(Me)CH— |
| 6404 | 2-Me-5-iBuO—Ph(Me)CH— |
| 6405 | 2-Me-6-iBuO—Ph(Me)CH— |
| 6406 | 2-F-3-PentylO—Ph(Me)CH— |
| 6407 | 2-F-4-PentylO—Ph(Me)CH— |
| 6408 | 2-F-5-PentylO—Ph(Me)CH— |
| 6409 | 2-F-6-PentylO—Ph(Me)CH— |
| 6410 | 2-Cl-3-PentylO—Ph(Me)CH— |
| 6411 | 2-Cl-4-PentylO—Ph(Me)CH— |
| 6412 | 2-Cl-5-PentylO—Ph(Me)CH— |
| 6413 | 2-Cl-6-PentylO—Ph(Me)CH— |
| 6414 | 2-Br-3-PentylO—Ph(Me)CH— |
| 6415 | 2-Br-4-PentylO—Ph(Me)CH— |
| 6416 | 2-Br-5-PentylO—Ph(Me)CH— |
| 6417 | 2-Br-6-PentylO—Ph(Me)CH— |
| 6418 | 2-I-3-PentylO—Ph(Me)CH— |
| 6419 | 2-I-4-PentylO—Ph(Me)CH— |
| 6420 | 2-I-5-PentylO—Ph(Me)CH— |
| 6421 | 2-I-6-PentylO—Ph(Me)CH— |
| 6422 | 2-Me-3-PentylO—Ph(Me)CH— |
| 6423 | 2-Me-4-PentylO—Ph(Me)CH— |
| 6424 | 2-Me-5-PentylO—Ph(Me)CH— |
| 6425 | 2-Me-6-PentylO—Ph(Me)CH— |
| 6426 | 2-F-3-N≡CCH2O—Ph(Me)CH— |
| 6427 | 2-F-4-N≡CCH2O—Ph(Me)CH— |
| 6428 | 2-F-5-N≡CCH2O—Ph(Me)CH— |
| 6429 | 2-F-6-N≡CCH2O—Ph(Me)CH— |

TABLE 2-continued

| No. | Z |
|---|---|
| 6430 | 2-Cl-3-N≡CCH2O—Ph(Me)CH— |
| 6431 | 2-Cl-4-N≡CCH2O—Ph(Me)CH— |
| 6432 | 2-Cl-5-N≡CCH2O—Ph(Me)CH— |
| 6433 | 2-Cl-6-N≡CCH2O—Ph(Me)CH— |
| 6434 | 2-Br-3-N≡CCH2O—Ph(Me)CH— |
| 6435 | 2-Br-4-N≡CCH2O—Ph(Me)CH— |
| 6436 | 2-Br-5-N≡CCH2O—Ph(Me)CH— |
| 6437 | 2-Br-6-N≡CCH2O—Ph(Me)CH— |
| 6438 | 2-I-3-N≡CCH2O—Ph(Me)CH— |
| 6439 | 2-I-4-N≡CCH2O—Ph(Me)CH— |
| 6440 | 2-I-5-N≡CCH2O—Ph(Me)CH— |
| 6441 | 2-I-6-N≡CCH2O—Ph(Me)CH— |
| 6442 | 2-Me-3-N≡CCH2O—Ph(Me)CH— |
| 6443 | 2-Me-4-N≡CCH2O—Ph(Me)CH— |
| 6444 | 2-Me-5-N≡CCH2O—Ph(Me)CH— |
| 6445 | 2-Me-6-N≡CCH2O—Ph(Me)CH— |
| 6446 | 2-F-3-N≡CCH2CH2O—Ph(Me)CH— |
| 6447 | 2-F-4-N≡CCH2CH2O—Ph(Me)CH— |
| 6448 | 2-F-5-N≡CCH2CH2O—Ph(Me)CH— |
| 6449 | 2-F-6-N≡CCH2CH2O—Ph(Me)CH— |
| 6450 | 2-Cl-3-N≡CCH2CH2O—Ph(Me)CH— |
| 6451 | 2-Cl-4-N≡CCH2CH2O—Ph(Me)CH— |
| 6452 | 2-Cl-5-N≡CCH2CH2O—Ph(Me)CH— |
| 6453 | 2-Cl-6-N≡CCH2CH2O—Ph(Me)CH— |
| 6454 | 2-Br-3-N≡CCH2CH2O—Ph(Me)CH— |
| 6455 | 2-Br-4-N≡CCH2CH2O—Ph(Me)CH— |
| 6456 | 2-Br-5-N≡CCH2CH2O—Ph(Me)CH— |
| 6457 | 2-Br-6-N≡CCH2CH2O—Ph(Me)CH— |
| 6458 | 2-I-3-N≡CCH2CH2O—Ph(Me)CH— |
| 6459 | 2-I-4-N≡CCH2CH2O—Ph(Me)CH— |
| 6460 | 2-I-5-N≡CCH2CH2O—Ph(Me)CH— |
| 6461 | 2-I-6-N≡CCH2CH2O—Ph(Me)CH— |
| 6462 | 2-Me-3-N≡CCH2CH2O—Ph(Me)CH— |
| 6463 | 2-Me-4-N≡CCH2CH2O—Ph(Me)CH— |
| 6464 | 2-Me-5-N≡CCH2CH2O—Ph(Me)CH— |
| 6465 | 2-Me-6-N≡CCH2CH2O—Ph(Me)CH— |
| 6466 | 2-F-3-cPrCH2O—Ph(Me)CH— |
| 6467 | 2-F-4-cPrCH2O—Ph(Me)CH— |
| 6468 | 2-F-5-cPrCH2O—Ph(Me)CH— |
| 6469 | 2-F-6-cPrCH2O—Ph(Me)CH— |
| 6470 | 2-Cl-3-cPrCH2O—Ph(Me)CH— |
| 6471 | 2-Cl-4-cPrCH2O—Ph(Me)CH— |
| 6472 | 2-Cl-5-cPrCH2O—Ph(Me)CH— |
| 6473 | 2-Cl-6-cPrCH2O—Ph(Me)CH— |
| 6474 | 2-Br-3-cPrCH2O—Ph(Me)CH— |
| 6475 | 2-Br-4-cPrCH2O—Ph(Me)CH— |
| 6476 | 2-Br-5-cPrCH2O—Ph(Me)CH— |
| 6477 | 2-Br-6-cPrCH2O—Ph(Me)CH— |
| 6478 | 2-I-3-cPrCH2O—Ph(Me)CH— |
| 6479 | 2-I-4-cPrCH2O—Ph(Me)CH— |
| 6480 | 2-I-5-cPrCH2O—Ph(Me)CH— |
| 6481 | 2-I-6-cPrCH2O—Ph(Me)CH— |
| 6482 | 2-Me-3-cPrCH2O—Ph(Me)CH— |
| 6483 | 2-Me-4-cPrCH2O—Ph(Me)CH— |
| 6484 | 2-Me-5-cPrCH2O—Ph(Me)CH— |
| 6485 | 2-Me-6-cPrCH2O—Ph(Me)CH— |
| 6486 | 2-F-3-cBuCH2O—Ph(Me)CH— |
| 6487 | 2-F-4-cBuCH2O—Ph(Me)CH— |
| 6488 | 2-F-5-cBuCH2O—Ph(Me)CH— |
| 6489 | 2-F-6-cBuCH2O—Ph(Me)CH— |
| 6490 | 2-Cl-3-cBuCH2O—Ph(Me)CH— |
| 6491 | 2-Cl-4-cBuCH2O—Ph(Me)CH— |
| 6492 | 2-Cl-5-cBuCH2O—Ph(Me)CH— |
| 6493 | 2-Cl-6-cBuCH2O—Ph(Me)CH— |
| 6494 | 2-Br-3-cBuCH2O—Ph(Me)CH— |
| 6495 | 2-Br-4-cBuCH2O—Ph(Me)CH— |
| 6496 | 2-Br-5-cBuCH2O—Ph(Me)CH— |
| 6497 | 2-Br-6-cBuCH2O—Ph(Me)CH— |
| 6498 | 2-I-3-cBuCH2O—Ph(Me)CH— |
| 6499 | 2-I-4-cBuCH2O—Ph(Me)CH— |
| 6500 | 2-I-5-cBuCH2O—Ph(Me)CH— |
| 6501 | 2-I-6-cBuCH2O—Ph(Me)CH— |
| 6502 | 2-Me-3-cBuCH2O—Ph(Me)CH— |
| 6503 | 2-Me-4-cBuCH2O—Ph(Me)CH— |
| 6504 | 2-Me-5-cBuCH2O—Ph(Me)CH— |
| 6505 | 2-Me-6-cBuCH2O—Ph(Me)CH— |
| 6506 | 2-F-3-cPentylCH2O—Ph(Me)CH— |
| 6507 | 2-F-4-cPentylCH2O—Ph(Me)CH— |
| 6508 | 2-F-5-cPentylCH2O—Ph(Me)CH— |
| 6509 | 2-F-6-cPentylCH2O—Ph(Me)CH— |
| 6510 | 2-Cl-3-cPentylCH2O—Ph(Me)CH— |
| 6511 | 2-Cl-4-cPentylCH2O—Ph(Me)CH— |
| 6512 | 2-Cl-5-cPentylCH2O—Ph(Me)CH— |
| 6513 | 2-Cl-6-cPentylCH2O—Ph(Me)CH— |
| 6514 | 2-Br-3-cPentylCH2O—Ph(Me)CH— |
| 6515 | 2-Br-4-cPentylCH2O—Ph(Me)CH— |
| 6516 | 2-Br-5-cPentylCH2O—Ph(Me)CH— |
| 6517 | 2-Br-6-cPentylCH2O—Ph(Me)CH— |
| 6518 | 2-I-3-cPentylCH2O—Ph(Me)CH— |
| 6519 | 2-I-4-cPentylCH2O—Ph(Me)CH— |
| 6520 | 2-I-5-cPentylCH2O—Ph(Me)CH— |
| 6521 | 2-I-6-cPentylCH2O—Ph(Me)CH— |
| 6522 | 2-Me-3-cPentylCH2O—Ph(Me)CH— |
| 6523 | 2-Me-4-cPentylCH2O—Ph(Me)CH— |
| 6524 | 2-Me-5-cPentylCH2O—Ph(Me)CH— |
| 6525 | 2-Me-6-cPentylCH2O—Ph(Me)CH— |
| 6526 | 2-F-3-cHexylCH2O—Ph(Me)CH— |
| 6527 | 2-F-4-cHexylCH2O—Ph(Me)CH— |
| 6528 | 2-F-5-cHexylCH2O—Ph(Me)CH— |
| 6529 | 2-F-6-cHexylCH2O—Ph(Me)CH— |
| 6530 | 2-Cl-3-cHexylCH2O—Ph(Me)CH— |
| 6531 | 2-Cl-4-cHexylCH2O—Ph(Me)CH— |
| 6532 | 2-Cl-5-cHexylCH2O—Ph(Me)CH— |
| 6533 | 2-Cl-6-cHexylCH2O—Ph(Me)CH— |
| 6534 | 2-Br-3-cHexylCH2O—Ph(Me)CH— |
| 6535 | 2-Br-4-cHexylCH2O—Ph(Me)CH— |
| 6536 | 2-Br-5-cHexylCH2O—Ph(Me)CH— |
| 6537 | 2-Br-6-cHexylCH2O—Ph(Me)CH— |
| 6538 | 2-I-3-cHexylCH2O—Ph(Me)CH— |
| 6539 | 2-I-4-cHexylCH2O—Ph(Me)CH— |
| 6540 | 2-I-5-cHexylCH2O—Ph(Me)CH— |
| 6541 | 2-I-6-cHexylCH2O—Ph(Me)CH— |
| 6542 | 2-Me-3-cHexylCH2O—Ph(Me)CH— |
| 6543 | 2-Me-4-cHexylCH2O—Ph(Me)CH— |
| 6544 | 2-Me-5-cHexylCH2O—Ph(Me)CH— |
| 6545 | 2-Me-6-cHexylCH2O—Ph(Me)CH— |
| 6546 | 2-F-3-MeOCH2O—Ph(Me)CH— |
| 6547 | 2-F-4-MeOCH2O—Ph(Me)CH— |
| 6548 | 2-F-5-MeOCH2O—Ph(Me)CH— |
| 6549 | 2-F-6-MeOCH2O—Ph(Me)CH— |
| 6550 | 2-Cl-3-MeOCH2O—Ph(Me)CH— |
| 6551 | 2-Cl-4-MeOCH2O—Ph(Me)CH— |
| 6552 | 2-Cl-5-MeOCH2O—Ph(Me)CH— |
| 6553 | 2-Cl-6-MeOCH2O—Ph(Me)CH— |
| 6554 | 2-Br-3-MeOCH2O—Ph(Me)CH— |
| 6555 | 2-Br-4-MeOCH2O—Ph(Me)CH— |
| 6556 | 2-Br-5-MeOCH2O—Ph(Me)CH— |
| 6557 | 2-Br-6-MeOCH2O—Ph(Me)CH— |
| 6558 | 2-I-3-MeOCH2O—Ph(Me)CH— |
| 6559 | 2-I-4-MeOCH2O—Ph(Me)CH— |
| 6560 | 2-I-5-MeOCH2O—Ph(Me)CH— |
| 6561 | 2-I-6-MeOCH2O—Ph(Me)CH— |
| 6562 | 2-Me-3-MeOCH2O—Ph(Me)CH— |
| 6563 | 2-Me-4-MeOCH2O—Ph(Me)CH— |
| 6564 | 2-Me-5-MeOCH2O—Ph(Me)CH— |
| 6565 | 2-Me-6-MeOCH2O—Ph(Me)CH— |
| 6566 | 2-F-3-EtOCH2O—Ph(Me)CH— |
| 6567 | 2-F-4-EtOCH2O—Ph(Me)CH— |
| 6568 | 2-F-5-EtOCH2O—Ph(Me)CH— |
| 6569 | 2-F-6-EtOCH2O—Ph(Me)CH— |
| 6570 | 2-Cl-3-EtOCH2O—Ph(Me)CH— |
| 6571 | 2-Cl-4-EtOCH2O—Ph(Me)CH— |
| 6572 | 2-Cl-5-EtOCH2O—Ph(Me)CH— |
| 6573 | 2-Cl-6-EtOCH2O—Ph(Me)CH— |
| 6574 | 2-Br-3-EtOCH2O—Ph(Me)CH— |
| 6575 | 2-Br-4-EtOCH2O—Ph(Me)CH— |
| 6576 | 2-Br-5-EtOCH2O—Ph(Me)CH— |
| 6577 | 2-Br-6-EtOCH2O—Ph(Me)CH— |
| 6578 | 2-I-3-EtOCH2O—Ph(Me)CH— |
| 6579 | 2-I-4-EtOCH2O—Ph(Me)CH— |
| 6580 | 2-I-5-EtOCH2O—Ph(Me)CH— |
| 6581 | 2-I-6-EtOCH2O—Ph(Me)CH— |
| 6582 | 2-Me-3-EtOCH2O—Ph(Me)CH— |
| 6583 | 2-Me-4-EtOCH2O—Ph(Me)CH— |
| 6584 | 2-Me-5-EtOCH2O—Ph(Me)CH— |
| 6585 | 2-Me-6-EtOCH2O—Ph(Me)CH— |

TABLE 2-continued

| No. | Z |
|---|---|
| 6586 | 2-F-3-MeOCH2CH2O—Ph(Me)CH— |
| 6587 | 2-F-4-MeOCH2CH2O—Ph(Me)CH— |
| 6588 | 2-F-5-MeOCH2CH2O—Ph(Me)CH— |
| 6589 | 2-F-6-MeOCH2CH2O—Ph(Me)CH— |
| 6590 | 2-Cl-3-MeOCH2CH2O—Ph(Me)CH— |
| 6591 | 2-Cl-4-MeOCH2CH2O—Ph(Me)CH— |
| 6592 | 2-Cl-5-MeOCH2CH2O—Ph(Me)CH— |
| 6593 | 2-Cl-6-MeOCH2CH2O—Ph(Me)CH— |
| 6594 | 2-Br-3-MeOCH2CH2O—Ph(Me)CH— |
| 6595 | 2-Br-4-MeOCH2CH2O—Ph(Me)CH— |
| 6596 | 2-Br-5-MeOCH2CH2O—Ph(Me)CH— |
| 6597 | 2-Br-6-MeOCH2CH2O—Ph(Me)CH— |
| 6598 | 2-I-3-MeOCH2CH2O—Ph(Me)CH— |
| 6599 | 2-I-4-MeOCH2CH2O—Ph(Me)CH— |
| 6600 | 2-I-5-MeOCH2CH2O—Ph(Me)CH— |
| 6601 | 2-I-6-MeOCH2CH2O—Ph(Me)CH— |
| 6602 | 2-Me-3-MeOCH2CH2O—Ph(Me)CH— |
| 6603 | 2-Me-4-MeOCH2CH2O—Ph(Me)CH— |
| 6604 | 2-Me-5-MeOCH2CH2O—Ph(Me)CH— |
| 6605 | 2-Me-6-MeOCH2CH2O—Ph(Me)CH— |
| 6606 | 2-F-3-MeOCH2CH2CH2O—Ph(Me)CH— |
| 6607 | 2-F-4-MeOCH2CH2CH2O—Ph(Me)CH— |
| 6608 | 2-F-5-MeOCH2CH2CH2O—Ph(Me)CH— |
| 6609 | 2-F-6-MeOCH2CH2CH2O—Ph(Me)CH— |
| 6610 | 2-Cl-3-MeOCH2CH2CH2O—Ph(Me)CH— |
| 6611 | 2-Cl-4-MeOCH2CH2CH2O—Ph(Me)CH— |
| 6612 | 2-Cl-5-MeOCH2CH2CH2O—Ph(Me)CH— |
| 6613 | 2-Cl-6-MeOCH2CH2CH2O—Ph(Me)CH— |
| 6614 | 2-Br-3-MeOCH2CH2CH2O—Ph(Me)CH— |
| 6615 | 2-Br-4-MeOCH2CH2CH2O—Ph(Me)CH— |
| 6616 | 2-Br-5-MeOCH2CH2CH2O—Ph(Me)CH— |
| 6617 | 2-Br-6-MeOCH2CH2CH2O—Ph(Me)CH— |
| 6618 | 2-I-3-MeOCH2CH2CH2O—Ph(Me)CH— |
| 6619 | 2-I-4-MeOCH2CH2CH2O—Ph(Me)CH— |
| 6620 | 2-I-5-MeOCH2CH2CH2O—Ph(Me)CH— |
| 6621 | 2-I-6-MeOCH2CH2CH2O—Ph(Me)CH— |
| 6622 | 2-Me-3-MeOCH2CH2CH2O—Ph(Me)CH— |
| 6623 | 2-Me-4-MeOCH2CH2CH2O—Ph(Me)CH— |
| 6624 | 2-Me-5-MeOCH2CH2CH2O—Ph(Me)CH— |
| 6625 | 2-Me-6-MeOCH2CH2CH2O—Ph(Me)CH— |
| 6626 | 2-F-3-MeOCH2CH2OCH2O—Ph(Me)CH— |
| 6627 | 2-F-4-MeOCH2CH2OCH2O—Ph(Me)CH— |
| 6628 | 2-F-5-MeOCH2CH2OCH2O—Ph(Me)CH— |
| 6629 | 2-F-6-MeOCH2CH2OCH2O—Ph(Me)CH— |
| 6630 | 2-Cl-3-MeOCH2CH2OCH2O—Ph(Me)CH— |
| 6631 | 2-Cl-4-MeOCH2CH2OCH2O—Ph(Me)CH— |
| 6632 | 2-Cl-5-MeOCH2CH2OCH2O—Ph(Me)CH— |
| 6633 | 2-Cl-6-MeOCH2CH2OCH2O—Ph(Me)CH— |
| 6634 | 2-Br-3-MeOCH2CH2OCH2O—Ph(Me)CH— |
| 6635 | 2-Br-4-MeOCH2CH2OCH2O—Ph(Me)CH— |
| 6636 | 2-Br-5-MeOCH2CH2OCH2O—Ph(Me)CH— |
| 6637 | 2-Br-6-MeOCH2CH2OCH2O—Ph(Me)CH— |
| 6638 | 2-I-3-MeOCH2CH2OCH2O—Ph(Me)CH— |
| 6639 | 2-I-4-MeOCH2CH2OCH2O—Ph(Me)CH— |
| 6640 | 2-I-5-MeOCH2CH2OCH2O—Ph(Me)CH— |
| 6641 | 2-I-6-MeOCH2CH2OCH2O—Ph(Me)CH— |
| 6642 | 2-Me-3-MeOCH2CH2OCH2O—Ph(Me)CH— |
| 6643 | 2-Me-4-MeOCH2CH2OCH2O—Ph(Me)CH— |
| 6644 | 2-Me-5-MeOCH2CH2OCH2O—Ph(Me)CH— |
| 6645 | 2-Me-6-MeOCH2CH2OCH2O—Ph(Me)CH— |
| 6646 | 2-F-3-MeSCH2O—Ph(Me)CH— |
| 6647 | 2-F-4-MeSCH2O—Ph(Me)CH— |
| 6648 | 2-F-5-MeSCH2O—Ph(Me)CH— |
| 6649 | 2-F-6-MeSCH2O—Ph(Me)CH— |
| 6650 | 2-Cl-3-MeSCH2O—Ph(Me)CH— |
| 6651 | 2-Cl-4-MeSCH2O—Ph(Me)CH— |
| 6652 | 2-Cl-5-MeSCH2O—Ph(Me)CH— |
| 6653 | 2-Cl-6-MeSCH2O—Ph(Me)CH— |
| 6654 | 2-Br-3-MeSCH2O—Ph(Me)CH— |
| 6655 | 2-Br-4-MeSCH2O—Ph(Me)CH— |
| 6656 | 2-Br-5-MeSCH2O—Ph(Me)CH— |
| 6657 | 2-Br-6-MeSCH2O—Ph(Me)CH— |
| 6658 | 2-I-3-MeSCH2O—Ph(Me)CH— |
| 6659 | 2-I-4-MeSCH2O—Ph(Me)CH— |
| 6660 | 2-I-5-MeSCH2O—Ph(Me)CH— |
| 6661 | 2-I-6-MeSCH2O—Ph(Me)CH— |
| 6662 | 2-Me-3-MeSCH2O—Ph(Me)CH— |
| 6663 | 2-Me-4-MeSCH2O—Ph(Me)CH— |
| 6664 | 2-Me-5-MeSCH2O—Ph(Me)CH— |
| 6665 | 2-Me-6-MeSCH2O—Ph(Me)CH— |
| 6666 | 2-F-3-MeS(O)CH2O—Ph(Me)CH— |
| 6667 | 2-F-4-MeS(O)CH2O—Ph(Me)CH— |
| 6668 | 2-F-5-MeS(O)CH2O—Ph(Me)CH— |
| 6669 | 2-F-6-MeS(O)CH2O—Ph(Me)CH— |
| 6670 | 2-Cl-3-MeS(O)CH2O—Ph(Me)CH— |
| 6671 | 2-Cl-4-MeS(O)CH2O—Ph(Me)CH— |
| 6672 | 2-Cl-5-MeS(O)CH2O—Ph(Me)CH— |
| 6673 | 2-Cl-6-MeS(O)CH2O—Ph(Me)CH— |
| 6674 | 2-Br-3-MeS(O)CH2O—Ph(Me)CH— |
| 6675 | 2-Br-4-MeS(O)CH2O—Ph(Me)CH— |
| 6676 | 2-Br-5-MeS(O)CH2O—Ph(Me)CH— |
| 6677 | 2-Br-6-MeS(O)CH2O—Ph(Me)CH— |
| 6678 | 2-I-3-MeS(O)CH2O—Ph(Me)CH— |
| 6679 | 2-I-4-MeS(O)CH2O—Ph(Me)CH— |
| 6680 | 2-I-5-MeS(O)CH2O—Ph(Me)CH— |
| 6681 | 2-I-6-MeS(O)CH2O—Ph(Me)CH— |
| 6682 | 2-Me-3-MeS(OCH2O—Ph(Me)CH— |
| 6683 | 2-Me-4-MeS(O)CH2O—Ph(Me)CH— |
| 6684 | 2-Me-5-MeS(O)CH2O—Ph(Me)CH— |
| 6685 | 2-Me-6-MeS(O)CH2O—Ph(Me)CH— |
| 6686 | 2-F-3-MeSO2CH2O—Ph(Me)CH— |
| 6687 | 2-F-4-MeSO2CH2O—Ph(Me)CH— |
| 6688 | 2-F-5-MeSO2CH2O—Ph(Me)CH— |
| 6689 | 2-F-6-MeSO2CH2O—Ph(Me)CH— |
| 6690 | 2-Cl-3-MeSO2CH2O—Ph(Me)CH— |
| 6691 | 2-Cl-4-MeSO2CH2O—Ph(Me)CH— |
| 6692 | 2-Cl-5-MeSO2CH2O—Ph(Me)CH— |
| 6693 | 2-Cl-6-MeSO2CH2O—Ph(Me)CH— |
| 6694 | 2-Br-3-MeSO2CH2O—Ph(Me)CH— |
| 6695 | 2-Br-4-MeSO2CH2O—Ph(Me)CH— |
| 6696 | 2-Br-5-MeSO2CH2O—Ph(Me)CH— |
| 6697 | 2-Br-6-MeSO2CH2O—Ph(Me)CH— |
| 6698 | 2-I-3-MeSO2CH2O—Ph(Me)CH— |
| 6699 | 2-I-4-MeSO2CH2O—Ph(Me)CH— |
| 6700 | 2-I-5-MeSO2CH2O—Ph(Me)CH— |
| 6701 | 2-I-6-MeSO2CH2O—Ph(Me)CH— |
| 6702 | 2-Me-3-MeSO2CH2O—Ph(Me)CH— |
| 6703 | 2-Me-4-MeSO2CH2O—Ph(Me)CH— |
| 6704 | 2-Me-5-MeSO2CH2O—Ph(Me)CH— |
| 6705 | 2-Me-6-MeSO2CH2O—Ph(Me)CH— |
| 6706 | 2-F-3-AcCH2O—Ph(Me)CH— |
| 6707 | 2-F-4-AcCH2O—Ph(Me)CH— |
| 6708 | 2-F-5-AcCH2O—Ph(Me)CH— |
| 6709 | 2-F-6-AcCH2O—Ph(Me)CH— |
| 6710 | 2-Cl-3-AcCH2O—Ph(Me)CH— |
| 6711 | 2-Cl-4-AcCH2O—Ph(Me)CH— |
| 6712 | 2-Cl-5-AcCH2O—Ph(Me)CH— |
| 6713 | 2-Cl-6-AcCH2O—Ph(Me)CH— |
| 6714 | 2-Br-3-AcCH2O—Ph(Me)CH— |
| 6715 | 2-Br-4-AcCH2O—Ph(Me)CH— |
| 6716 | 2-Br-5-AcCH2O—Ph(Me)CH— |
| 6717 | 2-Br-6-AcCH2O—Ph(Me)CH— |
| 6718 | 2-I-3-AcCH2O—Ph(Me)CH— |
| 6719 | 2-I-4-AcCH2O—Ph(Me)CH— |
| 6720 | 2-I-5-AcCH2O—Ph(Me)CH— |
| 6721 | 2-I-6-AcCH2O—Ph(Me)CH— |
| 6722 | 2-Me-3-AcCH2O—Ph(Me)CH— |
| 6723 | 2-Me-4-AcCH2O—Ph(Me)CH— |
| 6724 | 2-Me-5-AcCH2O—Ph(Me)CH— |
| 6725 | 2-Me-6-AcCH2O—Ph(Me)CH— |
| 6726 | 2-F-3-MeOC(=O)CH2O—Ph(Me)CH— |
| 6727 | 2-F-4-MeOC(=O)CH2O—Ph(Me)CH— |
| 6728 | 2-F-5-MeOC(=O)CH2O—Ph(Me)CH— |
| 6729 | 2-F-6-MeOC(=O)CH2O—Ph(Me)CH— |
| 6730 | 2-Cl-3-MeOC(=O)CH2O—Ph(Me)CH— |
| 6731 | 2-Cl-4-MeOC(=O)CH2O—Ph(Me)CH— |
| 6732 | 2-Cl-5-MeOC(=O)CH2O—Ph(Me)CH— |
| 6733 | 2-Cl-6-MeOC(=O)CH2O—Ph(Me)CH— |
| 6734 | 2-Br-3-MeOC(=O)CH2O—Ph(Me)CH— |
| 6735 | 2-Br-4-MeOC(=O)CH2O—Ph(Me)CH— |
| 6736 | 2-Br-5-MeOC(=O)CH2O—Ph(Me)CH— |
| 6737 | 2-Br-6-MeOC(=O)CH2O—Ph(Me)CH— |
| 6738 | 2-I-3-MeOC(=O)CH2O—Ph(Me)CH— |
| 6739 | 2-I-4-MeOC(=O)CH2O—Ph(Me)CH— |
| 6740 | 2-I-5-MeOC(=O)CH2O—Ph(Me)CH— |
| 6741 | 2-I-6-MeOC(=O)CH2O—Ph(Me)CH— |

TABLE 2-continued

| No. | Z |
|---|---|
| 6742 | 2-Me-3-MeOC(=O)CH2O—Ph(Me)CH— |
| 6743 | 2-Me-4-MeOC(=O)CH2O—Ph(Me)CH— |
| 6744 | 2-Me-5-MeOC(=O)CH2O—Ph(Me)CH— |
| 6745 | 2-Me-6-MeOC(=O)CH2O—Ph(Me)CH— |
| 6746 | 2-F-3-EtOC(=O)CH2O—Ph(Me)CH— |
| 6747 | 2-F-4-EtOC(=O)CH2O—Ph(Me)CH— |
| 6748 | 2-F-5-EtOC(=O)CH2O—Ph(Me)CH— |
| 6749 | 2-F-6-EtOC(=O)CH2O—Ph(Me)CH— |
| 6750 | 2-Cl-3-EtOC(=O)CH2O—Ph(Me)CH— |
| 6751 | 2-Cl-4-EtOC(=O)CH2O—Ph(Me)CH— |
| 6752 | 2-Cl-5-EtOC(=O)CH2O—Ph(Me)CH— |
| 6753 | 2-Cl-6-EtOC(=O)CH2O—Ph(Me)CH— |
| 6754 | 2-Br-3EtOC(=O)CH2O—Ph(Me)CH— |
| 6755 | 2-Br-4-EtOC(=O)CH2O—Ph(Me)CH— |
| 6756 | 2-Br-5-EtOC(=O)CH2O—Ph(Me)CH— |
| 6757 | 2-Br-6-EtOC(=O)CH2O—Ph(Me)CH— |
| 6758 | 2-I-3-EtOC(=O)CH2O—Ph(Me)CH— |
| 6759 | 2-I-4-EtOC(=O)CH2O—Ph(Me)CH— |
| 6760 | 2-I-5-EtOC(=O)CH2O—Ph(Me)CH— |
| 6761 | 2-I-6-EtOC(=O)CH2O—Ph(Me)CH— |
| 6762 | 2-Me-3-EtOC(=O)CH2O—Ph(Me)CH— |
| 6763 | 2-Me-4-EtOC(=O)CH2O—Ph(Me)CH— |
| 6764 | 2-Me-5-EtOC(=O)CH2O—Ph(Me)CH— |
| 6765 | 2-Me-6-EtOC(=O)CH2O—Ph(Me)CH— |
| 6766 | 2-F-3-(1,3-dioxolan-2-yl)CH2O—Ph(Me)CH— |
| 6767 | 2-F-4-(1,3-dioxolan-2-yl)CH2O—Ph(Me)CH— |
| 6768 | 2-F-5-(1,3-dioxolan-2-yl)CH2O—Ph(Me)CH— |
| 6769 | 2-F-6-(1,3-dioxolan-2-yl)CH2O—Ph(Me)CH— |
| 6770 | 2-Cl-3-(1,3-dioxolan-2-yl)CH2O—Ph(Me)CH— |
| 6771 | 2-Cl-4-(1,3-dioxolan-2-yl)CH2O—Ph(Me)CH— |
| 6772 | 2-Cl-5-(1,3-dioxolan-2-yl)CH2O—Ph(Me)CH— |
| 6773 | 2-Cl-6-(1,3-dioxolan-2-yl)CH2O—Ph(Me)CH— |
| 6774 | 2-Br-3-(1,3-dioxolan-2-yl)CH2O—Ph(Me)CH— |
| 6775 | 2-Br-4-(1,3-dioxolan-2-yl)CH2O—Ph(Me)CH— |
| 6776 | 2-Br-5-(1,3-dioxolan-2-yl)CH2O—Ph(Me)CH— |
| 6777 | 2-Br-6-(1,3-dioxolan-2-yl)CH2O—Ph(Me)CH— |
| 6778 | 2-I-3-(1,3-dioxolan-2-yl)CH2O—Ph(Me)CH— |
| 6779 | 2-I-4-(1,3-dioxolan-2-yl)CH2O—Ph(Me)CH— |
| 6780 | 2-I-5-(1,3-dioxolan-2-yl)CH2O—Ph(Me)CH— |
| 6781 | 2-I-6-(1,3-dioxolan-2-yl)CH2O—Ph(Me)CH— |
| 6782 | 2-Me-3-(1,3-dioxolan-2-yl)CH2O—Ph(Me)CH— |
| 6783 | 2-Me-4-(1,3-dioxolan-2-yl)CH2O—Ph(Me)CH— |
| 6784 | 2-Me-5-(1,3-dioxolan-2-yl)CH2O—Ph(Me)CH— |
| 6785 | 2-Me-6-(1,3-dioxolan-2-yl)CH2O—Ph(Me)CH— |
| 6786 | 2-F-3-(1,3-dioxolan-2-yl)CH2CH2O—Ph(Me)CH— |
| 6787 | 2-F-4-(1,3-dioxolan-2-yl)CH2CH2O—Ph(Me)CH— |
| 6788 | 2-F-5-(1,3-dioxolan-2-yl)CH2CH2O—Ph(Me)CH— |
| 6789 | 2-F-6-(1,3-dioxolan-2-yl)CH2CH2O—Ph(Me)CH— |
| 6790 | 2-Cl-3-(1,3-dioxolan-2-yl)CH2CH2O—Ph(Me)CH— |
| 6791 | 2-Cl-4-(1,3-dioxolan-2-yl)CH2CH2O—Ph(Me)CH— |
| 6792 | 2-Cl-5-(1,3-dioxolan-2-yl)CH2CH2O—Ph(Me)CH— |
| 6793 | 2-Cl-6-(1,3-dioxolan-2-yl)CH2CH2O—Ph(Me)CH— |
| 6794 | 2-Br-3-(1,3-dioxolan-2-yl)CH2CH2O—Ph(Me)CH— |
| 6795 | 2-Br-4-(1,3-dioxolan-2-yl)CH2CH2O—Ph(Me)CH— |
| 6796 | 2-Br-5-(1,3-dioxolan-2-yl)CH2CH2O—Ph(Me)CH— |
| 6797 | 2-Br-6-(1,3-dioxolan-2-yl)CH2CH2O—Ph(Me)CH— |
| 6798 | 2-I-3-(1,3-dioxolan-2-yl)CH2CH2O—Ph(Me)CH— |
| 6799 | 2-I-4-(1,3-dioxolan-2-yl)CH2CH2O—Ph(Me)CH— |
| 6800 | 2-I-5-(1,3-dioxolan-2-yl)CH2CH2O—Ph(Me)CH— |
| 6801 | 2-I-6-(1,3-dioxolan-2-yl)CH2CH2O—Ph(Me)CH— |
| 6802 | 2-Me-3-(1,3-dioxolan-2-yl)CH2CH2O—Ph(Me)CH— |
| 6803 | 2-Me-4-(1,3-dioxolan-2-yl)CH2CH2O—Ph(Me)CH— |
| 6804 | 2-Me-5-(1,3-dioxolan-2-yl)CH2CH2O—Ph(Me)CH— |
| 6805 | 2-Me-6-(1,3-dioxolan-2-yl)CH2CH2O—Ph(Me)CH— |
| 6806 | 2-F-3-(1,3-dioxan-2-yl)CH2O—Ph(Me)CH— |
| 6807 | 2-F-4-(1,3-dioxan-2-yl)CH2O—Ph(Me)CH— |
| 6808 | 2-F-5-(1,3-dioxan-2-yl)CH2O—Ph(Me)CH— |
| 6809 | 2-F-6-(1,3-dioxan-2-yl)CH2O—Ph(Me)CH— |
| 6810 | 2-Cl-3-(1,3-dioxan-2-yl)CH2O—Ph(Me)CH— |
| 6811 | 2-Cl-4-(1,3-dioxan-2-yl)CH2O—Ph(Me)CH— |
| 6812 | 2-Cl-5-(1,3-dioxan-2-yl)CH2O—Ph(Me)CH— |
| 6813 | 2-Cl-6-(1,3-dioxan-2-yl)CH2O—Ph(Me)CH— |
| 6814 | 2-Br-3-(1,3-dioxan-2-yl)CH2O—Ph(Me)CH— |
| 6815 | 2-Br-4-(1,3-dioxan-2-yl)CH2O—Ph(Me)CH— |
| 6816 | 2-Br-5-(1,3-dioxan-2-yl)CH2O—Ph(Me)CH— |
| 6817 | 2-Br-6-(1,3-dioxan-2-yl)CH2O—Ph(Me)CH— |
| 6818 | 2-I-3-(1,3-dioxan-2-yl)CH2O—Ph(Me)CH— |
| 6819 | 2-I-4-(1,3-dioxan-2-yl)CH2O—Ph(Me)CH— |
| 6820 | 2-I-5-(1,3-dioxan-2-yl)CH2O—Ph(Me)CH— |
| 6821 | 2-I-6-(1,3-dioxan-2-yl)CH2O—Ph(Me)CH— |
| 6822 | 2-Me-3-(1,3-dioxan-2-yl)CH2O—Ph(Me)CH— |
| 6823 | 2-Me-4-(1,3-dioxan-2-yl)CH2O—Ph(Me)CH— |
| 6824 | 2-Me-5-(1,3-dioxan-2-yl)CH2O—Ph(Me)CH— |
| 6825 | 2-Me-6-(1,3-dioxan-2-yl)CH2O—Ph(Me)CH— |
| 6846 | 2-F-3-(1,3-dioxan-2-yl)CH2CH2O—Ph(Me)CH— |
| 6847 | 2-F-4-(1,3-dioxan-2-yl)CH2CH2O—Ph(Me)CH— |
| 6848 | 2-F-5-(1,3-dioxan-2-yl)CH2CH2O—Ph(Me)CH— |
| 6849 | 2-F-6-(1,3-dioxan-2-yl)CH2CH2O—Ph(Me)CH— |
| 6830 | 2-Cl-3-(1,3-dioxan-2-yl)CH2CH2O—Ph(Me)CH— |
| 6831 | 2-Cl-4-(1,3-dioxan-2-yl)CH2CH2O—Ph(Me)CH— |
| 6832 | 2-Cl-5-(1,3-dioxan-2-yl)CH2CH2O—Ph(Me)CH— |
| 6833 | 2-Cl-6-(1,3-dioxan-2-yl)CH2CH2O—Ph(Me)CH— |
| 6834 | 2-Br-3-(1,3-dioxan-2-yl)CH2CH2O—Ph(Me)CH— |
| 6835 | 2-Br-4-(1,3-dioxan-2-yl)CH2CH2O—Ph(Me)CH— |
| 6836 | 2-Br-5-(1,3-dioxan-2-yl)CH2CH2O—Ph(Me)CH— |
| 6837 | 2-Br-6-(1,3-dioxan-2-yl)CH2CH2O—Ph(Me)CH— |
| 6838 | 2-I-3-(1,3-dioxan-2-yl)CH2CH2O—Ph(Me)CH— |
| 6839 | 2-I-4-(1,3-dioxan-2-yl)CH2CH2O—Ph(Me)CH— |
| 6840 | 2-I-5-(1,3-dioxan-2-yl)CH2CH2O—Ph(Me)CH— |
| 6841 | 2-I-6-(1,3-dioxan-2-yl)CH2CH2O—Ph(Me)CH— |
| 6842 | 2-Me-3-(1,3-dioxan-2-yl)CH2CH2O—Ph(Me)CH— |
| 6843 | 2-Me-4-(1,3-dioxan-2-yl)CH2CH2O—Ph(Me)CH— |
| 6844 | 2-Me-5-(1,3-dioxan-2-yl)CH2CH2O—Ph(Me)CH— |
| 6845 | 2-Me-6-(1,3-dioxan-2-yl)CH2CH2O—Ph(Me)CH— |
| 6847 | 2-F-4-cPrO—Ph(Me)CH— |
| 6848 | 2-F-5-cPrO—Ph(Me)CH— |
| 6849 | 2-F-6-cPrO—Ph(Me)CH— |
| 6850 | 2-Cl-3-cPrO—Ph(Me)CH— |
| 6851 | 2-Cl-4-cPrO—Ph(Me)CH— |
| 6852 | 2-Cl-5-cPrO—Ph(Me)CH— |
| 6853 | 2-Cl-6-cPrO—Ph(Me)CH— |
| 6854 | 2-Br-3-cPrO—Ph(Me)CH— |
| 6855 | 2-Br-4-cPrO—Ph(Me)CH— |
| 6856 | 2-Br-5-cPrO—Ph(Me)CH— |
| 6857 | 2-Br-6-cPrO—Ph(Me)CH— |
| 6858 | 2-I-3-cPrO—Ph(Me)CH— |
| 6859 | 2-I-4-cPrO—Ph(Me)CH— |
| 6860 | 2-I-5-cPrO—Ph(Me)CH— |
| 6861 | 2-I-6-cPrO—Ph(Me)CH— |
| 6862 | 2-Me-3-cPrO—Ph(Me)CH— |
| 6863 | 2-Me-4-cPrO—Ph(Me)CH— |
| 6864 | 2-Me-5-cPrO—Ph(Me)CH— |
| 6865 | 2-Me-6-cPrO—Ph(Me)CH— |
| 6866 | 2-F-3-cBuO—Ph(Me)CH— |
| 6867 | 2-F-4-cBuO—Ph(Me)CH— |
| 6868 | 2-F-5-cBuO—Ph(Me)CH— |
| 6869 | 2-F-6-cBuO—Ph(Me)CH— |
| 6870 | 2-Cl-3-cBuO—Ph(Me)CH— |
| 6871 | 2-Cl-4-cBuO—Ph(Me)CH— |
| 6872 | 2-Cl-5-cBuO—Ph(Me)CH— |
| 6873 | 2-Cl-6-cBuO—Ph(Me)CH— |
| 6874 | 2-Br-3-cBuO—Ph(Me)CH— |
| 6875 | 2-Br-4-cBuO—Ph(Me)CH— |
| 6876 | 2-Br-5-cBuO—Ph(Me)CH— |
| 6877 | 2-Br-6-cBuO—Ph(Me)CH— |
| 6878 | 2-I-3-cBuO—Ph(Me)CH— |
| 6879 | 2-I-4-cBuO—Ph(Me)CH— |
| 6880 | 2-I-5-cBuO—Ph(Me)CH— |
| 6881 | 2-I-6-cBuO—Ph(Me)CH— |
| 6882 | 2-Me-3-cBuO—Ph(Me)CH— |
| 6883 | 2-Me-4-cBuO—Ph(Me)CH— |
| 6884 | 2-Me-5-cBuO—Ph(Me)CH— |
| 6885 | 2-Me-6-cBuO—Ph(Me)CH— |
| 6886 | 2-F-3-cPentylO—Ph(Me)CH— |
| 6887 | 2-F-4-cPentylO—Ph(Me)CH— |
| 6888 | 2-F-5-cPentylO—Ph(Me)CH— |
| 6889 | 2-F-6-cPentylO—Ph(Me)CH— |
| 6890 | 2-Cl-3-cPentylO—Ph(Me)CH— |
| 6891 | 2-Cl-4-cPentylO—Ph(Me)CH— |
| 6892 | 2-Cl-5-cPentylO—Ph(Me)CH— |
| 6893 | 2-Cl-6-cPentylO—Ph(Me)CH— |
| 6894 | 2-Br-3-cPentylO—Ph(Me)CH— |
| 6895 | 2-Br-4-cPentylO—Ph(Me)CH— |
| 6896 | 2-Br-5-cPentylO—Ph(Me)CH— |
| 6897 | 2-Br-6-cPentylO—Ph(Me)CH— |
| 6898 | 2-I-3-cPentylO—Ph(Me)CH— |

TABLE 2-continued

| No. | Z |
|---|---|
| 6899 | 2-I-4-cPentylO—Ph(Me)CH— |
| 6900 | 2-I-5-cPentylO—Ph(Me)CH— |
| 6901 | 2-I-6-cPentylO—Ph(Me)CH— |
| 6902 | 2-Me-3-cPentylO—Ph(Me)CH— |
| 6903 | 2-Me-4-cPentylO—Ph(Me)CH— |
| 6904 | 2-Me-5-cPentylO—Ph(Me)CH— |
| 6905 | 2-Me-6-cPentylO—Ph(Me)CH— |
| 6906 | 2-F-3-cHexylO—Ph(Me)CH— |
| 6907 | 2-F-4-cHexylO—Ph(Me)CH— |
| 6908 | 2-F-5-cHexylO—Ph(Me)CH— |
| 6909 | 2-F-6-cHexylO—Ph(Me)CH— |
| 6910 | 2-Cl-3-cHexylO—Ph(Me)CH— |
| 6911 | 2-Cl-4-cHexylO—Ph(Me)CH— |
| 6912 | 2-Cl-5-cHexylO—Ph(Me)CH— |
| 6913 | 2-Cl-6-cHexylO—Ph(Me)CH— |
| 6914 | 2-Br-3-cHexylO—Ph(Me)CH— |
| 6915 | 2-Br-4-cHexylO—Ph(Me)CH— |
| 6916 | 2-Br-5-cHexylO—Ph(Me)CH— |
| 6917 | 2-Br-6-cHexylO—Ph(Me)CH— |
| 6918 | 2-I-3-cHexylO—Ph(Me)CH— |
| 6919 | 2-I-4-cHexylO—Ph(Me)CH— |
| 6920 | 2-I-5-cHexylO—Ph(Me)CH— |
| 6921 | 2-I-6-cHexylO—Ph(Me)CH— |
| 6922 | 2-Me-3-cHexylO—Ph(Me)CH— |
| 6923 | 2-Me-4-cHexylO—Ph(Me)CH— |
| 6924 | 2-Me-5-cHexylO—Ph(Me)CH— |
| 6925 | 2-Me-6-cHexylO—Ph(Me)CH— |
| 6926 | 2-F-3-F3CO—Ph(Me)CH— |
| 6927 | 2-F-4-F3CO—Ph(Me)CH— |
| 6928 | 2-F-5-F3CO—Ph(Me)CH— |
| 6929 | 2-F-6-F3CO—Ph(Me)CH— |
| 6930 | 2-Cl-3-F3CO—Ph(Me)CH— |
| 6931 | 2-Cl-4-F3CO—Ph(Me)CH— |
| 6932 | 2-Cl-5-F3CO—Ph(Me)CH— |
| 6933 | 2-Cl-6-F3CO—Ph(Me)CH— |
| 6934 | 2-Br-3-F3CO—Ph(Me)CH— |
| 6935 | 2-Br-4-F3CO—Ph(Me)CH— |
| 6936 | 2-Br-5-F3CO—Ph(Me)CH— |
| 6937 | 2-Br-6-F3CO—Ph(Me)CH— |
| 6938 | 2-I-3-F3CO—Ph(Me)CH— |
| 6939 | 2-I-4-F3CO—Ph(Me)CH— |
| 6940 | 3-I-5-F3CO—Ph(Me)CH— |
| 6941 | 2-I-6-F3CO—Ph(Me)CH— |
| 6942 | 2-Me-3-F3CO—Ph(Me)CH— |
| 6943 | 2-Me-4-F3CO—Ph(Me)CH— |
| 6944 | 2-Me-5-F3CO—Ph(Me)CH— |
| 6945 | 2-Me-6-F3CO—Ph(Me)CH— |
| 6946 | 2-F-3-F2CHO—Ph(Me)CH— |
| 6947 | 2-F-4-F2CHO—Ph(Me)CH— |
| 6948 | 2-F-5-F2CHO—Ph(Me)CH— |
| 6949 | 2-F-6-F2CHO—Ph(Me)CH— |
| 6950 | 2-Cl-3-F2CHO—Ph(Me)CH— |
| 6951 | 2-Cl-4-F2CHO—Ph(Me)CH— |
| 6952 | 2-Cl-5-F2CHO—Ph(Me)CH— |
| 6953 | 2-Cl-6-F2CHO—Ph(Me)CH— |
| 6954 | 2-Br-3-F2CHO—Ph(Me)CH— |
| 6955 | 2-Br-4-F2CHO—Ph(Me)CH— |
| 6956 | 2-Br-5-F2CHO—Ph(Me)CH— |
| 6957 | 2-Br-6-F2CHO—Ph(Me)CH— |
| 6958 | 2-I-3-F2CHO—Ph(Me)CH— |
| 6959 | 2-I-4-F2CHO—Ph(Me)CH— |
| 6960 | 2-I-5-F2CHO—Ph(Me)CH— |
| 6961 | 2-I-6-F2CHO—Ph(Me)CH— |
| 6962 | 2-Me-3-F2CHO—Ph(Me)CH— |
| 6963 | 2-Me-4-F2CHO—Ph(Me)CH— |
| 6964 | 2-Me-5-F2CHO—Ph(Me)CH— |
| 6965 | 2-Me-6-F2CHO—Ph(Me)CH— |
| 6966 | 2-F-3-F3CCH2O—Ph(Me)CH— |
| 6967 | 2-F-4-F3CCH2O—Ph(Me)CH— |
| 6968 | 2-F-5-F3CCH2O—Ph(Me)CH— |
| 6969 | 2-F-6-F3CCH2O—Ph(Me)CH— |
| 6970 | 2-Cl-3-F3CCH2O—Ph(Me)CH— |
| 6971 | 2-Cl-4-F3CCH2O—Ph(Me)CH— |
| 6972 | 2-Cl-5-F3CCH2O—Ph(Me)CH— |
| 6973 | 2-Cl-6-F3CCH2O—Ph(Me)CH— |
| 6974 | 2-Br-3-F3CCH2O—Ph(Me)CH— |
| 6975 | 2-Br-4-F3CCH2O—Ph(Me)CH— |
| 6976 | 2-Br-5-F3CCH2O—Ph(Me)CH— |
| 6977 | 2-Br-6-F3CCH2O—Ph(Me)CH— |
| 6978 | 2-I-3-F3CCH2O—Ph(Me)CH— |
| 6979 | 2-I-4-F3CCH2O—Ph(Me)CH— |
| 6980 | 2-I-5-F3CCH2O—Ph(Me)CH— |
| 6981 | 2-I-6-F3CCH2O—Ph(Me)CH— |
| 6982 | 2-Me-3-F3CCH2O—Ph(Me)CH— |
| 6983 | 2-Me-4-F3CCH2O—Ph(Me)CH— |
| 6984 | 2-Me-5-F3CCH2O—Ph(Me)CH— |
| 6985 | 2-Me-6-F3CCH2O—Ph(Me)CH— |
| 6986 | 2-F-3-F2CHCH2O—Ph(Me)CH— |
| 6987 | 2-F-4-F2CHCH2O—Ph(Me)CH— |
| 6988 | 2-F-5-F2CHCH2O—Ph(Me)CH— |
| 6989 | 2-F-6-F2CHCH2O—Ph(Me)CH— |
| 6990 | 2-Cl-3-F2CHCH2O—Ph(Me)CH— |
| 6991 | 2-Cl-4-F2CHCH2O—Ph(Me)CH— |
| 6992 | 2-Cl-5-F2CHCH2O—Ph(Me)CH— |
| 6993 | 2-Cl-6-F2CHCH2O—Ph(Me)CH— |
| 6994 | 2-Br-3-F2CHCH2O—Ph(Me)CH— |
| 6995 | 2-Br-4-F2CHCH2O—Ph(Me)CH— |
| 6996 | 2-Br-5-F2CHCH2O—Ph(Me)CH— |
| 6997 | 2-Br-6-F2CHCH2O—Ph(Me)CH— |
| 6998 | 2-I-3-F2CHCH2O—Ph(Me)CH— |
| 6999 | 2-I-4-F2CHCH2O—Ph(Me)CH— |
| 7000 | 2-I-5-F2CHCH2O—Ph(Me)CH— |
| 7001 | 2-I-6-F2CHCH2O—Ph(Me)CH— |
| 7002 | 2-Me-3-F2CHCH2O—Ph(Me)CH— |
| 7003 | 2-Me-4-F2CHCH2O—Ph(Me)CH— |
| 7004 | 2-Me-5-F2CHCH2O—Ph(Me)CH— |
| 7005 | 2-Me-6-F2CHCH2O—Ph(Me)CH— |
| 7006 | 2-F-3-H2C=CHCH2O—Ph(Me)CH— |
| 7007 | 2-F-4-H2C=CHCH2O—Ph(Me)CH— |
| 7008 | 2-F-5-H2C=CHCH2O—Ph(Me)CH— |
| 7009 | 2-F-6-H2C=CHCH2O—Ph(Me)CH— |
| 7010 | 2-Cl-3-H2C=CHCH2O—Ph(Me)CH— |
| 7011 | 2-Cl-4-H2C=CHCH2O—Ph(Me)CH— |
| 7012 | 2-Cl-5-H2C=CHCH2O—Ph(Me)CH— |
| 7013 | 2-Cl-6-H2C=CHCH2O—Ph(Me)CH— |
| 7014 | 2-Br-3-H2C=CHCH2O—Ph(Me)CH— |
| 7015 | 2-Br-4-H2C=CHCH2O—Ph(Me)CH— |
| 7016 | 2-Br-5-H2C=CHCH2O—Ph(Me)CH— |
| 7017 | 2-Br-6-H2C=CHCH2O—Ph(Me)CH— |
| 7018 | 2-I-3-H2C=CHCH2O—Ph(Me)CH— |
| 7019 | 2-I-4-H2C=CHCH2O—Ph(Me)CH— |
| 7020 | 2-I-5-H2C=CHCH2O—Ph(Me)CH— |
| 7021 | 2-I-6-H2C=CHCH2O—Ph(Me)CH— |
| 7022 | 2-Me-3-H2C=CHCH2O—Ph(Me)CH— |
| 7023 | 2-Me-4-H2C=CHCH2O—Ph(Me)CH— |
| 7024 | 2-Me-5-H2C=CHCH2O—Ph(Me)CH— |
| 7025 | 2-Me-6-H2C=CHCH2O—Ph(Me)CH— |
| 7026 | 2-F-3-HC≡CCH2O—Ph(Me)CH— |
| 7027 | 2-F-4-HC≡CCH2O—Ph(Me)CH— |
| 7028 | 2-F-5-HC≡CCH2O—Ph(Me)CH— |
| 7029 | 2-F-6-HC≡CCH2O—Ph(Me)CH— |
| 7030 | 2-Cl-3-HC≡CCH2O—Ph(Me)CH— |
| 7031 | 2-Cl-4-HC≡CCH2O—Ph(Me)CH— |
| 7032 | 2-Cl-5-HC≡CCH2O—Ph(Me)CH— |
| 7033 | 2-Cl-6-HC≡CCH2O—Ph(Me)CH— |
| 7034 | 2-Br-3-HC≡CCH2O—Ph(Me)CH— |
| 7035 | 2-Br-4-HC≡CCH2O—Ph(Me)CH— |
| 7036 | 2-Br-5-HC≡CCH2O—Ph(Me)CH— |
| 7037 | 2-Br-6-HC≡CCH2O—Ph(Me)CH— |
| 7038 | 2-I-3-HC≡CCH2O—Ph(Me)CH— |
| 7039 | 2-I-4-HC≡CCH2O—Ph(Me)CH— |
| 7040 | 2-I-5-HC≡CCH2O—Ph(Me)CH— |
| 7041 | 2-I-6-HC≡CCH2O—Ph(Me)CH— |
| 7042 | 2-Me-3-HC≡CCH2O—Ph(Me)CH— |
| 7043 | 2-Me-4-HC≡CCH2O—Ph(Me)CH— |
| 7044 | 2-Me-5-HC≡CCH2O—Ph(Me)CH— |
| 7045 | 2-Me-6-HC≡CCH2O—Ph(Me)CH— |
| 7046 | 2-F-3-Ac—Ph(Me)CH— |
| 7047 | 2-F-4-Ac—Ph(Me)CH— |
| 7048 | 2-F-5-Ac—Ph(Me)CH— |
| 7049 | 2-F-6-Ac—Ph(Me)CH— |
| 7050 | 2-Cl-3-Ac—Ph(Me)CH— |
| 7051 | 2-Cl-4-Ac—Ph(Me)CH— |
| 7052 | 2-Cl-5-Ac—Ph(Me)CH— |
| 7053 | 2-Cl-6-Ac—Ph(Me)CH— |
| 7054 | 2-Br-3-Ac—Ph(Me)CH— |

TABLE 2-continued

| No. | Z |
|---|---|
| 7055 | 2-Br-4-Ac—Ph(Me)CH— |
| 7056 | 2-Br-5-Ac—Ph(Me)CH— |
| 7057 | 2-Br-6-Ac—Ph(Me)CH— |
| 7058 | 2-I-3-Ac—Ph(Me)CH— |
| 7059 | 2-I-4-Ac—Ph(Me)CH— |
| 7060 | 2-I-5-Ac—Ph(Me)CH— |
| 7061 | 2-I-6-Ac—Ph(Me)CH— |
| 7062 | 2-Me-3-Ac—Ph(Me)CH— |
| 7063 | 2-Me-4-Ac—Ph(Me)CH— |
| 7064 | 2-Me-5-Ac—Ph(Me)CH— |
| 7065 | 2-Me-6-Ac—Ph(Me)CH— |
| 7066 | 2-F-3-MeOC(=O)—Ph(Me)CH— |
| 7067 | 2-F-4-MeOC(=O)—Ph(Me)CH— |
| 7068 | 2-F-5-MeOC(=O)—Ph(Me)CH— |
| 7069 | 2-F-6-MeOC(=O)—Ph(Me)CH— |
| 7070 | 2-Cl-3-MeOC(=O)—Ph(Me)CH— |
| 7071 | 2-Cl-4-MeOC(=O)—Ph(Me)CH— |
| 7072 | 2-Cl-5-MeOC(=O)—Ph(Me)CH— |
| 7073 | 2-Cl-6-MeOC(=O)—Ph(Me)CH— |
| 7074 | 2-Br-3-MeOC(=O)—Ph(Me)CH— |
| 7075 | 2-Br-4-MeOC(=O)—Ph(Me)CH— |
| 7076 | 2-Br-5-MeOC(=O)—Ph(Me)CH— |
| 7077 | 2-Br-6-MeOC(=O)—Ph(Me)CH— |
| 7178 | 2-I-3-MeOC(=O)—Ph(Me)CH— |
| 7179 | 2-I-4-MeOC(=O)—Ph(Me)CH— |
| 7180 | 2-I-5-MeOC(=O)—Ph(Me)CH— |
| 7181 | 2-I-6-MeOC(=O)—Ph(Me)CH— |
| 7082 | 2-Me-3-MeOC(=O)—Ph(Me)CH— |
| 7083 | 2-Me-4-MeOC(=O)—Ph(Me)CH— |
| 7084 | 2-Me-5-MeOC(=O)—Ph(Me)CH— |
| 7085 | 2-Me-6-MeOC(=O)—Ph(Me)CH— |
| 7086 | 2-F-3-EtOC(=O)—Ph(Me)CH— |
| 7086 | 2-F-4-EtOC(=O)—Ph(Me)CH— |
| 7087 | 2-F-5-EtOC(=O)—Ph(Me)CH— |
| 7088 | 2-F-5-EtOC(=O)—Ph(Me)CH— |
| 7089 | 2-F-6-EtOC(=O)—Ph(Me)CH— |
| 7090 | 2-Cl-3-EtOC(=O)—Ph(Me)CH— |
| 7091 | 2-Cl-4-EtOC(=O)—Ph(Me)CH— |
| 7092 | 2-Cl-5-EtOC(=O)—Ph(Me)CH— |
| 7093 | 2-Cl-6-EtOC(=O)—Ph(Me)CH— |
| 7094 | 2-Br-3-EtOC(=O)—Ph(Me)CH— |
| 7095 | 2-Br-4-EtOC(=O)—Ph(Me)CH— |
| 7096 | 2-Br-5-EtOC(=O)—Ph(Me)CH— |
| 7097 | 2-Br-6-EtOC(=O)—Ph(Me)CH— |
| 7098 | 2-I-3-EtOC(=O)—Ph(Me)CH— |
| 7099 | 2-I-4-EtOC(=O)—Ph(Me)CH— |
| 7100 | 2-I-5-EtOC(=O)—Ph(Me)CH— |
| 7101 | 2-I-6-EtOC(=O)—Ph(Me)CH— |
| 7102 | 2-Me-3-EtOC(=O)—Ph(Me)CH— |
| 7103 | 2-Me-4-EtOC(=O)—Ph(Me)CH— |
| 7104 | 2-Me-5-EtOC(=O)—Ph(Me)CH— |
| 7105 | 2-Me-6-EtOC(=O)—Ph(Me)CH— |
| 7106 | 2-F-3-AcO—Ph(Me)CH— |
| 7107 | 2-F-4-AcO—Ph(Me)CH— |
| 7108 | 2-F-5-AcO—Ph(Me)CH— |
| 7109 | 2-F-6-AcO—Ph(Me)CH— |
| 7110 | 2-Cl-3-AcO—Ph(Me)CH— |
| 7111 | 2-Cl-4-AcO—Ph(Me)CH— |
| 7112 | 2-Cl-5-AcO—Ph(Me)CH— |
| 7113 | 2-Cl-6-AcO—Ph(Me)CH— |
| 7114 | 2-Br-3-AcO—Ph(Me)CH— |
| 7115 | 2-Br-4-AcO—Ph(Me)CH— |
| 7116 | 2-Br-5-AcO—Ph(Me)CH— |
| 7117 | 2-Br-6-AcO—Ph(Me)CH— |
| 7118 | 2-I-3-AcO—Ph(Me)CH— |
| 7119 | 2-I-4-AcO—Ph(Me)CH— |
| 7120 | 2-I-5-AcO—Ph(Me)CH— |
| 7121 | 2-I-6-AcO—Ph(Me)CH— |
| 7122 | 2-Me-3-AcO—Ph(Me)CH— |
| 7123 | 2-Me-4-AcO—Ph(Me)CH— |
| 7124 | 2-Me-5-AcO—Ph(Me)CH— |
| 7125 | 2-Me-6-AcO—Ph(Me)CH— |
| 7126 | 2-F-3-MeOC(=O)O—Ph(Me)CH— |
| 7127 | 2-F-4-MeOC(=O)O—Ph(Me)CH— |
| 7128 | 2-F-5-MeOC(=O)O—Ph(Me)CH— |
| 7129 | 2-F-6-MeOC(=O)O—Ph(Me)CH— |
| 7130 | 2-Cl-3-MeOC(=O)O—Ph(Me)CH— |
| 7131 | 2-Cl-4-MeOC(=O)O—Ph(Me)CH— |
| 7132 | 2-Cl-5-MeOC(=O)O—Ph(Me)CH— |
| 7133 | 2-Cl-6-MeOC(=O)O—Ph(Me)CH— |
| 7134 | 2-Br-3-MeOC(=O)O—Ph(Me)CH— |
| 7135 | 2-Br-4-MeOC(=O)O—Ph(Me)CH— |
| 7136 | 2-Br-5-MeOC(=O)O—Ph(Me)CH— |
| 7137 | 2-Br-6-MeOC(=O)O—Ph(Me)CH— |
| 7138 | 2-I-3-MeOC(=O)O—Ph(Me)CH— |
| 7139 | 2-I-4-MeOC(=O)O—Ph(Me)CH— |
| 7140 | 2-I-5-MeOC(=O)O—Ph(Me)CH— |
| 7141 | 2-I-6-MeOC(=O)O—Ph(Me)CH— |
| 7142 | 2-Me-3-MeOC(=O)O—Ph(Me)CH— |
| 7143 | 2-Me-4-MeOC(=O)O—Ph(Me)CH— |
| 7144 | 2-Me-5-MeOC(=O)O—Ph(Me)CH— |
| 7145 | 2-Me-6-MeOC(=O)O—Ph(Me)CH— |
| 7146 | 2-F-3-EtOC(=O)O—Ph(Me)CH— |
| 7147 | 2-F-4-EtOC(=O)O—Ph(Me)CH— |
| 7148 | 2-F-5-EtOC(=O)O—Ph(Me)CH— |
| 7149 | 2-F-6-EtOC(=O)O—Ph(Me)CH— |
| 7150 | 2-Cl-3-EtOC(=O)O—Ph(Me)CH— |
| 7151 | 2-Cl-4-EtOC(=O)O—Ph(Me)CH— |
| 7152 | 2-Cl-5-EtOC(=O)O—Ph(Me)CH— |
| 7153 | 2-Cl-6-EtOC(=O)O—Ph(Me)CH— |
| 7154 | 2-Br-3-EtOC(=O)O—Ph(Me)CH— |
| 7155 | 2-Br-4-EtOC(=O)O—Ph(Me)CH— |
| 7156 | 2-Br-5-EtOC(=O)O—Ph(Me)CH— |
| 7157 | 2-Br-6-EtOC(=O)O—Ph(Me)CH— |
| 7158 | 2-I-3-EtOC(=O)O—Ph(Me)CH— |
| 7159 | 2-I-4-EtOC(=O)O—Ph(Me)CH— |
| 7160 | 2-I-5-EtOC(=O)O—Ph(Me)CH— |
| 7161 | 2-I-6-EtOC(=O)O—Ph(Me)CH— |
| 7162 | 2-Me-3-EtOC(=O)O—Ph(Me)CH— |
| 7163 | 2-Me-4-EtOC(=O)O—Ph(Me)CH— |
| 7164 | 2-Me-5-EtOC(=O)O—Ph(Me)CH— |
| 7165 | 2-Me-6-EtOC(=O)O—Ph(Me)CH— |
| 7166 | 2-F-3-(1,3-dioxolan-2-yl)-Ph(Me)CH— |
| 7167 | 2-F-4-(1,3-dioxolan-2-yl)-Ph(Me)CH— |
| 7168 | 2-F-5-(1,3-dioxolan-2-yl)-Ph(Me)CH— |
| 7169 | 2-F-6-(1,3-dioxolan-2-yl)-Ph(Me)CH— |
| 7170 | 2-Cl-3-(1,3-dioxolan-2-yl)-Ph(Me)CH— |
| 7171 | 2-Cl-4-(1,3-dioxolan-2-yl)-Ph(Me)CH— |
| 7173 | 2-Cl-5-(1,3-dioxolan-2-yl)-Ph(Me)CH— |
| 7172 | 2-Cl-6-(1,3-dioxolan-2-yl)-Ph(Me)CH— |
| 7174 | 2-Br-3-(1,3-dioxolan-2-yl)-Ph(Me)CH— |
| 7175 | 2-Br-4-(1,3-dioxolan-2-yl)-Ph(Me)CH— |
| 7176 | 2-Br-5-(1,3-dioxolan-2-yl)-Ph(Me)CH— |
| 7177 | 2-Br-6-(1,3-dioxolan-2-yl)-Ph(Me)CH— |
| 7178 | 2-I-3-(1,3-dioxolan-2-yl)-Ph(Me)CH— |
| 7179 | 2-I-4-(1,3-dioxolan-2-yl)-Ph(Me)CH— |
| 7180 | 2-I-5-(1,3-dioxolan-2-yl)-Ph(Me)CH— |
| 7181 | 2-I-6-(1,3-dioxolan-2-yl)-Ph(Me)CH— |
| 7182 | 2-Me-3-(1,3-dioxolan-2-yl)-Ph(Me)CH— |
| 7183 | 2-Me-4-(1,3-dioxolan-2-yl)-Ph(Me)CH— |
| 7184 | 2-Me-5-(1,3-dioxolan-2-yl)-Ph(Me)CH— |
| 7185 | 2-Me-6-(1,3-dioxolan-2-yl)-Ph(Me)CH— |
| 7186 | 2-F-3-(1,3-dioxan-2-yl)-Ph(Me)CH— |
| 7187 | 2-F-4-(1,3-dioxan-2-yl)-Ph(Me)CH— |
| 7188 | 2-F-5-(1,3-dioxan-2-yl)-Ph(Me)CH— |
| 7189 | 2-F-6-(1,3-dioxan-2-yl)-Ph(Me)CH— |
| 7190 | 2-Cl-3-(1,3-dioxan-2-yl)-Ph(Me)CH— |
| 7191 | 2-Cl-4-(1,3-dioxan-2-yl)-Ph(Me)CH— |
| 7193 | 2-Cl-5-(1,3-dioxan-2-yl)-Ph(Me)CH— |
| 7192 | 2-Cl-6-(1,3-dioxan-2-yl)-Ph(Me)CH— |
| 7194 | 2-Br-3-(1,3-dioxan-2-yl)-Ph(Me)CH— |
| 7195 | 2-Br-4-(1,3-dioxan-2-yl)-Ph(Me)CH— |
| 7196 | 2-Br-5-(1,3-dioxan-2-yl)-Ph(Me)CH— |
| 7197 | 2-Br-6-(1,3-dioxan-2-yl)-Ph(Me)CH— |
| 7198 | 2-I-3-(1,3-dioxan-2-yl)-Ph(Me)CH— |
| 7199 | 2-I-4-(1,3-dioxan-2-yl)-Ph(Me)CH— |
| 7200 | 2-I-5-(1,3-dioxan-2-yl)-Ph(Me)CH— |
| 7201 | 2-I-6-(1,3-dioxan-2-yl)-Ph(Me)CH— |
| 7202 | 2-Me-3-(1,3-dioxan-2-yl)-Ph(Me)CH— |
| 7203 | 2-Me-4-(1,3-dioxan-2-yl)-Ph(Me)CH— |
| 7204 | 2-Me-5-(1,3-dioxan-2-yl)-Ph(Me)CH— |
| 7205 | 2-Me-6-(1,3-dioxan-2-yl)-Ph(Me)CH— |
| 7206 | 2-F-3-MeS—Ph(Me)CH— |
| 7207 | 2-F-4-MeS—Ph(Me)CH— |
| 7208 | 2-F-5-MeS—Ph(Me)CH— |
| 7209 | 2-F-6-MeS—Ph(Me)CH— |
| 7210 | 2-Cl-3-MeS—Ph(Me)CH— |

TABLE 2-continued

| No. | Z |
|---|---|
| 7211 | 2-Cl-4-MeS—Ph(Me)CH— |
| 7212 | 2-Cl-5-MeS—Ph(Me)CH— |
| 7213 | 2-Cl-6-MeS—Ph(Me)CH— |
| 7214 | 2-Br-3-MeS—Ph(Me)CH— |
| 7215 | 2-Br-4-MeS—Ph(Me)CH— |
| 7216 | 2-Br-5-MeS—Ph(Me)CH— |
| 7217 | 2-Br-6-MeS—Ph(Me)CH— |
| 7218 | 2-I-3-MeS—Ph(Me)CH— |
| 7219 | 2-I-4-MeS—Ph(Me)CH— |
| 7220 | 2-I-5-MeS—Ph(Me)CH— |
| 7221 | 2-I-6-MeS—Ph(Me)CH— |
| 7222 | 2-Me-3-MeS—Ph(Me)CH— |
| 7223 | 2-Me-4-MeS—Ph(Me)CH— |
| 7224 | 2-Me-5-MeS—Ph(Me)CH— |
| 7225 | 2-Me-6-MeS—Ph(Me)CH— |
| 7226 | 2-F-3-MeS(O)—Ph(Me)CH— |
| 7227 | 2-F-4-MeS(O)—Ph(Me)CH— |
| 7228 | 2-F-5-MeS(O)—Ph(Me)CH— |
| 7229 | 2-F-6-MeS(O)—Ph(Me)CH— |
| 7230 | 2-Cl-3-MeS(O)—Ph(Me)CH— |
| 7231 | 2-Cl-4-MeS(O)—Ph(Me)CH— |
| 7232 | 2-Cl-5-MeS(O)—Ph(Me)CH— |
| 7233 | 2-Cl-6-MeS(O)—Ph(Me)CH— |
| 7234 | 2-Br-3-MeS(O)—Ph(Me)CH— |
| 7235 | 2-Br-4-MeS(O)—Ph(Me)CH— |
| 7236 | 2-Br-5-MeS(O)—Ph(Me)CH— |
| 7237 | 2-Br-6-MeS(O)—Ph(Me)CH— |
| 7238 | 2-I-3-MeS(O)—Ph(Me)CH— |
| 7239 | 2-I-4-MeS(O)—Ph(Me)CH— |
| 7240 | 2-I-5-MeS(O)—Ph(Me)CH— |
| 7241 | 2-I-6-MeS(O)—Ph(Me)CH— |
| 7242 | 2-Me-3-MeS(O)—Ph(Me)CH— |
| 7243 | 2-Me-4-MeS(O)—Ph(Me)CH— |
| 7244 | 2-Me-5-MeS(O)—Ph(Me)CH— |
| 7245 | 2-Me-6-MeS(O)—Ph(Me)CH— |
| 7246 | 2-F-3-MeSO2—Ph(Me)CH— |
| 7247 | 2-F-4-MeSO2—Ph(Me)CH— |
| 7248 | 2-F-5-MeSO2—Ph(Me)CH— |
| 7249 | 2-F-6-MeSO2—Ph(Me)CH— |
| 7250 | 2-Cl-3-MeSO2—Ph(Me)CH— |
| 7251 | 2-Cl-4-MeSO2—Ph(Me)CH— |
| 7252 | 2-Cl-5-MeSO2—Ph(Me)CH— |
| 7253 | 2-Cl-6-MeSO2—Ph(Me)CH— |
| 7254 | 2-Br-3-MeSO2—Ph(Me)CH— |
| 7255 | 2-Br-4-MeSO2—Ph(Me)CH— |
| 7256 | 2-Br-5-MeSO2—Ph(Me)CH— |
| 7257 | 2-Br-6-MeSO2—Ph(Me)CH— |
| 7258 | 2-I-3-MeSO2—Ph(Me)CH— |
| 7259 | 2-I-4-MeSO2—Ph(Me)CH— |
| 7260 | 2-I-5-MeSO2—Ph(Me)CH— |
| 7261 | 2-I-6-MeSO2—Ph(Me)CH— |
| 7262 | 2-Me-3-MeSO2—Ph(Me)CH— |
| 7263 | 2-Me-4-MeSO2—Ph(Me)CH— |
| 7264 | 2-Me-5-MeSO2—Ph(Me)CH— |
| 7265 | 2-Me-6-MeSO2—Ph(Me)CH— |
| 7266 | 2-F-3-ClCH2S—Ph(Me)CH— |
| 7267 | 2-F-4-ClCH2S—Ph(Me)CH— |
| 7268 | 2-F-5-ClCH2S—Ph(Me)CH— |
| 7269 | 2-F-6-ClCH2S—Ph(Me)CH— |
| 7270 | 2-Cl-3-ClCH2S—Ph(Me)CH— |
| 7271 | 2-Cl-4-ClCH2S—Ph(Me)CH— |
| 7272 | 2-Cl-5-ClCH2S—Ph(Me)CH— |
| 7273 | 2-Cl-6-ClCH2S—Ph(Me)CH— |
| 7274 | 2-Br-3-ClCH2S—Ph(Me)CH— |
| 7275 | 2-Br-4-ClCH2S—Ph(Me)CH— |
| 7276 | 2-Br-5-ClCH2S—Ph(Me)CH— |
| 7277 | 2-Br-6-ClCH2S—Ph(Me)CH— |
| 7278 | 2-I-3-ClCH2S—Ph(Me)CH— |
| 7279 | 2-I-4-ClCH2S—Ph(Me)CH— |
| 7280 | 2-I-5-ClCH2S—Ph(Me)CH— |
| 7281 | 2-I-6-ClCH2S—Ph(Me)CH— |
| 7282 | 2-Me-3-ClCH2S—Ph(Me)CH— |
| 7283 | 2-Me-4-ClCH2S—Ph(Me)CH— |
| 7284 | 2-Me-5-ClCH2S—Ph(Me)CH— |
| 7285 | 2-Me-6-ClCH2S—Ph(Me)CH— |
| 7286 | 2-F-3-ClCH2S(O)—Ph(Me)CH— |
| 7287 | 2-F-4-ClCH2S(O)—Ph(Me)CH— |
| 7288 | 2-F-5-ClCH2S(O)—Ph(Me)CH— |
| 7289 | 2-F-6-ClCH2S(O)—Ph(Me)CH— |
| 7290 | 2-Cl-3-ClCH2S(O)—Ph(Me)CH— |
| 7291 | 2-Cl-4-ClCH2S(O)—Ph(Me)CH— |
| 7292 | 2-Cl-5-ClCH2S(O)—Ph(Me)CH— |
| 7293 | 2-Cl-6-ClCH2S(O)—Ph(Me)CH— |
| 7294 | 2-Br-3-ClCH2S(O)—Ph(Me)CH— |
| 7295 | 2-Br-4-ClCH2S(O)—Ph(Me)CH— |
| 7296 | 2-Br-5-ClCH2S(O)—Ph(Me)CH— |
| 7297 | 2-Br-6-ClCH2S(O)—Ph(Me)CH— |
| 7298 | 2-I-3-ClCH2S(O)—Ph(Me)CH— |
| 7299 | 2-I-4-ClCH2S(O)—Ph(Me)CH— |
| 7300 | 2-I-5-ClCH2S(O)—Ph(Me)CH— |
| 7301 | 2-I-6-ClCH2S(O)—Ph(Me)CH— |
| 7302 | 2-Me-3-ClCH2S(O)—Ph(Me)CH— |
| 7303 | 2-Me-4-ClCH2S(O)—Ph(Me)CH— |
| 7304 | 2-Me-5-ClCH2S(O)—Ph(Me)CH— |
| 7305 | 2-Me-6-ClCH2S(O)—Ph(Me)CH— |
| 7306 | 2-F-3-ClCH2SO2—Ph(Me)CH— |
| 7307 | 2-F-4-ClCH2SO2—Ph(Me)CH— |
| 7308 | 2-F-5-ClCH2SO2—Ph(Me)CH— |
| 7309 | 2-F-6-ClCH2SO2—Ph(Me)CH— |
| 7310 | 2-Cl-3-ClCH2SO2—Ph(Me)CH— |
| 7311 | 2-Cl-4-ClCH2SO2—Ph(Me)CH— |
| 7312 | 2-Cl-5-ClCH2SO2—Ph(Me)CH— |
| 7313 | 2-Cl-6-ClCH2SO2—Ph(Me)CH— |
| 7314 | 2-Br-3-ClCH2SO2—Ph(Me)CH— |
| 7315 | 2-Br-4-ClCH2SO2—Ph(Me)CH— |
| 7316 | 2-Br-5-ClCH2SO2—Ph(Me)CH— |
| 7317 | 2-Br-6-ClCH2SO2—Ph(Me)CH— |
| 7318 | 2-I-3-ClCH2SO2—Ph(Me)CH— |
| 7319 | 2-I-4-ClCH2SO2—Ph(Me)CH— |
| 7320 | 2-I-5-ClCH2SO2—Ph(Me)CH— |
| 7321 | 2-I-6-ClCH2SO2—Ph(Me)CH— |
| 7322 | 2-Me-3-ClCH2SO2—Ph(Me)CH— |
| 7323 | 2-Me-4-ClCH2SO2—Ph(Me)CH— |
| 7324 | 2-Me-5-ClCH2SO2—Ph(Me)CH— |
| 7325 | 2-Me-6-ClCH2SO2—Ph(Me)CH— |
| 7326 | 3,5-di-MeO—Ph(Me)CH— |
| 7327 | 3,5-di-EtO—Ph(Me)CH— |
| 7328 | 3,5-di-F—Ph(Me)CH— |
| 7329 | 3,5-di-Cl—Ph(Me)CH— |
| 7330 | 3,5-di-Br—Ph(Me)CH— |
| 7331 | 3,5-di-I—Ph(Me)CH— |
| 7332 | 3,5-di-Me—Ph(Me)CH— |
| 7333 | 3-F-5-Me—Ph(Me)CH— |
| 7334 | 3-Cl-5-Me—Ph(Me)CH— |
| 7335 | 3-Br-5-Me—Ph(Me)CH— |
| 7336 | 3-I-5-Me—Ph(Me)CH— |
| 7337 | 3-F-5-MeO—Ph(Me)CH— |
| 7338 | 3-Cl-5-MeO—Ph(Me)CH— |
| 7339 | 3-Br-5-MeO—Ph(Me)CH— |
| 7340 | 3-I-5-MeO—Ph(Me)CH— |
| 7341 | 5-F-3-EtO—Ph(Me)CH— |
| 7342 | 3-Cl-5-EtO—Ph(Me)CH— |
| 7343 | 3-Br-5-EtO—Ph(Me)CH— |
| 7344 | 5-I-3-EtO—Ph(Me)CH— |
| 7345 | 3-F-5-N≡CCH2O—Ph(Me)CH— |
| 7346 | 3-Cl-5-N≡CCH2O—Ph(Me)CH— |
| 7347 | 3-Br-5-N≡CCH2O—Ph(Me)CH— |
| 7348 | 3-I-5-N≡CCH2O—Ph(Me)CH— |
| 7349 | 3-F-5-MeOCH2O—Ph(Me)CH— |
| 7350 | 3-Cl-5-MeOCH2O—Ph(Me)CH— |
| 7351 | 3-Br-5-MeOCH2O—Ph(Me)CH— |
| 7352 | 3-I-5-MeOCH2O—Ph(Me)CH— |
| 7353 | 5-F-2-MeO—Ph(Me)CH— |
| 7354 | 5-Cl-2-MeO—Ph(Me)CH— |
| 7355 | 5-Br-2-MeO—Ph(Me)CH— |
| 7356 | 5-I-2-MeO—Ph(Me)CH— |
| 7357 | 5-Me-2-MeO—Ph(Me)CH— |
| 7358 | 2-F-3,5-di-MeO—Ph(Me)CH— |
| 7359 | 2-F-3,5-di-EtO—Ph(Me)CH— |
| 7360 | 2,3,5-tri-F—Ph(Me)CH— |
| 7361 | 2-F-3,5-di-Cl—Ph(Me)CH— |
| 7362 | 3,5-di-Br-2-F—Ph(Me)CH— |
| 7363 | 2-F-3,5-di-I—Ph(Me)CH— |
| 7364 | 2-F-3,5-di-Me—Ph(Me)CH— |
| 7365 | 2,3-di-F-5-Me—Ph(Me)CH— |
| 7366 | 2,5-di-F-3-Me—Ph(Me)CH— |

TABLE 2-continued

| No. | Z |
|---|---|
| 7367 | 3-Cl-2-F-5-Me—Ph(Me)CH— |
| 7368 | 5-Cl-2-F-3-Me—Ph(Me)CH— |
| 7369 | 3-Br-2-F-5-Me—Ph(Me)CH— |
| 7370 | 5-Br-2-F-3-Me—Ph(Me)CH— |
| 7371 | 2-F-3-I-5-Me—Ph(Me)CH— |
| 7372 | 2-F-5-I-3-Me—Ph(Me)CH— |
| 7373 | 2,3-di-F-5-MeO—Ph(Me)CH— |
| 7374 | 2,5-di-F-3-MeO—Ph(Me)CH— |
| 7375 | 3-Cl-2-F-5-MeO—Ph(Me)CH— |
| 7376 | 5-Cl-2-F-3-MeO—Ph(Me)CH— |
| 7377 | 3-Br-2-F-5-MeO—Ph(Me)CH— |
| 7378 | 5-Br-2-F-3-MeO—Ph(Me)CH— |
| 7379 | 2-F-3-I-5-MeO—Ph(Me)CH— |
| 7380 | 2-F-5-I-3-MeO—Ph(Me)CH— |
| 7381 | 2,3-di-F-5-EtO—Ph(Me)CH— |
| 7382 | 2,5-di-F-3-EtO—Ph(Me)CH— |
| 7383 | 3-Cl-2-F-5-EtO—Ph(Me)CH— |
| 7384 | 5-Cl-2-F-3-EtO—Ph(Me)CH— |
| 7385 | 3-Br-2-F-5-EtO—Ph(Me)CH— |
| 7386 | 5-Br-2-F-3-EtO—Ph(Me)CH— |
| 7387 | 2-F-3-I-5-EtO—Ph(Me)CH— |
| 7388 | 2-F-5-I-3-EtO—Ph(Me)CH— |
| 7389 | 2,3-di-F-5-N≡CCH2O—Ph(Me)CH— |
| 7390 | 2,5-di-F-3-N≡CCH2O—Ph(Me)CH— |
| 7391 | 3-Cl-2-F-5-N≡CCH2O—Ph(Me)CH— |
| 7392 | 5-Cl-2-F-3-N≡CCH2O—Ph(Me)CH— |
| 7393 | 3-Br-2-F-5-N≡CCH2O—Ph(Me)CH— |
| 7394 | 5-Br-2-F-3-N≡CCH2O—Ph(Me)CH— |
| 7395 | 2-F-3-I-5-N≡CCH2O—Ph(Me)CH— |
| 7396 | 2-F-5-I-3-N≡CCH2O—Ph(Me)CH— |
| 7397 | 2,3-di-F-5-MeOCH2O—Ph(Me)CH— |
| 7398 | 2,5-di-F-3-MeOCH2O—Ph(Me)CH— |
| 7399 | 3-Cl-2-F-5-MeOCH2O—Ph(Me)CH— |
| 7400 | 5-Cl-2-F-3-MeOCH2O—Ph(Me)CH— |
| 7401 | 3-Br-2-F-5-MeOCH2O—Ph(Me)CH— |
| 7402 | 5-Br-2-F-3-MeOCH2O—Ph(Me)CH— |
| 7403 | 2-F-3-I-5-MeOCH2O—Ph(Me)CH— |
| 7404 | 2-F-5-I-3-MeOCH2O—Ph(Me)CH— |
| 7405 | 2-Cl-3,5-di-MeO—Ph(Me)CH— |
| 7406 | 2-Cl-3,5-di-EtO—Ph(Me)CH— |
| 7407 | 2-Cl-3,5-di-F—Ph(Me)CH— |
| 7408 | 2,3,5-tri-Cl—Ph(Me)CH— |
| 7409 | 3,5-di-Br-2-Cl—Ph(Me)CH— |
| 7410 | 2-Cl-3,5-di-I—Ph(Me)CH— |
| 7411 | 2-Cl-3,5-di-Me—Ph(Me)CH— |
| 7412 | 2-Cl-3-F-5-Me—Ph(Me)CH— |
| 7413 | 2-Cl-5-F-3-Me—Ph(Me)CH— |
| 7414 | 2,3-di-Cl-5-Me—Ph(Me)CH— |
| 7415 | 2,5-di-Cl-3-Me—Ph(Me)CH— |
| 7416 | 3-Br-2-Cl-5-Me—Ph(Me)CH— |
| 7417 | 5-Br-2-Cl-3-Me—Ph(Me)CH— |
| 7418 | 2-Cl-3-I-5-Me—Ph(Me)CH— |
| 7419 | 2-Cl-5-I-3-Me—Ph(Me)CH— |
| 7420 | 2-Cl-3-F-5-MeO—Ph(Me)CH— |
| 7421 | 2-Cl-5-F-3-MeO—Ph(Me)CH— |
| 7422 | 2,3-di-Cl-5-MeO—Ph(Me)CH— |
| 7423 | 2,5-di-Cl-3-MeO—Ph(Me)CH— |
| 7424 | 3-Br-2-Cl-5-MeO—Ph(Me)CH— |
| 7425 | 5-Br-2-Cl-3-MeO—Ph(Me)CH— |
| 7426 | 2-Cl-3-I-5-MeO—Ph(Me)CH— |
| 7427 | 2-Cl-5-I-3-MeO—Ph(Me)CH— |
| 7428 | 2-Cl-3-F-5-EtO—Ph(Me)CH— |
| 7429 | 2-Cl-5-F-3-EtO—Ph(Me)CH— |
| 7430 | 2,3-di-Cl-5-EtO—Ph(Me)CH— |
| 7431 | 2,5-di-Cl-3-EtO—Ph(Me)CH— |
| 7432 | 3-Br-2-Cl-5-EtO—Ph(Me)CH— |
| 7433 | 5-Br-2-Cl-3-EtO—Ph(Me)CH— |
| 7434 | 2-Cl-3-I-5-EtO—Ph(Me)CH— |
| 7435 | 2-Cl-5-I-3-EtO—Ph(Me)CH— |
| 7436 | 2-Cl-3-F-5-N≡CCH2O—Ph(Me)CH— |
| 7437 | 2-Cl-5-F-3-N≡CCH2O—Ph(Me)CH— |
| 7438 | 2,3-di-Cl-5-N≡CCH2O—Ph(Me)CH— |
| 7439 | 2,5-di-Cl-3-N≡CCH2O—Ph(Me)CH— |
| 7440 | 3-Br-2-Cl-5-N≡CCH2O—Ph(Me)CH— |
| 7441 | 5-Br-2-Cl-3-N≡CCH2O—Ph(Me)CH— |
| 7442 | 2-Cl-3-I-5-N≡CCH2O—Ph(Me)CH— |
| 7443 | 2-Cl-5-I-3-N≡CCH2O—Ph(Me)CH— |
| 7444 | 2-Cl-3-F-5-MeOCH2O—Ph(Me)CH— |
| 7445 | 2-Cl-5-F-3-MeOCH2O—Ph(Me)CH— |
| 7446 | 2,3-di-Cl-5-MeOCH2O—Ph(Me)CH— |
| 7447 | 2,5-di-Cl-3-MeOCH2O—Ph(Me)CH— |
| 7448 | 3-Br-2-Cl-5-MeOCH2O—Ph(Me)CH— |
| 7449 | 5-Br-2-Cl-3-MeOCH2O—Ph(Me)CH— |
| 7450 | 2-Cl-3-I-5-MeOCH2O—Ph(Me)CH— |
| 7451 | 2-Cl-5-I-3-MeOCH2O—Ph(Me)CH— |
| 7452 | 2-Br-3,5-di-MeO—Ph(Me)CH— |
| 7453 | 2-Br-3,5-di-EtO—Ph(Me)CH— |
| 7454 | 2-Br-3,5-di-F—Ph(Me)CH— |
| 7455 | 2-Br-3,5-di-Cl—Ph(Me)CH— |
| 7456 | 2,3,5-tri-Br—Ph(Me)CH— |
| 7457 | 2-Br-3,5-di-I—Ph(Me)CH— |
| 7458 | 2-Br-3,5-di-Me—Ph(Me)CH— |
| 7459 | 2-Br-3-F-5-Me—Ph(Me)CH— |
| 7460 | 2-Br-5-F-3-Me—Ph(Me)CH— |
| 7461 | 2-Br-3-Cl-5-Me—Ph(Me)CH— |
| 7462 | 2-Br-5-Cl-3-Me—Ph(Me)CH— |
| 7463 | 2,3-di-Br-5-Me—Ph(Me)CH— |
| 7464 | 2,5-di-Br-3-Me—Ph(Me)CH— |
| 7465 | 2-Br-3-I-5-Me—Ph(Me)CH— |
| 7466 | 2-Br-5-I-3-Me—Ph(Me)CH— |
| 7467 | 2-Br-3-F-5-MeO—Ph(Me)CH— |
| 7468 | 2-Br-5-F-3-MeO—Ph(Me)CH— |
| 7469 | 2-Br-3-Cl-5-MeO—Ph(Me)CH— |
| 7470 | 2-Br-5-Cl-3-MeO—Ph(Me)CH— |
| 7471 | 2,3-di-Br-5-MeO—Ph(Me)CH— |
| 7472 | 2,5-di-Br-3-MeO—Ph(Me)CH— |
| 7473 | 2-Br-3-I-5-MeO—Ph(Me)CH— |
| 7474 | 2-Br-5-I-3-MeO—Ph(Me)CH— |
| 7475 | 2-Br-3-F-5-EtO—Ph(Me)CH— |
| 7476 | 2-Br-5-F-3-EtO—Ph(Me)CH— |
| 7477 | 2-Br-3-Cl-5-EtO—Ph(Me)CH— |
| 7478 | 2-Br-5-Cl-3-EtO—Ph(Me)CH— |
| 7479 | 2,3-di-Br-5-EtO—Ph(Me)CH— |
| 7480 | 2,5-di-Br-3-EtO—Ph(Me)CH— |
| 7481 | 2-Br-3-I-5-EtO—Ph(Me)CH— |
| 7482 | 2-Br-5-I-3-EtO—Ph(Me)CH— |
| 7483 | 2-Br-3-F-5-N≡CCH2O—Ph(Me)CH— |
| 7484 | 2-Br-5-F-3-N≡CCH2O—Ph(Me)CH— |
| 7485 | 2-Br-3-Cl-5-N≡CCH2O—Ph(Me)CH— |
| 7486 | 2-Br-5-Cl-3-N≡CCH2O—Ph(Me)CH— |
| 7487 | 2,3-di-Br-5-N≡CCH2O—Ph(Me)CH— |
| 7488 | 2,5-di-Br-3-N≡CCH2O—Ph(Me)CH— |
| 7489 | 2-Br-3-I-5-N≡CCH2O—Ph(Me)CH— |
| 7490 | 2-Br-5-I-3-N≡CCH2O—Ph(Me)CH— |
| 7491 | 2-Br-3-F-5-MeOCH2O—Ph(Me)CH— |
| 7492 | 2-Br-5-F-3-MeOCH2O—Ph(Me)CH— |
| 7493 | 2-Br-3-Cl-5-MeOCH2O—Ph(Me)CH— |
| 7494 | 2-Br-5-Cl-3-MeOCH2O—Ph(Me)CH— |
| 7495 | 2,3-di-Br-5-MeOCH2O—Ph(Me)CH— |
| 7496 | 2,5-di-Br-3-MeOCH2O—Ph(Me)CH— |
| 7497 | 2-Br-3-I-5-MeOCH2O—Ph(Me)CH— |
| 7498 | 2-Br-5-I-3-MeOCH2O—Ph(Me)CH— |
| 7499 | 2-I-3,5-di-MeO—Ph(Me)CH— |
| 7500 | 2-I-3,5-di-EtO—Ph(Me)CH— |
| 7501 | 3,5-di-F-2-I—Ph(Me)CH— |
| 7502 | 3,5-di-Cl-2-I—Ph(Me)CH— |
| 7503 | 3,5-di-Br-2-I—Ph(Me)CH— |
| 7504 | 2,3,5-Tri-I—Ph(Me)CH— |
| 7505 | 3,5-di-Me-2-I—Ph(Me)CH— |
| 7506 | 3-F-2-I-5-Me—Ph(Me)CH— |
| 7507 | 5-F-2-I-3-Me—Ph(Me)CH— |
| 7508 | 3-Cl-2-I-5-Me—Ph(Me)CH— |
| 7509 | 5-Cl-2-I-3-Me—Ph(Me)CH— |
| 7510 | 3-Br-2-I-5-Me—Ph(Me)CH— |
| 7511 | 5-Br-2-I-3-Me—Ph(Me)CH— |
| 7512 | 2,3-di-I-5-Me—Ph(Me)CH— |
| 7513 | 2,5-di-I-3-Me—Ph(Me)CH— |
| 7514 | 3-F-2-I-5-MeO—Ph(Me)CH— |
| 7515 | 5-F-2-I-3-MeO—Ph(Me)CH— |
| 7516 | 3-Cl-2-I-5-MeO—Ph(Me)CH— |
| 7517 | 5-Cl-2-I-3-MeO—Ph(Me)CH— |
| 7518 | 3-Br-2-I-5-MeO—Ph(Me)CH— |
| 7519 | 5-Br-2-I-3-MeO—Ph(Me)CH— |
| 7520 | 2,3-di-I-5-MeO—Ph(Me)CH— |
| 7521 | 2,5-di-I-3-MeO—Ph(Me)CH— |
| 7522 | 3-F-2-I-5-EtO—Ph(Me)CH— |

TABLE 2-continued

| No. | Z |
|---|---|
| 7523 | 5-F-2-I-3-EtO—Ph(Me)CH— |
| 7524 | 3-Cl-2-I-5-EtO—Ph(Me)CH— |
| 7525 | 5-Cl-2-I-3-EtO—Ph(Me)CH— |
| 7526 | 3-Br-2-I-5-EtO—Ph(Me)CH— |
| 7527 | 5-Br-2-I-3-EtO—Ph(Me)CH— |
| 7528 | 2,3-di-I-5-EtO—Ph(Me)CH— |
| 7529 | 2,5-di-I-3-EtO—Ph(Me)CH— |
| 7530 | 3-F-2-I-5-N≡CCH2O—Ph(Me)CH— |
| 7531 | 5-F-2-I-3-N≡CCH2O—Ph(Me)CH— |
| 7532 | 5-Cl-2-I-5-N≡CCH2O—Ph(Me)CH— |
| 7533 | 3-Cl-2-I-3-N≡CCH2O—Ph(Me)CH— |
| 7534 | 3-Br-2-I-5-N≡CCH2O—Ph(Me)CH— |
| 7535 | 5-Br-2-I-3-N≡CCH2O—Ph(Me)CH— |
| 7536 | 2,3-di-I-5-N≡CCH2O—Ph(Me)CH— |
| 7537 | 2,5-di-I-3-N≡CCH2O—Ph(Me)CH— |
| 7538 | 3-F-2-I-5-MeOCH2O—Ph(Me)CH— |
| 7539 | 5-F-2-I-3-MeOCH2O—Ph(Me)CH— |
| 7540 | 3-Cl-2-I-5-MeOCH2O—Ph(Me)CH— |
| 7541 | 5-Cl-2-I-3-MeOCH2O—Ph(Me)CH— |
| 7542 | 3-Br-2-I-5-MeOCH2O—Ph(Me)CH— |
| 7543 | 5-Br-2-I-3-MeOCH2O—Ph(Me)CH— |
| 7544 | 2,3-di-I-5-MeOCH2O—Ph(Me)CH— |
| 7545 | 2,5-di-I-3-MeOCH2O—Ph(Me)CH— |
| 7546 | 2-Me-3,5-di-MeO—Ph(Me)CH— |
| 7547 | 2-Me-3,5-di-EtO—Ph(Me)CH— |
| 7548 | 3,5-di-F-2-Me—Ph(Me)CH— |
| 7549 | 3,5-di-Cl-2-Me—Ph(Me)CH— |
| 7550 | 3,5-di-Br-2-Me—Ph(Me)CH— |
| 7551 | 3,5-di-I-2-Me—Ph(Me)CH— |
| 7552 | 2,3,5-tri-Me—Ph(Me)CH— |
| 7553 | 3-F-2,5-di-Me—Ph(Me)CH— |
| 7554 | 5-F-2,3-di-Me—Ph(Me)CH— |
| 7555 | 3-Cl-2,5-di-Me—Ph(Me)CH— |
| 7556 | 5-Cl-2,3-di-Me—Ph(Me)CH— |
| 7557 | 3-Br-2,5-di-Me—Ph(Me)CH— |
| 7558 | 5-Br-2,3-di-Me—Ph(Me)CH— |
| 7559 | 3-I-2,5-di-Me—Ph(Me)CH— |
| 7560 | 5-I-2,3-di-Me—Ph(Me)CH— |
| 7561 | 3-F-2-Me-5-MeO—Ph(Me)CH— |
| 7562 | 5-F-2-Me-3-MeO—Ph(Me)CH— |
| 7563 | 3-Cl-2-Me-5-MeO—Ph(Me)CH— |
| 7564 | 5-Cl-2-Me-3-MeO—Ph(Me)CH— |
| 7565 | 3-Br-2-Me-5-MeO—Ph(Me)CH— |
| 7566 | 5-Br-2-Me-3-MeO—Ph(Me)CH— |
| 7567 | 3-I-2-Me-5-MeO—Ph(Me)CH— |
| 7568 | 5-I-2-Me-3-MeO—Ph(Me)CH— |
| 7569 | 3-F-2-Me-5-EtO—Ph(Me)CH— |
| 7570 | 5-F-2-Me-3-EtO—Ph(Me)CH— |
| 7571 | 3-Cl-2-Me-5-EtO—Ph(Me)CH— |
| 7572 | 5-Cl-2-Me-3-EtO—Ph(Me)CH— |
| 7573 | 3-Br-2-Me-5-EtO—Ph(Me)CH— |
| 7574 | 5-Br-2-Me-3-EtO—Ph(Me)CH— |
| 7575 | 3-I-2-Me-5-EtO—Ph(Me)CH— |
| 7576 | 5-I-2-Me-3-EtO—Ph(Me)CH— |
| 7577 | 3-F-2-Me-5-N≡CCH2O—Ph(Me)CH— |
| 7578 | 5-F-2-Me-3-N≡CCH2O—Ph(Me)CH— |
| 7579 | 3-Cl-2-Me-5-N≡CCH2O—Ph(Me)CH— |
| 7580 | 5-Cl-2-Me-3-N≡CCH2O—Ph(Me)CH— |
| 7581 | 3-Br-2-Me-5-N≡CCH2O—Ph(Me)CH— |
| 7582 | 5-Br-2-Me-3-N≡CCH2O—Ph(Me)CH— |
| 7583 | 3-I-2-Me-5-N≡CCH2O—Ph(Me)CH— |
| 7584 | 5-I-2-Me-3-N≡CCH2O—Ph(Me)CH— |
| 7585 | 3-F-2-Me-5-MeOCH2O—Ph(Me)CH— |
| 7586 | 5-F-2-Me-3-MeOCH2O—Ph(Me)CH— |
| 7587 | 3-Cl-2-Me-5-MeOCH2O—Ph(Me)CH— |
| 7588 | 5-Cl-2-Me-3-MeOCH2O—Ph(Me)CH— |
| 7589 | 3-Br-2-Me-5-MeOCH2O—Ph(Me)CH— |
| 7590 | 5-Br-2-Me-3-MeOCH2O—Ph(Me)CH— |
| 7591 | 3-I-2-Me-5-MeOCH2O—Ph(Me)CH— |
| 7592 | 5-I-2-Me-3-MeOCH2O—Ph(Me)CH— |
| 7593 | 2,3,6-tri-F—Ph(Me)CH— |
| 7594 | 2,6-di-Cl-3-F—Ph(Me)CH— |
| 7595 | 2-Cl-3,6-di-F—Ph(Me)CH— |
| 7596 | 6-Cl-2,3-di-F—Ph(Me)CH— |
| 7597 | 3-Cl-2,6-di-F—Ph(Me)CH— |
| 7598 | 2,3,6-Tri-Cl—Ph(Me)CH— |
| 7599 | 2,3-di-Cl-6-F—Ph(Me)CH— |
| 7600 | 3,6-di-Cl-2-F—Ph(Me)CH— |
| 7601 | 3-Br-2,6-di-F—Ph(Me)CH— |
| 7602 | 3-Br-2,6-di-Cl—Ph(Me)CH— |
| 7603 | 3-Br-2-Cl-6-F—Ph(Me)CH— |
| 7604 | 3-Br-6-Cl-2-F—Ph(Me)CH— |
| 7605 | 2,6-di-F-3-I—Ph(Me)CH— |
| 7606 | 2,6-di-Cl-3-I—Ph(Me)CH— |
| 7607 | 2-Cl-6-F-3-I—Ph(Me)CH— |
| 7608 | 6-Cl-2-F-3-I—Ph(Me)CH— |
| 7609 | 2,6-di-F-3-Me—Ph(Me)CH— |
| 7610 | 2,6-di-Cl-3-Me—Ph(Me)CH— |
| 7611 | 2-Cl-6-F-3-Me—Ph(Me)CH— |
| 7612 | 6-Cl-2-F-3-Me—Ph(Me)CH— |
| 7613 | 2,6-di-F-3-MeO—Ph(Me)CH— |
| 7614 | 2,6-di-Cl-3-MeO—Ph(Me)CH— |
| 7615 | 2-Cl-6-F-3-MeO—Ph(Me)CH— |
| 7616 | 6-Cl-2-F-3-MeO—Ph(Me)CH— |
| 7617 | 2,6-di-F-3-EtO—Ph(Me)CH— |
| 7618 | 2,6-di-Cl-3-EtO—Ph(Me)CH— |
| 7619 | 2-Cl-6-F-3-EtO—Ph(Me)CH— |
| 7620 | 6-Cl-2-F-3-EtO—Ph(Me)CH— |
| 7621 | 2,6-di-F-3-N≡CCH2O—Ph(Me)CH— |
| 7622 | 2,6-di-Cl-3-N≡CCH2O—Ph(Me)CH— |
| 7623 | 2-Cl-6-F-3-N≡CCH2O—Ph(Me)CH— |
| 7624 | 6-Cl-2-F-3-N≡CCH2O—Ph(Me)CH— |
| 7625 | 2,6-di-F-3-MeOCH2O—Ph(Me)CH— |
| 7626 | 2,6-di-Cl-3-MeOCH2O—Ph(Me)CH— |
| 7627 | 2-Cl-6-F-3-MeOCH2O—Ph(Me)CH— |
| 7628 | 6-Cl-2-F-3-MeOCH2O—Ph(Me)CH— |
| 7629 | 3,4,5-tri-F—Ph(Me)CH— |
| 7630 | 4-Cl-3,5-di-F—Ph(Me)CH— |
| 7631 | 4-Br-3,5-di-F—Ph(Me)CH— |
| 7632 | 3,5-di-F-4-I—Ph(Me)CH— |
| 7633 | 3,5-di-F-4-Me—Ph(Me)CH— |
| 7634 | 3,5-di-Cl-4-F—Ph(Me)CH— |
| 7635 | 3,4,5-tri-Cl—Ph(Me)CH— |
| 7636 | 4-Br-3,5-di-Cl—Ph(Me)CH— |
| 7637 | 3,5-di-Cl-4-I—Ph(Me)CH— |
| 7638 | 3,5-di-Cl-4-Me—Ph(Me)CH— |
| 7639 | 3,5-di-Br-4-F—Ph(Me)CH— |
| 7640 | 3,5-di-Br-4-Cl—Ph(Me)CH— |
| 7641 | 3,4,5-tri-Br—Ph(Me)CH— |
| 7642 | 3,5-di-Br-4-I—Ph(Me)CH— |
| 7643 | 3,5-di-Br-4-Me—Ph(Me)CH— |
| 7644 | 4-F-3,5-di-I—Ph(Me)CH— |
| 7645 | 4-Cl-3,5-di-I—Ph(Me)CH— |
| 7646 | 4-Br-3,5-di-I—Ph(Me)CH— |
| 7647 | 3,4,5-tri-I—Ph(Me)CH— |
| 7648 | 4-Me-3,5-di-I—Ph(Me)CH— |
| 7649 | 4-F-3,5-di-Me—Ph(Me)CH— |
| 7650 | 4-Cl-3,5-di-Me—Ph(Me)CH— |
| 7651 | 4-Br-3,5-di-Me—Ph(Me)CH— |
| 7652 | 4-I-3,5-di-Me—Ph(Me)CH— |
| 7653 | 3,4,5-tri-Me—Ph(Me)CH— |
| 7654 | 4-F-3,5-di-Me—Ph(Me)CH— |
| 7655 | 4-Cl-3,5-di-Me—Ph(Me)CH— |
| 7656 | 4-Br-3,5-di-Me—Ph(Me)CH— |
| 7657 | 4-I-3,5-di-Me—Ph(Me)CH— |
| 7658 | 4-MeO-3,5-di-Me—Ph(Me)CH— |
| 7659 | 4-F-3,5-di-MeO—Ph(Me)CH— |
| 7660 | 4-Cl-3,5-di-MeO—Ph(Me)CH— |
| 7661 | 4-Br-3,5-di-MeO—Ph(Me)CH— |
| 7662 | 4-I-3,5-di-MeO—Ph(Me)CH— |
| 7663 | 4-Me-3,5-di-MeO—Ph(Me)CH— |
| 7664 | 4-F-3,5-di-EtO—Ph(Me)CH— |
| 7665 | 4-Cl-3,5-di-EtO—Ph(Me)CH— |
| 7666 | 4-Br-3,5-di-EtO—Ph(Me)CH— |
| 7667 | 4-I-3,5-di-EtO—Ph(Me)CH— |
| 7668 | 4-Me-3,5-di-EtO—Ph(Me)CH— |
| 7669 | 2,3,4-tri-F—Ph(Me)CH— |
| 7670 | 2-Cl-3,4-di-F—Ph(Me)CH— |
| 7671 | 2-Br-3,4-di-F—Ph(Me)CH— |
| 7672 | 3,4-di-F-2-I—Ph(Me)CH— |
| 7673 | 3,4-di-F-2-Me—Ph(Me)CH— |
| 7674 | 2,4,5-tri-F—Ph(Me)CH— |
| 7675 | 2-Cl-4,5-di-F—Ph(Me)CH— |
| 7676 | 2-Br-4,5-di-F—Ph(Me)CH— |
| 7677 | 4,5-di-F-2-I—Ph(Me)CH— |
| 7678 | 4,5-di-F-2-Me—Ph(Me)CH— |

TABLE 2-continued

| No. | Z |
|---|---|
| 7679 | 2,4-di-F-3-Cl—Ph(Me)CH— |
| 7680 | 2,3-di-Cl-4-F—Ph(Me)CH— |
| 7681 | 2-Br-3-Cl-4-F—Ph(Me)CH— |
| 7682 | 3-Cl-4-F-24—Ph(Me)CH— |
| 7683 | 3-Cl-4-F-2-Me—Ph(Me)CH— |
| 7684 | 2,4-di-F-5-Cl—Ph(Me)CH— |
| 7685 | 2,5-di-Cl-4-F—Ph(Me)CH— |
| 7686 | 2-Br-5-Cl-4-F—Ph(Me)CH— |
| 7687 | 5-Cl-4-F-2-I—Ph(Me)CH— |
| 7688 | 5-Cl-4-F-2-Me—Ph(Me)CH— |
| 7689 | 2-F-3,4-di-Cl—Ph(Me)CH— |
| 7690 | 2,3,4-tri-Cl—Ph(Me)CH— |
| 7691 | 2-Br-3,4-di-Cl—Ph(Me)CH— |
| 7692 | di-3,4-Cl-2-I—Ph(Me)CH— |
| 7693 | di-3,4-Cl-2-Me—Ph(Me)CH— |
| 7694 | 2-F-3,5-di-Cl—Ph(Me)CH— |
| 7695 | 2,3,5-tri-Cl—Ph(Me)CH— |
| 7696 | 2-Br-3,5-di-Cl—Ph(Me)CH— |
| 7697 | 3,5-di-Cl-2-I—Ph(Me)CH— |
| 7698 | 3,5-di-Cl-2-Me—Ph(Me)CH— |
| 7699 | 4-Cl-2,3-di-F—Ph(Me)CH— |
| 7700 | 2,4-di-Cl-3-F—Ph(Me)CH— |
| 7701 | 2-Br-4-Cl-3-F—Ph(Me)CH— |
| 7702 | 4-Cl-3-F-2-I—Ph(Me)CH— |
| 7703 | 4-Cl-3-F-2-Me—Ph(Me)CH— |
| 7704 | 4-Cl-2,5-di-F—Ph(Me)CH— |
| 7705 | 2,4-di-Cl-5-F—Ph(Me)CH— |
| 7706 | 2-Br-4-Cl-5-F—Ph(Me)CH— |
| 7707 | 4-Cl-5-F-2-I—Ph(Me)CH— |
| 7708 | 4-Cl-5-F-2-Me—Ph(Me)CH— |
| 7709 | 2,4-di-F-3-MeO—Ph(Me)CH— |
| 7710 | 2-Cl-4-F-3-MeO—Ph(Me)CH— |
| 7711 | 2-Br-4-F-3-MeO—Ph(Me)CH— |
| 7712 | 4-F-2-I-3-MeO—Ph(Me)CH— |
| 7713 | 4-F-2-Me-3-MeO—Ph(Me)CH— |
| 7714 | 2,4-F-5-MeO—Ph(Me)CH— |
| 7715 | 2-Cl-4-F-5-MeO—Ph(Me)CH— |
| 7716 | 2-Br-4-F-5-MeO—Ph(Me)CH— |
| 7717 | 4-F-2-I-5-MeO—Ph(Me)CH— |
| 7718 | 4-F-2-Me-5-MeO—Ph(Me)CH— |
| 7719 | 4-Cl-2-F-3-MeO—Ph(Me)CH— |
| 7720 | 2,4-di-Cl-3-MeO—Ph(Me)CH— |
| 7721 | 2-Br-4-Cl-3-MeO—Ph(Me)CH— |
| 7722 | 4-Cl-2-I-3-MeO—Ph(Me)CH— |
| 7723 | 4-Cl-2-Me-3-MeO—Ph(Me)CH— |
| 7724 | 4-Cl-2-F-5-MeO—Ph(Me)CH— |
| 7725 | 2,4-di-Cl-5-MeO—Ph(Me)CH— |
| 7726 | 2-Br-4-Cl-5-MeO—Ph(Me)CH— |
| 7727 | 4-Cl-2-I-5-MeO—Ph(Me)CH— |
| 7728 | 4-Cl-2-Me-5-MeO—Ph(Me)CH— |
| 7729 | 2,6-di-F-3,5-di-MeO—Ph(Me)CH— |
| 7730 | 2,6-di-Cl-3,5-di-MeO—Ph(Me)CH— |
| 7731 | 6-Cl-2-F-3,5-di-MeO—Ph(Me)CH— |
| 7732 | 6-Br-2-F-3,5-di-MeO—Ph(Me)CH— |
| 7733 | 2-Br-6-Cl-3,5-di-MeO—Ph(Me)CH— |
| 7734 | 2,3,4,5,-tetra-F—Ph(Me)CH— |
| 7735 | 2,3,5,6,-tetra-F—Ph(Me)CH— |
| 7736 | 2,3,4,5,6-penta-F—Ph(Me)CH— |
| 7737 | 2,3-di-F-5-MeS—Ph(Me)CH— |
| 7738 | 2-F-3-MeO-5-MeS—Ph(Me)CH— |
| 7739 | 2,5-di-F-3-MeS—Ph(Me)CH— |
| 7740 | 2-Cl-3-F-5-MeS—Ph(Me)CH— |
| 7741 | 2-Cl-5-F-3-MeS—Ph(Me)CH— |
| 7742 | 2-F-5-MeO-3-MeS—Ph(Me)CH— |
| 7743 | 2-Cl-5-MeO-3-MeS—Ph(Me)CH— |
| 7744 | 2-Br-3-F-5-MeS—Ph(Me)CH— |
| 7745 | 2-Cl-3-MeO-5-MeS—Ph(Me)CH— |
| 7746 | 2-Br-3-MeO-5-MeS—Ph(Me)CH— |
| 7747 | 2-Br-5-MeO-3-MeS—Ph(Me)CH— |
| 7748 | 2-Br-5-F-3-MeS—Ph(Me)CH— |
| 7749 | 2-I-5-F-3-MeS—Ph(Me)CH— |
| 7750 | 2-I-3-MeO-5-MeS—Ph(Me)CH— |
| 7751 | 2-I-3-F-5-MeS—Ph(Me)CH— |
| 7752 | 3-F-2-Me-5-MeS—Ph(Me)CH— |
| 7753 | 5-F-2-Me-3-MeS—Ph(Me)CH— |
| 7754 | 2-I-5-MeO-3-MeS—Ph(Me)CH— |
| 7755 | 2-Me-5-MeO-3-MeS—Ph(Me)CH— |
| 7756 | 2-F-3,5-di-MeS—Ph(Me)CH— |
| 7757 | 2-Me-3-MeO-5-MeS—Ph(Me)CH— |
| 7758 | 2-Br-3,5-di-MeS—Ph(Me)CH— |
| 7759 | 2-I-3,5-di-MeS—Ph(Me)CH— |
| 7760 | 2-Cl-3,5-di-MeS—Ph(Me)CH— |
| 7761 | 2,5-di-F-3-MeS(O)—Ph(Me)CH— |
| 7762 | 2,3-di-F-5-MeS(O)—Ph(Me)CH— |
| 7763 | 2-Me-3,5-di-MeS—Ph(Me)CH— |
| 7764 | 2-F-5-MeO-3-MeS(O)—Ph(Me)CH— |
| 7765 | 2-Cl-3-F-5-MeS(O)—Ph(Me)CH— |
| 7766 | 2-F-3-MeO-5-MeS(O)—Ph(Me)CH— |
| 7767 | 2-Cl-3-MeO-5-MeS(O)—Ph(Me)CH— |
| 7768 | 2-Cl-5-MeO-3-MeS(O)—Ph(Me)CH— |
| 7769 | 2-Cl-5-F-3-MeS(O)—Ph(Me)CH— |
| 7770 | 2-Br-5-F-3-MeS(O)—Ph(Me)CH— |
| 7771 | 2-Br-3-MeO-5-MeS(O)—Ph(Me)CH— |
| 7772 | 2-Br-3-F-5-MeS(O)—Ph(Me)CH— |
| 7773 | 2-I-3-F-5-MeS(O)—Ph(Me)CH— |
| 7774 | 5-F-2-I-3-MeS(O)—Ph(Me)CH— |
| 7775 | 2-Br-5-MeO-3-MeS(O)—Ph(Me)CH— |
| 7776 | 2-I-5-MeO-3-MeS(O)—Ph(Me)CH— |
| 7777 | 3-F-2-Me-5-MeS(O)—Ph(Me)CH— |
| 7778 | 2-I-3-MeO-5-MeS(O)—Ph(Me)CH— |
| 7779 | 2-Me-3-MeO-5-MeS(O)—Ph(Me)CH— |
| 7780 | 2-Me-5-MeO-3-MeS(O)—Ph(Me)CH— |
| 7781 | 5-F-2-Me-3-MeS(O)—Ph(Me)CH— |
| 7782 | 2-Cl-3,5-di-MeS(O)—Ph(Me)CH— |
| 7783 | 2-Br-3,5-di-MeS(O)—Ph(Me)CH— |
| 7784 | 2-F-3,5-di-MeS(O)—Ph(Me)CH— |
| 7785 | 2-Me-3,5-di-MeS(O)—Ph(Me)CH— |
| 7786 | 2,5-di-F-3-MeSO2—Ph(Me)CH— |
| 7787 | 2-I-3,5-di-MeS(O)—Ph(Me)CH— |
| 7788 | 2-F-3-MeO-5-MeSO2—Ph(Me)CH— |
| 7789 | 2-F-5-MeO-3-MeSO2—Ph(Me)CH— |
| 7790 | 2,3-di-F-5-MeSO2—Ph(Me)CH— |
| 7791 | 2-Cl-5-F-3-MeSO2—Ph(Me)CH— |
| 7792 | 2-Cl-3-MeO-5-MeSO2—Ph(Me)CH— |
| 7793 | 2-Cl-3-F-5-MeSO2—Ph(Me)CH— |
| 7794 | 2-Br-3-F-5-MeSO2—Ph(Me)CH— |
| 7795 | 2-Br-5-F-3-MeSO2—Ph(Me)CH— |
| 7796 | 2-Cl-5-MeO-3-MeSO2—Ph(Me)CH— |
| 7797 | 2-Br-5-MeO-3-MeSO2—Ph(Me)CH— |
| 7798 | 3-F-2-I-5-MeSO2—Ph(Me)CH— |
| 7799 | 2-Br-3-MeO-5-MeSO2—Ph(Me)CH— |
| 7800 | 2-I-3-MeO-5-MeSO2—Ph(Me)CH— |
| 7801 | 2-I-5-MeO-3-MeSO2—Ph(Me)CH— |
| 7802 | 5-F-2-I-3-MeSO2—Ph(Me)CH— |
| 7803 | 5-F-2-Me-3-MeSO2—Ph(Me)CH— |
| 7804 | 2-Me-3-MeO-5-MeSO2—Ph(Me)CH— |
| 7805 | 3-F-2-Me-5-MeSO2—Ph(Me)CH— |
| 7806 | 2-F-3,5-di-MeSO2—Ph(Me)CH— |
| 7807 | 2-Cl-3,5-di-MeSO2—Ph(Me)CH— |
| 7808 | 2-Me-5-MeO-3-MeSO—Ph(Me)CH— |
| 7809 | 2-I-3,5-di-MeSO2—Ph(Me)CH— |
| 7810 | 2-Me-3,5-di-MeSO2—Ph(Me)CH— |
| 7811 | 2-Br-3,5-di-MeSO2—Ph(Me)CH— |
| 7812 | 2,4,6-tri-F—Ph(Me)CH— |
| 7813 | PhCH2CH2— |
| 7814 | 2-F—PhCH2CH2— |
| 7815 | 3-F—PhCH2CH2— |
| 7816 | 4-F—PhCH2CH2— |
| 7817 | 2-Cl—PhCH2CH2— |
| 7818 | 3-Cl—PhCH2CH2— |
| 7819 | 4-Cl—PhCH2CH2— |
| 7820 | 2-Br—PhCH2CH2— |
| 7821 | 3-Br—PhCH2CH2— |
| 7822 | 4-Br—PhCH2CH2— |
| 7823 | 2-I—PhCH2CH2— |
| 7824 | 3-I—PhCH2CH2— |
| 7825 | 4-I—PhCH2CH2— |
| 7826 | 2-HO—PhCH2CH2— |
| 7827 | 3-HO—PhCH2CH2— |
| 7828 | 4-HO—PhCH2CH2— |
| 7829 | 2-NC—PhCH2CH2— |
| 7830 | 3-NC—PhCH2CH2— |
| 7831 | 4-NC—PhCH2CH2— |
| 7832 | 2-O2N—PhCH2CH2— |
| 7833 | 3-O2N—PhCH2CH2— |
| 7834 | 4-O2N—PhCH2CH2— |

TABLE 2-continued

| No. | Z |
|---|---|
| 7835 | 2-Me—PhCH2CH2— |
| 7836 | 3-Me—PhCH2CH2— |
| 7837 | 4-Me—PhCH2CH2— |
| 7838 | 2-Et—PhCH2CH2— |
| 7839 | 3-Et—PhCH2CH2— |
| 7840 | 4-Et—PhCH2CH2— |
| 7841 | 2-Pr—PhCH2CH2— |
| 7842 | 3-Pr—PhCH2CH2— |
| 7843 | 4-Pr—PhCH2CH2— |
| 7844 | 2-iPr—PhCH2CH2— |
| 7845 | 3-iPr—PhCH2CH2— |
| 7846 | 4-iPr—PhCH2CH2— |
| 7847 | 2-N≡CCH2—PhCH2CH2— |
| 7848 | 3-N≡CCH2—PhCH2CH2— |
| 7849 | 4-N≡CCH2—PhCH2CH2— |
| 7850 | 2-N≡CCH2CH2—PhCH2CH2— |
| 7851 | 3-N≡CCH2CH2—PhCH2CH2— |
| 7852 | 4-N≡CCH2CH2—PhCH2CH2— |
| 7852 | 2-cPrCH2—PhCH2CH2— |
| 7853 | 3-cPrCH2—PhCH2CH2— |
| 7854 | 4-cPrCH2—PhCH2CH2— |
| 7855 | 4-cPrCH2—PhCH2CH2— |
| 7856 | 2-cBuCH2—PhCH2CH2— |
| 7857 | 3-cBuCH2—PhCH2CH2— |
| 7858 | 4-cBuCH2—PhCH2CH2— |
| 7859 | 2-MeOCH2—PhCH2CH2— |
| 7860 | 3-MeOCH2—PhCH2CH2— |
| 7861 | 4-MeOCH2—PhCH2CH2— |
| 7862 | 2-MeOCH2CH2—PhCH2CH2— |
| 7863 | 3-MeOCH2CH2—PhCH2CH2— |
| 7864 | 4-MeOCH2CH2—PhCH2CH2— |
| 7865 | 2-MeOCH2CH2CH2—PhCH2CH2— |
| 7866 | 3-MeOCH2CH2CH2—PhCH2CH2— |
| 7867 | 4-MeOCH2CH2CH2—PhCH2CH2— |
| 7868 | 2-EtOCH2—PhCH2CH2— |
| 7869 | 3-EtOCH2—PhCH2CH2— |
| 7870 | 4-EtOCH2—PhCH2CH2— |
| 7871 | 2-EtOCH2CH2—PhCH2CH2— |
| 7872 | 3-EtOCH2CH2—PhCH2CH2— |
| 7873 | 4-EtOCH2CH2—PhCH2CH2— |
| 7874 | 2-cPrOCH2—PhCH2CH2— |
| 7875 | 3-cPrOCH2—PhCH2CH2— |
| 7876 | 4-cPrOCH2—PhCH2CH2— |
| 7877 | 2-F3COCH2—PhCH2CH2— |
| 7878 | 3-F3COCH2—PhCH2CH2— |
| 7879 | 4-F3COCH2—PhCH2CH2— |
| 7880 | 2-F2CHOCH2—PhCH2CH2— |
| 7881 | 3-F2CHOCH2—PhCH2CH2— |
| 7882 | 4-F2CHOCH2—PhCH2CH2— |
| 7883 | 2-MeOCH2CH2OCH2—PhCH2CH2— |
| 7884 | 3-MeOCH2CH2OCH2—PhCH2CH2— |
| 7885 | 4-MeOCH2CH2OCH2—PhCH2CH2— |
| 7886 | 2-Me2NCH2—PhCH2CH2— |
| 7887 | 3-Me2NCH2—PhCH2CH2— |
| 7888 | 4-Me2NCH2—PhCH2CH2— |
| 7889 | 2-MeSCH2—PhCH2CH2— |
| 7890 | 3-MeSCH2—PhCH2CH2— |
| 7891 | 4-MeSCH2—PhCH2CH2— |
| 7892 | 2-MeS(O)CH2—PhCH2CH2— |
| 7893 | 3-MeS(O)CH2—PhCH2CH2— |
| 7894 | 4-MeS(O)CH2—PhCH2CH2— |
| 7895 | 2-MeSO2CH2—PhCH2CH2— |
| 7896 | 3-MeSO2CH2—PhCH2CH2— |
| 7897 | 4-MeSO2CH2—PhCH2CH2— |
| 7898 | 2-cPr—PhCH2CH2— |
| 7899 | 3-cPr—PhCH2CH2— |
| 7900 | 4-cPr—PhCH2CH2— |
| 7901 | 2-cBu—PhCH2CH2— |
| 7902 | 3-cBu—PhCH2CH2— |
| 7903 | 4-cBu—PhCH2CH2— |
| 7904 | 2-F3C—PhCH2CH2— |
| 7905 | 3-F3C—PhCH2CH2— |
| 7906 | 4-F3C—PhCH2CH2— |
| 7907 | 2-F2CH—PhCH2CH2— |
| 7908 | 3-F2CH—PhCH2CH2— |
| 7909 | 4-F2CH—PhCH2CH2— |
| 7910 | 2-H2C=CH—PhCH2CH2— |
| 7911 | 3-H2C=CH—PhCH2CH2— |
| 7912 | 4-H2C=CH—PhCH2CH2— |
| 7913 | 2-H2C=CHCH2—PhCH2CH2— |
| 7914 | 3-H2C=CHCH2—PhCH2CH2— |
| 7915 | 4-H2C=CHCH2—PhCH2CH2— |
| 7916 | 2-F2C=CH—PhCH2CH2— |
| 7917 | 3-F2C=CH—PhCH2CH2— |
| 7918 | 4-F2C=CH—PhCH2CH2— |
| 7919 | 2-F2C=CHCH2—PhCH2CH2— |
| 7920 | 3-F2C=CHCH2—PhCH2CH2— |
| 7921 | 4-F2C=CHCH2—PhCH2CH2— |
| 7922 | 2-HC≡C—PhCH2CH2— |
| 7923 | 3-HC≡C—PhCH2CH2— |
| 7924 | 4-HC≡C—PhCH2CH2— |
| 7925 | 2-HC≡CCH2—PhCH2CH2— |
| 7926 | 3-HC≡CCH2—PhCH2CH2— |
| 7927 | 4-HC≡CCH2—PhCH2CH2— |
| 7928 | 2-F3CC≡C—PhCH2CH2— |
| 7929 | 3-F3CC≡C—PhCH2CH2— |
| 7930 | 4-F3CC≡C—PhCH2CH2— |
| 7931 | 2-F3CC≡CCH2—PhCH2CH2— |
| 7932 | 3-F3CC≡CCH2—PhCH2CH2— |
| 7933 | 4-F3CC≡CCH2—PhCH2CH2— |
| 7934 | 2-MeO—PhCH2CH2— |
| 7935 | 3-MeO—PhCH2CH2— |
| 7936 | 4-MeO—PhCH2CH2— |
| 7937 | 2-EtO—PhCH2CH2— |
| 7938 | 3-EtO—PhCH2CH2— |
| 7939 | 4-EtO—PhCH2CH2— |
| 7940 | 2-PrO—PhCH2CH2— |
| 7941 | 3-PrO—PhCH2CH2— |
| 7942 | 4-PrO—PhCH2CH2— |
| 7943 | 2-iPrO—PhCH2CH2— |
| 7944 | 3-iPrO—PhCH2CH2— |
| 7945 | 4-iPrO—PhCH2CH2— |
| 7946 | 2-BuO—PhCH2CH2— |
| 7947 | 3-BuO—PhCH2CH2— |
| 7948 | 4-BuO—PhCH2CH2— |
| 7949 | 2-iBuO—PhCH2CH2— |
| 7950 | 3-iBuO—PhCH2CH2— |
| 7951 | 4-iBuO—PhCH2CH2— |
| 7952 | 2-PentylO—PhCH2CH2— |
| 7953 | 3-PentylO—PhCH2CH2— |
| 7954 | 4-PentylO—PhCH2CH2— |
| 7955 | 2-N≡CCH2O—PhCH2CH2— |
| 7956 | 3-N≡CCH2O—PhCH2CH2— |
| 7957 | 4-N≡CCH2O—PhCH2CH2— |
| 7958 | 2-N≡CCH2CH2O—PhCH2CH2— |
| 7959 | 3-N≡CCH2CH2O—PhCH2CH2— |
| 7960 | 4-N≡CCH2CH2O—PhCH2CH2— |
| 7961 | 2-cPrCH2O—PhCH2CH2— |
| 7962 | 3-cPrCH2O—PhCH2CH2— |
| 7963 | 4-cPrCH2O—PhCH2CH2— |
| 7964 | 2-cBuCH2O—PhCH2CH2— |
| 7965 | 3-cBuCH2O—PhCH2CH2— |
| 7966 | 4-cBuCH2O—PhCH2CH2— |
| 7967 | 2-cPentylCH2O—PhCH2CH2— |
| 7968 | 3-cPentylCH2O—PhCH2CH2— |
| 7969 | 4-cPentylCH2O—PhCH2CH2— |
| 7970 | 2-cHexylCH2O—PhCH2CH2— |
| 7971 | 3-cHexylCH2O—PhCH2CH2— |
| 7972 | 4-cHexylCH2O—PhCH2CH2— |
| 7973 | 2-MeOCH2O—PhCH2CH2— |
| 7974 | 3-MeOCH2O—PhCH2CH2— |
| 7975 | 4-MeOCH2O—PhCH2CH2— |
| 7976 | 2-EtOCH2O—PhCH2CH2— |
| 7977 | 3-EtOCH2O—PhCH2CH2— |
| 7978 | 4-EtOCH2O—PhCH2CH2— |
| 7979 | 2-MeOCH2CH2O—PhCH2CH2— |
| 7980 | 3-MeOCH2CH2O—PhCH2CH2— |
| 7981 | 4-MeOCH2CH2O—PhCH2CH2— |
| 7982 | 2-MeOCH2CH2CH2O—PhCH2CH2— |
| 7983 | 3-MeOCH2CH2CH2O—PhCH2CH2— |
| 7984 | 4-MeOCH2CH2CH2O—PhCH2CH2— |
| 7985 | 2-MeOCH2CH2OCH2O—PhCH2CH2— |
| 7986 | 3-MeOCH2CH2OCH2O—PhCH2CH2— |
| 7987 | 4-MeOCH2CH2OCH2O—PhCH2CH2— |
| 7988 | 2-MeSCH2O—PhCH2CH2— |
| 7989 | 3-MeSCH2O—PhCH2CH2— |

TABLE 2-continued

| No. | Z |
|---|---|
| 7990 | 4-MeSCH2O—PhCH2CH2— |
| 7991 | 2-MeS(O)CH2O—PhCH2CH2— |
| 7992 | 3-MeS(O)CH2O—PhCH2CH2— |
| 7993 | 4-MeS(O)CH2O—PhCH2CH2— |
| 7994 | 2-MeSO2CH2O—PhCH2CH2— |
| 7995 | 3-MeSO2CH2O—PhCH2CH2— |
| 7996 | 4-MeSO2CH2O—PhCH2CH2— |
| 7997 | 2-AcCH2O—PhCH2CH2— |
| 7998 | 3-AcCH2O—PhCH2CH2— |
| 7999 | 4-AcCH2O—PhCH2CH2— |
| 8000 | 2-MeOC(=O)CH2O—PhCH2CH2— |
| 8001 | 3-MeOC(=O)CH2O—PhCH2CH2— |
| 8002 | 4-MeOC(=O)CH2O—PhCH2CH2— |
| 8003 | 2-EtOC(=O)CH2O—PhCH2CH2— |
| 8004 | 3-EtOC(=O)CH2O—PhCH2CH2— |
| 8005 | 4-EtOC(=O)CH2O—PhCH2CH2— |
| 8006 | 2-(1,3-dioxolan-2-yl)CH2O—PhCH2CH2— |
| 8007 | 3-(1,3-dioxolan-2-yl)CH2O—PhCH2CH2— |
| 8008 | 4-(1,3-dioxolan-2-yl)CH2O—PhCH2CH2— |
| 8009 | 2-(1,3-dioxolan-2-yl)CH2CH2O—PhCH2CH2— |
| 8010 | 3-(1,3-dioxolan-2-yl)CH2CH2O—PhCH2CH2— |
| 8011 | 4-(1,3-dioxolan-2-yl)CH2CH2O—PhCH2CH2— |
| 8012 | 2-(1,3-dioxan-2-yl)CH2O—PhCH2CH2— |
| 8013 | 3-(1,3-dioxan-2-yl)CH2O—PhCH2CH2— |
| 8014 | 4-(1,3-dioxan-2-yl)CH2O—PhCH2CH2— |
| 8015 | 2-(1,3-dioxan-2-yl)CH2CH2O—PhCH2CH2— |
| 8016 | 3-(1,3-dioxan-2-yl)CH2CH2O—PhCH2CH2— |
| 8017 | 4-(1,3-dioxan-2-yl)CH2CH2O—PhCH2CH2— |
| 8018 | 2-cPrO—PhCH2CH2— |
| 8019 | 3-cPrO—PhCH2CH2— |
| 8020 | 4-cPrO—PhCH2CH2— |
| 8021 | 2-cBuO—PhCH2CH2— |
| 8022 | 3-cBuO—PhCH2CH2— |
| 8023 | 4-cBuO—PhCH2CH2— |
| 8024 | 2-cPentylO—PhCH2CH2— |
| 8025 | 3-cPentylO—PhCH2CH2— |
| 8026 | 4-cPentylO—PhCH2CH2— |
| 8027 | 2-cHexylO—PhCH2CH2— |
| 8028 | 3-cHexylO—PhCH2CH2— |
| 8029 | 4-cHexylO—PhCH2CH2— |
| 8030 | 2-F3CO—PhCH2CH2— |
| 8031 | 3-F3CO—PhCH2CH2— |
| 8032 | 4-F3CO—PhCH2CH2— |
| 8033 | 2-F2CHO—PhCH2CH2— |
| 8034 | 3-F2CHO—PhCH2CH2— |
| 8035 | 4-F2CHO—PhCH2CH2— |
| 8036 | 2-F3CCH2O—PhCH2CH2— |
| 8037 | 3-F3CCH2O—PhCH2CH2— |
| 8038 | 4-F3CCH2O—PhCH2CH2— |
| 8039 | 2-F2CHCH2O—PhCH2CH2— |
| 8040 | 3-F2CHCH2O—PhCH2CH2— |
| 8041 | 4-F2CHCH2O—PhCH2CH2— |
| 8042 | 2-H2C=CHCH2O—PhCH2CH2— |
| 8043 | 3-H2C=CHCH2O—PhCH2CH2— |
| 8044 | 4-H2C=CHCH2O—PhCH2CH2— |
| 8045 | 2-HC≡CCH2O—PhCH2CH2— |
| 8046 | 3-HC≡CCH2O—PhCH2CH2— |
| 8047 | 4-HC≡CCH2O—PhCH2CH2— |
| 8048 | 2-AcPhCH2CH2— |
| 8049 | 3-AcPhCH2CH2— |
| 8050 | 4-AcPhCH2CH2— |
| 8051 | 2-MeOC(=O)—PhCH2CH2— |
| 8052 | 3-MeOC(=O)—PhCH2CH2— |
| 8053 | 4-MeOC(=O)—PhCH2CH2— |
| 8054 | 2-EtOC(=O)—PhCH2CH2— |
| 8055 | 3-EtOC(=O)—PhCH2CH2— |
| 8056 | 4-EtOC(=O)—PhCH2CH2— |
| 8057 | 2-AcO—PhCH2CH2— |
| 8058 | 3-AcO—PhCH2CH2— |
| 8059 | 4-AcO—PhCH2CH2— |
| 8060 | 2-MeOC(=O)O—PhCH2CH2— |
| 8061 | 3-MeOC(=O)O—PhCH2CH2— |
| 8062 | 4-MeOC(=O)O—PhCH2CH2— |
| 8063 | 2-EtOC(=O)O—PhCH2CH2— |
| 8064 | 3-EtOC(=O)O—PhCH2CH2— |
| 8065 | 4-EtOC(=O)O—PhCH2CH2— |
| 8066 | 2-(1,3-dioxolan-2-yl)-PhCH2CH2— |
| 8067 | 3-(1,3-dioxolan-2-yl)-PhCH2CH2— |
| 8068 | 4-(1,3-dioxolan-2-yl)-PhCH2CH2— |
| 8069 | 2-(1,3-dioxan-2-yl)-PhCH2CH2— |
| 8070 | 3-(1,3-dioxan-2-yl)-PhCH2CH2— |
| 8071 | 4-(1,3-dioxan-2-yl)-PhCH2CH2— |
| 8072 | 2-MeS—PhCH2CH2— |
| 8073 | 3-MeS—PhCH2CH2— |
| 8074 | 4-MeS—PhCH2CH2— |
| 8075 | 2-MeS(O)—PhCH2CH2— |
| 8076 | 3-MeS(O)—PhCH2CH2— |
| 8077 | 4-MeS(O)—PhCH2CH2— |
| 8078 | 2-MeSO2—PhCH2CH2— |
| 8079 | 3-MeSO2—PhCH2CH2— |
| 8080 | 4-MeSO2—PhCH2CH2— |
| 8081 | 2-ClCH2S—PhCH2CH2— |
| 8082 | 3-ClCH2S—PhCH2CH2— |
| 8083 | 4-ClCH2S—PhCH2CH2— |
| 8084 | 2-ClCH2S(O)—PhCH2CH2— |
| 8085 | 3-ClCH2S(O)—PhCH2CH2— |
| 8086 | 4-ClCH2S(O)—PhCH2CH2— |
| 8087 | 2-ClCH2SO2—PhCH2CH2— |
| 8088 | 3-ClCH2SO2—PhCH2CH2— |
| 8089 | 4-ClCH2SO2—PhCH2CH2— |
| 8090 | 2-F-3-HO—PhCH2CH2— |
| 8091 | 2-F-4-HO—PhCH2CH2— |
| 8092 | 2-F-5-HO—PhCH2CH2— |
| 8093 | 2-F-6-HO—PhCH2CH2— |
| 8094 | 2-Cl-3-HO—PhCH2CH2— |
| 8095 | 2-Cl-4-HO—PhCH2CH2— |
| 8096 | 2-Cl-5-HO—PhCH2CH2— |
| 8097 | 2-Cl-6-HO—PhCH2CH2— |
| 8098 | 2-Br-3-HO—PhCH2CH2— |
| 8099 | 2-Br-4-HO—PhCH2CH2— |
| 8100 | 2-Br-5-HO—PhCH2CH2— |
| 8101 | 2-Br-6-HO—PhCH2CH2— |
| 8102 | 2-I-3-HO—PhCH2CH2— |
| 8103 | 2-I-4-HO—PhCH2CH2— |
| 8104 | 2-I-5-HO—PhCH2CH2— |
| 8105 | 2-I-6-HO—PhCH2CH2— |
| 8106 | 2-Me-3-HO—PhCH2CH2— |
| 8107 | 2-Me-4-HO—PhCH2CH2— |
| 8108 | 2-Me-5-HO—PhCH2CH2— |
| 8109 | 2-Me-6-HO—PhCH2CH2— |
| 8110 | 2,3-di-F—PhCH2CH2— |
| 8111 | 2,4-di-F—PhCH2CH2— |
| 8112 | 2,5-di-F—PhCH2CH2— |
| 8113 | 2,6-di-F—PhCH2CH2— |
| 8114 | 2-Cl-3-F—PhCH2CH2— |
| 8115 | 2-Cl-4-F—PhCH2CH2— |
| 8116 | 2-Cl-5-F—PhCH2CH2— |
| 8117 | 2-Cl-6-F—PhCH2CH2— |
| 8118 | 2-Br-3-F—PhCH2CH2— |
| 8119 | 2-Br-4-F—PhCH2CH2— |
| 8120 | 2-Br-5-F—PhCH2CH2— |
| 8121 | 2-Br-6-F—PhCH2CH2— |
| 8122 | 3-F-2-I—PhCH2CH2— |
| 8123 | 4-F-2-I—PhCH2CH2— |
| 8124 | 5-F-2-I—PhCH2CH2— |
| 8125 | 6-F-2-I—PhCH2CH2— |
| 8126 | 3-F-2-Me—PhCH2CH2— |
| 8127 | 4-F-2-Me—PhCH2CH2— |
| 8128 | 5-F-2-Me—PhCH2CH2— |
| 8129 | 6-F-2-Me—PhCH2CH2— |
| 8130 | 3-Cl-2-F—PhCH2CH2— |
| 8131 | 4-Cl-2-F—PhCH2CH2— |
| 8132 | 5-Cl-2-F—PhCH2CH2— |
| 8133 | 6-Cl-2-F—PhCH2CH2— |
| 8134 | 2,3-di-Cl—PhCH2CH2— |
| 8135 | 2,4-di-Cl—PhCH2CH2— |
| 8136 | 2,5-di-Cl—PhCH2CH2— |
| 8137 | 2,6-di-Cl—PhCH2CH2— |
| 8138 | 2-Br-3-Cl—PhCH2CH2— |
| 8139 | 2-Br-4-Cl—PhCH2CH2— |
| 8140 | 2-Br-5-Cl—PhCH2CH2— |
| 8141 | 2-Br-6-Cl—PhCH2CH2— |
| 8142 | 3-Cl-2-I—PhCH2CH2— |
| 8143 | 4-Cl-2-I—PhCH2CH2— |
| 8144 | 5-Cl-2-I—PhCH2CH2— |
| 8145 | 6-Cl-2-I—PhCH2CH2— |

TABLE 2-continued

| No. | Z |
|---|---|
| 8146 | 3-Cl-2-Me—PhCH2CH2— |
| 8147 | 4-Cl-2-Me—PhCH2CH2— |
| 8148 | 5-Cl-2-Me—PhCH2CH2— |
| 8149 | 6-Cl-2-Me—PhCH2CH2— |
| 8150 | 3-Br-2-F—PhCH2CH2— |
| 8151 | 4-Br-2-F—PhCH2CH2— |
| 8152 | 5-Br-2-F—PhCH2CH2— |
| 8153 | 6-Br-2-F—PhCH2CH2— |
| 8154 | 3-Br-2-Cl—PhCH2CH2— |
| 8155 | 4-Br-2-Cl—PhCH2CH2— |
| 8156 | 5-Br-2-Cl—PhCH2CH2— |
| 8157 | 6-Br-2-Cl—PhCH2CH2— |
| 8158 | 2,3-di-Br—PhCH2CH2— |
| 8159 | 2,4-di-Br—PhCH2CH2— |
| 8160 | 2,5-di-Br—PhCH2CH2— |
| 8161 | 2,6-di-Br—PhCH2CH2— |
| 8162 | 3-Br-2-I—PhCH2CH2— |
| 8163 | 4-Br-2-I—PhCH2CH2— |
| 8164 | 5-Br-2-I—PhCH2CH2— |
| 8165 | 6-Br-2-I—PhCH2CH2— |
| 8166 | 3-Br-2-Me—PhCH2CH2— |
| 8167 | 4-Br-2-Me—PhCH2CH2— |
| 8168 | 5-Br-2-Me—PhCH2CH2— |
| 8169 | 6-Br-2-Me—PhCH2CH2— |
| 8170 | 2-F-3-I—PhCH2CH2— |
| 8171 | 2-F-4-I—PhCH2CH2— |
| 8172 | 2-F-5-I—PhCH2CH2— |
| 8173 | 2-F-6-I—PhCH2CH2— |
| 8174 | 2-Cl-3-I—PhCH2CH2— |
| 8175 | 2-Cl-4-I—PhCH2CH2— |
| 8176 | 2-Cl-5-I—PhCH2CH2— |
| 8177 | 2-Cl-6-I—PhCH2CH2— |
| 8178 | 2-Br-3-I—PhCH2CH2— |
| 8179 | 2-Br-4-I—PhCH2CH2— |
| 8180 | 2-Br-5-I—PhCH2CH2— |
| 8181 | 2-Br-6-I—PhCH2CH2— |
| 8182 | 2,3-di-I—PhCH2CH2— |
| 8183 | 2,4-di-I—PhCH2CH2— |
| 8184 | 2,5-di-I—PhCH2CH2— |
| 8185 | 2,6-di-I—PhCH2CH2— |
| 8186 | 2-Me-3-I—PhCH2CH2— |
| 8187 | 2-Me-4-I—PhCH2CH2— |
| 8188 | 2-Me-5-I—PhCH2CH2— |
| 8189 | 2-Me-6-I—PhCH2CH2— |
| 8190 | 2-F-3-N≡C—PhCH2CH2— |
| 8191 | 2-F-4-N≡C—PhCH2CH2— |
| 8192 | 2-F-5-N≡C—PhCH2CH2— |
| 8193 | 2-F-6-N≡C—PhCH2CH2— |
| 8194 | 2-Cl-3-N≡C—PhCH2CH2— |
| 8195 | 2-Cl-4-N≡C—PhCH2CH2— |
| 8196 | 2-Cl-5-N≡C—PhCH2CH2— |
| 8197 | 2-Cl-6-N≡C—PhCH2CH2— |
| 8198 | 2-Br-3-N≡C—PhCH2CH2— |
| 8199 | 2-Br-4-N≡C—PhCH2CH2— |
| 8200 | 2-Br-5-N≡C—PhCH2CH2— |
| 8201 | 2-Br-6-N≡C—PhCH2CH2— |
| 8202 | 2-I-3-N≡C—PhCH2CH2— |
| 8203 | 2-I-4-N≡C—PhCH2CH2— |
| 8204 | 2-I-5-N≡C—PhCH2CH2— |
| 8205 | 2-I-6-N≡C—PhCH2CH2— |
| 8206 | 2-Me-3-N≡C—PhCH2CH2— |
| 8207 | 2-Me-4-N≡C—PhCH2CH2— |
| 8208 | 2-Me-5-N≡C—PhCH2CH2— |
| 8209 | 2-Me-6-N≡C—PhCH2CH2— |
| 8210 | 2-F-3-O2N—PhCH2CH2— |
| 8211 | 2-F-4-O2N—PhCH2CH2— |
| 8212 | 2-F-5-O2N—PhCH2CH2— |
| 8213 | 2-F-6-O2N—PhCH2CH2— |
| 8214 | 2-Cl-3-O2N—PhCH2CH2— |
| 8215 | 2-Cl-4-O2N—PhCH2CH2— |
| 8216 | 2-Cl-5-O2N—PhCH2CH2— |
| 8217 | 2-Cl-6-O2N—PhCH2CH2— |
| 8218 | 2-Br-3-O2N—PhCH2CH2— |
| 8219 | 2-Br-4-O2N—PhCH2CH2— |
| 8220 | 2-Br-5-O2N—PhCH2CH2— |
| 8221 | 2-Br-6-O2N—PhCH2CH2— |
| 8222 | 2-I-3-O2N—PhCH2CH2— |
| 8223 | 2-I-4-O2N—PhCH2CH2— |
| 8224 | 2-I-5-O2N—PhCH2CH2— |
| 8225 | 2-I-6-O2N—PhCH2CH2— |
| 8226 | 2-Me-3-O2N—PhCH2CH2— |
| 8227 | 2-Me-4-O2N—PhCH2CH2— |
| 8228 | 2-Me-5-O2N—PhCH2CH2— |
| 8229 | 2-Me-6-O2N—PhCH2CH2— |
| 8230 | 2-F-3-Me—PhCH2CH2— |
| 8231 | 2-F-4-Me—PhCH2CH2— |
| 8232 | 2-F-5-Me—PhCH2CH2— |
| 8233 | 2-F-6-Me—PhCH2CH2— |
| 8234 | 2-Cl-3-Me—PhCH2CH2— |
| 8235 | 2-Cl-4-Me—PhCH2CH2— |
| 8236 | 2-Cl-5-Me—PhCH2CH2— |
| 8237 | 2-Cl-6-Me—PhCH2CH2— |
| 8238 | 2-Br-3-Me—PhCH2CH2— |
| 8239 | 2-Br-4-Me—PhCH2CH2— |
| 8240 | 2-Br-5-Me—PhCH2CH2— |
| 8241 | 2-Br-6-Me—PhCH2CH2— |
| 8242 | 2-I-3-Me—PhCH2CH2— |
| 8243 | 2-I-4-Me—PhCH2CH2— |
| 8244 | 2-I-5-Me—PhCH2CH2— |
| 8245 | 2-I-6-Me—PhCH2CH2— |
| 8246 | 2,3-di-Me—PhCH2CH2— |
| 8247 | 2,4-di-Me—PhCH2CH2— |
| 8248 | 2,5-di-Me—PhCH2CH2— |
| 8249 | 2,6-di-Me—PhCH2CH2— |
| 8250 | 2-F-3-Et—PhCH2CH2— |
| 8251 | 2-F-4-Et—PhCH2CH2— |
| 8252 | 2-F-5-Et—PhCH2CH2— |
| 8253 | 2-F-6-Et—PhCH2CH2— |
| 8254 | 2-Cl-3-Et—PhCH2CH2— |
| 8255 | 2-Cl-4-Et—PhCH2CH2— |
| 8256 | 2-Cl-5-Et—PhCH2CH2— |
| 8257 | 2-Cl-6-Et—PhCH2CH2— |
| 8258 | 2-Br-3-Et—PhCH2CH2— |
| 8259 | 2-Br-4-Et—PhCH2CH2— |
| 8260 | 2-Br-5-Et—PhCH2CH2— |
| 8261 | 2-Br-6-Et—PhCH2CH2— |
| 8262 | 2-I-3-Et—PhCH2CH2— |
| 8263 | 2-I-4-Et—PhCH2CH2— |
| 8264 | 2-I-5-Et—PhCH2CH2— |
| 8265 | 2-I-6-Et—PhCH2CH2— |
| 8266 | 2-Me-3-Et—PhCH2CH2— |
| 8267 | 2-Me-4-Et—PhCH2CH2— |
| 8268 | 2-Me-5-Et—PhCH2CH2— |
| 8269 | 2-Me-6-Et—PhCH2CH2— |
| 8270 | 2-F-3-Pr—PhCH2CH2— |
| 8271 | 2-F-4-Pr—PhCH2CH2— |
| 8272 | 2-F-5-Pr—PhCH2CH2— |
| 8273 | 2-F-6-Pr—PhCH2CH2— |
| 8274 | 2-Cl-3-Pr—PhCH2CH2— |
| 8275 | 2-Cl-4-Pr—PhCH2CH2— |
| 8276 | 2-Cl-5-Pr—PhCH2CH2— |
| 8277 | 2-Cl-6-Pr—PhCH2CH2— |
| 8278 | 2-Br-3-Pr—PhCH2CH2— |
| 8279 | 2-Br-4-Pr—PhCH2CH2— |
| 8280 | 2-Br-5-Pr—PhCH2CH2— |
| 8281 | 2-Br-6-Pr—PhCH2CH2— |
| 8282 | 2-I-3-Pr—PhCH2CH2— |
| 8283 | 2-I-4-Pr—PhCH2CH2— |
| 8284 | 2-I-5-Pr—PhCH2CH2— |
| 8285 | 2-I-6-Pr—PhCH2CH2— |
| 8286 | 2-Me-3-Pr—PhCH2CH2— |
| 8287 | 2-Me-4-Pr—PhCH2CH2— |
| 8288 | 2-Me-5-Pr—PhCH2CH2— |
| 8289 | 2-Me-6-Pr—PhCH2CH2— |
| 8290 | 2-F-3-iPr—PhCH2CH2— |
| 8291 | 2-F-4-iPr—PhCH2CH2— |
| 8292 | 2-F-5-iPr—PhCH2CH2— |
| 8293 | 2-F-6-iPr—PhCH2CH2— |
| 8294 | 2-Cl-3-iPr—PhCH2CH2— |
| 8295 | 2-Cl-4-iPr—PhCH2CH2— |
| 8296 | 2-Cl-5iPr—PhCH2CH2— |
| 8297 | 2-Cl-6-iPr—PhCH2CH2— |
| 8298 | 2-Br-3-iPr—PhCH2CH2— |
| 8299 | 2-Br-4-iPr—PhCH2CH2— |
| 8300 | 2-Br-5-iPr—PhCH2CH2— |
| 8301 | 2-Br-6-iPr—PhCH2CH2— |

TABLE 2-continued

| No. | Z |
|---|---|
| 8302 | 2-I-3-iPr—PhCH2CH2— |
| 8303 | 2-I-4-iPr—PhCH2CH2— |
| 8304 | 2-I-5-iPr—PhCH2CH2— |
| 8305 | 2-I-6-iPr—PhCH2CH2— |
| 8306 | 2-Me-3-iPr—PhCH2CH2— |
| 8307 | 2-Me-4-iPr—PhCH2CH2— |
| 8308 | 2-Me-5-iPr—PhCH2CH2— |
| 8309 | 2-Me-6-iPr—PhCH2CH2— |
| 8310 | 2-F-3-N≡CCH2—PhCH2CH2— |
| 8311 | 2-F-4-N≡CCH2—PhCH2CH2— |
| 8312 | 2-F-5-N≡CCH2—PhCH2CH2— |
| 8313 | 2-F-6-N≡CCH2—PhCH2CH2— |
| 8314 | 2-Cl-3-N≡CCH2—PhCH2CH2— |
| 8315 | 2-Cl-4-N≡CCH2—PhCH2CH2— |
| 8316 | 2-Cl-5-N≡CCH2—PhCH2CH2— |
| 8317 | 2-Cl-6-N≡CCH2—PhCH2CH2— |
| 8318 | 2-Br-3-N≡CCH2—PhCH2CH2— |
| 8319 | 2-Br-4-N≡CCH2—PhCH2CH2— |
| 8320 | 2-Br-5-N≡CCH2—PhCH2CH2— |
| 8321 | 2-Br-6-N≡CCH2—PhCH2CH2— |
| 8322 | 2-I-3-N≡CCH2—PhCH2CH2— |
| 8323 | 2-I-4-N≡CCH2—PhCH2CH2— |
| 8324 | 2-I-5-N≡CCH2—PhCH2CH2— |
| 8325 | 2-I-6-N≡CCH2—PhCH2CH2— |
| 8326 | 2-Me-3-N≡CCH2—PhCH2CH2— |
| 8327 | 2-Me-4-N≡CCH2—PhCH2CH2— |
| 8328 | 2-Me-5-N≡CCH2—PhCH2CH2— |
| 8329 | 2-Me-6-N≡CCH2—PhCH2CH2— |
| 8330 | 2-F-3-N≡CCH2CH2—PhCH2CH2— |
| 8331 | 2-F-4-N≡CCH2CH2—PhCH2CH2— |
| 8332 | 2-F-5-N≡CCH2CH2—PhCH2CH2— |
| 8333 | 2-F-6-N≡CCH2CH2—PhCH2CH2— |
| 8334 | 2-Cl-3-N≡CCH2CH2—PhCH2CH2— |
| 8335 | 2-Cl-4-N≡CCH2CH2—PhCH2CH2— |
| 8336 | 2-Cl-5-N≡CCH2CH2—PhCH2CH2— |
| 8337 | 2-Cl-6-N≡CCH2CH2—PhCH2CH2— |
| 8338 | 2-Br-3-N≡CCH2CH2—PhCH2CH2— |
| 8339 | 2-Br-4-N≡CCH2CH2—PhCH2CH2— |
| 8340 | 2-Br-5-N≡CCH2CH2—PhCH2CH2— |
| 8341 | 2-Br-6-N≡CCH2CH2—PhCH2CH2— |
| 8342 | 2-I-3-N≡CCH2CH2—PhCH2CH2— |
| 8343 | 2-I-4-N≡CCH2CH2—PhCH2CH2— |
| 8344 | 2-I-5-N≡CCH2CH2—PhCH2CH2— |
| 8345 | 2-I-6-N≡CCH2CH2—PhCH2CH2— |
| 8346 | 2-Me-3-N≡CCH2CH2—PhCH2CH2— |
| 8347 | 2-Me-4-N≡CCH2CH2—PhCH2CH2— |
| 8348 | 2-Me-5-N≡CCH2CH2—PhCH2CH2— |
| 8349 | 2-Me-6-N≡CCH2CH2—PhCH2CH2— |
| 8350 | 2-F-3-cPrCH2—PhCH2CH2— |
| 8351 | 2-F-4-cPrCH2—PhCH2CH2— |
| 8352 | 2-F-5-cPrCH2—PhCH2CH2— |
| 8353 | 2-F-6-cPrCH2—PhCH2CH2— |
| 8354 | 2-Cl-3-cPrCH2—PhCH2CH2— |
| 8355 | 2-Cl-4-cPrCH2—PhCH2CH2— |
| 8356 | 2-Cl-5-cPrCH2—PhCH2CH2— |
| 8357 | 2-Cl-6-cPrCH2—PhCH2CH2— |
| 8358 | 2-Br-3-cPrCH2—PhCH2CH2— |
| 8359 | 2-Br-4-cPrCH2—PhCH2CH2— |
| 8360 | 2-Br-5-cPrCH2—PhCH2CH2— |
| 8361 | 2-Br-6-cPrCH2—PhCH2CH2— |
| 8362 | 2-I-3-cPrCH2—PhCH2CH2— |
| 8363 | 2-I-4-cPrCH2—PhCH2CH2— |
| 8364 | 2-I-5-cPrCH2—PhCH2CH2— |
| 8365 | 2-I-6-cPrCH2—PhCH2CH2— |
| 8366 | 2-Me-3-cPrCH2—PhCH2CH2— |
| 8367 | 2-Me-4-cPrCH2—PhCH2CH2— |
| 8368 | 2-Me-5-cPrCH2—PhCH2CH2— |
| 8369 | 2-Me-6-cPrCH2—PhCH2CH2— |
| 8370 | 2-F-3-cBuCH2—PhCH2CH2— |
| 8371 | 2-F-4-cBuCH2—PhCH2CH2— |
| 8372 | 2-F-5-cBuCH2—PhCH2CH2— |
| 8373 | 2-F-6-cBuCH2—PhCH2CH2— |
| 8374 | 2-Cl-3-cBuCH2—PhCH2CH2— |
| 8375 | 2-Cl-4-cBuCH2—PhCH2CH2— |
| 8376 | 2-Cl-5-cBuCH2—PhCH2CH2— |
| 8377 | 2-Cl-6-cBuCH2—PhCH2CH2— |
| 8378 | 2-Br-3-cBuCH2—PhCH2CH2— |
| 8379 | 2-Br-4-cBuCH2—PhCH2CH2— |
| 8380 | 2-Br-5-cBuCH2—PhCH2CH2— |
| 8381 | 2-Br-6-cBuCH2—PhCH2CH2— |
| 8382 | 2-I-3-cBuCH2—PhCH2CH2— |
| 8383 | 2-I-4-cBuCH2—PhCH2CH2— |
| 8384 | 2-I-5-cBuCH2—PhCH2CH2— |
| 8385 | 2-I-6-cBuCH2—PhCH2CH2— |
| 8386 | 2-Me-3-cBuCH2—PhCH2CH2— |
| 8387 | 2-Me-4-cBuCH2—PhCH2CH2— |
| 8388 | 2-Me-5-cBuCH2—PhCH2CH2— |
| 8389 | 2-Me-6-cBuCH2—PhCH2CH2— |
| 8390 | 2-F-3-MeOCH2—PhCH2CH2— |
| 8391 | 2-F-4-MeOCH2—PhCH2CH2— |
| 8392 | 2-F-5-MeOCH2—PhCH2CH2— |
| 8393 | 2-F-6-MeOCH2—PhCH2CH2— |
| 8394 | 2-Cl-3-MeOCH2—PhCH2CH2— |
| 8395 | 2-Cl-4-MeOCH2—PhCH2CH2— |
| 8396 | 2-Cl-5-MeOCH2—PhCH2CH2— |
| 8397 | 2-Cl-6-MeOCH2—PhCH2CH2— |
| 8398 | 2-Br-3-MeOCH2—PhCH2CH2— |
| 8399 | 2-Br-4-MeOCH2—PhCH2CH2— |
| 8400 | 2-Br-5-MeOCH2—PhCH2CH2— |
| 8401 | 2-Br-6-MeOCH2—PhCH2CH2— |
| 8402 | 2-I-3-MeOCH2—PhCH2CH2— |
| 8403 | 2-I-4-MeOCH2—PhCH2CH2— |
| 8404 | 2-I-5-MeOCH2—PhCH2CH2— |
| 8405 | 2-I-6-MeOCH2—PhCH2CH2— |
| 8406 | 2-Me-3-MeOCH2—PhCH2CH2— |
| 8407 | 2-Me-4-MeOCH2—PhCH2CH2— |
| 8408 | 2-Me-5-MeOCH2—PhCH2CH2— |
| 8409 | 2-Me-6-MeOCH2—PhCH2CH2— |
| 8410 | 2-F-3-MeOCH2CH2—PhCH2CH2— |
| 8411 | 2-F-4-MeOCH2CH2—PhCH2CH2— |
| 8412 | 2-F-5-MeOCH2CH2—PhCH2CH2— |
| 8413 | 2-F-6-MeOCH2CH2—PhCH2CH2— |
| 8414 | 2-Cl-3-MeOCH2CH2—PhCH2CH2— |
| 8415 | 2-Cl-4-MeOCH2CH2—PhCH2CH2— |
| 8416 | 2-Cl-5-MeOCH2CH2—PhCH2CH2— |
| 8417 | 2-Cl-6-MeOCH2CH2—PhCH2CH2— |
| 8418 | 2-Br-3-MeOCH2CH2—PhCH2CH2— |
| 8419 | 2-Br-4-MeOCH2CH2—PhCH2CH2— |
| 8420 | 2-Br-5-MeOCH2CH2—PhCH2CH2— |
| 8421 | 2-Br-6-MeOCH2CH2—PhCH2CH2— |
| 8422 | 2-I-3-MeOCH2CH2—PhCH2CH2— |
| 8423 | 2-I-4-MeOCH2CH2—PhCH2CH2— |
| 8424 | 2-I-5-MeOCH2CH2—PhCH2CH2— |
| 8425 | 2-I-6-MeOCH2CH2—PhCH2CH2— |
| 8426 | 2-Me-3-MeOCH2CH2—PhCH2CH2— |
| 8427 | 2-Me-4-MeOCH2CH2—PhCH2CH2— |
| 8428 | 2-Me-5-MeOCH2CH2—PhCH2CH2— |
| 8429 | 2-Me-6-MeOCH2CH2—PhCH2CH2— |
| 8430 | 2-F-3-MeOCH2CH2CH2—PhCH2CH2— |
| 8431 | 2-F-4-MeOCH2CH2CH2—PhCH2CH2— |
| 8432 | 2-F-5-MeOCH2CH2CH2—PhCH2CH2— |
| 8433 | 2-F-6-MeOCH2CH2CH2—PhCH2CH2— |
| 8434 | 2-Cl-3-MeOCH2CH2CH2—PhCH2CH2— |
| 8435 | 2-Cl-4-MeOCH2CH2CH2—PhCH2CH2— |
| 8436 | 2-Cl-5-MeOCH2CH2CH2—PhCH2CH2— |
| 8437 | 2-Cl-6-MeOCH2CH2CH2—PhCH2CH2— |
| 8438 | 2-Br-3-MeOCH2CH2CH2—PhCH2CH2— |
| 8439 | 2-Br-4-MeOCH2CH2CH2—PhCH2CH2— |
| 8440 | 2-Br-5-MeOCH2CH2CH2—PhCH2CH2— |
| 8441 | 2-Br-6-MeOCH2CH2CH2—PhCH2CH2— |
| 8442 | 2-I-3-MeOCH2CH2CH2—PhCH2CH2— |
| 8443 | 2-I-4-MeOCH2CH2CH2—PhCH2CH2— |
| 8444 | 2-I-5-MeOCH2CH2CH2—PhCH2CH2— |
| 8445 | 2-I-6-MeOCH2CH2CH2—PhCH2CH2— |
| 8446 | 2-Me-3-MeOCH2CH2CH2—PhCH2CH2— |
| 8447 | 2-Me-4-MeOCH2CH2CH2—PhCH2CH2— |
| 8448 | 2-Me-5-MeOCH2CH2CH2—PhCH2CH2— |
| 8449 | 2-Me-6-MeOCH2CH2CH2—PhCH2CH2— |
| 8450 | 2-F-3-EtOCH2—PhCH2CH2— |
| 8451 | 2-F-4-EtOCH2—PhCH2CH2— |
| 8452 | 2-F-5-EtOCH2—PhCH2CH2— |
| 8453 | 2-F-6-EtOCH2—PhCH2CH2— |
| 8454 | 2-Cl-3-EtOCH2—PhCH2CH2— |
| 8455 | 2-Cl-4-EtOCH2—PhCH2CH2— |
| 8456 | 2-Cl-5-EtOCH2—PhCH2CH2— |
| 8457 | 2-Cl-6-EtOCH2—PhCH2CH2— |

TABLE 2-continued

| No. | Z |
|---|---|
| 8458 | 2-Br-3-EtOCH2—PhCH2CH2— |
| 8459 | 2-Br-4-EtOCH2—PhCH2CH2— |
| 8460 | 2-Br-5-EtOCH2—PhCH2CH2— |
| 8461 | 2-Br-6-EtOCH2—PhCH2CH2— |
| 8462 | 2-I-3-EtOCH2—PhCH2CH2— |
| 8463 | 2-I-4-EtOCH2—PhCH2CH2— |
| 8464 | 2-I-5-EtOCH2—PhCH2CH2— |
| 8465 | 2-I-6-EtOCH2—PhCH2CH2— |
| 8466 | 2-Me-3-EtOCH2—PhCH2CH2— |
| 8467 | 2-Me-4-EtOCH2—PhCH2CH2— |
| 8468 | 2-Me-5-EtOCH2—PhCH2CH2— |
| 8469 | 2-Me-6-EtOCH2—PhCH2CH2— |
| 8470 | 2-F-3-EtOCH2CH2—PhCH2CH2— |
| 8471 | 2-F-4-EtOCH2CH2—PhCH2CH2— |
| 8472 | 2-F-5-EtOCH2CH2—PhCH2CH2— |
| 8473 | 2-F-6-EtOCH2CH2—PhCH2CH2— |
| 8474 | 2-Cl-3-EtOCH2CH2—PhCH2CH2— |
| 8475 | 2-Cl-4-EtOCH2CH2—PhCH2CH2— |
| 8476 | 2-Cl-5-EtOCH2CH2—PhCH2CH2— |
| 8477 | 2-Cl-6-EtOCH2CH2—PhCH2CH2— |
| 8478 | 2-Br-3-EtOCH2CH2—PhCH2CH2— |
| 8479 | 2-Br-4-EtOCH2CH2—PhCH2CH2— |
| 8480 | 2-Br-5-EtOCH2CH2—PhCH2CH2— |
| 8481 | 2-Br-6-EtOCH2CH2—PhCH2CH2— |
| 8482 | 2-I-3-EtOCH2CH2—PhCH2CH2— |
| 8483 | 2-I-4-EtOCH2CH2—PhCH2CH2— |
| 8484 | 2-I-5-EtOCH2CH2—PhCH2CH2— |
| 8485 | 2-I-6-EtOCH2CH2—PhCH2CH2— |
| 8486 | 2-Me-3-EtOCH2CH2—PhCH2CH2— |
| 8487 | 2-Me-4-EtOCH2CH2—PhCH2CH2— |
| 8488 | 2-Me-5-EtOCH2CH2—PhCH2CH2— |
| 8489 | 2-Me-6-EtOCH2CH2—PhCH2CH2— |
| 8490 | 2-F-3-cPrOCH2—PhCH2CH2— |
| 8491 | 2-F-4-cPrOCH2—PhCH2CH2— |
| 8492 | 2-F-5-cPrOCH2—PhCH2CH2— |
| 8493 | 2-F-6-cPrOCH2—PhCH2CH2— |
| 8494 | 2-Cl-3-cPrOCH2—PhCH2CH2— |
| 8495 | 2-Cl-4-cPrOCH2—PhCH2CH2— |
| 8496 | 2-Cl-5-cPrOCH2—PhCH2CH2— |
| 8497 | 2-Cl-6-cPrOCH2—PhCH2CH2— |
| 8498 | 2-Br-3-cPrOCH2—PhCH2CH2— |
| 8499 | 2-Br-4-cPrOCH2—PhCH2CH2— |
| 8500 | 2-Br-5-cPrOCH2—PhCH2CH2— |
| 8501 | 2-Br-6-cPrOCH2—PhCH2CH2— |
| 8502 | 2-I-3-cPrOCH2—PhCH2CH2— |
| 8503 | 2-I-4-cPrOCH2—PhCH2CH2— |
| 8504 | 2-I-5-cPrOCH2—PhCH2CH2— |
| 8505 | 2-I-6-cPrOCH2—PhCH2CH2— |
| 8506 | 2-Me-3-cPrOCH2—PhCH2CH2— |
| 8507 | 2-Me-4-cPrOCH2—PhCH2CH2— |
| 8508 | 2-Me-5-cPrOCH2—PhCH2CH2— |
| 8509 | 2-Me-6-cPrOCH2—PhCH2CH2— |
| 8510 | 2-F-3-F3COCH2—PhCH2CH2— |
| 8511 | 2-F-4-F3COCH2—PhCH2CH2— |
| 8512 | 2-F-5-F3COCH2—PhCH2CH2— |
| 8513 | 2-F-6-F3COCH2—PhCH2CH2— |
| 8514 | 2-Cl-3-F3COCH2—PhCH2CH2— |
| 8515 | 2-Cl-4-F3COCH2—PhCH2CH2— |
| 8516 | 2-Cl-5-F3COCH2—PhCH2CH2— |
| 8517 | 2-Cl-6-F3COCH2—PhCH2CH2— |
| 8518 | 2-Br-3-F3COCH2—PhCH2CH2— |
| 8519 | 2-Br-4-F3COCH2—PhCH2CH2— |
| 8520 | 2-Br-5-F3COCH2—PhCH2CH2— |
| 8521 | 2-Br-6-F3COCH2—PhCH2CH2— |
| 8522 | 2-I-3-F3COCH2—PhCH2CH2— |
| 8523 | 2-I-4-F3COCH2—PhCH2CH2— |
| 8524 | 2-I-5-F3COCH2—PhCH2CH2— |
| 8525 | 2-I-6-F3COCH2—PhCH2CH2— |
| 8526 | 2-Me-3-F3COCH2—PhCH2CH2— |
| 8527 | 2-Me-4-F3COCH2—PhCH2CH2— |
| 8528 | 2-Me-5-F3COCH2—PhCH2CH2— |
| 8529 | 2-Me-6-F3COCH2—PhCH2CH2— |
| 8530 | 2-F-3-F2CHOCH2—PhCH2CH2— |
| 8531 | 2-F-4-F2CHOCH2—PhCH2CH2— |
| 8532 | 2-F-5-F2CHOCH2—PhCH2CH2— |
| 8533 | 2-F-6-F2CHOCH2—PhCH2CH2— |
| 8534 | 2-Cl-3-F2CHOCH2—PhCH2CH2— |
| 8535 | 2-Cl-4-F2CHOCH2—PhCH2CH2— |
| 8536 | 2-Cl-5-F2CHOCH2—PhCH2CH2— |
| 8537 | 2-Cl-6-F2CHOCH2—PhCH2CH2— |
| 8538 | 2-Br-3-F2CHOCH2—PhCH2CH2— |
| 8539 | 2-Br-4-F2CHOCH2—PhCH2CH2— |
| 8540 | 2-Br-5-F2CHOCH2—PhCH2CH2— |
| 8541 | 2-Br-6-F2CHOCH2—PhCH2CH2— |
| 8542 | 2-I-3-F2CHOCH2—PhCH2CH2— |
| 8543 | 2-I-4-F2CHOCH2—PhCH2CH2— |
| 8544 | 2-I-5-F2CHOCH2—PhCH2CH2— |
| 8545 | 2-I-6-F2CHOCH2—PhCH2CH2— |
| 8546 | 2-Me-3-F2CHOCH2—PhCH2CH2— |
| 8547 | 2-Me-4-F2CHOCH2—PhCH2CH2— |
| 8548 | 2-Me-5-F2CHOCH2—PhCH2CH2— |
| 8549 | 2-Me-6-F2CHOCH2—PhCH2CH2— |
| 8550 | 2-F-3-MeOCH2CH2OCH2—PhCH2CH2— |
| 8551 | 2-F-4-MeOCH2CH2OCH2—PhCH2CH2— |
| 8552 | 2-F-5-MeOCH2CH2OCH2—PhCH2CH2— |
| 8553 | 2-F-6-MeOCH2CH2OCH2—PhCH2CH2— |
| 8554 | 2-Cl-3-MeOCH2CH2OCH2—PhCH2CH2— |
| 8555 | 2-Cl-4-MeOCH2CH2OCH2—PhCH2CH2— |
| 8556 | 2-Cl-5-MeOCH2CH2OCH2—PhCH2CH2— |
| 8557 | 2-Cl-6-MeOCH2CH2OCH2—PhCH2CH2— |
| 8558 | 2-Br-3-MeOCH2CH2OCH2—PhCH2CH2— |
| 8559 | 2-Br-4-MeOCH2CH2OCH2—PhCH2CH2— |
| 8560 | 2-Br-5-MeOCH2CH2OCH2—PhCH2CH2— |
| 8561 | 2-Br-6-MeOCH2CH2OCH2—PhCH2CH2— |
| 8562 | 2-I-3-MeOCH2CH2OCH2—PhCH2CH2— |
| 8563 | 2-I-4-MeOCH2CH2OCH2—PhCH2CH2— |
| 8564 | 2-I-5-MeOCH2CH2OCH2—PhCH2CH2— |
| 8565 | 2-I-6-MeOCH2CH2OCH2—PhCH2CH2— |
| 8566 | 2-Me-3-MeOCH2CH2OCH2—PhCH2CH2— |
| 8567 | 2-Me-4-MeOCH2CH2OCH2—PhCH2CH2— |
| 8568 | 2-Me-5-MeOCH2CH2OCH2—PhCH2CH2— |
| 8569 | 2-Me-6-MeOCH2CH2OCH2—PhCH2CH2— |
| 8570 | 2-F-3-Me2NCH2—PhCH2CH2— |
| 8571 | 2-F-4-Me2NCH2—PhCH2CH2— |
| 8572 | 2-F-5-Me2NCH2—PhCH2CH2— |
| 8573 | 2-F-6-Me2NCH2—PhCH2CH2— |
| 8574 | 2-Cl-3-Me2NCH2—PhCH2CH2— |
| 8575 | 2-Cl-4-Me2NCH2—PhCH2CH2— |
| 8576 | 2-Cl-5-Me2NCH2—PhCH2CH2— |
| 8577 | 2-Cl-6-Me2NCH2—PhCH2CH2— |
| 8578 | 2-Br-3-Me2NCH2—PhCH2CH2— |
| 8579 | 2-Br-4-Me2NCH2—PhCH2CH2— |
| 8580 | 2-Br-5-Me2NCH2—PhCH2CH2— |
| 8581 | 2-Br-6-Me2NCH2—PhCH2CH2— |
| 8582 | 2-I-3-Me2NCH2—PhCH2CH2— |
| 8583 | 2-I-4-Me2NCH2—PhCH2CH2— |
| 8584 | 2-I-5-Me2NCH2—PhCH2CH2— |
| 8585 | 2-I-6-Me2NCH2—PhCH2CH2— |
| 8586 | 2-Me-3-Me2NCH2—PhCH2CH2— |
| 8587 | 2-Me-4-Me2NCH2—PhCH2CH2— |
| 8588 | 2-Me-5-Me2NCH2—PhCH2CH2— |
| 8589 | 2-Me-6-Me2NCH2—PhCH2CH2— |
| 8590 | 2-F-3-MeSCH2—PhCH2CH2— |
| 8591 | 2-F-4-MeSCH2—PhCH2CH2— |
| 8592 | 2-F-5-MeSCH2—PhCH2CH2— |
| 8593 | 2-F-6-MeSCH2—PhCH2CH2— |
| 8594 | 2-Cl-3-MeSCH2—PhCH2CH2— |
| 8595 | 2-Cl-4-MeSCH2—PhCH2CH2— |
| 8596 | 2-Cl-5-MeSCH2—PhCH2CH2— |
| 8597 | 2-Cl-6-MeSCH2—PhCH2CH2— |
| 8598 | 2-Br-3-MeSCH2—PhCH2CH2— |
| 8599 | 2-Br-4-MeSCH2—PhCH2CH2— |
| 8600 | 2-Br-5-MeSCH2—PhCH2CH2— |
| 8601 | 2-Br-6-MeSCH2—PhCH2CH2— |
| 8602 | 2-I-3-MeSCH2—PhCH2CH2— |
| 8603 | 2-I-4-MeSCH2—PhCH2CH2— |
| 8604 | 2-I-5-MeSCH2—PhCH2CH2— |
| 8605 | 2-I-6-MeSCH2—PhCH2CH2— |
| 8606 | 2-Me-3-MeSCH2—PhCH2CH2— |
| 8607 | 2-Me-4-MeSCH2—PhCH2CH2— |
| 8608 | 2-Me-5-MeSCH2—PhCH2CH2— |
| 8609 | 2-Me-6-MeSCH2—PhCH2CH2— |
| 8610 | 2-F-3-MeS(O)CH2—PhCH2CH2— |
| 8611 | 2-F-4-MeS(O)CH2—PhCH2CH2— |
| 8612 | 2-F-5-MeS(O)CH2—PhCH2CH2— |
| 8613 | 2-F-6-MeS(O)CH2—PhCH2CH2— |

TABLE 2-continued

| No. | Z |
|---|---|
| 8614 | 2-Cl-3-MeS(O)CH2—PhCH2CH2— |
| 8615 | 2-Cl-4-MeS(O)CH2—PhCH2CH2— |
| 8616 | 2-Cl-5-MeS(O)CH2—PhCH2CH2— |
| 8617 | 2-Cl-6-MeS(O)CH2—PhCH2CH2— |
| 8618 | 2-Br-3-MeS(O)CH2—PhCH2CH2— |
| 8619 | 2-Br-4-MeS(O)CH2—PhCH2CH2— |
| 8620 | 2-Br-5-MeS(O)CH2—PhCH2CH2— |
| 8621 | 2-Br-6-MeS(O)CH2—PhCH2CH2— |
| 8622 | 2-I-3-MeS(O)CH2—PhCH2CH2— |
| 8623 | 2-I-4-MeS(O)CH2—PhCH2CH2— |
| 8624 | 2-I-5-MeS(O)CH2—PhCH2CH2— |
| 8625 | 2-I-6-MeS(O)CH2—PhCH2CH2— |
| 8626 | 2-Me-3-MeS(O)CH2—PhCH2CH2— |
| 8627 | 2-Me-4-MeS(O)CH2—PhCH2CH2— |
| 8628 | 2-Me-5-MeS(O)CH2—PhCH2CH2— |
| 8629 | 2-Me-6-MeS(O)CH2—PhCH2CH2— |
| 8630 | 2-F-3-MeSO2CH2—PhCH2CH2— |
| 8631 | 2-F-4-MeSO2CH2—PhCH2CH2— |
| 8632 | 2-F-5-MeSO2CH2—PhCH2CH2— |
| 8633 | 2-F-6-MeSO2CH2—PhCH2CH2— |
| 8634 | 2-Cl-3-MeSO2CH2—PhCH2CH2— |
| 8635 | 2-Cl-4-MeSO2CH2—PhCH2CH2— |
| 8636 | 2-Cl-5-MeSO2CH2—PhCH2CH2— |
| 8637 | 2-Cl-6-MeSO2CH2—PhCH2CH2— |
| 8638 | 2-Br-3-MeSO2CH2—PhCH2CH2— |
| 8639 | 2-Br-4-MeSO2CH2—PhCH2CH2— |
| 8640 | 2-Br-5-MeSO2CH2—PhCH2CH2— |
| 8641 | 2-Br-6-MeSO2CH2—PhCH2CH2— |
| 8642 | 2-I-3-MeSO2CH2—PhCH2CH2— |
| 8643 | 2-I-4-MeSO2CH2—PhCH2CH2— |
| 8644 | 2-I-5-MeSO2CH2—PhCH2CH2— |
| 8645 | 2-I-6-MeSO2CH2—PhCH2CH2— |
| 8646 | 2-Me-3-MeSO2CH2—PhCH2CH2— |
| 8647 | 2-Me-4-MeSO2CH2—PhCH2CH2— |
| 8648 | 2-Me-5-MeSO2CH2—PhCH2CH2— |
| 8649 | 2-Me-6-MeSO2CH2—PhCH2CH2— |
| 8650 | 2-F-3-cPr—PhCH2CH2— |
| 8651 | 2-F-4-cPr—PhCH2CH2— |
| 8652 | 2-F-5-cPr—PhCH2CH2— |
| 8653 | 2-F-6-cPr—PhCH2CH2— |
| 8654 | 2-Cl-3-cPr—PhCH2CH2— |
| 8655 | 2-Cl-4-cPr—PhCH2CH2— |
| 8656 | 2-Cl-5-cPr—PhCH2CH2— |
| 8657 | 2-Cl-6-cPr—PhCH2CH2— |
| 8658 | 2-Br-3-cPr—PhCH2CH2— |
| 8659 | 2-Br-4-cPr—PhCH2CH2— |
| 8660 | 2-Br-5-cPr—PhCH2CH2— |
| 8661 | 2-Br-6-cPr—PhCH2CH2— |
| 8662 | 2-I-3-cPr—PhCH2CH2— |
| 8663 | 2-I-4-cPr—PhCH2CH2— |
| 8664 | 2-I-5-cPr—PhCH2CH2— |
| 8665 | 2-I-6-cPr—PhCH2CH2— |
| 8666 | 2-Me-3-cPr—PhCH2CH2— |
| 8667 | 2-Me-4-cPr—PhCH2CH2— |
| 8668 | 2-Me-5-cPr—PhCH2CH2— |
| 8669 | 2-Me-6-cPr—PhCH2CH2— |
| 8670 | 2-F-3-cBu—PhCH2CH2— |
| 8671 | 2-F-4-cBu—PhCH2CH2— |
| 8672 | 2-F-5-cBu—PhCH2CH2— |
| 8673 | 2-F-6-cBu—PhCH2CH2— |
| 8674 | 2-Cl-3-cBu—PhCH2CH2— |
| 8675 | 2-Cl-4-cBu—PhCH2CH2— |
| 8676 | 2-Cl-5-cBu—PhCH2CH2— |
| 8677 | 2-Cl-6-cBu—PhCH2CH2— |
| 8678 | 2-Br-3-cBu—PhCH2CH2— |
| 8679 | 2-Br-4-cBu—PhCH2CH2— |
| 8680 | 2-Br-5-cBu—PhCH2CH2— |
| 8681 | 2-Br-6-cBu—PhCH2CH2— |
| 8682 | 2-I-3-cBu—PhCH2CH2— |
| 8683 | 2-I-4-cBu—PhCH2CH2— |
| 8684 | 2-I-5-cBu—PhCH2CH2— |
| 8685 | 2-I-6-cBu—PhCH2CH2— |
| 8686 | 2-Me-3-cBu—PhCH2CH2— |
| 8687 | 2-Me-4-cBu—PhCH2CH2— |
| 8688 | 2-Me-5-cBu—PhCH2CH2— |
| 8689 | 2-Me-6-cBu—PhCH2CH2— |
| 8690 | 2-F-3-F3C—PhCH2CH2— |
| 8691 | 2-F-4-F3C—PhCH2CH2— |
| 8692 | 2-F-5-F3C—PhCH2CH2— |
| 8693 | 2-F-6-F3C—PhCH2CH2— |
| 8694 | 2-Cl-3-F3C—PhCH2CH2— |
| 8695 | 2-Cl-4-F3C—PhCH2CH2— |
| 8696 | 2-Cl-5-F3C—PhCH2CH2— |
| 8697 | 2-Cl-6-F3C—PhCH2CH2— |
| 8698 | 2-Br-3-F3C—PhCH2CH2— |
| 8699 | 2-Br-4-F3C—PhCH2CH2— |
| 8700 | 2-Br-5-F3C—PhCH2CH2— |
| 8701 | 2-Br-6-F3C—PhCH2CH2— |
| 8702 | 2-I-3-F3C—PhCH2CH2— |
| 8703 | 2-I-4-F3C—PhCH2CH2— |
| 8704 | 2-I-5-F3C—PhCH2CH2— |
| 8705 | 2-I-6-F3C—PhCH2CH2— |
| 8706 | 2-Me-3-F3C—PhCH2CH2— |
| 8707 | 2-Me-4-F3C—PhCH2CH2— |
| 8708 | 2-Me-5-F3C—PhCH2CH2— |
| 8709 | 2-Me-6-F3C—PhCH2CH2— |
| 8710 | 2-F-3-F2CH—PhCH2CH2— |
| 8711 | 2-F-4-F2CH—PhCH2CH2— |
| 8712 | 2-F-5-F2CH—PhCH2CH2— |
| 8713 | 2-F-6-F2CH—PhCH2CH2— |
| 8714 | 2-Cl-3-F2CH—PhCH2CH2— |
| 8715 | 2-Cl-4-F2CH—PhCH2CH2— |
| 8716 | 2-Cl-5-F2CH—PhCH2CH2— |
| 8717 | 2-Cl-6-F2CH—PhCH2CH2— |
| 8718 | 2-Br-3-F2CH—PhCH2CH2— |
| 8719 | 2-Br-4-F2CH—PhCH2CH2— |
| 8720 | 2-Br-5-F2CH—PhCH2CH2— |
| 8721 | 2-Br-6-F2CH—PhCH2CH2— |
| 8722 | 2-I-3-F2CH—PhCH2CH2— |
| 8723 | 2-I-4-F2CH—PhCH2CH2— |
| 8724 | 2-I-5-F2CH—PhCH2CH2— |
| 8725 | 2-I-6-F2CH—PhCH2CH2— |
| 8726 | 2-Me-3-F2CH—PhCH2CH2— |
| 8727 | 2-Me-4-F2CH—PhCH2CH2— |
| 8728 | 2-Me-5-F2CH—PhCH2CH2— |
| 8729 | 2-Me-6-F2CH—PhCH2CH2— |
| 8730 | 2-F-3-H2C=CH—PhCH2CH2— |
| 8731 | 2-F-4-H2C=CH—PhCH2CH2— |
| 8732 | 2-F-5-H2C=CH—PhCH2CH2— |
| 8733 | 2-F-6-H2C=CH—PhCH2CH2— |
| 8734 | 2-Cl-3-H2C=CH—PhCH2CH2— |
| 8735 | 2-Cl-4-H2C=CH—PhCH2CH2— |
| 8736 | 2-Cl-5-H2C=CH—PhCH2CH2— |
| 8737 | 2-Cl-6-H2C=CH—PhCH2CH2— |
| 8738 | 2-Br-3-H2C=CH—PhCH2CH2— |
| 8739 | 2-Br-4-H2C=CH—PhCH2CH2— |
| 8740 | 2-Br-5-H2C=CH—PhCH2CH2— |
| 8741 | 2-Br-6-H2C=CH—PhCH2CH2— |
| 8742 | 2-I-3-H2C=CH—PhCH2CH2— |
| 8743 | 2-I-4-H2C=CH—PhCH2CH2— |
| 8744 | 2-I-5-H2C=CH—PhCH2CH2— |
| 8745 | 2-I-6-H2C=CH—PhCH2CH2— |
| 8746 | 2-Me-3-H2C=CH—PhCH2CH2— |
| 8747 | 2-Me-4-H2C=CH—PhCH2CH2— |
| 8748 | 2-Me-5-H2C=CH—PhCH2CH2— |
| 8749 | 2-Me-6-H2C=CH—PhCH2CH2— |
| 8750 | 2-F-3-H2C=CHCH2—PhCH2CH2— |
| 8751 | 2-F-4-H2C=CHCH2—PhCH2CH2— |
| 8752 | 2-F-5-H2C=CHCH2—PhCH2CH2— |
| 8753 | 2-F-6-H2C=CHCH2—PhCH2CH2— |
| 8754 | 2-Cl-3-H2C=CHCH2—PhCH2CH2— |
| 8755 | 2-Cl-4-H2C=CHCH2—PhCH2CH2— |
| 8756 | 2-Cl-5-H2C=CHCH2—PhCH2CH2— |
| 8757 | 2-Cl-6-H2C=CHCH2—PhCH2CH2— |
| 8758 | 2-Br-3-H2C=CHCH2—PhCH2CH2— |
| 8759 | 2-Br-4-H2C=CHCH2—PhCH2CH2— |
| 8760 | 2-Br-5-H2C=CHCH2—PhCH2CH2— |
| 8761 | 2-Br-6-H2C=CHCH2—PhCH2CH2— |
| 8762 | 2-I-3-H2C=CHCH2—PhCH2CH2— |
| 8763 | 2-I-4-H2C=CHCH2—PhCH2CH2— |
| 8764 | 2-I-5-H2C=CHCH2—PhCH2CH2— |
| 8765 | 2-I-6-H2C=CHCH2—PhCH2CH2— |
| 8766 | 2-Me-3-H2C=CHCH2—PhCH2CH2— |
| 8767 | 2-Me-4-H2C=CHCH2—PhCH2CH2— |
| 8768 | 2-Me-5-H2C=CHCH2—PhCH2CH2— |
| 8769 | 2-Me-6-H2C=CHCH2—PhCH2CH2— |

TABLE 2-continued

| No. | Z |
|---|---|
| 8770 | 2-F-3-F2C=CH—PhCH2CH2— |
| 8771 | 2-F-4-F2C=CH—PhCH2CH2— |
| 8772 | 2-F-5-F2C=CH—PhCH2CH2— |
| 8773 | 2-F-6-F2C=CH—PhCH2CH2— |
| 8774 | 2-Cl-3-F2C=CH—PhCH2CH2— |
| 8775 | 2-Cl-4-F2C=CH—PhCH2CH2— |
| 8776 | 2-Cl-5-F2C=CH—PhCH2CH2— |
| 8777 | 2-Cl-6-F2C=CH—PhCH2CH2— |
| 8778 | 2-Br-3-F2C=CH—PhCH2CH2— |
| 8779 | 2-Br-4-F2C=CH—PhCH2CH2— |
| 8780 | 2-Br-5-F2C=CH—PhCH2CH2— |
| 8781 | 2-Br-6-F2C=CH—PhCH2CH2— |
| 8782 | 2-I-3-F2C=CH—PhCH2CH2— |
| 8783 | 2-I-4-F2C=CH—PhCH2CH2— |
| 8784 | 2-I-5-F2C=CH—PhCH2CH2— |
| 8785 | 2-I-6-F2C=CH—PhCH2CH2— |
| 8786 | 2-Me-3-F2C=CH—PhCH2CH2— |
| 8787 | 2-Me-4-F2C=CH—PhCH2CH2— |
| 8788 | 2-Me-5-F2C=CH—PhCH2CH2— |
| 8789 | 2-Me-6-F2C=CH—PhCH2CH2— |
| 8790 | 2-F-3-F2C=CHCH2—PhCH2CH2— |
| 8791 | 2-F-4-F2C=CHCH2—PhCH2CH2— |
| 8792 | 2-F-5-F2C=CHCH2—PhCH2CH2— |
| 8793 | 2-F-6-F2C=CHCH2—PhCH2CH2— |
| 8794 | 2-Cl-3-F2C=CHCH2—PhCH2CH2— |
| 8795 | 2-Cl-4-F2C=CHCH2—PhCH2CH2— |
| 8796 | 2-Cl-5-F2C=CHCH2—PhCH2CH2— |
| 8797 | 2-Cl-6-F2C=CHCH2—PhCH2CH2— |
| 8798 | 2-Br-3-F2C=CHCH2—PhCH2CH2— |
| 8799 | 2-Br-4-F2C=CHCH2—PhCH2CH2— |
| 8800 | 2-Br-5-F2C=CHCH2—PhCH2CH2— |
| 8801 | 2-Br-6-F2C=CHCH2—PhCH2CH2— |
| 8802 | 2-I-3-F2C=CHCH2—PhCH2CH2— |
| 8803 | 2-I-4-F2C=CHCH2—PhCH2CH2— |
| 8804 | 2-I-5-F2C=CHCH2—PhCH2CH2— |
| 8805 | 2-I-6-F2C=CHCH2—PhCH2CH2— |
| 8806 | 2-Me-3-F2C=CHCH2—PhCH2CH2— |
| 8807 | 2-Me-4-F2C=CHCH2—PhCH2CH2— |
| 8808 | 2-Me-5-F2C=CHCH2—PhCH2CH2— |
| 8809 | 2-Me-6-F2C=CHCH2—PhCH2CH2— |
| 8810 | 2-F-3-HC≡C—PhCH2CH2— |
| 8811 | 2-F-4-HC≡C—PhCH2CH2— |
| 8812 | 2-F-5-HC≡C—PhCH2CH2— |
| 8813 | 2-F-6-HC≡C—PhCH2CH2— |
| 8814 | 2-Cl-3-HC≡C—PhCH2CH2— |
| 8815 | 2-Cl-4-HC≡C—PhCH2CH2— |
| 8816 | 2-Cl-5-HC≡C—PhCH2CH2— |
| 8817 | 2-Cl-6-HC≡C—PhCH2CH2— |
| 8818 | 2-Br-3-HC≡C—PhCH2CH2— |
| 8819 | 2-Br-4-HC≡C—PhCH2CH2— |
| 8820 | 2-Br-5-HC≡C—PhCH2CH2— |
| 8821 | 2-Br-6-HC≡C—PhCH2CH2— |
| 8822 | 2-I-3-HC≡C—PhCH2CH2— |
| 8823 | 2-I-4-HC≡C—PhCH2CH2— |
| 8824 | 2-I-5-HC≡C—PhCH2CH2— |
| 8825 | 2-I-6-HC≡C—PhCH2CH2— |
| 8826 | 2-Me-3-HC≡C—PhCH2CH2— |
| 8827 | 2-Me-4-HC≡C—PhCH2CH2— |
| 8828 | 2-Me-5-HC≡C—PhCH2CH2— |
| 8829 | 2-Me-6-HC≡C—PhCH2CH2— |
| 8830 | 2-F-3-HC≡CCH2—PhCH2CH2— |
| 8831 | 2-F-4-HC≡CCH2—PhCH2CH2— |
| 8832 | 2-F-5-HC≡CCH2—PhCH2CH2— |
| 8833 | 2-F-6-HC≡CCH2—PhCH2CH2— |
| 8834 | 2-Cl-3-HC≡CCH2—PhCH2CH2— |
| 8835 | 2-Cl-4-HC≡CCH2—PhCH2CH2— |
| 8836 | 2-Cl-5-HC≡CCH2—PhCH2CH2— |
| 8837 | 2-Cl-6-HC≡CCH2—PhCH2CH2— |
| 8838 | 2-Br-3-HC≡CCH2—PhCH2CH2— |
| 8839 | 2-Br-4-HC≡CCH2—PhCH2CH2— |
| 8840 | 2-Br-5-HC≡CCH2—PhCH2CH2— |
| 8841 | 2-Br-6-HC≡CCH2—PhCH2CH2— |
| 8842 | 2-I-3-HC≡CCH2—PhCH2CH2— |
| 8843 | 2-I-4-HC≡CCH2—PhCH2CH2— |
| 8844 | 2-I-5-HC≡CCH2—PhCH2CH2— |
| 8845 | 2-I-5-HC≡CCH2—PhCH2CH2— |
| 8846 | 2-Me-3-HC≡CCH2—PhCH2CH2— |
| 8847 | 2-Me-4-HC≡CCH2—PhCH2CH2— |
| 8848 | 2-Me-5-HC≡CCH2—PhCH2CH2— |
| 8849 | 2-Me-6-HC≡CCH2—PhCH2CH2— |
| 8850 | 2-F-3-F3CC≡C—PhCH2CH2— |
| 8851 | 2-F-4-F3CC≡C—PhCH2CH2— |
| 8852 | 2-F-5-F3CC≡C—PhCH2CH2— |
| 8853 | 2-F-6-F3CC≡C—PhCH2CH2— |
| 8854 | 2-Cl-3-F3CC≡C—PhCH2CH2— |
| 8855 | 2-Cl-4-F3CC≡C—PhCH2CH2— |
| 8856 | 2-Cl-5-F3CC≡C—PhCH2CH2— |
| 8857 | 2-Cl-6-F3CC≡C—PhCH2CH2— |
| 8858 | 2-Br-3-F3CC≡C—PhCH2CH2— |
| 8859 | 2-Br-4-F3CC≡C—PhCH2CH2— |
| 8860 | 2-Br-5-F3CC≡C—PhCH2CH2— |
| 8861 | 2-Br-6-F3CC≡C—PhCH2CH2— |
| 8862 | 2-I-3-F3CC≡C—PhCH2CH2— |
| 8863 | 2-I-4-F3CC≡C—PhCH2CH2— |
| 8864 | 2-I-5-F3CC≡C—PhCH2CH2— |
| 8865 | 2-I-6-F3CC≡C—PhCH2CH2— |
| 8866 | 2-Me-3-F3CC≡C—PhCH2CH2— |
| 8867 | 2-Me-4-F3CC≡C—PhCH2CH2— |
| 8868 | 2-Me-5-F3CC≡C—PhCH2CH2— |
| 8869 | 2-Me-6-F3CC≡C—PhCH2CH2— |
| 8870 | 2-F-3-F3CC≡CCH2—PhCH2CH2— |
| 8871 | 2-F-4-F3CC≡CCH2—PhCH2CH2— |
| 8872 | 2-F-5-F3CC≡CCH2—PhCH2CH2— |
| 8873 | 2-F-6-F3CC≡CCH2—PhCH2CH2— |
| 8874 | 2-Cl-3-F3CC≡CCH2—PhCH2CH2— |
| 8875 | 2-Cl-4-F3CC≡CCH2—PhCH2CH2— |
| 8876 | 2-Cl-5-F3CC≡CCH2—PhCH2CH2— |
| 8877 | 2-Cl-6-F3CC≡CCH2—PhCH2CH2— |
| 8878 | 2-Br-3-F3CC≡CCH2—PhCH2CH2— |
| 8879 | 2-Br-4-F3CC≡CCH2—PhCH2CH2— |
| 8880 | 2-Br-5-F3CC≡CCH2—PhCH2CH2— |
| 8881 | 2-Br-6-F3CC≡CCH2—PhCH2CH2— |
| 8882 | 2-I-3-F3CC≡CCH2—PhCH2CH2— |
| 8883 | 2-I-4-F3CC≡CCH2—PhCH2CH2— |
| 8884 | 2-I-5-F3CC≡CCH2—PhCH2CH2— |
| 8885 | 2-I-6-F3CC≡CCH2—PhCH2CH2— |
| 8886 | 2-Me-3-F3CC≡CCH2—PhCH2CH2— |
| 8887 | 2-Me-4-F3CC≡CCH2—PhCH2CH2— |
| 8888 | 2-Me-5-F3CC≡CCH2—PhCH2CH2— |
| 8889 | 2-Me-6-F3CC≡CCH2—PhCH2CH2— |
| 8890 | 2-F-3-MeO—PhCH2CH2— |
| 8891 | 2-F-4-MeO—PhCH2CH2— |
| 8892 | 2-F-5-MeO—PhCH2CH2— |
| 8893 | 2-F-6-MeO—PhCH2CH2— |
| 8894 | 2-Cl-3-MeO—PhCH2CH2— |
| 8895 | 2-Cl-4-MeO—PhCH2CH2— |
| 8896 | 2-Cl-5-MeO—PhCH2CH2— |
| 8897 | 2-Cl-6-MeO—PhCH2CH2— |
| 8898 | 2-Br-3-MeO—PhCH2CH2— |
| 8899 | 2-Br-4-MeO—PhCH2CH2— |
| 8900 | 2-Br-5-MeO—PhCH2CH2— |
| 8901 | 2-Br-6-MeO—PhCH2CH2— |
| 8902 | 2-I-3-MeO—PhCH2CH2— |
| 8903 | 2-I-4-MeO—PhCH2CH2— |
| 8904 | 2-I-5-MeO—PhCH2CH2— |
| 8905 | 2-I-6-MeO—PhCH2CH2— |
| 8906 | 2-Me-3-MeO—PhCH2CH2— |
| 8907 | 2-Me-4-MeO—PhCH2CH2— |
| 8908 | 2-Me-5-MeO—PhCH2CH2— |
| 8909 | 2-Me-6-MeO—PhCH2CH2— |
| 8910 | 2-F-3-EtO—PhCH2CH2— |
| 8911 | 2-F-4-EtO—PhCH2CH2— |
| 8912 | 2-F-5-EtO—PhCH2CH2— |
| 8913 | 2-F-6-EtO—PhCH2CH2— |
| 8914 | 2-Cl-3-EtO—PhCH2CH2— |
| 8915 | 2-Cl-4-EtO—PhCH2CH2— |
| 8916 | 2-Cl-5-EtO—PhCH2CH2— |
| 8917 | 2-Cl-6-EtO—PhCH2CH2— |
| 8918 | 2-Br-3-EtO—PhCH2CH2— |
| 8919 | 2-Br-4-EtO—PhCH2CH2— |
| 8920 | 2-Br-5-EtO—PhCH2CH2— |
| 8921 | 2-Br-6-EtO—PhCH2CH2— |
| 8922 | 2-I-3-EtO—PhCH2CH2— |
| 8923 | 2-I-4-EtO—PhCH2CH2— |
| 8924 | 2-I-5-EtO—PhCH2CH2— |
| 8925 | 2-I-6-EtO—PhCH2CH2— |

TABLE 2-continued

| No. | Z |
|---|---|
| 8926 | 2-Me-3-EtO—PhCH2CH2— |
| 8927 | 2-Me-4-EtO—PhCH2CH2— |
| 8928 | 2-Me-5-EtO—PhCH2CH2— |
| 8929 | 2-Me-6-EtO—PhCH2CH2— |
| 8930 | 2-F-3-PrO—PhCH2CH2— |
| 8931 | 2-F-4-PrO—PhCH2CH2— |
| 8932 | 2-F-5-PrO—PhCH2CH2— |
| 8933 | 2-F-6-PrO—PhCH2CH2— |
| 8934 | 2-Cl-3-PrO—PhCH2CH2— |
| 8935 | 2-Cl-4-PrO—PhCH2CH2— |
| 8936 | 2-Cl-5-PrO—PhCH2CH2— |
| 8937 | 2-Cl-6-PrO—PhCH2CH2— |
| 8938 | 2-Br-3-PrO—PhCH2CH2— |
| 8939 | 2-Br-4-PrO—PhCH2CH2— |
| 8940 | 2-Br-5-PrO—PhCH2CH2— |
| 8941 | 2-Br-6-PrO—PhCH2CH2— |
| 8942 | 2-I-3-PrO—PhCH2CH2— |
| 8943 | 2-I-4-PrO—PhCH2CH2— |
| 8944 | 2-I-5-PrO—PhCH2CH2— |
| 8945 | 2-I-6-PrO—PhCH2CH2— |
| 8946 | 2-Me-3-PrO—PhCH2CH2— |
| 8947 | 2-Me-4-PrO—PhCH2CH2— |
| 8948 | 2-Me-5-PrO—PhCH2CH2— |
| 8949 | 2-Me-6-PrO—PhCH2CH2— |
| 8950 | 2-F-3-iPrO—PhCH2CH2— |
| 8951 | 2-F-4-iPrO—PhCH2CH2— |
| 8952 | 2-F-5-iPrO—PhCH2CH2— |
| 8953 | 2-F-6-iPrO—PhCH2CH2— |
| 8954 | 2-Cl-3-iPrO—PhCH2CH2— |
| 8955 | 2-Cl-4-iPrO—PhCH2CH2— |
| 8956 | 2-Cl-5-iPrO—PhCH2CH2— |
| 8957 | 2-Cl-6-iPrO—PhCH2CH2— |
| 8958 | 2-Br-3-iPrO—PhCH2CH2— |
| 8959 | 2-Br-4-iPrO—PhCH2CH2— |
| 8960 | 2-Br-5-iPrO—PhCH2CH2— |
| 8961 | 2-Br-6-iPrO—PhCH2CH2— |
| 8962 | 2-I-3-iPrO—PhCH2CH2— |
| 8963 | 2-I-4-iPrO—PhCH2CH2— |
| 8964 | 2-I-5-iPrO—PhCH2CH2— |
| 8965 | 2-I-6-iPrO—PhCH2CH2— |
| 8966 | 2-Me-3-iPrO—PhCH2CH2— |
| 8967 | 2-Me-4-iPrO—PhCH2CH2— |
| 8968 | 2-Me-5-iPrO—PhCH2CH2— |
| 8969 | 2-Me-6-iPrO—PhCH2CH2— |
| 8970 | 2-F-3-BuO—PhCH2CH2— |
| 8971 | 2-F-4-BuO—PhCH2CH2— |
| 8972 | 2-F-5-BuO—PhCH2CH2— |
| 8973 | 2-F-6-BuO—PhCH2CH2— |
| 8974 | 2-Cl-3-BuO—PhCH2CH2— |
| 8975 | 2-Cl-4-BuO—PhCH2CH2— |
| 8976 | 2-Cl-5-BuO—PhCH2CH2— |
| 8977 | 2-Cl-6-BuO—PhCH2CH2— |
| 8978 | 2-Br-3-BuO—PhCH2CH2— |
| 8979 | 2-Br-4-BuO—PhCH2CH2— |
| 8980 | 2-Br-5-BuO—PhCH2CH2— |
| 8981 | 2-Br-6-BuO—PhCH2CH2— |
| 8982 | 2-I-3-BuO—PhCH2CH2— |
| 8983 | 2-I-4-BuO—PhCH2CH2— |
| 8984 | 2-I-5-BuO—PhCH2CH2— |
| 8985 | 2-I-6-BuO—PhCH2CH2— |
| 8986 | 2-Me-3-BuO—PhCH2CH2— |
| 8987 | 2-Me-4-BuO—PhCH2CH2— |
| 8988 | 2-Me-5-BuO—PhCH2CH2— |
| 8989 | 2-Me-6-BuO—PhCH2CH2— |
| 8990 | 2-F-3-iBuO—PhCH2CH2— |
| 8991 | 2-F-4-iBuO—PhCH2CH2— |
| 8992 | 2-F-5-iBuO—PhCH2CH2— |
| 8993 | 2-F-6-iBuO—PhCH2CH2— |
| 8994 | 2-Cl-3-iBuO—PhCH2CH2— |
| 8995 | 2-Cl-4-iBuO—PhCH2CH2— |
| 8996 | 2-Cl-5-iBuO—PhCH2CH2— |
| 8997 | 2-Cl-6-iBuO—PhCH2CH2— |
| 8998 | 2-Br-3-iBuO—PhCH2CH2— |
| 8999 | 2-Br-4-iBuO—PhCH2CH2— |
| 9000 | 2-Br-5-iBuO—PhCH2CH2— |
| 9001 | 2-Br-6-iBuO—PhCH2CH2— |
| 9002 | 2-I-3-iBuO—PhCH2CH2— |
| 9003 | 2-I-4-iBuO—PhCH2CH2— |
| 9004 | 2-I-5-iBuO—PhCH2CH2— |
| 9005 | 2-I-6-iBuO—PhCH2CH2— |
| 9006 | 2-Me-3-iBuO—PhCH2CH2— |
| 9007 | 2-Me-4-iBuO—PhCH2CH2— |
| 9008 | 2-Me-5-iBuO—PhCH2CH2— |
| 9009 | 2-Me-6-iBuO—PhCH2CH2— |
| 9010 | 2-F-3-PentylO—PhCH2CH2— |
| 9011 | 2-F-4-PentylO—PhCH2CH2— |
| 9012 | 2-F-5-PentylO—PhCH2CH2— |
| 9013 | 2-F-6-PentylO—PhCH2CH2— |
| 9014 | 2-Cl-3-PentylO—PhCH2CH2— |
| 9015 | 2-Cl-4-PentylO—PhCH2CH2— |
| 9016 | 2-Cl-5-PentylO—PhCH2CH2— |
| 9017 | 2-Cl-6-PentylO—PhCH2CH2— |
| 9018 | 2-Br-3-PentylO—PhCH2CH2— |
| 9019 | 2-Br-4-PentylO—PhCH2CH2— |
| 9020 | 2-Br-5-PentylO—PhCH2CH2— |
| 9021 | 2-Br-6-PentylO—PhCH2CH2— |
| 9022 | 2-I-3-PentylO—PhCH2CH2— |
| 9023 | 2-I-4-PentylO—PhCH2CH2— |
| 9024 | 2-I-5-PentylO—PhCH2CH2— |
| 9025 | 2-I-6-PentylO—PhCH2CH2— |
| 9026 | 2-Me-3-PentylO—PhCH2CH2— |
| 9027 | 2-Me-4-PentylO—PhCH2CH2— |
| 9028 | 2-Me-5-PentylO—PhCH2CH2— |
| 9029 | 2-Me-6-PentylO—PhCH2CH2— |
| 9030 | 2-F-3-N≡CCH2O—PhCH2CH2— |
| 9031 | 2-F-4-N≡CCH2O—PhCH2CH2— |
| 9032 | 2-F-5-N≡CCH2O—PhCH2CH2— |
| 9033 | 2-F-6-N≡CCH2O—PhCH2CH2— |
| 9034 | 2-Cl-3-N≡CCH2O—PhCH2CH2— |
| 9035 | 2-Cl-4-N≡CCH2O—PhCH2CH2— |
| 9036 | 2-Cl-5-N≡CCH2O—PhCH2CH2— |
| 9037 | 2-Cl-6-N≡CCH2O—PhCH2CH2— |
| 9038 | 2-Br-3-N≡CCH2O—PhCH2CH2— |
| 9039 | 2-Br-4-N≡CCH2O—PhCH2CH2— |
| 9040 | 2-Br-5-N≡CCH2O—PhCH2CH2— |
| 9041 | 2-Br-6-N≡CCH2O—PhCH2CH2— |
| 9042 | 2-I-3-N≡CCH2O—PhCH2CH2— |
| 9043 | 2-I-4-N≡CCH2O—PhCH2CH2— |
| 9044 | 2-I-5-N≡CCH2O—PhCH2CH2— |
| 9045 | 2-I-6-N≡CCH2O—PhCH2CH2— |
| 9046 | 2-Me-3-N≡CCH2O—PhCH2CH2— |
| 9047 | 2-Me-4-N≡CCH2O—PhCH2CH2— |
| 9048 | 2-Me-5-N≡CCH2O—PhCH2CH2— |
| 9049 | 2-Me-6-N≡CCH2O—PhCH2CH2— |
| 9050 | 2-F-3-N≡CCH2CH2O—PhCH2CH2— |
| 9051 | 2-F-4-N≡CCH2CH2O—PhCH2CH2— |
| 9052 | 2-F-5-N≡CCH2CH2O—PhCH2CH2— |
| 9053 | 2-F-6-N≡CCH2CH2O—PhCH2CH2— |
| 9054 | 2-Cl-3-N≡CCH2CH2O—PhCH2CH2— |
| 9055 | 2-Cl-4-N≡CCH2CH2O—PhCH2CH2— |
| 9056 | 2-Cl-5-N≡CCH2CH2O—PhCH2CH2— |
| 9057 | 2-Cl-6-N≡CCH2CH2O—PhCH2CH2— |
| 9058 | 2-Br-3-N≡CCH2CH2O—PhCH2CH2— |
| 9059 | 2-Br-4-N≡CCH2CH2O—PhCH2CH2— |
| 9060 | 2-Br-5-N≡CCH2CH2O—PhCH2CH2— |
| 9061 | 2-Br-6-N≡CCH2CH2O—PhCH2CH2— |
| 9062 | 2-I-3-N≡CCH2CH2O—PhCH2CH2— |
| 9063 | 2-I-4-N≡CCH2CH2O—PhCH2CH2— |
| 9064 | 2-I-6-N≡CCH2CH2O—PhCH2CH2— |
| 9065 | 2-I-5-N≡CCH2CH2O—PhCH2CH2— |
| 9066 | 2-Me-3-N≡CCH2CH2O—PhCH2CH2— |
| 9067 | 2-Me-4-N≡CCH2CH2O—PhCH2CH2— |
| 9068 | 2-Me-5-N≡CCH2CH2O—PhCH2CH2— |
| 9069 | 2-Me-6-N≡CCH2CH2O—PhCH2CH2— |
| 9070 | 2-F-3-cPrCH2O—PhCH2CH2— |
| 9071 | 2-F-4-cPrCH2O—PhCH2CH2— |
| 9072 | 2-F-5-cPrCH2O—PhCH2CH2— |
| 9073 | 2-F-6-cPrCH2O—PhCH2CH2— |
| 9074 | 2-Cl-3-cPrCH2O—PhCH2CH2— |
| 9075 | 2-Cl-4-cPrCH2O—PhCH2CH2— |
| 9076 | 2-Cl-5-cPrCH2O—PhCH2CH2— |
| 9077 | 2-Cl-6-cPrCH2O—PhCH2CH2— |
| 9078 | 2-Br-3-cPrCH2O—PhCH2CH2— |
| 9079 | 2-Br-4-cPrCH2O—PhCH2CH2— |
| 9080 | 2-Br-5-cPrCH2O—PhCH2CH2— |
| 9081 | 2-Br-6-cPrCH2O—PhCH2CH2— |

TABLE 2-continued

| No. | Z |
|---|---|
| 9082 | 2-I-3-cPrCH2O—PhCH2CH2— |
| 9083 | 2-I-4-cPrCH2O—PhCH2CH2— |
| 9084 | 2-I-5-cPrCH2O—PhCH2CH2— |
| 9085 | 2-I-6-cPrCH2O—PhCH2CH2— |
| 9086 | 2-Me-3-cPrCH2O—PhCH2CH2— |
| 9087 | 2-Me-4-cPrCH2O—PhCH2CH2— |
| 9088 | 2-Me-5-cPrCH2O—PhCH2CH2— |
| 9089 | 2-Me-6-cPrCH2O—PhCH2CH2— |
| 9090 | 2-F-3-cBuCH2O—PhCH2CH2— |
| 9091 | 2-F-4-cBuCH2O—PhCH2CH2— |
| 9092 | 2-F-5-cBuCH2O—PhCH2CH2— |
| 9093 | 2-F-6-cBuCH2O—PhCH2CH2— |
| 9094 | 2-Cl-3-cBuCH2O—PhCH2CH2— |
| 9095 | 2-Cl-4-cBuCH2O—PhCH2CH2— |
| 9096 | 2-Cl-5-cBuCH2O—PhCH2CH2— |
| 9097 | 2-Cl-6-cBuCH2O—PhCH2CH2— |
| 9098 | 2-Br-3-cBuCH2O—PhCH2CH2— |
| 9099 | 2-Br-4-cBuCH2O—PhCH2CH2— |
| 9100 | 2-Br-5-cBuCH2O—PhCH2CH2— |
| 9101 | 2-Br-6-cBuCH2O—PhCH2CH2— |
| 9102 | 2-I-3-cBuCH2O—PhCH2CH2— |
| 9103 | 2-I-4-cBuCH2O—PhCH2CH2— |
| 9104 | 2-I-5-cBuCH2O—PhCH2CH2— |
| 9105 | 2-I-6-cBuCH2O—PhCH2CH2— |
| 9106 | 2-Me-3-cBuCH2O—PhCH2CH2— |
| 9107 | 2-Me-4-cBuCH2O—PhCH2CH2— |
| 9108 | 2-Me-5-cBuCH2O—PhCH2CH2— |
| 9109 | 2-Me-6-cBuCH2O—PhCH2CH2— |
| 9110 | 2-F-3-cPentylCH2O—PhCH2CH2— |
| 9111 | 2-F-4-cPentylCH2O—PhCH2CH2— |
| 9112 | 2-F-5-cPentylCH2O—PhCH2CH2— |
| 9113 | 2-F-6-cPentylCH2O—PhCH2CH2— |
| 9114 | 2-Cl-3-cPentylCH2O—PhCH2CH2— |
| 9115 | 2-Cl-4-cPentylCH2O—PhCH2CH2— |
| 9116 | 2-Cl-5-cPentylCH2O—PhCH2CH2— |
| 9117 | 2-Cl-6-cPentylCH2O—PhCH2CH2— |
| 9118 | 2-Br-3-cPentylCH2O—PhCH2CH2— |
| 9119 | 2-Br-4-cPentylCH2O—PhCH2CH2— |
| 9119 | 2-Br-5-cPentylCH2O—PhCH2CH2— |
| 9121 | 2-Br-6-cPentylCH2O—PhCH2CH2— |
| 9122 | 2-I-3-cPentylCH2O—PhCH2CH2— |
| 9123 | 2-I-4-cPentylCH2O—PhCH2CH2— |
| 9124 | 2-I-5-cPentylCH2O—PhCH2CH2— |
| 9125 | 2-I-6-cPentylCH2O—PhCH2CH2— |
| 9126 | 2-Me-3-cPentylCH2O—PhCH2CH2— |
| 9127 | 2-Me-4-cPentylCH2O—PhCH2CH2— |
| 9128 | 2-Me-5-cPentylCH2O—PhCH2CH2— |
| 9129 | 2-Me-6-cPentylCH2O—PhCH2CH2— |
| 9130 | 2-F-3-cHexylCH2O—PhCH2CH2— |
| 9131 | 2-F-4-cHexylCH2O—PhCH2CH2— |
| 9132 | 2-F-5-cHexylCH2O—PhCH2CH2— |
| 9133 | 2-F-6-cHexylCH2O—PhCH2CH2— |
| 9134 | 2-Cl-3-cHexylCH2O—PhCH2CH2— |
| 9135 | 2-Cl-4-cHexylCH2O—PhCH2CH2— |
| 9136 | 2-Cl-5-cHexylCH2O—PhCH2CH2— |
| 9137 | 2-Cl-6-cHexylCH2O—PhCH2CH2— |
| 9138 | 2-Br-3-cHexylCH2O—PhCH2CH2— |
| 9139 | 2-Br-4-cHexylCH2O—PhCH2CH2— |
| 9140 | 2-Br-5-cHexylCH2O—PhCH2CH2— |
| 9141 | 2-Br-6-cHexylCH2O—PhCH2CH2— |
| 9142 | 2-I-3-cHexylCH2O—PhCH2CH2— |
| 9143 | 2-I-4-cHexylCH2O—PhCH2CH2— |
| 9144 | 2-I-5-cHexylCH2O—PhCH2CH2— |
| 9145 | 2-I-6-cHexylCH2O—PhCH2CH2— |
| 9146 | 2-Me-3-cHexylCH2O—PhCH2CH2— |
| 9147 | 2-Me-4-cHexylCH2O—PhCH2CH2— |
| 9148 | 2-Me-5-cHexylCH2O—PhCH2CH2— |
| 9149 | 2-Me-6-cHexylCH2O—PhCH2CH2— |
| 9150 | 2-F-3-MeOCH2O—PhCH2CH2— |
| 9151 | 2-F-4-MeOCH2O—PhCH2CH2— |
| 9152 | 2-F-5-MeOCH2O—PhCH2CH2— |
| 9153 | 2-F-6-MeOCH2O—PhCH2CH2— |
| 9154 | 2-Cl-3-MeOCH2O—PhCH2CH2— |
| 9155 | 2-Cl-4-MeOCH2O—PhCH2CH2— |
| 9156 | 2-Cl-5-MeOCH2O—PhCH2CH2— |
| 9157 | 2-Cl-6-MeOCH2O—PhCH2CH2— |
| 9158 | 2-Br-3-MeOCH2O—PhCH2CH2— |
| 9159 | 2-Br-4-MeOCH2O—PhCH2CH2— |
| 9160 | 2-Br-5-MeOCH2O—PhCH2CH2— |
| 9161 | 2-Br-6-MeOCH2O—PhCH2CH2— |
| 9162 | 2-I-3-MeOCH2O—PhCH2CH2— |
| 9163 | 2-I-4-MeOCH2O—PhCH2CH2— |
| 9164 | 2-I-5-MeOCH2O—PhCH2CH2— |
| 9165 | 2-I-6-MeOCH2O—PhCH2CH2— |
| 9166 | 2-Me-3-MeOCH2O—PhCH2CH2— |
| 9167 | 2-Me-4-MeOCH2O—PhCH2CH2— |
| 9168 | 2-Me-5-MeOCH2O—PhCH2CH2— |
| 9169 | 2-Me-6-MeOCH2O—PhCH2CH2— |
| 9170 | 2-F-3-EtOCH2O—PhCH2CH2— |
| 9171 | 2-F-4-EtOCH2O—PhCH2CH2— |
| 9172 | 2-F-5-EtOCH2O—PhCH2CH2— |
| 9173 | 2-F-6-EtOCH2O—PhCH2CH2— |
| 9174 | 2-Cl-3-EtOCH2O—PhCH2CH2— |
| 9175 | 2-Cl-4-EtOCH2O—PhCH2CH2— |
| 9176 | 2-Cl-5-EtOCH2O—PhCH2CH2— |
| 9177 | 2-Cl-6-EtOCH2O—PhCH2CH2— |
| 9178 | 2-Br-3-EtOCH2O—PhCH2CH2— |
| 9179 | 2-Br-4-EtOCH2O—PhCH2CH2— |
| 9180 | 2-Br-5-EtOCH2O—PhCH2CH2— |
| 9181 | 2-Br-6-EtOCH2O—PhCH2CH2— |
| 9182 | 2-I-3-EtOCH2O—PhCH2CH2— |
| 9183 | 2-I-4-EtOCH2O—PhCH2CH2— |
| 9184 | 2-I-5-EtOCH2O—PhCH2CH2— |
| 9185 | 2-I-6-EtOCH2O—PhCH2CH2— |
| 9186 | 2-Me-3-EtOCH2O—PhCH2CH2— |
| 9187 | 2-Me-4-EtOCH2O—PhCH2CH2— |
| 9188 | 2-Me-5-EtOCH2O—PhCH2CH2— |
| 9189 | 2-Me-6-EtOCH2O—PhCH2CH2— |
| 9190 | 2-F-3-MeOCH2CH2O—PhCH2CH2— |
| 9191 | 2-F-4-MeOCH2CH2O—PhCH2CH2— |
| 9192 | 2-F-5-MeOCH2CH2O—PhCH2CH2— |
| 9193 | 2-F-6-MeOCH2CH2O—PhCH2CH2— |
| 9194 | 2-Cl-3-MeOCH2CH2O—PhCH2CH2— |
| 9195 | 2-Cl-4-MeOCH2CH2O—PhCH2CH2— |
| 9196 | 2-Cl-5-MeOCH2CH2O—PhCH2CH2— |
| 9197 | 2-Cl-6-MeOCH2CH2O—PhCH2CH2— |
| 9198 | 2-Br-3-MeOCH2CH2O—PhCH2CH2— |
| 9199 | 2-Br-4-MeOCH2CH2O—PhCH2CH2— |
| 9200 | 2-Br-5-MeOCH2CH2O—PhCH2CH2— |
| 9201 | 2-Br-6-MeOCH2CH2O—PhCH2CH2— |
| 9202 | 2-I-3-MeOCH2CH2O—PhCH2CH2— |
| 9203 | 2-I-4-MeOCH2CH2O—PhCH2CH2— |
| 9204 | 2-I-5-MeOCH2CH2O—PhCH2CH2— |
| 9205 | 2-I-6-MeOCH2CH2O—PhCH2CH2— |
| 9206 | 2-Me-3-MeOCH2CH2O—PhCH2CH2— |
| 9207 | 2-Me-4-MeOCH2CH2O—PhCH2CH2— |
| 9208 | 2-Me-5-MeOCH2CH2O—PhCH2CH2— |
| 9209 | 2-Me-6-MeOCH2CH2O—PhCH2CH2— |
| 9210 | 2-F-3-MeOCH2CH2CH2O—PhCH2CH2— |
| 9211 | 2-F-4-MeOCH2CH2CH2O—PhCH2CH2— |
| 9212 | 2-F-5-MeOCH2CH2CH2O—PhCH2CH2— |
| 9213 | 2-F-6-MeOCH2CH2CH2O—PhCH2CH2— |
| 9214 | 2-Cl-3-MeOCH2CH2CH2O—PhCH2CH2— |
| 9215 | 2-Cl-4-MeOCH2CH2CH2O—PhCH2CH2— |
| 9216 | 2-Cl-5-MeOCH2CH2CH2O—PhCH2CH2— |
| 9217 | 2-Cl-6-MeOCH2CH2CH2O—PhCH2CH2— |
| 9218 | 2-Br-3-MeOCH2CH2CH2O—PhCH2CH2— |
| 9219 | 2-Br-4-MeOCH2CH2CH2O—PhCH2CH2— |
| 9220 | 2-Br-5-MeOCH2CH2CH2O—PhCH2CH2— |
| 9221 | 2-Br-6-MeOCH2CH2CH2O—PhCH2CH2— |
| 9222 | 2-I-3-MeOCH2CH2CH2O—PhCH2CH2— |
| 9223 | 2-I-4-MeOCH2CH2CH2O—PhCH2CH2— |
| 9224 | 2-I-5-MeOCH2CH2CH2O—PhCH2CH2— |
| 9225 | 2-I-6-MeOCH2CH2CH2O—PhCH2CH2— |
| 9226 | 2-Me-3-MeOCH2CH2CH2O—PhCH2CH2— |
| 9227 | 2-Me-4-MeOCH2CH2CH2O—PhCH2CH2— |
| 9228 | 2-Me-5-MeOCH2CH2CH2O—PhCH2CH2— |
| 9229 | 2-Me-6-MeOCH2CH2CH2O—PhCH2CH2— |
| 9230 | 2-F-3-MeOCH2CH2OCH2O—PhCH2CH2— |
| 9231 | 2-F-4-MeOCH2CH2OCH2O—PhCH2CH2— |
| 9232 | 2-F-5-MeOCH2CH2OCH2O—PhCH2CH2— |
| 9233 | 2-F-6-MeOCH2CH2OCH2O—PhCH2CH2— |
| 9234 | 2-Cl-3-MeOCH2CH2OCH2O—PhCH2CH2— |
| 9235 | 2-Cl-4-MeOCH2CH2OCH2O—PhCH2CH2— |
| 9236 | 2-Cl-5-MeOCH2CH2OCH2O—PhCH2CH2— |
| 9237 | 2-Cl-6-MeOCH2CH2OCH2O—PhCH2CH2— |

TABLE 2-continued

| No. | Z |
|---|---|
| 9238 | 2-Br-3-MeOCH2CH2OCH2O—PhCH2CH2— |
| 9239 | 2-Br-4-MeOCH2CH2OCH2O—PhCH2CH2— |
| 9240 | 2-Br-5-MeOCH2CH2OCH2O—PhCH2CH2— |
| 9241 | 2-Br-6-MeOCH2CH2OCH2O—PhCH2CH2— |
| 9242 | 2-I-3-MeOCH2CH2OCH2O—PhCH2CH2— |
| 9243 | 2-I-4-MeOCH2CH2OCH2O—PhCH2CH2— |
| 9244 | 2-I-5-MeOCH2CH2OCH2O—PhCH2CH2— |
| 9245 | 2-I-6-MeOCH2CH2OCH2O—PhCH2CH2— |
| 9246 | 2-Me-3-MeOCH2CH2OCH2O—PhCH2CH2— |
| 9247 | 2-Me-4-MeOCH2CH2OCH2O—PhCH2CH2— |
| 9248 | 2-Me-5-MeOCH2CH2OCH2O—PhCH2CH2— |
| 9249 | 2-Me-6-MeOCH2CH2OCH2O—PhCH2CH2— |
| 9250 | 2-F-3-MeSCH2O—PhCH2CH2— |
| 9251 | 2-F-4-MeSCH2O—PhCH2CH2— |
| 9252 | 2-F-5-MeSCH2O—PhCH2CH2— |
| 9253 | 2-F-6-MeSCH2O—PhCH2CH2— |
| 9254 | 2-Cl-3-MeSCH2O—PhCH2CH2— |
| 9255 | 2-Cl-4-MeSCH2O—PhCH2CH2— |
| 9256 | 2-Cl-5-MeSCH2O—PhCH2CH2— |
| 9257 | 2-Cl-6-MeSCH2O—PhCH2CH2— |
| 9258 | 2-B1-3-MeSCH2O—PhCH2CH2— |
| 9259 | 2-Br-4-MeSCH2O—PhCH2CH2— |
| 9260 | 2-Br-5-MeSCH2O—PhCH2CH2— |
| 9261 | 2-Br-6-MeSCH2O—PhCH2CH2— |
| 9262 | 2-I-3-MeSCH2O—PhCH2CH2— |
| 9263 | 2-I-4-MeSCH2O—PhCH2CH2— |
| 9264 | 2-I-5-MeSCH2O—PhCH2CH2— |
| 9265 | 2-I-6-MeSCH2O—PhCH2CH2— |
| 9266 | 2-Me-3-MeSCH2O—PhCH2CH2— |
| 9267 | 2-Me-4-MeSCH2O—PhCH2CH2— |
| 9268 | 2-Me-5-MeSCH2O—PhCH2CH2— |
| 9269 | 2-Me-6-MeSCH2O—PhCH2CH2— |
| 9270 | 2-F-3-MeS(O)CH2O—PhCH2CH2— |
| 9271 | 2-F-4-MeS(O)CH2O—PhCH2CH2— |
| 9272 | 2-F-5-MeS(O)CH2O—PhCH2CH2— |
| 9273 | 2-F-6-MeS(O)CH2O—PhCH2CH2— |
| 9274 | 2-Cl-3-MeS(O)CH2O—PhCH2CH2— |
| 9275 | 2-Cl-4-MeS(O)CH2O—PhCH2CH2— |
| 9276 | 2-Cl-5-MeS(O)CH2O—PhCH2CH2— |
| 9277 | 2-Cl-6-MeS(O)CH2O—PhCH2CH2— |
| 9278 | 2-Br-3-MeS(O)CH2O—PhCH2CH2— |
| 9279 | 2-Br-4-MeS(O)CH2O—PhCH2CH2— |
| 9280 | 2-Br-5-MeS(O)CH2O—PhCH2CH2— |
| 9281 | 2-Br-6-MeS(O)CH2O—PhCH2CH2— |
| 9282 | 2-I-3-MeS(O)CH2O—PhCH2CH2— |
| 9283 | 2-I-4-MeS(O)CH2O—PhCH2CH2— |
| 9284 | 2-I-5-MeS(O)CH2O—PhCH2CH2— |
| 9285 | 2-I-6-MeS(O)CH2O—PhCH2CH2— |
| 9286 | 2-Me-3-MeS(O)CH2O—PhCH2CH2— |
| 9287 | 2-Me-4-MeS(O)CH2O—PhCH2CH2— |
| 9288 | 2-Me-5-MeS(O)CH2O—PhCH2CH2— |
| 9289 | 2-Me-6-MeS(O)CH2O—PhCH2CH2— |
| 9290 | 2-F-3-MeSO2CH2O—PhCH2CH2— |
| 9291 | 2-F-4-MeSO2CH2O—PhCH2CH2— |
| 9292 | 2-F-5-MeSO2CH2O—PhCH2CH2— |
| 9293 | 2-F-6-MeSO2CH2O—PhCH2CH2— |
| 9294 | 2-Cl-3-MeSO2CH2O—PhCH2CH2— |
| 9295 | 2-Cl-4-MeSO2CH2O—PhCH2CH2— |
| 9296 | 2-Cl-5-MeSO2CH2O—PhCH2CH2— |
| 9297 | 2-Cl-6-MeSO2CH2O—PhCH2CH2— |
| 9298 | 2-Br-3-MeSO2CH2O—PhCH2CH2— |
| 9299 | 2-Br-4-MeSO2CH2O—PhCH2CH2— |
| 9300 | 2-Br-5-MeSO2CH2O—PhCH2CH2— |
| 9301 | 2-Br-6-MeSO2CH2O—PhCH2CH2— |
| 9302 | 2-I-3-MeSO2CH2O—PhCH2CH2— |
| 9303 | 2-I-4-MeSO2CH2O—PhCH2CH2— |
| 9304 | 2-I-5-MeSO2CH2O—PhCH2CH2— |
| 9305 | 2-I-6-MeSO2CH2O—PhCH2CH2— |
| 9306 | 2-Me-3-MeSO2CH2O—PhCH2CH2— |
| 9307 | 2-Me-4-MeSO2CH2O—PhCH2CH2— |
| 9308 | 2-Me-5-MeSO2CH2O—PhCH2CH2— |
| 9309 | 2-Me-6-MeSO2CH2O—PhCH2CH2— |
| 9310 | 2-F-3-AcCH2O—PhCH2CH2— |
| 9311 | 2-F-4-AcCH2O—PhCH2CH2— |
| 9312 | 2-F-5-AcCH2O—PhCH2CH2— |
| 9313 | 2-F-6-AcCH2O—PhCH2CH2— |
| 9314 | 2-Cl-3-AcCH2O—PhCH2CH2— |
| 9315 | 2-Cl-4-AcCH2O—PhCH2CH2— |
| 9316 | 2-Cl-5-AcCH2O—PhCH2CH2— |
| 9317 | 2-Cl-6-AcCH2O—PhCH2CH2— |
| 9318 | 2-Br-3-AcCH2O—PhCH2CH2— |
| 9319 | 2-Br-4-AcCH2O—PhCH2CH2— |
| 9320 | 2-Br-5-AcCH2O—PhCH2CH2— |
| 9321 | 2-Br-6-AcCH2O—PhCH2CH2— |
| 9322 | 2-I-3-AcCH2O—PhCH2CH2— |
| 9323 | 2-I-4-AcCH2O—PhCH2CH2— |
| 9324 | 2-I-5-AcCH2O—PhCH2CH2— |
| 9325 | 2-I-6-AcCH2O—PhCH2CH2— |
| 9326 | 2-Me-3-AcCH2O—PhCH2CH2— |
| 9327 | 2-Me-4-AcCH2O—PhCH2CH2— |
| 9328 | 2-Me-5-AcCH2O—PhCH2CH2— |
| 9329 | 2-Me-6-AcCH2O—PhCH2CH2— |
| 9330 | 2-F-3-MeOC(=O)CH2O—PhCH2CH2— |
| 9331 | 2-F-4-MeOC(=O)CH2O—PhCH2CH2— |
| 9332 | 2-F-5-MeOC(=O)CH2O—PhCH2CH2— |
| 9333 | 2-F-6-MeOC(=O)CH2O—PhCH2CH2— |
| 9334 | 2-Cl-3-MeOC(=O)CH2O—PhCH2CH2— |
| 9335 | 2-Cl-4-MeOC(=O)CH2O—PhCH2CH2— |
| 9336 | 2-Cl-5-MeOC(=O)CH2O—PhCH2CH2— |
| 9337 | 2-Cl-6-MeOC(=O)CH2O—PhCH2CH2— |
| 9338 | 2-Br-3-MeOC(=O)CH2O—PhCH2CH2— |
| 9339 | 2-Br-4-MeOC(=O)CH2O—PhCH2CH2— |
| 9340 | 2-Br-5-MeOC(=O)CH2O—PhCH2CH2— |
| 9341 | 2-Br-6-MeOC(=O)CH2O—PhCH2CH2— |
| 9342 | 2-I-3-MeOC(=O)CH2O—PhCH2CH2— |
| 9343 | 2-I-4-MeOC(=O)CH2O—PhCH2CH2— |
| 9344 | 2-I-5-MeOC(=O)CH2O—PhCH2CH2— |
| 9345 | 2-I-6-MeOC(=O)CH2O—PhCH2CH2— |
| 9346 | 2-Me-3-MeOC(=O)CH2O—PhCH2CH2— |
| 9347 | 2-Me-4-MeOC(=O)CH2O—PhCH2CH2— |
| 9348 | 2-Me-5-MeOC(=O)CH2O—PhCH2CH2— |
| 9349 | 2-Me-6-MeOC(=O)CH2O—PhCH2CH2— |
| 9350 | 2-F-3-EtOC(=O)CH2O—PhCH2CH2— |
| 9351 | 2-F-4-EtOC(=O)CH2O—PhCH2CH2— |
| 9352 | 2-F-5-EtOC(=O)CH2O—PhCH2CH2— |
| 9353 | 2-F-6-EtOC(=O)CH2O—PhCH2CH2— |
| 9354 | 2-Cl-3-EtOC(=O)CH2O—PhCH2CH2— |
| 9355 | 2-Cl-4-EtOC(=O)CH2O—PhCH2CH2— |
| 9356 | 2-Cl-5-EtOC(=O)CH2O—PhCH2CH2— |
| 9357 | 2-Cl-6-EtOC(=O)CH2O—PhCH2CH2— |
| 9358 | 2-Br-3-EtOC(=O)CH2O—PhCH2CH2— |
| 9359 | 2-Br-4-EtOC(=O)CH2O—PhCH2CH2— |
| 9360 | 2-Br-5-EtOC(=O)CH2O—PhCH2CH2— |
| 9361 | 2-Br-6-EtOC(=O)CH2O—PhCH2CH2— |
| 9362 | 2-I-3-EtOC(=O)CH2O—PhCH2CH2— |
| 9363 | 2-I-4-EtOC(=O)CH2O—PhCH2CH2— |
| 9364 | 2-I-5-EtOC(=O)CH2O—PhCH2CH2— |
| 9365 | 2-I-6-EtOC(=O)CH2O—PhCH2CH2— |
| 9366 | 2-Me-3-EtOC(=O)CH2O—PhCH2CH2— |
| 9367 | 2-Me-4-EtOC(=O)CH2O—PhCH2CH2— |
| 9368 | 2-Me-5-EtOC(=O)CH2O—PhCH2CH2— |
| 9369 | 2-Me-6-EtOC(=O)CH2O—PhCH2CH2— |
| 9370 | 2-F-3-(1,3-dioxolan-2-yl)CH2O—PhCH2CH2— |
| 9371 | 2-F-4-(1,3-dioxolan-2-yl)CH2O—PhCH2CH2— |
| 9372 | 2-F-5-(1,3-dioxolan-2-yl)CH2O—PhCH2CH2— |
| 9373 | 2-F-6-(1,3-dioxolan-2-yl)CH2O—PhCH2CH2— |
| 9374 | 2-Cl-3-(1,3-dioxolan-2-yl)CH2O—PhCH2CH2— |
| 9375 | 2-Cl-4-(1,3-dioxolan-2-yl)CH2O—PhCH2CH2— |
| 9376 | 2-Cl-5-(1,3-dioxolan-2-yl)CH2O—PhCH2CH2— |
| 9377 | 2-Cl-6-(1,3-dioxolan-2-yl)CH2O—PhCH2CH2— |
| 9378 | 2-Br-3-(1,3-dioxolan-2-yl)CH2O—PhCH2CH2— |
| 9379 | 2-Br-4-(1,3-dioxolan-2-yl)CH2O—PhCH2CH2— |
| 9380 | 2-Br-5-(1,3-dioxolan-2-yl)CH2O—PhCH2CH2— |
| 9381 | 2-Br-6-(1,3-dioxolan-2-yl)CH2O—PhCH2CH2— |
| 9382 | 2-I-3-(1,3-dioxolan-2-yl)CH2O—PhCH2CH2— |
| 9383 | 2-I-4-(1,3-dioxolan-2-yl)CH2O—PhCH2CH2— |
| 9384 | 2-I-5-(1,3-dioxolan-2-yl)CH2O—PhCH2CH2— |
| 9385 | 2-I-6-(1,3-dioxolan-2-yl)CH2O—PhCH2CH2— |
| 9386 | 2-Me-3-(1,3-dioxolan-2-yl)CH2O—PhCH2CH2— |
| 9387 | 2-Me-4-(1,3-dioxolan-2-yl)CH2O—PhCH2CH2— |
| 9388 | 2-Me-5-(1,3-dioxolan-2-yl)CH2O—PhCH2CH2— |
| 9389 | 2-Me-6-(1,3-dioxolan-2-yl)CH2O—PhCH2CH2— |
| 9390 | 2-F-3-(1,3-dioxolan-2-yl)CH2CH2O—PhCH2CH2— |
| 9391 | 2-F-4-(1,3-dioxolan-2-yl)CH2CH2O—PhCH2CH2— |
| 9392 | 2-F-5-(1,3-dioxolan-2-yl)CH2CH2O—PhCH2CH2— |
| 9393 | 2-F-6-(1,3-dioxolan-2-yl)CH2CH2O—PhCH2CH2— |

TABLE 2-continued

| No. | Z |
|---|---|
| 9394 | 2-Cl-3-(1,3-dioxolan-2-yl)CH2CH2O—PhCH2CH2— |
| 9395 | 2-Cl-4-(1,3-dioxolan-2-yl)CH2CH2O—PhCH2CH2— |
| 9396 | 2-Cl-5-(1,3-dioxolan-2-yl)CH2CH2O—PhCH2CH2— |
| 9397 | 2-Cl-6-(1,3-dioxolan-2-yl)CH2CH2O—PhCH2CH2— |
| 9398 | 2-Br-3-(1,3-dioxolan-2-yl)CH2CH2O—PhCH2CH2— |
| 9399 | 2-Br-4-(1,3-dioxolan-2-yl)CH2CH2O—PhCH2CH2— |
| 9400 | 2-Br-5-(1,3-dioxolan-2-yl)CH2CH2O—PhCH2CH2— |
| 9401 | 2-Br-6-(1,3-dioxolan-2-yl)CH2CH2O—PhCH2CH2— |
| 9402 | 2-I-3-(1,3-dioxolan-2-yl)CH2CH2O—PhCH2CH2— |
| 9403 | 2-I-4-(1,3-dioxolan-2-yl)CH2CH2O—PhCH2CH2— |
| 9404 | 2-I-5-(1,3-dioxolan-2-yl)CH2CH2O—PhCH2CH2— |
| 9405 | 2-I-6-(1,3-dioxolan-2-yl)CH2CH2O—PhCH2CH2— |
| 9406 | 2-Me-3-(1,3-dioxolan-2-yl)CH2CH2O—PhCH2CH2— |
| 9407 | 2-Me-4-(1,3-dioxolan-2-yl)CH2CH2O—PhCH2CH2— |
| 9408 | 2-Me-5-(1,3-dioxolan-2-yl)CH2CH2O—PhCH2CH2— |
| 9409 | 2-Me-6-(1,3-dioxolan-2-yl)CH2CH2O—PhCH2CH2— |
| 9410 | 2-F-3-(1,3-dioxan-2-yl)CH2O—PhCH2CH2— |
| 9411 | 2-F-4-(1,3-dioxan-2-yl)CH2O—PhCH2CH2— |
| 9412 | 2-F-5-(1,3-dioxan-2-yl)CH2O—PhCH2CH2— |
| 9413 | 2-F-6-(1,3-dioxan-2-yl)CH2O—PhCH2CH2— |
| 9414 | 2-Cl-3-(1,3-dioxan-2-yl)CH2O—PhCH2CH2— |
| 9415 | 2-Cl-4-(1,3-dioxan-2-yl)CH2O—PhCH2CH2— |
| 9416 | 2-Cl-5-(1,3-dioxan-2-yl)CH2O—PhCH2CH2— |
| 9417 | 2-Cl-6-(1,3-dioxan-2-yl)CH2O—PhCH2CH2— |
| 9418 | 2-Br-3-(1,3-dioxan-2-yl)CH2O—PhCH2CH2— |
| 9419 | 2-Br-4-(1,3-dioxan-2-yl)CH2O—PhCH2CH2— |
| 9420 | 2-Br-5-(1,3-dioxan-2-yl)CH2O—PhCH2CH2— |
| 9421 | 2-Br-6-(1,3-dioxan-2-yl)CH2O—PhCH2CH2— |
| 9422 | 2-I-3-(1,3-dioxan-2-yl)CH2O—PhCH2CH2— |
| 9423 | 2-I-4-(1,3-dioxan-2-yl)CH2O—PhCH2CH2— |
| 9424 | 2-I-5-(1,3-dioxan-2-yl)CH2O—PhCH2CH2— |
| 9425 | 2-I-6-(1,3-dioxan-2-yl)CH2O—PhCH2CH2— |
| 9426 | 2-Me-3-(1,3-dioxan-2-yl)CH2O—PhCH2CH2— |
| 9427 | 2-Me-4-(1,3-dioxan-2-yl)CH2O—PhCH2CH2— |
| 9428 | 2-Me-5-(1,3-dioxan-2-yl)CH2O—PhCH2CH2— |
| 9429 | 2-Me-6-(1,3-dioxan-2-yl)CH2O—PhCH2CH2— |
| 9430 | 2-F-3-(1,3-dioxan-2-yl)CH2CH2O—PhCH2CH2— |
| 9431 | 2-F-4-(1,3-dioxan-2-yl)CH2CH2O—PhCH2CH2— |
| 9432 | 2-F-5-(1,3-dioxan-2-yl)CH2CH2O—PhCH2CH2— |
| 9433 | 2-F-6-(1,3-dioxan-2-yl)CH2CH2O—PhCH2CH2— |
| 9434 | 2-Cl-3-(1,3-dioxan-2-yl)CH2CH2O—PhCH2CH2— |
| 9435 | 2-Cl-4-(1,3-dioxan-2-yl)CH2CH2O—PhCH2CH2— |
| 9436 | 2-Cl-5-(1,3-dioxan-2-yl)CH2CH2O—PhCH2CH2— |
| 9437 | 2-Cl-6-(1,3-dioxan-2-yl)CH2CH2O—PhCH2CH2— |
| 9438 | 2-Br-3-(1,3-dioxan-2-yl)CH2CH2O—PhCH2CH2— |
| 9439 | 2-Br-4-(1,3-dioxan-2-yl)CH2CH2O—PhCH2CH2— |
| 9440 | 2-Br-5-(1,3-dioxan-2-yl)CH2CH2O—PhCH2CH2— |
| 9441 | 2-Br-6-(1,3-dioxan-2-yl)CH2CH2O—PhCH2CH2— |
| 9442 | 2-I-3-(1,3-dioxan-2-yl)CH2CH2O—PhCH2CH2— |
| 9443 | 2-I-4-(1,3-dioxan-2-yl)CH2CH2O—PhCH2CH2— |
| 9444 | 2-I-5-(1,3-dioxan-2-yl)CH2CH2O—PhCH2CH2— |
| 9445 | 2-I-6-(1,3-dioxan-2-yl)CH2CH2O—PhCH2CH2— |
| 9446 | 2-Me-3-(1,3-dioxan-2-yl)CH2CH2O—PhCH2CH2— |
| 9447 | 2-Me-4-(1,3-dioxan-2-yl)CH2CH2O—PhCH2CH2— |
| 9448 | 2-Me-5-(1,3-dioxan-2-yl)CH2CH2O—PhCH2CH2— |
| 9449 | 2-Me-6-(1,3-dioxan-2-yl)CH2CH2O—PhCH2CH2— |
| 9450 | 2-F-3-cPrO—PhCH2CH2— |
| 9451 | 2-F-4-cPrO—PhCH2CH2— |
| 9452 | 2-F-5-cPrO—PhCH2CH2— |
| 9453 | 2-F-6-cPrO—PhCH2CH2— |
| 9454 | 2-Cl-3-cPrO—PhCH2CH2— |
| 9455 | 2-Cl-4-cPrO—PhCH2CH2— |
| 9456 | 2-Cl-5-cPrO—PhCH2CH2— |
| 9457 | 2-Cl-6-cPrO—PhCH2CH2— |
| 9458 | 2-Br-3-cPrO—PhCH2CH2— |
| 9459 | 2-Br-4-cPrO—PhCH2CH2— |
| 9460 | 2-Br-5-cPrO—PhCH2CH2— |
| 9461 | 2-Br-6-cPrO—PhCH2CH2— |
| 9462 | 2-I-3-cPrO—PhCH2CH2— |
| 9463 | 2-I-4-cPrO—PhCH2CH2— |
| 9464 | 2-I-5-cPrO—PhCH2CH2— |
| 9465 | 2-I-6-cPrO—PhCH2CH2— |
| 9466 | 2-Me-3-cPrO—PhCH2CH2— |
| 9467 | 2-Me-4-cPrO—PhCH2CH2— |
| 9468 | 2-Me-5-cPrO—PhCH2CH2— |
| 9469 | 2-Me-6-cPrO—PhCH2CH2— |
| 9470 | 2-F-3-cBuO—PhCH2CH2— |
| 9471 | 2-F-4-cBuO—PhCH2CH2— |
| 9472 | 2-F-5-cBuO—PhCH2CH2— |
| 9473 | 2-F-6-cBuO—PhCH2CH2— |
| 9474 | 2-Cl-3-cBuO—PhCH2CH2— |
| 9475 | 2-Cl-4-cBuO—PhCH2CH2— |
| 9476 | 2-Cl-5-cBuO—PhCH2CH2— |
| 9477 | 2-Cl-6-cBuO—PhCH2CH2— |
| 9478 | 2-Br-3-cBuO—PhCH2CH2— |
| 9479 | 2-Br-4-cBuO—PhCH2CH2— |
| 9480 | 2-Br-5-cBuO—PhCH2CH2— |
| 9481 | 2-Br-6-cBuO—PhCH2CH2— |
| 9482 | 2-I-3-cBuO—PhCH2CH2— |
| 9483 | 2-I-4-cBuO—PhCH2CH2— |
| 9484 | 2-I-5-cBuO—PhCH2CH2— |
| 9485 | 2-I-6-cBuO—PhCH2CH2— |
| 9486 | 2-Me-3-cBuO—PhCH2CH2— |
| 9487 | 2-Me-4-cBuO—PhCH2CH2— |
| 9488 | 2-Me-5-cBuO—PhCH2CH2— |
| 9489 | 2-Me-6-cBuO—PhCH2CH2— |
| 9490 | 2-F-3-cPentylO—PhCH2CH2— |
| 9491 | 2-F-4-cPentylO—PhCH2CH2— |
| 9492 | 2-F-5-cPentylO—PhCH2CH2— |
| 9493 | 2-F-6-cPentylO—PhCH2CH2— |
| 9494 | 2-Cl-3-cPentylO—PhCH2CH2— |
| 9495 | 2-Cl-4-cPentylO—PhCH2CH2— |
| 9496 | 2-Cl-5-cPentylO—PhCH2CH2— |
| 9497 | 2-Cl-6-cPentylO—PhCH2CH2— |
| 9498 | 2-Br-3-cPentylO—PhCH2CH2— |
| 9499 | 2-Br-4-cPentylO—PhCH2CH2— |
| 9500 | 2-Br-5-cPentylO—PhCH2CH2— |
| 9501 | 2-Br-6-cPentylO—PhCH2CH2— |
| 9502 | 2-I-3-cPentylO—PhCH2CH2— |
| 9503 | 2-I-4-cPentylO—PhCH2CH2— |
| 9504 | 2-I-5-cPentylO—PhCH2CH2— |
| 9505 | 2-I-6-cPentylO—PhCH2CH2— |
| 9506 | 2-Me-3-cPentylO—PhCH2CH2— |
| 9507 | 2-Me-4-cPentylO—PhCH2CH2— |
| 9508 | 2-Me-5-cPentylO—PhCH2CH2— |
| 9509 | 2-Me-6-cPentylO—PhCH2CH2— |
| 9510 | 2-F-3-cHexylO—PhCH2CH2— |
| 9511 | 2-F-4-cHexylO—PhCH2CH2— |
| 9512 | 2-F-5-cHexylO—PhCH2CH2— |
| 9513 | 2-F-6-cHexylO—PhCH2CH2— |
| 9514 | 2-Cl-3-cHexylO—PhCH2CH2— |
| 9515 | 2-Cl-4-cHexylO—PhCH2CH2— |
| 9516 | 2-Cl-5-cHexylO—PhCH2CH2— |
| 9517 | 2-Cl-6-cHexylO—PhCH2CH2— |
| 9518 | 2-Br-3-cHexylO—PhCH2CH2— |
| 9519 | 2-Br-4-cHexylO—PhCH2CH2— |
| 9520 | 2-Br-5-cHexylO—PhCH2CH2— |
| 9521 | 2-Br-6-cHexylO—PhCH2CH2— |
| 9522 | 2-I-3-cHexylO—PhCH2CH2— |
| 9523 | 2-I-4-cHexylO—PhCH2CH2— |
| 9524 | 2-I-5-cHexylO—PhCH2CH2— |
| 9525 | 2-I-6-cHexylO—PhCH2CH2— |
| 9526 | 2-Me-3-cHexylO—PhCH2CH2— |
| 9527 | 2-Me-4-cHexylO—PhCH2CH2— |
| 9528 | 2-Me-5-cHexylO—PhCH2CH2— |
| 9529 | 2-Me-6-cHexylO—PhCH2CH2— |
| 9530 | 2-F-3-F3CO—PhCH2CH2— |
| 9531 | 2-F-4-F3CO—PhCH2CH2— |
| 9532 | 2-F-5-F3CO—PhCH2CH2— |
| 9533 | 2-F-6-F3CO—PhCH2CH2— |
| 9534 | 2-Cl-3-F3CO—PhCH2CH2— |
| 9535 | 2-Cl-4-F3CO—PhCH2CH2— |
| 9536 | 2-Cl-5-F3CO—PhCH2CH2— |
| 9537 | 2-Cl-6-F3CO—PhCH2CH2— |
| 9538 | 2-Br-3-F3CO—PhCH2CH2— |
| 9539 | 2-Br-4-F3CO—PhCH2CH2— |
| 9540 | 2-Br-5-F3CO—PhCH2CH2— |
| 9541 | 2-Br-6-F3CO—PhCH2CH2— |
| 9542 | 2-I-3-F3CO—PhCH2CH2— |
| 9543 | 2-I-4-F3CO—PhCH2CH2— |
| 9544 | 2-I-5-F3CO—PhCH2CH2— |
| 9545 | 2-I-6-F3CO—PhCH2CH2— |
| 9546 | 2-Me-3-F3CO—PhCH2CH2— |
| 9547 | 2-Me-4-F3CO—PhCH2CH2— |
| 9548 | 2-Me-5-F3CO—PhCH2CH2— |
| 9549 | 2-Me-6-F3CO—PhCH2CH2— |

TABLE 2-continued

| No. | Z |
|---|---|
| 9550 | 2-F-3-F2CHO—PhCH2CH2— |
| 9551 | 2-F-4-F2CHO—PhCH2CH2— |
| 9552 | 2-F-5-F2CHO—PhCH2CH2— |
| 9553 | 2-F-6-F2CHO—PhCH2CH2— |
| 9554 | 2-Cl-3-F2CHO—PhCH2CH2— |
| 9555 | 2-Cl-4-F2CHO—PhCH2CH2— |
| 9556 | 2-Cl-5-F2CHO—PhCH2CH2— |
| 9557 | 2-Cl-6-F2CHO—PhCH2CH2— |
| 9558 | 2-Br-3-F2CHO—PhCH2CH2— |
| 9559 | 2-Br-4-F2CHO—PhCH2CH2— |
| 9560 | 2-Br-5-F2CHO—PhCH2CH2— |
| 9561 | 2-Br-6-F2CHO—PhCH2CH2— |
| 9562 | 2-I-3-F2CHO—PhCH2CH2— |
| 9563 | 2-I-4-F2CHO—PhCH2CH2— |
| 9564 | 2-I-5-F2CHO—PhCH2CH2— |
| 9565 | 2-I-6-F2CHO—PhCH2CH2— |
| 9566 | 2-Me-3-F2CHO—PhCH2CH2— |
| 9567 | 2-Me-4-F2CHO—PhCH2CH2— |
| 9568 | 2-Me-5-F2CHO—PhCH2CH2— |
| 9569 | 2-Me-6-F2CHO—PhCH2CH2— |
| 9570 | 2-F-3-F3CCH2O—PhCH2CH2— |
| 9571 | 2-F-4-F3CCH2O—PhCH2CH2— |
| 9572 | 2-F-5-F3CCH2O—PhCH2CH2— |
| 9573 | 2-F-6-F3CCH2O—PhCH2CH2— |
| 9574 | 2-Cl-3-F3CCH2O—PhCH2CH2— |
| 9575 | 2-Cl-4-F3CCH2O—PhCH2CH2— |
| 9576 | 2-Cl-5-F3CCH2O—PhCH2CH2— |
| 9577 | 2-Cl-6-F3CCH2O—PhCH2CH2— |
| 9578 | 2-Br-3-F3CCH2O—PhCH2CH2— |
| 9579 | 2-Br-4-F3CCH2O—PhCH2CH2— |
| 9580 | 2-Br-5-F3CCH2O—PhCH2CH2— |
| 9581 | 2-Br-6-F3CCH2O—PhCH2CH2— |
| 9582 | 2-I-3-F3CCH2O—PhCH2CH2— |
| 9583 | 2-I-4-F3CCH2O—PhCH2CH2— |
| 9584 | 2-I-5-F3CCH2O—PhCH2CH2— |
| 9585 | 2-I-6-F3CCH2O—PhCH2CH2— |
| 9586 | 2-Me-3-F3CCH2O—PhCH2CH2— |
| 9587 | 2-Me-4-F3CCH2O—PhCH2CH2— |
| 9588 | 2-Me-5-F3CCH2O—PhCH2CH2— |
| 9589 | 2-Me-6-F3CCH2O—PhCH2CH2— |
| 9590 | 2-F-3-F2CHCH2O—PhCH2CH2— |
| 9591 | 2-F-4-F2CHCH2O—PhCH2CH2— |
| 9592 | 2-F-5-F2CHCH2O—PhCH2CH2— |
| 9593 | 2-F-6-F2CHCH2O—PhCH2CH2— |
| 9594 | 2-Cl-3-F2CHCH2O—PhCH2CH2— |
| 9595 | 2-Cl-4-F2CHCH2O—PhCH2CH2— |
| 9596 | 2-Cl-5-F2CHCH2O—PhCH2CH2— |
| 9597 | 2-Cl-6-F2CHCH2O—PhCH2CH2— |
| 9598 | 2-Br-3-F2CHCH2O—PhCH2CH2— |
| 9599 | 2-Br-4-F2CHCH2O—PhCH2CH2— |
| 9600 | 2-Br-5-F2CHCH2O—PhCH2CH2— |
| 9601 | 2-Br-6-F2CHCH2O—PhCH2CH2— |
| 9602 | 2-I-3-F2CHCH2O—PhCH2CH2— |
| 9603 | 2-I-4-F2CHCH2O—PhCH2CH2— |
| 9604 | 2-I-5-F2CHCH2O—PhCH2CH2— |
| 9605 | 2-I-6-F2CHCH2O—PhCH2CH2— |
| 9606 | 2-Me-3-F2CHCH2O—PhCH2CH2— |
| 9607 | 2-Me-4-F2CHCH2O—PhCH2CH2— |
| 9608 | 2-Me-5-F2CHCH2O—PhCH2CH2— |
| 9609 | 2-Me-6-F2CHCH2O—PhCH2CH2— |
| 9610 | 2-F-3-H2C=CHCH2O—PhCH2CH2— |
| 9611 | 2-F-4-H2C=CHCH2O—PhCH2CH2— |
| 9612 | 2-F-5-H2C=CHCH2O—PhCH2CH2— |
| 9613 | 2-F-6-H2C=CHCH2O—PhCH2CH2— |
| 9614 | 2-Cl-3-H2C=CHCH2O—PhCH2CH2— |
| 9615 | 2-Cl-4-H2C=CHCH2O—PhCH2CH2— |
| 9616 | 2-Cl-5-H2C=CHCH2O—PhCH2CH2— |
| 9617 | 2-Cl-6-H2C=CHCH2O—PhCH2CH2— |
| 9618 | 2-Br-3-H2C=CHCH2O—PhCH2CH2— |
| 9619 | 2-Br-4-H2C=CHCH2O—PhCH2CH2— |
| 9620 | 2-Br-5-H2C=CHCH2O—PhCH2CH2— |
| 9621 | 2-Br-6-H2C=CHCH2O—PhCH2CH2— |
| 9622 | 2-I-3-H2C=CHCH2O—PhCH2CH2— |
| 9623 | 2-I-4-H2C=CHCH2O—PhCH2CH2— |
| 9624 | 2-I-5-H2C=CHCH2O—PhCH2CH2— |
| 9625 | 2-I-6-H2C=CHCH2O—PhCH2CH2— |
| 9626 | 2-Me-3-H2C=CHCH2O—PhCH2CH2— |
| 9627 | 2-Me-4-H2C=CHCH2O—PhCH2CH2— |
| 9628 | 2-Me-5-H2C=CHCH2O—PhCH2CH2— |
| 9629 | 2-Me-6-H2C=CHCH2O—PhCH2CH2— |
| 9630 | 2-F-3-HC≡CCH2O—PhCH2CH2— |
| 9631 | 2-F-4-HC≡CCH2O—PhCH2CH2— |
| 9632 | 2-F-5-HC≡CCH2O—PhCH2CH2— |
| 9633 | 2-F-6-HC≡CCH2O—PhCH2CH2— |
| 9634 | 2-Cl-3-HC≡CCH2O—PhCH2CH2— |
| 9635 | 2-Cl-4-HC≡CCH2O—PhCH2CH2— |
| 9636 | 2-Cl-5-HC≡CCH2O—PhCH2CH2— |
| 9637 | 2-Cl-6-HC≡CCH2O—PhCH2CH2— |
| 9638 | 2-Br-3-HC≡CCH2O—PhCH2CH2— |
| 9639 | 2-Br-4-HC≡CCH2O—PhCH2CH2— |
| 9640 | 2-Br-5-HC≡CCH2O—PhCH2CH2— |
| 9641 | 2-Br-6-HC≡CCH2O—PhCH2CH2— |
| 9642 | 2-I-3-HC≡CCH2O—PhCH2CH2— |
| 9643 | 2-I-4-HC≡CCH2O—PhCH2CH2— |
| 9644 | 2-I-5-HC≡CCH2O—PhCH2CH2— |
| 9645 | 2-I-6-HC≡CCH2O—PhCH2CH2— |
| 9646 | 2-Me-3-HC≡CCH2O—PhCH2CH2— |
| 9647 | 2-Me-4-HC≡CCH2O—PhCH2CH2— |
| 9648 | 2-Me-5-HC≡CCH2O—PhCH2CH2— |
| 9649 | 2-Me-6-HC≡CCH2O—PhCH2CH2— |
| 9650 | 2-F-3-Ac—PhCH2CH2— |
| 9651 | 2-F-4-Ac—PhCH2CH2— |
| 9652 | 2-F-5-Ac—PhCH2CH2— |
| 9653 | 2-F-6-Ac—PhCH2CH2— |
| 9654 | 2-Cl-3-Ac—PhCH2CH2— |
| 9655 | 2-Cl-4-Ac—PhCH2CH2— |
| 9656 | 2-Cl-5-Ac—PhCH2CH2— |
| 9657 | 2-Cl-6-Ac—PhCH2CH2— |
| 9658 | 2-Br-3-Ac—PhCH2CH2— |
| 9659 | 2-Br-4-Ac—PhCH2CH2— |
| 9660 | 2-Br-5-Ac—PhCH2CH2— |
| 9661 | 2-Br-6-Ac—PhCH2CH2— |
| 9662 | 2-I-3-Ac—PhCH2CH2— |
| 9663 | 2-I-4-Ac—PhCH2CH2— |
| 9664 | 2-I-5-Ac—PhCH2CH2— |
| 9665 | 2-I-6-Ac—PhCH2CH2— |
| 9666 | 2-Me-3-Ac—PhCH2CH2— |
| 9667 | 2-Me-4-Ac—PhCH2CH2— |
| 9668 | 2-Me-5-Ac—PhCH2CH2— |
| 9669 | 2-Me-6-Ac—PhCH2CH2— |
| 9670 | 2-F-3-MeOC(=O)—PhCH2CH2— |
| 9671 | 2-F-4-MeOC(=O)—PhCH2CH2— |
| 9672 | 2-F-5-MeOC(=O)—PhCH2CH2— |
| 9673 | 2-F-6-MeOC(=O)—PhCH2CH2— |
| 9674 | 2-Cl-3-MeOC(=O)—PhCH2CH2— |
| 9675 | 2-Cl-4-MeOC(=O)—PhCH2CH2— |
| 9676 | 2-Cl-5-MeOC(=O)—PhCH2CH2— |
| 9677 | 2-Cl-6-MeOC(=O)—PhCH2CH2— |
| 9678 | 2-Br-3-MeOC(=O)—PhCH2CH2— |
| 9679 | 2-Br-4-MeOC(=O)—PhCH2CH2— |
| 9680 | 2-Br-5-MeOC(=O)—PhCH2CH2— |
| 9681 | 2-Br-6-MeOC(=O)—PhCH2CH2— |
| 9682 | 2-I-3-MeOC(=O)—PhCH2CH2— |
| 9683 | 2-I-4-MeOC(=O)—PhCH2CH2— |
| 9684 | 2-I-5-MeOC(=O)—PhCH2CH2— |
| 9685 | 2-I-6-MeOC(=O)—PhCH2CH2— |
| 9686 | 2-Me-3-MeOC(=O)—PhCH2CH2— |
| 9687 | 2-Me-4-MeOC(=O)—PhCH2CH2— |
| 9688 | 2-Me-5-MeOC(=O)—PhCH2CH2— |
| 9689 | 2-Me-6-MeOC(=O)—PhCH2CH2— |
| 9690 | 2-F-3-EtOC(=O)—PhCH2CH2— |
| 9691 | 2-F-4-EtOC(=O)—PhCH2CH2— |
| 9692 | 2-F-5-EtOC(=O)—PhCH2CH2— |
| 9693 | 2-F-6-EtOC(=O)—PhCH2CH2— |
| 9694 | 2-Cl-3-EtOC(=O)—PhCH2CH2— |
| 9695 | 2-Cl-4-EtOC(=O)—PhCH2CH2— |
| 9696 | 2-Cl-5-EtOC(=O)—PhCH2CH2— |
| 9697 | 2-Cl-6-EtOC(=O)—PhCH2CH2— |
| 9698 | 2-Br-3-EtOC(=O)—PhCH2CH2— |
| 9699 | 2-Br-4-EtOC(=O)—PhCH2CH2— |
| 9700 | 2-Br-5-EtOC(=O)—PhCH2CH2— |
| 9701 | 2-Br-6-EtOC(=O)—PhCH2CH2— |
| 9702 | 2-I-3-EtOC(=O)—PhCH2CH2— |
| 9703 | 2-I-4-EtOC(=O)—PhCH2CH2— |
| 9704 | 2-I-5-EtOC(=O)—PhCH2CH2— |
| 9705 | 2-I-6-EtOC(=O)—PhCH2CH2— |

TABLE 2-continued

| No. | Z |
|---|---|
| 9706 | 2-Me-3-EtOC(=O)—PhCH2CH2— |
| 9707 | 2-Me-4-EtOC(=O)—PhCH2CH2— |
| 9708 | 2-Me-5-EtOC(=O)—PhCH2CH2— |
| 9709 | 2-Me-6-EtOC(=O)—PhCH2CH2— |
| 9710 | 2-F-3-AcO—PhCH2CH2— |
| 9711 | 2-F-4-AcO—PhCH2CH2— |
| 9712 | 2-F-5-AcO—PhCH2CH2— |
| 9713 | 2-F-6-AcO—PhCH2CH2— |
| 9714 | 2-Cl-3-AcO—PhCH2CH2— |
| 9715 | 2-Cl-4-AcO—PhCH2CH2— |
| 9716 | 2-Cl-5-AcO—PhCH2CH2— |
| 9717 | 2-Cl-6-AcO—PhCH2CH2— |
| 9718 | 2-Br-3-AcO—PhCH2CH2— |
| 9719 | 2-Br-4-AcO—PhCH2CH2— |
| 9720 | 2-Br-5-AcO—PhCH2CH2— |
| 9721 | 2-Br-6-AcO—PhCH2CH2— |
| 9722 | 2-I-3-AcO—PhCH2CH2— |
| 9723 | 2-I-4-AcO—PhCH2CH2— |
| 9724 | 2-I-5-AcO—PhCH2CH2— |
| 9725 | 2-I-6-AcO—PhCH2CH2— |
| 9726 | 2-Me-3-AcO—PhCH2CH2— |
| 9727 | 2-Me-4-AcO—PhCH2CH2— |
| 9728 | 2-Me-5-AcO—PhCH2CH2— |
| 9729 | 2-Me-6-AcO—PhCH2CH2— |
| 9730 | 2-F-3-MeOC(=O)O—PhCH2CH2— |
| 9731 | 2-F-3-MeOC(=O)O—PhCH2CH2— |
| 9732 | 2-F-3-MeOC(=O)O—PhCH2CH2— |
| 9733 | 2-F-6-MeOC(=O)O—PhCH2CH2— |
| 9734 | 2-Cl-3-MeOC(=O)O—PhCH2CH2— |
| 9735 | 2-Cl-4-MeOC(=O)O—PhCH2CH2— |
| 9736 | 2-Cl-5-MeOC(=O)O—PhCH2CH2— |
| 9737 | 2-Cl-6-MeOC(=O)O—PhCH2CH2— |
| 9738 | 2-Br-3-MeOC(=O)O—PhCH2CH2— |
| 9739 | 2-Br-4-MeOC(=O)O—PhCH2CH2— |
| 9740 | 2-Br-5-MeOC(=O)O—PhCH2CH2— |
| 9741 | 2-Br-6-MeOC(=O)O—PhCH2CH2— |
| 9742 | 2-I-3-MeOC(=O)O—PhCH2CH2— |
| 9743 | 2-I-4-MeOC(=O)O—PhCH2CH2— |
| 9744 | 2-I-5-MeOC(=O)O—PhCH2CH2— |
| 9745 | 2-I-6-MeOC(=O)O—PhCH2CH2— |
| 9746 | 2-Me-3-MeOC(=O)O—PhCH2CH2— |
| 9747 | 2-Me-4-MeOC(=O)O—PhCH2CH2— |
| 9748 | 2-Me-5-MeOC(=O)O—PhCH2CH2— |
| 9749 | 2-Me-6-MeOC(=O)O—PhCH2CH2— |
| 9750 | 2-F-3-EtOC(=O)O—PhCH2CH2— |
| 9751 | 2-F-4-EtOC(=O)O—PhCH2CH2— |
| 9752 | 2-F-5-EtOC(=O)O—PhCH2CH2— |
| 9753 | 2-F-6-EtOC(=O)O—PhCH2CH2— |
| 9754 | 2-Cl-3-EtOC(=O)O—PhCH2CH2— |
| 9755 | 2-Cl-4-EtOC(=O)O—PhCH2CH2— |
| 9756 | 2-Cl-5-EtOC(=O)O—PhCH2CH2— |
| 9757 | 2-Cl-6-EtOC(=O)O—PhCH2CH2— |
| 9758 | 2-Br-3-EtOC(=O)O—PhCH2CH2— |
| 9759 | 2-Br-4-EtOC(=O)O—PhCH2CH2— |
| 9760 | 2-Br-5-EtOC(=O)O—PhCH2CH2— |
| 9761 | 2-Br-6-EtOC(=O)O—PhCH2CH2— |
| 9762 | 2-I-3-EtOC(=O)O—PhCH2CH2— |
| 9763 | 2-I-4-EtOC(=O)O—PhCH2CH2— |
| 9764 | 2-I-5-EtOC(=O)O—PhCH2CH2— |
| 9765 | 2-I-6-EtOC(=O)O—PhCH2CH2— |
| 9766 | 2-Me-3-EtOC(=O)O—PhCH2CH2— |
| 9767 | 2-Me-4-EtOC(=O)O—PhCH2CH2— |
| 9768 | 2-Me-5-EtOC(=O)O—PhCH2CH2— |
| 9769 | 2-Me-6-EtOC(=O)O—PhCH2CH2— |
| 9770 | 2-F-3-(1,3-dioxolan-2-yl)-PhCH2CH2— |
| 9771 | 2-F-4-(1,3-dioxolan-2-yl)-PhCH2CH2— |
| 9772 | 2-F-5-(1,3-dioxolan-2-yl)-PhCH2CH2— |
| 9773 | 2-F-6-(1,3-dioxolan-2-yl)-PhCH2CH2— |
| 9774 | 2-Cl-3-(1,3-dioxolan-2-yl)-PhCH2CH2— |
| 9775 | 2-Cl-4-(1,3-dioxolan-2-yl)-PhCH2CH2— |
| 9776 | 2-Cl-5-(1,3-dioxolan-2-yl)-PhCH2CH2— |
| 9777 | 2-Cl-6-(1,3-dioxolan-2-yl)-PhCH2CH2— |
| 9778 | 2-Br-3-(1,3-dioxolan-2-yl)-PhCH2CH2— |
| 9779 | 2-Br-4-(1,3-dioxolan-2-yl)-PhCH2CH2— |
| 9780 | 2-Br-5-(1,3-dioxolan-2-yl)-PhCH2CH2— |
| 9781 | 2-Br-6-(1,3-dioxolan-2-yl)-PhCH2CH2— |
| 9782 | 2-I-3-(1,3-dioxolan-2-yl)-PhCH2CH2— |
| 9783 | 2-I-4-(1,3-dioxolan-2-yl)-PhCH2CH2— |
| 9784 | 2-I-5-(1,3-dioxolan-2-yl)-PhCH2CH2— |
| 9785 | 2-I-6-(1,3-dioxolan-2-yl)-PhCH2CH2— |
| 9786 | 2-Me-3-(1,3-dioxolan-2-yl)-PhCH2CH2— |
| 9787 | 2-Me-4-(1,3-dioxolan-2-yl)-PhCH2CH2— |
| 9788 | 2-Me-5-(1,3-dioxolan-2-yl)-PhCH2CH2— |
| 9789 | 2-Me-6-(1,3-dioxolan-2-yl)-PhCH2CH2— |
| 9790 | 2-F-3-(1,3-dioxan-2-yl)-PhCH2CH2— |
| 9791 | 2-F-4-(1,3-dioxan-2-yl)-PhCH2CH2— |
| 9792 | 2-F-5-(1,3-dioxan-2-yl)-PhCH2CH2— |
| 9793 | 2-F-6-(1,3-dioxan-2-yl)-PhCH2CH2— |
| 9794 | 2-Cl-3-(1,3-dioxan-2-yl)-PhCH2CH2— |
| 9795 | 2-Cl-4-(1,3-dioxan-2-yl)-PhCH2CH2— |
| 9796 | 2-Cl-5-(1,3-dioxan-2-yl)-PhCH2CH2— |
| 9797 | 2-Cl-6-(1,3-dioxan-2-yl)-PhCH2CH2— |
| 9798 | 2-Br-3-(1,3-dioxan-2-yl)-PhCH2CH2— |
| 9799 | 2-Br-3-(1,3-dioxan-2-yl)-PhCH2CH2— |
| 9800 | 2-Br-4-(1,3-dioxan-2-yl)-PhCH2CH2— |
| 9801 | 2-Br-5-(1,3-dioxan-2-yl)-PhCH2CH2— |
| 9802 | 2-Br-6-(1,3-dioxan-2-yl)-PhCH2CH2— |
| 9803 | 2-I-3-(1,3-dioxan-2-yl)-PhCH2CH2— |
| 9804 | 2-I-4-(1,3-dioxan-2-yl)-PhCH2CH2— |
| 9805 | 2-I-5-(1,3-dioxan-2-yl)-PhCH2CH2— |
| 9806 | 2-I-6-(1,3-dioxan-2-yl)-PhCH2CH2— |
| 9807 | 2-Me-3-(1,3-dioxan-2-yl)-PhCH2CH2— |
| 9808 | 2-Me-4-(1,3-dioxan-2-yl)-PhCH2CH2— |
| 9809 | 2-Me-5-(1,3-dioxan-2-yl)-PhCH2CH2— |
| 9810 | 2-Me-6-(1,3-dioxan-2-yl)-PhCH2CH2— |
| 9811 | 2-F-4-MeS—PhCH2CH2— |
| 9812 | 2-F-5-MeS—PhCH2CH2— |
| 9813 | 2-F-6-MeS—PhCH2CH2— |
| 9814 | 2-Cl-3-MeS—PhCH2CH2— |
| 9815 | 2-Cl-4-MeS—PhCH2CH2— |
| 9816 | 2-Cl-5-MeS—PhCH2CH2— |
| 9817 | 2-Cl-6-MeS—PhCH2CH2— |
| 9818 | 2-Br-3-MeS—PhCH2CH2— |
| 9819 | 2-Br-4-MeS—PhCH2CH2— |
| 9820 | 2-Br-5-MeS—PhCH2CH2— |
| 9821 | 2-Br-6-MeS—PhCH2CH2— |
| 9822 | 2-I-3-MeS—PhCH2CH2— |
| 9823 | 2-I-4-MeS—PhCH2CH2— |
| 9824 | 2-I-5-MeS—PhCH2CH2— |
| 9825 | 2-I-6-MeS—PhCH2CH2— |
| 9826 | 2-Me-3-MeS—PhCH2CH2— |
| 9827 | 2-Me-4-MeS—PhCH2CH2— |
| 9828 | 2-Me-5-MeS—PhCH2CH2— |
| 9829 | 2-Me-6-MeS—PhCH2CH2— |
| 9830 | 2-F-3-MeS(O)—PhCH2CH2— |
| 9831 | 2-F-4-MeS(O)—PhCH2CH2— |
| 9832 | 2-F-5-MeS(O)—PhCH2CH2— |
| 9833 | 2-F-6-MeS(O)—PhCH2CH2— |
| 9834 | 2-Cl-3-MeS(O)—PhCH2CH2— |
| 9835 | 2-Cl-4-MeS(O)—PhCH2CH2— |
| 9836 | 2-Cl-5-MeS(O)—PhCH2CH2— |
| 9837 | 2-Cl-6-MeS(O)—PhCH2CH2— |
| 9838 | 2-Br-3-MeS(O)—PhCH2CH2— |
| 9839 | 2-Br-4-MeS(O)—PhCH2CH2— |
| 9840 | 2-Br-5-MeS(O)—PhCH2CH2— |
| 9841 | 2-Br-6-MeS(O)—PhCH2CH2— |
| 9842 | 2-I-3-MeS(O)—PhCH2CH2— |
| 9843 | 2-I-4-MeS(O)—PhCH2CH2— |
| 9844 | 2-I-5-MeS(O)—PhCH2CH2— |
| 9845 | 2-I-6-MeS(O)—PhCH2CH2— |
| 9846 | 2-Me-3-MeS(O)—PhCH2CH2— |
| 9847 | 2-Me-4-MeS(O)—PhCH2CH2— |
| 9848 | 2-Me-5-MeS(O)—PhCH2CH2— |
| 9849 | 2-Me-6-MeS(O)—PhCH2CH2— |
| 9850 | 2-F-3-MeSO2—PhCH2CH2— |
| 9851 | 2-F-4-MeSO2—PhCH2CH2— |
| 9852 | 2-F-5-MeSO2—PhCH2CH2— |
| 9853 | 2-F-6-MeSO2—PhCH2CH2— |
| 9854 | 2-Cl-3-MeSO2—PhCH2CH2— |
| 9855 | 2-Cl-4-MeSO2—PhCH2CH2— |
| 9856 | 2-Cl-5-MeSO2—PhCH2CH2— |
| 9857 | 2-Cl-6-MeSO2—PhCH2CH2— |
| 9858 | 2-Br-3-MeSO2—PhCH2CH2— |
| 9859 | 2-Br-4-MeSO2—PhCH2CH2— |
| 9860 | 2-Br-5-MeSO2—PhCH2CH2— |
| 9861 | 2-Br-6-MeSO2—PhCH2CH2— |

TABLE 2-continued

| No. | Z |
|---|---|
| 9862 | 2-I-3-MeSO2—PhCH2CH2— |
| 9863 | 2-I-4-MeSO2—PhCH2CH2— |
| 9864 | 2-I-5-MeSO2—PhCH2CH2— |
| 9865 | 2-I-6-MeSO2—PhCH2CH2— |
| 9866 | 2-Me-3-MeSO2—PhCH2CH2— |
| 9867 | 2-Me-4-MeSO2—PhCH2CH2— |
| 9868 | 2-Me-5-MeSO2—PhCH2CH2— |
| 9869 | 2-Me-6-MeSO2—PhCH2CH2— |
| 9870 | 2-F-3-ClCH2S—PhCH2CH2— |
| 9871 | 2-F-4-ClCH2S—PhCH2CH2— |
| 9872 | 2-F-5-ClCH2S—PhCH2CH2— |
| 9873 | 2-F-6-ClCH2S—PhCH2CH2— |
| 9874 | 2-Cl-3-ClCH2S—PhCH2CH2— |
| 9875 | 2-Cl-4-ClCH2S—PhCH2CH2— |
| 9876 | 2-Cl-5-ClCH2S—PhCH2CH2— |
| 9877 | 2-Cl-6-ClCH2S—PhCH2CH2— |
| 9878 | 2-Br-3-ClCH2S—PhCH2CH2— |
| 9879 | 2-Br-4-ClCH2S—PhCH2CH2— |
| 9880 | 2-Br-5-ClCH2S—PhCH2CH2— |
| 9881 | 2-Br-6-ClCH2S—PhCH2CH2— |
| 9882 | 2-I-3-ClCH2S—PhCH2CH2— |
| 9883 | 2-I-4-ClCH2S—PhCH2CH2— |
| 9884 | 2-I-5-ClCH2S—PhCH2CH2— |
| 9885 | 2-I-6-ClCH2S—PhCH2CH2— |
| 9886 | 2-Me-3-ClCH2S—PhCH2CH2— |
| 9887 | 2-Me-4-ClCH2S—PhCH2CH2— |
| 9888 | 2-Me-5-ClCH2S—PhCH2CH2— |
| 9889 | 2-Me-6-ClCH2S—PhCH2CH2— |
| 9890 | 2-F-3-ClCH2S(O)—PhCH2CH2— |
| 9891 | 2-F-4-ClCH2S(O)—PhCH2CH2— |
| 9892 | 2-F-5-ClCH2S(O)—PhCH2CH2— |
| 9893 | 2-F-6-ClCH2S(O)—PhCH2CH2— |
| 9894 | 2-Cl-3-ClCH2S(O)—PhCH2CH2— |
| 9895 | 2-Cl-4-ClCH2S(O)—PhCH2CH2— |
| 9896 | 2-Cl-5-ClCH2S(O)—PhCH2CH2— |
| 9897 | 2-Cl-6-ClCH2S(O)—PhCH2CH2— |
| 9898 | 2-Br-3-ClCH2S(O)—PhCH2CH2— |
| 9899 | 2-Br-4-ClCH2S(O)—PhCH2CH2— |
| 9900 | 2-Br-5-ClCH2S(O)—PhCH2CH2— |
| 9901 | 2-Br-6-ClCH2S(O)—PhCH2CH2— |
| 9902 | 2-I-3-ClCH2S(O)—PhCH2CH2— |
| 9903 | 2-I-4-ClCH2S(O)—PhCH2CH2— |
| 9904 | 2-I-5-ClCH2S(O)—PhCH2CH2— |
| 9905 | 2-I-6-ClCH2S(O)—PhCH2CH2— |
| 9906 | 2-Me-3-ClCH2S(O)—PhCH2CH2— |
| 9907 | 2-Me-4-ClCH2S(O)—PhCH2CH2— |
| 9908 | 2-Me-5-ClCH2S(O)—PhCH2CH2— |
| 9909 | 2-Me-6-ClCH2S(O)—PhCH2CH2— |
| 9910 | 2-F-3-ClCH2SO2—PhCH2CH2— |
| 9911 | 2-F-4-ClCH2SO2—PhCH2CH2— |
| 9912 | 2-F-5-ClCH2SO2—PhCH2CH2— |
| 9913 | 2-F-6-ClCH2SO2—PhCH2CH2— |
| 9914 | 2-Cl-3-ClCH2SO2—PhCH2CH2— |
| 9915 | 2-Cl-4-ClCH2SO2—PhCH2CH2— |
| 9916 | 2-Cl-5-ClCH2SO2—PhCH2CH2— |
| 9917 | 2-Cl-6-ClCH2SO2—PhCH2CH2— |
| 9918 | 2-Br-3-ClCH2SO2—PhCH2CH2— |
| 9919 | 2-Br-4-ClCH2SO2—PhCH2CH2— |
| 9920 | 2-Br-5-ClCH2SO2—PhCH2CH2— |
| 9921 | 2-Br-6-ClCH2SO2—PhCH2CH2— |
| 9922 | 2-I-3-ClCH2SO2—PhCH2CH2— |
| 9923 | 2-I-4-ClCH2SO2—PhCH2CH2— |
| 9924 | 2-I-5-ClCH2SO2—PhCH2CH2— |
| 9925 | 2-I-6-ClCH2SO2—PhCH2CH2— |
| 9926 | 2-Me-3-ClCH2SO2—PhCH2CH2— |
| 9927 | 2-Me-4-ClCH2SO2—PhCH2CH2— |
| 9928 | 2-Me-5-ClCH2SO2—PhCH2CH2— |
| 9929 | 2-Me-6-ClCH2SO2—PhCH2CH2— |
| 9930 | 3,5-di-MeO—PhCH2CH2— |
| 9931 | 3,5-di-EtO—PhCH2CH2— |
| 9932 | 3,5-di-F—PhCH2CH2— |
| 9933 | 3,5-di-Cl—PhCH2CH2— |
| 9934 | 3,5-di-Br—PhCH2CH2— |
| 9935 | 3,5-di-I—PhCH2CH2— |
| 9936 | 3,5-di-Me—PhCH2CH2 |
| 9937 | 3-F-5-Me—PhCH2CH2— |
| 9938 | 3-Cl-5-Me—PhCH2CH2— |
| 9939 | 3-Br-5-Me—PhCH2CH2— |
| 9940 | 3-I-5-Me—PhCH2CH2— |
| 9941 | 3-F-5-MeO—PhCH2CH2— |
| 9942 | 3-Cl-5-MeO—PhCH2CH2— |
| 9943 | 3-Br-5-MeO—PhCH2CH2— |
| 9944 | 3,4-5-MeO—PhCH2CH2— |
| 9945 | 5-F-3-EtO—PhCH2CH2— |
| 9946 | 3-Cl-5-EtO—PhCH2CH2— |
| 9947 | 3-Br-5-EtO—PhCH2CH2— |
| 9948 | 5-I-3-EtO—PhCH2CH2— |
| 9949 | 3-F-5-N≡CCH2O—PhCH2CH2— |
| 9950 | 3-Cl-5-N≡CCH2O—PhCH2CH2— |
| 9951 | 3-Br-5-N≡CCH2O—PhCH2CH2— |
| 9952 | 3-I-5-N≡CCH2O—PhCH2CH2— |
| 9953 | 3-F-5-MeOCH2O—PhCH2CH2— |
| 9954 | 3-Cl-5-MeOCH2O—PhCH2CH2— |
| 9955 | 3-Br-5-MeOCH2O—PhCH2CH2— |
| 9956 | 3-I-5-MeOCH2O—PhCH2CH2— |
| 9957 | 5-F-2-MeO—PhCH2CH2— |
| 9958 | 5-Cl-2-MeO—PhCH2CH2— |
| 9959 | 5-Br-2-MeO—PhCH2CH2— |
| 9960 | 5-I-2-MeO—PhCH2CH2— |
| 9961 | 5-Me-2-MeO—PhCH2CH2— |
| 9962 | 2-F-3,5-di-MeO—PhCH2CH2— |
| 9963 | 2-F-3,5-di-EtO—PhCH2CH2— |
| 9964 | 2,3,5-tri-F—PhCH2CH2— |
| 9965 | 2-F-3,5-di-Cl—PhCH2CH2— |
| 9966 | 3,5-di-Br-2-F—PhCH2CH2— |
| 9967 | 2-F-3,5-di-I—PhCH2CH2— |
| 9968 | 2-F-3,5-di-Me—PhCH2CH2— |
| 9969 | 2,3-di-F-5-Me—PhCH2CH2— |
| 9970 | 2,5-di-F-3-Me—PhCH2CH2— |
| 9971 | 3-Cl-2-F-5-Me—PhCH2CH2— |
| 9972 | 5-Cl-2-F-3-Me—PhCH2CH2— |
| 9973 | 3-Br-2-F-5-Me—PhCH2CH2— |
| 9974 | 5-Br-2-F-3-Me—PhCH2CH2— |
| 9975 | 2-F-3-I-5-Me—PhCH2CH2— |
| 9976 | 2-F-5-I-3-Me—PhCH2CH2— |
| 9977 | 2,3-di-F-5-MeO—PhCH2CH2— |
| 9978 | 2,5-di-F-3-MeO—PhCH2CH2— |
| 9979 | 3-Cl-2-F-5-MeO—PhCH2CH2— |
| 9980 | 5-Cl-2-F-3-MeO—PhCH2CH2— |
| 9981 | 3-Br-2-F-5-MeO—PhCH2CH2— |
| 9982 | 5-Br-2-F-3-MeO—PhCH2CH2— |
| 9983 | 2-F-3-I-5-MeO—PhCH2CH2— |
| 9984 | 2-F-5-I-3-MeO—PhCH2CH2— |
| 9985 | 2,3-di-F-5-EtO—PhCH2CH2— |
| 9986 | 2,5-di-F-3-EtO—PhCH2CH2— |
| 9987 | 3-Cl-2-F-5-EtO—PhCH2CH2— |
| 9988 | 5-Cl-2-F-3-EtO—PhCH2CH2— |
| 9989 | 3-Br-2-F-5-EtO—PhCH2CH2— |
| 9990 | 5-Br-2-F-3-EtO—PhCH2CH2— |
| 9991 | 2-F-3-I-5-EtO—PhCH2CH2— |
| 9992 | 2-F-5-I-3-EtO—PhCH2CH2— |
| 9993 | 2,3-di-F-5-N≡CCH2O—PhCH2CH2— |
| 9994 | 2,5-di-F-3-N≡CCH2O—PhCH2CH2— |
| 9995 | 3-Cl-2-F-5-N≡CCH2O—PhCH2CH2— |
| 9996 | 5-Cl-2-F-3-N≡CCH2O—PhCH2CH2— |
| 9997 | 3-Br-2-F-5-N≡CCH2O—PhCH2CH2— |
| 9998 | 5-Br-2-F-3-N≡CCH2O—PhCH2CH2— |
| 9999 | 2-F-3-I-5-N≡CCH2O—PhCH2CH2— |
| 10000 | 2-F-5-I-3-N≡CCH2O—PhCH2CH2— |
| 10001 | 2,3-di-F-5-MeOCH2O—PhCH2CH2— |
| 10002 | 2,5-di-F-3-MeOCH2O—PhCH2CH2— |
| 10003 | 3-Cl-2-F-5-MeOCH2O—PhCH2CH2— |
| 10004 | 5-Cl-2-F-3-MeOCH2O—PhCH2CH2— |
| 10005 | 3-Br-2-F-5-MeOCH2O—PhCH2CH2— |
| 10006 | 5-Br-2-F-3-MeOCH2O—PhCH2CH2— |
| 10007 | 2-F-3,4-5-MeOCH2O—PhCH2CH2— |
| 10008 | 2-F-5-I-3-MeOCH2O—PhCH2CH2— |
| 10009 | 2-Cl-3,5-di-MeO—PhCH2CH2— |
| 10010 | 2-Cl-3,5-di-EtO—PhCH2CH2— |
| 10011 | 2-Cl-3,5-di-F—PhCH2CH2— |
| 10012 | 2,3,5-tri-Cl—PhCH2CH2— |
| 10013 | 3,5-di-Br-2-Cl—PhCH2CH2— |
| 10014 | 2-Cl-3,5-di-I—PhCH2CH2— |
| 10015 | 2-Cl-3,5-di-Me—PhCH2CH2— |
| 10016 | 2-Cl-3-F-5-Me—PhCH2CH2— |
| 10017 | 2-Cl-5-F-3-Me—PhCH2CH2— |

TABLE 2-continued

| No. | Z |
|---|---|
| 10018 | 2,3-di-Cl-5-Me—PhCH2CH2— |
| 10019 | 2,5-di-Cl-3-Me—PhCH2CH2— |
| 10020 | 3-Br-2-Cl-5-Me—PhCH2CH2— |
| 10021 | 5-Br-2-Cl-3-Me—PhCH2CH2— |
| 10022 | 2-Cl-3,4-5-Me—PhCH2CH2— |
| 10023 | 2-Cl-5-I-3-Me—PhCH2CH2— |
| 10024 | 2-Cl-3-F-5-MeO—PhCH2CH2— |
| 10025 | 2-Cl-5-F-3-MeO—PhCH2CH2— |
| 10026 | 2,3-di-Cl-5-MeO—PhCH2CH2— |
| 10027 | 2,5-di-Cl-3-MeO—PhCH2CH2— |
| 10028 | 3-Br-2-Cl-5-MeO—PhCH2CH2— |
| 10029 | 5-Br-2-Cl-3-MeO—PhCH2CH2— |
| 10030 | 2-Cl-3-I-5-MeO—PhCH2CH2— |
| 10031 | 2-Cl-5-I-3-MeO—PhCH2CH2— |
| 10032 | 2-Cl-3-F-5-EtO—PhCH2CH2— |
| 10033 | 2-Cl-5-F-3-EtO—PhCH2CH2— |
| 10034 | 2,3-di-Cl-5-EtO—PhCH2CH2— |
| 10035 | 2,5-di-Cl-3-EtO—PhCH2CH2— |
| 10036 | 3-Br-2-Cl-5-EtO—PhCH2CH2— |
| 10037 | 5-Br-2-Cl-3-EtO—PhCH2CH2— |
| 10038 | 2-Cl-3-I-5-EtO—PhCH2CH2— |
| 10039 | 2-Cl-5-I-3-EtO—PhCH2CH2— |
| 10040 | 2-Cl-3-F-5-N≡CCH2O—PhCH2CH2— |
| 10041 | 2-Cl-5-F-3-N≡CCH2O—PhCH2CH2— |
| 10042 | 2-3-di-Cl-5-N≡CCH2O—PhCH2CH2— |
| 10043 | 2-5-di-Cl-3-N≡CCH2O—PhCH2CH2— |
| 10044 | 3-Br-2-Cl-5-N≡CCH2O—PhCH2CH2— |
| 10045 | 5-Br-2-Cl-3-N≡CCH2O—PhCH2CH2— |
| 10046 | 2-Cl-3-I-5-N≡CCH2O—PhCH2CH2— |
| 10047 | 2-Cl-5-I-3-N≡CCH2O—PhCH2CH2— |
| 10048 | 2-Cl-3-F-5-MeOCH2O—PhCH2CH2— |
| 10049 | 2-Cl-5-F-3-MeOCH2O—PhCH2CH2— |
| 10050 | 2,3-di-Cl-5-MeOCH2O—PhCH2CH2— |
| 10051 | 2,5-di-Cl-3-MeOCH2O—PhCH2CH2— |
| 10052 | 3-Br-2-Cl-5-MeOCH2O—PhCH2CH2— |
| 10053 | 5-Br-2-Cl-3-MeOCH2O—PhCH2CH2— |
| 10054 | 2-Cl-3-I-4-5-MeOCH2O—PhCH2CH2— |
| 10055 | 2-Cl-5-I-4-3-MeOCH2O—PhCH2CH2— |
| 10056 | 2-Br-3,5-di-MeO—PhCH2CH2— |
| 10057 | 2-Br-3,5-di-EtO—PhCH2CH2— |
| 10058 | 2-Br-3,5-di-F—PhCH2CH2— |
| 10059 | 2-Br-3,5-di-Cl—PhCH2CH2— |
| 10060 | 2,3-5-tri-Br—PhCH2CH2— |
| 10061 | 2-Br-3,5-di-I—PhCH2CH2— |
| 10062 | 2-Br-3,5-di-Me—PhCH2CH2— |
| 10063 | 2-Br-3-F-5-Me—PhCH2CH2— |
| 10064 | 2-Br-5-F-3-Me—PhCH2CH2— |
| 10065 | 2-Br-3-Cl-5-Me—PhCH2CH2— |
| 10066 | 2-Br-5-Cl-3-Me—PhCH2CH2— |
| 10067 | 2,3-di-Br-5-Me—PhCH2CH2— |
| 10068 | 2,5-di-Br-3-Me—PhCH2CH2— |
| 10069 | 2-Br-3-I-5-Me—PhCH2CH2— |
| 10070 | 2-Br-5-I-3-Me—PhCH2CH2— |
| 10071 | 2-Br-3-F-5-MeO—PhCH2CH2— |
| 10072 | 2-Br-5-F-3-MeO—PhCH2CH2— |
| 10073 | 2-Br-3-Cl-5-MeO—PhCH2CH2— |
| 10074 | 2-Br-5-Cl-3-MeO—PhCH2CH2— |
| 10075 | 2,3-di-Br-5-MeO—PhCH2CH2— |
| 10076 | 2,5-di-Br-3-MeO—PhCH2CH2— |
| 10077 | 2-Br-3,4-5-MeO—PhCH2CH2— |
| 10078 | 2-Br-5-I-3-MeO—PhCH2CH2— |
| 10079 | 2-Br-3-F-5-EtO—PhCH2CH2— |
| 10080 | 2-Br-5-F-3-EtO—PhCH2CH2— |
| 10081 | 2-Br-3-Cl-5-EtO—PhCH2CH2— |
| 10082 | 2-Br-5-Cl-3-EtO—PhCH2CH2— |
| 10083 | 2,3-di-Br-5-EtO—PhCH2CH2— |
| 10084 | 2,5-di-Br-3-EtO—PhCH2CH2— |
| 10085 | 2-Br-3-I-5-EtO—PhCH2CH2— |
| 10086 | 2-Br-5-I-3-EtO—PhCH2CH2— |
| 10087 | 2-Br-3-F-5-N≡CCH2O—PhCH2CH2— |
| 10088 | 2-Br-5-F-3-N≡CCH2O—PhCH2CH2— |
| 10089 | 2-Br-3-Cl-5-N≡CCH2O—PhCH2CH2— |
| 10090 | 2-Br-5-Cl-3-N≡CCH2O—PhCH2CH2— |
| 10091 | 2,3-di-Br-5-N≡CCH2O—PhCH2CH2— |
| 10092 | 2,5-di-Br-3-N≡CCH2O—PhCH2CH2— |
| 10093 | 2-Br-3-I-5-N≡CCH2O—PhCH2CH2— |
| 10094 | 2-Br-5-I-3-N≡CCH2O—PhCH2CH2— |
| 10095 | 2-Br-3-F-5-MeOCH2O—PhCH2CH2— |
| 10096 | 2-Br-5-F-3-MeOCH2O—PhCH2CH2— |
| 10097 | 2-Br-3-Cl-5-MeOCH2O—PhCH2CH2— |
| 10098 | 2-Br-5-Cl-3-MeOCH2O—PhCH2CH2— |
| 10099 | 2,3-di-Br-5-MeOCH2O—PhCH2CH2— |
| 10100 | 2,5-di-Br-3-MeOCH2O—PhCH2CH2— |
| 10101 | 2-Br-3,4-5-MeOCH2O—PhCH2CH2— |
| 10102 | 2-Br-5-I-3-MeOCH2O—PhCH2CH2— |
| 10103 | 2-I-3,5-di-MeO—PhCH2CH2— |
| 10104 | 2-I-3,5-di-EtO—PhCH2CH2— |
| 10105 | 3,5-di-F-2-I—PhCH2CH2— |
| 10106 | 3,5-di-Cl-2-I—PhCH2CH2— |
| 10107 | 3,5-di-Br-2-I—PhCH2CH2— |
| 10108 | 2,3-5-Tri-I—PhCH2CH2— |
| 10109 | 3,5-di-Me-2-I—PhCH2CH2— |
| 10110 | 3-F-2-I-5-Me—PhCH2CH2— |
| 10111 | 5-F-2-I-3-Me—PhCH2CH2— |
| 10112 | 3-Cl-2-I-5-Me—PhCH2CH2— |
| 10113 | 5-Cl-2-I-3-Me—PhCH2CH2— |
| 10114 | 3-Br-2-I-5-Me—PhCH2CH2— |
| 10115 | 5-Br-2-I-3-Me—PhCH2CH2— |
| 10116 | 2,3-di-I-5-Me—PhCH2CH2— |
| 10117 | 2,5-di-I-3-Me—PhCH2CH2— |
| 10118 | 3-F-2-I-5-MeO—PhCH2CH2— |
| 10119 | 5-F-2-I-3-MeO—PhCH2CH2— |
| 10120 | 3-Cl-2-I-5-MeO—PhCH2CH2— |
| 10121 | 5-Cl-2-I-3-MeO—PhCH2CH2— |
| 10122 | 3-Br-2-I-5-MeO—PhCH2CH2— |
| 10123 | 5-Br-2-I-3-MeO—PhCH2CH2— |
| 10124 | 2,3-di-I-5-MeO—PhCH2CH2— |
| 10125 | 2,5-di-I-3-MeO—PhCH2CH2— |
| 10126 | 3-F-2-I-5-EtO—PhCH2CH2— |
| 10127 | 5-F-2-I-3-EtO—PhCH2CH2— |
| 10128 | 3-Cl-2-I-5-EtO—PhCH2CH2— |
| 10129 | 5-Cl-2-I-3-EtO—PhCH2CH2— |
| 10130 | 3-Br-2-I-5-EtO—PhCH2CH2— |
| 10131 | 5-Br-2-I-3-EtO—PhCH2CH2— |
| 10132 | 2,3-di-I-5-EtO—PhCH2CH2— |
| 10133 | 2,5-di-I-3-EtO—PhCH2CH2— |
| 10134 | 3-F-2-I-5-N≡CCH2O—PhCH2CH2— |
| 10135 | 5-F-2-I-3-N≡CCH2O—PhCH2CH2— |
| 10136 | 3-Cl-2-I-5-N≡CCH2O—PhCH2CH2— |
| 10137 | 5-Cl-2-I-3-N≡CCH2O—PhCH2CH2— |
| 10138 | 3-Br-2-I-5-N≡CCH2O—PhCH2CH2— |
| 10139 | 5-Br-2-I-3-N≡CCH2O—PhCH2CH2— |
| 10140 | 2,3-di-I-5-N≡CCH2O—PhCH2CH2— |
| 10141 | 2,5-di-I-3-N≡CCH2O—PhCH2CH2— |
| 10142 | 3-F-2-I-5-MeOCH2O—PhCH2CH2— |
| 10143 | 5-F-2-I-3-MeOCH2O—PhCH2CH2— |
| 10144 | 3-Cl-2-I-5-MeOCH2O—PhCH2CH2— |
| 10145 | 5-Cl-2-I-3-MeOCH2O—PhCH2CH2— |
| 10146 | 3-Br-2-I-5-MeOCH2O—PhCH2CH2— |
| 10147 | 5-Br-2-I-3-MeOCH2O—PhCH2CH2— |
| 10148 | 2,3-di-I-5-MeOCH2O—PhCH2CH2— |
| 10149 | 2,5-di-I-3-MeOCH2O—PhCH2CH2— |
| 10150 | 2-Me-3,5-di-MeO—PhCH2CH2— |
| 10151 | 2-Me-3,5-di-EtO—PhCH2CH2— |
| 10152 | 3,5-di-F-2-Me—PhCH2CH2— |
| 10153 | 3,5-di-Cl-2-Me—PhCH2CH2— |
| 10154 | 3,5-di-Br-2-Me—PhCH2CH2— |
| 10155 | 3,5-di-I-2-Me—PhCH2CH2— |
| 10156 | 2,3,5-tri-Me—PhCH2CH2— |
| 10157 | 3-F-2,5-di-Me—PhCH2CH2— |
| 10158 | 5-F-2,3-di-Me—PhCH2CH2— |
| 10159 | 3-Cl-2,5-di-Me—PhCH2CH2— |
| 10160 | 5-Cl-2,3-di-Me—PhCH2CH2— |
| 10161 | 3-Br-2,5-di-Me—PhCH2CH2— |
| 10162 | 5-Br-2,3-di-Me—PhCH2CH2— |
| 10163 | 3-I-2,5-di-Me—PhCH2CH2— |
| 10164 | 5-I-2,3-di-Me—PhCH2CH2— |
| 10165 | 3-F-2-Me-5-MeO—PhCH2CH2— |
| 10166 | 5-F-2-Me-3-MeO—PhCH2CH2— |
| 10167 | 3-Cl-2-Me-5-MeO—PhCH2CH2— |
| 10168 | 5-Cl-2-Me-3-MeO—PhCH2CH2— |
| 10169 | 3-Br-2-Me-5-MeO—PhCH2CH2— |
| 10170 | 5-Br-2-Me-3-MeO—PhCH2CH2— |
| 10171 | 3-I-2-Me-5-MeO—PhCH2CH2— |
| 10172 | 5-I-2-Me-3-MeO—PhCH2CH2— |
| 10173 | 3-F-2-Me-5-EtO—PhCH2CH2— |

TABLE 2-continued

| No. | Z |
|---|---|
| 10174 | 5-F-2-Me-3-EtO—PhCH2CH2— |
| 10175 | 3-Cl-2-Me-5-EtO—PhCH2CH2— |
| 10176 | 5-Cl-2-Me-3-EtO—PhCH2CH2— |
| 10177 | 3-Br-2-Me-5-EtO—PhCH2CH2— |
| 10178 | 5-Br-2-Me-3-EtO—PhCH2CH2— |
| 10179 | 3,4-2-Me-5-EtO—PhCH2CH2— |
| 10180 | 5-I-2-Me-3-EtO—PhCH2CH2— |
| 10181 | 3-F-2-Me-5-N≡CCH2O—PhCH2CH2— |
| 10182 | 5-F-2-Me-3-N≡CCH2O—PhCH2CH2— |
| 10183 | 3-Cl-2-Me-5-N≡CCH2O—PhCH2CH2— |
| 10184 | 5-Cl-2-Me-3-N≡CCH2O—PhCH2CH2— |
| 10185 | 3-Br-2-Me-5-N≡CCH2O—PhCH2CH2— |
| 10186 | 5-Br-2-Me-3-N≡CCH2O—PhCH2CH2— |
| 10187 | 3-I-2-Me-5-N≡CCH2O—PhCH2CH2— |
| 10188 | 5-I-2-Me-3-N≡CCH2O—PhCH2CH2— |
| 10189 | 3-F-2-Me-5-MeOCH2O—PhCH2CH2— |
| 10190 | 5-F-2-Me-3-MeOCH2O—PhCH2CH2— |
| 10191 | 3-Cl-2-Me-5-MeOCH2O—PhCH2CH2— |
| 10192 | 5-Cl-2-Me-3-MeOCH2O—PhCH2CH2— |
| 10193 | 3-Br-2-Me-5-MeOCH2O—PhCH2CH2— |
| 10194 | 5-Br-2-Me-3-MeOCH2O—PhCH2CH2— |
| 10195 | 3-I-2-Me-5-MeOCH2O—PhCH2CH2— |
| 10196 | 5-I-2-Me-3-MeOCH2O—PhCH2CH2— |
| 10197 | 2,3,6-tri-F—PhCH2CH2— |
| 10198 | 2,6-di-Cl-3-F—PhCH2CH2— |
| 10199 | 2-Cl-3,6-di-F—PhCH2CH2— |
| 10200 | 6-Cl-2,3-di-F—PhCH2CH2— |
| 10201 | 3-Cl-2,6-di-F—PhCH2CH2— |
| 10202 | 2,3,6-Tri-Cl—PhCH2CH2— |
| 10203 | 2,3-di-Cl-6-F—PhCH2CH2— |
| 10204 | 3,6-di-Cl-2-F—PhCH2CH2— |
| 10205 | 3-Br-2,6-di-F—PhCH2CH2— |
| 10206 | 3-Br-2,6-di-Cl—PhCH2CH2— |
| 10207 | 3-Br-2-Cl-6-F—PhCH2CH2— |
| 10208 | 3-Br-6-Cl-2-F—PhCH2CH2— |
| 10209 | 2,6-di-F-3-I—PhCH2CH2— |
| 10210 | 2,6-di-Cl-3-I—PhCH2CH2— |
| 10211 | 2-Cl-6-F-3-I—PhCH2CH2— |
| 10212 | 6-Cl-2-F-3-I—PhCH2CH2— |
| 10213 | 2,6-di-F-3-Me—PhCH2CH2— |
| 10214 | 2,6-di-Cl-3-Me—PhCH2CH2— |
| 10215 | 2-Cl-6-F-3-Me—PhCH2CH2— |
| 10216 | 6-Cl-2-F-3-Me—PhCH2CH2— |
| 10217 | 2,6-di-F-3-MeO—PhCH2CH2— |
| 10218 | 2,6-di-Cl-3-MeO—PhCH2CH2— |
| 10219 | 2-Cl-6-F-3-MeO—PhCH2CH2— |
| 10220 | 6-Cl-2-F-3-MeO—PhCH2CH2— |
| 10221 | 2,6-di-F-3-EtO—PhCH2CH2— |
| 10222 | 2,6-di-Cl-3-EtO—PhCH2CH2— |
| 10223 | 2-Cl-6-F-3-EtO—PhCH2CH2— |
| 10224 | 6-Cl-2-F-3-EtO—PhCH2CH2— |
| 10225 | 2,6-di-F-3-N≡CCH2O—PhCH2CH2— |
| 10226 | 2,6-di-Cl-3-N≡CCH2O—PhCH2CH2— |
| 10227 | 2-Cl-6-F-3-N≡CCH2O—PhCH2CH2— |
| 10228 | 6-Cl-2-F-3-N≡CCH2O—PhCH2CH2— |
| 10229 | 2,6-di-F-3-MeOCH2O—PhCH2CH2— |
| 10230 | 2,6-di-Cl-3-MeOCH2O—PhCH2CH2— |
| 10231 | 2-Cl-6-F-3-MeOCH2O—PhCH2CH2— |
| 10232 | 6-Cl-2-F-3-MeOCH2O—PhCH2CH2— |
| 10233 | 3,4,5-tri-F—PhCH2CH2— |
| 10234 | 4-Cl-3,5-di-F—PhCH2CH2— |
| 10235 | 4-Br-3,5-di-F—PhCH2CH2— |
| 10236 | 3,5-di-F-4-I—PhCH2CH2— |
| 10237 | 3,5-di-F-4-Me—PhCH2CH2— |
| 10238 | 3,5-di-Cl-4-F—PhCH2CH2— |
| 10239 | 3,4,5-tri-Cl—PhCH2CH2— |
| 10240 | 4-Br-3,5-di-Cl—PhCH2CH2— |
| 10241 | 3,5-di-Cl-4-I—PhCH2CH2— |
| 10242 | 3,5-di-Cl-4-Me—PhCH2CH2— |
| 10243 | 3,5-di-Br-4-F—PhCH2CH2— |
| 10244 | 3,5-di-Br-4-Cl—PhCH2CH2— |
| 10245 | 3,4,5-tri-Br—PhCH2CH2— |
| 10246 | 3,5-di-Br-4-I—PhCH2CH2— |
| 10247 | 3,5-di-Br-4-Me—PhCH2CH2— |
| 10248 | 4-F-3,5-di-I—PhCH2CH2— |
| 10249 | 4-Cl-3,5-di-I—PhCH2CH2— |
| 10250 | 4-Br-3,5-di-I—PhCH2CH2— |
| 10251 | 3,4,5-tri-I—PhCH2CH2— |
| 10252 | 4-Me-3,5-di-I—PhCH2CH2— |
| 10253 | 4-F-3,5-di-Me—PhCH2CH2— |
| 10254 | 4-Cl-3,5-di-Me—PhCH2CH2— |
| 10255 | 4-Br-3,5-di-Me—PhCH2CH2— |
| 10256 | 4-I-3,5-di-Me—PhCH2CH2— |
| 10257 | 3,4,5-tri-Me—PhCH2CH2— |
| 10258 | 4-F-3,5-di-Me—PhCH2CH2— |
| 10259 | 4-Cl-3,5-di-Me—PhCH2CH2— |
| 10260 | 4-Br-3,5-di-Me—PhCH2CH2— |
| 10261 | 4-I-3,5-di-Me—PhCH2CH2— |
| 10262 | 4-MeO-3,5-di-Me—PhCH2CH2— |
| 10263 | 4-F-3,5-di-MeO—PhCH2CH2— |
| 10264 | 4-Cl-3,5-di-MeO—PhCH2CH2— |
| 10265 | 4-Br-3,5-di-MeO—PhCH2CH2— |
| 10266 | 4-I-3,5-di-MeO—PhCH2CH2— |
| 10267 | 4-Me-3,5-di-MeO—PhCH2CH2— |
| 10268 | 4-F-3,5-di-EtO—PhCH2CH2— |
| 10269 | 4-Cl-3,5-di-EtO—PhCH2CH2— |
| 10270 | 4-Br-3,5-di-EtO—PhCH2CH2— |
| 10271 | 4-I-3,5-di-EtO—PhCH2CH2— |
| 10272 | 4-Me-3,5-di-EtO—PhCH2CH2— |
| 10273 | 2,3,4-tri-F—PhCH2CH2— |
| 10274 | 2-Cl-3,4-di-F—PhCH2CH2— |
| 10275 | 2-Br-3,4-di-F—PhCH2CH2— |
| 10276 | 3,4-di-F-2-I—PhCH2CH2— |
| 10277 | 3,4-di-F-2-Me—PhCH2CH2— |
| 10278 | 2,4,5-tri-F—PhCH2CH2— |
| 10279 | 2-Cl-4,5-di-F—PhCH2CH2— |
| 10280 | 2-Br-4,5-di-F—PhCH2CH2— |
| 10281 | 4,5-di-F-2-I—PhCH2CH2— |
| 10282 | 4,5-di-F-2-Me—PhCH2CH2— |
| 10283 | 2,4-di-F-3-Cl—PhCH2CH2— |
| 10284 | 2,3-di-Cl-4-F—PhCH2CH2— |
| 10285 | 2-Br-3-Cl-4-F—PhCH2CH2— |
| 10286 | 3-Cl-4-F-2-I—PhCH2CH2— |
| 10287 | 3-Cl-4-F-2-Me—PhCH2CH2— |
| 10288 | 2,4-di-F-5-Cl—PhCH2CH2— |
| 10289 | 2,5-di-Cl-4-F—PhCH2CH2— |
| 10290 | 2-Br-5-Cl-4-F—PhCH2CH2— |
| 10291 | 5-Cl-4-F-2-I—PhCH2CH2— |
| 10292 | 5-Cl-4-F-2-Me—PhCH2CH2— |
| 10293 | 2-F-3,4-di-Cl—PhCH2CH2— |
| 10294 | 2,3,4-tri-Cl—PhCH2CH2— |
| 10295 | 2-Br-3,4-di-Cl—PhCH2CH2— |
| 10296 | di-3,4-Cl-2-I—PhCH2CH2— |
| 10297 | di-3,4-Cl-2-Me—PhCH2CH2— |
| 10298 | 2-F-3,5-di-Cl—PhCH2CH2— |
| 10299 | 2,3,5-tri-Cl—PhCH2CH2— |
| 10300 | 2-Br-3,5-di-Cl—PhCH2CH2— |
| 10301 | 3,5-di-Cl-2-I—PhCH2CH2— |
| 10302 | 3,5-di-Cl-2-Me—PhCH2CH2— |
| 10303 | 4-Cl-2,3-di-F—PhCH2CH2— |
| 10304 | 2,4-di-Cl-3-F—PhCH2CH2— |
| 10305 | 2-Br-4-Cl-3-F—PhCH2CH2— |
| 10306 | 4-Cl-3-F-2-I—PhCH2CH2— |
| 10307 | 4-Cl-3-F-2-Me—PhCH2CH2— |
| 10308 | 4-Cl-2,5-di-F—PhCH2CH2— |
| 10309 | 2,4-di-Cl-5-F—PhCH2CH2— |
| 10310 | 2-Br-4-Cl-5-F—PhCH2CH2— |
| 10311 | 4-Cl-5-F-2-I—PhCH2CH2— |
| 10312 | 4-Cl-5-F-2-Me—PhCH2CH2— |
| 10313 | 2,4-di-F-3-MeO—PhCH2CH2— |
| 10314 | 2-Cl-4-F-3-MeO—PhCH2CH2— |
| 10315 | 2-Br-4-F-3-MeO—PhCH2CH2— |
| 10316 | 4-F-2-I-3-MeO—PhCH2CH2— |
| 10317 | 4-F-2-Me-3-MeO—PhCH2CH2— |
| 10318 | 2,4-F-5-MeO—PhCH2CH2— |
| 10319 | 2-Cl-4-F-5-MeO—PhCH2CH2— |
| 10320 | 2-Br-4-F-5-MeO—PhCH2CH2— |
| 10321 | 4-F-2-I-5-MeO—PhCH2CH2— |
| 10322 | 4-F-2-Me-5-MeO—PhCH2CH2— |
| 10323 | 4-Cl-2-F-3-MeO—PhCH2CH2— |
| 10324 | 2,4-di-Cl-3-MeO—PhCH2CH2— |
| 10325 | 2-Br-4-Cl-3-MeO—PhCH2CH2— |
| 10326 | 4-Cl-2-I-3-MeO—PhCH2CH2— |
| 10327 | 4-Cl-2-Me-3-MeO—PhCH2CH2— |
| 10328 | 4-Cl-2-F-5-MeO—PhCH2CH2— |
| 10329 | 2,4-di-Cl-5-MeO—PhCH2CH2— |

TABLE 2-continued

| No. | Z |
|---|---|
| 10330 | 2-Br-4-Cl-5-MeO—PhCH2CH2— |
| 10331 | 4-Cl-2-I-5-MeO—PhCH2CH2— |
| 10332 | 4-Cl-2-Me-5-MeO—PhCH2CH2— |
| 10333 | 2,6-di-F-3,5-di-MeO—PhCH2CH2— |
| 10334 | 2,6-di-Cl-3,5-di-MeO—PhCH2CH2— |
| 10335 | 6-Cl-2-F-3,5-di-MeO—PhCH2CH2— |
| 10336 | 6-Br-2-F-3,5-di-MeO—PhCH2CH2— |
| 10337 | 2-Br-6-Cl-3,5-di-MeO—PhCH2CH2— |
| 10338 | 2,3,4,5,-tetra-F—PhCH2CH2— |
| 10339 | 2,3,5,6,-tetra-F—PhCH2CH2— |
| 10340 | 2,3,4,5,6-penta-F—PhCH2CH2— |
| 10341 | 2,3-di-F-5-MeS—PhCH2CH2— |
| 10342 | 2-F-3-MeO-5-MeS—PhCH2CH2— |
| 10343 | 2,5-di-F-3-MeS—PhCH2CH2— |
| 10344 | 2-Cl-3-F-5-MeS—PhCH2CH2— |
| 10345 | 2-Cl-5-F-3-MeS—PhCH2CH2— |
| 10346 | 2-F-5-MeO-3-MeS—PhCH2CH2— |
| 10347 | 2-Cl-5-MeO-3-MeS—PhCH2CH2— |
| 10348 | 2-Br-3-F-5-MeS—PhCH2CH2— |
| 10349 | 2-Cl-3-MeO-5-MeS—PhCH2CH2— |
| 10350 | 2-Br-3-MeO-5-MeS—PhCH2CH2— |
| 10351 | 2-Br-5-MeO-3-MeS—PhCH2CH2— |
| 10352 | 2-Br-5-F-3-MeS—PhCH2CH2— |
| 10353 | 2-I-5-F-3-MeS—PhCH2CH2— |
| 10354 | 2-I-3-MeO-5-MeS—PhCH2CH2— |
| 10355 | 2-I-3-F-5-MeS—PhCH2CH2— |
| 10356 | 3-F-2-Me-5-MeS—PhCH2CH2— |
| 10357 | 5-F-2-Me-3-MeS—PhCH2CH2— |
| 10358 | 2-I-5-MeO-3-MeS—PhCH2CH2— |
| 10359 | 2-Me-5-MeO-3-MeS—PhCH2CH2— |
| 10360 | 2-F-3,5-di-MeS—PhCH2CH2— |
| 10361 | 2-Me-3-MeO-5-MeS—PhCH2CH2— |
| 10362 | 2-Br-3,5-di-MeS—PhCH2CH2— |
| 10363 | 2-I-3,5-di-MeS—PhCH2CH2— |
| 10364 | 2-Cl-3,5-di-MeS—PhCH2CH2— |
| 10365 | 2,5-di-F-3-MeS(O)—PhCH2CH2— |
| 10366 | 2,3-di-F-5-MeS(O)—PhCH2CH2— |
| 10367 | 2-Me-3,5-di-MeS—PhCH2CH2— |
| 10368 | 2-F-5-MeO-3-MeS(O)—PhCH2CH2— |
| 10369 | 2-Cl-3-F-5-MeS(O)—PhCH2CH2— |
| 10370 | 2-F-3-MeO-5-MeS(O)—PhCH2CH2— |
| 10371 | 2-Cl-3-MeO-5-MeS(O)—PhCH2CH2— |
| 10372 | 2-Cl-5-MeO-3-MeS(O)—PhCH2CH2— |
| 10373 | 2-Cl-5-F-3-MeS(O)—PhCH2CH2— |
| 10374 | 2-Br-5-F-3-MeS(O)—PhCH2CH2— |
| 10375 | 2-Br-5-MeO-3-MeS(O)—PhCH2CH2— |
| 10376 | 2-Br-3-F-5-MeS(O)—PhCH2CH2— |
| 10377 | 2-I-3-F-5-MeS(O)—PhCH2CH2— |
| 10378 | 5-F-2-I-3-MeS(O)—PhCH2CH2— |
| 10379 | 2-Br-5-MeO-3-MeS(O)—PhCH2CH2— |
| 10380 | 2-I-5-MeO-3-MeS(O)—PhCH2CH2— |
| 10381 | 3-F-2-Me-5-MeS(O)—PhCH2CH2— |
| 10382 | 2-I-3-MeO-5-MeS(O)—PhCH2CH2— |
| 10383 | 2-Me-3-MeO-5-MeS(O)—PhCH2CH2— |
| 10384 | 2-Me-5-MeO-3-MeS(O)—PhCH2CH2— |
| 10385 | 5-F-2-Me-3-MeS(O)—PhCH2CH2— |
| 10386 | 2-Cl-3,5-di-MeS(O)—PhCH2CH2— |
| 10387 | 2-Br-3,5-di-MeS(O)—PhCH2CH2— |
| 10388 | 2-F-3,5-di-MeS(O)—PhCH2CH2— |
| 10389 | 2-Me-3,5-di-MeS(O)—PhCH2CH2— |
| 10390 | 2,5-di-F-3-MeSO2—PhCH2CH2— |
| 10391 | 2-I-3,5-di-MeS(O)—PhCH2CH2— |
| 10392 | 2-F-3-MeO-5-MeSO2—PhCH2CH2— |
| 10393 | 2-F-5-MeO-3-MeSO2—PhCH2CH2— |
| 10394 | 2,3-di-F-5-MeSO2—PhCH2CH2— |
| 10395 | 2-Cl-5-F-3-MeSO2—PhCH2CH2— |
| 10396 | 2-Cl-3-MeO-5-MeSO2—PhCH2CH2— |
| 10397 | 2-Cl-3-F-5-MeSO2—PhCH2CH2— |
| 10398 | 2-Br-3-F-5-MeSO2—PhCH2CH2— |
| 10399 | 2-Br-5-F-3-MeSO2—PhCH2CH2— |
| 10400 | 2-Cl-5-MeO-3-MeSO2—PhCH2CH2— |
| 10401 | 2-Br-5-MeO-3-MeSO2—PhCH2CH2— |
| 10402 | 3-F-2-I-5-MeSO2—PhCH2CH2— |
| 10403 | 2-Br-3-MeO-5-MeSO2—PhCH2CH2— |
| 10404 | 2-I-3-MeO-5-MeSO2—PhCH2CH2— |
| 10405 | 2-I-5-MeO-3-MeSO2—PhCH2CH2— |
| 10406 | 5-F-2-I-3-MeSO2—PhCH2CH2— |
| 10407 | 5-F-2-Me-3-MeSO2—PhCH2CH2— |
| 10408 | 2-Me-3-MeO-5-MeSO2—PhCH2CH2— |
| 10409 | 3-F-2-Me-5-MeSO2—PhCH2CH2— |
| 10410 | 2-F-3,5-di-MeSO2—PhCH2CH2— |
| 10411 | 2-Cl-3,5-di-MeSO2—PhCH2CH2— |
| 10412 | 2-Me-5-MeO-3-MeSO—PhCH2CH2— |
| 10413 | 2-I-3,5-di-MeSO2—PhCH2CH2— |
| 10414 | 2-Me-3,5-di-MeSO2—PhCH2CH2— |
| 10415 | 2-Br-3,5-di-MeSO2—PhCH2CH2— |
| 10416 | 2,4,6-tri-F—PhCH2CH2— |
| 10417 | Me |
| 10418 | Et |
| 10419 | Pr |
| 10420 | Bu |
| 10421 | Pent |
| 10422 | Hex |
| 10423 | Hept |
| 10424 | Oct |
| 10425 | Non |
| 10426 | iPr |
| 10427 | iBu |
| 10428 | secBu |
| 10429 | Pr(Me)CH |
| 10430 | Et(Et)CH— |
| 10431 | Et(Pr)CH— |
| 10432 | iPr(Me)CH— |
| 10433 | iPr(Et)CH— |
| 10434 | iPr(Pr)CH— |
| 10435 | cPr-CH2— |
| 10436 | cBuCH2— |
| 10437 | cPent- |
| 10438 | cHex-CH2— |
| 10439 | cHept-CH2— |
| 10440 | cOct-CH2— |
| 10441 | F3CCH2— |
| 10442 | F3CCH2CH2— |
| 10443 | F3CCH2CH2CH2— |
| 10444 | F3CCH2CH2CH2CH2— |
| 10445 | F2CHCH2— |
| 10446 | F2CHCH2CH2— |
| 10447 | F2CHCH2CH2CH2— |
| 10448 | F2CHCH2CH2CH2CH2— |
| 10449 | F2CHCH2CH2CH2CH2CH2— |
| 10450 | cPr |
| 10451 | cBu |
| 10452 | cPent |
| 10453 | cHex |
| 10454 | cHept |
| 10455 | cOct |
| 10456 | 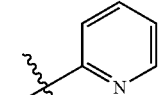 |
| 10457 | 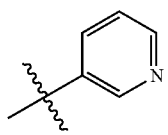 |
| 10458 | 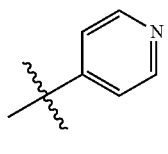 |
| 10459 | 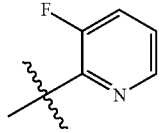 [SMILES: *c1ncccc1F] |

TABLE 2-continued
| No. | Z |
|---|---|
| 10460 | 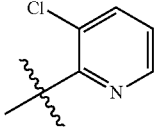 |
| 10461 | 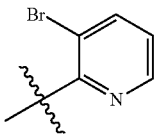 [SMILES: *c1ncccc1Br] |
| 10462 | 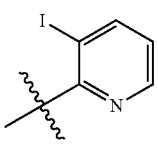 [SMILES: *c1ncccc1I] |
| 10463 | 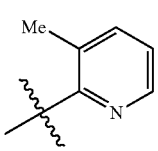 [SMILES: *c1ncccc1C] |
| 10464 | 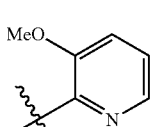 |
| 10465 | 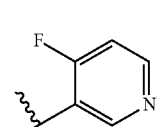 |
| 10466 | 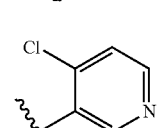 |
| 10467 | 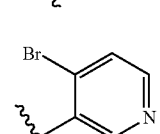 |
| 10468 | 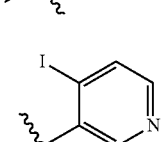 |
| 10469 | 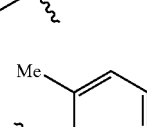 |
TABLE 2-continued
| No. | Z |
|---|---|
| 10470 | 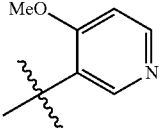 [SMILES: *c1cnccc1OC] |
| 10471 | 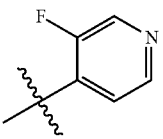 |
| 10472 | 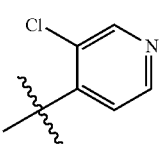 |
| 10473 | 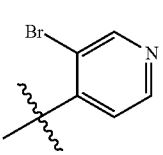 [SMILES: *c1ccncc1Br] |
| 10474 | 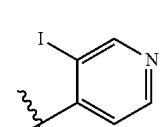 |
| 10475 | 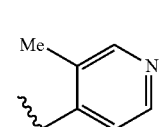 |
| 10476 | 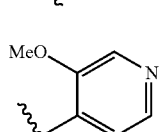 |
| 10477 | 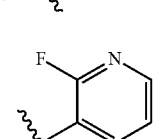 |
| 10478 | 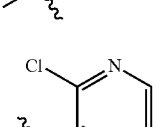 |
| 10479 | 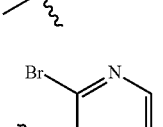 |

TABLE 2-continued

| No. | Z |
|---|---|
| 10480 | 2-I, 3-pyridyl |
| 10481 | 2-Me, 3-pyridyl |
| 10482 | 2-MeO, 3-pyridyl |
| 10483 | 4-F, 2-pyridyl |
| 10484 | 4-Cl, 2-pyridyl |
| 10485 | 4-Br, 2-pyridyl |
| 10486 | 3-I, 2-pyridyl |
| 10487 | 4-Me, 2-pyridyl |
| 10488 | 4-OMe, 2-pyridyl |
| 10489 | 5-F, 3-pyridyl |
| 10490 | 5-Cl, 3-pyridyl |
| 10491 | 5-Br, 3-pyridyl |
| 10492 | 5-I, 3-pyridyl |
| 10493 | 5-Me, 3-pyridyl |
| 10494 | 5-OMe, 3-pyridyl |
| 10495 | 2-F, 4-pyridyl |
| 10496 | 2-Cl, 4-pyridyl |

TABLE 2-continued
| No. | Z |
|---|---|
| 10497 | 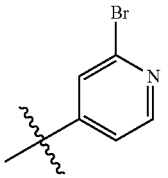 [SMILES: *c1ccnc(Br)c1] |
| 10498 | 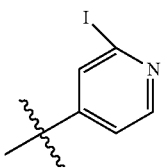 [SMILES: *c1ccnc(I)c1] |
| 10499 | 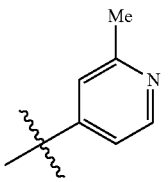 [SMILES: *c1ccnc(C)c1] |
| 10500 | 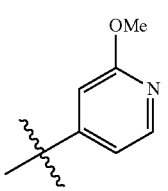 [SMILES: *c1ccnc(OC)c1] |
| 10501 | 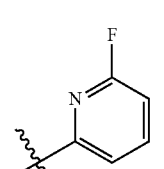 |
| 10502 | 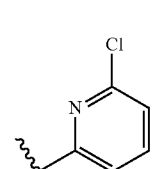 |
| 10503 | 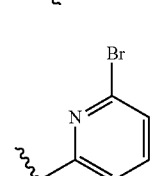 |
| 10504 | 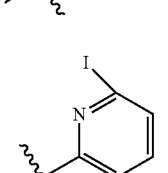 |
| 10505 | 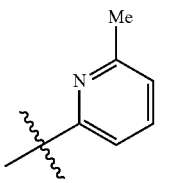 [SMILES: *c1cccc(C)n1] |
| 10506 | 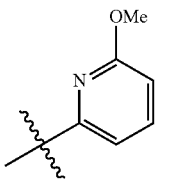 [SMILES: *c1cccc(OC)n1] |
| 10507 | 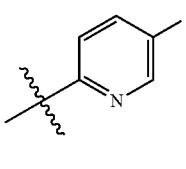 |
| 10508 | 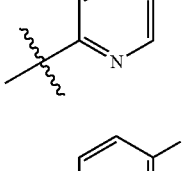 |
| 10509 | 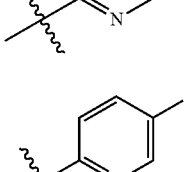 |
| 10510 | 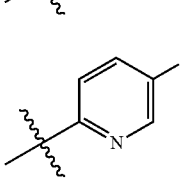 |
| 10511 | 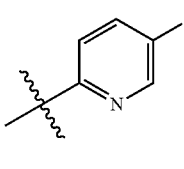 |
| 10512 | 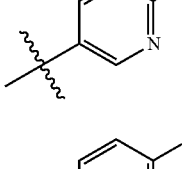 |
| 10513 | 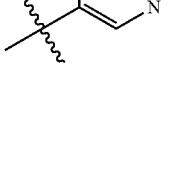 |
| 10514 |  |

TABLE 2-continued
| No. | Z |
|---|---|
| 10515 | 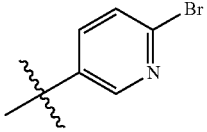 [SMILES: *c1ccc(Br)nc1] |
| 10516 | 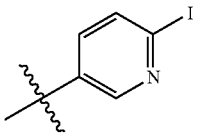 [SMILES: *c1ccc(I)nc1] |
| 10517 | 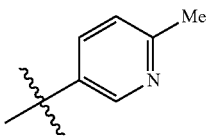 [SMILES: *c1ccc(C)nc1] |
| 10518 | 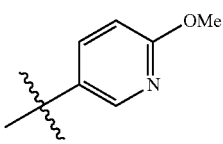 [SMILES: *c1ccc(OC)nc1] |
| 10519 | 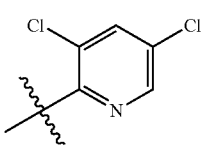 [SMILES: *c1ncc(Cl)cc1Cl] |
| 10520 | 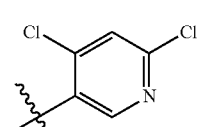 |
| 10521 | 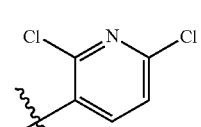 |
| 10522 | 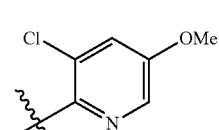 |
| 10523 | 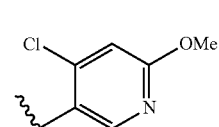 |
| 10524 | 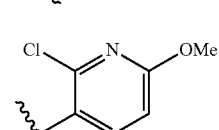 |
| 10525 | 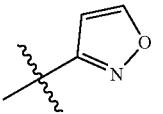 [SMILES: *c1ccon1] |
| 10526 | 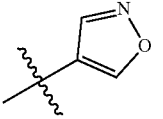 [SMILES: *c1cnoc1] |
| 10527 | 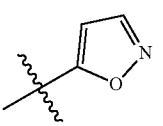 [SMILES: *c1ccno1] |
| 10528 | 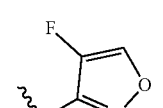 |
| 10529 | 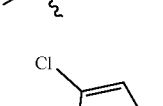 |
| 10530 | 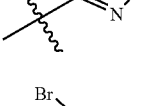 |
| 10531 | 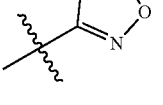 |
| 10532 | 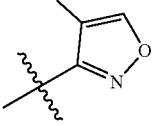 |
| 10533 | 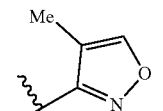 |
| 10534 | 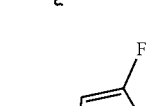 |

TABLE 2-continued
| No. | Z |
|---|---|
| 10535 | 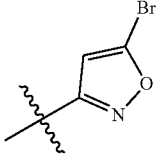 |
| 10536 | 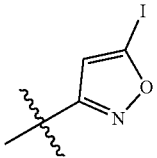 [SMILES: *c1cc(Cl)on1] |
| 10537 | 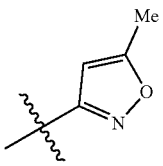 [SMILES: *c1cc(C)on1] |
| 10538 | 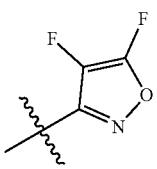 [SMILES: *c1noc(Cl)c1F] |
| 10539 | 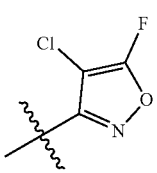 [SMILES: *c1noc(Cl)c1Cl] |
| 10540 | 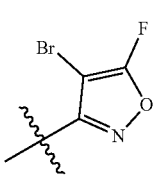 [SMILES: *c1noc(Cl)c1Br] |
| 10541 | 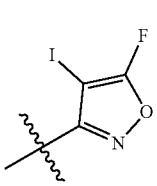 [SMILES: *c1noc(Cl)c1I] |
| 10542 | 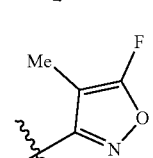 |
| 10543 | 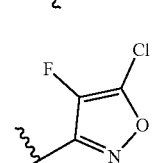 |
| 10544 | 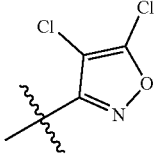 |
| 10545 | 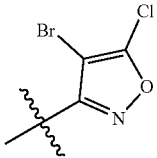 |
| 10546 | 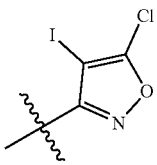 |
| 10547 | 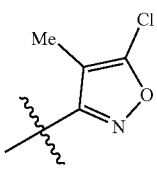 |
| 10548 | 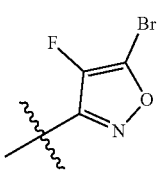 |
| 10549 | 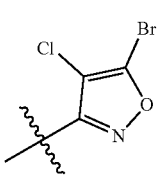 [SMILES: *c1noc(Br)c1Cl] |
| 10550 | 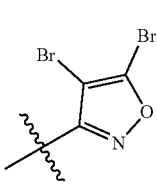 [SMILES: *c1noc(Br)c1Br] |
| 10551 | 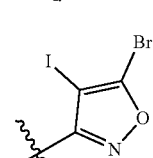 |
| 10552 | 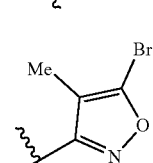 |

TABLE 2-continued
| No. | Z |
|---|---|
| 10553 | 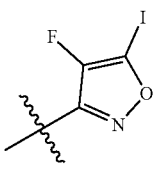 |
| 10554 | 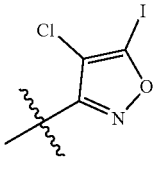 |
| 10555 | 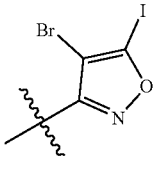 |
| 10556 | 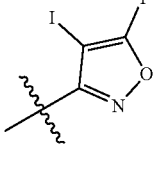 |
| 10557 | 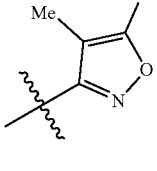 |
| 10558 | 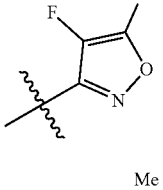 |
| 10559 | 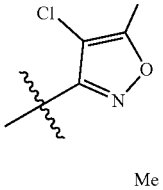 |
| 10560 | 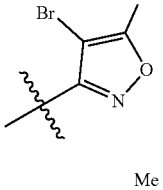 |
| 10561 | 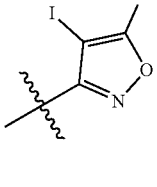 |
TABLE 2-continued
| No. | Z |
|---|---|
| 10562 | 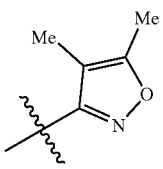 [SMILES: *c1noc(C)c1C] |
| 10563 | 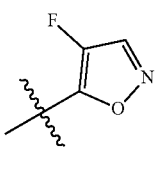 [SMILES: *c1oncc1I] |
| 10564 | 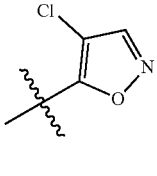 |
| 10565 | 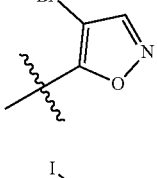 |
| 10566 | 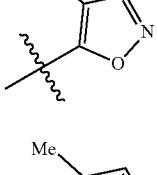 |
| 10567 | 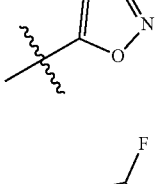 |
| 10568 | 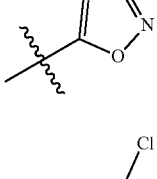 |
| 10569 | 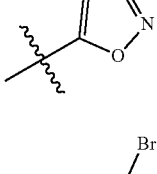 |
| 10570 | 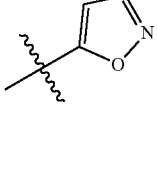 |

TABLE 2-continued
| No. | Z |
|---|---|
| 10571 | 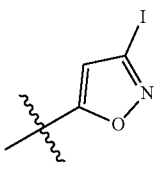 [SMILES: *c1cc(I)no1] 3-I isoxazole |
| 10572 | 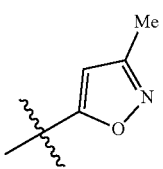 [SMILES: *c1cc(C)no1] 3-Me isoxazole |
| 10573 | 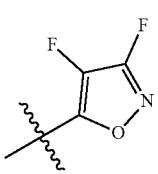 3-F, 4-F isoxazole |
| 10574 | 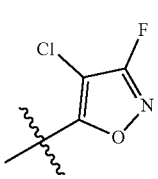 3-F, 4-Cl isoxazole |
| 10575 | 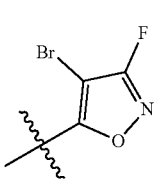 [SMILES: *c1onc(F)c1Br] 3-F, 4-Br isoxazole |
| 10576 | 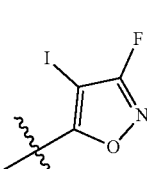 3-F, 4-I isoxazole |
| 10577 | 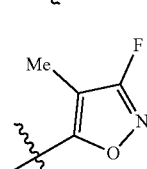 3-F, 4-Me isoxazole |
| 10578 | 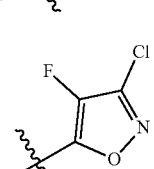 3-Cl, 4-F isoxazole |
| 10579 | 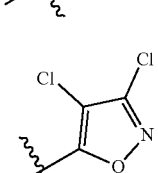 3-Cl, 4-Cl isoxazole |
| 10580 | 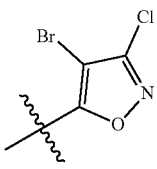 [SMILES: *c1onc(Cl)c1Cl] 3-Cl, 4-Br isoxazole |
| 10581 | 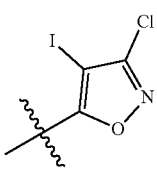 [SMILES: *c1onc(Cl)c1I] 3-Cl, 4-I isoxazole |
| 10582 | 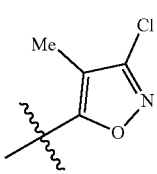 [SMILES: *c1onc(Cl)c1C] 3-Cl, 4-Me isoxazole |
| 10583 | 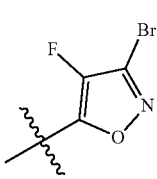 3-Br, 4-F isoxazole |
| 10584 | 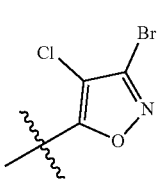 [SMILES: *c1onc(Br)c1Cl] 3-Br, 4-Cl isoxazole |
| 10585 | 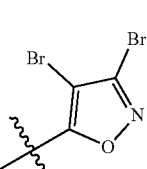 3-Br, 4-Br isoxazole |
| 10586 | 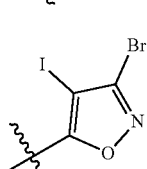 3-Br, 4-I isoxazole |
| 10587 | 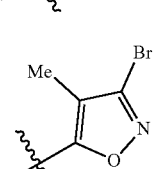 3-Br, 4-Me isoxazole |
| 10588 | 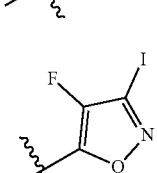 3-I, 4-F isoxazole |

TABLE 2-continued
| No. | Z |
|---|---|
| 10589 | 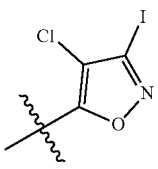 [SMILES: *c1onc(I)c1Cl] |
| 10590 | 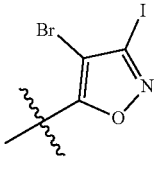 [SMILES: *c1onc(I)c1Br] |
| 10591 | 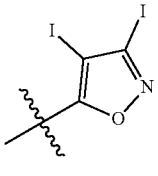 [SMILES: *c1onc(I)c1I] |
| 10592 | 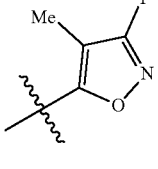 |
| 10593 | 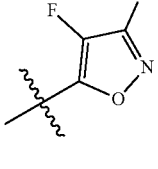 |
| 10594 | 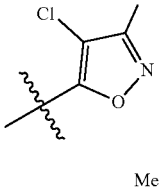 |
| 10595 | 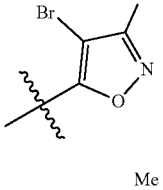 |
| 10596 | 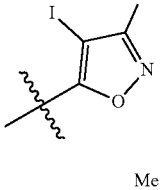 |
| 10597 | 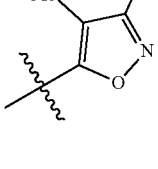 |
| 10598 | 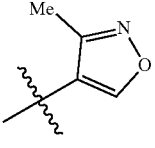 |
| 10599 | 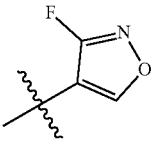 [SMILES: *c1conc1F] |
| 10600 | 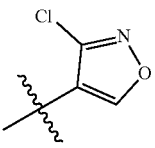 [SMILES: *c1conc1Cl] |
| 10601 | 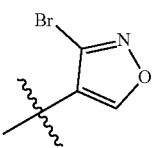 [SMILES: *c1conc1Br] |
| 10602 | 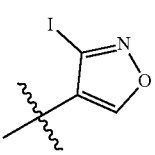 [SMILES: *c1conc1I] |
| 10603 | 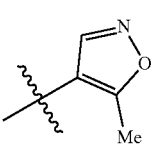 [SMILES: *c1cnoc1C] |
| 10604 | 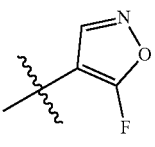 [SMILES: *c1cnoc1F] |
| 10605 | 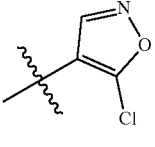 [SMILES: *c1cnoc1Cl] |
| 10606 | 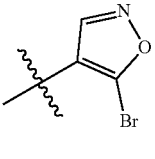 [SMILES: *c1cnoc1Br] |
| 10607 | 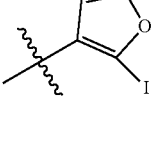 |

TABLE 2-continued
| No. | Z |
|---|---|
| 10608 | 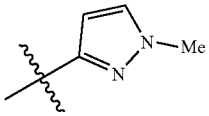 [SMILES: *c1ccn(C)n1] |
| 10609 | 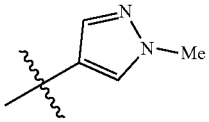 [SMILES: *c1cnn(C)c1] |
| 10610 | 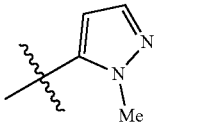 [SMILES: *c1ccnn1C] |
| 10611 | 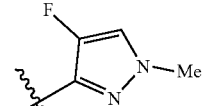 |
| 10612 | 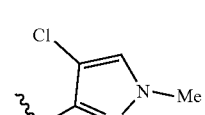 |
| 10613 | 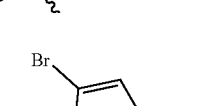 |
| 10614 | 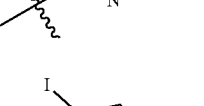 |
| 10615 | 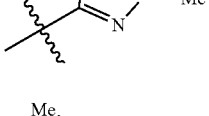 |
| 10616 | 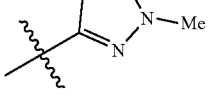 |
| 10617 | 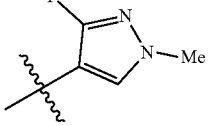 |
TABLE 2-continued
| No. | Z |
|---|---|
| 10618 | 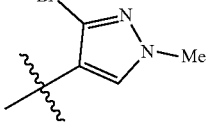 |
| 10619 | 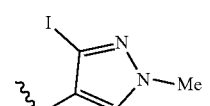 |
| 10620 | 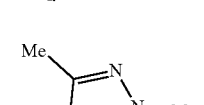 |
| 10621 |  |
| 10622 | 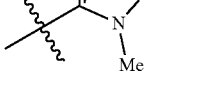 |
| 10623 | 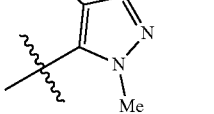 |
| 10624 | 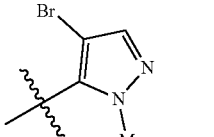 |
| 10625 | 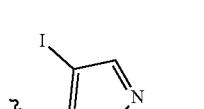 |
| 10626 |  |

TABLE 2-continued

| No. | Z |
|---|---|
| 10627 | 4-Cl, 5-Me, 1-Me pyrazol-3-yl |
| 10628 | 4-Br, 5-Me, 1-Me pyrazol-3-yl |
| 10629 | 4-I, 5-Me, 1-Me pyrazol-3-yl |
| 10630 | 4-Me, 5-Me, 1-Me pyrazol-3-yl |
| 10631 | 3-F, 5-Me, 1-Me pyrazol-4-yl |
| 10632 | 3-Cl, 5-Me, 1-Me pyrazol-4-yl |
| 10633 | 3-Br, 5-Me, 1-Me pyrazol-4-yl |
| 10634 | 3-I, 5-Me, 1-Me pyrazol-4-yl |
| 10635 | 3-Me, 5-Me, 1-Me pyrazol-4-yl |
| 10636 | 4-F, 3-Me, 1-Me pyrazol-5-yl |
| 10637 | 4-Cl, 3-Me, 1-Me pyrazol-5-yl |
| 10638 | 4-Br, 3-Me, 1-Me pyrazol-5-yl |
| 10639 | 4-I, 3-Me, 1-Me pyrazol-5-yl |
| 10640 | 4-Me, 3-Me, 1-Me pyrazol-5-yl |
| 10641 | 1,3,4-thiadiazol-2-yl |
| 10642 | thiazol-2-yl |
| 10643 | 4-Me, 5-Me thiazol-2-yl |
| 10644 | 4-Cl, 5-Cl thiazol-2-yl |

TABLE 2-continued

| No. | Z |
|---|---|
| 10645 | 2-(4-Me-5-Cl-thiazolyl) |
| 10646 | 2-(4-Cl-5-Me-thiazolyl) |
| 10647 | 2-pyrazinyl |
| 10648 | 2-(3-F-pyrazinyl) |
| 10649 | 2-(3-Cl-pyrazinyl) |
| 10650 | 2-(3-Br-pyrazinyl) |
| 10651 | 2-(3-I-pyrazinyl) |
| 10652 | 2-(3-Me-pyrazinyl) |
| 10653 | 2-Me—Bu |
| 10654 | 2-Me—Pent |
| 10655 | tBuCH2 |
| 10656 | tBuCH2CH2— |
| 10657 | iPrCH2CH2— |
| 10658 | N≡CCH2— |
| 10659 | N≡CCH2CH2— |
| 10660 | MeOCH2— |
| 10661 | MeOCH2CH2— |
| 10662 | MeOCH2CH2CH2— |
| 10663 | EtOCH2— |
| 10664 | EtOCH2CH2— |
| 10665 | EtOCH2CH2CH2— |
| 10666 | MeSCH2— |
| 10667 | MeSCH2CH2— |
| 10668 | MeSCH2CH2CH2— |
| 10669 | MeS(O)CH2— |
| 10670 | MeS(O)CH2CH2— |
| 10671 | MeS(O)CH2CH2CH2— |
| 10672 | MeSO2CH2— |
| 10673 | MeSO2CH2CH2— |
| 10674 | MeSO2CH2CH2CH2— |
| 10675 | MeOC(=O)CH2— |
| 10676 | MeOC(=O)CH2CH2— |
| 10677 | EtOC(=O)CH2— |
| 10678 | EtOC(=O)CH2CH2— |
| 10679 | 2-Me-cHex |
| 10680 | 3-Me-cHex |
| 10681 | 4-Me-cHex |
| 10682 | H2C=CH— |
| 10683 | H3CCH=CH— |
| 10684 | H2C=CHCH2— |
| 10685 | H3CHC=CHCH2— |
| 10686 | H2C=CHCH2CH2— |
| 10687 | HC≡CCH2— |
| 10688 | H3CC≡CCH2— |
| 10689 | HC≡CCH2CH2— |
| 10690 | H3CC≡CCH2CH2— |
| 10691 | 2-Et-3-HO—Ph |
| 10692 | 2-Et-4-HO—Ph |
| 10693 | 2-Et-5-HO—Ph |
| 10694 | 2-Et-3-MeO—Ph |
| 10695 | 2-Et-4-MeO—Ph |
| 10696 | 2-Et-5-MeO—Ph |
| 10697 | 2-Et-3-EtO—Ph |
| 10698 | 2-Et-4-EtO—Ph |
| 10699 | 2-Et-5-EtO—Ph |
| 10700 | 2-Et-3-N≡CCH2O—Ph |
| 10701 | 2-Et-4-N≡CCH2O—Ph |
| 10702 | 2-Et-5-N≡CCH2O—Ph |
| 10703 | 2-Et-3-MeOCH2O—Ph |
| 10704 | 2-Et-4-MeOCH2O—Ph |
| 10705 | 2-Et-5-MeOCH2O—Ph |
| 10706 | 2-Et-3-EtOCH2O—Ph |
| 10707 | 2-Et-4-EtOCH2O—Ph |
| 10708 | 2-Et-5-EtOCH2O—Ph |
| 10709 | 2-Et-3-MeOCH2CH2O—Ph |
| 10710 | 2-Et-4-MeOCH2CH2O—Ph |
| 10711 | 2-Et-5-MeOCH2CH2O—Ph |
| 10712 | 2-Et-3-EtOCH2CH2O—Ph |
| 10713 | 2-Et-4-EtOCH2CH2O—Ph |
| 10714 | 2-Et-5-EtOCH2CH2O—Ph |
| 10715 | 2-Et-3-HC≡CCH2O—Ph |
| 10716 | 2-Et-4-HC≡CCH2O—Ph |
| 10717 | 2-Et-5-HC≡CCH2O—Ph |
| 10718 | 2-Me-3-H2N—Ph |
| 10719 | 2-Me-4-H2N—Ph |
| 10720 | 2-Me-5-H2N—Ph |
| 10721 | 2-Et-3-H2N—Ph |
| 10722 | 2-Et-4-H2N—Ph |
| 10723 | 2-Et-5-H2N—Ph |
| 10724 | 2-Me-3-MeNH—Ph |
| 10725 | 2-Me-5-MeNH—Ph |
| 10726 | 2-Me-5-MeNH—Ph |
| 10727 | 2-Et-3-MeNH—Ph |
| 10728 | 2-Et-5-MeNH—Ph |
| 10729 | 2-Et-5-MeNH—Ph |
| 10730 | 2-Me-3-Me2N—Ph |
| 10731 | 2-Me-4-Me2N—Ph |
| 10732 | 2-Me-5-Me2N—Ph |
| 10733 | 2-Et-3-Me2N—Ph |
| 10734 | 2-Et-4-Me2N—Ph |
| 10735 | 2-Et-5-Me2N—Ph |
| 10736 | 2-Me-3-AcNH—Ph |
| 10737 | 2-Me-5-AcNH—Ph |
| 10738 | 2-Me-5-AcNH—Ph |
| 10739 | 2-Et-3-AcNH—Ph |
| 10740 | 2-Et-5-AcNH—Ph |
| 10741 | 2-Et-5-AcNH—Ph |
| 10742 | 4-Br-2-Me-3-O2N—Ph |
| 10743 | 4-Br-2-Et-3-O2N—Ph |
| 10744 | 4-Br-2-Me-5-MeO—Ph |
| 10745 | 4-Br-2-Et-5-MeO—Ph |
| 10746 | 2,3-di-MeO—PhCH2— |

TABLE 2-continued
| No. | Z |
|---|---|
| 10747 | 2,4-di-MeO—PhCH2— |
| 10748 | 2,5-di-MeO—PhCH2— |
TABLE 3
| Structure | Label |
|---|---|
| 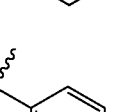 | Y-1 |
| phenyl, 2-F | Y-2 |
| phenyl, 2-Cl | Y-3 |
| phenyl, 2-Br | Y-4 |
| phenyl, 2-I | Y-5 |
| phenyl, 2-Me | Y-6 |
| phenyl, 2-OMe | Y-7 |
| phenyl, 2-CN | Y-8 |
| phenyl, 4-F | Y-9 |
| phenyl, 4-Cl | Y-10 |
| phenyl, 4-Br | Y-11 |
| phenyl, 4-I | Y-12 |
| phenyl, 4-Me | Y-13 |
| phenyl, 4-OMe | Y-14 |
| phenyl, 4-CN | Y-15 |
| phenyl, 2,4-di-F | Y-16 |
| phenyl, 2-F, 4-Cl | Y-17 |
| phenyl, 2-F, 4-Br | Y-18 |
| phenyl, 2-F, 4-I | Y-19 |

TABLE 3-continued

| Structure | Label |
|---|---|
| 2-F, 4-Me phenyl | Y-20 |
| 2-F, 4-OMe phenyl | Y-21 |
| 2-F, 4-CN phenyl | Y-22 |
| 2-Cl, 4-F phenyl | Y-23 |
| 2,4-diCl phenyl | Y-24 |
| 2-Cl, 4-Br phenyl | Y-25 |
| 2-Cl, 4-I phenyl | Y-26 |
| 2-Cl, 4-Me phenyl | Y-27 |
| 2-Cl, 4-OMe phenyl | Y-28 |
| 2-Cl, 4-CN phenyl | Y-29 |
| 2-Br, 4-F phenyl | Y-30 |
| 2-Br, 4-Cl phenyl | Y-31 |
| 2,4-diBr phenyl | Y-32 |
| 2-Br, 4-I phenyl | Y-33 |
| 2-Br, 4-Me phenyl | Y-34 |
| 2-Br, 4-OMe phenyl | Y-35 |
| 2-Br, 4-CN phenyl | Y-36 |
| 2-I, 4-F phenyl | Y-37 |
| 2-I, 4-Cl phenyl | Y-38 |
| 2-I, 4-Br phenyl | Y-39 |

TABLE 3-continued
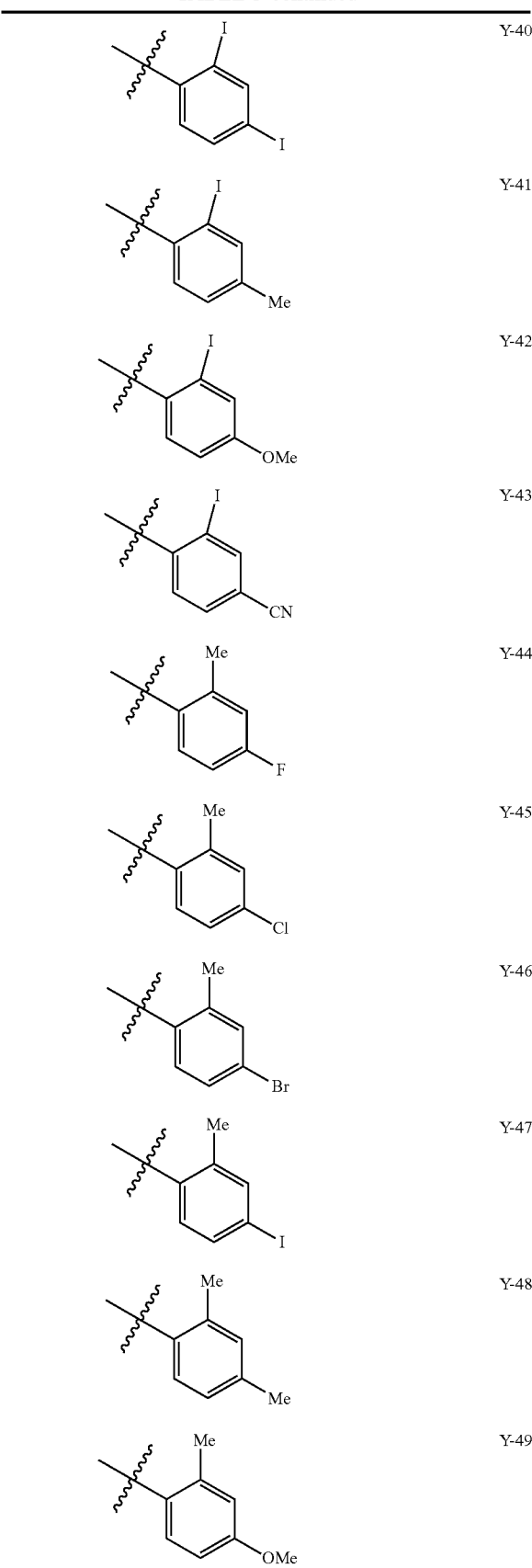
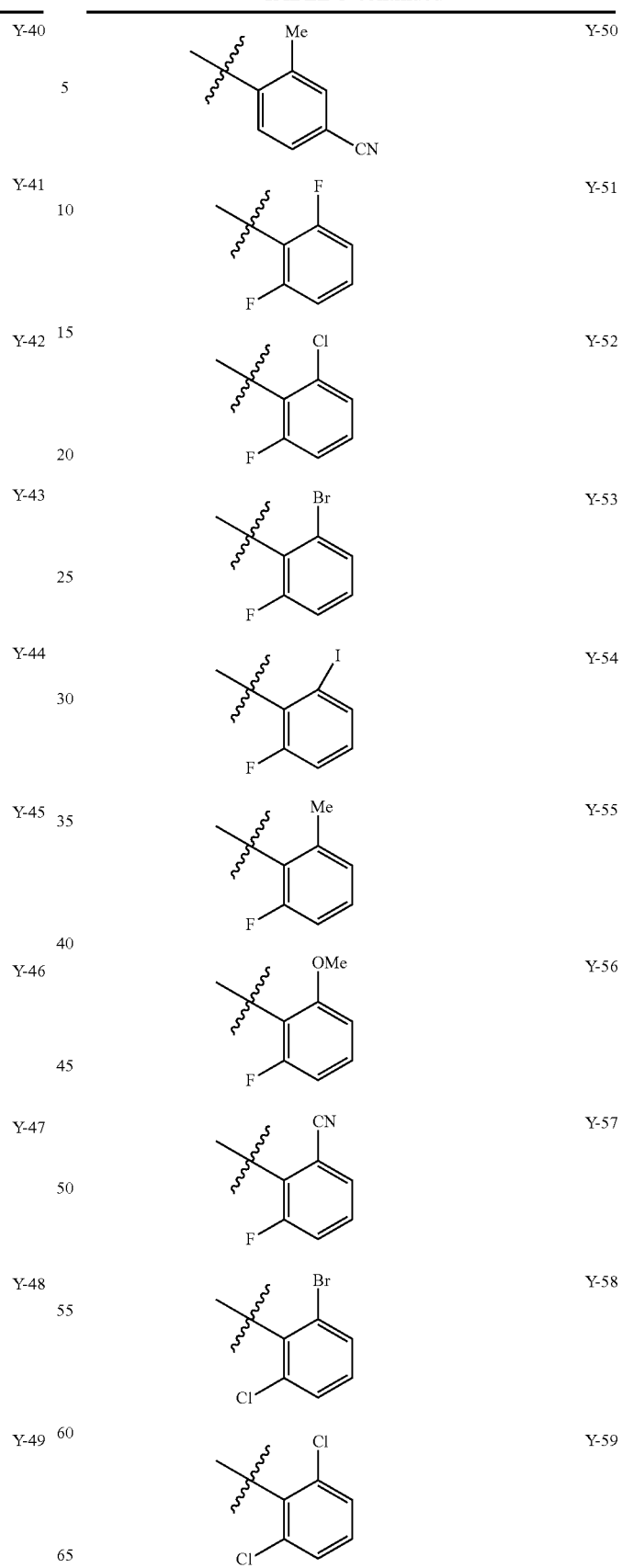

TABLE 3-continued
| | |
|---|---|
| 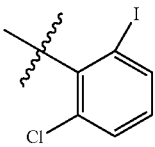 [SMILES: *c1c(Cl)cccc1I] | Y-60 |
| 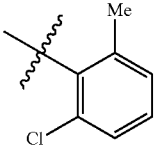 [SMILES: *c1c(C)cccc1Cl] | Y-61 |
| 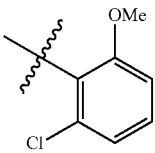 [SMILES: *c1c(Cl)cccc1OC] | Y-62 |
| 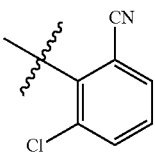 [SMILES: *c1c(Cl)cccc1C#N] | Y-63 |
| 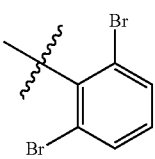 [SMILES: *c1c(Br)cccc1Br] | Y-64 |
| 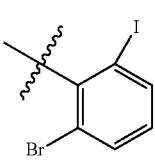 [SMILES: *c1c(Br)cccc1I] | Y-65 |
| 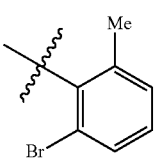 [SMILES: *c1c(C)cccc1I] | Y-66 |
| 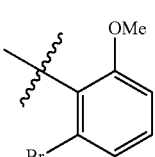 | Y-67 |
| 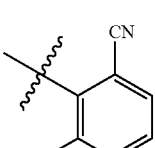 | Y-68 |
| 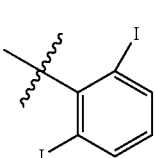 | Y-69 |
| 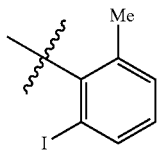 | Y-70 |
| 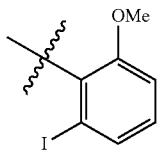 [SMILES: *c1c(I)cccc1OC] | Y-71 |
| 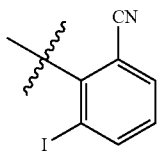 [SMILES: *c1c(I)cccc1C#N] | Y-72 |
| 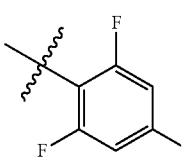 | Y-73 |
| 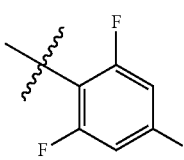 | Y-74 |
| 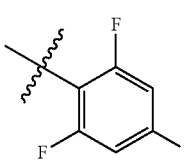 | Y-75 |
| 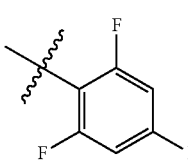 | Y-76 |
| 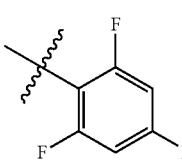 | Y-77 |
| 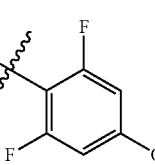 | Y-78 |
| 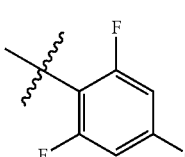 | Y-79 |

TABLE 3-continued
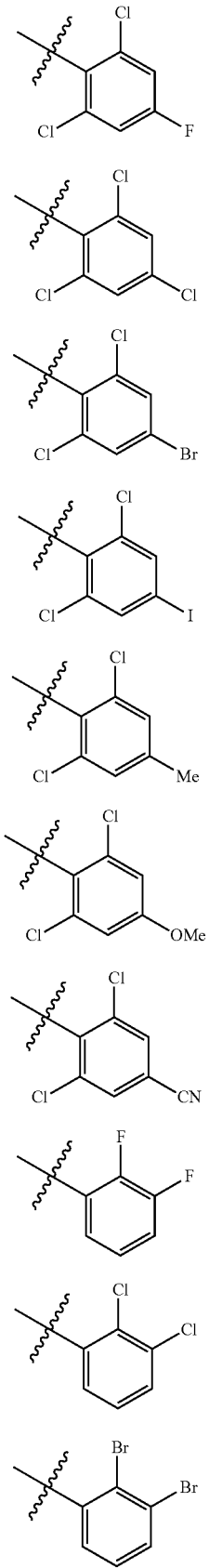
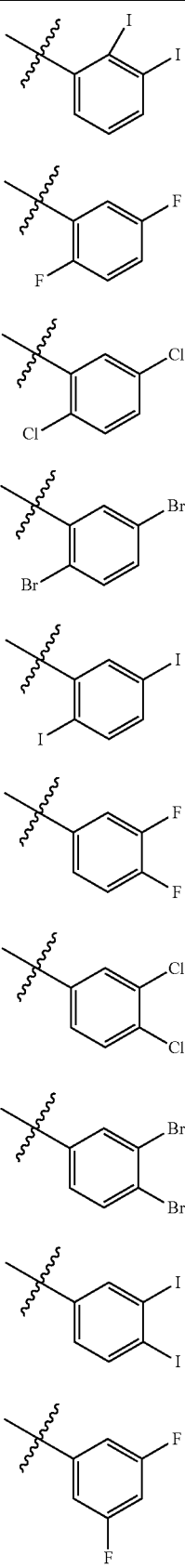

TABLE 3-continued
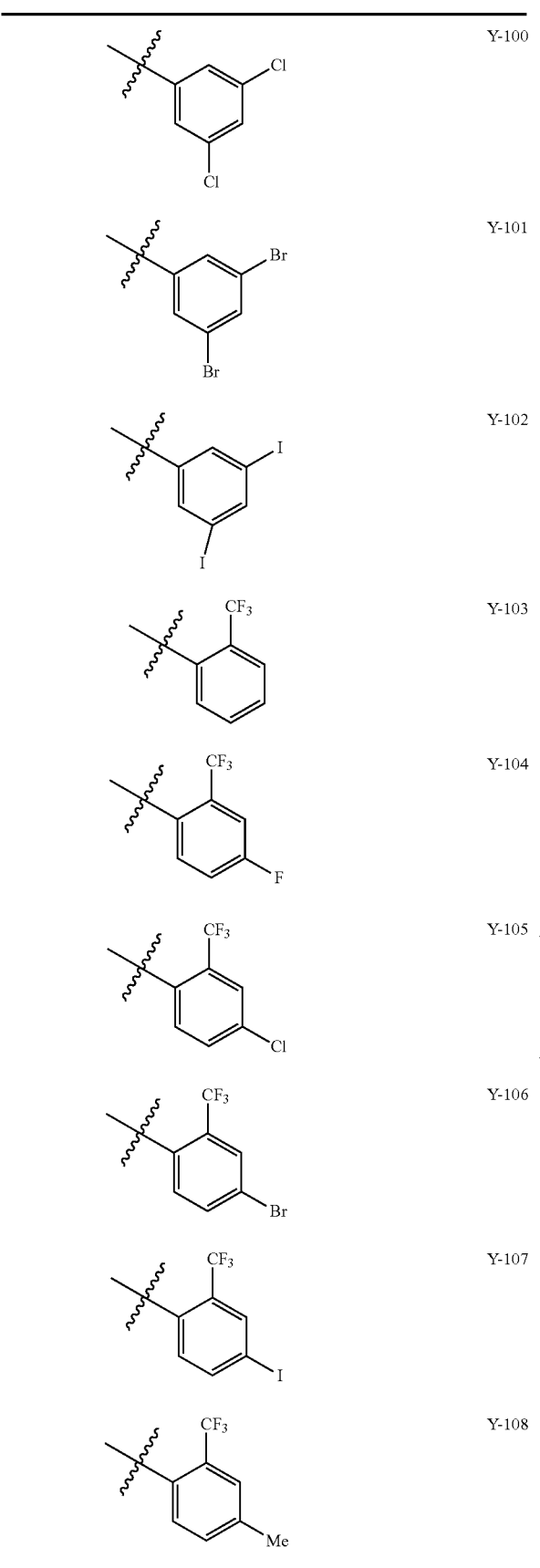
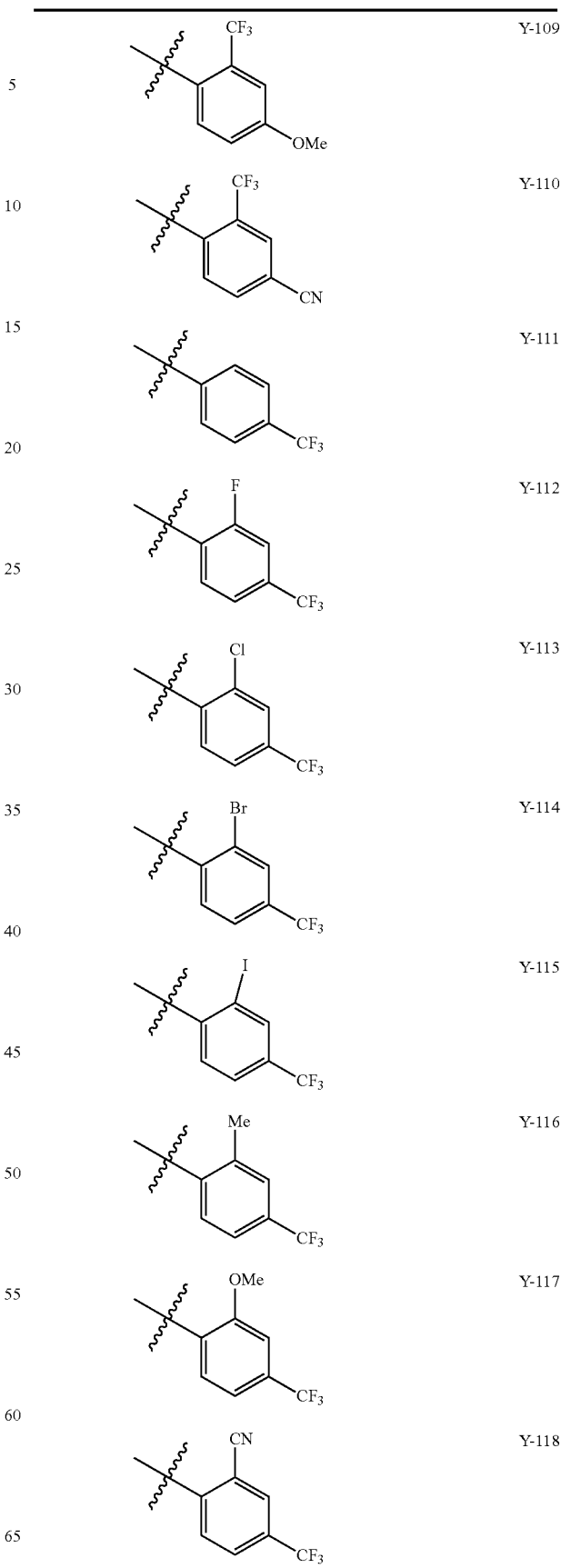

TABLE 3-continued
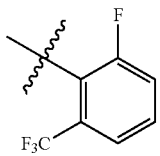 Y-119
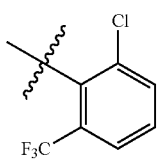 Y-120
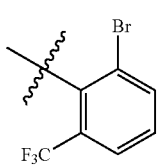 Y-121
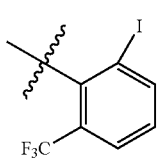 Y-122
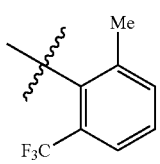 Y-123
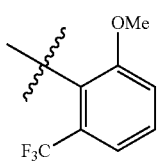 Y-124
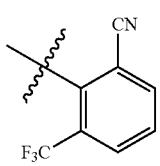 [SMILES: *c1c(C#N)cccc1C(F)(F)F] Y-125
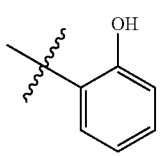 [SMILES: *c1ccccc1O] Y-126
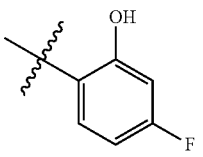 [SMILES: *c1ccc(F)cc1O] Y-127
TABLE 3-continued
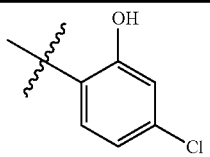 Y-128
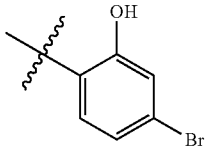 Y-129
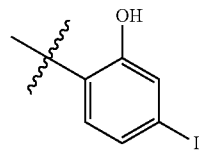 [SMILES: *c1ccc(I)cc1O] Y-130
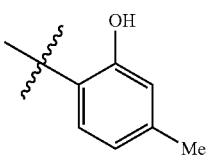 [SMILES: *c1ccc(C)cc1O] Y-131
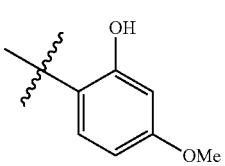 [SMILES: *c1ccc(OC)cc1O] Y-132
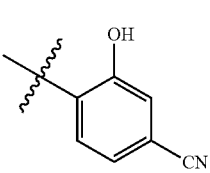 [SMILES: *c1ccc(C#N)cc1O] Y-133
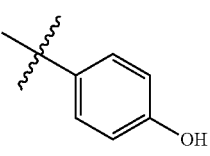 [SMILES: *c1ccc(O)cc1] Y-134
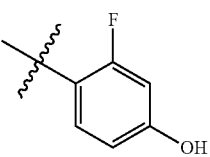 [SMILES: *c1ccc(O)cc1F] Y-135
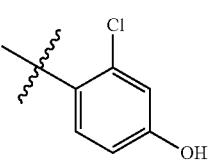 [SMILES: *c1ccc(O)cc1Cl] Y-136
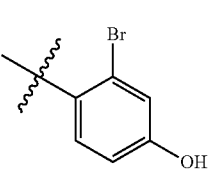 [SMILES: *c1ccc(O)cc1Br] Y-137

TABLE 3-continued
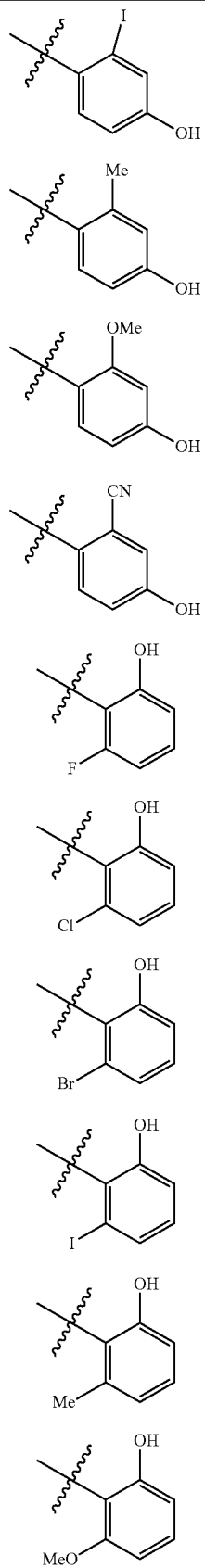
| | |
|---|---|
| | Y-138 |
| | Y-139 |
| | Y-140 |
| | Y-141 |
| | Y-142 |
| | Y-143 |
| | Y-144 |
| | Y-145 |
| | Y-146 |
| | Y-147 |
TABLE 3-continued
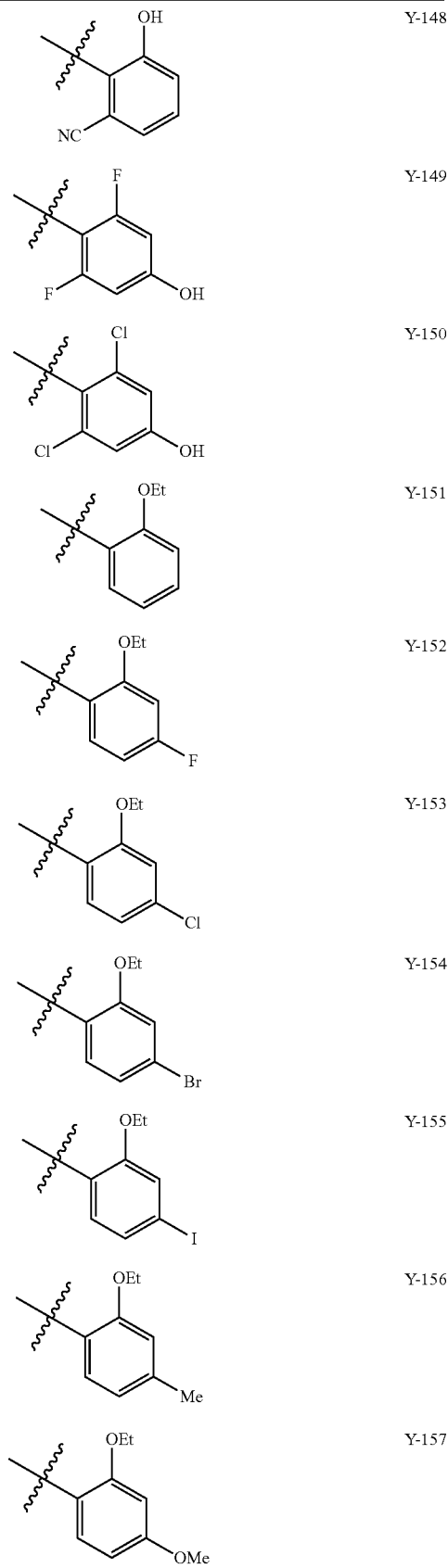
| | |
|---|---|
| | Y-148 |
| | Y-149 |
| | Y-150 |
| | Y-151 |
| | Y-152 |
| | Y-153 |
| | Y-154 |
| | Y-155 |
| | Y-156 |
| | Y-157 |

TABLE 3-continued
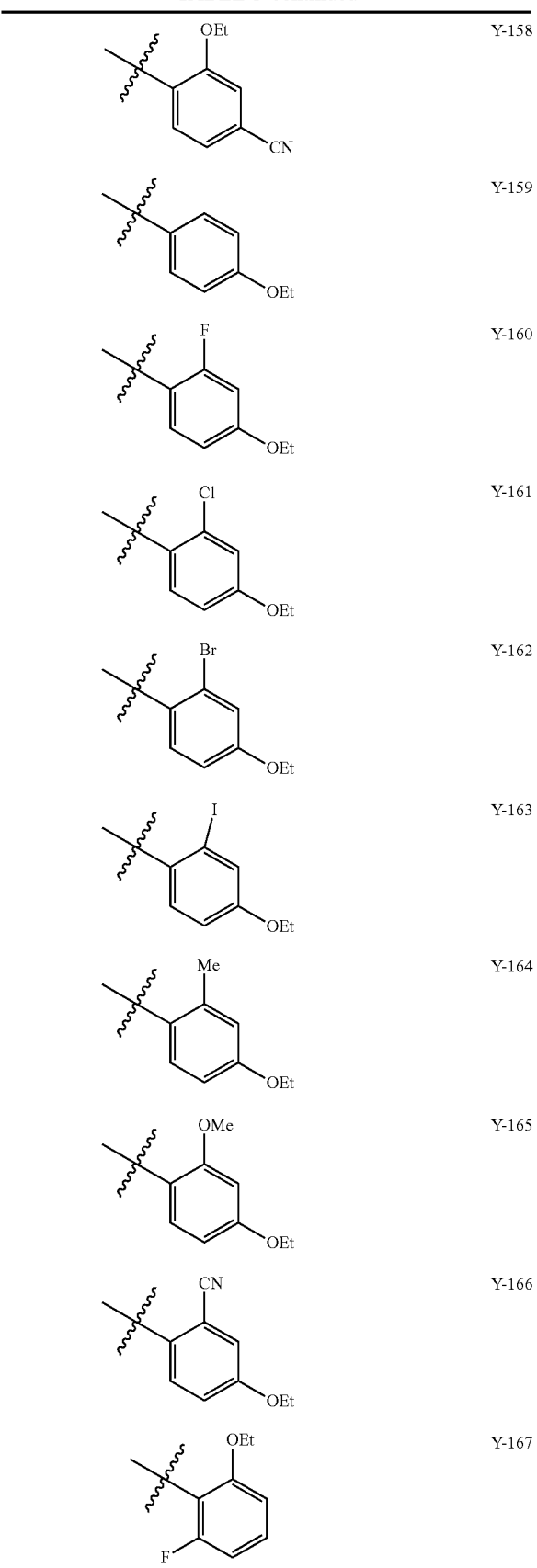
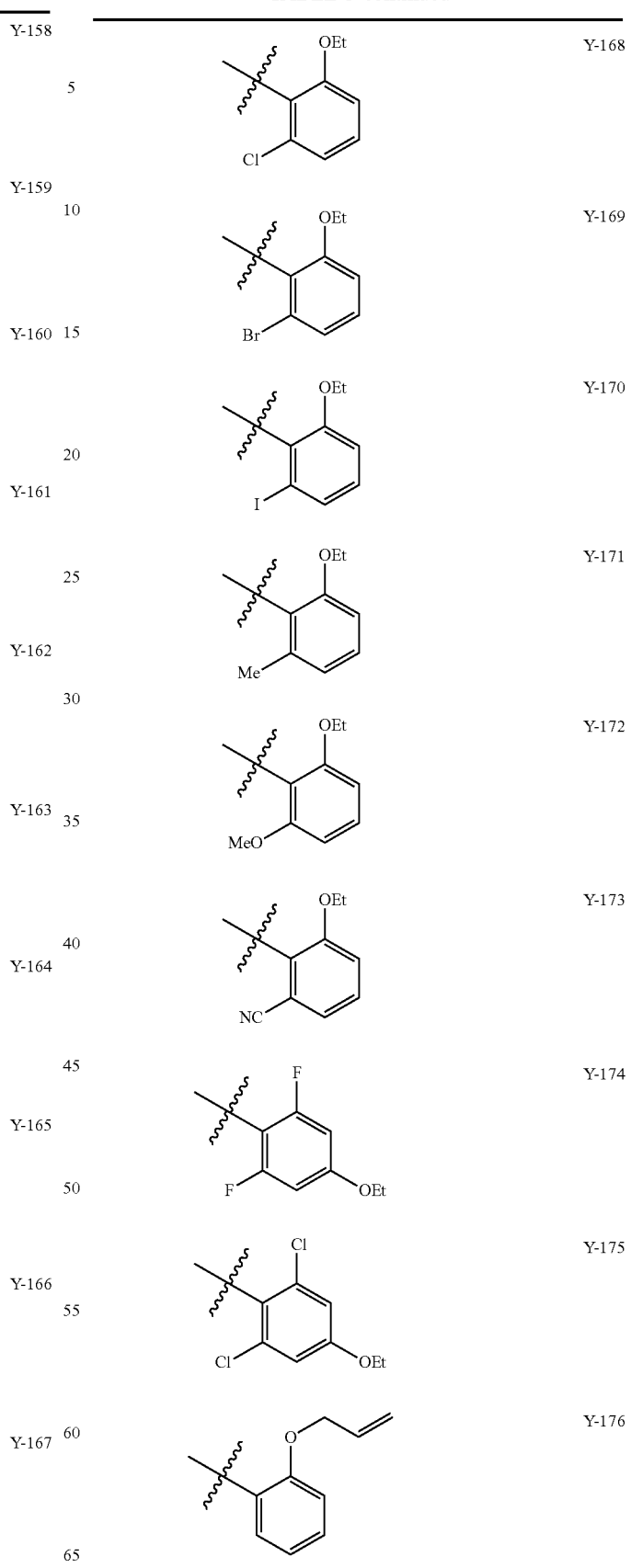

TABLE 3-continued
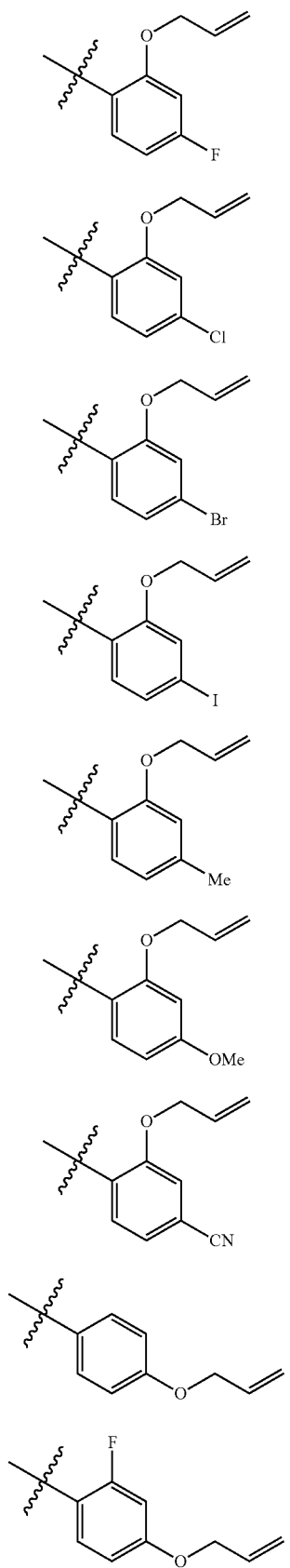
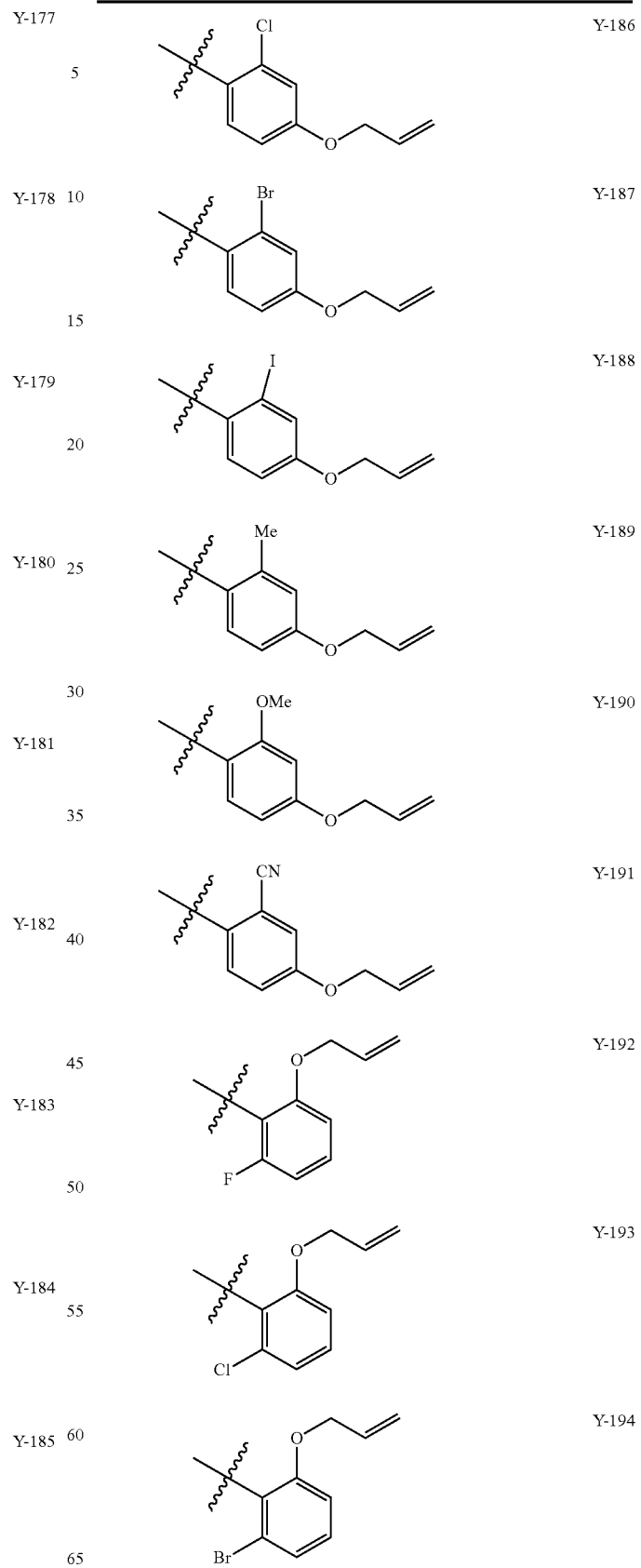

TABLE 3-continued
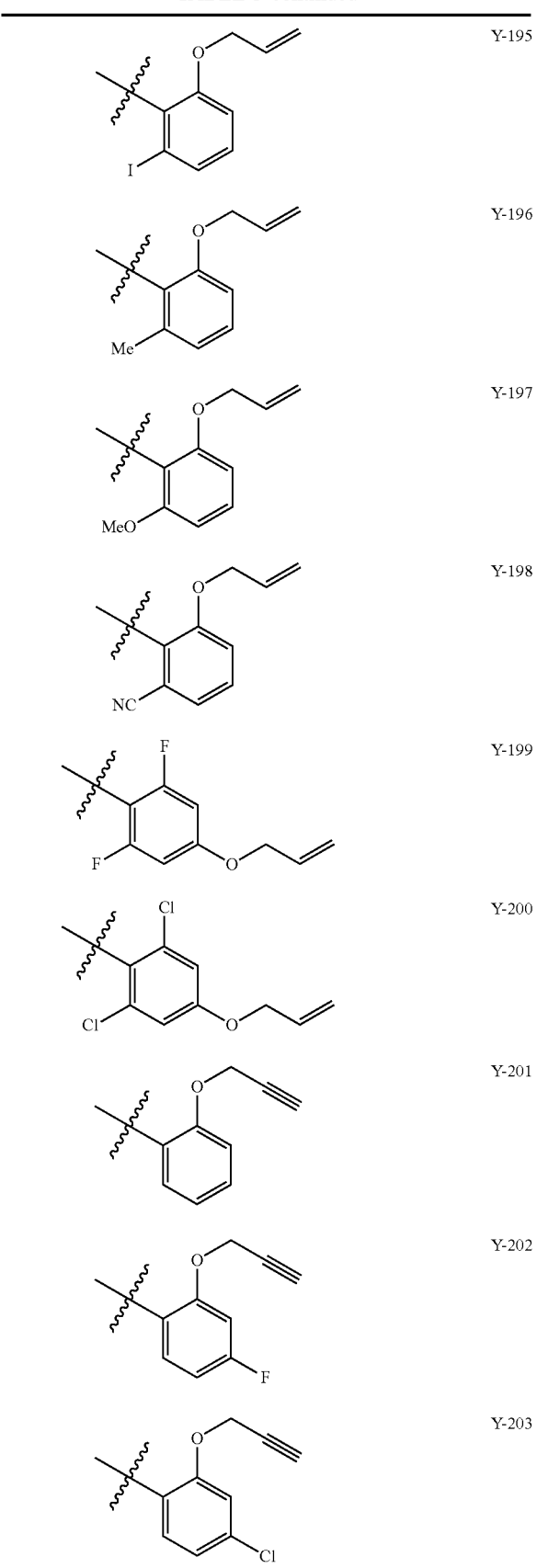
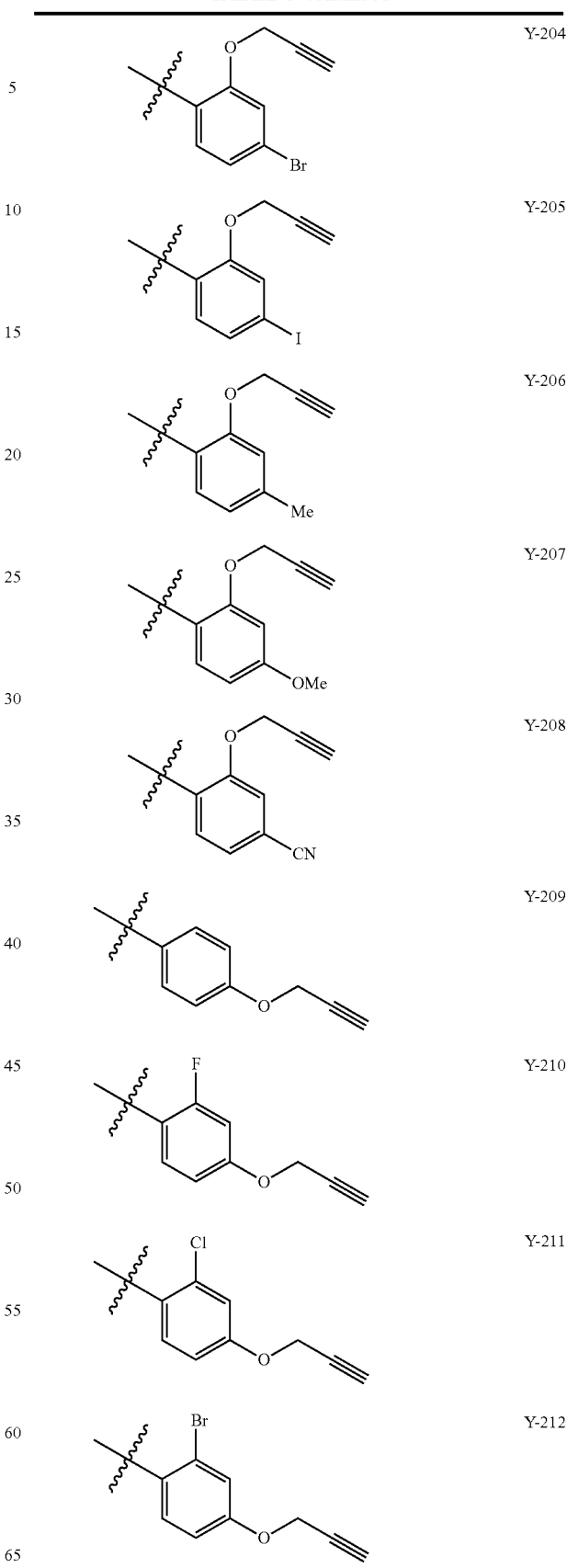

TABLE 3-continued
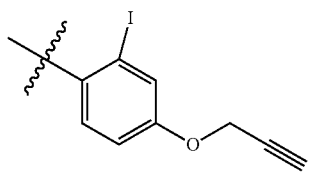 Y-213
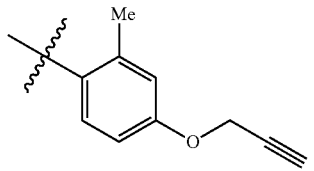 [SMILES: *c1ccc(OCC#C)cc1Br] Y-214
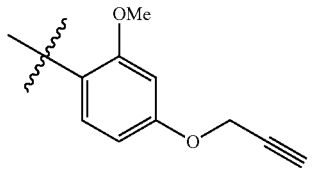 [SMILES: *c1ccc(OCC#C)cc1OC] Y-215
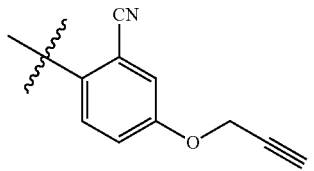 [SMILES: *c1ccc(OCC#C)cc1C#N] Y-216
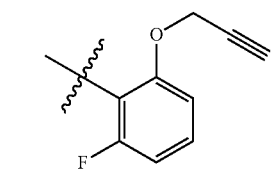 [SMILES: *c1c(F)cccc1OCC#C] Y-217
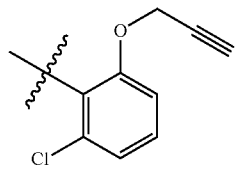 [SMILES: *c1c(Cl)cccc1OCC#C] Y-218
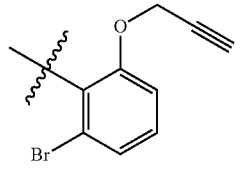 Y-219
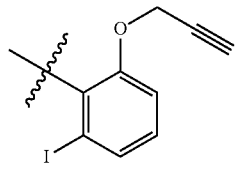 [SMILES: *c1c(I)cccc1OCC#C] Y-220
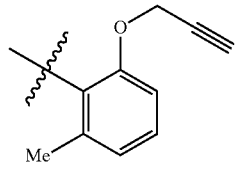 [SMILES: *c1c(C#N)cccc1OCC#C] Y-221
TABLE 3-continued
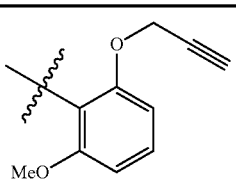 Y-222
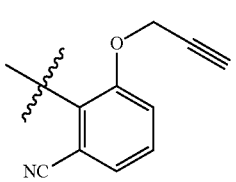 Y-223
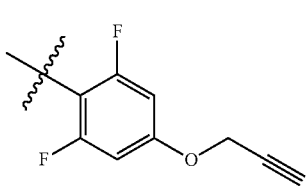 [SMILES: *c1c(F)cc(OCC#C)cc1F] Y-224
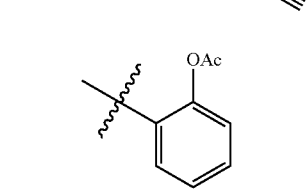 Y-225
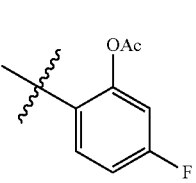 [SMILES: *c1ccc(F)cc1OC(C)=O] Y-226
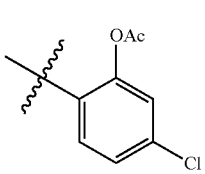 [SMILES: *c1ccc(Cl)cc1OC(C)=O] Y-227
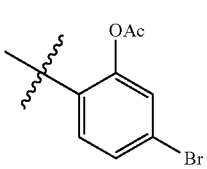 [SMILES: *c1ccc(Br)cc1OC(C)=O] Y-228
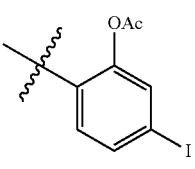 [SMILES: *c1ccc(I)cc1OC(C)=O] Y-229
 Y-230

TABLE 3-continued

| Structure | Label |
|---|---|
| 2-OAc, 4-Me phenyl | Y-231 |
| 2-OAc, 4-OMe phenyl | Y-232 |
| 2-OAc, 4-CN phenyl | Y-233 |
| 4-OAc phenyl | Y-234 |
| 2-F, 4-OAc phenyl | Y-235 |
| 2-Cl, 4-OAc phenyl | Y-236 |
| 2-Br, 4-OAc phenyl | Y-237 |
| 2-I, 4-OAc phenyl | Y-238 |
| 2-Me, 4-OAc phenyl | Y-239 |
| 2-OMe, 4-OAc phenyl | Y-240 |
| 2-CN, 4-OAc phenyl | Y-241 |
| 2-OAc, 3-F phenyl | Y-242 |
| 2-OAc, 3-Cl phenyl | Y-243 |
| 2-OAc, 3-Br phenyl | Y-244 |
| 2-OAc, 3-I phenyl | Y-245 |
| 2-OAc, 3-Me phenyl | Y-246 |
| 2-OAc, 3-OMe phenyl | Y-247 |
| 2-OAc, 3-CN phenyl | Y-248 |
| 2-F, 6-F, 4-OAc phenyl | Y-249 |
| 2-Cl, 6-Cl, 4-OAc phenyl | Y-250 |

TABLE 3-continued
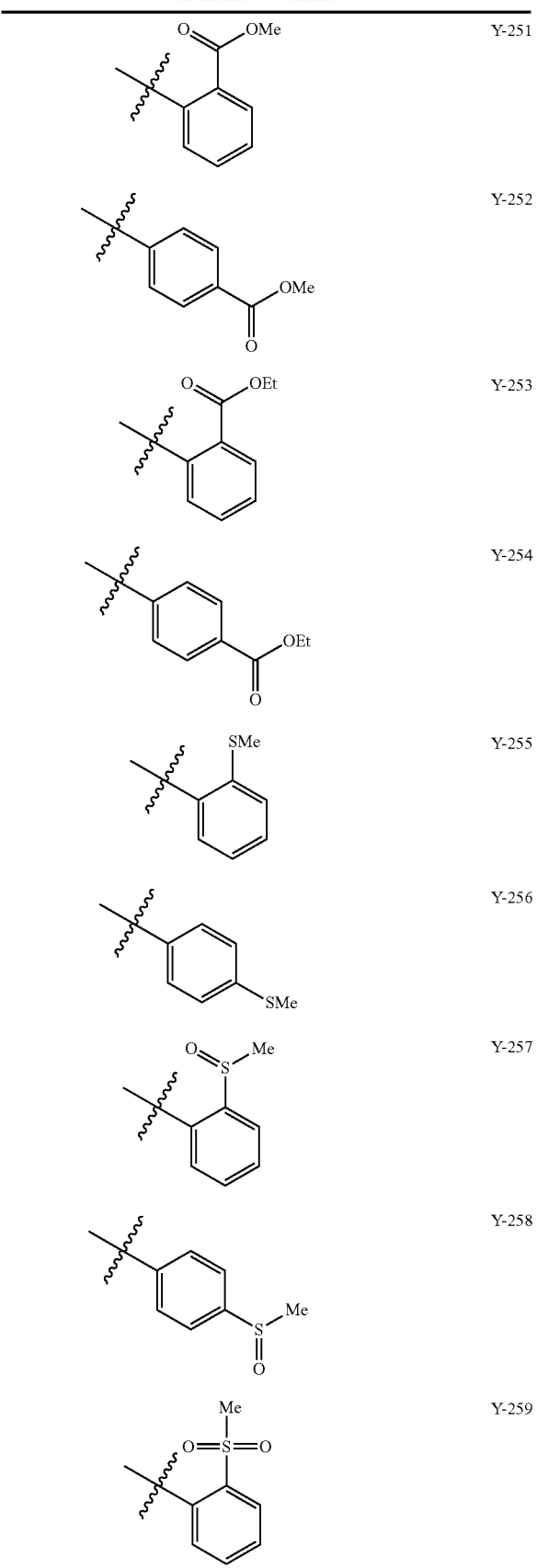
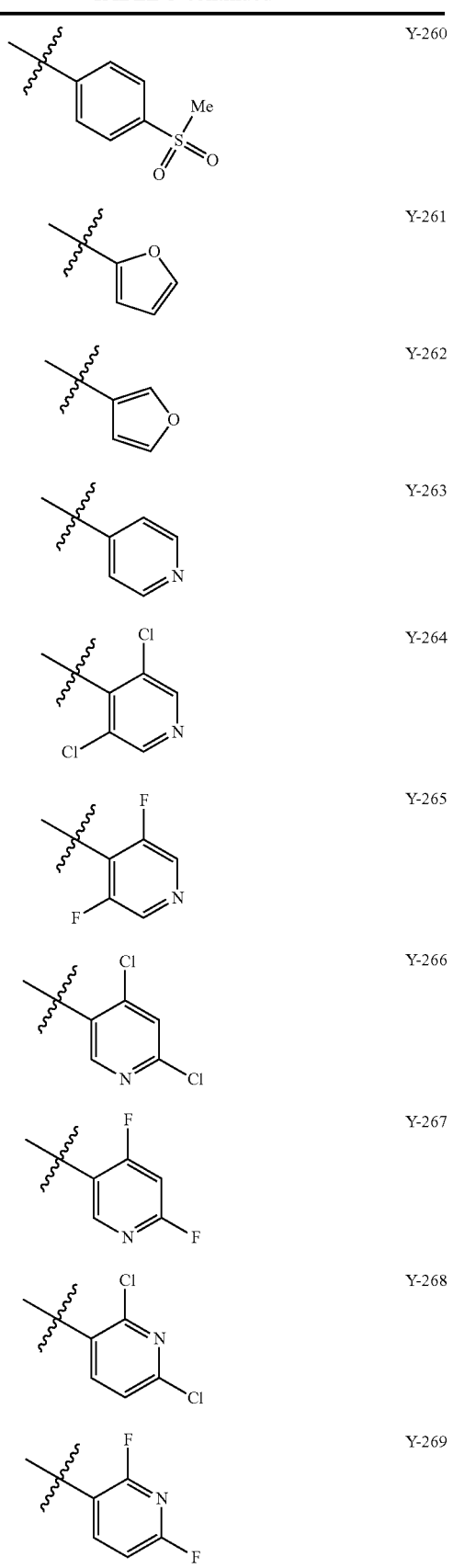

TABLE 3-continued

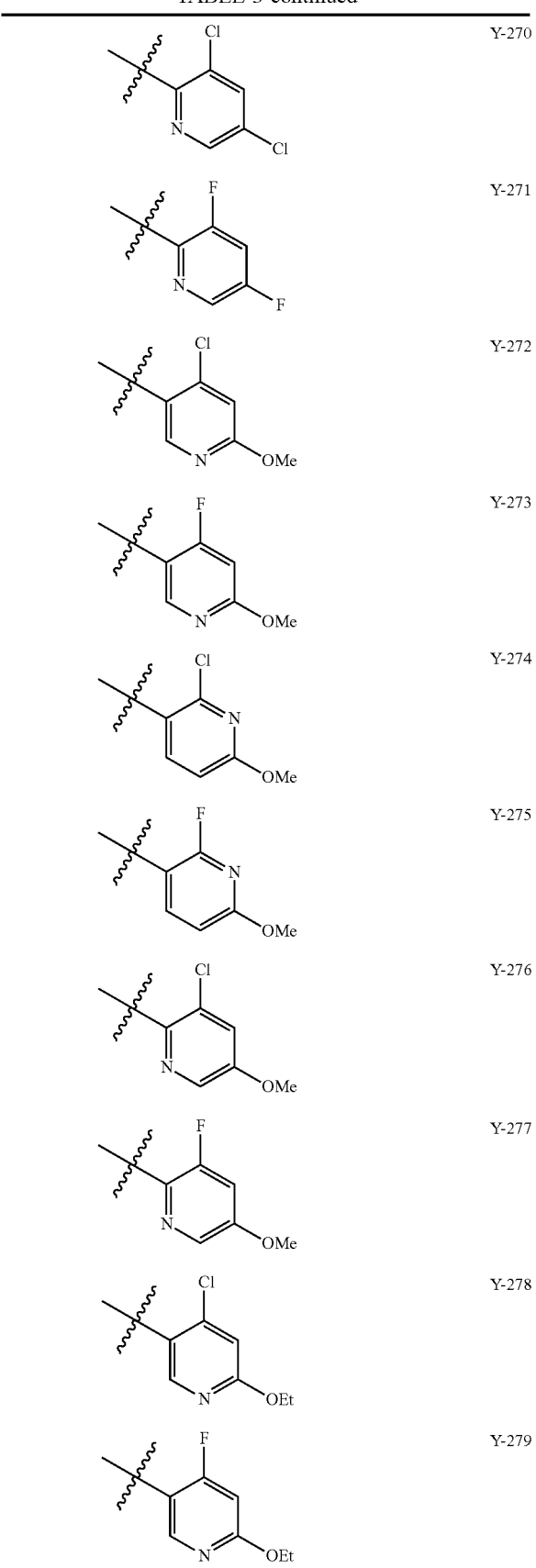

Y-270, Y-271, Y-272, Y-273, Y-274, Y-275, Y-276, Y-277, Y-278, Y-279

TABLE 3-continued

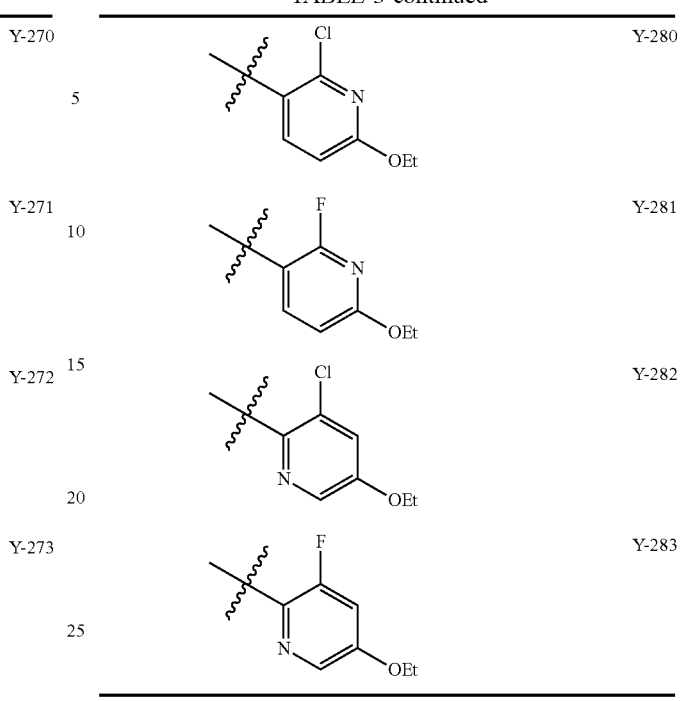

Y-280, Y-281, Y-282, Y-283

Hereinbelow, the method for producing the compound represented by Formula (1) is illustrated. The method for producing the compound of the present invention is not limited to Production Method A to Production Method U.

[Production Method A]

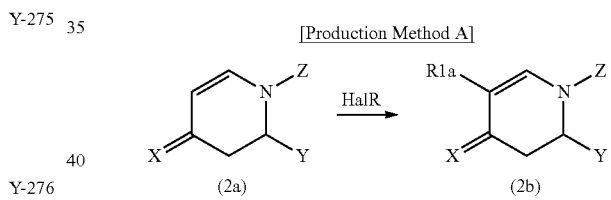

In the formula, R1a represents a halogen atom, HalR represents a halogenating agent, and X, Y and Z are the same as defined above.

Production Method A is a method for obtaining a production intermediate represented by Formula (2b), which comprises reacting a compound represented by Formula (2a) with a halogenating agent (HalR) in a solvent.

The compound represented by Formula (2a) used in this reaction can be obtained with reference to, for example, non-patent documents such as Synthesis, vol. 44, pp. 2181-2184 (2012), Organic Letters, vol. 4, No. 10, pp. 3309-3311 (2002), or Tetrahedron Letters, vol. 40, pp. 7831-7834 (1999), etc., and Reference Examples.

Examples of the halogenating agent used in this reaction include Selectfluor (N-fluoro-N'-triethylenediamine bis(tetrafluoroborate)), N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, bromine, iodine, and the like.

The amount of the halogenating agent used in this reaction is not particularly limited as long as the amount is 1 equivalent or more relative to the compound represented by Formula (2a) and the intended reaction proceeds. The amount is usually 1 equivalent or more and 20 equivalents or less. However, with respect to the halogenating agent comprising a hydantoin compound, the amount of the halogenating agent is not particularly limited as long as the amount is 0.5 equivalent or more and the intended reaction proceeds. The amount is usually 1 equivalent or more and 10 equivalents or less.

When the halogenating agent used in this reaction is an iodinating agent, an acid, for example, an inorganic acid, such as hydrochloric acid and sulfuric acid; or an organic acid, such as acetic acid, trifluoroacetic acid, methanesulfonic acid and trifluoromethanesulfonic acid, can be added.

The amount of the acid used in the case wherein the halogenating agent used in this reaction is an iodinating agent is not particularly limited as long as the amount is 0.01 equivalent or more relative to the compound represented by Formula (2a) and the intended reaction proceeds. The amount is usually 0.1 equivalent or more and 3 equivalents or less.

The solvent used in this reaction is not particularly limited as long as the intended reaction proceeds, and examples of the solvent include acidic solvents, such as sulfuric acid, acetic acid, trifluoroacetic acid, methanesulfonic acid and trifluoromethanesulfonic acid; ether solvents, such as diethyl ether, diisopropyl ether, methyl-t-butyl ether, dimethoxyethane, tetrahydrofuran and dioxane; alcohol solvent, such as methanol, ethanol and isopropanol; benzene-based solvents, such as benzene, toluene, xylene, mesitylene, chlorobenzene and dichlorobenzene; ester solvents, such as ethyl acetate, isopropyl acetate and butyl acetate; nitrile solvents, such as acetonitrile; amide solvents, such as N-methylpyrrolidone, N,N-dimethylformamide and N,N-dimethylacetamide; urea solvents, such as 1,3-dimethyl-2-imidazolidinone; halogen-based solvents, such as dichloromethane, dichloroethane, chloroform and carbon tetrachloride; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (2a).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield.

The reaction mixture obtained above, which contains the compound represented by Formula (2b), may be dehydrated with a drying agent, such as sodium sulfate and magnesium sulfate, but this is not essential.

With respect to the reaction mixture obtained above, which contains the compound represented by Formula (2b), the solvent may be evaporated under reduced pressure as long as the compound is not decomposed.

The reaction mixture obtained after the evaporation of the solvent, which contains the compound represented by Formula (2b), may be purified by washing, reprecipitation, recrystallization, column chromatography or the like using an appropriate solvent. The purification method may be appropriately selected depending on the desired purity.

[Production Method B]

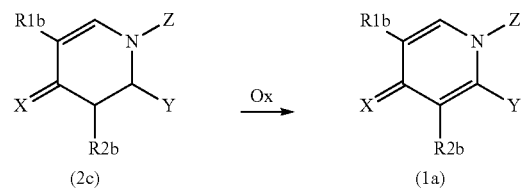

In the formula, Ox represents an oxidizing agent, R1b represents a hydrogen atom, a cyano group, a halogen atom, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, a C1-C6 alkoxy group optionally substituted with substituent A, a C1-C6 haloalkoxy group, a C3-C8 cycloalkoxy group optionally substituted with substituent A, a C2-C6 alkenyloxy group optionally substituted with substituent A, a C2-C6 haloalkenyloxy group, a C3-C6 alkynyloxy group optionally substituted with substituent A, a C3-C6 haloalkynyloxy group, an Rc-L- (wherein Rc and L are the same as defined above) or an RgC(=O)— (wherein Rg is the same as defined above), R2b represents a hydrogen atom, a cyano group, a halogen atom, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, an Rc-L- (wherein Rc and L are the same as defined above) or an RgC(=O)— (wherein Rg is the same as defined above), and X, Y and Z are the same as defined above.

Production Method B is a method for obtaining a compound represented by Formula (1a), which comprises reacting a compound represented by Formula (2c) with an oxidizing agent (Ox) in a solvent.

As the oxidizing agent for this reaction, it is possible to use a metal oxide, such as manganese dioxide; a benzoquinone, such as 2,3-dichloro-5,6-dicyano-p-benzoquinone; a halogen, such as chlorine, bromine and iodine; a hypervalent iodine compound, such as IBX (2-iodoxybenzoic acid) and DMP (1,1,1-triacetoxy-1,1-dihydro-1,2-benziodoxol-3(1H)- one); a peroxy acid, such as potassium peroxodisulfate; a combination of a radical initiator (such as azobisisobutyronitrile and benzoyl peroxide) and a halogenating agent (such as N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin are combined); and the like.

A method in which the oxidizing agent is a metal oxide is explained below. Here, manganese dioxide is described.

The amount of the oxidizing agent used in this reaction is not particularly limited as long as the amount is 1 equivalent or more relative to the compound represented by Formula (2c) and the intended reaction proceeds. The amount is usually 1 equivalent or more and 200 equivalents or less.

The solvent used in this reaction is not particularly limited as long as the intended reaction proceeds, and examples of the solvent include benzene-based solvents, such as benzene, toluene, xylene, mesitylene, chlorobenzene and dichlorobenzene; halogen-based solvents, such as dichloromethane, dichloroethane, chloroform and carbon tetrachloride; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (2c).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to remove an undissolved metal by filtration. Further, it is also possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield. In this reaction, the liquid separating operation is not essential.

The reaction mixture obtained above, which contains the compound represented by Formula (2b), may be dehydrated with a drying agent, such as sodium sulfate and magnesium sulfate, but this is not essential.

With respect to the reaction mixture obtained above, which contains the compound represented by Formula (2b), the solvent may be evaporated under reduced pressure as long as the compound is not decomposed.

The reaction mixture obtained after the evaporation of the solvent, which contains the compound represented by Formula (2b), may be purified by washing, reprecipitation, recrystallization, column chromatography or the like using an appropriate solvent. The purification method may be appropriately selected depending on the desired purity.

A method in which the oxidizing agent is a benzoquinone is explained below.

The amount of the oxidizing agent used in this reaction is not particularly limited as long as the amount is 1 equivalent or more relative to the compound represented by Formula (2c) and the intended reaction proceeds. The amount is usually 1 equivalent or more and 20 equivalents or less.

The solvent used in this reaction is not particularly limited as long as the intended reaction proceeds, and examples of the solvent include benzene-based solvents, such as benzene, toluene, xylene, mesitylene, chlorobenzene and dichlorobenzene; halogen-based solvents, such as dichloromethane, dichloroethane, chloroform and carbon tetrachloride; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (2c).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield. In this reaction, the liquid separating operation is not essential.

The reaction mixture obtained above, which contains the compound represented by Formula (1a), may be dehydrated with a drying agent, such as sodium sulfate and magnesium sulfate, but this is not essential.

With respect to the reaction mixture obtained above, which contains the compound represented by Formula (1a), the solvent may be evaporated under reduced pressure as long as the compound is not decomposed.

The reaction mixture obtained after the evaporation of the solvent, which contains the compound represented by Formula (1a), may be purified by washing, reprecipitation, recrystallization, column chromatography or the like using an appropriate solvent. The purification method may be appropriately selected depending on the desired purity.

A method in which the oxidizing agent is a halogen is explained below.

The amount of the oxidizing agent used in this reaction is not particularly limited as long as the amount is 1 equivalent or more relative to the compound represented by Formula (2c) and the intended reaction proceeds. The amount is usually 1 equivalent or more and 20 equivalents or less.

The solvent used in this reaction is not particularly limited as long as the intended reaction proceeds, and examples of the solvent include acidic solvents, such as acetic acid; benzene-based solvents, such as benzene, toluene, xylene, mesitylene, chlorobenzene and dichlorobenzene; halogen-based solvents, such as dichloromethane, dichloroethane, chloroform and carbon tetrachloride; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (2c).

The temperature for carrying out this reaction is not particularly limited as long as the intended reaction proceeds, and is usually −10° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield. In this reaction, the liquid separating operation is not essential.

The reaction mixture obtained above, which contains the compound represented by Formula (1a), may be dehydrated with a drying agent, such as sodium sulfate and magnesium sulfate, but this is not essential.

With respect to the reaction mixture obtained above, which contains the compound represented by Formula (1a), the solvent may be evaporated under reduced pressure as long as the compound is not decomposed.

The reaction mixture obtained after the evaporation of the solvent, which contains the compound represented by Formula (1a), may be purified by washing, reprecipitation, recrystallization, column chromatography or the like using an appropriate solvent. The purification method may be appropriately selected depending on the desired purity.

A method in which the oxidizing agent is a hypervalent iodine compound is explained below, and IBX is herein described.

The amount of the oxidizing agent used in this reaction is not particularly limited as long as the amount is 1 equivalent or more relative to the compound represented by Formula (2c) and the intended reaction proceeds. The amount is usually 1 equivalent or more and 20 equivalents or less.

The solvent used in this reaction is not particularly limited as long as the intended reaction proceeds, and examples of the solvent include ester solvents, such as ethyl acetate, isopropyl acetate and butyl acetate; sulfur-based solvents, such as dimethylsulfoxide and sulfolane; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (2c).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield. In this reaction, the liquid separating operation is not essential.

The reaction mixture obtained above, which contains the compound represented by Formula (1a), may be dehydrated with a drying agent, such as sodium sulfate and magnesium sulfate, but this is not essential.

With respect to the reaction mixture obtained above, which contains the compound represented by Formula (1a), the solvent may be evaporated under reduced pressure as long as the compound is not decomposed.

The reaction mixture obtained after the evaporation of the solvent, which contains the compound represented by Formula (1a), may be purified by washing, reprecipitation, recrystallization, column chromatography or the like using an appropriate solvent. The purification method may be appropriately selected depending on the desired purity.

A method in which the oxidizing agent is a peroxy acid is explained below. Here, potassium peroxodisulfate is described.

The amount of potassium peroxodisulfate used in this reaction is not particularly limited as long as the amount is 1 equivalent or more relative to the compound represented by Formula (2c) and the intended reaction proceeds. The amount is usually 1 equivalent or more and 10 equivalents or less.

When this reaction is to be carried out, it is necessary to add an acid, such as hydrochloric acid and sulfuric acid. In this case, the amount of the acid is not particularly limited as long as, when the acid is a monobasic acid, the amount is 2 equivalents or more (when the acid is a dibasic acid, 1 equivalent or more) relative to potassium peroxodisulfate and the intended reaction proceeds.

The solvent used in this reaction is not particularly limited as long as the intended reaction proceeds, and examples of the solvent include alcohol solvent, such as methanol, ethanol and isopropanol; nitrile solvent, such as acetonitrile; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (2c).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield.

The reaction mixture obtained above, which contains the compound represented by Formula (1a), may be dehydrated with a drying agent, such as sodium sulfate and magnesium sulfate, but this is not essential.

With respect to the reaction mixture obtained above, which contains the compound represented by Formula (1a), the solvent may be evaporated under reduced pressure as long as the compound is not decomposed.

The reaction mixture obtained after the evaporation of the solvent, which contains the compound represented by Formula (1a), may be purified by washing, reprecipitation, recrystallization, column chromatography or the like using an appropriate solvent. The purification method may be appropriately selected depending on the desired purity.

A method in which the oxidizing agent is a combination of a radical initiator and a halogenating agent is explained below.

The amounts of the radical initiator and halogenating agent used in this reaction are not particularly limited as long as the amount of the former is 0.01 equivalent or more and the amount of the latter is 1 equivalent or more, respectively, relative to the compound represented by Formula (2c), and the intended reaction proceeds. The amount of the radical initiator is usually 0.01 equivalent or more and 1 equivalents or less, and the amount the halogenating agent is usually 1 equivalent or more and 3 equivalents or less.

The solvent used in this reaction is not particularly limited as long as the intended reaction proceeds, and examples of the solvent include halogenated benzene-based solvents, such as chlorobenzene and dichlorobenzene; ester solvents, such as ethyl acetate, isopropyl acetate and butyl acetate; halogen-based solvents, such as dichloromethane, dichloroethane, chloroform and carbon tetrachloride; hydrocarbon solvents, such as hexane, heptane, cyclohexane and methylcyclohexane; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (2c).

The temperature for carrying out this reaction is not particularly limited as long as the intended reaction proceeds, and is usually 20° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane and chloroform; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield.

The reaction mixture obtained above, which contains the compound represented by Formula (1a), may be dehydrated with a drying agent, such as sodium sulfate and magnesium sulfate, but this is not essential.

With respect to the reaction mixture obtained above, which contains the compound represented by Formula (1a), the solvent may be evaporated under reduced pressure as long as the compound is not decomposed.

The reaction mixture obtained after the evaporation of the solvent, which contains the compound represented by Formula (1a), may be purified by washing, reprecipitation, recrystallization, column chromatography or the like using an appropriate solvent. The purification method may be appropriately selected depending on the desired purity.

[Production Method C]

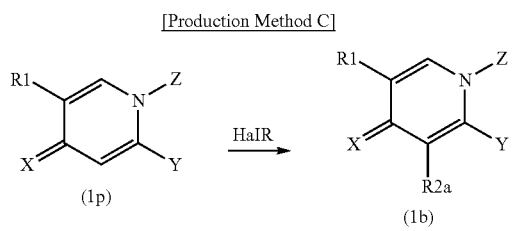

In the formula, R2a represents a halogen atom, HalR represents a halogenating agent, and R1, X, Y and Z are the same as defined above.

Production Method C is a method for obtaining a compound represented by Formula (1b), which comprises reacting a compound represented by Formula (1p) with a halogenating agent (HalR) in a solvent.

Production Method C can be carried out in substantially the same manner as in Production Method A, except that the compound represented by Formula (1p) is used in place of the compound represented by Formula (2a) in Production Method A.

[Production Method D]

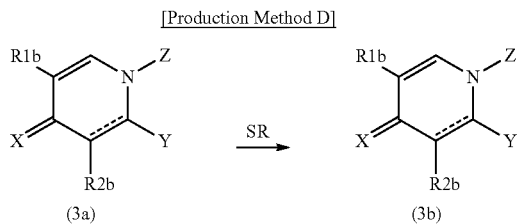

In the formula, SR represents a sulfurizing agent, a bond with a broken line portion represents a single bond or double bond, and R1b, R2b, Y and Z are the same as defined above.

Here, the bond with a broken line portion represents the portion represented by: ----

Production Method D is a method for obtaining a compound represented by Formula (3b) containing a sulfur atom, which comprises reacting a compound represented by Formula (3a) with a sulfurizing agent (SR) in a solvent.

Examples of the sulfurizing agent used in this reaction include Lawesson's reagent (2,4-bis(4-methoxyphenyl)-1,3-dithia-2,4-diphosphetane-2,4-disulfide) and the like.

The amount of the sulfurizing agent used in this reaction is not particularly limited as long as the amount is 0.5 equivalent or more relative to the compound represented by Formula (3a) and the intended reaction proceeds. The amount is usually 1 equivalent or more and 10 equivalents or less.

The solvent used in this reaction is not particularly limited as long as the intended reaction proceeds, and examples of the solvent include ether solvents, such as diethyl ether, diisopropyl ether, methyl-t-butyl ether, dimethoxyethane, tetrahydrofuran and dioxane; benzene-based solvents, such as benzene, toluene, xylene, mesitylene, chlorobenzene and dichlorobenzene; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (3a).

The temperature for carrying out this reaction is not particularly limited as long as the intended reaction proceeds, and is usually 50° C. or higher and 180° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield. In this reaction, the liquid separating operation is not essential.

The reaction mixture obtained above, which contains the compound represented by Formula (3b), may be dehydrated with a drying agent, such as sodium sulfate and magnesium sulfate, but this is not essential.

With respect to the reaction mixture obtained above, which contains the compound represented by Formula (3b), the solvent may be evaporated under reduced pressure as long as the compound is not decomposed.

The reaction mixture obtained after the evaporation of the solvent, which contains the compound represented by Formula (3b), may be purified by washing, reprecipitation, recrystallization, column chromatography or the like using an appropriate solvent. The purification method may be appropriately selected depending on the desired purity.

[Production Method E]

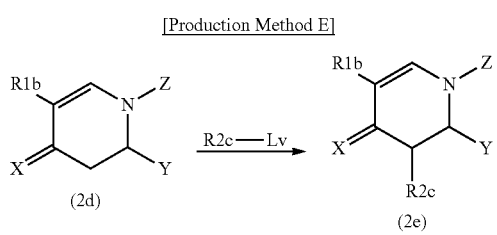

In the formula, R2c represents a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, an Rc-L- (wherein Rc and L are the same as defined above) or an RgC(=O)— (wherein Rg is the same as defined above), Lv represents a leaving group such as a methanesulfonyl group, a trifluoromethanesulfonyl group, a p-toluenesulfonyl group or a halogen atom, and R1b, X, Y and Z are the same as defined above.

Production Method E is a method for obtaining a production intermediate represented by Formula (2e) in which R2c is a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, an Rc-L- (wherein Rc and L are the same as defined above) or an RgC(=O)— (wherein Rg is the same as defined above), which method comprises reacting a compound represented by Formula (2d) with R2c-Lv in a solvent in the presence of a base.

The R2c-Lv used in this reaction is commercially available or can be produced by a conventionally known method.

The amount of R2c-Lv used in this reaction is not particularly limited as long as the amount is 1 equivalent or more relative to the compound represented by Formula (2d) and the intended reaction proceeds. The amount is usually 1 equivalent or more and 50 equivalents or less.

Examples of the base used in this reaction include a metal hydride, such as sodium hydride: an organolithium, such as methyllithium, butyllithium, sec-butyllithium, t-butyllithium and hexyllithium; and a metal amide, such as lithium diisopropylamide, hexamethyldisilazane lithium, hexamethyldisilazane sodium and hexamethyldisilazane potassium.

The amount of the base used in this reaction is not particularly limited as long as the amount is 1 equivalent or more relative to the compound represented by Formula (2d) and the intended reaction proceeds. The amount is usually 1 equivalent or more and 20 equivalents or less.

In order to smoothly proceed with the reaction, it is possible to add an additive such as HMPA (hexamethylphosphoric triamide), DMPU (N,N'-dimethylurea) and TMEDA (tetramethylethylenediamine), but this is not essential.

When the additive is used in this reaction, the amount of the additive is 1 equivalent or more and 100 equivalents or less, relative to the compound represented by Formula (2d).

The solvent used in this reaction is not particularly limited as long as the intended reaction proceeds, and examples of the solvent include ether solvents, such as diethyl ether, diisopropyl ether, methyl-t-butyl ether, dimethoxyethane, tetrahydrofuran and dioxane; benzene-based solvents, such as benzene, toluene, xylene, mesitylene, chlorobenzene and dichlorobenzene; hydrocarbon solvents, such as hexane, heptane, cyclohexane and methylcyclohexane; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (2d).

The temperature for carrying out this reaction is not particularly limited as long as the intended reaction proceeds, and is usually −80° C. or higher and 100° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane and chloroform; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield.

The reaction mixture obtained above, which contains the compound represented by Formula (2e), may be dehydrated with a drying agent, such as sodium sulfate and magnesium sulfate, but this is not essential.

With respect to the reaction mixture obtained above, which contains the compound represented by Formula (2e), the solvent may be evaporated under reduced pressure as long as the compound is not decomposed.

The reaction mixture obtained after the evaporation of the solvent, which contains the compound represented by Formula (2e), may be purified by washing, reprecipitation, recrystallization, column chromatography or the like using an appropriate solvent. The purification method may be appropriately selected depending on the desired purity.

[Production Method F]

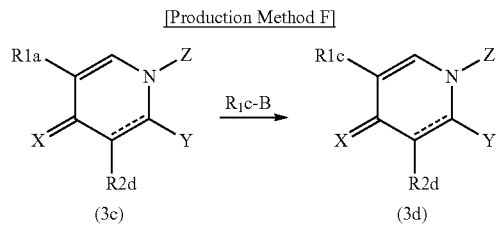

In the formula, R1c represents a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A or a C2-C6 haloalkenyl group, R1c-B represents an organic boronic acid derivative, R2d represents a hydrogen atom, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, an Rc-L- (wherein Rc and L are the same as defined above) or an RgC(=O)— (wherein Rg is the same as defined above), and R1a, X, Y, Z and the broken line portion are the same as defined above.

Production Method F is a method for obtaining a compound represented by Formula (3d) wherein R1c is a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A or a C2-C6 haloalkenyl group, which comprises obtaining it by Suzuki-Miyaura coupling in which a compound represented by Formula (3c) is reacted with an organic boronic acid derivative (R1c-B) in a solvent in the presence of a transition metal and a base.

In the compound represented by Formula (3c), preferred R1a is a chlorine atom, a bromine atom, an iodine atom, and the like.

The R1c-B used in this reaction represents an organic boronic acid derivative, such as an organic boronic acid and organic boronic acid ester, and is commercially available or can be produced by a conventionally known method.

The amount of the R1c-B used in this reaction is not particularly limited as long as the amount is 1 equivalent or more relative to the compound represented by Formula (3c) and the intended reaction proceeds. The amount is usually 1 equivalent or more and 10 equivalents or less.

Examples of the transition metal used in this reaction, which may have a ligand, include palladium, nickel and ruthenium, and the like. As preferred examples, there can be mentioned palladium compounds, such as palladium acetate, [1,1'-bis(diphenylphosphino)ferrocene]palladium dichloride, tris(dibenzylideneacetone)dipalladium, tetrakis(triphenylphosphine)palladium, bis(triphenylphosphine)palladium dichloride and the like.

The amount of the transition metal used in this reaction is usually 0.001 equivalent or more and 1 equivalent or less relative to the compound represented by Formula (3c), and not particularly limited as long as the intended reaction proceeds.

In order to efficiently proceed with this reaction, it is possible to add a phosphine ligand, such as triphenylphosphine and tricyclohexylphosphine.

The amount of the phosphine ligand used in this reaction is usually 0.001 equivalent or more and 1 equivalent or less relative to the compound represented by Formula (3c) and not particularly limited as long as the intended reaction proceeds.

Examples of the base used in this reaction include an inorganic base, such as sodium carbonate, potassium carbonate, cesium carbonate and tripotassium phosphate; and a metal alkoxide, such as sodium methoxide, sodium ethoxide and potassium t-butoxide.

The amount of the base used in this reaction is not particularly limited as long as the amount is 1 equivalent or more relative to the compound represented by Formula (3c) and the intended reaction proceeds. The amount is usually 1 equivalent or more and 50 equivalents or less.

The solvent used in this reaction is not particularly limited as long as the intended reaction proceeds, and examples of the solvent include water solvent, ether solvents, such as diethyl ether, diisopropyl ether, methyl-t-butyl ether, dimethoxyethane, tetrahydrofuran and dioxane; benzene-based solvents, such as benzene, toluene, xylene, mesitylene, chlorobenzene and dichlorobenzene; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (3c).

The temperature for carrying out this reaction is not particularly limited as long as the intended reaction proceeds, and is usually 30° C. or higher and 200° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield. It is also possible to remove insoluble materials by carrying out filtration operation, but this is not essential.

With respect to the reaction mixture obtained above, which contains the compound represented by Formula (3d), the solvent may be evaporated under reduced pressure as long as the compound is not decomposed.

The reaction mixture obtained after the evaporation of the solvent, which contains the compound represented by Formula (3d), may be purified by washing, reprecipitation, recrystallization, column chromatography or the like using an appropriate solvent. The purification method may be appropriately selected depending on the desired purity.

[Production Method G]

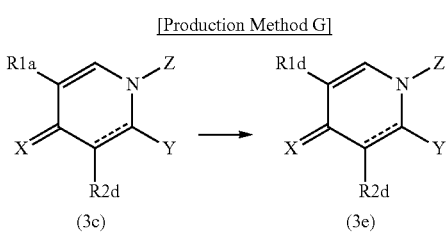

(3c) → (3e)

In the formula, R1d represents a C2-C6 alkynyl group optionally substituted with substituent A or a C2-C6 haloalkynyl group, and R1a, R2d, X, Y, Z and the broken line portion are the same as defined above.

Production Method G is a method for obtaining a compound represented by Formula (3e) wherein R1d is a C2-C6 alkynyl group optionally substituted with substituent A or a C2-C6 haloalkynyl group, which comprises obtaining it by Sonogashira coupling in which a compound represented by Formula (3c) is reacted with a terminal-alkyne compound in a solvent in the presence of a transition metal and a base.

In Formula (3c), preferred R1a is a chlorine atom, a bromine atom, an iodine atom, and the like.

The terminal-alkyne compound used in this reaction is commercially available or can be produced by a conventionally known method. As the terminal-alkyne compound, trimethylsilylacetylene may also be used. In this case, after introducing trimethylsilylethynyl group into the compound represented by Formula (3c), it is necessary to conduct desilylation. The desilylation may be carried out with reference to non-patent documents, such as Journal of the American Chemical Society, vol. 131, No. 2, pp. 634-643 (2009) and Journal of Organometallic Chemistry, vol. 696, No. 25, pp. 4039-4045 (2011).

The amount of the terminal-alkyne compound used in this reaction is not particularly limited as long as the amount is 1 equivalent or more relative to the compound represented by Formula (3c) and the intended reaction proceeds. The amount is usually 1 equivalent or more and 10 equivalents or less.

Examples of the transition metal used in this reaction, which may have a ligand, include, for example, a palladium compound, such as palladium acetate, [1,1'-bis(diphenylphosphino)ferrocene]palladium dichloride, tris(dibenzylideneacetone)dipalladium, tetrakis(triphenylphosphine)palladium and bis(triphenylphosphine)palladium dichloride. In addition, a copper compound, such as copper chloride, copper bromide and copper iodide, is simultaneously used.

The amount of each of the transition metals used in this reaction is not particularly limited as long as, with respect to each of the palladium compounds and copper compounds, usually, the amount is 0.001 equivalent or more relative to the compound represented by Formula (3c) and the intended reaction proceeds. The amount of each of these compounds is preferably 0.001 equivalent or more and 1 equivalent or less.

Examples of the base used in this reaction include organic amines, such as triethylamine, tributylamine, isopropylamine, diethylamine, diisopropylamine and diisopropylethylamine; inorganic bases, such as sodium carbonate, potassium carbonate and cesium carbonate; and the like.

The amount of the halogenating agent used in this reaction is not particularly limited as long as the amount is 1 equivalent or more relative to the compound represented by Formula (3c) and the intended reaction proceeds. The amount is usually 1 equivalent or more and 50 equivalents or less. An organic base in a liquid state can be used as a solvent.

In order to efficiently proceed with this reaction, it is possible to add a phosphine ligand, such as tri-t-butylphosphine and 2-dicyclohexylphosphino-2'4'6'-triisopropylbiphenyl, but this is not essential.

The amount of the phosphine ligand used in this reaction is usually 0.001 equivalent or more and 1 equivalent or less relative to the compound represented by Formula (3c) and not particularly limited as long as the intended reaction proceeds.

The solvent used in this reaction is not particularly limited as long as the intended reaction proceeds, and examples of the solvent include ether solvents, such as diethyl ether, diisopropyl ether, methyl-t-butyl ether, dimethoxyethane, tetrahydrofuran and dioxane; benzene-based solvents, such as benzene, toluene, xylene, mesitylene, chlorobenzene and dichlorobenzene; ester solvents, such as ethyl acetate, isopropyl acetate and butyl acetate; nitrile solvents, such as acetonitrile; amide solvents, such as N-methylpyrrolidone, N,N-dimethylformamide and N,N-dimethylacetamide; urea solvents, such as 1,3-dimethyl-2-imidazolidinone; halogen-based solvents, such as dichloromethane, dichloroethane, chloroform and carbon tetrachloride; organic amine solvents, such as triethylamine, tributylamine, isopropylamine, diethylamine, diisopropylamine and diisopropylethylamine; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (3c).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield. It is also possible to remove insoluble materials by carrying out filtration operation, but this is not essential.

With respect to the reaction mixture obtained above, which contains the compound represented by Formula (3e), the solvent may be evaporated under reduced pressure as long as the compound is not decomposed.

The reaction mixture obtained after the evaporation of the solvent, which contains the compound represented by Formula (3e), may be purified by washing, reprecipitation, recrystallization, column chromatography or the like using an appropriate solvent. The purification method may be appropriately selected depending on the desired purity.

[Production Method H]

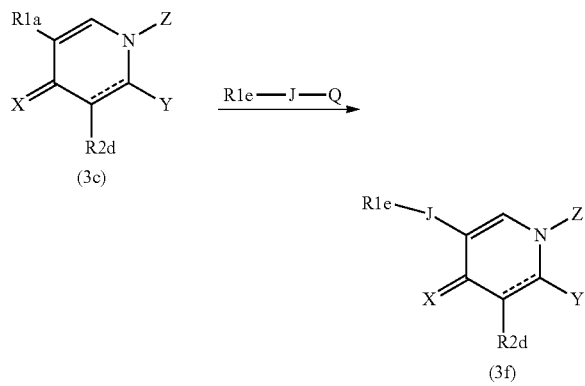

In the formula, J represents an oxygen atom or a sulfur atom, when J is an oxygen atom, R1e represents a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A or a C2-C6 haloalkynyl group, when J is a sulfur atom, R1e represents a C1-C6 alkyl group or a C1-C6 haloalkyl group, Q represents a hydrogen atom or a metal, and R1a, R2d, X, Y, Z and the broken line portion are the same as defined above.

Production Method H is a method for obtaining a compound represented by Formula (3f) wherein J represents an oxygen atom or a sulfur atom, when J is an oxygen atom, R1e represents a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A or a C2-C6 haloalkynyl group, when J is a sulfur atom, R1e represents a C1-C6 alkyl group or a C1-C6 haloalkyl group, which comprises obtaining it a coupling reaction in which a compound represented by Formula (3c) is reacted with R1e-J-Q in a solvent in the presence of a transition metal and a base.

In the compound represented by Formula (3c), preferred R1a is a chlorine atom, a bromine atom and an iodine atom.

The R1e-J-Q compound used in this reaction is commercially available or can be produced by a conventionally known method. Preferred Q is a hydrogen atom or an alkali metal, such as sodium, potassium and the like.

The amount of the R1e-J-Q used in this reaction is not particularly limited as long as the amount is 1 equivalent or more relative to the compound represented by Formula (3c) and the intended reaction proceeds. The R1e-J-Q can be used also as a solvent when Q is a hydrogen atom.

Examples of the transition metal used in this reaction, which may have a ligand, include, for example, a palladium compound, such as palladium acetate, [1,1'-bis(diphenylphosphino)ferrocene]palladium dichloride, tris(dibenzylideneacetone)dipalladium, tetrakis(triphenylphosphine)palladium and bis(triphenylphosphine)palladium dichloride.

The amount of the transition metal used in this reaction is usually 0.001 equivalent or more and 1 equivalent or less relative to the compound represented by Formula (3c) and not particularly limited as long as the intended reaction proceeds.

In order to efficiently proceed with this reaction, it is possible to add a phosphine ligand, such as triphenylphosphine, 1,1'-bis(diphenylphosphino)ferrocene, 2-dicyclohexylphosphino-2'4'6'-triisopropylbiphenyl and 2-di-t-butylphosphino-2'4'6'-triisopropylbiphenyl.

The amount of the phosphine ligand used in this reaction is usually 0.001 equivalent or more and 1 equivalent or less relative to the compound represented by Formula (3c) and not particularly limited as long as the intended reaction proceeds.

Examples of the base used in this reaction include an inorganic base, such as sodium carbonate, potassium carbonate and cesium carbonate; and an organic base, such as triethylamine, tributylamine and diisopropylethylamine.

The amount of the base used in this reaction is not particularly limited as long as the amount is 1 equivalent or more relative to the compound represented by Formula (3c) and the intended reaction proceeds. The amount is usually 1 equivalent or more and 50 equivalents or less.

The solvent used in this reaction is not particularly limited as long as the intended reaction proceeds, and examples of the solvent include the alcohol solvent represented by R1e-J-H (wherein R1e is the same as defined above and J is an oxygen atom); ether solvents, such as diethyl ether, diisopropyl ether, methyl-t-butyl ether, dimethoxyethane, tetrahydrofuran and dioxane; benzene-based solvents, such as benzene, toluene, xylene, mesitylene, chlorobenzene and dichlorobenzene; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (3c).

The temperature for carrying out this reaction is not particularly limited as long as the intended reaction proceeds, and is usually 30° C. or higher and 200° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield. It is also possible to remove insoluble materials by carrying out filtration operation, but this is not essential.

With respect to the reaction mixture obtained above, which contains the compound represented by Formula (3f), the solvent may be evaporated under reduced pressure as long as the compound is not decomposed.

The reaction mixture obtained after the evaporation of the solvent, which contains the compound represented by Formula (3f), may be purified by washing, reprecipitation, recrystallization, column chromatography or the like using an appropriate solvent. The purification method may be appropriately selected depending on the desired purity.

[Production Method I]

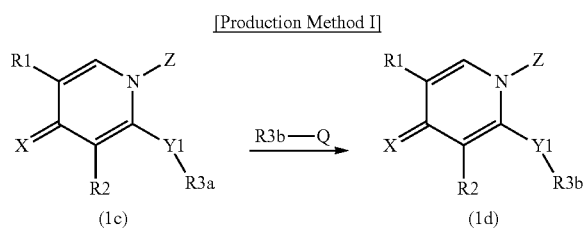

In the formula, R3a represents a halogen atom, R3b represents a C1-C6 alkoxy group optionally substituted with substituent C, a C1-C6 haloalkoxy group, a C3-C8 cycloalkoxy group optionally substituted with substituent C, a C2-C6 alkenyloxy group optionally substituted with substituent C, a C2-C6 haloalkenyloxy group, a C3-C6 alkynyloxy group optionally substituted with substituent C or a C3-C6 haloalkynyloxy group, Y1 represents a phenyl group optionally substituted with 0 to 4 R3 (with the proviso that when there are two or more substituents R3, they are independent to each other), a pyridyl group optionally substituted with 0 to 3 R3 (with the proviso that when there are two or more substituents R3, they are independent to each other), a pyridazinyl group optionally substituted with 0 to 2 R3 (with the proviso that when there are two substituents R3, they are independent to each other), a pyrimidinyl group optionally substituted with 0 to 2 R3 (with the proviso that when there are two substituents R3, they are independent to each other), a pyrazinyl group optionally substituted with 0 to 2 R3 (with the proviso that when there are two substituents R3, they are independent to each other), a triazinyl group optionally substituted with R3, a tetrazinyl group, a thienyl group optionally substituted with 0 to 2 R3 (with the proviso that when there are two substituents R3, they are independent to each other), a thiazolyl group optionally substituted with R3, an isothiazolyl group optionally substituted with R3 or a thiadiazolyl group, R1, R2, Q, X and Z are the same as defined above.

Production Method I is a method for obtaining a compound represented by Formula (1d) wherein R3b is a C1-C6 alkoxy group optionally substituted with substituent C, a C1-C6 haloalkoxy group, a C3-C8 cycloalkoxy group optionally substituted with substituent C, a C2-C6 alkenyloxy group optionally substituted with substituent C, a C2-C6 haloalkenyloxy group, a C3-C6 alkynyloxy group optionally substituted with substituent C or a C3-C6 haloalkynyloxy group, and Y1 is a phenyl group optionally substituted with 0 to 4 R3 (with the proviso that when there are two or more substituents R3, they are independent to each other), a pyridyl group optionally substituted with 0 to 3 R3 (with the proviso that when there are two or more substituents R3, they are independent to each other), a pyridazinyl group optionally substituted with 0 to 2 R3 (with the proviso that in the case of R3 with two substitutions, they are independent to each other), a pyrimidinyl group optionally substituted with 0 to 2 R3 (with the proviso that when there are two substituents R3, they are independent to each other), a pyrazinyl group optionally substituted with 0 to 2 R3 (with the proviso that when there are two substituents R3, they are independent to each other), a triazinyl group optionally substituted with R3, a tetrazinyl group, a thienyl group optionally substituted with 0 to 2 R3 (with the proviso that when there are two substituents R3, they are independent to each other), a thiazolyl group optionally substituted with R3, an isothiazolyl group optionally substituted with R3 or a thiadiazolyl group, which comprises reacting a compound represented by Formula (1c) with R3b-Q in a solvent.

The R3b-Q used in this reaction is commercially available or can be produced by a conventionally known method. Preferred Q is a hydrogen atom or an alkali metal, such as sodium, potassium and the like.

The amount of the R3b-Q used in this reaction is not particularly limited as long as the amount is 1 equivalent or more relative to the compound represented by Formula (1c) and the intended reaction proceeds. The amount is usually 1 equivalent or more and 30 equivalents or less. R3b-Q can be also used also as a solvent when Q represents a hydrogen atom.

It is preferred that the base used in this reaction is an inorganic base, such as sodium carbonate, potassium carbonate, cesium carbonate and sodium hydride. When Q is an alkali metal, use of the base is not essential.

The amount of the base used in this reaction is not particularly limited as long as the amount is 1 equivalent or more relative to the compound represented by Formula (1c) and the intended reaction proceeds. The amount is usually 1 equivalent or more and 30 equivalents or less.

The solvent used in this reaction is not particularly limited as long as the intended reaction proceeds, and examples of the solvent include the alcohol solvent represented by R3b-H (wherein R3b is the same as defined above); ether solvents, such as diethyl ether, diisopropyl ether, methyl-t-butyl ether, dimethoxyethane, tetrahydrofuran and dioxane; benzene-based solvents, such as benzene, toluene, xylene, mesitylene, chlorobenzene and dichlorobenzene; ester solvents, such as ethyl acetate, isopropyl acetate and butyl acetate; nitrile solvents, such as acetonitrile; amide solvents, such as N-methylpyrrolidone, N,N-dimethylformamide and N,N-dimethylacetamide; urea solvents, such as 1,3-dimethyl-2-imidazolidinone; halogen-based solvents, such as dichloromethane, dichloroethane, chloroform and carbon tetrachloride; sulfur-based solvents, such as dimethylsulfoxide and sulfolane; ketone solvents, such as acetone, methyl ethyl ketone and methyl isobutyl ketone; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (1c).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane.

These solvents may be used individually or in combination in any ratio. The number of times of the liquid separating operation is not particularly limited, and the operation can be carried out depending on the desired purity and yield.

The reaction mixture obtained above, which contains the compound represented by Formula (1d), may be dehydrated with a drying agent, such as sodium sulfate and magnesium sulfate, but this is not essential.

With respect to the reaction mixture obtained above, which contains the compound represented by Formula (1d), the solvent may be evaporated under reduced pressure as long as the compound is not decomposed.

The reaction mixture obtained after the evaporation of the solvent, which contains the compound represented by Formula (1d), may be purified by washing, reprecipitation, recrystallization, column chromatography or the like using an appropriate solvent. The purification method may be appropriately selected depending on the desired purity.

[Production Method J]

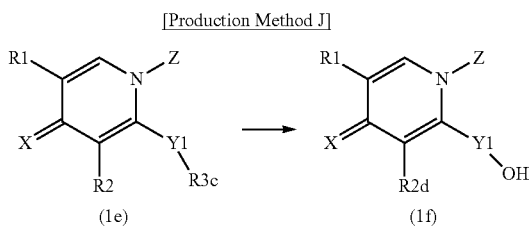

In the formula, R3c represents a C1-C6 alkoxy group, and R1, R2, Y1, X and Z are the same as defined above.

Production Method J is a method for obtaining a compound represented by Formula (1f) having a hydroxyl group, which comprises obtaining it by reacting a compound represented by Formula (1e) with an acid in a solvent.

Examples of the acid used in this reaction include boron halides, such as boron trichloride and boron tribromide.

The amount of the acid used in this reaction is not particularly limited as long as the amount is 1 equivalent or more relative to the compound represented by Formula (1e) and the intended reaction proceeds. The amount is usually 1 equivalent or more and 10 equivalents or less.

The solvent used in this reaction is not particularly limited as long as the intended reaction proceeds, and examples of the solvent include benzene-based solvents, such as benzene, toluene, xylene, mesitylene, chlorobenzene and dichlorobenzene; nitrile solvents, such as acetonitrile; halogen-based solvents, such as dichloromethane, dichloroethane, chloroform and carbon tetrachloride; hydrocarbon solvents, such as hexane, heptane, cyclohexane and methylcyclohexane; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (1e).

The temperature for carrying out this reaction is not particularly limited as long as the intended reaction proceeds, and is usually −80° C. or higher and 100° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield.

The reaction mixture obtained above, which contains the compound represented by Formula (1f), may be dehydrated with a drying agent, such as sodium sulfate and magnesium sulfate, but this is not essential.

With respect to the reaction mixture obtained above, which contains the compound represented by Formula (1f), the solvent may be evaporated under reduced pressure as long as the compound is not decomposed.

The reaction mixture obtained after the evaporation of the solvent, which contains the compound represented by Formula (1f), may be purified by washing, reprecipitation, recrystallization, column chromatography or the like using an appropriate solvent. The purification method may be appropriately selected depending on the desired purity.

[Production Method K]

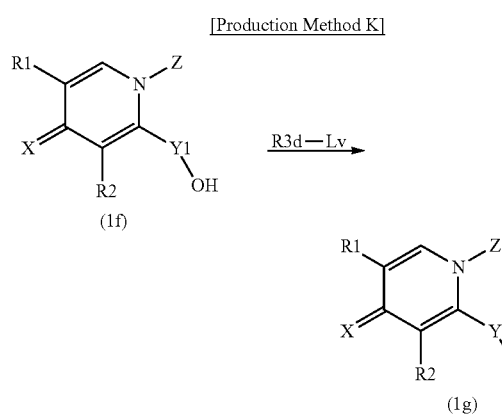

In the formula, Kid represents a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C3-C6 alkynyl group optionally substituted with substituent C, a C3-C6 haloalkynyl group or an RdC(=O)— (wherein Rd is the same as defined above), and R1, R2, Y1, Lv, X and Z are the same as defined above.

Production Method K is a method for obtaining a compound represented by Formula (1g) wherein R3d is a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C3-C6 alkynyl group optionally substituted with substituent C, a C3-C6 haloalkynyl group or an RdC(=O)—(Rd is the same as defined above), which comprises reacting a compound represented by Formula (1f) with R3d-Lv in a solvent in the presence of a base.

The R3d-Lv used in this reaction is commercially available or can be produced by a conventionally known method.

The amount of the R3d-Lv used in this reaction is not particularly limited as long as the amount is 1 equivalent or more relative to the compound represented by Formula (1f) and the intended reaction proceeds. This is usually 1 equivalent or more and 10 equivalents or less.

Examples of the base used in this reaction include inorganic bases, such as sodium carbonate, potassium carbonate, cesium carbonate and sodium hydride; and organic bases, such as triethylamine, tributylamine, diisopropylethylamine, pyridine, 4-dimethylaminopyridine, collidine and lutidine, and the base is not particularly limited as long as the intended reaction proceeds.

The amount of the base used in this reaction is not particularly limited as long as the amount is 1 equivalent or more relative to the compound represented by Formula (1f) and the intended reaction proceeds. This is usually 1 equivalent or more and 10 equivalents or less.

The solvent used in this reaction is not particularly limited as long as the intended reaction proceeds, and examples of the solvent include ether solvents, such as diethyl ether, diisopropyl ether, methyl-t-butyl ether, dimethoxyethane, tetrahydrofuran and dioxane; alcohol solvent, such as methanol, ethanol and isopropanol; benzene-based solvents, such as benzene, toluene, xylene, mesitylene, chlorobenzene and dichlorobenzene; ester solvents, such as ethyl acetate, isopropyl acetate and butyl acetate; nitrile solvents, such as acetonitrile; amide solvents, such as N-methylpyrrolidone, N,N-dimethylformamide and N,N-dimethylacetamide; urea solvents, such as 1,3-dimethyl-2-imidazolidinone; halogen-based solvents, such as dichloromethane, dichloroethane, chloroform and carbon tetrachloride; sulfur-based solvents, such as dimethylsulfoxide and sulfolane; ketone solvents, such as acetone, methyl ethyl ketone and methyl isobutyl ketone; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (1f).

The temperature for carrying out this reaction is not particularly limited as long as the intended reaction proceeds, and is usually −20° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield.

The reaction mixture obtained above, which contains the compound represented by Formula (1g), may be dehydrated with a drying agent, such as sodium sulfate and magnesium sulfate, but this is not essential.

With respect to the reaction mixture obtained above, which contains the compound represented by Formula (1g), the solvent may be evaporated under reduced pressure as long as the compound is not decomposed.

The reaction mixture obtained after the evaporation of the solvent, which contains the compound represented by Formula (1g), may be purified by washing, reprecipitation, recrystallization, column chromatography or the like using an appropriate solvent. The purification method may be appropriately selected depending on the desired purity.

[Production Method L]

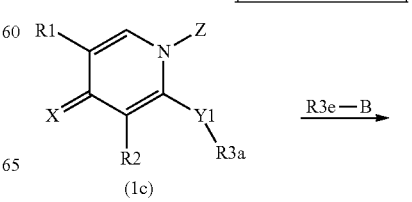

-continued

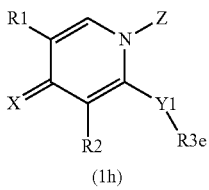

(1h)

In the formula, R3e represents a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C or a C2-C6 haloalkenyl group, R3e-B represents an organic boronic acid derivative, and R1, R2, R3a, Y1, X and Z are the same as defined above.

Production Method L is a method for obtaining a compound represented by Formula (1h) wherein R3e is a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C or a C2-C6 haloalkenyl group, which comprises obtaining it by Suzuki-Miyaura coupling in which a compound represented by Formula (1c) is reacted with an organic boronic acid derivative (R3e-B) in a solvent in the presence of a transition metal and a base.

In Formula (1c), preferred R3a is a chlorine atom, a bromine atom or an iodine atom.

The R3e-B used in this reaction represents an organic boronic acid derivative, such as an organic boronic acid and an organic boronic acid ester, and is commercially available or can be produced by a conventionally known method.

Production Method L can be carried out in substantially the same manner as in Production Method F, except that the compound represented by Formula (1c) and R3e-B are used in place of the compound represented by Formula (3c) and R1c-B in Production Method F, respectively.

[Production Method M]

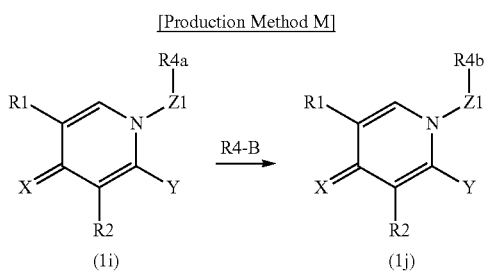

In the formula, R4a represents a halogen atom, R4b represents a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C or a C2-C6 haloalkenyl group, R4b-B represents an organic boronic acid derivative, Z1 represents a phenyl group optionally substituted with 0 to 4 R4 (with the proviso that when there are two or more substituents R4, they are independent to each other), a C1-C6 alkyl group having a phenyl group optionally substituted with 0 to 4 R4 (with the proviso that when there are two or more substituents R4, they are independent to each other), a C1-C6 haloalkyl group having a phenyl group optionally substituted with 0 to 4 R4 (with the proviso that when there are two or more substituents R4, they are independent to each other), a pyridyl group optionally substituted with 0 to 3 R4 (with the proviso that when there are two or more substituents R4, they are independent to each other), a pyridazinyl group optionally substituted with 0 to 3 R4 (with the proviso that when there are two or more substituents R4, they are independent to each other), a pyrimidinyl group optionally substituted with 0 to 2 R4 (with the proviso that when there are two substituents R4, they are independent to each other), a pyrazinyl group optionally substituted with 0 to 2 R4 (with the proviso that when there are two substituents R4, they are independent to each other), a triazinyl group optionally substituted with R4, a tetrazinyl group, a thienyl group optionally substituted with 0 to 2 R4 (with the proviso that when there are two substituents R4, they are independent to each other), a thiazolyl group optionally substituted with R4, an isothiazolyl group optionally substituted with R4, a thiadiazolyl group, an oxazolyl group optionally substituted with R4, an isoxazolyl group optionally substituted with R4, an oxadiazolyl group or a pyrazolyl group optionally substituted with R4, and R1, R2, X and Y are the same as defined above.

Production Method M is a method for obtaining a compound represented by Formula (1j) wherein R4b is a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C or a C2-C6 haloalkenyl group, which comprises obtaining it by Suzuki-Miyaura coupling in which a compound represented by Formula (1i) is reacted with an organic boronic acid derivative (R4b-B) in a solvent in the presence of a transition metal and a base.

In Formula (1i), preferred R4a is a chlorine atom, a bromine atom or an iodine atom.

The R4b-B used in this reaction represents an organic boronic acid derivative, such as an organic boronic acid and an organic boronic acid ester, and is commercially available or can be produced by a conventionally known method.

Production Method M can be carried out in substantially the same manner as in Production Method F, except that the compound represented by Formula (1i) and R4b-B are used in place of the compound represented by Formula (3c) and R1c-B in Production Method F, respectively.

[Production Method N]

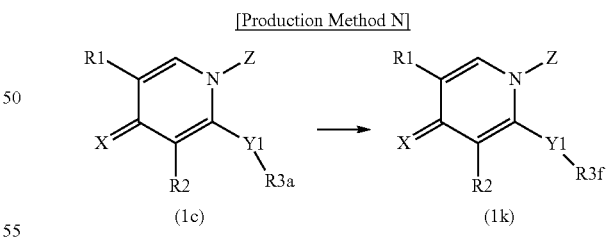

In the formula, R3f represents a C2-C6 alkynyl group optionally substituted with substituent C or a C2-C6 haloalkynyl group, and R1, R2, R3a, Y1, X and Z are the same as defined above.

Production Method N is a method for obtaining a compound represented by Formula (1k) wherein R3f is a C2-C6 alkynyl group optionally substituted with substituent C or a C2-C6 haloalkynyl group, which comprises obtaining it by Sonogashira coupling in which a compound represented by Formula (1c) is reacted with a terminal-alkyne compound in a solvent in the presence of a transition metal and a base.

In Formula (1c), preferred R3a is a chlorine atom, a bromine atom or an iodine atom.

The terminal-alkyne compound used in this reaction is commercially available or can be produced by a conventionally known method. As the terminal-alkyne compound, trimethylsilylacetylene may also be used.

Production Method N can be carried out in substantially the same manner as in Production Method G, except that the compound represented by Formula (1c) is used in place of the compound represented by Formula (3c) in Production Method G.

[Production Method O]

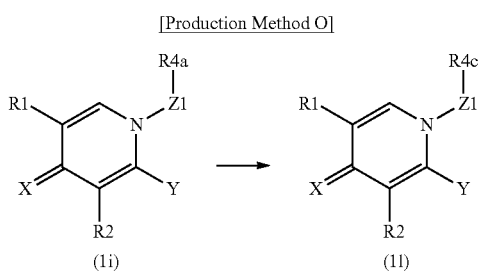

In the formula, R4c represents a C2-C6 alkynyl group optionally substituted with substituent C or a C2-C6 haloalkynyl group, and R1, R2, R4a, Z1, X and Y are the same as defined above.

Production Method O is a method for obtaining a compound represented by Formula (1l) wherein R4c is a C2-C6 alkynyl group optionally substituted with substituent C or a C2-C6 haloalkynyl group, which comprises obtaining it by Sonogashira coupling in which a compound represented by Formula (1i) is reacted with a terminal-alkyne compound in a solvent in the presence of a transition metal and a base.

In Formula (1i), preferred R4a is a chlorine atom, a bromine atom or an iodine atom.

The terminal-alkyne compound used in this reaction is commercially available or can be produced by a conventionally known method. As the terminal-alkyne compound, trimethylsilylacetylene may also be used.

Production Method O can be carried out in substantially the same manner as in Production Method G, except that the compound represented by Formula (1i) is used in place of the compound represented by Formula (3c) in Production Method G.

[Production Method P]

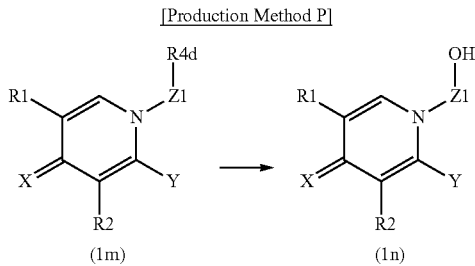

In the formula, R4d represents a C1-C6 alkoxy group, and R1, R2, Z1, X and Y are the same as defined above.

Production Method P is a method for obtaining a compound represented by Formula (1n) having a hydroxyl group, which comprises reacting a compound represented by Formula (1m) with an acid in a solvent.

Examples of the acid used in this reaction include boron halides, such as boron trichloride and boron tribromide.

Production Method P can be carried out in substantially the same manner as in

Production Method J, except that the compound represented by Formula (1m) is used in place of the compound represented by Formula (1e) in Production Method J.

[Production Method Q]

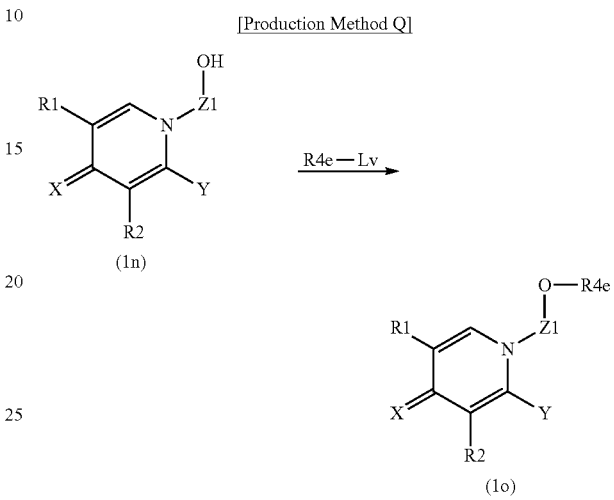

In the formula, R4e represents a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C3-C6 alkynyl group optionally substituted with substituent C, a C3-C6 haloalkynyl group or an RdC(=O)—(Rd is the same as defined above), and R1, R2, Z1, Lv, X and Y are the same as defined above.

Production Method Q is a method for obtaining a compound represented by Formula (1o) wherein R4e is a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C3-C6 alkynyl group optionally substituted with substituent C, a C3-C6 haloalkynyl group or an RdC(=O)—(Rd is the same as defined above), which comprises reacting a compound represented by Formula (1n) with R4e-Lv in a solvent in the presence of a base.

Production Method Q can be carried out in substantially the same manner as in Production Method K, except that the compound represented by Formula (1n) and R4e-Lv are used in place of the compound represented by Formula (1f) and R3d-Lv in Production Method K, respectively.

[Production Method R]

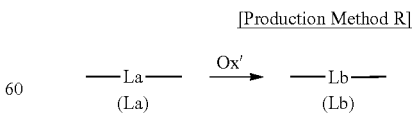

In the formula, La represents S, Lb represents SO or $SO_2$, and Ox' represents an oxidizing agent.

Production Method R is a method for obtaining a compound represented by Formula (Lb) among the compounds represented by Formula (1) wherein each Lb contained in R1, R2, Y and Z is SO or SO$_2$, which comprises reacting a compound represented by Formula (La) among the compounds represented by Formula (1) wherein La contained in R1, R2, Y and Z is S with an oxidizing agent (Ox') in a solvent.

Examples of the oxidizing agent used in this reaction include peroxides, such as hydrogen peroxide solution and meta-chloroperoxybenzoic acid. It is also possible to add a transition metal, such as sodium tungstate.

The amount of the oxidizing agent used in this reaction is usually 1.0 equivalent or more and 1.2 equivalents or less relative to the compound represented by Formula (La) when SO is produced, and usually 2 equivalents or more and 20 equivalents or less when SO$_2$ is produced. When a transition metal is added, the amount is usually 0.001 equivalent or more and 1 equivalent or less.

The solvent used in this reaction is not particularly limited as long as the intended reaction proceeds, and examples of the solvent include water solvent, acidic solvents, such as acetic acid; benzene-based solvents, such as benzene, toluene, xylene, mesitylene, chlorobenzene and dichlorobenzene; nitrile solvents, such as acetonitrile; halogen-based solvents, such as dichloromethane, dichloroethane, chloroform and carbon tetrachloride; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (La).

The temperature for carrying out this reaction is not particularly limited as long as the intended reaction proceeds, and is usually −10° C. or higher and 120° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane.

These solvents may be used individually or in combination in any ratio. The number of times of the liquid separating operation is not particularly limited, and the operation can be carried out depending on the desired purity and yield.

The reaction mixture obtained above, which contains the compound represented by Formula (Lb), may be dehydrated with a drying agent, such as sodium sulfate and magnesium sulfate, but this is not essential.

With respect to the reaction mixture obtained above, which contains the compound represented by Formula (Lb), the solvent may be evaporated under reduced pressure as long as the compound is not decomposed.

The reaction mixture obtained after the evaporation of the solvent, which contains the compound represented by Formula (Lb), may be purified by washing, reprecipitation, recrystallization, column chromatography or the like using an appropriate solvent. The purification method may be appropriately selected depending on the desired purity.

[Production Method S]

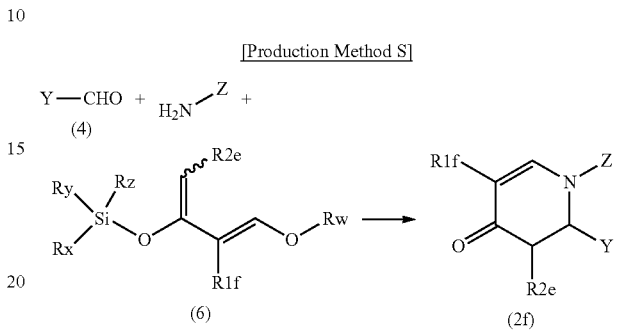

In the formula, R1f represents a hydrogen atom or a C1-C6 alkyl group, R2e represents a hydrogen atom or a C1-C6 alkyl group, Rx, Ry and Ry are independent to each other and each represent a C1-C6 alkyl group, Rw represents a C1-C6 alkyl group, and Y and Z are the same as defined above.

Production Method S is a method for obtaining a compound represented by Formula (2f) wherein R1f represents a hydrogen atom or a C1-C6 alkyl group, and R2e represents a hydrogen atom or a C1-C6 alkyl group, which comprises reacting a compound represented by Formula (4), a compound represented by Formula (5) and a compound represented by Formula (6) in a solvent.

The compound represented by Formula (4) used in this reaction is commercially available or can be produced by a conventionally known method.

The compound represented by Formula (5) used in this reaction is commercially available or can be produced by a conventionally known method.

The amount of the compound represented by Formula (5) used in this reaction is not particularly limited as long as the amount is 1 equivalent or more relative to the compound represented by Formula (4) and the intended reaction proceeds. The amount is usually 1 equivalent or more and 1.5 equivalents or less.

The compound represented by Formula (6) used in this reaction is commercially available or can be produced by a conventionally known method.

The amount of the compound represented by Formula (6) used in this reaction is not particularly limited as long as the amount is 1 equivalent or more relative to the compound represented by Formula (4) and the intended reaction proceeds. The amount is usually 1 equivalent or more and 3 equivalents or less.

It is possible to smoothly proceed with this reaction by adding an acid or surfactant, although this is not essential. Examples of the acid to be used include tetrafluoroboric acid and the like. The amount of the acid used in this reaction is not particularly limited as long as the intended reaction proceeds, and catalytic amount relative to the compound represented by Formula (4) is satisfactory. The amount is usually 0.01 equivalent or more and 1 equivalent or less. Examples of the surfactant to be used include sodium dodecyl sulfate and the like. The amount of the surfactant used in this reaction is not particularly limited as long as the intended reaction proceeds, and catalytic amount relative to the compound represented by Formula (4) is satisfactory. The amount is usually 0.01 equivalent or more and 1 equivalent or less. The acid and the surfactant may be simultaneously used, and only one of them may be used.

The solvent used in this reaction is not particularly limited as long as the intended reaction proceeds, and examples of the solvent include water; ether solvents, such as diethyl ether, diisopropyl ether, methyl-t-butyl ether, dimethoxyethane, tetrahydrofuran and dioxane; alcohol solvents, such as methanol, ethanol and isopropanol; benzene-based solvents, such as benzene, toluene, xylene, mesitylene, chlorobenzene and dichlorobenzene; ester solvents, such as ethyl acetate, isopropyl acetate and butyl acetate; nitrile solvents, such as acetonitrile; amide solvents, such as N-methylpyrrolidone, N,N-dimethylformamide and N,N-dimethylacetamide; urea solvents, such as 1,3-dimethyl-2-imidazolidinone; halogen-based solvents, such as dichloromethane, dichloroethane, chloroform and carbon tetrachloride; and the like. These solvents may be used individually or in combination in any ratio. The solvent is not essential for this reaction.

The amount of the solvent used in this reaction is not particularly limited as long as the intended reaction proceeds, and is usually 3 times by weight or more and 200 times by weight or less, relative to the compound represented by Formula (4).

The temperature for carrying out this reaction is not particularly limited as long as the intended reaction proceeds, and is usually −80° C. or higher and 150° C. or lower, or the boiling point of the solvent or lower.

With regard to the order of the reactions in this reaction, the compound represented by Formula (4), the compound represented by Formula (5) and the compound represented by Formula (6) may be simultaneously reacted. The compound represented by Formula (4) may be reacted with the compound represented by Formula (5) in advance to thereby convert them to an imine, with which the compound represented by Formula (6) is then reacted. Preparation of an imine can be carried out by a conventionally known method. In this case, this reaction can be carried out in substantially the same method as described above, except that the imine is used in place of the compound represented by Formula (4) and the compound represented by Formula (5).

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield.

The reaction mixture obtained above, which contains the compound represented by Formula (2f), may be dehydrated with a drying agent, such as sodium sulfate and magnesium sulfate, but this is not essential.

With respect to the reaction mixture obtained above, which contains the compound represented by Formula (2f), the solvent may be evaporated under reduced pressure as long as the compound is not decomposed.

The reaction mixture obtained after the evaporation of the solvent, which contains the compound represented by Formula (2f), may be purified by washing, reprecipitation, recrystallization, column chromatography or the like using an appropriate solvent. The purification method may be appropriately selected depending on the desired purity.

[Production Method T]

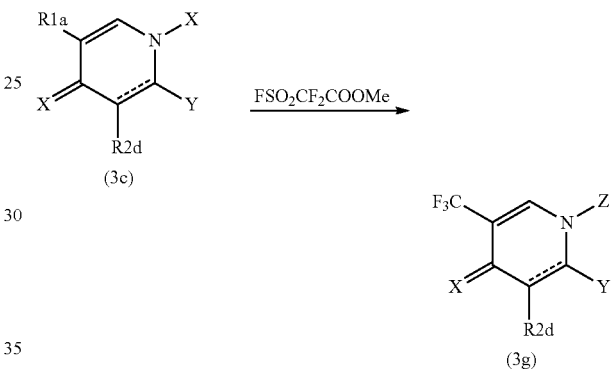

In the formula, R1a, R2d, X, Y and Z are the same as defined above.

Production Method T is a method for obtaining a compound represented by Formula (3g) having a trifluoromethyl group, which comprises reacting a compound represented by Formula (3c) with methyl difluoro(fluorosulfonyl)acetate in a solvent in the presence of a transition metal.

In the compound represented by Formula (3c), preferred R1a is a chlorine atom, a bromine atom or an iodine atom.

Methyl difluoro(fluorosulfonyl)acetate used in this reaction is commercially available or can be produced by a conventionally known method.

The amount of methyl difluoro(fluorosulfonyl)acetate used in this reaction is not particularly limited as long as the amount is 1 equivalent or more relative to the compound represented by Formula (3c) and the intended reaction proceeds. The amount is usually 1 equivalent or more and 50 equivalents or less.

Examples of the transition metals used in this reaction include copper compounds and the like. Examples of preferred transition metals used include copper bromide, copper iodide and the like.

The amount of the transition metal used in this reaction is not particularly limited as long as the amount is 1 equivalent or more relative to the compound represented by Formula (3c) and the intended reaction proceeds. The amount is usually 1 equivalent or more and 50 equivalents or less.

In order to efficiently proceed with this reaction, it is possible to add an additive, such as ethyldiisopropylamine and hexamethylphosphoric triamide, but this is not essential.

The amount of the additive used in this reaction is not particularly limited as long as the amount is 50 equivalents or less relative to the compound represented by Formula (3c) and the intended reaction proceeds.

The solvent used in this reaction is not particularly limited as long as the intended reaction proceeds, and examples of the solvent include amide solvents, such as N-methylpyrrolidone, N,N-dimethylformamide and N,N-dimethylacetamide; sulfur-based solvents, such as dimethylsulfoxide and sulfolane; and the like. These solvents may be used individually or in combination in any ratio.

The amount of the solvent used in this reaction is not particularly limited as long as the intended reaction proceeds, and is usually 3 times by weight or more and 200 times by weight or less, relative to the compound represented by Formula (3c).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein ammonia, potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield.

The reaction mixture obtained above, which contains the compound represented by Formula (3g), may be dehydrated with a drying agent, such as sodium sulfate and magnesium sulfate, but this is not essential.

With respect to the reaction mixture obtained above, which contains the compound represented by Formula (3g), the solvent may be evaporated under reduced pressure as long as the compound is not decomposed.

The reaction mixture obtained after the evaporation of the solvent, which contains the compound represented by Formula (3g), may be purified by washing, reprecipitation, recrystallization, column chromatography or the like using an appropriate solvent. The purification method may be appropriately selected depending on the desired purity.

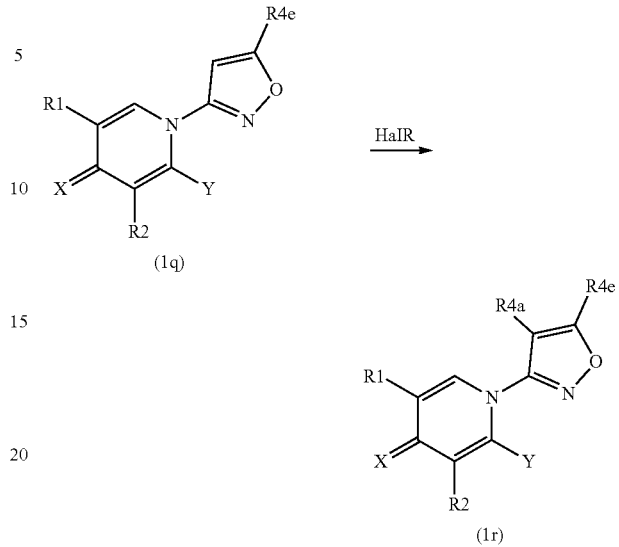

[Production Method U]

In the formula, R4e represents a hydrogen atom, a hydroxyl group, a cyano group, a nitro group, a halogen atom, a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C, a C2-C6 haloalkynyl group, a C1-C6 alkoxy group optionally substituted with substituent C, a C1-C6 haloalkoxy group, a C3-C8 cycloalkoxy group optionally substituted with substituent C, a C2-C6 alkenyloxy group optionally substituted with substituent C, a C2-C6 haloalkenyloxy group, a C3-C6 alkynyloxy group optionally substituted with substituent C, a C3-C6 haloalkynyloxy group, an RdC(=O)— (wherein Rd is the same as defined above), RdC(=O)O— (wherein Rd is the same as defined above), a group of a 3-6 membered ring containing 1-2 oxygen atoms, an Rc-L-(wherein Rc and L are the same as defined above), an RaRbN— (wherein Ra and Rb are the same as defined above) or ReC(=O)N(Rf)— (wherein Re and Rf are the same as defined above), and HalR, R1, R2, R4a, X and Y are the same as defined above.

Production Method U is a method for obtaining a compound represented by Formula (1r) wherein R4a is a halogen atom, which comprises reacting a compound represented by Formula (1q) with a halogenating agent (HalR) in a solvent.

Examples of the halogenating agent used in this reaction include chlorine, bromine, iodine and the like.

The amount of the halogenating agent used in this reaction is not particularly limited as long as the amount is 1 equivalent or more relative to the compound represented by Formula (1q) and the intended reaction proceeds. The amount is usually 1 equivalent or more and 200 equivalents or less.

The solvent used in this reaction is not particularly limited as long as the intended reaction proceeds, and examples of the solvent include acidic solvents, such as sulfuric acid, acetic acid, trifluoroacetic acid, methanesulfonic acid and trifluoromethanesulfonic acid; and the like.

The amount of the solvent used in this reaction is not particularly limited as long as the intended reaction proceeds, and is usually 3 times by weight or more and 200 times by weight or less, relative to the compound represented by Formula (1q).

The temperature for carrying out this reaction is not particularly limited as long as the intended reaction proceeds, and is usually 0° C. or higher and 150° C. or lower, or the boiling point of the solvent or lower.

As a post treatment after the reaction, it is possible to add water or an appropriate aqueous solution to the reaction mixture for carrying out liquid separating operation. When an aqueous solution is used, it is possible to use any aqueous solution, such as an acidic aqueous solution having dissolved therein hydrochloric acid, sulfuric acid, ammonium chloride or the like; an alkaline aqueous solution having dissolved therein potassium hydroxide, sodium hydroxide, sodium carbonate, potassium carbonate, sodium hydrogen carbonate, potassium hydrogen carbonate or the like; an aqueous solution having dissolved therein a salt containing a sulfur atom, such as sodium thiosulfate and sodium sulfite; or brine. At the time of the liquid separating operation, it is possible to add, if necessary, a solvent which is immiscible with water, such as a benzene-based solvent, such as toluene, xylene, benzene, chlorobenzene and dichlorobenzene; an ester solvent, such as ethyl acetate, isopropyl acetate and butyl acetate; an ether solvent, such as diethyl ether, diisopropyl ether and methyl-t-butyl ether; a halogen-based solvent, such as dichloromethane, dichloroethane, chloroform and carbon tetrachloride; or a hydrocarbon solvent, such as hexane, heptane, cyclohexane and methylcyclohexane. These solvents may be used individually or in combination in any ratio. The number of times of the liquid separating operation is not particularly limited, and the operation can be carried out depending on the desired purity and yield.

The reaction mixture obtained above, which contains the compound represented by Formula (1r), may be dehydrated with a drying agent, such as sodium sulfate and magnesium sulfate, but this is not essential.

With respect to the reaction mixture obtained above, which contains the compound represented by Formula (1r), the solvent may be evaporated under reduced pressure as long as the compound is not decomposed.

The reaction mixture obtained after the evaporation of the solvent, which contains the compound represented by Formula (1r), may be purified by washing, reprecipitation, recrystallization, column chromatography or the like using an appropriate solvent. The purification method may be appropriately selected depending on the desired purity.

The compound represented by Formula (1) can be produced by arbitrarily combining Production Method A to Production Method U shown above. Alternatively, the compound represented by Formula (1) can be also produced by arbitrarily combining a conventionally known method with Production Method A to Production Method U.

The compound of the present invention can control pests harmful to plants, and thus can be used as a pesticide, particularly an agricultural and horticultural pest control agent. Specific examples of such agents include fungicides, insecticides, herbicides, plant growth regulators and the like. A fungicide is preferred.

The compound of the present invention can be used as an agricultural and horticultural fungicide in farms, paddy fields, tea gardens, orchards, meadows, grasses, forests, gardens, roadside trees, etc. for plant disease control. A plant disease referred to in the present invention means that a systemic, abnormal pathological symptom, such as wilting, damping-off, yellowing, dwarfism and spindly growth, or a partial pathological symptom, such as spotting, leaf blight, mosaic pattern, leaf rolling, die back, root rot, club root and knotting, is induced in a plant including crops, flowering plants, flowering trees, and shrubs and trees. That is, this term means that a plant becomes ill. Examples of major pathogens that cause plant diseases include fungi, bacteria, spiroplasmas, phytoplasmas, viruses, viroids, parasitic higher plants, nematodes and the like. The compound of the present invention is effective against fungi, but the effectiveness may not be limited to that against fungi.

Major diseases caused by fungi are fungal diseases. Examples of fungi (pathogens) that cause fungal diseases include *Plasmodiophora, Oomycetes, Zygomycetes, Ascomycetes, Basidiomycetes* and *Deuteromycetes*. Examples of *Plasmodiophora* include club root fungus, potato powdery scab fungus and beet necrotic yellow vein virus; examples of *Oomycetes* include blight fungus, downy mildew fungus, *Pythium* species fungus and *Aphanomyces* species fungus; examples of *Zygomycetes* include *Rhizopus* species fungus; examples of *Ascomycetes* include peach leaf curl fungus, corn brown spot fungus, rice blast fungus, powdery mildew fungus, anthracnose fungus, *Fusarium* head blight fungus, bakanae disease fungus and sclerotial disease fungus; examples of *Basidiomycetes* include rust disease fungus, smut fungus, violet root rot fungus, blister blight fungus and rice sheath blight fungus; and examples of *Deuteromycetes* include gray mold fungus, *Alternaria* species fungus, *Fusarium* species fungus, *Penicillium* species fungus, *Rhizoctonia* species fungus and southern blight fungus.

The compound of the present invention is effective against various plant diseases. With respect to the names of diseases and their pathogens, specific examples are given bellow.

Rice: blast (*Magnaporthe grisea*), sheath blight (*Thanatephorus cucumeris*), brown sclerotial disease (*Ceratobasidium setariae*), brown small sclerotial disease (*Waitea circinata*), brown sheath blight (*Thanatephorus cucumeris*), globular sclerotial disease (*Sclerotium hydrophilum*), red sclerotial disease (*Wairea circinata*), black leaf blight (*Entyloma dactylidis*), stem rot (*Magnaporthe salvinii*), gray sclerotial disease (*Ceratobasidium cornigerum*), brown spot (*Cochliobolus miyabeanus*), cercospora leaf spot (*Sphaerulina oryzina*), bakanae disease (*Gibberella fujikuroi*), seedling blight (*Pythium* spp., *Fusarium* spp., *Trichoderma* spp., *Rhizopus* spp., *Rhizoctonia solani, Mucor* sp., *Phoma* sp.), seedling rot (*Pythium* spp., *Achlya* spp., *Dictyuchus* spp.), rice false smut (*Claviceps virens*), kernel smut (*Tilletia barclayana*), discolored rice grains (*Curvularia* spp., *Alternaria* spp.), crazy top (*Sclerophthora macrospora*), bacterial leaf blight (*Xanthomonas oryzae* pv. *oryzae*), bacterial brown stripe (*Acidovorax avenae* subsp. *avenae*), bacterial palea browning (*Erwinia ananas*), bacterial seedling blight (*Burkholderia plantarii*), bacterial grain rot (*Burkholderia glumae*), sheath brown rot (*Pseudomonas fuscovaginae*), bacterial halo blight (*Pseudomonas syringae* pv. *oryzae*), bacterial foot rot (*Erwinia chrysanthemi*), yellow dwarf (*Phytoplasma oryzae*), rice stripe (Rice stripe tenuivirus), rice dwarf (Rice dwarf reovirus);

wheat and barley: powdery mildew (*Blumeria graminis* f.sp. *hordei*; f.sp. *tritici*), rust (*Puccinia striiformis, Puccinia graminis, Puccinia recondita, Puccinia hordei*), barley stripe (*Pyrenophora graminea*), net blotch (*Pyrenophora teres*), *Fusarium* head blight (*Gibberella zeae, Fusarium culmorum, Fusarium avenaceum, Monographella nivalis*), *Typhula* snow blight (*Typhula incarnata, Typhula ishikariensis, Monographella nivalis*), loose smut (*Ustilago nuda*), stinking smut (*Tilletia caries, Tilletia controversa*), eye spot (*Pseudocercosporella herpotrichoides*), foot rot (*Ceratoba-* sidium gramineum), leaf scald (Rhynchosporium secalis), speckled leaf blotch (Septoria tritici), glume blotch (Phaeosphaeria nodorum), damping-off (Fusarium spp., Pythium spp., Rhizoctonia spp., Septoria spp., Pyrenophora spp.), seedling blight (Gaeumannomyces graminis), anthracnose (Colletotrichum graminicola), ergot (Claviceps purpurea), leaf spot (Cochliobolus sativus), bacterial black node (Pseudomonas syringae pv. syringae); corn: ear rot (Gibberella zeae, etc.), damping-off (Fusarium avenaceum, Penicillium spp., Pythium spp., Rhizoctonia spp.), rust (Puccinia sorghi), brown spot (Cochliobolus heterostrophus), smut (Ustilago maydis), anthracnose (Colletotrichum graminicola), northern leaf spot (Cochliobolus carbonum), bacterial brown stripe (Acidovorax avenae subsp. avenae), bacterial stripe (Burkholderia andropogonis), bacterial stalk rot (Erwinia chrysanthemi pv. zeae), bacterial wilt (Erwinia stewartii); grapes: downy mildew (Plasmopara viticola), rust (Physopella ampelopsidis), powdery mildew (Uncinula necator), scab (Elsinoe ampelina), ripe rot (Glomerella cingulata, Colletotrichum acutatum), black rot (Guignardia bidwellii), Phomopsis leaf spot (Phomopsis viticola), fly speck (Zygophiala jamaicensis), gray mold (Botrytis cinerea), twig blight (Diaporthe medusaea), violet root rot (Helicobasidium mompa), white root rot (Rosellinia necatrix), crown gall (Agrobacterium vitis); apples: powdery mildew (Podosphaera leucotricha), black spot disease (Venturia inaequalis), Alternaria leaf spot (Alternaria mali), rust (Gymnosporangium yamadae), blossom blight (Monilinia mali), apple canker (Valsa ceratosperma), ring spot (Botryosphaeria berengeriana), anthracnose (Colletotrichum acutatum, Glomerella cingulata), fly speck (Zygophiala jamaicensis), sooty spot (Gloeodes pomigena), fruit spot (Mycosphaerella pomi), violet root rot (Helicobasidium mompa), white root rot (Rosellinia necatrix), canker (Phomopsis mali, Diaporthe tanakae), apple blotch (Diplocarpon mali), apples: fire blight (Erwinia amylovora), crown gall (Agrobacterium tumefaciens), hairy root disease (Agrobacterium rhizogenes); Japanese pears: black spot (Alternaria kikuchiana), pear scab (Venturia nashicola), rust (Gymnosporangium asiaticum), ring spot (Botryosphaeria berengeriana f.sp. piricola), pear canker (Phomopsis fukushii), bacterial shoot blight (Erwinia sp.), crown gall (Agrobacterium tumefaciens), rusty canker (Erwinia chrysanthemi pv. chrysanthemi), bacterial petal blight (Pseudomonas syringae pv. syringae); European pears: blight (Phytophthora cactorum, Phytophthora syringae), bacterial shoot blight (Erwinia sp.); peaches: black spot (Cladosporium carpophilum), Phomopsis rot (Phomopsis sp.), blight (Phytophthora sp.), anthracnose (Colletotrichum gloeosporioides), leaf curl (Taphrina deformans), bacterial shot hole (Xanthomonas campestris pv. pruni), crown gall (Agrobacterium tumefaciens); cherries: anthracnose (Glomerella cingulata), young fruit sclerotial disease (Monilinia kusanoi), gray spot (Monilinia fructicola), crown gall (Agrobacterium tumefaciens), bacterial gummosis (Pseudomonas syringae pv. syringae); persimmons: anthracnose (Glomerella cingulata), leaf spot (Cercospora kaki; Mycosphaerella nawae), powdery mildew (Phyllactinia kakikora), crown gall (Agrobacterium tumefaciens); citrus fruits: melanose (Diaporthe citri), green mold disease (Penicillium digitatum), blue mold disease (Penicillium italicum), scab (Elsinoe fawcettii), brown rot (Phytophthora citrophthora), canker (Xanthomonas campestris pv. citri), bacterial brown spot (Pseudomonas syringae pv. syringae), greening disease (Liberibactor asiaticus), crown gall (Agrobacterium tumefaciens); tomatoes, cucumbers, beans, strawberries, potatoes, cabbage, eggplants, lettuce and the like: gray mold (Botrytis cinerea); tomatoes, cucumbers, beans, strawberries, potatoes, rapeseed, cabbage, eggplants, lettuce and the like: sclerotial disease (Sclerotinia sclerotiorum); various vegetables such as tomatoes, cucumbers, beans, Japanese radishes, watermelons, eggplants, rapeseed, green peppers, spinach, beets and the like: seedling damping-off (Rhizoctonia spp., Pythium spp., Fusarium spp., Phythophthora spp., Sclerotinia sclerotiorum, etc.); solanaceous plants: bacterial wilt (Ralstonia solanacearum); melons: downy mildew (Pseudoperonospora cubensis), powdery mildew (Sphaerotheca fuliginea), anthracnose (Colletotrichum orbiculare), gummy stem blight (Didymella bryoniae), stem rot (Fusarium oxysporum), late blight (Phytophthora parasitica, Phytophthora melonis, Phytophthora nicotianae, Phytophthora drechsleri, Phytophthora capsici, etc.), bacterial brown spot (Xanthomonas campestris pv. cucurbitae), soft rot (Erwinia carotovora subsp. carotovora), bacterial spot (Pseudomonas syringae pv. lachrymans), marginal blight (Pseudomonas marginalis pv. marginalis), canker (Streptomyces sp.), hairy root disease (Agrobacterium rhizogenes), cucumber mosaic virus (Cucumber mosaic virus); tomatoes: ring spot (Alternaria solani), leaf mold (Fulvia fulva), late blight (Phytophthora infestans), wilt disease (Fusarium oxysporum), root rot (Pythium myriotylum, Pythium dissotocum), anthracnose (Colletotrichum gloeosporioides), canker (Clavibacter michiganensis), pith necrosis (Pseudomonas corrugata), bacterial black spot (Pseudomonas viridiflava), soft rot (Erwinia carotovora subsp. carotovora), bacterial leaf gall (Crynebacterium sp.), yellowing wilt (Phytoplasma asteris), yellow dwarf (Tobacco leaf curl subgroup III geminivirus); eggplants: powdery mildew (Sphaerotheca fuliginea, etc.), leaf mold (Mycovellosiella nattrassii), blight (Phytophthora infestans), brown rot (Phytophthora capsici), bacterial brown spot (Pseudomonas cichorii), necrotic leaf spot (Pseudomonas corrugata), bacterial stem rot (Erwinia chrysanthemi), soft rot (Erwinia carotovora subsp. carotovora), bacterial spot (Pseudomonas sp.); rapeseed: black spot (Alternaria brassicae), black rot (Xanthomonas campestris pv. campestris), bacterial black spot (Pseudomonas syringae pv. maculicola), soft rot (Erwinia carotovora); cruciferous vegetables: black spot (Alternaria brassicae, etc.), white spot (Cercosporella brassicae), black leg (Phoma lingam), club root (Plasmodiophora brassicae), downy mildew (Peronospora parasitica), black rot (Xanthomonas campestris pv. campestris), bacterial black spot (Pseudomonas syringae pv. maculicola), soft rot (Erwinia carotovora subsp. carotovora); cabbage: club foot (Thanatephorus cucumeris), yellowing wilt (Fusarium oxysporum), Alternaria sooty spot (Alternaria brassisicola); Chinese cabbage: bottom rot (Rhizoctonia solani), yellowing (Verticillium dahliae); green onions: rust (Puccinia allii), black spot (Alternaria porri), southern blight (Sclerotium rolfsii), white rot (Phytophthora porri), black rot (Sclerotium cepivorum); onions: canker (Curtobacterium flaccumfaciens), soft rot (Erwinia carotovora subsp. carotovora), bacterial spot (Pseudomonas syringae pv. syringae), rot (Erwinia rhapontici), scale rot (Burkholderia gladioli), yellowing wilt (Phytoplasma asteris); garlic: soft rot (Erwinia carotovora subsp. carotovora), spring rot (Pseudomonas marginalis pv. marginalis); soybeans: purple seed stain (Cercospora kikuchii), scab (Elsinoe glycines), black spot (Diaporthe phaseolorum), Rhizoctonia root rot (Rhizoctonia solani), stem rot (Phytophthora sojae), downy mildew (Peronospora manshurica), rust (Phakopsora pachyrhizi), anthracnose (Colletotrichum truncatum, etc.), leaf scald (Xanthomonas campestris pv. glycines), bacterial spot (Pseudomonas syringae pv. glycinea); green beans: anthracnose (Colletotrichum lindemuthianum), bacterial wilt (*Ralstonia solanacearum*), halo blight (*Pseudomonas syringae* pv. *phaseolicola*), bacterial brown spot (*Pseudomonas viridiflava*), leaf scald (*Xanthomonas campestris* pv. *phaseoli*); peanuts: leaf spot (*Mycosphaerella berkeleyi*), brown spot (*Mycosphaerella arachidis*), bacterial wilt (*Ralstonia solanacearum*); garden peas: powdery mildew (*Erysiphe pisi*), downy mildew (*Peronospora pisi*), bacterial stem blight (*Pseudomonas syringae* pv. *pisi*), bacterial stem rot (*Xanthomonas campestris* pv. *pisi*); broad beans: downy mildew (*Peronospora viciae*), blight (*Phytophthora nicotianae*); potatoes: early blight (*Alternaria solani*), black scurf (*Thanatephorus cucumeris*), blight (*Phytophthora infestans*), silver scurf (*Helminthosporium solani*), soft rot (*Fusarium oxysporum, Fusarium solani*), powdery scab (*Spongospora subterranea*), bacterial wilt (*Ralstonia solanacearum*), black foot disease (*Erwinia carotovora* subsp. *atroseptica*), common scab (*Streptomyces scabies, Streptomyces acidiscabies*), soft rot (*Erwinia carotovora* subsp. *carotovora*), slimy rot (*Crostridium* spp.), ring rot (*Clavibacter michiganensis* subsp. *sepedonicus*); sweet potatoes: damping-off (*Streptomyces ipomoeae*); beets: brown spot (*Cercospora beticola*), downy mildew (*Peronospora schachtii*), black root rot (*Aphanomyces cochioides*), leaf spot (*Phoma betae*), crown gall (*Agrobacterium tumefaciens*), scab (*Streptomyces scabies*), bacterial spot (*Pseudomonas syringae* pv. *aptata*); carrots: leaf blight (*Alternaria dauci*), bacterial gall (*Rhizobacter dauci*), crown gall (*Agrobacterium tumefaciens*), *Streptomyces* scab (*Streptomyces* spp.), soft rot (*Erwinia carotovora* subsp. *carotovora*); strawberries: powdery mildew (*Sphaerotheca aphanis* var. *aphanis*), blight (*Phytophthora nicotianae*, etc.), anthracnose (*Glomerella cingulata*, etc.), fruit rot (*Pythium ultimum*), bacterial wilt (*Ralstonia solanacearum*), angular leaf spot (*Xanthomonas campestris*), bacterial bud blight (*Pseudomonas marginalis* pv. *marginalis*); tea: net blister blight (*Exobasidium reticulatum*), white scab (*Elsinoe leucospila*), anthracnose (*Colletotrichum theae-sinensis*), ring spot (*Pestalotiopsis longiseta*), red blight (*Pseudomonas syringae* pv. *theae*), canker (*Xanthomonas campestris* pv. *theicola*), witch's broom (*Pseudomonas* sp.); tobacco: red spot (*Alternaria alternata*), powdery mildew (*Erysiphe cichoracearum*), anthracnose (*Colletotrichum gloeosporioides*), blight (*Phytophthora nicotianae*), wildfire (*Pseudomonas syringae* pv. *tabaci*), bacterial leaf spot (*Pseudomonas syringae* pv. *mellea*), hollow root (*Erwinia carotovora* subsp. *carotovora*), bacterial wilt (*Ralstonia solanacearum*), tobacco mosaic virus (Tobacco mosaic virus); coffee: rust (*Hemileia vastatrix*); banana: black sigatoka (*Mycosphaerella fijiensis*), panama disease (*Fusarium oxysporum* fsp *cubense*); cotton: damping-off (*Fusarium oxysporum*), frosty mildew (*Ramularia areola*); sunflowers: sclerotial disease (*Sclerotinia sclerotiorum*), angular leaf spot (*Xanthomonas campestris* pv. *malvacearum*), hollow root (*Erwinia carotovora* subsp. *carotovora*), bacterial spot (*Pseudomonas syringae* pv. *helianthi*); roses: black spot (*Diplocarpon rosae*), powdery mildew (*Sphaerotheca pannosa*, etc.), blight (*Phytophthora megasperma*), downy mildew (*Peronospora sparsa*), crown gall (*Agrobacterium tumefaciens*); chrysanthemums: brown spot (*Septoria obesa*), white rust (*Puccinia horiana*), blight (*Phytophthora cactorum*), bacterial spot (*Pseudomonas cichorii*), soft rot (*Erwinia carotovora* subsp. *carotovora*), crown gall (*Agrobacterium tumefaciens*), hairy root disease (*Agrobacterium rhizogenes*), Chrysanthemum virescence (*Phytoplasma aurantifolia*); grasses: brown patch disease (*Rhizoctonia solani*), dollar spot disease (*Sclerotinia homoeocarpa*), *Curvularia* leaf blight (*Curvularia* sp.), rust (*Puccinia zoysiae*), *helminthosporium* leaf blight (*Cochliobolus* sp.), scald (*Rhynchosporium secalis*), Zoysia decline (*Gaeumannomyces graminis*), anthracnose (*Colletotrichum* sp.), *Typhula* brown snow blight (*Typhula incarnata*), *Typhula* black snow blight (*Typhula ishikariensis*), *Sclerotinia* (*Myriosclerotinia borealis*), fairy ring disease (*Marasmius oreades*, etc.), *Pythium* blight (*Pythium aphanidermatum*, etc.), blast (*Pyricularia grisea*) and the like.

The compound of the present invention may be used with the present compound alone, but preferably can be mixed with a solid carrier, liquid carrier, gas carrier, surfactant, adhesive agent, dispersant, stabilizer, or the like and used as a composition, such as a powder, a water-dispersible powder, water-dispersible granules, a water-soluble powder, water-soluble granules, granules, an emulsion, a liquid, a microemulsion, an aqueous suspension preparation, an aqueous emulsion preparation or a suspoemulsion preparation. The form of the composition is not limited to the above-mentioned ones as long as the effects are exhibited.

Specific examples of formulations, which are not limitative, are given below.

Preparation Example 1: Flowable

The compound of the present invention (10 parts by mass), a sodium salt of naphthalene sulfonate formaldehyde condensate (5 parts by mass), polyoxyethylene aryl phenyl ether (1 part by mass), propylene glycol (5 parts by mass), a silicone antifoaming agent (0.1 part by mass), xanthan gum (0.2 part by mass) and ion exchanged water (78.7 parts by mass) are mixed to thereby obtain a slurry. The resultant slurry is wet-milled with Dyno-Mill KDL using glass beads having a diameter of 1.0 mm to thereby obtain a flowable.

Preparation Example 2: Emulsion

The compound of the present invention (5 parts by mass) is dissolved in a mixed solution of xylene (40 parts by mass) and cyclohexane (35 parts by mass). Tween 20 (20 parts by mass) is added to and mixed with the resultant solution to thereby obtain an emulsion.

Preparation Example 3: Water-Dispersible Powder

The compound of the present invention (10 parts by mass), white carbon (10 parts by mass), polyvinyl alcohol (2 parts by mass), dioctylsulfosuccinic acid sodium salt (0.5 part by mass), alkylbenzene sulfonic acid sodium salt (5 parts by mass), calcined diatomaceous earth (10 parts by mass) and kaolinite clay (62.5 parts by mass) are mixed thoroughly, and the resultant mixture is pulverized by an air mill to thereby obtain a water-dispersible powder.

Hereinbelow, explanation is made with respect to application of the composition comprising the compound of the present invention (such as an agricultural and horticultural pest control agent and an agricultural and horticultural fungicide).

As an example of a method for applying the composition comprising the compound of the present invention, there can be mentioned a method comprising bringing the composition into contact with a plant body or seeds, or a method comprising preparing cultivation soil containing the composition and bringing the cultivation soil into contact with the roots or underground stem of a plant. Specific examples of such method include a treatment of spraying the composition onto the stem and leaves of a plant individual, an injection treatment, a treatment of seedling nursery boxes, a cell tray treatment, a treatment of spraying the composition to plant seeds, a treatment of coating plant seeds with the composition, a treatment of immersing plant seeds into the composition, a treatment of dressing plant seeds with the composition, a treatment of spraying the composition onto the surface of soil, soil mixing after the treatment of spraying the composition onto the surface of the soil, a treatment of injecting the composition into soil, soil mixing after the treatment of injecting the composition into soil, a treatment of irrigating the composition into soil, soil mixing after the treatment of irrigating the composition into soil, and the like. The composition exhibits adequate effects when applied by any method usually used by a person skilled in the art.

The term "plant" referred to in the present invention means a creature which thrives by photosynthesis without moving. Specific examples of the plants include rice, wheat, barley, corn, coffee, bananas, grapes, apples, Japanese pears, peaches, cherries, persimmons, citrus fruits, soybeans, green beans, cotton, strawberries, potatoes, cabbage, lettuce, tomatoes, cucumbers, eggplants, watermelons, beets, spinach, poded peas, squash, sugar cane, tobacco, green peppers, sweet potatoes, taro potatoes, konjak, cotton, sunflowers, roses, tulips, chrysanthemums, turf grasses and the like, and F1 hybrids thereof and the like. Also included are gene recombinant crops created by artificially manipulating gene or the like, which does not occur in nature and, as examples, there can be mentioned agricultural and horticultural crops including soybeans, corn, cotton and the like to which resistance to herbicides had been imparted; rice, tobacco and the like acclimated to cold climates; corn, cotton and the like to which an ability to produce insecticidal substances had been imparted; and the like. Further, there can also be mentioned trees, such as pines, ash trees, ginkgos, maples, oaks, poplars and zelkova. The term "plant body" referred to in the present invention collectively means all the parts constituting an individual of the above-mentioned plant, and examples of such parts include stems, leaves, roots, seeds, flowers, fruits and the like.

The term "seed" referred to in the present invention means a matter which stores nutrients for germination of young plant and is used for agricultural breeding. Specific examples of seeds include seeds of corn, soybeans, cotton, rice, beets, wheat, barley, sunflowers, tomato, cucumbers, eggplants, spinach, poded peas, squash, sugar cane, tobacco, green peppers, rape and the like and F1 hybrids thereof and the like; seed potatoes of taro potatoes, potatoes, sweet potatoes, konjak and the like; bulbs of edible lilies, tulips and the like; seed bulbs of scallions and the like; and seeds, tubers and the like of gene recombinant crops.

The amount and concentration for the application of the composition comprising the compound of the present invention may vary depending on the target crop, target disease, degree of occurrence of the disease, dosage form of the compound, application method, various environmental conditions and the like and, in the case of spraying or irrigating, 0.1 to 10,000 g per hectare as the amount of the active ingredient is suitable, and 10 to 1,000 g per hectare is preferred. The amount used for the seed treatment is 0.0001 to 1,000 g, preferably 0.001 to 100 g, per 1 kg of seeds as an amount of effective ingredient. When the composition comprising the compound of the present invention is used for a treatment of spraying the composition onto the stem and leaves of a plant individual, a treatment of spraying the composition onto the surface of soil, a treatment of injecting the composition into soil or a treatment of irrigating the composition into soil, the treatment may be carried out after the composition is diluted with a suitable carrier to a suitable concentration. When the composition comprising the compound of the present invention is brought into contact with the plant seeds, the plant seeds may be subjected to immersion, dressing, spraying or coating treatment after the composition is diluted to a suitable concentration. The amount of the composition used for the immersion, dressing, spraying or coating treatment as the amount of the effective ingredient is usually approximately 0.05 to 50%, preferably 0.1 to 30%, relative to the dry weight of the plant seeds. However, the amount may be appropriately set depending on the form of the composition or the kind of the plant seeds to be treated and is not limited to these ranges.

If necessary, the composition comprising the compound of the present invention can be used in the form of a mixture with or in combination with another agricultural chemical, such as pesticides including fungicides, insecticides, acaricides, nematicides, herbicides, biological pesticides and plant growth regulators; disease control agents comprising nucleic acids as an active ingredient (WO 2014/062775); soil improvers; and fertilizing substances. As examples of methods in which the compound of the present invention is used in the form of a mixture with another agricultural chemical, there can be mentioned: a method in which the compound of the present invention formulated into one preparation together with another agricultural chemical is used; a method in which both of them each separately formulated into one preparation are mixed prior to use and used as the resultant mixture; a method in which both of them each separately formulated into one preparation are simultaneously but separately used; and a method in which both of them are each separately formulated into one preparation and, after one of these preparations is used, the rest of these preparations is used.

Specific examples of components (including the salts, isomers and N-oxides thereof) contained in the fungicide which can be used in the form of a mixture with the compound of the present invention are indicated as Group b given below. However, the known fungicides are not limited to these examples.

Group b:
b-1: Phenylamide-Based Fungicides
As phenylamide-based fungicides, there can be mentioned [b-1.1] benalaxyl, [b-1.2] benalaxyl-M or kiralaxyl, [b-1.3] furalaxyl, [b-1.4] metalaxyl, [b-1.5] metalaxyl-M or mefenoxam, [b-1.6] oxadixyl, [b-1.7] ofurace, and the like.

b-2: Karyokinesis and Cell Division Inhibitors
As karyokinesis and cell division inhibitors, there can be mentioned [b-2.1] benomyl, [b-2.2] carbendazim, [b-2.3] fuberidazole, [b-2.4] thiabendazole, [b-2.5] thiophanate, [b-2.6] thiophanate-methyl, [b-2.7] diethofencarb, [b-2,8] zoxamide, [b-2.9] ethaboxam, [b-2.10] pencycuron, [b-2.11] fluopicolide, [b-2.12] phenamacril, and the like.

b-3: Succinate Dehydrogenase Inhibitors (SDHI Agent)
As succinate dehydrogenase inhibitors (SDHI agent), there can be mentioned [b-3.1] benodanil, [b-3.2] benzovindiflupyr, [b-3.3] bixafen, [b-3.4] boscalid, [b-3.5] carboxin, [b-3.6] fenfuram, [b-3.7] fluopyram, [b-3.8] flutolanil, [b-3.9] fluxapyroxad, [b-3.10] furametpyr, [b-3.11] isofetamid, [b-3.12] isopyrazam, [b-3.13] mepronil, [b-3.14] oxycarboxin, [b-3.15] penthiopyrad, [b-3.16] penflufen, [b-3.17] pydiflumetofen, [b-3.18] sedaxane, [b-3.19] thifluzamide, [b-3.20] pyraziflumid, and the like.

b-4: Quinone Outside Inhibitors (QoI Agent)
As quinone outside inhibitors (QoI agent), there can be mentioned [b-4.1] azoxystrobin, [b-4.2] coumoxystrobin, [b-4.3] dimoxystrobin, [b-4.4] enoxastrobin, [b-4.5] famoxadone, [b-4.6] fenamidone, [b-4.7] fenaminstrobin,

[b-4.8] flufenoxystrobin, [b-4.9] fluoxastrobin, [b-4.10] kresoxim-methyl, [b-4.11] mandestrobin, [b-4.12] metominostrobin, [b-4.13] orysastrobin, [b-4.14] picoxystrobin, [b-4.15] pyraclostrobin, [b-4.16] pyrametostrobin, [b-4.17] pyraoxystrobin, [b-4.18] pyribencarb, [b-4.19] triclopyricarb, [b-4.20] trifloxystrobin, and the like.

b-5: Quinone Inside Inhibitors (QiI Agent)

As quinone inside inhibitors (QiI agent), there can be mentioned [b-5.1] cyazofamid, [b-5.2] amisulbrom, and the like.

b-6: Oxidative Phosphorylation Uncoupling Inhibitors

As oxidative phosphorylation uncoupling inhibitors, there can be mentioned [b-6.1] binapacryl, [b-6.2] meptyldinocap, [b-6.3] dinocap, [b-6.4] fluazinam, and the like.

b-7: Quinone outside stigmaterin binding subsite inhibitors (QoSI agent)

As quinone outside stigmaterin binding subsite inhibitors (QoSI agent), there can be mentioned [b-7.1] ametoctradin, and the like.

b-8: Amino Acid Biosynthesis Inhibitors

As amino acid biosynthesis inhibitors, there can be mentioned [b-8.1] cyprodinil, [b-8.2] mepanipyrim, [b-8.3] pyrimethanil, and the like.

b-9: Protein Biosynthesis Inhibitors

As protein biosynthesis inhibitors, there can be mentioned [b-9.1] streptomycin, [b-9.2] blasticidin-S, [b-9.3] kasugamycin, [b-9.4] oxytetracycline, and the like.

b-10: Signal Transduction Inhibitors

As signal transduction inhibitors, there can be mentioned [b-10.1] fenpiclonil, [b-10.2] fludioxonil, [b-10.3] quinoxyfen, [b-10.4] proquinazid, [b-10.5] chlozolinate, [b-10.6] dimethachlone, [b-10.7] iprodione, [b-10.8] procymidone, [b-10.9] vinclozolin, and the like.

b-11: Lipid and Cell Membrane Biosynthesis Inhibitors

As lipid and cell membrane biosynthesis inhibitors, there can be mentioned [b-11.1] edifenphos, [b-11.2] iprobenfos, [b-11.3] pyrazophos, [b-11.4] isoprothiolane, [b-11.5] biphenyl, [b-11.6] chloroneb, [b-11.7] dicloran, [b-11.8] quintozene, [b-11.9] tecnazene, [b-11.10] tolclofos-methyl, [b-11.11] echlomezol or etridiazole, [b-11.12] iodocarb, [b-11.13] propamocarb, [b-11.14] prothiocarb, and the like.

b-12: Demethylation Inhibitors (DMI Agent)

As demethylation inhibitors (DMI agent), there can be mentioned [b-12.1] azaconazole, [b-12.2] bitertanol, [b-12.3] bromuconazole, [b-12.4] cyproconazole, [b-12.5] difenoconazole, [b-12.6] diniconazole, [b-12.7] diniconazole-M, [b-12.8] epoxiconazole, [b-12.9] etaconazole, [b-12.10] fenarimol, [b-12.11] fenbuconazole, [b-12.12] fluquinconazole, [b-12.13] quinconazole, [b-12.14] flusilazole, [b-12.15] flutriafol, [b-12.16] hexaconazole, [b-12.17] imazalil, [b-12.18] imibenconazole, [b-12.19] ipconazole, [b-12.20] metconazole, [b-12.21] myclobutanil, [b-12.22] nuarimol, [b-12.23] oxpoconazole, [b-12.24] oxpoconazole fumarate, [b-12.25] pefurazoate, [b-12.26] penconazole, [b-12.27] prochloraz, [b-12.28] propiconazole, [b-12.29] prothioconazole, [b-12.30] pyrifenox, [b-12.31] pyrisoxazole, [b-12.32] simeconazole, [b-12.33] tebuconazole, [b-12.34] tetraconazole, [b-12.35] triadimefon, [b-12.36] triadimenol, [b-12.37] triflumizole, [b-12.38] triforine, [b-12.39] triticonazole [b-12.40] mefentrifluconazole, [b-12.41] ipfentrifluconazole, and the like.

b-13: Amine-Based Fungicides

As amine-based fungicides, there can be mentioned [b-13.1] aldimorph, [b-13.2] dodemorph, [b-13.3] fenpropimorph, [b-13.4] tridemorph, [b-13.5] fenpropidin, [b-13.6] piperalin, [b-13.7] spiroxamine, and the like.

b-14: 3-Ketoreductase Inhibitors in C4-Position Demethylation of Sterol Biosynthesis As 3-ketoreductase inhibitors in C4-position demethylation of sterol biosynthesis, there can be mentioned [b-14.1] fenhexamid, [b-14.2] fenpyrazamine, and the like.

b-15: Squalene Epoxidase Inhibitors of Sterol Biosynthesis

As squalene epoxidase inhibitors of sterol biosynthesis, there can be mentioned [b-15.1] pyributicarb, [b-15.2] naftifine, [b-15.3] terbinafine, and the like.

b-16: Cell Wall Biosynthesis Inhibitors

As cell wall biosynthesis inhibitors, there can be mentioned [b-16.1] polyoxins, [b-16.2] dimethomorph, [b-16.3] flumorph, [b-16.4] pyrimorph, [b-16.5] benthiavalicarb, [b-16.6] benthivalicarb-isopropyl, [b-16.7] iprovalicarb, [b-16.8] mandipropamid, [b-17.9] valifenalate, and the like.

b-17: Melanine Biosynthesis Inhibitors

As melanine biosynthesis inhibitors, there can be mentioned [b-17.1] phthalide or fthalide, [b-17.2] pyroquilone, [b-17.3] tricyclazole, [b-17.4] carpropamid, [b-17.5] diclocymet, [b-17.6] fenoxanil, [b-17.7] tolprocarb, and the like.

b-18: Host Plant Resistance Inducers

As host plant resistance inducers, there can be mentioned [b-18.1] acibenzolar-S-methyl, [b-18.2] probenazole, [b-18.3] tiadinil, [b-18.4] isotianil, [b-18.5] laminarin, and the like.

b-19: Dithiocarbamate-Based Fungicides

As dithiocarbamate-based fungicides, there can be mentioned [b-19.1] mancozeb or manzeb, [b-19.2] maneb, [b-19.3] metiram, [b-19.4] propineb, [b-19.5] thiram, [b-19.6] zineb, [b-19.7] ziram, [b-19.8] ferbam, and the like.

b-20: Phthalimide-Based Fungicides

As phthalimide-based fungicides, there can be mentioned [b-20.1] captan, [b-20.2] captafol, [b-20.3] folpet, [b-20.4] fluorofolpet, and the like.

b-21: Guanidine-Based Fungicides

As guanidine-based fungicides, there can be mentioned [b-21.1] guazatine, [b-21.2] iminoctadine, [b-21.3] iminoctadine albesilate, [b-21.4] iminoctadine triacetate, and the like.

b-22: Multi-Site Contact Activity Type Fungicides

As multi-site contact activity type fungicides, there can be mentioned [b-22.1] basic copper chloride (copper oxychloride), [b-22.2] copper(II) hydroxide, [b-22.3] basic copper sulfate (copper hydroxide sulfate), [b-22.4] organocopper compound, [b-22.5] dodecylbenzenesulphonic acid bisethylenediamine copper[II] complex salt (DBEDC), [b-22.6] sulphur, [b-22.7] fluoroimide, [b-22.8] chlorothalonil, [b-22.9] dichlofluanid, [b-22.10] tolylfluanid, [b-22.11] anilazine, [b-22.12] dithianon, [b-22.13] chinomethionat or quinomethionate, [b-22.14] extract from the cotyledons of lupine plantlets (BLAD), and the like.

b-23: Other Fungicides

As the other fungicides, there can be mentioned [b-23.1] dichlobentiazox, [b-23.2] fenpicoxamid, [b-23.3] dipymetitrone, [b-23.4] bupirimate, [b-23.5] dimethirimol, [b-23.6] ethirimol, [b-23.7] triphenyl tin acetate (fentin acetate), [b-23.8] triphenyltin chloride (fentin chloride), [b-23.9] triphenyltin hydroxide (fentin hydroxide), [b-23.10] oxolinic acid, [b-23.11] hymexazol, [b-23.12] octhilinone, [b-23.13] fosetyl, [b-23.14] phosphorous acid, [b-23.15] sodium phosphite, [b-23.16] ammonium phosphite, [b-23.17] potassium phosphite, [b-23.18] tecloftalam, [b-23.19] triazoxide, [b-23.20] flusulfamide, [b-23.21] diclomezine, [b-23.22] silthiofam, [b-23.23] diflumetorim, [b-23.24] methasulfocarb, [b-23.25] cyflufenamid, [b-23.26] metrafenone, [b-23.27] pyriofenone, [b-23.28] dodine,

[b-23.29] flutianil, [b-23.30] ferimzone, [b-23.31] oxathiapiprolin, [b-23.32] tebufloquin, [b-23.33] picarbutrazox, [b-23.34] validamycins, [b-23.35] cymoxanil, [b-23.36] quinofumelin,

[b-23.37] the Compound Represented by Formula (s1)

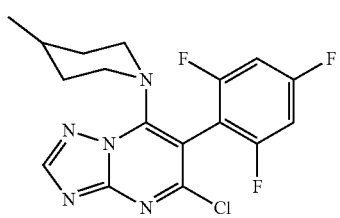

(see WO 98/046607),

[b-23.38] the Compound Represented by Formula (s2)

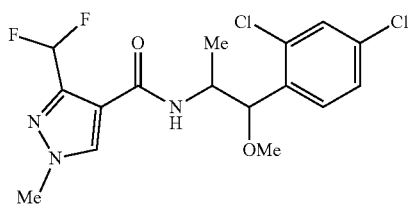

(see WO 08/148570),

[b-23.39] the Compound Represented by Formula (s3)

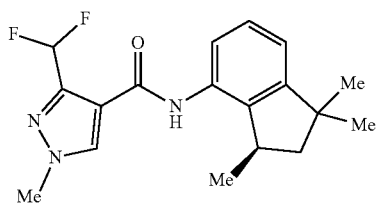

(see WO 92/012970),

[b-23.40] the Compound Represented by Formula (s4)

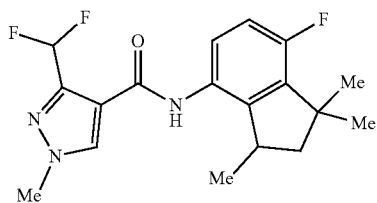

(see WO 12/084812),

[b-23.41] the Compound Represented by Formula (s5) (Gougerotin)

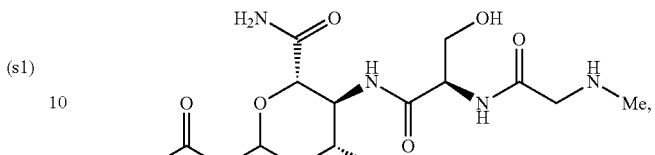

[b-23.42] the Compound Represented by Formula (s6) (Ningnanmycin)

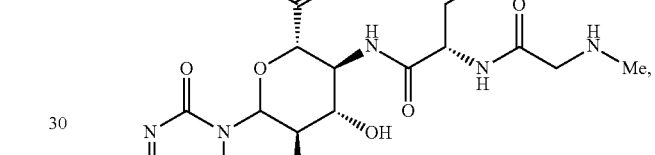

[b-23.43] the Compound Represented by Formula (s7)

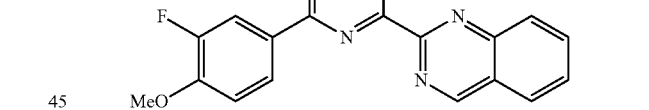

(see WO 10/136475),

[b-23.44] the Compound Represented by Formula (s8)

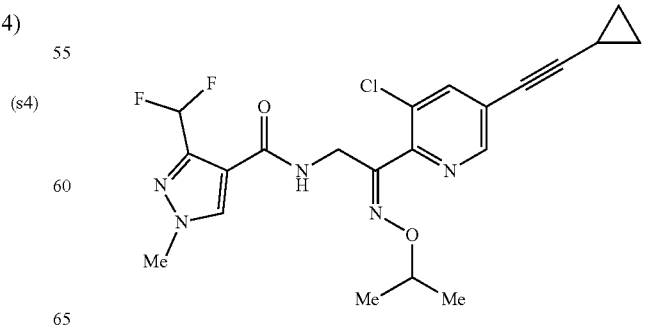

(see WO 14/010737),

[b-23.45] the Compound Represented by Formula (s9)

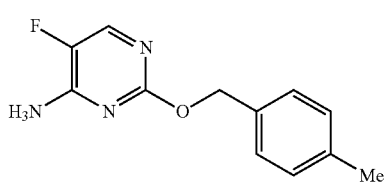

(see WO 11/085084),

[b-23.46] the Compound Represented by Formula (s10)

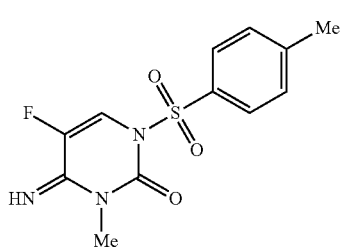

(see WO 11/137002),

[b-23.47] the Compound Represented by Formula (s11)

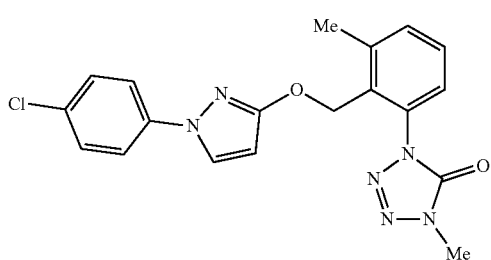

(see WO 13/162072),

[b-23.48] the Compound Represented by Formula (s12)

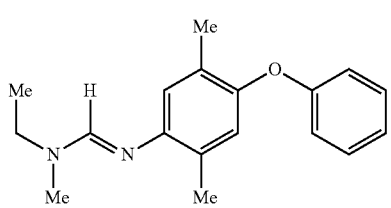

(see WO 08/110313),

[b-23.49] the Compound Represented by Formula (s13)

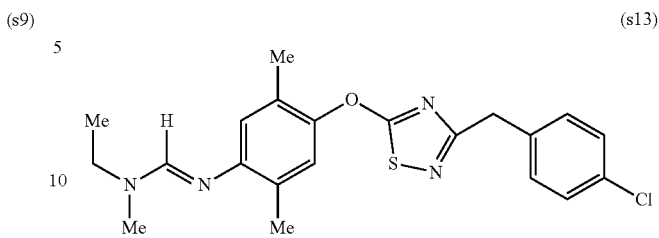

(see WO 09/156098),

[b-23.50] the Compound Represented by Formula (s14)

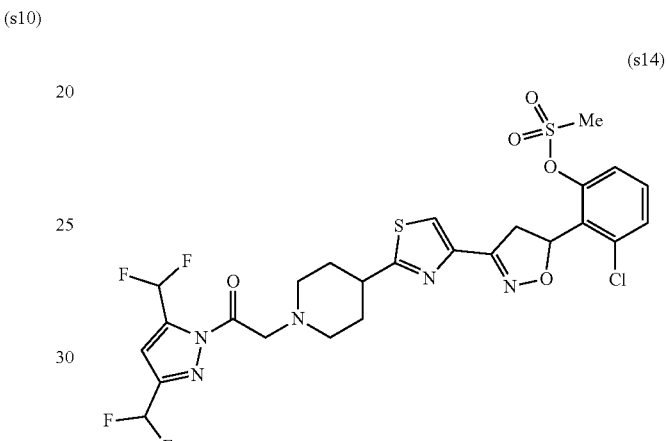

(see WO 12/025557),

[b-23.51] the Compound Represented by Formula (s15)

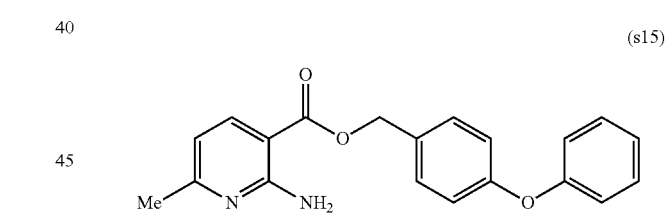

(see WO 14/006945),

[b-23.52] a Compound Represented by Formula (s16)

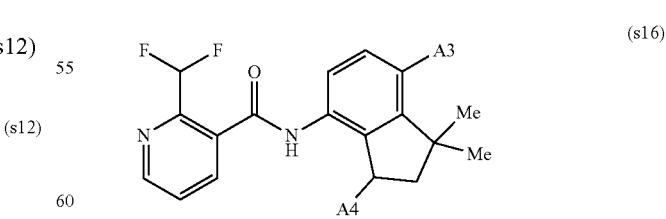

[wherein A3 represents a hydrogen atom, a halogen atom, a C1-C6 alkyl group, a C1-C6 haloalkyl group or a cyano group, and A4 represents a hydrogen atom, a C1-C6 alkyl group, a C1-C6 haloalkyl group or a C3-C8 cycloalkyl group] (see WO 14/095675),

[b-23.53] a Compound Represented by Formula (s17)

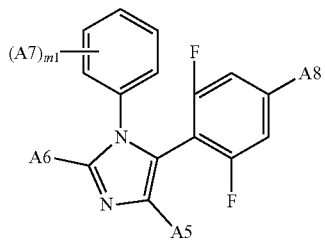

(s17)

[wherein m1 represents an integer of 0 to 3, A5 and A6 are independent to each other and each represent a halogen atom or a C1-C6 alkyl group, A7 and A8 are independent to each other and each represent a halogen atom or a C1-C6 alkoxy group and, when m1 is 2 or more, each of the 2 or more A7's independently represents a substituent which may be the same or different] (see WO 09/137538 and WO 09/137651),

[b-23.54] a Compound Represented by Formula (s18)

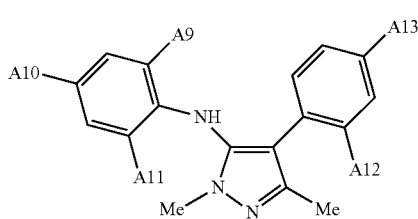

(s18)

[wherein A9 and A10 are independent to each other and each represent a hydrogen atom or halogen atom, A11 represents a halogen atom, A12 represents a halogen atom or a C1-C6 alkyl group, and A13 represents a halogen atom, a cyano group, a C1-C6 alkyl group or a C1-C6 alkoxy group] (see WO 12/031061),

[b-23.55] a Compound Represented by Formula (s19)

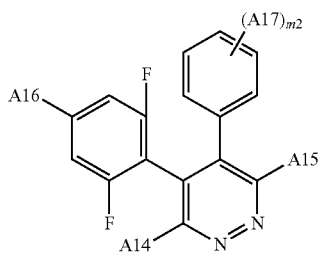

(s19)

[wherein m2 represents an integer of 0 to 6, A14 and A15 are independent to each other and each represent a halogen atom, a cyano group or C1-C6 alkyl group, A16 represents a hydrogen atom, a halogen atom or a C1-C6 alkoxy group, A17 represents a halogen atom or a C1-C6 alkoxy group, and when m2 is 2 or more, the 2 or more A17's each independently represent a substituent which may be the same or different] (see WO 05/121104),

[b-23.56] a Compound Represented by Formula (s20)

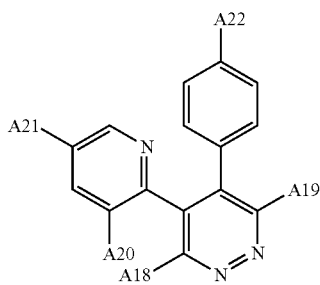

(s20)

[wherein A18 and A19 are independent to each other and each represent a halogen atom, a cyano group or a C1-C6 alkyl group, and A20, A21 and A22 are independent to each other and each represent a hydrogen atom, a halogen atom or a C1-C6 alkoxy group] (see WO 07/066601),

[b-23.57] a Compound Represented by Formula (s21)

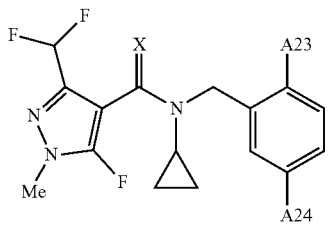

(s21)

[wherein A23 and A24 are independent to each other and each represent a hydrogen atom, a halogen atom, a C1-C6 alkyl group or a C3-C8 cycloalkyl group, and X represents an oxygen atom or a sulfur atom] (see WO 07/087906, WO 09/016220 and WO 10/130767),

[b-23.58] a Compound Represented by Formula (s22)

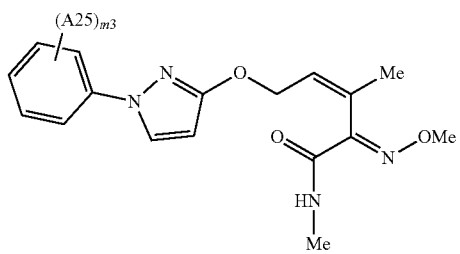

(s22)

[wherein m3 represents an integer of 0 to 5, A25 represents a halogen atom, a C1-C6 alkyl group, a C1-C6 haloalkyl group, a C1-C6 alkoxy group, a C1-C6 haloalkoxy group or a C3-C8 cycloalkyl group and, when m3 is 2 or more, each of the 2 or more A25's independently represents a substituent which may be the same or different] (see WO 13/092224),

[b-23.59] a Compound Represented by Formula (s23)

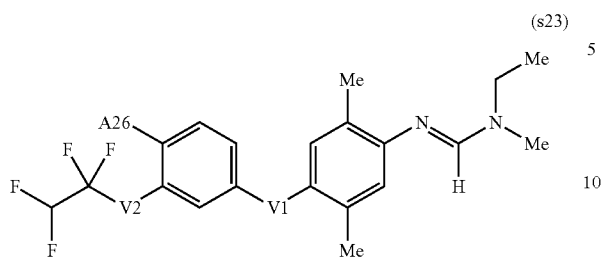

[wherein A26 represents a hydrogen atom or a halogen atom, and V1 and V2 are independent to each other and each represent an oxygen atom or a sulfur atom] (see WO 12/025450),

[b-23.60] a Compound Represented by Formula (s24) or Formula (s25)

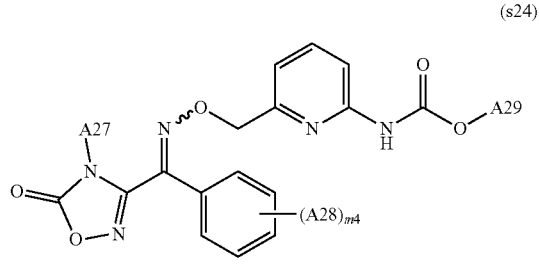

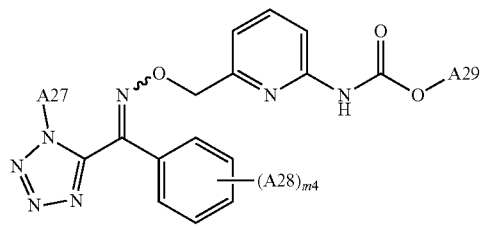

[wherein m4 represents an integer of 0 to 5, A27 represents a C1-C6 alkyl group, A28 represents a halogen atom, a cyano group, a C1-C6 alkyl group or a C1-C6 haloalkyl group, when m4 is 2 or more, each of the 2 or more A28's independently represents a substituent which may be the same or different, and A29 represents a C1-C6 alkyl group, a C2-C6 alkenyl group or a C3-C6 alkynyl group] (see WO 13/037717),

[b-23.61] a Compound Represented by Formula (s26) or Formula (s27)

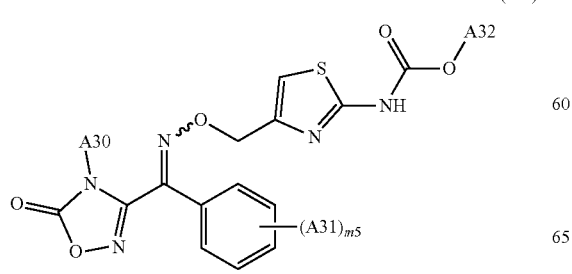

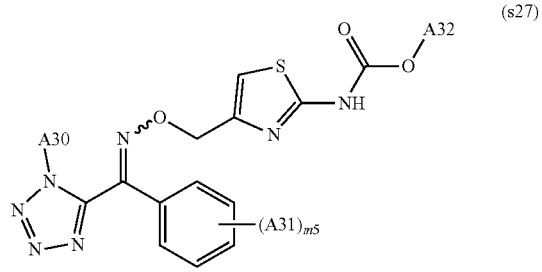

[wherein m5 represents an integer of 0 to 5, A30 represents a C1-C6 alkyl group, A31 represents a halogen atom, a cyano group, a C1-C6 alkyl group or a C1-C6 haloalkyl group, when m5 is 2 or more, each of the 2 or more A31's independently represents a substituent which may be the same or different, and A32 represents a C1-C6 alkyl group, a C2-C6 alkenyl group or a C3-C6 alkynyl group] (see WO 13/037717),

[b-23.62] a Compound Represented by Formula (s28)

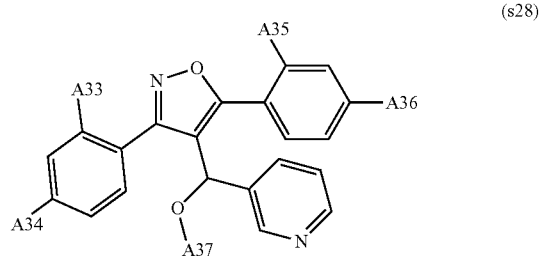

[wherein A33, A34, A35 and A36 are independent to each other and each represent a hydrogen atom or a halogen atom, and A37 represents a hydrogen atom, acetyl group or a benzoyl group] (see WO 06/031631 and WO 10/069882),

[b-23.63] a Compound Represented by Formula (s29)

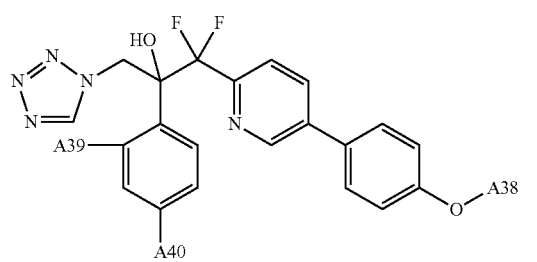

[wherein A38 represents a C1-C6 alkyl group or a C1-C6 haloalkyl group, and A39 and A40 are independent to each other and each represent a hydrogen atom or a halogen atom] (see WO 14/043376),

[b-23.64] a Compound Represented by Formula (s30)

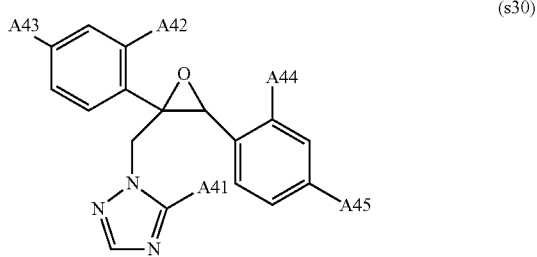

[wherein A41 represents a hydrogen atom, a sulfhydryl group (—SH), a thiocyanate group (—SCN) or a C1-C6 alkylthio group, and A42, A43, A44 and A45 are independent to each other and each represent a hydrogen atom or a halogen atom] (see WO 09/077443),

[b-23.65] a Compound Represented by Formula (s31) or Formula (s32)

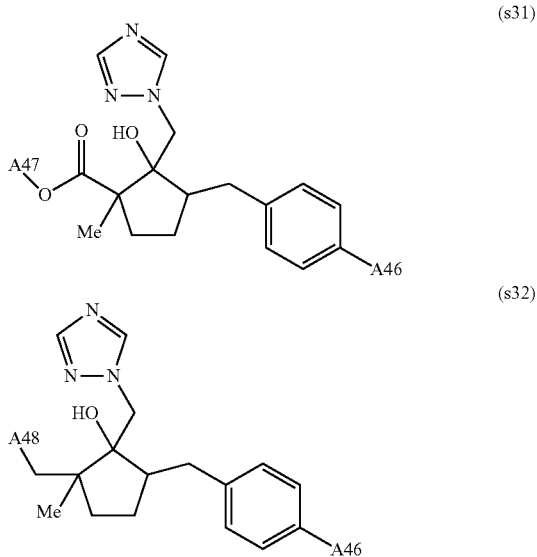

[wherein A46 represents a hydrogen atom or halogen atom, and A47 represents a C1-C6 alkyl group, and A48 represents a halogen atom] (see WO 11/070771),

[b-23.66] a Compound Represented by Formula (s33)

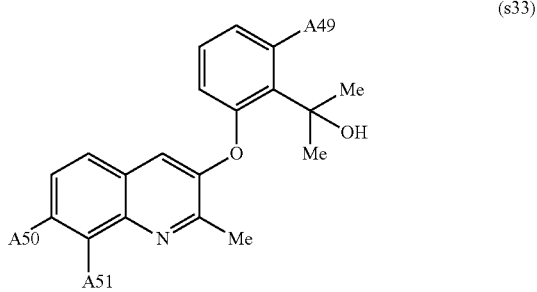

[wherein A49, A50 and A51 are independent to each other and each represent a hydrogen atom or a halogen atom] (see WO 11/081174), and the like.

Specific examples of components (including the salts, isomers and N-oxides thereof) contained in the insecticide which can be used in the form of a mixture with the compound of the present invention are indicated as Group c given below. However, the known insecticides are not limited to these examples.

Group c:

c-1: Carbamate-Based Acetylcholine Esterase (AChE) Inhibitors

As carbamate-based acetylcholine esterase (AChE) inhibitors, there can be mentioned [c-1.1] phosphocarb, [c-1.2] alanycarb, [c-1.3] butocarboxim, [c-1.4] butoxycarboxim, [c-1.5] thiodicarb, [c-1.6] thiofanox, [c-1.7] aldicarb, [c-1.8] bendiocarb, [c-1.9] benfuracarb, [c-1.10] carbaryl, [c-1.11] carbofuran, [c-1.12] carbosulfan, [c-1.13] ethiofencarb, [c-1.14] fenobucarb, [c-1.15] formetanate, [c-1.16] furathiocarb, [c-1.17] isoprocarb, [c-1.18] methiocarb, [c-1.19] methomyl, [c-1.20] oxamyl, [c-1.21] pirimicarb, [c-1.22] propoxur, [c-1.23] trimethacarb, [c-1.24] XMC (3,5-xylyl methylcarbamate), [c-1.25] allyxycarb, [c-1.26] aldoxycarb, [c-1.27] bufencarb, [c-1.28] butacarb, [c-1.29] carbanolate, [c-1.30] metolcarb, [c-1.31] xylylcarb, [c-1.32] fenothiocarb, [c-1.33] xylylcarb, [c-1.34] bendiocarb, and the like.

c-2: Organic Phosphorus-Based Acetylcholine Esterase (AChE) Inhibitors

As organic phosphorus-based acetylcholine esterase (AChE) inhibitors, there can be mentioned [c-2.1] acephate, [c-2.2] azamethiphos, [c-2.3] azinphos-methyl, [c-2.4] azinphos-ethyl, [c-2.5] ethephon, [c-2.6] cadusafos, [c-2.7] chlorethoxyfos, [c-2.8] chlorfenvinphos, [c-2.9] chlormephos, [c-2.10] chlorpyrifos, [c-2.11] chlorpyrifos-methyl, [c-2.12] coumaphos, [c-2.13] cyanophos, [c-2.14] demeton-S-methyl, [c-2.15] diazinon, [c-2.16] dichlofenthion, [c-2.17] dichlorvos, [c-2.18] dicrotophos, [c-2.19] dimethoate, [c-2.20] dimethylvinphos, [c-2.21] disulfoton, [c-2.22] O-ethyl O-4-nitrophenyl phenylphosphonothioate, [c-2.23] ethion, [c-2.24] ethoprophos, [c-2.25] famphur, [c-2.26] fenamiphos, [c-2.27] fenitrothion, [c-2.28] fenthion, [c-2.29] fosthiazate, [c-2.30] heptenophos, [c-2.31] isofenphos-methyl, [c-2.32] Isocarbophos, [c-2.33] isoxathion, [c-2.34] malathion, [c-2.35] mecarbam, [c-2.36] methamidophos, [c-2.37] methidathion, [c-2.38] mevinphos, [c-2.39] monocrotophos, [c-2.40] naled, [c-2.41] omethoate, [c-2.42] oxydemeton-methyl, [c-2.43] parathions, [c-2.44] parathion-methyl, [c-2.45] phenthoate, [c-2.46] phorate, [c-2.47] phosalone, [c-2.48] phosmet, [c-2.49] phosphamidon, [c-2.50] phoxim, [c-2.51] pirimiphos-methyl, [c-2.52] profenofos, [c-2.53] propetamphos, [c-2.54] prothiofos, [c-2.55] pyraclofos, [c-2.56] pyridaphenthion, [c-2.57] quinalphos, [c-2.58] sulfotep, [c-2.59] tebupirimfos, [c-2.60] temephos, [c-2.61] terbufos, [c-2.62] thiometon, [c-2.63] triazophos, [c-2.64] trichlorfon, [c-2.65] vamidothion, [c-2.66] chlorothion, [c-2.67] bromfenvinfos, [c-2.68] bromophos, [c-2.69] bromophos-ethyl, [c-2.70] butathiofos, [c-2.71] carbophenothion, [c-2.72] chlorphoxim, [c-2.73] sulprofos, [c-2.74] diamidafos, [c-2.75] tetrachlorvinphos, [c-2.76] propaphos, [c-2.77] mesulfenfos, [c-2.78] dioxabenzofos, [c-2.79] etrimfos, [c-2.80] oxydeprofos, [c-2.81] formothion, [c-2.82] fensulfothion, [c-2.83] isazofos, [c-2.84] imicyafos, [c-2.85] isamidofos, [c-2.86] thionazin, [c-2.87] fosthietan, and the like.

c-3: GABAergic Chlorine Ion Channel Blockers

As GABAergic chlorine ion channel blockers, there can be mentioned [c-3.1] chlordane, [c-3.2] endosulfan, [c-3.3] lindane, [c-3.4] dienochlor, [c-3.5] ethiprole, [c-3.6] fipronil, [c-3.7] acetoprole, and the like.

c-4: Sodium Channel Modulators

As sodium channel modulators, there can be mentioned [c-4.1] acrinathrin, [c-4.2] allethrin [(1R)-isomer], [c-4.3] bifenthrin, [c-4.4] bioallethrin, [c-4.5] bioallethrin S-cyclopentenyl isomer, [c-4.6] bioresmethrin, [c-4.7] cycloprothrin, [c-4.8] cyfluthrin, [c-4.9] beta-cyfluthrin, [c-4.10] cyhalothrin, [c-4.11] gamma-cyhalothrin, [c-4.12] lambda-cyhalothrin, [c-4.13] cypermethrin, [c-4.14] alpha-cypermethrin, [c-4.15] beta-cypermethrin, [c-4.16] theta-cypermethrin, [c-4.17] zeta-cypermethrin, [c-4.18] cyphenothrin [(1R)-trans-isomer], [c-4.19] deltamethrin, [c-4.20] empenthrin [(EZ)-(1R)-isomer], [c-4.21] esfenvalerate, [c-4.22] ethofenprox, [c-4.23] fenpropathrin, [c-4.24] fenvalerate, [c-4.25] flucythrinate, [c-4.26] flumethrin, [c-4.27] tau-fluvalinate, [c-4.28] halfenprox, [c-4.29] imiprothrin, [c-4.30] methothrin, [c-4.31] metofluthrin, [c-4.32] epsilon-metofluthrin, [c-4.33] momfluorothrin, [c-4.34] epsilon-momfluorothrin, [c-4.35] permethrin, [c-4.36] phenothrin [(1R)-trans-isomer], [c-4.37] prallethrin, [c-4.38] resmethrin, [c-4.39] kadethrin, [c-4.40] silafluofen, [c-4.41] tefluthrin, [c-4.42] tetramethrin, [c-4.43] tetramethrin [(1R)-isomer], [c-4.44] tralomethrin, [c-4.45] transfluthrin, [c-4.46] ZXI8901 (3-(4-bromophenoxy)phenyl]-cyanomethyl 4-(difluoromethoxy)-α-(1-methylethyl)benzeneacetate), [c-4.47] biopermethrin, [c-4.48] furamethrin, [c-4.49] profluthrin, [c-4.50] flubrocythrinate, [c-4.51] dimefluthrin, [c-4.52] DDT (dichloro-diphenyl-trichloroethane), [c-4.53] methoxychlor, [c-4.54] phenothrin, [c-4.55] fluvalinate, and the like.

c-5: Nicotinic Acetylcholine Receptor (nAChR) Competitive Modulators

As nicotinic acetylcholine receptor (nAChR) competitive modulators, there can be mentioned [c-5.1] acetamiprid, [c-5.2] clothianidin, [c-5.3] dinotefuran, [c-5.4] imidacloprid, [c-5.5] nitenpyram, [c-5.6] thiacloprid, [c-5.7] thiamethoxam, [c-5.8] nicotine, [c-5.9] nicotine sulfate, [c-5.10] sulfoxaflor, [c-5.11] flupyradifurone, [c-5.12] triflumezopyrim, and the like.

c-6: Nicotinic Acetylcholine Receptor (nAChR) Allosteric Modulators

As nicotinic acetylcholine receptor (nAChR) allosteric modulators, there can be mentioned [c-6.1] spinosad, [c-6.2] spinetoram, and the like.

c-7: Glutamate-Gated Chloride Ion Channel (GluCl) Allosteric Modulators

As glutamate-gated chloride ion channel (GluCl) allosteric modulators, there can be mentioned [c-7.1] abamectin, [c-7.2] emamectin benzoate, [c-7.3] lepimectin, [c-7.4] milbemectin, and the like.

c-8: Juvenile Hormone Analogues

As juvenile hormone analogues, there can be mentioned [c-8.1] hydroprene, [c-8.2] kinoprene, [c-8.3] methoprene, [c-8.4] fenoxycarb, [c-8.5] pyriproxyfen, and the like.

c-9: Nonspecific (Multisite) Inhibitors

As nonspecific (multisite) inhibitors, there can be mentioned [c-9.1] methyl bromide, [c-9.2] chloropicrin, [c-9.3] cryolite, [c-9.4] sulfuryl fluoride, [c-9.5] borax, [c-9.6] boric acid, [c-9.7] disodium octaborate, [c-9.8] sodium metaborate, [c-9.9] tartar emetic, [c-9.10] dazomet, [c-9.11] metam, [c-9.12] carbam sodium salt (metham sodium), and the like.

c-10: Chordotonal Organ TRPV Channel Modulators

Chordotonal organ TRPV channel modulators, there can be mentioned [c-10.1] pymetrozine, [c-10.2] pyrifluquinazon, and the like.

c-11: Acari Growth Inhibitors

As acari growth inhibitors, there can be mentioned [c-11.1] clofentezine, [c-11.2] diflovidazin, [c-11.3] hexythiazox, [c-11.4] etoxazole, and the like.

c-12: Mitochondrial ATP Synthase Inhibitors

As mitochondrial ATP synthase inhibitors, there can be mentioned [c-12.1] diafenthiuron, [c-12.2] azocyclotin, [c-12.3] cyhexatin, [c-12.4] fenbutatin oxide, [c-12.5] propargite, [c-12.6] tetradifon, and the like.

c-13: Uncouplers of Oxidative Phosphorylation Via Disruption of Proton Gradient

As uncouplers of oxidative phosphorylation via disruption of proton gradient, there can be mentioned [c-13.1] chlorfenapyr, [c-13.2] DNOC (dinitro-ortho-cresol), [c-13.3] binapacryl, [c-13.4] sulfluramid, and the like.

c-14: Nicotinic Acetylcholine Receptor (nAChR) Channel Blockers

As nicotinic acetylcholine receptor (nAChR) channel blockers, there can be mentioned [c-14.1] bensultap, [c-14.2] cartap hydrochloride, [c-14.3] thiocyclam, [c-14.4] monosultap, and the like.

c-15: Chitin Biosynthesis Inhibitors Type 0

As chitin biosynthesis inhibitors type 0, there can be mentioned [c-15.1] bistrifluron, [c-15.2] chlorfluazuron, [c-15.3] diflubenzuron, [c-15.4] flucycloxuron, [c-15.5] flufenoxuron, [c-15.6] hexaflumuron, [c-15.7] lufenuron, [c-15.8] novaluron, [c-15.9] noviflumuron, [c-15.10] teflubenzuron, [c-15.11] triflumuron, and the like.

c-16: Chitin Biosynthesis Inhibitor Type 1

As chitin biosynthesis inhibitor type 1, there can be mentioned [c-16.1] buprofezin, and the like.

c-17: Diptera Insect Molting Inhibitors

As diptera insect molting inhibitors, there can be mentioned [c-17.1] cyromazine, and the like.

c-18: Molting Hormone (Ecdysone) Receptor Agonists

As molting hormone (ecdysone) receptor agonists, there can be mentioned [c-18.1] chromafenozide, [c-18.2] halofenozide, [c-18.3] methoxyfenozide, [c-18.4] tebufenozide, and the like.

c-19: Octopamine Receptor Agonists

As octopamine receptor agonists, there can be mentioned [c-19.1] amitraz, and the like.

c-20: Mitochondrial Electron Transport System Complex III Inhibitors

As mitochondrial electron transport system complex III inhibitors, there can be mentioned [c-20.1] hydramethylnon, [c-20.2] acequinocyl, [c-20.3] fluacrypyrim, [c-20.4] bifenazate, and the like.

c-21: Mitochondrial Electron Transport System Complex I Inhibitors (METI)

As mitochondrial electron transport system complex I inhibitors (METI), there can be mentioned [c-21.1] fenazaquin, [c-21.2] fenpyroximate, [c-21.3] pyridaben, [c-21.4] pylimidifen, [c-21.5] tebufenpyrad, [c-21.6] tolfenpyrad, [c-21.7] rotenone, and the like.

c-22: Voltage-Gated Sodium Channel Blockers

As voltage-gated sodium channel blockers, there can be mentioned [c-22.1] indoxacarb, [c-22.2] metaflumizone, and the like.

c-23: Acetyl CoA Carboxylase Inhibitors

As acetyl CoA carboxylase inhibitors, there can be mentioned [c-23.1] spirodiclofen, [c-23.2] spiromesifen, [c-23.3] spirotetramat, and the like.

c-24: Mitochondrial Electron Transport System Complex IV Inhibitors

As mitochondrial electron transport system complex IV inhibitors, there can be mentioned [c-24.1] aluminum phosphide, [c-24.2] calcium phosphide, [c-24.3] hydrogen phosphide (phosphine), [c-24.4] zinc phosphide, [c-24.5] calcium cyanide, [c-24.6] sodium cyanide, [c-24.7] potassium cyanide, and the like.

c-25: Mitochondrial Electron Transport System Complex II Inhibitors

As mitochondrial electron transport system complex II inhibitors, there can be mentioned [c-25.1] cyenopyrafen, [c-25.2] cyflumetofen, [c-25.3] pyflubumide, and the like.

c-26: Ryanodine Receptor Modulators

As ryanodine receptor modulators, there can be mentioned [c-26.1] chlorantraniliprole, [c-26.2] cyantraniliprole, [c-26.3] flubendiamide, and the like.

c-27: Target Site-Unspecified Chordotonal Organ Modulators

As target site-unspecified chordotonal organ modulators, there can be mentioned [c-27.1] flonicamid, and the like.

c-28: Other Insecticides

As the other insecticides, there can be mentioned [c-28.1] azadirachtin, [c-28.2] benzoximate, [c-28.3] phenisobromolate, [c-28.4] chinomethionat, [c-28.5] dicofol, [c-28.6] pyridalyl, [c-28.7] bromopropylate, [c-28.8] triazamate, [c-28.9] dicyclanil, [c-28.10] dinobuton, [c-28.11] dinocap, [c-28.12] hydrogen cyanide, [c-28.13] methyl iodide, [c-28.14] karanjin, [c-28.15] mercury chloride, [c-28.16] methyl isothiocyanate, [c-28.17] pentachlorophenol, [c-28.18] phosphine, [c-28.19] piperonyl butoxide, [c-28.20] polynactin complex (polynactins), [c-28.21] sabadilla, [c-28.22] sulcofuron salt (sulcofuron-sodium), [c-28.23] tribufos, [c-28.24] aldrin, [c-28.25] amidithion, [c-28.26] amidothioate, [c-28.27] aminocarb, [c-28.28] amiton, [c-28.29] aramite, [c-28.30] athidathion, [c-28.31] azothoate, [c-28.32] barium polysulphide, [c-28.33] benclothiaz, [c-28.34] 5-(1,3-benzodioxol-5-yl)-3-hexylcyclohexa-2-enone, [c-28.35] 1,1-bis(4-chlorophenyl)-2-ethoxyethanol, [c-28.36] butonate, [c-28.37] butopyronoxyl, [c-28.38] 2-(2-butoxyethoxy)ethyl thiocyanate, [c-28.39] camphechlor, [c-28.40] chlorbenside, [c-28.41] chlordecone, [c-28.42] chlordimeform, [c-28.43] chlorfenethol, [c-28.44] chlorfenson, [c-28.45] fluazuron, [c-28.46] metaldehyde, [c-28.47] bialaphos, [c-28.48] levamisol hydrochloride (levamisol), [c-28.49] amidoflumet, [c-28.50] pyrafluprole, [c-28.51] pyriprole, [c-28.52] tralopyril, [c-28.53] flupyrazofos, [c-28.54] diofenolan, [c-28.55] chlorobenzilate, [c-28.56] flufenzine, [c-28.57] benzomate, [c-28.58] flufenerim, [c-28.59] albendazole, [c-28.60] oxibendazole, [c-28.61] fenbendazole, [c-28.62] metam-sodium, [c-28.63] 1,3-dichloropropene, [c-28.64] flometoquin, [c-28.65] cyclaniliprole, [c-28.66] tetraniliprole, [c-28.67] broflanilide, [c-28.68] dicloromezotiaz, [c-28.69] ethylene dibromide, [c-28.70] acrylonitrile, [c-28.71] bis(2-chloroethyl)ether, [c-28.72] 1-bromo-2-chloroethane, [c-28.73] 3-bromo-1-chloroprop-1-ene, [c-28.74] bromocyclen, [c-28.75] carbon disulfide, [c-28.76] carbon tetrachloride (tetrachloromethane), [c-28.77] nemadectin, [c-28.78] cymiazole, [c-28.79] calcium polysulfide, [c-28.80] cytokinin, [c-28.81] 2-(octylthio)ethanol, [c-28.82] potassium oleate, [c-28.83] sodium oleate, [c-28.84] machine oil, [c-28.85] tar oil, [c-28.86] anabasine, [c-28.87] morantel tartrate, [c-28.88] pyrethrum, [c-28.89] rape seed oil, [c-28.90] soybean lecithin, [c-28.91] starch, [c-28.92] hydroxypropyl starch, [c-28.93] fatty acid glyceride (decanoyloctanoylglycerol), [c-28.94] propylene glycol mono fatty acid ester (propylene glycol fatty acid ester), [c-28.95] diatomaceous earth (diatomite), [c-28.96] afoxolaner, [c-28.97] fluazaindolizine, [c-28.98] afidopyropen, [c-28.99] cyhalodiamide, [c-28.100] tioxazafen, [c-28.101] fluhexafon, [c-28.102] fluralaner, [c-28.103] fluxametamide, [c-28.104] tetrachlorantraniliprole, [c-28.105] sarolaner, [c-28.106] lotilaner, [c-28.107] cycloxaprid, [c-28.108] fluensulfone, [c-28.109] TPIC (tripropyl isocyanurate), [c-28.110] D-D (1,3-Dichloropropene), [c-28.111] peroxocarbonate, [c-28.112] MB-599 (verbutin), [c-28.113] bis(2,3,3,3-tetrachloropropyl)ether, [c-28.114] DCIP (bis(2-chloro-1-methylethyl)ether), [c-28.115] ENT-8184 (N-(2-Ethylhexyl)bicyclo[2.2.1] hept-5-ene-2,3-dicarboximide), [c-28.116] Bayer 22408 (O,O-diethyl O-naphthalimido phosphorothioate), [c-28.117] Bayer 32394 (tris(1-dodecyl-3-methyl-2-phenylbenzimidazolium)hexacyanoferrate),

[c-28.118] the Compound Represented by Formula (s34)

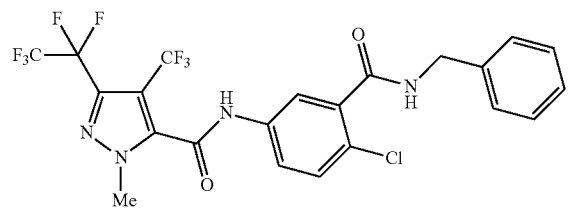

(s34)

(see WO 10/051926),

[c-28.119] the Compound Represented by Formula (s35)

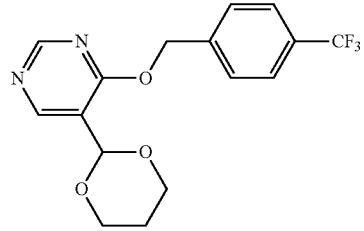

(s35)

(see WO 13/115391),

[c-28.120] the Compound Represented by Formula (s36)

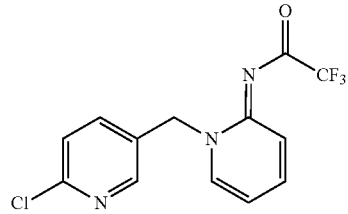

(s36)

(see WO 12/029672),

[c-28.121] the Compound Represented by Formula (s37)

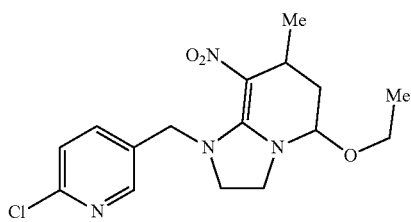

(see WO 06/056108),

[c-28.122] the Compound Represented by Formula (s38)

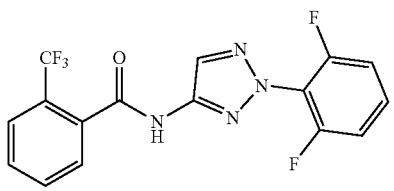

(see WO 14/053450 and WO 15/144683),

[c-28.123] the Compound Represented by Formula (s39)

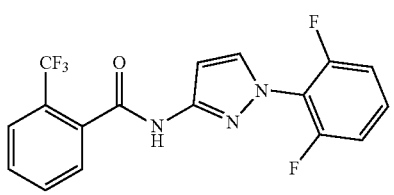

(see WO 14/053450 and WO 15/144683),

[c-28.124] the Compound Represented by Formula (s40)

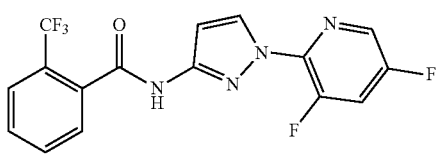

(see WO 14/053450 and WO 15/144683),

[c-28.125] a Compound Represented by Formula (s41)

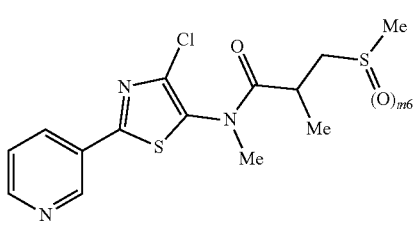

[wherein m6 represents an integer of 0 to 2] (see WO 10/129497),

[c-28.126] a Compound Represented by Formula (s42)

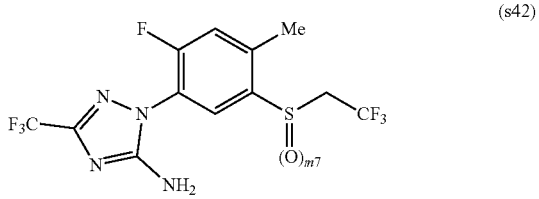

[wherein m7 represents an integer of 0 to 2] (see WO 11/152320),

[c-28.127] a compound represented by Formula (s43)

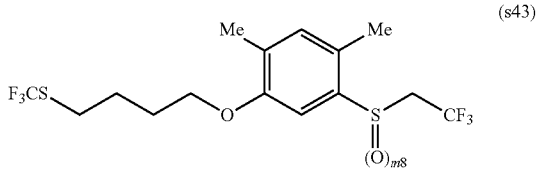

[wherein m8 represents an integer of 0 to 2] (see JP 2015-160813A),

[c-28.128] a compound represented by Formula (s44)

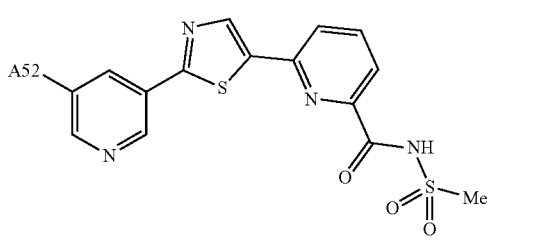

[wherein A52 represents a hydrogen atom or a fluorine atom] (see WO 11/134964 and WO 14/005982),

[c-28.129] a Compound Represented by Formula (s45)

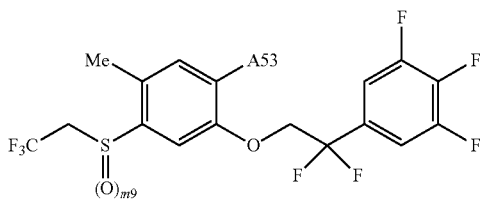

[wherein m9 represents an integer of 0 to 2, and A53 represents a fluorine atom or a chlorine atom] (see WO 15/025826),

[c-28.130] a Compound Represented by Formula (s46)

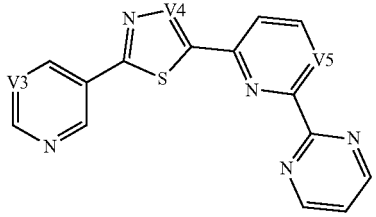
(s46)

[wherein V3 represents a nitrogen atom, a carbon atom or C—F, V4 and V5 are independent to each other and each represent a nitrogen atom or a carbon atom] (see WO 11/134964 and WO 14/005982),

[c-28.131] a Compound Represented by Formula (s47)

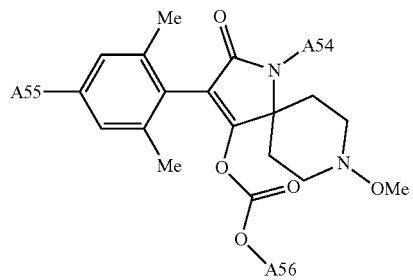
(s47)

[wherein A54 represents a hydrogen atom, a methyl group, a methoxy group or an ethoxy group, A55 represents a chlorine atom or a methyl group, and A56 represents a methyl group or an ethyl group] (see WO 09/049851),

[c-28.132] a Compound Represented by Formula (s48)

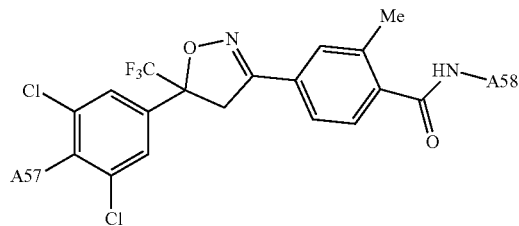
(s48)

[wherein A57 represents a hydrogen atom, a fluorine atom or a chlorine atom, and A58 represents one partial structure selected from the group consisting of

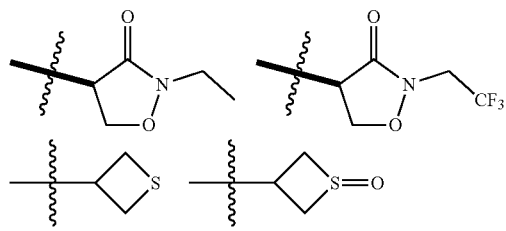

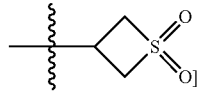

(see WO 11/067272),

[c-28.133] a Compound Represented by Formula (s49)

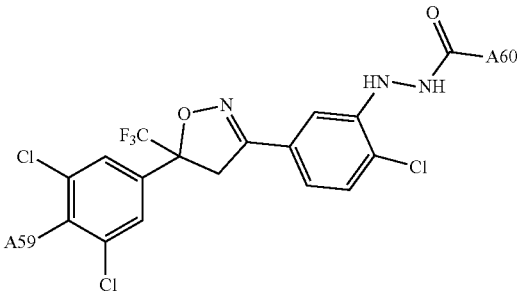
(s49)

[wherein A59 represents a hydrogen atom, a fluorine atom or a chlorine atom, and A60 represents a partial structure selected from the group consisting of

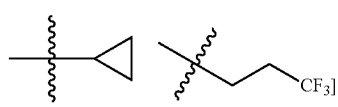

(see WO 10/090344),

[c-28.134] a Compound Represented by Formula (s50)

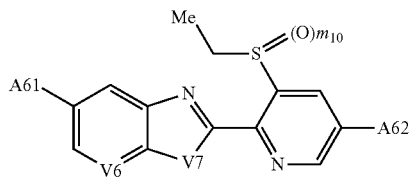
(s50)

[wherein m10 represents an integer of 0 to 2, A61 represents a trifluoromethyl group, a trifluoromethylthio group, a trifluoromethylsulfinyl group or a trifluoromethylsulfonyl group, A62 represents a hydrogen atom or a trifluoromethyl group, V6 represents a nitrogen atom or a carbon atom, and V7 represents an oxygen atom or an N-methyl group] (see WO 14/104407),

[c-28.135] a Compound Represented by Formula (s51)

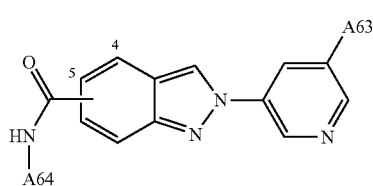
(s51)

[wherein A63 represents a hydrogen atom or a fluorine atom, the amide group is bonded to the 4-position or the 5-position, and A64 represents a partial structure selected from the group consisting of

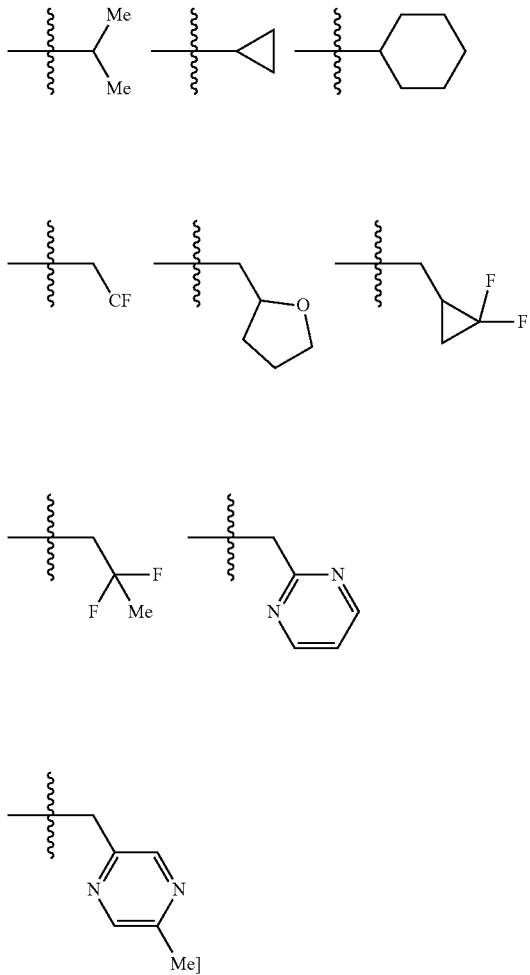

(see WO 15/038503, WO 16/144351 and WO 16/144678),
[c-28.136] a Compound Represented by Formula (s52)

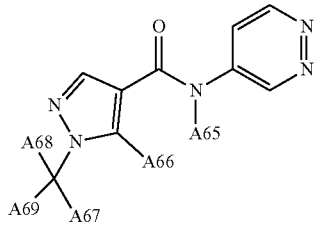

[wherein A65 represents a hydrogen atom, a C1-C6 alkyl group or a C1-C6 haloalkyl group, A66 represents a hydrogen atom, a halogen atom or a C1-C6 alkyl group, A67 and A68 are independent to each other and each represent a hydrogen atom, a C1-C6 alkyl group optionally substituted with a cyano group, an alkyl group optionally substituted with a methoxy group, an alkyl group optionally substituted with an ethoxy group or a C3-C8 cycloalkyl group, and A69 represents a hydrogen atom, a cyano group, a C1-C6 haloalkyl group optionally substituted with a cyano group, a C1-C6 alkyl group or a C3-C8 cycloalkyl group] (see WO 12/143317 and WO 16/016369),

[c-28.137] a Compound Represented by Formula (s53) or Formula (s54)

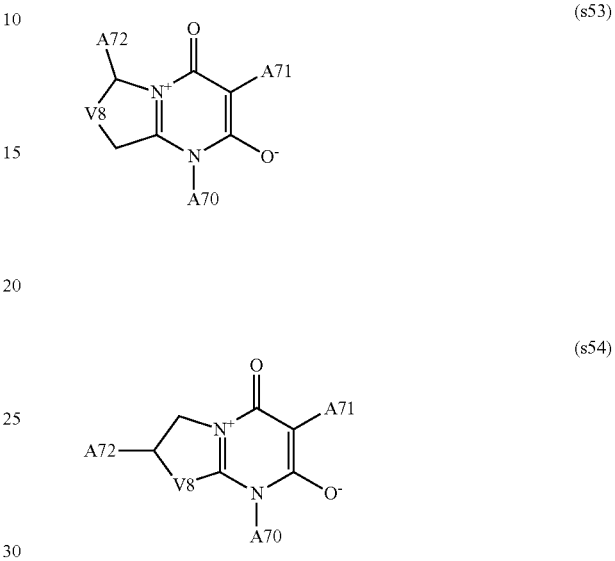

[wherein A70 represents a methyl group, an ethyl group, an isopropyl group, a 2,2,2-trifluoroethyl group or a phenyl group, A71 represents a partial structure selected from the group consisting of

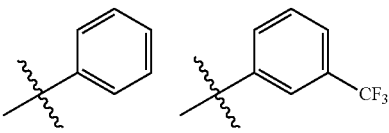

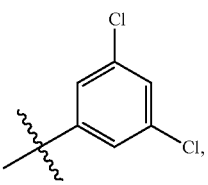

A72 represents a partial structure selected from the group consisting of

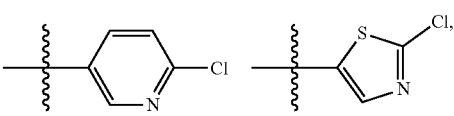 [SMILES: *c1ccc(Cl)nc1 ; *c1cnc(Cl)s1]

and V8 represents an oxygen atom, a sulfur atom, —CH$_2$— or —CH$_2$CH$_2$-] (see WO 14/167084 and WO 16/055431),

[c-28.138] a Compound Represented by Formula (s55)

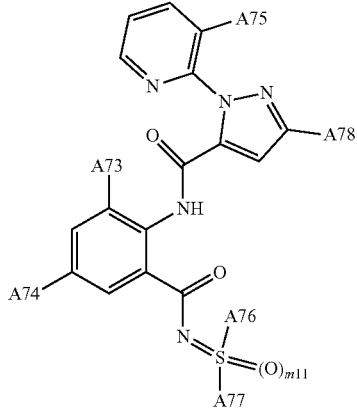
(s55)

[wherein m11 represents an integer of 0 to 1, A73 represents a chlorine atom, a bromine atom, a methyl group or a trifluoromethyl group, A74 represents a hydrogen atom, a chlorine atom, a bromine atom, a cyano group or a trifluoromethyl group, A75 represents a hydrogen atom, a chlorine atom or a bromine atom, A76 and A77 are independent to each other and each represent a C1-C6 alkyl group or a C3-C8 cycloalkyl group, and A78 represents a chlorine atom, a bromine atom, a cyano group, a nitro group, a difluoromethyl group or a trifluoromethyl group] (see WO 13/024009),

[c-28.139] a Compound Represented by Formula (s56)

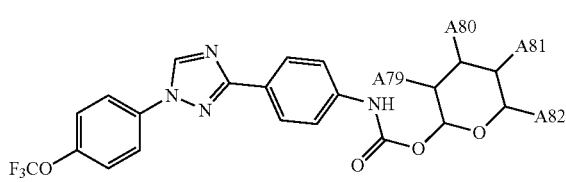
(s56)

[wherein A79, A80, A81 and A82 are independent to each other and each represent a hydrogen atom, a halogen atom, a C1-C6 alkyl group, a C1-C6 haloalkyl group, a C1-C6 alkoxy group or a C3-C8 cycloalkoxy group] (see WO 12/027521),

[c-28.140] a Compound Represented by Formula (s57)

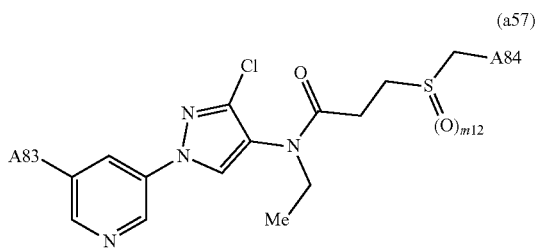
(a57)

[wherein m12 represents an integer of 0 to 2, A83 represents a hydrogen atom or a fluorine atom, and A84 represents a partial structure selected from the group consisting of

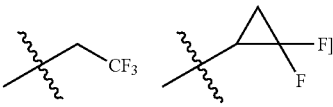

(see WO 13/162715),
[c-28.141] Acynonapyr,
[c-28.142] a Compound Represented by Formula (s59)

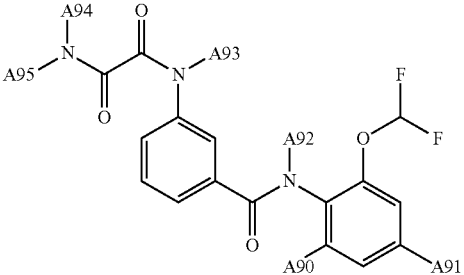
(s59)

[wherein A90 represents a halogen atom, a C1-C6 alkyl group or a C1-C6 haloalkyl group, A91 represents a C1-C6 haloalkyl group, A92 and A93 are independent to each other and each represent a hydrogen atom, a C1-C6 alkyl group, an acetyl group, a propionyl group, a methanesulfonylethyl group, a methoxycarbonyl group or an ethoxycarbonyl group, and A94 and A95 are independent to each other and each represent a hydrogen atom, a C1-C6 alkyl group or a C1-C6 haloalkyl group] (see WO 12/164698), and the like.

The ratio of mixing of the compound of the present invention with another agricultural chemical mentioned above, which may be used, if necessary, in the form of a mixture with the compound of the present invention, is not particularly limited, as long as the effects are effected. The weight ratio of another agricultural chemical relative to the compound of the present invention is usually 0.001 to 1,000, preferably 0.01 to 100.

EXAMPLES

Hereinbelow, the present invention will be described in more detail with reference to the following Examples, but not limited to these Examples.

Synthetic Example 1

Synthesis of 1-benzyl-3-bromo-5-chloro-2-(2,4,6-trifluorophenyl)pyridin-4(1H)-one (Compound No.: 49)

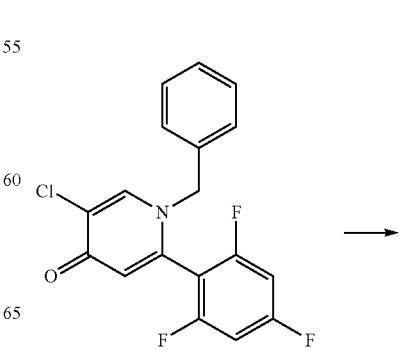

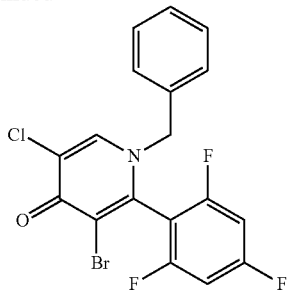

3 ml of a DMF solution containing 150 mg of 1-benzyl-5-chloro-2-(2,4,6-trifluorophenyl)pyridin-4(1H)-one and 145 mg of N-bromosuccinimide was stirred at 60° C. for 3 hours. The reaction mixture was cooled to room temperature, water and ethyl acetate were added and the layers were separated. The obtained organic layer was successively washed with an aqueous sodium thiosulfate solution and a saturated saline solution, and dried over sodium sulfate. The solvent was evaporated under reduced pressure, and the resultant residue was purified by silica gel column chromatography. The title compound was obtained as 141 mg of a white solid.

Synthetic Example 2

Synthesis of 3,5-dibromo-1-(2-chlorophenyl)-2-(2,4,6-trifluorophenyl)pyridin-4(1H)-one (Compound No.: 1)

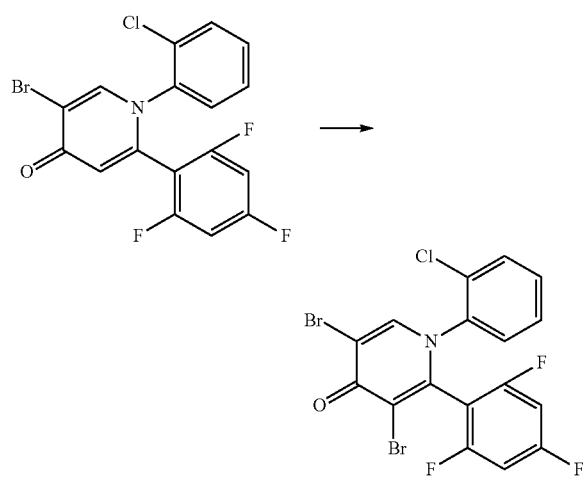

5 ml of a DMF solution containing 90 mg of 5-bromo-1-(2-chlorophenyl)-2-(2,4,6-trifluorophenyl)pyridin-4(1H)-one and 41 mg of N-bromosuccinimide was stirred at 70° C. for 1 hour. 80 mg of additional N-bromosuccinimide was added, and the resultant mixture was stirred for 2 hours. The reaction mixture was cooled to room temperature, water and ethyl acetate were added and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 89 mg of a white solid.

Synthetic Example 3

Synthesis of 5-bromo-3-chloro-1-(2-chlorophenyl)-2-(2,4,6-trifluorophenyl)pyridin-4(1H)-one (Compound No.: 2)

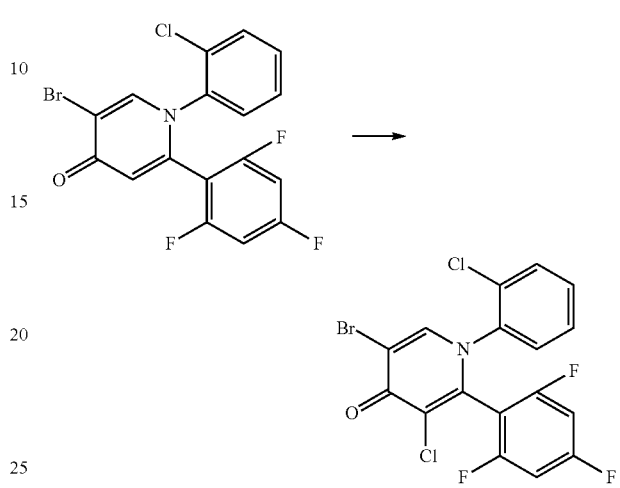

3 ml of a DMF solution containing 120 mg of 5-bromo-1-(2-chlorophenyl)-2-(2,4,6-trifluorophenyl)pyridin-4(1H)-one and 58 mg of N-chlorosuccinimide was stirred at 80° C. for 1 hour. 58 mg of additional N-chlorosuccinimide was added, and the resultant mixture was stirred for 1 hour. The reaction mixture was cooled to room temperature, water and ethyl acetate were added and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 104 mg of a white solid.

Synthetic Example 4

Synthesis of 3,5-dichloro-1-(2-chlorophenyl)-2-(2,4,6-trifluorophenyl)pyridin-4(1H)-one (Compound No.: 4)

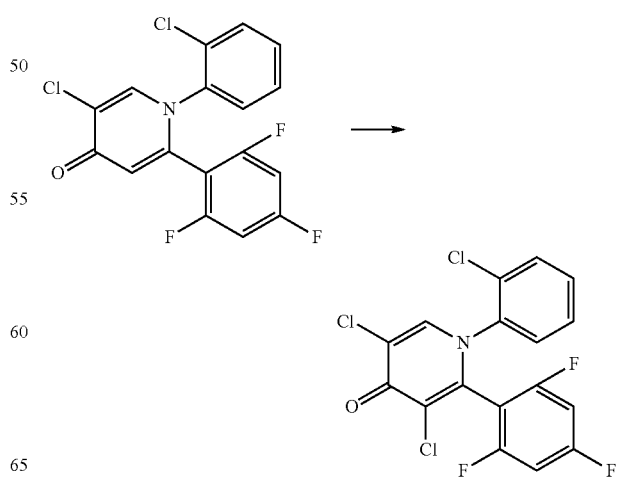

5 ml of a DMF solution containing 0.19 g of 5-chloro-1-(2-chlorophenyl)-2-(2,4,6-trifluorophenyl)pyridin-4(1H)-one and 0.21 g of N-chlorosuccinimide was stirred at 80° C. for 1.5 hours. The reaction mixture was cooled to room temperature, water and ethyl acetate were added and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 0.15 g of a white solid.

Synthetic Example 5

Synthesis of 3,5-dichloro-1-(2-chlorophenyl)-2-(2,6-difluoro-4-methoxyphenyl)pyridin-4(1H)-one (Compound No.: 5)

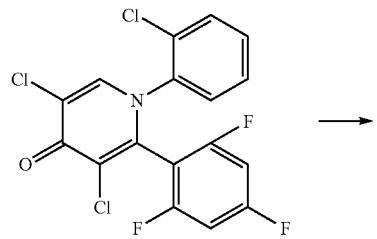

To 3 ml of a methanol solution containing 60 mg of 3,5-dichloro-1-(2-chlorophenyl)-2-(2,4,6-trifluorophenyl)pyridin-4(1H)-one was added 0.14 g of a 28% by weight methanol solution of sodium methoxide, and the resultant mixture was stirred under reflux for 1 hour. The reaction mixture was cooled to room temperature, 1N hydrochloric acid and ethyl acetate were added and the layers were separated. The obtained organic layer was washed with a saturated saline solution, and dried over sodium sulfate. The solvent was evaporated under reduced pressure, and the obtained residue was purified by silica gel column chromatography. The title compound was obtained as 59 mg of a white solid.

Synthetic Example 6

Synthesis of 3,5-dimethyl-1-(o-toluyl)-2-(2,4,6-trifluorophenyl)pyridin-4(1H)-one (Compound No.: 174)

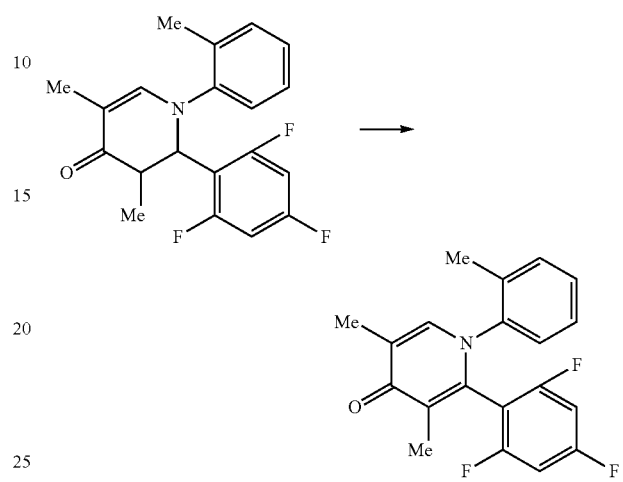

155 µl of bromine was added to 7 ml of an acetic acid solution containing 704 mg of 3,5-dimethyl-1-(o-toluyl)-2-(2,4,6-trifluorophenyl)-2,3-dihydropyridin-4(1H)-one obtained in Reference Example 9, and the resultant mixture was stirred at 80° C. for 30 minutes. The reaction mixture was cooled to room temperature, a saturated sodium hydrogen carbonate aqueous solution and ethyl acetate were added and the layers were separated. The obtained organic layer was washed with a saturated saline solution, and dried over magnesium sulfate. The solvent was evaporated under reduced pressure, and the obtained residue was purified by silica gel column chromatography. The title compound was obtained as 388 mg of a white solid.

Synthetic Example 7

Synthesis of 2-(2,6-difluoro-4-methoxyphenyl)-3,5-dimethyl-1-(o-toluyl)pyridin-4(1H)-one (Compound No.: 175)

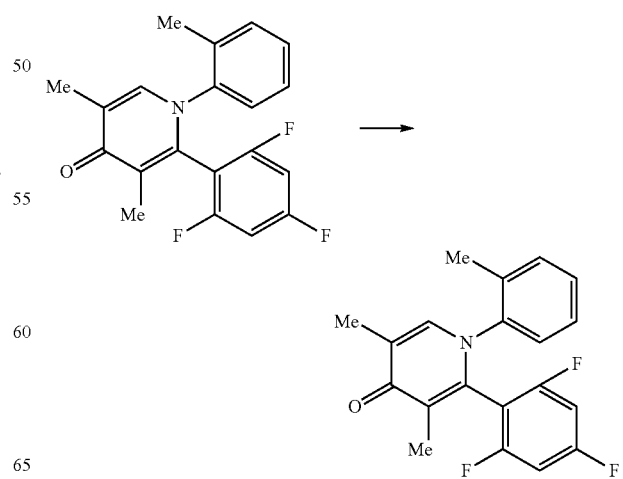

To 3 ml of a methanol solution containing 100 mg of 3,5-dimethyl-1-(o-toluyl)-2-(2,4,6-trifluorophenyl)pyridin-4(1H)-one was added 0.28 g of a 28% by weight methanol solution of sodium methoxide, and the resultant mixture was stirred under reflux for 3 hours. The reaction mixture was cooled to room temperature, water and ethyl acetate were added and the layers were separated. The obtained organic layer was washed with a saturated saline solution, and dried over magnesium sulfate. The solvent was evaporated under reduced pressure, and the obtained residue was purified by silica gel column chromatography. The title compound was obtained as 80 mg of a white solid.

Synthetic Example 8

Synthesis of 5-bromo-3-chloro-1-(5-methoxy-2-methylphenyl)-2-(2,4,6-trifluorophenyl)pyridin-4(1H)-one (Compound No.: 217)

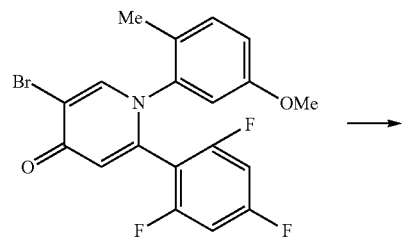

15 ml of a DMF solution containing 1.08 g of 5-bromo-1-(5-methoxy-2-methylphenyl)-2-(2,4,6-trifluorophenyl)pyridin-4(1H)-one and 0.38 g of N-chlorosuccinimide was stirred at 80° C. for 1.5 hours. The reaction mixture was cooled to room temperature, water and ethyl acetate were added and the layers were separated. The obtained organic layer was successively washed with an aqueous sodium thiosulfate solution and a saturated saline solution, and dried over magnesium sulfate. The solvent was evaporated under reduced pressure, and the obtained residue was purified by silica gel column chromatography. The title compound was obtained as 1.01 g of a white solid.

Synthetic Example 9

Synthesis of 5-bromo-3-chloro-1-(5-hydroxy-2-methylphenyl)-2-(2,4,6-trifluorophenyl)pyridin-4(1H)-one (Compound No.: 280)

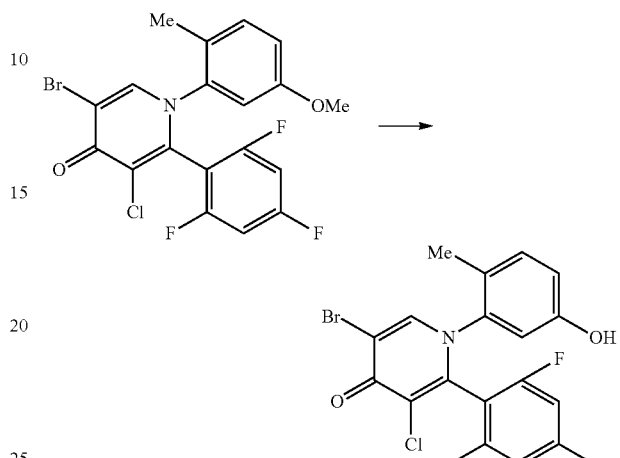

To 20 ml of a dichloromethane solution containing 1.01 g of 5-bromo-3-chloro-1-(5-methoxy-2-methylphenyl)-2-(2,4,6-trifluorophenyl)pyridin-4(1H)-one was added dropwise 4.40 ml of a 1.0 mol/l dichloromethane solution of boron tribromide. After stirring at room temperature for 2 hours, water and ethyl acetate were added to the reaction mixture and the layers were separated. The obtained organic layer was washed with a saturated saline solution, and dried over magnesium sulfate. The solvent was evaporated under reduced pressure, and the precipitate was washed with a mixed solution of ethyl acetate and diisopropyl ether (mixing ratio: 1/4). The title compound was obtained as 0.58 g of a white solid.

Synthetic Example 10

Synthesis of 5-bromo-3-chloro-1-(5-(methoxymethoxy)-2-methylphenyl)-2-(2,4,6-trifluorophenyl)pyridin-4(1H)-one (Compound No.: 285)

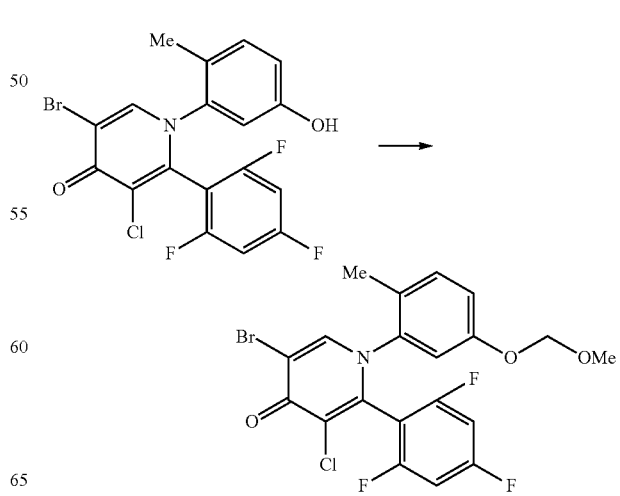

3 ml of a DMF solution containing 150 mg of 5-bromo-3-chloro-1-(5-hydroxy-2-methylphenyl)-2-(2,4,6-trifluorophenyl)pyridin-4(1H)-one was ice-cooled, and 20 mg of 60% sodium hydride and 38 μl of chloromethyl methyl ether was successively added. The temperature of the resultant mixture was raised from ice-cooling to room temperature, and then the reaction mixture was stirred for 2.5 hours, water and ethyl acetate were added and the layers were separated. The obtained organic layer was washed with a saturated saline solution, and dried over magnesium sulfate. The solvent was evaporated under reduced pressure, and the obtained residue was purified by silica gel column chromatography. The title compound was obtained as 99 mg of a white solid.

Synthetic Example 11

Synthesis of 5-bromo-3-chloro-2-(2,6-difluoro-4-methoxyphenyl)-1-(5-(methoxymethoxy)-2-methyl phenyl)pyridin-4(1H)-one (Compound No.: 286)

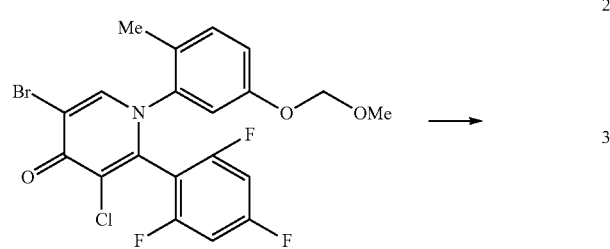

To 3 ml of a methanol solution containing 64 mg of 5-bromo-3-chloro-1-(5-(methoxymethoxy)-2-methylphenyl)-2-(2,4,6-trifluorophenyl)pyridin-4(1H)-one was added 0.50 g of a 28% by weight methanol solution of sodium methoxide, and the resultant mixture was stirred under reflux for 1.5 hours. The reaction mixture was cooled to room temperature, water and ethyl acetate were added and the layers were separated. The obtained organic layer was washed with a saturated saline solution, and dried over magnesium sulfate. The solvent was evaporated under reduced pressure, and the obtained residue was purified by silica gel column chromatography. The title compound was obtained as 62 mg white amorphous.

Synthetic Example 12

Synthesis of 5-bromo-1-(2,3-dimethylphenyl)-3-ethyl-2-(2,4,6-trifluorophenyl)pyridin-4(1H)-one (Compound No.: 528)

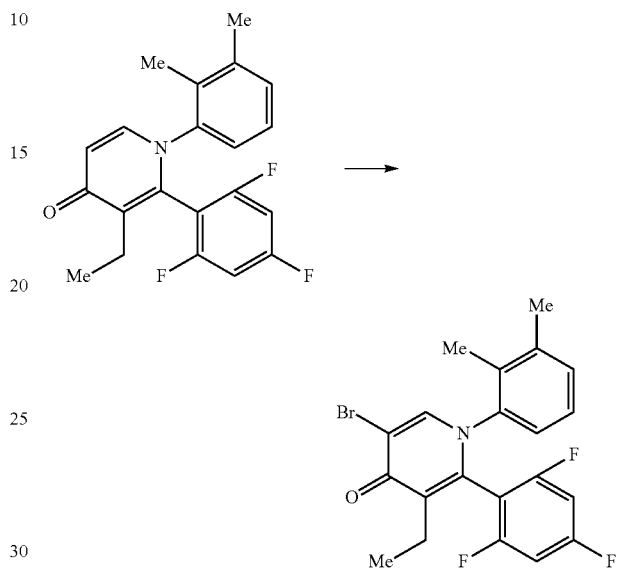

7 ml of a DMF solution containing 726 mg of 1-(2,3-dimethylphenyl)-3-ethyl-2-(2,4,6-trifluorophenyl)pyridin-4(1H)-one and 434 mg of N-bromosuccinimide was stirred at room temperature for 1 hour. Water and ethyl acetate were added to the reaction mixture and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 703 mg of a white solid.

Synthetic Example 13

Synthesis of 1-(2,3-dimethylphenyl)-3-ethyl-5-methyl-2-(2,4,6-trifluorophenyl)pyridin-4(1H)-one (Compound No.: 533)

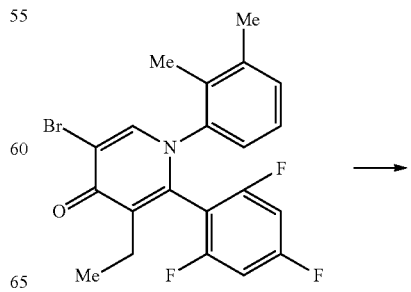

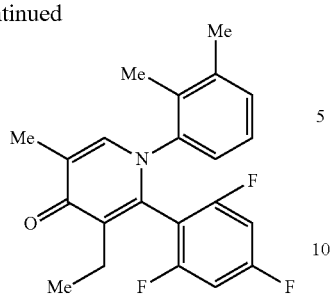

A solution of 277 mg of 5-bromo-1-(2,3-dimethylphenyl)-3-ethyl-2-(2,4,6-trifluorophenyl)pyridin-4(1H)-one, 152 mg of methylboronic acid, 14 mg of palladium acetate(II), 472 mg of tripotassium phosphate and 34 mg of tricyclohexylphosphine in a mixed solvent of 5 ml of toluene and 0.5 ml of water was stirred at 80° C. for 3.5 hours. The resultant mixture was further stirred at 100° C. for 2 hours and cooled to room temperature, and water and ethyl acetate were added to the reaction mixture and the layers were separated. The obtained organic layer was washed with a saturated saline solution, and dried over sodium sulfate. The solvent was evaporated under reduced pressure, and the obtained residue was purified by silica gel column chromatography. The title compound was obtained as 116 mg of a pale yellow solid.

Synthetic Example 14

Synthesis of 3,5-dichloro-1-(2-methylbutyl)-2-(2,4,6-trifluorophenyl)pyridin-4(1H)-one (Compound No.: 162)

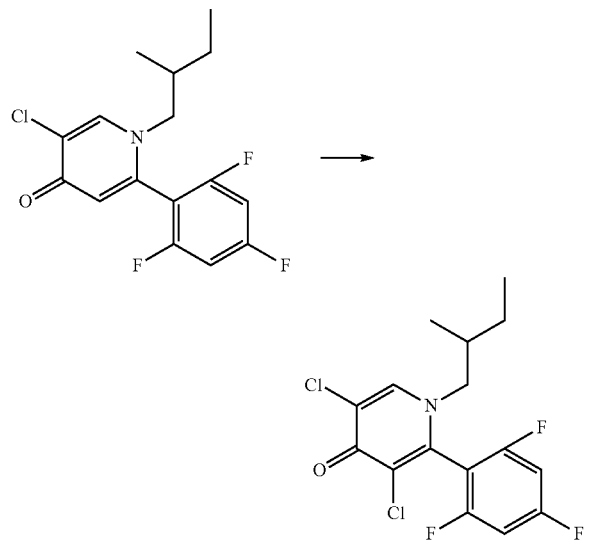

3 ml of a DMF solution containing 137 mg of 5-chloro-1-(2-methylbutyl)-2-(2,4,6-trifluorophenyl)pyridin-4(1H)-one and 83 mg of N-chlorosuccinimide was stirred at 80° C. for 2 hours. The reaction mixture was cooled to room temperature, water and ethyl acetate were added and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 46 mg of a pale yellow solid.

Synthetic Example 15

Synthesis of 3,5-dibromo-2'-chloro-2-(2,4,6-trifluorophenyl)-4H-[1,3'-bipyridin]-4-one (Compound No.: 38)

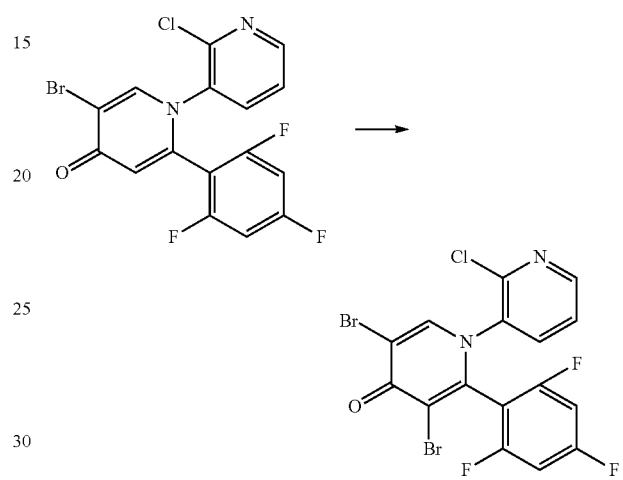

5 ml of a DMF solution containing 128 mg of 5-bromo-2'-chloro-2-(2,4,6-trifluorophenyl)-4H-[1,3'-bipyridin]-4-one and 82 mg of N-bromosuccinimide was stirred at 80° C. for 3 hours. 82 mg of additional N-bromosuccinimide was added, and the resultant mixture was stirred for 10 hours. The reaction mixture was cooled to room temperature, water and ethyl acetate were added and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 82 mg of a pale yellow solid.

Synthetic Example 16

Synthesis of 3-bromo-5-chloro-1-(5-methylisoxazol-3-yl)-2-(2,4,6-trifluorophenyl)pyridin-4(1H)-one (Compound No.: 141)

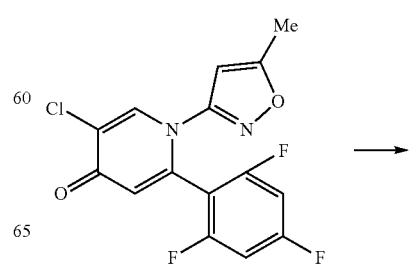

-continued

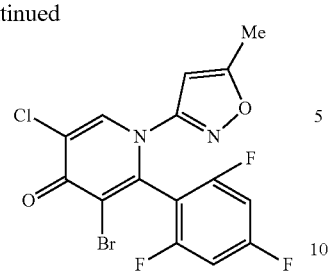

5 ml of a DMF solution containing 151 mg of 5-chloro-1-(5-methylisoxazol-3-yl)-2-(2,4,6-trifluorophenyl)pyridin-4(1H)-one and 789 mg of N-bromosuccinimide was stirred at 80° C. for 2 hours. The reaction mixture was cooled to room temperature, water and ethyl acetate were added and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 118 mg of a white solid.

Synthetic Example 17

Synthesis of 3-bromo-1-(4-bromo-5-methylisoxazol-3-yl)-5-chloro-2-(2,4,6-trifluorophenyl)pyridin-4(1H)-one (Compound No.: 142)

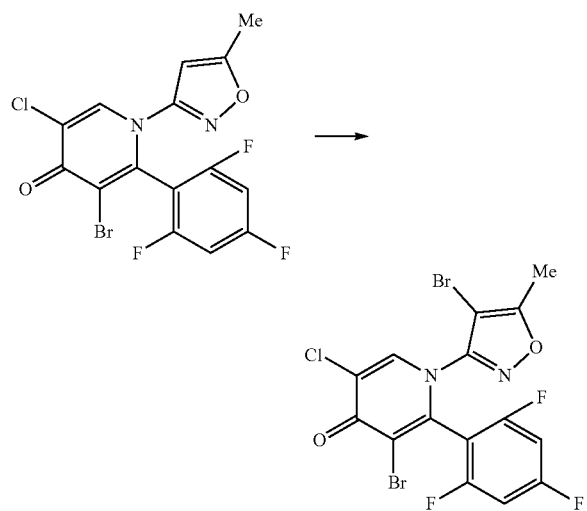

3 ml of an acetic acid solution containing 71 mg of 3-bromo-5-chloro-1-(5-methylisoxazol-3-yl)-2-(2,4,6-trifluorophenyl)pyridin-4(1H)-on e and 808 µl of bromine was stirred at 100° C. for 6.5 hours. 1.62 ml of additional bromine was added, and the resultant mixture was stirred at 100° C. for 2 hours. The reaction mixture was cooled to room temperature, an aqueous sodium thiosulfate solution and ethyl acetate were added and the layers were separated. The obtained organic layer was successively washed with a saturated sodium hydrogen carbonate aqueous solution and a saturated saline solution, and dried over sodium sulfate. The solvent was evaporated under reduced pressure, and the obtained residue was purified by silica gel column chromatography. The title compound was obtained as 14 mg of white amorphous.

Synthetic Example 18

Synthesis of 2-(4-chloro-2-fluorophenyl)-3,5-dimethyl-1-phenylpyridin-4(1H)-one (Compound No.: 577)

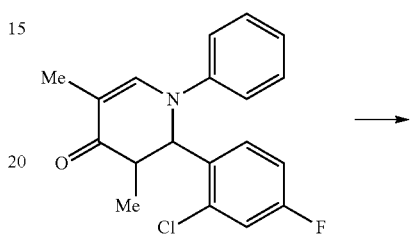

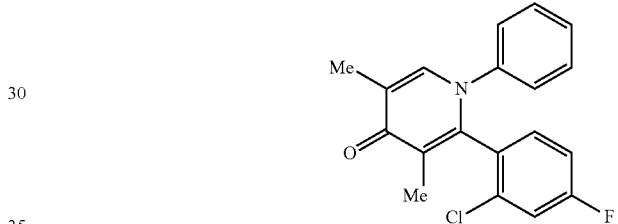

43 ml of an acetonitrile solution containing 2.14 g of 2-(4-chloro-2-fluorophenyl)-3,5-dimethyl-1-phenyl-2,3-dihydropyridin-4(1H)-one, 3.51 g of potassium peroxodisulfate ($K_2S_2O_8$) and 1.27 g of sulfuric acid was stirred for 1.5 hours under reflux. The reaction mixture was cooled to room temperature, a saturated sodium hydrogen carbonate aqueous solution and ethyl acetate were added and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 0.19 g of a pale brown solid.

Reference Example 1

Synthesis of 1-benzyl-2-(2,4,6-trifluorophenyl)-2,3-dihydropyridin-4(1H)-one

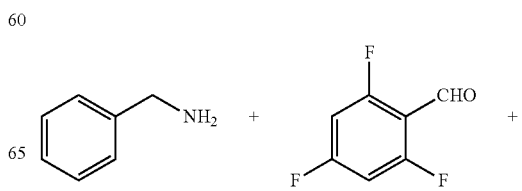

-continued

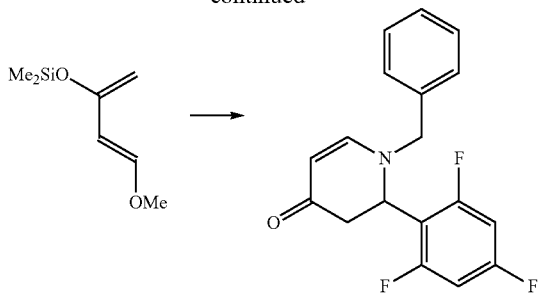

To 2.00 g of 2,4,6-trifluorobenzaldehyde was added 1.37 ml of benzylamine and the resultant mixture was stirred at 60° C. for 2.5 hours. The reaction mixture was cooled to room temperature, 30 ml of acetonitrile and 3.60 ml of 1-methoxy-3-(trimethoxysilyloxy)-1,3-butadiene were successively added to the reaction mixture, and then, the mixture resultant was ice-cooled. Then, 199 μl of 42% by weight aqueous solution of tetrafluoroboric acid was added, and the temperature of the resultant mixture was raised to 60° C. and the mixture was stirred for 2.5 hours. The reaction mixture was cooled to room temperature, a saturated sodium hydrogen carbonate aqueous solution and ethyl acetate were added and the layers were separated. The obtained organic layer was washed with a saturated saline solution, and dried over sodium sulfate. The solvent was evaporated under reduced pressure, and the obtained residue was purified by silica gel column chromatography. The title compound was obtained as 3.63 g of a yellow oil.

$^1$H-NMR (CDCl3) δ: 7.33-7.29 (3H, m), 7.26-7.24 (1H, m), 7.02-7.00 (2H, m), 6.70-6.63 (2H, m), 5.13 (1H, d, J=7.8 Hz), 4.96 (1H, dd, J=12.8, 6.3 Hz), 4.34 (1H, d, J=15.1 Hz), 4.05 (1H, d, J=15.1 Hz), 2.97 (1H, dd, J=16.5, 12.8 Hz), 2.56 (1H, dd, J=16.5, 6.3 Hz).

Reference Example 2

Synthesis of 1-benzyl-5-chloro-2-(2,4,6-trifluorophenyl)-2,3-dihydropyridin-4(1H)-one

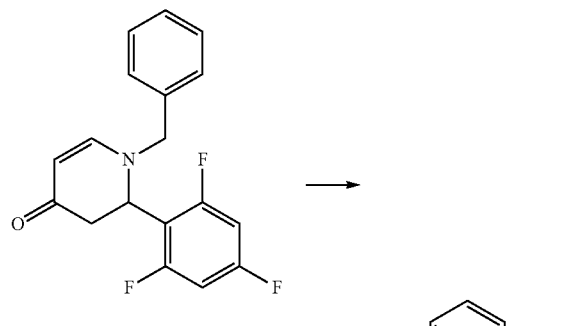

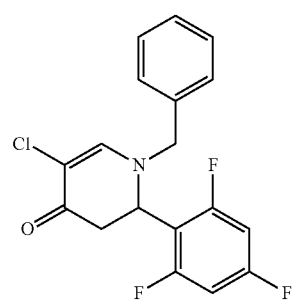

10 ml of DMF containing 1.00 g of 1-benzyl-2-(2,4,6-trifluorophenyl)-2,3-dihydropyridin-4(1H)-one and 463 mg of N-chlorosuccinimide was stirred at room temperature for 1 hour. Water and ethyl acetate were added to the reaction mixture and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 603 mg of a yellow oil.

$^1$H-NMR (CDCl3) δ: 7.51 (1H, s), 7.38-7.30 (3H, m), 7.03-7.01 (2H, m), 6.71-6.66 (2H, m), 4.99 (1H, dd, J=12.8, 6.2 Hz), 4.35 (1H, d, J=15.1 Hz), 4.07 (1H, d, J=15.1 Hz), 3.07 (1H, dd, J=16.6, 12.8 Hz), 2.72 (1H, dd, J=16.6, 6.2 Hz).

Reference Example 3

Synthesis of 1-benzyl-5-chloro-2-(2,4,6-trifluorophenyl)pyridin-4(1H)-one (Intermediate No.: a021)

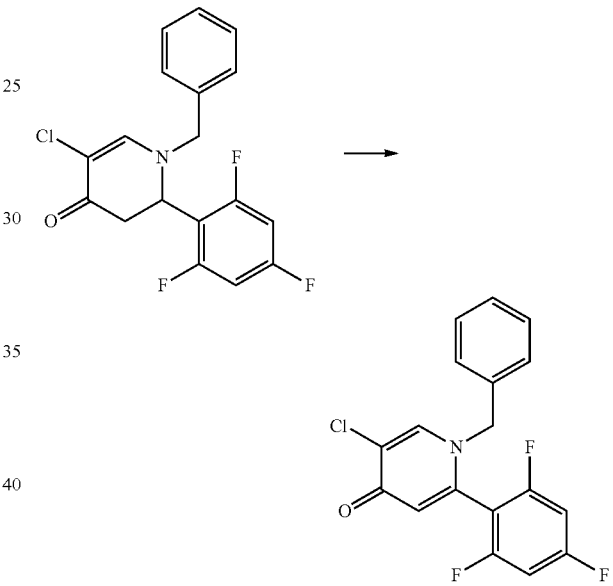

6 ml of a toluene solution containing 603 mg of 1-benzyl-5-chloro-2-(2,4,6-trifluorophenyl)-2,3-dihydropyridin-4(1H)-one and 584 mg of 2,3-dichloro-5,6-dicyano-p-benzoquinone was stirred at 100° C. for 3 hours. The reaction mixture was cooled to room temperature, and the solvent was evaporated under reduced pressure. The obtained residue was purified by silica gel column chromatography. The title compound was obtained as 353 mg of a white solid.

Among the compounds represented by Formula (1a), the compound represented by Formula (1a-a):

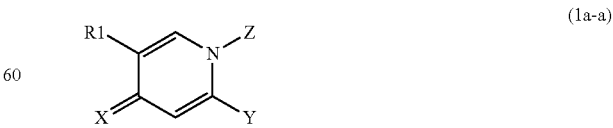

(wherein R1, X, Y and Z are the same as defined above) is an effective production intermediate for the production of the compound of the present invention. The production intermediate shown in Reference Example 3 (1-benzyl-5- chloro-2-(2,4,6-trifluorophenyl)pyridin-4(1H)-one) is encompassed by the compound represented by Formula (1a-a), and importance on the production is understood also from Synthetic Example 1.

Production intermediates represented by Formula (1a-a) are given in Table a, and corresponding $^1$H-NMR data of the compounds in Table a are given in Table A.

TABLE a

| Intermediate | R1 | Y | Z | X |
|---|---|---|---|---|
| a001 | Br | 2,4,6-tri-F—Ph | 2-Cl—Ph | O |
| a002 | Cl | 2,4,6-tri-F—Ph | 2-Cl—Ph | O |
| a003 | Cl | 2,4,6-tri-F—Ph | Pr | O |
| a004 | Br | 2,4,6-tri-F—Ph | Ph | O |
| a005 | Cl | 2,4,6-tri-F—Ph | iPr | O |
| a006 | Br | 2,4,6-tri-F—Ph | iPr | O |
| a007 | Cl | 2,4,6-tri-F—Ph | Ph | O |
| a008 | Cl | 2,6-di-F-4-MeO—Ph | Ph | O |
| a009 | Br | 2,4,6-tri-F—Ph | 2-F—Ph | O |
| a010 | Cl | 2,4,6-tri-F—Ph | 2-F—Ph | O |
| a011 | Br | 2,6-di-F-4-MeO—Ph | 2-F—Ph | O |
| a012 | Cl | 2,4,6-tri-F—Ph | cHex | O |
| a013 | Br | 2,4,6-tri-F—Ph | cHex | O |
| a014 | Cl | 2,6-di-F-4-MeO—Ph | 2-F—Ph | O |
| a015 | Cl | 2,4,6-tri-F—Ph | 2-Cl-3-Py | O |
| a016 | Br | 2,4,6-tri-F—Ph | 2-Cl-3-Py | O |
| a017 | Br | 2,4,6-tri-F—Ph | 2-Br—Ph | O |
| a018 | Cl | 2,4,6-tri-F—Ph | iPr(Me)CH— | O |
| a019 | Br | 2,4,6-tri-F—Ph | iPr(Me)CH— | O |
| a020 | Cl | 2,4,6-tri-F—Ph | 2-Br—Ph | O |
| a021 | Cl | 2,4,6-tri-F—Ph | PhCH2— | O |
| a022 | Br | 2,6-di-F—Ph | 2-Cl—Ph | O |
| a023 | Cl | 2,6-di-F—Ph | 2-Cl—Ph | O |
| a024 | Cl | 2,4,6-tri-F—Ph | 2-Me—Ph | O |
| a025 | Br | 2,4,6-tri-F—Ph | 2-Me—Ph | O |
| a026 | Cl | 2,4,6-tri-F—Ph | CF3CH2CH2CH2 | O |
| a027 | Br | 2,4,6-tri-F—Ph | CF3CH2CH2CH2 | O |
| a028 | Cl | 2,4,6-tri-F—Ph | Ph(Me)CH— | O |
| a029 | Br | 2,4,6-tri-F—Ph | Ph(Me)CH— | O |
| a030 | Cl | 2,4,6-tri-F—Ph | 2-MeO—Ph | O |
| a031 | Cl | 2,4,6-tri-F—Ph | (2-Cl—Ph)—CH2— | O |
| a032 | Br | 2,4,6-tri-F—Ph | (2-Cl—Ph)—CH2— | O |
| a033 | Br | 2,4,6-tri-F—Ph | 2-MeO—Ph | O |
| a034 | Br | 2,6-di-F-4-MeO—Ph | 2-MeO—Ph | O |
| a035 | Br | 2,6-di-F—Ph | 2-Br—Ph | O |
| a036 | Cl | 2,6-di-F—Ph | 2-Br—Ph | O |
| a037 | Cl | 2,4,6-tri-F—Ph | PhCH2CH2— | O |
| a038 | Br | 2,6-di-F—Ph | 2-Cl-4-F—Ph | O |
| a039 | Cl | 2,6-di-F—Ph | 2-Cl-4-F—Ph | O |
| a040 | Br | 2,4,6-tri-F—Ph | PhCH2CH2— | O |
| a041 | Br | 2,6-di-F—Ph | 2-Cl-5-F—Ph | O |
| a042 | Cl | 2,4,6-tri-F—Ph | iBu | O |
| a043 | Cl | 2,6-di-F—Ph | 2-Cl-5-F—Ph | O |
| a044 | Br | 2,6-di-F—Ph | 2-Me—Ph | O |
| a045 | Cl | 2,6-di-F—Ph | 2-Me—Ph | O |
| a046 | Cl | 2,4,6-tri-F—Ph | cHex—CH2— | O |
| a047 | Br | 2,4,6-tri-F—Ph | iBu | O |
| a048 | Br | 2,4,6-tri-F—Ph | 3-Br—Ph | O |
| a049 | Cl | 2,4,6-tri-F—Ph | 3-Br—Ph | O |
| a050 | Br | 2,4,6-tri-F—Ph | cHex—CH2— | O |
| a051 | Br | 2,4,6-tri-F—Ph | 3-Isoxazolyl | O |
| a052 | Cl | 2,4,6-tri-F—Ph | 3-Isoxazolyl | O |
| a053 | Cl | 2,4,6-tri-F—Ph | 5-Me-3-Isoxazolyl | O |
| a054 | Br | 2,4,6-tri-F—Ph | 3-Cl—Ph | O |
| a055 | Br | 2,4,6-tri-F—Ph | 5-Me-3-Isoxazolyl | O |
| a056 | Br | 2,4,6-tri-F—Ph | 2,5-di-Me—Ph | O |
| a057 | Cl | 2,4,6-tri-F—Ph | 2,5-di-Me—Ph | O |
| a058 | Cl | 2,4,6-tri-F—Ph | 2-Me—cHex | O |
| a059 | Br | 2,4,6-tri-F—Ph | 2-Me—cHex | O |
| a060 | Cl | 2,4,6-tri-F—Ph | 2-Me—Bu | O |
| a061 | Br | 2,4,6-tri-F—Ph | 2,3-di-Me—Ph | O |
| a062 | Br | 2,4,6-tri-F—Ph | 2-Me—Bu | O |
| a063 | Cl | 2,4,6-tri-F—Ph | 2,3-di-Me—Ph | O |
| a064 | Br | 2,4,6-tri-F—Ph | 5-F-2-Me—Ph | O |
| a065 | Cl | 2,4,6-tri-F—Ph | 5-F-2-Me—Ph | O |
| a066 | Br | 2,4,6-tri-F—Ph | 3-F-2-Me—Ph | O |
| a067 | Cl | 2,4,6-tri-F—Ph | 3-F-2-Me—Ph | O |
| a068 | Br | 2,4,6-tri-F—Ph | 2-F3C—Ph | O |

TABLE a-continued

| Intermediate | R1 | Y | Z | X |
|---|---|---|---|---|
| a069 | Cl | 2,4,6-tri-F—Ph | tBuCH2— | O |
| a070 | Br | 2,4,6-tri-F—Ph | tBuCH2— | O |
| a071 | Me | 2,4,6-tri-F—Ph | 2-Me—Ph | O |
| a072 | Cl | 2,4,6-tri-F—Ph | 2-F3C—Ph | O |
| a073 | Cl | 2,4,6-tri-F—Ph | iPrCH2CH2— | O |
| a074 | Br | 2,6-di-F—Ph | 2,5-di-Me—Ph | O |
| a075 | Cl | 2,6-di-F—Ph | 2,5-di-Me—Ph | O |
| a076 | Cl | 2,4,6-tri-F—Ph | MeOCH2CH2— | O |
| a077 | Br | 2,4,6-tri-F—Ph | MeOCH2CH2— | O |
| a078 | Br | 2,4,6-tri-F—Ph | 2-Me-5-MeO—Ph | O |
| a079 | Cl | 2,4,6-tri-F—Ph | 2-Me-5-MeO—Ph | O |
| a080 | Cl | 2,4,6-tri-F—Ph | Bu | O |
| a081 | Br | 2,4,6-tri-F—Ph | Bu | O |
| a082 | Br | 2,4,6-tri-F—Ph | 5-Cl-2-Me—Ph | O |
| a083 | Cl | 2,4,6-tri-F—Ph | 5-Cl-2-Me—Ph | O |
| a084 | Br | 2,4,6-tri-F—Ph | 5-Br-2-Me—Ph | O |
| a085 | Cl | 2,4,6-tri-F—Ph | 5-Br-2-Me—Ph | O |
| a086 | Br | 2,4,6-tri-F—Ph | 2,4-di-Me—Ph | O |
| a087 | Cl | 2,4,6-tri-F—Ph | 2,4-di-Me—Ph | O |
| a088 | Br | 2,4,6-tri-F—Ph | 2-Me-4-MeO—Ph | O |
| a089 | Cl | 2,4,6-tri-F—Ph | 2-Me-4-MeO—Ph | O |
| a090 | Br | 2,4,6-tri-F—Ph | 4-F-2-Me—Ph | O |
| a091 | Cl | 2,4,6-tri-F—Ph | 4-F-2-Me—Ph | O |
| a092 | Br | 2,4,6-tri-F—Ph | 2-F-6-Me—Ph | O |
| a093 | Cl | 2,4,6-tri-F—Ph | 2-F-6-Me—Ph | O |
| a094 | Br | 2,4,6-tri-F—Ph | 2,6-di-Me—Ph | O |
| a095 | Cl | 2,4,6-tri-F—Ph | 2,6-di-Me—Ph | O |
| a096 | Br | 2,4,6-tri-F—Ph | 2-Cl-6-Me—Ph | O |
| a097 | Br | 2,4,6-tri-F—Ph | 2-Me-5-F3C—Ph | O |
| a098 | Br | 2,4,6-tri-F—Ph | 2-Me-3-O2N—Ph | O |
| a099 | Cl | 2,4,6-tri-F—Ph | 2-Cl-6-Me—Ph | O |
| a100 | Br | 2,4,6-tri-F—Ph | 4-Cl-2-Me—Ph | O |
| a101 | Br | 2,4,6-tri-F—Ph | 3-Cl-2-Me—Ph | O |
| a102 | Br | 2,4,6-tri-F—Ph | 2-Me-5-O2N—Ph | O |
| a103 | Cl | 2,4,6-tri-F—Ph | 4-Cl-2-Me—Ph | O |
| a104 | Br | 2,4,6-tri-F—Ph | 2-Me-5-N≡C—Ph | O |
| a105 | Br | 2,4,6-tri-F—Ph | 3-Br-2-Me—Ph | O |
| a106 | Cl | 2,4,6-tri-F—Ph | 2-Et—Ph | O |
| a107 | Br | 4-F—Ph | 2,6-di-Me—Ph | O |
| a108 | Cl | 4-F—Ph | 2,6-di-Me—Ph | O |
| a109 | Br | 2,4,6-tri-F—Ph | 2-Me-3-F3C—Ph | O |
| a110 | Br | 2,4,6-tri-F—Ph | 2-Et—Ph | O |
| a111 | Br | 4-F—Ph | 2-F-6-Me—Ph | O |
| a112 | Cl | 4-F—Ph | 2-F-6-Me—Ph | O |
| a113 | Br | 2,6-di-F—Ph | Ph | O |
| a114 | Br | 2,4,6-tri-F—Ph | 2-Me-3-MeO—Ph | O |
| a115 | Br | 2,6-di-F—Ph | 2-F3C—Ph | O |
| a116 | Br | 4-F—Ph | 2-Cl-6-Me—Ph | O |
| a117 | Cl | 4-F—Ph | 2-Cl-6-Me—Ph | O |
| a118 | Br | 2,4,6-tri-F—Ph | 2-iPr—Ph | O |
| a119 | Cl | 2,4,6-tri-F—Ph | 2-iPr—Ph | O |
| a120 | Cl | 2,4,6-tri-F—Ph | 2-Me-3-O2N—Ph | O |
| a121 | Br | 4-Me—Ph | 2-Me—Ph | O |
| a122 | Cl | 2,4,6-tri-F—Ph | 2-Me-3-MeO—Ph | O |
| a123 | Cl | 2,4,6-tri-F—Ph | 2-Pr—Ph | O |
| a124 | Cl | 2,6-di-F—Ph | 5-F-2-Me—Ph | O |
| a125 | Br | Ph | 2,6-di-Me—Ph | O |
| a126 | Cl | Ph | 2,6-di-Me—Ph | O |
| a127 | Br | 2-Cl-4-F—Ph | Ph | O |
| a128 | Br | 4-F-2-Me—Ph | Ph | O |
| a129 | Br | 4-Cl-2-F—Ph | Ph | O |
| a130 | Br | 2,4-di-Cl—Ph | Ph | O |
| a131 | Br | 2,5-di-F—Ph | Ph | O |
| a132 | Br | 2,3-di-F—Ph | Ph | O |
| a133 | Br | 3,4-di-F—Ph | Ph | O |

TABLE A

| Intermediate | ¹H-NMR |
|---|---|
| a001 | ¹H-NMR (CDCl3) δ: 7.86 (1H, s), 7.42 (1H, dd, J = 8.4, 1.7 Hz), 7.36-7.33 (2H, m), 7.29-7.27 (1H, m), 6.61-6.55 (2H, m), 6.58 (1H, s). |
| a002 | ¹H-NMR (CDCl3) δ: 7.73 (1H, s), 7.43-7.41 (1H, m), 7.37-7.32 (2H, m), 7.28-7.27 (1H, m), 6.64-6.52 (2H, m), 6.60 (1H, s). |
| a003 | ¹H-NMR (CDCl3) δ: 7.75 (1H, s), 6.89-6.82 (2H, m), 6.45 (1H, s), 3.62-3.58 (2H, m), 1.66-1.61 (2H, m), 0.84 (3H, t, J = 7.4 Hz). |
| a004 | ¹H-NMR (CDCl3) δ: 8.00 (1H, s), 7.40-7.33 (3H, m), 7.21-7.18 (2H, m), 6.60-6.55 (3H, m). |
| a005 | ¹H-NMR (CDCl3) δ: 7.81 (1H, s), 6.89-6.83 (2H, m), 6.41 (1H, s), 4.05-3.99 (1H, m), 1.40 (6H, d, J = 6.8 Hz). |
| a006 | ¹H-NMR (CDCl3) δ: 7.94 (1H, s), 6.88-6.83 (2H, m), 6.39 (1H, s), 4.04-3.98 (1H, m), 1.40 (6H, d, J = 6.7 Hz). |
| a007 | ¹H-NMR (CDCl3) δ: 7.87 (1H, s), 7.40-7.33 (3H, m), 7.21-7.18 (2H, m), 6.61-6.54 (3H, m). |
| a008 | ¹H-NMR (CDCl3) δ: 7.86 (1H, s), 7.37-7.32 (3H, m), 7.19-7.19 (2H, m), 6.58 (1H, s), 6.33-6.30 (2H, m), 3.73 (3H, s). |
| a009 | ¹H-NMR (CDCl3) δ: 7.93 (1H, d, J = 0.6 Hz), 7.41-7.36 (1H, m), 7.30-7.29 (1H, m), 7.18-7.15 (1H, m), 7.12-7.08 (1H, m), 6.65-6.63 (1H, m), 6.58 (1H, s), 6.55-6.53 (1H, m). |
| a010 | ¹H-NMR (CDCl3) δ: 7.80 (1H, d, J = 0.7 Hz), 7.42-7.36 (1H, m), 7.30-7.28 (1H, m), 7.19-7.08 (2H, m), 6.65-6.62 (2H, m), 6.55-6.53 (1H, m). |
| a011 | ¹H-NMR (CDCl3) δ: 7.91 (1H, d, J = 0.6 Hz), 7.38-7.34 (1H, m), 7.29-7.27 (1H, m), 7.16-7.07 (2H, m), 6.58 (1H, s), 6.38-6.36 (1H, m), 6.30-6.27 (1H, m), 3.74 (3H, s). |
| a012 | ¹H-NMR (CDCl3) δ: 7.83 (1H, s), 6.90-6.83 (2H, m), 6.41 (1H, s), 3.49 (1H, tt, J = 12.2, 3.7 Hz), 1.95-1.87 (4H, br m), 1.67-1.58 (3H, br m), 1.20-1.12 (3H, br m). |
| a013 | ¹H-NMR (CDCl3) δ: 7.95 (1H, s), 6.88-6.83 (2H, m), 6.40 (1H, s), 3.52-3.45 (1H, m), 1.97-1.86 (4H, br m), 1.71-1.57 (3H, br m), 1.20-1.13 (3H, br m). |
| a014 | ¹H-NMR (CDCl3) δ: 7.79 (1H, d, J = 0.9 Hz), 7.39-7.34 (1H, m), 7.29-7.27 (1H, m), 7.15-7.14 (1H, m), 7.11-7.07 (1H, m), 6.60 (1H, s), 6.38-6.36 (1H, m), 6.30-6.28 (1H, m), 3.74 (3H, s). |
| a015 | ¹H-NMR (CDCl3) δ: 8.45 (1H, dd, J = 4.7, 1.7 Hz), 7.76 (1H, ddd, J = 7.9, 3.2, 1.7 Hz), 7.72 (1H, s), 7.33 (1H, dd, J = 7.9, 4.7 Hz), 6.68 (1H, tt, J = 8.8, 2.2 Hz), 6.62 (1H, s), 6.59-6.54 (1H, m). |
| a016 | ¹H-NMR (CDCl3) δ: 8.45 (1H, dd, J = 4.8, 1.7 Hz), 7.85 (1H, s), 7.76 (1H, ddd, J = 8.0, 3.4, 1.7 Hz), 7.33 (1H, dd, J = 8.0, 4.8 Hz), 6.69 (1H, tt, J = 8.7, 2.1 Hz), 6.60 (1H, s), 6.58-6.54 (1H, m). |
| a017 | ¹H-NMR (CDCl3) δ: 7.86 (1H, s), 7.61 (1H, dd, J = 7.7, 1.6 Hz), 7.37-7.25 (3H, m), 6.64-6.54 (3H, m). |
| a018 | ¹H-NMR (CDCl3) δ: 7.74 (1H, s), 6.89-6.81 (2H, m), 6.42 (1H, s), 3.41-3.34 (1H, m), 1.94-1.83 (1H, m), 1.45 (3H, d, J = 6.6 Hz), 0.92 (3H, d, J = 6.6 Hz), 0.71 (3H, dd, J = 6.6, 1.0 Hz). |
| a019 | ¹H-NMR (CDCl3) δ: 7.87 (1H, s), 6.89-6.81 (2H, m), 6.39 (1H, s), 3.40-3.33 (1H, m), 1.93-1.84 (1H, m), 1.45 (3H, d, J = 6.6 Hz), 0.92 (3H, d, J = 6.6 Hz), 0.71 (3H, dd, J = 6.6, 1.0 Hz). |
| a020 | ¹H-NMR (CDCl3) δ: 7.73 (1H, s), 7.61 (1H, dd, J = 7.8, 1.5 Hz), 7.38-7.25 (3H, m), 6.62-6.56 (3H, m). |
| a021 | ¹H-NMR (CDCl3) δ: 7.77 (1H, s), 7.33-7.31 (3H, m), 6.94-6.92 (2H, m), 6.77-6.72 (2H, m), 6.48 (1H, s), 4.83 (2H, s). |
| a022 | ¹H-NMR (CDCl3) δ: 7.88 (1H, s), 7.40 (1H, dd, J = 8.1, 1.4 Hz), 7.36-7.35 (1H, m), 7.29-7.26 (3H, m), 6.83-6.78 (2H, m), 6.60 (1H, s). |
| a023 | ¹H-NMR (CDCl3) δ: 7.75 (1H, s), 7.40 (1H, dd, J = 8.0, 1.5 Hz), 7.36-7.35 (1H, m), 7.29-7.26 (3H, m), 6.83-6.79 (2H, m), 6.62 (1H, s). |
| a024 | ¹H-NMR (CDCl3) δ: 7.74 (1H, s), 7.29-7.21 (2H, m), 7.15-7.13 (2H, m), 6.62-6.53 (3H, m), 2.18 (3H, s). |
| a025 | ¹H-NMR (CDCl3) δ: 7.87 (1H, s), 7.27-7.23 (2H, m), 7.16-7.13 (2H, m), 6.62-6.53 (3H, m), 2.18 (3H, s). |
| a026 | ¹H-NMR (CDCl3) δ: 7.74 (1H, s), 6.91-6.86 (2H, m), 6.46 (1H, s), 3.74-3.70 (2H, m), 2.08-1.98 (2H, m), 1.92-1.86 (2H, m). |
| a027 | ¹H-NMR (CDCl3) δ: 7.87 (1H, s), 6.91-6.85 (2H, m), 6.43 (1H, s), 3.73-3.71 (2H, m), 2.07-2.00 (3H, m), 1.93-1.85 (2H, m). |
| a028 | ¹H-NMR (CDCl3) δ: 7.57 (1H, s), 7.42-7.35 (3H, m), 7.16-7.13 (2H, m), 6.89 (1H, tt, J = 8.7, 2.1 Hz), 6.82 (1H, tt, J = 8.7, 2.1 Hz), 6.47 (1H, s), 5.08 (1H, q, J = 7.0 Hz), 1.76 (3H, d, J = 7.0 Hz). |
| a029 | ¹H-NMR (CDCl3) δ: 7.70 (1H, s), 7.42-7.35 (3H, m), 7.15-7.13 (2H, m), 6.89 (1H, tt, J = 8.7, 2.1 Hz), 6.82 (1H, tt, J = 8.7, 2.1 Hz), 6.45 (1H, s), 5.07 (1H, q, J = 6.8 Hz), 1.76 (3H, d, J = 6.8 Hz). |
| a030 | ¹H-NMR (CDCl3) δ: 7.75 (1H, s), 7.33-7.32 (1H, m), 7.27-7.25 (1H, m), 6.94-6.93 (1H, m), 6.81-6.79 (1H, m), 6.62-6.61 (1H, m), 6.57 (1H, s), 6.48-6.46 (1H, m), 3.69 (3H, s). |
| a031 | ¹H-NMR (CDCl3) δ: 7.72 (1H, s), 7.36-7.34 (1H, m), 7.32-7.27 (2H, m), 6.95-6.92 (1H, m), 6.78-6.73 (2H, m), 6.50 (1H, s), 4.96 (2H, s). |
| a032 | ¹H-NMR (CDCl3) δ: 7.86 (1H, s), 7.35-7.27 (3H, m), 6.94-6.91 (1H, m), 6.78-6.71 (2H, m), 6.48 (1H, s), 4.96 (2H, s). |

TABLE A-continued

| Intermediate | ¹H-NMR |
|---|---|
| a033 | ¹H-NMR (CDCl3) δ: 7.88 (1H, s), 7.33-7.31 (1H, m), 7.28-7.24 (1H, m), 6.94-6.92 (1H, m), 6.80-6.78 (1H, m), 6.62-6.60 (1H, m), 6.55 (1H, s), 6.47-6.45 (1H, m), 3.69 (3H, s). |
| a034 | ¹H-NMR (CDCl3) δ: 7.87 (1H, s), 7.31-7.29 (1H, m), 7.26-7.24 (1H, m), 6.92-6.91 (1H, m), 6.80-6.78 (1H, m), 6.55 (1H, s), 6.37-6.35 (1H, m), 6.23-6.20 (1H, m), 3.72 (3H, s), 3.69 (3H, s). |
| a035 | ¹H-NMR (CDCl3) δ: 7.87 (1H, s), 7.59 (1H, dd, J = 7.9, 1.6 Hz), 7.37-7.35 (1H, m), 7.30-7.20 (3H, m), 6.83-6.79 (2H, m), 6.60 (1H, s). |
| a036 | ¹H-NMR (CDCl3) δ: 7.74 (1H, s), 7.59 (1H, dd, J = 8.0, 1.5 Hz), 7.37-7.35 (1H, m), 7.29-7.24 (3H, m), 6.85-6.78 (2H, m), 6.62 (1H, s). |
| a037 | ¹H-NMR (CDCl3) δ: 7.42 (1H, s), 7.31-7.24 (3H, m), 6.94-6.84 (4H, m), 6.45 (1H, s), 3.85 (2H, t, J = 7.1 Hz), 2.82 (2H, t, J = 7.1 Hz). |
| a038 | ¹H-NMR (CDCl3) δ: 7.84 (1H, s), 7.40-7.28 (2H, m), 7.14 (1H, dd, J = 7.9, 2.8 Hz), 6.98-6.96 (1H, m), 6.86-6.82 (2H, m), 6.59 (1H, s). |
| a039 | ¹H-NMR (CDCl3) δ: 7.71 (1H, s), 7.40-7.36 (1H, m), 7.33-7.32 (1H, m), 7.14 (1H, dd, J = 8.0, 2.8 Hz), 6.98-6.96 (1H, m), 6.88-6.86 (1H, m), 6.82-6.80 (1H, m), 6.61 (1H, s). |
| a040 | ¹H-NMR (CDCl3) δ: 7.51 (1H, s), 7.28-7.22 (4H, m), 6.91-6.82 (3H, m), 6.40 (1H, s), 3.82 (2H, t, J = 7.2 Hz), 2.79 (2H, t, J = 7.2 Hz). |
| a041 | ¹H-NMR (CDCl3) δ: 7.85 (1H, s), 7.39-7.30 (2H, m), 7.15-7.14 (1H, m), 7.08-7.06 (1H, m), 6.89-6.82 (2H, m), 6.60 (1H, s). |
| a042 | ¹H-NMR (CDCl3) δ: 7.72 (1H, s), 6.90-6.83 (2H, m), 6.45 (1H, s), 3.45 (2H, d, J = 7.6 Hz), 1.86-1.78 (1H, m), 0.81 (6H, d, J = 6.7 Hz). |
| a043 | ¹H-NMR (CDCl3) δ: 7.73 (1H, s), 7.40-7.29 (2H, m), 7.15-7.14 (1H, m), 7.09-7.06 (1H, m), 6.89-6.82 (2H, m), 6.62 (1H, s). |
| a044 | ¹H-NMR (CDCl3) δ: 7.87 (1H, s), 7.28-7.16 (4H, m), 7.11-7.10 (1H, m), 6.83-6.76 (2H, m), 6.60 (1H, s), 2.19 (3H, s). |
| a045 | ¹H-NMR (CDCl3) δ: 7.74 (1H, s), 7.29-7.16 (4H, m), 7.12-7.09 (1H, m), 6.83-6.76 (2H, m), 6.62 (1H, s), 2.19 (3H, s). |
| a046 | ¹H-NMR (CDCl3) δ: 7.70 (1H, s), 6.86-6.84 (2H, m), 6.44 (1H, s), 3.46 (2H, d, J = 7.0 Hz), 1.69-1.66 (3H, m), 1.50-1.48 (3H, m), 1.14-1.09 (3H, m), 0.75-0.73 (2H, m). |
| a047 | ¹H-NMR (CDCl3) δ: 7.84 (1H, s), 6.88-6.82 (2H, m), 6.42 (1H, s), 3.44 (2H, d, J = 7.6 Hz), 1.86-1.76 (1H, m), 0.81 (6H, d, J = 6.8 Hz). |
| a048 | ¹H-NMR (CDCl3) δ: 7.97 (1H, s), 7.53-7.51 (1H, m), 7.41-7.40 (1H, m), 7.23 (1H, t, J = 8.1 Hz), 7.14-7.12 (1H, m), 6.66-6.60 (2H, m), 6.55 (1H, s). |
| a049 | ¹H-NMR (CDCl3) δ: 7.84 (1H, s), 7.53-7.52 (1H, m), 7.41-7.40 (1H, m), 7.23 (1H, t, J = 8.1 Hz), 7.14-7.13 (1H, m), 6.65-6.61 (2H, m), 6.57 (1H, s). |
| a050 | ¹H-NMR (CDCl3) δ: 7.83 (1H, s), 6.87-6.83 (2H, m), 6.41 (1H, s), 3.46 (2H, d, J = 7.3 Hz), 1.69-1.66 (3H, m), 1.51-1.44 (3H, m), 1.15-1.09 (3H, m), 0.76-0.74 (2H, m). |
| a051 | ¹H-NMR (CDCl3) δ: 8.39 (1H, d, J = 1.8 Hz), 8.16 (1H, s), 6.76-6.70 (2H, m), 6.58 (1H, s), 6.14 (1H, d, J = 1.8 Hz). |
| a052 | ¹H-NMR (CDCl3) δ: 8.39 (1H, d, J = 1.8 Hz), 8.04 (1H, s), 6.75-6.70 (2H, m), 6.60 (1H, s), 6.14 (1H, d, J = 1.8 Hz). |
| a053 | ¹H-NMR (CDCl3) δ: 8.00 (1H, s), 6.76-6.71 (2H, m), 6.57 (1H, s), 5.79 (1H, s), 2.41 (3H, s). |
| a054 | ¹H-NMR (CDCl3) δ: 7.97 (1H, s), 7.38-7.36 (1H, m), 7.29 (1H, t, J = 8.0 Hz), 7.26-7.24 (1H, m), 7.09-7.08 (1H, m), 6.65-6.60 (2H, m), 6.55 (1H, s). |
| a055 | ¹H-NMR (CDCl3) δ: 8.13 (1H, s), 6.75-6.70 (2H, m), 6.55 (1H, s), 5.79 (1H, s), 2.41 (3H, s). |
| a056 | ¹H-NMR (CDCl3) δ: 7.86 (1H, s), 7.08-7.06 (2H, m), 6.97 (1H, d, J = 2.7 Hz), 6.60-6.56 (3H, m), 2.24 (3H, s), 2.11 (3H, s). |
| a057 | ¹H-NMR (CDCl3) δ: 7.73 (1H, s), 7.10-7.05 (2H, m), 6.97 (1H, d, J = 2.7 Hz), 6.60-6.57 (3H, m), 2.24 (3H, s), 2.11 (3H, s). |
| a058 | ¹H-NMR (CDCl3) δ: 7.78-7.77 (1H, m), 6.88-6.82 (2H, m), 6.44-6.41 (1H, m), 3.16-3.11 (1H, m), 2.05-2.00 (1H, m), 1.91-1.83 (2H, m), 1.79-1.54 (7H, m), 1.34-1.11 (2H, m), 0.97-0.88 (1H, m), 0.72-0.69 (3H, m). |
| a059 | ¹H-NMR (CDCl3) δ: 7.90 (1H, s), 6.89-6.81 (2H, m), 6.39 (1H, s), 3.12 (1H, td, J = 11.7, 3.9 Hz), 2.04-2.00 (1H, m), 1.90-1.83 (2H, m), 1.77-1.64 (2H, br m), 1.34-1.09 (2H, m), 0.97-0.87 (2H, m), 0.71 (3H, dd, J = 6.5, 1.3 Hz). |
| a060 | ¹H-NMR (CDCl3) δ: 7.71 (1H, s), 6.88-6.82 (2H, m), 6.45 (1H, s), 3.62 (1H, dd, J = 14.2, 6.5 Hz), 3.35 (1H, dd, J = 14.2, 8.7 Hz), 1.56-1.51 (1H, m), 1.28-1.17 (1H, m), 1.05-1.00 (1H, m), 0.80-0.74 (6H, m). |
| a061 | ¹H-NMR (CDCl3) δ: 7.85 (1H, s), 7.15-7.14 (1H, m), 7.03-7.01 (2H, m), 6.60-6.53 (3H, m), 2.25 (3H, s), 2.03 (3H, d, J = 2.1 Hz). |
| a062 | ¹H-NMR (CDCl3) δ: 7.84 (1H, s), 6.87-6.83 (2H, m), 6.43 (1H, s), 3.62 (1H, dd, J = 14.4, 6.7 Hz), 3.35 (1H, dd, J = 14.4, 8.6 Hz), 1.58-1.51 (1H, m), 1.27-1.18 (1H, m), 1.09-0.99 (1H, m), 0.79-0.75 (6H, m). |
| a063 | ¹H-NMR (CDCl3) δ: 7.72 (1H, s), 7.16-7.14 (1H, m), 7.03-7.01 (2H, m), 6.61-6.53 (3H, m), 2.25 (3H, s), 2.03 (3H, d, J = 1.8 Hz). |
| a064 | ¹H-NMR (CDCl3) δ: 7.84 (1H, s), 7.21-7.19 (1H, m), 7.03-7.01 (1H, m), 6.95-6.93 (1H, m), 6.67-6.57 (2H, m), 6.57 (1H, s), 2.14 (3H, s). |

TABLE A-continued

| Intermediate | ¹H-NMR |
|---|---|
| a065 | ¹H-NMR (CDCl3) δ: 7.71 (1H, s), 7.22-7.19 (1H, m), 7.03-7.01 (1H, m), 6.95-6.93 (1H, m), 6.68-6.57 (3H, m), 2.14 (3H, s). |
| a066 | ¹H-NMR (CDCl3) δ: 7.85 (1H, s), 7.15-7.13 (1H, m), 7.09-7.05 (1H, m), 7.01-6.99 (1H, m), 6.63-6.57 (3H, m), 2.09 (3H, t, J = 1.8 Hz). |
| a067 | ¹H-NMR (CDCl3) δ: 7.73 (1H, s), 7.16-7.13 (1H, m), 7.08-7.06 (1H, m), 7.01-6.99 (1H, m), 6.64-6.57 (3H, m), 2.09 (3H, t, J = 1.8 Hz). |
| a068 | ¹H-NMR (CDCl3) δ: 7.89 (1H, m Hz), 7.72-7.71 (1H, m), 7.60-7.56 (2H, m), 7.44-7.42 (1H, m), 6.60-6.57 (2H, m), 6.55 (1H, s). |
| a069 | ¹H-NMR (CDCl3) δ: 7.71 (1H, s), 6.87-6.82 (2H, m), 6.45 (1H, s), 3.53 (2H, s), 0.84 (9H, s). |
| a070 | ¹H-NMR (CDCl3) δ: 7.84 (1H, s), 6.87-6.82 (2H, m), 6.43 (1H, s), 3.53 (2H, s), 0.84 (9H, s). |
| a071 | ¹H-NMR (CDCl3) δ: 7.36 (1H, q, J = 1.0 Hz), 7.24-7.19 (2H, m), 7.13-7.11 (2H, m), 6.59-6.51 (2H, m), 6.46 (1H, s), 2.15 (3H, s), 2.13 (3H, d, J = 1.0 Hz). |
| a072 | ¹H-NMR (CDCl3) δ: 7.76(1H, m), 7.73-7.71 (1H, m), 7.60-7.58 (2H, m), 7.44-7.43 (1H, m), 6.61-6.57 (3H, m). |
| a073 | ¹H-NMR (CDCl3) δ: 7.76-7.74 (1H, m), 6.89-6.84 (2H, m), 6.45 (1H, s), 3.64-3.61 (2H, m), 1.52-1.40 (3H, m), 0.78 (6H, d, J = 6.1 Hz). |
| a074 | ¹H-NMR (CDCl3) δ: 7.86 (1H, s), 7.29-7.23 (1H, m), 7.04-7.00 (3H, m), 6.83-6.77 (2H, m), 6.59 (1H, s), 2.22 (3H, s), 2.12 (3H, s). |
| a075 | ¹H-NMR (CDCl3) δ: 7.73 (1H, s), 7.29-7.23 (1H, m), 7.05-7.02 (2H, m), 6.99 (1H, br-s), 6.84-6.77 (2H, m), 6.61 (1H, s), 2.22 (3H, s), 2.12 (3H, s). |
| a076 | ¹H-NMR (CDCl3) δ: 7.86 (1H, s), 6.87-6.81 (2H, m), 6.44 (1H, s), 3.80 (2H, t, J = 5.0 Hz), 3.43 (2H, t, J = 5.0 Hz), 3.29 (3H, s). |
| a077 | ¹H-NMR (CDCl3) δ: 7.86 (1H, s), 6.87-6.81 (2H, m), 6.44 (1H, s), 3.80 (2H, t, J = 5.0 Hz), 3.43 (2H, t, J = 5.0 Hz), 3.29 (3H, s). |
| a078 | ¹H-NMR (CDCl3) δ: 7.87 (1H, s), 7.10 (1H, d, J = 8.5 Hz), 6.82 (1H, dd, J = 8.5, 2.7 Hz), 6.70 (1H, t, J = 2.7 Hz), 6.62-6.56 (3H, m), 3.72 (3H, s), 2.09 (3H, s). |
| a079 | ¹H-NMR (CDCl3) δ: 7.73 (1H, s), 7.10 (1H, d, J = 8.6 Hz), 6.82 (1H, dd, J = 8.6, 2.4 Hz), 6.70 (1H, t, J = 2.4 Hz), 6.64-6.56 (3H, m), 3.72 (3H, s), 2.08 (3H, s). |
| a080 | ¹H-NMR (CDCl3) δ: 7.75 (1H, s), 6.89-6.83 (2H, m), 6.45 (1H, s), 3.65-3.62 (2H, m), 2.05 (1H, s), 1.61-1.55 (2H, m), 1.24-1.18 (2H, m), 0.83 (3H, t, J = 7.3 Hz). |
| a081 | ¹H-NMR (CDCl3) δ: 7.87 (1H, s), 6.89-6.82 (2H, m), 6.42 (1H, s), 3.64-3.60 (2H, m), 1.61-1.54 (2H, m), 1.28-1.16 (2H, m), 0.83 (3H, t, J = 7.3 Hz). |
| a082 | ¹H-NMR (CDCl3) δ: 7.84 (1H, s), 7.26 (1H, dd, J = 8.3, 2.4 Hz), 7.21 (1H, t, J = 2.4 Hz), 7.17 (1H, d, J = 8.3 Hz), 6.68-6.58 (2H, m), 6.57 (1H, s), 2.14 (3H, s). |
| a083 | ¹H-NMR (CDCl3) δ: 7.70 (1H, s), 7.27 (1H, dd, J = 8.3, 2.1 Hz), 7.21 (1H, t, J = 2.1 Hz), 7.17 (1H, d, J = 8.3 Hz), 6.68-6.64 (1H, m), 6.63-6.58 (2H, m), 2.14 (3H, s). |
| a084 | ¹H-NMR (CDCl3) δ: 7.83 (1H, s), 7.41 (1H, dd, J = 8.3, 2.4 Hz), 7.36 (1H, t, J = 2.4 Hz), 7.10 (1H, d, J = 8.3 Hz), 6.69-6.57 (3H, m), 2.12 (3H, s). |
| a085 | ¹H-NMR (CDCl3) δ: 7.71 (1H, s), 7.41 (1H, dd, J = 8.3, 2.1 Hz), 7.36 (1H, t, J = 2.1 Hz), 7.11 (1H, d, J = 8.3 Hz), 6.69-6.58 (3H, m), 2.12 (3H, s). |
| a086 | ¹H-NMR (CDCl3) δ: 7.84 (1H, s), 7.03 7.01 (2H, m), 6.92-6.90 (1H, m), 6.59-6.56 (3H, m), 2.28 (3H, s), 2.12 (3H, s). |
| a087 | ¹H-NMR (CDCl3) δ: 7.71 (1H, s), 7.03-7.01 (2H, m), 6.92-6.90 (1H, m), 6.62-6.54 (3H, m), 2.28 (3H, s), 2.12 (3H, s). |
| a088 | ¹H-NMR (CDCl3) δ: 7.84 (1H, s), 7.07 (1H, dd, J = 8.7, 2.9 Hz), 6.68 (1H, d, J = 2.9 Hz), 6.62-6.57 (4H, m), 3.76 (3H, s), 2.13 (3H, s). |
| a089 | ¹H-NMR (CDCl3) δ: 7.71 (1H, s), 7.07 (1H, dd, J = 8.8, 2.9 Hz), 6.68 (1H, d, J = 2.9 Hz), 6.64-6.56 (4H, m), 3.76 (3H, s), 2.12 (3H, s). |
| a090 | ¹H-NMR (CDCl3) δ: 7.83 (1H, s), 7.19-7.15 (1H, m), 6.92 (1H, dd, J = 8.8, 2.9 Hz), 6.87-6.82 (1H, m), 6.62-6.59 (3H, m), 2.17 (3H, s). |
| a091 | ¹H-NMR (CDCl3) δ: 7.71 (1H, s), 7.19-7.15 (1H, m), 6.93 (1H, dd, J = 8.9, 2.8 Hz), 6.86-6.84 (1H, m), 6.64-6.58 (3H, m), 2.17 (3H, s). |
| a092 | ¹H-NMR (CDCl3) δ: 7.81 (1H, s), 7.27-7.25 (1H, m), 7.06-7.03 (1H, m), 6.91-6.87 (1H, m), 6.66-6.64 (1H, m), 6.61 (1H, s), 6.55-6.49 (1H, m), 2.24 (3H, t, J = 0.7 Hz). |
| a093 | ¹H-NMR (CDCl3) δ: 7.68 (1H, s), 7.27-7.25 (1H, m), 7.05 (1H, t, J = 3.8 Hz), 6.91-6.88 (1H, m), 6.68-6.63 (2H, m), 6.55-6.50 (1H, m), 2.24 (3H, t, J = 0.6 Hz). |
| a094 | ¹H-NMR (CDCl3) δ: 7.80 (1H, s), 7.16 (1H, t, J = 7.6 Hz), 7.03 (2H, d, J = 7.6 Hz), 6.60-6.56 (3H, m), 2.12 (3H, s), 2.11 (3H, s). |
| a095 | ¹H-NMR (CDCl3) δ: 7.67 (1H, s), 7.17 (1H, t, J = 7.6 Hz), 7.03-7.03 (2H, m), 6.64 (1H, s), 6.59-6.57 (2H, m), 2.12 (3H, s), 2.11 (3H, s). |
| a096 | ¹H-NMR (CDCl3) δ: 7.77 (1H, s), 7.27-7.16 (3H, m), 6.68-6.61 (2H, m), 6.54-6.48 (1H, m), 2.24 (3H, d, J = 2.2 Hz). |

TABLE A-continued

| Intermediate | ¹H-NMR |
|---|---|
| a097 | ¹H-NMR (CDCl3) δ: 7.86 (1H, s), 7.54 (1H, dd, J = 8.3, 1.4 Hz), 7.46 (1H, br s), 7.38 (1H, d, J = 8.3 Hz), 6.64-6.55 (2H, m), 6.59 (1H, s), 2.26 (3H, s). |
| a098 | ¹H-NMR (CDCl3) δ: 7.93 (1H, dd, J = 8.3, 1.2 Hz), 7.84 (1H, s), 7.51-7.48 (1H, m), 7.37 (1H, t, J = 8.3 Hz), 6.67-6.59 (2H, m), 6.59 (1H, s), 2.34 (3H, d, J = 1.5 Hz). |
| a099 | ¹H-NMR (CDCl3) δ: 7.65 (1H, s), 7.27-7.17 (3H, m), 6.66-6.64 (2H, m), 6.54-6.49 (1H, m), 2.24 (3H, d, J = 2.1 Hz). |
| a100 | ¹H-NMR (CDCl3) δ: 7.82 (1H, s), 7.23-7.23 (1H, m), 7.15-7.09 (2H, m), 6.64-6.59 (2H, m), 6.57 (1H, s), 2.16 (3H, s). |
| a101 | ¹H-NMR (CDCl3) δ: 7.83 (1H, s), 7.41-7.37 (1H, m), 7.13-7.10 (2H, m), 6.63-6.56 (3H, m), 2.19 (3H, d, J = 2.0 Hz). |
| a102 | ¹H-NMR (CDCl3) δ: 8.16 (1H, dd, J = 8.3, 2.3 Hz), 8.11 (1H, t, J = 2.3 Hz), 7.84 (1H, s), 7.45 (1H, d, J = 8.3 Hz), 6.67-6.57 (3H, m), 2.31 (3H, s). |
| a103 | ¹H-NMR (CDCl3) δ: 7.69 (1H, s), 7.23-(1H, m), 7.13-7.11 (2H, m), 6.63-6.61 (3H, m), 2.16 (3H, s). |
| a104 | ¹H-NMR (CDCl3) δ: 7.81 (1H, s), 7.58 (1H, dd, J = 8.1, 1.7 Hz), 7.52 (1H, dd, J = 2.7, 1.7 Hz), 7.38 (1H, d, J = 8.1 Hz), 6.70-6.59 (3H, m), 2.26 (3H, s). |
| a105 | ¹H-NMR (CDCl3) δ: 7.83 (1H, s), 7.58 (1H, dd, J = 8.1, 1.2 Hz), 7.17-7.15 (1H, m), 7.03 (1H, t, J = 8.1 Hz), 6.63-6.58 (2H, m), 6.57 (1H, s), 2.21 (3H, d, J = 1.8 Hz). |
| a106 | ¹H-NMR (CDCl3) δ: 7.74 (1H, s), 7.35-7.28 (2H, m), 7.19-7.12 (2H, m), 6.59-6.54 (3H, m), 2.47-2.41 (2H, m), 1.20 (3H, t, J = 7.6 Hz). |
| a107 | ¹H-NMR (CDCl3) δ: 7.70 (1H, s), 7.19 (1H, t, J = 7.7 Hz), 7.10-7.03 (4H, m), 6.90-6.88 (2H, m), 6.63 (1H, s), 2.09 (6H, s). |
| a108 | ¹H-NMR (CDCl3) δ: 7.57 (1H, s), 7.19 (1H, t, J = 7.6 Hz), 7.10-7.04 (4H, m), 6.90-6.89 (2H, m), 6.65 (1H, s), 2.09 (6H, s). |
| a109 | ¹H-NMR (CDCl3) δ: 7.85 (1H, s), 7.69-7.67 (1H, m), 7.40 (1H, dd, J = 8.0, 1.5 Hz), 7.31-7.28 (1H, m), 6.63-6.57 (3H, m), 2.27 (3H, s). |
| a110 | ¹H-NMR (CDCl3) δ: 7.87 (1H, s), 7.35-7.28 (2H, m), 7.18-7.12 (2H, m), 6.59-6.53 (3H, m), 2.48-2.41 (2H, m), 1.20 (3H, t, J = 7.6 Hz). |
| a111 | ¹H-NMR (CDCl3) δ: 7.73 (1H, s), 7.28-7.23 (1H, m), 7.18-7.16 (2H, m), 6.99-6.89 (4H, m), 6.58 (1H, s), 2.10 (3H, s). |
| a112 | ¹H-NMR (CDCl3) δ: 7.61 (1H, s), 7.28-7.24 (1H, m), 7.18-7.17 (2H, m), 6.99-6.90 (4H, m), 6.61 (1H, s), 2.10 (3H, s). |
| a113 | ¹H-NMR (CDCl3) δ: 8.00 (1H, s), 7.35-7.24 (4H, m), 7.21-7.20 (2H, m), 6.81-6.77 (2H, m), 6.58 (1H, s). |
| a114 | ¹H-NMR (CDCl3) δ: 7.84 (1H, s), 7.11-7.07 (1H, m), 6.81 (1H, d, J = 8.1 Hz), 6.78-6.75 (1H, m), 6.61-6.53 (3H, m), 3.82 (3H, s), 1.99 (3H, d, J = 2.0 Hz). |
| a115 | ¹H-NMR (CDCl3) δ: 7.89 (1H, d, J = 0.9 Hz), 7.70-7.68 (1H, m), 7.54-7.52 (2H, m), 7.45-7.42 (1H, m), 7.31-7.27 (1H, m), 6.83-6.78 (2H, m), 6.57 (1H, s). |
| a116 | ¹H-NMR (CDCl3) δ: 7.68 (1H, s), 7.32-7.30 (1H, m), 7.23-7.21 (3H, m), 7.09-7.07 (1H, m), 6.93-6.90 (2H, m), 6.59 (1H, s), 2.07 (3H, s). |
| a117 | ¹H-NMR (CDCl3) δ: 7.56 (1H, s), 7.32-7.30 (1H, m), 7.25-7.19 (3H, m), 7.09-7.07 (1H, m), 6.94-6.90 (2H, m), 6.62 (1H, s), 2.07 (3H, s). |
| a118 | ¹H-NMR (CDCl3) δ: 7.89 (1H, s), 7.38-7.35 (1H, m), 7.31-7.29 (1H, m), 7.23-7.21 (1H, m), 7.19-7.15 (1H, m), 6.63-6.54 (3H, m), 2.78-2.72 (1H, m), 1.15-1.12 (6H, m). |
| a119 | ¹H-NMR (CDCl3) δ: 7.74 (1H, s), 7.38-7.34 (1H, m), 7.29 (1H, dd, J = 8.0, 1.4 Hz), 7.22 (1H, ddd, J = 8.0, 3.7, 1.4 Hz), 7.18-7.15 (1H, m), 6.62-6.53 (3H, m), 2.77-2.72 (1H, m), 1.15-1.11 (6H, m). |
| a120 | ¹H-NMR (CDCl3) δ: 7.93 (1H, dd, J = 8.2, 1.3 Hz), 7.71 (1H, s), 7.49 (1H, ddd, J = 7.8, 2.7, 1.3 Hz), 7.39-7.35 (1H, m), 6.67-6.60 (3H, m), 2.34 (3H, d, J = 1.7 Hz). |
| a121 | ¹H-NMR (CDCl3) δ: 7.81 (1H, s), 7.28-7.18 (3H, m), 7.15-7.13 (1H, m), 6.99 (4H, s), 6.61 (1H, s), 2.78 (3H, s), 2.26 (3H, s). |
| a122 | ¹H-NMR (CDCl3) δ: 7.71 (1H, s), 7.11-7.07 (1H, m), 6.81 (1H, d, J = 8.3 Hz), 6.77 (1H, ddd, J = 8.1, 2.9, 0.7 Hz), 6.61-6.53 (3H, m), 3.82 (3H, s), 1.99 (3H, d, J = 1.7 Hz). |
| a123 | ¹H-NMR (CDCl3) δ: 7.74 (1H, s), 7.33-7.30 (1H, m), 7.26-7.23 (1H, m), 7.21-7.14 (2H, m), 6.59 (1H, s), 6.59-6.53 (2H, m), 2.36-2.33 (2H, m), 1.65-1.51 (2H, m), 0.94 (3H, t, J = 7.3 Hz). |
| a124 | ¹H-NMR (CDCl3) δ: 7.71 (1H, s), 7.34-7.28 (1H, m), 7.19-7.15 (1H, m), 7.00-6.94 (2H, m), 6.89-6.79 (2H, m), 6.61 (1H, s), 2.15 (3H, s). |
| a125 | ¹H-NMR (CDCl3) δ: 7.71 (1H, s), 7.29-7.27 (1H, m), 7.21-7.18 (2H, m), 7.15 (1H, d, J = 7.6 Hz), 7.11-7.09 (2H, m), 7.02 (2H, d, J = 8.0 Hz), 6.66 (1H, s), 2.10 (6H, s). |
| a126 | ¹H-NMR (CDCl3) δ: 7.58 (1H, s), 7.30-7.26 (1H, m), 7.20-7.17 (3H, m), 7.11-7.09 (2H, m), 7.02 (2H, d, J = 7.8 Hz), 6.68 (1H, s), 2.10 (6H, s). |
| a127 | ¹H-NMR (CDCl3) δ: 7.98 (1H, s), 7.34-7.19 (6H, m), 7.00 (1H, dd, J = 8.4, 2.6 Hz), 6.93-6.91 (1H, m), 6.48 (1H, s). |
| a128 | ¹H-NMR (CDCl3) δ: 7.99 (1H, s), 7.32-7.27 (3H, m), 7.07-7.04 (3H, m), 6.83-6.76 (2H, m), 6.47 (1H, s), 2.12 (3H, s). |

TABLE A-continued

| Intermediate | ¹H-NMR |
|---|---|
| a129 | ¹H-NMR (CDCl3) δ: 7.99 (1H, s), 7.35-7.32 (3H, m), 7.22-7.10 (4H, m), 6.91 (1H, dd, J = 9.3, 2.0 Hz), 6.54 (1H, s). |
| a130 | ¹H-NMR (CDCl3) δ: 7.98 (1H, s), 7.33-7.27 (4H, m), 7.20-7.19 (4H, m), 6.47 (1H, s). |
| a131 | ¹H-NMR (CDCl3) δ: 7.99 (1H, s), 7.34-7.30 (3H, m), 7.18-7.15 (2H, br m), 7.01-6.97 (2H, m), 6.86-6.83 (1H, m), 6.56 (1H, s). |
| a132 | ¹H-NMR (CDCl3) δ: 8.00 (1H, s), 7.35-7.33 (3H, m), 7.16-7.00 (5H, m), 6.57 (1H, s). |
| a133 | ¹H-NMR (CDCl3) δ: 7.99 (1H, s), 7.38-7.36 (3H, m), 7.14-7.01 (3H, m), 6.97-6.87 (2H, m), 6.56 (1H, s). |

Reference Example 4

Synthesis of 1-(2-chlorophenyl)-2-(2,4,6-trifluorophenyl)-2,3-dihydropyridin-4(1H)-one

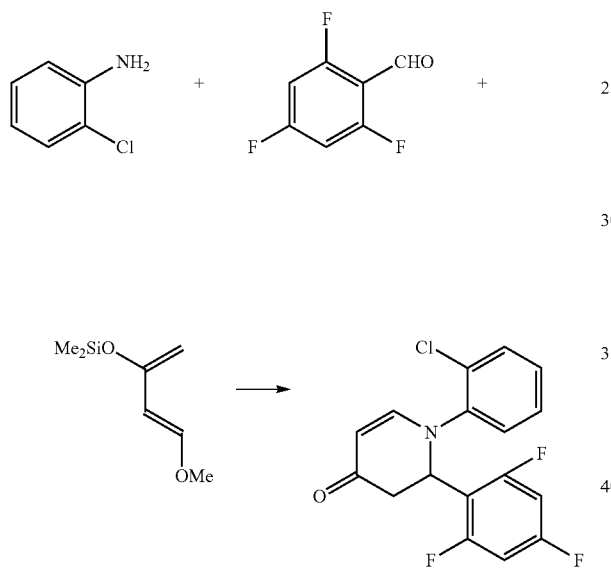

To 627 mg of 2,4,6-trifluorobenzaldehyde were added 500 mg of ortho-chloroaniline and 142 mg of magnesium sulfate, and the resultant mixture was stirred at 60° C. for 40 minutes. The reaction mixture was cooled to room temperature, dichloromethane was added and the mixture was sufficiently stirred. After removing the magnesium sulfate in the reaction mixture by filtration, the solvent of the obtained filtrate was evaporated under reduced pressure. To the residue were successively added 30 ml of acetonitrile and 1.12 ml of 1-methoxy-3-(trimethoxysilyloxy)-1,3-butadiene, and the resultant mixture was ice-cooled. Then, to the mixture were added 606 µl of water and 163 mg of 42% by weight aqueous solution of tetrafluoroboric acid, and the resultant mixture was stirred under ice-cooling for 30 minutes. To the reaction mixture were added a saturated sodium hydrogen carbonate aqueous solution and ethyl acetate followed by separation of the layers, and the obtained organic layer was washed with a saturated saline solution, and dried over sodium sulfate. The solvent was evaporated under reduced pressure, and the obtained residue was purified by silica gel column chromatography. The title compound was obtained as 1.23 g of a yellow oil.

¹H-NMR (CDCl3) δ: 7.37-7.35 (1H, m), 7.18-7.12 (4H, m), 6.57-6.51 (2H, m), 5.76 (1H, dd, J=13.4, 5.6 Hz), 5.30 (1H, d, J=8.1 Hz), 3.27 (1H, dd, J=16.4, 13.4 Hz), 2.72 (1H, dd, J=16.4, 5.6 Hz).

Reference Example 5

Synthesis of 5-bromo-1-(2-chlorophenyl)-2-(2,4,6-trifluorophenyl)-2,3-dihydropyridin-4(1H)-one

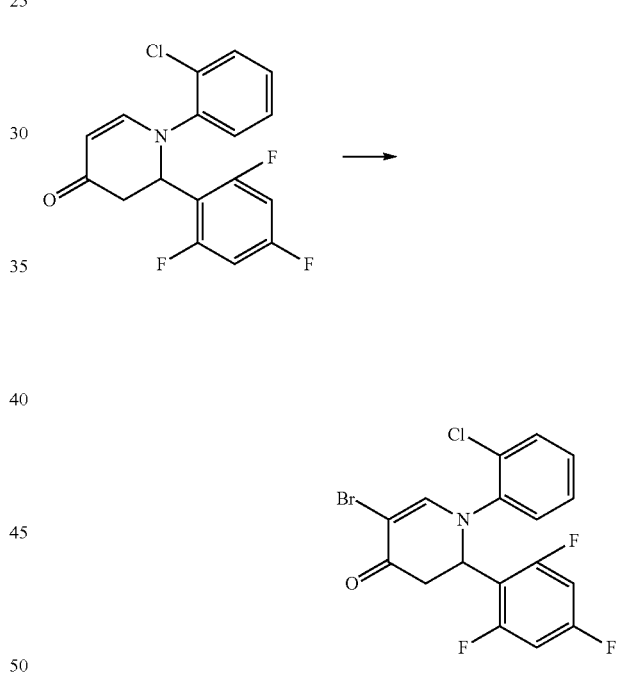

5 ml of a DMF solution containing 300 mg of 1-(2-chlorophenyl)-2-(2,4,6-trifluorophenyl)-2,3-dihydropyridin-4(1H)-one and 174 mg of N-bromosuccinimide was stirred at room temperature for 5 minutes. To the reaction mixture were added water and ethyl acetate followed by separation of the layers, and the obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 311 mg of pale yellow amorphous.

¹H-NMR (CDCl3) δ: 7.54 (1H, s), 7.38-7.37 (1H, m), 7.22-7.14 (3H, m), 6.59-6.53 (2H, m), 5.81 (1H, dd, J=13.2, 5.6 Hz), 3.38 (1H, dd, J=16.4, 13.2 Hz), 2.94 (1H, dd, J=16.4, 5.6 Hz).

Reference Example 6

Synthesis of 5-bromo-1-(2-chlorophenyl)-2-(2,4,6-trifluorophenyl)pyridin-4(1H)-one (Intermediate No.: a001)

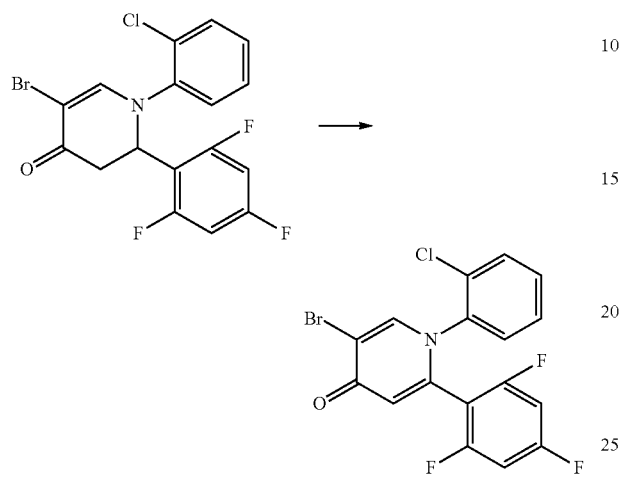

5 ml of a toluene solution containing 310 mg of 5-bromo-1-(2-chlorophenyl)-2-(2,4,6-trifluorophenyl)-2,3-dihydropyridin-4(1H)-one and 254 mg of 2,3-dichloro-5,6-dicyano-p-benzoquinone was stirred at 115° C. for 2 hours. 254 mg of additional 2,3-dichloro-5,6-dicyano-p-benzoquinone was added, and the resultant mixture was stirred at 115° C. for 2.5 hours. The reaction mixture was cooled to room temperature, and the precipitates were removed by filtration. The solvent of the filtrate was evaporated under reduced pressure, and the residue was purified by silica gel column chromatography. The title compound was obtained as 240 mg of a white solid.

Reference Example 7

Synthesis of 5-chloro-1-(2-chlorophenyl)-2-(2,4,6-trifluorophenyl)pyridin-4(1H)-one

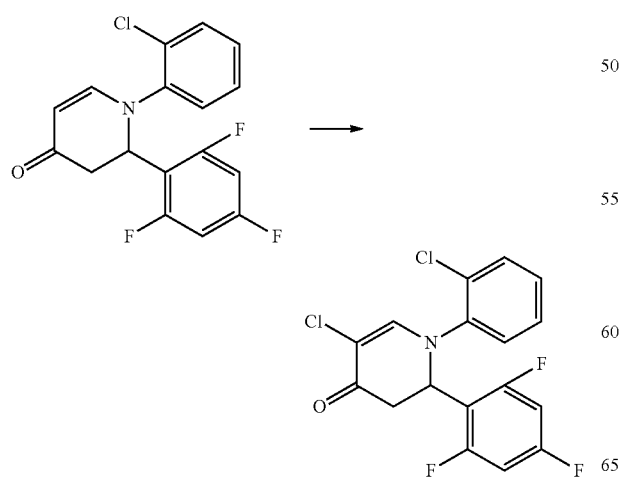

5 ml of a DMF solution containing 320 mg of 1-(2-chlorophenyl)-2-(2,4,6-trifluorophenyl)-2,3-dihydropyridin-4(1H)-one and 139 mg of N-chlorosuccinimide was stirred at room temperature for 2 hours. To the reaction mixture were added water and ethyl acetate followed by separation of the layers, and the obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 290 mg of a white solid.

$^1$H-NMR (CDCl3) δ: 7.43 (1H, s), 7.38-7.37 (1H, m), 7.21-7.13 (3H, m), 6.58-6.53 (2H, m), 5.79 (1H, dd, J=13.5, 5.5 Hz), 3.37 (1H, dd, J=16.8, 13.5 Hz), 2.89 (1H, dd, J=16.8, 5.5 Hz).

Reference Example 8

Synthesis of 5-chloro-1-(2-chlorophenyl)-2-(2,4,6-trifluorophenyl)pyridin-4(1H)-one (Intermediate No.: a002)

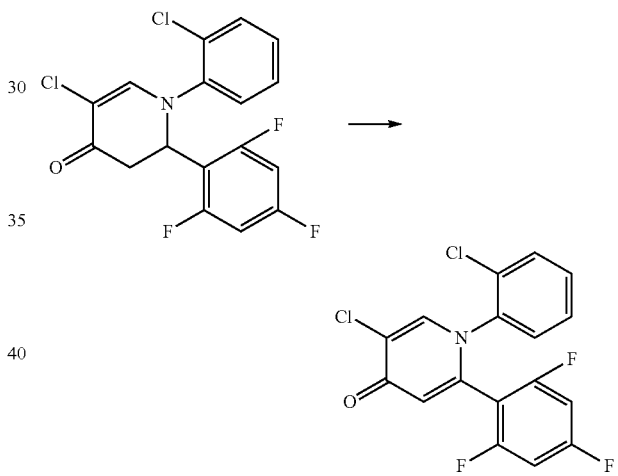

5 ml of a toluene solution containing 0.38 g of 5-chloro-1-(2-chlorophenyl)-2-(2,4,6-trifluorophenyl)pyridin-4(1H)-one and 0.69 g of 2,3-dichloro-5,6-dicyano-p-benzoquinone was stirred at 115° C. for 3 hours. The reaction mixture was cooled to room temperature, and the precipitates were removed by filtration. The solvent of the filtrate was evaporated under reduced pressure, and the residue was purified by silica gel column chromatography. The title compound was obtained as 0.33 g of a white solid.

Reference Example 9

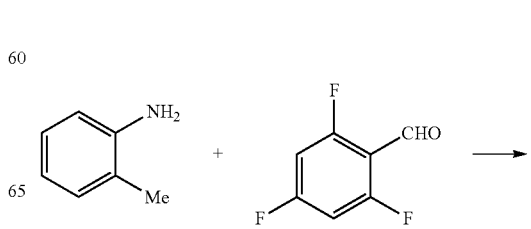

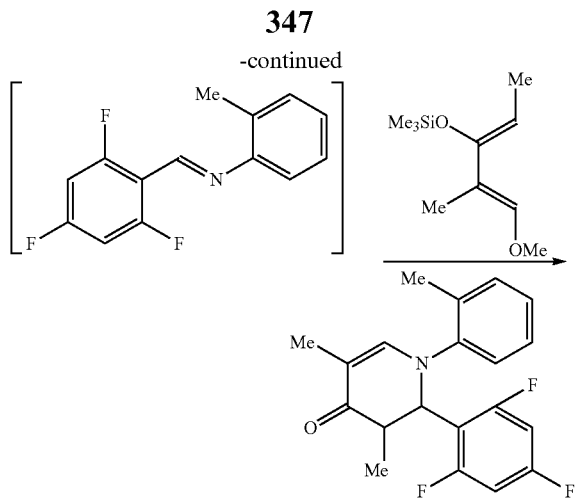
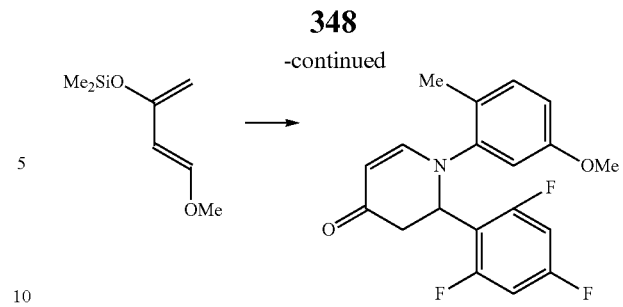

Step 1: Synthesis of N-o-toluyl-1-(2,4,6-trifluorophenyl)methaneimine 15 ml of a dichloroethane solution containing 3.00 g of 2,4,6-trifluorobenzaldehyde, 2.00 g of ortho-toluidine and 1.40 g of magnesium sulfate was stirred under reflux for 3 hours. The reaction mixture was cooled to room temperature, magnesium sulfate in the reaction mixture was removed by filtration, and the solvent of the obtained filtrate was evaporated under reduced pressure. The obtained orange solid was the title compound, and this was used in the next reaction without further purification.

$^1$H-NMR (CDCl3) δ: 8.50 (1H, s), 7.25-7.21 (2H, m), 7.17-7.14 (1H, m), 6.92 (1H, d, J=7.8 Hz), 6.79-6.77 (2H, m), 2.36 (3H, s).

Step 2: Synthesis of 3,5-dimethyl-1-(o-toluyl)-2-(2,4,6-trifluorophenyl)-2,3-dihydropyridin-4(1H)-one 5 ml of an acetonitrile solution containing 500 mg of N-o-toluyl-1-(2,4,6-trifluorophenyl)methaneimine and 3.02 ml of ((1-methoxy-2-methylpenta-1,3-dien-3-yl)oxy)trimethylsilane was ice-cooled and, after adding 86 mg of 42% by weight aqueous solution of tetrafluoroboric acid, the resultant mixture was stirred under ice-cooling for 1 hour. The temperature of the mixture was raised from ice-cooling to room temperature, and the mixture was stirred for 1.5 hours. To the reaction mixture were added a saturated sodium hydrogen carbonate aqueous solution and ethyl acetate followed by separation of the layers, and the obtained organic layer was washed with a saturated saline solution, and dried over magnesium sulfate. The solvent was evaporated under reduced pressure, and the obtained residue was purified by silica gel column chromatography. The title compound was obtained as 704 mg of a colorless oil. This was used in the next reaction without further purification.

Reference Example 10

Synthesis of 1-(5-methoxy-2-methylphenyl)-2-(2,4,6-trifluorophenyl)-2,3-dihydropyridin-4(1H)-one

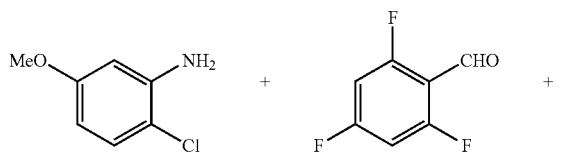

20 ml of a dichloroethane solution containing 2.91 g of 2,4,6-trifluorobenzaldehyde, 2.50 g of 5-methoxy-2-methylaniline and 2.19 g of magnesium sulfate was stirred under reflux for 4.5 hours. The reaction mixture was cooled to room temperature, followed by removing the magnesium sulfate in the reaction mixture by filtration, the solvent of the obtained filtrate was evaporated under reduced pressure. To 5.09 g of the obtained ocher solid were successively added 50 ml of acetonitrile and 5.23 ml of 1-methoxy-3-(trimethoxysilyloxy)-1,3-butadiene, and the resultant mixture was ice-cooled. Then, to the mixture was added 0.76 g of 42% by weight aqueous solution of tetrafluoroboric acid, the temperature of the mixture was raised from ice-cooling to room temperature and the mixture was stirred for 6 hours. To the reaction mixture were added a saturated sodium hydrogen carbonate aqueous solution and ethyl acetate followed by separation of the layers, and the obtained organic layer was washed with a saturated saline solution, and dried over magnesium sulfate. The solvent was evaporated under reduced pressure, and the obtained residue was purified by silica gel column chromatography. The title compound was obtained as 4.46 g of an orange solid.

$^1$H-NMR (CDCl3) δ: 7.09 (1H, dd, J=7.8, 0.7 Hz), 7.04 (1H, d, J=8.4 Hz), 6.64 (1H, dd, J=8.4, 2.6 Hz), 6.57-6.53 (3H, m), 5.60 (1H, dd, J=14.6, 5.2 Hz), 5.26 (1H, dd, J=7.8, 0.7 Hz), 3.67 (3H, s), 3.32 (1H, dd, J=16.4, 14.6 Hz), 2.64 (1H, ddd, J=16.4, 5.2, 1.0 Hz), 2.25 (3H, s).

Reference Example 11

Synthesis of 5-bromo-1-(5-methoxy-2-methylphenyl)-2-(2,4,6-trifluorophenyl)-2,3-dihydropyridin-4(1H)-one

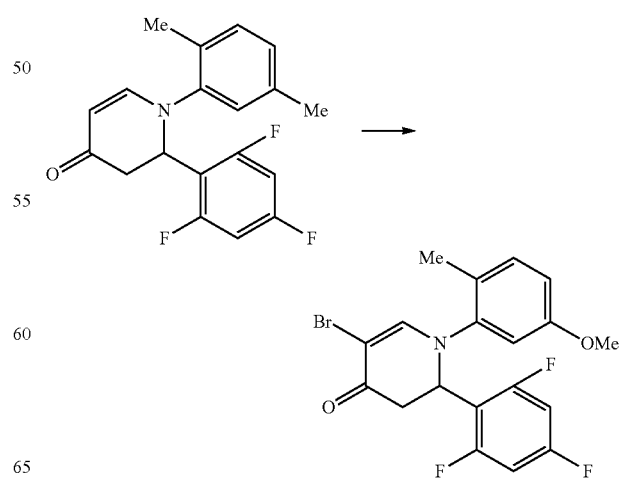

20 ml of a DMF solution containing 2.00 g of 1-(5-methoxy-2-methylphenyl)-2-(2,4,6-trifluorophenyl)-2,3-dihydropyridin-4(1H)-one and 1.23 g of N-bromosuccinimide was stirred at room temperature for 10 minutes. To the reaction mixture were added water and ethyl acetate followed by separation of the layers, and the obtained organic layer was successively washed with an aqueous sodium thiosulfate solution and a saturated saline solution, and dried over magnesium sulfate. The solvent was evaporated under reduced pressure, and the obtained residue was purified by silica gel column chromatography. The title compound was obtained as 1.78 g of pale yellow amorphous.

$^1$H-NMR (CDCl3) δ: 7.51 (1H, d, J=0.6 Hz), 7.06-7.05 (1H, m), 6.67 (1H, dd, J=8.4, 2.4 Hz), 6.59-6.54 (2H, m), 6.52 (1H, d, J=2.4 Hz), 5.66 (1H, dd, J=14.5, 5.5 Hz), 3.68 (3H,$), 3.42 (1H, dd, J=16.5, 14.5 Hz), 2.88 (1H, dd, J=16.5, 5.5 Hz), 2.26 (3H, s).

Reference Example 12

5-Bromo-1-(5-methoxy-2-methylphenyl)-2-(2,4,6-trifluorophenyl)pyridin-4(1H)-one (Intermediate No.: a078)

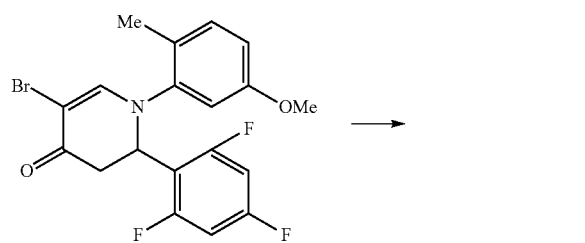

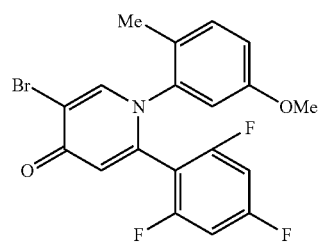

30 ml of a carbon tetrachloride solution containing 1.78 g of 5-bromo-1-(5-methoxy-2-methylphenyl)-2-(2,4,6-trifluorophenyl)-2,3-dihydropyridin-4 (1H)-one, 781 mg of N-bromosuccinimide and 69 mg of azobisisobutyronitrile was stirred under reflux for 3 hours. The reaction mixture was cooled to room temperature, to the reaction mixture were added dichloromethane and an aqueous sodium thiosulfate solution, and the layers were separated. The obtained organic layer was washed with a saturated saline solution, and dried over sodium sulfate. The solvent was evaporated under reduced pressure, and the obtained residue was purified by silica gel column chromatography. The title compound was obtained as 1.08 g of white amorphous.

Reference Example 13

Synthesis of 1-(2,3-dimethylphenyl)-2-(2,4,6-trifluorophenyl)-2,3-dihydropyridin-4(1H)-one

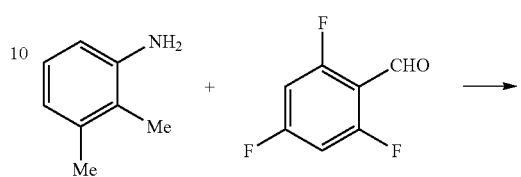

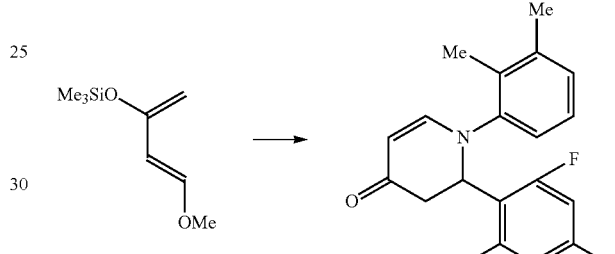

15 ml of a dichloroethane solution containing 3.00 g of 2,4,6-trifluorobenzaldehyde, 2.27 g of 2,3-dimethylaniline and 2.25 g of magnesium sulfate was stirred under reflux for 12 hours. The reaction mixture was cooled to room temperature, followed by removing the magnesium sulfate in the reaction mixture by filtration, and the solvent of the obtained filtrate was evaporated under reduced pressure. To the obtained brown solid were successively added 50 ml of acetonitrile and 5.37 ml of 1-methoxy-3-(trimethoxysilyloxy)-1,3-butadiene and the resultant mixture was ice-cooled. Then, to the mixture was added 0.32 g of 42% by weight aqueous solution of tetrafluoroboric acid, and the resultant mixture was stirred under ice-cooling for 1 hour. To the reaction mixture were added a saturated sodium hydrogen carbonate aqueous solution and ethyl acetate followed by separation of the layers, and the obtained organic layer was washed with a saturated saline solution, and dried over sodium sulfate. The solvent was evaporated under reduced pressure, and the obtained residue was purified by silica gel column chromatography. The title compound was obtained as 5.01 g of a yellow solid.

$^1$H-NMR (CDCl3) δ: 7.10-7.07 (1H, m), 6.98-6.96 (1H, m), 6.91 (1H, t, J=7.6 Hz), 6.84-6.82 (1H, m), 6.54-6.49 (2H, m), 5.60-5.57 (1H, br m), 5.24 (1H, d, J=7.3 Hz), 3.38-3.23 (1H, br m), 2.73-2.55 (1H, br m), 2.23 (3H, s), 2.22 (3H, s)

Reference Example 14

Synthesis of 1-(2,3-dimethylphenyl)-3-ethyl-2-(2,4,6-trifluorophenyl)-2,3-dihydropyridin-4(1H)-one

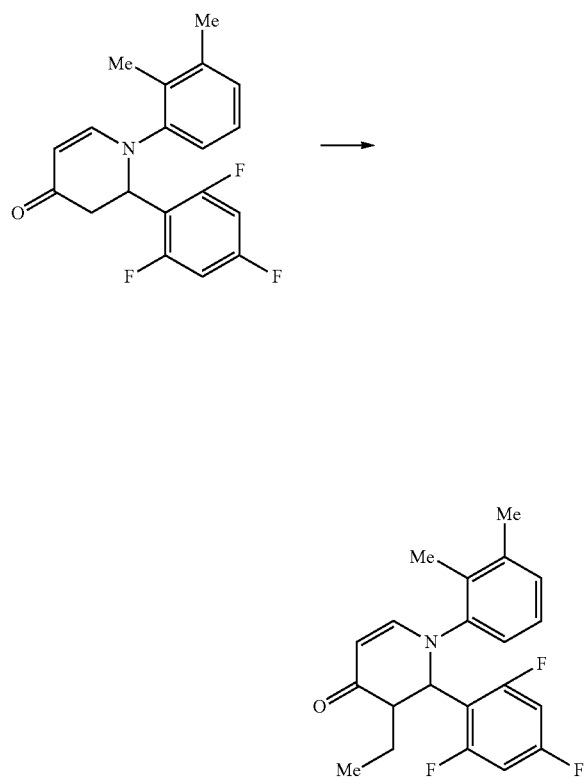

100 ml of a THF solution containing 5.01 g of 1-(2,3-dimethylphenyl)-2-(2,4,6-trifluorophenyl)-2,3-dihydropyridin-4(1H)-one, 24 ml of ethyl iodide and 5.25 ml of hexamethyl phosphoric acid triamide was cooled to −15° C. To the resultant mixture was added dropwise 23.00 ml of a 1.3 mol/l THF solution of lithium hexamethyldisilazane over 1 hour, and the mixture was stirred at −15° C. for 30 minutes. To the reaction mixture were added a saturated ammonium chloride aqueous solution and ethyl acetate followed by separation of the layers, and the obtained organic layer was washed with a saturated saline solution, and dried over sodium sulfate. The solvent was evaporated under reduced pressure, and the obtained residue was purified by silica gel column chromatography. The title compound was obtained as 3.13 g of a yellow oil.

$^1$H-NMR (CDCl3) δ: 7.00-6.99 (2H, m), 6.92 (1H, t, J=7.7 Hz), 6.85-6.83 (1H, m), 6.52 (2H, t, J=8.9 Hz), 5.38-5.36 (1H, m), 5.24 (1H, d, J=7.8 Hz), 2.99-2.96 (1H, br m), 2.23 (3H, s), 2.19 (3H, s), 1.94-1.84 (1H, m), 1.60-1.56 (1H, m), 0.95 (3H, t, J=7.3 Hz).

Reference Example 15

Synthesis of 1-(2,3-dimethylphenyl)-3-ethyl-2-(2,4,6-trifluorophenyl)pyridin-4(1H)-one (Intermediate No.: b020)

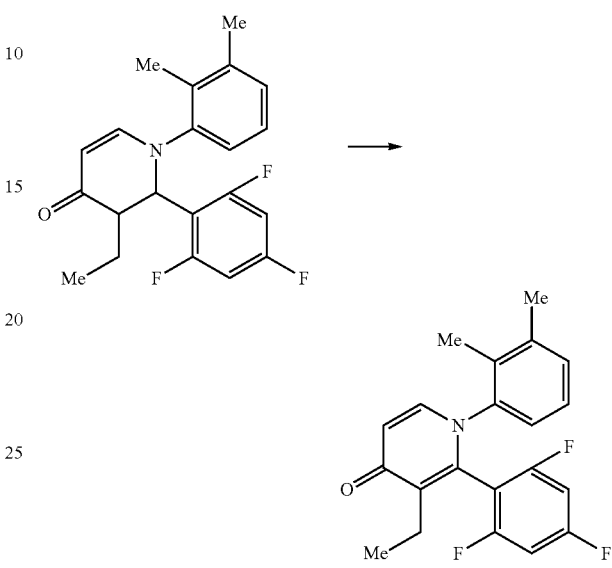

30 ml of a dimethylsulfoxide solution containing 3.11 g of 1-(2,3-dimethylphenyl)-3-ethyl-2-(2,4,6-trifluorophenyl)-2,3-dihydropyridin-4(1H)-one and 12.5 g of 39% by weight IBX (2-iodoxybenzoic acid) was stirred at 100° C. for 11 hours. The reaction mixture was cooled to room temperature, to the reaction mixture were added an aqueous sodium thiosulfate solution and ethyl acetate, and the layers were separated. The obtained organic layer was successively washed with a saturated sodium hydrogen carbonate aqueous solution and a saturated saline solution, and dried over sodium sulfate. The solvent was evaporated under reduced pressure, and the obtained residue was purified by silica gel column chromatography. The title compound was obtained as 0.78 g of an orange solid.

Among the compounds represented by Formula (1a), a compound represented by Formula (1a-b):

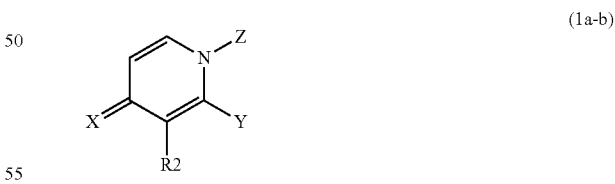

(1a-b)

(wherein R2, X, Y and Z are the same as defined above) is an effective production intermediate for the production of the compound of the present invention. The production intermediate shown in Reference Example 15 (1-(2,3-dimethylphenyl)-3-ethyl-2-(2,4,6-trifluorophenyl)pyridin-4(1H)-one) is encompassed by the compound represented by Formula (1a-b), and importance on production is understood also from Synthetic Example 12.

Production intermediates represented by Formula (1a-b) are given in Table b, and corresponding $^1$H-NMR data of the compounds in Table b are given in Table B.

TABLE b

| Intermediate | R2 | Y | Z | X |
|---|---|---|---|---|
| b001 | Me | 2,4,6-tri-F—Ph | iPr(Me)CH— | O |
| b002 | Me | 2,4,6-tri-F—Ph | iBu | O |
| b003 | Et | 2,4,6-tri-F—Ph | iBu | O |
| b004 | Me | 2,4,6-tri-F—Ph | 2-Me—Ph | O |
| b005 | Et | 2,4,6-tri-F—Ph | 2-Me—Ph | O |
| b006 | F3CCH2— | 2,4,6-tri-F—Ph | 2-Me—Ph | O |
| b007 | Et | 2,6-di-F—Ph | 2-Me—Ph | O |
| b008 | Et | Ph | 2-Me—Ph | O |
| b009 | Et | Ph | 2-Me-5-MeO—Ph | O |
| b010 | Et | Ph | 2,3-di-Me—Ph | O |
| b011 | Et | 2,4,6-tri-F—Ph | 2-Et—Ph | O |
| b012 | Et | 2,4,6-tri-F—Ph | 2-Cl—Ph | O |
| b013 | Et | 2,4,6-tri-F—Ph | Ph | O |
| b014 | Et | 2,6-di-F—Ph | 2,3-di-Me—Ph | O |
| b015 | Et | Ph | 2-Et—Ph | O |
| b016 | Et | Ph | 5-Br-2-Me—Ph | O |
| b017 | Et | 2,6-di-F—Ph | 5-Cl-2-Me—Ph | O |
| b018 | Et | Ph | 2-Cl—Ph | O |
| b019 | Et | 2,4,6-tri-F—Ph | 2-Me-5-MeO—Ph | O |
| b020 | Et | 2,4,6-tri-F—Ph | 2,3-di-Me—Ph | O |
| b021 | Et | 2,4,6-tri-F—Ph | 5-Br-2-Me—Ph | O |
| b022 | Et | Ph | 3-F-2-Me—Ph | O |
| b023 | Et | Ph | 3-Cl-2-Me—Ph | O |
| b024 | Et | 2,6-di-F—Ph | 2-Et—Ph | O |
| b025 | Et | 2,6-di-F—Ph | 2-Cl—Ph | O |
| b026 | Et | 2,6-di-F—Ph | 2,5-di-Me—Ph | O |
| b027 | Et | 2,4,6-tri-F—Ph | 2-Me-3-MeO—Ph | O |
| b028 | Et | 2,4,6-tri-F—Ph | 3-Cl-2-Me—Ph | O |
| b029 | Et | 2,4,6-tri-F—Ph | 2,5-di-Me—Ph | O |
| b030 | Et | 2,4,6-tri-F—Ph | 5-F-2-Me—Ph | O |
| b031 | Et | 2,6-di-F—Ph | 3-Cl-2-Me—Ph | O |
| b032 | Et | 2,6-di-F—Ph | 3-Br-2-Me—Ph | O |
| b033 | Et | 2,4,6-tri-F—Ph | 3-F-2-Me—Ph | O |
| b034 | Et | 2,6-di-F—Ph | Ph | O |
| b035 | Et | Ph | Ph | O |
| b036 | Et | 2,6-di-F—Ph | 2-Me-5-MeO—Ph | O |
| b037 | Et | 2,6-di-F—Ph | 5-F-2-Me—Ph | O |
| b038 | Et | Ph | 2-Me-3-MeO—Ph | O |
| b039 | Et | 2,4,6-tri-F—Ph | 3-Br-2-Me—Ph | O |
| b040 | Et | 2,6-di-F—Ph | 2-Me-3-MeO—Ph | O |
| b041 | Et | 2,6-di-F—Ph | 3-F-2-Me—Ph | O |
| b042 | Et | Ph | 5-Cl-2-Me—Ph | O |
| b043 | Et | 2,4,6-tri-F—Ph | 5-Cl-2-Me—Ph | O |
| b044 | Et | 2,6-di-F—Ph | 5-Br-2-Me—Ph | O |
| b045 | Et | Ph | 5-F-2-Me—Ph | O |
| b046 | Et | Ph | 3-Br-2-Me—Ph | O |
| b047 | Me | 2,4-di-F—Ph | Ph | O |
| b048 | Et | 2,4-di-F—Ph | Ph | O |
| b049 | Et | 2-Br-4-F—Ph | Ph | O |
| b050 | Et | 2-Cl-4-F—Ph | Ph | O |

TABLE B

| Intermediate | 1H-NMR |
|---|---|
| b001 | $^1$H-NMR (CDCl3) δ: 7.44 (1H, d, J = 7.6 Hz), 6.89-6.85 (2H, m), 6.53 (1H, d, J = 7.6 Hz), 3.29-3.28 (1H, m), 1.89-1.86 (1H, m), 1.81 (3H, s), 1.37 (3H, d, J = 6.7 Hz), 0.90 (3H, d, J = 6.4 Hz), 0.70 (3H, dd, J = 6.7, 1.2 Hz). |
| b002 | $^1$H-NMR (CDCl3) δ: 7.37 (1H, d, J = 7.6 Hz), 6.89-6.84 (2H, m), 6.44 (1H, d, J = 7.6 Hz), 3.37 (2H, d, J = 7.6 Hz), 1.82 (3H, s), 1.77-1.67 (1H, m), 0.78 (6H, d, J = 6.7 Hz). |
| b003 | $^1$H-NMR (CDCl3) δ: 7.35 (1H, d, J = 7.6 Hz), 6.89-6.83 (2H, m), 6.44 (1H, d, J = 7.6 Hz), 3.32 (2H, d, J = 7.6 Hz), 2.23 (2H, q, J = 7.4 Hz), 1.80-1.65 (4H, m), 0.93 (3H, t, J = 7.4 Hz), 0.80 (6H, d, J = 6.8 Hz). |
| b004 | $^1$H-NMR (CDCl3) δ: 7.36 (1H, d, J = 7.6 Hz), 7.24-7.18 (2H, m), 7.12-7.08 (2H, m), 6.63-6.51 (3H, m), 2.14 (3H, d, J = 1.0 Hz), 1.90 (3H, s). |
| b005 | $^1$H-NMR (CDCl3) δ: 7.34 (1H, d, J = 7.6 Hz), 7.23-7.17 (2H, m), 7.13-7.05 (2H, m), 6.63-6.58 (1H, m), 6.55-6.50 (2H, m), 2.37-2.24 (2H, m), 2.15 (3H, d, J = 1.2 Hz), 1.00 (3H, t, J = 7.4 Hz). |
| b006 | $^1$H-NMR (CDCl3) δ: 7.39 (1H, d, J = 7.8 Hz), 7.26-7.19 (2H, m), 7.14-7.07 (2H, m), 6.64-6.52 (3H, m), 3.41-3.18 (2H, m), 2.16 (3H, d, J = 1.2 Hz). |
| b007 | $^1$H-NMR (CDCl3) δ: 7.34 (1H, d, J = 7.6 Hz), 7.23-7.22 (1H, m), 7.16-7.14 (3H, m), 7.05-7.02 (1H, m), 6.83-6.81 (1H, m), 6.76-6.74 (1H, m), 6.53 (1H, d, J = 7.6 Hz), 2.33-2.29 (2H, m), 2.17 (3H, s), 1.00 (3H, t, J = 7.5 Hz). |
| b008 | $^1$H-NMR (CDCl3) δ: 7.28 (1H, d, J = 7.6 Hz), 7.25-6.98 (9H, m), 6.51 (1H, d, J = 7.6 Hz), 2.39-2.24 (2H, m), 2.11 (3H, s), 1.00 (3H, t, J = 7.4 Hz). |
| b009 | $^1$H-NMR (CDCl3) δ: 7.28-7.26 (2H, m), 7.25-7.22 (1H, m), 7.21-7.16 (2H, m), 7.04-7.02 (1H, m), 6.97 (1H, d, J = 8.5 Hz), 6.67 (1H, dd, J = 8.5, 2.7 Hz), 6.52 (1H, d, J = 2.7 Hz), 6.49 (1H, d, J = 7.6 Hz), 3.66 (3H, s), 2.38-2.25 (2H, m), 2.04 (3H, s), 1.00 (3H, t, J = 7.3 Hz). |
| b010 | $^1$H-NMR (CDCl3) δ: 7.27-7.26 (1H, m), 7.22-7.15 (3H, m), 7.12-7.11 (1H, m), 7.04-7.03 (1H, m), 6.99 (1H, d, J = 7.6 Hz), 6.93 (1H, t, J = 7.6 Hz), 6.87 (1H, d, J = 7.6 Hz), 6.49 (1H, d, J = 7.6 Hz), 2.33-2.29 (2H, m), 2.16 (3H, s), 1.96 (3H, s), 1.00 (3H, t, J = 7.3 Hz). |
| b011 | $^1$H-NMR (CDCl3) δ: 7.35 (1H, d, J = 7.6 Hz), 7.27-7.25 (2H, m), 7.14-7.13 (1H, m), 7.10-7.06 (1H, m), 6.60-6.56 (1H, m), 6.54-6.50 (2H, m), 2.44 (2H, q, J = 7.4 Hz), 2.38-2.34 (1H, m), 2.27-2.23 (1H, m), 1.18 (3H, t, J = 7.4 Hz), 1.00 (3H, t, J = 7.5 Hz). |
| b012 | $^1$H-NMR (CDCl3) δ: 7.41 (1H, dd, J = 8.4, 1.4 Hz), 7.33 (1H, d, J = 7.5 Hz), 7.30-7.26 (2H, m), 7.20 (1H, td, J = 7.6, 1.6 Hz), 6.59-6.57 (2H, m), 6.52 (1H, d, J = 7.5 Hz), 2.38-2.34 (1H, m), 2.28-2.24 (1H, m), 1.00 (3H, t, J = 7.5 Hz). |
| b013 | $^1$H-NMR (CDCl3) δ: 7.46 (1H, d, J = 7.5 Hz), 7.33-7.28 (3H, m), 7.18-7.16 (2H, m), 6.59-6.54 (2H, m), 6.51 (1H, d, J = 7.5 Hz), 2.31 (2H, q, J = 7.4 Hz), 1.00 (3H, t, J = 7.4 Hz). |

TABLE B-continued

| Intermediate | 1H-NMR |
|---|---|
| b014 | ¹H-NMR (CDCl3) δ: 7.32 (1H, d, J = 7.6 Hz), 7.22 (1H, tt, J = 8.3, 6.4 Hz), 7.05 (1H, d, J = 7.8 Hz), 7.02-7.00 (1H, m), 6.93 (1H, t, J = 7.8 Hz), 6.83-6.79 (1H, m), 6.77-6.73 (1H, m), 6.52 (1H, d, J = 7.6 Hz), 2.39-2.23 (2H, m), 2.22 (3H, s), 2.02 (3H, d, J = 2.1 Hz), 1.00 (3H, t, J = 7.5 Hz). |
| b015 | ¹H-NMR (CDCl3) δ: 7.30 (1H, d, J = 7.6 Hz), 7.22-7.09 (6H, m), 7.06-7.00 (3H, m), 6.49 (1H, d, J = 7.6 Hz), 2.46-2.24 (4H, m), 1.16 (3H t, J = 7.6 Hz), 1.00 (3H, t, J = 7.6 Hz) |
| b016 | ¹H-NMR (CDCl3) δ: 7.33-7.28 (1H, m), 7.26-7.14 (6H, m), 7.05-7.02 (1H, m), 6.96 (1H, d, J = 7.8 Hz), 6.50 (1H, d, J = 7.8 Hz), 2.39-2.23 (2H, m), 2.07 (3H, s), 1.00 (3H, t, J = 7.4 Hz). |
| b017 | ¹H-NMR (CDCl3) δ: 7.31-7.28 (2H, m), 7.18-7.14 (2H, m), 7.10 (1H, d, J = 8.3 Hz), 6.92-6.88 (1H, m), 6.80-6.76 (1H, m), 6.52 (1H, d, J = 7.6 Hz), 2.38-2.23 (2H, m), 2.14 (3H, s), 1.00 (3H, t, J = 7.3 Hz). |
| b018 | ¹H-NMR (CDCl3) δ: 7.33-7.30 (1H, m), 7.27-7.13 (7H, m), 7.11-7.09 (2H, m), 6.50 (1H, d, J = 7.6 Hz), 2.39-2.23 (2H, m), 1.01 (3H, t, J = 7.4 Hz). |
| b019 | ¹H-NMR (CDCl3) δ: 7.33 (1H, d, J = 7.6 Hz), 7.07 (1H, d, J = 8.5 Hz), 6.77 (1H, dd, J = 8.5, 2.7 Hz), 6.66-6.63 (2H, m), 6.57-6.55 (1H, m), 6.52 (1H, d, J = 7.6 Hz), 3.70 (3H, s), 2.34-2.26 (2H, m), 2.07 (3H, s), 1.00 (3H, t, J = 7.4 Hz). |
| b020 | ¹H-NMR (CDCl3) δ: 7.32 (1H, d, J = 7.6 Hz), 7.09-7.09 (1H, m), 6.97-6.96 (2H, m), 6.61-6.57 (1H, m), 6.54-6.52 (2H, m), 2.33-2.28 (5H, m), 2.00 (3H, d, J = 2.1 Hz), 1.00 (3H, t, J = 7.5 Hz). |
| b021 | ¹H-NMR (CDCl3) δ: 7.34 (1H, dd, J = 8.3, 2.1 Hz), 7.30-7.29 (2H, m), 7.08 (1H, d, J = 8.3 Hz), 6.71-6.67 (1H, m), 6.59-6.55 (1H, m), 6.52 (1H, d, J = 7.6 Hz), 2.36-2.33 (1H, m), 2.27-2.24 (1H, m), 2.11 (3H, s), 1.00 (3H, t, J = 7.3 Hz). |
| b022 | ¹H-NMR (CDCl3) δ: 7.26-7.25 (1H, m), 7.24-7.19 (3H, m), 7.14-7.11 (1H, m), 7.05-7.00 (2H, m), 6.90 (1H, t, J = 8.3 Hz), 6.85 (1H, d, J = 8.3 Hz), 6.50 (1H, d, J = 7.3 Hz), 2.34-2.28 (2H, m), 2.03 (3H, d, J = 2.1 Hz), 1.00 (3H, t, J = 7.5 Hz). |
| b023 | ¹H-NMR (CDCl3) δ: 7.25-7.20 (5H, m), 7.12-7.11 (1H, m), 7.03-7.02 (1H, m), 6.99 (1H, t, J = 8.0 Hz), 6.96 (1H, dd, J = 8.0, 1.5 Hz), 6.50 (1H, d, J = 7.3 Hz), 2.33-2.29 (2H, m), 2.13 (3H, s), 1.00 (3H, t, J = 7.3 Hz). |
| b024 | ¹H-NMR (CDCl3) δ: 7.35 (1H, d, J = 7.6 Hz), 7.23-7.20 (3H, m), 7.16-7.15 (1H, m), 7.06-7.03 (1H, m), 6.81-6.79 (1H, m), 6.75-6.73 (1H, m), 6.51 (1H, d, J = 7.6 Hz), 2.47-2.45 (2H, m), 2.38-2.34 (1H, m), 2.28-2.24 (1H, m), 1.18 (3H, t, J = 7.5 Hz), 1.00 (3H, t, J = 7.5 Hz). |
| b025 | ¹H-NMR (CDCl3) δ: 7.39-7.37 (1H, m), 7.34 (1H, d, J = 7.6 Hz), 7.31-7.21 (3H, m), 7.16-7.14 (1H, m), 6.83-6.77 (2H, m), 6.53 (1H, d, J = 7.6 Hz), 2.34-2.29 (2H, m), 1.00 (3H, t, J = 7.4 Hz). |
| b026 | ¹H-NMR (CDCl3) δ: 7.32 (1H, d, J = 7.6 Hz), 7.23-7.20 (1H, m), 7.04-7.02 (1H, m), 6.96-6.95 (2H, m), 6.85-6.81 (1H, m), 6.76-6.74 (1H, m), 6.51 (1H, d, J = 7.6 Hz), 2.33-2.28 (2H, m), 2.18 (3H, s), 2.11 (3H, s), 1.00 (3H, t, J = 7.4 Hz). |
| b027 | ¹H-NMR (CDCl3) δ: 7.31 (1H, d, J = 7.3 Hz), 7.05-7.00 (1H, m), 6.78-6.72 (2H, m), 6.60 (1H, tt, J = 8.7, 2.0 Hz), 6.56-6.50 (2H, m), 3.81 (3H, s), 2.35-2.25 (2H, m), 1.97 (3H, d, J = 2.1 Hz), 1.00 (3H, t, J = 7.5 Hz). |
| b028 | ¹H-NMR (CDCl3) δ: 7.35-7.32 (1H, m), 7.29 (1H, d, J = 7.6 Hz), 7.10-6.99 (2H, m), 6.64-6.56 (2H, m), 6.52 (1H, d, J = 7.6 Hz), 2.38-2.22 (2H, m), 2.17-2.14 (3H, m), 1.00 (3H, t, J = 7.3 Hz). |
| b029 | ¹H-NMR (CDCl3) δ: 7.32 (1H, d, J = 7.6 Hz), 7.05 (1H, d, J = 7.7 Hz), 7.00 (1H, dd, J = 7.7, 1.4 Hz), 6.92 (1H, s), 6.61 (1H, tt, J = 8.6, 2.1 Hz), 6.54-6.52 (2H, m), 2.33-2.28 (2H, m), 2.21 (3H, s), 2.10 (3H, s), 1.00 (3H, t, J = 7.5 Hz). |
| b030 | ¹H-NMR (CDCl3) δ: 7.30 (1H, d, J = 7.6 Hz), 7.17 (1H, dd, J = 8.7, 6.2 Hz), 6.96 (1H, td, J = 8.2, 2.6 Hz), 6.89 (1H, dt, J = 8.7, 2.6 Hz), 6.67 (1H, tt, J = 8.8. 2.1 Hz), 6.56 (1H, tt, J = 8.8, 2.1 Hz), 6.52 (1H, d, J = 7.6 Hz), 2.37-2.30 (1H, m), 2.27-2.22 (1H, m), 2.12 (3H, s), 1.00 (3H, t, J = 7.4 Hz). |
| b031 | ¹H-NMR (CDCl3) δ: 7.31-7.22 (3H, m), 7.12-7.09 (1H, m), 7.00 (1H, td, J = 8.1, 0.5 Hz), 6.85-6.77 (2H, m), 6.52 (1H, d, J = 7.6 Hz), 2.39-2.22 (2H, m), 2.17 (3H, d, J = 2.2 Hz), 1.00 (3H, t, J = 7.4 Hz). |
| b032 | ¹H-NMR (CDCl3) δ: 7.48 (1H, dd, J = 8.1, 1.0 Hz), 7.30-7.22 (2H, m), 7.15 (1H, ddd, J = 8.1, 2.4, 1.2 Hz), 6.95-6.91 (1H, m), 6.85-6.78 (2H, m), 6.52 (1H, d, J = 7.6 Hz), 2.40-2.22 (2H, m), 2.20 (3H, d, J = 2.2 Hz), 1.00 (3H, t, J = 7.4 Hz). |
| b033 | ¹H-NMR (CDCl3) δ: 7.31 (1H, d, J = 7.6 Hz), 7.05-6.98 (3H, m), 6.64-6.56 (2H, m), 6.52 (1H, d, J = 7.6 Hz), 2.33-2.27 (2H, m), 2.07 (3H, t, J = 2.0 Hz), 1.00 (3H, t, J = 7.3 Hz). |
| b034 | ¹H-NMR (CDCl3) δ: 7.46 (1H, d, J = 7.6 Hz), 7.25-7.20 (6H, m), 6.79-6.77 (2H, m), 6.51 (1H, d, J = 7.6 Hz), 2.31 (2H, q, J = 7.4 Hz), 0.99 (3H, t, J = 7.4 Hz). |

TABLE B-continued

| Intermediate | 1H-NMR |
| --- | --- |
| b035 | $^1$H-NMR (CDCl3) δ: 7.44 (1H, d, J = 7.6 Hz), 7.23-7.18 (6H, m), 7.09-7.07 (2H, m), 7.03-7.01 (2H, m), 6.49 (1H, d, J = 7.6 Hz), 2.34 (2H, q, J = 7.4 Hz), 1.00 (3H, t, J = 7.4 Hz). |
| b036 | $^1$H-NMR (CDCl3) δ: 7.34 (1H, d, J = 7.6 Hz), 7.29-7.22 (1H, m), 7.04 (1H, d, J = 8.4 Hz), 6.85 (1H, tt, J = 8.4, 1.0 Hz), 6.77 (1H, tt, J = 8.4, 1.0 Hz), 6.74-6.69 (2H, m), 6.52 (1H, d, J = 7.6 Hz), 3.68 (3H, s), 2.39-2.21 (2H, m), 2.09 (3H, s), 1.00 (3H, t, J = 7.4 Hz). |
| b037 | $^1$H-NMR (CDCl3) δ: 7.29-7.27 (2H, m), 7.15-7.13 (1H, m), 6.93-6.86 (3H, m), 6.81-6.76 (1H, m), 6.55 (1H, d, J = 7.6 Hz), 2.40-2.22 (2H, m), 2.13 (3H, s), 1.00 (3H, t, J = 7.4 Hz). |
| b038 | $^1$H-NMR (CDCl3) δ: 7.26-7.24 (1H, m), 7.23-7.12 (4H, m), 7.03 (1H, tt, J = 5.0, 1.3 Hz), 7.00-6.97 (1H, m), 6.67 (1H, d, J = 8.3 Hz), 6.63 (1H, d, J = 7.8 Hz), 6.48 (1H, d, J = 7.3 Hz), 3.75 (3H, s), 2.36-2.25 (2H, m), 1.94 (3H, s), 1.00 (3H, t, J = 7.4 Hz). |
| b039 | $^1$H-NMR (CDCl3) δ: 7.55-7.51 (1H, m), 7.30 (1H, d, J = 7.5 Hz), 7.15-7.10 (1H, m), 6.97 (1H, t, J = 8.3 Hz), 6.63-6.57 (2H, m), 6.52 (1H, d, J = 7.5 Hz), 2.38-2.21 (2H, m), 2.19 (3H, d, J = 2.1 Hz), 1.00 (3H, t, J = 7.5 Hz). |
| b040 | $^1$H-NMR (CDCl3) δ: 7.31 (1H, d, J = 7.6 Hz), 7.26-7.19 (1H, m), 6.99 (1H, t, J = 8.1 Hz), 6.84-6.71 (4H, m), 6.51 (1H, d, J = 7.6 Hz), 3.78 (3H, s), 2.38-2.23 (2H, m), 1.98 (3H, d, J = 2.0 Hz), 1.00 (3H, t, J = 7.4 Hz). |
| b041 | $^1$H-NMR (CDCl3) δ: 7.31 (1H, d, J = 7.6 Hz), 7.29-7.22 (1H, m), 7.06-6.94 (3H, m), 6.86-6.76 (2H, m), 6.53 (1H, d, J = 7.6 Hz), 2.38-2.23 (2H, m), 2.08 (3H, t, J = 2.1 Hz), 1.00 (3H, t, J = 7.4 Hz). |
| b042 | $^1$H-NMR (CDCl3) δ: 7.32-7.17 (4H, m), 7.16-7.14 (1H, m), 7.10 (1H, dd, J = 8.1, 2.2 Hz), 7.05-7.01 (3H, m), 6.50 (1H, d, J = 7.6 Hz), 2.39-2.23 (2H, m), 2.09 (3H, s), 1.00 (3H, t, J = 7.3 Hz). |
| b043 | $^1$H-NMR (CDCl3) δ: 7.29 (1H, d, J = 7.6 Hz), 7.20-7.19 (1H, m), 7.15-7.13 (2H, m), 6.70-6.66 (1H, m), 6.59-6.54 (1H, m), 6.52 (1H, d, J = 7.6 Hz), 2.34-2.28 (2H, m), 2.12 (3H, s), 1.00 (3H, t, J = 7.5 Hz). |
| b044 | $^1$H-NMR (CDCl3) δ: 7.33-7.24 (4H, m), 7.04 (1H, d, J = 7.9 Hz), 6.93-6.89 (1H, m), 6.80-6.76 (1H, m), 6.52 (1H, d, J = 7.9 Hz), 2.39-2.20 (2H, m), 2.12 (3H, s), 1.00 (3H, t, J = 7.4 Hz). |
| b045 | $^1$H-NMR (CDCl3) δ: 7.30-7.22 (3H, m), 7.21-7.19 (1H, m), 7.17-7.15 (1H, m), 7.05-7.04 (2H, m), 6.86 (1H, td, J = 8.6, 2.7 Hz), 6.76 (1H, dd, J = 8.6, 2.8 Hz), 6.50 (1H, d, J = 7.6 Hz), 2.34-2.28 (2H, m), 2.09 (3H, s), 1.00 (3H, t, J = 7.3 Hz). |
| b046 | $^1$H-NMR (CDCl3) δ: 7.41 (1H, dd, J = 8.0, 1.2 Hz), 7.25-7.20 (4H, m), 7.12-7.10 (1H, m), 7.01 (2H, dtd, J = 12.7, 4.3, 1.6 Hz), 6.91 (1H, t, J = 8.0 Hz), 6.50 (1H, d, J = 7.3 Hz), 2.32-2.28 (2H, m), 2.16 (3H, s), 1.00 (3H, t, J = 7.5 Hz). |
| b047 | $^1$H-NMR (CDCl3) δ: 7.48 (1H, d, J = 7.6 Hz), 7.28-7.25 (3H, m), 7.07-7.02 (3H, m), 6.81-6.76 (1H, m), 6.70 (1H, td, J = 9.2, 2.5 Hz), 6.50 (1H, d, J = 7.6 Hz), 1.88 (3H, s). |
| b048 | $^1$H-NMR (CDCl3) δ: 7.44 (1H, d, J = 7.6 Hz), 7.27-7.26 (3H, m), 7.10-7.08 (3H, m), 6.82-6.77 (1H, m), 6.68 (1H, td, J = 9.0, 2.4 Hz), 6.49 (1H, d, J = 7.6 Hz), 2.36-2.27 (2H, m), 0.99 (3H, t, J = 7.4 Hz). |
| b049 | $^1$H-NMR (CDCl3) δ: 7.43 (1H, d, J = 7.8 Hz), 7.26-7.15 (7H, m), 6.96 (1H, td, J = 8.3, 2.7 Hz), 6.51 (1H, d, J = 7.8 Hz), 2.52-2.43 (1H, m), 2.10-2.01 (1H, m), 0.99 (3H, t, J = 7.3 Hz). |
| b050 | $^1$H-NMR (CDCl3) δ: 7.44 (1H, d, J = 7.3 Hz), 7.27-7.09 (5H, m), 7.16 (1H, dd, J = 8.6, 5.8 Hz), 7.01 (1H, dd, J = 8.3, 2.6 Hz), 6.91 (1H, ddd, J = 8.6, 8.0, 2.6 Hz), 6.50 (1H, d, J = 7.3 Hz), 2.47-2.39 (1H, m), 2.14-2.07 (1H, m), 0.98 (3H, t, J = 7.5 Hz). |

Reference Example 16

Synthesis of 1-(2-methylbutyl)-2-(2,4,6-trifluorophenyl)-2,3-dihydropyridin-4(1H)-one

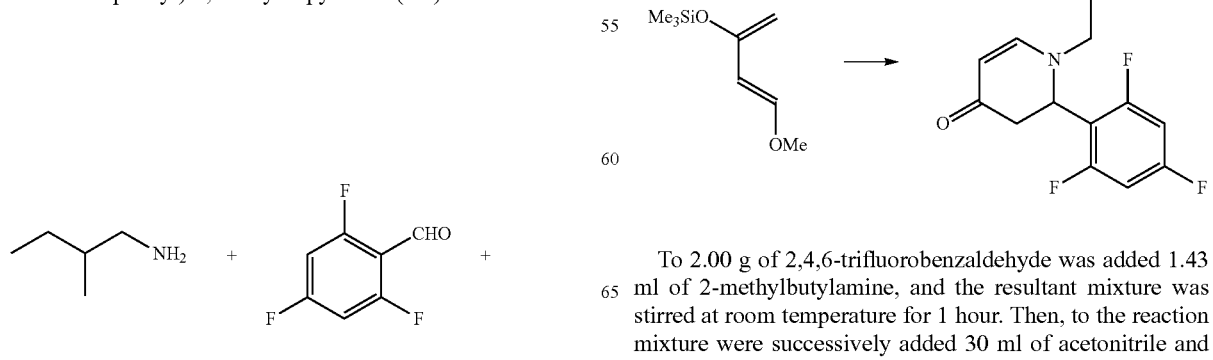

To 2.00 g of 2,4,6-trifluorobenzaldehyde was added 1.43 ml of 2-methylbutylamine, and the resultant mixture was stirred at room temperature for 1 hour. Then, to the reaction mixture were successively added 30 ml of acetonitrile and 3.60 ml of 1-methoxy-3-(trimethoxysilyloxy)-1,3-butadiene, and the resultant mixture was ice-cooled. Then, after adding 199 µl of 42% by weight aqueous solution of tetrafluoroboric acid to the mixture, the temperature of the mixture was raised to 60° C. and the mixture was stirred for 7 hours. The reaction mixture was cooled to room temperature, to the reaction mixture were added a saturated sodium hydrogen carbonate aqueous solution and ethyl acetate, and the layers were separated. The obtained organic layer was washed with a saturated saline solution, and dried over sodium sulfate. The solvent was evaporated under reduced pressure, and the obtained residue was purified by silica gel column chromatography. The title compound was obtained as 2.30 g of a brown oil.

$^1$H-NMR (CDCl3) δ: 7.05 (1H, dd, J=11.3, 7.6 Hz), 6.75-6.73 (2H, m), 5.09-5.02 (2H, m), 2.95-2.81 (2H, m), 2.67-2.63 (2H, m), 1.54-1.43 (2H, m), 1.13-0.67 (7H, m).

Reference Example 17

Synthesis of 5-chloro-1-(2-methylbutyl)-2-(2,4,6-trifluorophenyl)-2,3-dihydropyridin-4(1H)-one

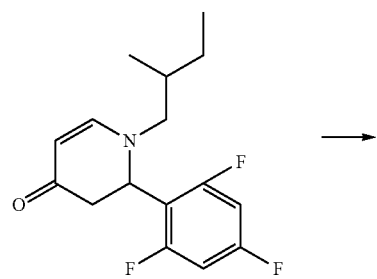

10 ml of a DMF solution containing 1.0 g of 1-(2-methylbutyl)-2-(2,4,6-trifluorophenyl)-2,3-dihydropyridin-4(1H)-one and 494 mg of N-chlorosuccinimide was stirred at room temperature for 1 hour. To the reaction mixture were added water and ethyl acetate followed by separation of the layers, and the obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 1.05 g of pale yellow amorphous. This was used in the next reaction without further purification.

Reference Example 18

5-Chloro-1-(2-methylbutyl)-2-(2,4,6-trifluorophenyl)pyridin-4(1H)-one (Intermediate No.: a060)

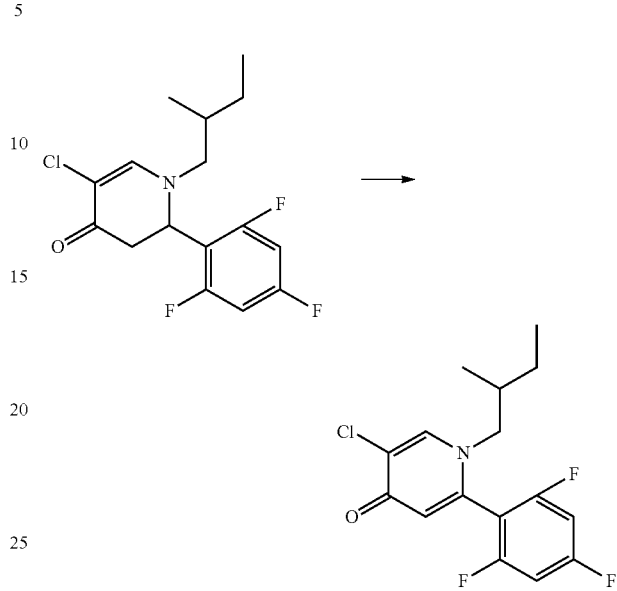

5 ml of a toluene solution containing 1.05 g of 5-chloro-1-(2-methylbutyl)-2-(2,4,6-trifluorophenyl)-2,3-dihydropyridin-4(1H)-one and 1.08 g of 2,3-dichloro-5,6-dicyano-p-benzoquinone was stirred at 110° C. for 30 minutes. The reaction mixture was cooled to room temperature and filtered. After the solvent of the filtrate was evaporated under reduced pressure, the residue was purified by silica gel column chromatography. The title compound was obtained as 0.53 g of a pale yellow solid.

Reference Example 19

Synthesis of 2'-chloro-2-(2,4,6-trifluorophenyl)-2,3-dihydro-4H-[1,3'-bipyridin]-4-one

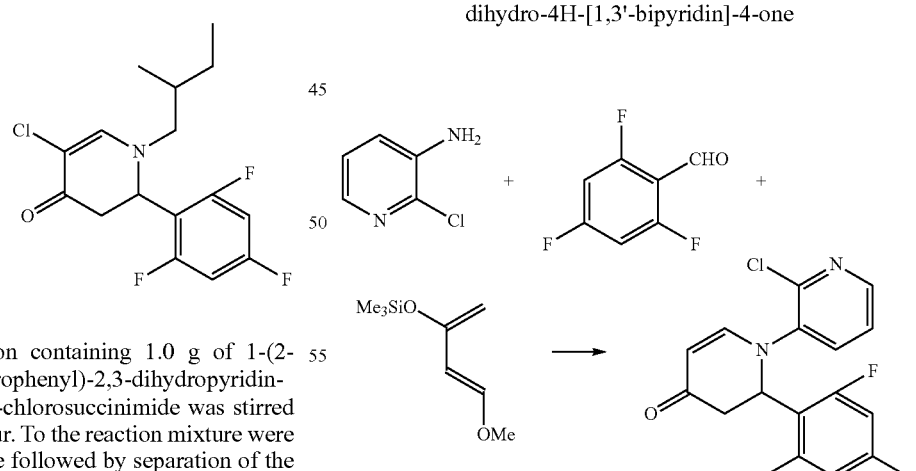

3 ml of an acetonitrile solution containing 2.50 g of 2,4,6-trifluorobenzaldehyde, 2.00 g of 3-amino-2-chloropyridine and 0.56 g of magnesium sulfate was stirred at 60° C. for 5 hours, and then further stirred at 80° C. for 6 hours. The reaction mixture was cooled to room temperature, to the reaction mixture were successively added 30 ml of acetonitrile and 4.48 ml of 1-methoxy-3-(trimethoxysilyloxy)-1,3-butadiene, and the mixture was ice-cooled. Then, 498 μl of 42% by weight aqueous solution of tetrafluoroboric acid was added and the resultant mixture was stirred under ice-cooling for 2 hours, and then the temperature of the mixture was raised to 60° C. and further stirred for 1 hour. The reaction mixture was cooled to room temperature, to the reaction mixture were added a saturated sodium hydrogen carbonate aqueous solution and ethyl acetate, and the layers were separated. The obtained organic layer was washed with a saturated saline solution, and dried over sodium sulfate. The solvent was evaporated under reduced pressure, and the obtained residue was purified by silica gel column chromatography. The title compound was obtained as 1.38 g of a yellow solid.

$^1$H-NMR (CDCl3) δ: 8.26 (1H, dd, J=4.7, 1.8 Hz), 7.49 (1H, d, J=8.0 Hz), 7.17 (1H, dd, J=8.0, 4.7 Hz), 7.11 (1H, d, J=8.0 Hz), 6.60-6.56 (2H, m), 5.76 (1H, dd, J=13.8, 5.2 Hz), 5.37 (1H, d, J=8.0 Hz), 3.29 (1H, dd, J=16.5, 13.8 Hz), 2.71 (1H, ddd, J=16.5, 5.2, 0.9 Hz).

Reference Example 20

Synthesis of 5-bromo-2'-chloro-2-(2,4,6-trifluorophenyl)-2,3-dihydro-4H-[1,3'-bipyridin]-4-one

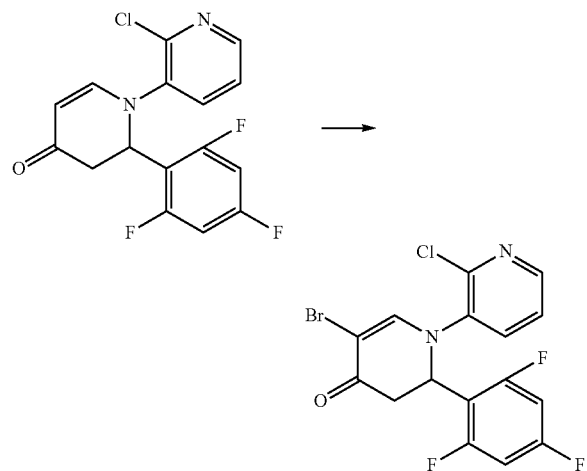

5 ml of DMF containing 500 mg of 2'-chloro-2-(2,4,6-trifluorophenyl)-2,3-dihydro-4H-[1,3'-bipyridin]-4-one and 289 mg of N-bromosuccinimide was stirred at room temperature for 1 hour. To the reaction mixture were added water and ethyl acetate, and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 475 mg of a pale yellow solid.

$^1$H-NMR (CDCl3) δ: 8.29 (1H, dd, J=4.7, 1.7 Hz), 7.52-7.50 (2H, m), 7.19 (1H, dd, J=7.8, 4.7 Hz), 6.62-6.56 (2H, m), 5.83 (1H, dd, J=13.7, 5.4 Hz), 2.94 (1H, dd, J=16.7, 5.4 Hz).

Reference Example 21

Synthesis of 5-bromo-2'-chloro-2-(2,4,6-trifluorophenyl)-4H-[1,3'-bipyridin]-4-one (Intermediate No.: a016)

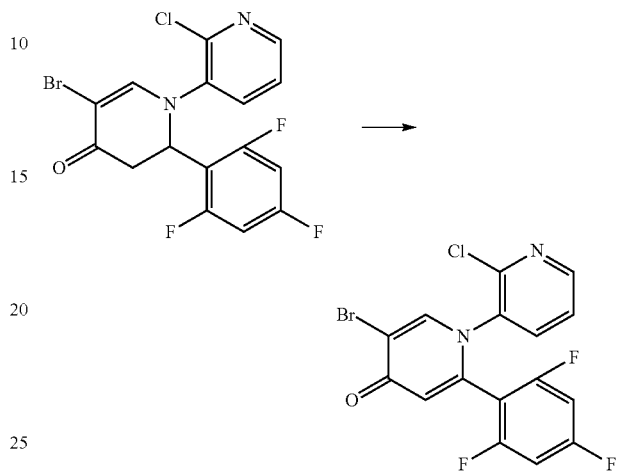

To 10 ml of carbon tetrachloride solution containing 475 mg of 5-bromo-2'-chloro-2-(2,4,6-trifluorophenyl)-2,3-dihydro-4H-[1,3'-bipyridin]-4-one were added 213 mg of N-bromosuccinimide and 19 mg of azobisisobutyronitrile, and the resultant mixture was stirred at 80° C. for 2 hours. The reaction mixture was cooled to room temperature, to the reaction mixture were added dichloromethane and water, and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 312 mg of a white solid.

Reference Example 22

Synthesis of 1-(5-methylisoxazol-3-yl)-2-(2,4,6-trifluorophenyl)-2,3-dihydropyridin-4(1H)-one

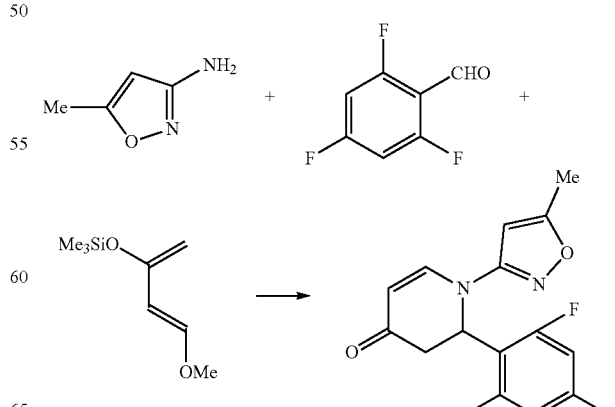

1 ml of acetonitrile solution containing 2.00 g of 2,4,6-trifluorobenzaldehyde and 1.84 g of 5-methylisoxazole-3-amine was stirred at 60° C. for 30 minutes. The reaction mixture was cooled to room temperature, to the reaction mixture were successively added 30 ml of acetonitrile, 3.60 ml of 1-methoxy-3-(trimethoxysilyloxy)-1,3-butadiene and 199 µl of 42% by weight aqueous solution of tetrafluoroboric acid, and the temperature of the mixture was raised to 60° C. and the mixture was stirred for 30 minutes. The reaction mixture was cooled to room temperature, to the reaction mixture were added a saturated sodium hydrogen carbonate aqueous solution and ethyl acetate, and the layers were separated. The obtained organic layer was washed with a saturated saline solution, and dried over sodium sulfate. The solvent was evaporated under reduced pressure, and the obtained residue was purified by silica gel column chromatography. The title compound was obtained as 2.73 g of a brown solid. This was used in the next reaction without further purification.

Reference Example 23

Synthesis of 5-chloro-1-(5-methylisoxazol-3-yl)-2-(2,4,6-trifluorophenyl)-2,3-dihydropyridin-4(1H)-one

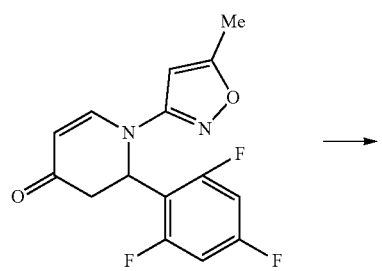

10 ml of a DMF solution containing 1.00 g of 1-(5-methylisoxazol-3-yl)-2-(2,4,6-trifluorophenyl)-2,3-dihydropyridin-4(1H)-one obtained in Reference Example 22 and 476 mg of N-chlorosuccinimide was stirred at 60° C. for 1 hour. The reaction mixture was cooled to room temperature, to the reaction mixture were added water and ethyl acetate, and the layers were separated. The obtained organic layer was successively washed with an aqueous sodium thiosulfate solution and a saturated saline solution, and dried over sodium sulfate. The solvent was evaporated under reduced pressure, and the obtained residue was purified by silica gel column chromatography. The title compound was obtained as 398 mg of a colorless transparent oil.

$^1$H-NMR (CDCl3) δ: 7.78 (1H, s), 6.70-6.63 (2H, m), 5.87-5.84 (2H, m), 3.32 (1H, dd, J=16.8, 8.8 Hz), 2.93 (1H, dd, J=16.8, 3.4 Hz), 2.37 (3H, d, J=0.7 Hz).

Reference Example 24

Synthesis of 5-chloro-1-(5-methylisoxazol-3-yl)-2-(2,4,6-trifluorophenyl)pyridin-4(1H)-one (Intermediate No.: a053)

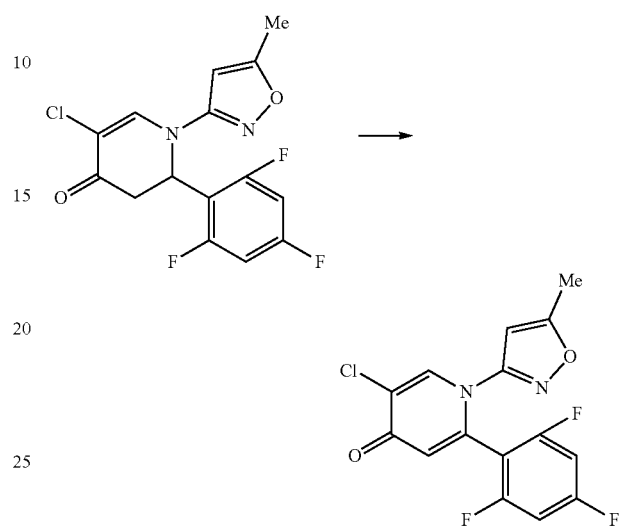

6 ml of a toluene solution containing 398 mg of 5-chloro-1-(5-methylisoxazol-3-yl)-2-(2,4,6-trifluorophenyl)-2,3-dihydropyridin-4(1H)-one and 395 mg of 2,3-dichloro-5,6-dicyano-p-benzoquinone was stirred at 110° C. for 2 hours. The reaction mixture was cooled to room temperature and, after the solvent of the filtrate was evaporated under reduced pressure, the residue was purified by silica gel column chromatography. The title compound was obtained as 293 mg of a white solid.

Reference Example 25

Synthesis of 2-(4-chloro-2-fluorophenyl)-3,5-dimethyl-1-phenyl-2,3-dihydropyridin-4(1H)-one

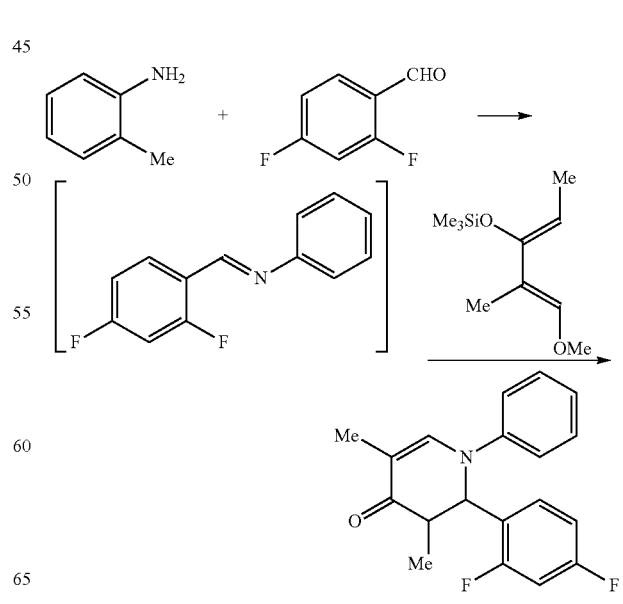

Step 1: Synthesis of
1-(2-chloro-4-fluorophenyl)-N-phenylmethaneimine 4.80 g of 2-chloro-4-fluorobenzaldehyde, 2.82 g of aniline and 1.10 g of magnesium sulfate were mixed, and the mixture was stirred at 80° C. for 2.5 hours. To the mixture was further added 10 ml of a dichloroethane solution, and the mixture was stirred under reflux for 5 hours. The reaction mixture was cooled to room temperature, magnesium sulfate in the reaction mixture was removed by filtration, and the solvent of the obtained filtrate was evaporated under reduced pressure. 6.70 g of the obtained pale brown oil was the title compound, and this was used in the next reaction without further purification.

$^1$H-NMR (CDCl3) δ: 8.84 (1H, s), 8.28 (1H, dd, J=9.0, 6.3 Hz), 7.42-7.40 (2H, m), 7.29-7.16 (4H, m), 7.11-7.08 (1H, m).

Step 2: Synthesis of 2-(2-chloro-4-fluorophenyl)-3,5-dimethyl-1-phenyl-2,3-dihydropyridin-4(1H)-one 30 ml of an acetonitrile solution containing 1.50 g of 1-(2-chloro-4-fluorophenyl)-N-phenylmethaneimine and 1.54 g of ((1-methoxy-2-methylpenta-1,3-dien-3-yl)oxy)trimethylsilane was ice-cooled and, after adding 0.27 g of 42% by weight aqueous solution of tetrafluoroboric acid thereto, the temperature of the mixture was raised from ice-cooling to room temperature, and the mixture was stirred for 6 hours. To the reaction mixture were added a saturated sodium hydrogen carbonate aqueous solution and ethyl acetate followed by separation of the layers, and the obtained organic layer was washed with a saturated saline solution, and dried over sodium sulfate. The solvent was evaporated under reduced pressure, and the obtained residue was purified by silica gel column chromatography. The title compound was obtained as 2.12 g of a pale yellow oil. This was used in the next reaction without further purification.

The compounds (compounds represented by Formula (1)) synthesized in substantially the same manner as in Examples described above are given in Table 4, but the present invention is not limited to these compounds.

TABLE 4

| Compound | R1 | R2 | Y | Z | X |
|---|---|---|---|---|---|
| 1 | Br | Br | 2,4,6-tri-F—Ph | 2-Cl—Ph | O |
| 2 | Br | Cl | 2,4,6-tri-F—Ph | 2-Cl—Ph | O |
| 3 | Cl | Br | 2,4,6-tri-F—Ph | 2-Cl—Ph | O |
| 4 | Cl | Cl | 2,4,6-tri-F—Ph | 2-Cl—Ph | O |
| 5 | Cl | Cl | 2,6-di-F-4-MeO—Ph | 2-Cl—Ph | O |
| 6 | Cl | Cl | 2,4,6-tri-F—Ph | Pr | O |
| 7 | Cl | Br | 2,4,6-tri-F—Ph | Pr | O |
| 8 | Br | Br | 2,4,6-tri-F—Ph | Ph | O |
| 9 | Br | Cl | 2,4,6-tri-F—Ph | Ph | O |
| 10 | Cl | Cl | 2,4,6-tri-F—Ph | iPr | O |
| 11 | Cl | Br | 2,4,6-tri-F—Ph | iPr | O |
| 12 | Br | Br | 2,4,6-tri-F—Ph | iPr | O |
| 13 | Br | Cl | 2,4,6-tri-F—Ph | iPr | O |
| 14 | Cl | Cl | 2,4,6-tri-F—Ph | Ph | O |
| 15 | Cl | Br | 2,4,6-tri-F—Ph | Ph | O |
| 16 | Cl | Cl | 2,6-di-F-4-MeO—Ph | Ph | O |
| 17 | Cl | Br | 2,6-di-F-4-MeO—Ph | Ph | O |
| 18 | Br | Br | 2,6-di-F-4-MeO—Ph | iPr | O |
| 19 | Br | Cl | 2,6-di-F-4-MeO—Ph | iPr | O |
| 20 | Br | Cl | 2,4,6-tri-F—Ph | 2-F—Ph | O |
| 21 | Br | Cl | 2,6-di-F-4-MeO—Ph | 2-F—Ph | O |
| 22 | Br | Br | 2,4,6-tri-F—Ph | 2-F—Ph | O |
| 23 | Br | Br | 2,6-di-F-4-MeO—Ph | 2-F—Ph | O |
| 24 | Cl | Cl | 2,4,6-tri-F—Ph | 2-F—Ph | O |
| 25 | Cl | Br | 2,4,6-tri-F—Ph | cHex | O |
| 26 | Cl | Cl | 2,4,6-tri-F—Ph | cHex | O |
| 27 | Cl | Br | 2,6-di-F-4-MeO—Ph | cHex | O |
| 28 | Cl | Cl | 2,6-di-F-4-MeO—Ph | cHex | O |
| 29 | Br | Cl | 2,4,6-tri-F—Ph | cHex | O |
| 30 | Br | Br | 2,4,6-tri-F—Ph | cHex | O |
| 31 | Cl | Br | 2,4,6-tri-F—Ph | 2-F—Ph | O |
| 32 | Cl | Cl | 2,6-di-F-4-MeO—Ph | 2-F—Ph | O |
| 33 | Cl | Br | 2,6-di-F-4-MeO—Ph | 2-F—Ph | O |
| 34 | Cl | Br | 2,4,6-tri-F—Ph | 2-Cl-3-Py | O |
| 35 | Cl | Cl | 2,4,6-tri-F—Ph | 2-Cl-3-Py | O |
| 36 | Br | Cl | 2,4,6-tri-F—Ph | 2-Cl-3-Py | O |
| 37 | Br | Cl | 2,4,6-tri-F—Ph | 2-Br—Ph | O |
| 38 | Br | Br | 2,4,6-tri-F—Ph | 2-Cl-3-Py | O |
| 39 | Cl | Br | 2,6-di-F-4-MeO—Ph | 2-MeO-3-Py | O |
| 40 | Br | Cl | 2,6-di-F-4-MeO—Ph | 2-MeO-3-Py | O |
| 41 | Cl | Cl | 2,4,6-tri-F—Ph | iPr(Me)CH— | O |
| 42 | Cl | Br | 2,4,6-tri-F—Ph | iPr(Me)CH— | O |
| 43 | Br | Cl | 2,4,6-tri-F—Ph | iPr(Me)CH— | O |
| 44 | Br | Br | 2,4,6-tri-F—Ph | 2-Br—Ph | O |
| 45 | Cl | Cl | 2,4,6-tri-F—Ph | 2-Br—Ph | O |
| 46 | Cl | Br | 2,4,6-tri-F—Ph | 2-Br—Ph | O |
| 47 | Br | Br | 2,4,6-tri-F—Ph | iPr(Me)CH— | O |
| 48 | Cl | Cl | 2,4,6-tri-F—Ph | PhCH2— | O |
| 49 | Cl | Br | 2,4,6-tri-F—Ph | PhCH2— | O |
| 50 | Cl | Br | 2,6-di-F-4-MeO—Ph | iPr(Me)CH— | O |

TABLE 4-continued

| Compound | R1 | R2 | Y | Z | X |
|---|---|---|---|---|---|
| 51 | Br | Cl | 2,6-di-F-4-MeO—Ph | iPr(Me)CH— | O |
| 52 | Cl | Cl | 2,6-di-F-4-MeO—Ph | iPr(Me)CH— | O |
| 53 | Br | Br | 2,6-di-F-4-MeO—Ph | iPr(Me)CH— | O |
| 54 | Br | Cl | 2,6-di-F—Ph | 2-Cl—Ph | O |
| 55 | Br | Br | 2,6-di-F—Ph | 2-Cl—Ph | O |
| 56 | Br | Cl | 2,4,6-tri-F—Ph | PhCH2— | O |
| 57 | Br | Br | 2,4,6-tri-F—Ph | PhCH2— | O |
| 58 | Cl | Cl | 2,6-di-F-4-MeO—Ph | PhCH2— | O |
| 59 | Cl | Br | 2,6-di-F-4-MeO—Ph | PhCH2— | O |
| 60 | Cl | Br | 2,6-di-F—Ph | 2-Cl—Ph | O |
| 61 | Cl | Cl | 2,6-di-F—Ph | 2-Cl—Ph | O |
| 62 | Cl | Br | 2,4,6-tri-F—Ph | 2-Me—Ph | O |
| 63 | Cl | Cl | 2,4,6-tri-F—Ph | 2-Me—Ph | O |
| 64 | Cl | Cl | 2,6-di-F-4-MeO—Ph | 2-Me—Ph | O |
| 65 | Cl | Br | 2,6-di-F-4-MeO—Ph | 2-Me—Ph | O |
| 66 | Br | Cl | 2,4,6-tri-F—Ph | 2-Me—Ph | O |
| 67 | Br | Br | 2,4,6-tri-F—Ph | 2-Me—Ph | O |
| 68 | Br | Br | 2,6-di-F-4-MeO—Ph | 2-Me—Ph | O |
| 69 | Cl | Cl | 2,4,6-tri-F—Ph | CF3CH2CH2CH2 | O |
| 70 | Cl | Br | 2,4,6-tri-F—Ph | CF3CH2CH2CH2 | O |
| 71 | Br | Cl | 2,4,6-tri-F—Ph | CF3CH2CH2CH2 | O |
| 72 | Br | Br | 2,4,6-tri-F—Ph | CF3CH2CH2CH2 | O |
| 73 | Cl | Br | 2,4,6-tri-F—Ph | Ph(Me)CH— | O |
| 74 | Cl | Cl | 2,4,6-tri-F—Ph | Ph(Me)CH— | O |
| 75 | Cl | Cl | 2,4,6-tri-F—Ph | 2-MeO—Ph | O |
| 76 | Cl | I | 2,4,6-tri-F—Ph | Ph(Me)CH— | O |
| 77 | Br | Cl | 2,4,6-tri-F—Ph | Ph(Me)CH— | O |
| 78 | Br | Br | 2,4,6-tri-F—Ph | Ph(Me)CH— | O |
| 79 | Cl | Cl | 2,4,6-tri-F—Ph | (2-Cl—Ph)—CH2— | O |
| 80 | Cl | Br | 2,4,6-tri-F—Ph | (2-Cl—Ph)—CH2— | O |
| 81 | Br | Cl | 2,4,6-tri-F—Ph | 2-MeO—Ph | O |
| 82 | Cl | Br | 2,6-di-F-4-MeO—Ph | Ph(Me)CH— | O |
| 83 | Cl | Cl | 2,6-di-F-4-MeO—Ph | Ph(Me)CH— | O |
| 84 | Cl | Br | 2,6-di-F-4-MeO—Ph | CF3CH2CH2CH2 | O |
| 85 | Cl | Cl | 2,6-di-F-4-MeO—Ph | CF3CH2CH2CH2 | O |
| 86 | Br | Cl | 2,4,6-tri-F—Ph | (2-Cl—Ph)—CH2— | O |
| 87 | Br | Br | 2,4,6-tri-F—Ph | (2-Cl—Ph)—CH2— | O |
| 88 | Cl | Br | 2,6-di-F-4-MeO—Ph | (2-Cl—Ph)—CH2— | O |
| 89 | Cl | I | 2,4,6-tri-F—Ph | (2-Cl—Ph)—CH2— | O |
| 90 | Br | Cl | 2,6-di-F—Ph | 2-Br—Ph | O |
| 91 | Br | Br | 2,6-di-F—Ph | 2-Br—Ph | O |
| 92 | Cl | Cl | 2,6-di-F—Ph | 2-Br—Ph | O |
| 93 | Cl | Br | 2,6-di-F—Ph | 2-Br—Ph | O |
| 94 | Cl | Cl | 2,4,6-tri-F—Ph | PhCH2CH2— | O |
| 95 | Cl | Br | 2,4,6-tri-F—Ph | PhCH2CH2— | O |
| 96 | Br | Cl | 2,6-di-F—Ph | 2-Cl-4-F—Ph | O |
| 97 | Br | Br | 2,6-di-F—Ph | 2-Cl-4-F—Ph | O |
| 98 | Cl | Br | 2,6-di-F—Ph | 2-Cl-4-F—Ph | O |
| 99 | Cl | Cl | 2,6-di-F—Ph | 2-Cl-4-F—Ph | O |
| 100 | Br | Cl | 2,4,6-tri-F—Ph | PhCH2CH2— | O |
| 101 | Br | Br | 2,4,6-tri-F—Ph | PhCH2CH2— | O |
| 102 | Cl | Cl | 2,6-di-F-4-MeO—Ph | PhCH2CH2— | O |
| 103 | Cl | Br | 2,6-di-F-4-MeO—Ph | PhCH2CH2— | O |
| 104 | Br | Br | 2,6-di-F-4-MeO—Ph | PhCH2CH2— | O |
| 105 | Br | Cl | 2,6-di-F—Ph | 2-Cl-5-F—Ph | O |
| 106 | Br | Br | 2,6-di-F—Ph | 2-Cl-5-F—Ph | O |
| 107 | Cl | Cl | 2,4,6-tri-F—Ph | iBu | O |
| 108 | Cl | Br | 2,4,6-tri-F—Ph | iBu | O |
| 109 | Cl | Br | 2,6-di-F—Ph | 2-Cl-5-F—Ph | O |
| 110 | Cl | Cl | 2,6-di-F—Ph | 2-Cl-5-F—Ph | O |
| 111 | Br | Cl | 2,6-di-F—Ph | 2-Me—Ph | O |
| 112 | Br | Br | 2,6-di-F—Ph | 2-Me—Ph | O |
| 113 | Cl | Br | 2,6-di-F—Ph | 2-Me—Ph | O |
| 114 | Cl | Cl | 2,6-di-F—Ph | 2-Me—Ph | O |
| 115 | Br | Cl | 2,4,6-tri-F—Ph | iBu | O |
| 116 | Br | Br | 2,4,6-tri-F—Ph | iBu | O |
| 117 | Br | Cl | 2,4,6-tri-F—Ph | 3-Br—Ph | O |
| 118 | Br | Br | 2,4,6-tri-F—Ph | 3-Br—Ph | O |
| 119 | Cl | Br | 2,4,6-tri-F—Ph | 3-Br—Ph | O |
| 120 | Cl | Cl | 2,4,6-tri-F—Ph | 3-Br—Ph | O |
| 121 | Cl | F | 2,4,6-tri-F—Ph | cHex—CH2— | O |
| 122 | Cl | Cl | 2,4,6-tri-F—Ph | cHex—CH2— | O |
| 123 | Cl | Br | 2,4,6-tri-F—Ph | cHex—CH2— | O |
| 124 | Br | Cl | 2,4,6-tri-F—Ph | cHex—CH2— | O |
| 125 | Br | Br | 2,4,6-tri-F—Ph | cHex—CH2— | O |
| 126 | Br | Cl | 2,4,6-tri-F—Ph | 3-Isoxazolyl | O |
| 127 | Br | Br | 2,4,6-tri-F—Ph | 3-Isoxazolyl | O |
| 128 | Cl | Cl | 2,4,6-tri-F-rh | 3-Isoxazolyl | O |

TABLE 4-continued

| Compound | R1 | R2 | Y | Z | X |
|---|---|---|---|---|---|
| 129 | Cl | Br | 2,4,6-tri-F—Ph | 3-Isoxazolyl | O |
| 130 | Br | Br | 2,6-di-F-4-MeO—Ph | 3-Isoxazolyl | O |
| 131 | Br | Cl | 2,6-di-F-4-MeO—Ph | 3-Isoxazolyl | O |
| 132 | Cl | Br | 2,6-di-F-4-MeO—Ph | iBu | O |
| 133 | Br | Br | 2,6-di-F-4-MeO—Ph | iBu | O |
| 134 | Br | F | 2,4,6-tri-F—Ph | iPr(Me)CH— | O |
| 135 | Me | Cl | 2,4,6-tri-F—Ph | iPr(Me)CH— | O |
| 136 | Ac | Cl | 2,4,6-tri-F—Ph | iPr(Me)CH— | O |
| 137 | F3C— | Cl | 2,4,6-tri-F—Ph | iPr(Me)CH— | O |
| 138 | Cl | Br | 2,4,6-tri-F—Ph | 5-Me-3-Isoxazolyl | O |
| 139 | Br | Cl | 2,4,6-tri-F—Ph | 3-Cl—Ph | O |
| 140 | Br | Br | 2,4,6-tri-F—Ph | 3-Cl—Ph | O |
| 141 | Cl | Br | 2,4,6-tri-F—Ph | 5-Me-3-Isoxazolyl | O |
| 142 | Cl | Br | 2,4,6-tri-F—Ph | 4-Br-5-Me-3-isoxazolyl | O |
| 143 | Br | Cl | 2,4,6-tri-F—Ph | 2,5-di-Me—Ph | O |
| 144 | Br | Br | 2,4,6-tri-F—Ph | 2,5-di-Me—Ph | O |
| 145 | Cl | Cl | 2,4,6-tri-F—Ph | EtOC(=O)CH2— | O |
| 146 | Br | Br | 2,4,6-tri-F—Ph | 5-Me-3-Isoxazolyl | O |
| 147 | Br | Br | 2,4,6-tri-F—Ph | 4-Br-5-Me-3-isoxazolyl | O |
| 148 | Cl | Br | 2,4,6-tri-F—Ph | 2,5-di-Me—Ph | O |
| 149 | Cl | Cl | 2,4,6-tri-F—Ph | 2,5-di-Me—Ph | O |
| 150 | Cl | Br | 2,4,6-tri-F—Ph | EtOC(=O)CH2— | O |
| 151 | Br | Me | 2,4,6-tri-F—Ph | iPr(Me)CH— | O |
| 152 | Me | Me | 2,4,6-tri-F—Ph | iPr(Me)CH— | O |
| 153 | Cl | Cl | 2,4,6-tri-F—Ph | 2-Me—cHex | O |
| 154 | Cl | Br | 2,4,6-tri-F—Ph | 2-Me—cHex | O |
| 155 | Me | Me | 2,6-di-F-4-MeO—Ph | iPr(Me)CH— | O |
| 156 | Cl | Me | 2,4,6-tri-F—Ph | iPr(Me)CH— | O |
| 157 | F3C— | Me | 2,4,6-tri-F—Ph | iPr(Me)CH— | O |
| 158 | Br | Et | 2,4,6-tri-F—Ph | iPr(Me)CH— | O |
| 159 | Br | Cl | 2,4,6-tri-F—Ph | 2-Me—cHex | O |
| 160 | Br | Br | 2,4,6-tri-F—Ph | 2-Me—cHex | O |
| 161 | Cl | Br | 2,4,6-tri-F—Ph | F2CHCH2— | O |
| 162 | Cl | Cl | 2,4,6-tri-F—Ph | 2-Me—Bu | O |
| 163 | Br | Cl | 2,4,6-tri-F—Ph | 2,3-di-Me—Ph | O |
| 164 | Br | Br | 2,4,6-tri-F—Ph | 2,3-di-Me—Ph | O |
| 165 | Cl | Br | 2,4,6-tri-F—Ph | 2-Me—Bu | O |
| 166 | Br | CL | 2,4,6-tri-F—Ph | 2-Me—Bu | O |
| 167 | Br | Br | 2,4,6-tri-F—Ph | 2-Me—Bu | O |
| 168 | Cl | Br | 2,6-di-F-4-MeO—Ph | 2-Me—Bu | O |
| 169 | Br | Cl | 2,6-di-F-4-MeO—Ph | 2-Me—Bu | O |
| 170 | Cl | Br | 2,6-di-F-4-MeO—Ph | 2-Me—cHex | O |
| 171 | Br | Cl | 2,6-di-F-4-MeO—Ph | 2-Me—cHex | O |
| 172 | Cl | Br | 2,4,6-tri-F—Ph | 2,3-di-Me—Ph | O |
| 173 | Cl | Cl | 2,4,6-tri-F—Ph | 2,3-di-Me—Ph | O |
| 174 | Me | Me | 2,4,6-tri-F—Ph | 2-Me—Ph | O |
| 175 | Me | Me | 2,6-di-F-4-MeO—Ph | 2-Me—Ph | O |
| 176 | Me | Me | 2,6-di-F-4-EtO—Ph | 2-Me—Ph | O |
| 177 | Br | Cl | 2,4,6-tri-F—Ph | 5-F-2-Me—Ph | O |
| 178 | Br | Br | 2,4,6-tri-F—Ph | 5-F-2-Me—Ph | O |
| 179 | Cl | Br | 2,4,6-tri-F—Ph | 5-F-2-Me—Ph | O |
| 180 | Cl | Cl | 2,4,6-tri-F—Ph | 5-F-2-Me—Ph | O |
| 181 | Br | Cl | 2,6-di-F-4-MeO—Ph | 2-Me—Ph | O |
| 182 | F3C— | Cl | 2,4,6-tri-F—Ph | 2-Me—Ph | O |
| 183 | Br | Me | 2,4,6-tri-F—Ph | 2-Me—Ph | O |
| 184 | F3C— | Me | 2,4,6-tri-F—Ph | 2-Me—Ph | O |
| 185 | Br | F | 2,4,6-tri-F—Ph | 2-Me—Ph | O |
| 186 | Br | Br | 2,4,6-tri-F—Ph | 3-F-2-Me—Ph | O |
| 187 | Br | Cl | 2,4,6-tri-F—Ph | 3-F-2-Me—Ph | O |
| 188 | Me | Cl | 2,4,6-tri-F—Ph | 2-Me—Ph | O |
| 189 | CL | Br | 2,4,6-tri-F—Ph | 3-F-2-Me—Ph | O |
| 190 | Cl | Cl | 2,4,6-tri-F—Ph | 3-F-2-Me—Ph | O |
| 191 | Br | Br | 2,4,6-tri-F—Ph | 2-F3C-Ph | O |
| 192 | Br | Cl | 2,4,6-tri-F—Ph | 2-F3C-Ph | O |
| 193 | Cl | Cl | 2,4,6-tri-F—Ph | tBuCH2— | O |
| 194 | Cl | Br | 2,4,6-tri-F—Ph | tBuCH2— | O |
| 195 | Br | Cl | 2,4,6-tri-F—Ph | tBuCH2— | O |
| 196 | Br | Br | 2,4,6-tri-F—Ph | tBuCH2— | O |
| 197 | Me | Br | 2,4,6-tri-F—Ph | 2-Me—Ph | O |
| 198 | Cl | Br | 2,4,6-tri-F—Ph | 2-F3C-Ph | O |
| 199 | Cl | Cl | 2,4,6-tri-F—Ph | 2-F3C-Ph | O |
| 200 | Cl | Cl | 2,4,6-tri-F—Ph | iPrCH2CH2— | O |
| 201 | Cl | Br | 2,4,6-tri-F—Ph | iPrCH2CH2— | O |
| 202 | Br | Cl | 2,4,6-tri-F—Ph | iPrCH2CH2— | O |
| 203 | Br | Br | 2,4,6-tri-F—Ph | iPrCH2CH2— | O |
| 204 | Cl | Br | 2,6-di-F-4-MeO—Ph | iPrCH2CH2— | O |
| 205 | Br | Et | 2,4,6-tri-F—Ph | 2-Me—Ph | O |
| 206 | Br | Cl | 2,6-di-F—Ph | 2,5-di-Me—Ph | O |

TABLE 4-continued

| Compound | R1 | R2 | Y | Z | X |
|---|---|---|---|---|---|
| 207 | Br | Br | 2,6-di-F—Ph | 2,5-di-Me—Ph | O |
| 208 | Cl | Br | 2,6-di-F—Ph | 2,5-di-Me—Ph | O |
| 209 | Cl | Cl | 2,6-di-F—Ph | 2,5-di-Me—Ph | O |
| 210 | Cl | Cl | 2,4,6-tri-F—Ph | MeOCH2CH2— | O |
| 211 | Cl | Br | 2,4,6-tri-F—Ph | MeOCH2CH2— | O |
| 212 | Br | Cl | 2,4,6-tri-F—Ph | MeOCH2CH2— | O |
| 213 | Br | Br | 2,4,6-tri-F—Ph | MeOCH2CH2— | O |
| 214 | Cl | Br | 2,6-di-F-4-MeO—Ph | tBuCH2— | O |
| 215 | Br | Cl | 2,6-di-F-4-MeO—Ph | tBuCH2— | O |
| 216 | Me | Me | 2,4,6-tri-F—Ph | 2-Me-5-MeO—Ph | S |
| 217 | Br | Cl | 2,4,6-tri-F—Ph | 2-Me-5-MeO—Ph | O |
| 218 | Br | Br | 2,4,6-tri-F—Ph | 2-Me-5-MeO—Ph | O |
| 219 | Br | Me | 2,4,6-tri-F—Ph | iBu | O |
| 220 | Br | Et | 2,4,6-tri-F—Ph | iBu | O |
| 221 | Cl | Cl | 2,4,6-tri-F—Ph | Bu | O |
| 222 | Cl | Br | 2,4,6-tri-F—Ph | Bu | O |
| 223 | Cl | Me | 2,4,6-tri-F—Ph | iBu | O |
| 224 | Cl | Et | 2,4,6-tri-F—Ph | iBu | O |
| 225 | Me | Me | 2,6-di-F-4-MeO—Ph | 2-Me—Ph | S |
| 226 | Me | Me | 4-F—Ph | 2-Me—Ph | O |
| 227 | Me | Me | 4-N≡C-Ph | 2-Me—Ph | O |
| 228 | Cl | Br | 2,4,6-tri-F—Ph | 2-Me-5-MeO—Ph | O |
| 229 | Cl | Cl | 2,4,6-tri-F—Ph | 2-Me-5-MeO—Ph | O |
| 230 | Br | Cl | 2,4,6-tri-F—Ph | 5-Cl-2-Me—Ph | O |
| 231 | Me | Et | 2,4,6-tri-F—Ph | iBu | O |
| 232 | Me | Et | 2,6-di-F-4-MeO—Ph | iBu | O |
| 233 | Br | Cl | 2,4,6-tri-F—Ph | Bu | O |
| 234 | Br | Br | 2,4,6-tri-F—Ph | Bu | O |
| 235 | Br | Cl | 4-F—Ph | 2-Me—Ph | O |
| 236 | Br | Br | 4-F—Ph | 2-Me—Ph | O |
| 237 | Br | Cl | 4-N≡C-Ph | 2-Me—Ph | O |
| 238 | Br | Br | 4-N≡C-Ph | 2-Me—Ph | O |
| 239 | Br | Br | 2,4,6-tri-F—Ph | 5-Cl-2-Me—Ph | O |
| 240 | Cl | Br | 2,4,6-tri-F—Ph | 5-Cl-2-Me—Ph | O |
| 241 | Cl | Cl | 2,4,6-tri-F—Ph | 5-Cl-2-Me—Ph | O |
| 242 | Me | Me | 4-MeO—Ph | 2-Me—Ph | O |
| 243 | Me | Me | 4-MeOC(=O)-Ph | 2-Me—Ph | O |
| 244 | Me | Me | 4-F3C-Ph | 2-Me—Ph | O |
| 245 | Me | Me | 2,4,6-tri-F—Ph | iBu | O |
| 246 | Me | Me | 2,4,6-tri-F—Ph | (2,4-di-MeO—Ph)—CH2— | O |
| 247 | Br | Cl | 2,4,6-tri-F—Ph | 5-Br-2-Me—Ph | O |
| 248 | Br | Br | 2,4,6-tri-F—Ph | 5-Br-2-Me—Ph | O |
| 249 | Cl | Br | 2,4,6-tri-F—Ph | 5-Br-2-Me—Ph | O |
| 250 | Cl | Cl | 2,4,6-tri-F—Ph | 5-Br-2-Me—Ph | O |
| 251 | Me | Me | 3,5-di-F-4-Py | 2-Me—Ph | O |
| 252 | Me | Me | 3,5-di-Cl-4-Py | 2-Me—Ph | O |
| 253 | Me | Me | Ph | 2-Me—Ph | O |
| 254 | Me | Me | 4-MeS-Ph | 2-Me—Ph | O |
| 255 | Me | Me | 2,4,6-tri-F—Ph | N≡CCH2— | O |
| 256 | Br | Cl | 2,4,6-tri-F—Ph | 2,4-di-Me—Ph | O |
| 257 | Br | Br | 2,4,6-tri-F—Ph | 2,4-di-Me—Ph | O |
| 258 | Cl | Br | 2,4,6-tri-F—Ph | 2,4-di-Me—Ph | O |
| 259 | Cl | Cl | 2,4,6-tri-F—Ph | 2,4-di-Me—Ph | O |
| 260 | Me | Me | 2,4,6-tri-F—Ph | MeOCH2— | O |
| 261 | I | Me | 2,4,6-tri-F—Ph | 2-Me—Ph | O |
| 262 | Me | Me | 4-MeS(=O)—Ph | 2-Me—Ph | O |
| 263 | Me | Me | 4-MeSO2-Ph | 2-Me—Ph | O |
| 264 | Br | Cl | 2,4,6-tri-F—Ph | 2-Me-4-MeO—Ph | O |
| 265 | Cl | Me | 2,4,6-tri-F—Ph | 2-Me—Ph | O |
| 266 | Br | Me | 2,6-di-F-4-MeO—Ph | 2-Me—Ph | O |
| 267 | Me | Me | 2,4,6-tri-F—Ph | HC≡CCH2— | O |
| 268 | Me | Me | 2,4,6-tri-F—Ph | H2C=CHCH2— | O |
| 269 | Me | Me | 2,4,6-tri-F—Ph | MeSCH2— | O |
| 270 | Cl | Cl | 2,4,6-tri-F—Ph | 2-Me-4-MeO—Ph | O |
| 271 | Me | Me | 4-Py | 2-Me—Ph | O |
| 272 | HC≡C— | Me | 2,4,6-tri-F—Ph | 2-Me—Ph | O |
| 273 | Br | Br | 2,4,6-tri-F—Ph | 4-F-2-Me—Ph | O |
| 274 | Br | Cl | 2,4,6-tri-F—Ph | 4-F-2-Me—Ph | O |
| 275 | Cl | Br | 2,4,6-tri-F—Ph | 4-F-2-Me—Ph | O |
| 276 | Cl | Cl | 2,4,6-tri-F—Ph | 4-F-2-Me—Ph | O |
| 277 | Ac | Me | 2,4,6-tri-F—Ph | 2-Me—Ph | O |
| 278 | F | Me | 2,4,6-tri-F—Ph | 2-Me—Ph | O |
| 279 | Br | Cl | 2,6-di-F-4-MeO—Ph | 2-Me-5-MeO—Ph | O |
| 230 | Br | Cl | 2,4,6-tri-F—Ph | 2-Me-5-HO—Ph | O |
| 281 | Et | Et | 2,4,6-tri-F—Ph | iBu | O |
| 282 | Br | Cl | 2,4,6-tri-F—Ph | 2-Me-5-MeOCH2CH2O—Ph | O |
| 283 | Br | Cl | 2,6-di-F-4-MeO—Ph | 2-Me-5-MeOCH2CH2O—Ph | O |
| 284 | Br | Cl | 2,4,6-tri-F—Ph | 2-Me-5-N≡CCH2O—Ph | O |

TABLE 4-continued

| Compound | R1 | R2 | Y | Z | X |
|---|---|---|---|---|---|
| 285 | Br | Cl | 2,4,6-tri-F—Ph | 2-Me-5-MeOCH2O—Ph | O |
| 286 | Br | Cl | 2,6-di-F-4-MeO—Ph | 2-Me-5-MeOCH2O—Ph | O |
| 287 | Me | Me | 3-furanyl | 2-Me—Ph | O |
| 288 | Br | Br | 2,4,6-tri-F—Ph | 2-F-6-Me—Ph | O |
| 289 | Br | Cl | 2,4,6-tri-F—Ph | 2-F-6-Me—Ph | O |
| 290 | Cl | Br | 2,4,6-tri-F—Ph | 2-F-6-Me—Ph | O |
| 291 | Cl | Cl | 2,4,6-tri-F—Ph | 2-F-6-Me—Ph | O |
| 292 | Br | Cl | 2,4,6-tri-F—Ph | 2-Me-5-EtOCH2O—Ph | O |
| 293 | Cl | Cl | 2,4,6-tri-F—Ph | 2-Me-5-HO—Ph | O |
| 294 | Cl | Cl | 2,6-di-F-4-MeO—Ph | 2-Me-5-MeO—Ph | O |
| 295 | Cl | Cl | 2,4,6-tri-F—Ph | 2-Me-5-MeOCH2CH2O—Ph | O |
| 296 | Cl | Cl | 2,6-di-F-4-MeO—Ph | 2-Me-5-MeOCH2CH2O—Ph | O |
| 297 | Cl | Cl | 2,4,6-tri-F—Ph | 2-Me-5-N≡CCH2O—Ph | O |
| 298 | Cl | Cl | 2,4,6-tri-F—Ph | 2-Me-5-MeOCH2O—Ph | O |
| 299 | Cl | Cl | 2,6-di-F-4-MeO—Ph | 2-Me-5-MeOCH2O—Ph | O |
| 300 | Me | Et | 2,4,6-tri-F—Ph | 2-Me—Ph | O |
| 301 | Br | Br | 2,4,6-tri-F—Ph | 2,6-di-Me—Ph | O |
| 302 | Br | Cl | 2,4,6-tri-F—Ph | 2,6-di-Me—Ph | O |
| 303 | Cl | Cl | 2,4,6-tri-F—Ph | 2-Me-5-EtOCH2O—Ph | O |
| 304 | Cl | Cl | 2,6-di-F-4-MeO—Ph | 2-Me-5-EtOCH2O—Ph | O |
| 305 | Cl | Cl | 2,4,6-tri-F—Ph | 2,6-di-Me—Ph | O |
| 306 | Cl | Br | 2,4,6-tri-F—Ph | 2,6-di-Me—Ph | O |
| 307 | Br | Cl | 2,4,6-tri-F—Ph | 2-Cl-6-Me—Ph | O |
| 308 | Br | Br | 2,4,6-tri-F—Ph | 2-Cl-6-Me—Ph | O |
| 309 | Br | Cl | 2,4,6-tri-F—Ph | 2-Me-5-F3C—Ph | O |
| 310 | Br | Br | 2,4,6-tri-F—Ph | 2-Me-5-F3C—Ph | O |
| 311 | Me | Et | 2,6-di-F-4-MeO—Ph | 2-Me—Ph | O |
| 312 | F3C— | Et | 2,4,6-tri-F—Ph | 2-Me—Ph | O |
| 313 | Me | Me | 2,4,6-tri-F—Ph | 2-Me-5-MeO—Ph | O |
| 314 | Me | Me | 2,4,6-tri-F—Ph | 2-Me-5-HO—Ph | O |
| 315 | Me | Me | 2,4,6-tri-F—Ph | 2-Me-5-MeOCH2CH2O—Ph | O |
| 316 | Me | Me | 2,6-di-F-4-MeO—Ph | 2-Me-5-MeOCH2CH2O—Ph | O |
| 317 | Et | Et | 2,4,6-tri-F—Ph | 2-Me—Ph | O |
| 318 | Cl | Br | 2,4,6-tri-F—Ph | 2-Cl-6-Me—Ph | O |
| 319 | Cl | Cl | 2,4,6-tri-F—Ph | 2-Cl-6-Me—Ph | O |
| 320 | Br | Cl | 2,4,6-tri-F—Ph | 2-Me-3-O2N-Ph | O |
| 321 | Br | Br | 2,4,6-tri-F—Ph | 2-Me-3-O2N-Ph | O |
| 322 | Br | Cl | 2,4,6-tri-F—Ph | 3-Cl-2-Me—Ph | O |
| 323 | Br | Br | 2,4,6-tri-F—Ph | 3-Cl-2-Me—Ph | O |
| 324 | Br | Cl | 2,4,6-tri-F—Ph | 2-Me-5-O2N—Ph | O |
| 325 | Br | Br | 2,4,6-tri-F—Ph | 2-Me-5-O2N—Ph | O |
| 326 | Me | Me | 2,4,6-tri-F—Ph | 2-Et—Ph | O |
| 327 | Ac | Et | 2,4,6-tri-F—Ph | 2-Me—Ph | O |
| 328 | Et | Me | 2,4,6-tri-F—Ph | 2-Me—Ph | O |
| 329 | Br | Cl | 2,4,6-tri-F—Ph | 4-Cl-2-Me—Ph | O |
| 330 | Br | Br | 2,4,6-tri-F—Ph | 4-Cl-2-Me—Ph | O |
| 331 | Cl | Br | 2,4,6-tri-F—Ph | 4-Cl-2-Me—Ph | O |
| 332 | Cl | Cl | 2,4,6-tri-F—Ph | 4-Cl-2-Me—Ph | O |
| 333 | Br | Cl | 2,4,6-tri-F—Ph | 2-Me-3-H2N—Ph | O |
| 334 | Br | Cl | 2,4,6-tri-F—Ph | 2-Me-3-MeNH—Ph | O |
| 335 | Br | Cl | 2,4,6-tri-F—Ph | 2-Me-3-Me2N—Ph | O |
| 336 | Br | Cl | 2,4,6-tri-F—Ph | 2-Me-5-N≡C—Ph | O |
| 337 | Br | Br | 2,4,6-tri-F—Ph | 2-Me-5-N≡C—Ph | O |
| 338 | Me | Me | 2,6-di-F-4-MeO—Ph | 2-Et—Ph | O |
| 339 | Cl | Cl | 2,4,6-tri-F—Ph | 2-Et—Ph | O |
| 340 | H2C=CH— | Me | 2,4,6-tri-F—Ph | 2-Me—Ph | O |
| 341 | Br | F3CCH2— | 2,4,6-tri-F—Ph | 2-Me—Ph | O |
| 342 | Br | Cl | 4-F—Ph | 2,6-di-Me—Ph | O |
| 343 | Br | Br | 4-F—Ph | 2,6-di-Me—Ph | O |
| 344 | Cl | Br | 4-F—Ph | 2,6-di-Me—Ph | O |
| 345 | Cl | Cl | 4-F—Ph | 2,6-di-Me—Ph | O |
| 346 | Br | Cl | 2,4,6-tri-F—Ph | 3-Br-2-Me—Ph | O |
| 347 | Br | Br | 2,4,6-tri-F—Ph | 3-Br-2-Me—Ph | O |
| 348 | Br | Cl | 2,4,6-tri-F—Ph | 2-Me-5-H2N-Ph | O |
| 349 | Cl | Br | 2,4,6-tri-F—Ph | 2-Et—Ph | O |
| 350 | Br | Cl | 2,4,6-tri-F—Ph | 2-Et—Ph | O |
| 351 | Me | Me | 2,6-di-F—Ph | 2-F—Ph | O |
| 352 | Br | Br | 2,4,6-tri-F—Ph | 2-Et—Ph | O |
| 353 | Me | Me | 2-F—Ph | 2-Me—Ph | O |
| 354 | Me | Me | 2-Cl—Ph | 2-Me—Ph | O |
| 355 | Me | F3CCH2— | 2,4,6-tri-F—Ph | 2-Me—Ph | O |
| 356 | Br | F3CCH2— | 2,6-di-F-4-MeO—Ph | 2-Me—Ph | O |
| 357 | Br | Me | Ph | 2-Me—Ph | O |
| 358 | Br | Cl | 4-F—Ph | 2-F-6-Me—Ph | O |
| 359 | Br | Br | 4-F—Ph | 2-F-6-Me—Ph | O |
| 360 | Me | Me | 2,6-di-F—Ph | Ph | O |
| 361 | Br | Cl | 2,6-di-F—Ph | 2-F—Ph | O |
| 362 | Br | Cl | 2,6-di-F—Ph | Ph | O |

TABLE 4-continued

| Compound | R1 | R2 | Y | Z | X |
|---|---|---|---|---|---|
| 363 | Br | Br | 2,6-di-F—Ph | Ph | O |
| 364 | Br | Cl | 2,4,6-tri-F—Ph | 2-Me-3-F3C—Ph | O |
| 365 | Br | Br | 2,4,6-tri-F—Ph | 2-Me-3-F3C—Ph | O |
| 366 | Br | Cl | 2,4,6-tri-F—Ph | 2-Me-3-MeO—Ph | O |
| 367 | Br | Br | 2,4,6-tri-F—Ph | 2-Me-3-MeO—Ph | O |
| 368 | Cl | Br | 4-F—Ph | 2-F-6-Me—Ph | O |
| 369 | Cl | Cl | 4-F—Ph | 2-F-6-Me—Ph | O |
| 370 | Me | Me | 2,6-di-F—Ph | 2-F3C—Ph | O |
| 371 | Br | Cl | 2,6-di-F—Ph | 2-F3C—Ph | O |
| 372 | Br | Br | 2,6-di-F—Ph | 2-F3C—Ph | O |
| 373 | Br | Cl | 2,4,6-tri-F—Ph | 2-Me-5-Me2N—Ph | O |
| 374 | Br | Cl | 2,4,6-tri-F—Ph | 2-Me-5-MeNH—Ph | O |
| 375 | Cl | Et | 2,4,6-tri-F—Ph | 2-Me—Ph | O |
| 376 | Br | Pr | 2,4,6-tri-F—Ph | 2-Me—Ph | O |
| 377 | Br | Cl | 2-F—Ph | 2-Me—Ph | O |
| 378 | Br | Cl | Ph | 2-Me—Ph | O |
| 379 | Br | Cl | 4-F—Ph | 2-Cl-6-Me—Ph | O |
| 380 | Br | Br | 4-F—Ph | 2-Cl-6-Me—Ph | O |
| 381 | Cl | Br | 4-F—Ph | 2-Cl-6-Me—Ph | O |
| 382 | Cl | Cl | 4-F—Ph | 2-Cl-6-Me—Ph | O |
| 383 | Me | Me | 2,6-di-F—Ph | 2-Me-5-MeO—Ph | O |
| 384 | Br | Br | 2,6-di-F—Ph | 4-Br-2-Me-5-MeO—Ph | O |
| 385 | Br | Br | 2,6-di-F—Ph | 2-Me-5-MeO—Ph | O |
| 386 | Br | Me | Ph | 4-Br-2-Cl—Ph | O |
| 387 | Br | Me | Ph | 2-Cl—Ph | O |
| 388 | Br | Cl | Ph | 2-Cl—Ph | O |
| 389 | Me | Me | Ph | 5-F-2-Me—Ph | O |
| 390 | Me | Me | 2,4,6-tri-F—Ph | 2,5-di-Me—Ph | O |
| 391 | Br | Cl | 2,6-di-F—Ph | 4-Br-2-Me-5-MeO—Ph | O |
| 392 | Br | Cl | 2,6-di-F—Ph | 2-Me-5-MeO—Ph | O |
| 393 | Br | Cl | 2,4,6-tri-F—Ph | 2-iPr—Ph | O |
| 394 | Br | Br | 2,4,6-tri-F—Ph | 2-iPr—Ph | O |
| 395 | Cl | Cl | 2,4,6-tri-F—Ph | 2-iPr—Ph | O |
| 396 | Cl | Br | 2,4,6-tri-F—Ph | 2-iPr—Ph | O |
| 397 | Me | Me | 2,4,6-tri-F—Ph | 2-iPr—Ph | O |
| 398 | Br | Me | Ph | 5-F-2-Me—Ph | O |
| 399 | Br | Cl | Ph | 5-F-2-Me—Ph | O |
| 400 | Br | Me | Ph | 2-Me-5-MeO—Ph | O |
| 401 | Me | Me | 2,6-di-F-4-MeO—Ph | 2,5-di-Me—Ph | O |
| 402 | Me | Me | 2,6-di-F—Ph | 2,5-di-Me—Ph | O |
| 403 | Me | Me | 2,6-di-F-4-HO—Ph | 2,5-di-Me—Ph | O |
| 404 | Me | Me | Ph | 2,5-di-Me—Ph | O |
| 405 | Me | Me | 2,6-di-F-4-H2C=CHCH2O—Ph | 2,5-di-Me—Ph | O |
| 406 | Me | Me | 2,6-di-F-4-HC≡CCH2O—Ph | 2,5-di-Me—Ph | O |
| 407 | Me | Me | 2,6-di-F-4-AcO—Ph | 2,5-di-Me—Ph | O |
| 408 | Br | Br | 4-Me—Ph | 2-Me—Ph | O |
| 409 | Br | Cl | 4-Me—Ph | 2-Me—Ph | O |
| 410 | Cl | Br | 4-Me—Ph | 2-Me—Ph | O |
| 411 | Cl | Cl | 4-Me—Ph | 2-Me—Ph | O |
| 412 | Br | Me | Ph | 3-F-2-Me—Ph | O |
| 413 | Br | Cl | Ph | 3-F-2-Me—Ph | O |
| 414 | Br | Cl | Ph | 4-Br-2-Me-5-MeO—Ph | O |
| 415 | Br | Me | Ph | 2-Cl-5-F—Ph | O |
| 416 | Me | Me | Ph | 2-Cl-5-F—Ph | O |
| 417 | Br | Cl | Ph | 2-Cl-5-F—Ph | O |
| 418 | Br | Br | Ph | 2-Cl-5-F—Ph | O |
| 419 | Br | Br | 2,4,6-tri-F—Ph | 2-Me-3-HO—Ph | O |
| 420 | Cl | Cl | 2,4,6-tri-F—Ph | 2-Me-3-O2N-Ph | O |
| 421 | Cl | Cl | 2,4,6-tri-F—Ph | 2-Me-3-H2N-Ph | O |
| 422 | Br | Br | 2,4,6-tri-F—Ph | 2-Me-3-EtO—Ph | O |
| 423 | Br | Br | 2,4,6-tri-F—Ph | 2-Me-3-PrO—Ph | O |
| 424 | Cl | Cl | 2,4,6-tri-F—Ph | 2-Me-3-AcNH-Ph | O |
| 425 | Me | Me | 2,4,6-tri-F—Ph | 4-Br-2-Me-3-O2N-Ph | O |
| 426 | Br | Cl | 2,6-di-F—Ph | 2-Me-5-HO—Ph | O |
| 427 | Br | Cl | 2,6-di-F—Ph | 2-Me-5-MeOCH2O—Ph | O |
| 428 | Br | Cl | 2,6-di-F—Ph | 2-Me-5-N≡CCH2O—Ph | O |
| 429 | Br | Cl | 2,6-di-F—Ph | 2-Me-5-HC≡CCH2O—Ph | O |
| 430 | Br | Cl | 2,6-di-F—Ph | 2-Me-5-H2C=CHCH2O—Ph | O |
| 431 | Br | Cl | 2,6-di-F—Ph | 2-Me-5-MeOCH2CH2O—Ph | O |
| 432 | Br | Cl | 2,6-di-F—Ph | 2-Me-5-EtOCH2O—Ph | O |
| 433 | Br | Cl | 2,6-di-F—Ph | 2-Me-5-EtO—Ph | O |
| 434 | Br | Cl | 2,6-di-F—Ph | 2-Me-5-iPrO—Ph | O |
| 435 | Me | Me | Ph | 2-Me-5-MeO—Ph | O |
| 436 | Cl | Br | 2,4,6-tri-F—Ph | 2-Me-3-MeO—Ph | O |
| 437 | Me | Me | 2,4,6-tri-F—Ph | 3-F-2-Me—Ph | O |
| 438 | Br | Br | 2,4,6-tri-F—Ph | 2-Me-3-iBuO—Ph | O |
| 439 | Me | Me | 2,4,6-tri-F—Ph | 2-Cl—Ph | O |
| 440 | Me | Me | 2,6-di-F-4-MeO—Ph | 3-F-2-Me—Ph | O |

TABLE 4-continued

| Compound | R1 | R2 | Y | Z | X |
|---|---|---|---|---|---|
| 441 | Me | Me | 2,4,6-tri-F—Ph | Ph | O |
| 442 | Me | Me | 2,6-di-F-4-MeO—Ph | 2-Cl—Ph | O |
| 443 | Br | Cl | 2,4,6-tri-F—Ph | 2-Pr—Ph | O |
| 444 | Br | Br | 2,4,6-tri-F—Ph | 2-Pr—Ph | O |
| 445 | Me | Me | 2,4,6-tri-F—Ph | 2-Pr—Ph | O |
| 446 | Cl | Cl | 2,4,6-tri-F—Ph | 2-Pr—Ph | O |
| 447 | Cl | Br | 2,4,6-tri-F—Ph | 2-Pr—Ph | O |
| 448 | Me | Me | 2,6-di-F—Ph | 5-F-2-Me—Ph | O |
| 449 | Cl | Br | 2,6-di-F—Ph | 5-F-2-Me—Ph | O |
| 450 | Cl | Cl | 2,6-di-F—Ph | 5-F-2-Me—Ph | O |
| 451 | Br | Br | Ph | 2,6-di-Me—Ph | O |
| 452 | Br | Cl | Ph | 2,6-di-Me—Ph | O |
| 453 | Me | Me | 2,4,6-tri-F—Ph | 2-Br—Ph | O |
| 454 | Me | Me | 2,6-di-F-4-MeO—Ph | Ph | O |
| 455 | Me | Me | 2,4,6-tri-F—Ph | 5-F-2-Me—Ph | O |
| 456 | Me | Me | 2,6-di-F-4-MeO—Ph | 2-Br—Ph | O |
| 457 | Br | Cl | 2,6-di-F—Ph | 5-F-2-Me—Ph | O |
| 458 | Br | Cl | 2,4,6-tri-F—Ph | 2-Me-3-Py | O |
| 459 | Br | Cl | Ph | 2,5-di-Me—Ph | O |
| 460 | Br | Br | Ph | 2,5-di-Me—Ph | O |
| 461 | Me | Me | 2,4,6-tri-F—Ph | 3-Cl-2-Me—Ph | O |
| 462 | Me | Me | 2,6-di-F-4-MeO—Ph | 5-F-2-Me—Ph | O |
| 463 | Me | Me | 2,4,6-tri-F—Ph | 5-Cl-2-Me—Ph | O |
| 464 | Me | Me | 2,6-di-F-4-MeO—Ph | 5-Cl-2-Me—Ph | O |
| 465 | Me | Me | 2,4,6-tri-F—Ph | 2,3-di-Me—Ph | O |
| 466 | Me | Me | 2,4-di-F—Ph | Ph | O |
| 467 | Br | Cl | 2-F—Ph | Ph | O |
| 468 | Br | Br | 2-F—Ph | Ph | O |
| 469 | Br | Cl | 2,4-di-F—Ph | Ph | O |
| 470 | Br | Br | 2,4-di-F—Ph | Ph | O |
| 471 | Me | Me | 2-F—Ph | Ph | O |
| 472 | Me | Me | 2,4,6-tri-F—Ph | 5-Br-2-Me—Ph | O |
| 473 | Me | Me | 2,6-di-F—Ph | 2-Cl—Ph | O |
| 474 | Me | Me | Ph | 2-Cl—Ph | O |
| 475 | Br | Et | Ph | 2-Me—Ph | O |
| 476 | Me | Me | 2,4,6-tri-F—Ph | 2-F3C—Ph | O |
| 477 | Me | Me | 2,6-di-F-4-MeO—Ph | 2,3-di-Me—Ph | O |
| 478 | Me | Me | 2,6-di-F—Ph | 2,3-di-Me—Ph | O |
| 479 | Me | Me | 2,6-di-F—Ph | 3-F-2-Me—Ph | O |
| 480 | Me | Me | 2,4,6-tri-F—Ph | 3-Br-2-Me—Ph | O |
| 481 | Me | Me | 2,4,6-tri-F—Ph | 2-Me-3-MeO—Ph | O |
| 482 | Me | Me | Ph | 2,3-di-Me—Ph | O |
| 483 | Me | Me | Ph | 3-F-2-Me—Ph | O |
| 484 | Me | Me | Ph | 3-Cl-2-Me—Ph | O |
| 485 | Me | Me | 2,6-di-F—Ph | 2-Et—Ph | O |
| 486 | Me | Me | 2,6-di-F—Ph | 5-Cl-2-Me—Ph | O |
| 487 | Me | Me | 2,6-di-F—Ph | 5-Br-2-Me—Ph | O |
| 488 | Br | Et | 2,4,6-tri-F—Ph | 2-Et—Ph | O |
| 489 | Me | Et | 2,4,6-tri-F—Ph | 2-Et—Ph | O |
| 490 | Br | Et | 2,4,6-tri-F—Ph | 2-Cl—Ph | O |
| 491 | Me | Et | 2,4,6-tri-F—Ph | 2-Cl—Ph | O |
| 492 | Br | Et | 2,4,6-tri-F—Ph | Ph | O |
| 493 | Me | Et | 2,4,6-tri-F—Ph | Ph | O |
| 494 | Me | Me | 2,6-di-F—Ph | 3-Cl-2-Me—Ph | O |
| 495 | Br | Et | 2,6-di-F—Ph | 2,3-di-Me—Ph | O |
| 496 | Me | Me | 2,6-di-F—Ph | 3-Br-2-Me—Ph | O |
| 497 | Me | Et | 2,6-di-F—Ph | 2,3-di-Me—Ph | O |
| 498 | Br | Et | Ph | 2-Et—Ph | O |
| 499 | Br | Et | Ph | 5-Br-2-Me—Ph | O |
| 500 | Me | Me | 2,6-di-F—Ph | 2-Me—Ph | O |
| 501 | Br | Et | 2,6-di-F—Ph | 5-Cl-2-Me—Ph | O |
| 502 | Br | Et | Ph | 2,3-di-Me—Ph | O |
| 503 | Me | Et | Ph | 2,3-di-Me—Ph | O |
| 504 | Br | Et | Ph | 2-Me-5-MeO—Ph | O |
| 505 | Br | Et | Ph | 3-F-2-Me—Ph | O |
| 506 | Br | Et | Ph | 3-Cl-2-Me—Ph | O |
| 507 | Br | Et | 2,6-di-F—Ph | 2-Me—Ph | O |
| 508 | Me | Et | 2,6-di-F—Ph | 2-Me—Ph | O |
| 509 | Br | Et | 2,6-di-F—Ph | 2-Et—Ph | O |
| 510 | Me | Et | 2,6-di-F—Ph | 2-Et—Ph | O |
| 511 | Br | Et | 2,6-di-F—Ph | 2-Cl—Ph | O |
| 512 | Me | Et | 2,6-di-F—Ph | 2-Cl—Ph | O |
| 513 | Br | Et | 2,4,6-tri-F—Ph | 2-Me-3-MeO—Ph | O |
| 514 | Me | Et | 2,4,6-tri-F—Ph | 2-Me-3-MeO—Ph | O |
| 515 | Br | Et | 2,4,6-tri-F—Ph | 3-Cl-2-Me—Ph | O |
| 516 | Me | Me | Ph | 2-Et—Ph | O |
| 517 | Me | Me | Ph | 5-Cl-2-Me—Ph | O |
| 518 | Me | Me | Ph | 5-Br-2-Me—Ph | O |

TABLE 4-continued

| Compound | R1 | R2 | Y | Z | X |
|---|---|---|---|---|---|
| 519 | Br | Et | 2,4,6-tri-F—Ph | 2,5-di-Me—Ph | O |
| 520 | Me | Et | 2,4,6-tri-F—Ph | 2,5-di-Me—Ph | O |
| 521 | Br | Et | 2,4,6-tri-F—Ph | 5-F-2-Me—Ph | O |
| 522 | Me | Et | 2,4,6-tri-F—Ph | 5-F-2-Me—Ph | O |
| 523 | Me | Me | 2,6-di-F—Ph | 2-Me-3-MeO—Ph | O |
| 524 | Br | Et | 2,6-di-F—Ph | 3-Cl-2-Me—Ph | O |
| 525 | Me | Et | 2,6-di-F—Ph | 3-Cl-2-Me—Ph | O |
| 526 | Br | Et | 2,6-di-F—Ph | 3-Br-2-Me—Ph | O |
| 527 | Br | Et | 2,4,6-tri-F—Ph | 2-Me-5-MeO—Ph | O |
| 528 | Br | Et | 2,4,6-tri-F—Ph | 2,3-di-Me—Ph | O |
| 529 | Br | Et | 2,4,6-tri-F—Ph | 5-Br-2-Me—Ph | O |
| 530 | Br | Et | 2,4,6-tri-F—Ph | 3-F-2-Me—Ph | O |
| 531 | Br | Et | 2,6-di-F—Ph | Ph | O |
| 532 | Me | Et | 2,4,6-tri-F—Ph | 2-Me-5-MeO—Ph | O |
| 533 | Me | Et | 2,4,6-tri-F—Ph | 2,3-di-Me—Ph | O |
| 534 | Me | Et | Ph | 2-Et—Ph | O |
| 535 | Br | Et | Ph | 2-Cl—Ph | O |
| 536 | Me | Et | 2,6-di-F—Ph | 5-Cl-2-Me—Ph | O |
| 537 | Me | Me | Ph | Ph | O |
| 538 | Me | Et | Ph | 2-Cl—Ph | O |
| 539 | Br | Et | 2,6-di-F—Ph | 2,5-di-Me—Ph | O |
| 540 | Me | Et | 2,6-di-F—Ph | 2,5-di-Me—Ph | O |
| 541 | Br | Et | 2,6-di-F—Ph | 5-F-2-Me—Ph | O |
| 542 | Me | Et | 2,6-di-F—Ph | 5-F-2-Me—Ph | O |
| 543 | Me | Et | Ph | 2-Me-5-MeO—Ph | O |
| 544 | Me | Et | Ph | 3-F-2-Me—Ph | O |
| 545 | Me | Et | Ph | 3-Cl-2-Me—Ph | O |
| 546 | Me | Me | Ph | 2-Me-3-MeO—Ph | O |
| 547 | Me | Et | 2,4,6-tri-F—Ph | 3-Cl-2-Me—Ph | O |
| 548 | Br | Et | 2,4,6-tri-F—Ph | 3-Br-2-Me—Ph | O |
| 549 | Br | Et | 2,6-di-F—Ph | 2-Me-3-MeO—Ph | O |
| 550 | Br | Et | 2,6-di-F—Ph | 3-F-2-Me—Ph | O |
| 551 | Me | Et | 2,6-di-F—Ph | 2-Me-3-MeO—Ph | O |
| 552 | Me | Et | 2,6-di-F—Ph | 3-F-2-Me—Ph | O |
| 553 | Br | Et | Ph | 5-Cl-2-Me—Ph | O |
| 554 | Me | Et | 2,4,6-tri-F—Ph | 3-F-2-Me—Ph | O |
| 555 | Me | Et | 2,6-di-F—Ph | Ph | O |
| 556 | Br | Et | 2,4,6-tri-F—Ph | 5-Cl-2-Me—Ph | O |
| 557 | Br | Et | Ph | Ph | O |
| 558 | Br | Et | 2,6-di-F—Ph | 2-Me-5-MeO—Ph | O |
| 559 | Me | Et | Ph | Ph | O |
| 560 | Me | Et | 2,6-di-F—Ph | 2-Me-5-MeO—Ph | O |
| 561 | Br | Et | 2,6-di-F—Ph | 5-Br-2-Me—Ph | O |
| 562 | Br | Et | Ph | 2-Me-3-MeO—Ph | O |
| 563 | Me | Et | Ph | 2-Me-3-MeO—Ph | O |
| 564 | Br | Et | Ph | 5-F-2-Me—Ph | O |
| 565 | Me | Me | Ph | 3-Br-2-Me—Ph | O |
| 566 | Me | Et | Ph | 2-Me—Ph | O |
| 567 | Br | Cl | 2-Cl-4-F—Ph | Ph | O |
| 568 | Me | Et | Ph | 5-Cl-2-Me—Ph | O |
| 569 | Br | Cl | 2-Br-4-F—Ph | Ph | O |
| 570 | Me | Et | 2,4,6-tri-F—Ph | 5-Cl-2-Me—Ph | O |
| 571 | Me | Me | 4-F-2-Me—Ph | Ph | O |
| 572 | Br | Et | Ph | 3-Br-2-Me—Ph | O |
| 573 | Me | Et | Ph | 5-F-2-Me—Ph | O |
| 574 | Br | Cl | 2-Cl—Ph | Ph | O |
| 575 | Me | Me | 2-Cl—Ph | Ph | O |
| 576 | Br | Cl | 2-Br—Ph | Ph | O |
| 577 | Me | Me | 2-Cl-4-F—Ph | Ph | O |
| 578 | Me | Me | 2-Br—Ph | Ph | O |
| 579 | Br | Cl | 2-Me—Ph | Ph | O |
| 580 | Me | Me | 2-Me—Ph | Ph | O |
| 581 | Me | Me | 2-F3C—Ph | Ph | O |
| 582 | Me | Me | 2-MeO—Ph | Ph | O |
| 583 | Br | Cl | 4-F-2-Me—Ph | Ph | O |
| 584 | Br | Br | 4-F-2-Me—Ph | Ph | O |
| 585 | Me | Me | 2-Br-4-F—Ph | Ph | O |
| 586 | Me | Me | 4-Cl-2-F—Ph | Ph | O |
| 587 | Br | Cl | 4-Cl-2-F—Ph | Ph | O |
| 588 | Br | Cl | 2,4-di-Cl—Ph | Ph | O |
| 589 | Me | Me | 2-Cl-6-F—Ph | Ph | O |
| 590 | Br | Cl | 2-Cl-6-F—Ph | Ph | O |
| 591 | Me | Me | 2-F-6-MeO—Ph | Ph | O |
| 592 | Br | Me | 2,4-di-F—Ph | Ph | O |
| 593 | I | Me | 2,4-di-F—Ph | Ph | O |
| 594 | Me | Me | 2-Br-4-MeO—Ph | Ph | O |
| 595 | Me | Me | 2,4-di-Cl—Ph | Ph | O |
| 596 | Br | Cl | 2,5-di-F—Ph | Ph | O |

TABLE 4-continued

| Compound | R1 | R2 | Y | Z | X |
|---|---|---|---|---|---|
| 597 | Br | Et | 2,4-di-F—Ph | Ph | O |
| 598 | Me | Et | 2,4-di-F—Ph | Ph | O |
| 599 | Br | Cl | 2-MeO—Ph | Ph | O |
| 600 | Br | Cl | 2-F3C—Ph | Ph | O |
| 601 | Me | Me | 2-F-6-F3C—Ph | Ph | O |
| 602 | Me | Me | 2,6-di-F—Ph | 2-Br-5-MeO—Ph | O |
| 603 | Br | Cl | 2,3-di-F—Ph | Ph | O |
| 604 | Br | Cl | 3,4-di-F—Ph | Ph | O |
| 605 | Me | Me | 2,6-di-F—Ph | 3-MeO—Ph | O |
| 606 | Me | Me | 4-MeO—Ph | 2-Me-5-MeO—Ph | O |
| 607 | Br | Cl | 2-Br-6-F—Ph | Ph | O |
| 608 | Me | Me | 2-Br-6-F—Ph | Ph | O |
| 609 | Br | Cl | 2-F-6-Me—Ph | Ph | O |
| 610 | Me | Me | 2-F-6-Me—Ph | Ph | O |
| 611 | Br | Cl | 2-F-6-MeO—Ph | Ph | O |
| 612 | Br | Cl | 2-F-6-MeO—Ph | 4-Br—Ph | O |
| 613 | Br | Et | 2-Br-4-F—Ph | Ph | O |
| 614 | Me | Me | 2,5-di-F—Ph | Ph | O |
| 615 | Me | Me | 2,3-di-F—Ph | Ph | O |
| 616 | Me | Me | 3,4-di-F—Ph | Ph | O |
| 617 | Me | Me | 2,6-di-F—Ph | 2-Et-5-MeO—Ph | O |
| 618 | Me | Me | 2,6-di-F—Ph | 2-Et-5-HO—Ph | O |
| 619 | Me | Me | 2,6-di-F—Ph | 2-Et-5-N≡CCH2O—Ph | O |
| 620 | Me | Me | 2,6-di-F—Ph | 2-Et-5-MeOCH2O—Ph | O |
| 621 | Br | Et | 2-Cl-4-F—Ph | Ph | O |
| 622 | Br | Et | 4-F-2-Me—Ph | Ph | O |
| 623 | Me | Et | 2-Cl-4-F—Ph | Ph | O |
| 624 | Me | Me | 3,5-di-Cl—Ph | Ph | O |
| 625 | Me | Me | 2,6-di-F—Ph | 2-Et-5-HC≡CCH2O—Ph | O |
| 626 | Me | Me | 2,6-di-F—Ph | 2-Et-5-MeOCH2CH2O—Ph | O |
| 627 | Br | Et | 2,6-di-F—Ph | 2-Et-5-MeO—Ph | O |
| 628 | Me | Et | 2,6-di-F—Ph | 2-Et-5-MeO—Ph | O |

Next, with regard to the compounds described in Table 4, $^1$H-NMR data thereof are shown in Table 5.

TABLE 5

| Compound | $^1$H-NMR |
|---|---|
| 1 | $^1$H-NMR (CDCl3) δ: 7.86 (1H, s), 7.44 (1H, dd, J = 8.3, 1.5 Hz), 7.36-7.34 (2H, m), 7.29-7.24 (1H, m), 6.63-6.58 (2H, m). |
| 2 | $^1$H-NMR (CDCl3) δ: 7.87 (1H, s), 7.45-7.44 (1H, m), 7.38-7.34 (2H, m), 7.29-7.28 (1H, m), 6.66-6.58 (2H, m). |
| 3 | $^1$H-NMR (CDCl3) δ: 7.74 (1H, s), 7.46-7.44 (1H, m), 7.37-7.33 (2H, m), 7.28-7.26 (1H, m), 6.61-6.60 (2H, m). |
| 4 | $^1$H-NMR (CDCl3) δ: 7.75 (1H, s), 7.46-7.44 (1H, m), 7.37-7.35 (2H, m), 7.30-7.28 (1H, m), 6.64-6.60 (2H, m). |
| 5 | $^1$H-NMR (CDCl3) δ: 7.73 (1H, s), 7.44-7.42 (1H, m), 7.36-7.32 (2H, m), 7.27-7.25 (1H, m), 6.39-6.32 (2H, m), 3.75 (3H, s). |
| 6 | $^1$H-NMR (CDCl3) δ: 7.77 (1H, s), 6.91-6.88 (2H, m), 3.66-3.62 (2H, m), 1.70-1.61 (2H, m), 0.85 (3H, t, J = 7.3 Hz). |
| 7 | $^1$H-NMR (CDCl3) δ: 7.77 (1H, s), 6.92-6.87 (2H, m), 3.67-3.64 (2H, m), 1.69-1.63 (2H, m), 0.86 (3H, t, J = 7.3 Hz). |
| 8 | $^1$H-NMR (CDCl3) δ: 7.99 (1H, s), 7.41-7.34 (3H, m), 7.22-7.20 (2H, m), 6.62-6.57 (2H, m). |
| 9 | $^1$H-NMR (CDCl3) δ: 8.00 (1H, s), 7.40-7.36 (3H, m), 7.22-7.21 (2H, m), 6.62-6.58 (2H, m). |
| 10 | $^1$H-NMR (CDCl3) δ: 7.80 (1H, s), 6.90-6.85 (2H, m), 4.12-4.02 (1H, m), 1.39 (6H, d, J = 6.7 Hz). |
| 11 | $^1$H-NMR (CDCl3) δ: 7.81 (1H, s), 6.90-6.84 (2H, m), 4.11-4.01 (1H, m), 1.39 (6H, d, J = 6.8 Hz). |
| 12 | $^1$H-NMR (CDCl3) δ: 7.94 (1H, s), 6.91-6.87 (2H, m), 4.11-4.03 (1H, m), 1.41 (6H, d, J = 6.7 Hz). |
| 13 | $^1$H-NMR (CDCl3) δ: 7.94 (1H, s), 6.92-6.87 (2H, m), 4.09-4.03 (1H, m), 1.42 (6H, d, J = 6.7 Hz). |
| 14 | $^1$H-NMR (CDCl3) δ: 7.88 (1H, s), 7.40-7.37 (3H, m), 7.23-7.21 (2H, m), 6.63-6.57 (2H, m). |
| 15 | $^1$H-NMR (CDCl3) δ: 7.87 (1H, s), 7.42-7.34 (3H, m), 7.23-7.20 (2H, m), 6.62-6.56 (2H, m). |
| 16 | $^1$H-NMR (CDCl3) δ: 7.86 (1H, s), 7.39-7.32 (3H, m), 7.22-7.20 (2H, m), 6.36-6.33 (2H, m), 3.74 (3H, s). |
| 17 | $^1$H-NMR (CDCl3) δ: 7.86 (1H, s), 7.39-7.32 (3H, m), 7.22-7.20 (2H, m), 6.36-6.32 (2H, m), 3.74 (3H, s). |

TABLE 5-continued

| Compound | ¹H-NMR |
|---|---|
| 18 | ¹H-NMR (CDCl3) δ: 7.93 (1H, s), 6.65-6.60 (2H, m), 4.17-4.10 (1H, m), 3.88 (3H, s), 1.40 (6H, d, J = 6.6 Hz). |
| 19 | ¹H-NMR (CDCl3) δ: 7.92 (1H, s), 6.65-6.61 (2H, m), 4.16-4.10 (1H, m), 3.88 (3H, s), 1.40 (6H, d, J = 6.6 Hz). |
| 20 | ¹H-NMR (CDCl3) δ: 7.93 (1H, d, J = 0.6 Hz), 7.41-7.40 (1H, m), 7.32-7.30 (1H, m), 7.19-7.16 (1H, m), 7.13-7.10 (1H, m), 6.67-6.65 (1H, m), 6.59-6.56 (1H, m). |
| 21 | ¹H-NMR (CDCl3) δ: 7.91 (1H, d, J = 0.6 Hz), 7.40-7.35 (1H, m), 7.30-7.29 (1H, m), 7.17-7.08 (2H, m), 6.41-6.39 (1H, m), 6.33-6.31 (1H, m), 3.75 (3H, s). |
| 22 | ¹H-NMR (CDCl3) δ: 7.93 (1H, d, J = 0.6 Hz), 7.42-7.38 (1H, m), 7.32-7.28 (1H, m), 7.17-7.16 (1H, m), 7.13-7.10 (1H, m), 6.66-6.64 (1H, m), 6.58-6.56 (1H, m). |
| 23 | ¹H-NMR (CDCl3) δ: 7.91 (1H, d, J = 0.6 Hz), 7.39-7.35 (1H, m), 7.29-7.28 (1H, m), 7.16-7.08 (2H, m), 6.40-6.38 (1H, m), 6.33-6.30 (1H, m), 3.75 (3H, s). |
| 24 | ¹H-NMR (CDCl3) δ: 7.81 (1H, d, J = 0.7 Hz), 7.44-7.38 (1H, m), 7.32-7.30 (1H, m), 7.20-7.15 (1H, m), 7.14-7.09 (1H, m), 6.67-6.65 (1H, m), 6.60-6.55 (1H, m). |
| 25 | ¹H-NMR (CDCl3) δ: 7.84 (1H, s), 6.92-6.86 (2H, m), 3.58-3.54 (1H, m), 1.97-1.88 (4H, br m), 1.71-1.55 (3H, br m), 1.21-1.09 (3H, br m). |
| 26 | ¹H-NMR (CDCl3) δ: 7.84 (1H, s), 6.93-6.87 (2H, m), 3.60-3.51 (1H, m), 1.97-1.89 (4H, br m), 1.69-1.61 (3H, br m), 1.18-1.12 (3H, br m). |
| 27 | ¹H-NMR (CDCl3) δ: 7.82 (1H, d, J = 5.6 Hz), 6.63-6.58 (2H, m), 3.87 (3H, s), 3.69-3.60 (1H, m), 1.94-1.54 (7H, br m), 1.14-1.09 (3H, br m). |
| 28 | ¹H-NMR (CDCl3) δ: 7.80 (1H, s), 6.63-6.59 (2H, m), 3.87 (3H, s), 3.69-3.59 (1H, m), 1.93-1.87 (4H, br m), 1.70-1.53 (3H, br m), 1.15-1.12 (3H, br m). |
| 29 | ¹H-NMR (CDCl3) δ: 7.93 (1H, s), 6.90-6.85 (2H, m), 3.54-3.48 (1H, m), 1.94-1.85 (4H, br m), 1.68-1.58 (3H, br m), 1.18-1.08 (3H, br m). |
| 30 | ¹H-NMR (CDCl3) δ: 7.96 (1H, s), 6.92-6.86 (2H, m), 3.54 (1H, tt, J = 12.0, 3.6 Hz), 1.96-1.88 (4H, br m), 1.72-1.61 (3H, br m), 1.21-1.11 (3H, br m). |
| 31 | ¹H-NMR (CDCl3) δ: 7.81 (1H, d, J = 0.9 Hz), 7.42-7.38 (1H, m), 7.30-7.29 (1H, m), 7.18-7.15 (1H, m), 7.14-7.10 (1H, m), 6.66-6.64 (1H, m), 6.58-6.56 (1H, m). |
| 32 | ¹H-NMR (CDCl3) δ: 7.80 (1H, d, J = 0.7 Hz), 7.41-7.35 (1H, m), 7.32-7.28 (1H, m), 7.16-7.10 (2H, m), 6.41-6.38 (1H, m), 6.34-6.31 (1H, m), 3.75 (3H, s). |
| 33 | ¹H-NMR (CDCl3) δ: 7.80 (1H, d, J = 0.9 Hz), 7.40-7.35 (1H, m), 7.30-7.27 (1H, m), 7.16-7.09 (2H, m), 6.40-6.38 (1H, m), 6.33-6.31 (1H, m), 3.75 (3H, s). |
| 34 | ¹H-NMR (CDCl3) δ: 8.46 (1H, dd, J = 4.8, 1.8 Hz), 7.75-7.72 (2H, m), 7.32 (1H, dd, J = 7.8, 4.8 Hz), 6.72-6.66 (1H, m), 6.64-6.58 (1H, m). |
| 35 | ¹H-NMR (CDCl3) δ: 8.47 (1H, dd, J = 4.7, 1.8 Hz), 7.76-7.73 (2H, m), 7.33 (1H, dd, J = 7.8, 4.7 Hz), 6.70 (1H, tt, J = 8.8, 2.1 Hz), 6.64-6.58 (1H, m). |
| 36 | ¹H-NMR (CDCl3) δ: 8.46 (1H, dd, J = 4.7, 1.7 Hz), 7.85 (1H, s), 7.76-7.73 (1H, m), 7.33 (1H, dd, J = 8.0, 4.7 Hz), 6.70 (1H, tt, J = 8.7, 2.1 Hz), 6.63-6.59 (1H, m). |
| 37 | ¹H-NMR (CDCl3) δ: 7.86 (1H, s), 7.63 (1H, dd, J = 7.8, 1.7 Hz), 7.37-7.26 (3H, m), 6.66-6.58 (2H, m). |
| 38 | ¹H-NMR (CDCl3) δ: 8.46 (1H, dd, J = 4.9, 1.9 Hz), 7.85 (1H, s), 7.75-7.72 (1H, m), 7.32 (1H, dd, J = 8.0, 4.9 Hz), 6.69 (1H, tt, J = 8.7, 2.0 Hz), 6.63-6.59 (1H, m). |
| 39 | ¹H-NMR (CDCl3) δ: 8.14 (1H, dd, J = 4.9, 1.7 Hz), 7.71 (1H, s), 7.58-7.55 (1H, m), 6.90 (1H, dd, J = 7.7, 5.0 Hz), 6.43-6.39 (1H, m), 6.29-6.25 (1H, m), 3.85 (3H, d, J = 10.5 Hz), 3.74 (3H, d, J = 4.2 Hz). |
| 40 | ¹H-NMR (CDCl3) δ: 8.14 (1H, dd, J = 5.0, 1.8 Hz), 7.83 (1H, s), 7.58 (1H, ddd, J = 7.7, 2.7, 1.8 Hz), 6.91 (1H, dd, J = 7.7, 5.0 Hz), 6.44-6.40 (1H, m), 6.29-6.25 (1H, m), 3.85 (3H, s), 3.75 (3H, s). |
| 41 | ¹H-NMR (CDCl3) δ: 7.76 (1H, s), 6.91-6.87 (2H, m), 3.47-3.41 (1H, m), 1.97-1.90 (1H, m), 1.42 (3H, d, J = 6.7 Hz), 0.94 (3H, d, J = 6.7 Hz), 0.75 (3H, dd, J = 6.7, 1.2 Hz). |
| 42 | ¹H-NMR (CDCl3) δ: 7.76 (1H, s), 6.91-6.87 (2H, m), 3.47-3.41 (1H, m), 1.97-1.90 (1H, m), 1.42 (3H, d, J = 6.7 Hz), 0.94 (3H, d, J = 6.7 Hz), 0.75 (3H, dd, J = 6.7, 1.2 Hz). |
| 43 | ¹H-NMR (CDCl3) δ: 7.87 (1H, s), 6.92-6.86 (2H, m), 3.45-3.37 (1H, m), 1.97-1.88 (1H, m), 1.44 (3H, d, J = 6.6 Hz), 0.93 (3H, d, J = 6.6 Hz), 0.74 (3H, dd, J = 6.6, 1.2 Hz). |
| 44 | ¹H-NMR (CDCl3) δ: 7.86 (1H, s), 7.63 (1H, dd, J = 7.8, 1.4 Hz), 7.36-7.26 (3H, m), 6.64-6.59 (2H, m). |
| 45 | ¹H-NMR (CDCl3) δ: 7.75 (1H, s), 7.64-7.62 (1H, m), 7.35-7.30 (3H, m), 6.64-6.61 (2H, m). |
| 46 | ¹H-NMR (CDCl3) δ: 7.75 (1H, s), 7.64-7.62 (1H, m), 7.36-7.26 (3H, m), 6.64-6.60 (2H, m). |
| 47 | ¹H-NMR (CDCl3) δ: 7.87 (1H, s), 6.91-6.86 (2H, m), 3.45-3.39 (1H, m), 1.97-1.90 (1H, m), 1.42 (3H, d, J = 6.6 Hz), 0.94 (3H, d, J = 6.6 Hz), 0.75 (3H, dd, J = 6.6, 1.2 Hz). |
| 48 | ¹H-NMR (CDCl3) δ: 7.79 (1H, s), 7.35-7.27 (3H, m), 6.91-6.87 (2H, m), 6.77-6.71 (2H, m), 4.85 (2H, s). |
| 49 | ¹H-NMR (CDCl3) δ: 7.78 (1H, s), 7.35-7.28 (3H, m), 6.91-6.89 (2H, m), 6.75-6.72 (2H, m), 4.85 (2H, s). |
| 50 | ¹H-NMR (CDCl3) δ: 7.73 (1H, s), 6.64-6.61 (2H, m), 3.89 (3H, s), 3.56-3.50 (1H, m), 1.95-1.87 (1H, m), 1.41 (3H, d, J = 6.7 Hz), 0.93 (3H, d, J = 6.7 Hz), 0.74 (3H, dd, J = 6.7, 1.2 Hz). |
| 51 | ¹H-NMR (CDCl3) δ: 7.85 (1H, s), 6.64-6.61 (2H, m), 3.89 (3H, s), 3.54-3.48 (1H, m), 1.94-1.87 (1H, m), 1.43 (3H, d, J = 6.7 Hz), 0.92 (3H, d, J = 6.7 Hz), 0.73 (3H, dd, J = 6.7, 0.9 Hz). |

TABLE 5-continued

| Compound | ¹H-NMR |
|---|---|
| 52 | ¹H-NMR (CDCl3) δ: 7.73 (1H, s), 6.65-6.61 (2H, m), 3.89 (3H, s), 3.56-3.49 (1H, m), 1.95-1.86 (1H, m), 1.43 (3H, d, J = 6.6 Hz), 0.93 (3H, d, J = 6.6 Hz), 0.73 (3H, dd, J = 6.6, 1.2 Hz). |
| 53 | ¹H-NMR (CDCl3) δ: 7.85 (1H, s), 6.64-6.60 (2H, m), 3.89 (3H, s), 3.55-3.47 (1H, m), 1.96-1.87 (1H, m), 1.41 (3H, d, J = 6.6 Hz), 0.93 (3H, d, J = 6.6 Hz), 0.74 (3H, dd, J = 6.6, 1.2 Hz). |
| 54 | ¹H-NMR (CDCl3) δ: 7.88 (1H, s), 7.42 (1H, dd, J = 8.1, 1.5 Hz), 7.35-7.31 (3H, m), 7.25-7.23 (1H, m), 6.85-6.82 (2H, m). |
| 55 | ¹H-NMR (CDCl3) δ: 7.88 (1H, s), 7.42 (1H, dd, J = 8.1, 1.4 Hz), 7.34-7.30 (3H, m), 7.24-7.22 (1H, m), 6.86-6.81 (2H, m). |
| 56 | ¹H-NMR (CDCl3) δ: 7.93 (1H, s), 7.36-7.30 (3H, m), 6.92-6.90 (2H, m), 6.78-6.74 (2H, m), 4.86 (2H, s). |
| 57 | ¹H-NMR (CDCl3) δ: 7.94 (1H, s), 7.36-7.31 (3H, m), 6.93-6.91 (2H, m), 6.77-6.73 (2H, m), 4.87 (2H, s). |
| 58 | ¹H-NMR (CDCl3) δ: 7.76 (1H, s), 7.35-7.31 (3H, m), 6.97-6.94 (2H, m), 6.55-6.51 (2H, m), 4.88 (2H, s), 3.85 (3H, s). |
| 59 | ¹H-NMR (CDCl3) δ: 7.76 (1H, s), 7.36-7.31 (3H, m), 6.98-6.94 (2H, m), 6.55-6.50 (2H, m), 4.89 (2H, s), 3.85 (3H, s). |
| 60 | ¹H-NMR (CDCl3) δ: 7.76 (1H, s), 7.42 (1H, dd, J = 8.1, 1.4 Hz), 7.34-7.31 (3H, m), 7.23 (1H, dt, J = 8.1, 1.4 Hz), 6.86-6.81 (2H, m). |
| 61 | ¹H-NMR (CDCl3) δ: 7.76 (1H, s), 7.42 (1H, dd, J = 8.1, 1.4 Hz), 7.37-7.30 (3H, m), 7.24 (1H, dt, J = 8.1, 1.4 Hz), 6.86-6.83 (2H, m). |
| 62 | ¹H-NMR (CDCl3) δ: 7.76 (1H, s), 7.30-7.26 (1H, m), 7.24-7.23 (1H, m), 7.17-7.12 (2H, m), 6.65-6.55 (2H, m), 2.19 (3H, d, J = 0.6 Hz). |
| 63 | ¹H-NMR (CDCl3) δ: 7.76 (1H, s), 7.30-7.27 (1H, m), 7.25-7.23 (1H, m), 7.16-7.14 (2H, m), 6.65-6.57 (2H, m), 2.18 (3H, s). |
| 64 | ¹H-NMR (CDCl3) δ: 7.74 (1H, s), 7.27-7.26 (1H, m), 7.23-7.21 (1H, m), 7.17-7.14 (2H, m), 6.39-6.32 (2H, m), 3.74 (3H, s), 2.17 (3H, s). |
| 65 | ¹H-NMR (CDCl3) δ: 7.74 (1H, s), 7.26-7.22 (2H, m), 7.18-7.12 (2H, m), 6.38-6.31 (2H, m), 3.74 (3H, s), 2.19 (3H, s). |
| 66 | ¹H-NMR (CDCl3) δ: 7.88 (1H, s), 7.30-7.27 (1H, m), 7.24-7.23 (1H, m), 7.18-7.13 (2H, m), 6.65-6.56 (2H, m), 2.19 (3H, s). |
| 67 | ¹H-NMR (CDCl3) δ: 7.88 (1H, s), 7.30-7.22 (2H, m), 7.17-7.11 (2H, m), 6.65-6.55 (2H, m), 2.19 (3H, d, J = 0.7 Hz). |
| 68 | ¹H-NMR (CDCl3) δ: 7.86 (1H, s), 7.28-7.11 (4H, m), 6.36-6.32 (2H, m), 3.74 (3H, s), 2.18 (3H, s). |
| 69 | ¹H-NMR (CDCl3) δ: 7.78 (1H, s), 6.95-6.89 (2H, m), 3.79-3.75 (2H, m), 2.11-2.00 (2H, m), 1.95-1.87 (2H, m). |
| 70 | ¹H-NMR (CDCl3) δ: 7.76 (1H, s), 6.93-6.90 (2H, m), 3.79-3.75 (2H, m), 2.09-1.99 (2H, m), 1.95-1.87 (2H, m). |
| 71 | ¹H-NMR (CDCl3) δ: 7.90 (1H, s), 6.94-6.90 (2H, m), 3.78-3.75 (2H, m), 2.09-2.00 (2H, m), 1.94-1.88 (2H, m). |
| 72 | ¹H-NMR (CDCl3) δ: 7.90 (1H, s), 6.94-6.89 (2H, m), 3.79-3.75 (2H, m), 2.10-2.01 (2H, m), 1.94-1.88 (2H, m). |
| 73 | ¹H-NMR (CDCl3) δ: 7.56 (1H, s), 7.43-7.37 (3H, m), 7.18-7.16 (2H, m), 6.93 (1H, tt, J = 8.8, 2.1 Hz), 6.86 (1H, tt, J = 8.8, 2.1 Hz), 5.15 (1H, q, J = 6.8 Hz), 1.76 (3H, d, J = 6.8 Hz). |
| 74 | ¹H-NMR (CDCl3) δ: 7.57 (1H, s), 7.43-7.37 (3H, m), 7.17-7.15 (2H, m), 6.94 (1H, tt, J = 8.7, 2.0 Hz), 6.87 (1H, tt, J = 8.7, 2.0 Hz), 5.14 (1H, q, J = 6.8 Hz), 1.77 (3H, d, J = 6.8 Hz). |
| 75 | ¹H-NMR (CDCl3) δ: 7.76 (1H, s), 7.35-7.33 (1H, m), 7.26-7.24 (1H, m), 6.94-6.92 (1H, m), 6.82-6.81 (1H, m), 6.65-6.61 (1H, m), 6.52-6.50 (1H, m), 3.72 (3H, s). |
| 76 | ¹H-NMR (CDCl3) δ: 7.54 (1H, s), 7.43-7.37 (3H, m), 7.18-7.17 (2H, m), 6.93 (1H, tt, J = 8.8, 2.0 Hz), 6.87 (1H, tt, J = 8.8, 2.0 Hz), 5.17 (1H, q, J = 7.0 Hz), 1.75 (3H, d, J = 7.0 Hz). |
| 77 | ¹H-NMR (CDCl3) δ: 7.69 (1H, s), 7.43-7.37 (3H, m), 7.16-7.15 (2H, m), 6.93 (1H, tt, J = 8.7, 2.0 Hz), 6.86 (1H, tt, J = 8.7, 2.0 Hz), 5.12 (1H, q, J = 7.0 Hz), 1.77 (3H, d, J = 7.0 Hz). |
| 78 | ¹H-NMR (CDCl3) δ: 7.68 (1H, s), 7.43-7.38 (3H, m), 7.17-7.16 (2H, m), 6.93 (1H, tt, J = 8.7, 2.0 Hz), 6.86 (1H, tt, J = 8.7, 2.0 Hz), 5.13 (1H, q, J = 7.0 Hz), 1.76 (3H, d, J = 7.0 Hz). |
| 79 | ¹H-NMR (CDCl3) δ: 7.75 (1H, s), 7.37-7.27 (3H, m), 6.94-6.92 (1H, m), 6.81-6.75 (2H, m), 5.00 (2H, s). |
| 80 | ¹H-NMR (CDCl3) δ: 7.76 (1H, s), 7.37-7.27 (3H, m), 6.95-6.92 (1H, m), 6.79-6.74 (2H, m), 5.00 (2H, s). |
| 81 | ¹H-NMR (CDCl3) δ: 7.88 (1H, s), 7.35-7.33 (1H, m), 7.27-7.24 (1H, m), 6.94-6.92 (1H, m), 6.82-6.80 (1H, m), 6.64-6.62 (1H, m), 6.51-6.49 (1H, m), 3.72 (3H, s). |
| 82 | ¹H-NMR (CDCl3) δ: 7.51 (1H, s), 7.43-7.36 (3H, m), 7.21-7.18 (2H, m), 6.69-6.60 (2H, m), 5.24 (1H, q, J = 6.9 Hz), 3.88 (3H, s), 1.75 (3H, d, J = 6.9 Hz). |
| 83 | ¹H-NMR (CDCl3) δ: 7.52 (1H, s), 7.43-7.35 (3H, m), 7.22-7.18 (2H, m), 6.69-6.60 (2H, m), 5.23 (1H, q, J = 6.9 Hz), 3.88 (3H, s), 1.75 (3H, d, J = 6.9 Hz). |
| 84 | ¹H-NMR (CDCl3) δ: 7.76 (1H, s), 6.66-6.63 (2H, m), 3.89 (3H, s), 3.81-3.78 (2H, m), 2.08-1.99 (2H, m), 1.93-1.87 (2H, m). |
| 85 | ¹H-NMR (CDCl3) δ: 7.75 (1H, s), 6.67-6.63 (2H, m), 3.89 (3H, s), 3.80-3.77 (2H, m), 2.07-1.98 (2H, m), 1.93-1.87 (2H, m). |
| 86 | ¹H-NMR (CDCl3) δ: 7.88 (1H, s), 7.37-7.28 (3H, m), 6.93-6.91 (1H, m), 6.79-6.74 (2H, m), 5.00 (2H, s). |

TABLE 5-continued

| Compound | ¹H-NMR |
|---|---|
| 87 | ¹H-NMR (CDCl3) δ: 7.88 (1H, s), 7.37-7.28 (3H, m), 6.94-6.91 (1H, m), 6.78-6.74 (2H, m), 5.00 (2H, s). |
| 88 | ¹H-NMR (CDCl3) δ: 7.71 (1H, s), 7.37-7.28 (3H, m), 6.95-6.92 (1H, m), 6.55-6.50 (2H, m), 5.02 (2H, s), 3.85 (3H, s). |
| 89 | ¹H-NMR (CDCl3) δ: 7.74 (1H, s), 7.37-7.27 (3H, m), 6.95-6.93 (1H, m), 6.78-6.74 (2H, m), 5.02 (2H, s). |
| 90 | ¹H-NMR (CDCl3) δ: 7.87 (1H, s), 7.60 (1H, dd, J = 8.0, 1.5 Hz), 7.37-7.36 (1H, m), 7.34-7.31 (1H, m), 7.29-7.22 (2H, m), 6.85-6.83 (2H, m). |
| 91 | ¹H-NMR (CDCl3) δ: 7.87 (1H, s), 7.60 (1H, dd, J = 7.8, 1.7 Hz), 7.36-7.35 (1H, m), 7.33-7.30 (1H, m), 7.29-7.21 (2H, m), 6.85-6.82 (2H, m). |
| 92 | ¹H-NMR (CDCl3) δ: 7.75 (1H, s), 7.60 (1H, dd, J = 7.4, 1.8 Hz), 7.38-7.22 (4H, m), 6.87-6.82 (2H, m). |
| 93 | ¹H-NMR (CDCl3) δ: 7.75 (1H, s), 7.62-7.59 (1H, m), 7.37-7.21 (4H, m), 6.87-6.82 (2H, m). |
| 94 | ¹H-NMR (CDCl3) δ: 7.36 (1H, s), 7.32-7.28 (3H, m), 6.95-6.92 (4H, m), 3.89 (2H, t, J = 7.2 Hz), 2.83 (2H, t, J = 7.2 Hz). |
| 95 | ¹H-NMR (CDCl3) δ: 7.35 (1H, s), 7.32-7.28 (3H, m), 6.95-6.91 (4H, m), 3.89 (2H, t, J = 7.2 Hz), 2.83 (2H, t, J = 7.2 Hz). |
| 96 | ¹H-NMR (CDCl3) δ: 7.85 (1H, s), 7.38-7.35 (2H, m), 7.16 (1H, dd, J = 7.8, 2.9 Hz), 6.97-6.96 (1H, m), 6.91-6.84 (2H, m). |
| 97 | ¹H-NMR (CDCl3) δ: 7.85 (1H, s), 7.39-7.33 (2H, m), 7.16 (1H, dd, J = 7.6, 2.8 Hz), 6.97-6.95 (1H, m), 6.90-6.83 (2H, m). |
| 98 | ¹H-NMR (CDCl3) δ: 7.72 (1H, s), 7.40-7.32 (2H, m), 7.16 (1H, dd, J = 7.8, 2.9 Hz), 6.97-6.95 (1H, m), 6.91-6.83 (2H, m). |
| 99 | ¹H-NMR (CDCl3) δ: 7.73 (1H, s), 7.40-7.34 (2H, m), 7.16 (1H, dd, J = 8.0, 2.8 Hz), 6.98-6.96 (1H, m), 6.91-6.84 (2H, m). |
| 100 | ¹H-NMR (CDCl3) δ: 7.47 (1H, s), 7.33-7.28 (3H, m), 6.96-6.91 (4H, m), 3.88 (2H, t, J = 7.2 Hz), 2.82 (2H, t, J = 7.2 Hz). |
| 101 | ¹H-NMR (CDCl3) δ: 7.47 (1H, s), 7.33-7.28 (3H, m), 6.95-6.91 (4H, m), 3.88 (2H, t ,1 = 7.2 Hz) 2.83 (2H, t, J = 7.2 Hz). |
| 102 | ¹H-NMR (CDCl3) δ: 7.33 (1H, s), 7.31-7.25 (3H, m), 6.95-6.92 (2H, m), 6.69-6.65 (2H, m), 3.92-3.89 (5H, m), 2.82 (2H, t, J = 7.0 Hz). |
| 103 | ¹H-NMR (CDCl3) δ: 7.33 (1H, s), 7.32-7.25 (3H, m), 6.95-6.92 (2H, m), 6.69-6.65 (2H, m), 3.92-3.87 (5H, m), 2.83 (2H, t, J = 7.2 Hz). |
| 104 | ¹H-NMR (CDCl3) δ: 7.44 (1H, s), 7.32-7.27 (3H, m), 6.95-6.93 (2H, m), 6.68-6.65 (2H, m), 3.92-3.88 (5H, m), 2.82 (2H, t, J = 7.2 Hz). |
| 105 | ¹H-NMR (CDCl3) δ: 7.86 (1H, s), 7.41-7.34 (2H, m), 7.16-7.14 (1H, m), 7.09-7.07 (1H, m), 6.91-6.87 (2H, m). |
| 106 | ¹H-NMR (CDCl3) δ: 7.86 (1H, s), 7.40-7.36 (2H, m), 7.14-7.13 (1H, m), 7.08-7.07 (1H, m), 6.91-6.86 (2H, m). |
| 107 | ¹H-NMR (CDCl3) δ: 7.73 (1H, s), 6.91-6.87 (2H, m), 3.48 (2H, d, J = 7.6 Hz), 1.86-1.78 (1H, m), 0.83 (6H, d, J = 6.7 Hz). |
| 108 | ¹H-NMR (CDCl3) δ: 7.74 (1H, s), 6.91-6.86 (2H, m), 3.49 (2H, d, J = 7.6 Hz), 1.87-1.78 (1H, m), 0.84 (6H, d, J = 6.7 Hz). |
| 109 | ¹H-NMR (CDCl3) δ: 7.74 (1H, s), 7.42-7.33 (2H, m), 7.14-7.13 (1H, m), 7.09-7.06 (1H, m), 6.92-6.86 (2H, m). |
| 110 | ¹H-NMR (CDCl3) δ: 7.74 (1H, s), 7.42-7.34 (2H, m), 7.16-7.14 (1H, m), 7.10-7.07 (1H, m), 6.90-6.88 (2H, m). |
| 111 | ¹H-NMR (CDCl3) δ: 7.88 (1H, s), 7.33-7.17 (4H, m), 7.11-7.10 (1H, m), 6.87-6.79 (2H, m), 2.20 (3H, s). |
| 112 | ¹H-NMR (CDCl3) δ: 7.88 (1H, s), 7.33-7.17 (4H, m), 7.11-7.09 (1H, m), 6.85-6.79 (2H, m), 2.20 (3H, s). |
| 113 | ¹H-NMR (CDCl3) δ: 7.76 (1H, s), 7.33-7.17 (4H, m), 7.12-7.08 (1H, m), 6.87-6.77 (2H, m), 2.20 (3H, s). |
| 114 | ¹H-NMR (CDCl3) δ: 7.76 (1H, s), 7.28-7.23 (4H, m), 7.13-7.09 (1H, m), 6.85-6.81 (2H, m), 2.20 (3H, s). |
| 115 | ¹H-NMR (CDCl3) δ: 7.86 (1H, s), 6.90-6.87 (2H, m), 3.48 (2H, d, J = 7.6 Hz), 1.86-1.77 (1H, m), 0.83 (6H, d, J = 6.7 Hz). |
| 116 | ¹H-NMR (CDCl3) δ: 7.86 (1H, s), 6.90-6.85 (2H, m), 3.48 (2H, d, J = 7.6 Hz), 1.86-1.78 (1H, m), 0.84 (6H, d, J = 6.7 Hz). |
| 117 | ¹H-NMR (CDCl3) δ: 7.97 (1H, s), 7.55-7.53 (1H, m), 7.42-7.42 (1H, m), 7.25 (1H, t, J = 8.1 Hz), 7.17-7.15 (1H, m), 6.67-6.65 (2H, m). |
| 118 | ¹H-NMR (CDCl3) δ: 7.97 (1H, s), 7.55-7.53 (1H, m), 7.41-7.41 (1H, m), 7.24 (1H, t, J = 8.1 Hz), 7.17-7.16 (1H, m), 6.66-6.64 (2H, m). |
| 119 | ¹H-NMR (CDCl3) δ: 7.85 (1H, s), 7.55-7.53 (1H, m), 7.42-7.41 (1H, m), 7.25 (1H, t, J = 8.0 Hz), 7.18-7.16 (1H, m), 6.66-6.64 (2H, m). |
| 120 | ¹H-NMR (CDCl3) δ: 7.85 (1H, s), 7.56-7.54 (1H, m), 7.42-7.42 (1H, m), 7.25 (1H, t, J = 7.9 Hz), 7.18-7.16 (1H, m), 6.68-6.64 (2H, m). |
| 121 | ¹H-NMR (CDCl3) δ: 7.71 (1H, d, J = 0.7 Hz), 6.92-6.89 (2H, m), 3.52 (2H, d, J = 7.1 Hz), 1.70-1.67 (3H, m), 1.50-1.44 (3H, m), 1.17-1.06 (3H, m), 0.78-0.75 (2H, m). |
| 122 | ¹H-NMR (CDCl3) δ: 7.72 (1H, s), 6.90-6.88 (2H, m), 3.50 (2H, d, J = 7.1 Hz), 1.73-1.70 (3H, m), 1.50-1.47 (3H, m), 1.18-1.07 (3H, m), 0.80-0.77 (2H, m). |
| 123 | ¹H-NMR (CDCl3) δ: 7.72 (1H, s), 6.91-6.86 (2H, m), 3.50 (2H, d, J = 7.1 Hz), 1.71-1.68 (3H, m), 1.51-1.46 (3H, m), 1.19-1.08 (3H, m), 0.81-0.78 (2H, m). |

TABLE 5-continued

| Compound | ¹H-NMR |
|---|---|
| 124 | ¹H-NMR (CDCl3) δ: 7.84 (1H, s), 6.91-6.87 (2H, m), 3.49 (2H, d, J = 7.0 Hz), 1.73-1.66 (3H, m), 1.51-1.44 (3H, m), 1.20-1.07 (3H, m), 0.79-0.76 (2H, m). |
| 125 | ¹H-NMR (CDCl3) δ: 7.84 (1H, s), 6.89-6.87 (2H, m), 3.49 (2H, d, J = 7.3 Hz), 1.71-1.68 (3H, m), 1.51-1.45 (3H, m), 1.18-1.08 (3H, m), 0.81-0.78 (2H, m). |
| 126 | ¹H-NMR (CDCl3) δ: 8.41 (1H, d, J = 1.5 Hz), 8.13 (1H, s), 6.78-6.73 (2H, m), 6.20 (1H, d, J = 1.5 Hz). |
| 127 | ¹H-NMR (CDCl3) δ: 8.41 (1H, d, J = 1.8 Hz), 8.12 (1H, s), 6.77-6.72 (2H, m), 6.21 (1H, d, J = 1.8 Hz). |
| 128 | ¹H-NMR (CDCl3) δ: 8.41 (1H, d, J = 1.7 Hz), 8.01 (1H, s), 6.79-6.73 (2H, m), 6.20 (1H, d, J = 1.7 Hz). |
| 129 | ¹H-NMR (CDCl3) δ: 8.41 (1H, d, J = 1.8 Hz), 8.00 (1H, s), 6.77-6.73 (2H, m), 6.22 (1H, d, J = 1.8 Hz). |
| 130 | ¹H-NMR (CDCl3) δ: 8.36 (1H, d, J = 1.8 Hz), 8.15 (1H, s), 6.51-6.47 (2H, m), 6.13 (1H, d, J = 1.8 Hz), 3.83 (3H, s). |
| 131 | ¹H-NMR (CDCl3) δ: 8.36 (1H, d, J = 1.8 Hz), 8.17 (1H, s), 6.52-6.48 (2H, m), 6.11 (1H, d, J = 1.8 Hz), 3.83 (3H, s). |
| 132 | ¹H-NMR (CDCl3) δ: 7.72 (1H, s), 6.63-6.60 (2H, m), 3.89 (3H, s), 3.51 (2H, d, J = 7.6 Hz), 1.88-1.79 (1H, m), 0.83 (6H, d, J = 6.4 Hz). |
| 133 | ¹H-NMR (CDCl3) δ: 7.84 (1H, s), 6.63-6.59 (2H, m), 3.89 (3H, s), 3.50(2H, d, J = 7.6 Hz), 1.87-1.79 (1H, m), 0.83 (6H, d, J = 6.7 Hz). |
| 134 | ¹H-NMR (CDCl3) δ: 7.88 (1H, s), 6.91-6.86 (2H, m), 3.46-3.38 (1H, m), 1.95-1.92 (1H, m), 1.42 (3H, d, J = 6.8 Hz), 0.94 (3H, d, J = 6.6 Hz), 0.75 (3H, dd, J = 6.6, 1.2 Hz). |
| 135 | ¹H-NMR (CDCl3) δ: 7.39 (1H, d, J = 1.0 Hz), 6.90-6.83 (2H, m), 3.37-3.34 (1H, m), 2.18 (3H, d, J = 1.0 Hz), 1.93 (1H, dt, J = 12.0, 4.9 Hz), 1.41 (3H, d, J = 6.8 Hz), 0.92 (3H, d, J = 6.6 Hz), 0.71 (3H, dd, J = 6.6, 1.2 Hz). |
| 136 | ¹H-NMR (CDCl3) δ: 8.32 (1H, s), 6.93-6.88 (2H, m), 3.44-3.41 (1H, m), 2.81 (3H, s), 2.00-1.98 (1H, m), 1.45 (3H, d, J = 6.7 Hz), 0.93 (3H, d, J = 6.4 Hz), 0.72 (3H, dd, J = 6.6, 1.1 Hz). |
| 137 | ¹H-NMR (CDCl3) δ: 7.83 (1H, d, J = 0.7 Hz), 6.94-6.88 (2H, m), 3.48-3.45 (1H, m), 1.97-1.88 (1H, m), 1.45 (3H, d, J = 6.6 Hz), 0.95 (3H, d, J = 6.6 Hz), 0.75 (3H, dd, J = 6.7, 1.1 Hz). |
| 138 | ¹H-NMR (CDCl3) δ: 7.98 (1H, s), 6.79-6.73 (2H, m), 5.84 (1H, s), 2.41 (3H, d, J = 1.0 Hz). |
| 139 | ¹H-NMR (CDCl3) δ: 7.97 (1H, s), 7.40-7.38 (1H, m), 7.31 (1H, t, J = 8.1 Hz), 7.27-7.26 (1H, m), 7.13-7.11 (1H, m), 6.66-6.65 (2H, m). |
| 140 | ¹H-NMR (CDCl3) δ: 7.97 (1H, s), 7.40-7.38 (1H, m), 7.31 (1H, t, J = 7.9 Hz), 7.27-7.26 (1H, m), 7.13-7.11 (1H, m), 6.67-6.62 (2H, m). |
| 141 | ¹H-NMR (CDCl3) δ: 7.96 (1H, s), 6.77-6.73 (2H, m), 5.86 (1H, s), 2.41 (3H, s). |
| 142 | ¹H-NMR (CDCl3) δ: 7.76 (1H, s), 6.74-6.69 (2H, m), 2.45 (3H, s). |
| 143 | ¹H-NMR (CDCl3) δ: 7.86 (1H, s), 7.11-7.06 (2H, m), 6.97 (1H, br s), 6.66-6.56 (2H, m), 2.24 (3H, s), 2.12 (3H, s). |
| 144 | ¹H-NMR (CDCl3) δ: 7.86 (1H, s), 7.09-7.06 (2H, m), 6.96 (1H, br s), 6.66-6.55 (2H, m), 2.24 (3H, s), 2.13 (3H, s). |
| 145 | ¹H-NMR (CDCl3) δ: 7.76 (1H, s), 6.90-6.86 (2H, m), 4.40 (2H, s), 4.18 (2H, q, J = 7.2 Hz), 1.22 (2H, t, J= 7.2 Hz). |
| 146 | ¹H-NMR (CDCl3) δ: 8.08 (1H, s), 6.77-6.72 (2H, m), 5.86 (1H, s), 2.41 (3H, d, J = 0.6 Hz). |
| 147 | ¹H-NMR (CDCl3) δ: 7.87 (1H, s), 6.75-6.68 (2H, m), 2.45 (3H, s). |
| 148 | ¹H-NMR (CDCl3) δ: 7.74 (1H, s), 7.10-7.07 (2H, m), 6.96 (1H, br s), 6.63-6.59 (2H, m), 2.24 (3H, s), 2.13 (3H, s). |
| 149 | ¹H-NMR (CDCl3) δ: 7.75 (1H, s), 7.11-7.07 (2H, m), 6.97 (1H, br s), 6.66-6.57 (2H, m), 2.25 (3H, s), 2.12 (3H, s). |
| 150 | ¹H-NMR (CDCl3) δ: 7.74 (1H, s), 6.88-6.86 (2H, m), 4.39 (2H, s), 4.18 (2H, q, J = 7.2 Hz), 1.23 (3H, t, J = 7.2 Hz). |
| 151 | ¹H-NMR (CDCl3) δ: 7.84 (1H, s), 6.89-6.86 (2H, m), 3.32-3.29 (1H, m), 1.92-1.87 (1H, m), 1.86 (3H, m), 1.40 (3H, d, J = 6.6 Hz), 0.91 (3H, d, J = 6.6 Hz), 0.71 (3H, dd, J = 6.8, 1.2 Hz). |
| 152 | ¹H-NMR (CDCl3) δ: 7.37 (1H, s), 6.86-6.84 (2H, m), 3.27-3.25 (1H, m), 2.13 (3H, d, J = 0.6 Hz), 1.91-1.89 (1H, m), 1.81 (3H, s), 1.37 (3H, d, J = 6.7 Hz), 0.90 (3H, d, J = 6.4 Hz), 0.67 (3H, dd, J = 6.6, 1.1 Hz). |
| 153 | ¹H-NMR (CDCl3) δ: 7.79 (1H, s), 6.93-6.86 (2H, m), 3.20 (1H, td, J = 11.5, 3.7 Hz), 2.03-1.98 (1H, m), 1.91-1.85 (2H, m), 1.81-1.64 (2H, m), 1.31-0.91 (4H, m), 0.74 (3H, dd, J = 6.3, 1.5 Hz). |
| 154 | ¹H-NMR (CDCl3) δ: 7.79 (1H, s), 6.92-6.86 (2H, m), 3.24-3.17 (1H, m), 2.02-1.98 (1H, m), 1.91-1.84 (2H, m), 1.82-1.65 (2H, m), 1.35-0.86 (4H, m), 0.75 (3H, dd, J = 6.5, 1.6 Hz). |
| 155 | ¹H-NMR (CDCl3) δ: 7.36 (1H, s), 6.60-6.58 (2H, m), 3.88 (3H, s), 3.36 (1H, t, J = 8.4 Hz), 2.13 (3H, s), 1.91-1.86 (1H, m), 1.83 (3H, s), 1.36 (3H, d, J = 6.6 Hz), 0.89 (3H, d, J = 6.6 Hz), 0.67 (3H, d, J = 6.6 Hz). |
| 156 | ¹H-NMR (CDCl3) δ: 7.72 (1H, s), 6.91-6.85 (2H, m), 3.35-3.31 (1H, m), 1.91-1.89 (4H, m), 1.40 (3H, d, J = 6.6 Hz), 0.91 (3H, d, J = 6.6 Hz), 0.70 (3H, dd, J = 6.6, 1.2 Hz). |

TABLE 5-continued

| Compound | ¹H-NMR |
|---|---|
| 157 | ¹H-NMR (CDCl3) δ: 7.80 (1H, s), 6.92-6.87 (2H, m), 3.38-3.36 (1H, m), 1.92-1.85 (1H, m), 1.82 (3H, s), 1.40 (3H, d, J = 6.7 Hz), 0.92 (3H, d, J = 6.7 Hz), 0.72 (3H, dd, J = 6.6, 1.1 Hz). |
| 158 | ¹H-NMR (CDCl3) δ: 7.83 (1H, s), 6.91-6.85 (2H, m), 3.27-3.24 (1H, m), 2.42-2.35 (1H, m), 2.13-2.10 (1H, m), 1.92-1.89 (1H, m), 1.37 (3H, d, J = 6.6 Hz), 0.96-0.87 (6H, m), 0.73 (3H, dd, J = 6.7, 1.3 Hz). |
| 159 | ¹H-NMR (CDCl3) δ: 7.90 (1H, s), 6.92-6.86 (2H, m), 3.18 (2H, td, J = 11.0, 3.2 Hz), 2.03-1.98 (1H, br m), 1.89-1.86 (2H, br m), 1.80-1.61 (2H, br m), 1.35-0.87 (4H, m), 0.74 (3H, dd, J = 6.3, 1.5 Hz). |
| 160 | ¹H-NMR (CDCl3) δ: 7.90 (1H, s), 6.91-6.86 (2H, m), 3.19 (1H, td, J = 11.4, 3.5 Hz), 2.02-1.96 (1H, br m), 1.89-1.85 (2H, br m), 1.78-1.66 (2H, m), 1.31-0.89 (4H, m), 0.75 (3H, dd, J = 6.5, 1.6 Hz). |
| 161 | ¹H-NMR (CDCl3) δ: 7.83 (1H, s), 6.95-6.88 (2H, m), 5.87 (1H, tt, J = 54.2, 3.7 Hz), 4.07 (2H, td, J = 13.4, 3.7 Hz). |
| 162 | ¹H-NMR (CDCl3) δ: 7.73 (1H, s), 6.91-6.87 (2H, m), 3.66 (1H, dd, J = 14.2, 6.6 Hz), 3.38 (1H, dd, J = 14.2, 8.7 Hz), 1.56-1.53 (1H, m), 1.28-1.18 (1H, m), 1.11-1.02 (1H, m), 0.81 (3H, d, J = 6.6 Hz), 0.76 (3H, t, J = 7.3 Hz). |
| 163 | ¹H-NMR (CDCl3) δ: 7.87 (1H, s), 7.17-7.16 (1H, m), 7.04-7.02 (2H, m), 6.64-6.56 (2H, m), 2.26 (3H, s), 2.03 (3H, d, J = 2.1 Hz). |
| 164 | ¹H-NMR (CDCl3) δ: 7.86 (1H, s), 7.16-7.15 (1H, m), 7.05-7.00 (2H, m), 6.64-6.55 (2H, m), 2.26 (3H, s), 2.04 (3H, d, J = 2.1 Hz). |
| 165 | ¹H-NMR (CDCl3) δ: 7.73 (1H, s), 6.90-6.84 (2H, m), 3.66 (1H, dd, J = 14.2, 6.6 Hz), 3.39 (1H, dd, J = 14.2, 8.6 Hz), 1.59-1.52 (1H, m), 1.25-1.20 (1H, m), 1.09-1.04 (1H, m), 0.82 (3H, d, J = 6.6 Hz), 0.76 (3H, t, J = 7.5 Hz). |
| 166 | ¹H-NMR (CDCl3) δ: 7.85 (1H, s), 6.91-6.87 (2H, m), 3.68-3.63 (1H, m), 3.40-3.35 (1H, m), 1.56-1.52 (1H, m), 1.28-1.18 (1H, m), 1.09-1.03 (1H, m), 0.81 (3H, d, J = 7.0 Hz), 0.76 (3H, t, J = 7.5 Hz). |
| 167 | ¹H-NMR (CDCl3) δ: 7.85 (1H, s), 6.91-6.85 (2H, m), 3.65 (1H, dd, J = 14.0, 6.3 Hz), 3.38 (1H, dd, J = 14.0, 8.8 Hz), 1.56-1.51 (1H, m), 1.28-1.17 (1H, m), 1.12-1.01 (1H, m), 0.82 (3H, d, J = 6.8 Hz), 0.76 (3H, t, J = 7.4 Hz). |
| 168 | ¹H-NMR (CDCl3) δ: 7.71 (1H, s), 6.63-6.60 (2H, m), 3.89 (3H, s), 3.68 (1H, dd, J = 14.0, 6.5 Hz), 1.58-1.54 (1H, m), 3.41 (1H, dd, J = 14.0, 8.8 Hz), 1.25-1.17 (1H, m), 1.10-1.00 (1H, m), 0.81 (3H, d, J = 6.5 Hz), 0.76 (3H, t, J = 7.4 Hz). |
| 169 | ¹H-NMR (CDCl3) δ: 7.83 (1H, s), 6.64-6.60 (2H, m), 3.88 (3H, s), 3.67 (1H, dd, J = 14.2, 6.6 Hz), 3.40 (1H, dd, J = 14.2, 8.8 Hz), 1.60-1.52 (1H, m), 1.27-1.20 (1H, m), 1.10-1.00 (1H, m), 0.81-0.74 (6H, m). |
| 170 | ¹H-NMR (CDCl3) δ: 7.76 (1H, s), 6.64-6.60 (2H, m), 3.89 (3H, s), 3.30 (1H, td, J = 11.4, 3.6 Hz), 2.02-1.66 (5H, m), 1.34-0.88 (4H, m), 0.74 (3H, dd, J = 6.5, 1.6 Hz). |
| 171 | ¹H-NMR (CDCl3) δ: 7.88 (1H, s), 6.65-6.60 (2H, m), 3.89 (3H, s), 3.31-3.24 (1H, m), 2.04-2.00 (1H, br m), 1.88-1.83 (2H, br m), 1.79-1.65 (2H, br m), 1.30-1.14 (3H, m), 0.98-0.88 (1H, m), 0.73 (3H, dd, J = 6.5, 1.3 Hz). |
| 172 | ¹H-NMR (CDCl3) δ: 7.74 (1H, s), 7.16-7.15 (1H, m), 7.05-7.00 (2H, m), 6.64-6.55 (2H, m), 2.26 (3H, s), 2.04 (3H, d, J = 2.1 Hz). |
| 173 | ¹H-NMR (CDCl3) δ: 7.74 (1H, s), 7.17-7.16 (1H, m), 7.04-7.02 (2H, m), 6.64-6.56 (2H, m), 2.26 (3H, s), 2.03 (3H, d, J = 2.1 Hz). |
| 174 | ¹H-NMR (CDCl3) δ: 7.33 (1H, d, J = 1.2 Hz), 7.20 (2H, tdd, J = 8.8, 5.9, 1.9 Hz), 7.12-7.05 (2H, m), 6.59-6.57 (1H, m), 6.55-6.51 (1H, m), 2.14 (3H, d, J = 1.2 Hz), 2.13 (3H, d, J = 0.9 Hz), 1.91 (3H, s). |
| 175 | ¹H-NMR (CDCl3) δ: 7.32 (1H, d, J = 0.9 Hz), 7.19-7.17 (2H, m), 7.13-7.12 (1H, m), 7.08-7.06 (1H, m), 6.35-6.27 (2H, m), 3.72 (3H, s), 2.13-2.13 (6H, m), 1.91 (3H, s). |
| 176 | ¹H-NMR (CDCl3) δ: 7.31 (1H, d, J = 1.0 Hz), 7.19-7.15 (2H, m), 7.13-7.12 (1H, m), 7.07 (1H, dd, J = 8.1, 2.2 Hz), 6.31-6.26 (2H, m), 3.91 (2H, q, J = 7.1 Hz), 2.13 (3H, d, J = 1.0 Hz), 2.12 (3H, s), 1.91 (3H, s), 1.36 (3H, t, J = 7.1 Hz). |
| 177 | ¹H-NMR (CDCl3) δ: 7.86 (1H, s), 7.23-7.21 (1H, m), 7.05-7.03 (1H, m), 6.95-6.94 (1H, m), 6.70-6.68 (1H, m), 6.63-6.62 (1H, m), 2.15 (3H, s). |
| 178 | ¹H-NMR (CDCl3) δ: 7.86 (1H, s), 7.23-7.21 (1H, m), 7.04-7.02 (1H, m), 6.94-6.93 (1H, m), 6.71-6.67 (1H, m), 6.64-6.59 (1H, m), 2.16 (3H, s). |
| 179 | ¹H-NMR (CDCl3) δ: 7.73 (1H, s), 7.23-7.21 (1H, m), 7.04-7.02 (1H, m), 6.94-6.93 (1H, m), 6.70-6.68 (1H, m), 6.63-6.60 (1H, m), 2.16 (3H, s). |
| 180 | ¹H-NMR (CDCl3) δ: 7.74 (1H, s), 7.23-7.22 (1H, m), 7.05-7.03 (1H, m), 6.95-6.94 (1H, m), 6.70-6.68 (1H, m), 6.64-6.61 (1H, m), 2.15 (3H, s). |
| 181 | ¹H-NMR (CDCl3) δ: 7.85 (1H, s), 7.25-7.21 (2H, m), 7.17-7.15 (2H, m), 6.38-6.31 (2H, m), 3.74 (3H, s), 2.18 (3H, s). |
| 182 | ¹H-NMR (CDCl3) δ: 7.83-7.83 (1H, m), 7.32-7.29 (1H, m), 7.25-7.25 (1H, m), 7.18-7.17 (2H, m), 6.66-6.58 (2H, m), 2.19 (3H, s). |

TABLE 5-continued

| Compound | ¹H-NMR |
|---|---|
| 183 | ¹H-NMR (CDCl3) δ: 7.83 (1H, s), 7.26-7.19 (2H, m), 7.13-7.11 (2H, m), 6.62-6.54 (2H, m), 2.16 (3H, d, J = 0.6 Hz), 1.95 (3H, s). |
| 184 | ¹H-NMR (CDCl3) δ: 7.78 (1H, d, J = 0.7 Hz), 7.28-7.24 (1H, m), 7.22-7.21 (1H, m) 7.15-7.13 (2H, m), 6.64-6.54 (2H, m), 2.16 (3H, d, J = 1.2 Hz), 1.91 (3H, s). |
| 185 | ¹H-NMR (CDCl3) δ: 7.87 (1H, s), 7.29-7.26 (1H, m), 7.24-7.22 (1H, m), 7.15-7.14 (2H, m), 6.62-6.57 (2H, m), 2.19 (3H, d, J = 0.7 Hz). |
| 186 | ¹H-NMR (CDCl3) δ: 7.87 (1H, s), 7.15-7.14 (1H, m), 7.09-7.07 (1H, m), 7.02-7.00 (1H, m), 6.66-6.60 (2H, m), 2.11 (3H, t, J = 1.8 Hz). |
| 187 | ¹H-NMR (CDCl3) δ: 7.87 (1H, s), 7.16-7.14 (1H, m), 7.09-7.07 (1H, m), 7.02-7.01 (1H, m), 6.67-6.61 (2H, m), 2.10 (3H, t, J = 1.8 Hz). |
| 188 | ¹H-NMR (CDCl3) δ: 7.37-7.36 (1H, m), 7.25-7.20 (2H, m), 7.15-7.11 (2H, m), 6.63-6.54 (2H, m), 2.19 (3H, d, J = 1.2 Hz), 2.15 (3H, s). |
| 189 | ¹H-NMR (CDCl3) δ: 7.74 (1H, s), 7.17-7.12 (1H, m), 7.09-7.07 (1H, m), 7.02-7.00 (1H, m), 6.66-6.60 (2H, m), 2.11 (3H, t, J = 1.8 Hz). |
| 190 | ¹H-NMR (CDCl3) δ: 7.75 (1H, s), 7.17-7.15 (1H, m), 7.10-7.07 (1H, m), 7.03-7.01 (1H, m), 6.68-6.60 (2H, m), 2.10 (3H, t, J = 1.8 Hz). |
| 191 | ¹H-NMR (CDCl3) δ: 7.91 (1H, m), 7.74-7.72 (1H, m), 7.60-7.58 (2H, m), 7.44-7.41 (1H, m), 6.65-6.57 (2H, m). |
| 192 | ¹H-NMR (CDCl3) δ: 7.91 (1H, m), 7.73-7.72 (1H, m), 7.61-7.58 (2H, m), 7.45-7.43 (1H, m), 6.66-6.58 (2H, m). |
| 193 | ¹H-NMR (CDCl3) δ: 7.74 (1H, s), 6.90-6.84 (2H, m), 3.57 (2H, s), 0.87 (9H, s). |
| 194 | ¹H-NMR (CDCl3) δ: 7.75 (1H, s), 6.89-6.84 (2H, m), 3.58 (2H, s), 0.87 (9H, s). |
| 195 | ¹H-NMR (CDCl3) δ: 7.87 (1H, s), 6.90-6.84 (2H, m), 3.56 (2H, s), 0.87 (9H, s). |
| 196 | ¹H-NMR (CDCl3) δ: 7.88 (1H, s), 6.89-6.84 (2H, m), 3.57 (2H, s), 0.87 (9H, s). |
| 197 | ¹H-NMR (CDCl3) δ: 7.36 (1H, q, J = 1.0 Hz), 7.23-7.22 (2H, m), 7.14-7.11 (2H, m), 6.60-6.55 (2H, m), 2.19 (3H, d, J = 1.0 Hz), 2.16 (3H, d, J = 0.6 Hz). |
| 198 | ¹H-NMR (CDCl3) δ: 7.79 (1H, m), 7.74-7.73 (1H, m), 7.60-7.58 (2H, m), 7.44-7.42 (1H, m), 6.66-6.58 (2H, m). |
| 199 | ¹H-NMR (CDCl3) δ: 7.79 (1H, m), 7.74-7.72 (1H, m), 7.61-7.59 (2H, m), 7.45-7.43 (1H, m), 6.66-6.59 (2H, m). |
| 200 | ¹H-NMR (CDCl3) δ: 7.77 (1H, s), 6.93-6.88 (2H, m), 3.68-3.65 (2H, m), 1.53-1.43 (3H, m), 0.79 (6H, d, J = 6.4 Hz). |
| 201 | ¹H-NMR (CDCl3) δ: 7.76 (1H, s), 6.93-6.87 (2H, m), 3.69-3.65 (2H, m), 1.54-1.41 (3H, m), 0.79 (6H, d, J = 6.3 Hz). |
| 202 | ¹H-NMR (CDCl2) δ: 7.89 (1H, s), 6.91-6.89 (2H, m), 3.67-3.65 (2H, m), 1.53-1.42 (3H, m), 0.79 (6H, d, J = 6.4 Hz). |
| 203 | ¹H-NMR (CDCl3) δ: 7.89 (1H, s), 6.92-6.87 (2H, m), 3.68-3.64 (2H, m), 1.54-1.43 (3H, m), 0.79 (6H, d, J = 6.3 Hz). |
| 204 | ¹H-NMR (CDCl3) δ: 7.75 (1H, s), 6.65-6.61 (2H, m), 3.89 (3H, s), 3.71-3.67 (2H, m), 1.56-1.41 (3H, m), 0.79 (6H, d, J = 6.3 Hz). |
| 205 | ¹H-NMR (CDCl3) δ: 7.82 (1H, s), 7.24-7.21 (2H, m), 7.14-7.07 (2H, m), 6.63-6.52 (2H, m), 2.37-2.32 (2H, m), 2.17 (3H, s), 1.01 (3H, t, J = 7.3 Hz). |
| 206 | ¹H-NMR (CDCl3) δ: 7.87 (1H, s), 7.33-7.30 (1H, m), 7.05-7.00 (3H, m), 6.88-6.79 (2H, m), 2.21 (3H, s), 2.13 (3H, s). |
| 207 | ¹H-NMR (CDCl3) δ: 7.87 (1H, s), 7.31-7.29 (1H, m), 7.06 (1H, d, J = 8.0 Hz), 7.03-7.01 (1H, m), 6.98(1H, m), 6.87-6.84 (1H, m), 6.81-6.79 (1H, m), 2.21 (3H, s), 2.14 (3H, s). |
| 208 | ¹H-NMR (CDCl3) δ: 7.74 (1H, s), 7.32-7.29 (1H, m), 7.06-7.03 (2H, m), 6.98 (1H, m), 6.88-6.84 (1H, m), 6.81-6.79 (1H, m), 2.21 (3H, s), 2.14 (3H, s). |
| 209 | ¹H-NMR (CDCl3) δ: 7.74 (1H, s), 7.33-7.30 (1H, m), 7.06-7.03 (2H, m), 6.99 (1H, m), 6.88-6.79 (2H, m), 2.21 (3H, s), 2.13 (3H, s). |
| 210 | ¹H-NMR (CDCl3) δ: 7.89 (1H, s), 6.91-6.85 (2H, m), 3.85 (2H, t, J = 5.0 Hz), 3.44 (2H, t, J = 5.0 Hz), 3.30 (3H, s). |
| 211 | ¹H-NMR (CDCl3) δ: 7.88 (1H, s), 6.91-6.85 (2H, m), 3.85 (2H, t, J = 4.9 Hz), 3.44 (2H, t, J = 4.9 Hz), 3.30 (3H, s). |
| 212 | ¹H-NMR (CDCl3) δ: 7.99 (1H, s), 6.90-6.85 (2H, m), 3.83 (2H, t, J = 4.9 Hz), 3.43 (2H, t, J = 4.9 Hz), 3.30 (3H, s). |
| 213 | ¹H-NMR (CDCl3) δ: 8.01 (1H, s), 6.90-6.84 (2H, m), 3.85 (2H, t, J = 4.9 Hz), 3.43 (2H, t, J = 4.9 Hz), 3.30 (3H, s). |
| 214 | ¹H-NMR (CDCl3) δ: 7.74 (1H, s), 6.62-6.58 (2H, m), 3.89 (3H, s), 3.61 (2H, s), 0.87 (9H, s). |
| 215 | ¹H-NMR (CDCl3) δ: 7.86 (1H, s), 6.62-6.59 (2H, m), 3.89 (3H, s), 3.59 (2H, s), 0.86 (9H, s). |
| 216 | ¹H-NMR (CDCl3) δ: 7.45 (1H, d, J = 0.9 Hz), 7.25-7.24 (1H, m), 7.23-7.21 (1H, m), 7.13-7.12 (2H, m), 6.63-6.54 (2H, m), 2.49 (3H, d, J = 0.9 Hz), 2.31 (3H, s), 2.13 (3H, d, J = 0.6 Hz). |
| 217 | ¹H-NMR (CDCl3) δ: 7.87 (1H, s), 7.11 (1H, d, J = 8.6 Hz), 6.83 (1H, dd, J = 8.6, 2.6 Hz), 6.70 (1H, t, J = 2.6 Hz), 6.66-6.61 (2H, m), 3.72 (3H, s), 2.10 (3H, s). |

TABLE 5-continued

| Compound | ¹H-NMR |
|---|---|
| 218 | ¹H-NMR (CDCl3) δ: 7.87 (1H, s), 7.11 (1H, d, J = 8.8 Hz), 6.83 (1H, dd, J = 8.8, 2.7 Hz), 6.70-6.57 (3H, m), 3.72 (3H, s), 2.10 (3H, s). |
| 219 | ¹H-NMR (CDCl3) δ: 7.82 (1H, s), 6.90-6.84 (2H, m), 3.39 (2H, d, J = 7.6 Hz), 1.87 (3H, s), 1.80-1.71 (1H, m), 0.80 (6H, d, J = 6.7 Hz). |
| 220 | ¹H-NMR (CDCl3) δ: 7.80 (1H, s), 6.90-6.85 (2H, m), 3.35 (2H, d, J = 7.6 Hz), 2.27 (2H, q, J = 7.3 Hz), 1.81-1.72 (1H, m), 0.94 (3H, t, J = 7.3 Hz), 0.81 (6H, d, J = 6.7 Hz). |
| 221 | ¹H-NMR (CDCl3) δ: 7.77 (1H, s), 6.93-6.87 (2H, m), 3.69-3.65 (2H, m), 1.64-1.56 (2H, m), 1.28-1.18 (2H, m), 0.84 (3H, t, J = 7.3 Hz). |
| 222 | ¹H-NMR (CDCl3) δ: 7.77 (1H, s), 6.92-6.86 (2H, m), 3.70-3.65 (2H, m), 1.63-1.56 (2H, m), 1.28-1.18 (2H, m), 0.84 (3H, t, J = 7.3 Hz). |
| 223 | ¹H-NMR (CDCl3) δ: 7.69 (1H, s), 6.90-6.85 (2H, m), 3.40 (2H, d, J = 7.6 Hz), 1.87 (3H, s), 1.80-1.72 (1H, m), 0.80 (6H, d, J = 6.7 Hz). |
| 224 | ¹H-NMR (CDCl3) δ: 7.68 (1H, s), 6.90-6.85 (2H, m), 3.35 (2H, d, J = 7.6 Hz), 2.27 (2H, q, J = 7.4 Hz), 1.81-1.73 (1H, m), 0.94 (3H, t, J = 7.4 Hz), 0.81 (6H, d, J = 6.7 Hz). |
| 225 | ¹H-NMR (CDCl3) δ: 7.44 (1H, d, J = 0.9 Hz), 7.26-7.19 (2H, m), 7.15-7.12 (2H, m), 6.37-6.30 (2H, m), 3.73 (3H, s), 2.49 (3H, d, J = 0.9 Hz), 2.32 (3H, s), 2.12 (3H, s). |
| 226 | ¹H-NMR (CDCl3) δ: 7.28-7.28 (1H, m), 7.15 (1H, td, J = 7.4, 1.3 Hz), 7.10-6.99 (5H, m), 6.90-6.88 (2H, m), 2.13 (3H, d, J = 1.2 Hz), 2.06 (3H, s), 1.90 (3H, s). |
| 227 | ¹H-NMR (CDCl3) δ: 7.51 (2H, dt, J = 13.9, 4.6 Hz), 7.30-7.30 (1H, m), 7.23-7.22 (2H, m), 7.17-7.15 (2H, m), 7.12-7.06 (2H, m), 6.99-6.99 (1H, m), 2.14 (3H, d, J = 0.9 Hz), 2.08 (3H, s), 1.87 (3H, s). |
| 228 | ¹H-NMR (CDCl3) δ: 7.75 (1H, s), 7.11 (1H, d, J = 8.6 Hz), 6.83 (1H, dd, J = 8.6, 2.8 Hz), 6.69 (1H, t, J = 2.8 Hz), 6.66-6.65 (1H, m), 6.61-6.59 (1H, m), 3.72 (3H, s), 2.10 (3H, s). |
| 229 | ¹H-NMR (CDCl3) δ: 7.75 (1H, s), 7.12 (1H, d, J = 8.6 Hz), 6.83 (1H, dd, J = 8.6, 2.4 Hz), 6.70 (1H, t, J = 2.4 Hz), 6.66-6.61 (2H, m), 3.72 (3H, s), 2.09 (3H, s). |
| 230 | ¹H-NMR (CDCl3) δ: 7.85 (1H, s), 7.28 (1H, dd, J = 8.6, 2.3 Hz), 7.21 (1H, t, J = 2.3 Hz), 7.18 (1H, d, J = 8.6 Hz), 6.72-6.68 (1H, m), 6.65-6.60 (1H, m), 2.15 (3H, s). |
| 231 | ¹H-NMR (CDCl3) δ: 7.33-7.30 (1H, m), 6.87-6.82 (2H, m), 3.31 (2H, d, J = 7.6 Hz), 2.24 (2H, q, J = 7.4 Hz), 2.10 (3H, d, J = 0.9 Hz), 1.79-1.71 (1H, m), 0.92 (3H, t, J = 7.4 Hz), 0.79 (6H, d, J = 6.7 Hz). |
| 232 | ¹H-NMR (CDCl3) δ: 7.67 (1H, s), 6.63-6.59 (2H, m), 3.89 (3H, s), 3.37 (2H, d, J = 7.6 Hz), 2.29 (2H, q, J = 7.4 Hz), 1.83-1.74 (1H, m), 0.94 (3H, t, J = 7.4 Hz), 0.80 (6H, d, J = 6.7 Hz). |
| 233 | ¹H-NMR (CDCl3) δ: 7.67 (1H, s), 6.63-6.59 (2H, m), 3.89 (3H, s), 3.37 (2H, d, J = 7.6 Hz), 2.29 (2H, q, J = 7.4 Hz), 1.83-1.74 (1H, m), 0.94 (3H, t, J = 7.4 Hz), 0.80 (6H, d, J = 6.7 Hz). |
| 234 | ¹H-NMR (CDCl3) δ: 7.90 (1H, s), 6.92-6.86 (2H, m), 3.67 (2H, t, J = 7.7 Hz), 1.63-1.55 (2H, m), 1.28-1.18 (2H, m), 0.84 (3H, t, J = 7.3 Hz). |
| 235 | ¹H-NMR (CDCl3) δ: 7.84 (1H, s), 7.23-7.22 (1H, m), 7.18-7.12 (5H, m), 6.97-6.92 (2H, m), 2.11 (3H, s). |
| 236 | ¹H-NMR (CDCl3) δ: 7.83 (1H, s), 7.23-7.21 (1H, m), 7.15-7.10 (4H, m), 7.05 (1H, d, J = 8.3 Hz), 6.97-6.91 (2H, m), 2.13 (3H, s). |
| 237 | ¹H-NMR (CDCl3) δ: 7.85 (1H, s), 7.57-7.54 (2H, m), 7.31 (1H, dd, J = 8.3, 1.8 Hz), 7.27-7.24 (2H, m), 7.16-7.15 (2H, m), 7.09-7.08 (1H, m), 2.13 (3H, s). |
| 238 | ¹H-NMR (CDCl3) δ: 7.85 (1H, s), 7.56-7.55 (2H, m), 7.30-7.28 (1H, m), 7.25-7.23 (2H, m), 7.16-7.12 (2H, m), 7.06-7.04 (1H, m), 2.14 (3H, s). |
| 239 | ¹H-NMR (CDCl3) δ: 7.85 (1H, s), 7.27 (1H, dd, J = 8.3, 2.1 Hz), 7.21-7.17 (2H, m), 6.71-6.69 (1H, m), 6.62-6.61 (1H, m), 2.16 (3H, s). |
| 240 | ¹H-NMR (CDCl3) δ: 7.73 (1H, s), 7.27 (1H, dd, J = 8.3, 2.2 Hz), 7.20-7.18 (2H, m), 6.73-6.67 (1H, m), 6.64-6.59 (1H, m), 2.16 (3H, s). |
| 241 | ¹H-NMR (CDCl3) δ: 7.73 (1H, s), 7.28 (1H, dd, J = 8.6, 2.4 Hz), 7.22-7.18 (2H, m), 6.73-6.68 (1H, m), 6.64-6.62 (1H, m), 2.15 (3H, s). |
| 242 | ¹H-NMR (CDCl3) δ: 7.27-7.27 (1H, m), 7.15-7.13 (1H, m), 7.08-7.06 (2H, m), 7.02-7.00 (1H, m), 6.97-6.95 (2H, m), 6.72-6.69 (2H, m), 3.73 (3H, s), 2.13 (3H, d, J = 0.9 Hz), 2.05 (3H, s), 1.91 (3H, s). |
| 243 | ¹H-NMR (CDCl3) δ: 7.88-7.86 (2H, m), 7.29-7.29 (1H, m), 7.18-7.17 (1H, m), 7.13-7.11 (2H, m), 7.08-7.03 (2H, m), 7.01 (1H, dd, J = 7.8, 1.4 Hz), 3.87 (3H, s), 2.14 (3H, d, J = 0.9 Hz), 2.08 (3H, s), 1.88 (3H, s). |
| 244 | ¹H-NMR (CDCl3) δ: 7.48-7.46 (2H, m), 7.30-7.30 (1H, m), 7.23-7.22 (1H, m), 7.17-7.14 (2H, m), 7.10-7.09 (1H, m), 7.07-7.05 (1H, m), 7.00 (1H, dd, J = 7.6, 1.2 Hz), 2.14 (3H, d, J = 0.9 Hz), 2.09 (3H, s), 1.88 (3H, s). |
| 245 | ¹H-NMR (CDCl3) δ: 7.33 (1H, q, J = 1.0 Hz), 6.88-6.81 (2H, m), 3.36 (2H, d, J = 7.6 Hz), 2.11 (3H, d, J = 1.0 Hz), 1.82 (3H, s), 1.79-1.70 (1H, m), 0.78 (6H, d, J = 6.6 Hz). |
| 246 | ¹H-NMR (CDCl3) δ: 7.42 (1H, d, J = 1.0 Hz), 6.78-6.71 (2H, m), 6.64 (1H, d, J = 8.3 Hz), 6.38-6.35 (2H, m), 4.69 (2H, s), 3.79 (3H, s), 3.65 (3H, s), 2.09 (3H, d, J = 1.0 Hz), 1.82 (3H, s). |

TABLE 5-continued

| Compound | ¹H-NMR |
|---|---|
| 247 | ¹H-NMR (CDCl3) δ: 7.85 (1H, s), 7.42 (1H, dd, J = 8.3, 1.8 Hz), 7.36 (1H, t, J = 1.8 Hz), 7.12 (1H, d, J = 8.3 Hz), 6.73-6.68 (1H, m), 6.65-6.60 (1H, m), 2.14 (3H, s). |
| 248 | ¹H-NMR (CDCl3) δ: 7.85 (1H, s), 7.41 (1H, dd, J = 8.3, 2.1 Hz), 7.35 (1H, t, J = 2.1 Hz), 7.12 (1H, d, J = 8.3 Hz), 6.71-6.69 (1H, m), 6.63-6.59 (1H, m), 2.14 (3H, s). |
| 249 | ¹H-NMR (CDCl3) δ: 7.73 (1H, s), 7.41 (1H, dd, J = 8.3, 2.3 Hz), 7.35 (1H, t, J = 2.3 Hz), 7.12 (1H, d, J = 8.3 Hz), 6.73-6.68 (1H, m), 6.64-6.59 (1H, m), 2.14 (3H, s). |
| 250 | ¹H-NMR (CDCl3) δ: 7.73 (1H, s), 7.42 (1H, dd, J = 8.3, 2.3 Hz), 7.36 (1H, t, J = 2.3 Hz), 7.12 (1H, d, J = 8.3 Hz), 6.73-6.68 (1H, m), 6.65-6.60 (1H, m), 2.13 (3H, s). |
| 251 | ¹H-NMR (CDCl3) δ: 8.28 (1H, s), 8.24 (1H, s), 7.36-7.35 (1H, m), 7.21-7.19 (2H, m), 7.13-7.10 (1H, m), 7.08-7.07 (1H, m), 2.16-2.14 (6H, m), 1.90 (3H, s). |
| 252 | ¹H-NMR (CDCl3) δ: 8.52 (1H, s), 8.35 (1H, s), 7.33-7.33 (1H, m), 7.23-7.20 (3H, m), 6.99-6.99 (1H, m), 2.28 (3H, s), 2.16 (3H, d, J = 0.9 Hz), 1.82 (3H, s). |
| 253 | ¹H-NMR (CDCl3) δ: 7.28 (1H, q, J = 1.2 Hz), 7.22-7.17 (3H, m), 7.13-7.11 (1H, m), 7.08-7.04 (1H, m), 7.03-7.00 (2H, m), 2.14 (3H, d, J = 1.2 Hz), 2.08 (3H, s), 1.90 (3H, s). |
| 254 | ¹H-NMR (CDCl3) δ: 7.27-7.27 (1H, m), 7.16-7.14 (1H, m), 7.09-7.07 (2H, m), 7.05-7.01 (3H, m), 6.97-6.93 (2H, m), 2.41 (3H, s), 2.13 (3H, d, J = 0.9 Hz), 2.06 (3H, s), 1.90 (3H, s). |
| 255 | ¹H-NMR (CDCl3) δ: 7.39 (1H, q, J = 1.0 Hz), 6.96-6.89 (2H, m), 4.46 (2H, s), 2.12 (3H, d, J = 1.0 Hz), 1.84 (3H, s). |
| 256 | ¹H-NMR (CDCl3) δ: 7.85 (1H, s), 7.04-7.02 (2H, m), 6.93-6.91 (1H, m), 6.66-6.56 (2H, m), 2.28 (3H, s), 2.13 (3H, s). |
| 257 | ¹H-NMR (CDCl3) δ: 7.85 (1H, s), 7.03-7.01 (2H, m), 6.92-6.90 (1H, m), 6.65-6.55 (2H, m), 2.28 (3H, s), 2.13 (3H, s). |
| 258 | ¹H-NMR (CDCl3) δ: 7.72 (1H, s), 7.03-7.01 (2H, m), 6.93-6.90 (1H, m), 6.66-6.56 (2H, m), 2.28 (3H, s), 2.13 (3H, s). |
| 259 | ¹H-NMR (CDCl3) δ: 7.72 (1H, s), 7.04-7.02 (2H, m), 6.93-6.91 (1H, m), 6.66-6.57 (2H, m), 2.28 (3H, s), 2.12 (3H, s). |
| 260 | ¹H-NMR (CDCl3) δ: 7.46-7.44 (1H, m), 6.86-6.79 (2H, m), 4.82 (2H, s), 3.20 (3H, s), 2.12-2.11 (3H, m), 1.83 (3H, s). |
| 261 | ¹H-NMR (CDCl3) δ: 7.96 (1H, s), 7.25-7.19 (2H, m), 7.13-7.09 (2H, m), 6.62-6.52 (2H, m), 2.15 (3H, d, J = 0.7 Hz), 1.95 (3H, s). |
| 262 | ¹H-NMR (CDCl3) δ: 7.59-7.57 (1H, m), 7.42-7.38 (1H, m), 7.31-7.30 (1H, m), 7.25-7.23 (1H, m), 7.17-7.14 (2H, m), 7.08-7.05 (2H, m), 7.00-6.99 (1H, m), 2.66 (3H, d, J = 1.0 Hz), 2.15 (3H, d, J = 1.0 Hz), 2.08 (3H, d, J = 1.7 Hz), 1.90 (3H, s). |
| 263 | ¹H-NMR (CDCl3) δ: 7.82-7.77 (2H, m), 7.33-7.31 (2H, m), 7.26-7.26 (1H, m), 7.17-7.13 (1H, m), 7.10-7.05 (2H, m), 7.01-6.99 (1H, m), 3.01 (3H, s), 2.15 (3H, d, J = 0.7 Hz), 2.08 (3H, s), 1.88 (3H, s). |
| 264 | ¹H-NMR (CDCl3) δ: 7.85 (1H, s), 7.08 (1H, dd, J = 8.8, 2.9 Hz), 6.69 (1H, d, J = 2.9 Hz), 6.66-6.58 (3H, m), 3.77 (3H, s), 2.13 (3H, s). |
| 265 | ¹H-NMR (CDCl3) δ: 7.70 (1H, s), 7.23-7.20 (2H, m), 7.13-7.11 (2H, m), 6.63-6.52 (2H, m), 2.15 (3H, d, J = 1.0 Hz), 1.95 (3H, s). |
| 266 | ¹H-NMR (CDCl3) δ: 7.81 (1H, s), 7.23-7.09 (4H, m), 6.36-6.28 (2H, m), 3.73 (3H, s), 2.15 (3H, s), 1.95 (3H, s). |
| 267 | ¹H-NMR (CDCl3) δ: 7.52-7.50 (1H, m), 6.89-6.82 (2H, m), 4.31 (2H, d, J = 2.6 Hz), 2.42 (1H, t, J = 2.6 Hz), 2.12 (3H, d, J = 1.0 Hz), 1.83 (3H, s). |
| 268 | ¹H-NMR (CDCl3) δ: 7.35 (1H, q, J = 1.0 Hz), 6.85-6.79 (2H, m), 5.76-5.66 (1H, m), 5.20-5.16 (1H, m), 4.98-4.92 (1H, m), 4.18-4.14 (2H, m), 2.11 (3H, d, J = 1.0 Hz), 1.83 (3H, s). |
| 269 | ¹H-NMR (CDCl3) δ: 7.52 (1H, q, J = 0.7 Hz), 6.87-6.80 (2H, m), 4.58 (2H, s), 2.12 (3H, d, J = 0.7 Hz), 2.02 (3H, s), 1.83 (3H, s). |
| 270 | ¹H-NMR (CDCl3) δ: 7.73 (1H, s), 7.08 (1H, dd, J = 8.8, 2.9 Hz), 6.69 (1H, d, J = 2.9 Hz), 6.67-6.58 (3H, m), 3.77 (3H, s), 2.13 (3H, s). |
| 271 | ¹H-NMR (CDCl3) δ: 8.49 (2H, dd, J = 8.3, 4.9 Hz), 7.30 (1H, d, J = 0.9 Hz), 7.17-7.16 (1H, m), 7.10-7.07 (2H, m), 7.03-7.02 (2H, m), 6.97 1H, d, J = 4.6 Hz), 2.14 (3H, d, J = 0.9 Hz), 2.09 (3H, s), 1.89 (3H, s). |
| 272 | ¹H-NMR (CDCl3) δ: 7.70 (1H, s), 7.25-7.19 (2H, m), 7.12-7.09 (2H, m), 6.59-6.55 (2H, m), 3.28 (3H, s), 2.16 (3H, s), 1.91 (3H, s). |
| 273 | ¹H-NMR (CDCl3) δ: 7.85 (1H, s), 7.19-7.15 (1H, m), 6.94 (1H, dd, J = 8.7, 2.9 Hz), 6.87-6.83 (1H, m), 6.67-6.59 (2H, m), 2.19 (3H, s). |
| 274 | ¹H-NMR (CDCl3) δ: 7.85 (1H, s), 7.20-7.16 (1H, m), 6.94 (1H, dd, J = 8.9, 2.8 Hz), 6.87-6.84 (1H, m), 6.68-6.61 (2H, m), 2.18 (3H, s). |
| 275 | ¹H-NMR (CDCl3) δ: 7.72 (1H, s), 7.19-7.15 (1H, m), 6.94 (1H, dd, J = 8.9, 2.8 Hz), 6.87-6.82 (1H, m), 6.68-6.59 (2H, m), 2.18 (3H, s). |
| 276 | ¹H-NMR (CDCl3) δ: 7.73 (1H, s), 7.20-7.16 (1H, m), 6.94 (1H, dd, J = 8.7, 2.9 Hz), 6.86-6.85 (1H, m), 6.68-6.61 (2H, m), 2.18 (3H, s). |
| 277 | ¹H-NMR (CDCl3) δ: 8.22 (1H, s), 7.23-7.20 (2H, m), 7.11-7.10 (2H, m), 6.63-6.54 (2H, m), 2.82 (3H, s), 2.14 (3H, d, J = 0.7 Hz), 1.93 (3H, s). |

TABLE 5-continued

| Compound | $^1$H-NMR |
|---|---|
| 278 | $^1$H-NMR (CDCl3) δ: 7.47 (1H, d, J = 6.1 Hz), 7.38 (1H, d, J = 1.8 Hz), 7.26-7.24 (2H, m), 7.01 (1H, dd, J = 8.4, 2.6 Hz), 6.64-6.61 (2H, m), 2.13 (3H, s), 1.94 (3H, s). |
| 279 | $^1$H-NMR (CDCl3) δ: 7.85 (1H, s), 7.09 (1H, d, J = 8.6 Hz), 6.81 (1H, dd, J = 8.6, 2.8 Hz), 6.71-6.71 (1H, m), 6.40-6.33 (2H, m), 3.75 (3H, s), 3.71 (3H, s), 2.08 (3H, s). |
| 280 | $^1$H-NMR (CDCl3) δ: 7.90 (1H, s), 7.07 (1H, d, J = 8.8 Hz), 6.81 (1H, dd, J = 8.8, 2.6 Hz), 6.66-6.62 (2H, m), 6.56-6.56 (1H, m), 6.41 (1H, br s), 2.08 (3H, s). |
| 281 | $^1$H-NMR (CDCl3) δ: 7.24 (1H, t, J = 0.9 Hz), 6.87-6.82 (2H, m), 3.33 (2H, d, J = 7.6 Hz), 2.60-2.56 (2H, m), 2.24 (2H, q, J = 7.6 Hz), 1.78-1.72 (1H, m), 1.21 (3H, t, J = 7.6 Hz), 0.92 (3H, t, J = 7.6 Hz), 0.79 (6H, d, J = 6.7 Hz). |
| 282 | $^1$H-NMR (CDCl3) δ: 7.85 (1H, s), 7.10 (1H, d, J = 8.6 Hz), 6.88 (1H, dd, J = 8.6, 2.4 Hz), 6.72-6.72 (1H, m), 6.65-6.61 (2H, m), 4.06-4.03 (1H, m), 3.96-3.92 (1H, m), 3.72-3.71 (2H, m), 3.44 (3H, s), 2.09 (3H, s). |
| 283 | $^1$H-NMR (CDCl3) δ: 7.84 (1H, s), 7.08 (1H, d, J = 8.4 Hz), 6.87 (1H, dd, J = 8.4, 2.6 Hz), 6.73-6.72 (1H, m), 6.40-6.34 (2H, m), 4.06-4.04 (1H, m), 3.96-3.94 (1H, m), 3.75 (3H, s), 3.73-3.70 (2H, m), 3.44 (3H, s), 2.08 (3H, s). |
| 284 | $^1$H-NMR (CDCl3) δ: 7.85 (1H, s), 7.22 (1H, d, J = 8.9 Hz), 6.96 (1H, dd, J = 8.6, 2.8 Hz), 6.85-6.84 (1H, m), 6.71-6.68 (1H, m), 6.63-6.61 (1H, m), 4.73 (2H, d, J = 5.2 Hz), 2.14 (3H, s). |
| 285 | $^1$H-NMR (CDCl3) δ: 7.87 (1H, s), 7.12 (1H, d, J = 8.6 Hz), 6.94 (1H, dd, J = 8.4, 2.6 Hz), 6.88-6.88 (1H, m), 6.67-6.57 (2H, m), 5.09 (1H, d, J = 7.0 Hz), 5.02 (1H, d, J = 7.0 Hz), 3.41 (3H, s), 2.11 (3H, s). |
| 286 | $^1$H-NMR (CDCl3) δ: 7.86 (1H, s), 7.10 (1H, d, J = 8.3 Hz), 6.93-6.90 (2H, m), 6.40-6.33 (2H, m), 5.08 (1H, d, J = 7.0 Hz), 5.04 (1H, d, J = 7.0 Hz), 3.75 (3H, s), 3.41 (3H, s), 2.10 (3H, s). |
| 287 | $^1$H-NMR (CDCl3) δ: 7.28-7.26 (1H, m), 7.25-7.22 (2H, m), 7.19-7.14 (3H, m), 7.09 (1H, d, J = 8.0 Hz), 6.08 (1H, dd, J = 1.8, 0.9 Hz), 2.11 (3H, d, J = 0.9 Hz), 2.05 (3H, s), 2.03 (3H, s). |
| 288 | $^1$H-NMR (CDCl3) δ: 7.82 (1H, s), 7.27-7.25 (1H, m), 7.06-7.04 (1H, m), 6.90-6.88 (1H, m), 6.69-6.67 (1H, m), 6.55-6.53 (1H, m), 2.25 (3H, d, J= 1.5 Hz). |
| 289 | $^1$H-NMR (CDCl3) δ: 7.82 (1H, s), 7.29-7.25 (1H, m), 7.07-7.05 (1H, m), 6.91-6.88 (1H, m), 6.70-6.68 (1H, m), 6.57-6.52 (1H, m), 2.25 (3H, d, J = 1.5 Hz). |
| 290 | $^1$H-NMR (CDCl3) δ: 7.70 (1H, s), 7.29-7.24 (1H, m), 7.07-7.04 (1H, m), 6.90-6.88 (1H, m), 6.71-6.66 (1H, m), 6.55-6.53 (1H, m), 2.24 (3H, d, J = 1.7 Hz). |
| 291 | $^1$H-NMR (CDCl3) δ: 7.71 (1H, s), 7.28-7.27 (1H, m), 7.06-7.05 (1H, m), 6.91-6.88 (1H, m), 6.70-6.68 (1H, m), 6.57-6.53 (1H, m), 2.25 (3H, d, J = 1.5 Hz). |
| 292 | $^1$H-NMR (CDCl3) δ: 7.85 (1H, s), 7.10-7.09 (1H, m), 6.93-6.90 (2H, m), 6.38-6.30 (2H, m), 5.13-5.08 (2H, m), 3.68-3.65 (2H, m), 2.09 (3H, s), 1.21-1.19 (3H, m). |
| 293 | $^1$H-NMR (CDCl3) δ: 7.82 (1H, s), 7.47 (1H, s), 7.06 (1H, d, J = 8.6 Hz), 6.84 (1H, dd, J = 8.4, 2.6 Hz), 6.64 (2H, dt, J = 24.2, 8.7 Hz), 6.58-6.58 (1H, m), 2.08 (3H, s). |
| 294 | $^1$H-NMR (CDCl3) δ: 7.73 (1H, s), 7.10 (1H, d, J = 8.6 Hz), 6.82 (1H, dd, J = 8.6, 2.8 Hz), 6.72-6.71 (1H, m), 6.41-6.34 (2H, m), 3.76 (3H, s), 3.72 (3H, s), 2.09 (3H, s). |
| 295 | $^1$H-NMR (CDCl3) δ: 7.73 (1H, s), 7.10 (1H, d, J = 8.5 Hz), 6.88 (1H, dd, J = 8.5, 2.7 Hz), 6.72-6.72 (1H, m), 6.68-6.59 (2H, m), 4.06-4.03 (1H, m), 3.97-3.92 (1H, m), 3.72-3.71 (2H, m), 3.44 (3H, s), 2.08 (3H, s). |
| 296 | $^1$H-NMR (CDCl3) δ: 7.72 (1H, s), 7.09 (1H, d, J = 8.6 Hz), 6.87 (1H, dd, J = 8.6, 2.8 Hz), 6.73 (1H, t, J = 2.8 Hz), 6.40-6.34 (2H, m), 4.06-4.04 (1H, m), 3.97-3.93 (1H, m), 3.75 (3H, s), 3.72-3.71 (2H, m), 3.44 (3H, s), 2.08 (3H, s). |
| 297 | $^1$H-NMR (CDCl3) δ: 7.73 (1H, s), 7.23 (1H, d, J = 8.6 Hz), 6.96 (1H, dd, J = 8.6, 2.8 Hz), 6.85-6.85 (1H, m), 6.71-6.69 (1H, m), 6.65-6.61 (1H, m), 4.75-4.71 (2H, m), 2.14 (3H, s). |
| 298 | $^1$H-NMR (CDCl3) δ: 7.75 (1H, s), 7.12 (1H, d, J = 8.4 Hz), 6.94 (1H, dd, J = 8.4, 2.6 Hz), 6.88 (1H, t, J = 2.6 Hz), 6.68-6.58 (2H, m), 5.09 (1H, d, J = 6.8 Hz), 5.02 (1H, d, J = 6.8 Hz), 3.41 (3H, s), 2.11 (3H, s). |
| 299 | $^1$H-NMR (CDCl3) δ: 7.74 (1H, s), 7.11 (1H, d, J = 8.3 Hz), 6.92 (2H, q, J = 10.1 Hz), 6.41-6.33 (2H, m), 5.08 (1H, d, J = 7.0 Hz), 5.04 (1H, d, J = 7.0 Hz), 3.75 (3H, s), 3.41 (3H, s), 2.10 (3H, s). |
| 300 | $^1$H-NMR (CDCl3) δ: 7.31-7.31 (1H, m), 7.21-7.18 (2H, m), 7.12-7.04 (2H, m), 6.58-6.53 (2H, m), 2.39-2.25 (2H, m), 2.14-2.13 (6H, m), 1.00 (3H, t, J = 7.4 Hz). |
| 301 | $^1$H-NMR (CDCl3) δ: 7.82 (1H, s), 7.17-7.15 (1H, m), 7.03-7.02 (2H, m), 6.61-6.58 (2H, m), 2.13 (3H, s), 2.12 (3H, s). |
| 302 | $^1$H-NMR (CDCl3) δ: 7.82 (1H, s), 7.17 (1H, t, J = 7.6 Hz), 7.04-7.03 (2H, m), 6.63-6.57 (2H, m), 2.12 (3H, s), 2.12 (3H, s). |

TABLE 5-continued

| Compound | ¹H-NMR |
|---|---|
| 303 | ¹H-NMR (CDCl3) δ: 7.75 (1H, s), 7.12 (1H, d, J = 8.5 Hz), 6.95 (1H, dd, J = 8.5, 2.4 Hz), 6.89 (1H, t, J = 2.4 Hz), 6.67-6.57 (2H, m), 5.13 (1H, d, J = 7.1 Hz), 5.08 (1H, d, J = 7.1 Hz), 3.66 (2H, q, J = 7.1 Hz), 2.10 (3H, s), 1.20 (3H, t, J = 7.1 Hz). |
| 304 | ¹H-NMR (CDCl3) δ: 7.73 (1H, s), 7.10 (1H, d, J = 8.3 Hz), 6.92 (2H, q, J = 10.0 Hz), 6.38-6.35 (2H, m), 5.12 (1H, d, J = 7.1 Hz), 5.09 (1H, d, J = 7.1 Hz), 3.75 (3H, s), 3.67 (2H, q, J = 7.1 Hz), 2.09 (3H, s), 1.20 (3H, t, J = 7.1 Hz). |
| 305 | ¹H-NMR (CDCl3) δ: 7.70 (1H, s), 7.17 (1H, t, J = 7.6 Hz), 7.04 (2H, d, J = 7.6 Hz), 6.63-6.58 (2H, m), 2.13 (3H, s), 2.12 (3H, s). |
| 306 | ¹H-NMR (CDCl3) δ: 7.70 (1H, s), 7.17 (1H, t, J = 7.6 Hz), 7.04-7.03 (2H, m), 6.62-6.58 (2H, m), 2.12 (3H, s), 2.12 (3H, s). |
| 307 | ¹H-NMR (CDCl3) δ: 7.78 (1H, s), 7.27-7.16 (3H, m), 6.68-6.66 (1H, m), 6.56-6.53 (1H, m), 2.23 (3H, d, J = 2.2 Hz). |
| 308 | ¹H-NMR (CDCl3) δ: 7.79 (1H, s), 7.27-7.16 (3H, m), 6.69-6.63 (1H, m), 6.57-6.51 (1H, m), 2.22 (3H, d, J = 2.4 Hz). |
| 309 | ¹H-NMR (CDCl3) δ: 7.87 (1H, s), 7.55 (1H, dd, J = 8.0, 1.5 Hz), 7.47 (1H, br s), 7.40 (1H, d, J = 8.0 Hz), 6.69-6.64 (1H, m), 6.62-6.58 (1H, m), 2.27 (3H, s). |
| 310 | ¹H-NMR (CDCl3) δ: 7.87 (1H, s), 7.55 (1H, dd, J = 8.0, 1.4 Hz), 7.46 (1H, br s), 7.40 (1H, d, J= 8.0 Hz), 6.68-6.64 (1H, m), 6.61-6.56 (1H, m), 2.28 (3H, s). |
| 311 | ¹H-NMR (CDCl3) δ: 7.30-7.30 (1H, m), 7.17-7.17 (2H, m), 7.13-7.12 (1H, m), 7.08-7.05 (1H, m), 6.34 (1H, dq, J = 10.5, 1.3 Hz), 6.27 (1H, dq, J = 10.8, 1.3 Hz), 3.72 (3H, s), 2.40-2.37 (1H, m), 2.31-2.27 (1H, m), 2.13-2.13 (6H, m), 1.00 (3H, t, J = 7.5 Hz). |
| 312 | ¹H-NMR (CDCl3) δ: 7.94 (1H, s), 7.23-7.20 (2H, m), 7.14-7.07 (2H, m), 6.63-6.52 (2H, m), 2.36-2.31 (2H, m), 2.17 (3H, s), 1.01 (3H, t, J = 7.5 Hz). |
| 313 | ¹H-NMR (CDCl3) δ: 7.33-7.33 (1H, m), 7.06 (1H, d, J = 8.5 Hz), 6.77 (1H, dd, J = 8.5, 2.7 Hz), 6.66-6.66 (1H, m), 6.64-6.53 (2H, m), 3.70 (3H, s), 2.14 (3H, d, J = 1.0 Hz), 2.04 (3H, d, J = 0.7 Hz), 1.90 (3H, s). |
| 314 | ¹H-NMR (CDCl3) δ: 9.42 (1H, s), 7.39-7.39 (1H, m), 6.99 (1H, d, J = 8.5 Hz), 6.80 (1H, dd, J = 8.4, 2.6 Hz), 6.61-6.52 (2H, m), 6.17-6.16 (1H, m), 2.11 (3H, d, J = 1.0 Hz), 2.00 (3H, s), 1.91 (3H, s). |
| 315 | ¹H-NMR (CDCl3) δ: 7.31-7.31 (1H, m), 7.05 (1H, d, J = 8.6 Hz), 6.81 (1H, dd, J = 8.4, 2.6 Hz), 6.68-6.68 (1H, m), 6.62-6.54 (2H, m), 4.04-4.02 (1H, m), 3.94-3.90 (1H, m), 3.71-3.70 (2H, m), 3.44 (3H, s), 2.13 (3H, d, J = 1.2 Hz), 2.03 (3H, s), 1.90 (3H, s). |
| 316 | ¹H-NMR (CDCl3) δ: 7.30-7.30 (1H, m), 7.04 (1H, d, J = 8.6 Hz), 6.80 (1H, dd, J = 8.6, 2.4 Hz), 6.69-6.69 (1H, m), 6.36-6.29 (2H, m), 4.03 (1H, ddd, J = 10.3, 5.4, 3.4 Hz), 3.95-3.91 (1H, m), 3.73 (3H, s), 3.72-3.69 (2H, m), 3.44 (3H, s), 2.13 (3H, d, J = 0.9 Hz), 2.03 (3H, s), 1.90 (3H, s). |
| 317 | ¹H-NMR (CDCl3) δ: 7.23 (1H, t, J = 1.0 Hz), 7.21-7.18 (2H, m), 7.13-7.05 (2H, m), 6.59 (1H, tt, J = 8.8, 2.2 Hz), 6.52 (1H, tt, J = 8.8, 2.2 Hz), 2.66-2.59 (2H, m), 2.39-2.23 (2H, m), 2.14 (3H, d, J = 1.0 Hz), 1.20 (3H, t, J = 7.6 Hz), 1.00 (3H, t, J = 7.4 Hz). |
| 318 | ¹H-NMR (CDCl3) δ: 7.67 (1H, s), 7.27-7.16 (3H, m), 6.67-6.65 (1H, m), 6.57-6.52 (1H, m), 2.22 (3H, d, J = 2.4 Hz). |
| 319 | ¹H-NMR (CDCl3) δ: 7.67 (1H, s), 7.27-7.17 (3H, m), 6.68-6.66 (1H, m), 6.57-6.53 (1H, m), 2.23 (3H, d, J = 2.4 Hz). |
| 320 | ¹H-NMR (CDCl3) δ: 7.94 (1H, dd, J = 8.3, 1.2 Hz), 7.85 (1H, s), 7.51-7.49 (1H, m), 7.40-7.36 (1H, m), 6.69-6.64 (2H, m), 2.35 (3H, d, J = 1.8 Hz). |
| 321 | ¹H-NMR (CDCl3) δ: 7.93 (1H, dd, J = 8.2, 1.1 Hz), 7.85 (1H, s), 7.51-7.48 (1H, m), 7.39-7.35 (1H, m), 6.68-6.63 (2H, m), 2.35 (3H, d, J = 1.7 Hz). |
| 322 | ¹H-NMR (CDCl3) δ: 7.84 (1H, s), 7.43-7.38 (1H, m), 7.14-7.09 (2H, m), 6.67-6.61 (2H, m), 2.19 (3H, d, J = 2.2 Hz). |
| 323 | ¹H-NMR (CDCl3) δ: 7.84 (1H, s), 7.41-7.38 (1H, m), 7.14-7.08 (2H, m), 6.66-6.60 (2H, m), 2.20 (3H, d, J = 2.2 Hz). |
| 324 | ¹H-NMR (CDCl3) δ: 8.17 (1H, dd, J = 8.4, 2.3 Hz), 8.11 (1H, t, J = 2.3 Hz), 7.85 (1H, s), 7.47 (1H, d, J = 8.4 Hz), 6.71-6.67 (1H, m), 6.65-6.60 (1H, m), 2.33 (3H, s). |
| 325 | ¹H-NMR (CDCl3) δ: 8.16 (1H, dd, J = 8.5, 2.3 Hz), 8.10 (1H, t, J = 2.3 Hz), 7.85 (1H, s), 7.47 (1H, d, J = 8.5 Hz), 6.71-6.66 (1H, m), 6.64-6.58 (1H, m), 2.33 (3H, s). |
| 326 | ¹H-NMR (CDCl3) δ: 7.34 (1H, d, J = 1.0 Hz), 7.29-7.22 (2H, m), 7.14-7.06 (2H, m), 6.59-6.50 (2H, m), 2.41 (2H, q, J = 7.6 Hz), 2.14 (3H, d, J = 1.0 Hz), 1.90 (3H, s), 1.16 (3H, t, J = 7.6 Hz). |
| 327 | ¹H-NMR (CDCl3) δ: 8.20 (1H, s), 7.25-7.19 (2H, m), 7.11-7.09 (2H, m), 6.64-6.53 (2H, m), 2.82 (3H, s), 2.40-2.38 (1H, m), 2.31-2.28 (1H, m), 2.15 (3H, s), 1.02 (3H, t, J = 7.5 Hz). |
| 328 | ¹H-NMR (CDCl3) δ: 7.28-7.25 (2H, m), 7.21-7.19 (2H, m), 7.13-7.06 (2H, m), 6.58-6.54 (2H, m), 2.65-2.59 (2H, m), 2.13 (3H, d, J = 1.0 Hz), 1.90 (3H, s), 1.21 (3H, t, J = 7.4 Hz). |

TABLE 5-continued

| Compound | ¹H-NMR |
|---|---|
| 329 | ¹H-NMR (CDCl3) δ: 7.83 (1H, s), 7.24 (1H, m), 7.15-7.11 (2H, m), 6.69-6.61 (2H, m), 2.17 (3H, s). |
| 330 | ¹H-NMR (CDCl3) δ: 7.83 (1H, s), 7.24 (1H, m), 7.14-7.10 (2H, m), 6.66-6.62 (2H, m), 2.18 (3H, s). |
| 331 | ¹H-NMR (CDCl3) δ: 7.71 (1H, s), 7.24 (1H, m), 7.13-7.11 (2H, m), 6.68-6.60 (2H, m), 2.18 (3H, s). |
| 332 | ¹H-NMR (CDCl3) δ: 7.71 (1H, s), 7.25-7.24 (1H, m), 7.15-7.11 (2H, m), 6.69-6.62 (2H, m), 2.17 (3H, s). |
| 333 | ¹H-NMR (CDCl3) δ: 7.86 (1H, s), 6.93 (1H, t, J = 7.9 Hz), 6.65-6.56 (4H, m), 3.77 (2H, s), 1.91 (3H, d, J = 2.2 Hz). |
| 334 | ¹H-NMR (CDCl3) δ: 7.86 (1H, s), 7.03 (1H, t, J = 8.0 Hz), 6.64-6.52 (4H, m), 3.74 (1H, br s), 2.87 (3H, s), 1.87 (3H, d, J = 2.4 Hz). |
| 335 | ¹H-NMR (CDCl3) δ: 7.89 (1H, s), 7.07 (1H, dd, J = 8.1, 7.9 Hz), 7.00 (1H, dd, J = 8.1, 1.1 Hz), 6.85 (1H, ddd, J = 7.9, 3.1, 1.1 Hz), 6.63-6.56 (2H, m), 2.63 (6H, s), 2.08 (3H, s). |
| 336 | ¹H-NMR (CDCl3) δ: 7.82 (1H, s), 7.60 (1H, dd, J = 8.0, 1.8 Hz), 7.53-7.52 (1H, m), 7.41-7.40 (1H, m), 6.74-6.70 (1H, m), 6.66-6.62 (1H, m), 2.28 (3H, s). |
| 337 | ¹H-NMR (CDCl3) δ: 7.82-7.82 (1H, m), 7.59 (1H, dd, J = 8.0, 1.7 Hz), 7.52-7.51 (1H, m), 7.41-7.39 (1H, m), 6.74-6.69 (1H, m), 6.64-6.60 (1H, m), 2.29 (3H, s). |
| 338 | ¹H-NMR (CDCl3) δ: 7.33 (1H, d, J = 1.0 Hz), 7.25-7.21 (2H, m), 7.16-7.13 (1H, m), 7.10-7.06 (1H, m), 6.33-6.26 (2H, m), 3.71 (3H, s), 2.41 (2H, q, J = 7.6 Hz), 2.13 (3H, s), 1.91 (3H, s), 1.16 (3H, t, J = 7.6 Hz). |
| 339 | ¹H-NMR (CDCl3) δ: 7.78 (1H, s), 7.37-7.34 (1H, m), 7.31-7.28 (1H, m), 7.19-7.14 (2H, m), 6.64-6.57 (2H, m), 2.45 (2H, q, J = 7.6 Hz), 1.21 (3H, t, J = 7.6 Hz). |
| 340 | ¹H-NMR (CDCl3) δ: 7.51 (1H, s), 7.23-7.19 (2H, m), 7.15-7.09 (2H, m), 6.85-6.77 (1H, m), 6.62-6.51 (2H, m), 6.14 (1H, dd, J = 17.6, 1.8 Hz), 5.34 (1H, dd, J = 11.4, 1.8 Hz), 2.15 (3H, d, J = 1.0 Hz), 1.92 (3H, s). |
| 341 | ¹H-NMR (CDCl3) δ: 7.87 (1H, s), 7.27-7.25 (1H, m), 7.22-7.21 (1H, m), 7.15-7.10 (2H, m), 6.61-6.57 (2H, m), 3.43-3.39 (1H, m), 3.28-3.23 (1H, m), 2.17 (3H, s). |
| 342 | ¹H-NMR (CDCl3) δ: 7.74 (1H, s), 7.15-7.13 (3H, m), 7.00 (2H, d, J = 7.3 Hz), 6.94-6.93 (2H, m), 2.12 (6H, s). |
| 343 | ¹H-NMR (CDCl3) δ: 7.74 (1H, s), 7.15-7.10 (3H, m), 6.99-6.98 (2H, m), 6.96-6.90 (2H, m), 2.13 (6H, s). |
| 344 | ¹H-NMR (CDCl3) δ: 7.61 (1H, s), 7.15-7.11 (3H, m), 6.97-6.93 (4H, m), 2.13 (6H, s). |
| 345 | ¹H-NMR (CDCl3) δ: 7.61 (1H, s), 7.15-7.13 (3H, m), 7.01-6.91 (4H, m), 2.12 (6H, s). |
| 346 | ¹H-NMR (CDCl3) δ: 7.84 (1H, s), 7.59 (1H, dd, J = 8.1, 1.1 Hz), 7.18-7.16 (1H, m), 7.06-7.02 (1H, m), 6.66-6.62 (2H, m), 2.22 (3H, d, J = 1.8 Hz). |
| 347 | ¹H-NMR (CDCl3) δ: 7.84 (1H, s), 7.59 (1H, dd, J = 8.1, 1.1 Hz), 7.17-7.15 (1H, m), 7.03 (1H, t, J = 8.1 Hz), 6.65-6.61 (2H, m), 2.23 (3H, d, J = 2.1 Hz). |
| 348 | ¹H-NMR (CDCl3) δ: 7.86 (1H, s), 6.96 (1H, d, J = 8.3 Hz), 6.68-6.60 (2H, m), 6.57 (1H, dd, J = 8.3, 2.4 Hz), 6.46-6.45 (1H, m), 3.69 (2H, br s), 2.02 (3H, s). |
| 349 | ¹H-NMR (CDCl3) δ: 7.76 (1H, s), 7.36-7.32 (1H, m), 7.30-7.28 (1H, m), 7.18-7.13 (2H, m), 6.63-6.55 (2H, m), 2.46 (2H, q, J = 7.6 Hz), 1.21 (3H, t, J = 7.6 Hz). |
| 350 | ¹H-NMR (CDCl3) δ: 7.88 (1H, s), 7.36-7.30 (2H, m), 7.19-7.13 (2H, m), 6.63-6.55 (2H, m), 2.45 (2H, q, J = 7.6 Hz), 1.21 (3H, t, J = 7.6 Hz). |
| 351 | ¹H-NMR (CDCl3) δ: 7.39 (1H, t, J = 1.0 Hz), 7.28-7.21 (3H, m), 7.07-7.00 (2H, m), 6.82 (1H, tt, J = 8.4, 1.0 Hz), 6.76 (1H, tt, J = 8.4, 1.0 Hz), 2.14 (3H, d, J = 1.0 Hz), 1.92 (3H, s). |
| 352 | ¹H-NMR (CDCl3) δ: 7.89 (1H, s), 7.36-7.32 (1H, m), 7.30-7.28 (1H, m), 7.18-7.13 (2H, m), 6.63-6.55 (2H, m), 2.46 (2H, q, J = 7.6 Hz), 1.21 (3H, t, J = 7.6 Hz). |
| 353 | ¹H-NMR (CDCl3) δ: 7.33 (1H, d, J = 1.0 Hz), 7.30 (1H, d, J = 1.0 Hz), 7.25-7.11 (6H, m), 7.10-7.06 (3H, m), 7.04-6.96 (5H, m), 6.94-6.88 (2H, m), 2.15-2.14 (6H, m), 2.11-2.11 (6H, m), 1.91-1.90 (3H, m), 1.88 (3H, s). |
| 354 | ¹H-NMR (CDCl3) δ: 7.31-7.29 (2.5H, m), 7.24-7.24 (1.5H, m), 7.19-7.13 (5.5H, m), 7.06 (1H, td, J = 7.5, 1.2 Hz), 7.03-6.97 (3H, m), 2.22 (1.5H, s), 2.17 (3H, s), 2.15 (4.5H, dd, J = 1.8, 0.9 Hz), 1.86 (1.5H, s), 1.84 (3H, s). |
| 355 | ¹H-NMR (CDCl3) δ: 7.36 (1H, q, J = 1.0 Hz), 7.21 (2H, tt, J = 9.9, 3.6 Hz), 7.13-7.07 (2H, m), 6.61-6.52 (2H, m), 3.40-3.33 (1H, m), 3.27-3.23 (1H, m), 2.15 (3H, d, J = 1.0 Hz), 2.14 (3H, s). |
| 356 | ¹H-NMR (CDCl3) δ: 7.85 (1H, s), 7.23-7.21 (2H, m), 7.17-7.15 (1H, m), 7.12-7.10 (1H, m), 6.36-6.29 (2H, m), 3.73 (3H, s), 3.46-3.39 (1H, m), 3.27-3.23 (1H, m), 2.16 (3H, s). |

TABLE 5-continued

| Compound | ¹H-NMR |
|---|---|
| 357 | ¹H-NMR (CDCl3) δ: 7.78 (1H, s), 7.23-7.19 (3H, m), 7.15 (1H, dd, J = 10.4, 4.6 Hz), 7.08-7.07 (3H, m), 7.04-7.02 (2H, m), 2.11 (3H, s), 1.94 (3H, s). |
| 358 | ¹H-NMR (CDCl3) δ: 7.76 (1H, s), 7.29-7.20 (2H, m), 7.17-7.13 (1H, m), 7.00-6.88 (4H, m), 2.17 (3H, s). |
| 359 | ¹H-NMR (CDCl3) δ: 7.76 (1H, s), 7.28-7.19 (2H, m), 7.15-7.11 (1H, m), 7.00-6.93 (3H, m), 6.91-6.88 (1H, m), 2.17 (3H, s). |
| 360 | ¹H-NMR (CDCl3) δ: 7.47 (1H, d, J = 1.0 Hz), 7.27-7.16 (6H, m), 6.80-6.75 (2H, m), 2.14 (3H, d, J = 1.0 Hz), 1.91 (3H, s). |
| 361 | ¹H-NMR (CDCl3) δ: 7.93 (1H, d, J = 0.7 Hz), 7.39-7.28 (3H, m), 7.15-7.06 (2H, m), 6.89-6.85 (1H, m), 6.82-6.78 (1H, m). |
| 362 | ¹H-NMR (CDCl3) δ: 8.00 (1H, s), 7.37-7.29 (4H, m), 7.23-7.22 (2H, m), 6.84-6.80 (2H, m). |
| 363 | ¹H-NMR (CDCl3) δ: 8.00 (1H, s), 7.36-7.28 (4H, m), 7.23-7.22 (2H, m), 6.83-6.80 (2H, m). |
| 364 | ¹H-NMR (CDCl3) δ: 7.86 (1H, s), 7.69 (1H, d, J = 8.0 Hz), 7.42-7.39 (1H, m), 7.30 (1H, t, J = 8.0 Hz), 6.65-6.60 (2H, m), 2.29 (3H, s). |
| 365 | ¹H-NMR (CDCl3) δ: 7.86 (1H, s), 7.69 (1H, d, J = 8.0 Hz), 7.42-7.39 (1H, m), 7.30 (1H, t, J = 8.0 Hz), 6.65-6.60 (2H, m), 2.29 (3H, s). |
| 366 | ¹H-NMR (CDCl3) δ: 7.85 (1H, s), 7.11-7.07 (1H, m), 6.82 (1H, d, J = 8.3 Hz), 6.78-6.76 (1H, m), 6.64-6.57 (2H, m), 3.82 (3H, s), 1.99 (3H, d, J = 1.8 Hz). |
| 367 | ¹H-NMR (CDCl3) δ: 7.85 (1H, s), 7.11-7.06 (1H, m), 6.81 (1H, d, J = 8.1 Hz), 6.78-6.75 (1H, m), 6.64-6.55 (2H, m), 3.82 (3H, s), 2.00 (3H, d, J = 2.2 Hz). |
| 368 | ¹H-NMR (CDCl3) δ: 7.64 (1H, s), 7.28-7.19 (2H, m), 7.14-7.13 (1H, m), 7.00-6.93 (3H, m), 6.90-6.89 (1H, m), 2.17 (3H, s). |
| 369 | ¹H-NMR (CDCl3) δ: 7.63 (1H, s), 7.26-7.22 (1H, m), 7.15-7.14 (1H, m), 7.01-6.88 (4H, m), 2.16 (3H, s). |
| 370 | ¹H-NMR (CDCl3) δ: 7.77 (1H, d, J = 2.2 Hz), 7.57 (1H, dd, J = 8.5, 2.2 Hz), 7.34-7.22 (4H, m), 6.87-6.79 (2H, m), 2.12 (3H, d, J = 1.0 Hz), 1.87 (3H, s). |
| 371 | ¹H-NMR (CDCl3) δ: 7.91 (1H, d, J = 1.0 Hz), 7.71-7.69 (1H, m), 7.56-7.52 (2H, m), 7.46-7.43 (1H, m), 7.37-7.29 (1H, m), 6.88-6.80 (2H, m). |
| 372 | ¹H-NMR (CDCl3) δ: 7.91 (1H, d, J = 0.7 Hz), 7.71-7.69 (1H, m), 7.55-7.52 (2H, m), 7.45-7.43 (1H, m), 7.36-7.29 (1H, m), 6.88-6.79 (2H, m). |
| 373 | ¹H-NMR (CDCl3) δ: 7.89 (1H, s), 7.02 (1H, d, J = 8.9 Hz), 6.65-6.58 (3H, m), 6.43 (1H, t, J = 2.6 Hz), 2.86 (6H, s), 2.04 (3H, s). |
| 374 | ¹H-NMR (CDCl3) δ: 7.88 (1H, s), 6.96 (1H, d, J = 8.3 Hz), 6.66-6.59 (2H, m), 6.50 (1H, dd, J = 8.3, 2.6 Hz), 6.34 (1H, t, J = 2.6 Hz), 3.76 (1H, s), 2.74 (3H, d, J = 3.4 Hz), 2.02 (3H, s). |
| 375 | ¹H-NMR (CDCl3) δ: 7.68 (1H, s), 7.22-7.20 (2H, m), 7.12-7.09 (2H, m), 6.61-6.54 (2H, m), 2.38-2.32 (2H, m), 2.17 (3H, d, J = 1.0 Hz), 1.02 (3H, t, J = 7.4 Hz). |
| 376 | ¹H-NMR (CDCl3) δ: 7.81 (1H, s), 7.24-7.19 (2H, m), 7.13-7.09 (2H, m), 6.60-6.54 (2H, m), 2.36-2.33 (1H, m), 2.27-2.21 (1H, m), 2.16 (3H, s), 1.46-1.44 (2H, m), 0.80 (3H, t, J = 7.5 Hz). |
| 377 | ¹H-NMR (CDCl3) δ: 7.86 (1H, s), 7.84 (1H, s), 7.31-7.27 (2H, m), 7.24-7.15 (4H, m), 7.14-7.02 (8H, m), 6.98-6.94 (2H, m), 2.18 (3H, s), 2.15 (3H, s). |
| 378 | ¹H-NMR (CDCl3) δ: 7.83 (1H, s), 7.24 (3H, dd, J = 4.8, 3.3 Hz), 7.21-7.17 (1H, m), 7.12 (4H, dt, J = 11.4, 3.7 Hz), 7.06-7.05 (1H, m), 2.13 (3H, s). |
| 379 | ¹H-NMR (CDCl3) δ: 7.71 (1H, s), 7.36-7.32 (1H, m), 7.27-7.17 (3H, m), 7.07-7.06 (1H, m), 6.99-6.92 (2H, m), 2.15 (3H, s). |
| 380 | ¹H-NMR (CDCl3) δ: 7.71 (1H, s), 7.36-7.34 (1H, m), 7.23-7.18 (3H, m), 7.07-7.05 (1H, m), 6.98-6.91 (2H, m), 2.17 (3H, s). |
| 381 | ¹H-NMR (CDCl3) δ: 7.58 (1H, s), 7.36-7.34 (1H, m), 7.25-7.17 (3H, m), 7.07-7.05 (1H, m), 6.99-6.92 (2H, m), 2.16 (3H, s). |
| 382 | ¹H-NMR (CDCl3) δ: 7.59 (1H, s), 7.36-7.32 (1H, m), 7.27-7.18 (3H, m), 7.08-7.06 (1H, m), 7.00-6.92 (2H, m), 2.15 (3H, s). |
| 383 | ¹H-NMR (CDCl3) δ: 7.35 (1H, d, J = 0.9 Hz), 7.29-7.22 (1H, m), 7.04 (1H, d, J = 8.5 Hz), 6.85-6.82 (1H, m), 6.79-6.76 (1H, m), 6.73 (1H, dd, J = 8.5, 2.6 Hz), 6.69 (1H, t, J = 2.6 Hz), 3.68 (3H, s), 2.15 (3H, d, J = 0.9 Hz), 2.06 (3H, s), 1.90 (3H, s). |
| 384 | ¹H-NMR (CDCl3) δ: 7.84 (1H, s), 7.39-7.34 (2H, m), 6.90-6.83 (2H, m), 6.71 (1H, d, J = 2.2 Hz), 3.78 (3H, s), 2.12 (3H, s). |
| 385 | ¹H-NMR (CDCl3) δ: 7.87 (1H, s), 7.35-7.28 (1H, m), 7.08 (1H, d, J = 8.5 Hz), 6.89-6.77 (3H, m), 6.71 (1H, t, J = 2.6 Hz), 3.70 (3H, s), 2.12 (3H, s). |
| 386 | ¹H-NMR (CDCl3) δ: 7.72-7.70 (1H, m), 7.51 (1H, d, J = 2.2 Hz), 7.30-7.27 (3H, m), 7.24 (1H, ddd, J = 6.3, 2.5, 1.8 Hz), 7.16-7.13 (1H, m), 7.10-7.09 (1H, m), 7.01 (1H, d, J = 8.3 Hz), 1.92 (3H, s). |
| 387 | ¹H-NMR (CDCl3) δ: 7.76 (1H, s), 7.34-7.33 (1H, m), 7.25-7.16 (5H, m), 7.14-7.12 (2H, m), 7.10-7.09 (1H, m), 1.93 (3H, s). |

TABLE 5-continued

| Compound | ¹H-NMR |
|---|---|
| 388 | ¹H-NMR (CDCl3) δ: 7.81 (1H, s), 7.37 (1H, dd, J = 4.9, 4.0 Hz), 7.28-7.27 (2H, m), 7.25-7.24 (3H, m), 7.20-7.18 (3H, m). |
| 389 | ¹H-NMR (CDCl3) δ: 7.27-7.24 (3H, m), 7.22-7.17 (1H, m), 7.11-7.08 (1H, m), 7.06-7.01 (2H, m), 6.86 (1H, td, J = 8.3, 2.7 Hz), 6.77 (1H, dd, J = 8.5, 2.7 Hz), 2.14 (3H, d, J = 1.0 Hz), 2.05 (3H, s), 1.89 (3H, s). |
| 390 | ¹H-NMR (CDCl3) δ: 7.33-7.32 (1H, m), 7.04 (1H, d, J = 8.0 Hz), 7.01-6.99 (1H, m), 6.92 (1H, br s), 6.62-6.57 (1H, m), 6.56-6.51 (1H, m), 2.21 (3H, s), 2.14 (3H, d, J = 0.9 Hz), 2.07 (3H, s), 1.90 (3H, s). |
| 391 | ¹H-NMR (CDCl3) δ: 7.86 (1H, s), 7.41-7.33 (2H, m), 6.88 (2H, q, J = 9.0 Hz), 6.72 (1H, d, J = 2.4 Hz), 3.78 (3H, s), 2.12 (3H, s). |
| 392 | ¹H-NMR (CDCl3) δ: 7.87 (1H, s), 7.34-7.30 (1H, m), 7.08 (1H, d, J = 8.8 Hz), 6.90-6.78 (3H, m), 6.72 (1H, t, J = 2.6 Hz), 3.70 (3H, s), 2.11 (3H, s). |
| 393 | ¹H-NMR (CDCl3) δ: 7.88 (1H, s), 7.39-7.35 (1H, m), 7.31 (1H, dd, J = 8.0, 1.5 Hz), 7.22-7.20 (1H, m), 7.18-7.14 (1H, m), 6.63-6.58 (2H, m), 2.77-2.72 (1H, m), 1.17-1.14 (6H, m). |
| 394 | ¹H-NMR (CDCl3) δ: 7.88 (1H, s), 7.38-7.34 (1H, m), 7.31 (1H, dd, J = 7.9, 1.6 Hz), 7.21-7.18 (1H, m), 7.17-7.13 (1H, m), 6.62-6.57 (2H, m), 2.79-2.72 (1H, m), 1.18-1.14 (6H, m). |
| 395 | ¹H-NMR (CDCl3) δ: 7.75 (1H, s), 7.39-7.35 (1H, m), 7.31 (1H, dd, J = 7.9, 1.6 Hz), 7.23-7.20 (1H, m), 7.18-7.14 (1H, m), 6.64-6.57 (2H, m), 2.77-2.71 (1H, m), 1.17-1.14 (6H, m). |
| 396 | ¹H-NMR (CDCl3) δ: 7.75 (1H, s), 7.38-7.35 (1H, m), 7.31 (1H, dd, J = 8.0, 1.5 Hz), 7.21-7.19 (1H, m), 7.17-7.14 (1H, m), 6.62-6.58 (2H, m), 2.78-2.73 (1H, m), 1.18-1.15 (6H, m). |
| 397 | ¹H-NMR (CDCl3) δ: 7.34 (1H, d, J = 0.7 Hz), 7.32-7.22 (2H, m), 7.17 (1H, ddd, J = 7.8, 3.5, 1.2 Hz), 7.12-7.08 (1H, m), 6.59-6.52 (2H, m), 2.78-2.71 (1H, m), 2.13 (3H, d, J = 1.0 Hz), 1.91 (3H, s), 1.13-1.10 (6H, m). |
| 398 | ¹H-NMR (CDCl3) δ: 7.76 (1H, s), 7.29-7.28 (1H, m), 7.26-7.20 (2H, m), 7.09-7.07 (2H, m), 7.03-7.02 (1H, m), 6.90 (1H, td, J = 8.3, 2.5 Hz), 6.79 (1H, dd, J = 8.3, 2.5 Hz), 2.08 (3H, s), 1.93 (3H, s). |
| 399 | ¹H-NMR (CDCl3) δ: 7.81 (1H, s), 7.32-7.30 (2H, m), 7.17-7.08 (4H, m), 6.94 (1H, td, J = 8.3, 2.7 Hz), 6.84 (1H, dd, J = 8.3, 2.7 Hz), 2.11 (3H, s). |
| 400 | ¹H-NMR (CDCl3) δ: 7.78 (1H, s), 7.25-7.19 (3H, m), 7.12-7.10 (1H, m), 7.03-7.00 (1H, m), 6.98 (1H, d, J = 8.5 Hz), 6.71 (1H, dd, J = 8.5, 2.7 Hz), 6.54 (1H, d, J = 2.7 Hz), 3.67 (3H, s), 2.03 (3H, s), 1.94 (3H, s). |
| 401 | ¹H-NMR (CDCl3) δ: 7.31 (1H, d, J = 1.0 Hz), 7.04-6.93 (3H, m), 6.36-6.27 (2H, m), 3.73 (3H, s), 2.21 (3H, s), 2.13 (3H, d, J = 1.0 Hz), 2.06 (3H, s), 1.91 (3H, s). |
| 402 | ¹H-NMR (CDCl3) δ: 7.32 (1H, d, J = 0.9 Hz), 7.22 (1H, tt, J = 8.4, 6.4 Hz), 7.02 (1H, d, J = 7.6 Hz), 6.97-6.94 (2H, m), 6.83-6.73 (2H, m), 2.18 (3H, s), 2.14 (3H, d, J = 0.9 Hz), 2.08 (3H, s), 1.91 (3H, s). |
| 403 | ¹H-NMR (CDCl3) δ: 7.43 (1H, d, J = 0.9 Hz), 7.04 (1H, d, J = 8.0 Hz), 7.01 (1H, dd, J = 8.0, 1.5 Hz), 6.94 (1H, br s), 6.51-6.47 (2H, m), 2.23 (3H, s), 2.14 (3H, d, J = 0.9 Hz), 2.04 (3H, s), 1.94 (3H, s). |
| 404 | ¹H-NMR (CDCl3) δ: 7.27-7.27 (1H, m), 7.23-7.16 (3H, m), 7.08-7.05 (1H, m), 7.04-7.02 (1H, m), 6.94 (1H, d, J = 8.0 Hz), 6.91 (1H, dd, J = 8.0, 1.5 Hz), 6.82 (1H, br s), 2.19 (3H, s), 2.14 (3H, d, J = 0.9 Hz), 2.02 (3H, s), 1.90 (3H, s). |
| 405 | ¹H-NMR (CDCl3) δ: 7.30 (1H, d, J = 1.0 Hz), 7.03 (1H, d, J = 7.8 Hz), 6.98 (1H, dd, J = 7.8, 1.5 Hz), 6.94-6.93 (1H, m), 6.35 (1H, ddd, J = 10.7, 2.2, 1.5 Hz), 6.30 (1H, ddd, J = 11.0, 2.4, 1.7 Hz), 6.01-5.91 (1H, m), 5.36 (1H, dq, J = 17.3, 1.5 Hz), 5.30 (1H, dq, J = 10.6, 1.3 Hz), 4.43 (2H, dt, J = 5.4, 1.5 Hz), 2.21 (3H, s), 2.13 (3H, d, J = 1.0 Hz), 2.06 (3H, s), 1.91 (3H, s). |
| 406 | ¹H-NMR (CDCl3) δ: 7.31 (1H, d, J = 1.0 Hz), 7.03 (1H, d, J = 7.8 Hz), 6.97 (1H, dd, J = 7.8, 1.5 Hz), 6.93-6.92 (1H, m), 6.44 (1H, ddd, J = 10.5, 2.2, 1.7 Hz), 6.38 (1H, ddd, J = 10.5, 2.4, 1.7 Hz), 4.60 (2H, d, J = 2.4 Hz), 2.55 (1H, t, J = 2.4 Hz), 2.20 (3H, s), 2.13 (3H, d, J = 1.0 Hz), 2.06 (3H, s), 1.91 (3H, s). |
| 407 | ¹H-NMR (CDCl3) δ: 7.32 (1H, d, J = 0.9 Hz), 7.03 (1H, d, J = 8.0 Hz), 6.98 (1H, dd, J = 8.0, 1.2 Hz), 6.92-6.91 (1H, m), 6.68 (1H, dt, J = 9.5, 2.0 Hz), 6.61 (1H, dt, J = 9.5, 1.8 Hz), 2.25 (3H, s), 2.20 (3H, s), 2.14 (3H, d, J = 0.9 Hz), 2.07 (3H, s), 1.92 (3H, s). |
| 408 | ¹H-NMR (CDCl3) δ: 7.81 (1H, s), 7.21-7.17 (1H, m), 7.13-7.09 (2H, m), 7.06-6.98 (5H, m), 2.26 (3H, s), 2.12 (3H, s). |
| 409 | ¹H-NMR (CDCl3) δ: 7.82 (1H, s), 7.21-7.20 (1H, m), 7.14-7.11 (2H, m), 7.09-6.99 (5H, m), 2.26 (3H, s), 2.11 (3H, s). |
| 410 | ¹H-NMR (CDCl3) δ: 7.69 (1H, s), 7.21-7.18 (1H, m), 7.13-7.10 (2H, m), 7.05-6.98 (5H, m), 2.26 (3H, s), 2.12 (3H, s). |
| 411 | ¹H-NMR (CDCl3) δ: 7.69 (1H, s), 7.22-7.19 (1H, m), 7.13-7.11 (2H, m), 7.06-7.00 (5H, m), 2.26 (3H, s), 2.11 (3H, s). |
| 412 | ¹H-NMR (CDCl3) δ: 7.77 (1H, s), 7.24-7.23 (3H, m), 7.07-7.01 (3H, m), 6.94 (1H, t, J = 8.6 Hz), 6.88 (1H, d, J = 8.6 Hz), 2.02 (3H, d, J = 2.1 Hz), 1.94 (3H, s). |

TABLE 5-continued

| Compound | ¹H-NMR |
|---|---|
| 413 | ¹H-NMR (CDCl3) δ: 7.82 (1H, s), 7.29-7.25 (3H, m), 7.14-7.08 (3H, m), 6.98 (1H, t, J = 8.0 Hz), 6.93 (1H, d, J = 8.0 Hz), 2.04 (3H, d, J = 2.1 Hz). |
| 414 | ¹H-NMR (CDCl3) δ: 7.80 (1H, s), 7.31 (4H, m), 7.26-7.24 (1H, m), 7.06 (1H, dd, J = 5.1, 3.9 Hz), 6.71 (1H, s), 3.79 (3H, s), 2.07 (3H, s). |
| 415 | ¹H-NMR (CDCl3) δ: 7.74 (1H, s), 7.32-7.30 (2H, m), 7.28-7.25 (1H, m), 7.25-7.21 (1H, m), 7.17-7.15 (1H, m), 7.13-7.11 (1H, m), 6.97-6.95 (1H, m), 6.89 (1H, dd, J = 7.8, 2.9 Hz), 1.93 (3H, s). |
| 416 | ¹H-NMR (CDCl3) δ: 7.29-7.27 (2H, m), 7.24-7.19 (3H, m), 7.17-7.15 (1H, m), 7.13-7.11 (1H, m), 6.93-6.91 (1H, m), 6.85 (1H, dd, J = 8.1, 2.9 Hz), 2.14 (3H, d, J = 0.9 Hz), 1.89 (3H, s). |
| 417 | ¹H-NMR (CDCl3) δ: 7.78 (1H, s), 7.33-7.29 (4H, m), 7.24-7.22 (2H, m), 7.02-7.00 (1H, m), 6.96 (1H, dd, J = 7.8, 2.9 Hz). |
| 418 | ¹H-NMR (CDCl3) δ: 7.78 (1H, s), 7.36-7.29 (3H, m), 7.27-7.23 (1H, m), 7.23-7.21 (1H, m), 7.20-7.19 (1H, m), 7.01-6.99 (1H, m), 6.94 (1H, dd, J = 7.8, 2.9 Hz). |
| 419 | ¹H-NMR (CDCl3) δ: 8.81 (1H, s), 7.87 (1H, s), 6.92 (1H, dd, J = 8.3, 8.0 Hz), 6.84 (1H, dd, J = 8.3, 0.9 Hz), 6.65 (1H, ddd, J = 8.0, 2.8, 0.9 Hz), 6.63-6.56 (2H, m), 2.00 (3H, d, J = 1.8 Hz). |
| 420 | ¹H-NMR (CDCl3) δ: 7.95 (1H, dd, J = 8.3, 1.2 Hz), 7.74 (1H, s), 7.51 (1H, ddd, J = 8.0, 2.7, 1.2 Hz), 7.38 (1H, ddd, J = 8.3, 8.0, 0.5 Hz), 6.70-6.64 (2H, m), 2.35 (3H, d, J = 2.0 Hz). |
| 421 | ¹H-NMR (CDCl3) δ: 7.74 (1H, s), 6.93 (1H, t, J = 7.9 Hz), 6.65-6.56 (4H, m), 3.78 (2H, s), 1.91 (3H, d, J = 2.4 Hz). |
| 422 | ¹H-NMR (CDCl3) δ: 7.85 (1H, s), 7.05 (1H, dd, J = 8.3, 7.9 Hz), 6.79 (1H, d, J = 8.3 Hz), 6.75 (1H, dd, J = 7.9, 2.3 Hz), 6.64-6.55 (2H, m), 4.05-3.94 (2H, m), 2.00 (3H, d, J = 2.0 Hz), 1.42 (3H, t, J = 7.0 Hz). |
| 423 | ¹H-NMR (CDCl3) δ: 7.85 (1H, s), 7.07-7.03 (1H, m), 6.79 (1H, d, J = 8.1 Hz), 6.75 (1H, dd, J = 8.1, 2.7 Hz), 6.64-6.55 (2H, m), 3.95-3.84 (2H, m), 2.01 (3H, d, J = 2.0 Hz), 1.87-1.77 (2H, m), 1.04 (3H, t, J = 7.4 Hz). |
| 424 | ¹H-NMR (CDCl3) δ: 7.88 (1H, d, J = 8.1 Hz), 7.74 (1H, s), 7.18 (1H, t, J = 8.1 Hz), 7.10 (1H, br s), 7.05-7.02 (1H, m), 6.67-6.57 (2H, m), 2.23 (3H, s), 2.05 (3H, s). |
| 425 | ¹H-NMR (CDCl3) δ: 7.46 (2H, dd, J = 8.5, 0.6 Hz), 7.25-7.24 (1H, m), 7.17 (1H, dd, J = 8.5, 2.4 Hz), 6.69-6.64 (2H, m), 2.13 (3H, d, J = 1.0 Hz), 2.12 (3H, d, J = 1.5 Hz), 1.89 (3H, s). |
| 426 | ¹H-NMR (DMSO-D6) δ: 8.68 (1H, s), 7.56-7.50 (1H, m), 7.20 (1H, t, J = 8.7 Hz), 7.12 (1H, t, J = 8.9 Hz), 7.06 (1H, d, J = 8.3 Hz), 6.68 (1H, dd, J = 8.4, 2.6 Hz), 6.62-6.61 (1H, m), 1.99 (3H, s). |
| 427 | ¹H-NMR (CDCl3) δ: 7.89 (1H, s), 7.36-7.27 (1H, m), 7.10 (1H, d, J = 8.3 Hz), 6.91-6.80 (4H, m), 5.03 (2H, dd, J = 19.3, 6.8 Hz), 3.40 (3H, s), 2.12 (3H, s). |
| 428 | ¹H-NMR (CDCl3) δ: 7.89 (1H, s), 7.39-7.31 (1H, m), 7.19 (1H, d, J = 8.5 Hz), 6.94-6.83 (4H, m), 4.76 (2H, s), 2.15 (3H, s). |
| 429 | ¹H-NMR (CDCl3) δ: 7.88 (1H, s), 7.37-7.27 (1H, m), 7.11 (1H, d, J = 8.3 Hz), 6.89-6.82 (4H, m), 4.58 (2H, d, J = 1.7 Hz), 2.55 (1H, s), 2.12 (3H, s). |
| 430 | ¹H-NMR (CDCl3) δ: 7.86 (1H, s), 7.36-7.29 (1H, m), 7.07 (1H, d, J = 8.5 Hz), 6.90-6.80 (3H, m), 6.72 (1H, t, J = 2.6 Hz), 6.01-5.92 (1H, m), 5.37-5.27 (2H, m), 4.47-4.35 (2H, m). |
| 431 | ¹H-NMR (CDCl3) δ: 7.86 (1H, s), 7.36-7.28 (1H, m), 7.07 (1H, d, J = 8.8 Hz), 6.89-6.81 (3H, m), 6.73 (1H, t, J = 2.6 Hz), 4.05-4.01 (1H, m), 3.94-3.89 (1H, m), 3.72-3.68 (2H, m), 3.44 (3H, s), 2.10 (3H, s). |
| 432 | ¹H-NMR (CDCl3) δ: 7.88 (1H, s), 7.35-7.28 (1H, m), 7.08 (1H, d, J = 8.1 Hz), 6.92-6.80 (4H, m), 5.08 (2H, q, J = 7.0 Hz), 3.65 (2H, q, J = 7.0 Hz), 2.11 (3H, s), 1.20 (3H, t, J = 7.0 Hz). |
| 433 | ¹H-NMR (CDCl3) δ: 7.87 (1H, s), 7.35-7.29 (1H, m), 7.06 (1H, d, J = 8.6 Hz), 6.89-6.81 (2H, m), 6.78 (1H, dd, J = 8.6, 2.8 Hz), 6.70 (1H, t, J = 2.8 Hz), 3.98-3.92 (1H, m), 3.87-3.80 (1H, m), 2.10 (3H, s), 1.36 (3H, t, J = 7.0 Hz). |
| 434 | ¹H-NMR (CDCl3) δ: 7.87 (1H, s), 7.36-7.28 (1H, m), 7.06 (1H, d, J = 8.5 Hz), 6.88-6.81 (2H, m), 6.77 (1H, dd, J = 8.5, 2.7 Hz), 6.69 (1H, t, J = 2.4 Hz), 4.41-4.32 (1H, m), 2.10 (3H, s), 1.27 (3H, d, J = 6.1 Hz), 1.21 (3H, d, J = 6.1 Hz). |
| 435 | ¹H-NMR (CDCl3) δ: 7.28-7.28 (1H, m), 7.25-7.17 (3H, m), 7.12-7.11 (1H, m), 7.02-7.00 (1H, m), 6.97 (1H, d, J = 8.4 Hz), 6.68 (1H, dd, J = 8.4, 2.4 Hz), 6.53 (1H, d, J = 2.8 Hz), 3.66 (3H, s), 2.14 (3H, d, J = 0.9 Hz), 2.01 (3H, s), 1.90 (3H, s). |
| 436 | ¹H-NMR (CDCl3) δ: 7.72 (1H, s), 7.09 (1H, dd, J = 8.3, 8.1 Hz), 6.81 (1H, d, J = 8.3 Hz), 6.77 (1H, ddd, J = 8.1, 2.9, 0.7 Hz), 6.64-6.55 (2H, m), 3.82 (3H, s), 2.00 (3H, d, J = 2.2 Hz). |
| 437 | ¹H-NMR (CDCl3) δ: 7.30 (1H, q, J = 1.0 Hz), 7.09-6.94 (3H, m), 6.62-6.54 (2H, m), 2.14 (3H, d, J = 1.0 Hz), 2.05-2.04 (3H, m), 1.90 (3H, s). |
| 438 | ¹H-NMR (CDCl3) δ: 7.85 (1H, s), 7.05 (1H, t, J = 8.1 Hz), 6.78 (1H, d, J = 8.1 Hz), 6.74 (1H, dd, J = 8.1, 2.2 Hz), 6.64-6.55 (2H, m), 3.74 (1H, dd, J = 8.8, 6.1 Hz), 3.65 (1H, dd, J = 8.8, 6.6 Hz), 2.15-2.05 (1H, |

TABLE 5-continued

| Compound | ¹H-NMR |
|---|---|
| | m), 2.02 (3H, d, J = 2.2 Hz), 1.03 (3H, d, J = 6.8 Hz), 1.03 (3H, d, J = 6.8 Hz). |
| 439 | ¹H-NMR (CDCl3) δ: 7.40-7.38 (1H, m), 7.33 (1H, q, J = 0.9 Hz), 7.30-7.26 (2H, m), 7.22-7.19 (1H, m), 6.61-6.53 (2H, m), 2.14 (3H, d, J = 0.9 Hz), 1.91 (3H, s). |
| 440 | ¹H-NMR (CDCl3) δ: 7.29 (1H, q, J = 0.9 Hz), 7.08-7.04 (1H, m), 7.00-6.96 (2H, m), 6.36-6.30 (2H, m), 3.74 (3H, s), 2.13 (3H, d, J = 0.9 Hz), 2.03 (3H, t, J = 1.8 Hz), 1.91 (3H, s). |
| 441 | ¹H-NMR (CDCl3) δ: 7.47-7.46 (1H, m), 7.32-7.28 (3H, m), 7.17-7.15 (2H, m), 6.58-6.53 (2H, m), 2.14 (3H, d, J = 0.9 Hz), 1.91 (3H, s). |
| 442 | ¹H-NMR (CDCl3) δ: 7.38 (1H, dd, J = 8.0, 1.5 Hz), 7.32 (1H, q, J = 0.9 Hz), 7.30-7.26 (1H, m), 7.24 (1H, dd, J = 7.7, 1.8 Hz), 7.19 (1H, td, J = 7.7, 1.5 Hz), 6.35-6.29 (2H, m), 3.73 (3H, s), 2.14 (3H, d, J = 0.9 Hz), 1.92 (3H, s). |
| 443 | ¹H-NMR (CDCl3) δ: 7.88 (1H, s), 7.34-7.31 (1H, m), 7.27-7.25 (1H, m), 7.20-7.14 (2H, m), 6.62-6.56 (2H, m), 2.41-2.31 (2H, m), 1.65-1.52 (2H, m), 0.95 (3H, t, J = 7.3 Hz). |
| 444 | ¹H-NMR (CDCl3) δ: 7.88 (1H, s), 7.34-7.30 (1H, m), 7.27-7.25 (1H, m), 7.19-7.13 (2H, m), 6.62-6.55 (2H, m), 2.42-2.32 (2H, m), 1.65-1.52 (2H, m), 0.96 (3H, t, J = 7.3 Hz). |
| 445 | ¹H-NMR (CDCl3) δ: 7.34 (1H, d, J = 1.0 Hz), 7.27-7.19 (2H, m), 7.16-7.07 (2H, m), 6.57-6.51 (2H, m), 2.34-2.30 (2H, m), 2.14 (3H, d, J = 1.0 Hz), 1.91 (3H, s), 1.63-1.48 (2H, m), 0.91 (3H, t, J = 7.3 Hz). |
| 446 | ¹H-NMR (CDCl3) δ: 7.75 (1H, s), 7.35-7.31 (1H, m), 7.27-7.25 (1H, m), 7.21-7.14 (2H, m), 6.62-6.57 (2H, m), 2.40-2.31 (2H, m), 1.66-1.53 Z(2H, m), 0.95 (3H, t, J = 7.3 Hz). |
| 447 | ¹H-NMR (CDCl3) δ: 7.76 (1H, s), 7.34-7.31 (1H, m), 7.27-7.25 (1H, m), 7.20-7.13 (2H, m), 6.62-6.55 (2H, m), 2.41-2.32 (2H, m), 1.68-1.52 (2H, m), 0.96 (3H, t, J = 7.3 Hz). |
| 448 | ¹H-NMR (CDCl3) δ: 7.30 (1H, d, J = 1.0 Hz), 7.28-7.22 (1H, m), 7.14-7.10 (1H, m), 6.93-6.84 (3H, m), 6.80-6.76 (1H, m), 2.14 (3H, d, J = 0.7 Hz), 2.10 (3H, s), 1.90 (3H, s). |
| 449 | ¹H-NMR (CDCl3) δ: 7.73 (1H, s), 7.38-7.30 (1H, m), 7.19 (1H, dd, J = 8.4, 6.0 Hz), 7.01-6.94 (2H, m), 6.91 (1H, tt, J = 8.5, 1.0 Hz), 6.85-6.81 (1H, m), 2.17 (3H, s). |
| 450 | ¹H-NMR (CDCl3) δ: 7.73 (1H, s), 7.39-7.31 (1H, m), 7.19 (1H, dd, J = 8.6, 6.0 Hz), 7.02-6.95 (2H, m), 6.91 (1H, tt, J = 8.6, 1.0 Hz), 6.84 (1H, tt, J = 8.6, 1.0 Hz), 2.16 (3H, s). |
| 451 | ¹H-NMR (CDCl3) δ: 7.74 (1H, s), 7.29-7.22 (3H, m), 7.16-7.13 (2H, m), 7.09 (1H, t, J = 7.6 Hz), 6.96 (2H, d, J = 7.6 Hz), 2.14 (6H, s). |
| 452 | ¹H-NMR (CDCl3) δ: 7.74 (1H, s), 7.28-7.21 (3H, m), 7.17-7.13 (2H, m), 7.11-7.09 (1H, m), 6.97-6.96 (2H, m), 2.13 (6H, s). |
| 453 | ¹H-NMR (CDCl3) δ: 7.58 (1H, dd, J = 7.8, 1.5 Hz), 7.32 (1H, q, J = 1.0 Hz), 7.31-7.27 (1H, m), 7.26-7.22 (1H, m), 7.19 (1H, ddd, J = 7.8, 7.3, 2.0 Hz), 6.61-6.54 (2H, m), 2.14 (3H, d, J = 1.0 Hz), 1.91 (3H, s). |
| 454 | ¹H-NMR (CDCl3) δ: 7.45 (1H, q, J = 0.9 Hz), 7.29-7.27 (3H, m), 7.18-7.14 (2H, m), 6.33-6.29 (2H, m), 3.72 (3H, s), 2.13 (3H, d, J = 0.9 Hz), 1.91 (3H, s). |
| 455 | ¹H-NMR (CDCl3) δ: 7.30 (1H, q, J = 0.9 Hz), 7.15 (1H, dd, J = 8.4, 6.1 Hz), 6.95 (1H, td, J = 8.4, 2.8 Hz), 6.89 (1H, dt, J = 8.6, 2.8 Hz), 6.64 (1H, tt, J = 8.9, 2.1 Hz), 6.57 (1H, tt, J = 8.9, 2.1 Hz), 2.14 (3H, d, J = 0.9 Hz), 2.09 (3H, s), 1.90 (3H, s). |
| 456 | ¹H-NMR (CDCl3) δ: 7.57 (1H, dd, J = 8.0, 1.5 Hz), 7.31 (1H, q, J = 0.9 Hz), 7.29 (1H, ddd, J = 7.7, 2.8, 1.8 Hz), 7.25-7.21 (1H, m), 7.19-7.15 (1H, m), 6.34-6.31 (2H, m), 3.73 (3H, s), 2.14 (3H, d, J = 0.9 Hz), 1.91 (3H, s). |
| 457 | ¹H-NMR (CDCl3) δ: 7.85 (1H, s), 7.38-7.32 (1H, m), 7.18 (1H, dd, J = 8.4, 6.0 Hz), 7.01-6.95 (2H, m), 6.93-6.89 (1H, m), 6.86-6.82 (1H, m), 2.16 (3H, s). |
| 458 | ¹H-NMR (CDCl3) δ: 8.55 (1H, dd, J = 4.8, 1.6 Hz), 7.53 (1H, dq, J = 8.1, 1.4 Hz), 7.17-7.15 (1H, m), 6.68-6.61 (2H, m), 2.43 (3H, d, J = 1.2 Hz). |
| 459 | ¹H-NMR (CDCl3) δ: 7.82 (1H, s), 7.26-7.25 (3H, m), 7.14-7.12 (2H, m), 6.98 (2H, s), 6.87 (1H, s), 2.22 (3H, s), 2.07 (3H, s). |
| 460 | ¹H-NMR (CDCl3) δ: 7.82 (1H, s), 7.29-7.22 (3H, m), 7.12-7.11 (2H, m), 6.98-6.97 (2H, m), 6.85 (1H, s), 2.21 (3H, s), 2.08 (3H, s). |
| 461 | ¹H-NMR (CDCl3) δ: 7.33 (1H, dd, J = 7.5, 1.7 Hz), 7.30 (1H, q, J = 0.9 Hz), 7.09-7.02 (2H, m), 6.62-6.56 (2H, m), 2.15-2.12 (6H, m), 1.90 (3H, s). |
| 462 | ¹H-NMR (CDCl3) δ: 7.29 (1H, q, J = 0.9 Hz), 7.13 (1H, dd, J = 8.4, 6.0 Hz), 6.95-6.89 (2H, m), 6.39 (1H, ddd, J = 10.7, 2.4, 1.5 Hz), 6.31 (1H, ddd, J = 11.0, 2.1, 1.5 Hz), 3.74 (3H, s), 2.13 (3H, d, J = 0.9 Hz), 2.08 (3H, s), 1.9 (3H, s). |
| 463 | ¹H-NMR (CDCl3) δ: 7.29 (1H, q, J = 0.9 Hz), 7.20 (1H, dd, J = 8.4, 2.3 Hz), 7.15 (1H, t, J = 2.3 Hz), 7.12 (1H, d, J = 8.4 Hz), 6.68-6.63 (1H, m), 6.59-6.55 (1H, m), 2.13 (3H, d, J = 0.9 Hz), 2.09 (3H, s), 1.90 (3H, s). |

TABLE 5-continued

| Compound | ¹H-NMR |
|---|---|
| 464 | ¹H-NMR (CDCl3) δ: 7.28 (1H, q, J = 0.9 Hz), 7.19-7.17 (2H, m), 7.10 (1H, d, J = 9.2 Hz), 6.40 (1H, ddd, J = 10.7, 2.4, 1.5 Hz), 6.32 (1H, ddd, J = 10.7, 2.4, 1.5 Hz), 3.75 (3H, s), 2.13 (3H, d, J = 0.9 Hz), 2.08 (3H, s), 1.91 (3H, s). |
| 465 | ¹H-NMR (CDCl3) δ: 7.32 (1H, q, J = 0.9 Hz), 7.10-7.07 (1H, m), 6.98-6.97 (2H, m), 6.59-6.51 (2H, m), 2.23 (3H, s), 2.14 (3H, d, J = 0.9 Hz), 1.98 (3H, d, J = 2.1 Hz), 1.90 (3H, s). |
| 466 | ¹H-NMR (CDCl3) δ: 7.45 (1H, d, J = 1.0 Hz), 7.27-7.24 (3H, m), 7.08-6.99 (3H, m), 6.79-6.74 (1H, m), 6.69 (1H, td, J = 9.0, 2.4 Hz), 2.14 (3H, d, J = 1.0 Hz), 1.89 (3H, s). |
| 467 | ¹H-NMR (CDCl3) δ: 7.99 (1H, s), 7.33-7.28 (4H, m), 7.17-7.13 (3H, m), 7.08 (1H, td, J = 7.6, 1.0 Hz), 6.98-6.94 (1H, m). |
| 468 | ¹H-NMR (CDCl3) δ: 7.98 (1H, s), 7.32-7.27 (4H, m), 7.16-7.06 (4H, m), 6.97-6.93 (1H, m). |
| 469 | ¹H-NMR (CDCl3) δ: 7.98 (1H, s), 7.35-7.30 (3H, m), 7.18-7.13 (3H, m), 6.86-6.81 (1H, m), 6.74-6.69 (1H, m). |
| 470 | ¹H-NMR (CDCl3) δ: 7.98 (1H, s), 7.33-7.30 (3H, m), 7.17-7.11 (3H, m), 6.85-6.80 (1H, m), 6.71 (1H, td, J = 9.1, 2.5 Hz). |
| 471 | ¹H-NMR (CDCl3) δ: 7.46 (1H, d, J = 1.0 Hz), 7.26-7.20 (4H, m), 7.10 (2H, s), 7.06-6.99 (2H, m), 6.92 (1H, t, J = 9.0 Hz), 2.14 (3H, d, J = 0.7 Hz), 1.90 (3H, s). |
| 472 | ¹H-NMR (CDCl3) δ: 7.34 (1H, dd, J = 8.1, 2.0 Hz), 7.30 (2H, dd, J = 4.7, 1.7 Hz), 7.06 (1H, d, J = 8.0 Hz), 6.67-6.65 (1H, m), 6.58-6.56 (1H, m), 2.13 (3H, d, J = 0.9 Hz), 2.08 (3H, s), 1.90 (3H, s). |
| 473 | ¹H-NMR (CDCl3) δ: 7.37-7.35 (2H, m), 7.25-7.20 (4H, m), 6.82-6.76 (2H, m), 2.15 (3H, d, J = 1.2 Hz), 1.91 (3H, s). |
| 474 | ¹H-NMR (CDCl3) δ: 7.32 (1H, dd, J = 8.1, 1.2 Hz), 7.25-7.07 (9H, m), 2.14 (3H, d, J = 1.2 Hz), 1.90 (3H, s). |
| 475 | ¹H-NMR (CDCl3) δ: 7.76 (1H, s), 7.25-7.00 (9H, m), 2.43-2.28 (2H, m), 2.13 (3H, s), 1.01 (3H, t, J = 7.3 Hz). |
| 476 | ¹H-NMR (CDCl3) δ: 7.70-7.65 (1H, m), 7.52-7.47 (2H, m), 7.36-7.33 (2H, m), 6.62-6.52 (2H, m), 2.12 (3H, d, J = 1.0 Hz), 1.88 (3H, s). |
| 477 | ¹H-NMR (CDCl3) δ: 7.30 (1H, q, J = 0.9 Hz), 7.08-7.06 (1H, m), 7.01-6.95 (2H, m), 6.33 (1H, ddd, J = 10.7, 2.4, 1.5 Hz), 6.28 (1H, ddd, J = 10.7, 2.4, 1.5 Hz), 3.72 (3H, s), 2.23 (3H, s), 2.13 (3H, d, J = 0.9 Hz), 1.97 (3H, d, J = 2.1 Hz), 1.91 (3H, s). |
| 478 | ¹H-NMR (CDCl3) δ: 7.32 (1H, q, J = 1.0 Hz), 7.25-7.17 (1H, m), 7.05 (1H, d, J = 7.3 Hz), 7.01-6.99 (1H, m), 6.96-6.92 (1H, m), 6.82-6.72 (2H, m), 2.21 (3H, s), 2.14 (3H, d, J = 1.0 Hz), 1.99 (3H, d, J = 2.2 Hz), 1.90 (3H, s). |
| 479 | ¹H-NMR (CDCl3) δ: 7.31 (1H, q, J = 1.0 Hz), 7.25 (2H, tt, J = 8.5, 6.6 Hz), 7.06-6.93 (3H, m), 6.76-6.84 (2H, m), 2.14 (3H, d, J = 1.0 Hz), 2.06 (3H, t, J = 2.0 Hz), 1.90 (3H, s). |
| 480 | ¹H-NMR (CDCl3) δ: 7.53-7.51 (1H, m), 7.30 (1H, q, J = 1.0 Hz), 7.13-7.10 (1H, m), 7.00-6.94 (1H, m), 6.62-6.55 (2H, m), 2.17-2.15 (3H, br m), 2.14 (3H, d, J = 1.0 Hz), 1.90 (3H, s). |
| 481 | ¹H-NMR (CDCl3) δ: 7.31 (1H, q, J = 0.9 Hz), 7.03 (1H, t, J = 8.1 Hz), 6.77-6.72 (2H, m), 6.60-6.51 (2H, m), 3.80 (3H, s), 2.13 (3H, d, J = 0.9 Hz), 1.95-1.94 (3H, br m), 1.90 (3H, s). |
| 482 | ¹H-NMR (CDCl3) δ: 7.27-7.27 (1H, m), 7.20-7.16 (3H, m), 7.06-7.04 (1H, m), 7.01-7.00 (2H, m), 6.94 (1H, t, J = 7.6 Hz), 6.88 (1H, d, J = 7.6 Hz), 2.15 (3H, s), 2.14 (3H, d, J = 0.9 Hz), 1.93 (3H, s), 1.89 (3H, s). |
| 483 | ¹H-NMR (CDCl3) δ: 7.26-7.26 (1H, m), 7.23-7.20 (3H, m), 7.07-7.00 (3H, m), 6.92-6.89 (1H, m), 6.86 (1H, d, J = 7.8 Hz), 2.14 (3H, d, J = 1.0 Hz), 1.99 (3H, d, J = 2.4 Hz), 1.90 (3H, s). |
| 484 | ¹H-NMR (CDCl3) δ: 7.25-7.20 (5H, m), 7.07-7.04 (1H, m), 7.01-6.99 (2H, m), 6.96 (1H, dd, J = 8.0, 1.2 Hz), 2.14 (3H, d, J = 0.9 Hz), 2.10 (3H, s), 1.89 (3H, s). |
| 485 | ¹H-NMR (CDCl3) δ: 7.35 (1H, d, J = 0.9 Hz), 7.24-7.18 (3H, m), 7.16-7.15 (1H, m), 7.07-7.04 (1H, m), 6.80-6.73 (2H, m), 2.46-2.41 (2H, m), 2.14 (3H, d, J = 1.2 Hz), 1.90 (3H, s), 1.16 (3H, t, J = 7.5 Hz). |
| 486 | ¹H-NMR (CDCl3) δ: 7.31-7.23 (2H, m), 7.17-7.15 (2H, m), 7.09 (1H, d, J = 8.1 Hz), 6.88-6.86 (1H, m), 6.80-6.77 (1H, m), 2.14 (3H, d, J = 1.0 Hz), 2.11 (3H, s), 1.90 (3H, s). |
| 487 | ¹H-NMR (CDCl3) δ: 7.32-7.24 (4H, m), 7.03 (1H, d, J = 8.3 Hz), 6.89-6.87 (1H, m), 6.79-6.77 (1H, m), 2.14 (3H, d, J = 1.2 Hz), 2.09 (3H, s), 1.90 (3H, s). |
| 488 | ¹H-NMR (CDCl3) δ: 7.82 (1H, s), 7.31-7.25 (2H, m), 7.14 (1H, ddd, J = 7.9, 2.8, 1.4 Hz), 7.11-7.09 (1H, m), 6.59 (1H, tt, J = 8.8, 2.1 Hz), 6.54 (1H, tt, J = 8.8, 2.1 Hz), 2.45-2.39 (3H, m), 2.31-2.27 (1H, m), 1.20 (3H, t, J = 7.5 Hz), 1.01 (3H, t, J = 7.5 Hz). |
| 489 | ¹H-NMR (CDCl3) δ: 7.32 (1H, d, J = 0.9 Hz), 7.27-7.22 (2H, m), 7.14-7.12 (1H, m), 7.08-7.06 (1H, m), 6.57 (1H, tt, J = 8.9, 2.1 Hz), 6.51 (1H, tt, J = 8.9, 2.1 Hz), 2.43 (2H, q, J = 7.5 Hz), 2.39-2.34 (1H, m), 2.28-2.24 (1H, m), 2.13 (3H, d, J = 0.9 Hz), 1.17 (3H, t, J = 7.5 Hz), 1.00 (3H, t, J = 7.5 Hz). |

TABLE 5-continued

| Compound | ¹H-NMR |
|---|---|
| 490 | ¹H-NMR (CDCl3) δ: 7.81 (1H, s), 7.42-7.41 (1H, m), 7.32-7.29 (2H, m), 7.24-7.20 (1H, m), 6.62-6.56 (2H, m), 2.43-2.39 (1H, m), 2.31-2.27 (1H, m), 1.01 (3H, t, J = 7.3 Hz). |
| 491 | ¹H-NMR (CDCl3) δ: 7.39 (1H, dd, J = 8.1, 1.4 Hz), 7.31 (1H, d, J = 1.2 Hz), 7.29-7.25 (2H, m), 7.21-7.17 (1H, m), 6.60-6.54 (2H, m), 2.40-2.37 (1H, m), 2.29-2.26 (1H, m), 2.13 (3H, d, J = 1.2 Hz), 1.00 (3H, t, J = 7.5 Hz). |
| 492 | ¹H-NMR (CDCl3) δ: 7.93 (1H, s), 7.36-7.29 (3H, m), 7.19 (2H, d, J = 6.7 Hz), 6.57 (2H, tt, J = 9.6, 2.4 Hz), 2.35 (2H, q, J = 7.4 Hz), 1.01 (3H, t, J = 7.4 Hz). |
| 493 | ¹H-NMR (CDCl3) δ: 7.44 (1H, d, J = 0.9 Hz), 7.32-7.27 (3H, m), 7.18-7.16 (2H, m), 6.56-6.54 (2H, m), 2.32(2H, q, J = 7.4 Hz), 2.13 (3H, d, J = 0.9 Hz), 1.00 (3H, t, J = 7.4 Hz). |
| 494 | ¹H-NMR (CDCl3) δ: 7.30-7.28 (2H, m), 7.27-7.22 (1H, m), 7.10 (1H, ddd, J = 8.0, 2.4, 1.2 Hz), 7.01 (1H, td, J = 8.0, 0.6 Hz), 6.83-6.78 (2H, m), 2.15-2.14 (6H, m), 1.90 (3H, s). |
| 495 | ¹H-NMR (CDCl3) δ: 7.80 (1H, s), 7.27-7.20 (1H, m), 7.08-7.06 (1H, m), 7.03-7.00 (1H, m), 6.95 (1H, t, J = 7.7 Hz), 6.84-6.74 (2H, m), 2.44-2.26 (2H, m), 2.22 (3H, s), 2.03 (3H, d, J = 2.2 Hz), 1.01 (3H, t, J = 7.4 Hz). |
| 496 | ¹H-NMR (CDCl3) δ: 7.47 (1H, dd, J = 8.0, 0.9 Hz), 7.29 (1H, q, J = 0.9 Hz), 7.28-7.22 (1H, m), 7.15-7.13 (1H, m), 6.95-6.92 (1H, m), 6.83-6.78 (2H, m), 2.17 (3H, d, J = 2.1 Hz), 2.14 (3H, d, J = 0.9 Hz), 1.90 (3H, s). |
| 497 | ¹H-NMR (CDCl3) δ: 7.30 (1H, q, J = 0.9 Hz), 7.24-7.18 (1H, m), 7.05-7.03 (1H, m), 7.02-7.00 (1H, m), 6.93 (1H, t, J = 7.8 Hz), 6.81-6.78 (1H, m), 6.76-6.72 (1H, m), 2.40-2.34 (1H, m), 2.31-2.24 (1H, m), 2.21 (3H, s), 2.14 (3H, d, J = 0.9 Hz), 2.00 (3H, d, J = 2.1 Hz), 1.00 (3H, t, J = 7.5 Hz). |
| 498 | ¹H-NMR (CDCl3) δ: 7.77 (1H, s), 7.23-7.12 (5H, m), 7.10-7.00 (4H, m), 2.48-2.28 (4H, m), 1.18 (3H, t, J = 7.6 Hz), 1.01 (3H, t, J = 7.3 Hz). |
| 499 | ¹H-NMR (CDCl3) δ: 7.73 (1H, s), 7.33-7.19 (5H, m), 7.14-7.11 (1H, m), 7.06-7.03 (1H, m), 6.97 (1H, d, J = 8.5 Hz), 2.42-2.27 (2H, m), 2.08 (3H, s), 1.01 (3H, t, J = 7.4 Hz). |
| 500 | ¹H-NMR (CDCl3) δ: 7.33 (1H, d, J = 1.0 Hz), 7.25-7.18 (1H, m), 7.17-7.12 (3H, m), 7.06-7.02 (1H, m), 6.80 (1H, tt, J = 8.6, 1.0 Hz), 6.75 (1H, tt, J = 8.6, 1.0 Hz), 2.15-2.14 (6H, m), 1.91 (3H, s). |
| 501 | ¹H-NMR (CDCl3) δ: 7.78 (1H, s), 7.34-7.26 (1H, m), 7.20-7.16 (2H, m), 7.13-7.10 (1H, m), 6.90 (1H, tt, J = 8.5, 1.1 Hz), 6.80 (1H, tt, J = 8.5, 1.1 Hz), 2.44-2.25 (2H, m), 2.16 (3H, s), 1.01 (3H, t, J = 7.4 Hz). |
| 502 | ¹H-NMR (CDCl3) δ: 7.75 (1H, s), 7.22-7.17 (3H, m), 7.09-7.07 (1H, m), 7.05-7.00 (2H, m), 6.95 (1H, t, J = 7.6 Hz), 6.89 (1H, d, J = 7.6 Hz), 2.39-2.30 (2H, m), 2.16 (3H, s), 1.97 (3H, s), 1.01 (3H, t, J = 7.3 Hz). |
| 503 | ¹H-NMR (CDCl3) δ: 7.24-7.24 (1H, m), 7.19-7.16 (3H, m), 7.10-7.08 (1H, m), 7.04-7.02 (1H, m), 6.98 (1H, d, J = 7.6 Hz), 6.93 (1H, t, J = 7.6 Hz), 6.87 (1H, d, J = 7.6 Hz), 2.38-2.27 (2H, m), 2.15 (3H, s), 2.13 (3H, d, J = 0.9 Hz), 1.94 (3H, s), 1.00 (3H, t, J = 7.3 Hz). |
| 504 | ¹H-NMR (CDCl3) δ: 7.75 (1H, s), 7.24-7.20 (3H, m), 7.15-7.14 (1H, m), 7.05-7.03 (1H, m), 6.98 (1H, d, J = 8.6 Hz), 6.69 (1H, dd, J = 8.6, 2.6 Hz), 6.53 (1H, d, J = 2.6 Hz), 3.67 (3H, s), 2.40-2.30 (2H, m), 2.05 (3H, s), 1.01 (3H, t, J = 7.3 Hz). |
| 505 | ¹H-NMR (CDCl3) δ: 7.74 (1H, s), 7.25-7.20 (3H, m), 7.10-7.02 (3H, m), 6.94-6.91 (1H, m), 6.88 (1H, d, J = 8.0 Hz), 2.39-2.30 (2H, m), 2.04 (3H, d, J = 2.1 Hz), 1.01 (3H, t, J = 7.3 Hz). |
| 506 | ¹H-NMR (CDCl3) δ: 7.73 (1H, s), 7.26-7.21 (4H, m), 7.09-7.08 (1H, m), 7.04-7.03 (1H, m), 7.01 (1H, d, J = 8.0 Hz), 6.98 (1H, dd, J = 8.0, 1.8 Hz), 2.39-2.30 (2H, m), 2.14 (3H, s), 1.01 (3H, t, J = 7.3 Hz). |
| 507 | ¹H-NMR (CDCl3) δ: 7.82 (1H, s), 7.27-7.20 (1H, m), 7.19-7.15 (3H, m), 7.07-7.04 (1H, m), 6.83-6.82 (1H, m), 6.77-6.75 (1H, m), 2.41-2.36 (1H, m), 2.33-2.29 (1H, m), 2.18 (3H, s), 1.01 (3H, t, J = 7.5 Hz). |
| 508 | ¹H-NMR (CDCl3) δ: 7.31 (1H, s), 7.26-7.13 (4H, m), 7.03-7.01 (1H, m), 6.82-6.80 (1H, m), 6.75-6.73 (1H, m), 2.35-2.30 (2H, m), 2.15-2.14 (6H, m), 1.01 (3H, t, J = 7.4 Hz). |
| 509 | ¹H-NMR (CDCl3) δ: 7.82 (1H, s), 7.25-7.23 (3H, m), 7.18-7.16 (1H, m), 7.08-7.04 (1H, m), 6.81-6.80 (1H, m), 6.76-6.75 (1H, m), 2.47 (2H, q, J = 7.5 Hz), 2.42-2.39 (1H, m), 2.31-2.28 (1H, m), 1.19 (3H, t, J = 7.5 Hz), 1.01 (3H, t, J = 7.3 Hz). |
| 510 | ¹H-NMR (CDCl3) δ: 7.32 (1H, s), 7.22-7.14 (4H, m), 7.07-7.02 (1H, m), 6.80-6.78 (1H, m), 6.74-6.72 (1H, m), 2.45 (2H, q, J = 7.6 Hz), 2.40-2.33 (1H, m), 2.29-2.24 (1H, m), 2.14 (3H, s), 1.17 (3H, t, J = 7.6 Hz), 1.00 (3H, t, J = 7.4 Hz). |
| 511 | ¹H-NMR (CDCl3) δ: 7.82 (1H, s), 7.40-7.38 (1H, m), 7.32-7.31 (1H, m), 7.29-7.24 (2H, m), 7.18-7.17 (1H, m), 6.82-6.80 (2H, m), 2.43-2.37 (1H, m), 2.34-2.29 (1H, m), 1.01 (3H, t, J = 7.5 Hz). |
| 512 | ¹H-NMR (CDCl3) δ: 7.37 (1H, dd, J = 8.1, 1.4 Hz), 7.32-7.31 (1H, m), 7.31-7.28 (1H, m), 7.25-7.20 (2H, m), 7.16-7.13 (1H, m), 6.80-6.78 |

TABLE 5-continued

| Compound | ¹H-NMR |
|---|---|
| | (2H, m), 2.39-2.36 (1H, m), 2.32-2.27 (1H, m), 2.14 (3H, d, J = 1.2 Hz), 1.00 (3H, t, J = 7.5 Hz). |
| 513 | ¹H-NMR (CDCl3) δ: 7.79 (1H, s), 7.05 (1H, t, J = 8.3 Hz), 6.79-6.74 (2H, m), 6.62-6.53 (2H, m), 3.81 (3H, s), 2.43-2.25 (2H, m), 1.98 (3H, d, J = 2.2 Hz), 1.01 (3H, t, J = 7.3 Hz). |
| 514 | ¹H-NMR (CDCl3) δ: 7.29 (1H, q, J = 1.0 Hz), 7.05-6.99 (1H, m), 6.76-6.73 (2H, m), 6.61-6.50 (2H, m), 3.80 (3H, s), 2.39-2.23 (2H, m), 2.13 (3H, d, J = 1.0 Hz), 1.97-1.93 (3H, m), 1.00 (3H, t, J = 7.3 Hz). |
| 515 | ¹H-NMR (CDCl3) δ: 7.78 (1H, s), 7.36 (1H, dd, J = 7.6, 1.5 Hz), 7.12-7.03 (2H, m), 6.64-6.57 (2H, m), 2.39-2.30 (2H, m), 2.19-2.17 (3H, m), 1.01 (3H, t, J = 7.3 Hz). |
| 516 | ¹H-NMR (CDCl3) δ: 7.31-7.31 (1H, m), 7.20-7.16 (4H, m), 7.13-7.12 (1H, m), 7.08-7.00 (4H, m), 2.38-2.34 (2H, m), 2.14 (3H, d, J = 0.9 Hz), 1.90 (3H, s), 1.14 (3H, t, J = 7.5 Hz). |
| 517 | ¹H-NMR (CDCl3) δ: 7.29-7.19 (4H, m), 7.11-7.07 (2H, m), 7.05-7.01 (3H, m), 2.13 (3H, d, J = 0.9 Hz), 2.05 (3H, s), 1.89 (3H, s). |
| 518 | ¹H-NMR (CDCl3) δ: 7.30-7.18 (6H, m), 7.09-7.07 (1H, m), 7.03-7.01 (1H, m), 6.95 (1H, d, J = 8.3 Hz), 2.13 (3H, d, J = 1.0 Hz), 2.03 (3H, s), 1.89 (3H, s). |
| 519 | ¹H-NMR (CDCl3) δ: 7.80 (1H, s), 7.06 (1H, d, J = 7.8 Hz), 7.02 (1H, dd, J = 7.8, 0.9 Hz), 6.94 (1H, s), 6.61 (1H, tt, J = 8.8, 2.1 Hz), 6.55 (1H, tt, J = 8.8, 2.1 Hz), 2.37-2.32 (2H, m), 2.22 (3H, s), 2.11 (3H, s), 1.01 (3H, t, J = 7.4 Hz). |
| 520 | ¹H-NMR (CDCl3) δ: 7.30 (1H, d, J = 1.1 Hz), 7.04 (1H, d, J = 7.6 Hz), 6.99 (1H, dd, J = 7.6, 1.4 Hz), 6.92 (1H, s), 6.59 (1H, tt, J = 8.7, 2.1 Hz), 6.53 (1H, tt, J = 8.7, 2.1 Hz), 2.38-2.34 (1H, m), 2.29-2.26 (1H, m), 2.21 (3H, s), 2.13 (3H, d, J = 1.1 Hz), 2.08 (3H, s), 1.00 (3H, t, J = 7.5 Hz). |
| 521 | ¹H-NMR (CDCl3) δ: 7.78 (1H, s), 7.18 (1H, dd, J = 8.7, 6.0 Hz), 6.98 (1H, td, J = 8.3, 2.6 Hz), 6.91 (1H, dt, J = 8.3, 2.6 Hz), 6.67 (1H, tt, J = 8.8, 2.1 Hz), 6.58 (1H, tt, J = 8.8, 2.1 Hz), 2.42-2.37 (1H, m), 2.31-2.26 (1H, m), 2.14 (3H, s), 1.01 (3H, t, J = 7.4 Hz). |
| 522 | ¹H-NMR (CDCl3) δ: 7.28 (1H, d, J = 0.9 Hz), 7.15 (1H, dd, J = 8.4, 6.3 Hz), 6.94 (1H, td, J = 8.4, 2.9 Hz), 6.89 (1H, dt, J = 8.6, 2.9 Hz), 6.65 (1H, tt, J = 8.8, 2.1 Hz), 6.56 (1H, tt, J = 8.8, 2.1 Hz), 2.38-2.34 (1H, m), 2.28-2.24 (1H, m), 2.13 (3H, d, J = 0.9 Hz), 2.10 (3H, s), 1.00 (3H, t, J = 7.5 Hz). |
| 523 | ¹H-NMR (CDCl3) δ: 7.31 (1H, q, J = 0.9 Hz), 7.25-7.19 (1H, m), 7.01-6.98 (1H, m), 6.80 (1H, tt, J = 8.4, 1.0 Hz), 6.77-6.71 (3H, m), 3.78 (3H, s), 2.14 (3H, d, J = 0.9 Hz), 1.96 (3H, d, J = 1.8 Hz), 1.90 (3H, s). |
| 524 | ¹H-NMR (CDCl3) δ: 7.78 (1H, s), 7.32-7.25 (2H, m), 7.13-7.11 (1H, m), 7.04-7.01 (1H, m), 6.85-6.80 (2H, m), 2.42-2.35 (1H, m), 2.33-2.26 (1H, m), 2.19 (3H, d, J = 1.8 Hz), 1.01 (3H, t, J = 7.3 Hz). |
| 525 | ¹H-NMR (CDCl3) δ: 7.29-7.22 (3H, m), 7.11-7.09 (1H, m), 7.01-6.98 (1H, m), 6.83-6.77 (2H, m), 2.39-2.32 (1H, m), 2.31-2.24 (1H, m), 2.16 (3H, d, J = 2.1 Hz), 2.13 (3H, d, J = 0.9 Hz), 1.00 (3H, t, J = 7.3 Hz). |
| 526 | ¹H-NMR (CDCl3) δ: 7.78 (1H, s), 7.50 (1H, dd, J = 8.1, 1.0 Hz), 7.32-7.24 (1H, m), 7.18-7.15 (1H, m), 6.97-6.93 (1H, m), 6.85-6.80 (2H, m), 2.44-2.26 (2H, m), 2.22 (3H, d, J = 2.0 Hz), 1.01 (3H, t, J = 7.4 Hz). |
| 527 | ¹H-NMR (CDCl3) δ: 7.81 (1H, s), 7.08 (1H, d, J = 8.6 Hz), 6.79 (1H, dd, J = 8.6, 2.6 Hz), 6.68 (1H, t, J = 2.6 Hz), 6.64-6.62 (1H, m), 6.58-6.56 (1H, m), 3.70 (3H, s), 2.41-2.37 (1H, m), 2.31-2.27 (1H, m), 2.09 (3H, s), 1.01 (3H, t, J = 7.5 Hz). |
| 528 | ¹H-NMR (CDCl3) δ: 7.80 (1H, s), 7.11-7.10 (1H, m), 6.99-6.99 (2H, m), 6.62-6.57 (1H, m), 6.55-6.53 (1H, m) 2.41-2.36 (1H, m), 2.31-2.28 (1H, m), 2.24 (3H, s), 2.02 (3H, d, J = 2.1 Hz), 1.01 (3H, t, J = 7.5 Hz). |
| 529 | ¹H-NMR (CDCl3) δ: 7.78 (1H, s), 7.37 (1H, dd, J = 8.3, 2.1 Hz), 7.32-7.32 (1H, m), 7.09 (1H, d, J = 8.3 Hz), 6.70-6.68 (1H, m), 6.59-6.57 (1H, m), 2.40-2.38 (1H, m), 2.30-2.28 (1H, m), 2.13 (3H, s), 1.01 (3H, t, J = 7.5 Hz). |
| 530 | ¹H-NMR (CDCl3) δ: 7.79 (1H, s), 7.07-7.00 (3H, m), 6.64-6.57 (2H, m), 2.38-2.31 (2H, m), 2.09 (3H, t, J = 2.1 Hz), 1.01 (3H, t, J = 7.3 Hz). |
| 531 | ¹H-NMR (CDCl3) δ: 7.93 (1H, s), 7.29-7.19 (6H, m), 6.80-6.77 (2H, m), 2.35 (2H, q, J = 7.4 Hz), 1.01 (3H, t, J = 7.4 Hz). |
| 532 | ¹H-NMR (CDCl3) δ: 7.33 (1H, q, J = 1.2 Hz), 7.07 (1H, d, J = 8.6 Hz), 6.76 (1H, dd, J = 8.6, 2.8 Hz), 6.67-6.67 (1H, m), 6.63-6.61 (1H, m), 6.56-6.54 (1H, m), 3.70 (3H, s), 2.36 (1H, dt, J = 20.5, 7.3 Hz), 2.27 (1H, dt, J = 20.5, 7.3 Hz), 2.14 (3H, d, J = 1.2 Hz), 2.06 (3H, s), 1.00 (3H, t, J = 7.3 Hz). |
| 533 | ¹H-NMR (CDCl3) δ: 7.30 (1H, q, J = 1.0 Hz), 7.09-7.07 (1H, m), 6.98-6.95 (2H, m), 6.60-6.49 (2H, m), 2.35-2.30 (2H, m), 2.23 (3H, s), 2.13 (3H, d, J = 1.0 Hz), 1.99 (3H, d, J = 2.2 Hz), 1.00 (3H, t, J = 7.4 Hz). |
| 534 | ¹H-NMR (CDCl3) δ: 7.26-6.99 (10H, m), 2.44-2.26 (4H, m), 2.12 (3H, d, J = 1.0 Hz), 1.15 (3H, t, J = 7.6 Hz), 1.00 (3H, t, J = 7.3 Hz). |

TABLE 5-continued

| Compound | ¹H-NMR |
|---|---|
| 535 | ¹H-NMR (CDCl3) δ: 7.74 (1H, s), 7.33 (1H, dt, J = 7.8, 0.9 Hz), 7.25-7.18 (5H, m), 7.14-7.11 (3H, m), 2.41-2.28 (2H, m), 1.02 (3H, t, J = 7.3 Hz). |
| 536 | ¹H-NMR (CDCl3) δ: 7.29-7.23 (2H, m), 7.17 (1H, t, J = 2.0 Hz), 7.14 (1H, dd, J = 8.4, 2.0 Hz), 7.09 (1H, d, J = 8.4 Hz), 6.88 (1H, t, J = 8.4 Hz), 6.77 (1H, t, J = 8.4 Hz), 2.40-2.24 (2H, m), 2.13-2.13 (6H, m), 1.00 (3H, t, J = 7.5 Hz). |
| 537 | ¹H-NMR (CDCl3) δ: 7.45 (1H, d, J = 1.1 Hz), 7.23-7.18 (6H, m), 7.05-7.01 (4H, m), 2.15 (3H, d, J = 1.1 Hz), 1.92 (3H, s). |
| 538 | ¹H-NMR (CDCl3) δ: 7.32-7.30 (1H, m), 7.24-7.12 (7H, m), 7.11-7.09 (2H, m), 2.39-2.26 (2H, m), 2.13 (3H, d, J = 0.9 Hz), 1.01 (3H, t, J = 7.3 Hz). |
| 539 | ¹H-NMR (CDCl3) δ: 7.80 (1H, s), 7.26-7.24 (1H, m), 7.04-7.02 (1H, m), 6.98-6.96 (2H, m), 6.84-6.82 (1H, m), 6.78-6.76 (1H, m), 2.43-2.27 (2H, m), 2.19 (3H, s), 2.12 (3H, s), 1.01 (3H, t, J = 7.4 Hz). |
| 540 | ¹H-NMR (CDCl3) δ: 7.304-7.301 (1H, m), 7.22-7.20 (1H, m), 7.02-7.00 (1H, m), 6.95-6.94 (2H, m), 6.82-6.80 (1H, m), 6.75-6.73 (1H, m), 2.41-2.23 (2H, m), 2.18 (3H, s), 2.13 (3H, d, J = 1.0 Hz), 2.10 (3H, s), 1.00 (3H, t, J = 7.3 Hz). |
| 541 | ¹H-NMR (CDCl3) δ: 7.79 (1H, s), 7.30-7.28 (1H, m), 7.16-7.14 (1H, m), 6.95-6.93 (2H, m), 6.90-6.88 (1H, m), 6.81-6.79 (1H, m), 2.41-2.37 (1H, m), 2.31-2.27 (1H, m), 2.15 (3H, s), 1.01 (3H, t, J = 7.3 Hz). |
| 542 | ¹H-NMR (CDCl3) δ: 7.28-7.24 (2H, m), 7.13-7.11 (1H, m), 6.92-6.84 (3H, m), 6.78-6.76 (1H, m), 2.38-2.35 (1H, m), 2.28-2.25 (1H, m), 2.14 (3H, d, J = 1.0 Hz), 2.12 (3H, s), 1.00 (3H, t, J = 7.4 Hz). |
| 543 | ¹H-NMR (CDCl3) δ: 7.25-7.21 (3H, m), 7.19-7.18 (1H, m), 7.16-7.15 (1H, m), 7.04-7.02 (1H, m), 6.96 (1H, d, J = 8.6 Hz), 6.67 (1H, dd, J = 8.6, 2.8 Hz), 6.52 (1H, d, J = 2.8 Hz), 3.66 (3H, s), 2.39-2.27 (2H, m), 2.13 (3H, d, J = 0.9 Hz), 2.02 (3H, s). |
| 544 | ¹H-NMR (CDCl3) δ: 7.23-7.19 (4H, m), 7.11-7.09 (1H, m), 7.05-6.99 (2H, m), 6.89 (1H, t, J = 8.0 Hz), 6.85 (1H, d, J = 8.0 Hz), 2.35-2.30 (2H, m), 2.13 (3H, d, J = 0.9 Hz), 2.01 (3H, d, J = 2.4 Hz), 1.00 (3H, t, J = 7.3 Hz). |
| 545 | ¹H-NMR (CDCl3) δ: 7.24-7.18 (5H, m), 7.11-7.08 (1H, m), 7.04-7.01 (1H, m), 6.98-6.96 (2H, m), 2.38-2.26 (2H, m), 2.13 (3H, d, J = 1.0 Hz), 2.11 (3H, s), 1.00 (3H, t, J = 7.4 Hz). |
| 546 | ¹H-NMR (CDCl3) δ: 7.26-7.26 (1H, m), 7.21-7.18 (3H, m), 7.09-7.07 (1H, m), 7.01-6.99 (2H, m), 6.67 (1H, d, J = 8.1 Hz), 6.65-6.63 (1H, m), 3.75 (3H, s), 2.13 (3H, d, J = 1.0 Hz), 1.91 (3H, s), 1.89 (3H, s). |
| 547 | ¹H-NMR (CDCl3) δ: 7.34-7.31 (1H, m), 7.28-7.27 (1H, m), 7.10-7.00 (2H, m), 6.63-6.55 (2H, m), 2.38-2.32 (1H, m), 2.30-2.22 (1H, m), 2.16-2.12 (6H, m), 1.00 (3H, t, J = 7.3 Hz). |
| 548 | ¹H-NMR (CDCl3) δ: 7.78 (1H, s), 7.54 (1H, dd, J = 8.0, 0.9 Hz), 7.14 (1H, ddd, J = 8.0, 2.1, 0.9 Hz), 7.01-6.97 (1H, m), 6.64-6.58 (2H, m), 2.41-2.35 (1H, m), 2.33-2.27 (1H, m), 2.20 (3H, d, J = 2.1 Hz), 1.01 (3H, t, J = 7.5 Hz). |
| 549 | ¹H-NMR (CDCl3) δ: 7.79 (1H, s), 7.27-7.21 (1H, m), 7.01 (1H, t, J = 8.1 Hz), 6.83-6.73 (4H, m), 3.79 (3H, s), 2.41-2.27 (2H, m), 2.00 (3H, d, J = 1.8 Hz), 1.01 (3H, t, J = 7.5 Hz). |
| 550 | ¹H-NMR (CDCl3) δ: 7.79 (1H, s), 7.31-7.24 (1H, m), 7.08-6.96 (3H, m), 6.86-6.78 (2H, m), 2.43-2.26 (2H, m), 2.10 (3H, t, J = 2.0 Hz), 1.01 (3H, t, J = 7.4 Hz). |
| 551 | ¹H-NMR (CDCl3) δ: 7.29 (1H, q, J = 1.0 Hz), 7.25-7.17 (1H, m), 7.00-6.96 (1H, m), 6.82-6.70 (4H, m), 3.78 (3H, s), 2.40-2.24 (2H, m), 2.13 (3H, d, J = 0.7 Hz), 1.97 (3H, d, J = 2.0 Hz), 1.00 (3H, t, J = 7.3 Hz). |
| 552 | ¹H-NMR (CDCl3) δ: 7.29 (1H, q, J = 1.0 Hz), 7.28-7.20 (1H, m), 7.05-6.92 (3H, m), 6.84-6.75 (2H, m), 2.40-2.24 (2H, m), 2.14 (3H, d, J = 1.0 Hz), 2.07 (3H, t, J = 2.1 Hz), 1.00 (3H, t, J = 7.4 Hz). |
| 553 | ¹H-NMR (CDCl3) δ: 7.72 (1H, s), 7.32-7.19 (3H, m), 7.13-7.11 (2H, m), 7.06-7.01 (3H, m), 2.43-2.27 (2H, m), 2.10 (3H, s), 1.01 (3H, t, J = 7.3 Hz). |
| 554 | ¹H-NMR (CDCl3) δ: 7.28 (1H, q, J = 1.0 Hz), 7.09-6.94 (3H, m), 6.60-6.56 (2H, m), 2.40-2.23 (2H, m), 2.13 (3H, d, J = 1.0 Hz), 2.06 (3H, t, J = 2.3 Hz), 1.00 (3H, t, J = 7.3 Hz). |
| 555 | ¹H-NMR (CDCl3) δ: 7.45 (1H, q, J = 1.0 Hz), 7.24-7.19 (6H, m), 6.79-6.75 (2H, m), 2.33 (2H, q, J = 7.4 Hz), 2.14 (3H, d, J = 1.0 Hz), 0.99 (3H, t, J = 7.4 Hz). |
| 556 | ¹H-NMR (CDCl3) δ: 7.78 (1H, s), 7.21-7.17 (3H, m), 6.71-6.66 (1H, m), 6.60-6.57 (1H, m), 2.42-2.26 (2H, m), 2.14 (3H, s), 1.01 (3H, t, J = 7.4 Hz). |
| 557 | ¹H-NMR (CDCl3) δ: 7.91 (1H, s), 7.24-7.20 (6H, m), 7.08-7.02 (4H, m), 2.37 (2H, q, J = 7.4 Hz), 1.01 (3H, t, J = 7.3 Hz). |
| 558 | ¹H-NMR (CDCl3) δ: 7.82 (1H, s), 7.31-7.24 (1H, m), 7.05 (1H, d, J = 8.5 Hz), 6.87-6.83 (1H, m), 6.81-6.73 (2H, m), 6.70 (1H, t, J = 2.4 Hz), 3.68 (3H, s), 2.43-2.26 (2H, m), 2.10 (3H, s), 1.01 (3H, t, J = 7.4 Hz). |

TABLE 5-continued

| Compound | ¹H-NMR |
|---|---|
| 559 | ¹H-NMR (CDCl3) δ: 7.42 (1H, d, J = 0.9 Hz), 7.22-7.16 (6H, m), 7.08-7.06 (2H, m), 7.03-7.01 (2H, m), 2.35 (2H, q, J = 7.3 Hz), 2.14 (3H, d, J = 0.9 Hz), 1.01 (3H, t, J = 7.3 Hz). |
| 560 | ¹H-NMR (CDCl3) δ: 7.31 (1H, d, J = 1.0 Hz), 7.28-7.20 (1H, m), 7.03 (1H, d, J = 8.4 Hz), 6.83 (1H, t, J = 8.4 Hz), 6.76 (1H, t, J = 8.4 Hz), 6.73-6.69 (2H, m), 3.67 (3H, s), 2.41-2.23 (2H, m), 2.14 (3H, d, J = 1.0 Hz), 2.08 (3H, s), 1.00 (3H, t, J = 7.4 Hz). |
| 561 | ¹H-NMR (CDCl3) δ: 7.78 (1H, s), 7.34-7.27 (3H, m), 7.05 (1H, d, J = 8.4 Hz), 6.91 (1H, t, J = 8.4 Hz), 6.79 (1H, t, J = 8.4 Hz), 2.43-2.36 (1H, m), 2.34-2.27 (1H, m), 2.14 (3H, s), 1.01 (3H, t, J = 7.3 Hz). |
| 562 | ¹H-NMR (CDCl3) δ: 7.74 (1H, s), 7.24-7.17 (3H, m), 7.11-7.10 (1H, m), 7.05-7.03 (1H, m), 7.00 (1H, t, J = 8.1 Hz), 6.68 (1H, d, J = 8.1 Hz), 6.65 (1H, d, J = 8.1 Hz), 3.75 (3H, s), 2.39-2.29 (2H, m), 1.94 (3H, s), 1.01 (3H, t, J = 7.3 Hz). |
| 563 | ¹H-NMR (CDCl3) δ: 7.23-7.23 (1H, m), 7.22-7.15 (3H, m), 7.13-7.10 (1H, m), 7.05-7.02 (1H, m), 7.00-6.96 (1H, m), 6.66-6.63 (2H, m), 3.75 (3H, s), 2.37-2.26 (2H, m), 2.12 (3H, d, J = 1.0 Hz), 1.92 (3H, s), 1.00 (3H, t, J = 7.3 Hz). |
| 564 | ¹H-NMR (CDCl3) δ: 7.73 (1H, s), 7.31-7.23 (2H, m), 7.22-7.19 (1H, m), 7.13-7.12 (1H, m), 7.06-7.05 (2H, m), 6.88 (1H, td, J = 8.4, 2.7 Hz), 6.78 (1H, dd, J = 8.4, 2.7 Hz), 2.40-2.30 (2H, m), 2.10 (3H, s), 1.01 (3H, t, J= 7.5 Hz). |
| 565 | ¹H-NMR (CDCl3) δ: 7.42 (1H, dd, J = 8.1, 1.3 Hz), 7.24-7.24 (1H, m), 7.22-7.21 (3H, m), 7.07-7.04 (1H, m), 7.01-6.98 (2H, m), 6.92 (1H, dd, J = 8.1, 7.6 Hz), 2.13 (3H, d, J = 1.0 Hz), 2.13 (3H, s), 1.89 (3H, s). |
| 566 | ¹H-NMR (CDCl3) δ: 7.26-6.99 (10H, m), 2.41-2.26 (2H, m), 2.13 (3H, d, J = 1.0 Hz), 2.10 (3H, s), 1.01 (3H, t, J = 7.3 Hz). |
| 567 | ¹H-NMR (CDCl3) δ: 7.98 (1H, s), 7.33-7.27 (6H, m), 7.05 (1H, dd, J = 8.3, 2.4 Hz), 6.94-6.92 (1H, m). |
| 568 | ¹H-NMR (CDCl3) δ: 7.29-7.26 (1H, m), 7.25-7.16 (3H, m), 7.13-7.11 (1H, m), 7.09 (1H, dd, J = 8.3, 2.3 Hz), 7.05-7.03 (2H, m), 7.00 (1H, d, J = 8.3 Hz), 2.39-2.26 (2H, m), 2.13 (3H, d, J = 0.9 Hz), 2.07 (3H, s), 1.00 (3H, t, J = 7.3 Hz). |
| 569 | ¹H-NMR (CDCl3) δ: 7.97 (1H, s), 7.33-7.23 (6H, m), 7.16 (1H, dd, J = 8.7, 5.7 Hz), 6.97 (1H, ddd, J = 8.7, 7.8, 2.4 Hz). |
| 570 | ¹H-NMR (CDCl3) δ: 7.27 (1H, q, J = 1.0 Hz), 7.17-7.14 (3H, m), 6.67-6.65 (1H, m), 6.57-6.55 (1H, m), 2.36-2.26 (2H, m), 2.13 (3H, d, J = 1.0 Hz), 2.11 (3H, s), 1.00 (3H, t, J = 7.4 Hz). |
| 571 | ¹H-NMR (CDCl3) δ: 7.44 (1H, d, J = 0.9 Hz), 7.23-7.22 (3H, m), 7.03-7.01 (2H, m), 6.97-6.94 (1H, m), 6.78-6.75 (2H, m), 2.14 (3H, d, J = 0.9 Hz), 2.07 (3H, s), 1.81 (3H, s). |
| 572 | ¹H-NMR (CDCl3) δ: 7.73 (1H, s), 7.44 (1H, dd, J = 7.9, 1.3 Hz), 7.25-7.22 (3H, m), 7.09-7.07 (1H, m), 7.04-7.01 (2H, m), 6.94 (1H, t, J = 7.9 Hz), 2.36-2.32 (2H, m), 2.17 (3H, s), 1.01 (3H, t, J = 7.3 Hz). |
| 573 | ¹H-NMR (CDCl3) δ: 7.27-7.26 (1H, m), 7.23-7.21 (2H, m), 7.20-7.17 (1H, m), 7.14-7.13 (1H, m), 7.04-7.03 (2H, m), 6.84 (1H, td, J = 8.7, 2.5 Hz), 6.76 (1H, dd, J = 8.7, 2.6 Hz), 2.38-2.27 (2H, m), 2.13 (3H, d, J = 0.9 Hz), 2.07 (3H, s), 1.00 (3H, t, J = 7.3 Hz). |
| 574 | ¹H-NMR (CDCl3) δ: 7.97 (1H, s), 7.30-7.29 (5H, m), 7.24-7.22 (2H, m), 7.18 (1H, dd, J = 7.3, 1.5 Hz), 7.15-7.12 (1H, m). |
| 575 | ¹H-NMR (CDCl3) δ: 7.44-7.44 (1H, m), 7.29-7.27 (1H, m), 7.24-7.21 (3H, m), 7.19-7.15 (3H, m), 7.12 (1H, dd, J = 7.6, 1.5 Hz), 7.06-7.04 (1H, m), 2.15 (3H, d, J = 1.0 Hz), 1.85 (3H, s). |
| 576 | ¹H-NMR (CDCl3) δ: 7.97 (1H, s), 7.50-7.48 (1H, m), 7.29-7.29 (4H, m), 7.25-7.22 (2H, m), 7.16-7.14 (2H, m). |
| 577 | ¹H-NMR (CDCl3) δ: 7.44-7.44 (1H, m), 7.25-7.25 (3H, m), 7.14 (2H, br s), 7.07-7.02 (2H, m), 6.89-6.84 (1H, m), 2.14 (3H, d, J = 1.0 Hz), 1.84 (3H, s). |
| 578 | ¹H-NMR (CDCl3) δ: 7.46 (1H, dd, J = 8.1, 1.0 Hz), 7.44-7.43 (1H, m), 7.22-7.16 (6H, m), 7.09 (1H, dd, J = 7.8, 2.0 Hz), 7.07-7.05 (1H, m), 2.15 (3H, d, J = 1.0 Hz), 1.84 (3H, s). |
| 579 | ¹H-NMR (CDCl3) δ: 7.98 (1H, s), 7.27-7.25 (3H, m), 7.21-7.17 (1H, m), 7.12-7.07 (4H, m), 6.99 (1H, dd, J = 7.7, 1.3 Hz), 2.17 (3H, s). |
| 580 | ¹H-NMR (CDCl3) δ: 7.45-7.45 (1H, m), 7.20-7.19 (3H, m), 7.13-7.11 (1H, m), 7.06-7.04 (4H, m), 6.99-6.98 (1H, m), 2.15 (3H, d, J = 1.0 Hz), 2.07 (3H, s), 1.82 (3H, s). |
| 581 | ¹H-NMR (CDCl3) δ: 7.56-7.55 (1H, m), 7.46-7.45 (1H, m), 7.42-7.41 (1H, m), 7.39-7.38 (1H, m), 7.22-7.20 (4H, m), 7.09-7.07 (2H, m), 2.14 (3H, d, J = 1.2 Hz), 1.78 (3H, s). |
| 582 | ¹H-NMR (CDCl3) δ: 7.44-7.44 (1H, m), 7.22-7.17 (4H, m), 7.07-7.05 (2H, br m), 6.99 (1H, dd, J = 7.5, 1.7 Hz), 6.84-6.83 (1H, m), 6.68 (1H, d, J = 8.3 Hz), 3.63 (3H, s), 2.14 (3H, d, J = 1.2 Hz), 1.87 (3H, s). |
| 583 | ¹H-NMR (CDCl3) δ: 7.98 (1H, s), 7.33-7.27 (3H, m), 7.08-7.07 (2H, m), 6.98 (1H, dd, J = 8.4, 5.7 Hz), 6.84-6.78 (2H, m), 2.17 (3H, s). |
| 584 | ¹H-NMR (CDCl3) δ: 7.97 (1H, s), 7.31-7.27 (3H, m), 7.08-7.06 (2H, m), 6.99 (1H, dd, J = 9.0, 5.7 Hz), 6.82-6.78 (2H, m), 2.15 (3H, s). |

TABLE 5-continued

| Compound | ¹H-NMR |
|---|---|
| 585 | ¹H-NMR (CDCl3) δ: 7.43 (1H, q, J = 0.9 Hz), 7.26-7.16 (6H, m), 7.05 (1H, dd, J = 8.6, 5.8 Hz), 6.91 (1H, ddd, J = 8.6, 8.0, 2.4 Hz), 2.14 (3H, d, J = 0.9 Hz), 1.84 (3H, s). |
| 586 | ¹H-NMR (CDCl3) δ: 7.46-7.45 (1H, m), 7.28-7.25 (3H, m), 7.09-6.96 (5H, m), 2.13 (3H, d, J = 1.0 Hz), 1.88 (3H, s). |
| 587 | ¹H-NMR (CDCl3) δ: 7.98 (1H, s), 7.36-7.32 (3H, m), 7.28-7.23 (3H, m), 7.10-7.08 (1H, m), 6.99 (1H, dd, J = 9.0, 2.0 Hz). |
| 588 | ¹H-NMR (CDCl3) δ: 7.97 (1H, s), 7.34-7.29 (7H, m), 7.19 (1H, dd, J = 8.3, 2.1 Hz). |
| 589 | ¹H-NMR (CDCl3) δ: 7.45-7.45 (1H, m), 7.25-7.23 (6H, m), 7.20-7.18 (1H, m), 7.11-7.09 (1H, m), 6.87 (1H, td, J = 8.4, 1.1 Hz), 2.15 (3H, d, J = 1.0 Hz), 1.87 (3H, s). |
| 590 | ¹H-NMR (CDCl3) δ: 7.98 (1H, s), 7.35-7.24 (6H, m), 7.14 (1H, dt, J = 8.3, 0.9 Hz), 6.94-6.90 (1H, m). |
| 591 | ¹H-NMR (CDCl3) δ: 7.45-7.45 (1H, m), 7.23-7.20 (3H, m), 7.18 (1H, dd, J = 8.5, 1.7 Hz), 7.15-7.13 (2H, m), 6.58-6.56 (1H, m) 6.50 (1H, d, J = 8.5 Hz), 3.68 (3H, s), 2.14 (3H, d, J = 0.9 Hz), 1.87 (3H, s). |
| 592 | ¹H-NMR (CDCl3) δ: 7.94 (1H, s), 7.30-7.27 (3H, m), 7.11 (2H, br s), 7.06-7.01 (1H, m), 6.81-6.77 (1H, m), 6.70 (1H, td, J = 9.0, 2.4 Hz), 1.93 (3H, s). |
| 593 | ¹H-NMR (CDCl3) δ: 8.07 (1H, s), 7.30-7.28 (3H, m), 7.10 (2H, br s), 7.04-7.02 (1H, m), 6.81-6.77 (1H, m), 6.72-6.68 (1H, m), 1.93 (3H, s). |
| 594 | ¹H-NMR (CDCl3) δ: 7.42 (1H, d, J = 1.0 Hz), 7.26-7.18 (5H, m), 6.99 (1H, d, J = 2.4 Hz), 6.94 (1H, d, J = 8.5 Hz), 6.71 (1H, dd, J = 8.5, 2.4 Hz), 3.73 (3H, s), 2.14 (3H, d, J = 1.0 Hz), 1.85 (3H, s). |
| 595 | ¹H-NMR (CDCl3) δ: 7.44 (1H, s), 7.31 (1H, d, J = 2.1 Hz), 7.26-7.26 (3H, m), 7.14-7.12 (3H, m), 7.01 (1H, d, J = 8.3 Hz), 2.13 (3H, s), 1.82 (3H, s). |
| 596 | ¹H-NMR (CDCl3) δ: 7.98 (1H, s), 7.34-7.24 (5H, m), 7.01-6.90 (3H, m). |
| 597 | ¹H-NMR (CDCl3) δ: 7.92 (1H, s), 7.29-7.28 (3H, m), 7.09-7.07 (3H, m), 6.83-6.78 (1H, m), 6.69 (1H, td, J = 9.0, 2.4 Hz), 2.36-2.32 (2H, m), 1.00 (3H, t, J = 7.4 Hz). |
| 598 | ¹H-NMR (CDCl3) δ: 7.42-7.42 (1H, m), 7.26-7.25 (3H, m), 7.08-7.06 (3H, m), 6.79-6.76 (1H, m), 6.67 (1H, td, J = 9.0, 2.5 Hz), 2.38-2.26 (2H, m), 2.13 (3H, d, J = 1.0 Hz), 0.99 (3H, t, J = 7.3 Hz). |
| 599 | ¹H-NMR (CDCl3) δ: 7.96 (1H, s), 7.27-7.24 (4H, m), 7.12-7.06 (3H, m), 6.89-6.87 (1H, m), 6.72 (1H, d, J = 8.1 Hz), 3.67 (3H, s). |
| 600 | ¹H-NMR (CDCl3) δ: 7.95 (1H, s), 7.58-7.56 (1H, m), 7.53-7.51 (1H, m), 7.47-7.45 (1H, m), 7.29-7.28 (4H, m), 7.14-7.13 (2H, m). |
| 601 | ¹H-NMR (CDCl3) δ: 7.42-7.39 (3H, m), 7.24-7.23 (3H, m), 7.20-7.19 (3H, m), 2.14 (3H, d, J = 0.9 Hz), 1.81 (3H, s). |
| 602 | ¹H-NMR (CDCl3) δ: 7.40 (1H, d, J = 8.9 Hz), 7.33 (1H, d, J = 0.9 Hz), 7.30-7.24 (1H, m), 6.85-6.80 (3H, m), 6.71 (1H, dd, J = 8.9, 3.1 Hz), 3.70 (3H, s), 2.15 (3H, s), 1.90 (3H, s). |
| 603 | ¹H-NMR (CDCl3) δ: 7.99 (1H, s), 7.33-7.32 (3H, m), 7.24-7.23 (2H, m), 7.13-7.11 (1H, m), 7.06-7.00 (2H, m). |
| 604 | ¹H-NMR (DMSO-D6) δ: 8.59 (1H, s), 7.57-7.54 (1H, m), 7.43-7.32 (6H, m), 7.24-7.20 (1H, m). |
| 605 | ¹H-NMR (CDCl3) δ: 7.47 (1H, s), 7.29-7.21 (1H, m), 7.14 (1H, t, J = 8.1 Hz), 6.82-6.71 (4H, m), 3.72 (3H, s), 2.14 (3H, s), 1.90 (3H, s). |
| 606 | ¹H-NMR (CDCl3) δ: 7.26 (1H, s), 7.03-6.93 (3H, m), 6.76-6.68 (3H, m), 6.54 (1H, d, J = 2.7 Hz), 3.74 (3H, s), 3.69 (3H, s), 2.13 (3H, d, J = 0.7 Hz), 1.98 (3H, s), 1.91 (3H, s). |
| 607 | ¹H-NMR (CDCl3) δ: 7.98 (1H, s), 7.33-7.32 (6H, m), 7.20-7.18 (1H, m), 6.99-6.95 (1H, m). |
| 608 | ¹H-NMR (CDCl3) δ: 7.45-7.44 (1H, m), 7.28-7.27 (6H, m), 7.13-7.11 (1H, m), 6.92 (1H, td, J = 8.5, 1.0 Hz), 2.15 (3H, d, J = 0.9 Hz), 1.86 (3H, d, J = 3.1 Hz). |
| 609 | ¹H-NMR (CDCl3) δ: 7.99 (1H, s), 7.32-7.30 (3H, m), 7.20-7.18 (3H, m), 6.91 (1H, d, J = 8.7 Hz), 6.80 (1H, t, J = 8.7 Hz), 2.17 (3H, s). |
| 610 | ¹H-NMR (CDCl3) δ: 7.46-7.46 (1H, m), 7.25-7.22 (3H, m), 7.13-7.11 (3H, m) 6.86 (1H, d, J = 7.6 Hz), 6.78 (1H, t, J = 8.7 Hz), 2.15 (3H, d, J = 1.0 Hz), 2.07 (3H, s), 1.84 (3H, s). |
| 611 | ¹H-NMR (CDCl3) δ: 7.97 (1H, s), 7.33-7.22 (5H, m), 7.20-7.19 (2H, m), 6.60 (1H, td, J = 8.6, 0.9 Hz), 6.54 (1H, d, J = 8.6 Hz), 3.74 (3H, s). |
| 612 | ¹H-NMR (CDCl3) δ: 7.91 (1H, s), 7.42-7.41 (2H, m), 7.31-7.29 (1H, m), 7.09-7.07 (2H, m), 6.64-6.60 (2H, m), 3.75 (3H, s). |
| 613 | ¹H-NMR (CDCl3) δ: 7.90 (1H, s), 7.29-7.14 (5H, m), 7.20 (1H, dd, J = 8.1, 2.5 Hz), 7.15 (1H, dd, J = 8.5, 5.6 Hz), 6.97 (1H, ddd, J = 8.5, 8.1, 2.5 Hz), 2.56-2.47 (1H, m), 2.13-2.05 (1H, m), 1.00 (3H, t, J = 7.4 Hz). |
| 614 | ¹H-NMR (CDCl3) δ: 7.45(1H, m), 7.28-7.26 (3H, m), 7.13-7.11 (2H, br m), 6.96-6.88 (2H, m), 6.78-6.74 (1H, m), 2.13 (3H, d, J = 1.2 Hz), 1.91 (3H, s). |

TABLE 5-continued

| Compound | $^1$H-NMR |
|---|---|
| 615 | $^1$H-NMR (CDCl3) δ: 7.46(1H, m), 7.28-7.25 (3H, m), 7.08-7.05 (3H, m), 7.00-6.94 (1H, m), 6.83-6.79 (1H, m), 2.14 (3H, d, J = 1.0 Hz), 1.90 (3H, s). |
| 616 | $^1$H-NMR (CDCl3) δ: 7.45 (1H, d, J = 0.9 Hz), 7.27-7.25 (3H, m), 7.06-7.01 (3H, m), 6.91-6.87 (1H, m), 6.81-6.80 (1H, m), 2.13 (3H, d, J = 0.9 Hz), 1.91 (3H, s). |
| 617 | $^1$H-NMR (CDCl3) δ: 7.35 (1H, d, J = 1.0 Hz), 7.27-7.20 (1H, m), 7.09 (1H, d, J = 8.5 Hz), 6.83-6.74 (3H, m), 6.70 (1H, t, J = 2.8 Hz), 3.69 (3H, s), 2.36 (2H, q, J = 7.6 Hz), 2.14 (3H, d, J = 1.0 Hz), 1.90 (3H, s), 1.13 (3H, t, J = 7.6 Hz). |
| 618 | $^1$H-NMR (DMSO D6) δ: 9.66 (1H, s), 7.76 (1H, d, J = 1.0 Hz), 7.48-7.40 (1H, m), 7.13-7.04 (3H, m), 6.68 (1H, dd, J = 8.5, 2.5 Hz), 6.54 (1H, t, J = 2.5 Hz), 2.22 (2H, q, J = 7.6 Hz), 1.96 (3H, s), 1.68 (3H, s), 1.06 (3H, t, J = 7.6 Hz). |
| 619 | $^1$H-NMR (CDCl3) δ: 7.32 (1H, d, J = 0.9 Hz), 7.28-7.22 (1H, m), 7.19 (1H, d, J = 8.9 Hz), 6.90 (1H, dd, J = 8.6, 2.8 Hz), 6.86-6.82 (2H, m), 6.78 (1H, t, J = 8.6 Hz), 4.68 (2H, d, J = 3.1 Hz), 2.39 (2H, q, J = 7.6 Hz), 2.14 (3H, s), 1.90 (3H, s), 1.14 (3H, t, J = 7.6 Hz). |
| 620 | $^1$H-NMR (CDCl3) δ: 7.35 (1H, d, J = 1.0 Hz), 7.26-7.20 (1H, m), 7.10 (1H, d, J = 9.2 Hz), 6.90-6.88 (2H, m), 6.81 (1H, t, J = 8.5 Hz), 6.76 (1H, t, J = 8.5 Hz), 5.03 (2H, q, J = 6.8 Hz), 3.40 (3H, s), 2.37 (2H, q, J = 7.6 Hz), 2.14 (3H, d, J = 1.0 Hz), 1.90 (3H, s), 1.14 (3H, t, J = 7.6 Hz). |
| 621 | $^1$H-NMR (CDCl3) δ: 7.91 (1H, s), 7.33-6.98 (5H, m), 7.15 (1H, dd, J = 8.6, 5.8 Hz), 7.02 (1H, dd, J = 8.4, 2.8 Hz), 6.92 (1H, ddd, J = 8.6, 8.0, 2.8 Hz), 2.46 (1H, dq, J = 13.1, 7.3 Hz), 2.14 (1H, dq, J = 13.1, 7.3 Hz), 0.99 (3H, t, J = 7.3 Hz). |
| 622 | $^1$H-NMR (CDCl3) δ: 8.32-8.30 (1H, m), 8.17-8.12 (2H, m), 7.83 (1H, dd, J = 9.9, 2.6 Hz), 7.67 (1H, d, J = 8.6 Hz), 7.60-7.57 (1H, m), 7.44-7.40 (1H, m), 7.28-7.24 (2H, m), 3.02 (2H, q, J = 7.2 Hz), 2.26 (3H, d, J = 1.2 Hz), 1.48 (3H, t, J = 7.2 Hz). |
| 623 | $^1$H-NMR (CDCl3) δ: 7.41 (1H, d, J = 0.7 Hz), 7.25-7.12 (5H, m), 7.14 (1H, dd, J = 8.4, 6.1 Hz), 7.01 (1H, dd, J = 8.4, 2.6 Hz), 6.90 (1H, td, J = 8.2, 2.6 Hz), 2.50-2.41 (1H, m), 2.15-2.05 (1H, m), 2.13 (3H, d, J = 0.7 Hz), 0.98 (3H, t, J = 7.3 Hz). |
| 624 | $^1$H-NMR (CDCl3) δ: 7.45 (1H, m), 7.32-7.27 (3H, m), 7.21 (1H, t, J = 1.8 Hz), 7.05-7.02 (2H, m), 6.96 (2H, d, J = 1.8 Hz), 2.12 (3H, s), 1.91 (3H, s). |
| 625 | $^1$H-NMR (CDCl3) δ: 7.34 (1H, d, J = 1.0 Hz), 7.27-7.20 (3H, m), 7.11 (1H, d, J = 8.5 Hz), 6.87 (1H, dd, J = 8.5, 2.7 Hz), 6.83-6.75 (3H, m), 4.56 (2H, t, J = 1.8 Hz), 2.53 (1H, t, J = 2.4 Hz), 2.36 (2H, q, J = 7.6 Hz), 2.14 (3H, d, J = 1.0 Hz), 1.90 (3H, s), 1.13 (3H, t, J = 7.6 Hz). |
| 626 | $^1$H-NMR (CDCl3) δ: 7.33 (1H, d, J = 1.0 Hz), 7.26-7.19 (1H, m), 7.08 (1H, d, J = 8.5 Hz), 6.85-6.75 (3H, m), 6.71 (1H, t, J = 2.7 Hz), 4.05-4.01 (1H, m), 3.95-3.90 (1H, m), 3.72-3.68 (2H, m), 3.44 (3H, s), 2.35 (2H, q, J = 7.6 Hz), 2.14 (3H, d, J = 1.0 Hz), 1.89 (3H, s), 1.12 (3H, t, J = 7.6 Hz). |
| 627 | $^1$H-NMR (CDCl3) δ: 7.83 (1H, s), 7.30-7.23 (1H, m), 7.11 (1H, d, J = 8.8 Hz), 6.86-6.76 (3H, m), 6.71 (1H, t, J = 2.7 Hz), 3.70 (3H, s), 2.44-2.24 (4H, m), 1.16 (3H, t, J = 7.5 Hz), 1.01 (3H, t, J = 7.5 Hz). |
| 628 | $^1$H-NMR (CDCl3) δ: 7.33 (1H, d, J = 1.0 Hz), 7.26-7.19 (1H, m), 7.09 (1H, d, J = 8.5 Hz), 6.83-6.73 (3H, m), 6.70 (1H, t, J = 2.7 Hz), 3.69 (3H, s), 2.40-2.24 (4H, m), 2.14 (3H, d, J = 1.0 Hz), 1.14 (3H, t, J = 7.6 Hz), 1.00 (3H, t, J = 7.6 Hz). |

Next, it is specifically shown that the compounds of the present invention are effective against plant diseases, but the compounds are not limited to these examples.

[Test Example A] Rice Blast

Test plants (rice variety: Sachikaze) were cultivated until the second leaves appeared after the sowing of seeds. In the test, the chemical solution was obtained by dissolving the compound of the present invention in a dimethylsulfoxide-methanol mixed solvent (volume ratio: 9/1) and appropriately diluting the resultant solution with well water so that the concentration was 250 ppm. The obtained chemical solution was sprayed to the test plants (2.5 ml/pot). The plants after the drying of the chemical liquid were inoculated with rice blast fungi (*Magnaporthe grisea*) by spraying a conidial suspension of 1 to 2×10$^5$ conidia/ml. After the inoculation, the plants were allowed to stand, for about 24 hours, in a moist chamber with the room temperature of 20 to 23° C. to promote the onset of disease. The degree of disease development after 6 to 10 days from the inoculation was investigated to evaluate the effect of the chemical solution.

[Test Example B] Tomato Gray Mold

Test plants (tomato variety: Oogata Fukuju) were cultivated until three to five first leaves (true leaves) appeared after the sowing of seeds. In the test, the chemical solution was obtained by dissolving the compound of the present invention in a dimethylsulfoxide-methanol mixed solvent (volume ratio: 9/1) and appropriately diluting the resultant solution with well water so that the concentration was 250 ppm. The obtained chemical solution was sprayed to the test plants (2.5 ml/pot). The plants after the drying of the chemical liquid were inoculated with gray mold fungi (*Botrytis cinerea*) by spraying a conidial suspension of 4 to 8×10$^5$ conidia/ml. After the inoculation, the plants were allowed to stand, for about 48 hours, in a moist chamber with the room temperature of 20 to 23° C. to promote the onset of disease. The degree of disease development after 2 to 3 days from the inoculation was investigated to evaluate the effect of the chemical solution.

[Test Example C] Cabbage *Alternaria* Sooty Spot

Test plants (cabbage variety: Shikidori) were cultivated until the cotyledons extended after the sowing of seeds. In the test, the chemical solution was obtained by dissolving the compound of the present invention in a dimethylsulfoxide-methanol mixed solvent (volume ratio: 9/1) and appropriately diluting the resultant solution with well water so that the concentration was 250 ppm. The obtained chemical solution was sprayed to the test plants (2.5 ml/pot). The plants after the drying of the chemical liquid were inoculated with cabbage *Alternaria* sooty spot fungi (*Alternaia brassicicola*) by spraying a conidial suspension of 4 to 8×10$^5$ conidia/ml. After the inoculation, the plants were allowed to stand, for about 48 hours, in a moist chamber with the room temperature of 20 to 23° C. to promote the onset of disease. The degree of disease development after 2 to 3 days from the inoculation was investigated to evaluate the effect of the chemical solution.

[Test Example D] Barley Powdery Mildew

Test plants (barley variety: Akashinriki) were cultivated until the first leaves appeared after the sowing of seeds. In the test, the chemical solution was obtained by dissolving the compound of the present invention in a dimethylsulfoxide-methanol mixed solvent (volume ratio: 9/1) and appropriately diluting the resultant solution with well water so that the concentration was 250 ppm. The obtained chemical solution was sprayed to the test plants (2.5 ml/pot). The plants after the drying of the chemical liquid were inoculated with barley powdery mildew fungi (*Blumeria graminis* f. sp. *hordei*) by dusting method. The degree of disease development after 6 to 10 days from the inoculation was investigated to evaluate the effect of the chemical solution.

[Test Example E] Wheat Brown Rust

Test plants (wheat variety: Norin 61) were cultivated until the first leaves appeared after the sowing of seeds. In the test, the chemical solution was obtained by dissolving the compound of the present invention in a dimethylsulfoxide-methanol mixed solvent (volume ratio: 9/1) and appropriately diluting the resultant solution with well water so that the concentration was 250 ppm. The obtained chemical solution was sprayed to the test plants (2.5 ml/pot). The plants after the drying of the chemical liquid were inoculated with wheat brown rust fungi (*Puccinia recondita*) by spraying a uredospore suspension of 1 to 2×10$^5$ spores/ml. After the inoculation, the plants were allowed to stand, for about 24 hours, in a moist chamber with the room temperature of 20 to 23° C. to promote the onset of disease. The degree of disease development after 7 to 10 days from the inoculation was investigated to evaluate the effect of the chemical solution.

[Test Example F] Tomato Late Blight

Test plants (tomato variety: Oogata Fukuju) were cultivated until three to five first leaves appeared after the sowing of seeds. In the test, the chemical solution was obtained by dissolving the compound of the present invention in a dimethylsulfoxide-methanol mixed solvent (volume ratio: 9/1) and appropriately diluting the resultant solution with well water so that the concentration was 250 ppm. The obtained chemical solution was sprayed to the test plants (2.5 ml/pot). The plants after the drying of the chemical liquid were inoculated with tomato late blight fungi (*Phytophthora infestans*) by spraying a zoosporangial suspension of 8×10$^3$ zoosporangia/ml. After the inoculation, the plants were allowed to stand, for about 24 hours, in a moist chamber with the room temperature of 20° C. to promote the onset of disease. The degree of disease development after 5 to 10 days from the inoculation was investigated to evaluate the effect of the chemical solution.

[Test Example G] Grape Downy Mildew

Test plants (grape variety: Neomuscat) were cultivated until three to four first leaves appeared after the sowing of seeds. In the test, the chemical solution was obtained by dissolving the compound of the present invention in a dimethylsulfoxide-methanol mixed solvent (volume ratio: 9/1) and appropriately diluting the resultant solution with well water so that the concentration was 250 ppm. The obtained chemical solution was sprayed to the test plants (2.5 ml/pot). The plants after the drying of the chemical liquid were inoculated with grape downy mildew fungus (*Plasmopara viticola*) by spraying a zoosporangial suspension of 1 to 2×10$^4$ zoosporangia/ml. After the inoculation, the plants were allowed to stand, for about 24 hours, in a moist chamber with the room temperature of 20° C. to promote the onset of disease. The degree of disease development after 7 to 10 days from the inoculation was investigated to evaluate the effect of the chemical solution.

[Test Example H] Cucumber Anthracnose

Test plants (cucumber variety: Sagami Hanjiro) were cultivated until one first leaf appeared after the sowing of seeds. In the test, the chemical solution was obtained by dissolving the compound of the present invention in a dimethylsulfoxide-methanol mixed solvent (volume ratio: 9/1) and appropriately diluting the resultant solution with well water so that the concentration was 250 ppm. The obtained chemical solution was sprayed to the test plants (2.5 ml/pot). The plants after the drying of the chemical liquid were inoculated with cucumber anthracnose fungi (*Colletotrichum orbiculare*) by spraying a conidial suspension of 2 to 4×10$^5$ conidia/ml. After the inoculation, the plants were allowed to stand, for about 24 hours, in a moist chamber with the room temperature of 20 to 23° C. to promote the onset of disease. The degree of disease development after 6 to 10 days from the inoculation was investigated to evaluate the effect of the chemical solution.

With respect to each Test Example described above, the degree of disease development was evaluated as a value with increments of 0.05, regarding the degree of disease development for plants with no onset of disease as 0 and that for plants of untreated group as 3. Further, from the degrees of disease development, a control value was calculated according to the calculation formula below.

<Control Value>

Control value=100{1−(n/3)} n=Degree of disease development of each chemical treated group

The results of the described above test are summarized in Table 6, wherein H shows the control value of more than 50%, L shows the control value of 50% or less, and nt shows that no test was performed.

TABLE 6

| Compound | Test A | Test B | Test C | Test D | Test E | Test F | Test G | Test H |
|---|---|---|---|---|---|---|---|---|
| 1 | H | H | H | H | H | L | H | H |
| 2 | H | H | H | H | H | L | H | H |
| 3 | H | H | H | H | H | L | H | H |
| 4 | H | H | H | H | H | L | H | H |
| 5 | H | H | H | H | H | L | H | H |
| 6 | H | H | H | L | H | L | L | L |
| 7 | H | H | H | L | H | L | H | H |
| 8 | H | H | H | L | H | L | L | H |
| 9 | H | H | H | H | H | L | H | H |
| 10 | H | L | H | H | H | L | L | H |
| 11 | H | L | H | H | H | L | L | H |
| 12 | H | H | H | L | H | L | L | H |
| 13 | L | L | H | H | H | L | H | H |
| 14 | H | H | H | H | H | L | H | H |
| 15 | H | H | H | L | H | L | L | H |
| 16 | H | H | H | L | H | L | L | H |
| 17 | H | H | H | L | H | L | L | H |
| 18 | H | H | H | L | H | L | L | H |
| 19 | H | H | H | L | H | L | H | H |
| 20 | H | H | H | L | H | L | L | H |
| 21 | H | H | H | L | H | L | L | H |
| 22 | H | H | H | L | H | L | L | H |
| 23 | H | H | H | L | H | L | L | H |
| 24 | H | H | H | L | H | L | H | H |
| 25 | H | H | H | L | H | L | L | H |
| 26 | H | H | H | L | H | L | L | L |
| 27 | H | H | H | H | H | L | H | H |
| 28 | H | H | H | H | H | L | H | H |
| 29 | H | L | H | L | H | L | L | H |
| 30 | H | H | H | H | H | L | L | H |
| 31 | H | H | H | H | H | L | L | H |
| 32 | H | H | H | L | H | L | L | H |
| 33 | H | H | H | L | H | L | L | H |
| 34 | H | H | H | H | H | H | H | H |
| 35 | H | H | H | H | H | H | H | H |
| 36 | H | H | H | H | H | L | H | H |
| 37 | H | H | H | H | H | L | H | H |
| 38 | H | H | H | H | H | H | H | H |
| 39 | H | H | H | H | H | L | H | H |
| 40 | H | H | H | L | H | L | L | H |
| 41 | H | H | H | H | H | L | H | H |
| 42 | H | H | H | H | H | L | H | H |
| 43 | H | H | H | H | H | L | L | H |
| 44 | H | H | H | H | H | L | L | H |
| 45 | H | H | H | H | H | L | H | H |
| 46 | H | H | H | H | H | L | H | H |
| 47 | H | H | H | H | H | L | L | H |
| 48 | H | H | H | H | H | L | H | H |
| 49 | H | H | H | H | H | H | H | H |
| 50 | H | H | H | H | H | L | H | H |
| 51 | L | H | H | H | H | L | L | H |
| 52 | H | H | H | H | H | L | L | H |
| 53 | H | H | H | L | H | L | L | H |
| 54 | H | H | H | H | H | L | H | H |
| 55 | H | H | H | H | H | L | H | H |
| 56 | H | H | H | H | H | L | L | L |
| 57 | H | H | H | H | H | L | H | H |
| 58 | H | H | H | H | H | H | H | H |
| 59 | H | H | H | L | H | H | H | H |
| 60 | H | H | H | L | H | L | L | H |
| 61 | H | H | H | H | H | L | L | H |
| 62 | H | H | H | H | H | L | H | H |
| 63 | H | H | H | H | H | L | L | H |
| 64 | H | H | H | H | H | L | H | H |
| 65 | H | H | H | H | H | L | L | H |
| 66 | H | H | H | H | H | L | L | H |
| 67 | H | H | H | L | H | L | H | H |
| 68 | H | H | H | H | H | L | H | H |
| 69 | L | L | H | L | H | L | L | L |
| 70 | L | L | H | L | H | L | L | L |
| 71 | L | L | L | L | L | L | L | H |
| 72 | L | L | H | H | L | L | L | L |
| 73 | H | H | H | L | H | L | L | L |
| 74 | H | H | H | L | H | L | L | L |
| 75 | H | H | H | L | H | L | L | H |
| 76 | H | H | L | L | H | L | L | L |
| 77 | H | H | L | L | H | L | L | L |
| 78 | H | H | L | L | H | L | H | L |

TABLE 6-continued

| Compound | Test A | Test B | Test C | Test D | Test E | Test F | Test G | Test H |
|---|---|---|---|---|---|---|---|---|
| 79 | H | L | H | L | L | L | L | L |
| 80 | H | L | H | L | H | L | L | L |
| 81 | H | H | H | H | H | L | L | H |
| 82 | H | H | H | L | H | H | H | H |
| 83 | H | H | H | L | H | H | H | H |
| 84 | L | H | H | L | H | L | H | L |
| 85 | L | H | H | L | H | L | H | L |
| 86 | L | L | H | L | L | L | L | L |
| 87 | H | L | H | L | H | L | L | H |
| 88 | H | H | H | L | H | L | H | H |
| 89 | H | H | H | L | H | L | H | H |
| 90 | H | H | H | H | H | L | H | H |
| 91 | H | H | H | L | H | L | L | H |
| 92 | H | H | H | H | H | L | L | H |
| 93 | H | H | H | L | H | L | L | H |
| 94 | L | L | L | L | H | L | L | L |
| 95 | L | L | L | L | H | L | L | L |
| 96 | H | H | H | L | H | L | H | H |
| 97 | H | H | H | L | H | L | L | H |
| 98 | H | H | H | L | H | L | L | H |
| 99 | H | H | H | L | H | L | L | H |
| 100 | L | L | L | L | H | L | L | L |
| 101 | L | L | L | L | H | L | L | L |
| 102 | L | H | H | L | H | L | L | L |
| 103 | H | H | H | L | H | L | L | L |
| 104 | L | H | H | L | H | L | L | L |
| 105 | H | H | H | H | H | L | L | H |
| 106 | H | H | H | L | H | L | L | H |
| 107 | H | H | H | H | H | L | H | H |
| 108 | H | H | H | H | H | L | H | H |
| 109 | H | H | H | L | H | L | L | H |
| 110 | H | H | H | H | H | L | L | H |
| 111 | L | H | H | L | H | L | L | H |
| 112 | L | H | H | L | H | L | L | H |
| 113 | H | H | H | L | H | L | L | H |
| 114 | H | H | H | L | H | L | L | H |
| 115 | H | H | H | H | H | L | H | H |
| 116 | H | H | H | H | H | L | H | H |
| 117 | H | L | H | L | H | L | L | H |
| 118 | L | L | H | L | L | L | L | L |
| 119 | H | L | H | L | L | L | L | L |
| 120 | H | H | H | L | H | L | L | H |
| 121 | L | L | H | L | H | L | L | L |
| 122 | H | H | H | L | L | L | L | L |
| 123 | H | H | H | L | H | L | H | L |
| 124 | H | L | H | L | L | L | L | L |
| 125 | H | H | H | L | H | L | L | L |
| 126 | H | H | H | L | H | L | L | H |
| 127 | H | H | H | L | H | L | L | H |
| 128 | H | H | H | L | H | L | L | H |
| 129 | H | H | H | L | H | L | L | H |
| 130 | H | H | H | L | H | H | L | H |
| 131 | H | H | H | L | H | L | L | H |
| 132 | H | H | H | L | H | H | L | H |
| 133 | H | H | H | L | H | L | L | H |
| 134 | H | H | H | H | H | L | L | H |
| 135 | H | H | H | H | H | L | L | H |
| 136 | L | H | H | L | H | H | H | H |
| 137 | L | H | L | H | L | L | L | L |
| 138 | H | H | H | L | H | L | L | H |
| 139 | H | H | H | L | H | L | L | H |
| 140 | H | L | H | L | L | L | L | L |
| 141 | L | H | H | L | H | L | L | L |
| 142 | H | H | H | H | H | H | H | H |
| 143 | H | H | H | H | H | L | H | H |
| 144 | H | H | H | H | H | L | H | H |
| 145 | L | L | H | L | H | L | H | L |
| 146 | H | L | H | L | H | L | L | L |
| 147 | H | H | H | H | H | H | H | H |
| 148 | H | H | H | H | H | L | H | H |
| 149 | H | H | H | H | H | L | H | H |
| 150 | L | H | H | L | H | L | L | L |
| 151 | H | H | H | H | H | L | L | H |
| 152 | H | H | H | H | H | L | L | H |
| 153 | H | H | H | L | H | L | L | L |
| 154 | H | H | H | H | H | L | L | L |
| 155 | H | H | H | H | H | L | L | H |
| 156 | H | H | H | H | H | L | L | H |

TABLE 6-continued

| Compound | Test A | Test B | Test C | Test D | Test E | Test F | Test G | Test H |
|---|---|---|---|---|---|---|---|---|
| 157 | H | H | H | H | L | nt | L | L |
| 158 | H | nt | H | nt | nt | nt | H | H |
| 159 | L | H | H | L | H | L | L | L |
| 160 | L | H | H | L | H | L | L | L |
| 161 | L | H | H | L | H | L | L | L |
| 162 | H | H | H | H | H | L | H | H |
| 163 | H | H | H | H | H | L | H | H |
| 164 | H | H | H | H | H | L | H | H |
| 165 | H | H | H | H | H | H | H | H |
| 166 | H | H | H | H | H | L | H | H |
| 167 | H | H | H | H | H | L | H | H |
| 168 | H | H | H | L | H | L | H | H |
| 169 | H | H | H | L | H | H | H | H |
| 170 | H | H | H | L | H | L | L | L |
| 171 | L | H | H | L | H | L | L | L |
| 172 | H | H | H | H | H | H | L | H |
| 173 | H | H | H | H | H | L | L | H |
| 174 | H | H | H | H | H | L | H | H |
| 175 | H | H | H | H | H | L | H | H |
| 176 | H | H | H | H | H | L | H | H |
| 177 | H | H | H | L | H | L | L | H |
| 178 | H | H | H | L | H | L | H | H |
| 179 | H | H | H | H | H | L | L | H |
| 180 | H | H | H | H | H | L | L | H |
| 181 | H | H | H | H | H | L | L | H |
| 182 | H | H | L | H | H | L | L | L |
| 183 | H | H | H | H | H | L | L | H |
| 184 | H | H | L | H | H | L | L | H |
| 185 | H | nt | H | nt | nt | L | L | H |
| 186 | H | H | H | H | H | L | L | H |
| 187 | H | H | H | H | H | L | L | H |
| 188 | H | H | H | H | H | L | L | H |
| 189 | H | H | H | H | H | L | L | H |
| 190 | H | H | H | H | H | L | L | H |
| 191 | L | H | H | L | H | L | L | L |
| 192 | H | H | H | L | H | L | L | L |
| 193 | H | H | H | H | H | L | L | L |
| 194 | H | H | H | L | H | L | L | L |
| 195 | H | H | H | H | H | L | H | L |
| 196 | H | H | H | H | H | L | L | L |
| 197 | H | H | H | H | H | L | H | H |
| 198 | H | H | H | L | H | L | L | L |
| 199 | H | H | H | L | H | L | L | H |
| 200 | L | L | H | L | L | L | L | L |
| 201 | L | L | H | L | L | L | L | L |
| 202 | L | L | H | L | L | L | L | L |
| 203 | H | H | H | L | L | L | L | L |
| 204 | H | H | H | L | L | L | L | L |
| 205 | H | H | H | H | H | L | L | H |
| 206 | H | H | H | L | H | L | L | L |
| 207 | H | L | L | L | H | L | L | L |
| 208 | H | L | L | L | H | L | L | L |
| 209 | H | H | H | L | H | L | L | L |
| 210 | L | L | L | L | H | L | H | L |
| 211 | L | L | L | L | H | L | H | L |
| 212 | L | L | L | L | H | L | H | L |
| 213 | L | L | H | L | H | L | H | L |
| 214 | H | H | H | L | H | H | L | H |
| 215 | H | H | H | L | H | L | L | L |
| 216 | H | H | H | H | H | L | H | H |
| 217 | H | H | H | H | H | L | H | H |
| 218 | H | H | H | H | H | L | H | H |
| 219 | H | H | H | H | H | L | H | H |
| 220 | H | H | H | H | H | L | H | H |
| 221 | H | H | H | L | H | H | H | H |
| 222 | H | H | H | L | H | L | H | H |
| 223 | H | H | H | H | H | L | H | H |
| 224 | H | H | H | H | H | L | L | H |
| 225 | H | H | H | L | L | L | L | H |
| 226 | H | H | H | L | H | L | L | H |
| 227 | H | L | H | L | H | L | L | L |
| 228 | H | H | H | H | H | L | H | H |
| 229 | H | H | H | H | H | L | H | H |
| 230 | H | H | H | L | H | L | L | H |
| 231 | H | H | H | H | H | L | L | H |
| 232 | H | H | H | H | H | L | L | H |
| 233 | H | H | H | L | H | L | L | H |
| 234 | H | H | H | L | H | L | L | L |

TABLE 6-continued

| Compound | Test A | Test B | Test C | Test D | Test E | Test F | Test G | Test H |
|---|---|---|---|---|---|---|---|---|
| 235 | H | H | H | L | H | L | H | H |
| 236 | H | H | H | L | H | L | L | H |
| 237 | H | L | L | L | L | L | L | L |
| 238 | H | L | L | L | L | L | L | L |
| 239 | H | H | H | L | H | L | L | H |
| 240 | H | H | H | L | H | L | H | H |
| 241 | H | H | H | H | H | L | H | H |
| 242 | H | H | H | L | H | H | L | H |
| 243 | L | H | H | L | L | L | L | L |
| 244 | L | L | H | L | L | L | L | H |
| 245 | H | H | H | H | H | L | L | H |
| 246 | H | L | H | L | H | L | H | L |
| 247 | H | H | H | L | H | L | L | H |
| 248 | H | H | H | L | H | L | L | H |
| 249 | H | H | H | L | H | L | H | H |
| 250 | H | H | H | L | H | L | L | H |
| 251 | H | H | H | L | H | L | L | H |
| 252 | H | H | H | L | H | L | L | H |
| 253 | L | H | H | L | H | L | H | L |
| 254 | L | H | L | L | L | L | L | L |
| 255 | L | L | L | L | H | L | L | L |
| 256 | H | H | H | L | H | L | L | H |
| 257 | L | H | H | L | H | L | L | H |
| 258 | H | H | H | L | H | L | L | H |
| 259 | H | H | H | L | H | L | L | H |
| 260 | L | H | L | L | L | L | L | L |
| 261 | H | H | H | H | H | L | H | H |
| 262 | L | H | L | L | L | L | L | L |
| 263 | L | H | L | L | L | L | L | L |
| 264 | H | H | H | H | H | H | H | H |
| 265 | H | H | H | H | H | L | L | H |
| 266 | H | H | H | H | H | L | H | H |
| 267 | L | L | L | L | H | L | L | H |
| 268 | L | H | L | H | H | L | L | L |
| 269 | L | H | L | L | H | L | L | L |
| 270 | H | H | H | H | H | L | H | H |
| 271 | H | L | L | L | L | L | L | L |
| 272 | H | H | H | H | H | L | L | H |
| 273 | H | H | H | H | H | L | L | H |
| 274 | H | H | H | H | H | L | L | H |
| 275 | H | H | H | H | H | L | H | H |
| 276 | H | H | H | L | H | L | L | H |
| 277 | L | H | H | L | H | L | L | H |
| 278 | H | H | H | H | H | L | H | H |
| 279 | H | H | H | H | H | H | L | H |
| 280 | H | H | H | L | H | L | L | H |
| 281 | H | H | H | H | H | L | L | H |
| 282 | H | H | L | H | H | L | H | H |
| 283 | H | H | H | L | H | L | L | H |
| 284 | H | H | H | H | H | L | H | H |
| 285 | H | H | H | L | H | L | H | H |
| 286 | H | H | H | H | H | H | H | H |
| 287 | L | L | L | L | H | L | H | L |
| 288 | H | H | H | L | H | L | L | L |
| 289 | H | L | H | L | H | L | L | H |
| 290 | L | H | H | L | H | L | L | H |
| 291 | H | H | H | L | H | L | L | H |
| 292 | H | H | H | L | H | L | L | H |
| 293 | H | H | H | L | H | L | L | H |
| 294 | H | H | H | H | H | L | L | H |
| 295 | H | H | H | H | H | L | H | H |
| 296 | H | H | H | L | H | L | L | L |
| 297 | H | H | H | H | H | L | L | H |
| 298 | H | H | H | H | H | H | H | H |
| 299 | H | H | H | H | H | H | H | H |
| 300 | H | nt | H | nt | nt | L | L | H |
| 301 | H | L | H | L | H | L | H | H |
| 302 | H | H | H | L | H | L | L | H |
| 303 | H | H | H | L | H | L | L | H |
| 304 | H | H | H | H | H | L | H | H |
| 305 | L | H | L | L | L | L | L | H |
| 306 | H | L | L | L | H | L | L | L |
| 307 | H | H | L | L | H | L | L | H |
| 308 | H | H | L | L | H | L | L | H |
| 309 | L | H | H | L | H | L | L | H |
| 310 | L | H | L | L | H | L | L | H |
| 311 | H | H | H | H | H | L | H | H |
| 312 | L | H | H | H | H | L | L | H |

TABLE 6-continued

| Compound | Test A | Test B | Test C | Test D | Test E | Test F | Test G | Test H |
|---|---|---|---|---|---|---|---|---|
| 313 | H | H | H | H | H | L | H | H |
| 314 | H | H | H | H | H | L | H | H |
| 315 | H | H | H | H | H | L | L | H |
| 316 | H | H | H | H | H | L | L | H |
| 317 | H | H | H | H | H | L | H | H |
| 318 | H | L | H | L | L | L | L | H |
| 319 | L | L | L | L | H | L | L | L |
| 320 | H | H | H | L | H | L | L | L |
| 321 | H | L | H | L | H | L | L | L |
| 322 | H | H | H | H | H | L | H | H |
| 323 | H | H | H | H | H | H | H | H |
| 324 | H | H | H | L | H | H | H | H |
| 325 | H | H | H | L | H | L | H | H |
| 326 | H | H | H | H | H | L | L | H |
| 327 | H | H | H | L | H | L | H | H |
| 328 | H | H | H | H | H | L | L | H |
| 329 | H | H | H | L | H | L | L | H |
| 330 | H | H | H | L | H | L | L | L |
| 331 | H | H | H | L | H | L | L | H |
| 332 | H | H | H | L | H | L | L | H |
| 333 | H | H | H | L | H | L | L | H |
| 334 | H | H | H | H | H | L | H | H |
| 335 | H | H | H | L | H | L | H | L |
| 336 | H | H | L | L | H | L | L | H |
| 337 | H | H | L | L | H | L | L | L |
| 338 | H | H | H | H | H | L | H | H |
| 339 | H | H | H | H | H | L | H | H |
| 340 | H | H | H | H | H | L | L | H |
| 341 | H | L | L | L | L | L | L | L |
| 342 | L | L | H | L | L | L | L | H |
| 343 | L | L | L | L | L | L | L | H |
| 344 | L | L | H | L | L | L | L | H |
| 345 | L | L | L | L | L | L | L | H |
| 346 | H | H | H | H | H | L | L | H |
| 347 | H | H | H | L | H | L | H | H |
| 348 | L | L | H | L | L | L | L | L |
| 349 | H | H | H | H | H | L | L | H |
| 350 | H | H | H | H | H | L | L | H |
| 351 | H | H | H | H | H | L | L | H |
| 352 | H | H | H | H | H | L | H | H |
| 353 | H | H | H | L | H | L | L | H |
| 354 | H | H | H | H | H | L | L | H |
| 355 | H | L | H | L | L | L | L | L |
| 356 | H | H | H | H | H | L | H | H |
| 357 | L | H | L | L | H | L | H | L |
| 358 | L | H | L | L | L | L | L | L |
| 359 | L | H | L | L | L | L | L | H |
| 360 | H | H | H | L | H | L | H | H |
| 361 | L | H | H | L | H | L | H | H |
| 362 | H | H | H | L | H | L | H | H |
| 363 | L | H | H | L | H | L | H | L |
| 364 | H | H | H | H | H | L | H | H |
| 365 | L | H | H | L | L | L | L | L |
| 366 | H | H | H | H | H | H | H | H |
| 367 | H | H | H | H | H | H | H | H |
| 368 | H | H | H | L | H | L | H | H |
| 369 | L | H | L | L | H | L | H | H |
| 370 | L | L | H | L | L | L | L | H |
| 371 | H | H | H | H | H | L | L | H |
| 372 | H | H | H | L | H | L | L | H |
| 373 | H | L | H | L | L | L | L | H |
| 374 | H | H | H | L | L | L | L | H |
| 375 | H | H | H | H | H | L | L | H |
| 376 | L | H | H | H | L | L | L | L |
| 377 | L | H | H | L | L | L | L | H |
| 378 | L | L | L | L | L | L | L | H |
| 379 | H | H | L | L | H | L | H | L |
| 380 | H | H | L | L | H | L | L | L |
| 381 | H | L | L | L | H | L | L | L |
| 382 | H | H | L | L | H | L | L | H |
| 383 | H | H | H | L | H | L | L | H |
| 384 | H | L | L | L | H | L | L | H |
| 385 | H | H | H | L | H | L | L | H |
| 386 | H | H | H | L | H | L | H | H |
| 387 | H | H | H | L | H | L | H | H |
| 388 | H | H | L | L | H | L | L | H |
| 389 | L | H | H | L | H | L | L | H |
| 390 | H | H | H | H | H | L | L | H |

TABLE 6-continued

| Compound | Test A | Test B | Test C | Test D | Test E | Test F | Test G | Test H |
|---|---|---|---|---|---|---|---|---|
| 391 | H | H | H | L | H | L | H | H |
| 392 | H | H | H | L | H | L | L | H |
| 393 | H | H | H | H | H | L | H | H |
| 394 | H | H | H | L | H | L | H | H |
| 395 | H | H | H | H | H | L | H | H |
| 396 | H | H | H | L | H | L | L | L |
| 397 | L | L | H | L | L | L | L | L |
| 398 | H | L | L | L | H | L | L | L |
| 399 | L | L | L | L | L | L | L | H |
| 400 | H | H | H | L | H | L | H | H |
| 401 | H | H | H | H | H | L | H | H |
| 402 | L | H | L | L | H | L | L | L |
| 403 | L | H | H | L | H | L | L | L |
| 404 | L | H | L | L | H | L | H | L |
| 405 | H | H | H | H | H | L | L | H |
| 406 | L | H | H | H | H | H | H | H |
| 407 | L | H | L | L | H | L | L | L |
| 408 | L | L | L | L | H | L | L | L |
| 409 | L | L | L | L | H | L | L | L |
| 410 | L | L | L | L | L | L | H | L |
| 411 | L | L | L | L | H | L | L | L |
| 412 | L | H | H | L | H | L | L | L |
| 413 | L | H | L | L | H | L | L | L |
| 414 | L | L | H | L | L | L | L | L |
| 415 | H | H | H | L | H | L | H | H |
| 416 | L | H | H | L | H | L | L | H |
| 417 | L | H | H | L | H | L | H | H |
| 418 | L | H | H | L | H | L | L | H |
| 419 | L | H | H | L | H | L | H | H |
| 420 | L | H | H | L | H | L | L | H |
| 421 | L | L | H | L | H | L | L | L |
| 422 | H | H | H | H | H | L | H | H |
| 423 | L | H | L | H | H | L | H | H |
| 424 | H | L | H | L | L | L | L | L |
| 425 | H | L | L | L | L | L | H | L |
| 426 | L | L | H | L | H | L | L | L |
| 427 | H | H | H | H | H | H | H | H |
| 428 | H | H | H | H | H | H | H | H |
| 429 | H | H | H | L | H | L | H | H |
| 430 | H | H | L | L | H | L | L | H |
| 431 | L | H | L | L | H | L | L | H |
| 432 | H | H | H | H | H | L | L | H |
| 433 | L | H | H | L | H | L | L | H |
| 434 | L | L | L | L | H | L | H | L |
| 435 | H | H | H | H | H | L | L | H |
| 436 | H | H | H | H | H | H | H | H |
| 437 | H | H | H | H | H | L | L | H |
| 438 | L | H | H | L | H | L | L | L |
| 439 | H | H | H | H | H | L | L | H |
| 440 | H | H | H | H | H | L | L | H |
| 441 | H | H | H | H | H | L | H | H |
| 442 | H | H | H | H | H | L | L | H |
| 443 | H | H | H | H | H | L | L | H |
| 444 | H | H | H | H | H | L | L | H |
| 445 | H | H | H | H | H | L | H | H |
| 446 | H | H | H | H | H | L | H | H |
| 447 | L | H | H | H | H | L | L | H |
| 448 | H | H | H | H | H | L | L | H |
| 449 | L | H | H | L | H | L | L | L |
| 450 | H | H | H | L | H | L | L | H |
| 451 | L | L | L | L | L | L | L | H |
| 452 | L | L | L | L | L | L | L | H |
| 453 | H | H | H | H | H | L | H | H |
| 454 | H | H | H | H | H | L | H | H |
| 455 | H | H | H | H | H | L | H | H |
| 456 | H | H | H | H | H | L | H | H |
| 457 | L | H | H | L | H | L | L | H |
| 458 | H | H | H | H | H | L | H | H |
| 459 | L | H | L | L | L | L | L | L |
| 460 | H | H | L | L | L | L | L | L |
| 461 | H | H | H | H | H | L | L | H |
| 462 | H | H | H | H | H | L | L | H |
| 463 | H | H | H | H | H | L | L | H |
| 464 | H | H | H | H | H | L | L | H |
| 465 | H | H | H | H | H | L | H | H |
| 466 | H | H | H | H | H | L | L | H |
| 467 | L | H | H | L | L | L | L | L |
| 468 | H | H | H | L | L | L | L | L |

TABLE 6-continued

| Compound | Test A | Test B | Test C | Test D | Test E | Test F | Test G | Test H |
|---|---|---|---|---|---|---|---|---|
| 469 | H | H | H | L | H | L | L | H |
| 470 | H | H | H | L | H | L | L | H |
| 471 | H | H | H | H | H | L | L | H |
| 472 | H | H | H | H | H | L | L | H |
| 473 | H | H | H | H | H | L | L | H |
| 474 | H | H | H | H | H | L | H | H |
| 475 | H | H | H | L | H | L | L | H |
| 476 | H | H | H | H | H | L | L | H |
| 477 | H | H | H | H | H | L | H | H |
| 478 | H | H | H | H | H | L | H | H |
| 479 | H | H | H | H | H | L | H | H |
| 480 | H | H | H | H | H | L | H | H |
| 481 | H | H | H | H | H | H | H | H |
| 482 | L | H | H | L | H | L | L | H |
| 483 | L | H | H | H | H | L | H | H |
| 484 | L | H | H | H | H | L | L | H |
| 485 | H | H | H | L | H | L | L | H |
| 486 | L | H | L | H | H | L | L | L |
| 487 | H | H | H | L | H | L | L | L |
| 488 | H | H | H | H | H | L | H | H |
| 489 | H | H | H | H | H | H | H | H |
| 490 | H | H | H | H | H | H | L | H |
| 491 | H | H | H | H | H | L | L | H |
| 492 | H | H | H | L | H | L | L | H |
| 493 | H | H | H | H | H | L | L | H |
| 494 | H | H | H | H | H | L | L | H |
| 495 | L | L | H | L | L | L | L | L |
| 496 | H | H | H | H | H | L | L | L |
| 497 | H | H | H | L | H | L | L | L |
| 498 | H | L | L | L | L | L | L | L |
| 499 | H | L | L | L | L | L | L | L |
| 500 | H | H | H | H | H | L | L | H |
| 501 | H | H | L | L | H | L | L | L |
| 502 | L | H | H | L | H | L | L | L |
| 503 | L | L | H | L | L | L | L | H |
| 504 | L | H | H | L | H | L | L | H |
| 505 | L | H | H | H | H | L | L | H |
| 506 | H | H | H | H | H | L | L | L |
| 507 | L | H | H | L | L | L | L | L |
| 508 | H | H | H | L | H | L | L | H |
| 509 | H | H | H | H | H | L | L | H |
| 510 | H | H | H | L | L | L | L | H |
| 511 | L | H | H | H | H | L | L | H |
| 512 | H | H | H | H | H | L | L | H |
| 513 | H | H | H | H | H | L | H | H |
| 514 | H | H | H | H | H | L | H | H |
| 515 | H | H | H | H | H | H | L | H |
| 516 | L | L | L | L | L | H | L | H |
| 517 | L | H | L | L | L | H | L | L |
| 518 | H | H | L | L | L | L | L | H |
| 519 | H | H | H | H | H | L | L | H |
| 520 | H | H | H | H | H | L | L | H |
| 521 | H | H | H | L | H | L | L | H |
| 522 | H | H | H | H | H | L | L | H |
| 523 | H | H | H | H | H | L | H | H |
| 524 | H | H | H | L | H | L | L | L |
| 525 | H | H | H | H | H | L | L | H |
| 526 | H | H | H | L | H | L | L | H |
| 527 | H | H | H | H | H | L | H | H |
| 528 | H | L | H | H | H | L | L | H |
| 529 | H | H | H | H | H | L | L | H |
| 530 | H | H | H | H | H | L | L | H |
| 531 | H | H | H | L | L | L | L | H |
| 532 | H | H | H | H | H | L | L | H |
| 533 | H | H | H | H | H | L | L | H |
| 534 | L | H | H | L | L | L | L | H |
| 535 | L | H | H | L | H | L | L | H |
| 536 | L | H | H | L | H | L | L | H |
| 537 | L | H | H | L | H | H | L | L |
| 538 | L | H | H | H | H | L | L | H |
| 539 | L | H | H | L | H | L | L | H |
| 540 | L | H | H | L | L | L | L | H |
| 541 | L | L | H | H | L | L | L | L |
| 542 | L | H | H | L | L | L | L | L |
| 543 | H | H | H | H | H | L | L | H |
| 544 | L | H | H | H | L | H | L | H |
| 545 | L | H | H | L | L | L | L | H |
| 546 | H | H | H | H | H | L | L | H |

TABLE 6-continued

| Compound | Test A | Test B | Test C | Test D | Test E | Test F | Test G | Test H |
|---|---|---|---|---|---|---|---|---|
| 547 | H | H | H | H | H | L | H | H |
| 548 | H | H | H | H | H | L | L | H |
| 549 | L | H | H | H | H | H | L | H |
| 550 | H | H | H | L | H | L | L | H |
| 551 | H | H | H | H | H | H | L | H |
| 552 | H | H | H | H | H | L | H | H |
| 553 | L | H | L | L | L | L | L | L |
| 554 | H | H | H | H | H | H | L | H |
| 555 | H | H | H | H | H | H | L | H |
| 556 | H | H | H | H | H | H | L | H |
| 557 | L | H | H | L | H | L | L | H |
| 558 | H | H | H | H | H | H | H | H |
| 559 | L | L | H | H | L | L | H | H |
| 560 | H | H | H | H | H | L | L | H |
| 561 | H | H | H | L | H | L | H | H |
| 562 | L | H | H | L | H | L | L | L |
| 563 | H | H | H | H | H | L | L | H |
| 564 | L | H | H | L | H | L | L | H |
| 565 | H | H | H | L | H | L | H | L |
| 566 | H | H | H | H | H | L | L | H |
| 567 | H | H | H | L | H | L | L | H |
| 568 | H | H | H | H | H | L | L | H |
| 569 | H | H | H | L | H | L | L | H |
| 570 | H | H | H | H | H | L | L | H |
| 571 | H | H | H | H | H | L | L | H |
| 572 | L | H | H | H | H | L | L | L |
| 573 | H | H | H | H | H | L | L | L |
| 574 | H | H | H | L | H | L | L | H |
| 575 | H | H | H | L | H | L | L | H |
| 576 | L | H | L | L | H | L | L | H |
| 577 | H | H | H | H | H | L | L | H |
| 578 | L | H | H | L | H | L | L | H |
| 579 | H | H | H | L | H | L | L | L |
| 580 | H | H | H | L | H | L | H | H |
| 581 | L | H | H | L | H | L | L | H |
| 582 | L | L | H | L | L | L | L | L |
| 583 | L | H | H | L | H | L | L | H |
| 584 | H | H | H | L | H | L | L | H |
| 585 | L | H | H | L | H | L | L | H |
| 586 | H | H | H | H | H | L | H | H |
| 587 | H | L | H | L | H | L | L | H |
| 588 | H | H | H | L | H | L | H | H |
| 589 | H | H | H | H | H | L | L | H |
| 590 | H | H | H | L | H | L | L | H |
| 591 | L | L | L | L | L | L | H | L |
| 592 | L | H | H | L | H | L | L | H |
| 593 | H | H | H | L | L | L | L | L |
| 594 | L | H | H | L | H | H | H | H |
| 595 | H | H | H | L | H | L | L | H |
| 596 | L | L | H | L | L | L | L | L |
| 597 | H | H | H | L | H | L | L | H |
| 598 | H | H | H | H | H | L | L | H |
| 599 | L | H | L | L | L | L | L | L |
| 600 | H | L | L | L | L | L | L | H |
| 601 | H | H | H | H | H | L | L | H |
| 602 | H | H | H | L | H | L | L | H |
| 603 | L | H | H | L | H | L | L | L |
| 604 | L | L | H | L | L | L | L | L |
| 605 | H | H | H | H | H | L | L | H |
| 606 | H | H | H | H | H | L | H | H |
| 607 | H | H | H | L | H | L | L | H |
| 608 | H | H | H | L | H | L | H | H |
| 609 | H | H | H | L | H | L | L | H |
| 610 | L | H | H | L | H | L | L | H |
| 611 | L | L | L | L | L | L | L | L |
| 612 | L | L | L | L | L | H | H | L |
| 613 | H | H | H | L | H | L | L | L |
| 614 | H | H | H | H | H | L | L | H |
| 615 | L | H | H | L | H | L | H | H |
| 616 | L | H | H | L | H | L | H | L |
| 617 | H | H | H | H | H | L | H | H |
| 618 | H | L | L | L | L | L | L | L |
| 619 | H | H | H | H | H | L | L | H |
| 620 | H | H | H | H | H | L | H | H |
| 621 | H | H | H | H | H | L | L | H |
| 622 | L | L | H | L | L | L | H | L |
| 623 | H | H | H | H | H | L | L | H |
| 624 | L | H | H | L | L | L | L | L |

TABLE 6-continued

| Compound | Test A | Test B | Test C | Test D | Test E | Test F | Test G | Test H |
|---|---|---|---|---|---|---|---|---|
| 625 | L | H | H | H | H | H | L | L |
| 626 | L | H | H | H | H | L | H | L |
| 627 | L | H | H | H | H | L | H | H |
| 628 | L | H | H | H | H | L | L | H |

INDUSTRIAL APPLICABILITY

The pyridone compound of the present invention is a novel compound and can control plant diseases. Therefore, the compound is valuable as a pesticide, for example, an agricultural and horticultural pest control agent, in particular an agricultural and horticultural fungicide.

The disclosure in Japanese Patent Application No. 2017-77802 (filing date: Apr. 10, 2017) is entirely incorporated herein by reference.

All publications, patent applications and technical standards mentioned in the present specification are herein incorporated by reference to the same extent as if each individual publication, patent application or technical standard was specifically and individually indicated to be incorporated by reference.

The invention claimed is:

1. A compound represented by Formula (1), or a salt thereof:

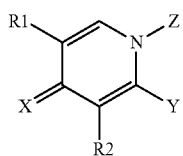

(1)

wherein R1 represents
a cyano group,
a halogen atom,
a C1-C6 alkyl group optionally substituted with substituent A,
a C1-C6 haloalkyl group,
a C3-C8 cycloalkyl group optionally substituted with substituent A,
a C2-C6 alkenyl group optionally substituted with substituent A,
a C2-C6 haloalkenyl group,
a C2-C6 alkynyl group optionally substituted with substituent A,
a C2-C6 haloalkynyl group,
a C1-C6 alkoxy group optionally substituted with substituent A,
a C1-C6 haloalkoxy group,
a C3-C8 cycloalkoxy group optionally substituted with substituent A,
a C2-C6 alkenyloxy group optionally substituted with substituent A,
a C2-C6 haloalkenyloxy group,
a C3-C6 alkynyloxy group optionally substituted with substituent A,
a C3-C6 haloalkynyloxy group,
an Rc-L- (wherein Rc represents a C1-C6 alkyl group or a C1-C6 haloalkyl group, and L represents S, SO or SO$_2$), or
an RgC(=O)— (wherein Rg represents a C1-C6 alkyl group optionally substituted with substituent B, a C1-C6 haloalkyl group or a C3-C8 cycloalkyl group);

R2 represents
a cyano group,
a halogen atom,
a C1-C6 alkyl group optionally substituted with substituent A,
a C1-C6 haloalkyl group,
a C3-C8 cycloalkyl group optionally substituted with substituent A,
a C2-C6 alkenyl group optionally substituted with substituent A,
a C2-C6 haloalkenyl group,
a C2-C6 alkynyl group optionally substituted with substituent A,
a C2-C6 haloalkynyl group,
an Rc-L- (wherein Rc and L are the same as defined above), or
an RgC(=O)— (wherein Rg is the same as defined above);

X represents an oxygen atom or a sulfur atom;

Y represents
a phenyl group optionally substituted with 0 to 5 R3 (with the proviso that when there are two or more substituents R3, they are independent to each other),
a pyridyl group optionally substituted with 0 to 4 R3 (with the proviso that when there are two or more substituents R3, they are independent to each other),
a pyridazinyl group optionally substituted with 0 to 3 R3 (with the proviso that when there are two or more substituents R3, they are independent to each other),
a pyrimidinyl group optionally substituted with 0 to 3 R3 (with the proviso that when there are two or more substituents R3, they are independent to each other),
a pyrazinyl group optionally substituted with 0 to 3 R3 (with the proviso that when there are two or more substituents R3, they are independent to each other),
a triazinyl group optionally substituted with 0 to 2 R3 (with the proviso that when there are two substituents R3, they are independent to each other),
a tetrazinyl group optionally substituted with R3,
a thienyl group optionally substituted with 0 to 3 R3 (with the proviso that when there are two or more substituents R3, they are independent to each other),
a thiazolyl group optionally substituted with 0 to 2 R3 (with the proviso that when there are two substituents R3, they are independent to each other),
an isothiazolyl group optionally substituted with 0 to 2 R3 (with the proviso that when there are two substituents R3, they are independent to each other),
a thiadiazolyl group optionally substituted with R3,
a furanyl group optionally substituted with 0 to 3 R3 (with the proviso that when there are two or more substituents R3, they are independent to each other), an oxazolyl group optionally substituted with 0 to 2 R3 (with the proviso that when there are two substituents R3, they are independent to each other),
an isoxazolyl group optionally substituted with 0 to 2 R3 (with the proviso that when there are two substituents R3, they are independent to each other), or
an oxadiazolyl group optionally substituted with R3, R3 represents
a hydroxyl group,
a cyano group,
a nitro group,
a halogen atom,
a C1-C6 alkyl group optionally substituted with substituent C,
a C1-C6 haloalkyl group,
a C3-C8 cycloalkyl group optionally substituted with substituent C,
a C2-C6 alkenyl group optionally substituted with substituent C,
a C2-C6 haloalkenyl group,
a C2-C6 alkynyl group optionally substituted with substituent C,
a C2-C6 haloalkynyl group,
a C1-C6 alkoxy group optionally substituted with substituent C,
a C1-C6 haloalkoxy group,
a C3-C8 cycloalkoxy group optionally substituted with substituent C,
a C2-C6 alkenyloxy group optionally substituted with substituent C,
a C2-C6 haloalkenyloxy group,
a C3-C6 alkynyloxy group optionally substituted with substituent C,
a C3-C6 haloalkynyloxy group,
an RdC(=O)— (wherein Rd represents a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group)),
an RdC(=O)O— (wherein Rd is the same as defined above),
a group of a 3-6 membered ring containing 1-2 oxygen atoms,
an Rc-L- (wherein Rc and L are the same as defined above),
an RaRbN— (wherein Ra and Rb are the same as defined above), or
an ReC(=O)N(Rf)— (wherein Re and Rf are independent to each other, and each represents a hydrogen atom, a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are the same as defined above));

Z represents
a C1-C9 alkyl group optionally substituted with substituent C,
a C1-C6 haloalkyl group,
a C3-C8 cycloalkyl group optionally substituted with substituent D,
a C2-C6 alkenyl group optionally substituted with substituent C,
a C2-C6 haloalkenyl group,
a C2-C6 alkynyl group optionally substituted with substituent C,
a C2-C6 haloalkynyl group,
a phenyl group optionally substituted with 0 to 5 R4 (with the proviso that when there are two or more substituents R4, they are independent to each other),
a C1-C6 alkyl group having a phenyl group optionally substituted with 0 to 5 R4 (with the proviso that when there are two or more substituents R4, they are independent to each other),
a C1-C6 haloalkyl group having a phenyl group optionally substituted with 0 to 5 R4 (with the proviso that when there are two or more substituents R4, they are independent to each other),
a pyridyl group optionally substituted with 0 to 4 R4 (with the proviso that when there are two or more substituents R4, they are independent to each other),
a pyridazinyl group optionally substituted with 0 to 3 R4 (with the proviso that when there are two or more substituents R4, they are independent to each other),
a pyrimidinyl group optionally substituted with 0 to 3 R4 (with the proviso that when there are two or more substituents R4, they are independent to each other),
a pyrazinyl group optionally substituted with 0 to 3 R4 (with the proviso that when there are two or more substituents R4, they are independent to each other),
a triazinyl group optionally substituted with 0 to 2 R4 (with the proviso that when there are two substituents R4, they are independent to each other),
a tetrazinyl group optionally substituted with R4,
a thienyl group optionally substituted with 0 to 3 R4 (with the proviso that when there are two or more substituents R4, they are independent to each other),
a thiazolyl group optionally substituted with 0 to 2 R4 (with the proviso that when there are two substituents R4, they are independent to each other),
an isothiazolyl group optionally substituted with 0 to 2 R4 (with the proviso that when there are two substituents R4, they are independent to each other),
a thiadiazolyl group optionally substituted with R4,
an oxazolyl group optionally substituted with 0 to 2 R4 (with the proviso that when there are two substituents R4, they are independent to each other),
an isoxazolyl group optionally substituted with 0 to 2 R4 (with the proviso that when there are two substituents R4, they are independent to each other),
an oxadiazolyl group optionally substituted with R4, or
a pyrazolyl group optionally substituted with 0 to 2 R4 (with the proviso that when there are two substituents R4, they are independent to each other), R4 has the same meaning as R3; and
the substituent A is at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, an RaRbN— (wherein Ra and Rb are the same as defined above) and an Rc-L- (wherein Rc and L are the same as defined above);
the substituent B is at least one member selected from the group consisting of a cyano group, a C1-C6 alkoxy group, a C1-C6 haloalkoxy group and a C3-C8 cycloalkoxy group;

the substituent C is at least one member selected from the group consisting of a hydroxyl group, a cyano group, a C3-C8 cycloalkyl group, a C1-C6 alkoxy group, a C1-C6 haloalkoxy group, a C3-C8 cycloalkoxy group, a C2-C5 alkoxyalkoxy group, an RaRbN— (wherein Ra and Rb are the same as defined above), an Rc-L- (wherein Rc and L are the same as defined above), an RdC(=O)— (wherein Rd is the same as defined above) and a group of a 3-6 membered ring containing 1-2 oxygen atoms; and the substituent D is at least one member selected from the group consisting of a cyano group, a C1-C6 alkyl group, a C1-C6 alkoxy group, a C1-C6 haloalkoxy group and a C3-C8 cycloalkoxy group.

2. The compound, or a salt thereof according to claim 1, wherein:

R1 represents
  a halogen atom,
  a C1-C6 alkyl group optionally substituted with substituent A,
  a C1-C6 haloalkyl group,
  a C3-C8 cycloalkyl group optionally substituted with substituent A,
  a C2-C6 alkenyl group optionally substituted with substituent A,
  a C2-C6 haloalkenyl group,
  a C2-C6 alkynyl group optionally substituted with substituent A,
  a C2-C6 haloalkynyl group,
  a C1-C6 alkoxy group optionally substituted with substituent A,
  a C1-C6 haloalkoxy group,
  a C2-C6 alkenyloxy group optionally substituted with substituent A,
  a C3-C6 alkynyloxy group optionally substituted with substituent A, or
  an RgC(=O)— (wherein Rg represents a C1-C6 alkyl group optionally substituted with substituent B, a C1-C6 haloalkyl group or a C3-C8 cycloalkyl group);

R2 represents
  a halogen atom,
  a C1-C6 alkyl group optionally substituted with substituent A,
  a C1-C6 haloalkyl group,
  a C3-C8 cycloalkyl group optionally substituted with substituent A,
  a C2-C6 alkenyl group optionally substituted with substituent A,
  a C2-C6 haloalkenyl group,
  a C2-C6 alkynyl group optionally substituted with substituent A, or
  a C2-C6 haloalkynyl group;

Y represents
  a phenyl group optionally substituted with 0 to 5 R3 (with the proviso that when there are two or more substituents R3, they are independent to each other),
  a pyridyl group optionally substituted with 0 to 4 R3 (with the proviso that when there are two or more substituents R3, they are independent to each other), or
  a furanyl group optionally substituted with 0 to 3 R3 (with the proviso that when there are two or more substituents R3, they are independent to each other), R3 represents
  a hydroxyl group,
  a cyano group,
  a halogen atom,
  a C1-C6 alkyl group optionally substituted with substituent C,
  a C1-C6 haloalkyl group,
  a C1-C6 alkoxy group optionally substituted with substituent C,
  a C1-C6 haloalkoxy group,
  a C2-C6 alkenyloxy group optionally substituted with substituent C,
  a C2-C6 haloalkenyloxy group,
  a C3-C6 alkynyloxy group optionally substituted with substituent C,
  a C3-C6 haloalkynyloxy group,
  an RdC(=O)— (wherein Rd represents a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group)),
  an RdC(=O)O— (wherein Rd is the same as defined above), or
  an Rc-L- (wherein Rc represents a C1-C6 alkyl group or a C1-C6 haloalkyl group, and L represents S, SO or SO₂);

Z represents
  a C1-C9 alkyl group optionally substituted with substituent C,
  a C1-C6 haloalkyl group,
  a C3-C8 cycloalkyl group optionally substituted with substituent D,
  a C2-C6 alkenyl group optionally substituted with substituent C,
  a C2-C6 alkynyl group optionally substituted with substituent C,
  a phenyl group optionally substituted with 0 to 5 R4 (with the proviso that when there are two or more substituents R4, they are independent to each other),
  a C1-C6 alkyl group having a phenyl group optionally substituted with 0 to 5 R4 (with the proviso that when there are two or more substituents R4, they are independent to each other),
  a pyridyl group optionally substituted with 0 to 4 R4 (with the proviso that when there are two or more substituents R4, they are independent to each other),
  an oxazolyl group optionally substituted with 0 to 2 R4 (with the proviso that when there are two substituents R4, they are independent to each other),
  an isoxazolyl group optionally substituted with 0 to 2 R4 (with the proviso that when there are two substituents R4, they are independent to each other),
  or an oxadiazolyl group optionally substituted with R4, R4 represents
  a hydroxyl group,
  a cyano group,
  a nitro group,
  a halogen atom, a C1-C6 alkyl group optionally substituted with substituent C,
a C1-C6 haloalkyl group,
a C2-C6 alkenyl group optionally substituted with substituent C,
a C2-C6 alkynyl group optionally substituted with substituent C,
a C1-C6 alkoxy group optionally substituted with substituent C,
a C1-C6 haloalkoxy group,
a C2-C6 alkenyloxy group optionally substituted with substituent C,
a C3-C6 alkynyloxy group optionally substituted with substituent C,
an RdC(=O)O— (wherein Rd is the same as defined above),
an RaRbN— (wherein Ra and Rb are the same as defined above), or
an ReC(=O)N(Rf)— (wherein Re and Rf are independent to each other, and each represents a hydrogen atom, a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are the same as defined above)).

3. The compound, or a salt thereof according to claim 2, wherein:
R1 represents
a halogen atom,
a C1-C6 alkyl group optionally substituted with substituent A,
a C1-C6 haloalkyl group,
a C2-C6 alkenyl group optionally substituted with substituent A,
a C2-C6 alkynyl group optionally substituted with substituent A,
or an RgC(=O)— (wherein Rg represents a C1-C6 alkyl group optionally substituted with substituent B, a C1-C6 haloalkyl group or a C3-C8 cycloalkyl group);
R2 represents
a halogen atom,
a C1-C6 alkyl group optionally substituted with substituent A, or
a C1-C6 haloalkyl group;
Y represents
a phenyl group optionally substituted with 0 to 5 R3 (with the proviso that when there are two or more substituents R3, they are independent to each other),
a pyridyl group optionally substituted with 0 to 4 R3 (with the proviso that when there are two or more substituents R3, they are independent to each other), or
a furanyl group optionally substituted with 0 to 3 R3 (with the proviso that when there are two or more substituents R3, they are independent to each other),
R3 represents
a hydroxyl group,
a cyano group,
a halogen atom,
a C1-C6 alkyl group optionally substituted with substituent C,
a C1-C6 haloalkyl group,
a C1-C6 alkoxy group optionally substituted with substituent C,
a C2-C6 alkenyloxy group optionally substituted with substituent C,
a C3-C6 alkynyloxy group optionally substituted with substituent C,
an RdC(=O)— (wherein Rd represents a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are independent to each other, and each represents a hydrogen atom, a C1-C6 alkyl group optionally substituted with substituent B, a C1-C6 haloalkyl group or a C3-C8 cycloalkyl group, or Ra and Rb in combination with the nitrogen atom to which they are bonded form an aziridinyl group, an azetidinyl group, a pyrrolidinyl group, a piperidinyl group, a homopiperidinyl group or an azocanyl group)),
an RdC(=O)O— (wherein Rd is the same as defined above), or
an Rc-L- (wherein Rc represents a C1-C6 alkyl group or a C1-C6 haloalkyl group, and L represents S, SO or $SO_2$);
Z represents
a C1-C9 alkyl group optionally substituted with substituent C,
a C1-C6 haloalkyl group,
a C3-C8 cycloalkyl group optionally substituted with substituent D,
a C2-C6 alkenyl group optionally substituted with substituent C,
a C2-C6 alkynyl group optionally substituted with substituent C,
a phenyl group optionally substituted with 0 to 5 R4 (with the proviso that when there are two or more substituents R4, they are independent to each other),
a C1-C6 alkyl group having a phenyl group optionally substituted with 0 to 5 R4 (with the proviso that when there are two or more substituents R4, they are independent to each other),
a pyridyl group optionally substituted with 0 to 4 R4 (with the proviso that when there are two or more substituents R4, they are independent to each other), or
an isoxazolyl group optionally substituted with 0 to 2 R4 (with the proviso that when there are two substituents R4, they are independent to each other),
R4 represents
a hydroxyl group,
a cyano group,
a nitro group,
a halogen atom,
a C1-C6 alkyl group optionally substituted with substituent C,
a C1-C6 haloalkyl group,
a C1-C6 alkoxy group optionally substituted with substituent C,
a C2-C6 alkenyloxy group optionally substituted with substituent C,
a C3-C6 alkynyloxy group optionally substituted with substituent C,
an RaRbN— (wherein Ra and Rb are the same as defined above) or
an ReC(=O)N(Rf)— (wherein Re and Rf are independent to each other, and each represents a hydrogen atom, a C1-C6 alkyl group optionally substituted with substituent B, a C1-C6 haloalkyl group, a C3-C8 cycloalkyl group, a C1-C6 alkoxy group, a C1-C6 haloalkoxy group, a C3-C8 cycloalkoxy group or an RaRbN— (wherein Ra and Rb are the same as defined above)).

4. An agricultural and horticultural pest control agent comprising the compound or a salt thereof according to claim 1 as an active ingredient.

5. An agricultural and horticultural fungicide comprising the compound or a salt thereof according to claim 1 as an active ingredient.

6. A method for controlling a plant disease, comprising applying the agricultural and horticultural pest control agent of claim 4.

7. A method for controlling a plant disease, comprising applying the agricultural and horticultural fungicide of claim 5.

* * * * *